US009802927B2

(12) United States Patent
Acharya et al.

(10) Patent No.: US 9,802,927 B2
(45) Date of Patent: Oct. 31, 2017

(54) OXADIAZINE COMPOUNDS AND METHODS OF USE THEREOF

(71) Applicant: Denali Therapeutics, Inc., South San Francisco, CA (US)

(72) Inventors: Raksha Acharya, Bedford, MA (US); Duane A. Burnett, Wayland, MA (US); Matthew Gregory Bursavich, Needham, MA (US); Andrew Simon Cook, Stow, MA (US); Bryce Alden Harrison, Framingham, MA (US); Andrew J. McRiner, Melrose, MA (US)

(73) Assignee: DENALI THERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 15/178,626

(22) Filed: Jun. 10, 2016

(65) Prior Publication Data
US 2017/0066753 A1 Mar. 9, 2017

Related U.S. Application Data

(60) Provisional application No. 62/279,384, filed on Jan. 15, 2016, provisional application No. 62/173,723, filed on Jun. 10, 2015.

(51) Int. Cl.
C07D 498/04 (2006.01)
C07D 413/14 (2006.01)
A61K 31/535 (2006.01)
C07D 247/02 (2006.01)
C07D 271/02 (2006.01)
C07D 273/02 (2006.01)
C07D 273/04 (2006.01)
C07D 413/04 (2006.01)
C07D 417/14 (2006.01)
C07D 471/04 (2006.01)

(52) U.S. Cl.
CPC .......... C07D 413/14 (2013.01); A61K 31/535 (2013.01); C07D 247/02 (2013.01); C07D 271/02 (2013.01); C07D 273/02 (2013.01); C07D 273/04 (2013.01); C07D 413/04 (2013.01); C07D 417/14 (2013.01); C07D 471/04 (2013.01)

(58) Field of Classification Search
CPC .............................. C07D 498/04; C07D 413/14
See application file for complete search history.

(56) References Cited

U.S. PATENT DOCUMENTS

| 6,143,741 A | 11/2000 | Jednakovits et al. |
| 2004/0019019 A1 | 1/2004 | Hansen et al. |
| 2012/0058891 A1 | 3/2012 | Kruge et al. |
| 2014/0179691 A1 | 6/2014 | Cho et al. |

FOREIGN PATENT DOCUMENTS

| EP | 0184752 A2 | 6/1986 |
| EP | 1847524 A1 | 10/2007 |
| EP | 1849762 A1 | 10/2007 |
| GB | 2482502 A | 2/2012 |
| WO | 2004074232 | 9/2004 |
| WO | 2004110350 | 12/2004 |
| WO | 2005054193 | 6/2005 |
| WO | 2005108362 | 11/2005 |
| WO | 2005115990 | 12/2005 |
| WO | 2006008558 | 1/2006 |
| WO | 2006021441 | 3/2006 |
| WO | 2006041874 | 4/2006 |
| WO | 2006045554 | 5/2006 |
| WO | 2007110667 | 10/2007 |
| WO | 2007116228 | 10/2007 |
| WO | 2007124394 | 11/2007 |
| WO | 2007125364 | 11/2007 |
| WO | 2009086277 | 7/2009 |
| WO | 2012131539 | 10/2012 |
| WO | 2014045156 | 3/2014 |
| WO | 2014096212 | 6/2014 |
| WO | 2014111457 | 7/2014 |

OTHER PUBLICATIONS

Asberom, et al., "Discovery of γ-secretase inhibitors efficacious in a transgenic animal model of Alzheimer's disease", Bioorganic & Medicinal Chemistry Letters 17, 511-516 (2007).
Chen, et al., "Discovery of 2-methylpyridine-based biaryl amides as γ-secretase modulators for the treatment of Alzheimer's disease", Bioorganic & Medicinal Chemistry Letters 23, 6447-6465 (2013).
De Strooper, "Aph-1, Pen-2, and Nicastrin with Presenilin generate an active gamma-Secretase complex", Neuron 38 (1), 9-12 (2003).
Huang, et al., "Efficient synthesis and reaction pathway studies of novel fused morpholine oxadiazolines for use as gamma secretase modulators", Tetrahedron Letters 53, 6451-6455 (2012).
Huang, et al., "Synthesis and SAR Studies of Fused Oxadiazines as γ-Secretase Modulators for Treatment of Alzheimer's Disease", ACS Med Chem Lett 3, 931-935 (2012).
Kobayashi, et al., "Design and synthesis of an aminopiperidine series of γ-secretase modulators", Bioorganic & Medicinal Chemistry Letters 24, 378-381 (2014).
Li, et al., "The discovery of fused oxadiazepines as gamma secretase modulators for treatment of Alzheimer's disease", Bioorganic & Medicinal Chemistry Letters 23, 466-471 (2013).
Patent Cooperation Treaty, International Searching Authority, Search Report and Written Opinion for PCT/US2016/036801, 11 pages, Nov. 3, 2016.

(Continued)

Primary Examiner — Kahsay Habte
(74) Attorney, Agent, or Firm — Viksnins Harris Padys Malen LLP

(57) ABSTRACT

The present disclosure relates to oxadiazine compounds, pharmaceutical compositions comprising an effective amount of an oxadiazine compound and methods for using an oxadiazine compound in the treatment of a neurodegenerative disease, comprising administering to a subject in need thereof an effective amount of an oxadiazine compound.

19 Claims, No Drawings

(56) References Cited

OTHER PUBLICATIONS

Peretto, et al., "Synthesis and Biological Activity of Flurbiprofen Analogues as Selective Inhibitors of β-Amyloid1-42 Secretion", J Med Chem 48 (18), 5705-5720 (2005).

Pettersson, et al., "Design and synthesis of dihydrobenzofuran amides as orally bioavailable, centrally active γ-secretase modulators", Bioorganic & Medicinal Chemistry Letters 22, 2906-2911 (2012).

Pettersson, et al., "Design of Pyridopyrazine-1,6-dione γ-Secretase Modulators that Align Potency, MDR Efflux Ratio, and Metabolic Stability", ACS Med Chem Lett 6, 596-601 (2015).

Pettersson, et al., "Design, Synthesis, and Pharmacological Evaluation of a Novel Series of Pyridopyrazine-1,6-dione γ-Secretase Modulators", J Med Chem 57, 1046-1062 (2014).

Pettersson, et al., "Discovery of indole-derived pyridopyrazine-1,6-dione γ-secretase modulators that target presenilin", Bioorganic & Medicinal Chemistry Letters 25, 908-913 (2015).

Stock, et al., "The geminal dimethyl analogue of Flurbiprofen as a novel Abeta42 inhibitor and potential Alzheimer's disease modifying agent", Bioorg Med Chem Lett 16 (8), 2219-2223 (2006).

Thompson, et al., "Synthesis and evaluation of succinoyl-caprolactam gamma-secretase inhibitors", Bioorg Med Chem Lett 16, 2357-2363 (2006).

OXADIAZINE COMPOUNDS AND METHODS OF USE THEREOF

1. CROSS-REFERENCE TO RELATED APPLICATIONS

This application claims priority to U.S. Provisional Application Ser. No. 62/173,723, filed Jun. 10, 2015, and to U.S. Provisional Application Ser. No. 62/279,384, filed Jan. 15, 2016, both of which are herein incorporated by reference in their entirety.

2. FIELD

This disclosure relates generally to oxadiazine compounds. More specifically, the disclosure relates to the use of the oxadiazine compounds for the treatment of neurological disease.

3. BACKGROUND

Alzheimer's disease (AD) is the most prevalent form of dementia. It is a neurodegenerative disease that is associated (though not exclusively) with aging. The disease is clinically characterized by a progressive loss of memory, cognition, reasoning and judgment that leads to an extreme mental deterioration and ultimately death. The disease is pathologically characterized by the deposition of extracellular plaques and the presence of neurofibrillary tangles. The plaques mainly consist of fibrillar aggregates of β-amyloid peptide (Aβ), which are products of the amyloid precursor protein (APP). APP is initially processed by β-secretase forming a secreted peptide and a membrane bound C99 fragment. The C99 fragment is subsequently processed by the proteolytic activity of γ-secretase. Multiple sites of proteolysis on the C99 fragment lead to the production of a range of smaller peptides (Aβ 37-42 amino acids). N-terminal truncations can also be found e.g., Aβ (4-42). For convenience, notations Aβ40 and Aβ42, as used herein, include these N-terminal truncated peptides. Upon secretion, the Aβ peptides initially form soluble aggregates which ultimately lead to the formation of insoluble deposits and plaques. Aβ42 is believed to be the most neurotoxic; the shorter peptides have less propensity to aggregate and form plaques. Aβ plaques in the brain are also associated with cerebral amyloid angiopathy, hereditary cerebral hemorrhage with amyloidosis, multi infarct dementia, dementia pugilistica and Down's Syndrome.

γ-secretase is an association of four proteins: Aph1, nicastrin, presenilin and Pen-2 (review De Strooper, *Neuron* 38:9-12 (2003)). Subjects carrying particular mutations in one of these components, presenilin, show increased Aβ42/Aβ40 ratio. These mutations are correlated with early onset familial AD. Inhibition of γ-secretase resulting in the lowering of Aβ42 has been investigated by the pharmaceutical community, and numerous inhibitors have been found. See, e.g., Thompson et al. (*Bioorg. Med. Chem. Lett.* 2006, 16, 2357-63), Shaw et al. (*Bioorg. Med. Chem. Lett.* 2006, 17, 511-16) and Asberom et al. (*Bioorg. Med. Chem. Lett.* 2007, 15, 2219-2223). Inhibition of γ-secretase, though, is not without side-effects, some of which are due to the γ-secretase complex processing substrates other than C99, e.g., Notch. A more desirable approach is to modulate the proteolytic activity of the γ-secretase complex in a manner that lowers Aβ42 in favor of shorter peptides without significantly affecting the activity of γ-secretase on substrates such as Notch.

Compounds that have shown modulation of γ-secretase include certain non-steroidal, anti-inflammatory drugs (NSAIDs), for example Flurbiprofen, (Stock et al., *Bioorg. Med. Chem. Lett.* 2006, 16, 2219-2223). Other publications that disclose agents said to reduce Aβ42 through the modulation of γ-secretase include: WO 2004/074232, WO 2005/054193, Perreto et al., *Journal of Medicinal Chemistry* 2005, 48, 5705-20, WO 2005/108362, WO 2006/008558, WO 2006/021441, WO 2006/041874, WO 2006/045554, WO 2004/110350, WO 2006/043964, WO 2005/115990, EP 1847524, WO 2007/116228, WO 2007/110667, WO 2007/124394, EP 184752, EP 1849762, WO 2007/125364, WO 2009/086277 and others.

4. SUMMARY

It is understood that any of the embodiments described below can be combined in any desired way, and that any embodiment or combination of embodiments can be applied to each of the aspects described below, unless the context indicates otherwise.

In one aspect, the invention provides a compound of Formula (I)

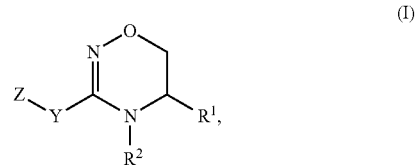

or a pharmaceutically acceptable salt thereof, wherein: $R^1$ is —$C_1$-$C_6$ alkyl, —$C_3$-$C_8$ monocyclic cycloalkyl, —$C_1$-$C_4$ alkylene-$C_3$-$C_8$ monocyclic cycloalkyl, phenyl, 5- to 6-membered aromatic heterocycle, 3- to 7-membered monocyclic heterocycle, 8- to 10-membered bicyclic heterocycle, each of which is unsubstituted or substituted with one or more substituents independently selected from the group consisting of -halo, —CN, —$C_1$-$C_4$ alkyl, —$C_3$-$C_8$ monocyclic cycloalkyl, halo-substituted $C_1$-$C_4$ alkyl, —$C_1$-$C_4$ alkoxy, halo-substituted $C_1$-$C_4$ alkoxy and oxo; $R^2$ is hydrogen or —$C_1$-$C_4$ alkyl; Y is pyridinyl which is unsubstituted or substituted with one or more substituents independently selected from the group consisting of -halo, —$C_1$-$C_4$ alkoxy, halo-substituted $C_1$-$C_4$ alkoxy, —$C_1$-$C_4$ alkyl, halo-substituted $C_1$-$C_4$ alkyl, —CN and —OH; and Z is nitrogen-containing 3- to 7-membered monocyclic heterocycle which is unsubstituted or substituted with one or more substituents independently selected from the group consisting of -halo, —$C_1$-$C_4$ alkyl, halo-substituted $C_1$-$C_4$ alkyl, —$C_1$-$C_4$ alkoxy and —$OCF_3$.

In some embodiments, $R^1$ is —$C_1$-$C_6$ alkyl, —$C_3$-$C_8$ monocyclic cycloalkyl, phenyl, 8- to 10-membered bicyclic heterocycle, each of which is unsubstituted or substituted with one or more substituents independently selected from the group consisting of -halo, —CN, —$C_1$-$C_4$ alkyl, —$C_3$-$C_8$ monocyclic cycloalkyl, halo-substituted $C_1$-$C_4$ alkyl, —$C_1$-$C_4$ alkoxy and halo-substituted $C_1$-$C_4$ alkoxy; or a pharmaceutically acceptable salt thereof.

In some embodiments, $R^1$ is —$C_3$-$C_8$ monocyclic cycloalkyl, phenyl, 8- to 10-membered bicyclic heterocycle, each of which is unsubstituted or substituted with one or more substituents independently selected from the group consisting of -halo, —$C_1$-$C_4$ alkyl, —$C_3$-$C_8$ monocyclic cycloalkyl, halo-substituted $C_1$-$C_4$ alkyl, and halo-substituted $C_1$-$C_4$ alkoxy; or a pharmaceutically acceptable salt thereof.

In some embodiments, $R^1$ is 8- to 10-membered bicyclic heterocycle, each of which is unsubstituted or substituted with one or more substituents independently selected from the group consisting of -halo, —$C_1$-$C_4$ alkyl, and halo-substituted $C_1$-$C_4$ alkyl; or a pharmaceutically acceptable salt thereof.

In some embodiments, $R^1$ is phenyl, each of which is unsubstituted or substituted with one or more substituents independently selected from the group consisting of -halo, —CN, —$C_1$-$C_4$ alkyl, —$C_3$-$C_8$ monocyclic cycloalkyl, halo-substituted $C_1$-$C_4$ alkyl, —$C_1$-$C_4$ alkoxy and halo-substituted $C_1$-$C_4$ alkoxy; or a pharmaceutically acceptable salt thereof.

In some embodiments, $R^1$ is phenyl, each of which is unsubstituted or substituted with one or more substituents independently selected from the group consisting of -halo, —$C_3$-$C_8$ monocyclic cycloalkyl, halo-substituted $C_1$-$C_4$ alkyl, and halo-substituted $C_1$-$C_4$ alkoxy; or a pharmaceutically acceptable salt thereof.

In some embodiments, $R^1$ is —$C_1$-$C_6$ alkyl which is unsubstituted; or a pharmaceutically acceptable salt thereof.

In some embodiments, $R^1$ is —$C_3$-$C_8$ monocyclic cycloalkyl, each of which is unsubstituted or substituted with one or more -halo; or a pharmaceutically acceptable salt thereof.

In some embodiments, $R^1$ is —$C_3$-$C_8$ monocyclic cycloalkyl which is unsubstituted; or a pharmaceutically acceptable salt thereof.

In some embodiments, Y is pyridinyl which is unsubstituted or substituted with one or more —$C_1$-$C_4$ alkoxy, halo-substituted $C_1$-$C_4$ alkoxy; or a pharmaceutically acceptable salt thereof.

In some embodiments, Y is pyridinyl which is substituted with one —$C_1$-$C_4$ alkoxy; or a pharmaceutically acceptable salt thereof.

In some embodiments, Y is pyridinyl which is substituted with one methoxy; or a pharmaceutically acceptable salt thereof.

In some embodiments, Z is nitrogen-containing 3- to 7-membered monocyclic heterocycle which is unsubstituted or substituted with one or more —$C_1$-$C_4$ alkyl; or a pharmaceutically acceptable salt thereof.

In some embodiments, Z is nitrogen-containing 3- to 7-membered monocyclic heterocycle which is substituted with one —$C_1$-$C_4$ alkyl; or a pharmaceutically acceptable salt thereof.

In some embodiments, Z is nitrogen-containing 3- to 7-membered monocyclic heterocycle which is substituted with one methyl; or a pharmaceutically acceptable salt thereof.

In some embodiments, Z is imidazolyl which is unsubstituted or substituted with one methyl; or a pharmaceutically acceptable salt thereof.

In some embodiments, $R^1$ is

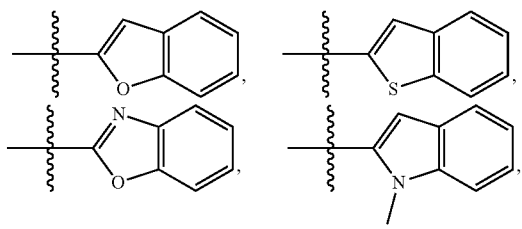

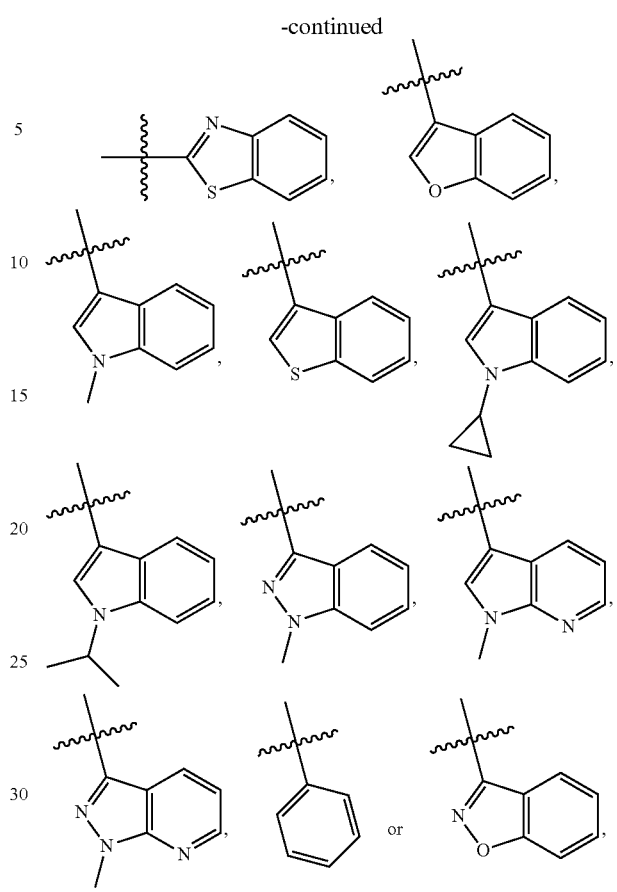

each of which is optionally further substituted with -halo, —$CF_3$ or —$C_1$-$C_4$ alkyl; and Z is

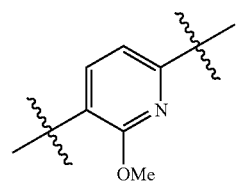 [SMILES: *c1ccc(*)c(OC)n1]

or a pharmaceutically acceptable salt thereof.

In some embodiments, Y is

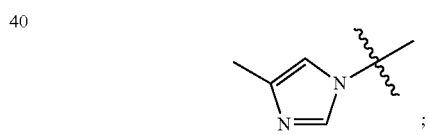

wherein the left most radical is connected to the Z group in Formula (I); or a pharmaceutically acceptable salt thereof.

In one aspect, the invention provides a pharmaceutical composition comprising a pharmaceutically acceptable carrier or vehicle and an effective amount of a compound of Formula (I); or a pharmaceutically acceptable salt thereof.

In one aspect, the invention provides a method for treating a neurodegenerative disease, comprising administering to a subject in need thereof an effective amount of a compound of Formula (I); or a pharmaceutically acceptable salt thereof.

In some embodiments, the neurodegenerative disease is panic disorder, obsessive compulsive disorder, delusional disorder, drug-induced psychosis, post-traumatic stress disorder, age-related cognitive decline, attention deficit/hyperactivity disorder, personality disorder of the paranoid type, personality disorder of the schizoid type, dyskinesia, choreiform condition, psychosis associated with Parkinson's disease, psychotic symptoms associated with Alzheimer's disease, mood disorder, or dementia.

In some embodiments, the invention provides a method for treating Alzheimer's disease, comprising administering to a subject in need thereof an effective amount of a compound of Formula (I) or a pharmaceutically acceptable salt thereof.

In some embodiments, the invention provides a method for improving an impaired cognitive function, comprising administering to a subject having impaired cognitive function an effective amount of a compound of Formula (I); or a pharmaceutically acceptable salt thereof.

In some embodiments, the cognitive function impaired is one or more of attention, learning, delayed memory, working memory, visual learning, speed of processing, vigilance, verbal learning, visual motor function, social cognition, long term memory or executive function.

In some embodiments, the invention provides a method for ameliorating a symptom of Alzheimer's disease, comprising administering to a subject in need thereof an effective amount of a compound of Formula (I) or a pharmaceutically acceptable salt thereof.

In some embodiments, the symptom is progressive loss of memory, progressive loss of cognition, progressive loss of reasoning and/or progressive loss of judgment.

In some embodiments, the compound of Formula (I) is a compound selected from the list of compounds in Table I or a pharmaceutically acceptable salt thereof.

In some embodiments, the compound of Formula (I) is selected from the group consisting of: (R)-5-(benzofuran-2-yl)-3-(6-methoxy-5-(4-methyl-1H-imidazol-1-yl)pyridin-2-yl)-5,6-dihydro-4H-1,2,4-oxadiazine; 3-(6-Methoxy-5-(4-methyl-1H-imidazol-1-yl)pyridin-2-yl)-5-(7-methylbenzofuran-2-yl)-5,6-dihydro-4H-1,2,4-oxadiazine; (R)-3-(6-methoxy-5-(4-methyl-1H-imidazol-1-yl)pyridin-2-yl)-5-(5-methylbenzofuran-2-yl)-5,6-dihydro-4H-1,2,4-oxadiazine; (R)-5-(benzo[b]thiophen-2-yl)-3-(6-methoxy-5-(4-methyl-1H-imidazol-1-yl)pyridin-2-yl)-5,6-dihydro-4H-1,2,4-oxadiazine; (+)-3-(6-methoxy-5-(4-methyl-1H-imidazol-1-yl)pyridin-2-yl)-5-(3-methylbenzofuran-2-yl)-5,6-dihydro-4H-1,2,4-oxadiazine; (R)-3-(6-methoxy-5-(4-methyl-1H-imidazol-1-yl)pyridin-2-yl)-5-(4-methylbenzofuran-2-yl)-5,6-dihydro-4H-1,2,4-oxadiazine; (R)-3-(6-methoxy-5-(4-methyl-1H-imidazol-1-yl)pyridin-2-yl)-5-(6-methylbenzofuran-2-yl)-5,6-dihydro-4H-1,2,4-oxadiazine; (+)-3-(6-methoxy-5-(4-methyl-1H-imidazol-1-yl)pyridin-2-yl)-4-methyl-5-(7-methylbenzofuran-2-yl)-5,6-dihydro-4H-1,2,4-oxadiazine; (+)-3-(5-(4-chloro-1H-imidazol-1-yl)-6-methoxypyridin-2-yl)-5-(7-methylbenzofuran-2-yl)-5,6-dihydro-4H-1,2,4-oxadiazine; 5-(4-chloro-2-methylphenyl)-3-(6-methoxy-5-(4-methyl-1H-imidazol-1-yl) pyridin-2-yl)-4-methyl-5,6-dihydro-4H-1,2,4-oxadiazine; 3-(6-methoxy-5-(4-methyl-1H-imidazol-1-yl) pyridin-2-yl)-4-methyl-5-(3-(trifluoromethyl) phenyl)-5,6-dihydro-4H-1,2,4-oxadiazine; (+)-3-(6-methoxy-5-(4-methoxy-1H-imidazol-1-yl)pyridin-2-yl)-5-(7-methylbenzofuran-2-yl)-5,6-dihydro-4H-1,2,4-oxadiazine; 3-(6-methoxy-5-(4-methyl-1H-imidazol-1-yl)pyridin-2-yl)-5-phenyl-5,6-dihydro-4H-1,2,4-oxadiazine; 5-(benzofuran-3-yl)-3-(6-methoxy-5-(4-methyl-1H-imidazol-1-yl)pyridin-2-yl)-5,6-dihydro-4H-1,2,4-oxadiazine; 5-(4-fluorophenyl)-3-(6-methoxy-5-(4-methyl-1H-imidazol-1-yl)pyridin-2-yl)-5,6-dihydro-4H-1,2,4-oxadiazine; 5-(4-chlorophenyl)-3-(6-methoxy-5-(4-methyl-1H-imidazol-1-yl)pyridin-2-yl)-5,6-dihydro-4H-1,2,4-oxadiazine; 5-(4-fluoro-3-(trifluoromethyl)phenyl)-3-(6-methoxy-5-(4-methyl-1H-imidazol-1-yl)pyridin-2-yl)-5,6-dihydro-4H-1,2,4-oxadiazine; 5-(1H-indol-3-yl)-3-(6-methoxy-5-(4-methyl-1H-imidazol-1-yl)pyridin-2-yl)-5,6-dihydro-4H-1,2,4-oxadiazine; (+)-5-(3,4-dichlorophenyl)-3-(6-methoxy-5-(4-methyl-1H-imidazol-1-yl) pyridin-2-yl)-5,6-dihydro-4H-1,2,4-oxadiazine; (+)-5-(6-fluorobenzofuran-2-yl)-3-(6-methoxy-5-(4-methyl-1H-imidazol-1-yl) pyridin-2-yl)-5,6-dihydro-4H-1,2,4-oxadiazine; (+)-3-(6-methoxy-5-(4-methyl-1H-imidazol-1-yl) pyridin-2-yl)-5-(4-methoxyphenyl)-5,6-dihydro-4H-1,2,4-oxadiazine; (+)-5-(5-chlorobenzofuran-2-yl)-3-(6-methoxy-5-(4-methyl-1H-imidazol-1-yl) pyridin-2-yl)-5,6-dihydro-4H-1,2,4-oxadiazine; (+)-3-(6-methoxy-5-(4-methyl-1H-imidazol-1-yl) pyridin-2-yl)-5-(4-(trifluoromethyl) phenyl)-5,6-dihydro-4H-1,2,4-oxadiazine; (+)-5-cyclohexyl-3-(6-methoxy-5-(4-methyl-1H-imidazol-1-yl) pyridin-2-yl)-5,6-dihydro-4H-1,2,4-oxadiazine; (+)-5-(7-chlorobenzofuran-2-yl)-3-(6-methoxy-5-(4-methyl-1H-imidazol-1-yl) pyridin-2-yl)-5,6-dihydro-4H-1,2,4-oxadiazine; (+)-3-(6-methoxy-5-(4-methyl-1H-imidazol-1-yl) pyridin-2-yl)-5-(3-methylbenzo [b] thiophen-2-yl)-5,6-dihydro-4H-1,2,4-oxadiazine; (+)-5-(benzo [b] thiophen-3-yl)-3-(6-methoxy-5-(4-methyl-1H-imidazol-1-yl) pyridin-2-yl)-5,6-dihydro-4H-1,2,4-oxadiazine; (+)-3-(6-methoxy-5-(4-methyl-1H-imidazol-1-yl) pyridin-2-yl)-5-(4-(trifluoromethoxy) phenyl)-5,6-dihydro-4H-1,2,4-oxadiazine; (−)-5-(5-chloro-1-ethyl-6-fluoro-1H-indol-3-yl)-3-(6-methoxy-5-(4-methyl-1H-imidazol-1-yl) pyridin-2-yl)-5,6-dihydro-4H-1,2,4-oxadiazine; (+)-5-(5-chloro-1-ethyl-6-fluoro-1H-indol-3-yl)-3-(6-methoxy-5-(4-methyl-1H-imidazol-1-yl) pyridin-2-yl)-5,6-dihydro-4H-1,2,4-oxadiazine; (+)-5-(3,4-difluorophenyl)-3-(6-methoxy-5-(4-methyl-1H-imidazol-1-yl) pyridin-2-yl)-5,6-dihydro-4H-1,2,4-oxadiazine; (+)-5-(6-chlorobenzofuran-2-yl)-3-(6-methoxy-5-(4-methyl-1H-imidazol-1-yl) pyridin-2-yl)-5,6-dihydro-4H-1,2,4-oxadiazine; (+)-5-(3,5-difluorophenyl)-3-(6-methoxy-5-(4-methyl-1H-imidazol-1-yl) pyridin-2-yl)-5,6-dihydro-4H-1,2,4-oxadiazine; (+)-5-(5-fluorobenzofuran-2-yl)-3-(6-methoxy-5-(4-methyl-1H-imidazol-1-yl) pyridin-2-yl)-5,6-dihydro-4H-1,2,4-oxadiazine; (+)-5-(4-chloro-3-methylphenyl)-3-(6-methoxy-5-(4-methyl-1H-imidazol-1-yl) pyridin-2-yl)-5,6-dihydro-4H-1,2,4-oxadiazine; (+)-5-(7-fluorobenzofuran-2-yl)-3-(6-methoxy-5-(4-methyl-1H-imidazol-1-yl) pyridin-2-yl)-5,6-dihydro-4H-1,2,4-oxadiazine; (+)-3-(6-methoxy-5-(4-methyl-1H-imidazol-1-yl) pyridin-2-yl)-5-(3,4,5-trifluorophenyl)-5,6-dihydro-4H-1,2,4-oxadiazine; (+)-5-(4-(difluoromethoxy) phenyl)-3-(6-methoxy-5-(4-methyl-1H-imidazol-1-yl) pyridin-2-yl)-5,6-dihydro-4H-1,2,4-oxadiazine; (+)-5-(4-chlorobenzofuran-2-yl)-3-(6-methoxy-5-(4-methyl-1H-imidazol-1-yl) pyridin-2-yl)-5,6-dihydro-4H-1,2,4-oxadiazine; (−)-5-(4-fluorobenzofuran-2-yl)-3-(6-methoxy-5-(4-methyl-1H-imidazol-1-yl) pyridin-2-yl)-5,6-dihydro-4H-1,2,4-oxadiazine; (+)-5-(5-fluoro-3-methylbenzofuran-2-yl)-3-(6-methoxy-5-(4-methyl-1H-imidazol-1-yl) pyridin-2-yl)-5,6-dihydro-4H-1,2,4-oxadiazine; (−)-5-(6-fluoro-1-methyl-5-(trifluoromethyl)-1H-indol-3-yl)-3-(6-methoxy-5-(4-methyl-1H-imidazol-1-yl) pyridin-2-yl)-5,6-dihydro-4H-1,2,4-oxadiazine; (+)-5-(6-fluoro-1-methyl-5-(trifluoromethyl)-1H-indol-3-yl)-3-(6-methoxy-5-(4-methyl-1H-imidazol-1-yl) pyridin-2-yl)-5,6-dihydro-4H-1, 2,4-oxadiazine; (+)-5-(4-chloro-3-fluorophenyl)-3-(6-methoxy-5-(4-methyl-1H-imidazol-1-yl) pyridin-2-yl)-5,6-dihydro-4H-1,2,4-oxadiazine; (+)-5-(3-chloro-4-fluorophenyl)-3-(6-methoxy-5-(4-methyl-1H-imidazol-1-yl) pyridin-2-yl)-5,6-dihydro-4H-1,2,4-oxadiazine; (+)-5-(3-chloro-5-fluorophenyl)-3-(6-methoxy-5-(4-methyl-1H-imidazol-1-yl) pyridin-2-yl)-5,6-dihydro-4H-1,2,4-oxadiazine; (+)-3-(6-methoxy-5-(4-methyl-1H-imidazol-1-yl) pyridin-2-yl)-5-(3-(trifluoromethyl) phenyl)-5,6-dihydro-4H-1,2,4-oxadiazine; (+)-5-(4-cyclopropylphenyl)-3-(6-methoxy-5-(4-methyl-1H-imidazol-1-yl) pyridin-2-yl)-5,6-dihydro-4H-1,2,4-oxadiazine; (+)-5-(3,5-dichlorophenyl)-3-(6-methoxy-5-(4-methyl-1H-imidazol-1-yl) pyridin-2-yl)-5,6-dihydro-4H-1,2,4-oxadiazine; (+)-5-(3-fluoro-4-(trifluoromethyl) phenyl)-3-(6-methoxy-5-(4-methyl-1H-imidazol-1-yl) pyridin-2-yl)-5,6-dihydro-4H-1,2,4-oxadiazine; (+)-3-(6-methoxy-5-(4-methyl-1H-imidazol-1-yl) pyridin-2-yl)-5-(1-methyl-1H-indazol-3-yl)-5,6-dihydro-4H-1,2,4-oxadiazine; (+)-5-(3-cyclopropylphenyl)-3-(6-methoxy-5-(4-methyl-1H-imidazol-1-yl) pyridin-2-yl)-5,6-dihydro-4H-1,2,4-oxadiazine; 5-(2,4-difluorophenyl)-3-(6-methoxy-5-(4-methyl-1H-imidazol-1-yl)pyridin-2-yl)-5,6-dihydro-4H-1,2,4-oxadiazine; (+)-3-(6-methoxy-5-(4-methyl-1H-imidazol-1-yl) pyridin-2-yl)-5-(o-tolyl)-5,6-dihydro-4H-1,2,4-oxadiazine; 5-(2-chlorophenyl)-3-(6-methoxy-5-(4-methyl-1H-imidazol-1-yl) pyridin-2-yl)-5,6-dihydro-4H-1,2,4-oxadiazine: (+)-5-(4,4-difluorocyclohexyl)-3-(6-methoxy-5-(4-methyl-1H-imidazol-1-yl) pyridin-2-yl)-5,6-dihydro-4H-1,2,4-oxadiazine; (+)-3-(3-(6-methoxy-5-(4-methyl-1H-imidazol-1-yl) pyridin-2-yl)-5,6-dihydro-4H-1,2,4-oxadiazin-5-yl) benzonitrile; (+)-3-(6-methoxy-5-(4-methyl-1H-imidazol-1-yl) pyridin-2-yl)-5-(3-methoxyphenyl)-5,6-dihydro-4H-1,2,4-oxadiazine; (−)-5-(tert-butyl)-3-(6-methoxy-5-(4-methyl-1H-imidazol-1-yl) pyridin-2-yl)-5,6-dihydro-4H-1,2,4-oxadiazine; (−)-5-isobutyl-3-(6-methoxy-5-(4-methyl-1H-imidazol-1-yl) pyridin-2-yl)-5,6-dihydro-4H-1,2,4-oxadiazine; (−)-5-cyclopentyl-3-(6-methoxy-5-(4-methyl-1H-imidazol-1-yl) pyridin-2-yl)-5,6-dihydro-4H-1,2,4-oxadiazine; (+)-3-(6-methoxy-5-(4-methyl-1H-imidazol-1-yl)pyridin-2-yl)-5-(1-methyl-1H-indol-3-yl)-5,6-dihydro-4H-1,2,4-oxadiazine; (−)-3-(6-methoxy-5-(4-methyl-1H-imidazol-1-yl)pyridin-2-yl)-5-(1-methyl-1H-indol-3-yl)-5,6-dihydro-4H-1,2,4-oxadiazine; (+)-5-(5-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine; (+)-5-(4-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine; (−)-5-(4-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine; (−)-5-(6-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine; (+)-5-(6-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine; (−)-5-(5-chloro-1-methyl-1H-indol-3-yl)-3-(6-methoxy-5-(4-methyl-1H-imidazol-1-yl) pyridin-2-yl)-5,6-dihydro-4H-1,2,4-oxadiazine; (+)-5-(5-chloro-1-methyl-1H-indol-3-yl)-3-(6-methoxy-5-(4-methyl-1H-imidazol-1-yl) pyridin-2-yl)-5,6-dihydro-4H-1,2,4-oxadiazine; (+)-5-(6-chloro-1-methyl-1H-indol-3-yl)-3-(6-methoxy-5-(4-methyl-1H-imidazol-1-yl) pyridin-2-yl)-5,6-dihydro-4H-1,2,4-oxadiazine; (−)-5-(6-chloro-1-methyl-1H-indol-3-yl)-3-(6-methoxy-5-(4-methyl-1H-imidazol-1-yl) pyridin-2-yl)-5,6-dihydro-4H-1,2,4-oxadiazine; (+)-3-(6-methoxy-5-(4-methyl-1H-imidazol-1-yl) pyridin-2-yl)-5-(1-methyl-1H-pyrrolo [2,3-b] pyridin-3-yl)-5,6-dihydro-4H-1,2,4-oxadiazine; (+)-5-(4-fluoro-1-isopropyl-1H-indol-3-yl)-3-(6-methoxy-5-(4-methyl-1H-imidazol-1-yl) pyridin-2-yl)-5,6-dihydro-4H-1,2,4-oxadiazine; (−)-5-(4-fluoro-1-isopropyl-1H-indol-3-yl)-3-(6-methoxy-5-(4-methyl-1H-imidazol-1-yl) pyridin-2-yl)-5,6-dihydro-4H-1,2,4-oxadiazine; (+)-3-(6-methoxy-5-(4-methyl-1H-imidazol-1-yl) pyridin-2-yl)-5-(1-methyl-6-(trifluoromethyl)-1H-indol-3-yl)-5,6-dihydro-4H-1,2,4-oxadiazine; (−)-3-(6-methoxy-5-(4-methyl-1H-imidazol-1-yl) pyridin-2-yl)-5-(1-methyl-6-(trifluoromethyl)-1H-indol-3-yl)-5,6-dihydro-4H-1,2,4-oxadiazine; (+)-3-(6-methoxy-5-(4-methyl-1H-imidazol-1-yl)pyridin-2-yl)-4-methyl-5-(1-methyl-1H-indol-3-yl)-5,6-dihydro-4H-1,2,4-oxadiazine; (+)-2-(3-(6-methoxy-5-(4-methyl-1H-imidazol-1-yl)pyridin-2-yl)-5,6-dihydro-4H-1,2,4-oxadiazin-5-yl)benzo[d]oxazole; (+)-3-(6-methoxy-5-(4-methyl-1H-imidazol-1-yl)pyridin-2-yl)-5-(1-methyl-1H-indol-2-yl)-5,6-dihydro-4H-1,2,4-oxadiazine; (+)-3-(6-methoxy-5-(4-methyl-1H-imidazol-1-yl) pyridin-2-yl)-5-(1-methyl-5-(trifluoromethyl)-1H-pyrrolo [2,3-b] pyridin-3-yl)-5,6-dihydro-4H-1,2,4-oxadiazine; (+)-5-(benzo[d]thiazol-2-yl)-3-(6-methoxy-5-(4-methyl-1H-imidazol-1-yl) pyridin-2-yl)-5,6-dihydro-4H-1,2,4-oxadiazine; (+)3-(6-methoxy-5-(4-methyl-1H-imidazol-1-yl)pyridin-2-yl)-5-(1-methyl-5-(chloro)-1H-indazol-3-yl)-5,6-dihydro-4H-1,2,4-oxadiazine; and (+) 3-(6-methoxy-5-(4-methyl-1H-imidazol-1-yl)pyridin-2-yl)-5-(1-methyl-5-(trifluoromethyl)-1H-indazol-3-yl)-5,6-dihydro-4H-1,2,4-oxadiazine; or a pharmaceutically acceptable salt thereof.

In one embodiment, the compound of Formula (I) is selected from the group consisting of: (R)-5-(benzofuran-2-yl)-3-(6-methoxy-5-(4-methyl-1H-imidazol-1-yl)pyridin-2-yl)-5,6-dihydro-4H-1,2,4-oxadiazine; 3-(6-Methoxy-5-(4-methyl-1H-imidazol-1-yl)pyridin-2-yl)-5-(7-methylbenzofuran-2-yl)-5,6-dihydro-4H-1,2,4-oxadiazine; (R)-3-(6-methoxy-5-(4-methyl-1H-imidazol-1-yl)pyridin-2-yl)-5-(5-methylbenzofuran-2-yl)-5,6-dihydro-4H-1,2,4-oxadiazine; (R)-5-(benzo[b]thiophen-2-yl)-3-(6-methoxy-5-(4-methyl-1H-imidazol-1-yl)pyridin-2-yl)-5,6-dihydro-4H-1,2,4-oxadiazine; (+)-3-(6-methoxy-5-(4-methyl-1H-imidazol-1-yl)pyridin-2-yl)-5-(3-methylbenzofuran-2-yl)-5,6-dihydro-4H-1,2,4-oxadiazine; (R)-3-(6-methoxy-5-(4-methyl-1H-imidazol-1-yl)pyridin-2-yl)-5-(4-methylbenzofuran-2-yl)-5,6-dihydro-4H-1,2,4-oxadiazine; (R)-3-(6-methoxy-5-(4-methyl-1H-imidazol-1-yl)pyridin-2-yl)-5-(6-methylbenzofuran-2-yl)-5,6-dihydro-4H-1,2,4-oxadiazine; (+)-3-(5-(4-chloro-1H-imidazol-1-yl)-6-methoxypyridin-2-yl)-5-(7-methylbenzofuran-2-yl)-5,6-dihydro-4H-1,2,4-oxadiazine; 5-(4-chloro-2-methylphenyl)-3-(6-methoxy-5-(4-methyl-1H-imidazol-1-yl) pyridin-2-yl)-4-methyl-5,6-dihydro-4H-1,2,4-oxadiazine; 3-(6-methoxy-5-(4-methyl-1H-imidazol-1-yl) pyridin-2-yl)-4-methyl-5-(3-(trifluoromethyl) phenyl)-5,6-dihydro-4H-1,2,4-oxadiazine; 5-(benzofuran-3-yl)-3-(6-methoxy-5-(4-methyl-1H-imidazol-1-yl)pyridin-2-yl)-5,6-dihydro-4H-1,2,4-oxadiazine; 5-(4-fluorophenyl)-3-(6-methoxy-5-(4-methyl-1H-imidazol-1-yl)pyridin-2-yl)-5,6-dihydro-4H-1,2,4-oxadiazine; 5-(4-fluoro-3-(trifluoromethyl)phenyl)-3-(6-methoxy-5-(4-methyl-1H-imidazol-1-yl)pyridin-2-yl)-5,6-dihydro-4H-1,2,4-oxadiazine; 5-(1H-indol-3-yl)-3-(6-methoxy-5-(4-methyl-1H-imidazol-1-yl)pyridin-2-yl)-5,6-dihydro-4H-1,2,4-oxadiazine; (+)-5-(3,4-dichlorophenyl)-3-(6-methoxy-5-(4-methyl-1H-imidazol-1-yl) pyridin-2-yl)-5,6-dihydro-4H-1,2,4-oxadiazine; (+)-5-(6-fluorobenzofuran-2-yl)-3-(6-methoxy-5-(4-methyl-1H-imidazol-1-yl) pyridin-2-yl)-5,6-dihydro-4H-1,2,4-oxadiazine; (+)-5-(5-chlorobenzofuran-2-yl)-3-(6-methoxy-5-(4-methyl-1H-imidazol-1-yl) pyridin-2-yl)-5,6-dihydro-4H-1,2,4-oxadiazine; (+)-3-(6-methoxy-5-

(4-methyl-1H-imidazol-1-yl) pyridin-2-yl)-5-(4-(trifluoromethyl) phenyl)-5,6-dihydro-4H-1,2,4-oxadiazine; (+)-5-cyclohexyl-3-(6-methoxy-5-(4-methyl-1H-imidazol-1-yl) pyridin-2-yl)-5,6-dihydro-4H-1,2,4-oxadiazine; (+)-5-(7-chlorobenzofuran-2-yl)-3-(6-methoxy-5-(4-methyl-1H-imidazol-1-yl) pyridin-2-yl)-5,6-dihydro-4H-1,2,4-oxadiazine; (+)-3-(6-methoxy-5-(4-methyl-1H-imidazol-1-yl) pyridin-2-yl)-5-(3-methylbenzo [b] thiophen-2-yl)-5,6-dihydro-4H-1,2,4-oxadiazine; (+)-5-(benzo [b] thiophen-3-yl)-3-(6-methoxy-5-(4-methyl-1H-imidazol-1-yl) pyridin-2-yl)-5,6-dihydro-4H-1,2,4-oxadiazine; (+)-3-(6-methoxy-5-(4-methyl-1H-imidazol-1-yl) pyridin-2-yl)-5-(4-(trifluoromethoxy) phenyl)-5,6-dihydro-4H-1,2,4-oxadiazine; (−)-5-(5-chloro-1-ethyl-6-fluoro-1H-indol-3-yl)-3-(6-methoxy-5-(4-methyl-1H-imidazol-1-yl) pyridin-2-yl)-5,6-dihydro-4H-1,2,4-oxadiazine; (+)-5-(5-chloro-1-ethyl-6-fluoro-1H-indol-3-yl)-3-(6-methoxy-5-(4-methyl-1H-imidazol-1-yl) pyridin-2-yl)-5,6-dihydro-4H-1,2,4-oxadiazine; (+)-5-(6-chlorobenzofuran-2-yl)-3-(6-methoxy-5-(4-methyl-1H-imidazol-1-yl) pyridin-2-yl)-5,6-dihydro-4H-1,2,4-oxadiazine; (+)-5-(3,5-difluorophenyl)-3-(6-methoxy-5-(4-methyl-1H-imidazol-1-yl) pyridin-2-yl)-5,6-dihydro-4H-1,2,4-oxadiazine; (+)-5-(5-fluorobenzofuran-2-yl)-3-(6-methoxy-5-(4-methyl-1H-imidazol-1-yl) pyridin-2-yl)-5,6-dihydro-4H-1,2,4-oxadiazine; (+)-5-(4-chloro-3-methylphenyl)-3-(6-methoxy-5-(4-methyl-1H-imidazol-1-yl) pyridin-2-yl)-5,6-dihydro-4H-1,2,4-oxadiazine; (+)-5-(7-fluorobenzofuran-2-yl)-3-(6-methoxy-5-(4-methyl-1H-imidazol-1-yl) pyridin-2-yl)-5,6-dihydro-4H-1,2,4-oxadiazine; (+)-3-(6-methoxy-5-(4-methyl-1H-imidazol-1-yl) pyridin-2-yl)-5-(3,4,5-trifluorophenyl)-5,6-dihydro-4H-1,2,4-oxadiazine; (+)-5-(4-chlorobenzofuran-2-yl)-3-(6-methoxy-5-(4-methyl-1H-imidazol-1-yl) pyridin-2-yl)-5,6-dihydro-4H-1,2,4-oxadiazine; (−)-5-(4-fluorobenzofuran-2-yl)-3-(6-methoxy-5-(4-methyl-1H-imidazol-1-yl) pyridin-2-yl)-5,6-dihydro-4H-1,2,4-oxadiazine; (+)-5-(5-fluoro-3-methylbenzofuran-2-yl)-3-(6-methoxy-5-(4-methyl-1H-imidazol-1-yl) pyridin-2-yl)-5,6-dihydro-4H-1,2,4-oxadiazine; (+)-5-(6-fluoro-1-methyl-5-(trifluoromethyl)-1H-indol-3-yl)-3-(6-methoxy-5-(4-methyl-1H-imidazol-1-yl) pyridin-2-yl)-5,6-dihydro-4H-1,2,4-oxadiazine; (+)-5-(4-chloro-3-fluorophenyl)-3-(6-methoxy-5-(4-methyl-1H-imidazol-1-yl) pyridin-2-yl)-5,6-dihydro-4H-1,2,4-oxadiazine; (+)-5-(3-chloro-4-fluorophenyl)-3-(6-methoxy-5-(4-methyl-1H-imidazol-1-yl) pyridin-2-yl)-5,6-dihydro-4H-1,2,4-oxadiazine; (+)-5-(3-chloro-5-fluorophenyl)-3-(6-methoxy-5-(4-methyl-1H-imidazol-1-yl) pyridin-2-yl)-5,6-dihydro-4H-1,2,4-oxadiazine; (+)-3-(6-methoxy-5-(4-methyl-1H-imidazol-1-yl) pyridin-2-yl)-5-(3-(trifluoromethyl) phenyl)-5,6-dihydro-4H-1,2,4-oxadiazine; (+)-5-(4-cyclopropylphenyl)-3-(6-methoxy-5-(4-methyl-1H-imidazol-1-yl) pyridin-2-yl)-5,6-dihydro-4H-1,2,4-oxadiazine; (+)-5-(3,5-dichlorophenyl)-3-(6-methoxy-5-(4-methyl-1H-imidazol-1-yl) pyridin-2-yl)-5,6-dihydro-4H-1,2,4-oxadiazine; (+)-5-(3-fluoro-4-(trifluoromethyl) phenyl)-3-(6-methoxy-5-(4-methyl-1H-imidazol-1-yl) pyridin-2-yl)-5,6-dihydro-4H-1,2,4-oxadiazine; (+)-3-(6-methoxy-5-(4-methyl-1H-imidazol-1-yl) pyridin-2-yl)-5-(1-methyl-1H-indazol-3-yl)-5,6-dihydro-4H-1,2,4-oxadiazine; (+)-5-(3-cyclopropylphenyl)-3-(6-methoxy-5-(4-methyl-1H-imidazol-1-yl) pyridin-2-yl)-5,6-dihydro-4H-1,2,4-oxadiazine; (+)-3-(6-methoxy-5-(4-methyl-1H-imidazol-1-yl)pyridin-2-yl)-5-(1-methyl-1H-indol-3-yl)-5,6-dihydro-4H-1,2,4-oxadiazine; (+)-5-(5-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine; (+)-5-(4-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine; (+)-5-(6-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine; (+)-5-(5-chloro-1-methyl-1H-indol-3-yl)-3-(6-methoxy-5-(4-methyl-1H-imidazol-1-yl) pyridin-2-yl)-5,6-dihydro-4H-1,2,4-oxadiazine; (+)-5-(6-chloro-1-methyl-1H-indol-3-yl)-3-(6-methoxy-5-(4-methyl-1H-imidazol-1-yl) pyridin-2-yl)-5,6-dihydro-4H-1,2,4-oxadiazine; (+)-5-(4-fluoro-1-isopropyl-1H-indol-3-yl)-3-(6-methoxy-5-(4-methyl-1H-imidazol-1-yl) pyridin-2-yl)-5,6-dihydro-4H-1,2,4-oxadiazine; (+)-3-(6-methoxy-5-(4-methyl-1H-imidazol-1-yl) pyridin-2-yl)-5-(1-methyl-6-(trifluoromethyl)-1H-indol-3-yl)-5,6-dihydro-4H-1,2,4-oxadiazine; (+)-3-(6-methoxy-5-(4-methyl-1H-imidazol-1-yl)pyridin-2-yl)-5-(1-methyl-1H-indol-2-yl)-5,6-dihydro-4H-1,2,4-oxadiazine; (+)-3-(6-methoxy-5-(4-methyl-1H-imidazol-1-yl) pyridin-2-yl)-5-(1-methyl-5-(trifluoromethyl)-1H-pyrrolo [2,3-b] pyridin-3-yl)-5,6-dihydro-4H-1,2,4-oxadiazine; (+)3-(6-methoxy-5-(4-methyl-1H-imidazol-1-yl)pyridin-2-yl)-5-(1-methyl-5-(chloro)-1H-indazol-3-yl)-5,6-dihydro-4H-1,2,4-oxadiazine; and (+) 3-(6-methoxy-5-(4-methyl-1H-imidazol-1-yl)pyridin-2-yl)-5-(1-methyl-5-(trifluoromethyl)-1H-indazol-3-yl)-5,6-dihydro-4H-1,2,4-oxadiazine; or a pharmaceutically acceptable salt thereof.

In some embodiments, the invention provides a levorotatory isomer of the compound of Formula (I); or a pharmaceutically acceptable salt thereof.

In some embodiments, the invention provides a dextrorotatory isomer of the compound of Formula (I); or a pharmaceutically acceptable salt thereof.

In some embodiments, Alzheimer's disease is early onset Alzheimer's disease.

In some embodiments, the subject is a human.

In some embodiments, the subject is 65 years old or older. In other embodiments, the subject is 55 years old or older. In still other embodiments, the subject is 55 years old or younger, or 50 years old or younger.

A compound of Formula (I) or a pharmaceutically acceptable salt thereof (also referred to herein as an "Oxadiazine Compound") is useful for treating, preventing or ameliorating one or more symptoms of a neurodegenerative disease.

A pharmaceutical composition comprising an effective amount of an Oxadiazine Compound and a pharmaceutically acceptable carrier or vehicle is useful for treating, preventing or ameliorating one or more symptoms of a neurodegenerative disease.

The details of the invention are set forth in the accompanying description below.

All patents and publications cited in this specification are hereby incorporated by reference in their entirety.

5. DETAILED DESCRIPTION

5.1 Definitions and Abbreviations

The following are definitions of terms used in the present specification. The initial definition provided for a group or term herein applies to that group or term throughout the present specification individually or as part of another group, unless otherwise indicated. Unless otherwise defined, all technical and scientific terms used herein have the same meaning as commonly understood by one of ordinary skill in the art.

The term "$C_1$-$C_4$ alkyl" as used herein, refers to a straight chain or branched non-cyclic hydrocarbon having from 1 to 4 carbon atoms, wherein one of the hydrocarbon's hydrogen atoms has been replaced by a single bond. Representative straight chain C$_1$-C$_4$ alkyls include -methyl, -ethyl, -n-propyl and -n-butyl. Representative branched C$_1$-C$_4$ alkyls include -isopropyl, -sec-butyl, -isobutyl and -tert-butyl.

The term "—C$_1$-C$_6$ alkyl" as used herein, refers to a straight chain or branched non-cyclic hydrocarbon having from 1 to 6 carbon atoms, wherein one of the hydrocarbon's hydrogen atoms has been replaced by a single bond. Representative straight chain —C$_1$-C$_6$ alkyls include -methyl, -ethyl, -n-propyl, -n-butyl, -n-pentyl and -n-hexyl. Representative branched —C$_1$-C$_6$ alkyls include -isopropyl, -sec-butyl, -isobutyl, -tert-butyl, -isopentyl, -neopentyl, -1-methylbutyl, -isohexyl, -neohexyl, -2-methylbutyl, -3-methylbutyl, -1,1-dimethylpropyl and -1,2-dimethylpropyl.

The term "C$_1$-C$_4$ alkylene" as used herein, refers to a straight or branched chain saturated hydrocarbon containing 1-4 carbon atoms, wherein two of the hydrocarbon's hydrogen atoms have been replaced by a single a bond. Representative C$_1$-C$_4$ alkylene groups include, methylene, ethylene, n-propylene, isopropylene, n-butylene and isobutylene.

The term "C$_1$-C$_4$ alkylene-phenyl" as used herein, refers to a C$_1$-C$_4$ alkyl group, as defined above, wherein one of the C$_1$-C$_4$ alkyl group's hydrogen atoms has been replaced with phenyl.

The term "C$_1$-C$_4$ alkoxy" as used herein, refers to a C$_1$-C$_4$ alkyl-O— group wherein the C$_1$-C$_4$ alkyl is as defined above. Examples of C$_1$-C$_4$ alkoxy include, but are not limited to methoxy, ethoxy, propoxy or butoxy.

The terms "halogen" or "halo" as used herein, refer to chlorine, bromine, fluorine or iodine.

The term "halo-substituted C$_1$-C$_4$ alkyl" as used herein, refers to a C$_1$-C$_4$ alkyl group, as defined above, wherein one or more of the C$_1$-C$_4$ alkyl group's hydrogen atoms have been replaced with —F, —Cl, —Br or —I. Examples of a halo-substituted C$_1$-C$_4$ alkyl include, but are not limited to, —CH$_2$F, —CCl$_3$, —CF$_3$, —CH$_2$Cl, —CH$_2$CH$_2$Br, —CH$_2$CH$_2$I, —CF$_2$CF$_3$, —CH$_2$CH$_2$CH$_2$F, —CH$_2$CH$_2$CH$_2$Cl, —CH$_2$CH$_2$CH$_2$CH$_2$Br, —CH$_2$CH$_2$CH$_2$CH$_2$I, —CH$_2$CH(Br)CH$_3$, —CH$_2$CH(Cl)CH$_2$CH$_3$, —CH(F)CH$_2$CH$_3$, —CH$_2$CF$_3$ and —C(CH$_3$)$_2$(CH$_2$Cl).

The term "halo-substituted C$_1$-C$_4$ alkoxy" as used herein, refers to a C$_1$-C$_4$ alkoxy group, as defined above, wherein one or more of the C$_1$-C$_4$ alkoxy group's hydrogen atoms have been replaced with —F, —Cl, —Br or —I. Examples of a halo-substituted C$_1$-C$_4$ alkoxy include, but are not limited to, —O—CH$_2$F, —O—CCl$_3$, —O—CF$_3$, —O—CH$_2$Cl, —O—CH$_2$CH$_2$Br, —O—CH$_2$CH$_2$I, —O—CF$_2$CF$_3$, —O—CH$_2$CH$_2$CH$_2$F, —O—CH$_2$CH$_2$CH$_2$Cl, —O—CH$_2$CH$_2$CH$_2$CH$_2$Br, —O—CH$_2$CH$_2$CH$_2$CH$_2$I, —O—CH$_2$CH(Br)CH$_3$, —O—CH$_2$CH(Cl)CH$_2$CH$_3$, —O—CH(F)CH$_2$CH$_3$, —OCH$_2$CF$_3$ and —O—C(CH$_3$)$_2$(CH$_2$Cl).

A "5- to 6-membered aromatic heterocycle" refers to a monocyclic 5- to 6-membered aromatic cycloalkyl group in which 1-4 of the cycloalkyl group's ring carbon atoms have been independently replaced with a N, O or S atom. The 5- to 6-membered aromatic heterocycles can be attached via a nitrogen or carbon atom. Representative examples of a 5- to 6-membered aromatic heterocycle group include, but are not limited to thiophenyl, furanyl, thiazolyl, isothiazolyl, oxazolyl, isoxazolyl, 1,2,4-oxadiazolyl, 1,3,4-oxadiazolyl, oxatriazolyl, pyrrazolyl, pyrrolyl, imidazolyl, tetrazolyl, 1,2,3-triazolyl, 1,3,4-triazolyl, thiadiazolyl, thiazolyl, pyridinyl, pyrimidinyl, pyrazinyl and pyridazinyl.

A "8- to 10-membered bicyclic heterocycle" refers to a bicyclic 8- to 10-membered bridged, aromatic or non-aromatic cycloalkyl group in which 1-4 of the cycloalkyl group's ring carbon atoms have been independently replaced with a N, O or S atom. The 8- to 10-membered bicyclic heterocycles can be attached via a nitrogen or carbon atom. Representative examples of a 8- to 10-membered bicyclic heterocycle group include, but are not limited to benzimidazolyl, benzothiophenyl, benzthiazolyl, benzoxazolyl, benzofuranyl, quinolinyl, isoquinolinyl, tetrahydroquinolinyl, tetrahydroisoquinolinyl, cinnolinyl, quinazolinyl, tetrahydroquinazolinyl, quinoxalinyl, tetrahydroquinoxazolinyl, indolyl, indolinyl, 1,5-naphthyridinyl, 1,2,3,4-tetrahydro-1,5-naphthyridine, 1,6-naphthyridinyl, 1,2,3,4-tetrahydro-1,6-naphthyridine, 1,7-naphthyridinyl, 1,2,3,4-tetrahydro-1,7-naphthyridine, 1,8-naphthyridinyl, 1,2,3,4-tetrahydro-1,8-naphthyridine, indazolyl, azaindazolyl and azaindolyl.

The term "3- to 7-membered monocyclic heterocycle" as used herein, refers to a monocyclic 3- to 7-membered aromatic or non-aromatic monocyclic cycloalkyl group in which 1-4 of the cycloalkyl group's ring carbon atoms have been independently replaced with a N, O or S atom. The 3- to 7-membered monocyclic heterocycles can be attached via a nitrogen or carbon atom. Representative examples of a 3- to 7-membered monocyclic heterocycle group include, but are not limited to, nitrogen-containing 3- to 7-membered monocyclic heterocycles discussed above, tetrahydrofuranyl, dihydrofuranyl, pyranyl, dihydropyranyl, tetrahydropyranyl, thiopyranyl, dihydrothiopyranyl, tetrahydrothiopyranyl, dioxanyl, dithianyl, trithianyl, dioxolanyl, furanyl and thiophenyl. In one embodiment, the 3- to 7-membered monocyclic heterocycle is a nitrogen-containing 3- to 7-membered monocyclic heterocycle. In another embodiment, the 3- to 7-membered monocyclic heterocycle is fully saturated or partially saturated.

A "4- to 6-membered nonaromatic heterocycle" refers to a monocyclic 4- to 6-membered nonaromatic monocyclic cycloalkyl group in which 1-3 of the cycloalkyl group's ring carbon atoms have been independently replaced with a N, O or S atom. The 4- to 6-membered nonaromatic heterocycles can be attached via a nitrogen or carbon atom. Representative examples of nitrogen-containing 4- to 6-membered nonaromatic heterocycles include, but are not limited to, azetidinyl, piperidinyl, oxazinyl, morpholinyl, imidazolidinyl, pyrazolidinyl, thiomorpholinyl, oxetanyl, tetrahydrofuranyl, tetrahydropyranyl and dioxanyl.

The term "C$_3$-C$_8$ monocyclic cycloalkyl" as used herein, refers to a saturated cyclic hydrocarbon having from 3 to 8 carbon atoms. Representative C$_3$-C$_8$ monocyclic cycloalkyls include -cyclopropyl, -cyclobutyl, -cyclopentyl, -cyclohexyl, -cycloheptyl and -cyclooctyl.

The term "nitrogen-containing 5- to 6-membered aromatic monocyclic heterocycle" as used herein, refers to a 5- or 6-membered aromatic monocyclic cycloalkyl group in which from 1 to 4 of the cycloalkyl group's ring carbon atoms have been independently replaced with a nitrogen atom and 0-4 of the cycloalkyl group's remaining ring carbon atoms have been independently replaced with an O or S atom. The nitrogen-containing 5- to 6-membered aromatic monocyclic heterocycle can be attached via a nitrogen or carbon atom. Representative examples of a 5- to 6-membered aromatic monocyclic heterocycles include, but are not limited to, imidazolyl, isothiazolyl, isoxazolyl, oxazolyl, oxadiazolyl, pyrimidinyl, pyrazolyl, pyrazinyl, pyridazinyl, pyridinyl, pyrrolyl, thiazolyl, thiadiazolyl, triazinyl, and triazolyl. Unless otherwise indicated, the nitrogen-containing 5- to 6-membered aromatic monocyclic heterocycle is unsubstituted.

A "nitrogen-containing 4- to 6-membered nonaromatic heterocycle" refers to a monocyclic 4- to 6-membered nonaromatic monocyclic cycloalkyl group in which one of the cycloalkyl group's ring carbon atoms has been replaced with a nitrogen atom and 0-3 of the cycloalkyl group's remaining ring carbon atoms have been independently replaced with a N, O or S atom. The nitrogen-containing 4- to 6-membered nonaromatic heterocycles can be attached via a nitrogen or carbon atom. Representative examples of nitrogen-containing 4- to 6-membered nonaromatic heterocycles include, but are not limited to, azetidinyl, piperidinyl, oxazinyl, morpholinyl, imidazolidinyl, pyrazolidinyl and thiomorpholinyl.

The term "oxo" refers to =O group.

Unless otherwise indicated, any heteroatom with unsatisfied valences is assumed to have hydrogen atoms sufficient to satisfy the valences.

The phrase "pharmaceutically acceptable carrier or vehicle" as used herein, refers to a pharmaceutically acceptable material, composition or vehicle, such as a liquid or solid filler, diluent, excipient, solvent or encapsulating material, involved in carrying or transporting the Oxadiazine Compound from one organ, or portion of the body, to another organ, or portion of the body. Each carrier or vehicle must be "acceptable" in the sense of being compatible with the other ingredients of the formulation and not injurious to the subject. Some examples of materials which can serve as pharmaceutically acceptable carriers or vehicles include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as butylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The compounds described herein may form salts which are also within the scope of this invention. Reference to a compound described herein is understood to include reference to salts thereof, unless otherwise indicated. The term "salt(s)", as employed herein, denotes acidic and/or basic salts formed with inorganic and/or organic acids and bases. In addition, when a compound described herein contains both a basic moiety, such as, but not limited to, amine, pyridine or imidazole and an acidic moiety, such as, but not limited to, a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds described herein may be formed, for example, by reacting a compound with an amount of acid or base, such as an equivalent amount, in a medium, such as one in which the salt precipitates or in an aqueous medium followed by lyophilization.

The compounds described herein which contain a basic moiety, such as, but not limited to, an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates, such as tosylates, undecanoates and the like.

The compounds described herein which contain an acidic moiety, such as, but not limited to, a carboxylic acid, may form salts with a variety of organic and inorganic bases. Exemplary basic salts include ammonium salts, alkali metal salts, such as sodium, lithium and potassium salts, alkaline earth metal salts, such as calcium and magnesium salts, salts with organic bases (for example, organic amines), such as benzathines, dicyclohexylamines, hydrabamines (formed with N,N-bis(dehydroabietyl) ethylenediamine), N-methyl-D-glucamines, N-methyl-D-glycamides, t-butyl amines and salts with amino acids, such as arginine, lysine and the like. Basic nitrogen-containing groups may be quaternized with agents, such as lower alkyl halides (e.g., methyl, ethyl, propyl and butyl chlorides, bromides and iodides), dialkyl sulfates (e.g., dimethyl, diethyl, dibutyl and diamyl sulfates), long chain halides (e.g., decyl, lauryl, myristyl and stearyl chlorides, bromides and iodides), aralkyl halides (e.g., benzyl and phenethyl bromides), and others.

Prodrugs and solvates of the compounds described herein are also contemplated herein. The term "prodrug" as employed herein denotes a compound that, upon administration to a subject, undergoes chemical conversion by metabolic or chemical processes to yield a compound described herein, or a salt and/or solvate thereof. Solvates of the compounds described herein include, for example, hydrates.

Compounds described herein are, subsequent to their preparation, preferably isolated and purified to obtain a composition containing an amount by weight equal to or greater than 90%, for example, equal to or greater than 95%, equal to or greater than 97%, equal to or greater than 98%, or equal to or greater than 99% of the compounds ("substantially pure" compounds), which is then used or formulated as described herein. Such "substantially pure" compounds described herein are also contemplated herein as part of the present invention.

All stereoisomers of the present compounds (for example, those which may exist due to asymmetric carbons on various substituents), including enantiomeric forms and diastereomeric forms, are contemplated within the scope of this invention. Individual stereoisomers of the compounds described herein may, for example, be substantially free of other isomers (e.g., as a pure or substantially pure optical isomer having a specified activity), or may be admixed, for example, as racemates or with all other, or other selected, stereoisomers. The chiral centers of the compounds described herein may have the S or R configuration as defined by the International Union of Pure and Applied Chemistry (IUPAC) 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

If, for instance, a particular enantiomer of a compound described herein is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

All configurational isomers of the compounds described herein are contemplated, either in admixture or in pure or substantially pure form. Certain compounds described herein may exist in particular geometric or stereoisomeric forms. The present invention contemplates all such compounds, including cis- and trans-isomers, cis (Z) and trans (E) alkene isomers R- and S-enantiomers, diastereomers, (D)-isomers, (L)-isomers, the racemic mixtures thereof, and other mixtures thereof, as falling within the scope of the invention. Additional asymmetric carbon atoms may be present in a substituent, such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

Throughout the specifications, groups and substituents thereof may be chosen to provide stable moieties and compounds. Compounds useful in the treatment, for example, are neurodegenerative disorders. The term "stable", as used herein, refers to compounds which possess stability sufficient to allow manufacture and which maintain the integrity of the compound for a sufficient period of time to be detected and preferably for a sufficient period of time to be useful for the purposes detailed herein.

Definitions of specific functional groups and chemical terms are described in more detail above. For purposes of this invention, the chemical elements are identified in accordance with the Periodic Table of the Elements, CAS version, *Handbook of Chemistry and Physics,* 75$^{th}$ Ed., inside cover, and specific functional groups are generally defined as described therein. Additionally, general principles of organic chemistry, as well as specific functional moieties and reactivity, are described in *Organic Chemistry,* Thomas Sorrell, University Science Books, Sausalito, 1999, the entire contents of which are incorporated herein by reference.

In some embodiments, the present invention also includes isotopically labeled compounds, which are identical to the compounds disclosed herein, but for the fact that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorous, sulfur, fluorine and chlorine, such as $^{2}$H, $^{3}$H, $^{13}$C, $^{11}$C, $^{14}$C, $^{15}$N, $^{18}$O, $^{17}$O, $^{31}$P, $^{32}$P, $^{35}$S, $^{18}$F and $^{36}$Cl, respectively. Compounds described herein, or an enantiomer, diastereomer, tautomer, or pharmaceutically acceptable salt or solvate thereof, which contain the aforementioned isotopes and/or other isotopes of other atoms, are within the scope of this invention. Certain isotopically labeled compounds described herein, for example those into which radioactive isotopes, such as $^{3}$H and $^{14}$C are incorporated, are useful in drug and/or substrate tissue distribution assays. Tritiated, i.e., $^{3}$H, and carbon-14, i.e., $^{14}$C, isotopes are particularly preferred for their ease of preparation and detectability. Further, substitution with heavier isotopes, such as deuterium, i.e., $^{2}$H, can afford certain therapeutic advantages resulting from greater metabolic stability, for example increased in vivo half-life or reduced dosage requirements, and hence, may be preferred in some circumstances. Isotopically labeled compounds can generally be prepared by carrying out the procedures disclosed in the Schemes and/or in the Examples below, by substituting a readily available isotopically labeled reagent for a non-isotopically labeled reagent.

When more than one position in any given structure may be substituted with more than one substituent selected from a specified group, the substituent may be either the same or different at every position.

As used herein, "effective amount" refers to any amount that is necessary or sufficient for achieving or promoting a desired outcome, e.g., for treating, preventing, or ameliorating a symptom of a neurodegenerative disease. In some instances an effective amount is a therapeutically effective amount. A therapeutically effective amount is any amount that is necessary or sufficient for promoting or achieving a desired biological response in a subject. The effective amount for any particular application can vary depending on such factors as the disease or condition being treated, the particular agent being administered, the size of the subject, or the severity of the disease or condition.

As used herein, "treat" or "treating" includes stopping the progression and/or reducing or ameliorating a symptom of a neurodegenerative disease, for example, improving cognitive function.

As used herein, the term "subject" refers to a vertebrate animal. In one embodiment the subject is a mammal. In one embodiment the subject is a human. In other embodiments the subject is a non-human vertebrate animal, including, without limitation, non-human primates, laboratory animals, livestock, domesticated animals and non-domesticated animals. Non-limiting examples of subject include a mammal, e g, a human, mouse, rat, guinea pig, dog, cat, horse, cow, pig, and non-human primate, such as a monkey, chimpanzee, baboon or rhesus. In one embodiment, the subject is a human.

Practitioners of the art will recognize that certain chemical groups may exist in multiple tautomeric forms (for example, as an amide or imino ether). The scope of this disclosure is meant to include all such tautomeric forms. For example, a tetrazole may exist in two tautomeric forms, 1-H tetrazole and a 2-H tetrazole. This is depicted in the figure below. This example is not meant to be limiting in the scope of tautomeric forms.

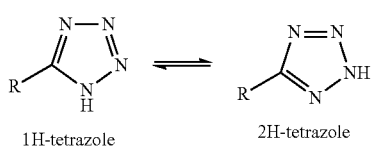

1H-tetrazole        2H-tetrazole

Practitioners of the art will recognize that certain electrophilic ketones, may exist in a hydrated form. The scope of this disclosure is to include all such hydrated forms. For example, a trifluoromethyl ketone may exist in a hydrated form via addition of water to the carbonyl group. This is depicted in the figure below. This example is not meant to be limiting in the scope of hydrated forms.

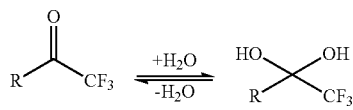

Abbreviations

Abbreviations used in the following examples and preparations include:
Aβ Amyloid-beta
Ac Acyl (Me-C(O)—)
ACN Acetonitrile
AD Alzheimer's Disease
APP Amyloid Precursor Protein
Aq Aqueous
Bn Benzyl
Boc Tert-butyloxycarbonyl
BSA Bovine Serum Albumin
Bu Butyl
BuLi Butyllithium
Cyclo
cBu Cylcobutyl
Conc. Concentrated
cPr Cyclopropyl
CSF Cerebrospinal Fluid
Day(s)
Doublet
dba Dibenzylideneacetorte
DCE 1, 2-Dichloroethane
DCM Dichloromethane
DEA Di-ethylamine
DIAD Diisopropyl Azodicarboxylate
DIBALH Diisobutylaluminium Hydride
DIPEA N, N-Diisopropylethylamine
DMAP 4-Dimethylaminopyridine
DMF Dimethylformamide
DMS Dimethylsulfate
DMSO Dimethyl Sulfoxide
dppf 1,1'-Bis(diphenylphosphino)ferrocene
EDC 1-[3-(Dimethylamino)propyl]-3-ethylcarbodiimide
ELISA Enzyme-Linked Immuno Sorbent Assay
ESI Electrospray Ionization
Et Ethyl
Et₃N Triethylamine
Eq. Equivalent
Grams(s)
HATU 1-[Bis(dimethylamino)methylene]-1H-1,2,3-triazolo[4,5-b]pyridinium 3-oxid Hexafluorophosphate
HOAt 1-Hydroxy-7-azabenzotriazole
HPLC High Pressure Liquid Chromatography
Hour(s)
IPA Isopropyl Alcohol
iPr Isopropyl
i.v or IV. Intravenous
LAH Lithium Aluminum Hydride
LC-MS Liquid Chromatography-Mass Spectrometry
LC/MS Liquid Chromatography Mass Spectrometry
LG Leaving Group
LRMS Low Resolution Mass Spectrometry
Multiplet
Me Methyl
MeOH Methanol
min Minute(s)
mmol Millimoles
μl Microliter
ul Microliter
μm Micrometer
MS Mass Spectrometry
MW Molecular Weight (all values are ±0.05)
n Normal
N Normal
NaHMDS Sodium Hexamethyldisilazane
NB S N-Bromosuccinimide
NCS N-Chlorosuccinimide
NIS N-Iodosuccinimide
NMP 1-Methylpyrrolidin-2-one
NMR Nuclear Magnetic Resonance
NSAIDS Non-Steroidal Anti-Inflammatory Drugs
o/n Overnight
PBS Phosphate Buffered Saline
PPA Poly Phosphoric Acid
Ph Phenyl
Phth Phthalimide
Pr Propyl
PS-BEMP Polystyrene 2-Tert-butylimino-2-diethylamino-1,3-dimethyl-perhydro-1,3,2-diazaphosphorine
Py Pyridine
Ra—Ni Raney Nickel
Rf Retention Factor
RT (or rt) Room Temperature (about 20-25° C.) or Retention Time
RT Retention Time
Singlet
sat. Saturated
SEM-Cl 2-(Trimethylsilyl)ethoxymethyl Chloride
Triplet
TBAF Tetrabutylammonium Fluoride
t-Bu Tertiary Butyl
tert Tertiary
TFA Trifluoroacetic Acid
TFAA Trifluoroacetic Anhydride
THF Tetrahydrofuran
TLC Thin Layer Chromatography
TMS Trimethylsilyl
TPP Triphenylphosphine UPLC Ultra Performance Liquid Chromatography
v/v Volume/volume
wt/v Weight/volume
XPhos 2-Dicyclohexylphosphino-2',4',6'-triisopropylbiphenyl

5.2 Oxadiazine Compounds

Described below are Oxadiazine Compounds, i.e., compounds according to Formula (I) and compounds in Table I-1, and pharmaceutically acceptable salts thereof, as well as methods for preparing the compounds and using the compounds to treat one or more neurodegenerative diseases, e.g., reducing a symptom of Alzheimer's disease (such as improving cognitive function). The compounds of the disclosure are believed to be gamma secretase modulators (GSMs), i.e., compounds that act to shift the relative levels of Aβ peptides produced by γ-secretase. In some embodiments, the compounds alter the relative levels of Aβ peptides produced by γ-secretase, for example the level of Aβ42 peptide, without significantly changing the total level of Aβ peptides produced.

In one aspect, described herein are compounds according to Formula (I), below:

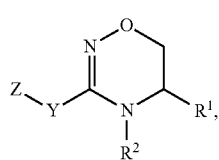

(I)

and pharmaceutically acceptable salts thereof,
wherein $R^1$, $R^2$, Y and Z are as defined above for the compounds of Formula (I).

In some embodiments, $R^1$ is $-C_1-C_6$ alkyl, $-C_3-C_8$ monocyclic cycloalkyl, phenyl, 8- to 10-membered bicyclic heterocycle, each of which is unsubstituted or substituted with one or more substituents independently selected from the group consisting of -halo, $-CN$, $-C_1-C_4$ alkyl, $-C_3-C_8$ monocyclic cycloalkyl, halo-substituted $C_1-C_4$ alkyl, $-C_1-C_4$ alkoxy and halo-substituted $C_1-C_4$ alkoxy; or a pharmaceutically acceptable salt thereof.

In some embodiments, $R^1$ is $-C_3-C_8$ monocyclic cycloalkyl, phenyl, 8- to 10-membered bicyclic heterocycle, each of which is unsubstituted or substituted with one or more substituents independently selected from the group consisting of -halo, $-C_1-C_4$ alkyl, $-C_3-C_8$ monocyclic cycloalkyl, halo-substituted $C_1-C_4$ alkyl, and halo-substituted $C_1-C_4$ alkoxy; or a pharmaceutically acceptable salt thereof.

In some embodiments, $R^1$ is 8- to 10-membered bicyclic heterocycle, each of which is unsubstituted or substituted with one or more substituents independently selected from the group consisting of -halo, $-C_1-C_4$ alkyl, and halo-substituted $C_1-C_4$ alkyl; or a pharmaceutically acceptable salt thereof.

In some embodiments, $R^1$ is phenyl, each of which is unsubstituted or substituted with one or more substituents independently selected from the group consisting of -halo, $-CN$, $-C_1-C_4$ alkyl, $-C_3-C_8$ monocyclic cycloalkyl, halo-substituted $C_1-C_4$ alkyl, $-C_1-C_4$ alkoxy and halo-substituted $C_1-C_4$ alkoxy; or a pharmaceutically acceptable salt thereof.

In some embodiments, $R^1$ is phenyl, each of which is unsubstituted or substituted with one or more substituents independently selected from the group consisting of -halo, $-C_3-C_8$ monocyclic cycloalkyl, halo-substituted $C_1-C_4$ alkyl, and halo-substituted $C_1-C_4$ alkoxy; or a pharmaceutically acceptable salt thereof.

In some embodiments, $R^1$ is $-C_1-C_6$ alkyl which is unsubstituted; or a pharmaceutically acceptable salt thereof.

In some embodiments, $R^1$ is $-C_3-C_8$ monocyclic cycloalkyl, each of which is unsubstituted or substituted with one or more -halo; or a pharmaceutically acceptable salt thereof.

In some embodiments, $R^1$ is $-C_3-C_8$ monocyclic cycloalkyl which is unsubstituted; or a pharmaceutically acceptable salt thereof.

In some embodiments, Y is pyridinyl which is unsubstituted or substituted with one or more $-C_1-C_4$ alkoxy, halo-substituted $C_1-C_4$ alkoxy; or a pharmaceutically acceptable salt thereof.

In some embodiments, Y is pyridinyl which is substituted with one $-C_1-C_4$ alkoxy; or a pharmaceutically acceptable salt thereof.

In some embodiments, Y is pyridinyl which is substituted with one methoxy; or a pharmaceutically acceptable salt thereof.

In some embodiments, Z is nitrogen-containing 3- to 7-membered monocyclic heterocycle which is unsubstituted or substituted with one or more $-C_1-C_4$ alkyl; or a pharmaceutically acceptable salt thereof.

In some embodiments, Z is nitrogen-containing 3- to 7-membered monocyclic heterocycle which is substituted with one $-C_1-C_4$ alkyl; or a pharmaceutically acceptable salt thereof.

In some embodiments, Z is nitrogen-containing 3- to 7-membered monocyclic heterocycle which is substituted with one methyl; or a pharmaceutically acceptable salt thereof.

In some embodiments, Z is imidazolyl which is unsubstituted or substituted with one methyl; or a pharmaceutically acceptable salt thereof.

In some embodiments, $R^1$ is

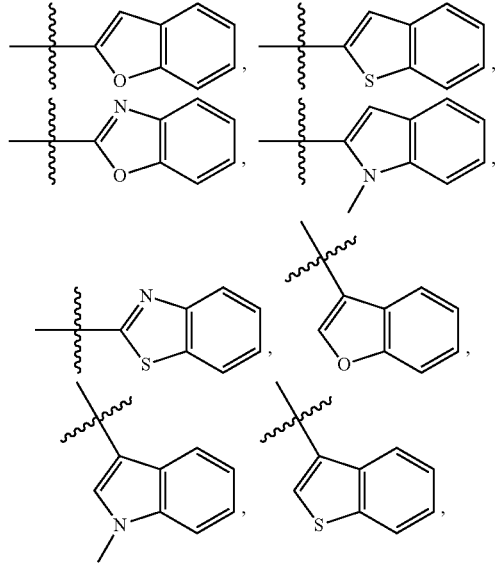

-continued

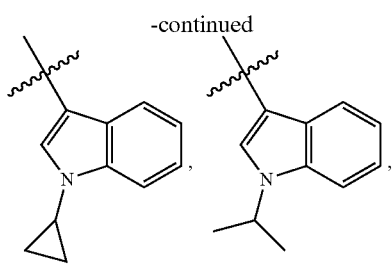

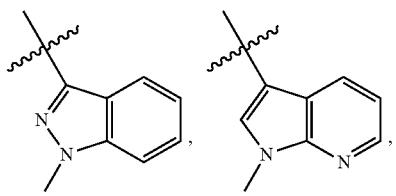

each of which is optionally further substituted with -halo, —CF$_3$ or —C$_1$-C$_4$ alkyl; and Z is

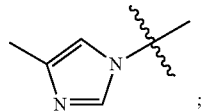 [SMILES: *n1cnc(C)c1]

or a pharmaceutically acceptable salt thereof.

In some embodiments, Y is

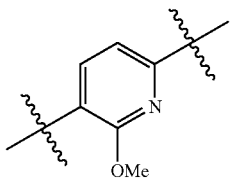 [SMILES: *c1ccc(*)c(OC)n1]

wherein the left most radical is connected to the Z group in Formula (I); or a pharmaceutically acceptable salt thereof.

In some embodiments, the invention provides a levorotatory isomer of the compound of Formula (I); or a pharmaceutically acceptable salt thereof.

In some embodiments, the invention provides a dextrorotatory isomer of the compound of Formula (I); or a pharmaceutically acceptable salt thereof.

In some embodiments, the invention provides a compound of Formula (I) in which one or more hydrogen atoms have been replaced with deuterium atoms.

In some embodiments, the compound of Formula (I) is a compound selected from the compounds in Table I. In some embodiments, the compound of Formula (I) is a pharmaceutically acceptable salt of a compound selected from the compounds in Table I.

TABLE I

Exemplary Oxadiazine Compounds of Formula (I)

| Compound of Example | Structure | Name |
| --- | --- | --- |
| 4 | 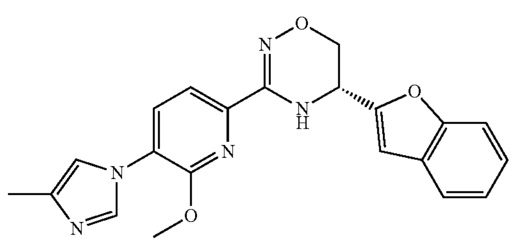 [SMILES: COc1nc(C2=NOC[C@H](c3cc4ccccc4s3)N2)ccc1-n1cnc(C)c1] | (R)-5-(benzofuran-2-yl)-3-(6-methoxy-5-(4-methyl-1H-imidazol-1-yl)pyridin-2-yl)-5,6-dihydro-4H-1,2,4-oxadiazine |
| 7A | 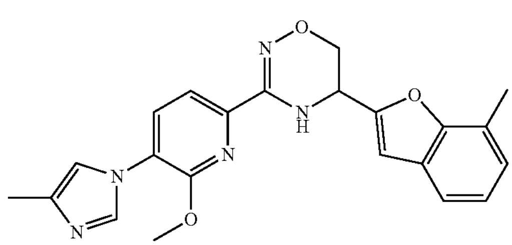 | 3-(6-methoxy-5-(4-methyl-1H-imidazol-1-yl)pyridin-2-yl)-5-(7-methylbenzofuran-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 7B | 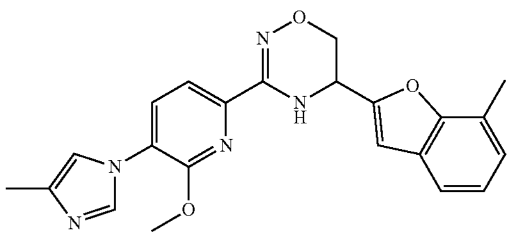 | 3-(6-Methoxy-5-(4-methyl-1H-imidazol-1-yl)pyridin-2-yl)-5-(7-methylbenzofuran-2-yl)-5,6-dihydro-4H-1,2,4-oxadiazine |
| 10 | 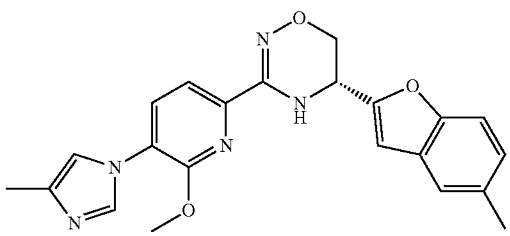 | (R)-3-(6-methoxy-5-(4-methyl-1H-imidazol-1-yl)pyridin-2-yl)-5-(5-methylbenzofuran-2-yl)-5,6-dihydro-4H-1,2,4-oxadiazine |
| 13 | 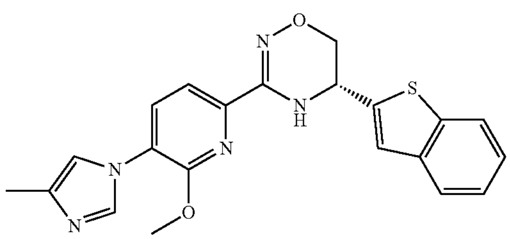 | (R)-5-(benzo[b]thiophen-2-yl)-3-(6-methoxy-5-(4-methyl-1H-imidazol-1-yl)pyridin-2-yl)-5,6-dihydro-4H-1,2,4-oxadiazine |
| 16A | 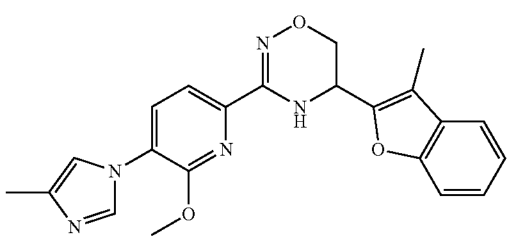 | (−)-3-(6-methoxy-5-(4-methyl-1H-imidazol-1-yl)pyridin-2-yl)-5-(3-methylbenzofuran-2-yl)-5,6-dihydro-4H-1,2,4-oxadiazine |
| 16B | 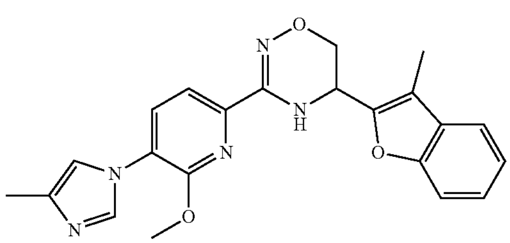 | (+)-3-(6-methoxy-5-(4-methyl-1H-imidazol-1-yl)pyridin-2-yl)-5-(4-methylbenzofuran-2-yl)-5,6-dihydro-4H-1,2,4-oxadiazine |
| 19 | 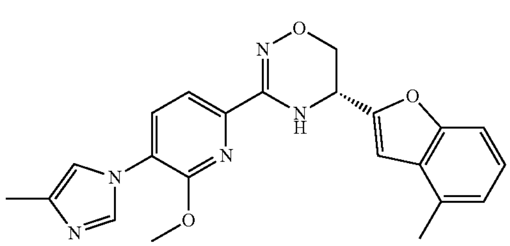 [SMILES: COc1nc(C2=NOC[C@H](c3cc4c(C)cccc4o3)N2)ccc1-n1cnc(C)c1] | (R)-3-(6-methoxy-5-(4-methyl-1H-imidazol-1-yl)pyridin-2-yl)-5-(4-methylbenzofuran-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 22 | 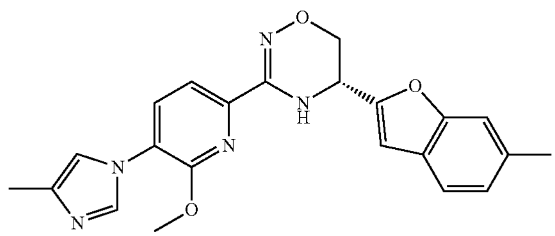 | (R)-3-(6-methoxy-5-(4-methyl-1H-imidazol-1-yl)pyridin-2-yl)-5-(6-methylbenzofuran-2-yl)-5,6-dihydro-4H-1,2,4-oxadiazine |
| 23 | 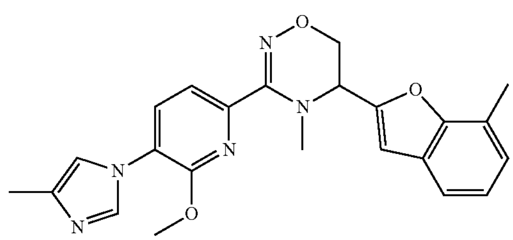 | (+)-3-(6-methoxy-5-(4-methyl-1H-imidazol-1-yl)pyridin-2-yl)-4-methyl-5-(7-methylbenzofuran-2-yl)-5,6-dihydro-4H-1,2,4-oxadiazine |
| 24 | 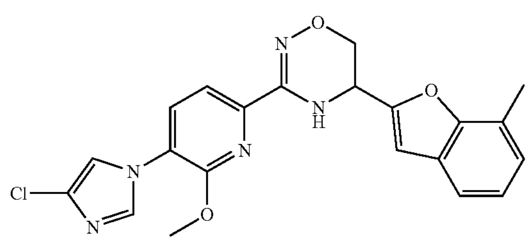 [SMILES: COc1nc(C2=NOCC(c3cc4cccc(C)c4o3)N2)ccc1-n1cnc(Cl)c1] | (+)-3-(5-(4-chloro-1H-imidazol-1-yl)-6-methoxypyridin-2-yl)-5-(7-methylbenzofuran-2-yl)-5,6-dihydro-4H-1,2,4-oxadiazine |
| 27A | 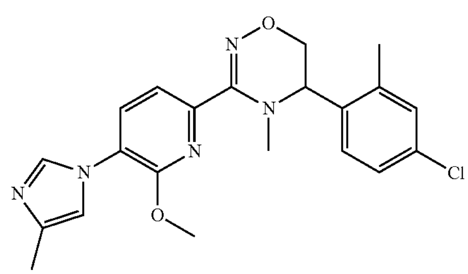 [SMILES: COc1nc(C2=NOCC(c3ccc(Cl)cc3C)N2C)ccc1-n1cnc(C)c1] | 5-(4-chloro-2-methylphenyl)-3-(6-methoxy-5-(4-methyl-1H-imidazol-1-yl)pyridin-2-yl)-4-methyl-5,6-dihydro-4H-1,2,4-oxadiazine |
| 27B | 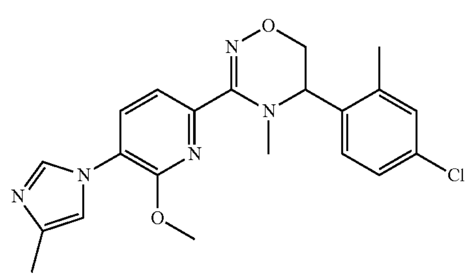 [SMILES: COc1nc(C2=NOCC(c3ccc(Cl)cc3C)N2C)ccc1-n1cnc(C)c1] | 5-(4-chloro-2-methylphenyl)-3-(6-methoxy-5-(4-methyl-1H-imidazol-1-yl)pyridin-2-yl)-4-methyl-5,6-dihydro-4H-1,2,4-oxadiazine |
| 30A | 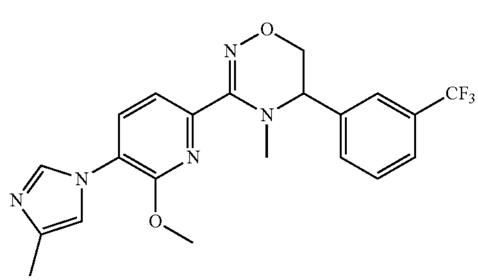 [SMILES: COc1nc(C2=NOCC(c3cccc(C(F)(F)F)c3)N2C)ccc1-n1cnc(C)c1] | 3-(6-methoxy-5-(4-methyl-1H-imidazol-1-yl)pyridin-2-yl)-4-methyl-5-(3-(trifluoromethyl)phenyl)-5,6-dihydro-4H-1,2,4-oxadiazine |

TABLE I-continued

Exemplary Oxadiazine Compounds of Formula (I)

| Compound of Example | Structure | Name |
|---|---|---|
| 30B | 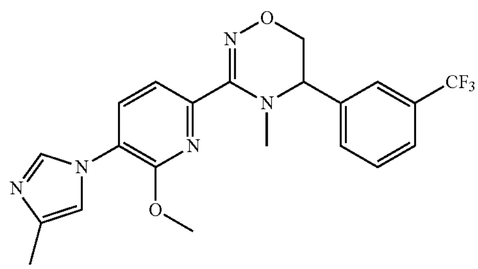 [SMILES: COc1nc(C2=NOCC(c3cccc(C(F)(F)F)c3)N2C)ccc1-n1cnc(C)c1] | 3-(6-methoxy-5-(4-methyl-1H-imidazol-1-yl)pyridin-2-yl)-4-methyl-5-(3-(trifluoromethyl)phenyl)-5,6-dihydro-4H-1,2,4-oxadiazine |
| 31A | 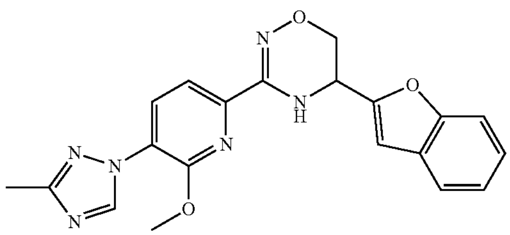 [SMILES: COc1nc(C2=NOCC(c3cc4ccccc4o3)N2)ccc1-n1cnc(C)n1] | (−)-5-(Benzofuran-2-yl)-3-(6-methoxy-5-(3-methyl-1H-1,2,4-triazol-1-yl)pyridin-2-yl)-5,6-dihydro-4H-1,2,4-oxadiazine |
| 31B | 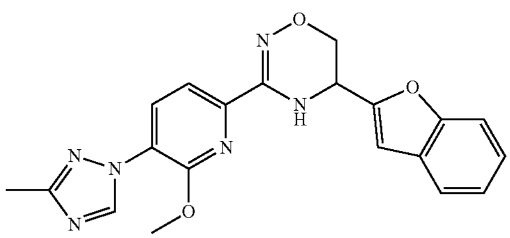 | (+)-5-(Benzofuran-2-yl)-3-(6-methoxy-5-(3-methyl-1H-1,2,4-triazol-1-yl)pyridin-2-yl)-5,6-dihydro-4H-1,2,4-oxadiazine |
| 32 | 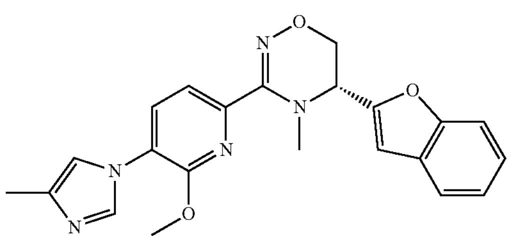 [SMILES: COc1nc(C2=NOC[C@H](c3cc4ccccc4o3)N2C)ccc1-n1cnc(C)c1] | (R)-5-(benzofuran-2-yl)-3-(6-methoxy-5-(4-methyl-1H-imidazol-1-yl)pyridin-2-yl)-4-methyl-5,6-dihydro-4H-1,2,4-oxadiazine |
| 33 | 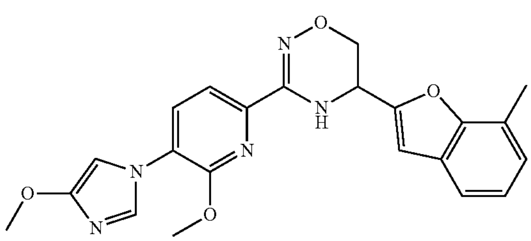 | (+)-3-(6-methoxy-5-(4-methoxy-1H-imidazol-1-yl)pyridin-2-yl)-5-(7-methylbenzofuran-2-yl)-5,6-dihydro-4H-1,2,4-oxadiazine |
| 36A | 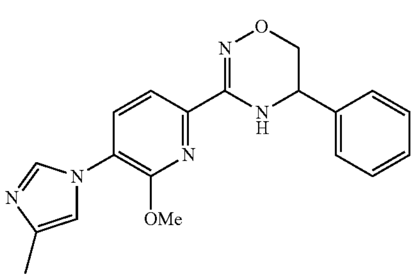 [SMILES: COc1nc(C2=NOCC(c3ccccc3)N2)ccc1-n1cnc(C)c1] | 3-(6-methoxy-5-(4-methyl-1H-imidazol-1-yl)pyridin-2-yl)-5-phenyl-5,6-dihydro-4H-1,2,4-oxadiazine |

TABLE I-continued

Exemplary Oxadiazine Compounds of Formula (I)

| Compound of Example | Structure | Name |
|---|---|---|
| 36B | 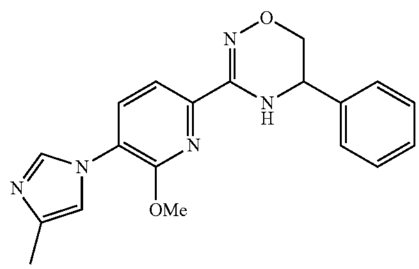 [SMILES: COc1nc(C2=NOCC(c3ccccc3)N2)ccc1-n1cnc(C)c1] | 3-(6-methoxy-5-(4-methyl-1H-imidazol-1-yl)pyridin-2-yl)-5-phenyl-5,6-dihydro-4H-1,2,4-oxadiazine |
| 38A | 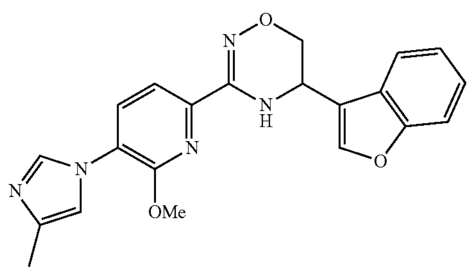 [SMILES: COc1nc(C2=NOCC(c3coc4ccccc34)N2)ccc1-n1cnc(C)c1] | 5-(benzofuran-3-yl)-3-(6-methoxy-5-(4-methyl-1H-imidazol-1-yl)pyridin-2-yl)-5,6-dihydro-4H-1,2,4-oxadiazine |
| 38B | 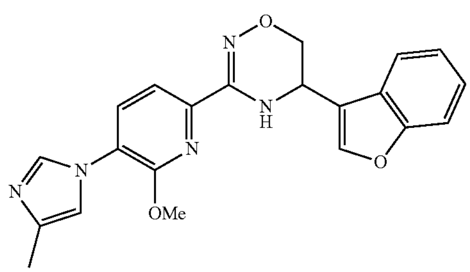 [SMILES: COc1nc(C2=NOCC(c3coc4ccccc34)N2)ccc1-n1cnc(C)c1] | 5-(benzofuran-3-yl)-3-(6-methoxy-5-(4-methyl-1H-imidazol-1-yl)pyridin-2-yl)-5,6-dihydro-4H-1,2,4-oxadiazine |
| 40A | 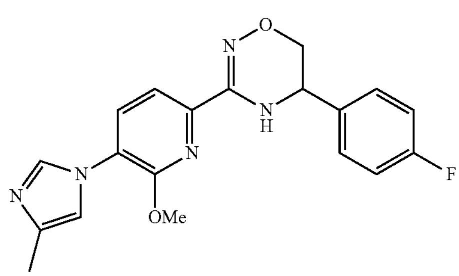 [SMILES: COc1nc(C2=NOCC(c3ccc(F)cc3)N2)ccc1-n1cnc(C)c1] | 5-(4-fluorophenyl)-3-(6-methoxy-5-(4-methyl-1H-imidazol-1-yl)pyridin-2-yl)-5,6-dihydro-4H-1,2,4-oxadiazine |
| 40B | 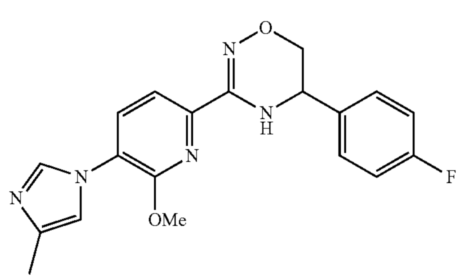 [SMILES: COc1nc(C2=NOCC(c3ccc(F)cc3)N2)ccc1-n1cnc(C)c1] | 5-(4-fluorophenyl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 42A | 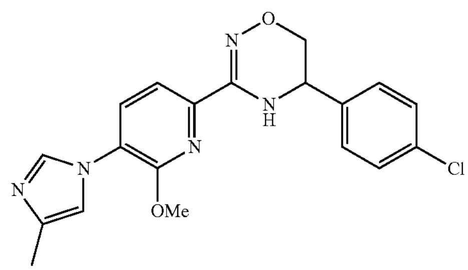 [SMILES: COc1nc(C2=NOCC(c3ccc(Cl)cc3)N2)ccc1-n1cnc(C)c1] | 5-(4-chlorophenyl)-3-(6-methoxy-5-(4-methyl-1H-imidazol-1-yl)pyridin-2-yl)-5,6-dihydro-4H-1,2,4-oxadiazine |
| 42B | 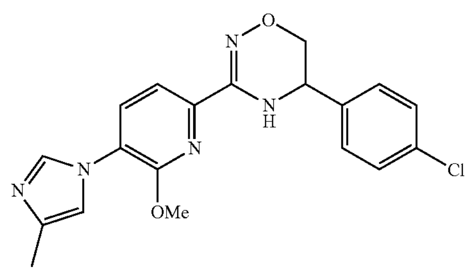 [SMILES: COc1nc(C2=NOCC(c3ccc(Cl)cc3)N2)ccc1-n1cnc(C)c1] | 5-(4-chlorophenyl)-3-(6-methoxy-5-(4-methyl-1H-imidazol-1-yl)pyridin-2-yl)-5,6-dihydro-4H-1,2,4-oxadiazine |
| 44A | 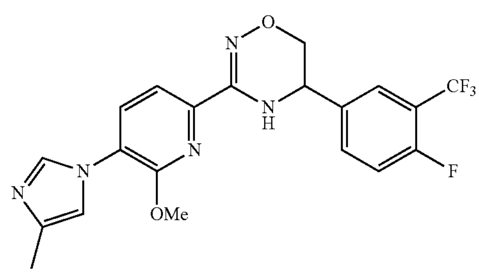 [SMILES: COc1nc(C2=NOCC(c3ccc(F)c(C(F)(F)F)c3)N2)ccc1-n1cnc(C)c1] | 5-(4-fluoro-3-(trifluoromethyl)phenyl)-3-(6-methoxy-5-(4-methyl-1H-imidazol-1-yl)pyridin-2-yl)-5,6-dihydro-4H-1,2,4-oxadiazine |
| 44B | 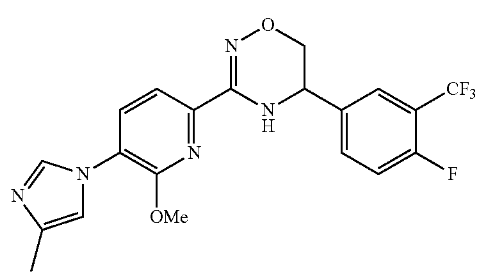 [SMILES: COc1nc(C2=NOCC(c3ccc(F)c(C(F)(F)F)c3)N2)ccc1-n1cnc(C)c1] | 5-(4-fluoro-3-(trifluoromethyl)phenyl)-3-(6-methoxy-5-(4-methyl-1H-imidazol-1-yl)pyridin-2-yl)-5,6-dihydro-4H-1,2,4-oxadiazine |
| 47A | 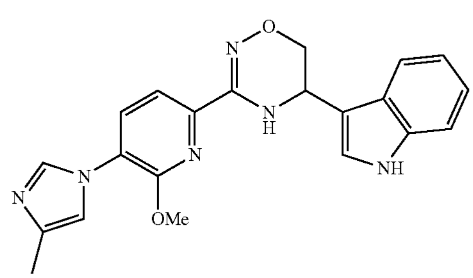 [SMILES: COc1nc(C2=NOCC(c3c[nH]c4ccccc34)N2)ccc1-n1cnc(C)c1] | 5-(1H-indol-3-yl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 47B | 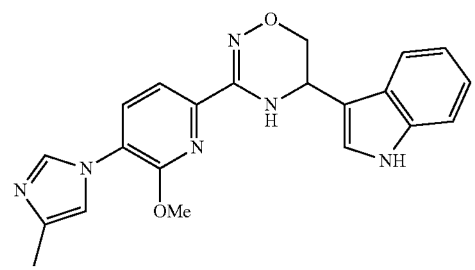 [SMILES: COc1nc(C2=NOCC(c3c[nH]c4ccccc34)N2)ccc1-n1cnc(C)c1] | 5-(1H-indol-3-yl)-3-(6-methoxy-5-(4-methyl-1H-imidazol-1-yl)pyridin-2-yl)-5,6-dihydro-4H-1,2,4-oxadiazine |
| 49A | 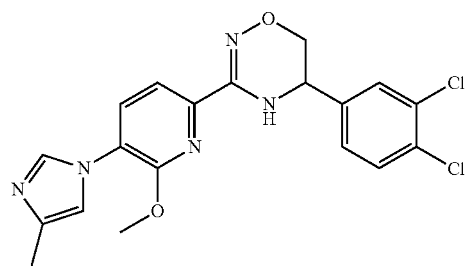 [SMILES: COc1nc(C2=NOCC(c3ccc(Cl)c(Cl)c3)N2)ccc1-n1cnc(C)c1] | (−)-5-(3,4-dichlorophenyl)-3-(6-methoxy-5-(4-methyl-1H-imidazol-1-yl)pyridin-2-yl)-5,6-dihydro-4H-1,2,4-oxadiazine |
| 49B | 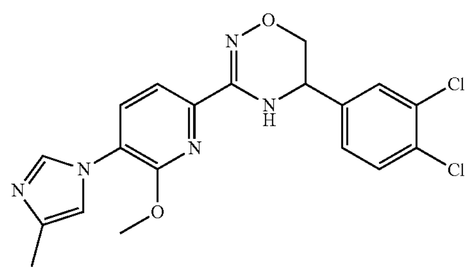 | (+)-5-(3,4-dichlorophenyl)-3-(6-methoxy-5-(4-methyl-1H-imidazol-1-yl)pyridin-2-yl)-5,6-dihydro-4H-1,2,4-oxadiazine |
| 52A | 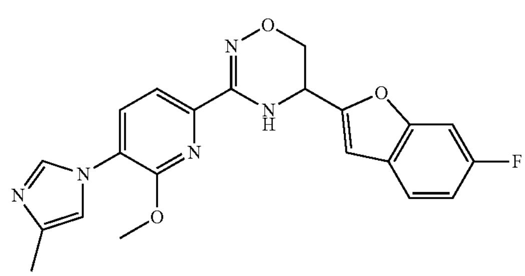 [SMILES: COc1nc(C2=NOCC(c3cc4ccc(F)cc4o3)N2)ccc1-n1cnc(C)c1] | (−)-5-(6-fluorobenzofuran-2-yl)-3-(6-methoxy-5-(4-methyl-1H-imidazol-1-yl)pyridin-2-yl)-5,6-dihydro-4H-1,2,4-oxadiazine |
| 52B | 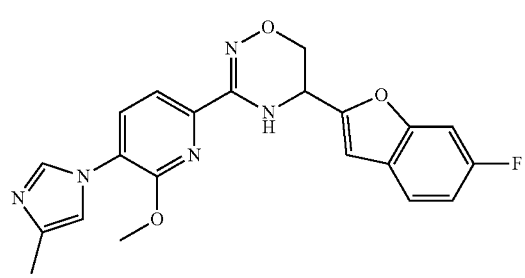 [SMILES: COc1nc(C2=NOCC(c3cc4ccc(F)cc4o3)N2)ccc1-n1cnc(C)c1] | (+)-5-(6-fluorobenzofuran-2-yl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 54A | 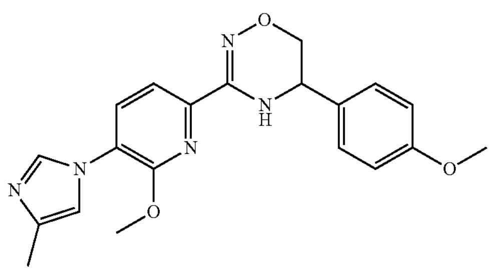 [SMILES: COc1ccc(C2CON=C(c3ccc(-n4cnc(C)c4)c(OC)n3)N2)cc1] | (−)-3-(6-methoxy-5-(4-methyl-1H-imidazol-1-yl)pyridin-2-yl)-5-(4-methoxyphenyl)-5,6-dihydro-4H-1,2,4-oxadiazine |
| 54B | 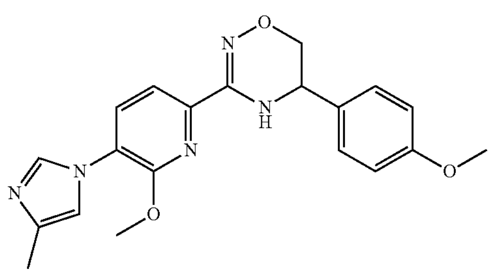 [SMILES: COc1ccc(C2CON=C(c3ccc(-n4cnc(C)c4)c(OC)n3)N2)cc1] | (+)-3-(6-methoxy-5-(4-methyl-1H-imidazol-1-yl)pyridin-2-yl)-5-(4-methoxyphenyl)-5,6-dihydro-4H-1,2,4-oxadiazine |
| 57A | 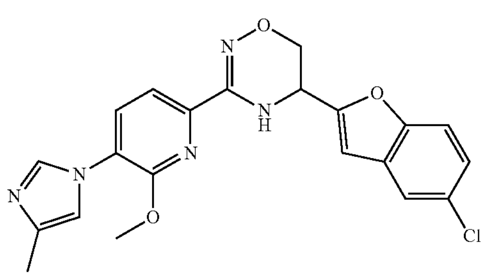 [SMILES: COc1nc(C2=NOCC(c3cc4cc(Cl)ccc4o3)N2)ccc1-n1cnc(C)c1] | (−)-5-(5-chlorobenzofuran-2-yl)-3-(6-methoxy-5-(4-methyl-1H-imidazol-1-yl)pyridin-2-yl)-5,6-dihydro-4H-1,2,4-oxadiazine |
| 57B | 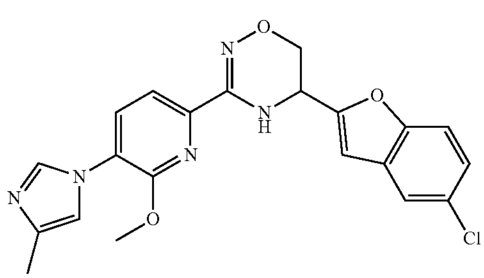 [SMILES: COc1nc(C2=NOCC(c3cc4cc(Cl)ccc4o3)N2)ccc1-n1cnc(C)c1] | (+)-5-(5-chlorobenzofuran-2-yl)-3-(6-methoxy-5-(4-methyl-1H-imidazol-1-yl)pyridin-2-yl)-5,6-dihydro-4H-1,2,4-oxadiazine |
| 59A | 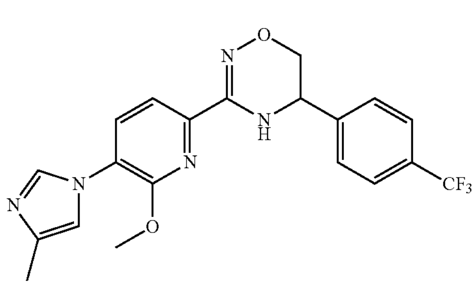 [SMILES: COc1nc(C2=NOCC(c3ccc(C(F)(F)F)cc3)N2)ccc1-n1cnc(C)c1] | (−)-3-(6-methoxy-5-(4-methyl-1H-imidazol-1-yl)pyridin-2-yl)-5-(4-(trifluoromethyl)phenyl)-5,6-dihydro-4H-1,2,4-oxadiazine |

TABLE I-continued

Exemplary Oxadiazine Compounds of Formula (I)

| Compound of Example | Structure | Name |
|---|---|---|
| 59B | 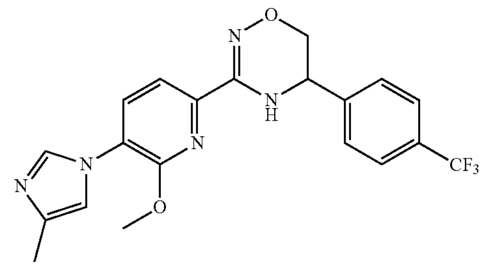 [SMILES: COc1nc(C2=NOCC(c3ccc(C(F)(F)F)cc3)N2)ccc1-n1cnc(C)c1] | (+)-3-(6-methoxy-5-(4-methyl-1H-imidazol-1-yl)pyridin-2-yl)-5-(4-(trifluoromethyl)phenyl)-5,6-dihydro-4H-1,2,4-oxadiazine |
| 61A | 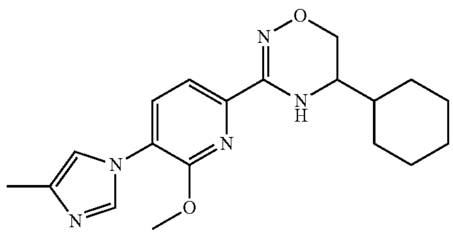 [SMILES: COc1nc(C2=NOCC(C3CCCCC3)N2)ccc1-n1cnc(C)c1] | (−)-5-cyclohexyl-3-(6-methoxy-5-(4-methyl-1H-imidazol-1-yl)pyridin-2-yl)-5,6-dihydro-4H-1,2,4-oxadiazine |
| 61B | 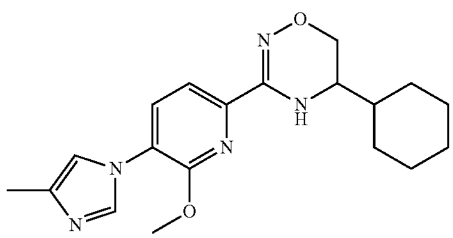 [SMILES: COc1nc(C2=NOCC(C3CCCCC3)N2)ccc1-n1cnc(C)c1] | (+)-5-cyclohexyl-3-(6-methoxy-5-(4-methyl-1H-imidazol-1-yl)pyridin-2-yl)-5,6-dihydro-4H-1,2,4-oxadiazine |
| 64A | 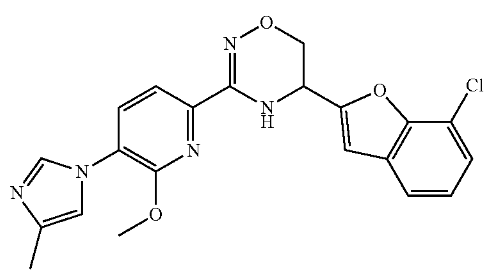 [SMILES: COc1nc(C2=NOCC(c3cc4cccc(Cl)c4o3)N2)ccc1-n1cnc(C)c1] | (−)-5-(7-chlorobenzofuran-2-yl)-3-(6-methoxy-5-(4-methyl-1H-imidazol-1-yl)pyridin-2-yl)-5,6-dihydro-4H-1,2,4-oxadiazine |
| 64B | 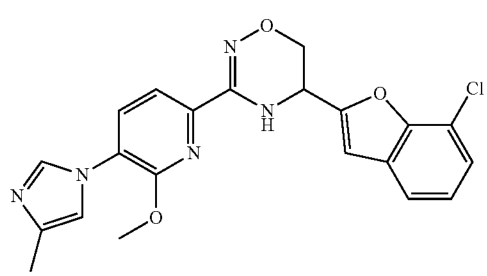 [SMILES: COc1nc(C2=NOCC(c3cc4cccc(Cl)c4o3)N2)ccc1-n1cnc(C)c1] | (+)-5-(7-chlorobenzofuran-2-yl)-3-(6-methoxy-5-(4-methyl-1H-imidazol-1-yl)pyridin-2-yl)-5,6-dihydro-4H-1,2,4-oxadiazine |
| 66A | 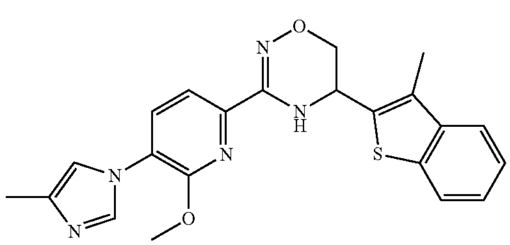 | (−)-3-(6-methoxy-5-(4-methyl-1H-imidazol-1-yl)pyridin-2-yl)-5-(3-methylbenzo[b]thiophen-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 66B | 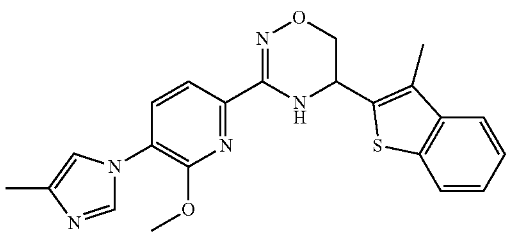 | (+)-3-(6-methoxy-5-(4-methyl-1H-imidazol-1-yl)pyridin-2-yl)-5-(3-methylbenzo[b]thiophen-2-yl)-5,6-dihydro-4H-1,2,4-oxadiazine |
| 68A | 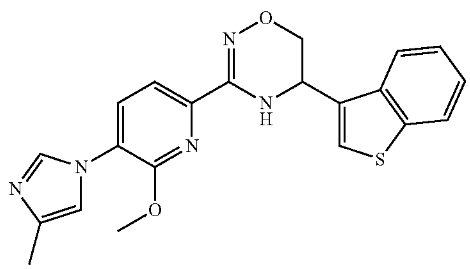 [SMILES: COc1nc(C2=NOCC(c3csc4ccccc34)N2)ccc1-n1cnc(C)c1] | (−)-5-(benzo[b]thiophen-3-yl)-3-(6-methoxy-5-(4-methyl-1H-imidazol-1-yl)pyridin-2-yl)-5,6-dihydro-4H-1,2,4-oxadiazine |
| 68B | 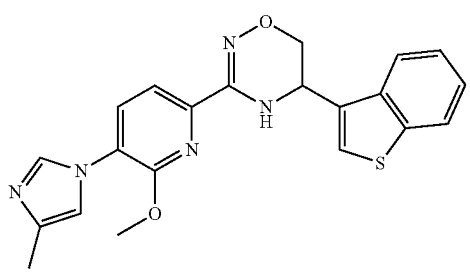 [SMILES: COc1nc(C2=NOCC(c3csc4ccccc34)N2)ccc1-n1cnc(C)c1] | (+)-5-(benzo[b]thiophen-3-yl)-3-(6-methoxy-5-(4-methyl-1H-imidazol-1-yl)pyridin-2-yl)-5,6-dihydro-4H-1,2,4-oxadiazine |
| 70A | 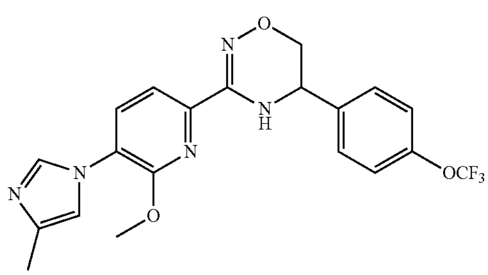 [SMILES: COc1nc(C2=NOCC(c3ccc(OC(F)(F)F)cc3)N2)ccc1-n1cnc(C)c1] | (−)-3-(6-methoxy-5-(4-methyl-1H-imidazol-1-yl)pyridin-2-yl)-5-(4-(trifluoromethoxy)phenyl)-5,6-dihydro-4H-1,2,4-oxadiazine |
| 70B | 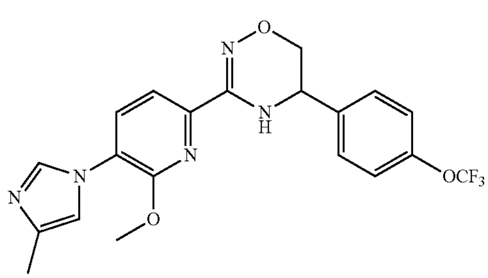 [SMILES: COc1nc(C2=NOCC(c3ccc(OC(F)(F)F)cc3)N2)ccc1-n1cnc(C)c1] | (+)-3-(6-methoxy-5-(4-methyl-1H-imidazol-1-yl)pyridin-2-yl)-5-(4-(trifluoromethoxy)phenyl)-5,6-dihydro-4H-1,2,4-oxadiazine |

TABLE I-continued

Exemplary Oxadiazine Compounds of Formula (I)

| Compound of Example | Structure | Name |
|---|---|---|
| 73A | 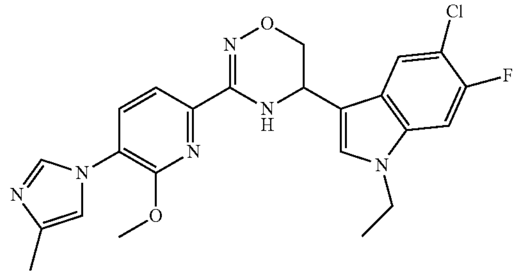 [SMILES: CCn1cc(C2CON=C(c3ccc(-n4cnc(C)c4)c(OC)n3)N2)c2cc(Cl)c(F)cc21] | (−)-5-(5-chloro-1-ethyl-6-fluoro-1H-indol-3-yl)-3-(6-methoxy-5-(4-methyl-1H-imidazol-1-yl)pyridin-2-yl)-5,6-dihydro-4H-1,2,4-oxadiazine |
| 73B | 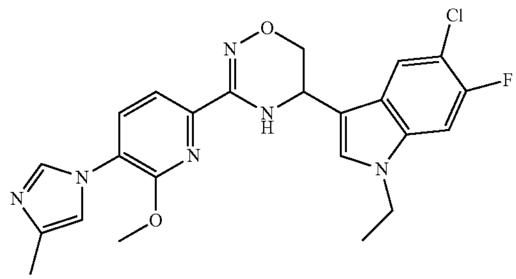 [SMILES: CCn1cc(C2CON=C(c3ccc(-n4cnc(C)c4)c(OC)n3)N2)c2cc(Cl)c(F)cc21] | (+)-5-(5-chloro-1-ethyl-6-fluoro-1H-indol-3-yl)-3-(6-methoxy-5-(4-methyl-1H-imidazol-1-yl)pyridin-2-yl)-5,6-dihydro-4H-1,2,4-oxadiazine |
| 75A | 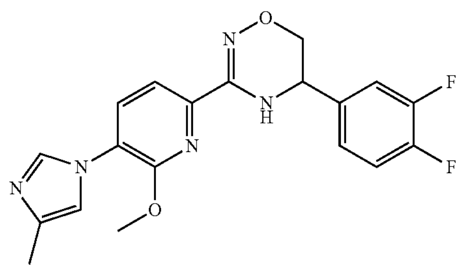 [SMILES: COc1nc(C2=NOCC(c3ccc(F)c(F)c3)N2)ccc1-n1cnc(C)c1] | (−)-5-(3,4-difluorophenyl)-3-(6-methoxy-5-(4-methyl-1H-imidazol-1-yl)pyridin-2-yl)-5,6-dihydro-4H-1,2,4-oxadiazine |
| 75B | 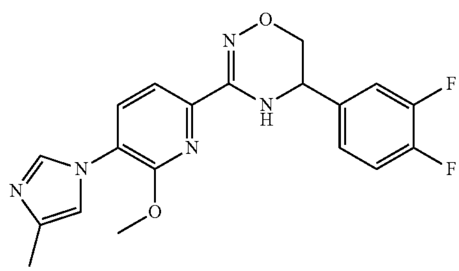 [SMILES: COc1nc(C2=NOCC(c3ccc(F)c(F)c3)N2)ccc1-n1cnc(C)c1] | (+)-5-(3,4-difluorophenyl)-3-(6-methoxy-5-(4-methyl-1H-imidazol-1-yl)pyridin-2-yl)-5,6-dihydro-4H-1,2,4-oxadiazine |
| 78A | 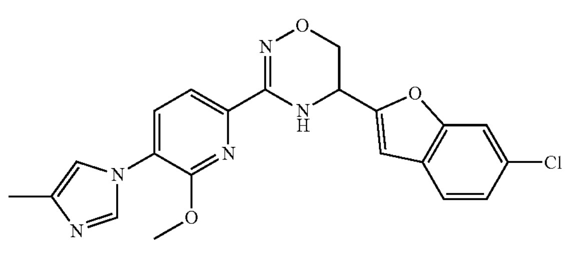 [SMILES: COc1nc(C2=NOCC(c3cc4ccc(Cl)cc4o3)N2)ccc1-n1cnc(C)c1] | (−)-5-(6-chlorobenzofuran-2-yl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 78B | 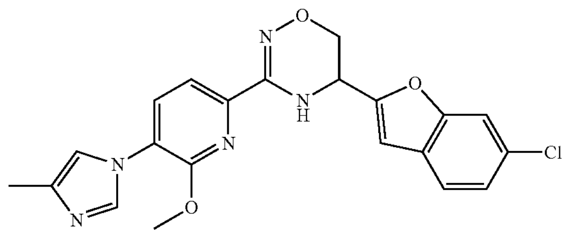 [SMILES: COc1nc(C2=NOCC(c3cc4ccc(Cl)cc4o3)N2)ccc1-n1cnc(C)c1] | (+)-5-(6-chlorobenzofuran-2-yl)-3-(6-methoxy-5-(4-methyl-1H-imidazol-1-yl)pyridin-2-yl)-5,6-dihydro-4H-1,2,4-oxadiazine |
| 81A | 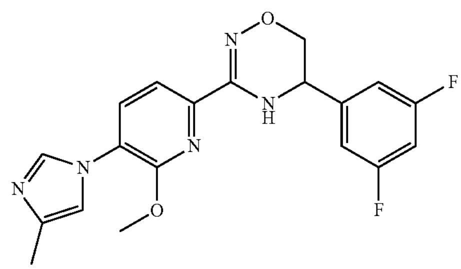 [SMILES: COc1nc(C2=NOCC(c3cc(F)cc(F)c3)N2)ccc1-n1cnc(C)c1] | (−)-5-(3,5-difluorophenyl)-3-(6-methoxy-5-(4-methyl-1H-imidazol-1-yl)pyridin-2-yl)-5,6-dihydro-4H-1,2,4-oxadiazine |
| 81B | 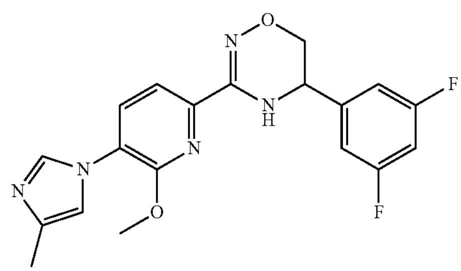 [SMILES: COc1nc(C2=NOCC(c3cc(F)cc(F)c3)N2)ccc1-n1cnc(C)c1] | (+)-5-(3,5-difluorophenyl)-3-(6-methoxy-5-(4-methyl-1H-imidazol-1-yl)pyridin-2-yl)-5,6-dihydro-4H-1,2,4-oxadiazine |
| 84A | 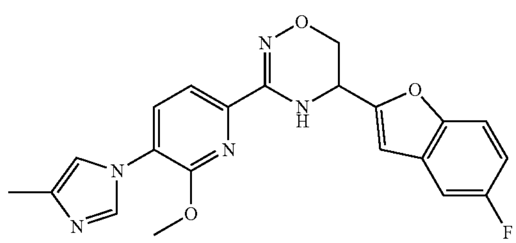 [SMILES: COc1nc(C2=NOCC(c3cc4cc(F)ccc4o3)N2)ccc1-n1cnc(C)c1] | (−)-5-(5-fluorobenzofuran-2-yl)-3-(6-methoxy-5-(4-methyl-1H-imidazol-1-yl)pyridin-2-yl)-5,6-dihydro-4H-1,2,4-oxadiazine |
| 84B | 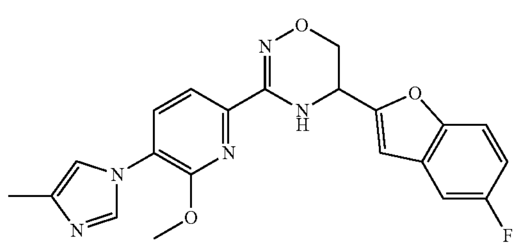 [SMILES: COc1nc(C2=NOCC(c3cc4cc(F)ccc4o3)N2)ccc1-n1cnc(C)c1] | (+)-5-(5-fluorobenzofuran-2-yl)-3-(6-methoxy-5-(4-methyl-1H-imidazol-1-yl)pyridin-2-yl)-5,6-dihydro-4H-1,2,4-oxadiazine |
| 86A | 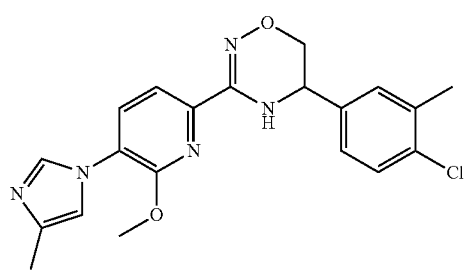 [SMILES: COc1nc(C2=NOCC(c3ccc(Cl)c(C)c3)N2)ccc1-n1cnc(C)c1] | (−)-5-(4-chloro-3-methylphenyl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 86B | 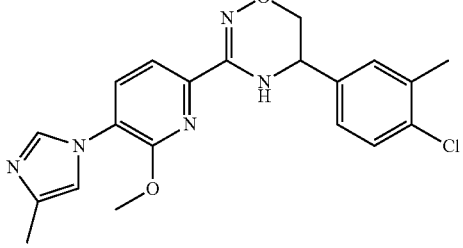 | (+)-5-(4-chloro-3-methylphenyl)-3-(6-methoxy-5-(4-methyl-1H-imidazol-1-yl)pyridin-2-yl)-5,6-dihydro-4H-1,2,4-oxadiazine |
| 89A | 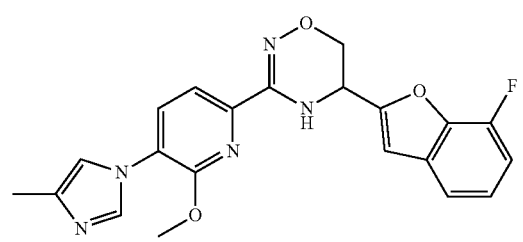 [SMILES: COc1nc(C2=NOCC(c3cc4cccc(F)c4o3)N2)ccc1-n1cnc(C)c1] | (−)-5-(7-fluorobenzofuran-2-yl)-3-(6-methoxy-5-(4-methyl-1H-imidazol-1-yl)pyridin-2-yl)-5,6-dihydro-4H-1,2,4-oxadiazine |
| 89B | 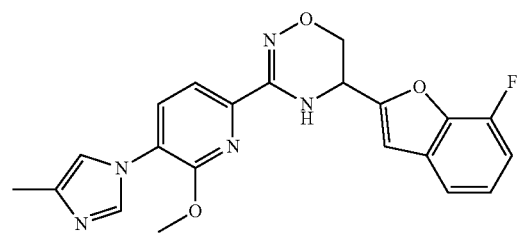 [SMILES: COc1nc(C2=NOCC(c3cc4cccc(F)c4o3)N2)ccc1-n1cnc(C)c1] | (+)-5-(7-fluorobenzofuran-2-yl)-3-(6-methoxy-5-(4-methyl-1H-imidazol-1-yl)pyridin-2-yl)-5,6-dihydro-4H-1,2,4-oxadiazine |
| 91A | 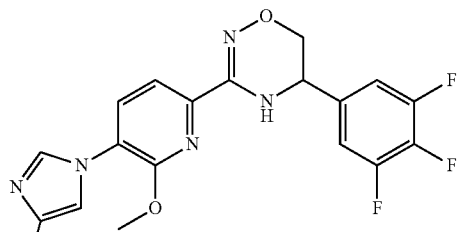 | (−)-3-(6-methoxy-5-(4-methyl-1H-imidazol-1-yl)pyridin-2-yl)-5-(3,4,5-trifluorophenyl)-5,6-dihydro-4H-1,2,4-oxadiazine |
| 91B | 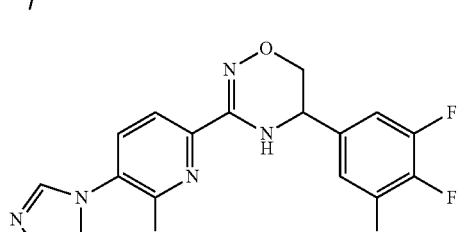 | (+)-3-(6-methoxy-5-(4-methyl-1H-imidazol-1-yl)pyridin-2-yl)-5-(3,4,5-trifluorophenyl)-5,6-dihydro-4H-1,2,4-oxadiazine |
| 93A | 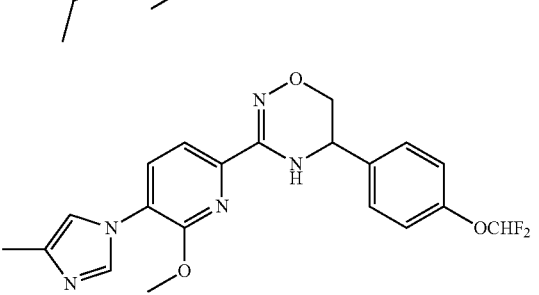 | (−)-5-(4-(difluoromethoxy)phenyl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 93B | 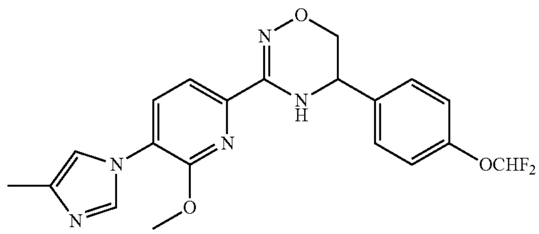 [SMILES: COc1nc(C2=NOCC(c3ccc(OC(F)F)cc3)N2)ccc1-n1cnc(C)c1] | (+)-5-(4-(difluoromethoxy)phenyl)-3-(6-methoxy-5-(4-methyl-1H-imidazol-1-yl)pyridin-2-yl)-5,6-dihydro-4H-1,2,4-oxadiazine |
| 96A | 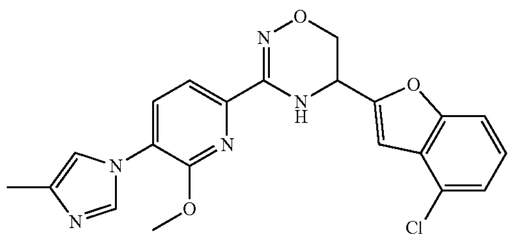 [SMILES: COc1nc(C2=NOCC(c3cc4c(Cl)cccc4o3)N2)ccc1-n1cnc(C)c1] | (−)-5-(4-chlorobenzofuran-2-yl)-3-(6-methoxy-5-(4-methyl-1H-imidazol-1-yl)pyridin-2-yl)-5,6-dihydro-4H-1,2,4-oxadiazine |
| 96B | 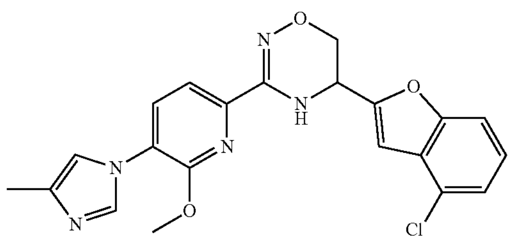 [SMILES: COc1nc(C2=NOCC(c3cc4c(Cl)cccc4o3)N2)ccc1-n1cnc(C)c1] | (+)-5-(4-chlorobenzofuran-2-yl)-3-(6-methoxy-5-(4-methyl-1H-imidazol-1-yl)pyridin-2-yl)-5,6-dihydro-4H-1,2,4-oxadiazine |
| 99A | 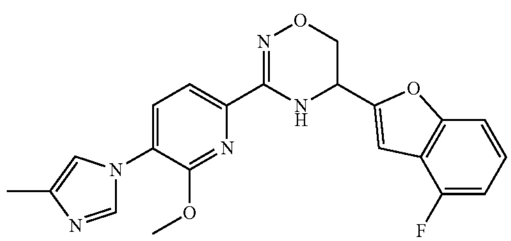 [SMILES: COc1nc(C2=NOCC(c3cc4c(F)cccc4o3)N2)ccc1-n1cnc(C)c1] | (+)-5-(4-fluorobenzofuran-2-yl)-3-(6-methoxy-5-(4-methyl-1H-imidazol-1-yl)pyridin-2-yl)-5,6-dihydro-4H-1,2,4-oxadiazine |
| 99B | 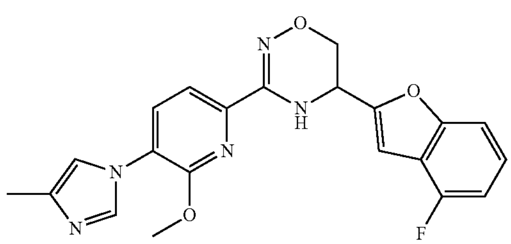 | (−)-5-(4-fluorobenzofuran-2-yl)-3-(6-methoxy-5-(4-methyl-1H-imidazol-1-yl)pyridin-2-yl)-5,6-dihydro-4H-1,2,4-oxadiazine |
| 101A | 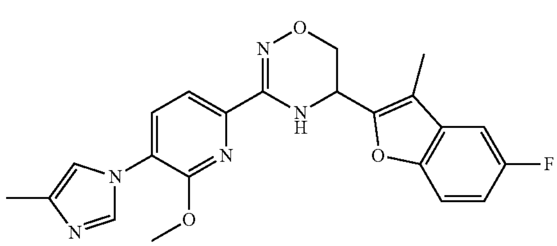 [SMILES: COc1nc(C2=NOCC(c3oc4ccc(F)cc4c3C)N2)ccc1-n1cnc(C)c1] | (−)-5-(5-fluoro-3-methylbenzofuran-2-yl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
| --- | --- | --- |
| 101B | 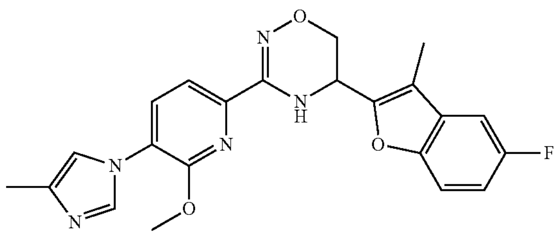 [SMILES: COc1nc(C2=NOCC(c3oc4ccc(F)cc4c3C)N2)ccc1-n1cnc(C)c1] | (+)-5-(5-fluoro-3-methylbenzofuran-2-yl)-3-(6-methoxy-5-(4-methyl-1H-imidazol-1-yl)pyridin-2-yl)-5,6-dihydro-4H-1,2,4-oxadiazine |
| 104A | 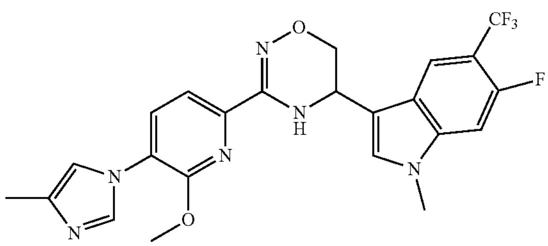 [SMILES: COc1nc(C2=NOCC(c3cn(C)c4cc(F)c(C(F)(F)F)cc34)N2)ccc1-n1cnc(C)c1] | (−)-5-(6-fluoro-1-methyl-5-(trifluoromethyl)-1H-indol-3-yl)-3-(6-methoxy-5-(4-methyl-1H-imidazol-1-yl)pyridin-2-yl)-5,6-dihydro-4H-1,2,4-oxadiazine |
| 104B | 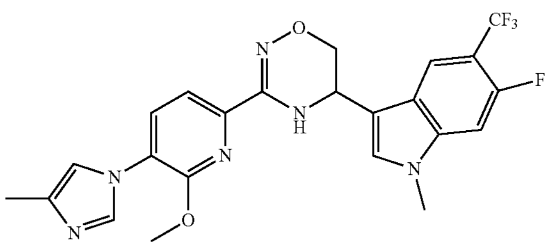 [SMILES: COc1nc(C2=NOCC(c3cn(C)c4cc(F)c(C(F)(F)F)cc34)N2)ccc1-n1cnc(C)c1] | (+)-5-(6-fluoro-1-methyl-5-(trifluoromethyl)-1H-indol-3-yl)-3-(6-methoxy-5-(4-methyl-1H-imidazol-1-yl)pyridin-2-yl)-5,6-dihydro-4H-1,2,4-oxadiazine |
| 106A | 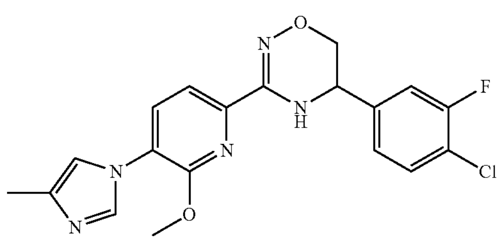 [SMILES: COc1nc(C2=NOCC(c3ccc(Cl)c(F)c3)N2)ccc1-n1cnc(C)c1] | (−)-5-(4-chloro-3-fluorophenyl)-3-(6-methoxy-5-(4-methyl-1H-imidazol-1-yl)pyridin-2-yl)-5,6-dihydro-4H-1,2,4-oxadiazine |
| 106B | 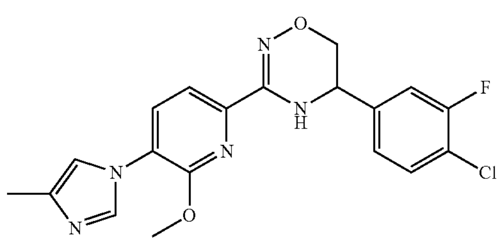 [SMILES: COc1nc(C2=NOCC(c3ccc(F)c(Cl)c3)N2)ccc1-n1cnc(C)c1] | (+)-5-(4-chloro-3-fluorophenyl)-3-(6-methoxy-5-(4-methyl-1H-imidazol-1-yl)pyridin-2-yl)-5,6-dihydro-4H-1,2,4-oxadiazine |
| 108A | 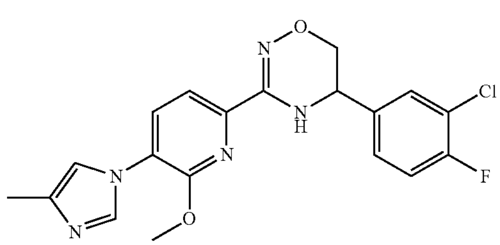 [SMILES: COc1nc(C2=NOCC(c3ccc(F)c(Cl)c3)N2)ccc1-n1cnc(C)c1] | (−)-5-(3-chloro-4-fluorophenyl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 108B | 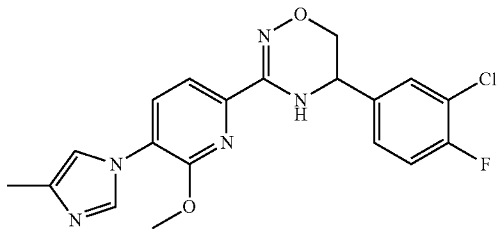 | (+)-5-(3-chloro-4-fluorophenyl)-3-(6-methoxy-5-(4-methyl-1H-imidazol-1-yl)pyridin-2-yl)-5,6-dihydro-4H-1,2,4-oxadiazine |
| 111A | 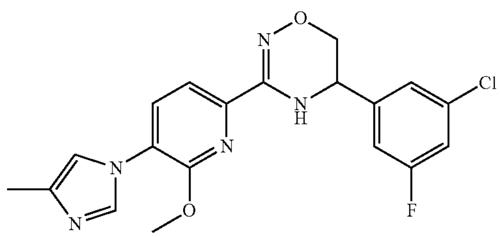 [SMILES: COc1nc(C2=NOCC(c3cc(F)cc(Cl)c3)N2)ccc1-n1cnc(C)c1] | (−)-5-(3-chloro-5-fluorophenyl)-3-(6-methoxy-5-(4-methyl-1H-imidazol-1-yl)pyridin-2-yl)-5,6-dihydro-4H-1,2,4-oxadiazine |
| 111B | 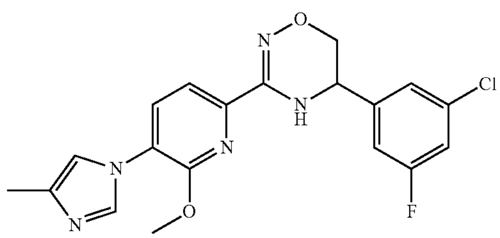 [SMILES: COc1nc(C2=NOCC(c3cc(F)cc(Cl)c3)N2)ccc1-n1cnc(C)c1] | (+)-5-(3-chloro-5-fluorophenyl)-3-(6-methoxy-5-(4-methyl-1H-imidazol-1-yl)pyridin-2-yl)-5,6-dihydro-4H-1,2,4-oxadiazine |
| 113A | 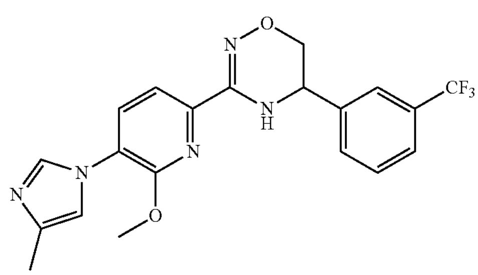 [SMILES: COc1nc(C2=NOCC(c3cccc(C(F)(F)F)c3)N2)ccc1-n1cnc(C)c1] | (−)-3-(6-methoxy-5-(4-methyl-1H-imidazol-1-yl)pyridin-2-yl)-5-(3-(trifluoromethyl)phenyl)-5,6-dihydro-4H-1,2,4-oxadiazine |
| 113B | 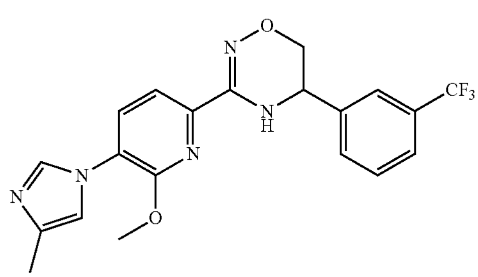 [SMILES: COc1nc(C2=NOCC(c3cccc(C(F)(F)F)c3)N2)ccc1-n1cnc(C)c1] | (+)-3-(6-methoxy-5-(4-methyl-1H-imidazol-1-yl)pyridin-2-yl)-5-(3-(trifluoromethyl)phenyl)-5,6-dihydro-4H-1,2,4-oxadiazine |
| 116A | 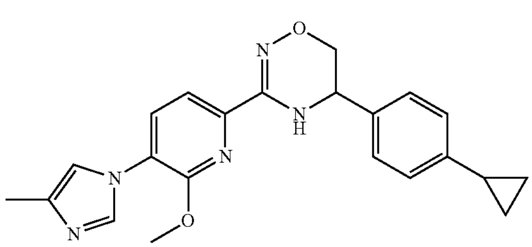 [SMILES: COc1nc(C2=NOCC(c3ccc(C4CC4)cc3)N2)ccc1-n1cnc(C)c1] | (−)-5-(4-cyclopropylphenyl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 116B | 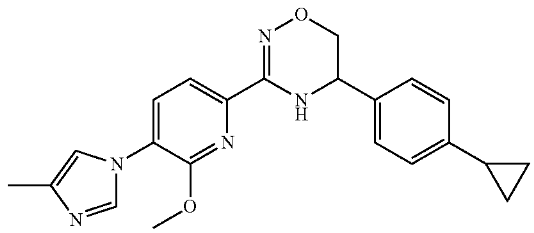 [SMILES: COc1nc(C2=NOCC(c3ccc(C4CC4)cc3)N2)ccc1-n1cnc(C)c1] | (+)-5-(4-cyclopropylphenyl)-3-(6-methoxy-5-(4-methyl-1H-imidazol-1-yl)pyridin-2-yl)-5,6-dihydro-4H-1,2,4-oxadiazine |
| 118A | 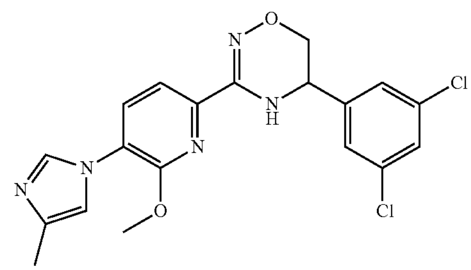 [SMILES: COc1nc(C2=NOCC(c3cc(Cl)cc(Cl)c3)N2)ccc1-n1cnc(C)c1] | (−)-5-(3,5-dichlorophenyl)-3-(6-methoxy-5-(4-methyl-1H-imidazol-1-yl)pyridin-2-yl)-5,6-dihydro-4H-1,2,4-oxadiazine |
| 118B | 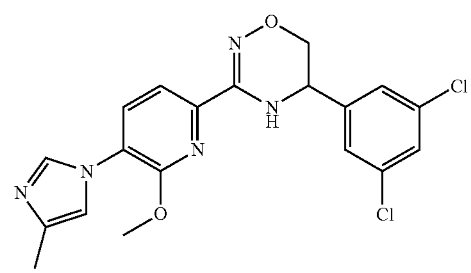 [SMILES: COc1nc(C2=NOCC(c3cc(Cl)cc(Cl)c3)N2)ccc1-n1cnc(C)c1] | (+)-5-(3,5-dichlorophenyl)-3-(6-methoxy-5-(4-methyl-1H-imidazol-1-yl)pyridin-2-yl)-5,6-dihydro-4H-1,2,4-oxadiazine |
| 121A | 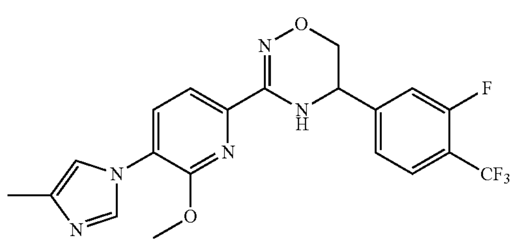 [SMILES: COc1nc(C2=NOCC(c3ccc(C(F)(F)F)c(F)c3)N2)ccc1-n1cnc(C)c1] | (−)-5-(3-fluoro-4-(trifluoromethyl)phenyl)-3-(6-methoxy-5-(4-methyl-1H-imidazol-1-yl)pyridin-2-yl)-5,6-dihydro-4H-1,2,4-oxadiazine |
| 121B | 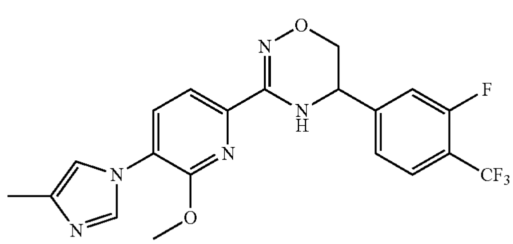 [SMILES: COc1nc(C2=NOCC(c3ccc(C(F)(F)F)c(F)c3)N2)ccc1-n1cnc(C)c1] | (+)-5-(3-fluoro-4-(trifluoromethyl)phenyl)-3-(6-methoxy-5-(4-methyl-1H-imidazol-1-yl)pyridin-2-yl)-5,6-dihydro-4H-1,2,4-oxadiazine |
| 124A | 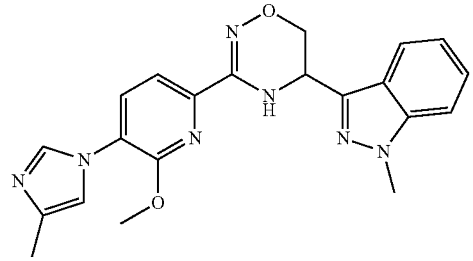 [SMILES: COc1nc(C2=NOCC(c3nn(C)c4ccccc34)N2)ccc1-n1cnc(C)c1] | (−)-3-(6-methoxy-5-(4-methyl-1H-imidazol-1-yl)pyridin-2-yl)-5-(1-methyl-1H-indazol-3-yl)-5,6-dihydro-4H-1,2,4-oxadiazine |

TABLE I-continued

Exemplary Oxadiazine Compounds of Formula (I)

| Compound of Example | Structure | Name |
| --- | --- | --- |
| 124B | 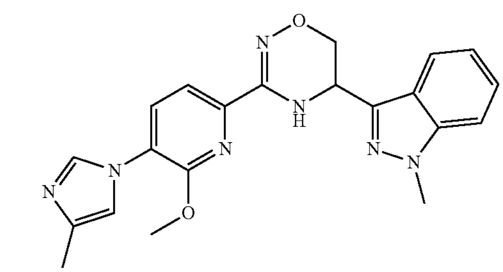 [SMILES: COc1nc(C2=NOCC(c3nn(C)c4ccccc34)N2)ccc1-n1cnc(C)c1] | (+)-3-(6-methoxy-5-(4-methyl-1H-imidazol-1-yl)pyridin-2-yl)-5-(1-methyl-1H-indazol-3-yl)-5,6-dihydro-4H-1,2,4-oxadiazine |
| 127A | 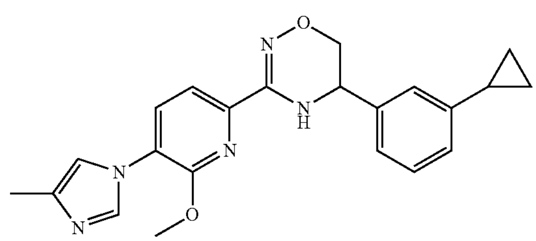 [SMILES: COc1nc(C2=NOCC(c3cccc(C4CC4)c3)N2)ccc1-n1cnc(C)c1] | (−)-5-(3-cyclopropylphenyl)-3-(6-methoxy-5-(4-methyl-1H-imidazol-1-yl)pyridin-2-yl)-5,6-dihydro-4H-1,2,4-oxadiazine |
| 127B | 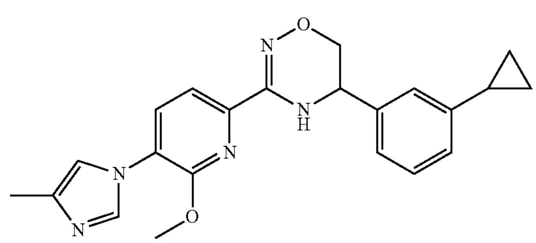 [SMILES: COc1nc(C2=NOCC(c3cccc(C4CC4)c3)N2)ccc1-n1cnc(C)c1] | (+)-5-(3-cyclopropylphenyl)-3-(6-methoxy-5-(4-methyl-1H-imidazol-1-yl)pyridin-2-yl)-5,6-dihydro-4H-1,2,4-oxadiazine |
| 129A | 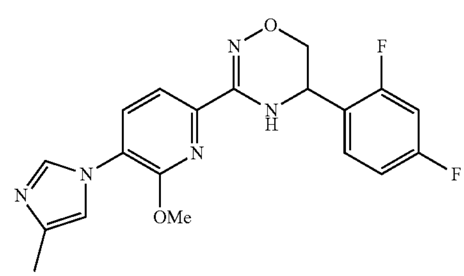 [SMILES: COc1nc(C2=NOCC(c3ccc(F)cc3F)N2)ccc1-n1cnc(C)c1] | 5-(2,4-difluorophenyl)-3-(6-methoxy-5-(4-methyl-1H-imidazol-1-yl)pyridin-2-yl)-5,6-dihydro-4H-1,2,4-oxadiazine |
| 129B | 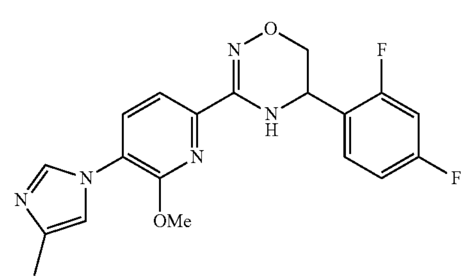 [SMILES: COc1nc(C2=NOCC(c3ccc(F)cc3F)N2)ccc1-n1cnc(C)c1] | 5-(2,4-difluorophenyl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 131A | 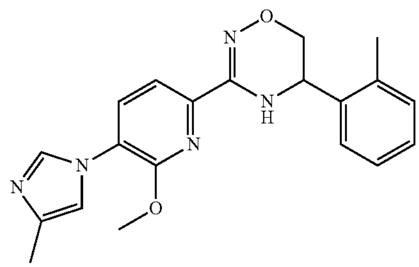 [SMILES: COc1nc(C2=NOCC(c3ccccc3C)N2)ccc1-n1cnc(C)c1] | (+)-3-(6-methoxy-5-(4-methyl-1H-imidazol-1-yl)pyridin-2-yl)-5-(o-tolyl)-5,6-dihydro-4H-1,2,4-oxadiazine |
| 131B | 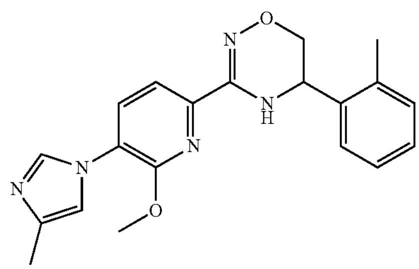 [SMILES: COc1nc(C2=NOCC(c3ccccc3C)N2)ccc1-n1cnc(C)c1] | (−)-3-(6-methoxy-5-(4-methyl-1H-imidazol-1-yl)pyridin-2-yl)-5-(o-tolyl)-5,6-dihydro-4H-1,2,4-oxadiazine |
| 133A | 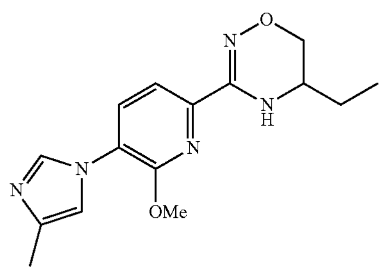 [SMILES: CCC1CON=C(c2ccc(-n3cnc(C)c3)c(OC)n2)N1] | 5-ethyl-3-(6-methoxy-5-(4-methyl-1H-imidazol-1-yl)pyridin-2-yl)-5,6-dihydro-4H-1,2,4-oxadiazine |
| 133B | 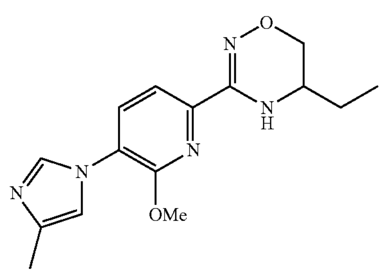 [SMILES: CCC1CON=C(c2ccc(-n3cnc(C)c3)c(OC)n2)N1] | 5-ethyl-3-(6-methoxy-5-(4-methyl-1H-imidazol-1-yl)pyridin-2-yl)-5,6-dihydro-4H-1,2,4-oxadiazine |
| 134A | 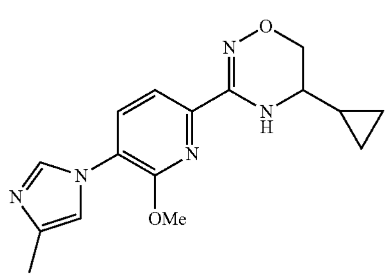 [SMILES: COc1nc(C2=NOCC(C3CC3)N2)ccc1-n1cnc(C)c1] | 5-cyclopropyl-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 134B | 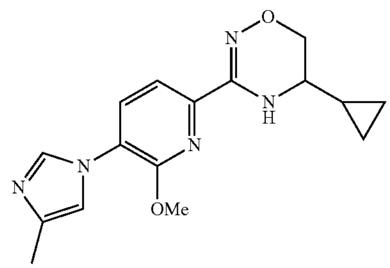 [SMILES: COc1nc(C2=NOCC(C3CC3)N2)ccc1-n1cnc(C)c1] | 5-cyclopropyl-3-(6-methoxy-5-(4-methyl-1H-imidazol-1-yl)pyridin-2-yl)-5,6-dihydro-4H-1,2,4-oxadiazine |
| 136A | 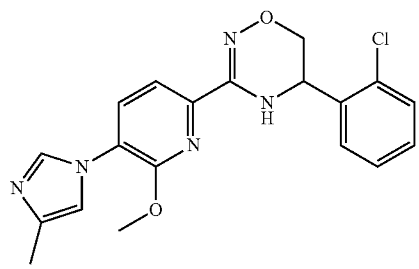 [SMILES: COc1nc(C2=NOCC(c3ccccc3Cl)N2)ccc1-n1cnc(C)c1] | 5-(2-chlorophenyl)-3-(6-methoxy-5-(4-methyl-1H-imidazol-1-yl)pyridin-2-yl)-5,6-dihydro-4H-1,2,4-oxadiazine |
| 136B | 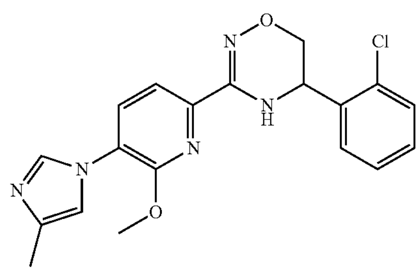 [SMILES: COc1nc(C2=NOCC(c3ccccc3Cl)N2)ccc1-n1cnc(C)c1] | 5-(2-chlorophenyl)-3-(6-methoxy-5-(4-methyl-1H-imidazol-1-yl)pyridin-2-yl)-5,6-dihydro-4H-1,2,4-oxadiazine |
| 139A | 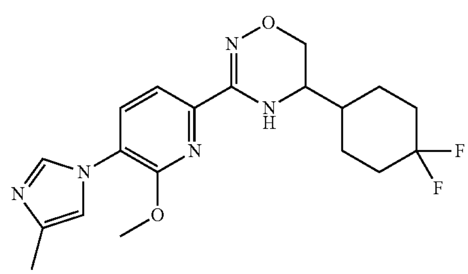 [SMILES: COc1nc(C2=NOCC(C3CCC(F)(F)CC3)N2)ccc1-n1cnc(C)c1] | (−)-5-(4,4-difluorocyclohexyl)-3-(6-methoxy-5-(4-methyl-1H-imidazol-1-yl)pyridin-2-yl)-5,6-dihydro-4H-1,2,4-oxadiazine |
| 139B | 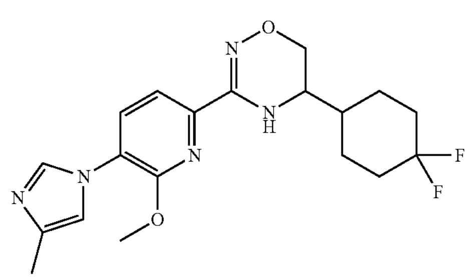 [SMILES: COc1nc(C2=NOCC(C3CCC(F)(F)CC3)N2)ccc1-n1cnc(C)c1] | (+)-5-(4, 4-difluorocyclohexyl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 141A | 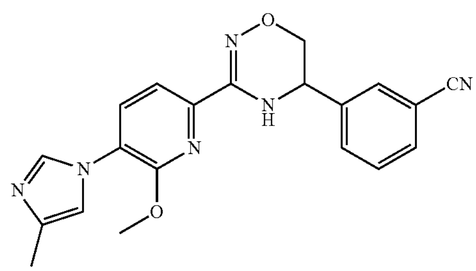 [SMILES: COc1nc(C2=NOCC(c3cccc(C#N)c3)N2)ccc1-n1cnc(C)c1] | (−)-3-(3-(6-methoxy-5-(4-methyl-1H-imidazol-1-yl)pyridin-2-yl)-5,6-dihydro-4H-1,2,4-oxadiazin-5-yl)benzonitrile |
| 141B | 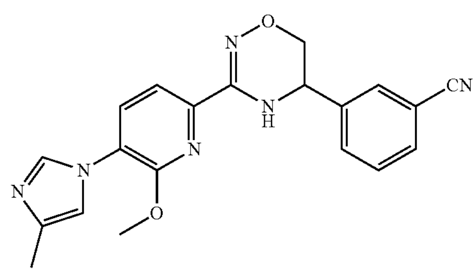 [SMILES: COc1nc(C2=NOCC(c3cccc(C#N)c3)N2)ccc1-n1cnc(C)c1] | (+)-3-(3-(6-methoxy-5-(4-methyl-1H-imidazol-1-yl)pyridin-2-yl)-5,6-dihydro-4H-1,2,4-oxadiazin-5-yl)benzonitrile |
| 143A | 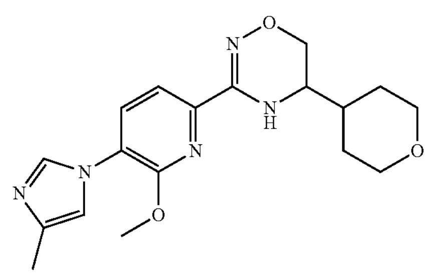 [SMILES: COc1nc(C2=NOCC(C3CCOCC3)N2)ccc1-n1cnc(C)c1] | (−)-3-(6-methoxy-5-(4-methyl-1H-imidazol-1-yl)pyridin-2-yl)-5-(tetrahydro-2H-pyran-4-yl)-5,6-dihydro-4H-1,2,4-oxadiazine |
| 143B | 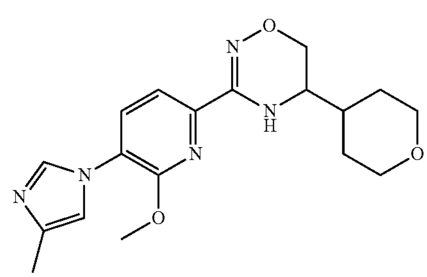 [SMILES: COc1nc(C2=NOCC(C3CCOCC3)N2)ccc1-n1cnc(C)c1] | (+)-3-(6-methoxy-5-(4-methyl-1H-imidazol-1-yl)pyridin-2-yl)-5-(tetrahydro-2H-pyran-4-yl)-5,6-dihydro-4H-1,2,4-oxadiazine |
| 145A | 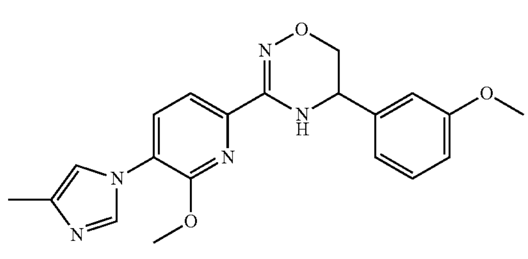 | (−)-3-(6-methoxy-5-(4-methyl-1H-imidazol-1-yl)pyridin-2-yl)-5-(3-methoxyphenyl)-5,6-dihydro-4H-1,2,4-oxadiazine |

TABLE I-continued

Exemplary Oxadiazine Compounds of Formula (I)

| Compound of Example | Structure | Name |
|---|---|---|
| 145B | 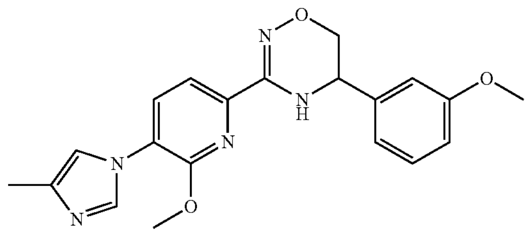 | (+)-3-(6-methoxy-5-(4-methyl-1H-imidazol-1-yl)pyridin-2-yl)-5-(3-methoxyphenyl)-5,6-dihydro-4H-1,2,4-oxadiazine |
| 147A | 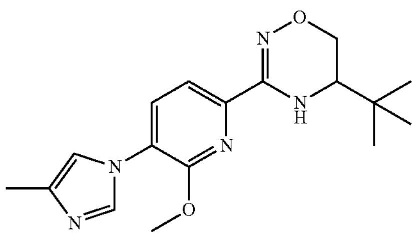 [SMILES: COc1nc(C2=NOCC(C(C)(C)C)N2)ccc1-n1cnc(C)c1] | (−)-5-(tert-butyl)-3-(6-methoxy-5-(4-methyl-1H-imidazol-1-yl)pyridin-2-yl)-5,6-dihydro-4H-1,2,4-oxadiazine |
| 147B | 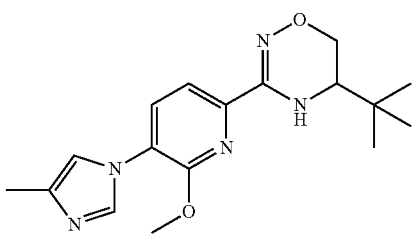 [SMILES: COc1nc(C2=NOCC(C(C)(C)C)N2)ccc1-n1cnc(C)c1] | (+)-5-(tert-butyl)-3-(6-methoxy-5-(4-methyl-1H-imidazol-1-yl)pyridin-2-yl)-5,6-dihydro-4H-1,2,4-oxadiazine |
| 149A | 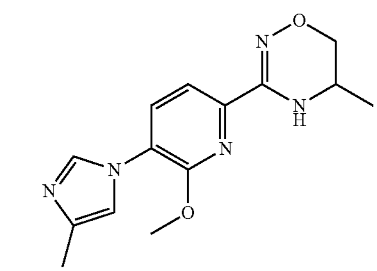 [SMILES: COc1nc(C2=NOCC(C)N2)ccc1-n1cnc(C)c1] | (+)-3-(6-methoxy-5-(4-methyl-1H-imidazol-1-yl)pyridin-2-yl)-5-methyl-5,6-dihydro-4H-1,2,4-oxadiazine |
| 149B | 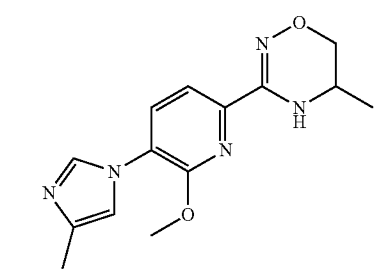 [SMILES: COc1nc(C2=NOCC(C)N2)ccc1-n1cnc(C)c1] | (−)-3-(6-methoxy-5-(4-methyl-1H-imidazol-1-yl)pyridin-2-yl)-5-methyl-5,6-dihydro-4H-1,2,4-oxadiazine |
| 151A | 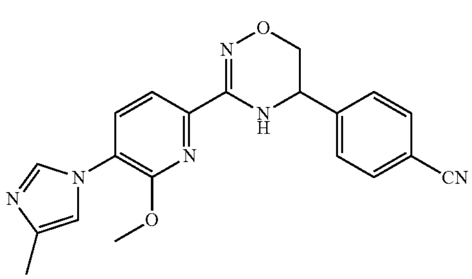 [SMILES: COc1nc(C2=NOCC(c3ccc(C#N)cc3)N2)ccc1-n1cnc(C)c1] | (−)-4-(3-(6-methoxy-5-(4-methyl-1H-imidazol-1-yl)pyridin-2-yl)-5,6-dihydro-4H-1,2,4-oxadiazin-5-yl)benzonitrile |

TABLE I-continued

Exemplary Oxadiazine Compounds of Formula (I)

| Compound of Example | Structure | Name |
|---|---|---|
| 151B | 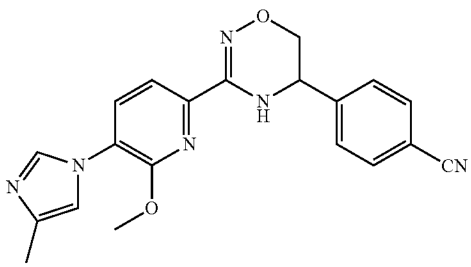 [SMILES: COc1nc(C2=NOCC(c3ccc(C#N)cc3)N2)ccc1-n1cnc(C)c1] | (+)-4-(3-(6-methoxy-5-(4-methyl-1H-imidazol-1-yl)pyridin-2-yl)-5,6-dihydro-4H-1,2,4-oxadiazin-5-yl)benzonitrile |
| 154A | 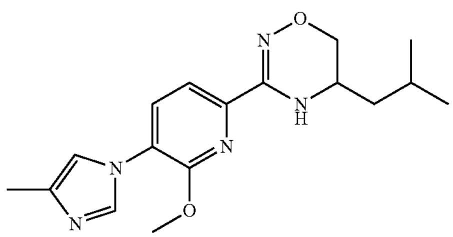 [SMILES: COc1nc(C2=NOCC(CC(C)C)N2)ccc1-n1cnc(C)c1] | (+)-5-isobutyl-3-(6-methoxy-5-(4-methyl-1H-imidazol-1-yl)pyridin-2-yl)-5,6-dihydro-4H-1,2,4-oxadiazine |
| 154B | 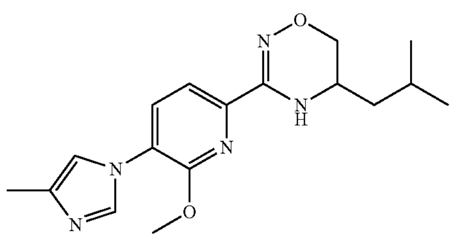 [SMILES: COc1nc(C2=NOCC(CC(C)C)N2)ccc1-n1cnc(C)c1] | (−)-5-isobutyl-3-(6-methoxy-5-(4-methyl-1H-imidazol-1-yl)pyridin-2-yl)-5,6-dihydro-4H-1,2,4-oxadiazine |
| 156A | 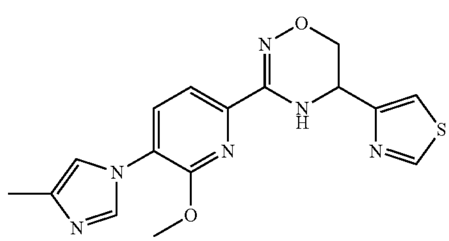 [SMILES: COc1nc(C2=NOCC(c3cscn3)N2)ccc1-n1cnc(C)c1] | (+)-3-(6-methoxy-5-(4-methyl-1H-imidazol-1-yl)pyridin-2-yl)-5-(thiazol-4-yl)-5,6-dihydro-4H-1,2,4-oxadiazine |
| 156B | 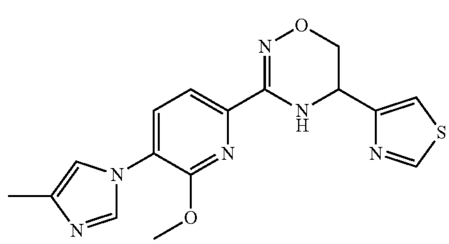 [SMILES: COc1nc(C2=NOCC(c3cscn3)N2)ccc1-n1cnc(C)c1] | (−)-3-(6-methoxy-5-(4-methyl-1H-imidazol-1-yl)pyridin-2-yl)-5-(thiazol-4-yl)-5,6-dihydro-4H-1,2,4-oxadiazine |
| 159A | 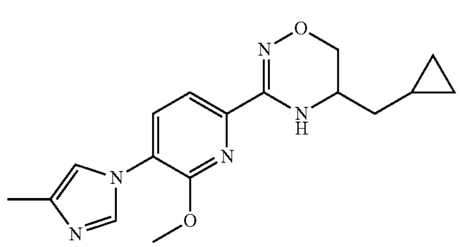 [SMILES: COc1nc(C2=NOCC(CC3CC3)N2)ccc1-n1cnc(C)c1] | 5-(cyclopropylmethyl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 159B | 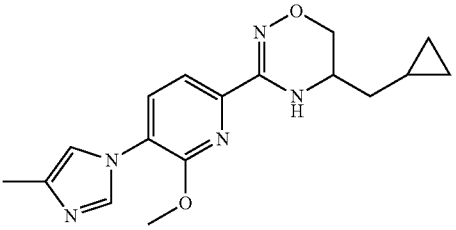 | 5-(cyclopropylmethyl)-3-(6-methoxy-5-(4-methyl-1H-imidazol-1-yl)pyridin-2-yl)-5,6-dihydro-4H-1,2,4-oxadiazine |
| 161A | 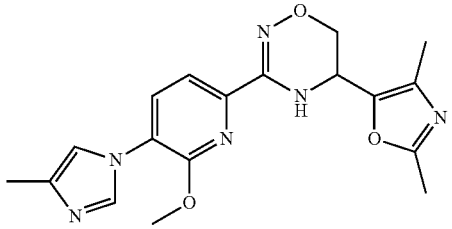 [SMILES: COc1nc(C2=NOCC(c3oc(C)nc3C)N2)ccc1-n1cnc(C)c1] | (−)-5-(2,4-dimethyloxazol-5-yl)-3-(6-methoxy-5-(4-methyl-1H-imidazol-1-yl)pyridin-2-yl)-5,6-dihydro-4H-1,2,4-oxadiazine |
| 161B | 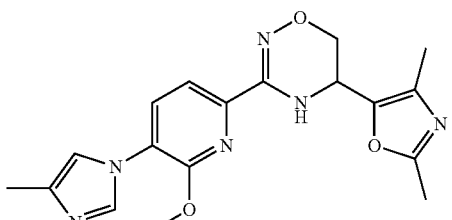 | (+)-5-(2,4-dimethyloxazol-5-yl)-3-(6-methoxy-5-(4-methyl-1H-imidazol-1-yl)pyridin-2-yl)-5,6-dihydro-4H-1,2,4-oxadiazine |
| 163A | 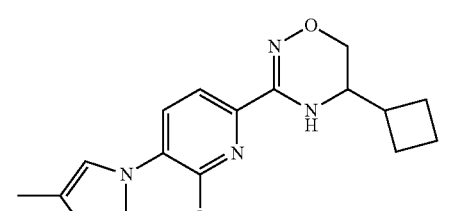 | (+)-5-cyclobutyl-3-(6-methoxy-5-(4-methyl-1H-imidazol-1-yl)pyridin-2-yl)-5,6-dihydro-4H-1,2,4-oxadiazine |
| 163B | 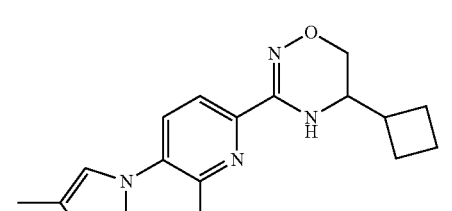 | (−)-5-cyclobutyl-3-(6-methoxy-5-(4-methyl-1H-imidazol-1-yl)pyridin-2-yl)-5,6-dihydro-4H-1,2,4-oxadiazine |
| 166A | 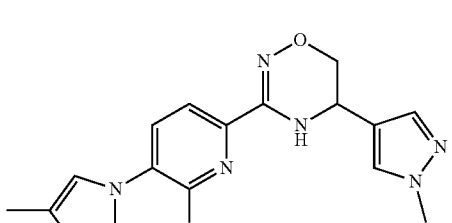 | (−)-3-(6-methoxy-5-(4-methyl-1H-imidazol-1-yl)pyridin-2-yl)-5-(1-methyl-1H-pyrazol-4-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 166B | 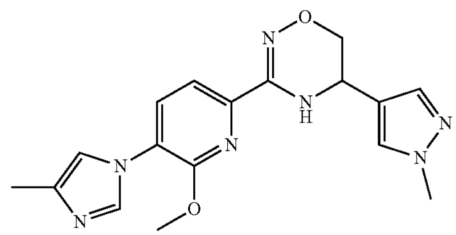 [SMILES: COc1nc(C2=NOCC(c3cnn(C)c3)N2)ccc1-n1cnc(C)c1] | (+)-3-(6-methoxy-5-(4-methyl-1H-imidazol-1-yl)pyridin-2-yl)-5-(1-methyl-1H-pyrazol-4-yl)-5,6-dihydro-4H-1,2,4-oxadiazine |
| 168A | 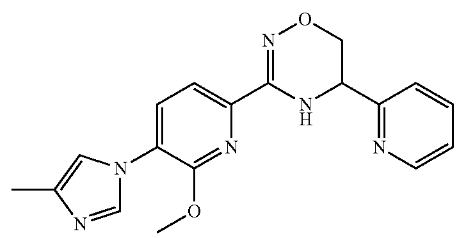 [SMILES: COc1nc(C2=NOCC(c3ccccn3)N2)ccc1-n1cnc(C)c1] | (+)-3-(6-methoxy-5-(4-methyl-1H-imidazol-1-yl)pyridin-2-yl)-5-(pyridin-2-yl)-5,6-dihydro-4H-1,2,4-oxadiazine |
| 168B | 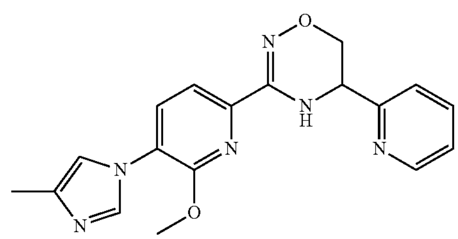 [SMILES: COc1nc(C2=NOCC(c3ccccn3)N2)ccc1-n1cnc(C)c1] | (−)-3-(6-methoxy-5-(4-methyl-1H-imidazol-1-yl)pyridin-2-yl)-5-(pyridin-2-yl)-5,6-dihydro-4H-1,2,4-oxadiazine |
| 171A | 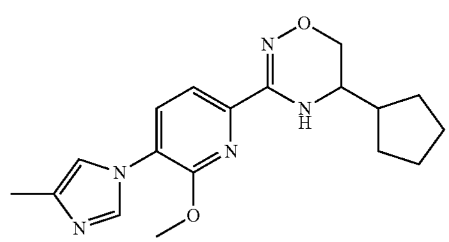 [SMILES: COc1nc(C2=NOCC(C3CCCC3)N2)ccc1-n1cnc(C)c1] | (+)-5-cyclopentyl-3-(6-methoxy-5-(4-methyl-1H-imidazol-1-yl)pyridin-2-yl)-5,6-dihydro-4H-1,2,4-oxadiazine |
| 171B | 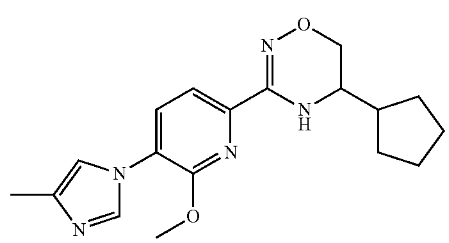 [SMILES: COc1nc(C2=NOCC(C3CCCC3)N2)ccc1-n1cnc(C)c1] | (−)-5-cyclopentyl-3-(6-methoxy-5-(4-methyl-1H-imidazol-1-yl)pyridin-2-yl)-5,6-dihydro-4H-1,2,4-oxadiazine |
| 174A | 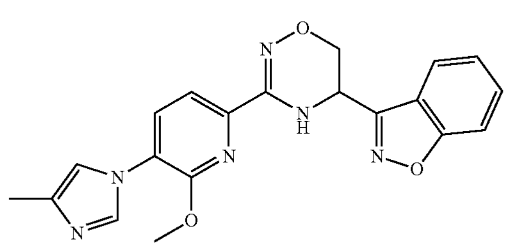 [SMILES: COc1nc(C2=NOCC(c3noc4ccccc34)N2)ccc1-n1cnc(C)c1] | 3-(3-(6-methoxy-5-(4-methyl-1H-imidazol-1-yl)pyridin-2-yl)-5,6-dihydro-4H-1,2,4-oxadiazin-5-yl)benzo[d]isoxazole |

TABLE I-continued

Exemplary Oxadiazine Compounds of Formula (I)

| Compound of Example | Structure | Name |
|---|---|---|
| 174B | 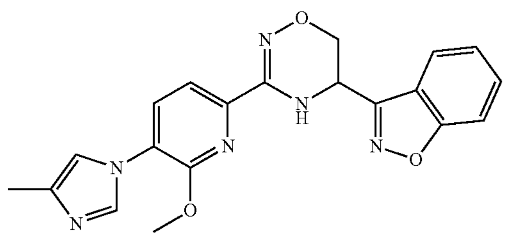 [SMILES: COc1nc(C2=NOCC(c3noc4ccccc34)N2)ccc1-n1cnc(C)c1] | 3-(3-(6-methoxy-5-(4-methyl-1H-imidazol-1-yl)pyridin-2-yl)-5,6-dihydro-4H-1,2,4-oxadiazin-5-yl)benzo[d]isoxazole |
| 177A | 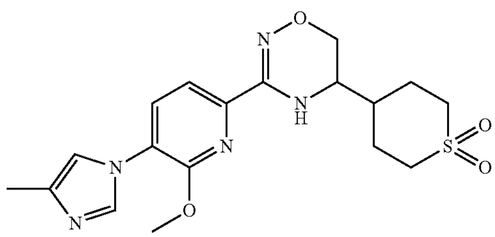 [SMILES: COc1nc(C2=NOCC(C3CCS(=O)(=O)CC3)N2)ccc1-n1cnc(C)c1] | (+)-4-(3-(6-methoxy-5-(4-methyl-1H-imidazol-1-yl)pyridin-2-yl)-5,6-dihydro-4H-1,2,4-oxadiazin-5-yl)tetrahydro-2H-thiopyran 1,1-dioxide |
| 177B | 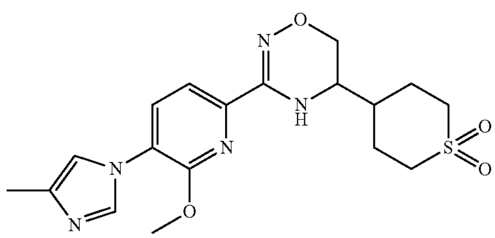 [SMILES: COc1nc(C2=NOCC(C3CCS(=O)(=O)CC3)N2)ccc1-n1cnc(C)c1] | (−)-4-(3-(6-methoxy-5-(4-methyl-1H-imidazol-1-yl)pyridin-2-yl)-5,6-dihydro-4H-1,2,4-oxadiazin-5-yl)tetrahydro-2H-thiopyran 1,1-dioxide |
| 180A | 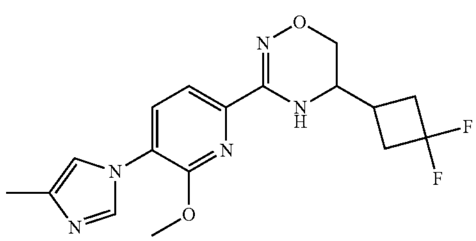 [SMILES: COc1nc(C2=NOCC(C3CC(F)(F)C3)N2)ccc1-n1cnc(C)c1] | (−)-5-(3,3-difluorocyclobutyl)-3-(6-methoxy-5-(4-methyl-1H-imidazol-1-yl)pyridin-2-yl)-5,6-dihydro-4H-1,2,4-oxadiazine |
| 180B | 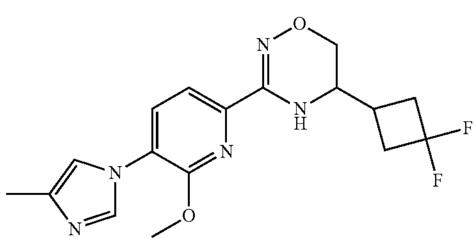 [SMILES: COc1nc(C2=NOCC(C3CC(F)(F)C3)N2)ccc1-n1cnc(C)c1] | (+)-5-(3,3-difluorocyclobutyl)-3-(6-methoxy-5-(4-methyl-1H-imidazol-1-yl)pyridin-2-yl)-5,6-dihydro-4H-1,2,4-oxadiazine |
| 183A | 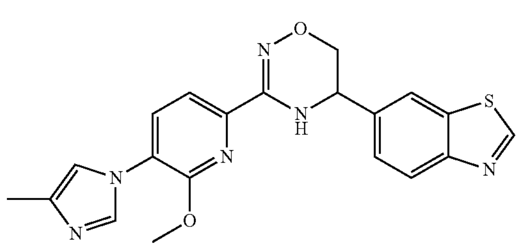 [SMILES: COc1nc(C2=NOCC(c3ccc4ncsc4c3)N2)ccc1-n1cnc(C)c1] | (−)-5-(benzo[d]thiazol-6-yl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
| --- | --- | --- |
| 183B | 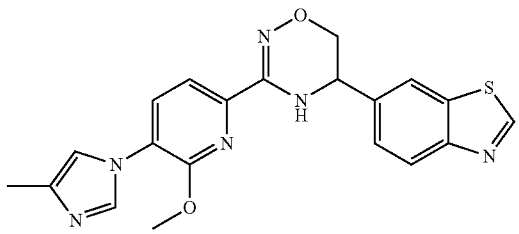 [SMILES: COc1nc(C2=NOCC(c3ccc4ncsc4c3)N2)ccc1-n1cnc(C)c1] | (+)-5-(benzo[d]thiazol-6-yl)-3-(6-methoxy-5-(4-methyl-1H-imidazol-1-yl)pyridin-2-yl)-5,6-dihydro-4H-1,2,4-oxadiazine |
| 186A | 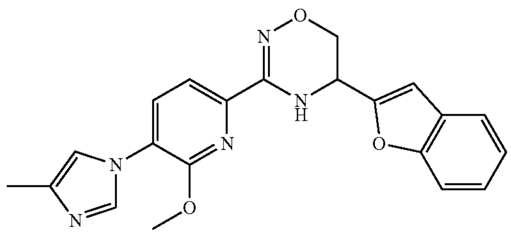 [SMILES: COc1nc(C2=NOCC(c3cc4ccccc4o3)N2)ccc1-n1cnc(C)c1] | (−)-5-(benzofuran-2-yl)-3-(6-methoxy-5-(4-methyl-1H-imidazol-1-yl)pyridin-2-yl)-5,6-dihydro-4H-1,2,4-oxadiazine |
| 186B | 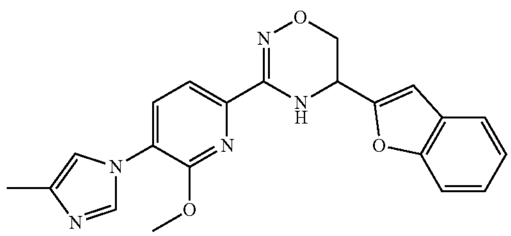 | (+)-5-(benzofuran-2-yl)-3-(6-methoxy-5-(4-methyl-1H-imidazol-1-yl)pyridin-2-yl)-5,6-dihydro-4H-1,2,4-oxadiazine |
| 189A | 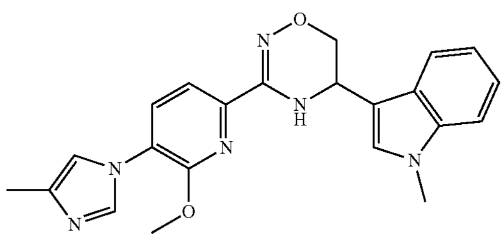 | (+)-3-(6-methoxy-5-(4-methyl-1H-imidazol-1-yl)pyridin-2-yl)-5-(1-methyl-1H-indol-3-yl)-5,6-dihydro-4H-1,2,4-oxadiazine |
| 189B | 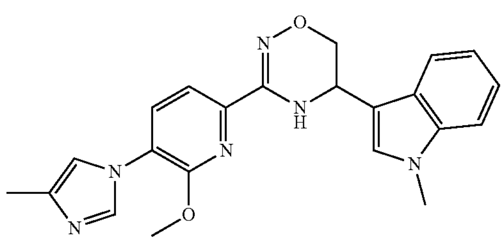 | (−)-3-(6-methoxy-5-(4-methyl-1H-imidazol-1-yl)pyridin-2-yl)-5-(1-methyl-1H-idol-3-yl)-5,6-dihydro-4H-1,2,4-oxadiazine |
| 190A | 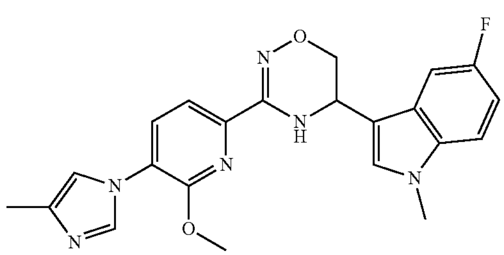 [SMILES: COc1nc(C2=NOCC(c3cn(C)c4ccc(F)cc34)N2)ccc1-n1cnc(C)c1] | (−)-5-(5-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 190B | 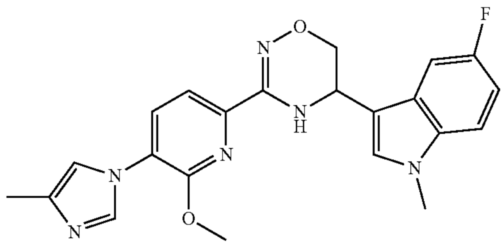 [SMILES: COc1nc(C2=NOCC(c3cn(C)c4ccc(F)cc34)N2)ccc1-n1cnc(C)c1] | (+)-5-(5-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 191A | 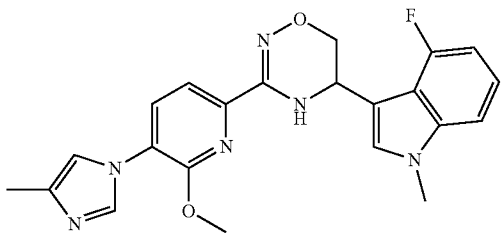 [SMILES: COc1nc(C2=NOCC(c3cn(C)c4cccc(F)c34)N2)ccc1-n1cnc(C)c1] | (+)-5-(4-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 191B | 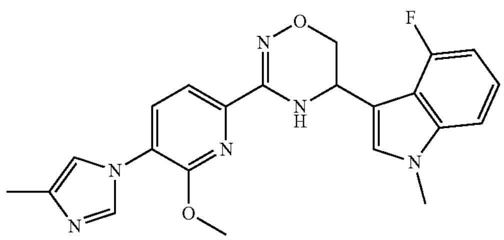 [SMILES: COc1nc(C2=NOCC(c3cn(C)c4cccc(F)c34)N2)ccc1-n1cnc(C)c1] | (−)-5-(4-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 192A | 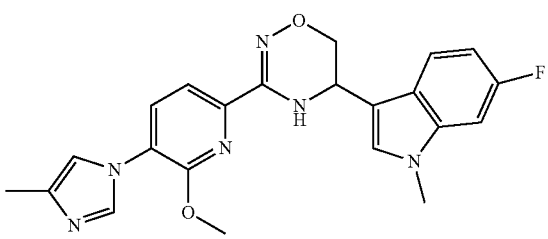 [SMILES: COc1nc(C2=NOCC(c3cn(C)c4cc(F)ccc34)N2)ccc1-n1cnc(C)c1] | (−)-5-(6-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 192B | 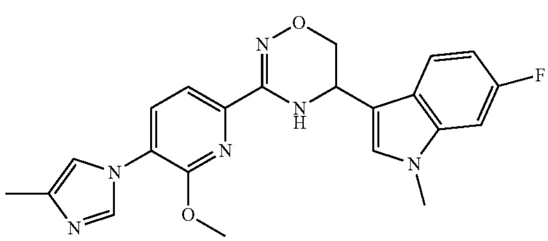 [SMILES: COc1nc(C2=NOCC(c3cn(C)c4cc(F)ccc34)N2)ccc1-n1cnc(C)c1] | (+)-5-(6-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 193A | 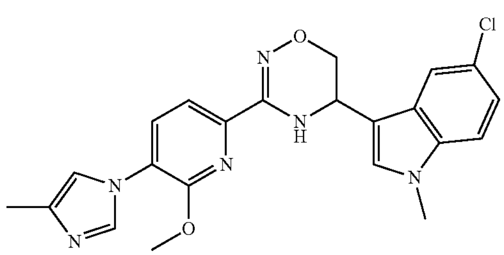 [SMILES: COc1nc(C2=NOCC(c3cn(C)c4ccc(Cl)cc34)N2)ccc1-n1cnc(C)c1] | (−)-5-(5-chloro-1-methyl-1H-indol-3-yl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 193B | 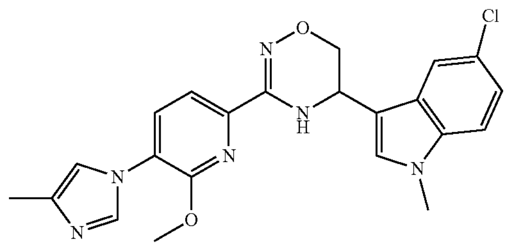 [SMILES: COc1nc(C2=NOCC(c3cn(C)c4ccc(Cl)cc34)N2)ccc1-n1cnc(C)c1] | (+)-5-(5-chloro-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 194A | 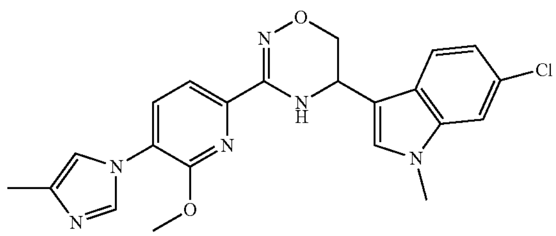 [SMILES: COc1nc(C2=NOCC(c3cn(C)c4cc(Cl)ccc34)N2)ccc1-n1cnc(C)c1] | (+)-5-(6-chloro-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 194B | 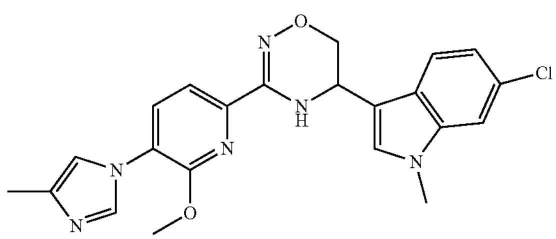 [SMILES: COc1nc(C2=NOCC(c3cn(C)c4cc(Cl)ccc34)N2)ccc1-n1cnc(C)c1] | (−)-5-(6-chloro-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 195A | 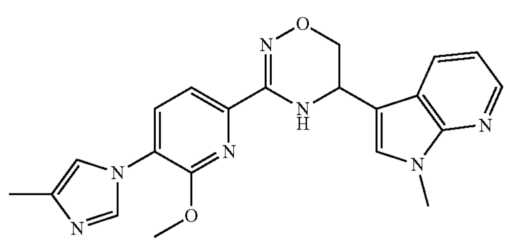 [SMILES: COc1nc(C2=NOCC(c3cn(C)c4ncccc34)N2)ccc1-n1cnc(C)c1] | (−)-3-(6-methoxy-5-(4-methyl-1H-imidazol-1-yl)pyridin-2-yl)-5-(1-methyl-1H-pyrrolo[2,3-b]pyridin-3-yl)-5,6-dihydro-4H-1,2,4-oxadiazine |
| 195B | 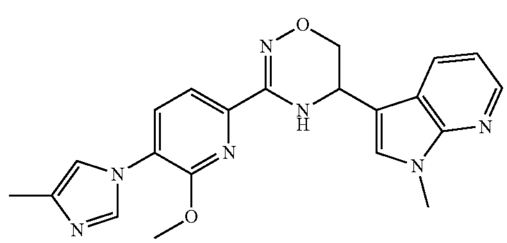 [SMILES: COc1nc(C2=NOCC(c3cn(C)c4ncccc34)N2)ccc1-n1cnc(C)c1] | (+)-3-(6-methoxy-5-(4-methyl-1H-imidazol-1-yl)pyridin-2-yl)-5-(1-methyl-1H-pyrrolo[2,3-b]pyridin-3-yl)-5,6-dihydro-4H-1,2,4-oxadiazine |
| 196A | 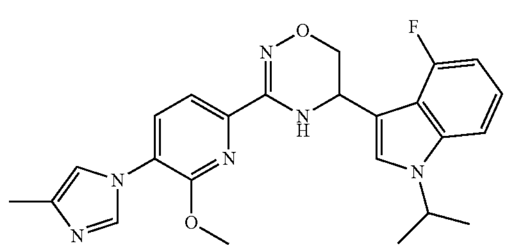 [SMILES: COc1nc(C2=NOCC(c3cn(C(C)C)c4cccc(F)c34)N2)ccc1-n1cnc(C)c1] | (+)-5-(4-fluoro-1-isopropyl-1H-indol-3-yl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 196B | 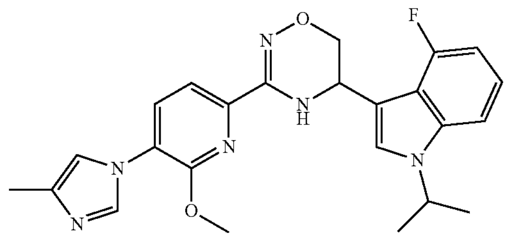 [SMILES: COc1nc(C2=NOCC(c3cn(C(C)C)c4cccc(F)c34)N2)ccc1-n1cnc(C)c1] | (−)-5-(4-fluoro-1-isopropyl-1H-indol-3-yl)-3-(6-methoxy-5-(4-methyl-1H-imidazol-1-yl)pyridin-2-yl)-5,6-dihydro-4H-1,2,4-oxadiazine |
| 197A | 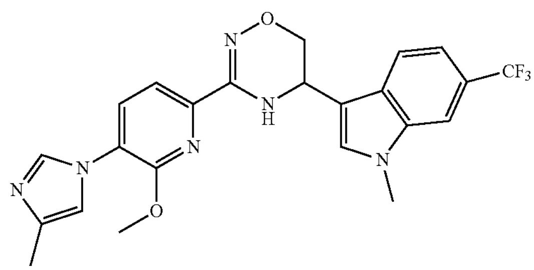 [SMILES: COc1nc(C2=NOCC(c3cn(C)c4cc(C(F)(F)F)ccc34)N2)ccc1-n1cnc(C)c1] | (+)-3-(6-methoxy-5-(4-methyl-1H-imidazol-1-yl)pyridin-2-yl)-5-(1-methyl-6-(trifluoromethyl)-1H-indol-3-yl)-5,6-dihydro-4H-1,2,4-oxadiazine |
| 197B | 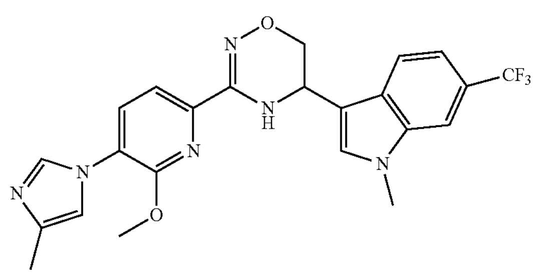 [SMILES: COc1nc(C2=NOCC(c3cn(C)c4cc(C(F)(F)F)ccc34)N2)ccc1-n1cnc(C)c1] | (−)-3-(6-methoxy-5-(4-methyl-1H-imidazol-1-yl)pyridin-2-yl)-5-(1-methyl-6-(trifluoromethyl)-1H-indol-3-yl)-5,6-dihydro-4H-1,2,4-oxadiazine |
| 200A | 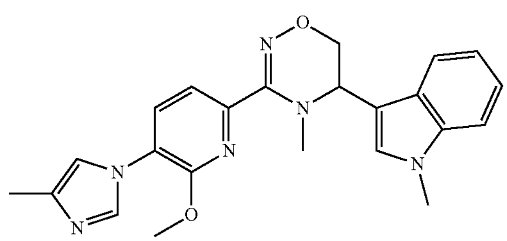 [SMILES: COc1nc(C2=NOCC(c3cn(C)c4ccccc34)N2C)ccc1-n1cnc(C)c1] | (+)-3-(6-methoxy-5-(4-methyl-1H-imidazol-1-yl)pyridin-2-yl)-4-methyl-5-(1-methyl-1H-indol-3-yl)-5,6-dihydro-4H-1,2,4-oxadiazine |
| 200B | 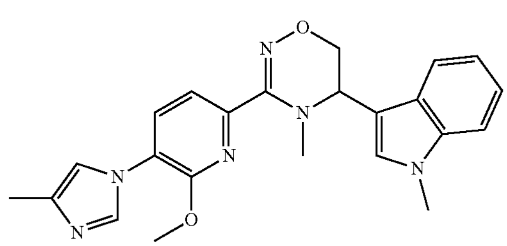 [SMILES: COc1nc(C2=NOCC(c3cn(C)c4ccccc34)N2C)ccc1-n1cnc(C)c1] | (−)-3-(6-methoxy-5-(4-methyl-1H-imidazol-1-yl)pyridin-2-yl)-4-methyl-5-(1-methyl-1H-indol-3-yl)-5,6-dihydro-4H-1,2,4-oxadiazine |
| 203A | 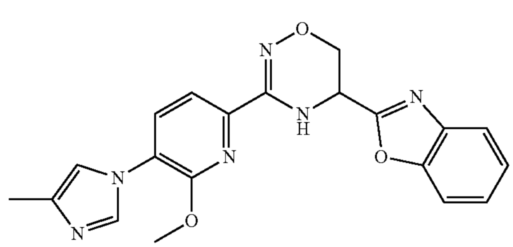 | (−)-2-(3-(6-methoxy-5-(4-methyl-1H-imidazol-1-yl)pyridin-2-yl)-5,6-dihydro-4H-1,2,4-oxadiazin-5-yl)benzo[d]oxazole |

TABLE I-continued

Exemplary Oxadiazine Compounds of Formula (I)

| Compound of Example | Structure | Name |
|---|---|---|
| 203B | 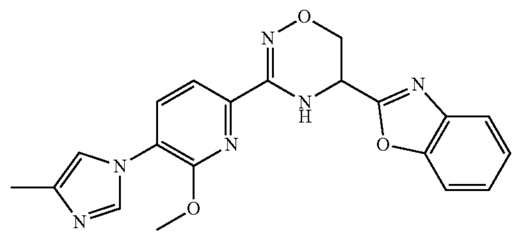 | (+)-2-(3-(6-methoxy-5-(4-methyl-1H-imidazol-1-yl)pyridin-2-yl)-5,6-dihydro-4H-1,2,4-oxadiazin-5-yl)benzo[d]oxazole |
| 205A | 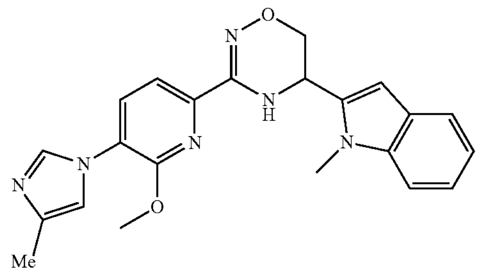 [SMILES: COc1nc(C2=NOCC(c3cc4ccccc4n3C)N2)ccc1-n1cnc(C)c1] | (−)-3-(6-methoxy-5-(4-methyl-1H-imidazol-1-yl)pyridin-2-yl)-5-(1-methyl-1H-indol-2-yl)-5,6-dihydro-4H-1,2,4-oxadiazine |
| 205B | 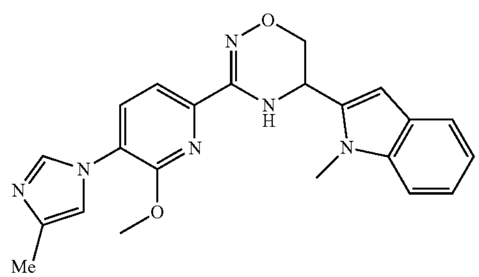 [SMILES: COc1nc(C2=NOCC(c3cc4ccccc4n3C)N2)ccc1-n1cnc(C)c1] | (+)-3-(6-methoxy-5-(4-methyl-1H-imidazol-1-yl)pyridin-2-yl)-5-(1-methyl-1H-indol-2-yl)-5,6-dihydro-4H-1,2,4-oxadiazine |
| 206A | 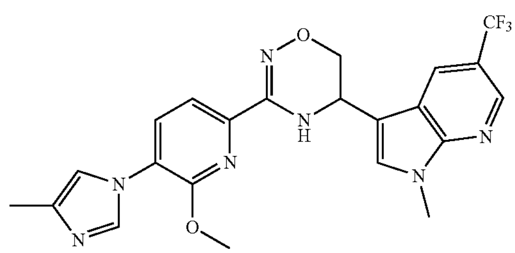 [SMILES: COc1nc(C2=NOCC(c3cn(C)c4ncc(C(F)(F)F)cc34)N2)ccc1-n1cnc(C)c1] | (−)-3-(6-methoxy-5-(4-methyl-1H-imidazol-1-yl)pyridin-2-yl)-5-(1-methyl-5-(trifluoromethyl)-1H-pyrrolo[2,3-b]pyridin-3-yl)-5,6-dihydro-4H-1,2,4-oxadiazine |
| 206B | 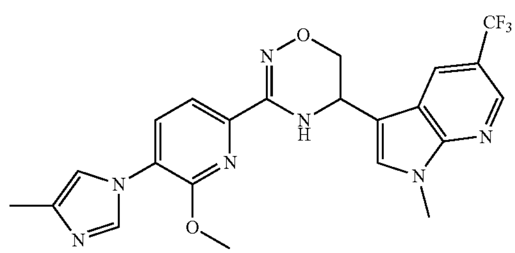 [SMILES: COc1nc(C2=NOCC(c3cn(C)c4ncc(C(F)(F)F)cc34)N2)ccc1-n1cnc(C)c1] | (+)-3-(6-methoxy-5-(4-methyl-1H-imidazol-1-yl)pyridin-2-yl)-5-(1-methyl-5-(trifluoromethyl)-1H-pyrrolo[2,3-b]pyridin-3-yl)-5,6-dihydro-4H-1,2,4-oxadiazine |
| 208A | 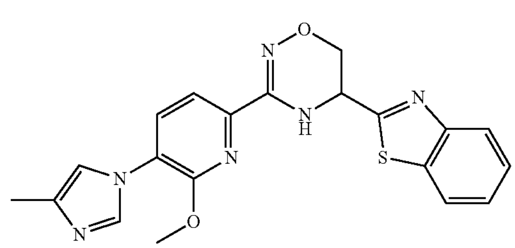 | (−)-5-(benzo[d]thiazol-2-yl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 208B | 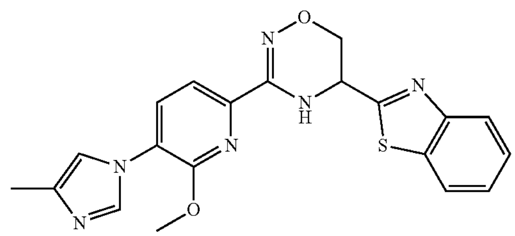 | (+)-5-(benzo[d]thiazol-2-yl)-3-(6-methoxy-5-(4-methyl-1H-imidazol-1-yl)pyridin-2-yl)-5,6-dihydro-4H-1,2,4-oxadiazine |
| 210 | 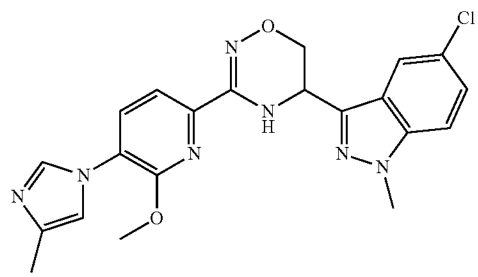 [SMILES: COc1nc(C2=NOCC(c3nn(C)c4ccc(Cl)cc34)N2)ccc1-n1cnc(C)c1] | (+)-3-(6-methoxy-5-(4-methyl-1H-imidazol-1-yl)pyridin-2-yl)-5-(1-methyl-5-(chloro)-1H-indazol-3-yl)-5,6-dihydro-4H-1,2,4-oxadiazine |
| 211 | 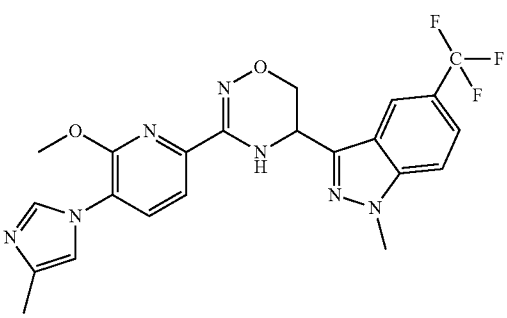 [SMILES: COc1nc(C2=NOCC(c3nn(C)c4ccc(C(F)(F)F)cc34)N2)ccc1-n1cnc(C)c1] | (+)-3-(6-methoxy-5-(4-methyl-1H-imidazol-1-yl)pyridin-2-yl)-5-(1-methyl-5-(trifluoromethyl)-1H-indazol-3-yl)-5,6-dihydro-4H-1,2,4-oxadiazine |
| 213 | 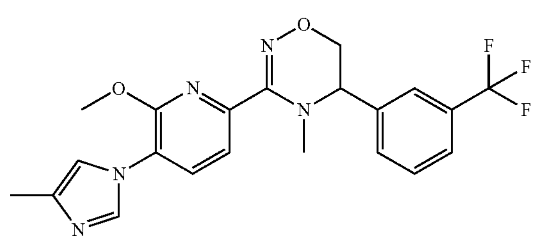 [SMILES: COc1nc(C2=NOCC(c3cccc(C(F)(F)F)c3)N2C)ccc1-n1cnc(C)c1] | 3-(6-methoxy-5-(4-methyl-1H-imidazol-1-yl)pyridin-2-yl)-4-methyl-5-(3-(trifluoromethyl)phenyl)-5,6-dihydro-4H-1,2,4-oxadiazine |
| 215A | 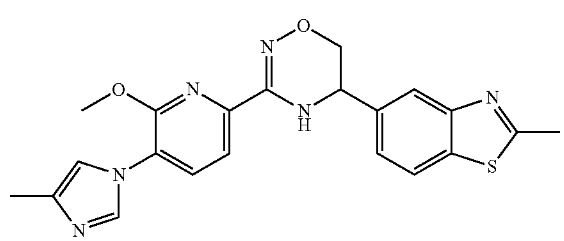 | (−)-3-(6-methoxy-5-(4-methyl-1H-imidazol-1-yl)pyridin-2-yl)-5-(2-methylbenzo[d]thiazol-5-yl)-5,6-dihydro-4H-1,2,4-oxadiazine |
| 215B | 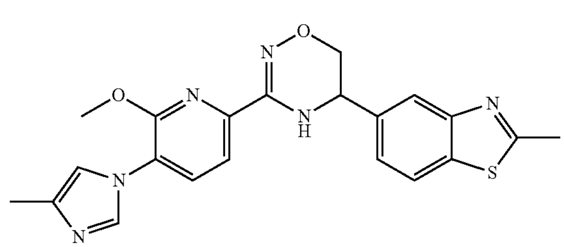 | (+)-3-(6-methoxy-5-(4-methyl-1H-imidazol-1-yl)pyridin-2-yl)-5-(2-methylbenzo[d]thiazol-5-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 216A | 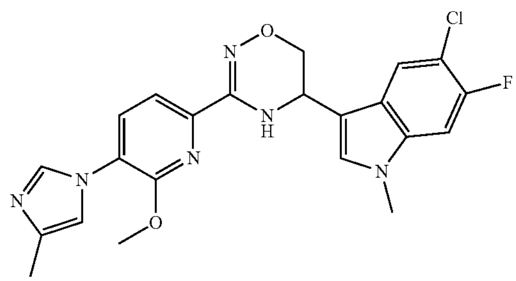 [SMILES: COc1nc(C2=NOCC(c3cn(C)c4cc(F)c(Cl)cc34)N2)ccc1-n1cnc(C)c1] | (−)-5-(5-chloro-6-fluoro-1-methyl-1H-indol-3-yl)-3-(6-melhoxy-5-(4-methyl-1H-imidazol-1-yl)pyridin-2-yl)-5,6-dihydro-4H-1,2,4-oxadiazine |
| 216B | 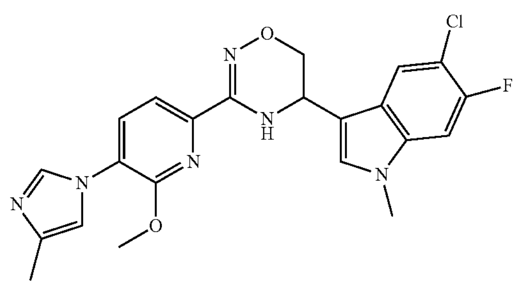 | (+)-5-(5-chloro-6-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 218A | 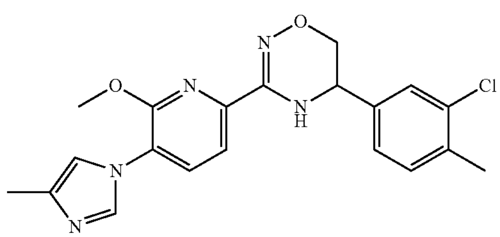 [SMILES: COc1nc(C2=NOCC(c3ccc(C)c(Cl)c3)N2)ccc1-n1cnc(C)c1] | (−)-5-(3-chloro-4-methylphenyl)-3-(6-methoxy-5-(4-methyl-1H-imidazol-1-yl)pyridin-2-yl)-5,6-dihydro-4H-1,2,4-oxadiazine |
| 218B | 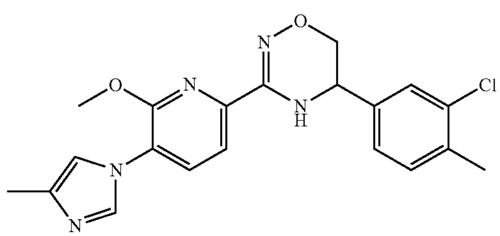 [SMILES: COc1nc(C2=NOCC(c3ccc(C)c(Cl)c3)N2)ccc1-n1cnc(C)c1] | (+)-5-(3-chloro-4-methylphenyl)-3-(6-methoxy-5-(4-methyl-1H-imidazol-1-yl)pyridin-2-yl)-5,6-dihydro-4H-1,2,4-oxadiazine |
| 219A | 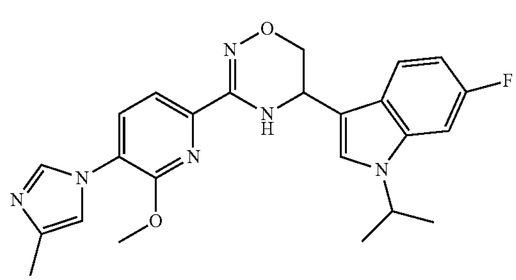 [SMILES: COc1nc(C2=NOCC(c3cn(C(C)C)c4cc(F)ccc34)N2)ccc1-n1cnc(C)c1] | (+)-5-(6-fluoro-1-isopropyl-1H-indol-3-yl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 219B | 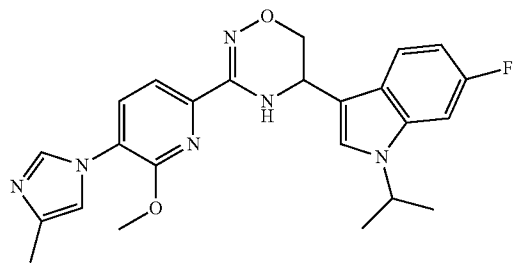 [SMILES: COc1nc(C2=NOCC(c3cn(C(C)C)c4cc(F)ccc34)N2)ccc1-n1cnc(C)c1] | (−)-5-(6-fluoro-1-isopropyl-1H-indol-3-yl)-3-(6-methoxy-5-(4-methyl-1H-imidazol-1-yl)pyridin-2-yl)-5,6-dihydro-4H-1,2,4-oxadiazine |
| 220A | 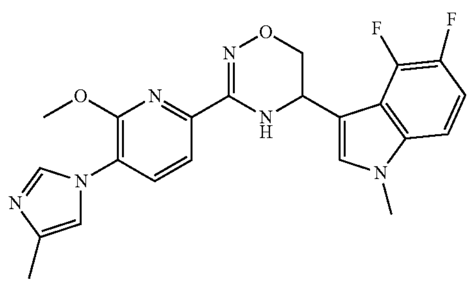 [SMILES: COc1nc(C2=NOCC(c3cn(C)c4ccc(F)c(F)c34)N2)ccc1-n1cnc(C)c1] | (−)-5-(4,5-difluoro-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 220B | 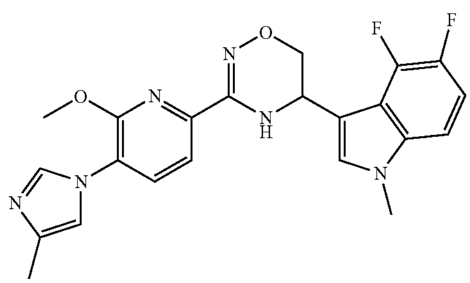 [SMILES: COc1nc(C2=NOCC(c3cn(C)c4ccc(F)c(F)c34)N2)ccc1-n1cnc(C)c1] | (+)-5-(4,5-difluoro-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 221A | 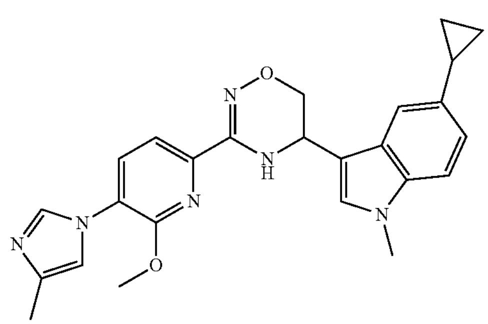 [SMILES: COc1nc(C2=NOCC(c3cn(C)c4ccc(C5CC5)cc34)N2)ccc1-n1cnc(C)c1] | (−)-5-(5-cyclopropyl-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 221B | 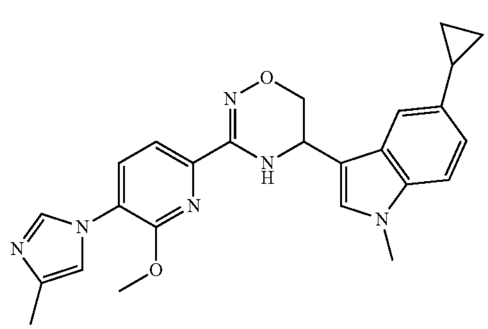 [SMILES: COc1nc(C2=NOCC(c3cn(C)c4ccc(C5CC5)cc34)N2)ccc1-n1cnc(C)c1] | (+)-5-(5-cyclopropyl-1-methyl-1H-indol-3-yl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 222A | 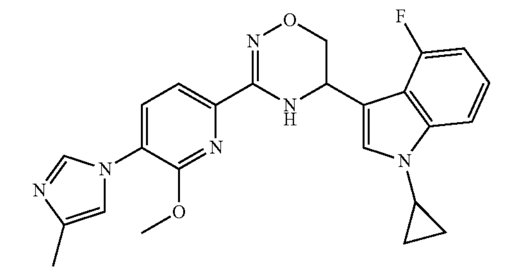 [SMILES: COc1nc(C2=NOCC(c3cn(C4CC4)c4cccc(F)c34)N2)ccc1-n1cnc(C)c1] | (+)-5-(1-cyclopropyl-4-fluoro-1H-indol-3-yl)-3-(6-methoxy-5-(4-methyl-1H-imidazol-1-yl)pyridin-2-yl)-5,6-dihydro-4H-1,2,4-oxadiazine |
| 222B | 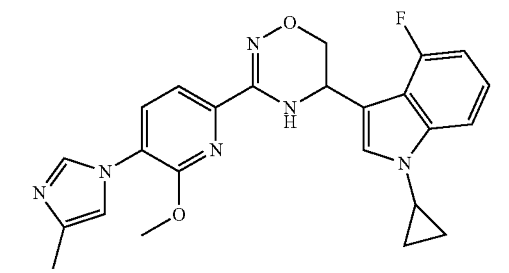 [SMILES: COc1nc(C2=NOCC(c3cn(C4CC4)c4cccc(F)c34)N2)ccc1-n1cnc(C)c1] | (−)-5-(1-cyclopropyl-4-fluoro-1H-indol-3-yl)-3-(6-methoxy-5-(4-methyl-1H-imidazol-1-yl)pyridin-2-yl)-5,6-dihydro-4H-1,2,4-oxadiazine |
| 223A | 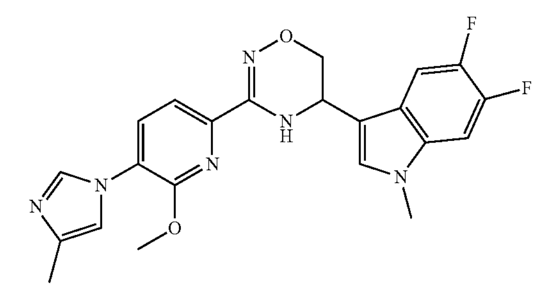 [SMILES: COc1nc(C2=NOCC(c3cn(C)c4cc(F)c(F)cc34)N2)ccc1-n1cnc(C)c1] | (−)-5-(5,6-difluoro-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 223B | 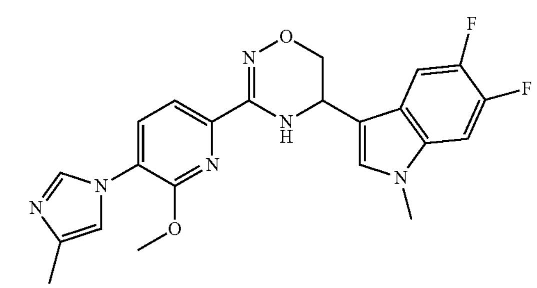 [SMILES: COc1nc(C2=NOCC(c3cn(C)c4cc(F)c(F)cc34)N2)ccc1-n1cnc(C)c1] | (+)-5-(5,6-difluoro-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 224A | 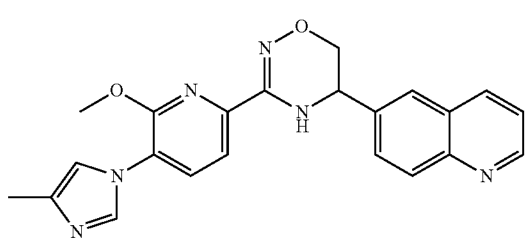 [SMILES: COc1nc(C2=NOCC(c3ccc4ncccc4c3)N2)ccc1-n1cnc(C)c1] | (−)-3-(6-methoxy-5-(4-methyl-1H-imidazol-1-yl)pyridin-2-yl)-5-(quinolin-6-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 224B | 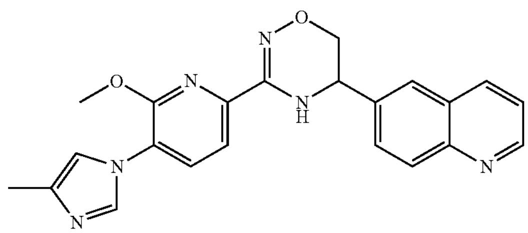 [SMILES: COc1nc(C2=NOCC(c3ccc4ncccc4c3)N2)ccc1-n1cnc(C)c1] | (+)-3-(6-methoxy-5-(4-methyl-1H-imidazol-1-yl)pyridin-2-yl)-5-(quinolin-6-yl)-5,6-dihydro-4H-1,2,4-oxadiaxine |
| 225A | 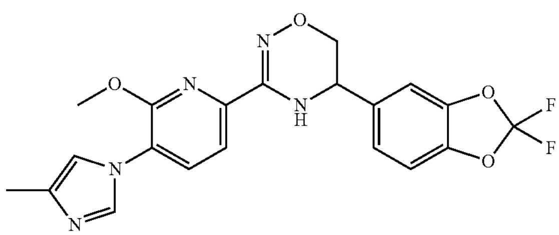 [SMILES: COc1nc(C2=NOCC(c3ccc4c(c3)OC(F)(F)O4)N2)ccc1-n1cnc(C)c1] | (−)-5-(2,2-difluorobenzo[d][1,3]dioxol-5-yl)-3-(6-methoxy-5-(4-methyl-1H-imidazol-1-yl)pyridin-2-yl)-5,6-dihydro-4H-1,2,4-oxadiazine |
| 225B | 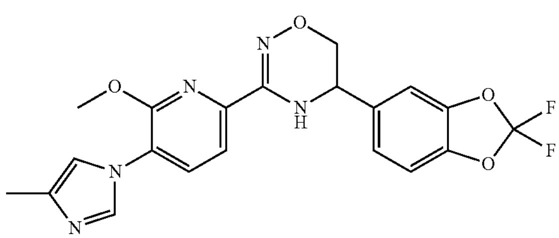 [SMILES: COc1nc(C2=NOCC(c3ccc4c(c3)OC(F)(F)O4)N2)ccc1-n1cnc(C)c1] | (+)-5-(2,2-difluorobenzo[d][1,3]dioxol-5-yl)-3-(6-methoxy-5-(4-methyl-1H-imidazol-1-yl)pyridin-2-yl)-5,6-dihydro-4H-1,2,4-oxadiazine |
| 226A | 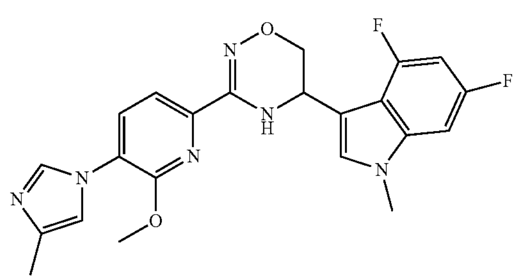 [SMILES: COc1nc(C2=NOCC(c3cn(C)c4cc(F)cc(F)c34)N2)ccc1-n1cnc(C)c1] | (+)-5-(4,6-difluoro-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 226B | 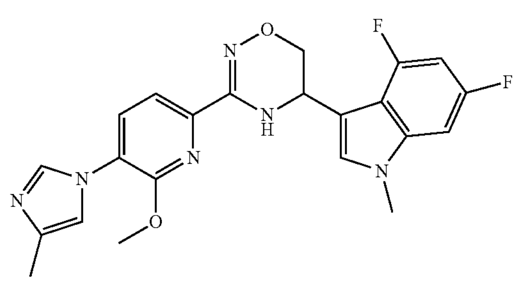 [SMILES: COc1nc(C2=NOCC(c3cn(C)c4cc(F)cc(F)c34)N2)ccc1-n1cnc(C)c1] | (−)-5-(4,6-difluoro-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 227A | 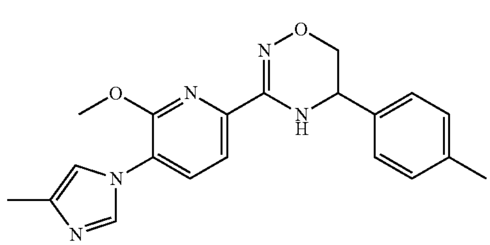 | (−)-3-(6-methoxy-5-(4-methyl-1H-imidazol-1-yl)pyridin-2-yl)-5-(p-tolyl)-5,6-dihydro-4H-1,2,4-oxadiazine |

TABLE I-continued

Exemplary Oxadiazine Compounds of Formula (I)

| Compound of Example | Structure | Name |
|---|---|---|
| 227B | 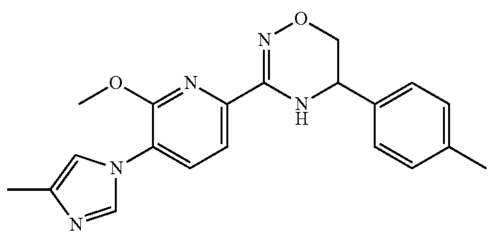 | (+)-3-(6-methoxy-5-(4-methyl-1H-imidazol-1-yl)pyridin-2-yl)-5-(p-tolyl)-5,6-dihydro-4H-1,2,4-oxadiazine |
| 228A | 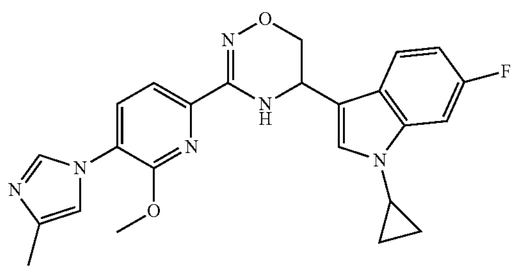 [SMILES: COc1nc(C2=NOCC(c3cn(C4CC4)c4cc(F)ccc34)N2)ccc1-n1cnc(C)c1] | (−)-5-(1-cyclopropyl-6-fluoro-1H-indol-3-yl)-3-(6-methoxy-5-(4-methyl-1H-imidazol-1-yl)pyridin-2-yl)-5,6-dihydro-4H-1,2,4-oxadiazine |
| 228B | 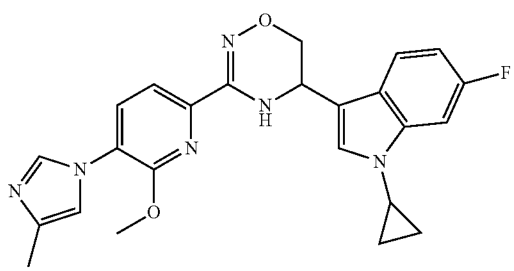 [SMILES: COc1nc(C2=NOCC(c3cn(C4CC4)c4cc(F)ccc34)N2)ccc1-n1cnc(C)c1] | (+)-5-(1-cyclopropyl-6-fluoro-1H-indol-3-yl)-3-(6-methoxy-5-(4-methyl-1H-imidazol-1-yl)pyridin-2-yl)-5,6-dihydro-4H-1,2,4-oxadiazine |
| 229A | 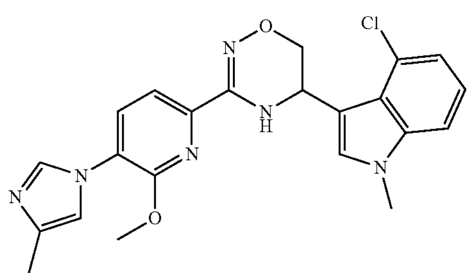 [SMILES: COc1nc(C2=NOCC(c3cn(C)c4cccc(Cl)c34)N2)ccc1-n1cnc(C)c1] | (+)-5-(4-chloro-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 229B | 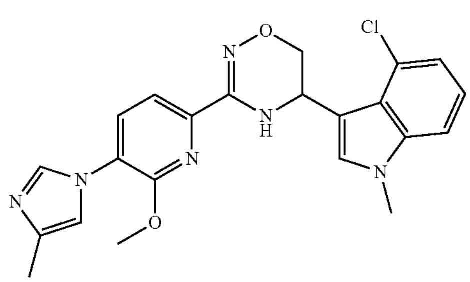 [SMILES: COc1nc(C2=NOCC(c3cn(C)c4cccc(Cl)c34)N2)ccc1-n1cnc(C)c1] | (−)-5-(4-chloro-1-methyl-1H-indol-3-yl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 230A | 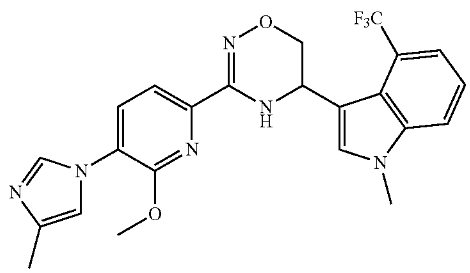 [SMILES: COc1nc(C2=NOCC(c3cn(C)c4cccc(C(F)(F)F)c34)N2)ccc1-n1cnc(C)c1] | (+)-3-(6-methoxy-5-(4-methyl-1H-imidazol-1-yl)pyridin-2-yl)-5-(1-methyl-4-(trifluoromethyl)-1H-indol-3-yl)-5,6-dihydro-4H-1,2,4-oxadiazine |
| 230B | 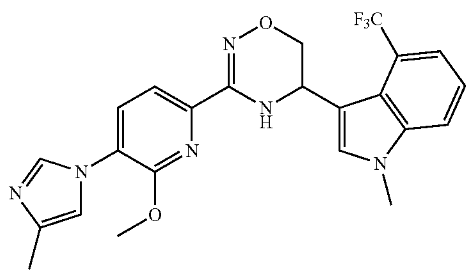 [SMILES: COc1nc(C2=NOCC(c3cn(C)c4cccc(C(F)(F)F)c34)N2)ccc1-n1cnc(C)c1] | (−)-3-(6-methoxy-5-(4-methyl-1H-imidazol-1-yl)pyridin-2-yl)-5-(1-methyl-4-(trifluoromethyl)-1H-indol-3-yl)-5,6-dihydro-4H-1,2,4-oxadiazine |
| 231A | 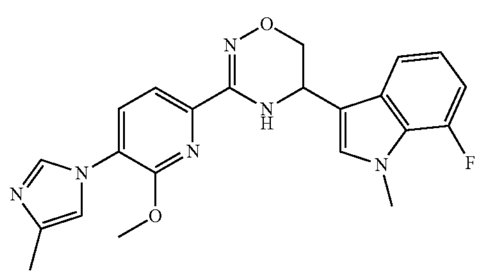 [SMILES: COc1nc(C2=NOCC(c3cn(C)c4c(F)cccc34)N2)ccc1-n1cnc(C)c1] | (−)-5-(7-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 231B | 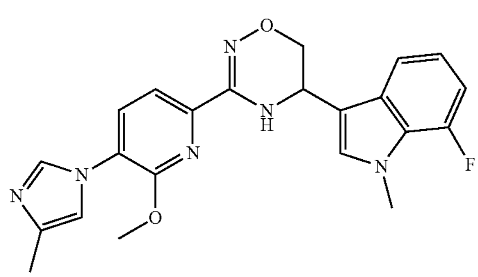 [SMILES: COc1nc(C2=NOCC(c3cn(C)c4c(F)cccc34)N2)ccc1-n1cnc(C)c1] | (+)-5-(7-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 232A | 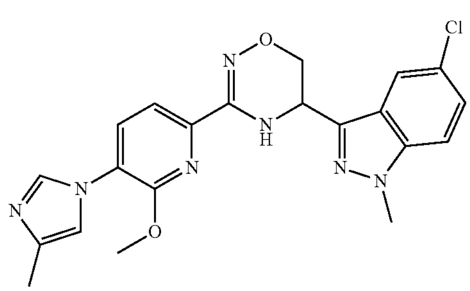 [SMILES: COc1nc(C2=NOCC(c3nn(C)c4ccc(Cl)cc34)N2)ccc1-n1cnc(C)c1] | (−)-5-(5-chloro-1-methyl-1H-indazol-3-yl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 232B | 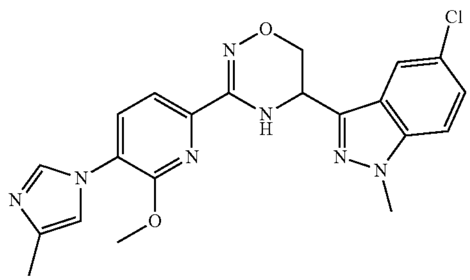 [SMILES: COc1nc(C2=NOCC(c3nn(C)c4ccc(Cl)cc34)N2)ccc1-n1cnc(C)c1] | (+)-5-(5-chloro-1-methyl-1H-indazol-3-yl)-3-(6-methoxy-5-(4-methyl-1H-imidazol-1-yl)pyridin-2-yl)-5,6-dihydro-4H-1,2,4-oxadiazine |
| 233A | 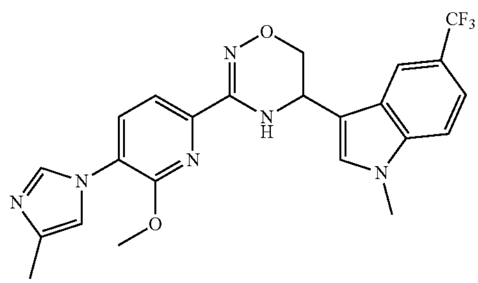 [SMILES: COc1nc(C2=NOCC(c3cn(C)c4ccc(C(F)(F)F)cc34)N2)ccc1-n1cnc(C)c1] | (−)-3-(6-methoxy-5-(4-methyl-1H-imidazol-1-yl)pyridin-2-yl)-5-(1-methyl-5-(trifluoromethyl)-1H-indol-3-yl)-5,6-dihydro-4H-1,2,4-oxadiazine |
| 233B | 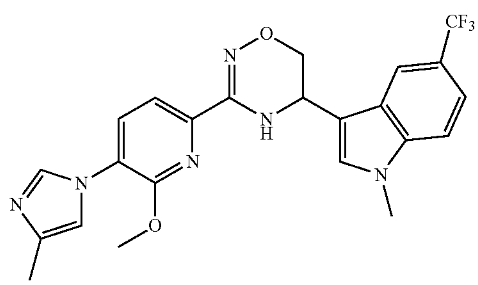 [SMILES: COc1nc(C2=NOCC(c3cn(C)c4ccc(C(F)(F)F)cc34)N2)ccc1-n1cnc(C)c1] | (+)-3-(6-methoxy-5-(4-methyl-1H-imidazol-1-yl)pyridin-2-yl)-5-(1-methyl-5-(trifluoromethyl)-1H-indol-3-yl)-5,6-dihydro-4H-1,2,4-oxadiazine |
| 234A | 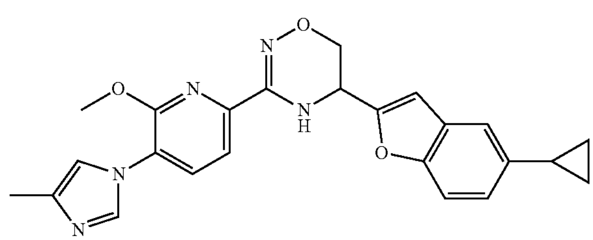 [SMILES: COc1nc(C2=NOCC(c3cc4cc(C5CC5)ccc4o3)N2)ccc1-n1cnc(C)c1] | (−)-5-(5-cyclopropylbenzofuran-2-yl)-3-(6-methoxy-5-(4-methyl-1H-imidazol-1-yl)pyridin-2-yl)-5,6-dihydro-4H-1,2,4-oxadiazine |
| 234B | 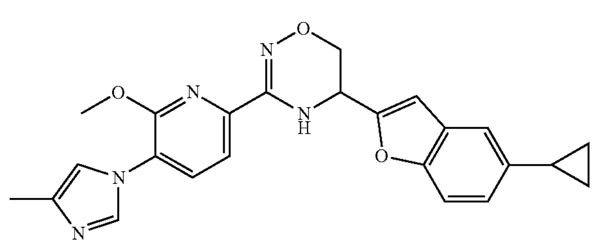 [SMILES: COc1nc(C2=NOCC(c3cc4cc(C5CC5)ccc4o3)N2)ccc1-n1cnc(C)c1] | (+)-5-(5-cyclopropylbenzofuran-2-yl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 235A | 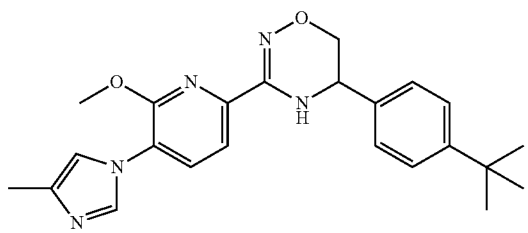 [SMILES: COc1nc(C2=NOCC(c3ccc(C(C)(C)C)cc3)N2)ccc1-n1cnc(C)c1] | (−)-5-(4-(tert-butyl)phenyl)-3-(6-methoxy-5-(4-methyl-1H-imidazol-1-yl)pyridin-2-yl)-5,6-dihydro-4H-1,2,4-oxadiazine |
| 235B | 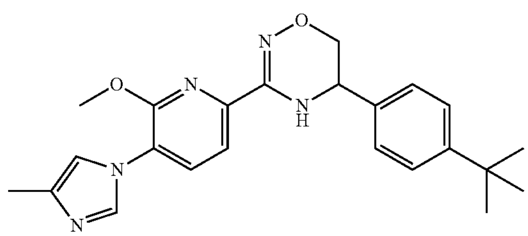 [SMILES: COc1nc(C2=NOCC(c3ccc(C(C)(C)C)cc3)N2)ccc1-n1cnc(C)c1] | (+)-5-(4-(tert-butyl)phenyl)-3-(6-methoxy-5-(4-methyl-1H-imidazol-1-yl)pyridin-2-yl)-5,6-dihydro-4H-1,2,4-oxadiazine |
| 236A | 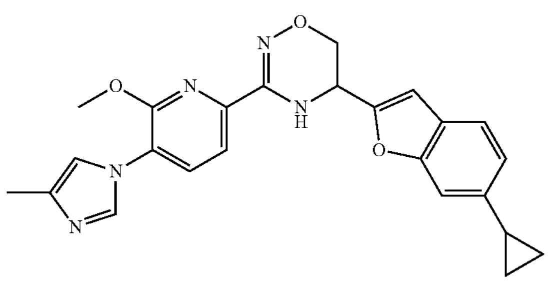 [SMILES: COc1nc(C2=NOCC(c3cc4ccc(C5CC5)cc4o3)N2)ccc1-n1cnc(C)c1] | (−)-5-(6-cyclopropylbenzofuran-2-yl)-3-(6-methoxy-5-(4-methyl-1H-imidazol-1-yl)pyridin-2-yl)-5,6-dihydro-4H-1,2,4-oxadiazine |
| 236B | 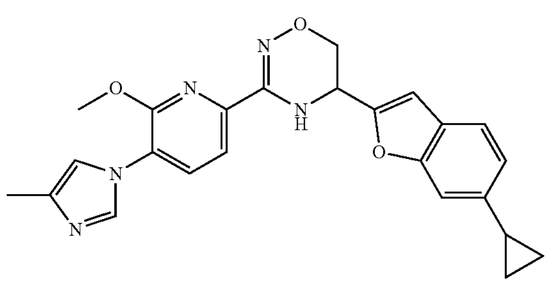 [SMILES: COc1nc(C2=NOCC(c3cc4ccc(C5CC5)cc4o3)N2)ccc1-n1cnc(C)c1] | (+)-5-(6-cyclopropylbenzofuran-2-yl)-3-(6-methoxy-5-(4-methyl-1H-imidazol-1-yl)pyridin-2-yl)-5,6-dihydro-4H-1,2,4-oxadiazine |
| 237A | 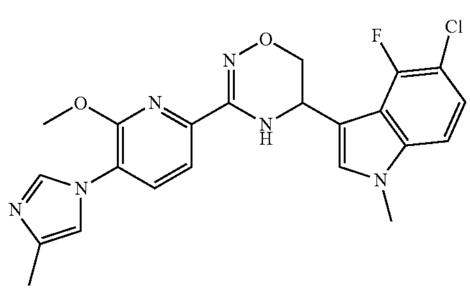 [SMILES: COc1nc(C2=NOCC(c3cn(C)c4ccc(Cl)c(F)c34)N2)ccc1-n1cnc(C)c1] | (+)-5-(5-chloro-4-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 237B | 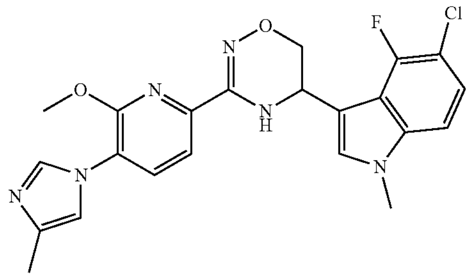 [SMILES: COc1nc(C2=NOCC(c3cn(C)c4ccc(Cl)c(F)c34)N2)ccc1-n1cnc(C)c1] | (−)-5-(5-chloro-4-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 238A | 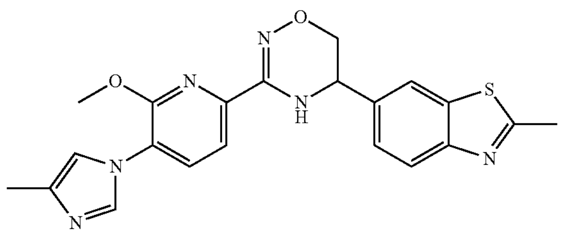 | (−)-3-(6-methoxy-5-(4-methyl-1H-imidazol-1-yl)pyridin-2-yl)-5-(2-methylbenzo[d]thiazol-6-yl)-5,6-dihydro-4H-1,2,4-oxadiazine |
| 238B | 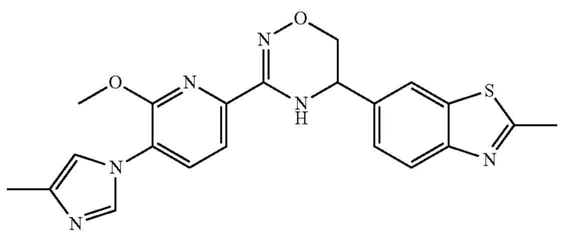 | (+)-3-(6-methoxy-5-(4-methyl-1H-imidazol-1-yl)pyridin-2-yl)-5-(2-methylbenzo[d]thiazol-6-yl)-5,6-dihydro-4H-1,2,4-oxadiazine |
| 239A | 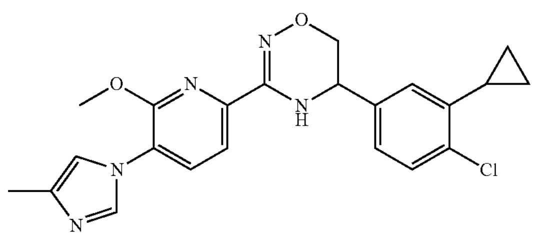 [SMILES: COc1nc(C2=NOCC(c3ccc(Cl)c(C4CC4)c3)N2)ccc1-n1cnc(C)c1] | (−)-5-(4-chloro-3-cyclopropylphenyl)-3-(6-methoxy-5-(4-methyl-1H-imidazol-1-yl)pyridin-2-yl)-5,6-dihydro-4H-1,2,4-oxadiazine |
| 239B | 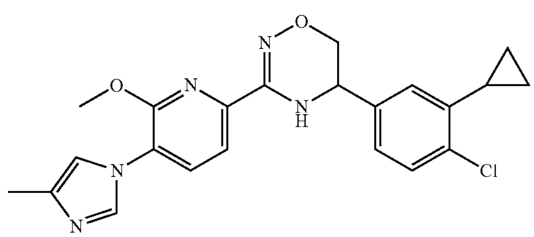 [SMILES: COc1nc(C2=NOCC(c3ccc(Cl)c(C4CC4)c3)N2)ccc1-n1cnc(C)c1] | (+)-5-(4-chloro-3-cyclopropylphenyl)-3-(6-methoxy-5-(4-methyl-1H-imidazol-1-yl)pyridin-2-yl)-5,6-dihydro-4H-1,2,4-oxadiazine |
| 240A | 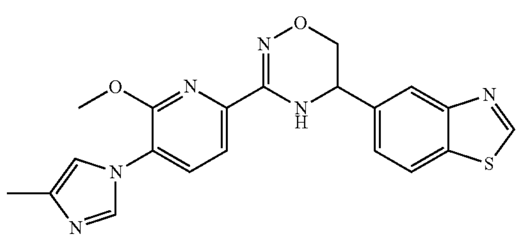 [SMILES: COc1nc(C2=NOCC(c3ccc4scnc4c3)N2)ccc1-n1cnc(C)c1] | (−)-5-(benzo[d]thiazol-5-yl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 240B | 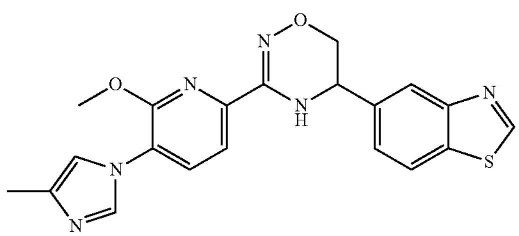 [SMILES: COc1nc(C2=NOCC(c3ccc4scnc4c3)N2)ccc1-n1cnc(C)c1] | (+)-5-(benzo[d]thiazol-5-yl)-3-(6-methoxy-5-(4-methyl-1H-imidazol-1-yl)pyridin-2-yl)-5,6-dihydro-4H-1,2,4-oxadiazine |
| 241A | 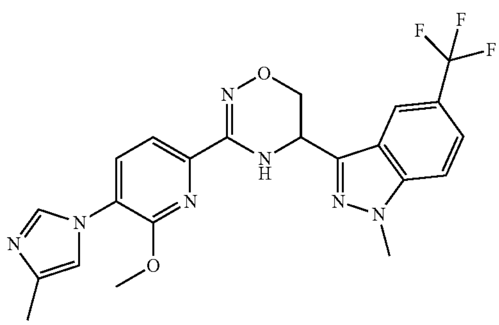 [SMILES: COc1nc(C2=NOCC(c3nn(C)c4ccc(C(F)(F)F)cc34)N2)ccc1-n1cnc(C)c1] | (−)-3-(6-methoxy-5-(4-methyl-1H-imidazol-1-yl)pyridin-2-yl)-5-(1-methyl-5-(trifluoromethyl)-1H-indazol-3-yl)-5,6-dihydro-4H-1,2,4-oxadiazine |
| 241B | 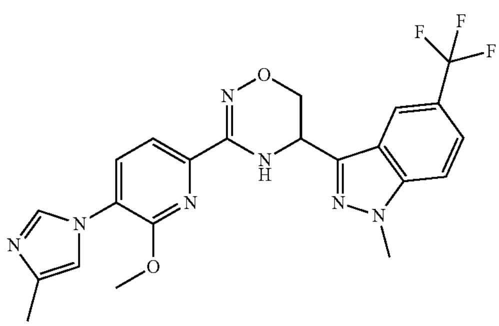 [SMILES: COc1nc(C2=NOCC(c3nn(C)c4ccc(C(F)(F)F)cc34)N2)ccc1-n1cnc(C)c1] | (+)-3-(6-methoxy-5-(4-methyl-1H-imidazol-1-yl)pyridin-2-yl)-5-(1-methyl-5-(trifluoromethyl)-1H-indazol-3-yl)-5,6-dihydro-4H-1,2,4-oxadiazine |
| 242A | 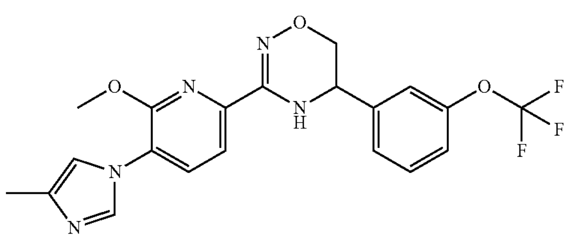 [SMILES: COc1nc(C2=NOCC(c3cccc(OC(F)(F)F)c3)N2)ccc1-n1cnc(C)c1] | (−)-3-(6-methoxy-5-(4-methyl-1H-imidazol-1-yl)pyridin-2-yl)-5-(3-(trifluoromethoxy)phenyl)-5,6-dihydro-4H-1,2,4-oxadiazine |
| 242B | 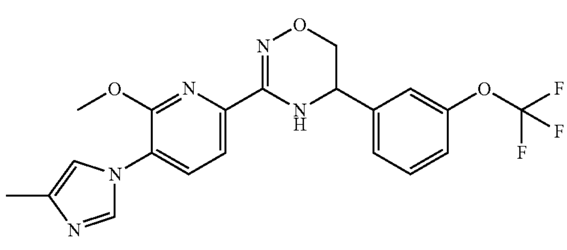 [SMILES: COc1nc(C2=NOCC(c3cccc(OC(F)(F)F)c3)N2)ccc1-n1cnc(C)c1] | (+)-3-(6-methoxy-5-(4-methyl-1H-imidazol-1-yl)pyridin-2-yl)-5-(3-(trifluoromethoxy)phenyl)-5,6-dihydro-4H-1,2,4-oxadiazine |

TABLE I-continued

Exemplary Oxadiazine Compounds of Formula (I)

| Compound of Example | Structure | Name |
|---|---|---|
| 243A | 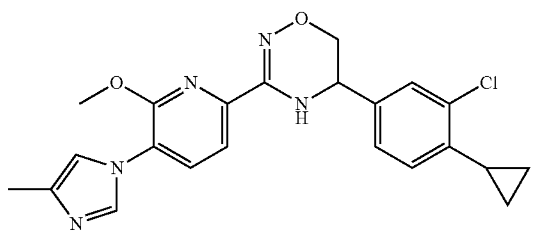 [SMILES: COc1nc(C2=NOCC(c3ccc(C4CC4)c(Cl)c3)N2)ccc1-n1cnc(C)c1] | (−)-5-(3-chloro-4-cyclopropylphenyl)-3-(6-methoxy-5-(4-methyl-1H-imidazol-1-yl)pyridin-2-yl)-5,6-dihydro-4H-1,2,4-oxadiazine |
| 243B | 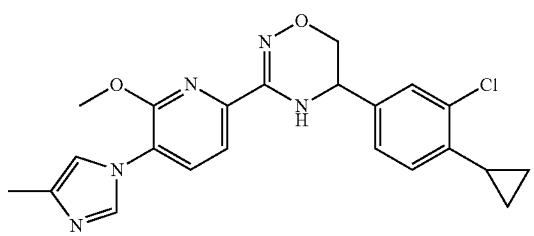 [SMILES: COc1nc(C2=NOCC(c3ccc(C4CC4)c(Cl)c3)N2)ccc1-n1cnc(C)c1] | (+)-5-(3-chloro-4-cyclopropylphenyl)-3-(6-methoxy-5-(4-methyl-1H-imidazol-1-yl)pyridin-2-yl)-5,6-dihydro-4H-1,2,4-oxadiazine |
| 244A | 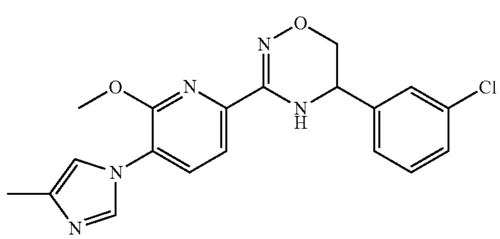 [SMILES: COc1nc(C2=NOCC(c3cccc(Cl)c3)N2)ccc1-n1cnc(C)c1] | (−)-5-(3-chlorophenyl)-3-(6-methoxy-5-(4-methyl-1H-imidazol-1-yl)pyridin-2-yl)-5,6-dihydro-4H-1,2,4-oxadiazine |
| 244B | 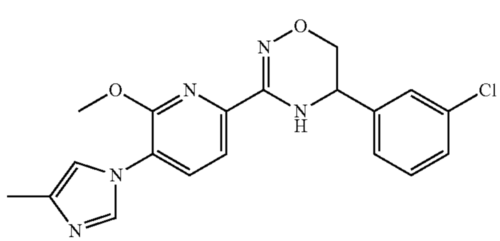 [SMILES: COc1nc(C2=NOCC(c3cccc(Cl)c3)N2)ccc1-n1cnc(C)c1] | (+)-5-(3-chlorophenyl)-3-(6-methoxy-5-(4-methyl-1H-imidazol-1-yl)pyridin-2-yl)-5,6-dihydro-4H-1,2,4-oxadiazine |
| 245A | 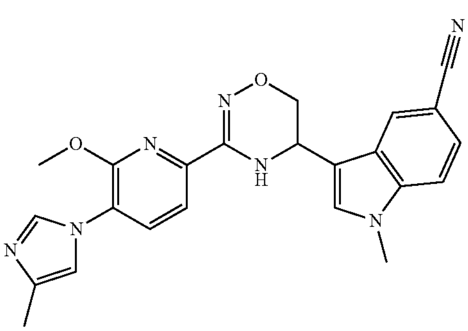 [SMILES: COc1nc(C2=NOCC(c3cn(C)c4ccc(C#N)cc34)N2)ccc1-n1cnc(C)c1] | (−)-3-(3-(6-methoxy-5-(4-methyl-1H-imidazol-1-yl)pyridin-2-yl)-5,6-dihydro-4H-1,2,4-oxadiazin-5-yl)-1-methyl-1H-indole-5-carbonitrile |

TABLE I-continued

Exemplary Oxadiazine Compounds of Formula (I)

| Compound of Example | Structure | Name |
|---|---|---|
| 245B | 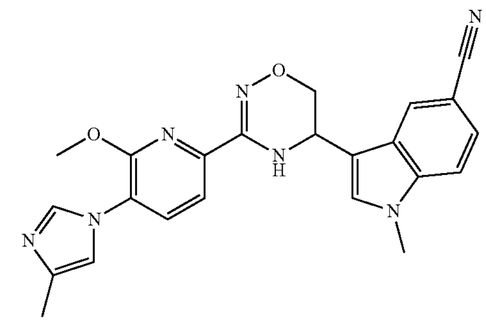 [SMILES: COc1nc(C2=NOCC(c3cn(C)c4ccc(C#N)cc34)N2)ccc1-n1cnc(C)c1] | (+)-3-(3-(6-methoxy-5-(4-methyl-1H-imidazol-1-yl)pyridin-2-yl)-5,6-dihydro-4H-1,2,4-oxadiazin-5-yl)-1-methyl-1H-indole-5-carbonitrile |
| 247A | 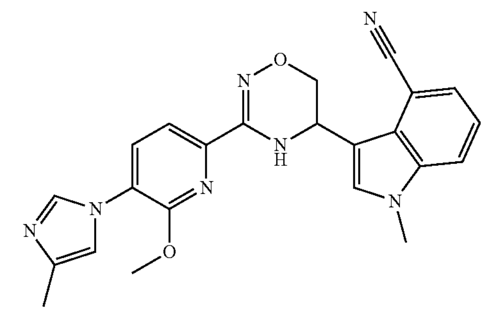 [SMILES: COc1nc(C2=NOCC(c3cn(C)c4cccc(C#N)c34)N2)ccc1-n1cnc(C)c1] | (+)-3-(3-(6-methoxy-5-(4-methyl-1H-imidazol-1-yl)pyridin-2-yl)-5,6-dihydro-4H-1,2,4-oxadiazin-5-yl)-1-methyl-1H-indole-4-carbonitrile |
| 247B | 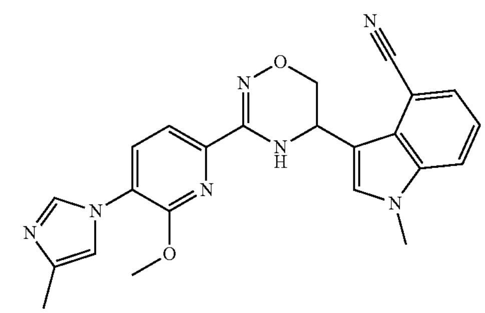 [SMILES: COc1nc(C2=NOCC(c3cn(C)c4cccc(C#N)c34)N2)ccc1-n1cnc(C)c1] | (−)-3-(3-(6-methoxy-5-(4-methyl-1H-imidazol-1-yl)pyridin-2-yl)-5,6-dihydro-4H-1,2,4-oxadiazin-5-yl)-1-methyl-1H-indole-4-carbonitrile |
| 248A | 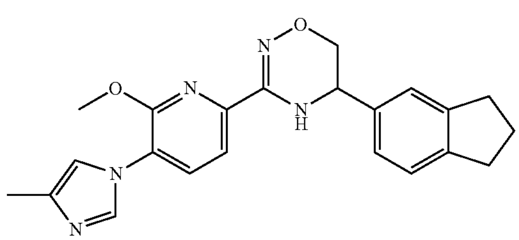 [SMILES: COc1nc(C2=NOCC(c3ccc4c(c3)CCC4)N2)ccc1-n1cnc(C)c1] | (−)-5-(2,3-dihydro-1H-inden-5-yl)-3-(6-methoxy-5-(4-methyl-1H-imidazol-1-yl)pyridin-2-yl)-5,6-dihydro-4H-1,2,4-oxadiazine |
| 248B | 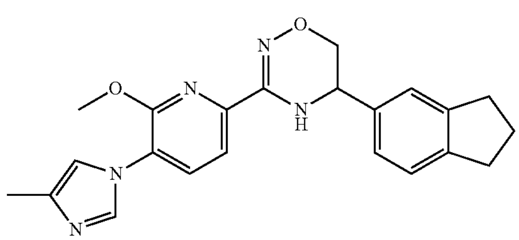 [SMILES: COc1nc(C2=NOCC(c3ccc4c(c3)CCC4)N2)ccc1-n1cnc(C)c1] | (+)-5-(2,3-dihydro-1H-inden-5-yl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 249A | 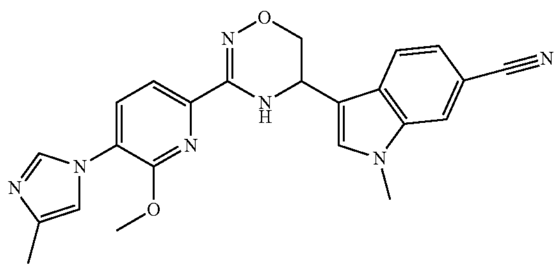 [SMILES: COc1nc(C2=NOCC(c3cn(C)c4cc(C#N)ccc34)N2)ccc1-n1cnc(C)c1] | (−)-3-(3-(6-methoxy-5-(4-methyl-1H-imidazol-1-yl)pyridin-2-yl)-5,6-dihydro-4H-1,2,4-oxadiazin-5-yl)-1-methyl-1H-indole-6-carbonitrile |
| 249B | 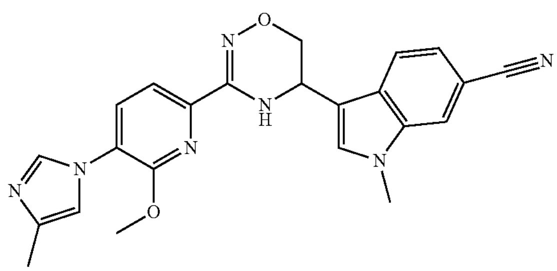 [SMILES: COc1nc(C2=NOCC(c3cn(C)c4cc(C#N)ccc34)N2)ccc1-n1cnc(C)c1] | (+)-3-(3-(6-methoxy-5-(4-methyl-1H-imidazol-1-yl)pyridin-2-yl)-5,6-dihydro-4H-1,2,4-oxadiazin-5-yl)-1-methyl-1H-indole-6-carbonitrile |
| 250A | 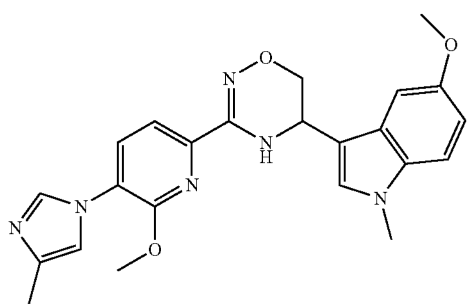 [SMILES: COc1ccc2c(c1)c(C1CON=C(c3ccc(-n4cnc(C)c4)c(OC)n3)N1)cn2C] | (−)-5-(5-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 250B | 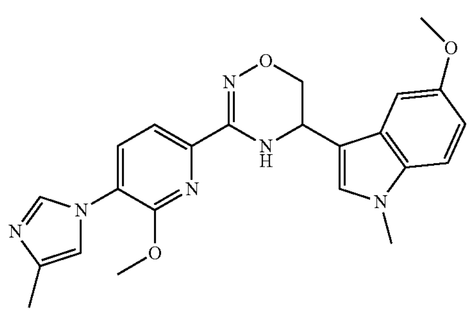 [SMILES: COc1ccc2c(c1)c(C1CON=C(c3ccc(-n4cnc(C)c4)c(OC)n3)N1)cn2C] | (+)-5-(5-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 252A | 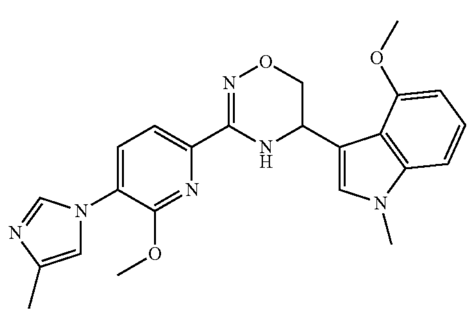 [SMILES: COc1nc(C2=NOCC(c3cn(C)c4cccc(OC)c34)N2)ccc1-n1cnc(C)c1] | (−)-5-(4-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 252B | 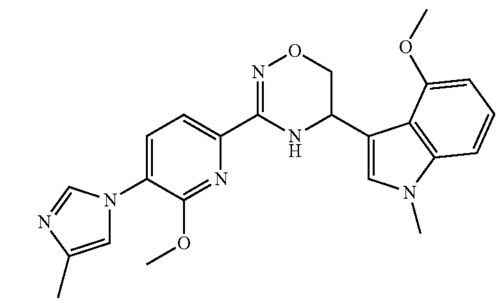 [SMILES: COc1nc(C2=NOCC(c3cn(C)c4cccc(OC)c34)N2)ccc1-n1cnc(C)c1] | (+)-5-(4-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 253A | 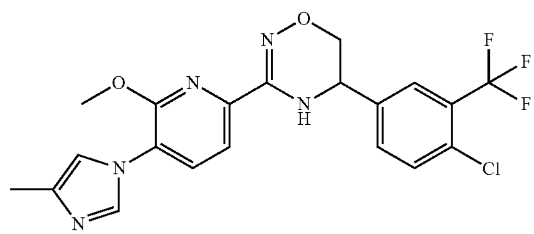 [SMILES: COc1nc(C2=NOCC(c3ccc(Cl)c(C(F)(F)F)c3)N2)ccc1-n1cnc(C)c1] | 5-(4-chloro-3-(trifluoromethyl)phenyl)-3-(6-methoxy-5-(4-methyl-1H-imidazol-1-yl)pyridin-2-yl)-5,6-dihydro-4H-1,2,4-oxadiazine |
| 253B | 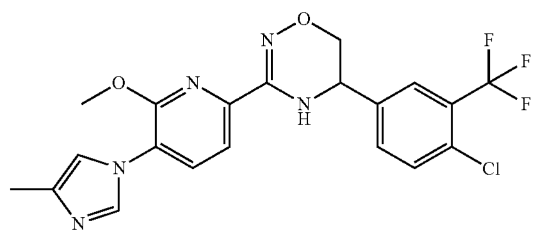 [SMILES: COc1nc(C2=NOCC(c3ccc(Cl)c(C(F)(F)F)c3)N2)ccc1-n1cnc(C)c1] | 5-(4-chloro-3-(trifluoromethyl)phenyl)-3-(6-methoxy-5-(4-methyl-1H-imidazol-1-yl)pyridin-2-yl)-5,6-dihydro-4H-1,2,4-oxadiazine |
| 254A | 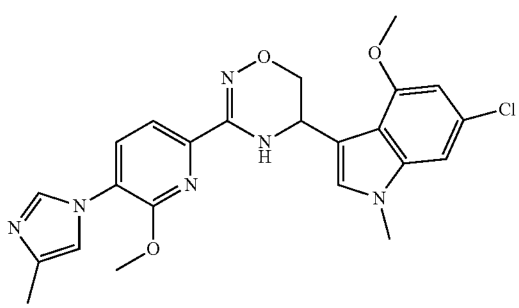 [SMILES: COc1nc(C2=NOCC(c3cn(C)c4cc(Cl)cc(OC)c34)N2)ccc1-n1cnc(C)c1] | (−)-5-(6-chloro-4-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 254B | 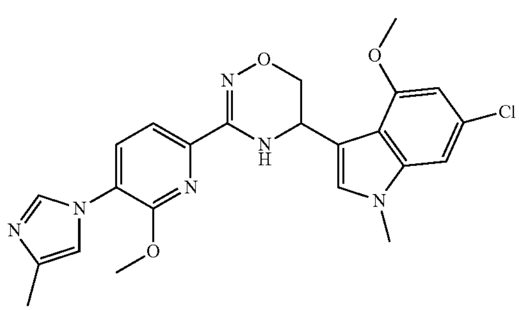 [SMILES: COc1nc(C2=NOCC(c3cn(C)c4cc(Cl)cc(OC)c34)N2)ccc1-n1cnc(C)c1] | (+)-5-(6-chloro-4-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 255A | 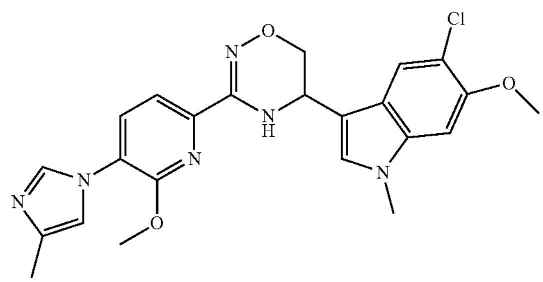 [SMILES: COc1cc2c(cc1Cl)c(C1CON=C(c3ccc(-n4cnc(C)c4)c(OC)n3)N1)cn2C] | (−)-5-(5-chloro-6-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 255B | 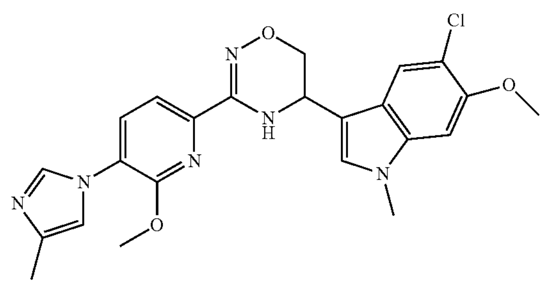 [SMILES: COc1cc2c(cc1Cl)c(C1CON=C(c3ccc(-n4cnc(C)c4)c(OC)n3)N1)cn2C] | (+)-5-(5-chloro-6-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 257A | 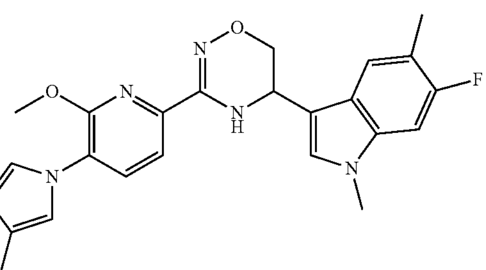 | (−)-5-(6-fluoro-1,5-dimethyl-1H-indol-3-yl)-3-(6-methoxy-5-(4-methyl-1H-imidazol-1-yl)pyridin-2-yl)-5,6-dihydro-4H-1,2,4-oxadiazine |
| 257B | 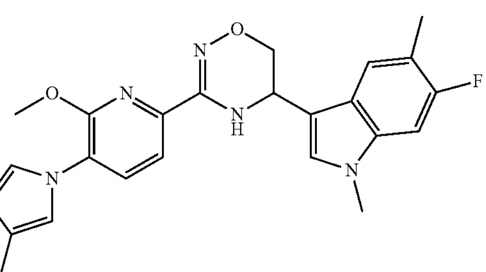 | (+)-5-(6-fluoro-1,5-dimethyl-1H-indol-3-yl)-3-(6-methoxy-5-(4-methyl-1H-imidazol-1-yl)pyridin-2-yl)-5,6-dihydro-4H-1,2,4-oxadiazine |
| 258A | 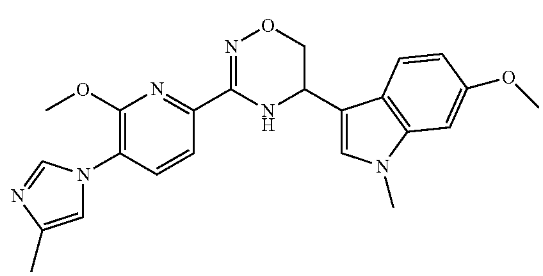 [SMILES: COc1ccc2c(C3CON=C(c4ccc(-n5cnc(C)c5)c(OC)n4)N3)cn(C)c2c1] | (−)-5-(6-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 258B | 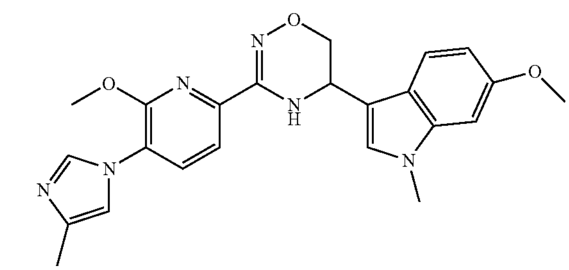 [SMILES: COc1ccc2c(C3CON=C(c4ccc(-n5cnc(C)c5)c(OC)n4)N3)cn(C)c2c1] | (+)-5-(6-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 259A | 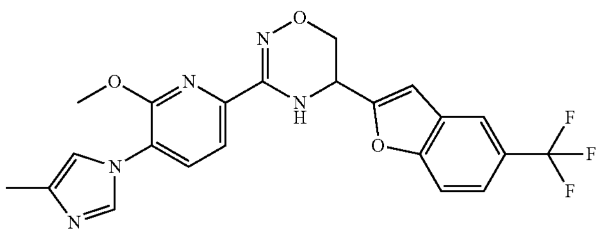 [SMILES: COc1nc(C2=NOCC(c3cc4cc(C(F)(F)F)ccc4o3)N2)ccc1-n1cnc(C)c1] | (−)-3-(6-methoxy-5-(4-methyl-1H-imidazol-1-yl)pyridin-2-yl)-5-(5-(trifluoromethyl)benzofuran-2-yl)-5,6-dihydro-4H-1,2,4-oxadiazine |
| 259B | 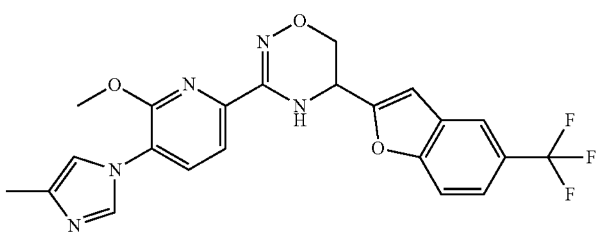 [SMILES: COc1nc(C2=NOCC(c3cc4cc(C(F)(F)F)ccc4o3)N2)ccc1-n1cnc(C)c1] | (+)-3-(6-methoxy-5-(4-methyl-1H-imidazol-1-yl)pyridin-2-yl)-5-(5-(trifluoromethyl)benzofuran-2-yl)-5,6-dihydro-4H-1,2,4-oxadiazine |
| 260A | 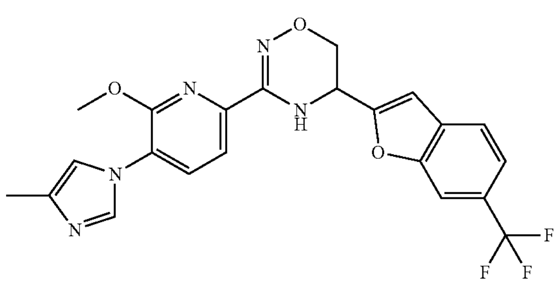 [SMILES: COc1nc(C2=NOCC(c3cc4ccc(C(F)(F)F)cc4o3)N2)ccc1-n1cnc(C)c1] | (−)-3-(6-methoxy-5-(4-methyl-1H-imidazol-1-yl)pyridin-2-yl)-5-(6-(trifluoromethyl)benzofuran-2-yl)-5,6-dihydro-4H-1,2,4-oxadiazine |
| 260B | 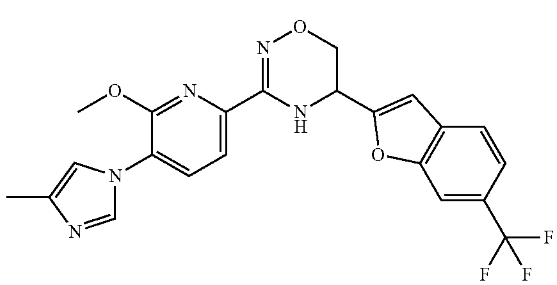 [SMILES: COc1nc(C2=NOCC(c3cc4ccc(C(F)(F)F)cc4o3)N2)ccc1-n1cnc(C)c1] | (+)-3-(6-methoxy-5-(4-methyl-1H-imidazol-1-yl)pyridin-2-yl)-5-(6-(trifluoromethyl)benzofurun-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 261A | 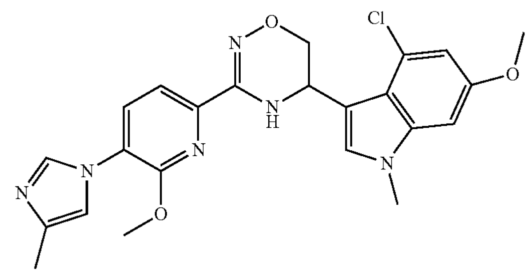 [SMILES: COc1cc(Cl)c2c(C3CON=C(c4ccc(-n5cnc(C)c5)c(OC)n4)N3)cn(C)c2c1] | (+)-5-(4-chloro-6-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine |
| 261B | 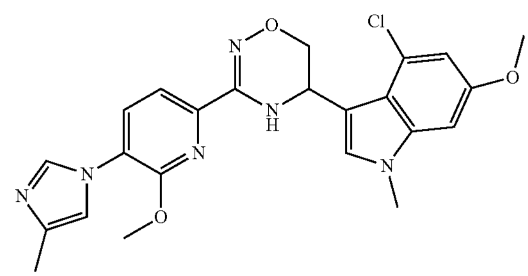 [SMILES: COc1cc(Cl)c2c(C3CON=C(c4ccc(-n5cnc(C)c5)c(OC)n4)N3)cn(C)c2c1] | (−)-5-(4-chloro-6-methoxy-1-methyl-1H-indol-3-yl)-3-(6-methoxy-5-(4-meihyl-1H-imidazol-1-yl)pyridin-2-yl)-5,6-dihydro-4H-1,2,4-oxadiazine |
| 262A | 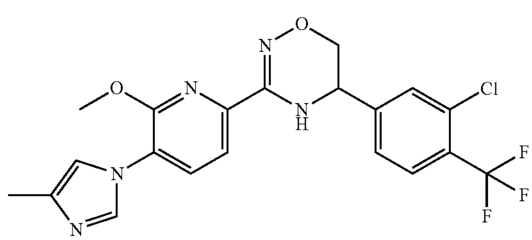 [SMILES: COc1nc(C2=NOCC(c3ccc(C(F)(F)F)c(Cl)c3)N2)ccc1-n1cnc(C)c1] | (−)-5-(3-chloro-4-(trifluoromethyl)phenyl)-3-(6-methoxy-5-(4-methyl-1H-imidazol-1-yl)pyridin-2-yl)-5,6-dihydro-4H-1,2,4-oxadiazine |
| 262B | 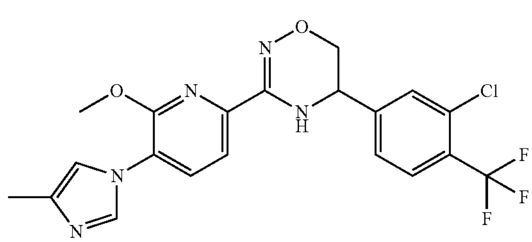 [SMILES: COc1nc(C2=NOCC(c3ccc(C(F)(F)F)c(Cl)c3)N2)ccc1-n1cnc(C)c1] | (+)-5-(3-chloro-4-(trifluoromethyl)phenyl)-3-(6-methoxy-5-(4-methyl-1H-imidazol-1-yl)pyridin-2-yl)-5,6-dihydro-4H-1,2,4-oxadiazine |
| 264A | 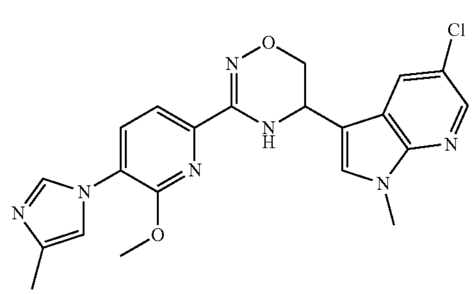 [SMILES: COc1nc(C2=NOCC(c3cn(C)c4ncc(Cl)cc34)N2)ccc1-n1cnc(C)c1] | (−)-5-(5-chloro-1-methyl-1H-pyrrolo[2,3-b]pyridin-3-yl)-3-(6-methoxy-5-(4-methyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 264B | 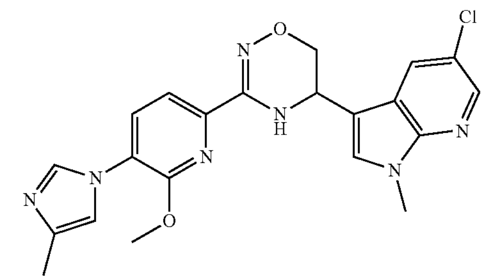 [SMILES: COc1nc(C2=NOCC(c3cn(C)c4ncc(Cl)cc34)N2)ccc1-n1cnc(C)c1] | (+)-5-(5-chloro-1-methyl-1H-pyrrolo[2,3-b]pyridin-3-yl)-3-(6-methoxy-5-(4-methyl-1H-imidazol-1-yl)pyridin-2-yl)-5,6-dihydro-4H-1,2,4-oxadiazine |
| 266A | 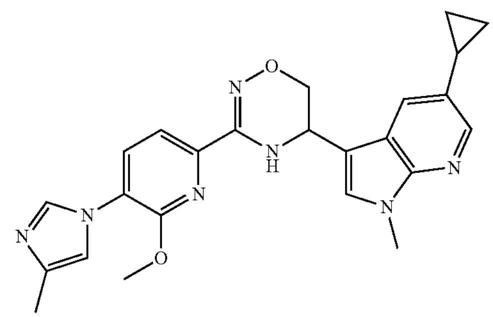 | (−)-5-(5-cyclopropyl-1-methyl-1H-pyrrolo[2,3-b]pyridin-3-yl)-3-(6-methoxy-5-(4-methyl-1H-imidazol-1-yl)pyridin-2-yl)-5,6-dihydro-4H-1,2,4-oxadiazine |
| 266B | 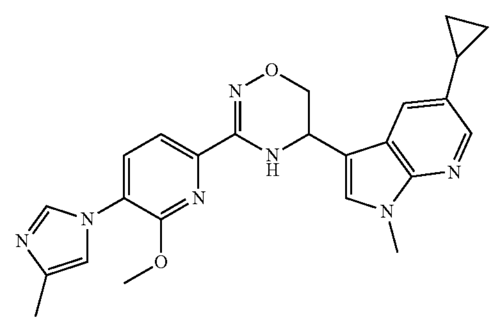 [SMILES: COc1nc(C2=NOCC(c3cn(C)c4ncc(C5CC5)cc34)N2)ccc1-n1cnc(C)c1] | (+)-5-(5-cyclopropyl-1-methyl-1H-pyrrolo[2,3-b]pyridin-3-yl)-3-(6-methoxy-5-(4-methyl-1H-imidazol-1-yl)pyridin-2-yl)-5,6-dihydro-4H-1,2,4-oxadiazine |
| 267A | 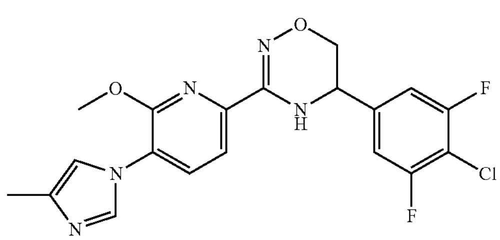 [SMILES: COc1nc(C2=NOCC(c3cc(F)c(Cl)c(F)c3)N2)ccc1-n1cnc(C)c1] | (−)-5-(4-chloro-3,5-difluorophenyl)-3-(6-methoxy-5-(4-methyl-1H-imidazol-1-yl)pyridin-2-yl)-5,6-dihydro-4H-1,2,4-oxadiazine |
| 267B | 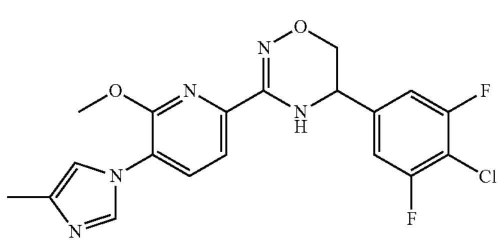 [SMILES: COc1nc(C2=NOCC(c3cc(F)c(Cl)c(F)c3)N2)ccc1-n1cnc(C)c1] | (+)-5-(4-chloro-3,5-difluoromethyl)-3-(6-methoxy-5-(4-niethyl-1H-imidazol-1-yl)pyridin-2-yl)-5,6-dihydro-4H-1,2,4-oxadiazine |

TABLE I-continued

Exemplary Oxadiazine Compounds of Formula (I)

| Compound of Example | Structure | Name |
|---|---|---|
| 269A | 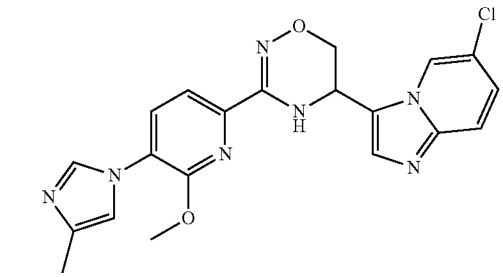 [SMILES: COc1nc(C2=NOCC(c3cnc4ccc(Cl)cn34)N2)ccc1-n1cnc(C)c1] | (−)-5-(6-chloroimidazo[1,2-a]pyridin-3-yl)-3-(6-methoxy-5-(4-methyl-1H-imidazol-1-yl)pyridin-2-yl)-5,6-dihydro-4H-1,2,4-oxadiazine |
| 269B | 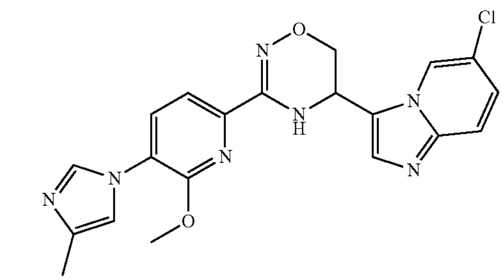 [SMILES: COc1nc(C2=NOCC(c3cnc4ccc(Cl)cn34)N2)ccc1-n1cnc(C)c1] | (+)-5-(6-chloroimidazo[1,2-a]pyridin-3-yl)-3-(6-methoxy-5-(4-methyl-1H-imidazol-1-yl)pyridin-2-yl)-5,6-dihydro-4H-1,2,4-oxadiazine |
| 270A | 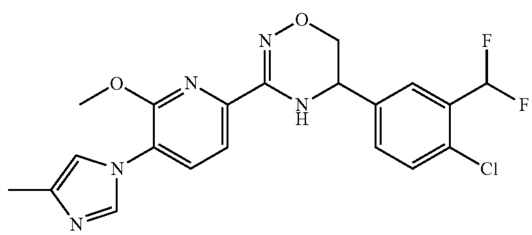 [SMILES: COc1nc(C2=NOCC(c3ccc(Cl)c(C(F)F)c3)N2)ccc1-n1cnc(C)c1] | (−)-5-(4-chloro-3-(difluoromethyl)phenyl)-3-(6-methoxy-5-(4-methyl-1H-imidazol-1-yl)pyridin-2-yl)-5,6-dihydro-4H-1,2,4-oxadiazine |
| 270B | 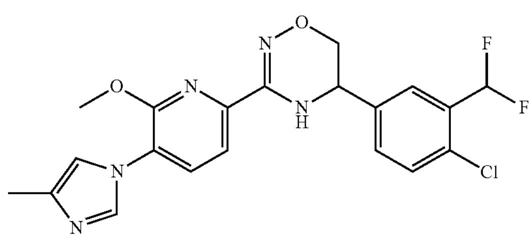 [SMILES: COc1nc(C2=NOCC(c3ccc(Cl)c(C(F)F)c3)N2)ccc1-n1cnc(C)c1] | (+)-5-(4-chloro-3-(difluoromethyl)phenyl)-3-(6-methoxy-5-(4-methyl-1H-imidazol-1-yl)pyridin-2-yl)-5,6-dihydro-4H-1,2,4-oxadiazine |

Additional exemplary Oxadizine Compounds are shown in Table I-1.

TABLE I-1

Additional Exemplary Oxadiazine Compounds

| Compound of Example | Structure | Name |
|---|---|---|
| 212A | 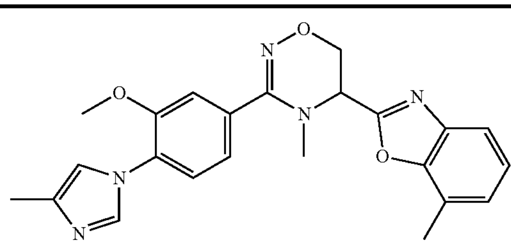 | (+)-2-(3-(3-methoxy-4-(4-methyl-1H-imidazol-1-yl)phenyl)-4-methyl-5,6-dihydro-4H-1,2,4-oxadiazin-5-yl)-7-methylbenzo[d]oxazole |

TABLE I-1-continued

Additional Exemplary Oxadiazine Compounds

| Compound of Example | Structure | Name |
|---|---|---|
| 212B | 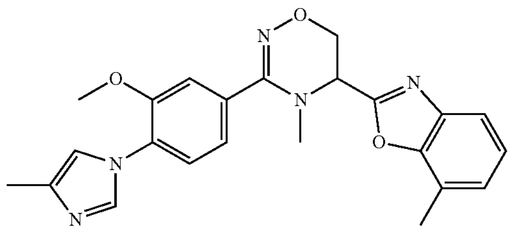 [SMILES: COc1cc(C2=NOCC(c3nc4cccc(C)c4o3)N2C)ccc1-n1cnc(C)c1] | (−)-2-(3-(3-methoxy-4-(4-methyl-1H-imidazol-1-yl)phenyl)-4-methyl-5,6-dihydro-4H-1,2,4-oxadiazin-5-yl)-7-methylbenzo[d]oxazole |
| 214A | 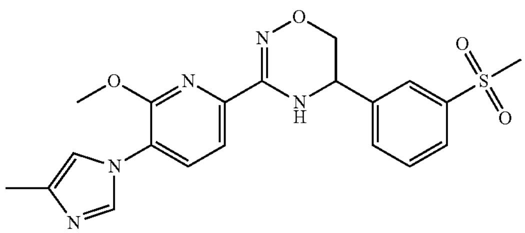 | (−)-3-(6-methoxy-5-(4-methyl-1H-imidazol-1-yl)pyridin-2-yl)-5-(3-(methylsulfonyl)phenyl)-5,6-dihydro-4H-1,2,4-oxadiazine |
| 214B | 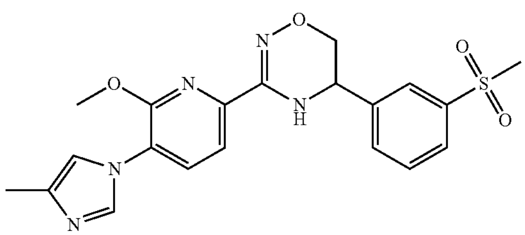 | (+)-3-(6-methoxy-5-(4-methyl-1H-imidazol-1-yl)pyridin-2-yl)-5-(3-(methylsulfonyl)phenyl)-5,6-dihydro-4H-1,2,4-oxadiazine |
| 217A | 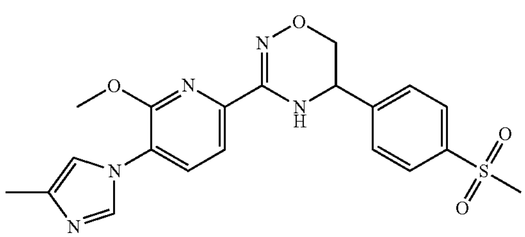 | (−)-3-(6-methoxy-5-(4-methyl-1H-imidazol-1-yl)pyridin-2-yl)-5-(4-(methylsulfonyl)phenyl)-5,6-dihydro-4H-1,2,4-oxadiazine |
| 217B | 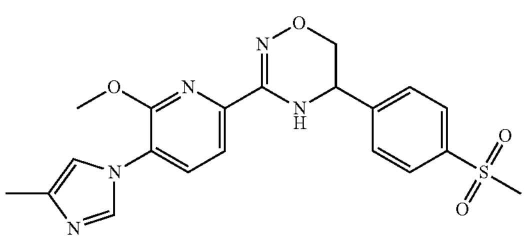 | (+)-3-(6-methoxy-5-(4-methyl-1H-imidazol-1-yl)pyridin-2-yl)-5-(4-(methylsulfonyl)phenyl)-5,6-dihydro-4H-1,2,4-oxadiazine |
| 246A | 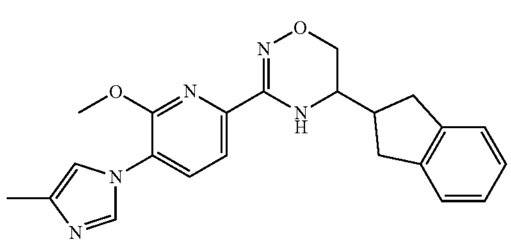 [SMILES: COc1nc(C2=NOCC(C3Cc4ccccc4C3)N2)ccc1-n1cnc(C)c1] | (−)-5-(2,3-dihydro-1H-inden-2-yl)-3-(6-methoxy-5-(4-methyl-1H-imidazol-1-yl)pyridin-2-yl)-5,6-dihydro-4H-1,2,4-oxadiazin |

TABLE I-1-continued

Additional Exemplary Oxadiazine Compounds

| Compound of Example | Structure | Name |
|---|---|---|
| 246B | 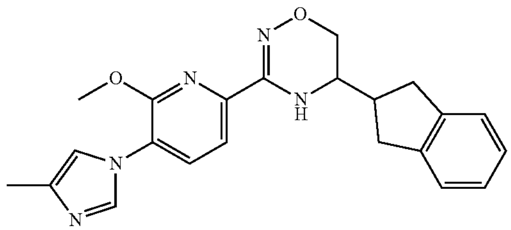 [SMILES: COc1nc(C2=NOCC(C3Cc4ccccc4C3)N2)ccc1-n1cnc(C)c1] | (+)-5-(2,3-dihydro-1H-inden-2-yl)-3-(6-methoxy-5-(4-methyl-1H-imidazol-1-yl)pyridin-2-yl)-5,6-dihydro-4H-1,2,4-oxadiazine |
| 256A | 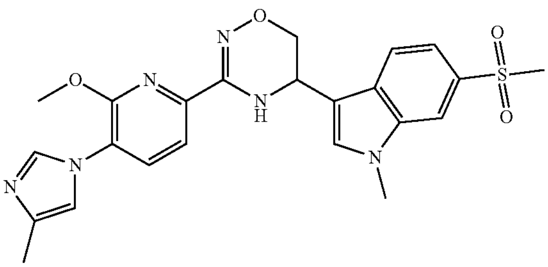 [SMILES: COc1nc(C2=NOCC(c3cn(C)c4cc(S(C)(=O)=O)ccc34)N2)ccc1-n1cnc(C)c1] | (−)-3-(6-methoxy-5-(4-methyl-1H-imidazol-1-yl)pyridin-2-yl)-5-(1-methyl-6-(methylsulfonyl)-1H-indol-3-yl)-5,6-dihydro-4H-1,2,4-oxadiazine |
| 256B | 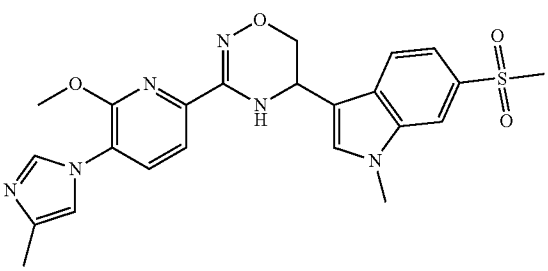 [SMILES: COc1nc(C2=NOCC(c3cn(C)c4cc(S(C)(=O)=O)ccc34)N2)ccc1-n1cnc(C)c1] | (+)-3-(6-methoxy-5-(4-methyl-1H-imidazol-1-yl)pyridin-2-yl)-5-(1-methyl-6-(methylsulfonyl)-1H-indol-3-yl)-5,6-dihydro-4H-1,2,4-oxadiazine |
| 268A | 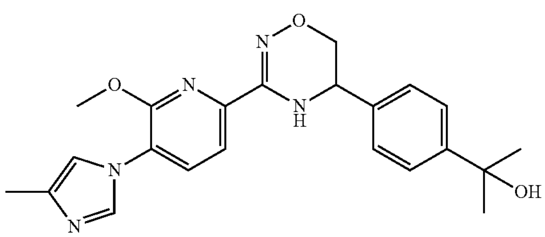 [SMILES: COc1nc(C2=NOCC(c3ccc(C(C)(C)O)cc3)N2)ccc1-n1cnc(C)c1] | (−)-2-(4-(3-(6-methoxy-5-(4-methyl-1H-imidazol-1-yl)pyridin-2-yl)-5,6-dihydro-4H-1,2,4-oxadiazin-5-yl)phenyl)propan-2-ol |
| 268B | 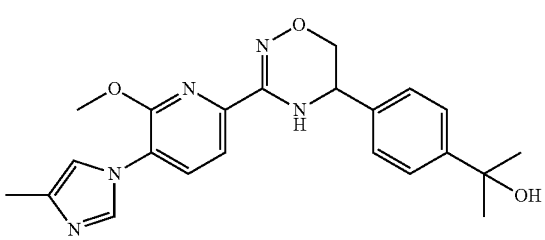 [SMILES: COc1nc(C2=NOCC(c3ccc(C(C)(C)O)cc3)N2)ccc1-n1cnc(C)c1] | (+)-2-(4-(3-(6-methoxy-5-(4-methyl-1H-imidazol-1-yl)pyridin-2-yl)-5,6-dihydro-4H-1,2,4-oxadiazin-5-yl)phenyl)propan-2-ol |

5.3 Methods for Making Oxadiazine Compounds

Methods useful for making the Oxadiazine Compounds are set forth in the Examples below and generalized in Schemes 1-4 for the compounds of Formula (I).

Schemes 1-4 represent general synthetic schemes for manufacturing Oxadiazine Compounds. These schemes are illustrative and are not meant to limit the possible techniques one skilled in the art may use to manufacture compounds disclosed herein. Different methods will be evident to those skilled in the art. Additionally, the various steps in the synthesis may be performed in an alternate sequence or order to provide the compound(s). Various modifications to these methods may be envisioned by those skilled in the art to achieve similar results to that of the inventors provided below. For example, optional protecting groups can be used as described, for example, in Greene et al., *Protective Groups in Organic Synthesis* (3$^{rd}$ ed. 1999).

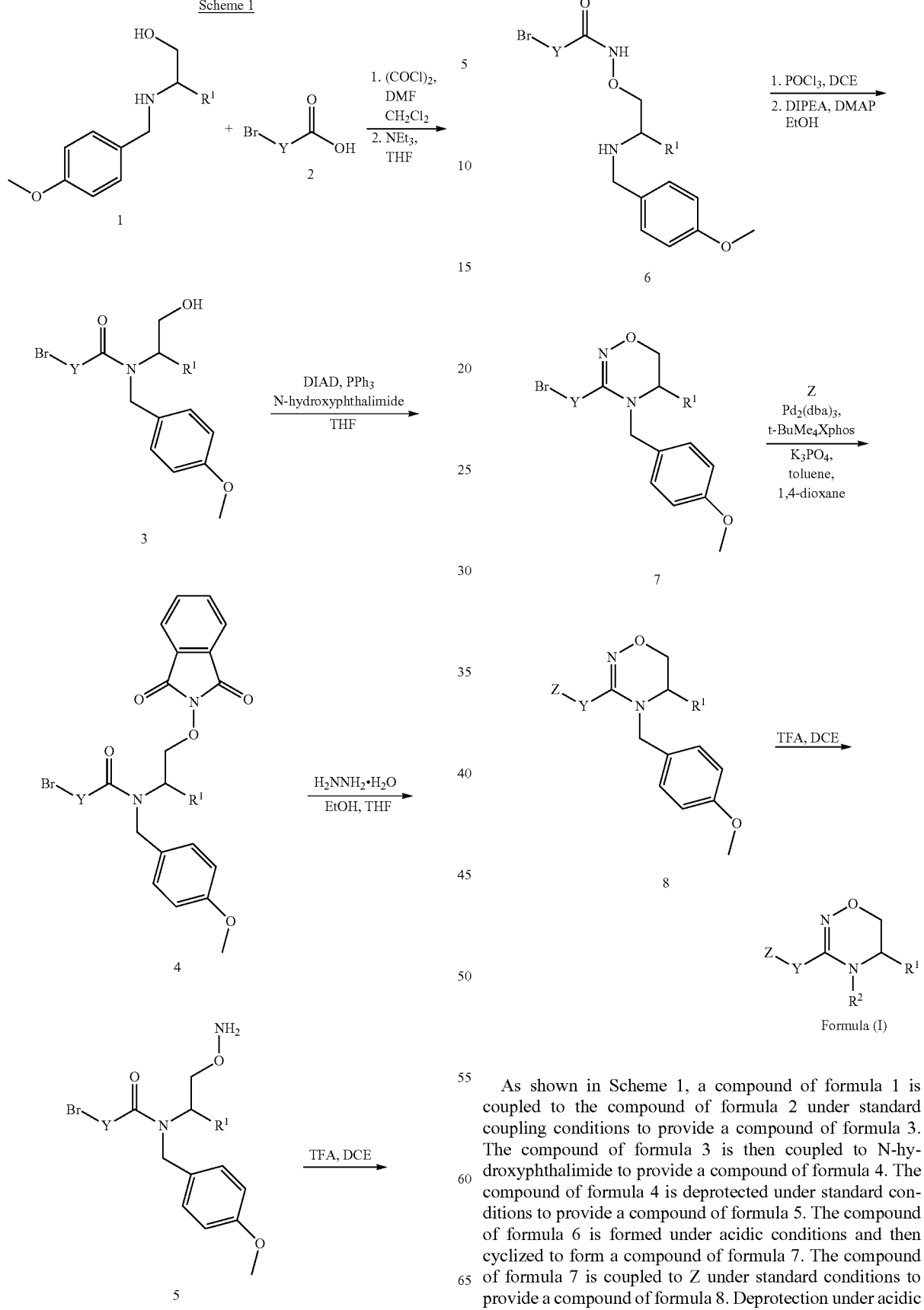

As shown in Scheme 1, a compound of formula 1 is coupled to the compound of formula 2 under standard coupling conditions to provide a compound of formula 3. The compound of formula 3 is then coupled to N-hydroxyphthalimide to provide a compound of formula 4. The compound of formula 4 is deprotected under standard conditions to provide a compound of formula 5. The compound of formula 6 is formed under acidic conditions and then cyclized to form a compound of formula 7. The compound of formula 7 is coupled to Z under standard conditions to provide a compound of formula 8. Deprotection under acidic conditions provides an Oxadiazine Compound.

Scheme 2

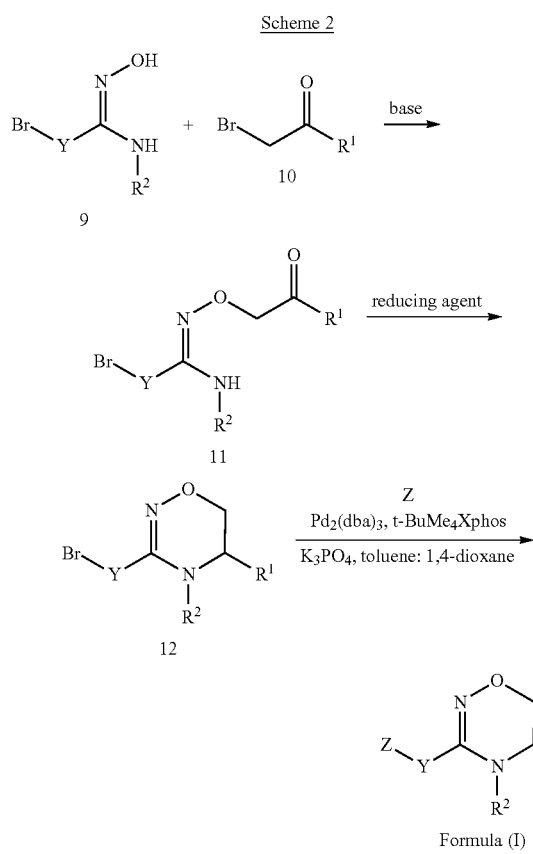

As shown in Scheme 2, a compound of formula 9 is reacted with a compound of formula 10 under basic conditions to provide a compound of formula 11. The compound of formula 11 is then reduced under standard conditions to provide a compound of formula 12. The compound of formula 12 is coupled to Z under standard conditions to provide an Oxadiazine Compound.

Scheme 3

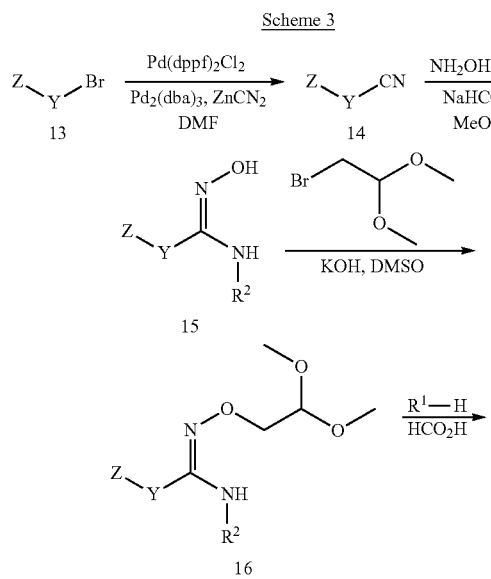

As shown in Scheme 3, a compound of formula 13 is reacted with $ZnCN_2$ to provide a compound of formula 14. The compound of formula 14 is then reacted with $NH_2OH$ under basic conditions to provide a compound of formula 15. The compound of formula 15 is coupled under standard conditions to provide a compound of formula 16. The compound of formula 16 is then cyclized in the presence of $R^1$—H to provide an Oxadiazine Compound.

Scheme 4

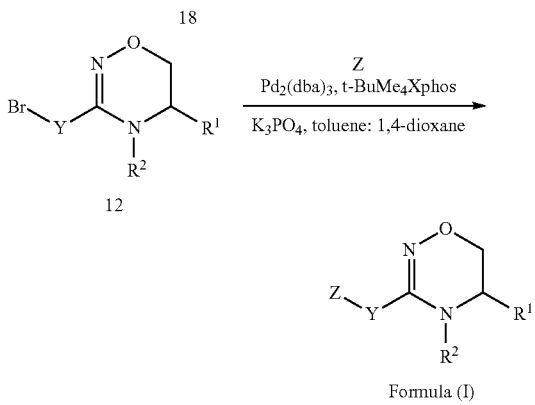

As shown in Scheme 4, a compound of formula 9 is coupled under standard conditions to provide a compound of formula 17. The compound of formula 17 is then cyclized under acidic conditions to form compound 18. The compound of formula 18 is reacted with $R^1$—H under acidic conditions to provide a compound of formula 12. The compound of formula 12 is then coupled to Z under standard conditions to provide an Oxadiazine Compound.

5.4 Pharmaceutical Compositions Comprising an Oxadiazine Compound

In another aspect, the present disclosure provides pharmaceutical compositions for treating, preventing, or ameliorating a symptom of a neurodegenerative disease in a subject having a neurodegenerative disease, wherein the pharmaceutical composition comprises a therapeutically effective amount of an Oxadiazine Compound, and a pharmaceutically acceptable carrier or vehicle.

As set out above, in some embodiments, Oxadiazine Compounds are provided in the form of pharmaceutically acceptable salts. These salts can be prepared in situ during the final isolation and purification of the compounds described herein, or by separately reacting a purified compound described herein in its free base or acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, laurylsulphonate, ammonium, amine salts and the like. See, for example, Berge, et al., (1977) "Pharmaceutical Salts", *J. Pharm. Sci.* 66:1-19.

The pharmaceutically acceptable salts of Oxadiazine Compounds include the conventional nontoxic salts or acid salts of the compounds, e.g., from non-toxic organic or inorganic acids. For example, such conventional nontoxic salts include those derived from inorganic acids, such as hydrochloride, hydrobromic, sulfuric, sulfamic, phosphoric, nitric, and the like; and the salts prepared from organic acids, such as acetic, butionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic and the like.

In general, a suitable dose of an Oxadiazine Compound will be in the range of 0.01 to 100 mg per kilogram body weight of the recipient per day or in the range of 0.2 to 10 mg per kilogram body weight per day. The desired dose can be administered once daily, but may be dosed as two, three, four, five, six or more sub-doses administered at appropriate intervals throughout the day.

The concentration of compounds included in compositions used in the methods described herein can range from about 1 nM to about 100 μM. Effective doses are believed to range from about 10 picomole/kg to about 100 micromole/kg.

An Oxadiazine Compound can be administered as the sole active agent, or in combination with other known therapeutics to be beneficial in the treatment of neurodegenerative diseases. In any event, the administering physician can provide a method of treatment that is prophylactic or therapeutic by adjusting the amount and timing of drug administration on the basis of observations of one or more symptoms (e.g., motor or cognitive function as measured by standard clinical scales or assessments) of the disease being treated.

Details on techniques for formulation and administration are well described in the scientific and patent literature, see, e.g., Remington: The Science and Practice of Pharmacy (2 Volumes), (22nd Edition, 2012), Pharmaceutical Press ("Remington's"). After a pharmaceutical composition has been formulated in an acceptable carrier, it can be placed in an appropriate container and labeled for treatment of an indicated condition. For administration of an Oxadiazine Compound, such labeling would include, e.g., instructions concerning the amount, frequency, and method of administration.

The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration. The amount of active ingredient, which can be combined with a carrier or vehicle material to produce a single dosage form will generally be that amount of the compound which produces a therapeutic effect. Generally, out of 100%, this amount will range from about 1% to about 99% of active ingredient, preferably from about 5% to about 70%, most preferably from about 10% to about 30%.

The compounds and pharmaceutical compositions described herein can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved.

Methods of preparing these formulations or compositions include the step of bringing into association a compound described herein with the carrier and, optionally, one or more accessory ingredients. In general, the formulations are prepared by uniformly and intimately bringing into association a compound described herein with liquid carriers, or finely divided solid carriers, or both, and then, if necessary, shaping the product.

When an Oxadiazine Compound is administered as pharmaceuticals to humans and animals, it can be given per se or as a pharmaceutical composition containing, for example, 0.1% to 99.5% (more preferably, 0.5% to 90%) of active ingredient in combination with a pharmaceutically acceptable carrier.

The pharmaceutical compositions described herein can be administered in a variety of dosage forms including, but not limited to, a solid dosage form, a liquid dosage form, an oral dosage form, a parenteral dosage form, an intranasal dosage form, a suppository, a lozenge, a troche, a buccal dosage form, a controlled release dosage form, a pulsed release dosage form, an immediate release dosage form, an intravenous solution, a suspension or combinations thereof.

Oral Formulations and Administration

Pharmaceutical formulations described herein suitable for oral administration can be in the form of capsules, cachets, pills, tablets, caplet, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes and the like, each containing a predetermined amount of a compound described herein as an active ingredient. The dosage can be an oral dosage form that is a controlled release dosage form. An Oxadiazine Compound can also be administered as a bolus, electuary or paste.

In solid dosage forms described herein for oral administration (capsules, tablets, pills, dragees, powders, granules and the like), the active ingredient is mixed with one or more pharmaceutically acceptable carriers and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, sodium carbonate, and sodium starch glycolate; solution retarding agents, such as paraffin; absorption accelerators, such as quaternary ammonium compounds; wetting agents, such as, for example, cetyl alcohol, glycerol monostearate, and polyethylene oxide-polybutylene oxide copolymer; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions can also comprise buffering agents. Solid compositions of a similar type can also be employed as fillers in soft and hard-filled gelatin capsules using such excipients as lactose or milk sugars, as well as high molecular weight polyethylene glycols and the like.

A tablet can be made by compression or molding, optionally with one or more accessory ingredients. Compressed tablets can be prepared using a binder (for example, gelatin or hydroxybutylmethyl cellulose), lubricant, inert diluent, preservative, disintegrant (for example, sodium starch glycolate or cross-linked sodium carboxymethyl cellulose), surface-active or dispersing agent. Molded tablets can be made by molding in a suitable machine a mixture of the powdered compound moistened with an inert liquid diluent.

Tablets, and other solid dosage forms of the pharmaceutical compositions described herein, such as dragees, capsules, pills and granules, can optionally be scored or prepared with coatings and shells, such as enteric coatings and other coatings well known in the pharmaceutical-formulating art. They can also be formulated so as to provide slow or controlled release of the active ingredient therein using, for example, hydroxybutylmethyl cellulose in varying proportions to provide the desired release profile, other polymer matrices, liposomes and/or microspheres. They can be sterilized by, for example, filtration through a bacteria-retaining filter, or by incorporating sterilizing agents in the form of sterile solid compositions, which can be dissolved in sterile water, or some other sterile injectable medium immediately before use. These compositions can also optionally contain opacifying agents and may be of a composition that they release the active ingredient(s) only, or preferentially, in a certain portion of the gastrointestinal tract, optionally, in a delayed manner Examples of embedding compositions which can be used include polymeric substances and waxes. The active ingredient can also be in micro-encapsulated form, if appropriate, with one or more of the above-described excipients.

Capsules for oral use include hard gelatin capsules in which the active ingredient is mixed with a solid diluent, and soft gelatin capsules, wherein the active ingredients is mixed with water or an oil, such as peanut oil, liquid paraffin or olive oil.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Liquid dosage forms for oral administration of the compounds described herein include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isobutyl alcohol, ethyl carbonate, ethyl acetate, benzyl alcohol, benzyl benzoate, butylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Additionally, cyclodextrins, e.g., hydroxybutyl-β-cyclodextrin, may be used to solubilize compounds.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar and tragacanth, and mixtures thereof.

Besides inert diluents, the oral compositions can also include adjuvants, such as wetting agents, emulsifying and suspending agents, sweetening, flavoring, coloring, perfuming and preservative agents.

Pharmaceutical preparations for oral use can be obtained through combination of an Oxadiazine Compound with a solid excipient, optionally grinding a resultant mixture, and processing the mixture of granules, after adding suitable additional compounds, if desired, to obtain tablets or dragee cores. Suitable solid excipients in addition to those previously mentioned are carbohydrate or protein fillers that include, but are not limited to, sugars, including lactose, sucrose, mannitol, or sorbitol; starch from corn, wheat, rice, potato, or other plants; cellulose, such as methyl cellulose, hydroxypropylmethyl-cellulose or sodium carboxymethylcellulose; and gums including arabic and tragacanth; as well as proteins, such as gelatin and collagen. If desired, disintegrating or solubilizing agents can be added, such as the cross-linked polyvinyl pyrrolidone, agar, alginic acid, or a salt thereof, such as sodium alginate.

Pharmaceutical preparations for oral use can be presented as aqueous or liposome formulations. Aqueous suspensions can contain an Oxadiazine Compound in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents, such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives, such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending an Oxadiazine Compound in a vegetable oil, such as arachis oil, olive oil, sesame oil or coconut oil, or in a mineral oil, such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant, such as ascorbic acid. As an example of an injectable oil vehicle, see Minto, *J. Pharmacol. Exp. Ther.* 281:93-102, 1997. The pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

Parenteral Formulations and Administration

In another embodiment, an Oxadiazine Compound can be administered parenterally, such as intravenous (IV) or intramuscular (IM) administration. The formulations for administration will commonly comprise a solution of an Oxadiazine Compound dissolved in a pharmaceutically acceptable carrier. Administration of an Oxadiazine Compound to any of the above mentioned sites can be achieved by direct injection of the pharmaceutical composition comprising the Oxadiazine Compound or by the use of infusion pumps. The pharmaceutical compositions can be formulated in solid form and re-dissolved or suspended immediately prior to use. Lyophilized forms are also included. The injection can be, for example, in the form of a bolus injection or continuous infusion (e.g., using infusion pumps) of pharmaceutical composition.

Pharmaceutical compositions suitable for parenteral administration comprise one or more compounds described herein in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Among the acceptable vehicles and solvents that can be employed for formulation and/or reconstitution are water (e.g., water for injection) and Ringer's solution, an isotonic sodium chloride. In addition, sterile fixed oils can conventionally be employed as a solvent or suspending medium. For this purpose, any bland fixed oil can be employed including synthetic mono- or diglycerides. In addition, fatty acids, such as oleic acid can likewise be used in the preparation of injectables. These solutions are sterile and generally free of undesirable matter. These formulations may be sterilized by conventional, well known sterilization techniques such as gamma-radiation or electron beam sterilization. The formulations can contain pharmaceutically acceptable auxiliary substances as required to approximate physiological conditions, such as pH adjusting and buffering agents, toxicity adjusting agents, e.g., sodium acetate, sodium chloride, potassium chloride, calcium chloride, sodium lactate and the like. The concentration of an Oxadiazine Compound in these formulations can vary widely, and will be selected primarily based on fluid volumes, viscosities, body weight, and the like, in accordance with the particular mode of administration selected and the subject's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In some embodiments, an Oxadiazine Compound can be administered by introduction into the central nervous system of the subject, e.g., into the cerebrospinal fluid of the subject. The formulations for administration will commonly comprise a solution of the Oxadiazine Compound dissolved in a pharmaceutically acceptable carrier. In certain aspects, the Oxadiazine Compound is introduced intrathecally, e.g., into a cerebral ventricle, the lumbar region, or the cisterna magna.

In some embodiments, the pharmaceutical composition comprising an Oxadiazine Compound is administered into a subject intrathecally. As used herein, the term "intrathecal administration" is intended to include delivering a pharmaceutical composition comprising an Oxadiazine Compound directly into the cerebrospinal fluid of a subject, by techniques including lateral cerebroventricular injection through a borehole or cisternal or lumbar puncture or the like (described in Lazorthes et al., Advances in Drug Delivery Systems and Applications in Neurosurgery, 1991, 18:143-192 and Omaya et al., Cancer Drug Delivery, 1984, 1:169-179, the contents of which are incorporated herein by reference). The term "lumbar region" is intended to include the area between the third and fourth lumbar (lower back) vertebrae. The term "cisterna magna" is intended to include the area where the skull ends and the spinal cord begins at the back of the head. The term "cerebral ventricle" is intended to include the cavities in the brain that are continuous with the central canal of the spinal cord. In some embodiments, the pharmaceutical composition is administered by injection into the cisterna magna, or lumbar area of a subject.

Depot Formulations and Administration

An Oxadiazine Compound can be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle. One strategy for depot injections includes the use of polyethylene oxide-polybutylene oxide copolymers, wherein the vehicle is fluid at room temperature and solidifies at body temperature.

Injectable depot forms can be made by forming microencapsule matrices of the subject compounds in biodegradable polymers, such as polylactide-polyglycolide. Depending on the ratio of drug to polymer, and the nature of the particular polymer employed, the rate of drug release can be controlled. Examples of other biodegradable polymers include poly (orthoesters) and poly (anhydrides). Depot injectable formulations can also be prepared by entrapping the drug in liposomes or microemulsions, which are compatible with body tissue.

Intranasal Formulations and Administration

For administration by inhalation, the compounds are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base, such as lactose or starch.

Other Formulations and Modes of Administration

For transmucosal administration (e.g., buccal, rectal, nasal, ocular, etc.), penetrants appropriate to the barrier to be permeated are used in the formulation. Such penetrants are generally known in the art.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid and polyanhydrides. Microcapsules of the foregoing polymers containing drugs are described in, for example, U.S. Pat. No. 5,075,109. Delivery systems also include non-polymer systems that are: lipids including sterols, such as cholesterol, cholesterol esters and fatty acids or neutral fats, such as mono-, di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an agent described herein is contained in a form within a matrix, such as those described in U.S. Pat. Nos. 4,452,775, 4,675,189, and 5,736,152, and (b) diffusional systems in which an active component permeates at a controlled rate from a polymer, such as described in U.S. Pat. Nos. 3,854,480, 5,133,974 and 5,407,686. In addition, pump-based hardware delivery systems can be used, some of which are adapted for implantation.

5.5 Treatment, Prevention or Amelioration of Symptoms of a Neurodegenerative Disease In another aspect, a method for treating a neurodegenerative disease is described, comprising administering to a subject an effective amount a pharmaceutical composition comprising an effective amount of an Oxadiazine Compound.

In some embodiments, the method for treating a neurodegenerative disease is a method for reducing or ameliorating a symptom of the neurodegenerative disease.

In some embodiments, a method for reducing or ameliorating a symptom of a neurological disease is described, comprising administering to a subject in need thereof an effective amount of an Oxadiazine Compound. Ameliorating or reducing the symptoms can be manifested in a variety of ways, for example, by improvement in cognitive function. Such improvement can be assessed relative to the cognitive function of the subject prior to being treated or being administered an Oxadiazine Compound or a pharmaceutical composition comprising an effective amount of an Oxadiazine Compound.

In some embodiments, a method for preventing a neurological disease is described, comprising administering to a subject in need thereof an effective amount of an Oxadiazine Compound.

In some embodiments, a method for stopping progression of a neurological disease is described, comprising administering to a subject in need thereof an effective amount of an Oxadiazine Compound.

Exemplary symptoms of neurological disease that can be reduced or ameliorated by administration of an Oxadiazine Compound include, but are not limited to, loss of memory, loss of cognition, loss of reasoning and/or loss of judgment. The loss of each of memory, cognition, reasoning and/or judgment can be progressive or sudden. Dementia is an exemplary symptom of neurodegenerative disease. Administration of an Oxadiazine Compound can reduce or improve one or more of these symptoms.

Exemplary cognitive functions that can be improved by administration of an Oxadiazine Compound are attention, learning, delayed memory, working memory, visual learning, speed of processing, vigilance, verbal learning, visual motor function, social cognition, long term memory or executive function.

In one embodiment, the neurodegenerative disease is Alzheimer's disease. In some embodiments, the neurodegenerative disease is early onset Alzheimer's disease. In some embodiments, the early onset Alzheimer's disease is autosomal dominant early onset Alzheimer's disease.

In some embodiments, the subject is 65 years or older. In some embodiments, the subject is 55 years old or younger, or 50 years old or younger. In some embodiments, the subject is older than 55 years and younger than 65 years. In some embodiments, the subject is older than 55 years.

In some embodiments, the neurodegenerative disease is panic disorder, obsessive compulsive disorder, delusional disorder, drug-induced psychosis, post-traumatic stress disorder, age-related cognitive decline, attention deficit/hyperactivity disorder, personality disorder of the paranoid type, personality disorder of the schizoid type, dyskinesia, choreiform condition, psychosis associated with Parkinson's disease, psychotic symptoms associated with Alzheimer's disease, mood disorder, or dementia.

In some embodiments, the neurodegenerative disease is cognitive impairment, myclonus, seizures, Parkinsonism, extrapyramidal signs (EPS), apraxia, dystonia, dementia with Lewy bodies (DLB), aphasia, visual agnosia, or ataxia.

In some embodiments, the subject has impaired cognitive function including one or more of attention, learning, delayed memory, working memory, visual learning, speed of processing, vigilance, verbal learning, visual motor function, social cognition, long term memory or executive function.

In some embodiments, the subject has a mutation in at least one gene selected from PSEN1, PSEN2 and APP. In some embodiments, the mutation in PSEN1, PSEN2 or APP is a missense mutation.

In some embodiments, the invention provides a method for treating or ameliorating a symptom of neurodegenerative disease (e.g., Alzheimer's disease) in a subject with an increased level of Aβ42 in cerebrospinal fluid, the method comprising administering to a subject in need thereof an effective amount of an Oxadiazine Compound. In such subject, the increased level of Aβ42 in cerebrospinal fluid can be detected relative to the level of Aβ42 in cerebrospinal fluid of a healthy subject.

In some embodiments, the invention provides a method for lowering Aβ42 concentration in a subject, the method comprising administering to a subject in need thereof an effective amount of an Oxadiazine Compound. In some embodiments, the subject has a lower Aβ42 concentration relative to a healthy subject.

In some embodiments, the invention provides a method for decreasing of Aβ42 concentration in a subject, the method comprising administering to a subject in need thereof an effective amount of an Oxadiazine Compound.

5.6 Kits

Described herein are kits that can simplify the administration of an Oxadiazine Compound to a subject. The kit can comprise one or more containers filled with one or more of the ingredients of the pharmaceutical compositions described herein. Optionally associated with such container(s) can be a notice in the form prescribed by a governmental agency regulating the manufacture, use or sale of pharmaceuticals or biological products, which notice reflects approval by the agency of manufacture, use or sale for human administration.

A typical kit comprises a unit dosage form of an Oxadiazine Compound. In one embodiment, the unit dosage form is a container, which can be sterile, containing an effective amount of an Oxadiazine Compound and a pharmaceutically acceptable carrier or vehicle. The kit can further comprise a label or printed instructions instructing the use of the Oxadiazine Compound to treat or prevent a neurodegenerative disease. The kit can also further comprise a unit dosage form of another prophylactic or therapeutic agent, for example, a container containing an effective amount of the other prophylactic or therapeutic agent. In one embodiment, the kit comprises a container containing an effective amount of an Oxadiazine Compound and an effective amount of another prophylactic or therapeutic agent. Examples of other prophylactic or therapeutic agents include, but are not limited to, those listed above.

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. The following examples contain additional information, exemplification and guidance which can be adapted to the practice of this invention in its various embodiments and equivalents thereof. The examples do not limit the scope of the invention described in the claims.

6. EXAMPLES

General Experimental Techniques

All reactions were carried out using commercial materials and reagents without further purification unless otherwise noted. All reactions were monitored by thin layer chromatography (TLC) on silica gel plates (Keiselgel 60 F254, Merck), high-performance liquid chromatography (HPLC), liquid chromatography mass spectrometry (LCMS) or ultraperformance liquid chromatography (UPLC). Visualisation of the spots on TLC plates was achieved by UV light and by staining the TLC plates in potassium permanganate and charring with a heat gun. LCMS: (Short Basic) column: XBridge C18 IS 2.5 µm 2.1×2.0 mm; Waters Alliance 2695 HPLC Pump (Flow: 1 mL/min); Waters 996 PDA 215-350 nm; run Time: 3.10 min; solvents: A) 10 mM ammonium bicarbonate pH 10, B) MeCN; gradient: 0% B to 0.18 min, 0-95% B to 2.00 min, hold at 95% B to 2.60 min; (Long Basic) Column. XBridge C18 3×100 3.5 um; Waters alliance 2695 HPLC pump (Flow 1 ml/min); Waters 2996 PDA 215-350 nm); run time: 11.0 min; solvents: A) 10 mM ammonium bicarbonate pH 10, B) MeCN; gradient: 5-95% B in 8.0 min, hold at 95% B to 11.0 min. UPLC: column: XBridge BEH C18 2.5 µm 2.1×50 mm; Waters Acquity (Flow 0.8 mL/min); Waters Acquity Auto sampler (UPLC LG 500 nm); (Short Basic) run Time: 1.30 min; solvents: A) 10 mM ammonium bicarbonate pH 10, B) MeCN; gradient: 2-98% B in 0.8 min, hold at 98% B to 1.30 min; (Long Basic) run time: 4.70 min; solvents: A) 10 mM ammonium bicarbonate pH 10, B) MeCN; gradient: 2-98% B in 4.0 min, hold at 98% B to 4.7 min. All products were characterised by $^1$H NMR. $^1$H NMR spectral data was recorded on a JEOL ECX300 MHz or JEOL ECX400 MHz spectrometer. Chemical shifts are expressed in parts per million values (ppm) and are designated as s (singlet); br s (broad singlet); d (doublet); t (triplet); q (quartet); quint (quintet) or m (multiplet). Coupling constants (J) are expressed as values in Hertz (Hz). Flash column chromatography was performed on silica gel using Fluorochem silicagel LC60A 40-63 micron and reagent grade heptane, ethyl acetate, dichloromethane, methanol and 2-propanol as eluent. Chiral preparative HPLC was carried out using a Waters 2525 Binary Gradient module with a Waters 2487 Dual absorbance detector (set at 254 and 210 nm) and Waters 2767 sample manager with Chiralpak IA, IB or IC column (20×250 mm) and HPLC grade tert-butylmethyl ether, methanol, heptane, ethanol and reagent grade diethyl amine and ethanolamine. Chiral analysis was carried out using a Waters Alliance 2695 HPLC Pump with a Waters 2487 dual wavelength PDA with Chiralpak IA, IB or IC column (0.6×250 mm) and HPLC grade tert-butylmethyl ether, methanol, heptane, ethanol and reagent grade diethyl amine and ethanolamine.

Reactions were Monitored and Final Products were Characterized Using One of the Following Methods:

LCMS A, standard conditions: Waters HPLC system equipped with an Alliance 2695 main module, Waters 2998 diode array detector and ZQ micromass ESI-MS detector. Mobile phase A: $H_2O$, mobile phase B: $CH_3CN$ were prepared with 0.1% formic acid (FA). HPLC conditions were: XTerra RP18 column, 3.0×50 mm, 3.5 µm; 0-1 min isocratic (5% B), 1-6 min gradient (5-95% B), 6-7 min isocratic (95% B); flow rate: 1 mL/min; UV channel: 254 nm. LCMS B, standard conditions: Waters HPLC system equipped with an Alliance 2695 main module, Waters 996 diode array detector and ZQ micromass ESI-MS detector. Mobile phase A: $H_2O$ (10.0 mM $NH_4HCO_2$), mobile phase B: $CH_3CN$. HPLC conditions were: XBridge C18 column, 4.6×30 mm, 3.5 µm, 0.0-0.2 min isocratic (5% B), 0.2-2.0 min. gradient (5-100% B), 3.0-3.0 min isocratic (100% B); flow rate: 3.0 mL/min; UV channel: 254 nm.

Purification of Some Racemic Products was Performed Using the Following Instruments:

Semi preparative HPLC A: Gilson 215 system equipped with a Waters 996 diode array detector and a Waters 2525 pump.

Products Homogeneity and Enantiomeric Excess Determination were Performed Using the Following Instrument:

Analytical HPLC A: Agilent 1100 HPLC system equipped with an Agilent G1315A diode array detector.

Nuclear Magnetic Resonance:

NMR spectra were recorded on Bruker Avance II Ultra shield spectrometer (500 MHz).

Optical Rotation:

Optical rotations were taken on a Rudolph Research Analytical; Autopol III automatic polarimeter; Model A21101 AIII/2W.

Analytical Methods:

LCMS method A: column: Waters XSelect (C18, 30×2.1 mm, particle size 3.5μ); flow: 1 mL/min; Column temp: 25° C.; Eluent A: 95% acetonitrile+5% 10 mM ammoniumbicarbonate in water; Eluent B: 10 mM ammoniumbicarbonate in water pH=9.0; Linear Gradient: t=0 min 5% A, t=1.6 min 98% A, t=3 min 98% A; detection: DAD (220-320 nm). LCMS method B: Column: Phenomenex Gemini NX (C18, 50×2.0 mm, particle size: 3μ); Flow: 0.8 mL/min; Column temp: 25° C.; Eluent A: 95% acetonitrile+5% 10 mM ammoniumbicarbonate in water; Eluent B: 10 mM ammoniumbicarbonate in water pH=9.0; Linear Gradient: t=0 min 5% A, t=3.5 mM 98% A, t=6 mM 98% A; detection: DAD (220-320 nm). LCMS method D: Column. Waters XSelect (C18, 50×2.1 mm, particle size: 3.5μ); Flow: 0.8 mL/min; Column temp: 25° C.; Eluent A: 95% acetonitrile+5% 10 mM ammoniumbicarbonate in water; Eluent B: 10 mM ammoniumbicarbonate in water pH=9.0; Linear Gradient: t=0 min 5% A, t=3.5 mM 98% A, t=6 mM 98% A; detection: DAD (220-320 nm).

Preparative Methods:

Basic preparative MPLC was performed on a Reveleris Prep system: column: Waters Xselect CSH (C18 145×25 mm, particle size 10μ); Flow: 40 mL/min; Column temp: room temperature; Eluent A: 99% acetonitrile+1% 10 mM ammoniumbicarbonate in water; Eluent B: 10 mM ammoniumbicarbonate in water pH=9.0), using the indicated gradient and detection wavelength.

Example 1

Synthesis of 5-bromo-6-methoxypicolinic acid

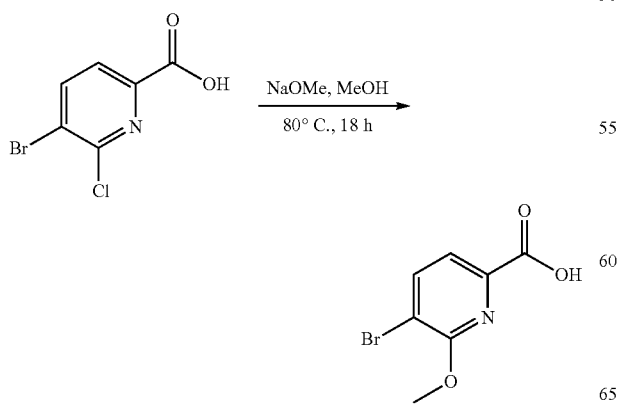

5-bromo-6-methoxypicolinic acid

A suspension of 5-bromo-6-chloropicolinic acid (15.0 g, 63.4 mmol, 1.0 equiv.) in MeOH (130 mL) at ambient temperature was treated with a 4.37 M sodium methoxide solution in MeOH (58.0 mL, 253 mmol, 4.0 equiv.). The resultant mixture was heated at 80° C. for 18 hours, resulting in a thick mixture. The reaction was diluted with MeOH (100 mL) and stirred at 80° C. for 24 hours. The reaction mixture was cooled to ambient temperature, acidified to pH=3 with concentrated aqueous HCl, diluted with water and extracted with EtOAc (three times). The combined organic layers were dried over MgSO$_4$, filtered and concentrated to afford a residue that was co-evaporated with DCM/hexanes (1:1 mixture, 200 mL, three times) to afford 5-bromo-6-methoxypicolinic acid (13.9 g, 94%) as a white solid. $^1$H NMR (500 MHz, CDCl$_3$) δ 10.22 (br s, 1H), 8.06 (d, J=7.7 Hz, 1H), 7.73 (d, J=7.7 Hz, 1H), 4.10 (s, 3H). LCMS (ES−) [M−H]+: 229.9/231.9.

Example 2

Synthesis of (R)-2-(Benzofuran-2-yl)-2-(4-methoxybenzylamino)ethanol

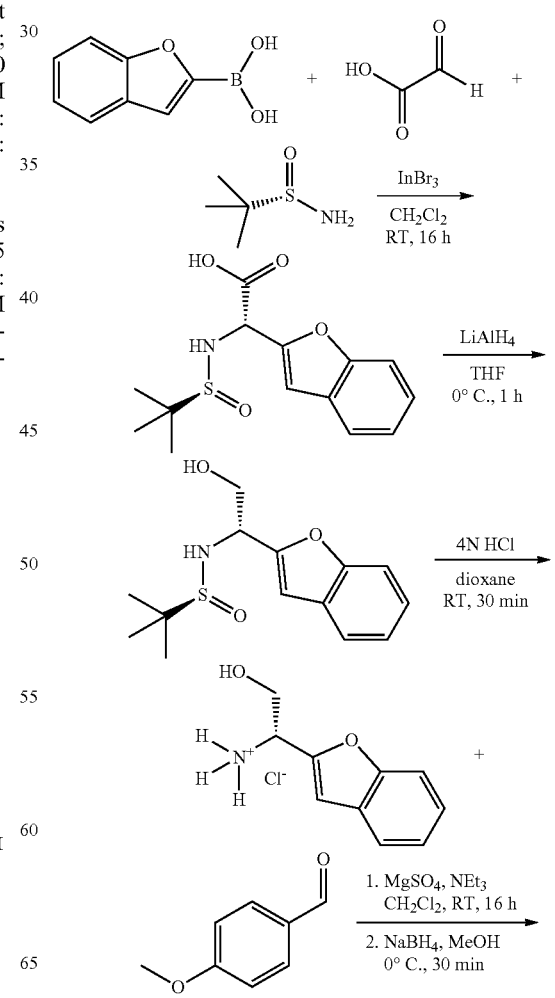

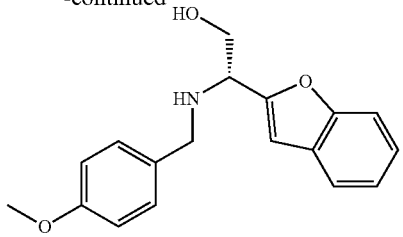

(S)-2-(Benzofuran-2-yl)-2-((S)-1,1-dimethylethyl-sulfinamido)acetic acid

A suspension of benzofuran-2-ylboronic acid (5.0 g, 30.9 mmol, 1.0 equiv), glyoxylic acid monohydrate (3.16 g, 34.3 mmol, 1.1 equiv) and (S)-2-methylpropane-2-sulfinamide (4.16 g, 34.3 mmol, 1.1 equiv) in anhydrous DCM (100 mL) at ambient temperature was treated with InBr₃ (1.22 g, 3.43 mmol, 0.11 equiv). The resultant mixture was stirred for 16 h at ambient temperature. To the mixture was added MgSO₄ (3 g), the suspension was stirred for 5 minutes and filtered through a pad of celite, which was washed with EtOAc. The filtrate was concentrated under vacuum to afford the corresponding intermediate as an orange solid that was used directly in the next step. LCMS (ES+) [M+H]+: 296.1.

(S)—N—((R)-1-(Benzofuran-2-yl)-2-hydroxyethyl)-2-methylpropane-2-sulfinamide A THF (80 mL) solution of crude (S)-2-(benzofuran-2-yl)-2-((S)-1,1-dimethylethylsulfinamido)acetic acid from the previous reaction was slowly added to a cooled (0° C.) suspension of LiAlH₄ (5.86 g, 154 mmol, 5.0 equiv) in THF (120 mL). The resultant mixture was stirred for 1 h at 0° C. before being diluted with Et₂O (300 mL). While maintained at 0° C. the reaction mixture was quenched by sequential addition of water (5.60 mL), sodium hydroxide (2 N, 5.60 mL) and water (16.8 mL). The mixture was allowed to warm to RT, stirred for 1 hour and MgSO₄ was added. The mixture was stirred for 10 minutes, and the solids were filtered and rinsed thoroughly with 10% MeOH/DCM (500 mL). The filtrate was concentrated and the residue was purified by normal phase chromatography on silica (0-5% MeOH/DCM) to afford the alcohol as pale yellow oil (1.85 g, 21%). ¹H NMR (500 MHz, CDCl₃) δ 7.54 (ddd, J=7.6, 1.4, 0.7 Hz, 1H), 7.47-7.43 (m, 1H), 7.30-7.26 (m, 1H), 7.25-7.21 (m, 1H), 6.65 (t, J=0.9 Hz, 1H), 4.69-4.64 (m, 1H), 4.14 (dd, J=11.9, 3.6 Hz, 1H), 3.95-3.88 (m, 2H), 1.29 (s, 9H). LCMS (ES+) [M+H]+: 282.0.

(R)-1-(Benzofuran-2-yl)-2-hydroxyethanaminium chloride (S)—N—((R)-1-(benzofuran-2-yl)-2-hydroxyethyl)-2-methylpropane-2-sulfinamide (1.85 g, 6.58 mmol, 1.0 equiv) was dissolved in a 4 N solution of HCl in 1,4-dioxane (40.0 mL) at ambient temperature. The resultant mixture was stirred at ambient temperature for 30 minutes and concentrated to dryness to afford the hydrochloride salt which was used directly in the next step. LCMS (ES+) [M–H₂O]+: 161.0.

(R)-2-(Benzofuran-2-yl)-2-(4-methoxybenzylamino)ethanol

A solution of crude (R)-1-(benzofuran-2-yl)-2-hydroxyethanaminium chloride from previous step in DCM (40.0 mL) at ambient temperature was treated successively with triethylamine (1.83 mL, 13.2 mmol, 2.0 equiv), MgSO₄ (5.6 g) and anisaldehyde (800 μL, 6.58 mmol, 1.0 equiv). The resultant suspension was stirred for 16 hours at ambient temperature and filtered through a pad of celite which was washed with EtOAc. The filtrate was concentrated under vacuum to afford the corresponding imine intermediate. This intermediate was dissolved in MeOH (50.0 mL) and cooled to 0° C. Solid NaBH₄ (730 mg, 19.7 mmol, 3.0 equiv) was added portion wise over 5 minutes. The resultant mixture was stirred for 30 minutes at 0° C., then quenched by the slow addition of a saturated aqueous solution of NaHCO₃. Water and DCM were added. The layers were separated, and the aqueous layer was extracted with DCM twice. The combined organic layers were dried over MgSO₄, filtered and concentrated to afford a residue that was purified by normal phase chromatography on silica (0-10% MeOH/DCM) to afford (R)-2-(Benzofuran-2-yl)-2-(4-methoxybenzylamino)ethanol (1.96 g, 68%) as an off-white solid. ¹H NMR (500 MHz, CDCl₃) δ 7.55 (ddd, J=7.5, 1.4, 0.7 Hz, 1H), 7.49-7.43 (m, 1H), 7.31-7.26 (m, 1H), 7.25-7.21 (m, 3H), 6.88-6.82 (m, 2H), 6.63-6.62 (m, 1H), 3.97 (dd, J=8.4, 4.4 Hz, 1H), 3.89-3.73 (m, 6H), 3.70-3.61 (m, 1H). LCMS (ES+) [M+H]+: 298.1.

Example 3

Synthesis of (R)-5-(Benzofuran-2-yl)-3-(5-bromo-6-methoxypyridin-2-yl)-4-(4-methoxybenzyl)-5,6-dihydro-4H-1,2,4-oxadiazine

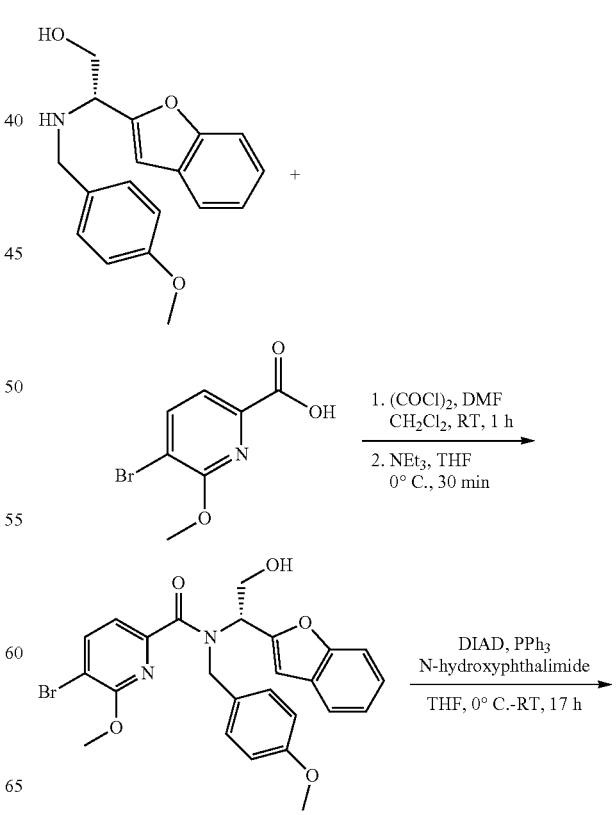

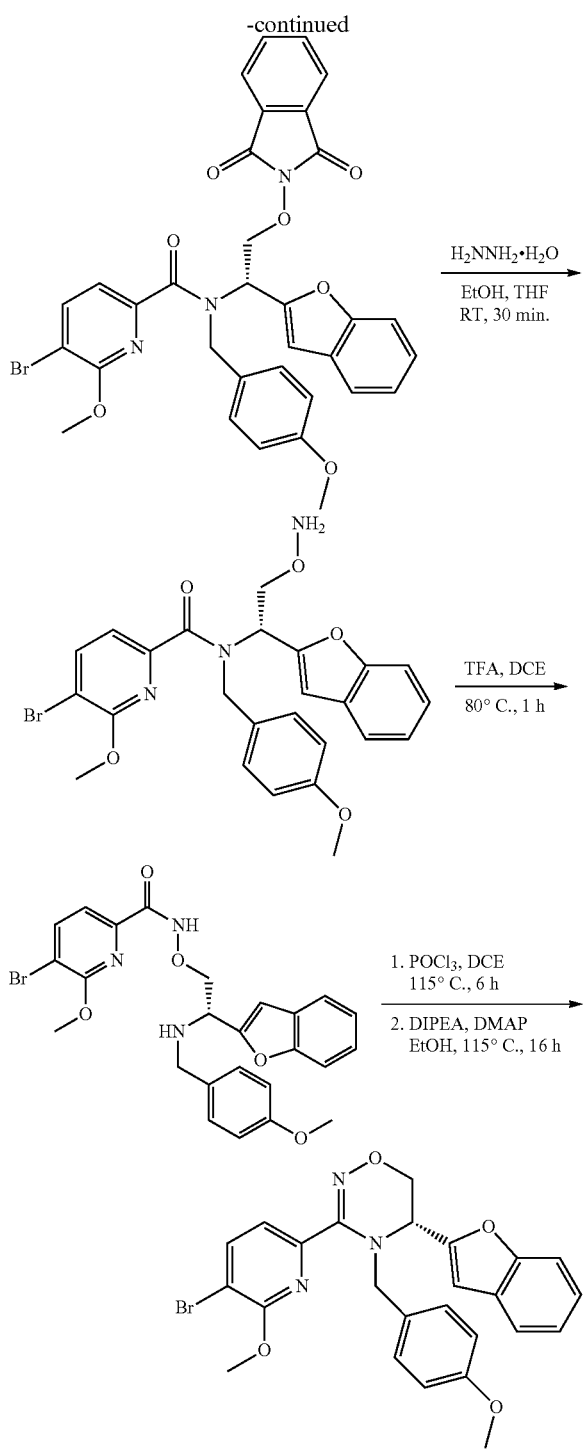

(R)—N-(1-(Benzofuran-2-yl)-2-hydroxyethyl)-5-bromo-6-methoxy-N-(4-methoxybenzyl) picolinamide A solution of 5-bromo-6-methoxypicolinic acid (1.08 g, 4.45 mmol, 1.05 equiv.) in DCM (40.0 mL) at ambient temperature was treated with a catalytic amount of DMF (4 drops) and oxalyl chloride (1.17 mL, 13.4 mmol, 3.0 equiv.). The resultant mixture was stirred at ambient temperature for 1 h at which point LCMS monitoring showed completion of the reaction. The mixture was concentrated, diluted with anhydrous THF (20.0 mL), concentrated again and dried under high vacuum for 1 hour. The residue was diluted in anhydrous THF (20.0 ml), treated with triethylamine (1.86 mL, 13.4 mmol, 3.0 equiv.) and cooled to 0° C. A solution of (R)-2-(benzofuran-2-yl)-2-(4-methoxybenzylamino)ethanol (1.32 g, 4.45 mmol, 1.0 equiv.) in THF (20.0 ml) was quickly added and the resultant mixture was stirred at 0° C. for 30 minutes. A saturated aqueous solution of NaHCO$_3$ and EtOAc were then successively added. The layers were separated, and the aqueous layer was extracted with EtOAc twice. The combined organic layers were dried over MgSO$_4$, filtered and concentrated. The residue was purified by normal phase chromatography on silica (0-40% EtOAc/hexanes) to afford amide as white foam (1.78 g, 78%). LCMS (ES+) [M+H]+: 511.2/513.2.

(R)—N-(1-(benzofuran-2-yl)-2-(1, 3-dioxoisoindolin-2-yloxy)ethyl)-5-bromo-6-methoxy-N-(4-methoxybenzyl)picolinamide DIAD (828 uL, 4.18 mmol, 1.2 equiv.) was added to a solution of triphenylphosphine (PPh$_3$) (1.10 g, 4.18 mmol, 1.2 equiv.), (R)—N-(1-(benzofuran-2-yl)-2-hydroxyethyl)-5-bromo-6-methoxy-N-(4-methoxybenzyl)picolinamide (1.78 g, 3.48 mmol, 1.0 equiv.) and N-hydroxylphtalimide (681 mg, 4.18 mmol, 1.2 equiv.) in THF (20.0 mL) at 0° C. The resultant mixture was kept at 0° C. for 1 h, then warmed to ambient temperature and stirred for 16 h. EtOAc was added, and the organic layer was washed with 1 N aqueous NaOH (twice), water, and brine, dried over MgSO$_4$, filtered, and concentrated. The residue was purified by normal phase chromatography on silica (0-40% EtOAc/hexanes) to afford product as beige foam (1.61 g, 71%). LCMS (ES+) [M+H]+: 656.2/658.2.

(R)—N-(2-(Aminooxy)-1-(benzofuran-2-yl)ethyl)-5-bromo-6-methoxy-N-(4-methoxybenzyl) picolinamide A suspension of (R)—N-(1-(benzofuran-2-yl)-2-(1,3-dioxoisoindolin-2-yloxy)ethyl)-5-bromo-6-methoxy-N-(4-methoxybenzyl)picolinamide (1.61 g, 2.45 mmol, 1.0 equiv.) in ethanol (90%, 15.0 mL) and THF (2.25 mL) at ambient temperature was treated with hydrazine hydrate (50-60%, 2.50 mL). The resultant mixture was stirred for 30 minutes, then water was added. The mixture was extracted with EtOAc (three times), and the combined organic layers were dried over MgSO$_4$, filtered, and concentrated to afford product (1.24 g, 96%) as off-white foam that was used directly in the next step. LCMS (ES+) [M+H]+: 526.0/528.0.

(S)—N-(2-(Benzofuran-2-yl)-2-(4-methoxybenzylamino)ethoxy)-5-bromo-6-methoxy picolinamide A solution of (R)—N-(2-(aminooxy)-1-(benzofuran-2-yl)ethyl)-5-bromo-6-methoxy-N-(4-methoxybenzyl)picolinamide (1.24 g, 2.34 mmol, 1.0 equiv.) in DCE (20.0 mL) was treated with TFA (1.00 mL). The resultant mixture was stirred at 80° C. for 1 h, then cooled to ambient temperature and concentrated to dryness. The residue was diluted with EtOAc, washed with saturated aqueous solution of NaHCO$_3$ and brine, dried over MgSO$_4$, filtered and concentrated to afford product (1.21 g, 98%) as pale yellow oil that was used directly in the next step. LCMS (ES+) [M+H]+: 526.1/528.0.

(R)-5-(Benzofuran-2-yl)-3-(5-bromo-6-methoxypyridin-2-yl)-4-(4-methoxybenzyl)-5,6-dihydro-4H-1,2,4-oxadiazine A solution of (S)—N-(2-(benzofuran-2-yl)-2-(4-methoxybenzylamino)ethoxy)-5-bromo-6-methoxypicolinamide (1.20 g, 2.28 mmol, 1.0 equiv.) in anhydrous DCE (20.0 ml) at ambient temperature was treated with POCl$_3$ (3.2 mL, 34.3 mmol, 15.0 equiv.). The vial was sealed and heated at 115° C. for 6 h. The reaction mixture was evaporated, dried under high vacuum for 10 minutes, dissolved in EtOH (15.0 mL) and treated with DIPEA (2.0 mL, 11.5 mmol, 5.0 equiv.) and DMAP (140 mg, 1.15 mmol, 0.5 equiv.). The resultant mixture was heated to 115° C. for 16 h. The reaction mixture was cooled to ambient temperature and diluted with EtOAc. The organic layer was washed with 1 N aqueous NaOH, water (twice) and brine, dried over MgSO$_4$, filtered and concentrated. The residue was purified by normal phase chromatography on silica (0-30% EtOAc/hexanes) to afford (R)-5-(Benzofuran-2-yl)-3-(5-bromo-6-methoxypyridin-2-yl)-4-(4-methoxybenzyl)-5,6-dihydro-4H-1,2,4-oxadiazine (442 mg, 38%) as a pale orange foam. $^1$H NMR (500 MHz, CDCl$_3$) δ 7.88 (d, J=7.8 Hz, 1H), 7.56 (ddd, J=7.5, 1.4, 0.6 Hz, 1H), 7.46 (dd, J=8.1, 0.8 Hz, 1H), 7.31-7.27 (m, 1H), 7.25-7.22 (m, 2H), 7.21-7.17 (m, 2H), 6.86-6.82 (m, 2H), 6.79 (t, J=0.8 Hz, 1H), 4.70 (d, J=15.6 Hz, 1H), 4.62 (t, J=2.9 Hz, 1H), 4.46 (dd, J=11.1, 3.1 Hz, 1H), 4.14 (d, J=15.6 Hz, 1H), 4.04 (dd, J=11.1, 3.2 Hz, 1H), 3.94 (s, J=5.3 Hz, 3H), 3.79 (s, 3H). LCMS (ES+) [M+H]+: 508.1/510.0.

Example 4

Synthesis of (R)-5-(Benzofuran-2-yl)-3-(6-methoxy-5-(4-methyl-1H-imidazol-1-yl)pyridin-2-yl)-5,6-dihydro-4H-1,2,4-oxadiazine

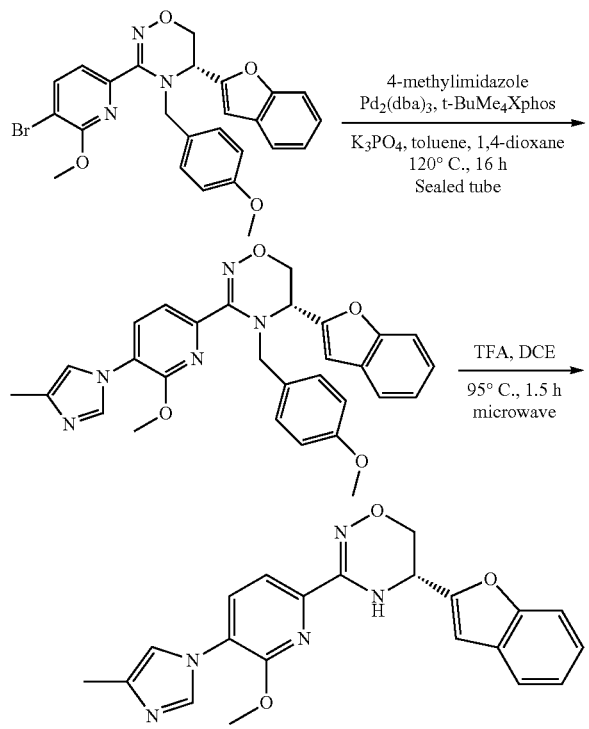

(R)-5-(Benzofuran-2-yl)-3-(6-methoxy-5-(4-methyl-1H-imidazol-1-yl)pyridin-2-yl)-4-(4-methoxybenzyl)-5,6-dihydro-4H-1,2,4-oxadiazine To a vial charged with (R)-5-(benzofuran-2-yl)-3-(5-bromo-6-methoxypyridin-2-yl)-4-(4-methoxybenzyl)-5,6-dihydro-4H-1,2,4-oxadiazine (442 mg, 0.87 mmol, 1.0 equiv.), 4(5)-methylimidazole (143 mg, 1.74 mmol, 2.0 equiv.), and K$_3$PO$_4$ (369 mg, 1.74 mmol, 2.0 equiv.) under N$_2$ atmosphere was added degassed 4:1 PhMe:dioxane solvent mixture (4.00 mL). To a second vial charged with Pd$_2$(dba)$_3$ (31.8 mg, 0.035 mmol, 4.0 mol %) and Me$_4$-di-t-BuXPhos (CAS#857356-94-6, 33.4 mg, 0.07 mmol, 8.0 mol %) under N$_2$ atmosphere was added degassed 4:1 PhMe:dioxane solvent mixture (2.00 mL). This mixture was stirred for 3 minutes at 120° C. to provide a dark red solution which was cooled to RT and transferred to the first vial. The reaction was degassed by bubbling with N$_2$ for 5 minutes and then sealed. The reaction mixture was stirred at 120° C. for 16 h. The reaction was cooled to RT and filtered through a pad of celite which was washed thoroughly with EtOAc. The filtrate was concentrated, and the residue was purified by normal phase chromatography on silica (0-5% MeOH/DCM) to afford the product (322 mg, 73%) as an off-white solid. LCMS (ES+) [M+H]+: 510.4.

(R)-5-(Benzofuran-2-yl)-3-(6-methoxy-5-(4-methyl-1H-imidazol-1-yl)pyridin-2-yl)-5,6-dihydro-4H-1,2,4-oxadiazine A solution of (R)-5-(benzofuran-2-yl)-3-(6-methoxy-5-(4-methyl-1H-imidazol-1-yl)pyridin-2-yl)-4-(4-methoxybenzyl)-5,6-dihydro-4H-1,2,4-oxadiazine (320 mg, 0.63 mmol, 1.0 equiv.) in DCE (4.00 mL) at ambient temperature was treated with TFA (4.00 mL). The resultant mixture was stirred at 95° C. for 1.5 h in a microwave reactor. The reaction mixture was cooled to RT, concentrated and dissolved in EtOAc. The organic layer was washed with 1 N aqueous NaOH and brine, dried over MgSO$_4$, filtered, and concentrated. The residue was purified by normal phase chromatography on silica (0-10% MeOH/DCM) to afford the product (225 mg) as an off-white solid. A portion (100 mg) of this material was dissolved in DMF (1.50 mL) and further purified using reverse phase chromatography on C18 resin (5-100% MeCN/H$_2$O+0.1% HCOOH) to provide, after lyophilisation (R)-5-(Benzofuran-2-yl)-3-(6-methoxy-5-(4-methyl-1H-imidazol-1-yl)pyridin-2-yl)-5,6-dihydro-4H-1,2,4-oxadiazine as a white solid (70.0 mg, 70%).

(R)-5-(Benzofuran-2-yl)-3-(6-methoxy-5-(4-methyl-1H-imidazol-1-yl)pyridin-2-yl)-5,6-dihydro-4H-1,2,4-oxadiazine: $^1$H NMR (500 MHz, CDCl$_3$) δ 7.82 (d, J=1.3 Hz, 1H), 7.81 (d, J=8.0 Hz, 1H), 7.63 (d, J=8.0 Hz, 1H), 7.56 (ddd, J=7.7, 1.3, 0.7 Hz, 1H), 7.48 (dd, J=8.2, 0.8 Hz, 1H), 7.30 (ddd, J=8.3, 7.3, 1.4 Hz, 1H), 7.24 (dd, J=7.4, 1.0 Hz, 1H), 7.00-6.98 (m, 1H), 6.75 (t, J=0.8 Hz, 1H), 6.70 (d, J=2.5 Hz, 1H), 5.04 (dt, J=5.6, 2.9 Hz, 1H), 4.33 (dd, J=10.9, 3.7 Hz, 1H), 4.21 (dd, J=11.0, 5.3 Hz, 1H), 4.05 (s, 3H), 2.30 (d, J=0.9 Hz, 3H); LCMS analysis using LCMS A, standard conditions: t$_r$=3.78 min, LCMS (ES+) [M+H]+: 390.3; [α]$_D$=+435 (c=0.11, MeOH).

Example 5

Synthesis of 2-(4-Methoxybenzylamino)-2-(7-methylbenzofuran-2-yl)ethanol

7-Methylbenzofuran-2-ylboronic acid

To a solution of 7-methylbenzofuran (7.90 g, 59.7 mmol, 1.0 equiv.) in THF (299 mL) at −78° C. was slowly added 2.5 M nBuLi in hexanes (28.7 mL, 69.4 mmol, 1.2 equiv).

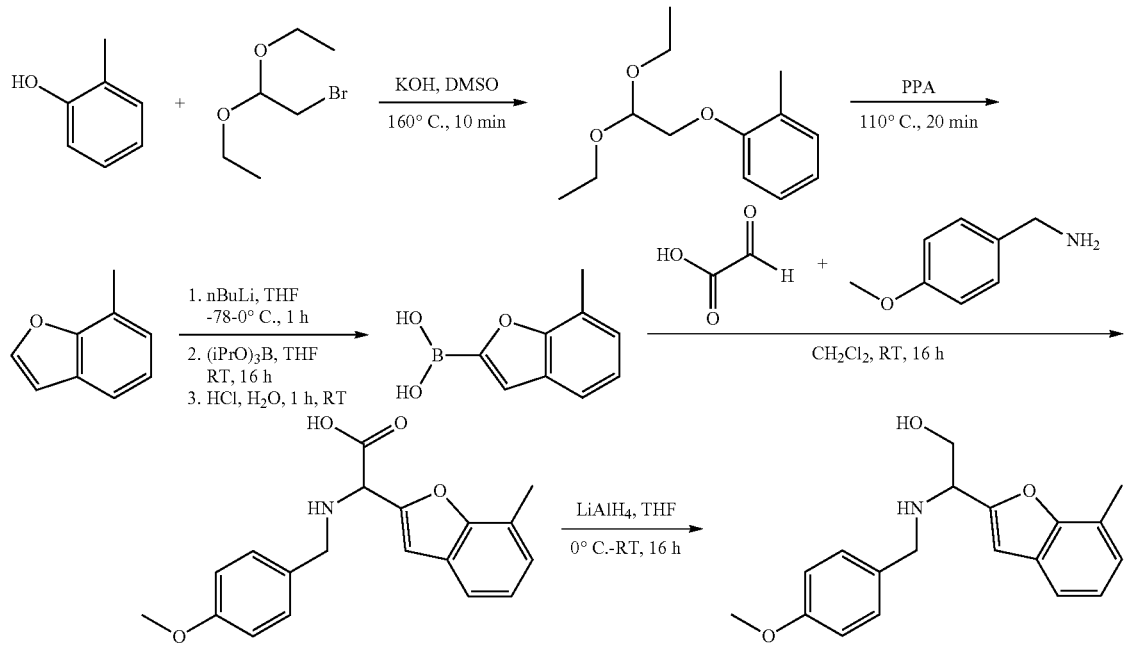

1-(2,2-Diethoxyethoxy)-2-methylbenzene

To a solution of 2-methylphenol (10.0 g, 92.5 mmol, 1.0 equiv) in DMSO (46.0 mL) was added 2-bromo-1,1-diethoxyethane (13.2 mL, 139 mmol, 1.5 equiv), followed by KOH (7.78 g, 139 mmol, 1.5 equiv). The resultant mixture was stirred at 160° C. for 10 min. LCMS analysis showed 74% conversion to the product. The reaction was cooled to RT, and water was added. The mixture was extracted with EtOAc, and the organic layer was washed with 1 N aqueous NaOH, dried over $Na_2SO_4$, filtered and evaporated to afford the product as an oil (16.6 g, 80%) that was used directly in the next step. $^1$H NMR (500 MHz, $CDCl_3$) δ 7.17-7.11 (m, 2H), 6.86 (td, J=7.4, 1.0 Hz, 1H), 6.81 (d, J=8.4 Hz, 1H), 4.86 (t, J=5.3 Hz, 1H), 4.01 (d, J=5.3 Hz, 2H), 3.79 (dq, J=9.4, 7.1 Hz, 2H), 3.66 (dq, J=9.4, 7.1 Hz, 2H), 2.24 (s, J=8.1 Hz, 3H), 1.25 (dd, J=9.7, 4.4 Hz, 6H).

7-Methylbenzofuran

To a solution of polyphosphoric acid (6.00 g) in toluene (134 mL) was added 1-(2,2-diethoxyethoxy)-2-methylbenzene (6.00 g, 26.7 mmol, 1.0 equiv). The resultant mixture was allowed to stir at 110° C. for 20 min, then cooled to RT and diluted with water. The mixture was extracted with EtOAc, and the organic layer was washed with 1 N aqueous NaOH, dried over $Na_2SO_4$ and evaporated to afford the product as an oil (4.22 g, 119%) that was used directly in the next step (toluene still present). $^1$H NMR (500 MHz, $CDCl_3$) δ 7.63 (d, J=2.2 Hz, 1H), 7.45-7.42 (m, 1H), 7.14 (d, J=7.5 Hz, 1H), 7.10 (d, J=7.3 Hz, 1H), 6.76 (d, J=2.2 Hz, 1H), 2.54 (s, 3H).

The resultant mixture was stirred for 1 h at 0° C., then cooled back to −78° C. and treated with triisopropylborate (41.4 mL, 179 mmol, 3.0 equiv). The reaction was allowed to warm to RT and stirred for 16 hours, then quenched with 2 N aqueous HCl. The reaction mixture was stirred for 1 h, and the pH was adjusted to 5 using a 1 N aqueous NaOH solution. The aqueous medium was extracted with EtOAc, and the organic extracts were dried over $Na_2SO_4$, filtered and evaporated. The residue was purified by trituration in DCM/Hexanes mixture, and the resultant white solid was collected by filtration and rinsed with hexanes to afford the product (9.68 g, 92%). $^1$H NMR (500 MHz, DMSO) δ 8.47 (s, 1H), 7.46 (ddd, J=7.2, 1.7, 0.6 Hz, 1H), 7.42 (s, 1H), 7.15-7.06 (m, 2H), 3.33 (s, 1H), 2.48 (s, 3H).

2-(4-Methoxybenzylamino)-2-(7-methylbenzofuran-2-yl)acetic acid

A suspension of benzofuran-2-ylboronic acid (1.20 g, 6.81 mmol, 1.0 equiv), glyoxylic acid monohydrate (627 mg, 6.81 mmol, 1.0 equiv) and 4-methoxybenzylamine (934, 6.81 mmol, 1.0 equiv) in anhydrous DCM (40.0 mL) was stirred for 16 h at ambient temperature. To the mixture was added $MgSO_4$ (2 g), the suspension was stirred for 5 minutes and filtered through a pad of celite, which was washed with EtOAc. The filtrate was concentrated under vacuum to afford the corresponding intermediate as a white solid that was used directly in the next step. LCMS (ES+) [M+H]+: 326.2.

2-(4-Methoxybenzylamino)-2-(7-methylbenzofuran-2-yl)ethanol

Crude 2-(4-methoxy benzylamino)-2-(7-methylbenzofuran-2-yl)acetic acid (17.9 g, 55.0 mmol, 1.0 equiv.) from the previous reaction was portion wise added to a cooled (0° C.) suspension of LiAlH₄ (6.26 g, 165 mmol, 3.0 equiv) in THF (300 mL). The resultant mixture was stirred at RT for 16 h before being diluted with Et₂O (600 mL). While maintained at 0° C. the reaction mixture was quenched by sequential addition of water (6.30 mL), aqueous sodium hydroxide (2 N, 6.30 mL) and water (19.0 mL). The mixture was allowed to warm to RT, stirred for 2 hour and MgSO₄ was added. The mixture was stirred for 10 minutes, and the solids were filtered and rinsed thoroughly with EtOAc (150 mL). The filtrate was concentrated and the residue was purified by normal phase chromatography on silica (0-5% MeOH/DCM) to afford 2-(4-Methoxybenzylamino)-2-(7-methylbenzofuran-2-yl)ethanol as orange oil (6.86 g, 40%). ¹H NMR (500 MHz, CDCl₃) δ 7.38 (ddd, J=7.6, 1.2, 0.5 Hz, 1H), 7.26-7.23 (m, 2H), 7.13 (t, J=7.5 Hz, 1H), 7.08 (ddd, J=7.3, 1.2, 0.8 Hz, 1H), 6.88-6.85 (m, 2H), 6.61 (d, J=0.4 Hz, 1H), 4.01-3.97 (m, 1H), 3.88-3.84 (m, 2H), 3.82-3.77 (m, 4H), 3.69 (d, J=12.7 Hz, 1H), 2.52 (s, 3H). LCMS (ES+) [M+H]+: 312.1.

Example 6

Synthesis of 3-(5-Bromo-6-methoxypyridin-2-yl)-4-(4-methoxybenzyl)-5-(7-methylbenzofuran-2-yl)-5,6-dihydro-4H-1,2,4-oxadiazine

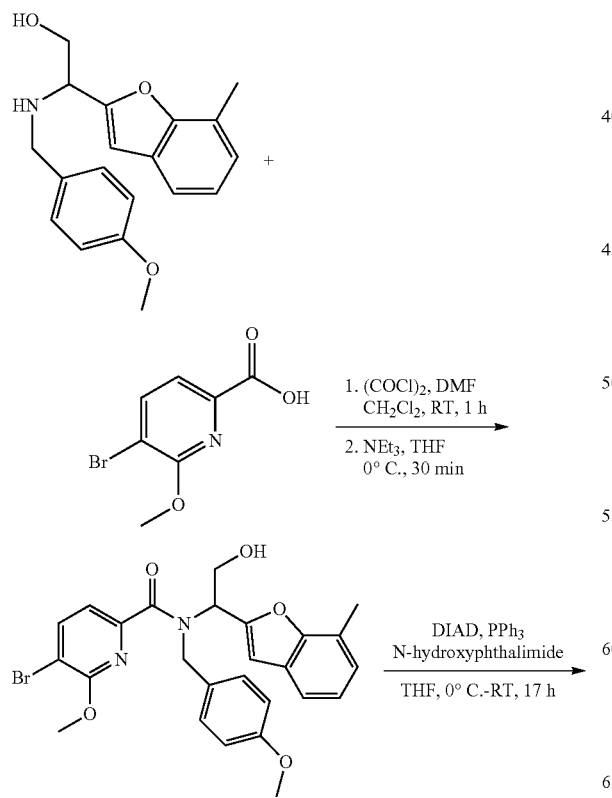

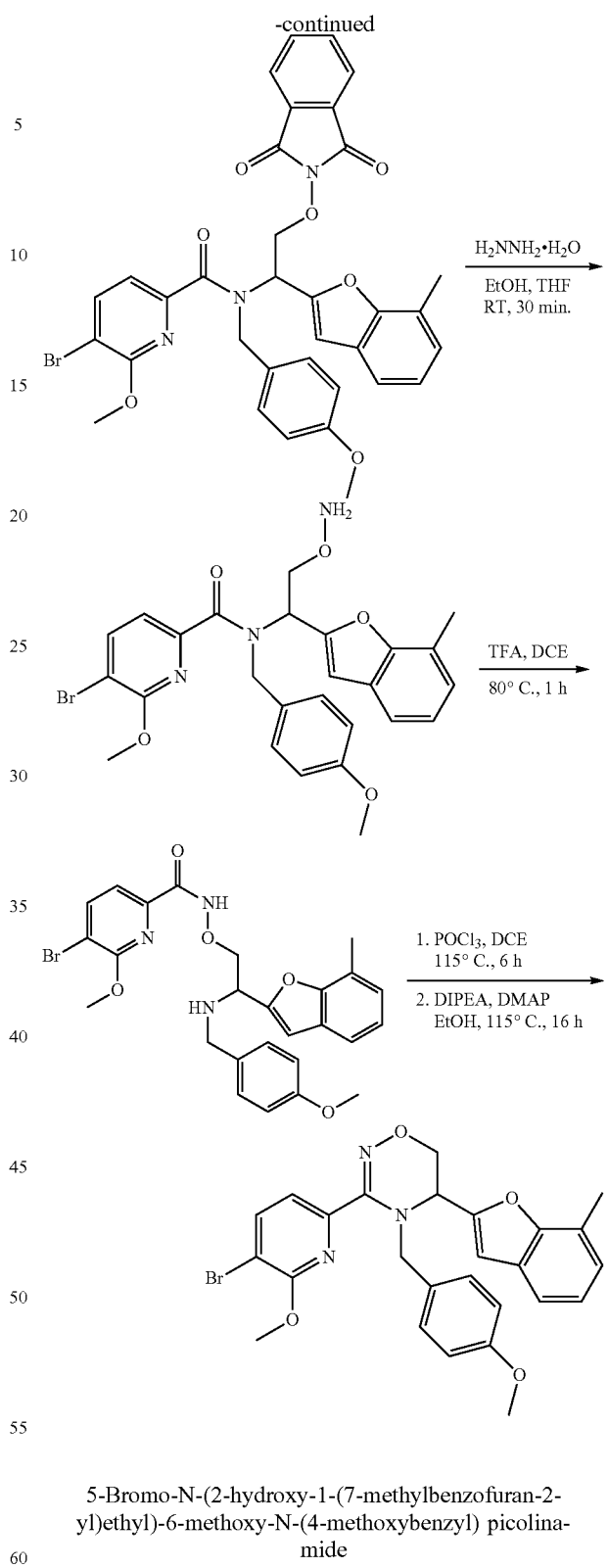

5-Bromo-N-(2-hydroxy-1-(7-methylbenzofuran-2-yl)ethyl)-6-methoxy-N-(4-methoxybenzyl) picolinamide A solution of 5-bromo-6-methoxypicolinic acid (407 mg, 1.75 mmol, 1.05 equiv.) in DCM (13 mL) at ambient temperature was treated with a catalytic amount of DMF (4 drops) and oxalyl chloride (437 uL, 5.01 mmol, 3.0 equiv.). The resultant mixture was stirred at ambient temperature for 1 h at which point LCMS monitoring showed completion of the reaction. The mixture was concentrated, diluted with anhydrous THF (25.0 mL), concentrated again and dried under high vacuum for 1 hour. The residue was diluted in anhydrous THF (10.0 mL), treated with triethylamine (698 uL, 5.01 mmol, 3.0 equiv.) and cooled to 0° C. A solution of 2-(4-methoxybenzylamino)-2-(7-methylbenzofuran-2-yl) ethanol (520 mg, 1.67 mmol, 1.0 equiv.) in THF (3.00 ml) was quickly added and the resultant mixture was stirred at 0° C. for 30 minutes. A saturated aqueous solution of NaHCO$_3$ and EtOAc were then successively added. The layers were separated, and the aqueous layer was extracted with EtOAc twice. The combined organic layers were dried over MgSO$_4$, filtered and concentrated. The residue was purified by normal phase chromatography on silica (0-60% EtOAc/hexanes) to afford the amide as white solid (877 mg, 64%). LCMS (ES+) [M+H]+: 525.2/527.2.

5-Bromo-N-(2-(1,3-dioxoisoindolin-2-yloxy)-1-(7-methylbenzofuran-2-yl)ethyl)-6-methoxy-N-(4-methoxybenzyl)picolinamide DIAD (254 uL, 1.28 mmol, 1.2 equiv.) was added to a solution of PPh$_3$ (356 mg, 1.28 mmol, 1.2 equiv.), 5-bromo-N-(2-hydroxy-1-(7-methylbenzofuran-2-yl)ethyl)-6-methoxy-N-(4-methoxybenzyl)picolinamide (560 mg, 1.07 mmol, 1.0 equiv.) and N-hydroxylphtalimide (209 mg, 1.28 mmol, 1.2 equiv.) in THF (7.00 mL) at 0° C. The resultant mixture was kept at 0° C. for 1 h, then warmed to ambient temperature and stirred for 16 h. EtOAc was added, and the organic layer was washed with 1 N aqueous NaOH (twice), water, and brine, dried over MgSO$_4$, filtered, and concentrated. The residue was purified by normal phase chromatography on silica (5-50% EtOAc/hexanes) to afford the product as foamy white solid (440 mg, 62%). LCMS (ES+) [M+MeOH+H]+: 702.1/704.1.

N-(2-(Aminooxy)-1-(7-methylbenzofuran-2-yl) ethyl)-5-bromo-6-methoxy-N-(4-methoxy benzyl) picolinamide A suspension of 5-bromo-N-(2-(1,3-dioxoisoindolin-2-yloxy)-1-(7-methylbenzofuran-2-yl)ethyl)-6-methoxy-N-(4-methoxybenzyl)picolinamide (440 mg, 0.66 mmol, 1.0 equiv.) in ethanol (90%, 5.0 mL) and THF (0.75 mL) at ambient temperature was treated with hydrazine hydrate (50-60%, 0.80 mL). The resultant mixture was stirred for 30 minutes, then water was added. The mixture was extracted with EtOAc (three times), and the combined organic layers were dried over MgSO$_4$, filtered, and concentrated to afford the product (355 mg, 99%) as a pale yellow oil that was used directly in the next step. LCMS (ES+) [M+H]+: 540.2/542.2.

5-Bromo-6-methoxy-N-(2-(4-methoxybenzylamino)-2-(7-methylbenzofuran-2-yl)ethoxy) picolinamide A solution of N-(2-(aminooxy)-1-(7-methylbenzofuran-2-yl)ethyl)-5-bromo-6-methoxy-N-(4-methoxybenzyl)picolinamide (355 mg, 0.66 mmol, 1.0 equiv.) in DCE (7.00 mL) was treated with TFA (0.35 mL). The resultant mixture was stirred at 80° C. for 60 min, then cooled to ambient temperature and concentrated to dryness. The residue was diluted with EtOAc, washed with saturated aqueous solution of NaHCO$_3$ and brine, dried over MgSO$_4$, filtered and concentrated to afford the product (350 mg, 99%) as pale yellow foam that was used directly in the next step. LCMS (ES+) [M+H]+: 540.3/542.2.

3-(5-Bromo-6-methoxypyridin-2-yl)-4-(4-methoxybenzyl)-5-(7-methylbenzofuran-2-yl)-5,6-dihydro-4H-1,2,4-oxadiazine A solution of 5-bromo-6-methoxy-N-(2-(4-methoxybenzylamino)-2-(7-methylbenzofuran-2-yl)ethoxy) picolinamide (351 mg, 0.65 mmol, 1.0 equiv.) in anhydrous DCE (6.00 mL) at ambient temperature was treated with POCl$_3$ (908 uL, 9.74 mmol, 15.0 equiv.). The vial was sealed and heated at 115° C. for 6 h. The reaction mixture was evaporated, dried under high vacuum for 20 minutes, dissolved in EtOH (5.00 mL) and treated with DIPEA (453 uL, 2.60 mmol, 4.0 equiv.) and DMAP (39.7 mg, 0.33 mmol, 0.5 equiv.). The resultant mixture was heated to 115° C. for 16 h. The reaction mixture was cooled to ambient temperature and diluted with EtOAc. The organic layer was washed with 1 N aqueous NaOH, water (twice) and brine, dried over MgSO$_4$, filtered and concentrated. The residue was purified by normal phase chromatography on silica (2.5-40% EtOAc/hexanes) to afford the product as white solid.

The racemate was separated using chiral semi preparative HPLC A (Chiral pak IA column, 5 um, 20×250 mm, 15 mL/min, 90% Hexanes/5% MeOH/5% DCM) to afford the compounds of Example 6A (Fraction (I)) and Example 6B (Fraction (II)).

Example 6A, 3-(5-bromo-6-methoxypyridin-2-yl)-4-(4-methoxybenzyl)-5-(7-methylbenzofuran-2-yl)-5,6-dihydro-4H-1,2,4-oxadiazine, fraction (I): (34.0 mg of a white solid, 10%, t$_r$=15.8 min). LCMS (ES+) [M+H]+: 522.2/524.3.

Example 6B, 3-(5-bromo-6-methoxypyridin-2-yl)-4-(4-methoxybenzyl)-5-(7-methylbenzofuran-2-yl)-5,6-dihydro-4H-1,2,4-oxadiazine, fraction (II): (30.0 mg of a white solid, 9%, t$_r$=17.5 min). $^1$H NMR (500 MHz, CDCl$_3$) δ 7.81 (d, J=7.8 Hz, 1H), 7.31 (d, J=7.6 Hz, 1H), 7.16 (d, J=7.7 Hz, 1H), 7.12 (d, J=8.5 Hz, 2H), 7.07 (t, J=7.5 Hz, 1H), 7.01 (d, J=7.3 Hz, 1H), 6.77 (d, J=8.6 Hz, 2H), 6.72 (s, 1H), 4.62 (d, J=15.6 Hz, 1H), 4.57 (t, J=3.2 Hz, 1H), 4.41 (dd, J=11.1, 3.2 Hz, 1H), 4.08 (d, J=15.6 Hz, 1H), 3.99 (dd, J=11.1, 3.3 Hz, 1H), 3.87 (s, 3H), 3.72 (s, 3H), 2.42 (s, 3H). LCMS (ES+) [M+H]+: 522.2/524.3.

Example 7A

Synthesis of 3-(6-Methoxy-5-(4-methyl-1H-imidazol-1-yl)pyridin-2-yl)-5-(7-methylbenzofuran-2-yl)-5,6-dihydro-4H-1,2,4-oxadiazine, fraction (I)

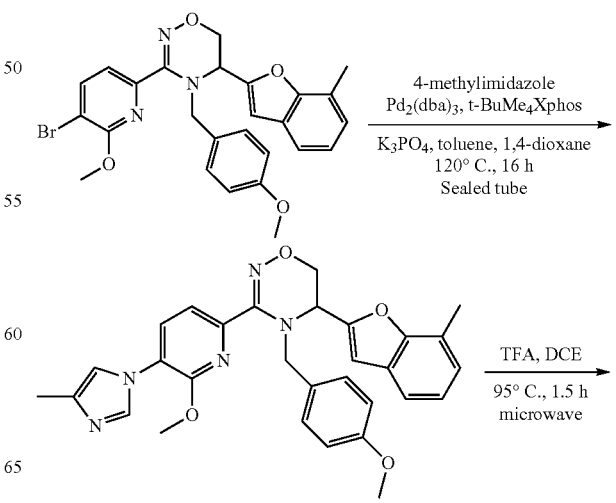

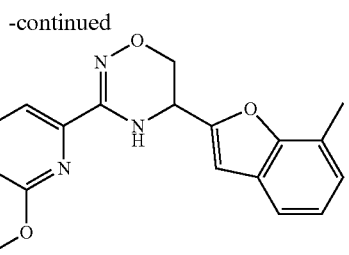

3-(6-Methoxy-5-(4-methyl-1H-imidazol-1-yl)pyridin-2-yl)-4-(4-methoxybenzyl)-5-(7-methylbenzofuran-2-yl)-5,6-dihydro-4H-1,2,4-oxadiazine, fraction (I)

The title compound (21.4 mg, 63%) was prepared as a white solid from 3-(5-bromo-6-methoxypyridin-2-yl)-4-(4-methoxybenzyl)-5-(7-methylbenzofuran-2-yl)-5,6-dihydro-4H-1,2,4-oxadiazine, fraction (I) according to the procedure in Example 7B. LCMS (ES+) [M+H]+: 524.4.

3-(6-Methoxy-5-(4-methyl-1H-imidazol-1-yl)pyridin-2-yl)-5-(7-methylbenzofuran-2-yl)-5,6-dihydro-4H-1,2,4-oxadiazine, fraction (I): Example 7A (7.0 mg, 40%) was prepared as a white solid from 3-(6-methoxy-5-(4-methyl-1H-imidazol-1-yl)pyridin-2-yl)-4-(4-methoxybenzyl)-5-(7-methylbenzofuran-2-yl)-5,6-dihydro-4H-1,2,4-oxadiazine, fraction (I) according to the procedure for Example 7B.

Example 7A, 3-(6-Methoxy-5-(4-methyl-1H-imidazol-1-yl)pyridin-2-yl)-5-(7-methylbenzofuran-2-yl)-5,6-dihydro-4H-1,2,4-oxadiazine, fraction (I): LCMS analysis using LCMS A, standard conditions: $t_r$=3.88 mM, LCMS (ES+) [M+H]+: 404.2; $[\alpha]_D$=−304 (c=0.10, MeOH).

Example 7B

Synthesis of 3-(6-Methoxy-5-(4-methyl-1H-imidazol-1-yl)pyridin-2-yl)-5-(7-methylbenzofuran-2-yl)-5,6-dihydro-4H-1,2,4-oxadiazine, fraction (II)

3-(6-Methoxy-5-(4-methyl-1H-imidazol-1-yl)pyridin-2-yl)-4-(4-methoxybenzyl)-5-(7-methylbenzofuran-2-yl)-5,6-dihydro-4H-1,2,4-oxadiazine, fraction (II)

To a vial charged with 3-(5-bromo-6-methoxypyridin-2-yl)-4-(4-methoxybenzyl)-5-(7-methylbenzofuran-2-yl)-5,6-dihydro-4H-1,2,4-oxadiazine, fraction (II) Example 6B (30 mg, 0.06 mmol, 1.0 equiv.), 4(5)-methylimidazole (9.40 mg, 0.12 mmol, 2.0 equiv.), and $K_3PO_4$ (24.3 mg, 0.12 mmol, 2.0 equiv.) under $N_2$ atmosphere was added degassed 4:1 PhMe:dioxane solvent mixture (0.20 mL). To a second vial charged with $Pd_2(dba)_3$ (2.10 mg, 0.002 mmol, 4.0 mol %) and $Me_4$-di-t-BuXPhos (CAS#857356-94-6, 2.20 mg, 0.005 mmol, 8.0 mol %) under $N_2$ atmosphere was added degassed 4:1 PhMe:dioxane solvent mixture (0.2 mL). This mixture was stirred for 3 minutes at 120° C. to provide a dark red solution which was cooled to RT and transferred to the first vial. The reaction was degassed by bubbling with $N_2$ for 5 minutes and then sealed. The reaction mixture was stirred at 120° C. for 16 h. The reaction was cooled to RT and filtered through a pad of celite which was washed thoroughly with EtOAc. The filtrate was concentrated, and the residue was purified by normal phase chromatography on silica (0-5% MeOH/DCM) to afford the product (20.0 mg, 67%) as a white solid. LCMS (ES+) [M+H]+: 524.4.

3-(6-Methoxy-5-(4-methyl-1H-imidazol-1-yl)pyridin-2-yl)-5-(7-methylbenzofuran-2-yl)-5,6-dihydro-4H-1,2,4-oxadiazine, fraction (II)

A solution of 3-(6-methoxy-5-(4-methyl-1H-imidazol-1-yl)pyridin-2-yl)-4-(4-methoxybenzyl)-5-(7-methylbenzofuran-2-yl)-5,6-dihydro-4H-1,2,4-oxadiazine, fraction (II) (20.0 mg, 0.04 mmol, 1.0 equiv.) in DCE (0.50 mL) at ambient temperature was treated with TFA (0.50 mL). The resultant mixture was stirred at 95° C. for 1.5 h in a microwave reactor. The reaction mixture was cooled to RT, concentrated and dissolved in EtOAc. The organic layer was washed with 1 N aqueous NaOH and brine, dried over $MgSO_4$, filtered, and concentrated. The residue was purified by normal phase chromatography on silica (0-10% MeOH/DCM) to afford the product (15.0 mg) as oil. This material was dissolved in DMF (1.50 mL) and further purified using reverse phase chromatography on C18 resin (5-100% $MeCN/H_2O$+0.1% HCOOH) to provide, after lyophilisation, the compound of Example 7B as a white solid (6.1 mg, 40%).

Example 7B, 3-(6-Methoxy-5-(4-methyl-1H-imidazol-1-yl)pyridin-2-yl)-5-(7-methylbenzofuran-2-yl)-5,6-dihydro-4H-1,2,4-oxadiazine, fraction (II): $^1$H NMR (500 MHz, $CDCl_3$) δ 7.87 (s, 1H), 7.81 (d, J=8.0 Hz, 1H), 7.64 (d, J=8.0 Hz, 1H), 7.38 (d, J=7.5 Hz, 1H), 7.17-7.08 (m, 2H), 6.99 (s, 1H), 6.73 (s, 1H), 6.71 (s, 1H), 5.08-5.03 (m, 1H), 4.37 (dd, J=11.0, 3.8 Hz, 1H), 4.19 (dd, J=11.0, 5.5 Hz, 1H), 4.06 (s, 3H), 2.52 (s, 3H), 2.31 (s, 3H); LCMS analysis using LCMS A, standard conditions: $t_r$=3.88 min, LCMS (ES+) [M+H]+: 404.2; $[\alpha]_D$=+285 (c=0.10, MeOH).

Example 8

Synthesis of (R)-2-(4-Methoxybenzylamino)-2-(5-methylbenzofuran-2-yl)ethanol

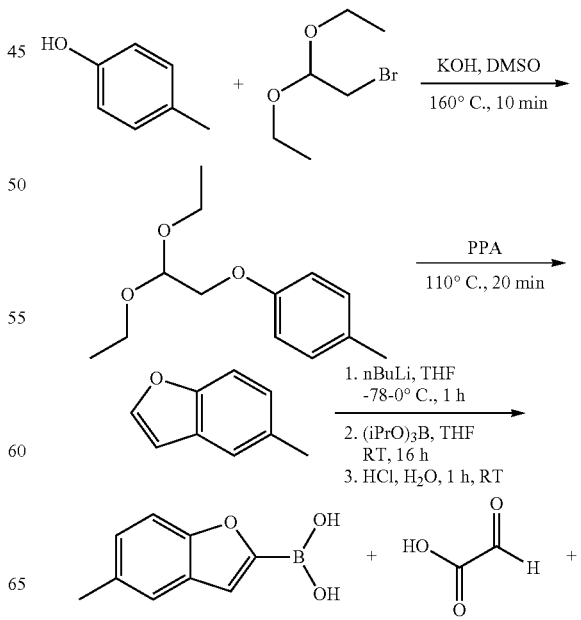

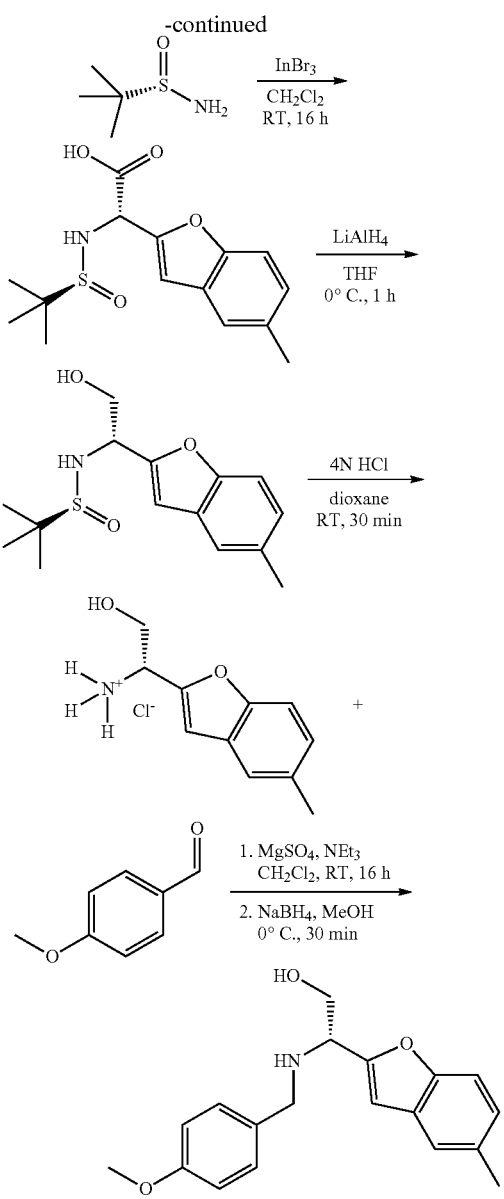

1-(2,2-Diethoxyethoxy)-4-methylbenzene

To a solution of 4-methylphenol (10.0 g, 92.5 mmol, 1.0 equiv) in DMSO (46.0 mL) was added 2-bromo-1,1-diethoxyethane (13.2 mL, 139 mmol, 1.5 equiv), followed by KOH (7.78 g, 139 mmol, 1.5 equiv). The resultant mixture was stirred at 160° C. for 10 min. LCMS analysis showed 69% conversion to the product. The reaction was cooled to RT, and water was added. The mixture was extracted with EtOAc, and the organic layer was washed with 1 N aqueous NaOH, dried over Na₂SO₄, filtered and evaporated to afford the product as an oil (16.2 g, 78%) that was used directly in the next step. ¹H NMR (500 MHz, CDCl₃) δ 7.07 (d, J=8.6 Hz, 2H), 6.82 (d, J=8.6 Hz, 2H), 4.82 (t, J=5.2 Hz, 1H), 3.98 (d, J=5.2 Hz, 2H), 3.76 (dq, J=9.4, 7.1 Hz, 2H), 3.63 (dq, J=9.4, 7.1 Hz, 2H), 2.28 (s, 3H), 1.25 (t, J=7.1 Hz, 6H).

4-Methylbenzofuran

To a solution of polyphosphoric acid (9.23 g) in toluene (103 mL) was added 1-(2,2-diethoxyethoxy)-4-methylben-zene (9.23 g, 41.1 mmol, 1.0 equiv). The resultant mixture was allowed to stir at 110° C. for 45 min, then cooled to RT and diluted with water. The mixture was extracted with EtOAc, and the organic layer was washed with 1 N aqueous NaOH, dried over Na₂SO₄ and evaporated to afford the product as an oil (5.92 g, 109%) that was used directly in the next step (toluene still present). ¹H NMR (500 MHz, CDCl₃) δ 7.58 (d, J=2.2 Hz, 1H), 7.40-7.37 (m, 2H), 7.10 (ddd, J=8.5, 1.2, 0.4 Hz, 1H), 6.70 (dd, J=2.2, 0.9 Hz, 1H), 2.45 (s, 3H).

4-Methylbenzofuran-2-ylboronic acid

To a solution of 7-methylbenzofuran (8.30 g, 62.8 mmol, 1.0 equiv.) in THF (314 mL) at −78° C. was slowly added 2.5 M nBuLi in hexanes (30.1 mL, 75.4 mmol, 1.2 equiv). The resultant mixture was stirred for 1 h at 0° C., then cooled back to −78° C. and treated with triisopropylborate (43.5 mL, 188 mmol, 3.0 equiv). The reaction was allowed to warm to RT and stirred for 16 hours, then quenched with 2 N aqueous HCl. The reaction mixture was stirred for 1 h, and the pH was adjusted to 5 using a 1 N aqueous NaOH solution. The aqueous medium was extracted with EtOAc, and the organic extracts were dried over Na₂SO₄, filtered and evaporated. The residue was purified by trituration in DCM/Hexanes mixture, and the resultant white solid was collected by filtration and rinsed with hexanes to afford the product (9.43 g, 85%). ¹H NMR (500 MHz, DMSO) δ 8.49 (s, 2H), 7.46-7.43 (m, 2H), 7.36 (d, J=1.0 Hz, 1H), 7.15 (ddd, J=8.4, 1.8, 0.5 Hz, 1H), 2.39 (s, 3H).

(S)-2-((S)-1,1-Dimethylethylsulfinamido)-2-(5-methylbenzofuran-2-yl)acetic acid

A suspension of 4-methylbenzofuran-2-ylboronic acid (9.23 g, 52.4 mmol, 1.0 equiv), glyoxylic acid monohydrate (5.36 g, 58.3 mmol, 1.1 equiv) and (S)-2-methylpropane-2-sulfinamide (7.06 g, 58.3 mmol, 1.1 equiv) in anhydrous DCM (175 mL) at ambient temperature was treated with InBr₃ (2.07 g, 5.83 mmol, 0.11 equiv). The resultant mixture was stirred for 16 h at ambient temperature. To the mixture was added MgSO₄ (4.0 g), the suspension was stirred for 5 minutes and filtered through a pad of celite, which was washed with EtOAc. The filtrate was concentrated under vacuum to afford the corresponding intermediate as an orange solid that was used directly in the next step. LCMS (ES+) [M+H]+: 310.2.

(S)—N—((R)-2-Hydroxy-1-(5-methylbenzofuran-2-yl)ethyl)-2-methylpropane-2-sulfinamide A THF (150 mL) solution of crude (S)-2-((S)-1,1-dim-ethylethylsulfinamido)-2-(5-methylbenzofuran-2-yl)acetic acid from the previous reaction was slowly added to a cooled (0° C.) suspension of LiAlH₄ (9.94 g, 262 mmol, 5.0 equiv) in THF (150 mL). The resultant mixture was stirred for 1 h at 0° C. before being diluted with Et₂O (300 mL). While maintained at 0° C. the reaction mixture was quenched by sequential addition of water (10.0 mL), sodium hydroxide (2 N, 10.0 mL) and water (30.0 mL). The mixture was allowed to warm to RT, stirred for 1 hour and MgSO₄ was added. The mixture was stirred for 10 minutes, and the solids were filtered and rinsed thoroughly with 10% MeOH/DCM (200 mL). The filtrate was concentrated and the residue was purified by normal phase chromatography on silica (0-7% MeOH/DCM) to afford the alcohol as a pale yellow oil (4.55 g, 29%). ¹H NMR (500 MHz, CDCl₃) δ 7.34-7.30 (m, 2H), 7.08 (dd, J=8.0, 1.8 Hz, 1H), 6.56 (s, 1H), 4.67-4.60 (m, 1H), 4.12 (dd, J=11.7, 3.2 Hz, 1H), 3.94-3.85 (m, 2H), 3.64 (s, 1H), 2.43 (s, 3H), 1.29 (s, 9H).

(R)-2-hydroxy-1-(5-methylbenzofuran-2-yl)ethanaminium chloride ((S)—N—((R)-2-Hydroxy-1-(5-methylbenzofuran-2-yl)ethyl)-2-methylpropane-2-sulfinamide (4.56 g, 15.4 mmol, 1.0 equiv) was dissolved in a 4 N solution of HCl in 1,4-dioxane (80.0 mL) at ambient temperature. The resultant mixture was stirred at ambient temperature for 30 minutes and concentrated to dryness to afford the hydrochloride salt which was used directly in the next step. LCMS (ES+) [M–H₂O]+: 175.1.

(R)-2-(4-Methoxybenzylamino)-2-(5-methylbenzofuran-2-yl)ethanol

A solution of crude (R)-2-hydroxy-1-(5-methylbenzofuran-2-yl)ethanaminium chloride from previous step in DCM (100 mL) at ambient temperature was treated successively with triethylamine (4.30 mL, 30.8 mmol, 2.0 equiv), MgSO₄ (14.0 g) and anisaldehyde (1.88 mL, 15.4 mmol, 1.0 equiv). The resultant suspension was stirred for 16 hours at ambient temperature and filtered through a pad of celite which was washed with EtOAc. The filtrate was concentrated under vacuum to afford the corresponding imine intermediate. This intermediate was dissolved in MeOH (120 mL) and cooled to 0° C. Solid NaBH₄ (1.71 g, 46.3 mmol, 3.0 equiv) was added portion wise over 5 minutes. The resultant mixture was stirred for 30 minutes at 0° C., then quenched by the slow addition of a saturated aqueous solution of NaHCO₃. Water and DCM were added. The layers were separated, and the aqueous layer was extracted with DCM twice. The combined organic layers were dried over MgSO₄, filtered and concentrated to afford a residue that was purified by normal phase chromatography on silica (0-10% MeOH/DCM) to afford (R)-2-(4-methoxybenzylamino)-2-(5-methylbenzofuran-2-yl)ethanol (4.37 g, 91%) as an off-white solid. ¹H NMR (500 MHz, CDCl₃) δ 7.35-7.30 (m, 2H), 7.23 (d, J=8.7 Hz, 2H), 7.08 (dd, J=8.5, 1.3 Hz, 1H), 6.86 (d, J=8.7 Hz, 2H), 6.55 (s, 1H), 3.95 (dd, J=8.4, 4.6 Hz, 1H), 3.86-3.81 (m, 2H), 3.80 (s, 3H), 3.78-3.75 (m, 2H), 3.68-3.62 (m, 2H), 2.44 (s, 3H). LCMS (ES+) [M+H]+: 312.1.

Example 9

Synthesis of (R)-3-(5-Bromo-6-methoxypyridin-2-yl)-4-(4-methoxybenzyl)-5-(5-methylbenzofuran-2-yl)-5,6-dihydro-4H-1,2,4-oxadiazine

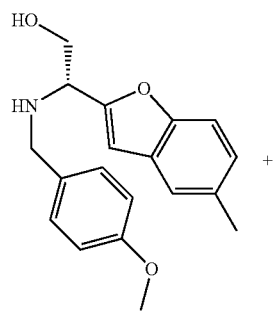

+

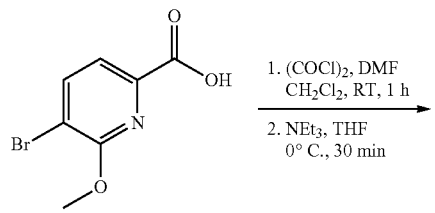

1. (COCl)₂, DMF
CH₂Cl₂, RT, 1 h

2. NEt₃, THF
0° C., 30 min

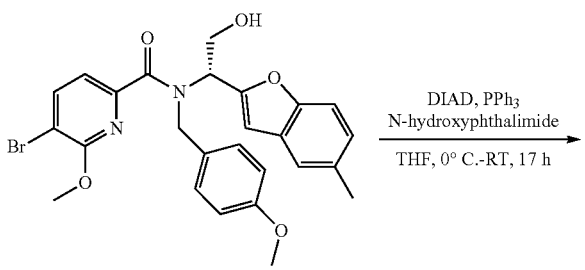

DIAD, PPh₃
N-hydroxyphthalimide

THF, 0° C.-RT, 17 h

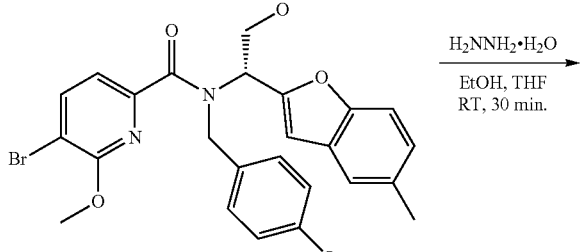

H₂NNH₂·H₂O

EtOH, THF
RT, 30 min.

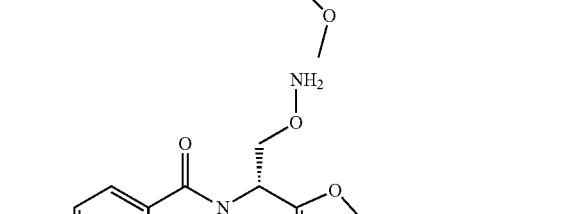

TFA, DCE

80° C., 1 h

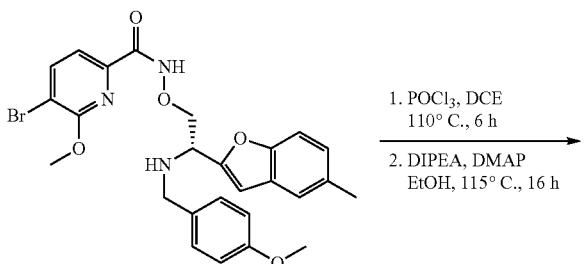

1. POCl₃, DCE
110° C., 6 h

2. DIPEA, DMAP
EtOH, 115° C., 16 h

-continued

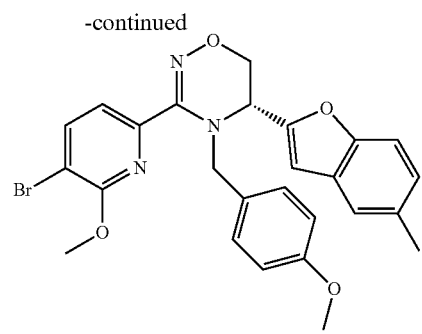

(R)-5-Bromo-N-(2-hydroxy-1-(5-methylbenzofuran-2-yl)ethyl)-6-methoxy-N-(4-methoxy benzyl)picolinamide A solution of 5-bromo-6-methoxypicolinic acid (3.42 g, 14.7 mmol, 1.05 equiv.) in DCM (100 mL) at ambient temperature was treated with a catalytic amount of DMF (4 drops) and oxalyl chloride (3.67 mL, 42.1 mmol, 3.0 equiv.). The resultant mixture was stirred at ambient temperature for 1 h at which point LCMS monitoring showed completion of the reaction. The mixture was concentrated, diluted with anhydrous THF (30.0 mL), concentrated again and dried under high vacuum for 1 hour. The residue was diluted in anhydrous THF (70.0 ml), treated with triethylamine (5.87 mL, 42.1 mmol, 3.0 equiv.) and cooled to 0° C. A solution of (R)-2-(4-methoxybenzylamino)-2-(5-methylbenzofuran-2-yl)ethanol (4.37 g, 14.0 mmol, 1.0 equiv.) in THF (30.0 ml) was quickly added and the resultant mixture was stirred at 0° C. for 30 minutes. A saturated aqueous solution of NaHCO₃ and EtOAc were then successively added. The layers were separated, and the aqueous layer was extracted with EtOAc twice. The combined organic layers were dried over MgSO₄, filtered and concentrated. The residue was purified by normal phase chromatography on silica (0-40% EtOAc/hexanes) to afford the amide as beige foam (4.23 g, 57%). LCMS (ES+) [M+H]+: 525.2/527.2.

(R)-5-Bromo-N-(2-(1, 3-dioxoisoindolin-2-yloxy)-1-(5-methylbenzofuran-2-yl)ethyl)-6-methoxy-N-(4-methoxybenzyl)picolinamide DIAD (1.92 mL, 4.18 mmol, 1.2 equiv.) was added to a solution of triphenylphosphine (2.53 g, 9.66 mmol, 1.2 equiv.), (R)-5-bromo-N-(2-hydroxy-1-(5-methylbenzofuran-2-yl)ethyl)-6-methoxy-N-(4-methoxybenzyl)picolinamide (4.23 g, 8.05 mmol, 1.0 equiv.) and N-hydroxylphtalimide (1.58 g, 9.66 mmol, 1.2 equiv.) in THF (45.0 mL) at 0° C. The resultant mixture was kept at 0° C. for 1 h, then warmed to ambient temperature and stirred for 2 h. EtOAc was added, and the organic layer was washed with 1 N aqueous NaOH (twice), water, and brine, dried over MgSO₄, filtered, and concentrated. The residue was purified by normal phase chromatography on silica (0-40% EtOAc/hexanes) to afford the product as a white foamy solid (2.0 g, 37%). LCMS (ES+) [M+H]+: 670.3/672.2.

(R)—N-(2-(Aminooxy)-1-(5-methylbenzofuran-2-yl)ethyl)-5-bromo-6-methoxy-N-(4-methoxy benzyl)picolinamide A suspension of (R)-5-bromo-N-(2-(1,3-dioxoisoindolin-2-yloxy)-1-(5-methylbenzofuran-2-yl)ethyl)-6-methoxy-N-(4-methoxybenzyl)picolinamide (2.00 g, 2.98 mmol, 1.0 equiv.) in ethanol (90%, 30.0 mL) and THF (4.00 mL) at ambient temperature was treated with hydrazine hydrate (50-60%, 3.00 mL). The resultant mixture was stirred for 30 minutes, then water was added. The mixture was extracted with EtOAc (three times), and the combined organic layers were dried over MgSO₄, filtered, and concentrated to afford the product (1.61 g, 99%) as an off-white foam that was used directly in the next step. LCMS (ES+) [M+H]+: 540.1/542.1.

(R)-5-Bromo-6-methoxy-N-(2-(4-methoxybenzylamino)-2-(5-methylbenzofuran-2-yl)ethoxy) picolinamide A solution of (R)—N-(2-(aminooxy)-1-(5-methylbenzofuran-2-yl)ethyl)-5-bromo-6-methoxy-N-(4-methoxybenzyl)picolinamide (1.61 g, 2.98 mmol, 1.0 equiv.) in DCE (20.0 mL) was treated with TFA (1.05 mL). The resultant mixture was stirred at 80° C. for 1 h, then cooled to ambient temperature and concentrated to dryness. The residue was diluted with EtOAc, washed with saturated aqueous solution of NaHCO₃ and brine, dried over MgSO₄, filtered and concentrated to afford the product (1.52 g, 94%) as pale yellow oil that was used directly in the next step. LCMS (ES+) [M+H]+: 540.0/542.0.

(R)-3-(5-Bromo-6-methoxypyridin-2-yl)-4-(4-methoxybenzyl)-5-(5-methylbenzofuran-2-yl)-5,6-dihydro-4H-1,2,4-oxadiazine A solution of (R)-5-bromo-6-methoxy-N-(2-(4-methoxy benzylamino)-2-(5-methylbenzofuran-2-yl)ethoxy)picolinamide (1.52 g, 2.81 mmol, 1.0 equiv.) in anhydrous DCE (20.0 ml) at ambient temperature was treated with POCl₃ (3.93 mL, 42.2 mmol, 15.0 equiv.). The vial was sealed and heated at 110° C. for 6 h. The reaction mixture was evaporated, dried under high vacuum for 10 minutes, dissolved in EtOH (30.0 mL) and treated with DIPEA (1.96 mL, 11.3 mmol, 4.0 equiv.) and DMAP (172 mg, 1.41 mmol, 0.5 equiv.). The resultant mixture was heated to 115° C. for 16 h. The reaction mixture was cooled to ambient temperature and diluted with EtOAc. The organic layer was washed with 1 N aqueous NaOH, water (twice) and brine, dried over MgSO₄, filtered and concentrated. The residue was purified by normal phase chromatography on silica (0-30% EtOAc/hexanes) to afford (R)-3-(5-Bromo-6-methoxypyridin-2-yl)-4-(4-methoxybenzyl)-5-(5-methylbenzofuran-2-yl)-5,6-dihydro-4H-1,2,4-oxadiazine (693 mg, 60%) as a pale beige foam. ¹H NMR (500 MHz, CDCl₃) δ 7.88 (d, J=7.8 Hz, 1H), 7.35-7.31 (m, 2H), 7.23 (d, J=7.8 Hz, 1H), 7.18 (d, J=8.6 Hz, 2H), 7.10-7.08 (m, 1H), 6.84 (d, J=8.7 Hz, 2H), 6.71 (s, 1H), 4.68 (d, J=15.6 Hz, 1H), 4.59 (t, J=3.0 Hz, 1H), 4.44 (dd, J=11.1, 3.2 Hz, 1H), 4.11 (d, J=15.6 Hz, 1H), 4.04 (dd, J=11.1, 3.3 Hz, 1H), 3.93 (s, J=5.4 Hz, 3H), 3.79 (s, 3H), 2.44 (s, 3H). LCMS (ES+) [M+H]+: 522.0/524.0.

Example 10

Synthesis of (R)-3-(6-Methoxy-5-(4-methyl-1H-imidazol-1-yl)pyridin-2-yl)-5-(5-methylbenzofuran-2-yl)-5,6-dihydro-4H-1,2,4-oxadiazine

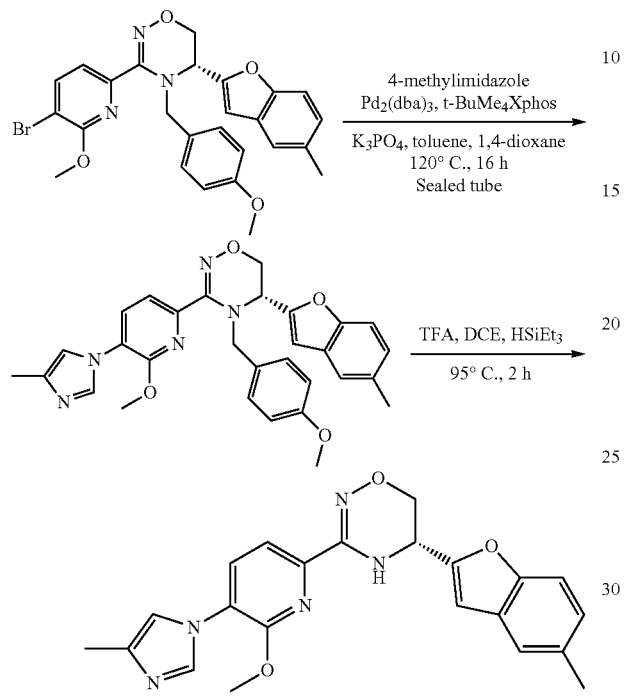

(R)-3-(6-Methoxy-5-(4-methyl-1H-imidazol-1-yl)pyridin-2-yl)-4-(4-methoxybenzyl)-5-(5-methylbenzofuran-2-yl)-5,6-dihydro-4H-1,2,4-oxadiazine To a vial charged with (R)-3-(5-bromo-6-methoxypyridin-2-yl)-4-(4-methoxybenzyl)-5-(5-methylbenzofuran-2-yl)-5,6-dihydro-4H-1,2,4-oxadiazine (400 mg, 0.77 mmol, 1.0 equiv.), 4(5)-methylimidazole (125.7 mg, 1.53 mmol, 2.0 equiv.), and K$_3$PO$_4$ (325 mg, 1.53 mmol, 2.0 equiv.) under N$_2$ atmosphere was added degassed 4:1 PhMe:dioxane solvent mixture (4.00 mL). To a second vial charged with Pd$_2$(dba)$_3$ (28.0 mg, 0.03 mmol, 4.0 mol %) and Me$_4$-di-t-BuXPhos (CAS#857356-94-6, 29.5 mg, 0.06 mmol, 8.0 mol %) under N$_2$ atmosphere was added degassed 4:1 PhMe:dioxane solvent mixture (1.00 mL). This mixture was stirred for 3 minutes at 120° C. to provide a dark red solution which was cooled to RT and transferred to the first vial. The reaction was degassed by bubbling with N$_2$ for 5 minutes and then sealed. The reaction mixture was stirred at 120° C. for 16 h. The reaction was cooled to RT and filtered through a pad of celite which was washed thoroughly with EtOAc. The filtrate was concentrated, and the residue was purified by normal phase chromatography on silica (0-5% MeOH/DCM) to afford the product (182 mg, 45%) as an off-white solid. LCMS (ES+) [M+H]+: 524.4.

(R)-3-(6-Methoxy-5-(4-methyl-1H-imidazol-1-yl)pyridin-2-yl)-5-(5-methylbenzofuran-2-yl)-5,6-dihydro-4H-1,2,4-oxadiazine A solution of (R)-3-(6-methoxy-5-(4-methyl-1H-imidazol-1-yl)pyridin-2-yl)-4-(4-methoxybenzyl)-5-(5-methylbenzofuran-2-yl)-5,6-dihydro-4H-1,2,4-oxadiazine (100 mg, 0.19 mmol, 1.0 equiv.) in DCE (1.00 mL) at ambient temperature was treated with triethylsilane (91.5 uL, 0.57 mmol, 3.0 equiv.) and TFA (1.00 mL). The resultant mixture was stirred at 95° C. for 2 h. The reaction mixture was cooled to RT, concentrated and dissolved in EtOAc. The organic layer washed with 1 N aqueous NaOH, brine and dried over MgSO$_4$, filtered and concentrated. The residue was purified by normal phase chromatography on silica (0-10% MeOH/DCM) to afford the product as an off-white solid. This material was dissolved in DMF and further purified using reverse phase chromatography on C18 resin (5-100% MeCN/H$_2$O+0.1% HCOOH) to provide, after lyophilisation, the compound of Example 10 as a white solid (55.0 mg, 71%).

Example 10, (R)-3-(6-Methoxy-5-(4-methyl-1H-imidazol-1-yl)pyridin-2-yl)-5-(5-methylbenzofuran-2-yl)-5,6-dihydro-4H-1,2,4-oxadiazine: $^1$H NMR (500 MHz, CDCl$_3$) δ 7.86 (s, 1H), 7.81 (d, J=8.0 Hz, 1H), 7.64 (d, J=8.0 Hz, 1H), 7.34 (dd, J=6.5, 5.0 Hz, 2H), 7.11 (dd, J=8.4, 1.4 Hz, 1H), 6.99 (s, 1H), 6.70-6.64 (m, 2H), 5.01 (dt, J=5.7, 3.0 Hz, 1H), 4.33 (dd, J=11.0, 3.7 Hz, 1H), 4.17 (dd, J=11.0, 5.5 Hz, 1H), 4.05 (s, 3H), 2.44 (s, 3H), 2.31 (d, J=0.8 Hz, 3H). LCMS analysis using LCMS A, standard conditions: t$_r$=3.91 min, LCMS (ES+) [M+H]+: 404.2; [α]$_D$=+319 (c=0.10, MeOH).

Example 11

Synthesis of (R)-2-(Benzo[b]thiophen-2-yl)-2-(4-methoxybenzylamino)ethanol

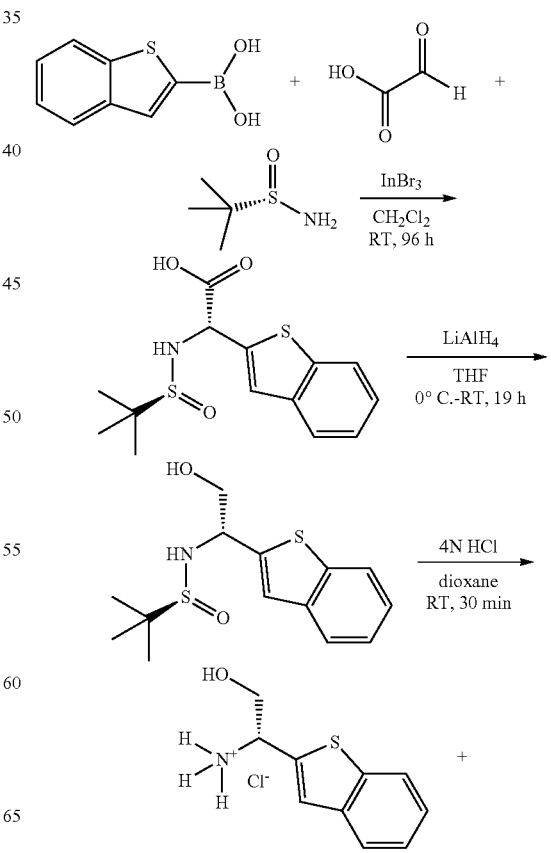

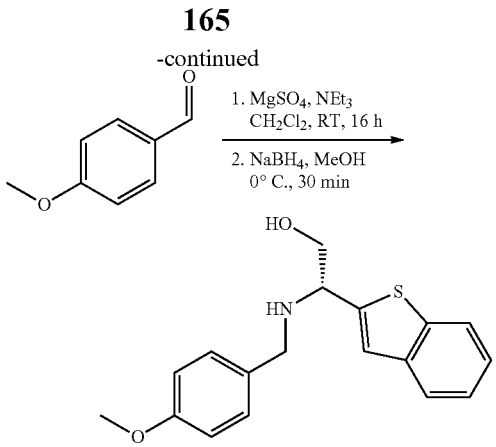

(R)-2-(Benzo[b]thiophen-2-yl)-2-((S)-1,1-dimethyl-ethylsulfinamido)acetic acid A suspension of benzo[b]thien-2-ylboronic acid (9.72 g, 54.6 mmol, 1.0 equiv), glyoxylic acid monohydrate (5.03 g, 54.6 mmol, 1.0 equiv) and (S)-2-methylpropane-2-sulfinamide (6.62 g, 54.6 mmol, 1.1 equiv) in anhydrous DCM (180 mL) at RT was treated with InBr$_3$ (1.94 g, 5.46 mmol, 0.10 equiv). The resultant mixture was stirred for 96 h at RT. The reaction mixture was filtered and the solid that was collected was washed with a small amount of DCM to afford the product as a white solid (9.40 g, 55%) that was used directly in the next step without further purification. LCMS (ES+) [M+H]+: 312.0.

(S)—N—((R)-1-(Benzo[b]thiophen-2-yl)-2-hydroxyethyl)-2-methylpropane-2-sulfinamide (R)-2-(Benzo[b]thiophen-2-yl)-2-((S)-1,1-dimethylethylsulfinamido)acetic acid (9.40 g, 30.2 mmol, 1.0 equiv.) from the previous reaction was added portion wise to a cooled (0° C.) suspension of LiAlH$_4$ (5.73 g, 151 mmol, 5.0 equiv) in THF (300 mL). The resultant mixture was allowed to warm to RT over 3 h and stirred for 16 h before being diluted with Et$_2$O (300 mL). The reaction mixture was cooled to 0° C. and quenched by sequential addition of water (5.7 ml), an aqueous sodium hydroxide solution (2 N, 5.7 ml) and water (17.1 ml). The mixture was allowed to warm to RT, stirred for 1 h and MgSO4 was added. The mixture was stirred for 10 min, the solids were filtered and rinsed thoroughly with 10% MeOH/DCM (500 mL). The filtrate was concentrated and the residue was purified by normal phase chromatography on silica (0-6% MeOH/DCM) to afford the alcohol as a white solid (2.71 g, 30%). 1H NMR (500 MHz, CDCl3) δ 7.80 (dd, J=8.0, 1.0 Hz, 1H), 7.73 (dd, J=7.1, 1.3 Hz, 1H), 7.35 (td, J=7.5, 1.4 Hz, 1H), 7.32 (td, J=7.2, 1.3 Hz, 1H), 7.23 (s, 1H), 4.85-4.80 (m, 1H), 4.16 (ddd, J=11.8, 8.2, 3.6 Hz, 1H), 4.03 (d, J=7.2 Hz, 1H), 3.84 (ddd, J=11.9, 8.0, 5.3 Hz, 1H), 3.62 (dd, J=8.2, 5.4 Hz, 1H), 1.32 (s, 9H); LCMS (ES+) [M+H]+: 298.0.

(R)-2-Amino-2-(benzo[b]thiophen-2-yl)ethanol hydrochloride (S)—N—((R)-1-(benzo[b]thioph-en-2-yl)-2-hydroxyethyl)-2-methylpropane-2-sulfinamide (2.71 g, 9.11 mmol, 1.0 equiv) was dissolved in a 4 N solution of HCl in 1,4-dioxane (46 mL) at RT. The resultant mixture was stirred at RT for 30 min and concentrated to dryness to afford the hydrochloride salt (2.47 g) which was used directly in the next step. LCMS (ES+) [M−OH]+: 176.9.

(R)-2-(Benzo[b]thiophen-2-yl)-2-(4-methoxybenzylamino)ethanol

A solution of crude (R)-2-amino-2-(benzo[b]thiophen-2-yl)ethanol hydrochloride from previous step in DCM (40 mL) at RT was treated successively with triethylamine (2.99 mL, 21.5 mmol, 2.0 equiv), MgSO$_4$ (2.6 g) and p-anisaldehyde (1.44 mL, 11.8 mmol, 1.1 equiv). The resultant suspension was stirred for 16 h at RT and filtered through a pad of celite which was washed with EtOAc. The filtrate was concentrated under vacuum to afford the corresponding imine intermediate. This intermediate was dissolved in MeOH (40 mL) and cooled to 0° C. NaBH$_4$ (1.23 g, 32.3 mmol, 3.0 equiv) was added portion wise over 5 min. The resultant mixture was stirred for 30 min at 0° C. and then quenched by the slow addition of a saturated aqueous solution of NaHCO$_3$. Water and DCM were added. The layers were separated and the aqueous layer was extracted with DCM twice. The combined organic layers were dried over MgSO$_4$, filtered and concentrated. The residue was purified by normal phase chromatography on silica (0-6% MeOH/DCM) to afford (R)-2-(Benzo[b]thiophen-2-yl)-2-(4-methoxybenzylamino)ethanol (2.41 g, 84% over 2 steps) as a white solid. $^1$H NMR (500 MHz, CDCl$_3$) δ 7.83 (ddt, J=7.7, 1.4, 0.7 Hz, 1H), 7.74-7.72 (m, 1H), 7.37-7.30 (m, 2H), 7.26-7.23 (m, 2H), 7.22 (s, 1H), 6.89-6.85 (m, 2H), 4.15 (ddd, J=8.1, 4.7, 0.6 Hz, 1H), 3.86 (d, J=12.8 Hz, H), 3.84 (dd, J=10.8, 4.7 Hz, 1H), 3.80 (s, 3H), 3.73 (dd, J=10.8, 8.1 Hz, 1H), 3.67 (d, J=12.7 Hz, 1H); LCMS (ES+) [M+H]+: 314.1.

Example 12

Synthesis of (R)-5-(Benzo[b]thiophen-2-yl)-3-(5-bromo-6-methoxypyridin-2-yl)-4-(4-methoxybenzyl)-5,6-dihydro-4H-1,2,4-oxadiazine

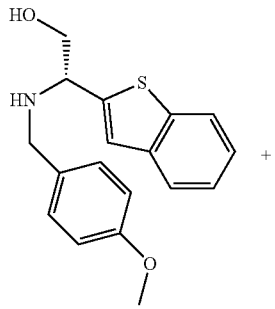

+

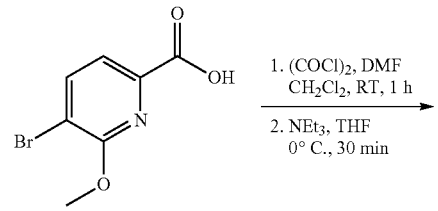

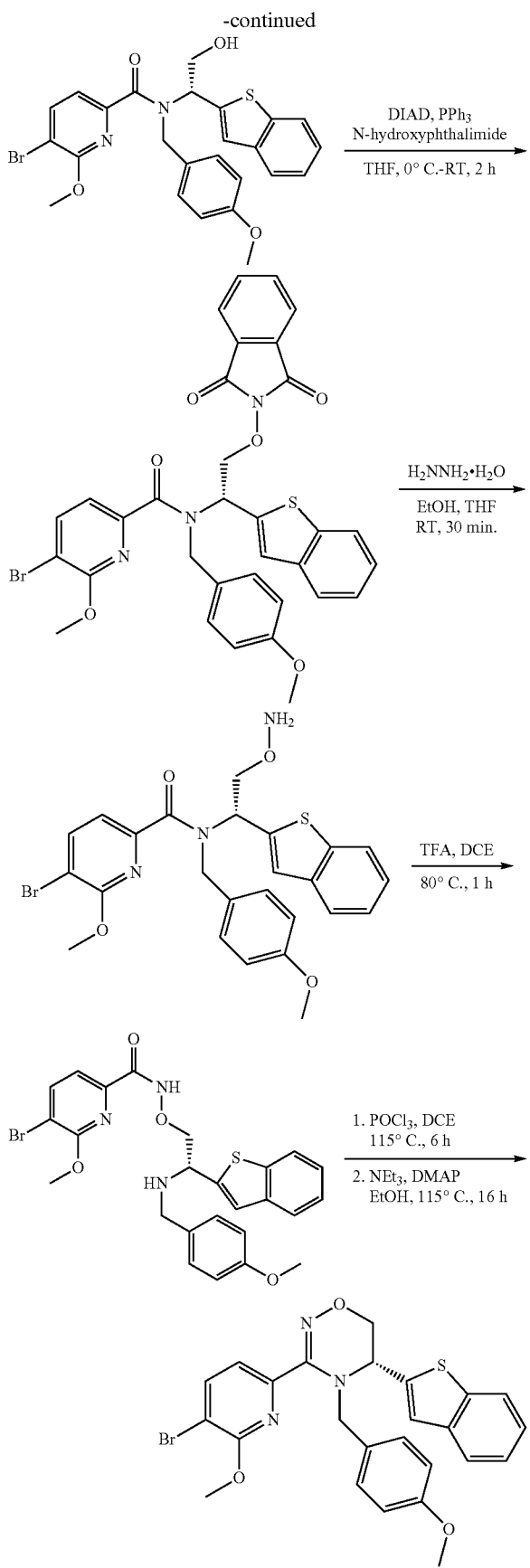

(R)—N-(1-(Benzo[b] thiophen-2-yl)-2-hydroxy-ethyl)-5-bromo-6-methoxy-N-(4-methoxyben-zyl) picolinamide A solution of 5-bromo-6-methoxypicolinic acid (1.96 g, 8.46 mmol, 1.10 equiv.) in DCM (50 mL) at RT was treated with a catalytic amount of DMF (1 drop) and oxalyl chloride (1.98 mL, 23.1 mmol, 3.0 equiv.). The resultant mixture was stirred at RT for 1 h at which point LCMS monitoring showed completion of the reaction. The mixture was concentrated, diluted with anhydrous THF (20 mL), concentrated again and dried under high vacuum for 1 h. The residue was diluted in anhydrous THF (35 ml), treated with triethylamine (3.22 mL, 23.1 mmol, 3.0 equiv.) and cooled to 0° C. A solution of (R)-2-(benzo[b]thiophen-2-yl)-2-(4-methoxybenzylamino)ethanol (2.41 g, 7.69 mmol, 1.0 equiv.) in THF (15 ml) was quickly added and the resultant mixture was stirred at 0° C. for 30 min. The reaction mixture was diluted with 120 mL of MeOH and $K_2CO_3$ (1.50 g) was added. The resultant mixture was then allowed to warm to RT and stirred for 16 h. A saturated aqueous solution of $NaHCO_3$ and EtOAc were then successively added. The layers were separated, and the aqueous layer was extracted with EtOAc twice. The combined organic layers were dried over $MgSO_4$, filtered and concentrated. The residue was purified by normal phase chromatography on silica (0-30% EtOAc/DCM) to afford the amide as a white foam (2.94 g, 82%). LCMS (ES+) [M+H]+: 527.1/528.9.

(R)—N-(1-(Benzo[b] thiophen-2-yl)-2-(1,3-diox-oisoindolin-2-yloxy)ethyl)-5-bromo-6-methoxy-N-(4-methoxybenzyl)picolinamide DIAD (1.22 mL, 6.19 mmol, 1.2 equiv.) was added to a solution of triphenylphosphine (1.62 g, 6.19 mmol, 1.2 equiv.), (R)—N-(1-(benzo[b]thiophen-2-yl)-2-hydroxy-ethyl)-5-bromo-6-methoxy-N-(4-methoxyben-zyl)picolinamide (2.72 g, 5.17 mmol, 1.0 equiv.) and N-hydroxyphthalimide (1.01 g, 6.19 mmol, 1.2 equiv.) in THF (35 mL) at 0° C. The resultant mixture was kept at 0° C. for 1 h, then warmed to RT and stirred for 2 h. EtOAc was added, and the organic layer was washed with 1 N aqueous NaOH twice, water and brine, dried over $MgSO_4$, filtered and concentrated. The residue was purified by normal phase chromatography on silica (0-45% EtOAc/hexanes) to afford the product as a light brown foam (1.93 g, 53%). LCMS (ES+) [M+H]+: 672.2/674.0.

(R)—N-(2-(Aminooxy)-1-(benzo[b] thiophen-2-yl) ethyl)-5-bromo-6-methoxy-N-(4-metho-xybenzyl) picolinamide A suspension of (R)—N-(1-(benzo[b]thiophen-2-yl)-2-(1,3-dioxoisoin-dolin-2-yloxy)ethyl)-5-bromo-6-methoxy-N-(4-methoxybenzyl)picolinamide (1.93 g, 2.87 mmol, 1.0 equiv.) in ethanol (90%, 20 mL) and THF (10 mL) at RT was treated with hydrazine hydrate (50-60%, 1.5 mL). The resultant mixture was stirred for 30 min and then water was added. The mixture was extracted with EtOAc three times, the combined organic layers were dried over $MgSO_4$, filtered and concentrated to afford the product (1.49 g, 96%) as light brown foam that was used directly in the next step. LCMS (ES+) [M+H]+: 542.1/544.0.

(R)—N-(2-(Benzo[b] thiophen-2-yl)-2-(4-methoxy-benzylamino)ethoxy)-5-bromo-6-methoxypicolina-mide A solution of (R)—N-(2-(aminooxy)-1-(benzo[b]thio-phen-2-yl)ethyl)-5-bromo-6-methoxy-N-(4-methoxybenzyl)picolinamide (1.49 g, 2.75 mmol, 1.0 equiv.) in DCE (20 mL) was treated with TFA (1.0 mL). The resultant mixture was stirred at 80° C. for 1 h, then cooled to RT and concentrated to dryness. The residue was diluted with EtOAc, washed with saturated aqueous solution of NaHCO$_3$ and brine, dried over MgSO$_4$, filtered and concentrated to afford the product (1.49 g, 100%) as pale yellow foam that was used directly in the next step. LCMS (ES+) [M+H]+: 542.1/544.1.

(R)-5-(Benzo[b] thiophen-2-yl)-3-(5-bromo-6-methoxypyridin-2-yl)-4-(4-methoxyben-zyl)-5,6-dihydro-4H-1,2,4-oxadiazine A solution of (R)—N-(2-(benzo[b]thiophen-2-yl)-2-(4-methoxybenzylamino)ethoxy)-5-bromo-6-methoxypicolinamide (1.49 g, 2.75 mmol, 1.0 equiv.) in anhydrous DCE (20 mL) at RT was treated with POCl$_3$ (3.8 mL, 41.2 mmol, 15.0 equiv.). The vial was sealed and heated at 115° C. for 6 h. The reaction mixture was evaporated, dried under high vacuum for 10 min, dissolved in EtOH (20 mL) and treated with Et$_3$N (1.53 mL, 11.0 mmol, 4.0 equiv.) and DMAP (168 mg, 1.37 mmol, 0.50 equiv.). The resultant mixture was heated to 115° C. for 16 h. The reaction mixture was cooled to RT and diluted with EtOAc. The organic layer was washed with 1 N aqueous NaOH, water twice and brine, dried over MgSO$_4$, filtered and concentrated. The residue was purified by normal phase chromatography on silica (0-45% EtOAc/hexanes) to afford (R)-5-(Benzo[b]thiophen-2-yl)-3-(5-bromo-6-methoxypyridin-2-yl)-4-(4-methoxy-ben-zyl)-5,6-dihydro-4H-1,2,4-oxadiazine (460 mg, 32%) as a pale yellow foam. $^1$H NMR (500 MHz, CDCl$_3$) δ 7.88 (d, J=7.8 Hz, 1H), 7.86-7.83 (m, 1H), 7.75-7.73 (m, 1H), 7.39-7.32 (m, 2H), 7.25-7.18 (m, 4H), 6.88-6.85 (m, 2H), 4.76 (t, J=3.5 Hz, 1H), 4.62 (d, J=15.7 Hz, 1H), 4.27 (dd, J=11.4, 3.7 Hz, 1H), 4.18 (dd, J=11.4, 3.6 Hz, 1H), 4.02 (d, J=15.6 Hz, 1H), 3.93 (s, J=5.2 Hz, 3H), 3.81 (s, J=4.0 Hz, 3H); LCMS (ES+) [M+H]+: 524.0/526.0.

Example 13

Synthesis of (R)-5-(Benzo[b]thiophen-2-yl)-3-(6-methoxy-5-(4-methyl-1H-imidazol-1-yl)pyridin-2-yl)-5,6-dihydro-4H-1,2,4-oxadiazine

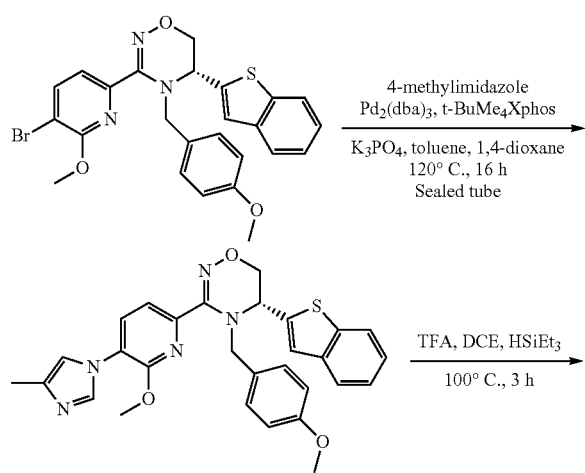

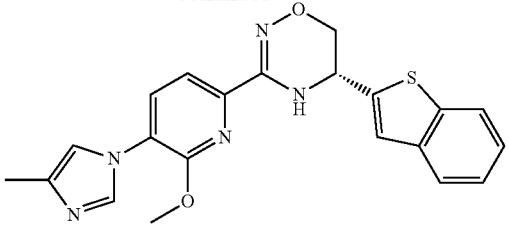

(R)-5-(Benzo[b]thiophen-2-yl)-3-(6-methoxy-5-(4-methyl-1H-imidazol-1-yl)pyridin-2-yl)-4-(4-methoxybenzyl)-5,6-dihydro-4H-1,2,4-oxadiazine To a vial charged with (R)-5-(benzo[b]thiophen-2-yl)-3-(5-bromo-6-methoxypyridin-2-yl)-4-(4-methoxybenzyl)-5,6-dihydro-4H-1,2,4-oxadiazine (200 mg, 0.381 mmol, 1.0 equiv.), 4(5)-methylimidazole (38 mg, 0.458 mmol, 1.2 equiv.), and K$_3$PO$_4$ (162 mg, 0.763 mmol, 2.0 equiv.) under N$_2$ atmosphere was added degassed 4:1 PhMe:dioxane solvent mixture (1.5 mL). To a second vial charged with Pd$_2$(dba)$_3$ (14.0 mg, 0.015 mmol, 4.0 mol %) and Me$_4$-di-t-BuXPhos (CAS#857356-94-6, 14.7 mg, 0.031 mmol, 8.0 mol %) under N$_2$ atmosphere was added degassed 4:1 PhMe:dioxane solvent mixture (1.5 mL). This mixture was stirred for 3 min at 120° C. to provide a dark red solution which was cooled to RT and transferred to the first vial. The reaction was degassed by bubbling with N$_2$ for 5 minutes and then sealed. The reaction mixture was stirred at 120° C. for 16 h. The reaction was cooled to RT and filtered through a pad of celite which was washed thoroughly with EtOAc. The filtrate was concentrated, and the residue was purified by normal phase chromatography on silica (0-5% MeOH/DCM) to afford the product (140 mg, 70%) as an off-white solid. LCMS (ES+) [M+H]+: 526.4.

(R)-5-(Benzo[b]thiophen-2-yl)-3-(6-methoxy-5-(4-methyl-1H-imidazol-1-yl)pyridin-2-yl)-5,6-dihydro-4H-1,2,4-oxadiazine A solution of (R)-5-(benzo[b]thiophen-2-yl)-3-(6-methoxy-5-(4-methyl-1H-imidazol-1-yl)pyridin-2-yl)-4-(4-methoxybenzyl)-5,6-dihydro-4H-1,2,4-oxadiazine (140 mg, 0.266 mmol, 1.0 equiv.) and Et$_3$SiH (127 μL, 0.799 mmol, 3.0 equiv.) in DCE (4.0 mL) at RT was treated with TFA (4.0 mL). The resultant mixture was stirred at 100° C. for 3 h. The reaction mixture was cooled to RT, concentrated and dissolved in EtOAc. The organic layer was washed with 1 N aqueous NaOH and brine, dried over MgSO$_4$, filtered and concentrated. The residue was purified by normal phase chromatography on silica (0-5% MeOH/DCM) to afford the product (72 mg) as an off-white solid. The product was dissolved in DMF (1.5 mL) and further purified using reverse phase chromatography on C18 resin (5-100% MeCN/H$_2$O+0.1% HCOOH) to provide, after lyophilisation, the compound of Example 13 as a white solid (66 mg, 61%).

Example 13, (R)-5-(Benzo[b]thiophen-2-yl)-3-(6-methoxy-5-(4-methyl-1H-imidazol-1-yl)pyridin-2-yl)-5,6-dihydro-4H-1,2,4-oxadiazine: $^1$H NMR (500 MHz, CDCl$_3$) δ 7.87-7.80 (m, 3H), 7.78-7.75 (m, 1H), 7.64 (d, J=8.0 Hz, 1H), 7.40-7.33 (m, 3H), 7.00-6.98 (m, 1H), 6.74 (s, 1H), 5.19-5.16 (m, 1H), 4.37 (ddd, J=11.0, 3.9, 0.8 Hz, 1H), 4.03 (s, 3H), 4.00 (dd, J=11.0, 6.2 Hz, 1H), 2.30 (d, J=1.0 Hz,

Example 14

Synthesis of 2-(4-Methoxybenzylamino)-2-(3-methylbenzofuran-2-yl)ethanol

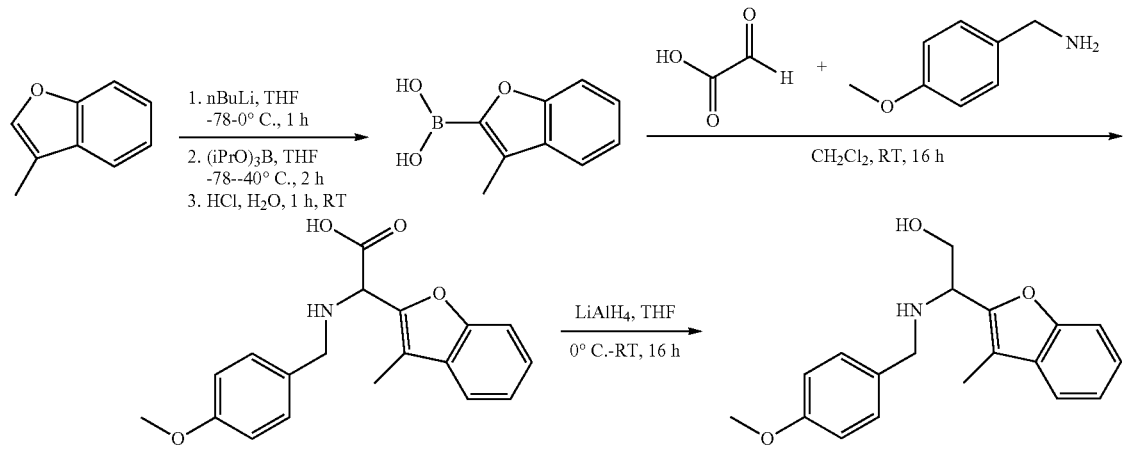

3-Methylbenzofuran-2-ylboronic acid

To a solution of 3-methylbenzofuran (10.3 g, 77.9 mmol, 1.0 equiv.) in THF (260 mL) at −78° C. was slowly added 2.5 M nBuLi in hexanes (37.4 mL, 93.5 mmol, 1.2 equiv). The resultant mixture was stirred for 1 h at 0° C. and then cooled back to −78° C. and treated with triisopropylborate (27.0 mL, 117 mmol, 1.5 equiv). The reaction was allowed to warm to −40° C. over 2 h and quenched with water. The reaction mixture was allowed to warm to RT, a 2 N aqueous HCl solution (60 mL) was added and the resultant mixture was stirred for 1 h. The pH was adjusted to 5 using a 1 N aqueous NaOH solution. EtOAc was added ant the layers were separated. The aqueous phase was extracted with EtOAc, the combined organic extracts were washed with brine, dried over $MgSO_4$, filtered and concentrated. The residue was purified by trituration in DCM/Hexanes mixture and the resultant white solid was collected by filtration and rinsed with hexanes to afford the product (8.71 g, 64%) as a white solid. $^1$H NMR (500 MHz, DMSO-d6) δ 8.41 (s, 2H), 7.62 (d, J=7.7 Hz, 1H), 7.50 (d, J=8.2 Hz, 1H), 7.34 (ddd, J=8.3, 7.2, 1.3 Hz, 1H), 7.25-7.22 (m, 1H), 2.40 (s, 3H); LCMS (ES−) [M−H]−: 174.9.

2-(4-Methoxybenzylamino)-2-(3-methylbenzofuran-2-yl)acetic acid

A suspension of 3-methylbenzofuran-2-ylboronic acid (8.27 g, 47.0 mmol, 1.0 equiv), glyoxylic acid monohydrate (4.33 g, 47.0 mmol, 1.0 equiv) and 4-methoxybenzylamine (6.14 mL, 47.0 mmol, 1.0 equiv) in anhydrous DCM (230 mL) was stirred for 16 h at RT. Hexanes (250 mL) was added, the solid that precipitated was collected by filtration and washed with 300 mL of DCM/hexanes 1:1 to provide the amino acid (15.8 g) as a white solid that was used directly in the next step without further purification. LCMS (ES+) [M+H]+: 326.2.

2-(4-Methoxybenzylamino)-2-(3-methylbenzofuran-2-yl)ethanol

Crude 2-(4-methoxybenzyl amino)-2-(3-methylbenzofuran-2-yl)acetic acid (16.2 g, 49.7 mmol, 1.0 equiv.) from the previous reaction was added portion wise to a cooled (0° C.) suspension of $LiAlH_4$ (5.66 g, 149 mmol, 3.0 equiv) in THF (250 mL). The resultant mixture was stirred at RT for 16 h before being diluted with $Et_2O$ (300 mL). While maintained at 0° C., the reaction mixture was quenched by sequential addition of water (5.7 mL), aqueous sodium hydroxide (2 N, 5.7 mL) and water (17.1 mL). The mixture was allowed to warm to RT, stirred for 2 h and $MgSO_4$ was added. The mixture was stirred for 10 min, the solids were filtered and rinsed thoroughly with 4:1 DCM/MeOH (750 mL). The filtrate was concentrated and the residue was purified by normal phase chromatography on silica (0-6% MeOH/DCM) to afford 2-(4-Methoxybenzylamino)-2-(3-methylbenzofuran-2-yl)ethanol as a white solid (7.71 g, 50%). $^1$H NMR (500 MHz, $CDCl_3$) δ 7.50-7.47 (m, 1H), 7.43-7.40 (m, 1H), 7.30-7.22 (m, 2H), 7.22-7.18 (m, 2H), 6.86-6.82 (m, 2H), 3.99 (dd, J=9.0, 5.0 Hz, 1H), 3.85-3.71 (m, 6H), 3.56 (d, J=12.8 Hz, 1H), 2.18 (s, 3H); LCMS (ES+) [M+H]+: 312.1.

Example 15

Synthesis of 3-(5-Bromo-6-methoxypyridin-2-yl)-4-(4-methoxybenzyl)-5-(3-methylbenzofu-ran-2-yl)-5,6-dihydro-4H-1,2,4-oxadiazine

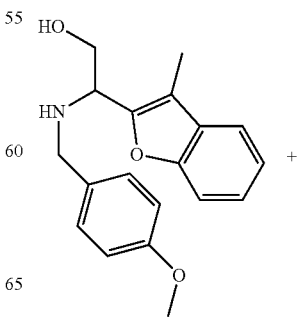

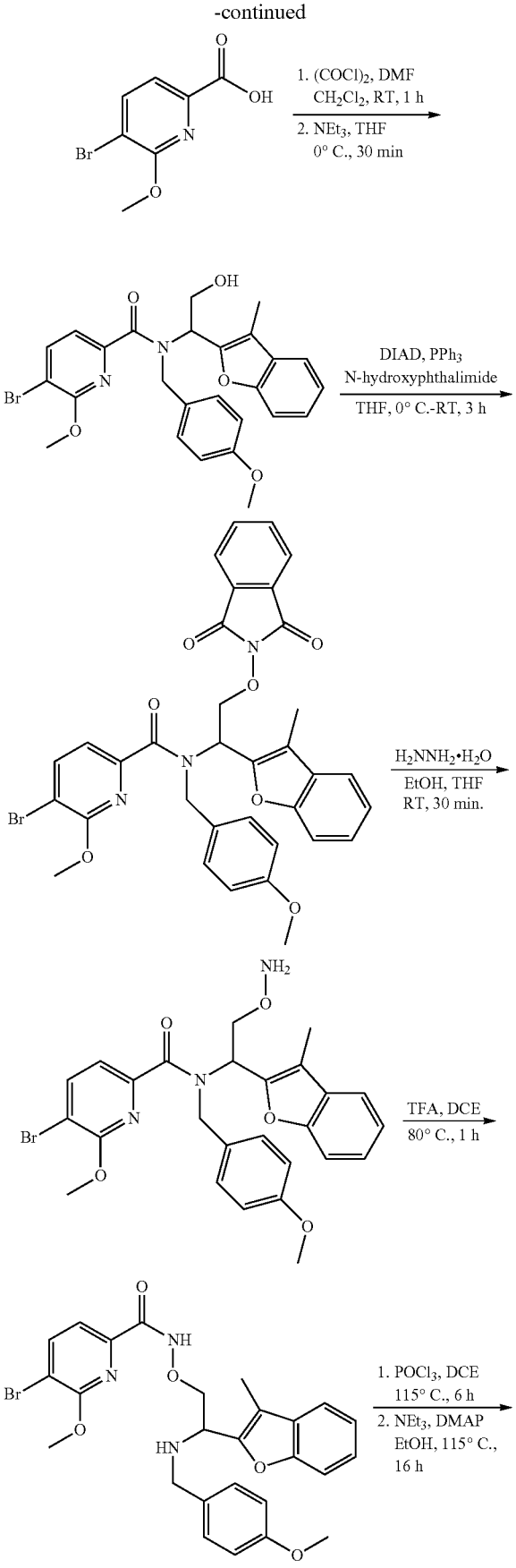

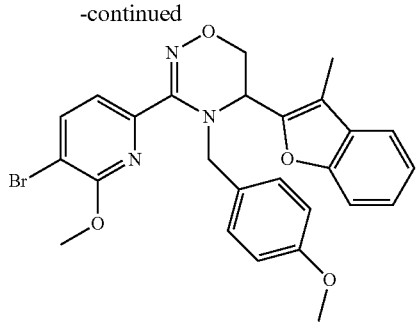

5-Bromo-N-(2-hydroxy-1-(3-methylbenzofuran-2-yl)ethyl)-6-methoxy-N-(4-methoxybenzyl) picolinamide A solution of 5-bromo-6-methoxypicolinic acid (2.87 g, 12.4 mmol, 1.10 equiv.) in DCM (75 mL) at RT was treated with a catalytic amount of DMF (4 drops) and oxalyl chloride (2.89 mL, 33.7 mmol, 3.0 equiv.). The resultant mixture was stirred at RT for 1 h at which point LCMS monitoring showed completion of the reaction. The mixture was concentrated, diluted with anhydrous THF (50 mL), concentrated again and dried under high vacuum for 1 h. The residue was diluted in anhydrous THF (50 ml), treated with triethylamine (4.70 mL, 33.7 mmol, 3.0 equiv.) and cooled to 0° C. A solution of 2-(4-methoxybenzylamino)-2-(3-methylbenzofuran-2-yl)ethanol (3.50 g, 11.2 mmol, 1.0 equiv.) in THF (25 ml) was quickly added and the resultant mixture was stirred at 0° C. for 30 min. A saturated aqueous solution of $NaHCO_3$ and EtOAc were then successively added. The layers were separated, and the aqueous layer was extracted with EtOAc twice. The combined organic layers were dried over $MgSO_4$, filtered and concentrated. The residue was dissolved in MeOH (60 mL), cooled to 0° C. and $K_2CO_3$ (1.50 g) was added. The resultant mixture was stirred for 30 min at 0° C., diluted with EtOAc and water was added. The layers were separated, and the aqueous layer was extracted with EtOAc twice. The combined organic layers were washed with brine, dried over $MgSO_4$, filtered and concentrated. The residue was purified by normal phase chromatography on silica (0-25% EtOAc/DCM) to afford the amide as white solid (4.86 g, 82%). LCMS (ES+) [M+H]+: 525.1/526.9.

5-Bromo-N-(2-(1,3-dioxoisoindolin-2-yloxy)-1-(3-methylbenzofuran-2-yl)ethyl)-6-methoxy-N-(4-methoxybenzyl)picolinamide DIAD (2.10 mL, 10.7 mmol, 1.2 equiv.) was added to a solution of triphenylphosphine (2.80 g, 10.7 mmol, 1.2 equiv.), 5-bromo-N-(2-hydroxy-1-(3-methylbenzofuran-2-yl)ethyl)-6-methoxy-N-(4-methoxybenzyl)picolinamide (4.67 g, 8.89 mmol, 1.0 equiv.) and N-hydroxylphtalimide (1.74 g, 10.7 mmol, 1.2 equiv.) in THF (45 mL) at 0° C. The resultant mixture was kept at 0° C. for 1 h, then warmed to RT and stirred for 2 h. EtOAc was added, and the organic layer was washed with 1 N aqueous NaOH twice, water and brine, dried over $MgSO_4$, filtered and concentrated. The residue was purified by normal phase chromatography on silica (10-45% EtOAc/hexanes) to afford the product as white solid (4.54 g, 76%). LCMS (ES+) [M+H]+: 670.2/672.0.

N-(2-(Aminooxy)-1-(3-methylbenzofuran-2-yl)ethyl)-5-bromo-6-methoxy-N-(4-methoxy benzyl) picolinamide A suspension of 5-bromo-N-(2-(1,3-dioxoisoindolin-2-yloxy)-1-(3-methyl benzofuran-2-yl)ethyl)-6-methoxy-N-(4-methoxybenzyl)picolinamide (4.54 g, 6.77 mmol, 1.0 equiv.) in ethanol (90%, 30 mL) and THF (15 mL) at 0° C. was treated with hydrazine hydrate (50-60%, 3.0 mL). The resultant mixture was stirred for 30 min at 0° C. and then water was added. The mixture was extracted with EtOAc three times, the combined organic layers were dried over MgSO$_4$, filtered and concentrated to afford the product (3.69 g, 99%) as a pale yellow foam that was used directly in the next step. LCMS (ES+) [M+H]+: 540.1/542.0.

5-Bromo-6-methoxy-N-(2-(4-methoxybenzylamino)-2-(3-methylbenzofuran-2-yl)ethoxy) picolinamide A solution of N-(2-(aminooxy)-1-(3-methylbenzofuran-2-yl)ethyl)-5-bromo-6-methoxy-N-(4-methoxybenzyl)picolinamide (3.33 g, 6.16 mmol, 1.0 equiv.) in DCE (30 mL) was treated with TFA (2.20 mL). The resultant mixture was stirred at 80° C. for 60 min, then cooled to RT and concentrated to dryness. The residue was diluted with EtOAc, washed with saturated aqueous solution of NaHCO$_3$ and brine, dried over MgSO$_4$, filtered and concentrated to afford the product (3.33 g, 100%) as orange foam that was used directly in the next step. LCMS (ES+) [M+H]+: 540.1/542.0.

3-(5-Bromo-6-methoxypyridin-2-yl)-4-(4-methoxybenzyl)-5-(3-methylbenzofu-ran-2-yl)-5,6-dihydro-4H-1,2,4-oxadiazine A solution of 5-bromo-6-methoxy-N-(2-(4-methoxybenzylamino)-2-(3-methylbenzofuran-2-yl)ethoxy)picoli-namide (3.36 g, 6.22 mmol, 1.0 equiv.) in anhydrous DCE (40 mL) at RT was treated with POCl$_3$ (8.7 mL, 93.3 mmol, 15.0 equiv.). The vial was sealed and heated at 115° C. for 6 h. The reaction mixture was evaporated, dried under high vacuum for 20 min, dissolved in EtOH (40 mL) and treated with Et$_3$N (3.47 mL, 24.9 mmol, 4.0 equiv.) and DMAP (380 mg, 3.11 mmol, 0.50 equiv.). The resultant mixture was heated to 115° C. for 16 h. The reaction mixture was cooled to RT and diluted with EtOAc. The organic layer was washed with 1 N aqueous NaOH, water twice and brine, dried over MgSO$_4$, filtered and concentrated. The residue was purified by normal phase chromatography on silica (0-45% EtOAc/hexanes) to afford the product (1.38 g, 43%) as white solid.

The racemate was separated using semi preparative HPLC A (ChiralPak IB column, 5 uM, 20×250 mm, 15 mL/min, 76% Hexanes/12% MeOH/12% DCM) to afford the compounds of Example 15A (Fraction (I)) and Example 15B (Fraction (II)).

Example 15A, 3-(5-bromo-6-methoxypyridin-2-yl)-4-(4-methoxybenzyl)-5-(3-methylbenzofuran-2-yl)-5,6-dihydro-4H-1,2,4-oxadiazine, fraction (I): (400 mg of a white solid, T$_R$=9.3 min); LCMS (ES+) [M+H]+: 522.0/524.0.

Example 15B, 3-(5-bromo-6-methoxypyridin-2-yl)-4-(4-methoxybenzyl)-5-(3-methylbenzofuran-2-yl)-5,6-dihydro-4H-1,2,4-oxadiazine, fraction (II): (410 mg of a white solid, T$_R$=10.9 min). $^1$H NMR (500 MHz, CDCl$_3$) δ 7.91-7.86 (m, 1H), 7.51-7.48 (m, 1H), 7.46-7.44 (m, 1H), 7.33-7.24 (m, 3H), 7.08-7.05 (m, 2H), 6.84-6.77 (m, 2H), 4.77 (dd, J=5.5, 4.2 Hz, 1H), 4.67 (d, J=15.7 Hz, 1H), 4.32 (dd, J=11.4, 5.6 Hz, 1H), 4.19 (dd, J=11.4, 4.2 Hz, 1H), 3.93 (s, J=5.5 Hz, 3H), 3.89 (d, J=15.8 Hz, 1H), 3.78 (s, 3H), 2.15 (s, 3H); LCMS (ES+) [M+H]+: 522.0/524.0.

Example 16A

Synthesis of 3-(6-methoxy-5-(4-methyl-1H-imidazol-1-yl)pyridin-2-yl)-5-(3-methylbenzofuran-2-yl)-5,6-dihydro-4H-1,2,4-oxadiazine, fraction (I)

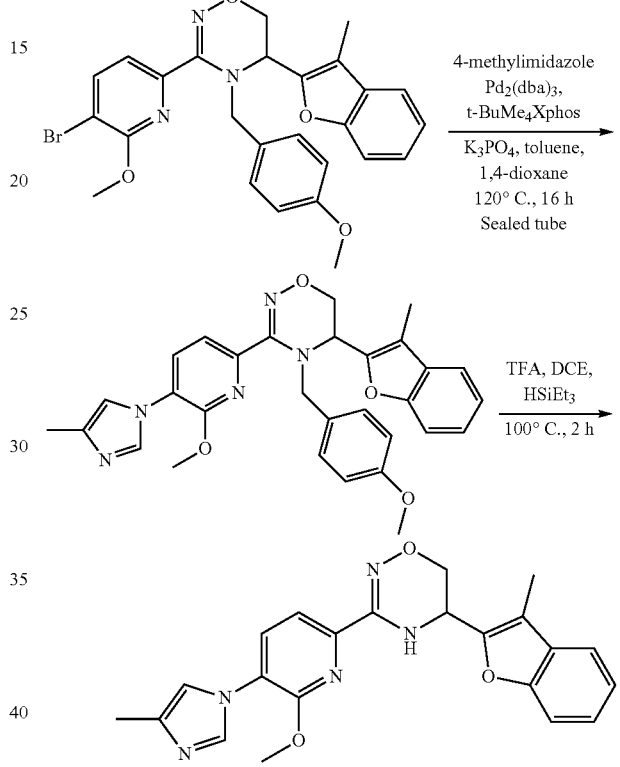

3-(6-Methoxy-5-(4-methyl-1H-imidazol-1-yl)pyridin-2-yl)-4-(4-methoxybenzyl)-5-(3-methylbenzofuran-2-yl)-5,6-dihydro-4H-1,2,4-oxadiazine, fraction (I)

The title compound (98 mg, 66%) was prepared as a white solid from 3-(5-bromo-6-methoxypyridin-2-yl)-4-(4-methoxybenzyl)-5-(3-methylbenzofuran-2-yl)-5,6-dihydro-4H-1,2,4-oxadiazine, fraction (I) Example 15A according to the procedure for Example 16B. LCMS (ES+) [M+H]+: 524.3.

3-(6-Methoxy-5-(4-methyl-1H-imidazol-1-yl)pyridin-2-yl)-5-(3-methylbenzofuran-2-yl)-5,6-dihydro-4H-1,2,4-oxadiazine, fraction (I)

Example 16A (55 mg, 73%) was prepared as a white solid from 3-(6-methoxy-5-(4-methyl-1H-imidazol-1-yl)pyridin-2-yl)-4-(4-methoxybenzyl)-5-(3-methylbenzofuran-2-yl)-5,6-dihydro-4H-1,2,4-oxadiazine, fraction (I) according to the procedure for Example 16B.

Example 16A, (−)-3-(6-methoxy-5-(4-methyl-1H-imidazol-1-yl)pyridin-2-yl)-5-(3-methylbenzofuran-2-yl)-5,6-dihydro-4H-1,2,4-oxadiazine, fraction (I): LCMS analysis using LCMS B, standard conditions: $T_R$=1.45 min, LCMS (ES+) [M+H]+: 404.3; $[\alpha]_D$=−221 (c=0.63, MeOH).

Example 16B

Synthesis of 3-(6-methoxy-5-(4-methyl-1H-imidazol-1-yl)pyridin-2-yl)-5-(3-methylbenzofuran-2-yl)-5,6-dihydro-4H-1,2,4-oxadiazine, fraction (II)

(6-Methoxy-5-(4-methyl-1H-imidazol-1-yl)pyridin-2-yl)-4-(4-methoxybenzyl)-5-(3-methylbenzofuran-2-yl)-5,6-dihydro-4H-1,2,4-oxadiazine, fraction (II)

To a vial charged with 3-(5-bromo-6-methoxypyridin-2-yl)-4-(4-methoxybenzyl)-5-(3-methylbenzofuran-2-yl)-5,6-dihydro-4H-1,2,4-oxadiazine, fraction (II) Example 15B (150 mg, 287 mmol, 1.0 equiv.), 4(5)-methylimidazole (28 mg, 0.345 mmol, 1.2 equiv.), and $K_3PO_4$ (122 mg, 0.574 mmol, 2.0 equiv.) under $N_2$ atmosphere was added degassed 4:1 PhMe:dioxane solvent mixture (1.20 mL). To a second vial charged with $Pd_2(dba)_3$ 10.5 mg, 0.011 mmol, 4.0 mol %) and $Me_4$-di-t-BuXPhos (CAS#857356-94-6, 11.0 mg, 0.023 mmol, 8.0 mol %) under $N_2$ atmosphere was added degassed 4:1 PhMe:dioxane solvent mixture (1.2 mL). This mixture was stirred for 3 min at 120° C. to provide a dark red solution which was cooled to RT and transferred to the first vial. The reaction was degassed by bubbling with $N_2$ for 5 min and then sealed. The reaction mixture was stirred at 120° C. for 16 h. The reaction was cooled to RT and filtered through a pad of celite which was washed thoroughly with EtOAc. The filtrate was concentrated and the residue was purified by normal phase chromatography on silica (0-5% MeOH/DCM) to afford the product (99 mg, 67%) as a white solid. LCMS (ES+) [M+H]+: 524.3.

(6-Methoxy-5-(4-methyl-1H-imidazol-1-yl)pyridin-2-yl)-5-(3-methylbenzofuran-2-yl)-5,6-dihydro-4H-1,2,4-oxadiazine, fraction (II)

A solution of 3-(6-methoxy-5-(4-methyl-1H-imidazol-1-yl)pyridin-2-yl)-4-(4-methoxybenzyl)-5-(3-methylbenzofuran-2-yl)-5,6-dihydro-4H-1,2,4-oxadiazine, fraction (II) (99 mg, 0.189 mmol, 1.0 equiv.) and $Et_3SiH$ (91 µL, 0.567 mmol, 3.0 equiv.) in DCE (4 mL) at RT was treated with TFA (4 mL). The resultant mixture was stirred at 100° C. for 2 h, cooled to RT, concentrated and dissolved in EtOAc. The organic layer was washed with 1 N aqueous NaOH and brine, dried over $MgSO_4$, filtered and concentrated. The residue was purified by normal phase chromatography on silica (0-5% MeOH/DCM) to afford the product (60 mg) as an oil. This material was dissolved in DMF (1.5 mL) and further purified using reverse phase chromatography on C18 resin (5-100% MeCN/$H_2O$+0.1% HCOOH) to provide, after lyophilisation, the compound of Example 16B as a white solid (51 mg, 67%).

Example 16B, (+)-(6-methoxy-5-(4-methyl-1H-imidazol-1-yl)pyridin-2-yl)-5-(3-methylbenzofuran-2-yl)-5,6-dihydro-4H-1,2,4-oxadiazine, fraction (II): $^1$H NMR (500 MHz, $CDCl_3$) δ 7.85 (d, J=1.3 Hz, 1H), 7.83 (d, J=8.0 Hz, 1H), 7.64 (d, J=8.0 Hz, 1H), 7.53 (ddd, J=7.5, 1.4, 0.7 Hz, 1H), 7.44-7.42 (m, 1H), 7.34-7.30 (m, 1H), 7.28 (dd, J=7.6, 1.1 Hz, 1H), 6.99-6.97 (m, 1H), 6.52 (s, 1H), 5.11 (ddd, J=7.4, 4.2, 1.8 Hz, 1H), 4.36 (ddd, J=11.0, 4.2, 1.0 Hz, 1H), 4.06 (dd, J=11.0, 7.5 Hz, 1H), 4.00 (s, 3H), 2.32 (s, 3H), 2.30 (d, J=1.0 Hz, 3H); LCMS analysis using LCMS B, standard conditions: $T_R$=1.45 min, LCMS (ES+) [M+H]+: 404.3; $[\alpha]_D$=+234 (c=0.63, MeOH).

Example 17

Synthesis of (R)-2-(4-Methoxybenzylamino)-2-(4-methylbenzofuran-2-yl)ethanol

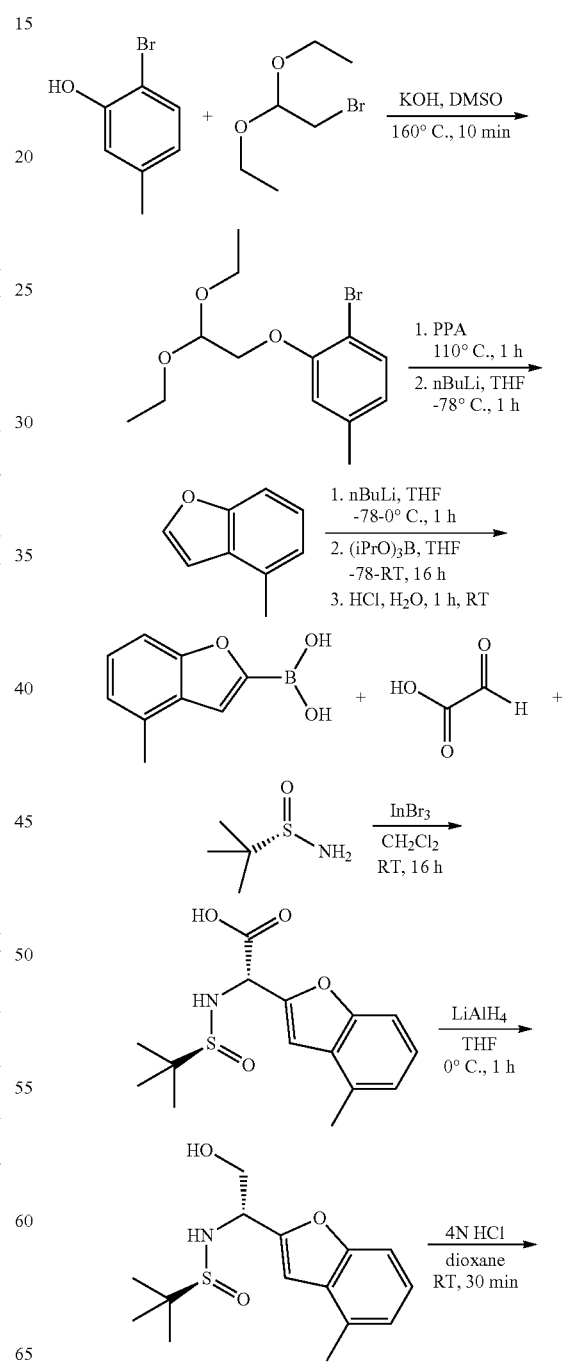

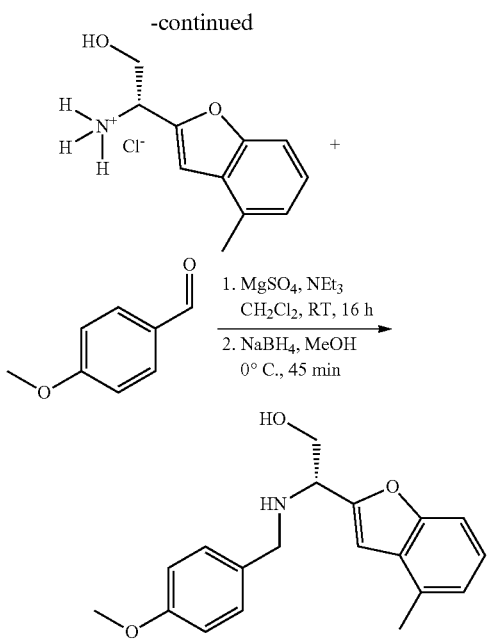

1-Bromo-2-(2,2-diethoxyethoxy)-4-methylbenzene

To a solution of 2-bromo-5-methylphenol (9.37 g, 50.1 mmol, 1.0 equiv) in DMSO (25.0 mL) was added 2-bromo-1,1-diethoxyethane (7.17 mL, 75.1 mmol, 1.5 equiv), followed by KOH (4.22 g, 75.1 mmol, 1.5 equiv). The resultant mixture was stirred at 160° C. for 10 min. LCMS analysis showed 77% conversion to the product. The reaction was cooled to RT, and water was added. The mixture was extracted with EtOAc, and the organic layer was washed with 1 N aqueous NaOH, dried over $Na_2SO_4$, filtered and evaporated to afford the product as an oil (12.2 g, 80%) that was used directly in the next step. $^1H$ NMR (500 MHz, $CDCl_3$) δ 7.38 (d, J=8.0 Hz, 1H), 6.73 (d, J=1.5 Hz, 1H), 6.65 (ddd, J=8.0, 1.9, 0.7 Hz, 1H), 4.87 (t, J=5.2 Hz, 1H), 4.03 (d, J=5.2 Hz, 2H), 3.81 (dq, J=9.4, 7.1 Hz, 2H), 3.70 (dq, J=9.4, 7.0 Hz, 2H), 2.29 (s, 3H), 1.26 (t, J=7.1 Hz, 6H).

7-Bromo-4-methylbenzofuran

To a solution of polyphosphoric acid (12.2 g) in toluene (100 mL) was added 1-bromo-2-(2,2-diethoxyethoxy)-4-methylbenzene (12.2 g, 40.3 mmol, 1.0 equiv). The resultant mixture was allowed to stir at 110° C. for 1 h, then cooled to RT and diluted with water. The mixture was extracted with EtOAc, and the organic layer was washed with 1 N aqueous NaOH, dried over $Na_2SO_4$ and evaporated to afford the product as an oil (7.06 g, 83%) that was used directly in the next step. $^1H$ NMR (500 MHz, $CDCl_3$) δ7.68 (d, J=2.2 Hz, 1H), 7.34 (d, J=7.8 Hz, 1H), 6.92 (dq, J=7.9, 0.7 Hz, 1H), 6.85 (d, J=2.2 Hz, 1H), 2.48 (d, J=0.6 Hz, 3H).

4-Methylbenzofuran

To a solution of 7-bromo-4-methylbenzofuran (9.61 g) in THF (228 mL) at −78° C. was slowly added 2.5 M nBuLi in hexanes (21.9 mL, 54.6 mmol, 1.2 equiv). The resultant reaction mixture was stirred for 1 h, then quenched by the addition of water. The mixture was allowed to warm to RT extracted with EtOAc. The organic extracts were dried over $Na_2SO_4$ and evaporated. The oily residue was heated at 80° C. in the presence of $CaH_2$, then distilled under vacuum at 110° C. to afford the product as a clear oil (4.51 g, 75%). $^1H$ NMR (500 MHz, $CDCl_3$) δ7.64 (d, J=2.2 Hz, 1H), 7.40 (d, J=7.8 Hz, 1H), 7.22 (dd, J=8.2, 7.3 Hz, 1H), 7.06 (m, 1H), 6.81 (d, J=2.2 Hz, 1H), 2.54 (s, 3H).

4-Methylbenzofuran-2-ylboronic acid

To a solution of 4-methylbenzofuran (7.65 g, 57.8 mmol, 1.0 equiv.) in THF (193 mL) at −78° C. was slowly added 2.5 M nBuLi in hexanes (27.8 mL, 69.4 mmol, 1.2 equiv). The resultant mixture was stirred for 1 h at 0° C., then cooled back to −78° C. and treated with triisopropylborate (20.1 mL, 86.8 mmol, 1.5 equiv). The reaction was allowed to warm to RT and stirred for 16 hours, then quenched with 2 N aqueous HCl. The reaction mixture was stirred for 1 h, and the pH was adjusted to 5 using a 1 N aqueous NaOH solution. The aqueous medium was extracted with EtOAc, and the organic extracts were dried over $Na_2SO_4$, filtered and evaporated. The residue was purified by trituration in DCM/Hexanes mixture, and the resultant white solid was collected by filtration and rinsed with hexanes to afford the product (4.51 g, 75%). $^1H$ NMR (500 MHz, DMSO) δ 8.50 (s, 2H), 7.50 (d, J=1.0 Hz, 1H), 7.38 (dd, J=8.3, 0.6 Hz, 1H), 7.23 (dd, J=8.2, 7.3 Hz, 1H), 7.04-7.01 (m, 1H), 2.49 (s, 3H).

(2S)-2-(1,1-Dimethylethylsulfinamido)-2-(4-methyl-benzofuran-2-yl)acetic acid A suspension of 4-methylbenzofuran-2-ylboronic acid (8.22 g, 46.7 mmol, 1.0 equiv), glyoxylic acid monohydrate (4.78 g, 51.9 mmol, 1.1 equiv) and (S)-2-methylpropane-2-sulfinamide (6.29 g, 51.9 mmol, 1.1 equiv) in anhydrous DCM (156 mL) at ambient temperature was treated with $InBr_3$ (1.84 g, 5.19 mmol, 0.11 equiv). The resultant mixture was stirred for 16 h at ambient temperature. To the mixture was added $MgSO_4$ (5 g), the mixture was stirred for 5 minutes and filtered through a pad of celite, which was washed with EtOAc. The filtrate was concentrated under vacuum to afford the corresponding intermediate as an orange solid that was used directly in the next step. LCMS (ES+) [M+H]+: 310.0.

N—((R)-2-Hydroxy-1-(4-methylbenzofuran-2-yl)ethyl)-2-methylpropane-2-sulfinamide A crude solution of (2S)-2-(1,1-dimethylethylsulfinamido)-2-(4-methylbenzofuran-2-yl)acetic acid from previous reaction in THF (100 mL) was slowly added to a cooled (0° C.) suspension of $LiAlH_4$ (8.86 g, 233 mmol, 5.0 equiv) in THF (175 mL). The reaction mixture was stirred for 1 h at 0° C. LCMS analysis shown 10% of starting material remaining. More $LiAlH_4$ (1.77 g, 46.6 mmol, 1.0 equiv) was added and the reaction was stirred for another hour before being diluted with $Et_2O$ (300 mL). While maintained at 0° C. the reaction mixture was quenched by sequential addition of water (11.0 mL), aqueous sodium hydroxide (2 N, 11.0 mL) and water (33.0 mL). The mixture was warmed to ambient temperature, stirred for 1 hour and then $MgSO_4$ was added. The mixture was stirred for 10 minutes and the solids were filtered and rinsed thoroughly with 10% MeOH/DCM (500 mL). The filtrate was concentrated and the residue was purified by normal phase chromatography on silica (0-7% MeOH/DCM) to afford the alcohol as a pale yellow oil (6.16 g, 45%, 70% pure by LCMS). LCMS (ES+) [M+H]+: 296.1.

(R)-2-Hydroxy-1-(4-methylbenzofuran-2-yl)ethanaminium chloride

N—((R)-2-hydroxy-1-(4-methylbenzofuran-2-yl)ethyl)-2-methylpropane-2-sulfinamide (5.02 g, 17.0 mmol, 1.0 equiv) was dissolved in a 4 N solution of HCl in 1,4-dioxane (85.0 mL) at ambient temperature. The resultant mixture was stirred at this temperature for 30 minutes and concentrated to dryness to afford the hydrochloride salt which was used directly in the next step. LCMS (ES+) [M−H₂O]+: 175.1.

(R)-2-(4-Methoxybenzylamino)-2-(4-methylbenzofuran-2-yl)ethanol

A solution of crude (R)-2-hydroxy-1-(4-methylbenzofuran-2-yl)ethanaminium chloride from previous step in DCM (113 mL) at ambient temperature was treated successively with triethylamine (7.11 mL, 51.0 mmol, 3.0 equiv), MgSO₄ (15.0 g) and anisaldehyde (2.07 mL, 17.0 mmol, 1.0 equiv). The resultant mixture was stirred for 16 hours at ambient temperature and filtered through a pad of celite which was washed with DCM. The filtrate was concentrated under vacuum to afford the corresponding imine intermediate. This intermediate was dissolved in MeOH (113 mL) and cooled to 0° C. Solid NaBH₄ (1.89 g, 51.0 mmol, 3.0 equiv) was added portion wise over 5 minutes. The resultant mixture was stirred for 45 minutes at 0° C., then quenched by the slow addition of a saturated aqueous solution of NaHCO₃. Water and DCM were added. Layers were separated and the aqueous layer was extracted with DCM twice. The combined organic layers were dried over MgSO₄, filtered and concentrated to provide a residue that was purified by normal phase chromatography on silica (0-4% MeOH/DCM) to afford (R)-2-(4-methoxybenzylamino)-2-(4-methylbenzofuran-2-yl)ethanol (3.72 g, 70%) as an off-white solid. ¹H NMR (500 MHz, CDCl₃) δ 7.29 (dd, J=8.2, 0.6 Hz, 1H), 7.25-7.22 (m, 2H), 7.19-7.15 (m, 1H), 7.04-7.01 (m, 1H), 6.89-6.83 (m, 2H), 6.64 (s, 1H), 3.98 (dd, J=8.3, 4.7 Hz, 1H), 3.88-3.75 (m, 7H), 3.67-3.62 (m, 1H), 2.51 (s, 3H). LCMS (ES+) [M+H]+: 312.1.

Example 18

Synthesis of (R)-3-(5-Bromo-6-methoxypyridin-2-yl)-4-(4-methoxybenzyl)-5-(4-methylbenzofuran-2-yl)-5,6-dihydro-4H-1,2,4-oxadiazine

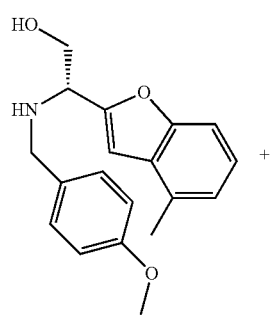

+

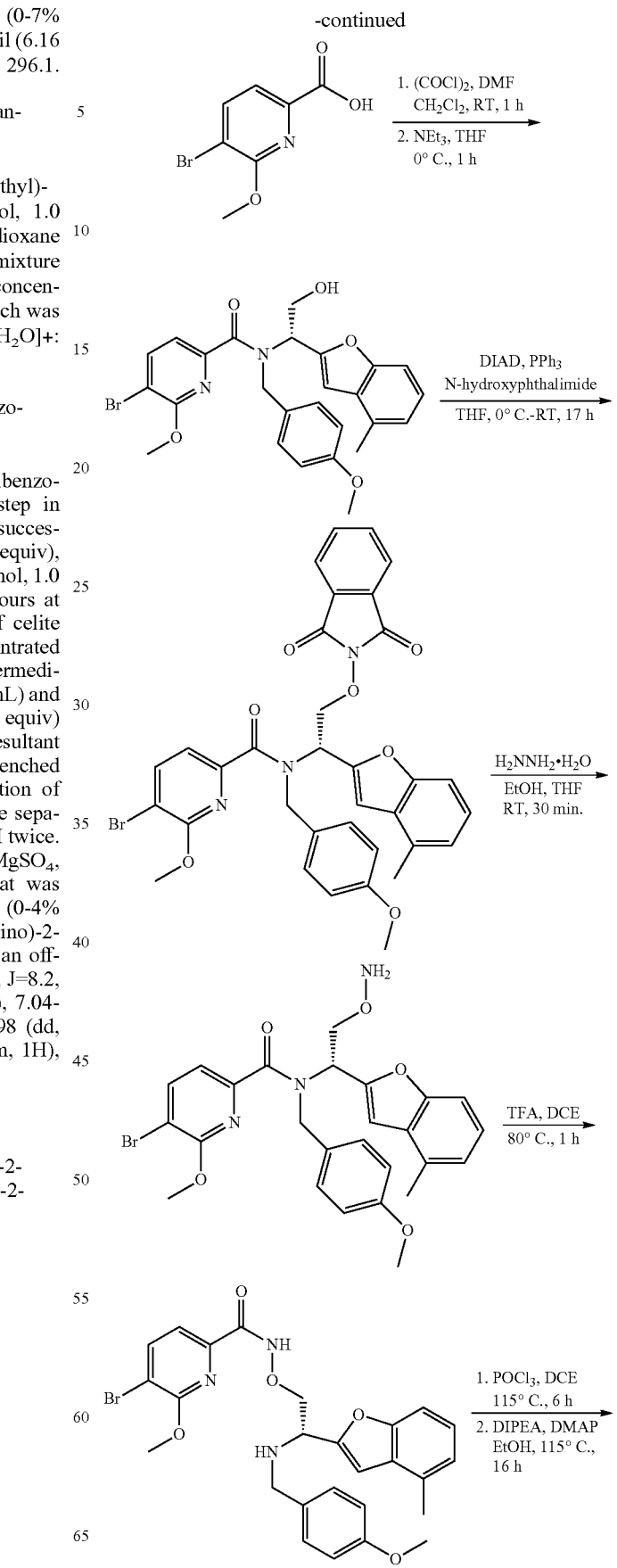

-continued

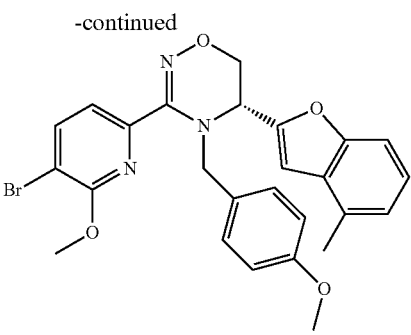

(R)-5-Bromo-N-(2-hydroxy-1-(4-methylbenzofuran-2-yl)ethyl)-6-methoxy-N-(4-methoxy benzyl)picolinamide A solution of 5-bromo-6-methoxypicolinic acid (3.24 g, 14.0 mmol, 1.1 equiv.) in DCM (63.5 mL) at ambient temperature was treated with a catalytic amount of DMF (7 drops) and oxalyl chloride (3.32 mL, 38.1 mmol, 3.0 equiv.). The resultant mixture was stirred at ambient temperature for 1 h at which point LCMS monitoring showed completion of the reaction. The mixture was concentrated, diluted with anhydrous THF (40.0 mL), concentrated again before being dried under high vacuum for 1 hour. The residue was diluted in anhydrous THF (40.0 ml), treated with triethylamine (6.18 mL, 44.4 mmol, 3.5 equiv.) and cooled to 0° C. A solution of (R)-2-(4-methoxybenzylamino)-2-(4-methylbenzofuran-2-yl)ethanol (3.95 g, 12.7 mmol, 1.0 equiv.) in THF (45.0 ml) was then quickly added and the resultant mixture was stirred at 0° C. for 1 h. Volatiles were removed under vacuum and MeOH (80.0 mL) was added, followed by $K_2CO_3$ (1.75 g, 12.7 mmol, 1.0 equiv.). The reaction mixture was stirred at ambient temperature for 16 hours before water and EtOAc were successively added, layers were separated, and the aqueous layer was extracted with EtOAc twice. The combined organic layers were dried over $MgSO_4$, filtered and concentrated. The residue was purified by normal phase chromatography on silica (10-50% EtOAc/hexanes) to afford the amide (4.58 g, 69%) as white foam. LCMS (ES+) [M+H]+: 525.1/526.9.

(R)-5-Bromo-N-(2-(1,3-dioxoisoindolin-2-yloxy)-1-(4-methylbenzofuran-2-yl)ethyl)-6-methoxy-N-(4-methoxybenzyl)picolinamide DIAD (1.89 mL, 9.59 mmol, 1.2 equiv.) was added to a solution of triphenylphosphine ($PPh_3$) (2.52 g, 9.59 mmol, 1.2 equiv.), (R)-5-bromo-N-(2-hydroxy-1-(4-methylbenzofuran-2-yl)ethyl)-6-methoxy-N-(4-methoxybenzyl)picolinamide (4.20 g, 7.99 mmol, 1.0 equiv.) and N-hydroxylphtalimide (1.56 g, 9.59 mmol, 1.2 equiv.) in THF (53.2 mL) at 0° C., then warmed to ambient temperature and stirred for 17 hours. EtOAc was added, and the organic layer was washed with 1 N aqueous NaOH (twice), water, and brine, dried over $MgSO_4$, filtered and concentrated. The residue was purified by normal phase chromatography on silica (10-40% EtOAc/hexanes) to afford the product (3.4 g, 63%) as an off-white foam. LCMS (ES+) [M+H]+: 670.2/672.0.

(R)—N-(2-(Aminooxy)-1-(4-methylbenzofuran-2-yl)ethyl)-5-bromo-6-methoxy-N-(4-methoxy benzyl)picolinamide A suspension of (R)-5-bromo-N-(2-(1,3-dioxoisoindolin-2-yloxy)-1-(4-methylbenzofuran-2-yl)ethyl)-6-methoxy-N-(4-methoxybenzyl)picolinamide (3.40 g, 6.47 mmol, 1.0 equiv.) in ethanol (90%, 65.0 mL) and THF (5.00 mL) at ambient temperature was treated with hydrazine hydrate (50-60%, 5.00 mL). The resultant mixture was stirred for 30 minutes, then water was added. The mixture was extracted with EtOAc (three times), and combined organic layers were dried over $MgSO_4$. Filtration and solvent evaporation to afford the product (2.65 g, 76%) as an off-white foam that was used directly in the next step. LCMS (ES+) [M+H]+: 540.0/542.0.

(R)-5-Bromo-6-methoxy-N-(2-(4-methoxybenzylamino)-2-(4-methylbenzofuran-2-yl)ethoxy) picolinamide A solution of (R)—N-(2-(aminooxy)-1-(4-methylbenzofuran-2-yl)ethyl)-5-bromo-6-methoxy-N-(4-methoxybenzyl)picolinamide (2.45 g, 4.53 mmol, 1.0 equiv.) in DCE (30.2 mL) was treated with TFA (1.60 mL). The resultant mixture was stirred at 80° C. for 1 h, then cooled to ambient temperature, concentrated to dryness, diluted with EtOAc, washed with saturated aqueous solution of $NaHCO_3$, brine and dried over $MgSO_4$, filtered and concentrated to afford the product as pale yellow oil that was used directly in the next step. LCMS (ES+) [M+H]+: 540.0/542.0.

(R)-3-(5-Bromo-6-methoxypyridin-2-yl)-4-(4-methoxybenzyl)-5-(4-methylbenzofuran-2-yl)-5,6-dihydro-4H-1,2,4-oxadiazine A solution of (R)-5-bromo-6-methoxy-N-(2-(4-methoxy benzylamino)-2-(4-methylbenzofuran-2-yl)ethoxy)picolinamide crude form previous step in anhydrous DCE (37.8 mL) at ambient temperature was treated with $POCl_3$ (6.34 mL, 68.0 mmol, 15.0 equiv.). The vial was sealed and heated at 115° C. for 6 h. The reaction mixture was evaporated, dried under high vacuum for 10 minutes, dissolved in EtOH (37.8 mL) and treated with DIPEA (3.16 mL, 18.1 mmol, 4.0 equiv.) and DMAP (277 mg, 2.27 mmol, 0.5 equiv.). The resultant mixture was heated to 115° C. for 16 h. The reaction mixture was cooled to ambient temperature and diluted with EtOAc. The organic layer was washed with 1 N aqueous NaOH, water (twice), brine and dried over $MgSO_4$, filtered and concentrated. The residue was purified by normal phase chromatography on silica (5-30% EtOAc/hexanes) to afford (R)-3-(5-Bromo-6-methoxypyridin-2-yl)-4-(4-methoxybenzyl)-5-(4-methylbenzofuran-2-yl)-5,6-dihydro-4H-1,2,4-oxadiazine (1.10 g, 47%) as a pale orange foam. $^1$H NMR (500 MHz, $CDCl_3$) δ 7.89 (d, J=7.8 Hz, 1H), 7.28 (d, J=8.3 Hz, 1H), 7.24 (d, J=7.8 Hz, 1H), 7.21-7.16 (m, 3H), 7.04-7.01 (m, 1H), 6.86-6.80 (m, 3H), 4.70 (d, J=15.6 Hz, 1H), 4.61 (t, J=2.9 Hz, 1H), 4.46 (dd, J=11.1, 3.0 Hz, 1H), 4.16-4.13 (m, 1H), 4.05 (dd, J=11.1, 3.3 Hz, 1H), 3.93 (s, J=5.3 Hz, 3H), 3.80 (s, J=5.2 Hz, 3H), 2.51 (s, J=4.9 Hz, 3H). LCMS (ES+) [M+H]+: 522.0/524.0.

Example 19

Synthesis of (R)-3-(6-Methoxy-5-(4-methyl-1H-imidazol-1-yl)pyridin-2-yl)-5-(4-methylbenzofuran-2-yl)-5,6-dihydro-4H-1,2,4-oxadiazine

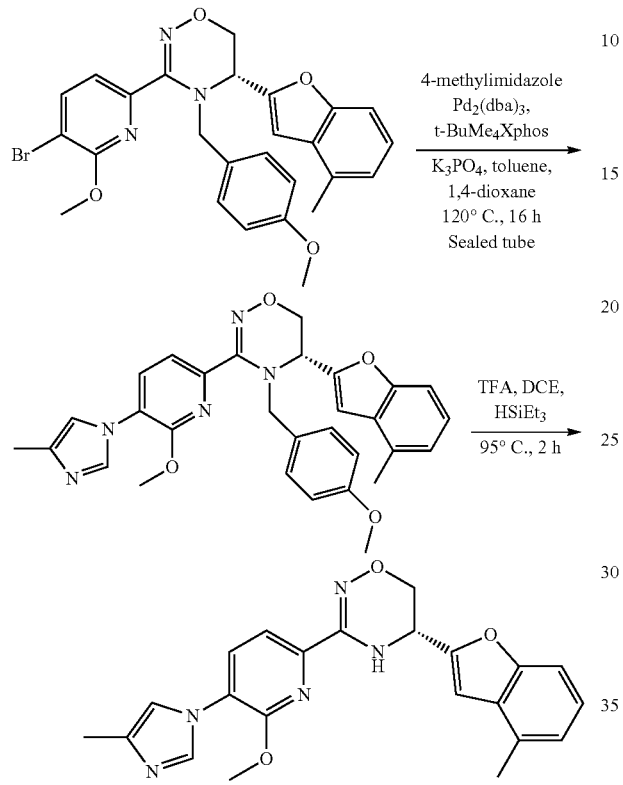

(R)-3-(6-Methoxy-5-(4-methyl-1H-imidazol-1-yl)pyridin-2-yl)-4-(4-methoxybenzyl)-5-(4-methylbenzofuran-2-yl)-5,6-dihydro-4H-1,2,4-oxadiazine To a vial charged with (R)-3-(5-bromo-6-methoxypyridin-2-yl)-4-(4-methoxybenzyl)-5-(4-methylbenzofuran-2-yl)-5,6-dihydro-4H-1,2,4-oxadiazine (300 mg, 0.57 mmol, 1.0 equiv.), 4(5)-methylimidazole (71.6 mg, 0.86 mmol, 1.5 equiv.), and $K_3PO_4$ (243.5 mg, 1.15 mmol, 2.0 equiv.). The vial was then equipped with a septum and put under $N_2$ atmosphere was added degassed 4:1 PhMe:dioxane solvent mixture (3.00 mL). To a second vial charged with $Pd_2(dba)_3$ (21.0 mg, 0.02 mmol, 4.0 mol %) and $Me_4$-di-t-BuXPhos (CAS#857356-94-6, 22.1 mg, 0.05 mmol, 8.0 mol %). The vial was equipped with a septum, put under $N_2$ atmosphere was added degassed 4:1 PhMe:dioxane solvent mixture (0.83 mL). This mixture was stirred for 3 minutes at 120° C. to provide a dark red solution which was cooled to RT before being transferred to the first vial. The reaction was degassed by bubbling with $N_2$ for 5 minutes before it was sealed. The reaction mixture was stirred at 120° C. for 16 h. The reaction was cooled to ambient temperature, filtered through a pad of celite and washed thoroughly with EtOAc. The filtrate was concentrated, and the residue that purified by normal phase chromatography on silica (0-5% MeOH/DCM) to afford the product (200 mg, 66%) as an off-white solid. LCMS (ES+) [M+H]+: 524.3.

(R)-3-(6-Methoxy-5-(4-methyl-1H-imidazol-1-yl)pyridin-2-yl)-5-(4-methylbenzofuran-2-yl)-5,6-dihydro-4H-1,2,4-oxadiazine A solution of (R)-3-(6-methoxy-5-(4-methyl-1H-imidazol-1-yl)pyridin-2-yl)-4-(4-methoxybenzyl)-5-(4-methylbenzofuran-2-yl)-5,6-dihydro-4H-1,2,4-oxadiazine (100 mg, 0.19 mmol, 1.0 equiv.) in DCE (1.00 mL) at ambient temperature was treated with triethylsilane (91.5 uL, 0.57 mmol, 3.0 equiv.) and TFA (1.00 mL). The resultant mixture was stirred at 95° C. for 2 h. The reaction mixture was cooled to RT, concentrated and dissolved in EtOAc. The organic layer washed with 1 N aqueous NaOH, brine and dried over $MgSO_4$, filtered and concentrated. The residue was purified by normal phase chromatography on silica (0-10% MeOH/DCM) to afford the product as an off-white solid. This material was dissolved in DMF and further purified using reverse phase chromatography on C18 resin (5-100% $MeCN/H_2O$+0.1% HCOOH) to provide, after lyophilisation, the compound of Example 19 as a white solid (62 mg, 81%).

Example 19, (R)-3-(6-Methoxy-5-(4-methyl-1H-imidazol-1-yl)pyridin-2-yl)-5-(4-methylbenzofuran-2-yl)-5,6-dihydro-4H-1,2,4-oxadiazine: $^1$H NMR (500 MHz, $CDCl_3$) δ □7.83 (s, 1H), 7.81 (d, J=8.0 Hz, 1H), 7.64 (d, J=8.0 Hz, 1H), 7.30 (d, J=8.3 Hz, 1H), 7.22-7.18 (m, 1H), 7.05-7.02 (m, 1H), 6.99 (s, 1H), 6.76 (s, 1H), 6.71 (d, J=2.4 Hz, 1H), 5.05-5.02 (m, 1H), 4.31 (dd, J=11.0, 3.7 Hz, 1H), 4.23 (dd, J=11.0, 5.1 Hz, 1H), 4.05 (s, 3H), 2.50 (s, 3H), 2.30 (d, J=0.9 Hz, 3H). LCMS analysis using LCMS A, standard conditions: $t_r$=3.85 min, LCMS (ES+) [M+H]+: 404.2; $[α]_D$=+284 (c=0.10, MeOH).

Example 20

Synthesis of (R)-2-(4-Methoxybenzylamino)-2-(6-methylbenzofuran-2-yl)ethanol

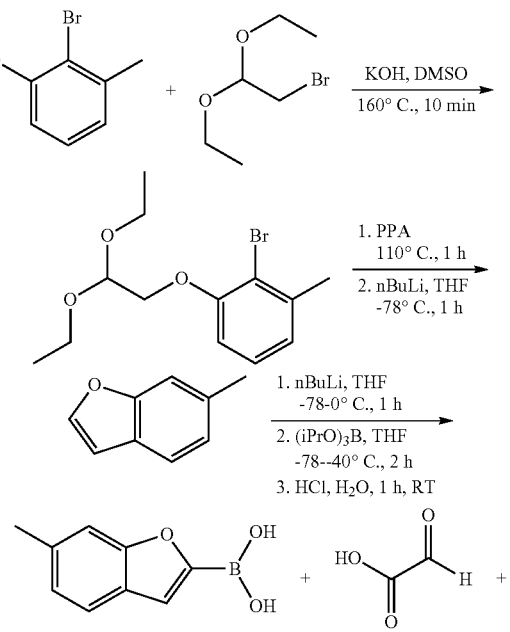

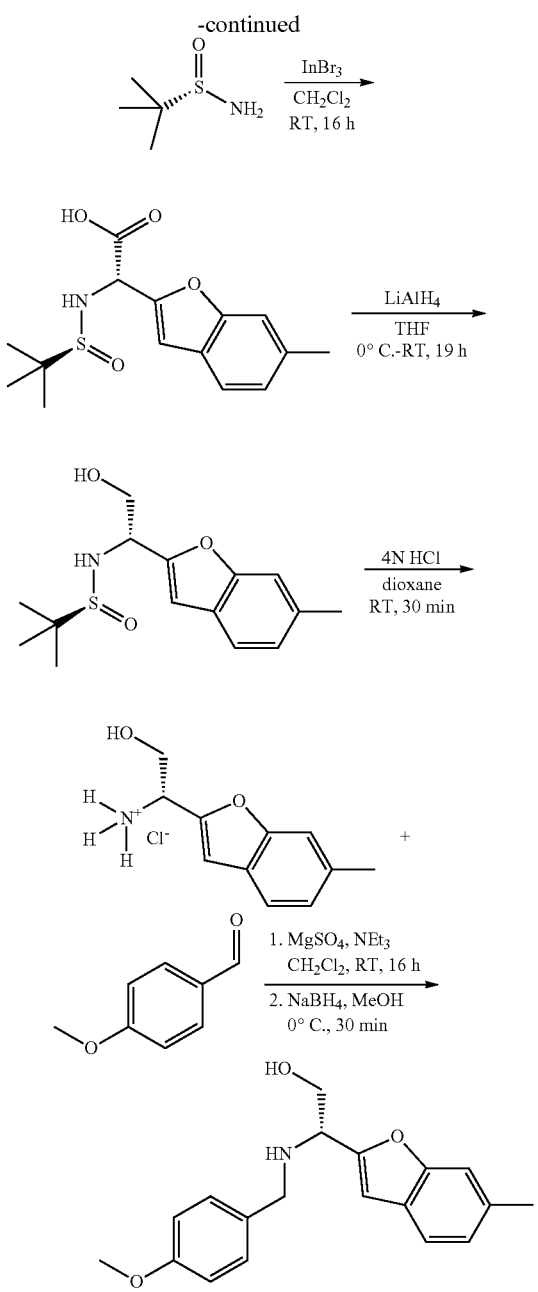

4.04 (d, J=5.2 Hz, 2H), 3.81 (dq, J=9.4, 7.1 Hz, 2H), 3.71 (dq, J=9.4, 7.0 Hz, 2H), 2.41 (s, 3H), 1.26 (t, J=7.0 Hz, 6H).

7-Bromo-6-methylbenzofuran

To a mixture of polyphosphoric acid (12.0 g) in toluene (100 mL) was added 2-bromo-1-(2,2-diethoxyethoxy)-3-methylbenzene (12.0 g, 39.5 mmol, 1.0 equiv). The resultant mixture was stirred at 110° C. for 1 h, cooled to RT and diluted with water. The mixture was extracted with EtOAc, the organic layer was washed with 1 N aqueous NaOH, dried over $Na_2SO_4$ and evaporated to afford the product as a colorless oil (8.74 g) that was used directly in the next step without further purification. $^1$H NMR (500 MHz, $CDCl_3$) δ7.97 (d, J=2.2 Hz, 1H), 7.75 (d, J=7.9 Hz, 1H), 7.47 (dd, J=7.9, 0.5 Hz, 1H), 7.14 (d, J=2.2 Hz, 1H), 2.87 (s, 3H).

6-Methylbenzofuran

To a solution of 7-bromo-6-methylbenzofuran (15.9 g) in THF (380 mL) at −78° C. was slowly added 2.5 M nBuLi in hexanes (36.2 mL, 90.6 mmol, 1.2 equiv). The resultant reaction mixture was stirred for 1 h and then quenched by the addition of water. The mixture was allowed to warm to RT extracted with EtOAc. The organic extracts were dried over $Na_2SO_4$ and evaporated. The oily residue was heated at 80° C. in the presence of CaH and then distilled under vacuum at [1110° C.-130° C.] to afford the product as a clear oil (7.40 g, 74% over 2 steps). $^1$H NMR (500 MHz, $CDCl_3$) δ 7.55 (d, J=2.2 Hz, 1H), 7.47 (d, J=7.9 Hz, 1H), 7.32 (d, J=0.7 Hz, 1H), 7.06 (ddd, J=7.9, 1.3, 0.5 Hz, 1H), 6.72 (dd, J=2.2, 1.0 Hz, 1H), 2.48 (s, 3H).

6-Methylbenzofuran-2-ylboronic acid

To a solution of 6-methylbenzofuran (7.40 g, 66.0 mmol, 1.0 equiv.) in THF (180 mL) at −78° C. was slowly added 2.5 M nBuLi in hexanes (26.9 mL, 67.2 mmol, 1.2 equiv). The resultant mixture was stirred for 1 h at 0° C., cooled back to −78° C. and treated with triisopropylborate (19.4 mL, 84.0 mmol, 1.5 equiv). The reaction was allowed to warm to −40° C. over 2 h and quenched with water. The reaction mixture was allowed to warm to RT, a 2 N aqueous HCl solution (50 mL) was added and the resultant mixture was stirred for 1 h. The pH was adjusted to 5 using a 1 N aqueous NaOH solution. EtOAc was added and the layers were separated. The aqueous phase was extracted with EtOAc, the combined organic extracts were washed with brine, dried over $MgSO_4$, filtered and concentrated. The residue was purified by trituration in DCM/Hexanes mixture and the resultant white solid was collected by filtration and rinsed with hexanes to afford the product (8.43 g, 86%). $^1$H NMR (500 MHz, DMSO-d6) 8.48 (s, 2H), 7.54 (d, J=7.9 Hz, 1H), 7.39 (d, J=1.0 Hz, 1H), 7.37 (s, 1H), 7.06 (d, J=7.9 Hz, 1H), 2.43 (s, 3H).

(S)-2-((S)-1,1-Dimethylethylsulfinamido)-2-(6-methylbenzofuran-2-yl)acetic acid

2-Bromo-1-(2,2-diethoxyethoxy)-3-methylbenzene

To a solution of 2-bromo-3-methylphenol (10.0 g, 53.5 mmol, 1.0 equiv) in DMSO (27 mL) was added 2-bromo-1,1-diethoxyethane (7.66 mL, 80.2 mmol, 1.5 equiv) and KOH (4.50 g, 80.2 mmol, 1.5 equiv). The resultant mixture was stirred at 160° C. for 10 min. LCMS analysis showed 75% conversion to the product. The reaction mixture was cooled to RT and water was added. The mixture was extracted with EtOAc, the organic layer was washed with 1 N aqueous NaOH, dried over $Na_2SO_4$, filtered and evaporated to afford the product as a colorless oil (12.0 g, 74%) that was used directly in the next step. $^1$H NMR (500 MHz, $CDCl_3$) δ 7.13 (t, J=7.9 Hz, 1H), 6.86 (ddd, J=7.6, 1.4, 0.7 Hz, 1H), 6.74 (dd, J=8.2, 0.8 Hz, 1H), 4.89 (t, J=5.2 Hz, 1H), A suspension of 6-methylbenzofuran-2-ylboronic acid (9.20 g, 52.3 mmol, 0.9 equiv), glyoxylic acid monohydrate (5.35 g, 58.1 mmol, 1.0 equiv) and (S)-2-methylpropane-2-sulfinamide (7.04 g, 58.1 mmol, 1.0 equiv) in anhydrous DCM (170 mL) at RT was treated with $InBr_3$ (2.06 g, 5.81 mmol, 0.10 equiv). The resultant mixture was stirred for 16 h at RT. $MgSO_4$ was added and the reaction mixture was filtered over a small pad of celite. The celite pad was washed with 500 mL of 4:1 DCM/MeOH and the filtrate was concentrated to afford the product as a white solid (17.2 g) that was used directly in the next step without further purification. LCMS (ES+) [M+H]+: 310.1.

(S)—N—((R)-2-Hydroxy-1-(6-methylbenzofuran-2-yl)ethyl)-2-methylpropane-2-sulfinamide (S)-2-((S)-1,1-dimethylethylsulfinamido)-2-(6-methylbenzofuran-2-yl)acetic acid (17.2 g, 55.6 mmol, 1.0 equiv.) from the previous reaction was added portion wise to a cooled (0° C.) suspension of LiAlH$_4$ (9.92 g, 261 mmol, 4.7 equiv) in THF (300 mL). The resultant mixture was allowed to warm to RT over 3 h and stirred for 16 h before being diluted with Et$_2$O (300 mL). The reaction mixture was cooled to 0° C. and quenched by sequential addition of water (10.0 mL), an aqueous sodium hydroxide solution (2 N, 10.0 mL) and water (30.0 mL). The mixture was allowed to warm to RT, stirred for 1 h and MgSO$_4$ was added. The mixture was stirred for 10 min, and the solids were filtered and rinsed thoroughly with 10% MeOH/DCM (500 mL). The filtrate was concentrated and the residue was purified by normal phase chromatography on silica (0-7% MeOH/DCM) to afford the alcohol as a thick orange oil (6.88 g, 45% over 2 steps). LCMS (ES+) [M+H]+: 296.1.

(R)-2-Amino-2-(6-methylbenzofuran-2-yl)ethanol hydrochloride (S)—N—((R)-2-hydroxy-1-(6-methylbenzofuran-2-yl)ethyl)-2-methylpropane-2-sulfinamide (6.88 g, 23.3 mmol, 1.0 equiv) was dissolved in a 4 N solution of HCl in 1,4-dioxane (50 mL) at RT. The resultant mixture was stirred at RT for 30 min and concentrated to dryness to afford the hydrochloride salt (5.30 g) as a beige solid which was used directly in the next step. LCMS (ES+) [M−OH]+: 175.1.

(R)-2-(4-Methoxybenzylamino)-2-(6-methylbenzofuran-2-yl)ethanol

A solution of crude (R)-2-amino-2-(6-methylbenzofuran-2-yl)ethanol hydrochloride (5.30 g, 23.3 mmol) from the previous step in DCM (150 mL) at RT was treated successively with triethylamine (6.50 mL, 46.8 mmol, 2.0 equiv), MgSO$_4$ (21 g) and p-anisaldehyde (2.85 mL, 23.3 mmol, 1.0 equiv). The resultant suspension was stirred for 16 h at RT and filtered through a pad of celite which was washed with EtOAc. The filtrate was concentrated under vacuum to afford the corresponding imine intermediate. This intermediate was dissolved in MeOH (200 mL) and cooled to 0° C. NaBH$_4$ (2.60 g, 70.2 mmol, 3.0 equiv) was added portion wise over 5 minutes. The resultant mixture was stirred for 30 min at 0° C. and then quenched by the slow addition of a saturated aqueous solution of NaHCO$_3$. Water and DCM were added. The layers were separated, and the aqueous layer was extracted with DCM twice. The combined organic layers were dried over MgSO$_4$, filtered and concentrated. The residue was purified by normal phase chromatography on silica (0-5% MeOH/DCM) to afford (R)-2-(4-Methoxybenzylamino)-2-(6-methylbenzofuran-2-yl)ethanol (2.78 g, 38% over 2 steps) as a pale yellow solid. $^1$H NMR (500 MHz, CDCl$_3$) δ 7.41 (d, J=7.9 Hz, 1H), 7.27 (d, J=0.7 Hz, 1H), 7.25-7.21 (m, 2H), 7.06 (ddd, J=7.9, 1.4, 0.6 Hz, 1H), 6.87-6.84 (m, 2H), 6.57 (s, 1H), 3.94 (dd, J=8.3, 4.8 Hz, 1H), 3.86-3.81 (m, 2H), 3.81-3.75 (m, 5H), 3.67-3.62 (m, 2H), 2.47 (s, 3H); LCMS (ES+) [M+H]+: 312.0.

Example 21

Synthesis of (R)-3-(5-Bromo-6-methoxypyridin-2-yl)-4-(4-methoxybenzyl)-5-(6-methylbenzofuran-2-yl)-5,6-dihydro-4H-1,2,4-oxadiazine

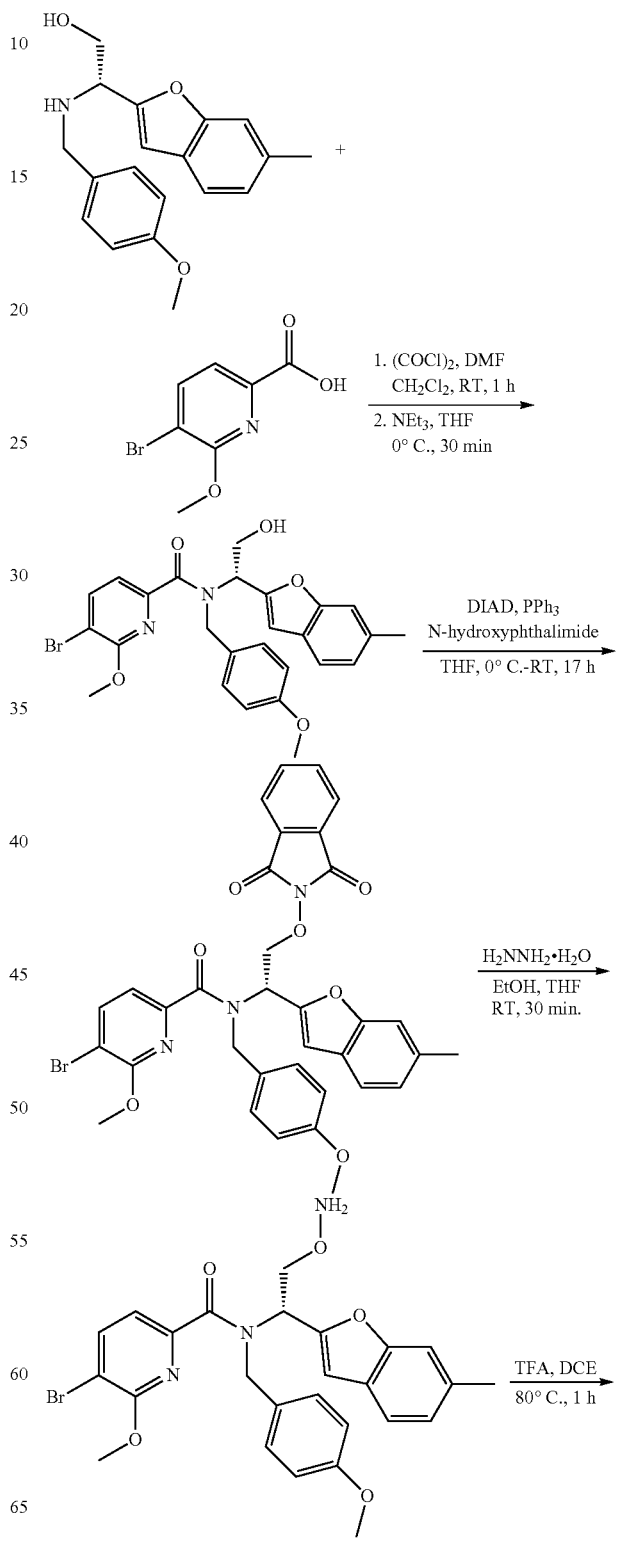

-continued

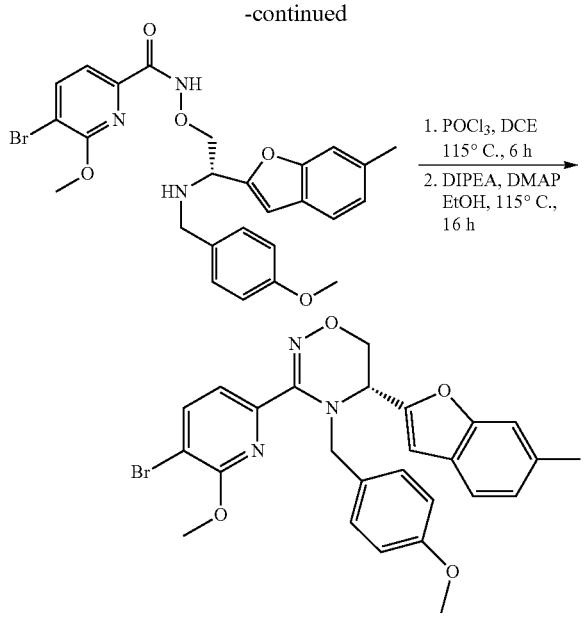

(R)-5-Bromo-N-(2-hydroxy-1-(6-methylbenzofuran-2-yl)ethyl)-6-methoxy-N-(4-methoxy benzyl)picolinamide A solution of 5-bromo-6-methoxypicolinic acid (2.28 g, 9.82 mmol, 1.1 equiv.) in DCM (60 mL) at RT was treated with a catalytic amount of DMF (1 drop) and oxalyl chloride (2.34 mL, 26.8 mmol, 3.0 equiv.). The resultant mixture was stirred at RT for 1 h at which point LCMS monitoring showed completion of the reaction. The mixture was concentrated, diluted with anhydrous THF (40 mL), concentrated again and dried under high vacuum for 1 h. The residue was diluted in anhydrous THF (55 mL), treated with triethylamine (3.70 mL, 26.8 mmol, 3.0 equiv.) and cooled to 0° C. A solution of (R)-2-(4-methoxybenzylamino)-2-(6-methylbenzofuran-2-yl)ethanol (2.78 g, 8.92 mmol, 1.0 equiv.) in THF (15 ml) was quickly added and the resultant mixture was stirred at 0° C. for 30 min. A saturated aqueous solution of NaHCO$_3$ and EtOAc were then successively added. The layers were separated, and the aqueous layer was extracted with EtOAc twice. The combined organic layers were dried over MgSO$_4$, filtered and concentrated. The residue was dissolved in MeOH (60 mL), cooled to 0° C. and K$_2$CO$_3$ (1.50 g) was added. The resultant mixture was stirred for 30 min at 0° C., diluted with EtOAc and water was added. The layers were separated, and the aqueous layer was extracted with EtOAc twice. The combined organic layers were washed with brine, dried over MgSO$_4$, filtered and concentrated. The residue was purified by normal phase chromatography on silica (0-40% EtOAc/hexanes) to afford the amide as white solid (3.45 g, 74%). LCMS (ES+) [M+H]+: 524.9/526.9.

(R)-5-Bromo-N-(2-(1, 3-dioxoisoindolin-2-yloxy)-1-(6-methylbenzofuran-2-yl)ethyl)-6-methoxy-N-(4-methoxybenzyl)picolinamide DIAD (1.56 mL, 7.88 mmol, 1.2 equiv.) was added to a solution of triphenylphosphine (2.07 g, 7.88 mmol, 1.2 equiv.), (R)-5-bromo-N-(2-hydroxy-1-(6-methylbenzofuran-2-yl)ethyl)-6-methoxy-N-(4-methoxybenzyl)picolinamide (3.45 g, 6.57 mmol, 1.0 equiv.) and N-hydroxyphthalimide (1.29 g, 7.88 mmol, 1.2 equiv.) in THF (35 mL) at 0° C. The resultant mixture was kept at 0° C. for 1 h, then warmed to RT and stirred for 16 h. EtOAc was added, and the organic layer was washed with 1 N aqueous NaOH twice, water and brine, dried over MgSO$_4$, filtered and concentrated. The residue was purified by normal phase chromatography on silica (0-40% EtOAc/hexanes) to afford the product as a light brown foam (2.59 g, 59%). LCMS (ES+) [M+H]+: 670.2/672.2.

(R)—N-(2-(Aminooxy)-1-(6-methylbenzofuran-2-yl)ethyl)-5-bromo-6-methoxy-N-(4-methoxy benzyl)picolinamide A suspension of (R)-5-bromo-N-(2-(1,3-dioxoisoindolin-2-yloxy)-1-(6-methylbenzofuran-2-yl)ethyl)-6-methoxy-N-(4-methoxybenzyl)picolinamide (2.59 g, 3.86 mmol, 1.0 equiv.) in ethanol (90%, 20 mL) and THF (10 mL) at RT was treated with hydrazine hydrate (50-60%, 3.0 mL). The resultant mixture was stirred for 30 min and then water was added. The mixture was extracted with EtOAc three times, the combined organic layers were dried over MgSO$_4$, filtered and concentrated to afford the product (2.09 g, 100%) as a brown foam that was used directly in the next step. LCMS (ES+) [M+H]+: 540.0/542.0.

(R)-5-Bromo-6-methoxy-N-(2-(4-methoxybenzylamino)-2-(6-methylbenzofuran-2-yl)ethoxy) picolinamide A solution of (R)—N-(2-(aminooxy)-1-(6-methylbenzofuran-2-yl)ethyl)-5-bromo-6-methoxy-N-(4-methoxybenzyl)picolinamide (2.09 g, 3.86 mmol, 1.0 equiv.) in DCE (25 mL) was treated with TFA (1.25 mL). The resultant mixture was stirred at 80° C. for 1 h, then cooled to RT and concentrated to dryness. The residue was diluted with EtOAc, washed with saturated aqueous solution of NaHCO$_3$ and brine, dried over MgSO$_4$, filtered and concentrated to afford the product (2.09 g, 100%) as a beige solid that was used directly in the next step. LCMS (ES+) [M+H]+: 539.9/541.9.

(R)-3-(5-Bromo-6-methoxypyridin-2-yl)-4-(4-methoxybenzyl)-5-(6-methylbenzofuran-2-yl)-5,6-dihydro-4H-1,2,4-oxadiazine A solution of (R)-5-bromo-6-methoxy-N-(2-(4-methoxy benzylamino)-2-(6-methylbenzofuran-2-yl)ethoxy)picolinamide (2.09 g, 3.86 mmol, 1.0 equiv.) in anhydrous DCE (25 ml) at RT was treated with POCl$_3$ (5.40 mL, 57.9 mmol, 15.0 equiv.). The vial was sealed and heated at 115° C. for 6 h. The reaction mixture was evaporated, dried under high vacuum for 10 min, dissolved in EtOH (35 mL) and treated with DIPEA (2.69 mL, 15.4 mmol, 4.0 equiv.) and DMAP (260 mg, 1.93 mmol, 0.50 equiv.). The resultant mixture was heated to 115° C. for 16 h. The reaction mixture was cooled to RT and diluted with EtOAc. The organic layer was washed with 1 N aqueous NaOH, water twice and brine, dried over MgSO$_4$, filtered and concentrated. The residue was purified by normal phase chromatography on silica (0-40% EtOAc/hexanes) to afford (R)-3-(5-Bromo-6-methoxypyridin-2-yl)-4-(4-methoxybenzyl)-5-(6-methylbenzofuran-2-yl)-5,6-dihydro-4H-1,2,4-oxadiazine (1.11 g, 55%) as a pale yellow foam. $^1$H NMR (500 MHz, CDCl$_3$) δ 7.88 (d, J=7.8 Hz, 1H), 7.42 (d, J=7.9 Hz, 1H), 7.26 (s, 1H), 7.23 (d, J=7.8 Hz, 1H), 7.20-7.16 (m, 2H), 7.06 (dd, J=7.9, 0.8 Hz, 1H), 6.86-6.82 (m, 2H), 6.72 (s, 1H), 4.68 (d, J=15.6 Hz, 1H), 4.59 (t, J=3.1 Hz, 1H), 4.44 (dd, J=11.2, 3.2 Hz, 1H), 4.11 (d, J=15.6 Hz, 1H), 4.04 (dd, J=11.1, 3.3 Hz, 1H), 3.93 (s, 3H), 3.79 (d, J=4.6 Hz, 3H), 2.47 (s, 3H); LCMS (ES+) [M+H]+: 522.0/524.0.

Example 22

Synthesis of (R)-3-(6-Methoxy-5-(4-methyl-1H-imidazol-1-yl)pyridin-2-yl)-5-(6-methylbenzofuran-2-yl)-5,6-dihydro-4H-1,2,4-oxadiazine

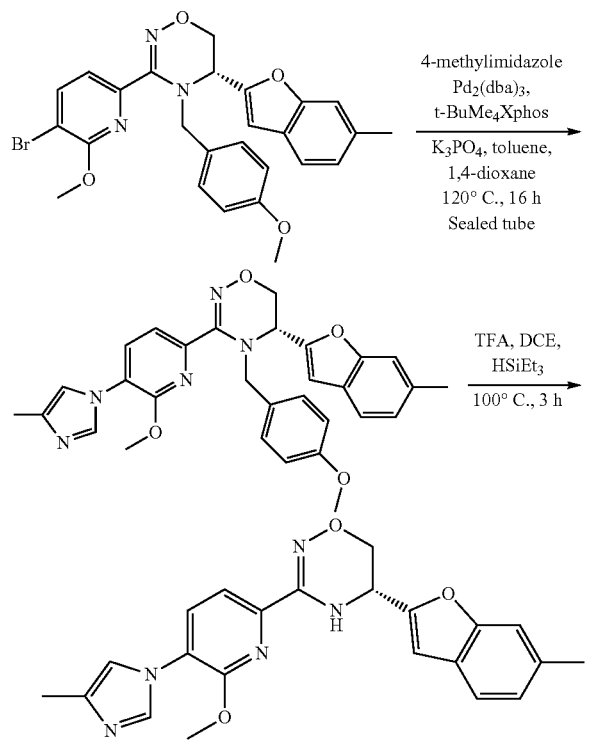

(R)-3-(6-Methoxy-5-(4-methyl-1H-imidazol-1-yl)pyridin-2-yl)-4-(4-methoxybenzyl)-5-(6-methylbenzofuran-2-yl)-5,6-dihydro-4H-1,2,4-oxadiazine To a vial charged with (R)-3-(5-bromo-6-methoxypyridin-2-yl)-4-(4-methoxybenzyl)-5-(6-methylbenzofuran-2-yl)-5,6-dihydro-4H-1,2,4-oxadiazine (300 mg, 0.381 mmol, 1.0 equiv.), 4(5)-methylimidazole (57 mg, 0.689 mmol, 1.2 equiv.), and K₃PO₄ (244 mg, 1.15 mmol, 2.0 equiv.) under N₂ atmosphere was added degassed 4:1 PhMe:dioxane solvent mixture (2.0 mL). To a second vial charged with Pd₂(dba)₃ (21.0 mg, 0.023 mmol, 4.0 mol %) and Me₄-di-t-BuXPhos (CAS#857356-94-6, 22.1 mg, 0.046 mmol, 8.0 mol %) under N₂ atmosphere was added degassed 4:1 PhMe:dioxane solvent mixture (2.0 mL). This mixture was stirred for 3 min at 120° C. to provide a dark red solution which was cooled to RT and transferred to the first vial. The reaction was degassed by bubbling with N₂ for 5 min and then sealed. The reaction mixture was stirred at 120° C. for 16 h. The reaction was cooled to RT and filtered through a pad of celite which was washed thoroughly with EtOAc. The filtrate was concentrated and the residue was purified by normal phase chromatography on silica (0-5% MeOH/DCM) to afford the product (235 mg, 78%) as a white foam. LCMS (ES+) [M+H]+: 524.3.

(R)-3-(6-Methoxy-5-(4-methyl-1H-imidazol-1-yl)pyridin-2-yl)-5-(6-methylbenzofuran-2-yl)-5,6-dihydro-4H-1,2,4-oxadiazine A solution of (R)-3-(6-methoxy-5-(4-methyl-1H-imidazol-1-yl)pyridin-2-yl)-4-(4-methoxybenzyl)-5-(6-methylbenzofuran-2-yl)-5,6-dihydro-4H-1,2,4-oxadiazine (233 mg, 0.445 mmol, 1.0 equiv.) and Et₃SiH (0.21 mL, 1.34 mmol, 3.0 equiv.) in DCE (4.0 mL) at RT was treated with TFA (4.0 mL). The resultant mixture was stirred at 100° C. for 3 h. The reaction mixture was cooled to RT, concentrated and dissolved in EtOAc. The organic layer was washed with 1 N aqueous NaOH and brine, dried over MgSO₄, filtered and concentrated. The residue was purified by normal phase chromatography on silica (0-5% MeOH/DCM) to afford the product (150 mg) as a white solid. The product was dissolved in DMF (1.5 mL) and further purified using reverse phase chromatography on C18 resin (5-100% MeCN/H₂O+ 0.1% HCOOH) to provide, after lyophilisation, the compound of Example 22 as a white solid (140 mg, 78%).

Example 22, (R)-3-(6-Methoxy-5-(4-methyl-1H-imidazol-1-yl)pyridin-2-yl)-5-(6-methylbenzofuran-2-yl)-5,6-dihydro-4H-1,2,4-oxadiazine: ¹H NMR (500 MHz, CDCl₃) δ 7.84 (s, 1H), 7.81 (d, J=8.0 Hz, 1H), 7.65-7.61 (m, 1H), 7.42 (d, J=7.9 Hz, 1H), 7.28 (d, J=0.7 Hz, 1H), 7.07 (ddd, J=8.0, 1.3, 0.6 Hz, 1H), 6.99 (s, 1H), 6.69 (t, J=0.8 Hz, 1H), 6.67 (d, J=2.0 Hz, 1H), 5.03-5.00 (m, 1H), 4.33 (dd, J=11.0, 3.8 Hz, 1H), 4.17 (dd, J=11.0, 5.6 Hz, 1H), 4.05 (s, 3H), 2.47 (s, 3H), 2.30 (d, J=0.9 Hz, 3H); LCMS analysis using LCMS B, standard conditions: T_R=1.49 mM, LCMS (ES+) [M+H]+: 404.3; [α]_D=+304 (c=0.26, MeOH).

Example 23

3-(6-Methoxy-5-(4-methyl-1H-imidazol-1-yl)pyridin-2-yl)-4-methyl-5-(7-methylbenzo furan-2-yl)-5,6-dihydro-4H-1,2,4-oxadiazine

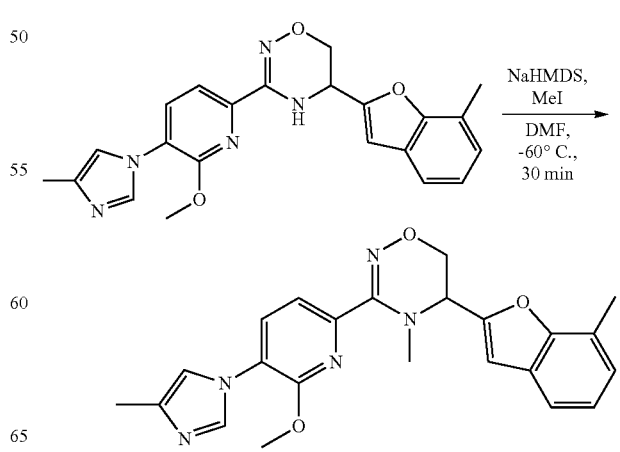

3-(6-Methoxy-5-(4-methyl-1H-imidazol-1-yl)pyridin-2-yl)-4-methyl-5-(7-methylbenzofuran-2-yl)-5,6-dihydro-4H-1,2,4-oxadiazine A solution of 3-(6-methoxy-5-(4-methyl-1H-imidazol-1-yl)pyridin-2-yl)-5-(7-methylbenzofuran-2-yl)-5,6-dihydro-4H-1,2,4-oxadiazine, fraction (II) Example 7B (35 mg, 0.09 mmol, 1.0 equiv.) in DMF (1.00 mL) at −60° C. was treated with a 1 M solution of NaHMDS in THF (0.09 mL, 0.09 mmol, 1.0 equiv.). After 60 min, at this temperature, MeI (0.04 mL, 0.64 mmol, 2.0 equiv.) was added. The resultant mixture was stirred for another 30 minutes, then water was added. The mixture was extracted with EtOAc (three times), and the combined organic layers were dried over MgSO$_4$, filtered, and concentrated. The residue was purified by normal phase chromatography on silica (0-10% MeOH/DCM) to afford the product. This material was dissolved in DMF (1.50 mL) and further purified using reverse phase chromatography on C18 resin (5-100% MeCN/H$_2$O+0.1% HCOOH) to provide, after lyophilisation, the compound of Example 23 as a white solid (10.3 mg, 29%).

Example 23, (+)-3-(6-Methoxy-5-(4-methyl-1H-imidazol-1-yl)pyridin-2-yl)-4-methyl-5-(7-methylbenzofuran-2-yl)-5,6-dihydro-4H-1,2,4-oxadiazine: $^1$H NMR (500 MHz, CDCl$_3$) δ 7.84 (d, J=1.3 Hz, 1H), 7.62 (d, J=7.8 Hz, 1H), 7.42-7.38 (m, 2H), 7.15 (t, J=7.5 Hz, 1H), 7.12-7.08 (m, 1H), 7.00-6.98 (m, 1H), 6.80 (d, J=0.6 Hz, 1H), 4.77 (t, J=3.7 Hz, 1H), 4.44 (dd, J=11.4, 4.1 Hz, 1H), 4.27 (dd, J=11.4, 3.7 Hz, 1H), 4.07 (s, 3H), 3.01 (s, 3H), 2.53 (s, 3H), 2.31 (d, J=0.9 Hz, 3H); LCMS analysis using LCMS A, standard conditions: t$_r$=3.85 min, LCMS (ES+) [M+H]+: 418.2; [α]$_D$=+124 (c=0.10, MeOH).

Example 24

3-(5-(4-Chloro-1H-imidazol-1-yl)-6-methoxypyridin-2-yl)-5-(7-methylbenzofuran-2-yl)-5,6-dihydro-4H-1,2,4-oxadiazine

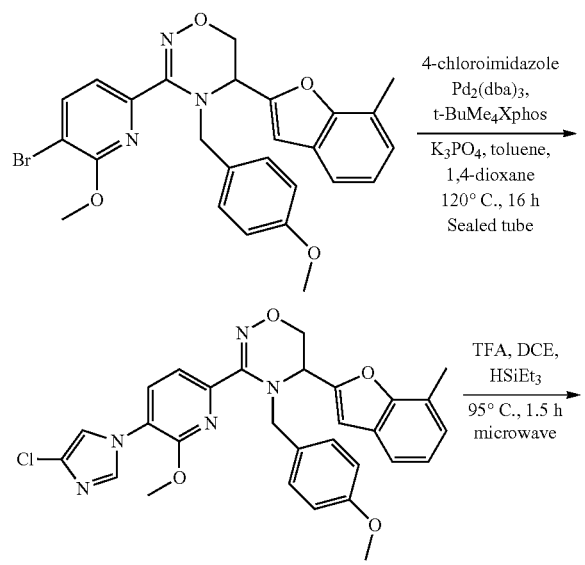

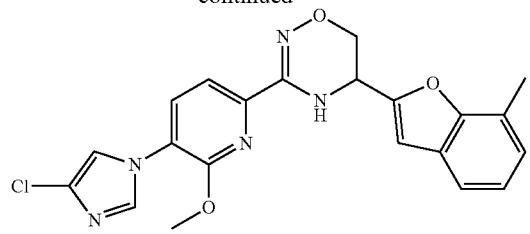

3-(5-(4-Chloro-1H-imidazol-1-yl)-6-methoxypyridin-2-yl)-4-(4-methoxybenzyl)-5-(7-methylbenzofuran-2-yl)-5,6-dihydro-4H-1,2,4-oxadiazine To a vial charged with 3-(5-bromo-6-methoxypyridin-2-yl)-4-(4-methoxybenzyl)-5-(7-methylbenzofuran-2-yl)-5,6-dihydro-4H-1,2,4-oxadiazine, fraction (II) Example 6B (100 mg, 0.19 mmol, 1.0 equiv.), 4-chloro-1H-imidazole (40.4 mg, 0.38 mmol, 2.0 equiv.), and K$_3$PO$_4$ (81.2 mg, 0.38 mmol, 2.0 equiv.) under N$_2$ atmosphere was added degassed 4:1 PhMe:dioxane solvent mixture (0.80 mL). To a second vial charged with Pd$_2$(dba)$_3$ (7.00 mg, 0.008 mmol, 4.0 mol %) and Me$_4$-di-t-BuXPhos (CAS#857356-94-6, 7.40 mg, 0.02 mmol, 8.0 mol %) under N$_2$ atmosphere was added degassed 4:1 PhMe:dioxane solvent mixture (0.40 mL). This mixture was stirred for 3 minutes at 120° C. to provide a dark red solution which was cooled to RT and transferred to the first vial. The reaction was degassed by bubbling with N$_2$ for 5 minutes and then sealed. The reaction mixture was stirred at 120° C. for 16 h. The reaction was cooled to RT and filtered through a pad of celite which was washed thoroughly with EtOAc. The filtrate was concentrated, and the residue was purified by normal phase chromatography on silica (0-5% MeOH/DCM) to afford the product (90.0 mg, 86%) as a white solid. LCMS (ES+) [M+H]+: 544.2/546.1.

3-(5-(4-Chloro-1H-imidazol-1-yl)-6-methoxypyridin-2-yl)-5-(7-methylbenzofuran-2-yl)-5,6-dihydro-4H-1,2,4-oxadiazine A solution of 3-(5-(4-chloro-1H-imidazol-1-yl)-6-methoxypyridin-2-yl)-4-(4-methoxybenzyl)-5-(7-methylbenzofuran-2-yl)-5,6-dihydro-4H-1,2,4-oxadiazine (90.0 mg, 0.17 mmol, 1.0 equiv.) in DCE (1.00 mL) at ambient temperature was treated with TFA (1.00 mL). The resultant mixture was stirred at 95° C. for 1.5 h in a microwave reactor. The reaction mixture was cooled to RT, concentrated and dissolved in EtOAc. The organic layer was washed with 1 N aqueous NaOH and brine, dried over MgSO$_4$, filtered, and concentrated. The residue was purified by normal phase chromatography on silica (0-10% MeOH/DCM) to afford the product (79.0 mg) as oil. This material was dissolved in DMF (1.50 mL) and further purified using reverse phase chromatography on C18 resin (5-100% MeCN/H$_2$O+0.1% HCOOH) to provide, after lyophilisation, the compound of Example 24 as a white solid (44.0 mg, 63%).

Example 24, (+)-3-(5-(4-Chloro-1H-imidazol-1-yl)-6-methoxypyridin-2-yl)-5-(7-methylbenzofuran-2-yl)-5,6-dihydro-4H-1,2,4-oxadiazine: $^1$H NMR (500 MHz, CDCl$_3$) δ 7.84 (d, J=8.0 Hz, 1H), 7.75 (d, J=1.6 Hz, 1H), 7.66 (d, J=8.0 Hz, 1H), 7.38 (d, J=7.6 Hz, 1H), 7.19 (d, J=1.6 Hz, 1H), 7.17-7.09 (m, 2H), 6.73 (d, J=0.7 Hz, 1H), 6.69 (d, J=1.9 Hz, 1H), 5.06 (dt, J=5.8, 2.9 Hz, 1H), 4.37 (dd, J=11.0, 3.7 Hz, 1H), 4.19 (dd, J=11.0, 5.6 Hz, 1H), 4.07 (s, 3H), 2.52 (s, 3H);

LCMS analysis using LCMS A, standard conditions: $t_r$=5.26 min, LCMS (ES+) [M+H]+: 424.2/426.2; $[\alpha]_D$=+224 (c=0.10, MeOH).

Example 25

Synthesis of tert-butyl (1-(4-chloro-2-methylphenyl)-2-hydroxyethyl) (methyl) carbamate

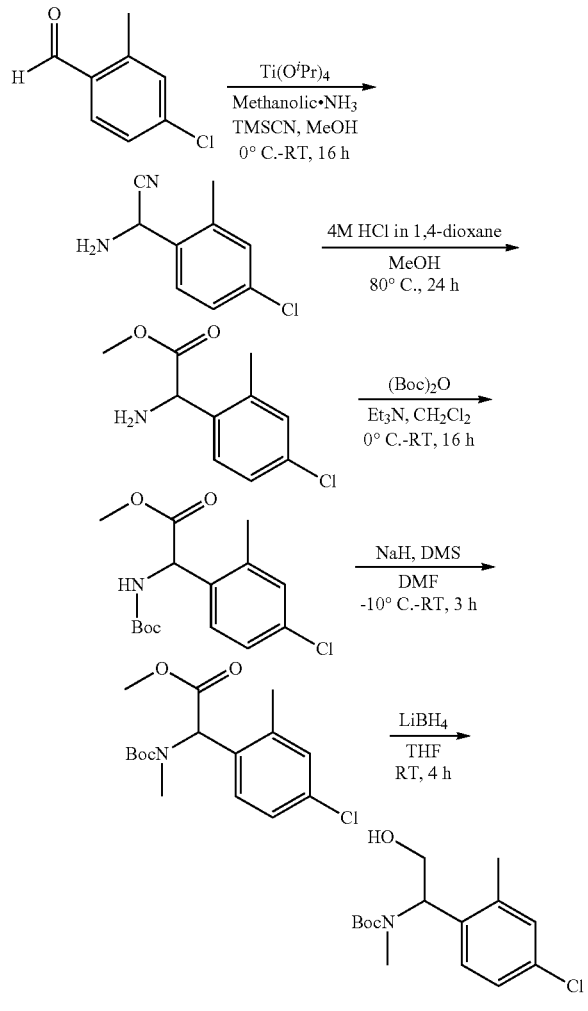

2-amino-2-(4-chloro-2-methylphenyl) acetonitrile

To a stirred solution of 4-chloro-2-methylbenzaldehyde (7.5 g, 49 mmol) in MeOH (30 mL) at 0° C. under an argon atmosphere were added methanolic ammonia (60 mL) and titanium isopropoxide (16.6 g, 59 mmol). The reaction mixture warmed to room temperature and stirred for 1 h. Then TMSCN (9.6 g, 97 mmol) was added to the reaction mixture at 0° C. The reaction mixture was warmed to room temperature and stirred for 16 h. After consumption of starting material (monitored by TLC), the volatiles were evaporated in vacuo. The residue was diluted with water (300 mL) and extracted with EtOAc (2×150 mL). The combined organic extracts were dried over sodium sulfate, filtered and concentrated in vacuo to afford 2-amino-2-(4-chloro-2-methylphenyl) acetonitrile (11 g, crude) as a brown solid used in the next step without further purification. $^1$H NMR (DMSO-$d_6$, 400 MHz): δ 7.54 (d, 1H), 7.36-7.33 (m, 1H), 7.32 (s, 1H), 5.09 (s, 1H), 2.79 (br s, 1H), 2.36 (s, 3H), 2.34-2.31 (m, 1H); TLC: 30% EtOAc/Hexane ($R_f$: 0.3).

Methyl 2-amino-2-(4-chloro-2-methylphenyl) acetate

To a stirred solution of 2-amino-2-(4-chloro-2-methylphenyl) acetonitrile (7.6 g, 42 mmol) in methanol (35 mL) at 0° C. was added 4M HCl in 1,4-dioxane (75 mL). The reaction mixture was stirred at 80° C. for 24 h. After consumption of starting material (monitored by TLC), the volatiles were evaporated in vacuo. The residue was diluted with saturated sodium bicarbonate solution (250 mL) and extracted with EtOAc (2×200 mL). The combined organic extracts were dried over sodium sulfate, filtered and concentrated in vacuo. The crude material was purified by column chromatography using 40% EtOAc: Hexane to afford methyl 2-amino-2-(4-chloro-2-methylphenyl) acetate (4.4 g, 49%) as a brown solid. $^1$H NMR (DMSO-$d_6$, 400 MHz): δ 7.31 (d, 1H), 7.28-7.18 (m, 2H), 4.69 (s, 1H), 3.59 (s, 3H), 2.33 (s, 3H), 2.24 (br s, 2H); TLC: 50% EtOAc/Hexane ($R_f$: 0.3).

Methyl 2-((tert-butoxycarbonyl) amino)-2-(4-chloro-2-methylphenyl) acetate

To a stirred solution of methyl 2-amino-2-(4-chloro-2-methylphenyl) acetate (4.4 g, 21 mmol) in CH$_2$Cl$_2$ (50 mL) at 0° C. under an argon atmosphere was added triethylamine (14.2 mL, 104 mmol). The reaction mixture was stirred for 10 min, and di-tert-butyl dicarbonate (5 g, 25 mmol) was added to the reaction mixture at 0° C. The reaction mixture was warmed to room temperature and stirred for 16 h. After consumption of starting material (monitored by TLC), the reaction mixture was diluted with water (100 mL) and extracted CH$_2$Cl$_2$ (2×100 mL). The combined organic extracts were dried over sodium sulfate, filtered and concentrated in vacuo. The crude material was purified by column chromatography using 10% EtOAc: Hexane to afford methyl 2-((tert-butoxycarbonyl) amino)-2-(4-chloro-2-methylphenyl) acetate (5.25 g, 81%) as a white solid. $^1$H NMR (CDCl$_3$, 400 MHz): δ 7.26 (s, 1H), 7.21-7.11 (m, 2H), 5.50 (br s, 2H), 3.71 (s, 3H), 2.46 (s, 3H), 1.42 (s, 9H); LCMS: 98.4%; 214 (M-Boc); (column; X-Select CSH C-18 (50×3.0 mm, 3.5 µm); RT 4.53 min; mobile phase: 5 mM NH$_4$OAc in water: ACN; T/B %: 0.01/10, 0.5/10, 4/90, 8/90; flow rate: 0.80 mL/min) (Gradient); TLC: 20% EtOAc/Hexane ($R_f$: 0.6).

Methyl 2-((tert-butoxycarbonyl) (methyl) amino)-2-(4-chloro-2-methylphenyl) acetate To a stirred solution of methyl 2-((tert-butoxycarbonyl) amino)-2-(4-chloro-2-methylphenyl) acetate (5 g, 16 mmol) in DMF (50 mL) at –10° C. under an argon atmosphere was added sodium hydride (575 mg, 24 mmol). The reaction mixture was stirred for 15 min. Then dimethylsulfate (3.01 g, 24 mmol) was added to the reaction mixture at –10° C. The reaction mixture was warmed to room temperature and stirred for 3 h. After consumption of starting material (monitored by TLC), the reaction mixture was quenched with a saturated ammonium chloride: 1N HCl solution (1:3, 50 mL) and extracted with EtOAc (2×100 mL). The combined organic extracts were dried over sodium sulfate, filtered and concentrated in vacuo. The crude material was purified by column chromatography using 3% EtOAc: Hexane to afford methyl 2-((tert-butoxycarbonyl) (methyl) amino)-2-(4-chloro-2-methylphenyl) acetate (3.3 g, 63%) as white solid. $^1$H NMR (CDCl$_3$, 400 MHz): δ 7.24-7.22 (m, 1H), 7.16 (d, 1H), 6.95 (d, 1H), 6.12 (br s, 1H), 3.78 (s, 3H), 2.68 (s, 3H), 2.27 (s, 3H), 1.49 (s, 9H); LCMS: 98.9%; 228 (M-Boc); (column; X-select CSH C-18 (50×3.0 mm, 3.5 μm); RT 4.55 min; mobile phase: 5 mM NH$_4$OAc in water: ACN; T/B %: 0.01/10, 0.5/10, 4/90, 8/90; flow rate: 0.8 mL/min) (Gradient); TLC: 5% EtOAc/Hexane (R$_f$: 0.4).

Tert-butyl (1-(4-chloro-2-methylphenyl)-2-hydroxyethyl) (methyl) carbamate

To a stirred solution of methyl 2-((tert-butoxycarbonyl) (methyl) amino)-2-(4-chloro-2-methylphenyl) acetate (3.3 g, 10 mmol) in THF (33 mL) at 0° C. under an argon atmosphere was added lithium borohydride (9.9 mL, 20 mmol, 2M solution in THF). The reaction mixture was warmed to room temperature and stirred for 4 h. After consumption of starting material (monitored by TLC), the reaction mixture was quenched with saturated ammonium chloride solution (100 mL) and extracted with EtOAc (2×100 mL). The combined organic extract were dried over sodium sulfate, filtered and concentrated in vacuo. The crude material was purified by column chromatography using 15% EtOAc: Hexane to afford tert-butyl (1-(4-chloro-2-methylphenyl)-2-hydroxyethyl) (methyl) carbamate (2.3 g, 76%) as an off-white solid. $^1$H NMR (CDCl$_3$, 400 MHz): δ 7.22-7.14 (m, 2H), 7.13-7.09 (m, 1H), 5.36 (br s, 1H), 4.13-4.00 (m, 2H), 2.53 (br s, 3H), 2.26 (s, 3H), 1.49 (s, 9H); LCMS: 96.0%; 200 (M-Boc); (column; X-select CSH C-18 (50×3.0 mm, 3.5 μm); RT 4.13 min; mobile phase: 5 mM NH$_4$OAc in water: ACN; T/B %: 0.01/10, 0.5/10, 4/90, 8/90; flow rate: 0.8 mL/min) (Gradient); TLC: 20% EtOAc/Hexane (R$_f$: 0.2).

Example 26

Synthesis of 3-(5-bromo-6-methoxypyridin-2-yl)-5-(4-chloro-2-methylphenyl)-4-methyl-5,6-dihydro-4H-1,2,4-oxadiazine

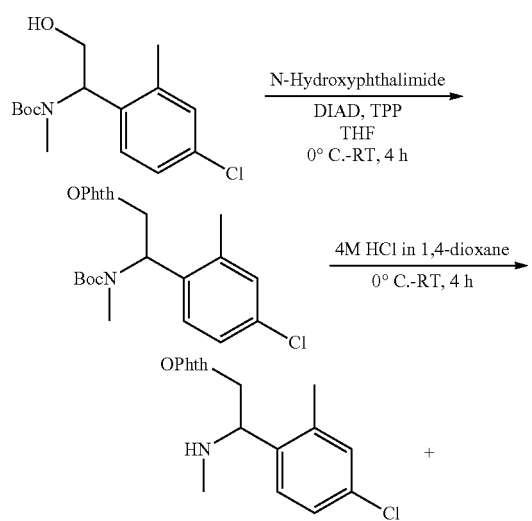

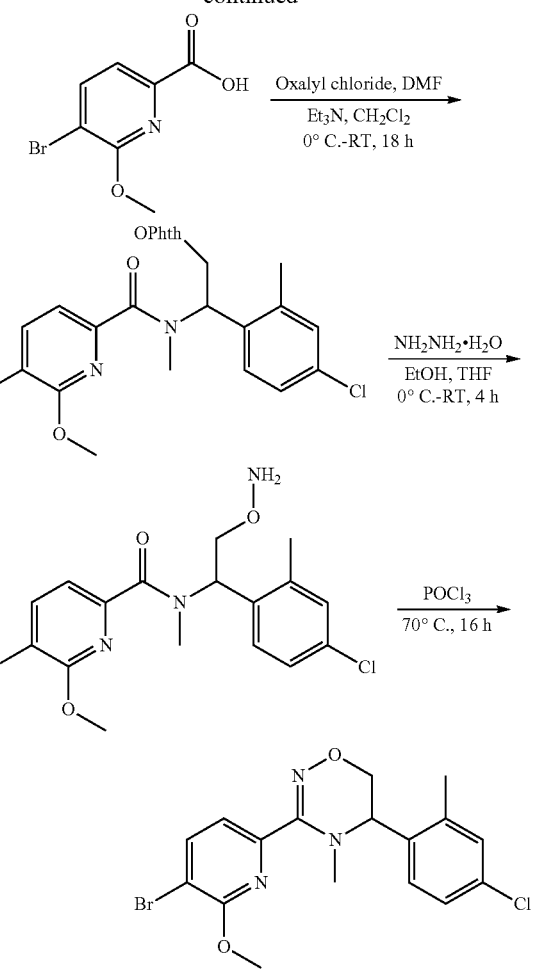

Tert-butyl (1-(4-chloro-2-methylphenyl)-2-((1,3-dioxoisoindolin-2-yl) oxy) ethyl) (methyl) carbamate To a stirred solution of tert-butyl (1-(4-chloro-2-methylphenyl)-2-hydroxyethyl) (methyl) carbamate (2 g, 7 mmol) in THF (25 mL) at 0° C. under an argon atmosphere were added N-hydroxyphthalimide (1.2 g, 7 mmol) in THF (5 mL), triphenylphosphine (2 g, 10 mmol) and diisopropylazodicarboxylate (2.6 g, 10 mmol). The reaction mixture was warmed to room temperature and stirred for 4 h. After consumption of starting material (monitored by TLC), the volatiles were evaporated in vacuo. The crude material was purified by column chromatography using 15% EtOAc: Hexanes to afford tert-butyl (1-(4-chloro-2-methylphenyl)-2-((1,3-dioxoisoindolin-2-yl) oxy) ethyl) (methyl) carbamate (1 g, 34%) as an off-white solid. $^1$H NMR (CDCl$_3$, 400 MHz): δ 7.89-7.80 (m, 2H), 7.79-7.70 (m, 2H), 7.52-7.36 (m, 1H), 7.24-7.20 (m, 2H), 5.71 (br s, 1H), 4.70-4.53 (m, 2H), 2.68 (s, 3H), 2.31 (s, 3H), 1.49 (s, 9H); LCMS: 93.3%; 345.2 (M-Boc); (column; X-Select CSH C-18 (50×3.0 mm, 3.5 μm); RT 4.67 min; mobile phase: 5 mM Aq NH$_4$OAc in water: ACN; T/B %: 0.01/10, 0.5/10, 4/90, 8/90; flow rate: 0.80 mL/min) (Gradient); TLC: 30% EtOAc/Hexane (R$_f$: 0.6).

2-(2-(4-chloro-2-methylphenyl)-2-(methylamino) ethoxy) isoindoline-1,3-dione hydrochloride To a stirred solution of tert-butyl (1-(4-chloro-2-methylphenyl)-2-((1,3-dioxoisoindolin-2-yl) oxy) ethyl) (methyl) carbamate (1 g, 2 mmol) in CH$_2$Cl$_2$ (20 mL) at 0° C. under an argon atmosphere was added 4M HCl in 1,4-dioxane (5 mL). The reaction mixture was warmed to room temperature and stirred for 4 h. After consumption of starting material (monitored by TLC), the volatiles were evaporated in vacuo. The residue was washed with ether (2×30 mL) to afford 2-(2-(4-chloro-2-methylphenyl)-2-(methylamino) ethoxy) isoindoline-1,3-dione hydrochloride (500 mg as HCl salt) as an off-white solid, used in the next step without further purification. LCMS: 94.9%; 344.9 (M+1); (column; Ascentis Express C-18 (50×30 mm, 2.7 μm); RT 1.90 min; mobile phase: 0.025% Aq TFA+5% CH$_3$CN: 5% CH$_3$CN+0.025% Aq TFA; T/B %: 0.01/5, 0.5/5, 3/100, 5/100; flow rate: 1.2 mL/min) (Gradient); TLC: 30% EtOAc/Hexane ($R_f$: 0.2).

5-bromo-N-(1-(4-chloro-2-methylphenyl)-2-((1,3-dioxoisoindolin-2-yl) oxy) ethyl)-6-methoxy-N-methylpicolinamide To a stirred solution of 5-bromo-6-methoxypicolinic acid (440 mg, 2 mmol) in CH$_2$Cl$_2$ (10 mL) at 0° C. under an argon atmosphere were added oxalyl chloride (722 mg, 6 mmol) and DMF (catalytic amount). The reaction mixture was warmed to room temperature and stirred for 2 h. After consumption of acid (monitored by TLC), the volatiles were evaporated in vacuo to afford 5-bromo-6-methoxypicolinoyl chloride.

5-bromo-N-(1-(4-chloro-2-methylphenyl)-2-((1,3-dioxoisoindolin-2-yl) oxy) ethyl)-6-methoxy-N-methylpicolinamide To a stirred solution of 2-(2-(4-chloro-2-methylphenyl)-2-(methylamino) ethoxy) isoindoline-1,3-dione hydrochloride (500 mg, 1 mmol) in CH$_2$Cl$_2$ (10 mL) at 0° C. were added triethylamine (740 mg, 7 mmol) and 5-bromo-6-methoxypicolinoyl chloride (434 mg, 2 mmol). The reaction mixture was warmed to room temperature and stirred for 16 h. After consumption of the starting material (monitored by TLC), the reaction mixture was diluted with water (50 mL) and extracted with CH$_2$Cl$_2$ (2×50 mL). The combined organic extracts were washed with sodium bicarbonate solution (20 mL) and water (20 mL). The organic layer was dried over sodium sulfate, filtered and concentrated in vacuo. The crude material was purified by column chromatography using 10% EtOAc: Hexanes to afford 5-bromo-N-(1-(4-chloro-2-methylphenyl)-2-((1,3-dioxoisoindolin-2-yl) oxy) ethyl)-6-methoxy-N-methylpicolinamide (450 mg, 55%) as an off-white solid. $^1$H NMR (CDCl$_3$, 500 MHz): δ 7.93 (d, 1H), 7.88-7.81 (m, 2H), 7.78-7.75 (m, 2H), 7.30-7.27 (m, 4H), 6.19-6.17 (m, 1H), 4.84 (d, 2H), 3.98 (s, 3H), 2.85 (s, 3H), 2.39 (s, 3H); LCMS: 99.3%; 559.8 (M+2); (column; Ascentis Express C-18 (50×30 mm, 2.7 μm); RT 3.10 min; mobile phase: 0.025% Aq TFA+5% CH$_3$CN: 5% CH$_3$CN+0.025% Aq TFA; T/B %: 0.01/5, 0.5/5, 3/100, 5/100; flow rate: 1.2 mL/min) (Gradient); TLC: 50% EtOAc/Hexanes ($R_f$: 0.7).

N-(2-(aminooxy)-1-(4-chloro-2-methylphenyl) ethyl)-5-bromo-6-methoxy-N-methylpicolinamide To a stirred solution of 5-bromo-N-(1-(4-chloro-2-methylphenyl)-2-((1,3-dioxoisoindolin-2-yl) oxy) ethyl)-6-methoxy-N-methylpicolinamide (450 mg, 0.8 mmol) in EtOH: THF (2:1, 13.5 mL) at 0° C. under an argon atmosphere was added hydrazine hydrate (6.75 mL). The reaction mixture was warmed to room temperature and stirred for 4 h. After consumption of starting material (monitored by TLC), the volatiles were evaporated in vacuo. The residue was dissolved in ether and filtered to remove solids. The filtrate was washed with water (30 mL), and the aqueous phase was back extracted with EtOAc (2×20 mL). The combined organic phases were dried over sodium sulfate, filtered and concentrated in vacuo to afford N-(2-(aminooxy)-1-(4-chloro-2-methylphenyl) ethyl)-5-bromo-6-methoxy-N-methylpicolinamide (350 mg, crude) as white solid used in the next step without further purification. LCMS: 98.1%; 429.8 (M+2); (column; Ascentis Express C-18 (50×30 mm, 2.7 μm); RT 2.27 min; mobile phase: 0.025% Aq TFA+5% CH$_3$CN: 5% CH$_3$CN+0.025% Aq TFA; T/B %: 0.01/5, 0.5/5, 3/100, 5/100; flow rate: 1.2 mL/min) (Gradient); TLC: 50% EtOAc/Hexane ($R_f$: 0.5).

3-(5-bromo-6-methoxypyridin-2-yl)-5-(4-chloro-2-methylphenyl)-4-methyl-5,6-dihydro-4H-1,2,4-oxadiazine A mixture of N-(2-(aminooxy)-1-(4-chloro-2-methylphenyl) ethyl)-5-bromo-6-methoxy-N-methylpicolinamide (350 mg, 0.8 mmol) and POCl$_3$ (3.5 mL) was heated at 70° C. for 16 h under an argon atmosphere. After consumption of starting material (monitored by TLC), the reaction mixture was cooled to 0° C., basified with a saturated sodium carbonate solution (50 mL) and extracted with EtOAc (2×50 mL). The combined organic extract were dried over sodium sulfate, filtered and concentrated in vacuo. The crude material was purified by column chromatography using 10% EtOAc: Hexane to afford 3-(5-bromo-6-methoxypyridin-2-yl)-5-(4-chloro-2-methylphenyl)-4-methyl-5,6-dihydro-4H-1,2,4-oxadiazine (140 mg, 42%) as an off-white solid. $^1$H NMR (CDCl$_3$, 400 MHz): δ 7.89 (d, 1H), 7.39 (d, 1H), 7.23-7.21 (m, 3H), 4.82-4.79 (m, 1H), 4.24 (dd, 1H), 4.04 (s, 3H), 3.88-3.84 (m, 1H), 2.72 (s, 3H), 2.4 (s, 3H); LCMS: 92.6%; 411.7 (M+2); (column; Ascentis Express C-18 (50×30 mm, 2.7 μm); RT 2.87 min; mobile phase: 0.025% Aq TFA+5% CH$_3$CN: 5% CH$_3$CN+0.025% Aq TFA; T/B %: 0.01/5, 0.5/5, 3/100, 5/100; flow rate: 1.2 mL/min) (Gradient); TLC: 30% EtOAc/Hexane ($R_f$: 0.7).

Example 27

Synthesis of 5-(4-chloro-2-methylphenyl)-3-(6-methoxy-5-(4-methyl-1H-imidazol-1-yl) pyridin-2-yl)-4-methyl-5,6-dihydro-4H-1,2,4-oxadiazine

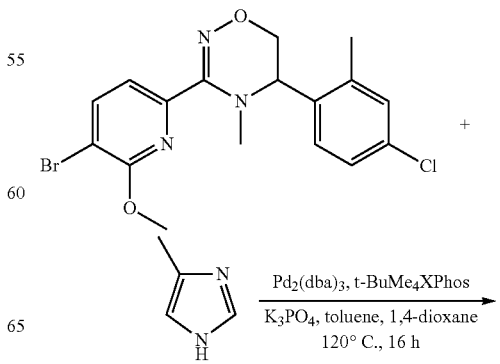

-continued

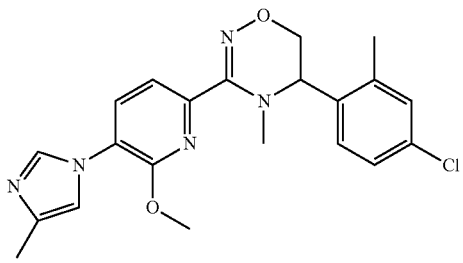

5-(4-chloro-2-methylphenyl)-3-(6-methoxy-5-(4-methyl-1H-imidazol-1-yl) pyridin-2-yl)-4-methyl-5,6-dihydro-4H-1,2,4-oxadiazine To a dry vial was added a suspension of Pd$_2$(dba)$_3$ (16 mg, 0.02 mmol) and tert-butyl tetramethyl XPhos (25 mg, 0.05 mmol) in toluene:1,4-dioxane (2:1, 1.5 mL) at room temperature. The suspension was degassed with argon, heated to 120° C., and stirred at 120° C. for 3 min. A mixture of 3-(5-bromo-6-methoxypyridin-2-yl)-5-(4-chloro-2-methylphenyl)-4-methyl-5,6-dihydro-4H-1,2,4-oxadiazine (140 mg, 0.3 mmol), 4-methyl-1H-imidazole (31 mg, 0.4 mmol) and potassium phosphate (144 mg, 0.7 mmol) in toluene:1,4-dioxane (2:1, 1.5 mL) was degassed, and the catalyst premixture was added. The resultant mixture was stirred at 120° C. for 16 h in a sealed tube. After consumption of the starting material (monitored by TLC and LCMS), the volatiles were evaporated in vacuo. The crude material was purified by column chromatography using 5-8% MeOH:CH$_2$Cl$_2$ to afford 5-(4-chloro-2-methylphenyl)-3-(6-methoxy-5-(4-methyl-1H-imidazol-1-yl) pyridin-2-yl)-4-methyl-5,6-dihydro-4H-1,2,4-oxadiazine (40 mg, 28%) as an off-white solid.

Racemic compound of Example 27 was separated using a Chiralpak IC column (250×4.6 min. 5 µm; (20 mg loading; 0.1% DEA in n-Hexane: CH$_2$Cl$_2$:MeOH (50:50); (A:B: 70:30) as mobile phase) to afford the compounds of Example 27A (Fraction (I)) and Example 27B (Fraction (II)).

Analytical conditions for Example 27A and Example 27B: HPLC (column; Acquity UPLC BEH C-18, 50×2.1 mm, 1.7µ); mobile phase: ACN: 0.025% Aq TFA; flow rate: 0.5 mL/min; Gradient program: T/B % 0.01/90, 0.5/90, 3/10, 6/10; diluent: CH$_3$CN:Water; Chiral HPLC: (Chiralpak-IC (250×4.6 mm, 5 µm; mobile phase (A) 0.1% DEA in n-Hexane (B) CH$_2$Cl$_2$:MeOH (50:50) (A:B; 70:30); flow Rate: 1.0 mL/min).

Example 27A, 5-(4-chloro-2-methylphenyl)-3-(6-methoxy-5-(4-methyl-1H-imidazol-1-yl) pyridin-2-yl)-4-methyl-5,6-dihydro-4H-1,2,4-oxadiazine, fraction (I): Mass (ESI): 412.5 [M+1]; HPLC (purity): 99.0%, RT 2.02 min; Chiral HPLC: 98.1% RT=25.05 min.

Example 27B, 5-(4-chloro-2-methylphenyl)-3-(6-methoxy-5-(4-methyl-1H-imidazol-1-yl) pyridin-2-yl)-4-methyl-5,6-dihydro-4H-1,2,4-oxadiazine, fraction (II): $^1$H NMR (CD$_3$OD, 400 MHz): δ 8.00 (s, 1H), 7.91 (d, 1H), 7.38 (d, 2H), 7.28-7.19 (m, 3H), 4.92 (t, 1H), 4.21 (dd, 1H), 4.08 (s, 3H), 3.95 (dd, 1H), 2.79 (s, 3H), 2.42 (s, 3H), 2.25 (s, 3H); Mass (ESI): 412.5 [M+1]; HPLC (purity): 99.0%, RT 2.02 min; Chiral HPLC: 99.5% RT=30.22 min.

Example 28

Synthesis of 2-(methylamino)-2-(3-(trifluoromethyl) phenyl) ethan-1-ol

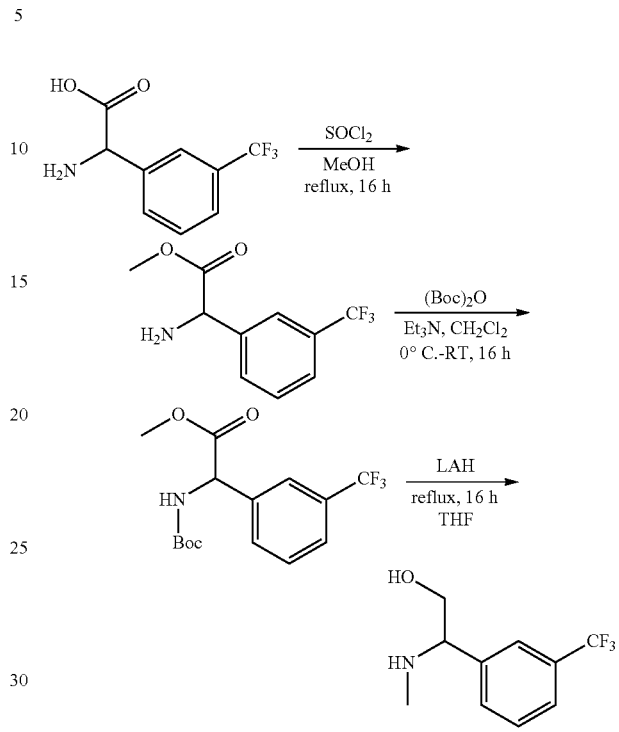

Methyl 2-amino-2-(3-(trifluoromethyl) phenyl) acetate

To a stirred solution of 2-amino-2-(3-(trifluoromethyl) phenyl) acetic acid (10 g, 46 mmol) in MeOH (200 mL) at 0° C. under an argon atmosphere was added thionyl chloride (10.4 mL, 137 mmol). The reaction mixture was stirred at reflux for 16 h. After consumption of starting material (monitored by TLC), the volatiles were evaporated in vacuo to afford methyl 2-amino-2-(3-(trifluoromethyl) phenyl) acetate (10.1 g, crude) as an off-white solid used in the next step without further purification. TLC: 50% EtOAc/Hexane (R$_f$: 0.5).

Methyl 2-((tert-butoxycarbonyl) amino)-2-(3-(trifluoromethyl) phenyl) acetate

To a stirred solution of methyl 2-amino-3-(2-(trifluoromethyl) phenyl) propanoate (4.3 g, 18 mmol) in CH$_2$Cl$_2$ (85 mL) at 0° C. under an argon atmosphere were added triethylamine (13 mL, 92 mmol), and di-tert-butyl dicarbonate (4.82 g, 22 mmol). The reaction mixture was warmed to room temperature and stirred for 16 h. After consumption of starting material (monitored by TLC), the reaction mixture was diluted with water (200 mL) and extracted with CH$_2$Cl$_2$ (2×200 mL). The combined organic extracts were dried over sodium sulfate, filtered and concentrated in vacuo to afford methyl 2-((tert-butoxycarbonyl) amino)-2-(3-(trifluoromethyl) phenyl) acetate (3.8 g, 62%) as an off-white solid. TLC: 50% EtOAc/Hexane (R$_f$: 0.6).

2-(methylamino)-2-(3-(trifluoromethyl) phenyl) ethan-1-ol

To a stirred solution of methyl 2-((tert-butoxycarbonyl) amino)-2-(3-(trifluoromethyl) phenyl) acetate (3 g, 9 mmol)

in THF (60 mL) at 0° C. under an argon atmosphere was added lithium aluminium hydride (1.36 g, 36 mmol). The reaction mixture was stirred at reflux for 16 h. After consumption of starting material (monitored by TLC), the reaction mixture was quenched with 1 N sodium hydroxide solution and stirred for 1 h. The reaction mixture was filtered and washed with THF (50 mL). The filtrate was concentrated in vacuo to afford 2-(methylamino)-2-(3-(trifluoromethyl) phenyl) ethan-1-ol (1.4 g, crude) as an off-white solid used in the next step without further purification. TLC: 50% EtOAc/Hexane ($R_f$: 0.3).

Example 29

Synthesis of 3-(5-bromo-6-methoxypyridin-2-yl)-4-methyl-5-(3-(trifluoromethyl) phenyl)-5,6-dihydro-4H-1, 2, 4-oxadiazine

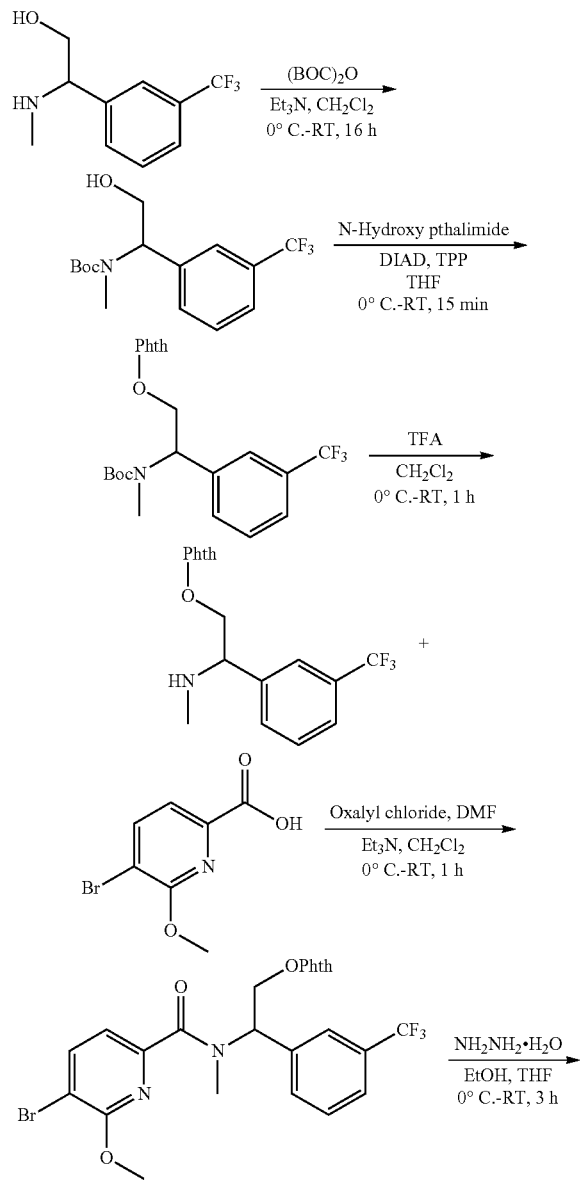

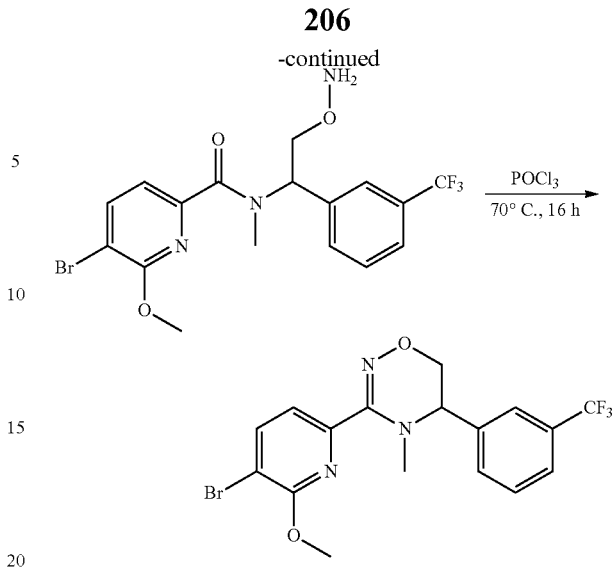

Tert-butyl (2-hydroxy-1-(3-(trifluoromethyl) phenyl) ethyl) (methyl) carbamate

To a stirred solution of 2-(methylamino)-2-(3-(trifluoromethyl) phenyl) ethan-1-ol (1.4 g, 6 mmol) in $CH_2Cl_2$ (30 mL) at 0° C. under an argon atmosphere were added triethylamine (2.7 mL, 19 mmol), and di-tert-butyl dicarbonate (1.67 g, 8 mmol). The reaction mixture was warmed to room temperature and stirred for 16 h. After consumption of starting material (monitored by TLC), the reaction mixture was diluted with water (200 mL) and extracted with $CH_2Cl_2$ (2×200 mL). The combined organic extracts were dried over sodium sulfate, filtered and concentrated in vacuo. The crude material was purified by column chromatography using 20-50% EtOAc: Hexane to afford tert-butyl (2-hydroxy-1-(3-(trifluoromethyl) phenyl) ethyl) (methyl) carbamate (1.3 g, 64%) as an off-white solid. $^1$H NMR ($CDCl_3$, 500 MHz): δ 7.59-7.56 (m, 1H), 7.54-7.49 (m, 3H), 5.27 (br s, 1H), 4.14-4.07 (m, 2H), 2.78-2.73 (m, 3H), 1.60 (s, 9H); TLC: 30% EtOAc/Hexane ($R_f$: 0.6).

Tert-butyl (2-((1,3-dioxoisoindolin-2-yl) oxy)-1-(3-(trifluoromethyl) phenyl) ethyl) (methyl) carbamate To a stirred solution of tert-butyl (2-hydroxy-1-(3-(trifluoromethyl) phenyl) ethyl) (methyl) carbamate (800 mg, 3 mmol) in THF (16 mL) at 0° C. under an argon atmosphere were added diisopropylazodicarboxylate (1.26 g, 6 mmol), triphenylphosphine (1.64 g, 6 mmol) and N-hydroxy phthalimide (613 mg, 4 mmol). The reaction mixture was warmed to room temperature and stirred for 15 min. After consumption of starting material (monitored by TLC), the reaction mixture was diluted with saturated ammonium chloride solution (50 mL) and extracted with EtOAc (2×50 mL). The combined organic extracts were dried over sodium sulfate, filtered and concentrated in vacuo. The crude material was purified by column chromatography using 20% EtOAc: Hexane to afford tert-butyl (2-((1, 3-dioxoisoindolin-2-yl) oxy)-1-(3-(trifluoromethyl) phenyl) ethyl) (methyl) carbamate (320 mg, 28%) as an off-white solid. $^1$H NMR ($CDCl_3$, 500 MHz): δ 7.90-7.83 (m, 2H), 7.82-7.75 (m, 2H), 7.72-7.63 (m, 2H), 7.63-7.56 (m, 1H), 7.55-7.48 (m, 1H), 5.79-5.51 (m, 1H), 4.73 (br s, 2H), 2.92 (br s, 3H), 1.57 (s, 9H); TLC: 30% EtOAc/Hexane ($R_f$: 0.5).

2-(2-(methyl (2,2,2-trifluoroacetyl)-14-azanyl)-2-(3-(trifluoromethyl) phenyl) ethoxy) isoindoline-1,3-dione To a stirred solution of tert-butyl (2-((1,3-dioxoisoindolin-2-yl) oxy)-1-(3-(trifluoromethyl) phenyl) ethyl) (methyl) carbamate (350 mg, 0.7 mmol) in CH$_2$Cl$_2$ (10 mL) at 0° C. under an argon atmosphere was added trifluoroacetic acid (860 mg, 8 mmol). The reaction mixture was stirred for 30 min at 0° C. The reaction mixture was warmed to room temperature and stirred for 30 min. After consumption of starting material (monitored by TLC), the volatiles were evaporated in vacuo to afford 2-(2-(methyl (2,2,2-trifluoroacetyl)-14-azanyl)-2-(3-(trifluoromethyl) phenyl) ethoxy) isoindoline-1,3-dione (280 mg, crude) as brown syrup used in the next step without further purification. TLC: 30% EtOAc/Hexanes (R$_f$: 0.1).

5-bromo-N-(2-((1,3-dioxoisoindolin-2-yl) oxy)-1-(3-(trifluoromethyl) phenyl) ethyl)-6-methoxy-N-methylpicolinamide To a stirred solution of 5-bromo-6-methoxypicolinic acid (250 mg, 1 mmol) in CH$_2$Cl$_2$ (5 mL) at 0° C. under an argon atmosphere were added oxalyl chloride (0.27 mL, 3 mmol) and DMF (catalytic amount). The reaction mixture warmed to room temperature and stirred for 2 h. After consumption of starting material (monitored by TLC), the volatiles were evaporated in vacuo to afford 5-bromo-6-methoxypicolinoyl chloride (288 mg, crude) as a pale yellow solid.

5-bromo-N-(2-((1,3-dioxoisoindolin-2-yl) oxy)-1-(3-(trifluoromethyl) phenyl) ethyl)-6-methoxy-N-methylpicolinamide To a stirred solution of 2-(2-(methyl (2,2,2-trifluoroacetyl)-14-azanyl)-2-(3-(trifluoromethyl) phenyl) ethoxy) isoindoline-1, 3-dione (280 mg, 0.8 mmol) in CH$_2$Cl$_2$ (15 mL) at 0° C. under an argon atmosphere was added triethylamine (1.07 mL, 7.7 mmol) and 5-bromo-6-methoxypicolinoyl chloride (288 mg, 1 mmol). The reaction mixture was stirred for 30 min at 0° C. The reaction mixture was warmed to room temperature and stirred for 30 min. After consumption of starting material (monitored by TLC), the reaction mixture was diluted with saturated sodium bicarbonate solution (20 mL) and extracted with CH$_2$Cl$_2$ (2×20 mL). The combined organic extracts were dried over sodium sulfate, filtered and concentrated in vacuo to afford 5-bromo-N-(2-((1,3-dioxoisoindolin-2-yl) oxy)-1-(3-(trifluoromethyl) phenyl) ethyl)-6-methoxy-N-methylpicolinamide (100 mg, 22%) as an off-white solid used in the next step without further purification. LCMS: 90.2%; 579.7 (M+2); (column; Ascentis Express C-18 (50×3.0 mm, 2.7 μm); RT 2.92 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexanes (R$_f$: 0.4).

N-(2-(aminooxy)-1-(3-(trifluoromethyl) phenyl) ethyl)-5-bromo-6-methoxy-N-methylpicolinamide To a stirred solution of 5-bromo-N-(2-((1,3-dioxoisoindolin-2-yl) oxy)-1-(3-(trifluoromethyl) phenyl) ethyl)-6-methoxy-N-methylpicolinamide (100 mg, 0.2 mmol) in toluene (3 mL) at room temperature under an argon atmosphere was added hydrazine hydrate (0.2 mL). The reaction mixture was stirred at room temperature for 3 h. After consumption of starting material (monitored by TLC), the volatiles were evaporated in vacuo. The residue was dissolved in ether and filtered to remove solids. The filtrate was washed with water (30 mL), and the aqueous phase was back extracted with EtOAc (2×20 mL). The combined organic extracts were dried over sodium sulfate, filtered and concentrated in vacuo to afford N-(2-(aminooxy)-1-(3-(trifluoromethyl) phenyl) ethyl)-5-bromo-6-methoxy-N-methylpicolinamide (56 mg, crude) as colorless thick syrup used in the next step without further purification. TLC: 50% EtOAc/Hexane (R$_f$: 0.3).

Synthesis of 3-(5-bromo-6-methoxypyridin-2-yl)-4-methyl-5-(3-(trifluoromethyl) phenyl)-5,6-dihydro-4H-1,2,4-oxadiazine To a stirred solution of N-(2-(aminooxy)-1-(3-(trifluoromethyl) phenyl) ethyl)-5-bromo-6-methoxy-N-methylpicolinamide (50 mg, 0.1 mmol) in POCl$_3$ (1 mL) under an argon atmosphere was stirred at 70° C. for 16 h. After consumption of starting material (monitored by TLC), the volatiles were evaporated in vacuo. The residue was diluted with a saturated sodium bicarbonate solution (20 mL) and extracted with EtOAc (2×20 mL). The combined organic extracts were dried over sodium sulfate, filtered and concentrated in vacuo to afford 3-(5-bromo-6-methoxypyridin-2-yl)-4-methyl-5-(3-(trifluoromethyl) phenyl)-5,6-dihydro-4H-1, 2, 4-oxadiazine (11 mg, 23%) as a pale yellow syrup used in the next step without further purification. LCMS: 71.7%; 429.9 (M+); (column; Ascentis Express C-18 (50×3.0 mm, 2.7 μm); RT 2.80 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.7).

Example 30

Synthesis of 3-(6-methoxy-5-(4-methyl-1H-imidazol-1-yl) pyridin-2-yl)-4-methyl-5-(3-(trifluoromethyl) phenyl)-5,6-dihydro-4H-1,2,4-oxadiazine

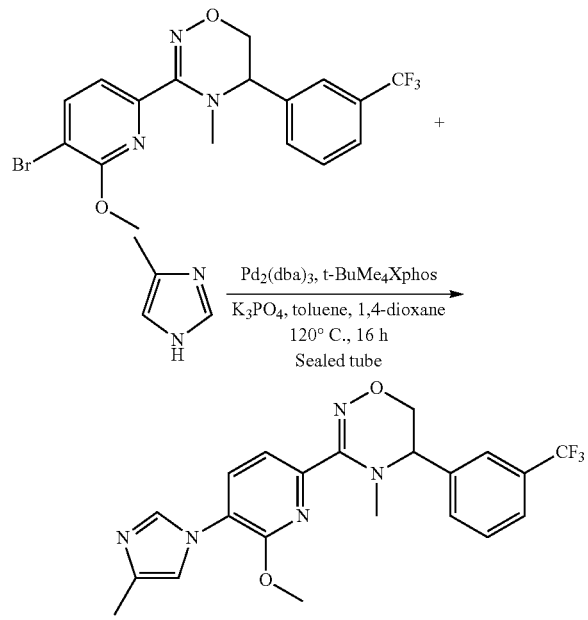

3-(6-methoxy-5-(4-methyl-1H-imidazol-1-yl) pyridin-2-yl)-4-methyl-5-(3-(trifluoromethyl) phenyl)-5,6-dihydro-4H-1,2,4-oxadiazine To a dry vial was added a suspension of Pd$_2$(dba)$_3$ (8.5 mg, 0.009 mmol) and tert-butyl tetramethyl Xphos (9 mg, 0.02 mmol) in toluene:1,4-dioxane (2:1, 1.5 mL) at room temperature. The suspension was degassed with argon, heated to 120° C., and stirred at 120° C. for 3 min. A mixture of 3-(5-bromo-6-methoxypyridin-2-yl)-4-methyl-5-(3-(trifluoromethyl) phenyl)-5,6-dihydro-4H-1, 2, 4-oxadiazine (80 mg, 0.2 mmol), 4-methyl-1H-imidazole (23 mg, 0.3 mmol) and potassium phosphate (79 mg, 0.4 mmol) in toluene:1, 4-dioxane (2:1, 1.5 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with MeOH: CH$_2$Cl$_2$ (2×20 mL). The combined organic extracts were dried over sodium sulfate, filtered and concentrated in vacuo. The crude material was purified by column chromatography using 2-5% MeOH: CH$_2$Cl$_2$ to afford 3-(6-methoxy-5-(4-methyl-1H-imidazol-1-yl) pyridin-2-yl)-4-methyl-5-(3-(trifluoromethyl) phenyl)-5,6-dihydro-4H-1,2,4-oxadiazine (40 mg, 50%) as yellow syrup.

Racemic compound of Example 30 was separated using a Chiralpak-IA column (250×4.6 mm, 5 μm) (15 mg loading; 0.1% DEA in n-Hexane: CH$_2$Cl$_2$:MeOH (80:20) (A:B: 80:20) as mobile phase) to afford the compounds of Example 30A (Fraction (I)) and Example 30B (Fraction (II)).

Analytical conditions for Example 30A and Example 30B: HPLC (column; Eclipse XDB-C-18, 150×4.6 mm, 5.0 μm); mobile phase: ACN: 0.05% Aq TFA; flow rate: 1.0 mL/min; Gradient program: T/B % 0.01/90, 2/90, 8/10, 15/10: diluent: CH$_3$CN:Water; Chiral HPLC: (Chiralpak-IA (250×4.6 mm, 5 μm; mobile phase (A) 0.1% DEA in n-Hexane (B) CH$_2$Cl$_2$:MeOH (80:20) (A:B; 80:20); flow Rate: 1.0 mL/min).

Example 30A, 3-(6-methoxy-5-(4-methyl-1H-imidazol-1-yl) pyridin-2-yl)-4-methyl-5-(3-(trifluoromethyl) phenyl)-5,6-dihydro-4H-1,2,4-oxadiazine, fraction (I): $^1$H NMR (CD$_3$OD, 400 MHz) δ 8.01 (s, 1H), 7.92 (d, 1H), 7.79 (s, 1H), 7.76-7.60 (m, 3H), 7.38 (d, 1H), 7.24 (s, 1H), 4.78 (t, 1H), 4.24 (dd, 1H), 4.13-4.11 (m, 1H), 4.10 (s, 3H), 2.87 (s, 3H), 2.26 (s, 3H); Mass (ESI): 432.4 [M+1]; HPLC (purity): 96.1%, RT 7.45 min; Chiral HPLC: 98.8%, RT=11.49 min.

Example 30B, 3-(6-methoxy-5-(4-methyl-1H-imidazol-1-yl) pyridin-2-yl)-4-methyl-5-(3-(trifluoromethyl) phenyl)-5,6-dihydro-4H-1,2,4-oxadiazine, fraction (II): Mass (ESI): 432.6 [M+1]; HPLC (purity): 99.3%, RT 7.49 min; Chiral HPLC: 99.1%, RT=13.77 min.

Example 31

Synthesis of 5-(Benzofuran-2-yl)-3-(6-methoxy-5-(3-methyl-1H-1,2,4-triazol-1-yl)pyridin-2-yl)-5,6-dihydro-4H-1,2,4-oxadiazine

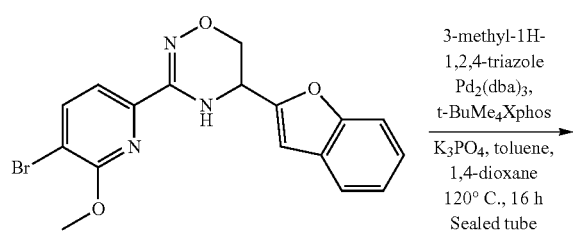

3-methyl-1H-1,2,4-triazole
Pd$_2$(dba)$_3$,
t-BuMe$_4$Xphos
K$_3$PO$_4$, toluene,
1,4-dioxane
120° C., 16 h
Sealed tube -continued

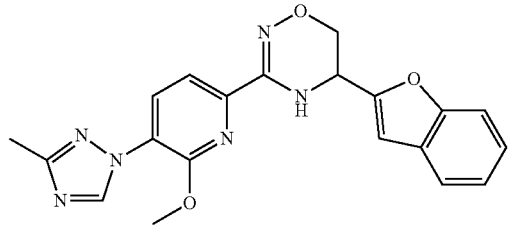

5-(Benzofuran-2-yl)-3-(6-methoxy-5-(3-methyl-1H-1,2,4-triazol-1-yl)pyridin-2-yl)-5,6-dihydro-4H-1,2,4-oxadiazine To a vial charged with racemic 5-(benzofuran-2-yl)-3-(5-bromo-6-methoxypyridin-2-yl)-5,6-dihydro-4H-1,2,4-oxadiazine (110 mg, 0.28 mmol, 1.0 equiv.), 3-methyl-1H-1,2,4-triazole (47.1 mg, 0.57 mmol, 2.0 equiv.), and K$_3$PO$_4$ (120 mg, 0.57 mmol, 2.0 equiv.) under N$_2$ atmosphere was added degassed 4:1 PhMe:dioxane solvent mixture (2.00 mL). To a second vial charged with Pd$_2$(dba)$_3$ (20.8 mg, 0.02 mmol, 8.0 mol %) and Me$_4$-di-t-BuXPhos (CAS#857356-94-6, 21.8 mg, 0.05 mmol, 16 mol %) under N$_2$ atmosphere was added degassed 4:1 PhMe:dioxane solvent mixture (0.83 mL). This mixture was stirred for 3 minutes at 120° C. to provide a dark red solution which was cooled to RT and transferred to the first vial. The reaction was degassed by bubbling with N$_2$ for 5 minutes and then sealed. The reaction mixture was stirred at 120° C. for 16 h. The reaction was cooled to RT and filtered through a pad of celite which was washed thoroughly with EtOAc. The filtrate was concentrated, and the residue was purified by normal phase chromatography on silica (0-5% MeOH/DCM) to afford 5-(Benzofuran-2-yl)-3-(6-methoxy-5-(3-methyl-1H-1,2,4-triazol-1-yl)pyridin-2-yl)-5,6-dihydro-4H-1,2,4-oxadiazine (77.4 mg, 70%) as an off-white solid.

The racemate was separated using semi preparative HPLC A (Chiralpak IB column, 5 um 20×250 mm, 15 mL/min, 80% Hexanes/10% MeOH/10% DCM) to afford the compounds of Example 31A (Fraction (I)(-)) (27.9 mg, 25%, t$_r$=22.2 min) and Example 31B (Fraction (II)(+)) (24.5 mg, 22%, t$_r$=26.6 min).

Example 31A, (-)-5-(Benzofuran-2-yl)-3-(6-methoxy-5-(3-methyl-1H-1,2,4-triazol-1-yl)pyridin-2-yl)-5,6-dihydro-4H-1,2,4-oxadiazine, fraction (I): Chiral HPLC A (Chiralpak IB column, 5 um, 4.6×250 mm, 1 mL/min, 80% Hexanes/10% MeOH/10% DCM), 99% cc, t$_r$=11.02 min; LCMS analysis using LCMS A, standard conditions: t$_r$=4.75 min, LCMS (ES+) [M+H]+: 391.3; [α]$_D$=-258 (c=0.11, MeOH).

Example 31B, (+)-5-(Benzofuran-2-yl)-3-(6-methoxy-5-(3-methyl-1H-1,2,4-triazol-1-yl)pyridin-2-yl)-5,6-dihydro-4H-1,2,4-oxadiazine, fraction (II): Chiral HPLC A (Chiralpak IB column, 5 um, 4.6×250 mm, 1 mL/min, 80% Hexanes/10% MeOH/10% DCM), >99% cc, t$_r$=13.03 min; $^1$H NMR (500 MHz, CDCl$_3$) δ 8.84 (s, 1H), 8.28 (d, J=8.2 Hz, 1H), 7.87 (d, J=8.2 Hz, 1H), 7.56 (ddd, J=7.7, 1.3, 0.7 Hz, 1H), 7.49-7.46 (m, 1H), 7.31 (ddd, J=8.3, 7.3, 1.4 Hz, 1H), 7.24 (dd, J=7.3, 1.0 Hz, 1H), 6.76 (t, J=0.8 Hz, 1H), 6.68 (d, J=2.2 Hz, 1H), 5.06-5.02 (m, 1H), 4.36-4.31 (m, 1H), 4.21 (dd, J=11.0, 5.3 Hz, 1H), 4.14 (s, 3H), 2.50 (s, 3H). LCMS analysis using LCMS A, standard conditions: t$_r$=4.75 min, LCMS (ES+) [M+H]+: 391.3; [α]$_D$=+236 (c=0.10, MeOH).

Example 32

Synthesis of (R)-5-(Benzofuran-2-yl)-3-(6-methoxy-5-(4-methyl-1H-imidazol-1-yl)pyridin-2-yl)-4-methyl-5,6-dihydro-4H-1,2,4-oxadiazine

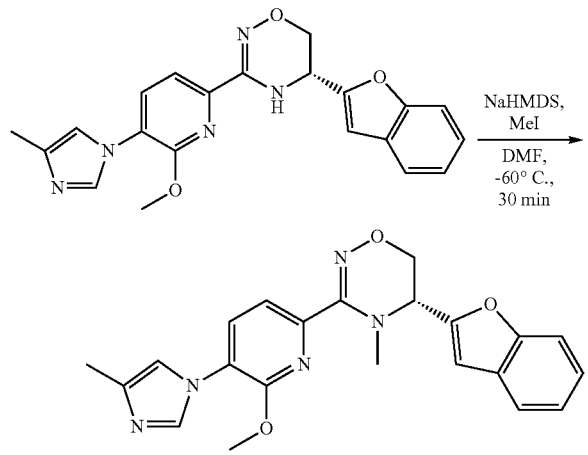

The title compound (61.0 mg, 47%) was prepared as a white solid from (R)-5-(benzofuran-2-yl)-3-(6-methoxy-5-(4-methyl-1H-imidazol-1-yl)pyridin-2-yl)-5,6-dihydro-4H-1,2,4-oxadiazine according to the procedure for Example 23.

Example 32, (R)-5-(Benzofuran-2-yl)-3-(6-methoxy-5-(4-methyl-1H-imidazol-1-yl)pyridin-2-yl)-4-methyl-5,6-dihydro-4H-1,2,4-oxadiazine: $^1$H NMR (500 MHz, CDCl$_3$) δ 7.83 (d, J=1.3 Hz, 1H), 7.62 (d, J=7.8 Hz, 1H), 7.57 (ddd, J=7.6, 1.3, 0.6 Hz, 1H), 7.51-7.47 (m, 1H), 7.41 (d, J=7.8 Hz, 1H), 7.33-7.28 (m, 1H), 7.26-7.23 (m, 1H), 7.00-6.98 (m, 1H), 6.82 (t, J=0.7 Hz, 1H), 4.74 (dd, J=3.8, 3.3 Hz, 1H), 4.45 (dd, J=11.4, 3.8 Hz, 1H), 4.26 (dd, J=11.4, 3.7 Hz, 1H), 4.06 (s, 3H), 3.01 (s, 3H), 2.31 (d, J=1.0 Hz, 3H); LCMS analysis using LCMS A, standard conditions: t$_r$=3.71 mM, LCMS (ES+) [M+H]+: 404.2; [α]$_D$=+189 (c=0.10, MeOH).

Example 33

Synthesis of (+)-3-(6-Methoxy-5-(4-methoxy-1H-imidazol-1-yl)pyridin-2-yl)-5-(7-methylbenzofuran-2-yl)-5,6-dihydro-4H-1,2,4-oxadiazine

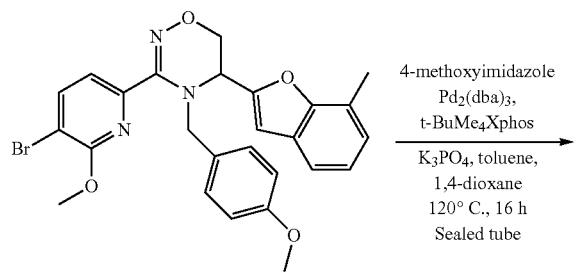

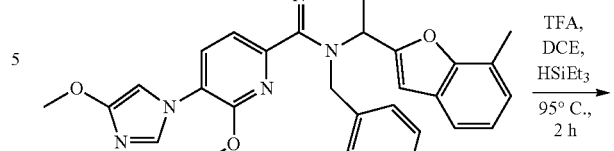

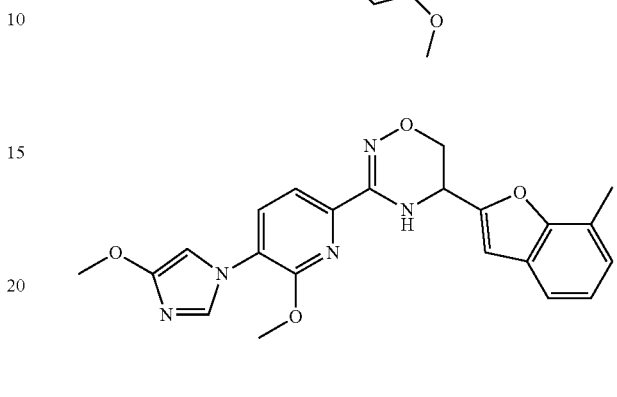

3-(6-Methoxy-5-(4-methoxy-1H-imidazol-1-yl)pyridin-2-yl)-4-(4-methoxybenzyl)-5-(7-methylbenzofuran-2-yl)-5,6-dihydro-4H-1,2,4-oxadiazine To a vial charged with 3-(5-bromo-6-methoxypyridin-2-yl)-4-(4-methoxybenzyl)-5-(7-methylbenzofuran-2-yl)-5,6-dihydro-4H-1,2,4-oxadiazine, fraction (II) Example 6B (80.0 mg, 0.15 mmol, 1.0 equiv.), 4-Methoxy-1H-imidazole (30.0 mg, 0.31 mmol, 2.0 equiv.), and K$_3$PO$_4$ (64.9 mg, 0.31 mmol, 2.0 equiv.) under N$_2$ atmosphere was added degassed 4:1 PhMe:dioxane solvent mixture (0.80 mL). To a second vial charged with Pd$_2$(dba)$_3$ (5.60 mg, 0.006 mmol, 4.0 mol %) and Me$_4$-di-t-BuXPhos (CAS#857356-94-6, 5.90 mg, 0.01 mmol, 8.0 mol %) under N$_2$ atmosphere was added degassed 4:1 PhMe:dioxane solvent mixture (0.40 mL). This mixture was stirred for 3 minutes at 120° C. to provide a dark red solution which was cooled to RT and transferred to the first vial. The reaction was degassed by bubbling with N$_2$ for 5 minutes and then sealed. The reaction mixture was stirred at 120° C. for 16 h. The reaction was cooled to RT and filtered through a pad of celite which was washed thoroughly with EtOAc. The filtrate was concentrated, and the residue was purified by normal phase chromatography on silica (0-5% MeOH/DCM) to afford the product (70.0 mg, 85%) as a white solid. LCMS (ES+) [M+H]+: 540.3.

(+)-3-(6-Methoxy-5-(4-methoxy-1H-imidazol-1-yl)pyridin-2-yl)-5-(7-methylbenzofuran-2-yl)-5,6-dihydro-4H-1,2,4-oxadiazine A solution of 3-(6-methoxy-5-(4-methoxy-1H-imidazol-1-yl)pyridin-2-yl)-4-(4-methoxybenzyl)-5-(7-methylbenzofuran-2-yl)-5,6-dihydro-4H-1,2,4-oxadiazine (57.0 mg, 0.11 mmol, 1.0 equiv.) in DCE (1.00 mL) at ambient temperature was treated with triethylsilane (50.6 uL, 0.32 mmol, 3.0 equiv.) and TFA (1.00 mL). The resultant mixture was stirred at 95° C. for 2 h. The reaction mixture was cooled to RT, concentrated and dissolved in EtOAc. The organic layer washed with 1 N aqueous NaOH, brine and dried over MgSO4, filtered and concentrated. The residue was purified by normal phase chromatography on silica (0-10% MeOH/DCM) to afford the product as an off-white solid. This material was dissolved in DMF and further purified using reverse phase chromatography on C18 resin (5-100% MeCN/H2O+0.1% HCOOH) to provide, after lyophilisation, the compound of Example 33 as a white solid (27.6 mg, 62%).

Example 33, (+)-3-(6-methoxy-5-(4-methoxy-1H-imidazol-1-yl)pyridin-2-yl)-5-(7-methylbenzofuran-2-yl)-5,6-dihydro-4H-1,2,4-oxadiazine: $^1$H NMR (500 MHz, CDCl$_3$) δ 7.82 (d, J=8.0 Hz, 1H), 7.67 (s, 1H), 7.66 (d, J=8.0 Hz, 1H), 7.38 (d, J=7.6 Hz, 1H), 7.17-7.08 (m, 2H), 6.73 (d, J=0.8 Hz, 1H), 6.70 (d, J=1.9 Hz, 1H), 6.59 (d, J=1.4 Hz, 1H), 5.06 (dt, J=5.8, 3.0 Hz, 1H), 4.37 (dd, J=10.9, 3.7 Hz, 1H), 4.19 (dd, J=11.0, 5.5 Hz, 1H), 4.07 (s, 3H), 3.88 (s, 3H), 2.52 (s, 3H). LCMS analysis using LCMS A, standard conditions: t$_r$=4.85 mM, LCMS (ES+) [M+H]+: 420.2; [α]$_D$=+284 (c=0.13, MeOH).

Example 34

Synthesis of 5-bromo-N'-hydroxy-6-methoxypicolinimidamide

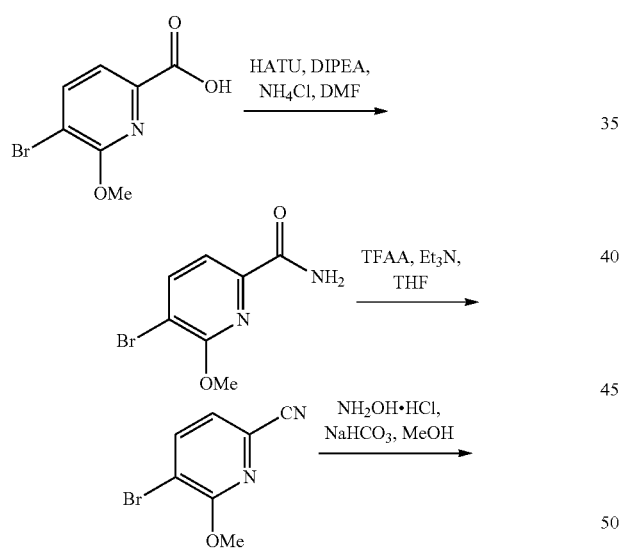

5-bromo-6-methoxypicolinamide 5-bromo-6-methoxypicolinic acid (5 g, 22 mmol) was dissolved in DMF (50 mL) and cooled to 0° C. under argon. DIPEA (7.66 mL, 44 mmol), ammonium chloride (1.77 g, 33 mmol) and HATU (12.6 g, 33 mmol) were added and the mixture was warmed to room temperature and stirred overnight. Water (50 mL) was added and the solid precipitate 5-bromo-6-methoxypicolinamide was collected by filtration (4.21 g, 83%). $^1$H NMR (DMSO, 400 MHz): δ 8.14 (d, 1H), 8.04 (br s, 1H), 7.71 (br s, 1H), 7.48 (d, 1H), 4.00 (s, 3H). LCMS (basic, 3.1 min): RT 1.64 mM, [MH]+ 232.9, purity 83%.

5-bromo-6-methoxypicolinonitrile 5-bromo-6-methoxypicolinamide (4.21 g, 18 mmol) was suspended in THF (50 mL) and cooled to −5° C. under argon. Triethylamine (6.27 mL, 45 mmol) and TFAA (3.02 mL, 21.6 mmol) were added and the mixture was then warmed to 0° C. and stirred for 2 hours. The reaction mixture was partitioned between ethyl acetate and water and the aqueous layer was re-extracted with ethyl acetate. The combined organics were dried over magnesium sulfate, filtered and the solvent was removed under reduced pressure to provide 5-bromo-6-methoxypicolinonitrile (3.83 g, 100%). $^1$H NMR (DMSO, 400 MHz): δ 8.28 (d, 1H), 7.58 (d, 1H), 3.94 (s, 3H). LCMS (basic, 3.1 min): RT 2.00 mM, [MH]+ 214.1, purity 97%.

5-bromo-N'-hydroxy-6-methoxypicolinimidamide 5-bromo-6-methoxypicolinonitrile (3.83 g, 18 mmol) was dissolved in methanol (65 mL) under argon. Hydroxylamine hydrochloride (1.63 g, 23.4 mmol) was added followed by sodium hydrogen carbonate (2.27 g, 27 mmol) and the mixture was warmed to 60° C. and stirred for 1 hour. It was quenched with ammonium chloride (5 mL, saturated aqueous) and partitioned between ethyl acetate and water; the aqueous layer was extracted with ethyl acetate and the combined organics were washed with brine, dried over magnesium sulfate, filtered and the solvent was removed under reduced pressure to afford 5-bromo-N'-hydroxy-6-methoxypicolinimidamide (4.09 g, 92%). $^1$H NMR (CDCl$_3$, 400 MHz): δ 7.81 (d, 1H), 7.40 (d, 1H), 5.50 (br s, 2H), 4.05 (s, 3H). UPLC (basic, 4.7 min): RT 1.53 min, [MH]+ 246.0, purity 97%.

Example 35

Synthesis of 3-(5-bromo-6-methoxypyridin-2-yl)-5-phenyl-5,6-dihydro-4H-1,2,4-oxadiazine

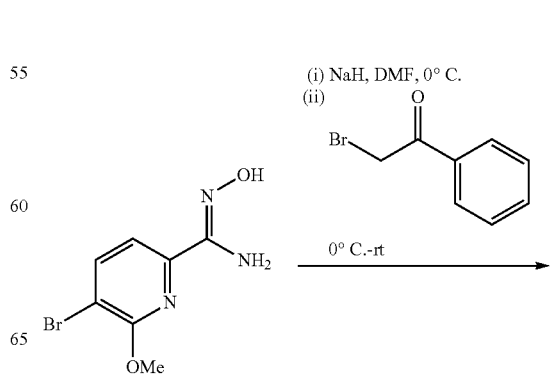

Example 36

Synthesis of 3-(6-methoxy-5-(4-methyl-1H-imidazol-1-yl)pyridin-2-yl)-5-phenyl-5,6-dihydro-4H-1,2,4-oxadiazine

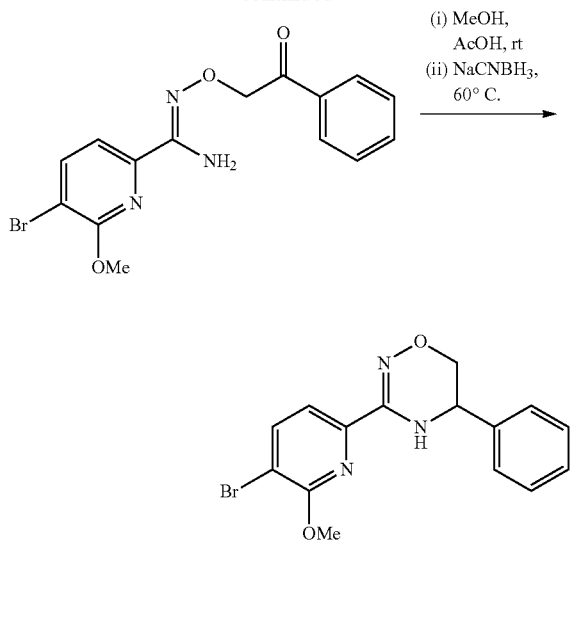

(Z)-5-bromo-6-methoxy-N'-(2-oxo-2-phenylethoxy)picolinimidamide

Sodium hydride (39 mg, 0.97 mmol, 60% dispersion in mineral oil) was added to a solution of 5-bromo-N'-hydroxy-6-methoxypicolinimidamide (200 mg, 0.81 mol) in DMF (4 mL) at 0° C. and the mixture was stirred at 0-10° C. for 10 minutes. A solution of 2-bromoacetophenone (242 mg, 1.21 mmol) in DMF (1 mL) was added dropwise and the mixture was warmed to room temperature and stirred for 20 minutes. The reaction mixture was diluted with water (10 mL) and extracted into ethyl acetate (2×10 mL). The combined organic extracts were washed with brine (3×10 mL), dried over magnesium sulfate, filtered, and the solvent was removed under reduced pressure to afford crude (Z)-5-bromo-6-methoxy-N'-(2-oxo-2-phenylethoxy)picolinimidamide which was used directly in the next step. UPLC (basic, 1.25 min): RT 0.87 min, [MH]+ 364.2, purity 61%.

3-(5-bromo-6-methoxypyridin-2-yl)-5-phenyl-5,6-dihydro-4H-1,2,4-oxadiazine

A mixture of crude (Z)-5-bromo-6-methoxy-N'-(2-oxo-2-phenylethoxy)picolinimidamide (max. 0.81 mmol), acetic acid (1 mL) and methanol (4 mL) were heated to 60° C. for 1 hour. To the mixture was added sodium cyanoborohydride (61 mg) and the mixture was stirred at 60° C. for 18 hours. The reaction mixture was diluted with water (10 mL) and extracted into ethyl acetate (2×10 mL). The combined organic extracts were washed with brine (10 mL), dried over magnesium sulfate, filtered, and the solvent was removed under reduced pressure. The crude material was purified by flash column chromatography on silica gel (eluting with 2:1→1:1 heptane:ethyl acetate) to afford 3-(5-bromo-6-methoxypyridin-2-yl)-5-phenyl-5,6-dihydro-4H-1,2,4-oxadiazine (146 mg, 52% over 2 steps). $^1$H (CDCl$_3$, 400 MHz) δ 7.87 (s, 1H), 7.60 (d, 1H), 7.45-7.33 (m, 5H), 6.55 (s, 1H), 4.80-4.73 (m, 1H), 4.28 (dd, 1H), 3.97 (s, 3H), 3.70 (dd, 1H). LCMS (basic, 3.1 min): RT 2.00 mM, [MH]+ 348.0, purity 80%.

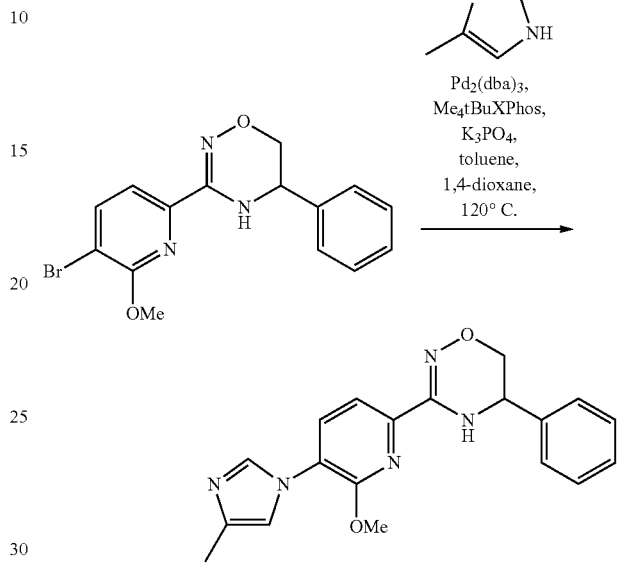

3-(6-methoxy-5-(4-methyl-1H-imidazol-1-yl)pyridin-2-yl)-5-phenyl-5,6-dihydro-4H-1,2,4-oxadiazine A solution of tris(dibenzylideneacetone)dipalladium(0) (1.3 mg, 1.4 µmol) and 2-di-tert-butylphosphino-3,4,5,6-tetramethyl-2',4',6'-triisopropyl-1,1'-biphenyl (1.3 mg, 2.8 mol) in toluene (500 µL) and 1,4-dioxane (100 µL) was heated at 120° C. for 3 minutes under an atmosphere of argon. To this mixture was added 3-(5-bromo-6-methoxy-pyridin-2-yl)-5-phenyl-5,6-dihydro-4H-1,2,4-oxadiazine (62 mg, 0.14 mol), 4-methyl-1H-imidazole (14 mg, 0.17 mmol) and potassium phosphate tribasic (59 mg, 0.28 mmol). The reaction mixture was heated at 120° C. for 18 hours then cooled to ambient temperature, diluted with 4:1 dichloromethane:methanol (50 mL), filtered through Celite (washing with 4:1 dichloromethane:methanol (100 mL)) and the filtrate was the solvent was removed under reduced pressure. The crude material was purified by flash column chromatography on silica gel eluting with neat dichloromethane→19:1 dichloromethane:methanol to afford the title compound (138 mg, 95%). The enantiomers were separated by chiral preparative high performance liquid chromatography (HPLC) (Chiralpak IB 20×250 mm) eluting with 9:1 tert-butylmethyl ether:methanol (0.1% diethylamine) over 20 minutes (18 mL per minute) to afford the compounds of Example 36A (Fraction (I)) and Example 36B (Fraction 2).

Example 36A, 3-(6-methoxy-5-(4-methyl-1H-imidazol-1-yl)pyridin-2-yl)-5-phenyl-5,6-dihydro-4H-1,2,4-oxadiazine, fraction (I): 23.4 mg; Chiral HPLC: RT 8.99 min, 100% e.e.; LCMS (basic, 11 min): RT 5.75 mM, [MH]+ 350.3, purity 99%.

Example 36B, 3-(6-methoxy-5-(4-methyl-1H-imidazol-1-yl)pyridin-2-yl)-5-phenyl-5,6-dihydro-4H-1,2,4-oxadiazine, fraction (II): 25.1 mg; ¹H NMR (CDCl₃, 400 MHz) δ 7.85-7.77 (m, 2H), 7.63 (d, 1H), 7.51-7.32 (m, 5H), 6.98 (s, 1H), 6.58 (s, 1H), 4.84-4.72 (m, 1H), 4.30 (dd, 1H), 3.99 (s, 3H), 3.72 (dd, 1H), 2.29 (s, 3H). Chiral HPLC: RT 13.0 min, 100% e.e.; LCMS (basic, 11 min): RT 5.74 min, [MH]+ 350.3, purity 99%.

Example 37

Synthesis of 5-(benzofuran-3-yl)-3-(5-bromo-6-methoxypyridin-2-yl)-5,6-dihydro-4H-1,2,4-oxadiazine

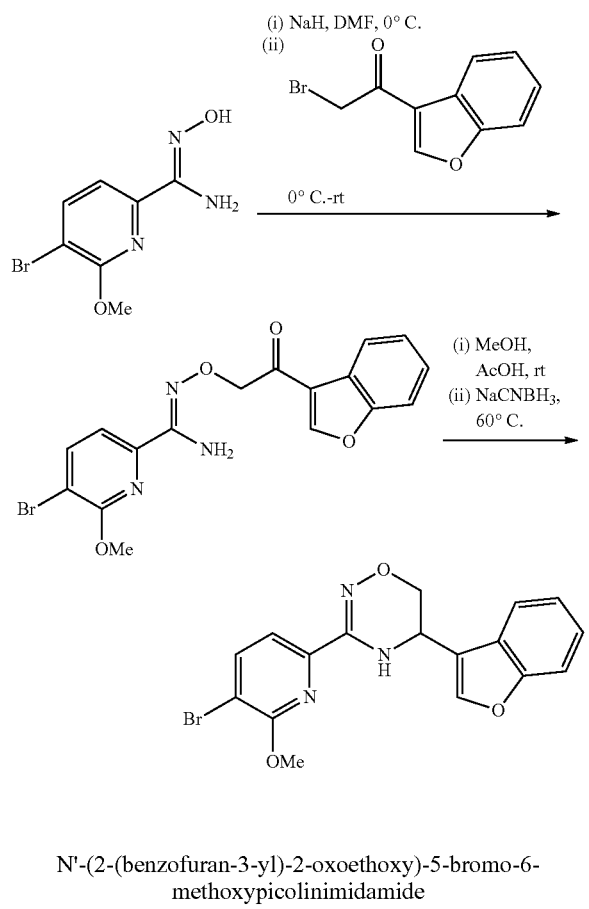

N'-(2-(benzofuran-3-yl)-2-oxoethoxy)-5-bromo-6-methoxypicolinimidamide

Sodium hydride (39.0 mg, 0.97 mmol, 60% dispersion in mineral oil) was added to a solution of 5-bromo-N'-hydroxy-6-methoxypicolinimidamide (200 mg, 0.81 mmol) in DMF (5 mL) at 0° C. and the mixture was stirred at 0-10° C. for 10 minutes. A solution of 1-(benzofuran-3-yl)-2-bromoethanone (289 mg, 1.22 mmol) in DMF (1.5 mL) was added dropwise and the mixture was warmed to room temperature and stirred for 20 minutes. The reaction mixture was diluted with water (10 mL) and extracted into ethyl acetate (2×10 mL). The combined organic extracts were washed with brine (3×10 mL), dried over magnesium sulfate, filtered, and the solvent was removed under reduced pressure to afford crude (Z)—N'-(2-(benzofuran-3-yl)-2-oxoethoxy)-5-bromo-6-methoxypicolinimidamide, which was used directly in the next step. UPLC (basic, 1.25 min): RT 0.93 min, [MH]+ 406.2, purity 53%.

5-(benzofuran-3-yl)-3-(5-bromo-6-methoxypyridin-2-yl)-5,6-dihydro-4H-1,2,4-oxadiazine A mixture of (Z)—N'-(2-(benzofuran-3-yl)-2-oxoethoxy)-5-bromo-6-methoxypicolinimidamide (max. 0.81 mmol), acetic acid (1 mL) and methanol (4 mL) were stirred at room temperature for 1 hour. To the mixture was added sodium cyanoborohydride (61.3 mg, 0.98 mmol) and heated at 60° C. for 18 hours. The reaction mixture was diluted with water (10 mL) and extracted into ethyl acetate (2×10 mL). The combined organic extracts were washed with brine (10 mL), dried over magnesium sulfate, filtered and the solvent removed under reduced pressure. The crude material was purified by flash column chromatography (silica), eluting with 3:1 to 2:1 heptane:ethyl acetate to afford 5-(benzofuran-3-yl)-3-(5-bromo-6-methoxypyridin-2-yl)-5,6-dihydro-4H-1,2,4-oxadiazine (130 mg, 41% over 2 steps). ¹H NMR (CDCl₃, 400 MHz): δ 7.90 (d, 1H), 7.67 (s, 1H), 7.63-7.58 (m, 2H), 7.52 (d, 1H), 7.34 (t, 1H), 7.28-7.21 (m, 1H), 6.57 (s, 1H), 5.09 (s, 1H), 4.35 (dd, 1H), 4.02 (dd, 1H), 3.94 (s, 3H).

Example 38

Synthesis of 5-(benzofuran-3-yl)-3-(6-methoxy-5-(4-methyl-1H-imidazol-1-yl)pyridin-2-yl)-5,6-dihydro-4H-1,2,4-oxadiazine

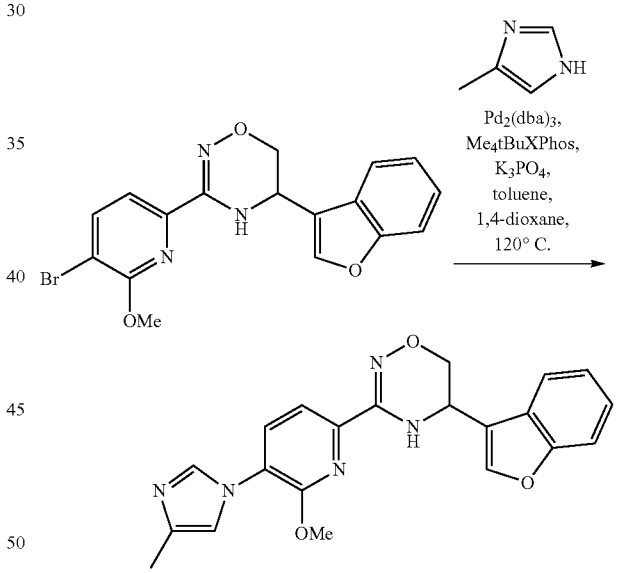

5-(benzofuran-3-yl)-3-(6-methoxy-5-(4-methyl-1H-imidazol-1-yl)pyridin-2-yl)-5,6-dihydro-4H-1,2,4-oxadiazine A solution of tris(dibenzylideneacetone)dipalladium(0) (2.45 mg, 2.68 µmol) and 2-di-tert-butylphosphino-3,4,5,6-tetramethyl-2',4',6'-triisopropyl-1,1'-biphenyl (2.58 mg, 5.36 mol) in toluene (1 mL) and 1,4-dioxane (200 µL) was heated at 120° C. for 3 minutes under an atmosphere of argon. To this mixture was added 5-(benzofuran-3-yl)-3-(5-bromo-6-methoxypyridin-2-yl)-5,6-dihydro-4H-1,2,4-oxadiazine (104 mg, 0.27 mmol), 4-methyl-1H-imidazole (26.4 mg, 321 µmol) and potassium phosphate tribasic (114 mg, 0.54 mmol). The reaction mixture was heated at 120° C. for 18 hours then cooled to ambient temperature, diluted with 4:1 dichloromethane:methanol (50 mL), filtered through Celite (washing with 4:1 dichloromethane:methanol (100 mL)) and the filtrate was the solvent was removed under reduced pressure under reduced pressure. The crude material was purified by flash column chromatography on silica gel eluting with neat DCM→19:1 dichloromethane:methanol to afford the title compound (80 mg, 76%). The enantiomers were separated by chiral preparative high performance liquid chromatography (HPLC) (Chiralpak IB 20×250 mm) eluting with 9:1 tert-butylmethyl ether:methanol (0.1% diethylamine) over 20 minutes (18 mL per minute) to afford the compounds of Example 38A (Fraction (I)) and Example 38B (Fraction (II)).

Example 38A, 5-(benzofuran-3-yl)-3-(6-methoxy-5-(4-methyl-1H-imidazol-1-yl)pyridin-2-yl)-5,6-dihydro-4H-1,2,4-oxadiazole, fraction (I): 31.6 mg; Chiral HPLC: RT 9.67 min 100% e.e.; LCMS (basic, 11 min): RT 6.07 mM, [MH]+ 390.3, purity 98%.

Example 38B, 5-(benzofuran-3-yl)-3-(6-methoxy-5-(4-methyl-1H-imidazol-1-yl)pyridin-2-yl)-5,6-dihydro-4H-1,2,4-oxadiazole, fraction (II): 19.0 mg; $^1$H NMR (CDCl$_3$, 400 MHz): δ 7.90-7.77 (m, 2H), 7.74-7.45 (m, 3H), 7.52 (d, 1H), 7.34 (t, 1H), 7.28-7.18 (m, 1H), 6.98 (s, 1H), 6.60 (s, 1H), 5.09 (s, 1H), 4.35 (dd, 1H), 4.02 (dd, 1H), 3.94 (s, 3H), 2.29 (s, 3H). Chiral HPLC: RT 12.8 min, 100% e.e.; LCMS (basic, 11 min): RT 6.08 mM, [MH]+ 390.3, purity 99%.

Example 39

Synthesis of 3-(5-bromo-6-methoxypyridin-2-yl)-5-(4-fluorophenyl)-5,6-dihydro-4H-1,2,4-oxadiazine

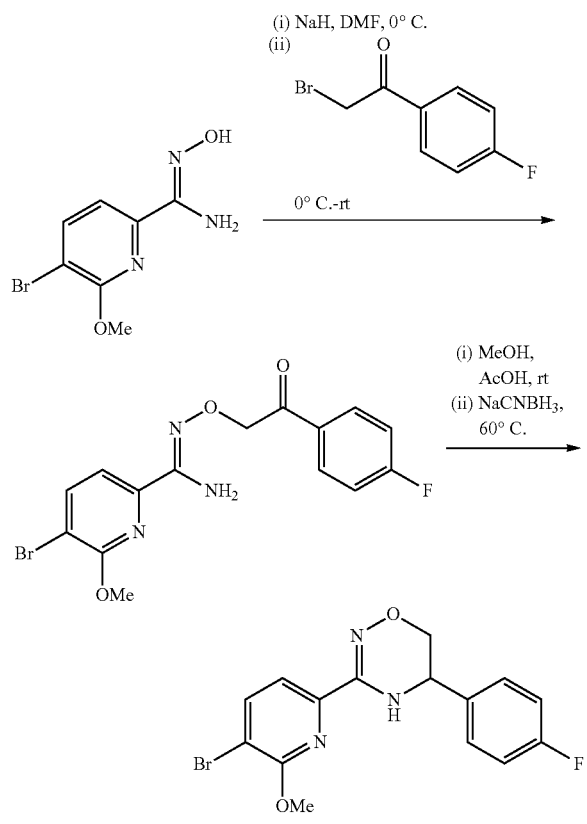

Synthesis of ((Z)-5-bromo-N'-(2-(4-fluorophenyl)-2-oxoethoxy)-6-methoxypicolinimidamide Sodium hydride (59 mg, 1.46 mmol, 60% dispersion in mineral oil) was added to a solution of bromo-N'-hydroxy-6-methoxypicolinimidamide (300 mg, 1.22 mmol) in DMF (5 mL) at 0° C. and the mixture was stirred at 0-10° C. for 10 minutes. A solution of 2-bromo-1-(4-fluorophenyl)ethanone (397 mg, 1.83 mmol) in DMF (1 mL) was added dropwise and the mixture was warmed to room temperature and stirred for 20 minutes. The reaction mixture was diluted with water (10 mL) and extracted into ethyl acetate (2×10 mL). The combined organic extracts were washed with brine (3×10 mL), dried over magnesium sulfate, filtered, and the solvent was removed under reduced pressure to afford crude ((Z)-5-bromo-N'-(2-(4-fluorophenyl)-2-oxoethoxy)-6-methoxypicolinimidamide which was used directly in the next step.

3-(5-bromo-6-methoxypyridin-2-yl)-5-(4-fluorophenyl)-5,6-dihydro-4H-1,2,4-oxadiazine A mixture of ((Z)-5-bromo-N'-(2-(4-fluorophenyl)-2-oxoethoxy)-6-methoxypicolinimidamide (max 1.22 mmol), acetic acid (2 mL) and methanol (8 mL) were heated to 60° C. for 1 hour. To the mixture was added sodium cyanoborohydride (92 mg, 1.46 mmol) and the mixture was stirred at 60° C. for 18 hours. The reaction mixture was diluted with water (20 mL) and extracted into ethyl acetate (2×20 mL). The combined organic extracts were washed with brine (20 mL), dried over magnesium sulfate, filtered, and the solvent was removed under reduced pressure. The crude material was purified by flash column chromatography on silica gel (eluting with 3:1→2:1 heptane:ethyl acetate) to afford 3-(5-bromo-6-methoxypyridin-2-yl)-5-(4-fluorophenyl)-5,6-dihydro-4H-1,2,4-oxadiazine (220 mg, 49% over 2 steps). $^1$H NMR (CDCl$_3$, 400 MHz) δ 7.87 (d, 1H), 7.59 (d, 1H), 7.36-7.30 (m, 2H), 7.09 (t, 2H), 6.53 (s, 1H), 4.77-4.72 (m, 1H), 4.23 (dd, 1H), 3.97 (s, 3H), 3.71 (dd, 1H).

Example 40

Synthesis of 5-(4-fluorophenyl)-3-(6-methoxy-5-(4-methyl-1H-imidazol-1-yl)pyridin-2-yl)-5,6-dihydro-4H-1,2,4-oxadiazine

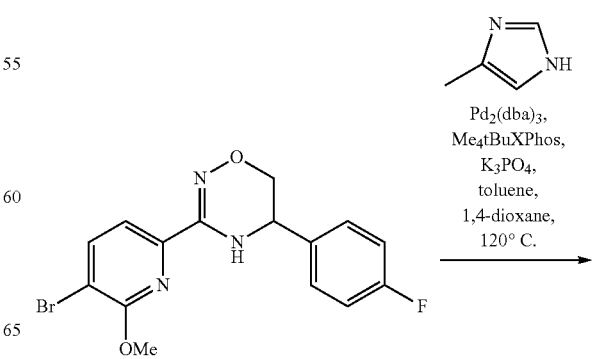

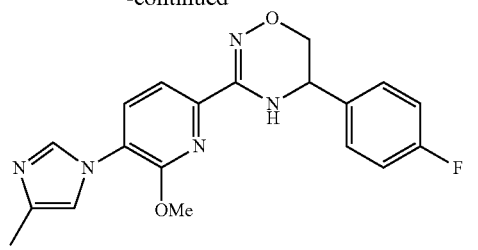

5-(4-fluorophenyl)-3-(6-methoxy-5-(4-methyl-1H-imidazol-1-yl)pyridin-2-yl)-5,6-dihydro-4H-1,2,4-oxadiazine A solution of tris(dibenzylideneacetone)dipalladium(0) (5.4 mg, 5.9 μmol) and 2-di-tert-butylphosphino-3,4,5,6-tetramethyl-2',4',6'-triisopropyl-1,1'-biphenyl (5.7 mg, 11.8 mol) in toluene (2 mL) and 1,4-dioxane (400 μL) was heated at 120° C. for 3 minutes under an atmosphere of argon. To this mixture was added 3-(5-bromo-6-methoxypyridin-2-yl)-5-(4-fluorophenyl)-5,6-dihydro-4H-1,2,4-oxadiazine (216 mg, 0.59 mmol), 4-methyl-1H-imidazole (58 mg, 0.71 mmol) and potassium phosphate tribasic (250 mg, 1.18 mmol). The reaction mixture was heated at 120° C. for 18 hours then cooled to ambient temperature, diluted with 4:1 dichloromethane:methanol (50 mL), filtered through Celite (washing with 4:1 dichloromethane:methanol (100 mL)) and the filtrate was the solvent was removed under reduced pressure under reduced pressure. The crude material was purified by flash column chromatography on silica gel eluting with neat dichloromethane→94:6 dichloromethane:methanol to afford the title compound (130 mg, 60%). The enantiomers were separated by chiral preparative high performance liquid chromatography (HPLC) (Chiralpak IB 20×250 mm) eluting with 9:1 tert-butylmethyl ether: methanol (0.1% diethylamine) over 20 minutes (18 mL per minute) to afford the compounds of Example 40A (Fraction (I)) and Example 40B (Fraction 2).

Example 40A, 5-(4-fluorophenyl)-3-(6-methoxy-5-(4-methyl-1H-imidazol-1-yl)pyridin-2-yl)-5,6-dihydro-4H-1,2,4-oxadiazine, fraction (I): 31.5 mg; Chiral HPLC: RT 8.67 min, 100% e.e.; LCMS (basic, 11 min): RT 5.85 mM, [MH]+ 368.3, purity 99%.

Example 40B, 5-(4-fluorophenyl)-3-(6-methoxy-5-(4-methyl-1H-imidazol-1-yl)pyridin-2-yl)-5,6-dihydro-4H-1,2,4-oxadiazine, fraction (II): 31.3 mg; $^1$H NMR (CDCl$_3$, 400 MHz) δ 7.87 (s, 1H), 7.81 (d, 1H), 7.64 (d, 1H), 7.38-7.31 (m, 2H), 7.10 (t, 2H), 6.99 (s, 1H), 6.55 (s, 1H), 4.81-4.75 (m, 1H), 4.25 (dd, 1H), 4.00 (s, 3H), 3.74 (dd, 1H), 2.31 (s, 3H). Chiral HPLC: RT 11.56 min, 100% e.e.; LCMS (basic, 11 min): RT 5.84 mM, [MH]+ 368.2, purity 99%.

Example 41

Synthesis of 3-(5-bromo-6-methoxypyridin-2-yl)-5-(4-chlorophenyl)-5,6-dihydro-4H-1,2,4-oxadiazine

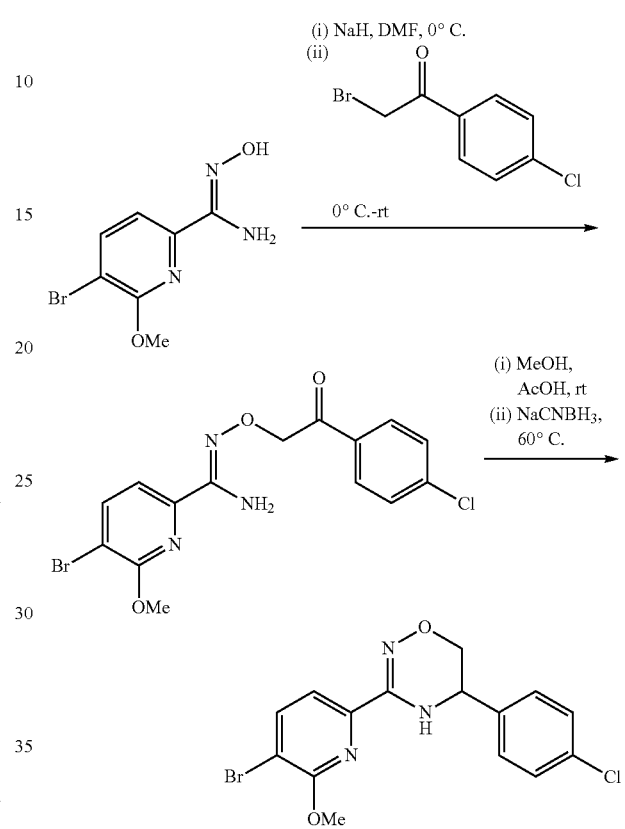

(Z)-5-bromo-N'-(2-(4-chlorophenyl)-2-oxoethoxy)-6-methoxypicolinimidamide

Sodium hydride (36 mg, 0.89 mmol, 60% dispersion in mineral oil) was added to a solution of bromo-N'-hydroxy-6-methoxypicolinimidamide (200 mg, 0.81 mol) in DMF (8 mL) at 0° C. and the mixture was stirred at 0-10° C. for 10 minutes. A solution of 2-bromo-1-(4-chlorophenyl)ethanone (247 mg, 1.06 mmol) in DMF (2 mL) was added dropwise and the mixture was warmed to room temperature and stirred for 15 minutes. The reaction mixture was diluted with water (10 mL) and extracted into ethyl acetate (2×10 mL). The combined organic extracts were washed with brine (3×10 mL), dried over magnesium sulfate, filtered, and the solvent was removed under reduced pressure to afford crude (Z)-5-bromo-N'-(2-(4-chlorophenyl)-2-oxoethoxy)-6-methoxypicolinimidamide which was used directly in the next step. UPLC (basic, 1.25 min): RT 0.92 mM, [MH]+ 400.1, purity 28%.

3-(5-bromo-6-methoxypyridin-2-yl)-5-(4-chlorophenyl)-5,6-dihydro-4H-1,2,4-oxadiazine A mixture of (Z)-5-bromo-N'-(2-(4-chlorophenyl)-2-oxoethoxy)-6-methoxypicolinimidamide (max. 0.81 mmol), acetic acid (2 mL) and methanol (8 mL) were heated to 60° C. for 1 hour. To the mixture was added sodium cyanoborohydride (61 mg, 0.98 mmol) and the mixture was stirred at 60° C. for 18 hours. The reaction mixture was diluted with water (20 mL) and extracted into ethyl acetate (2×20 mL). The combined organic extracts were washed with brine (20 mL), dried over magnesium sulfate, filtered, and the solvent was removed under reduced pressure. The crude material was purified by flash column chromatography on silica gel (eluting with neat heptane→4:1 heptane:ethyl acetate) to afford 3-(5-bromo-6-methoxypyridin-2-yl)-5-(4-chlorophenyl)-5,6-dihydro-4H-1,2,4-oxadiazine (130 mg, 42% over 2 steps). $^1$H NMR (CDCl$_3$, 400 MHz) δ 7.84 (d, 1H), 7.76 (d, 1H), 7.57 (d, 1H), 7.37-7.23 (d, 3H), 6.57 (s, 1H), 4.76-4.69 (m, 1H), 4.19 (dd, 1H), 3.95 (s, 3H), 3.70 (dd, 1H).

Example 42

Synthesis of 5-(4-chlorophenyl)-3-(6-methoxy-5-(4-methyl-1H-imidazol-1-yl)pyridin-2-yl)-5,6-dihydro-4H-1,2,4-oxadiazine

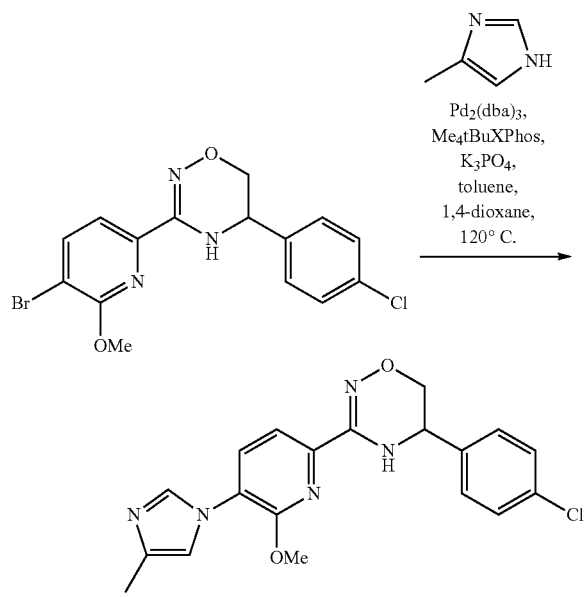

5-(4-chlorophenyl)-3-(6-methoxy-5-(4-methyl-1H-imidazol-1-yl)pyridin-2-yl)-5,6-dihydro-4H-1,2,4-oxadiazine A solution of tris(dibenzylideneacetone)dipalladium(0) (7.1 mg, 7.8 μmol) and 2-di-tert-butylphosphino-3,4,5,6-tetramethyl-2',4',6'-triisopropyl-1,1'-biphenyl (7.5 mg, 15.6 μmol) in toluene (2 mL) and 1,4-dioxane (2 mL) was heated at 120° C. for 3 minutes under an atmosphere of argon. To this mixture was added 3-(5-bromo-6-methoxypyridin-2-yl)-5-(4-chlorophenyl)-5,6-dihydro-4H-1,2,4-oxadiazine (200 mg, 0.52 mmol), 4-methyl-1H-imidazole (51 mg, 0.62 mmol) and potassium phosphate tribasic (221 mg, 1.04 mmol). The reaction mixture was heated at 120° C. for 18 hours then cooled to ambient temperature, diluted with 4:1 dichloromethane:methanol (50 mL), filtered through Celite (washing with 4:1 dichloromethane:methanol (100 mL)) and the filtrate was the solvent was removed under reduced pressure under reduced pressure. The crude material was purified by flash column chromatography on silica gel eluting with 1:1 heptane:ethyl acetate→99:1 dichloromethane:methanol→96:4 dichloromethane:methanol to afford the title compound (144 mg, 58%). The enantiomers were separated by chiral preparative high performance liquid chromatography (HPLC) (Chiralpak IB 20×250 mm) eluting with 9:1 tert-butylmethyl ether:methanol (0.1% diethylamine) over 20 minutes (18 mL per minute) to afford the compounds of Example 42A (Fraction (I)) and Example 42B (Fraction 2).

Example 42A, 5-(4-chlorophenyl)-3-(6-methoxy-5-(4-methyl-1H-imidazol-1-yl)pyridin-2-yl)-5,6-dihydro-4H-1,2,4-oxadiazine, fraction (I): 30.2 mg; Chiral HPLC: RT 8.61 min, 100% e.e.; LCMS (basic, 11 min): RT 6.26 mM, [MH]+ 384.2, purity 100%.

Example 42B, 5-(4-chlorophenyl)-3-(6-methoxy-5-(4-methyl-1H-imidazol-1-yl)pyridin-2-yl)-5,6-dihydro-4H-1,2,4-oxadiazine, fraction (II): 28.6 mg; $^1$H NMR (CDCl$_3$, 400 MHz) δ 7.91 (br s, 1H), 7.82 (d, 1H), 7.65 (d, 2H), 7.38 (d, 2H), 7.31 (d, 2H), 7.00 (s, 1H), 6.55 (s, 1H), 4.83-4.74 (m, 1H), 4.24 (dd, 1H), 4.00 (s, 3H), 3.75 (dd, 1H), 2.32 (s, 3H). Chiral HPLC: RT 11.56 min, 100% e.e.; LCMS (basic, 11 min): RT 6.26 mM, [MH]+ 384.1, purity 100%.

Example 43

Synthesis of 3-(5-bromo-6-methoxypyridin-2-yl)-5-(4-fluoro-3-(trifluoromethyl)phenyl)-5,6-dihydro-4H-1,2,4-oxadiazine

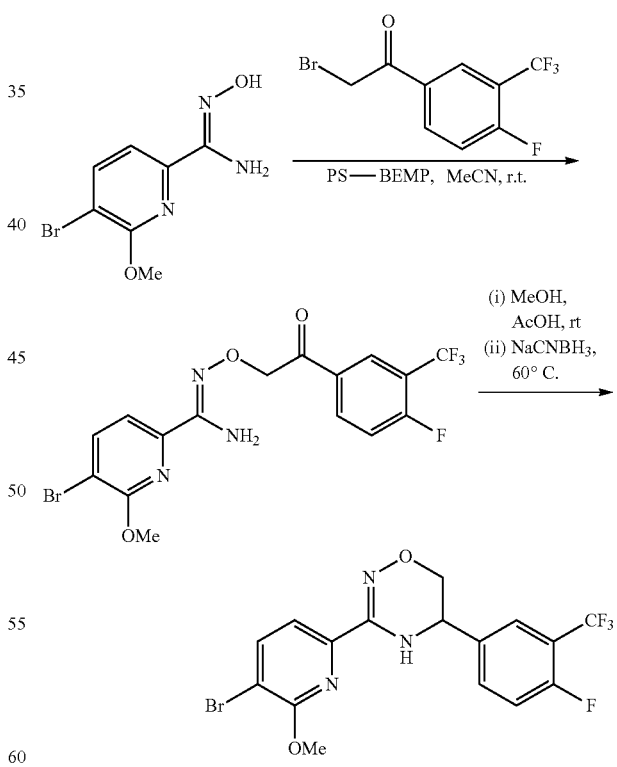

(Z)-5-bromo-N'-(2-(4-fluoro-3-(trifluoromethyl)phenyl)-2-oxoethoxy)-6-methoxypicolinimidamide bromo-N'-hydroxy-6-methoxypicolinimidamide (573 mg, 2.33 mmol) in acetonitrile (15 mL) was added to PS-BEMP (2.2 mmol/g, 1.27 g, 2.8 mmol). The mixture was stirred at room temperature for 5 minutes before the addition of 2-bromo-1-(3-fluoro-4-(trifluoromethyl)phenyl)ethanone (1 g, 3.5 mmol) in acetonitrile (5 mL). The reaction mixture was stirred for 2.5 hours, filtered, and the solvent was removed under reduced pressure to afford crude (Z)-5-bromo-N'-(2-(4-fluoro-3-(trifluoromethyl)phenyl)-2-oxoethoxy)-6-methoxypicolinimidamide which was used directly in the next step. UPLC (basic, 1.25 min): RT 0.94 mM, [MH]+ 450.2, purity 55%.

3-(5-bromo-6-methoxypyridin-2-yl)-5-(4-fluoro-3-(trifluoromethyl)phenyl)-5,6-dihydro-4H-1,2,4-oxadiazine A mixture of (Z)-5-bromo-N'-(2-(4-fluoro-3-(trifluoromethyl)phenyl)-2-oxoethoxy)-6-methoxypicolinimidamide (max. 2.33 mmol), acetic acid (5 mL) and methanol (20 mL) were heated to 60° C. for 18 hours. To the mixture was added sodium cyanoborohydride (220 mg, 3.5 mmol) and the mixture was stirred at 60° C. for 18 hours. The reaction mixture was diluted with water (100 mL) and extracted into ethyl acetate (2×100 mL). The combined organic extracts were washed with brine (100 mL), dried over magnesium sulfate, filtered, and the solvent was removed under reduced pressure. The crude material was purified by flash column chromatography on silica gel (eluting with 3:1 heptane:ethyl acetate) to afford 3-(5-bromo-6-methoxypyridin-2-yl)-5-(4-fluoro-3-(trifluoromethyl)phenyl)-5,6-dihydro-4H-1,2,4-oxadiazine (471 mg, 47%). $^1$H NMR (CDCl$_3$, 400 MHz) δ 7.89 (d, 1H), 7.61-7.50 (m, 3H), 6.59 (s, 1H), 4.86-4.80 (m, 1H), 4.19 (dd, 1H), 3.99 (s, 3H), 3.82 (dd, 1H). LCMS (basic, 3.1 min): RT 2.32 mM, [MH]+ 435.9, purity 53%.

Example 44

Synthesis of 5-(4-fluoro-3-(trifluoromethyl)phenyl)-3-(6-methoxy-5-(4-methyl-1H-imidazol-1-yl)pyridin-2-yl)-5,6-dihydro-4H-1,2,4-oxadiazine 5-(4-fluoro-3-(trifluoromethyl)phenyl)-3-(6-methoxy-5-(4-methyl-1H-imidazol-1-yl)pyridin-2-yl)-5,6-dihydro-4H-1,2,4-oxadiazine A solution of tris(dibenzylideneacetone) dipalladium(0) (12 mg, 13 μmol) and 2-di-tert-butylphosphino-3,4,5,6-tetramethyl-2',4',6'-triisopropyl-1,1'-biphenyl (12 mg, 26 μmol) in toluene (5 mL) and 1,4-dioxane (1 mL) was heated at 120° C. for 3 minutes under an atmosphere of argon. To this mixture was added 3-(5-bromo-6-methoxypyridin-2-yl)-5-(4-fluoro-3-(trifluoromethyl)phenyl)-5,6-dihydro-4H-1,2,4-oxadiazine (552 mg, 1.3 mol), 4-methyl-1H-imidazole (128 mg, 1.56 mmol) and potassium phosphate tribasic (552 mg, 2.6 mmol). The reaction mixture was heated at 120° C. for 18 hours then cooled to ambient temperature, diluted with 4:1 dichloromethane:methanol (50 mL), filtered through Celite (washing with 4:1 dichloromethane:methanol (100 mL)) and the filtrate was the solvent was removed under reduced pressure under reduced pressure. The crude material was purified by flash column chromatography on silica gel eluting with 98:2 dichloromethane:methanol to afford the title compound (222 mg, 39%). The enantiomers were separated by chiral preparative high performance liquid chromatography (HPLC) (Chiralpak IB 20×250 mm) eluting with 95:5 tert-butylmethyl ether:methanol (0.1% diethylamine) over 30 minutes (18 mL per minute) to afford the compounds of Example 44A (Fraction (I)) and Example 44B (Fraction (II)).

Example 44A, 5-(4-fluoro-3-(trifluoromethyl)phenyl)-3-(6-methoxy-5-(4-methyl-1H-imidazol-1-yl)pyridin-2-yl)-5,6-dihydro-4H-1,2,4-oxadiazine, fraction (I): 41.8 mg; Chiral HPLC: RT 11.94 min, 100% e.e.; LCMS (basic, 11 min): RT 6.45 mM, [MH]+ 436.1, purity 100%.

Example 44B, 5-(4-fluoro-3-(trifluoromethyl)phenyl)-3-(6-methoxy-5-(4-methyl-1H-imidazol-1-yl)pyridin-2-yl)-5,6-dihydro-4H-1,2,4-oxadiazine, fraction (II): 41.6 mg; $^1$H NMR (CDCl$_3$, 400 MHz) δ 7.84-7.79 (m, 2H), 7.65 (d, 1H), 7.62-7.54 (m, 3H), 6.99 (s, 1H), 6.63 (s, 1H), 4.89-4.82 (m, 1H), 4.21 (dd, 1H), 4.01 (s, 3H), 3.85 (dd, 1H), 2.29 (s, 3H). Chiral HPLC: RT 15.18 min, 99% e.e.; LCMS (basic, 11 min): RT 6.47 min, [MH]– 434.2, purity 99%.

Example 45

Synthesis of 2-chloro-1-(1-((2-(trimethylsilyl)ethoxy)methyl)-1H-indol-3-yl)ethanone

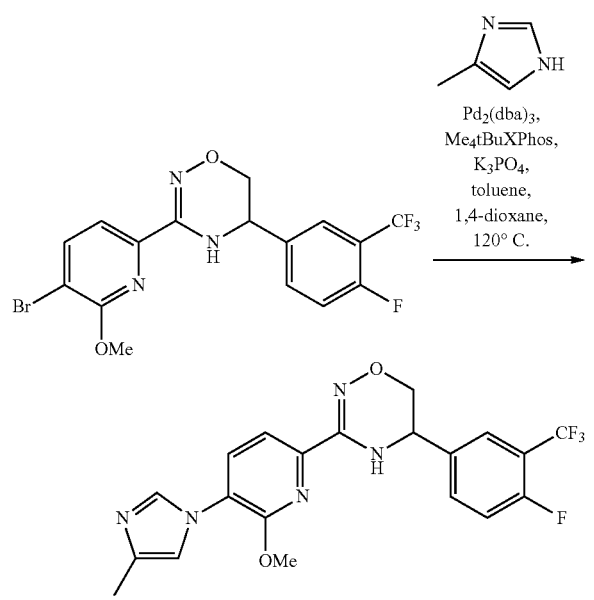

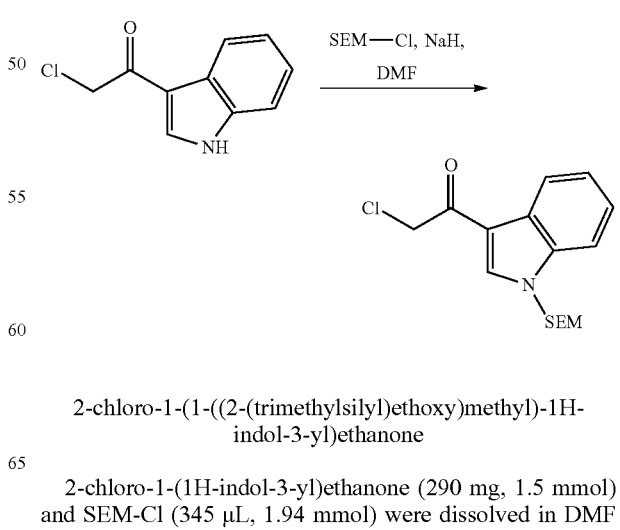

2-chloro-1-(1-((2-(trimethylsilyl)ethoxy)methyl)-1H-indol-3-yl)ethanone 2-chloro-1-(1H-indol-3-yl)ethanone (290 mg, 1.5 mmol) and SEM-Cl (345 μL, 1.94 mmol) were dissolved in DMF (25 mL) and cooled to 0° C. under Ar. Sodium hydride (72 mg, 1.8 mmol, 60% dispersion in mineral oil) was added portion wise and the reaction mixture was warmed to room temperature and stirred for 2 hours. The reaction mixture was partitioned between ammonium chloride (50 mL, saturated aqueous) and ethyl acetate (50 mL). The aqueous layer was extracted with ethyl acetate (50 mL) and the combined organics were washed with brine (50 mL), dried over magnesium sulfate, filtered and the solvent was removed under reduced pressure. The crude reaction mixture was purified by flash column chromatography in silica gel eluting with 4:1 heptane:ethyl acetate to afford 2-chloro-1-(1-((2-(trimethylsilyl)ethoxy)methyl)-1H-indol-3-yl)ethanone (331 mg, 68%). $^1$H NMR (CDCl$_3$, 400 MHz) δ 8.37-8.32 (m, 1H), 7.93 (s, 1H), 7.55-7.49 (m, 1H), 7.39-7.31 (m, 2H), 5.53 (s, 2H), 4.54 (s, 2H), 3.51 (dd, 2H), 0.90 (dd, 2H), −0.06 (s, 9H).

Example 46

Synthesis of 3-(5-bromo-6-methoxypyridin-2-yl)-5-(1-((2-(trimethylsilyl)ethoxy)methyl)-1H-indol-3-yl)-5,6-dihydro-4H-1,2,4-oxadiazine

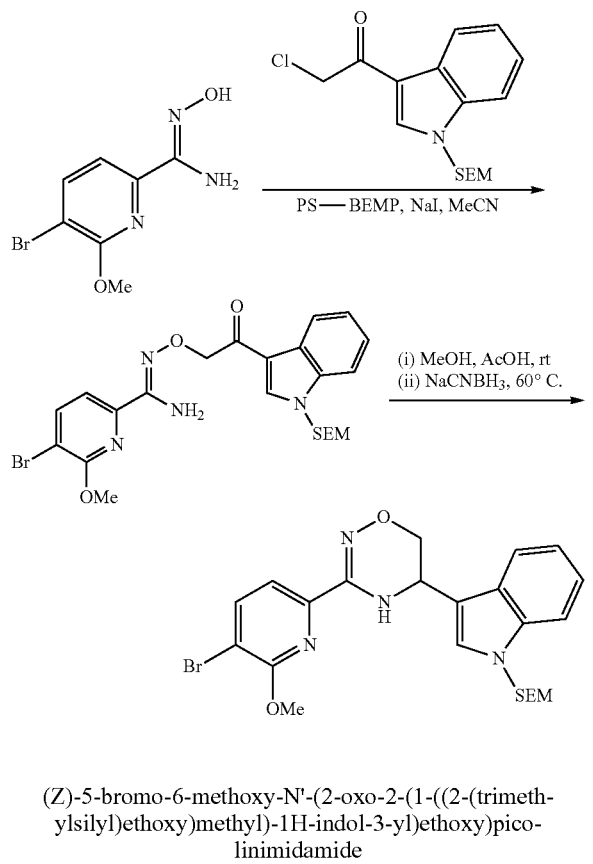

(Z)-5-bromo-6-methoxy-N'-(2-oxo-2-(1-((2-(trimethylsilyl)ethoxy)methyl)-1H-indol-3-yl)ethoxy)picolinimidamide bromo-N'-hydroxy-6-methoxypicolinimidamide (200 mg, 0.81 mmol) in acetonitrile (5 mL) was added to PS-BEMP (2.2 mmol/g, 450 mg, 0.98 mmol). The mixture was stirred at room temperature for 5 minutes. 2-chloro-1-(1-((2-(trimethylsilyl)ethoxy)methyl)-1H-indol-3-yl)ethanone (200 mg, 0.81 mmol) was dissolved in acetonitrile (5 mL) and sodium iodide (175 mg, 1.17 mmol) was added; the mixture was stirred for 5 minutes then added to the reaction mixture. It was stirred overnight, filtered and the solvent was removed under reduced pressure to afford crude (Z)-5-bromo-6-methoxy-N'-(2-oxo-2-(1-((2-(trimethylsilyl)ethoxy)methyl)-1H-indol-3-yl)ethoxy)picolinimidamide, which was used directly in the next step. UPLC (basic, 1.25 min): RT 1.03 mM, [MH]+ 533.3, purity 69%.

3-(5-bromo-6-methoxypyridin-2-yl)-5-(1-((2-(trimethylsilyl)ethoxy)methyl)-1H-indol-3-yl)-5,6-dihydro-4H-1,2,4-oxadiazine A mixture of (Z)-5-bromo-6-methoxy-N'-(2-oxo-2-(1-((2-(trimethylsilyl)ethoxy)methyl)-1H-indol-3-yl)ethoxy)picolinimidamide (max. 0.81 mmol), acetic acid (2 mL) and methanol (8 mL) were heated to 60° C. for 1 hour. To the mixture was added sodium cyanoborohydride (61 mg, 0.97 mmol) and the mixture was stirred at 60° C. for 18 hours. The reaction mixture was diluted with water (20 mL) and extracted into ethyl acetate (2×20 mL). The combined organic extracts were washed with brine (20 mL), dried over magnesium sulfate, filtered, and the solvent was removed under reduced pressure. The crude material was purified by flash column chromatography on silica gel (eluting with 4:1 heptane:ethyl acetate) to afford 3-(5-bromo-6-methoxypyridin-2-yl)-5-(1-((2-(trimethylsilyl)ethoxy)methyl)-1H-indol-3-yl)-5,6-dihydro-4H-1,2,4-oxadiazine (245 mg, 58% over 2 steps). LCMS (basic, 3.1 min): RT 2.66 mM, [MH]+ 516.0, purity 46%.

Example 47

5-(1H-indol-3-yl)-3-(6-methoxy-5-(4-methyl-1H-imidazol-1-yl)pyridin-2-yl)-5,6-dihydro-4H-1,2,4-oxadiazine

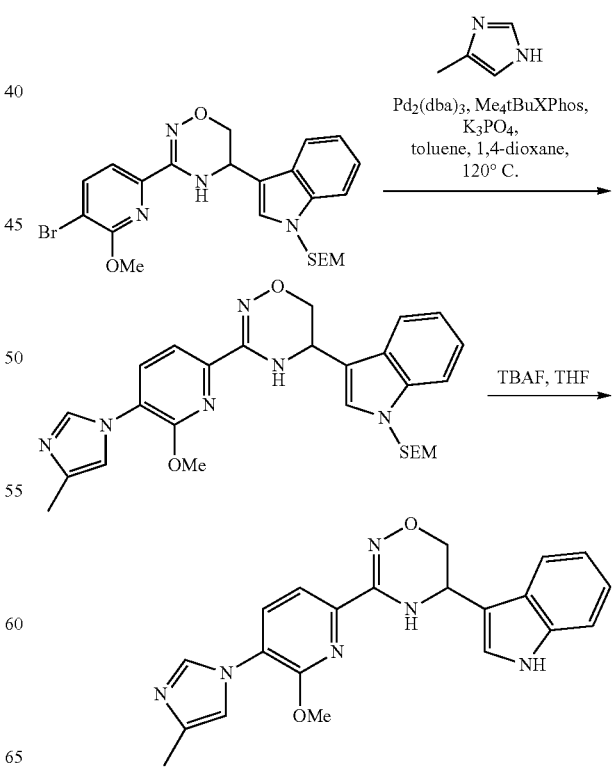

3-(6-methoxy-5-(4-methyl-1H-imidazol-1-yl)pyridin-2-yl)-5-(1-((2-(trimethylsilyl)ethoxy)methyl)-1H-indol-3-yl)-5,6-dihydro-4H-1,2,4-oxadiazine A solution of tris(dibenzylideneacetone)dipalladium(0) (4.2 mg, 10 mol) and 2-di-tert-butylphosphino-3,4,5,6-tetramethyl-2',4',6'-triisopropyl-1,1'-biphenyl (4.4 mg, 20 µmol) in toluene (2.5 mL) and 1,4-dioxane (500 µL) was heated at 120° C. for 3 minutes under an atmosphere of argon. To this mixture was added 3-(5-bromo-6-methoxypyridin-2-yl)-5-(1-((2-(trimethylsilyl)ethoxy)methyl)-1H-indol-3-yl)-5,6-dihydro-4H-1,2,4-oxadiazine (240 mg, 0.46 mmol), 4-methyl-1H-imidazole (46 mg, 0.56 mol) and potassium phosphate tribasic (195 mg, 0.92 mmol). The reaction mixture was heated at 120° C. for 18 hours then cooled to ambient temperature, diluted with 4:1 dichloromethane:methanol (50 mL), filtered through Celite (washing with 4:1 dichloromethane:methanol (100 mL)) and the filtrate was the solvent was removed under reduced pressure under reduced pressure. The crude material was purified by flash column chromatography on silica gel eluting with 97.5:2.5→95; 5 dichloromethane:methanol to afford 3-(6-methoxy-5-(4-methyl-1H-imidazol-1-yl)pyridin-2-yl)-5-(1-((2-(trimethylsilyl)ethoxy)methyl)-1H-indol-3-yl)-5,6-dihydro-4H-1,2,4-oxadiazine (157 mg, 66%). $^1$H NMR (CDCl$_3$, 400 MHz) δ 7.85-7.81 (m, 2H), 7.68-7.62 (m, 2H), 7.52 (d, 1H), 7.29 (t, 1H), 7.25-7.22 (t, 1H), 7.16 (t, 1H), 6.99 (s, 1H), 6.55 (s, 1H), 5.47 (s, 2H), 5.15-5.09 (m, 1H), 4.38 (dd, 1H), 3.97 (dd, 1H), 3.90 (s, 3H), 3.50 (dd, 2H), 2.29 (s, 3H), 0.89 (dd, 2H), −0.07 (s, 9H). UPLC (basic, 1.25 min): RT 0.95 min, [MH]+ 517.5, purity 97%.

5-(1H-indol-3-yl)-3-(6-methoxy-5-(4-methyl-1H-imidazol-1-yl)pyridin-2-yl)-5,6-dihydro-4H-1,2,4-oxadiazine 3-(6-methoxy-5-(4-methyl-1H-imidazol-1-yl)pyridin-2-yl)-5-(1-((2-(trimethylsilyl)ethoxy)methyl)-1H-indol-3-yl)-5,6-dihydro-4H-1,2,4-oxadiazine (150 mg, 0.29 mmol) was dissolved in THF (15 mL). TBAF (350 µL of a 1M solution in THF, 0.35 mmol) was added and the mixture was heated to reflux for 2 hours then left to stir at room temperature overnight. A further 200 µL of TBAF was added and the mixture was heated to reflux overnight. It was partitioned between ethyl acetate (20 mL) and water (20 mL). The aqueous was extracted with ethyl acetate (20 mL) and the combined organics were washed with brine (20 mL), dried over magnesium sulfate, filtered and the solvent was removed under reduced pressure. The crude reaction mixture was purified by flash column chromatography eluting with 97.5:2.5 dichloromethane:methanol to provide the title compound (56 mg, 50%). The enantiomers were separated by chiral preparative high performance liquid chromatography (HPLC) (Chiralpak IB 20×250 mm) eluting with 1:1 heptane:EtOH (0.1% diethylamine) over 30 minutes (18 mL per minute) to afford the compounds of Example 47A (Fraction (I)) and Example 47B (Fraction 2).

Example 47A, 5-(1H-indol-3-yl)-3-(6-methoxy-5-(4-methyl-1H-imidazol-1-yl)pyridin-2-yl)-5,6-dihydro-4H-1,2,4-oxadiazine, fraction (I): 14 mg; Chiral HPLC: RT 14.20 min, 100% e.e.; LCMS (basic, 11 min): RT 5.56 min, [MH]+ 389.1, purity 98%.

Example 47B, 5-(1H-indol-3-yl)-3-(6-methoxy-5-(4-methyl-1H-imidazol-1-yl)pyridin-2-yl)-5,6-dihydro-4H-1,2,4-oxadiazine, fraction (II): 9.8 mg; $^1$H NMR (CDCl$_3$, 400 MHz) δ 8.26 (br s, 1H), 7.85-7.79 (m, 2H), 7.70-7.61 (m, 2H), 7.43 (d, 1H), 7.30-7.22 (m, 2H), 7.14 (t, 1H), 6.98 (s, 1H), 6.56 (s, 1H), 5.14 (dd, 1H), 4.40 (dd, 1H), 3.96 (dd, 1H), 3.90 (s, 3H), 2.29 (s, 3H). Chiral HPLC: RT 17.30 min, 99% e.e.; LCMS (basic, 11 min): RT 5.64 min, [MH]− 387.3, purity 99%.

Example 48

Synthesis of 3-(5-bromo-6-methoxypyridin-2-yl)-5-(3,4-dichlorophenyl)-5,6-dihydro-4H-1,2,4-oxadiazine

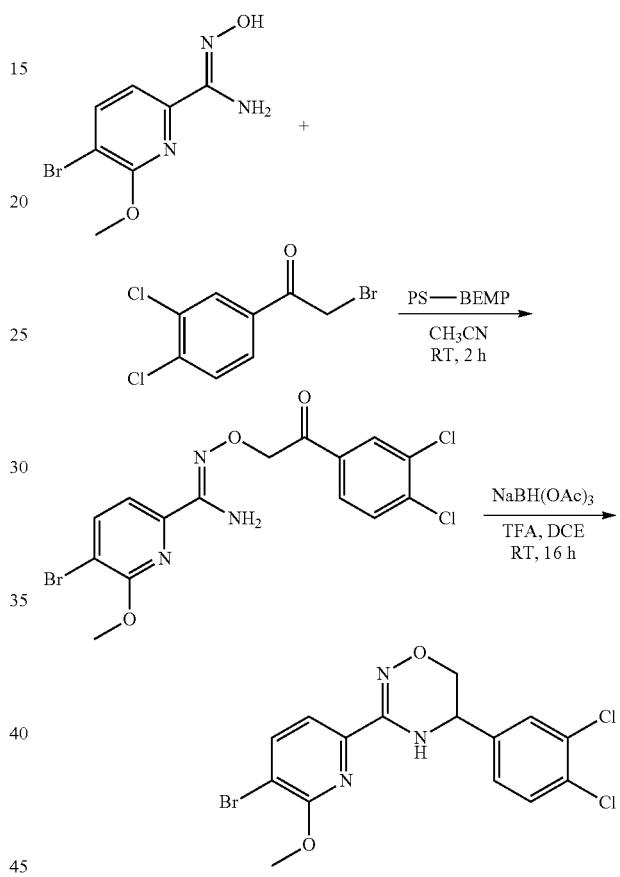

(Z)-5-bromo-N'-(2-(3,4-dichlorophenyl)-2-oxoethoxy)-6-methoxypicolinimidamide

To a stirred solution of 5-bromo-N'-hydroxy-6-methoxypicolinimidamide (500 mg, 2.0 mmol) in CH$_3$CN (12.5 mL) at room temperature under an argon atmosphere was added PS-BEMP (665 mg, 2.4 mmol). The reaction mixture was stirred for 10 min at room temperature. Then 2-bromo-1-(3, 4-dichlorophenyl) ethan-1-one (814 mg, 3.0 mmol) in CH$_3$CN (12.5 mL) was added to the reaction mixture at room temperature. The reaction mixture was stirred for 2 h at room temperature. After consumption of starting material (monitored by TLC), the reaction mixture was filtered and the filtrate was concentrated in vacuo to afford (Z)-5-bromo-N'-(2-(3,4-dichlorophenyl)-2-oxoethoxy)-6-methoxypicolinimidamide (600 mg, crude) as a brown syrup used in the next step without further purification.

LCMS: 22.0%; 433.7 (M+); (column; Ascentis Express C-18 (50×3.0 mm, 3.5 µm); RT 2.95 min; mobile phase:

0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.5).

3-(5-bromo-6-methoxypyridin-2-yl)-5-(3,4-dichlorophenyl)-5,6-dihydro-4H-1,2,4-oxadiazine To a stirred solution of (Z)-5-bromo-N'-(2-(3,4-dichlorophenyl)-2-oxoethoxy)-6-methoxypicolinimidamide (750 mg, crude) in dichloroethane (15 mL) at room temperature under an argon atmosphere was added trifluoroacetic acid (6.6 mL, 9 mmol) and sodium triacetoxyborohydride (1.1 g, 5 mmol). The reaction mixture was stirred for 16 h at room temperature. After consumption of starting material (monitored by TLC), the reaction mixture was diluted with water (20 mL), 1N sodium hydroxide solution (20 mL) and extracted with EtOAc (2×20 mL). The combined organic extracts were dried over sodium sulfate, filtered and concentrated in vacuo to afford 3-(5-bromo-6-methoxypyridin-2-yl)-5-(3,4-dichlorophenyl)-5,6-dihydro-4H-1,2,4-oxadiazine (700 mg, crude) as a brown syrup used in the next step without further purification.

LCMS: 49.3%; 417.8 (M+1); (column; Ascentis Express C-18 (50×3.0 mm, 3.5 µm); RT 2.94 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.5).

Example 49

Synthesis of 5-(3, 4-dichlorophenyl)-3-(6-methoxy-5-(4-methyl-1H-imidazol-1-yl) pyridin-2-yl)-5,6-dihydro-4H-1,2,4-oxadiazine

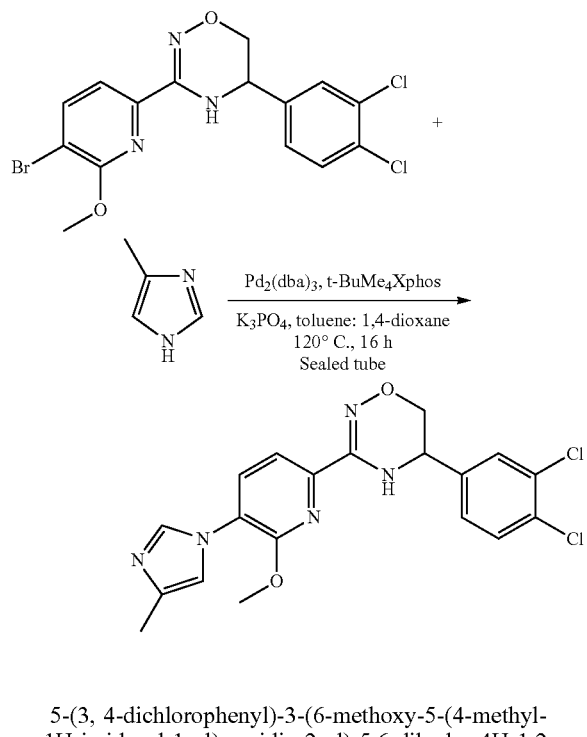

5-(3, 4-dichlorophenyl)-3-(6-methoxy-5-(4-methyl-1H-imidazol-1-yl) pyridin-2-yl)-5,6-dihydro-4H-1,2,4-oxadiazine To a dry vial was added a suspension of $Pd_2(dba)_3$ (44 mg, 0.05 mmol) and tert-butyl tetramethyl Xphos (46 mg, 0.09 mmol) in toluene:1,4-dioxane (2:1, 6 mL) at room temperature. The suspension was degassed with argon, heated to 120° C., and stirred at 120° C. for 3 min. A mixture of 3-(5-bromo-6-methoxypyridin-2-yl)-5-(3,4-dichlorophenyl)-5,6-dihydro-4H-1,2,4-oxadiazine (400 mg, 1.10 mmol), 4-methyl-1H-imidazole (118 mg, 1.44 mmol) and potassium phosphate (407 mg, 1.10 mmol) in toluene: 1,4-dioxane (2:1, 6 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with $CH_2Cl_2$ (2×10 mL). The combined organic extracts were dried over sodium sulfate, filtered and concentrated in vacuo. The crude material was purified by column chromatography using 2-5% MeOH: $CH_2Cl_2$ to afford 5-(3, 4-dichlorophenyl)-3-(6-methoxy-5-(4-methyl-1H-imidazol-1-yl) pyridin-2-yl)-5,6-dihydro-4H-1,2,4-oxadiazine (44 mg, 11%) as an off-white solid.

Racemic compound of Example 49 was separated using a Chiralpak-IB column (250×20 mm, 5 µm) (16 mg loading; 0.1% DEA in n-Hexane: $CH_2Cl_2$:MeOH (50:50) (A:B: 80:20) as mobile phase) to afford the compounds of Example 49A (Fraction (I) (−)) and Example 49B (Fraction (II) (+)).

Analytical conditions for Example 49A and Example 49B. HPLC: (column; Eclipse XDB C-18, 150×4.6 mm, 5.0 µm); mobile phase: ACN: 0.05% TFA; flow rate: 1.0 mL/min; Gradient program: T/B % 0.01/90, 2/90, 10/10, 15/10: diluent: $CH_3CN$:Water; Chiral HPLC: (Chiralpak-IB (250×4.6 mm, 5 µm; mobile phase (A) 0.1% DEA in n-Hexane (B) $CH_2Cl_2$:MeOH (50:50) (A:B; 80:20); flow Rate: 1.0 mL/min).

Example 49A, (−)-5-(3, 4-dichlorophenyl)-3-(6-methoxy-5-(4-methyl-1H-imidazol-1-yl) pyridin-2-yl)-5,6-dihydro-4H-1,2,4-oxadiazine, fraction (I) (−): Mass (ESI): 417.9 [M+1]; HPLC (purity): 98.0%, RT 7.58 min; Chiral HPLC: 95.0%, RT=14.96 min; Optical rotation $[\alpha]_D^{20.01}$: −171.44 (c=0.25, $CH_2Cl_2$).

Example 49B, (+)-5-(3, 4-dichlorophenyl)-3-(6-methoxy-5-(4-methyl-1H-imidazol-1-yl) pyridin-2-yl)-5,6-dihydro-4H-1,2,4-oxadiazine, fraction (II) (+): $^1$H NMR ($CD_3OD$, 400 MHz): δ 7.99 (s, 1H), 7.89 (d, 1H), 7.65 (d, 1H), 7.54 (d, 2H), 7.33 (dd, 1H), 7.23 (s, 1H), 4.92-4.85 (m, 1H), 4.10 (s, 3H), 4.06 (dd, 1H), 4.00 (dd, 1H), 2.26 (s, 3H); Mass (ESI): 417.9 [M+1]; HPLC (purity): 99.5%; RT 7.58 min; Chiral HPLC: 98.5%, RT=20.68 min; Optical rotation $[\alpha]_D^{19.99}$: +183.24 (c=0.25, $CH_2Cl_2$).

Example 50

Synthesis of 2-bromo-1-(6-fluorobenzofuran-2-yl) ethan-1-one

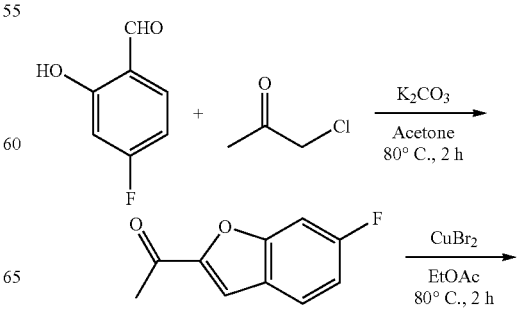

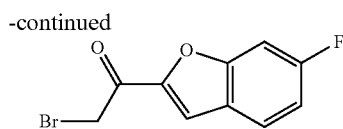

1-(6-fluorobenzofuran-2-yl) ethan-1-one

To a stirred solution of 4-fluoro-2-hydroxybenzaldehyde (3 g, 21 mmol) in acetone (60 mL) at room temperature under an argon atmosphere were added potassium carbonate (4 g, 16 mmol) and 1-chloropropan-2-one (2.21 mL, 26 mmol). The reaction mixture was stirred for 2 h at 80° C. After consumption of starting material (monitored by TLC), the reaction mixture was filtered. The filtrate was concentrated in vacuo. The residue was diluted with water (20 mL) and extracted with EtOAc (2×20 mL). The combined organic extracts were dried over sodium sulfate, filtered and concentrated in vacuo to afford 1-(6-fluorobenzofuran-2-yl) ethan-1-one (2.9 g, 76%) as an off-white solid used in the next step without further purification.

$^1$H NMR (CDCl$_3$, 500 MHz): δ 7.67 (dd, 1H), 7.50 (s, 1H), 7.32-7.27 (m, 1H), 7.11 (dt, 1H), 2.61 (s, 3H); LCMS: 96.7%; 179.7 (M+1); (column; X-select CSH C-18 (50×3.0 mm, 3.5 μm); RT 3.65 min; mobile phase: 5 mM Aq NH$_4$OAc: ACN; T/B %: 0.01/10, 0.5/10, 4/90, 9/90; flow rate: 0.8 mL/min) (Gradient); TLC: 5% EtOAc/Hexane (R$_f$: 0.3).

2-bromo-1-(6-fluorobenzofuran-2-yl) ethan-1-one

To a stirred solution of 1-(6-fluorobenzofuran-2-yl) ethan-1-one (2.8 g, 16 mmol) in EtOAc (140 mL) at room temperature under an argon atmosphere was added copper bromide (7.7 g, 35 mmol). The reaction mixture was stirred for 2 h at 80° C. After consumption of starting material (monitored by TLC), the reaction mixture was filtered. The filtrate was concentrated in vacuo. The crude material was purified by column chromatography using 2-3% EtOAc: Hexane to afford 2-bromo-1-(6-fluorobenzofuran-2-yl) ethan-1-one (2.7 g, 62%) as a pale yellow solid, used in the next step without further purification.

$^1$H NMR (CDCl$_3$, 400 MHz): δ 7.69 (dd, 1H), 7.64 (s, 1H), 7.30 (dd, 1H), 7.13 (dt, 1H), 4.41 (s, 2H); LCMS: 93.8%; 257.5 (M+1); (column; X-select CSH C-18 (50×3.0 mm, 3.5 μm); RT 4.06 min; mobile phase: 5 mM Aq NH$_4$OAc: ACN; T/B %: 0.01/10, 0.5/10, 4/90, 9/90; flow rate: 0.8 mL/min) (Gradient); TLC: 5% EtOAc/Hexane (R$_f$: 0.3).

Example 51

Synthesis of 3-(5-bromo-6-methoxypyridin-2-yl)-5-(6-fluorobenzofuran-2-yl)-5,6-dihydro-4H-1,2,4-oxadiazine

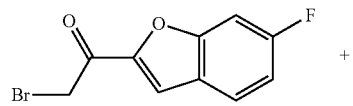

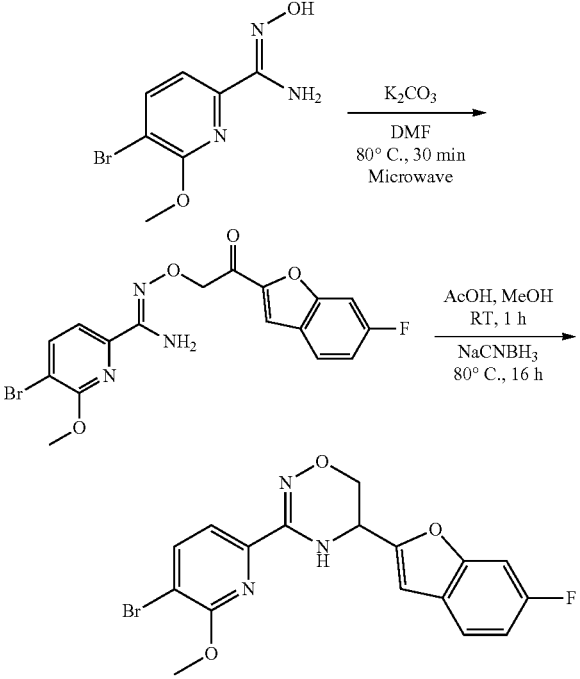

(Z)-5-bromo-N'-(2-(6-fluorobenzofuran-2-yl)-2-oxoethoxy)-6-methoxypicolinimidamide To a stirred solution of 2-bromo-1-(6-fluorobenzofuran-2-yl) ethan-1-one (600 mg, 2 mmol) in DMF (6 mL) at room temperature under an argon atmosphere were added potassium carbonate (670 mg, 5 mmol) and 2-bromo-1-(6-fluorobenzofuran-2-yl) ethan-1-one (936 mg, 4 mmol). The reaction mixture was stirred for 30 min at 80° C. in microwave. After consumption of starting material (monitored by TLC), the reaction mixture was diluted with water (20 mL) and extracted with EtOAc (2×20 mL). The combined organic extracts were dried over sodium sulfate, filtered and concentrated in vacuo to afford (Z)-5-bromo-N'-(2-(6-fluorobenzofuran-2-yl)-2-oxoethoxy)-6-methoxypicolinimidamide (1.1 g, crude) as a brown syrup used in the next step without further purification.

LCMS: 38.2%; 421.6 (M+1); (column; Ascentis Express C-18 (50×3.0 mm, 3.5 μm); RT 2.84 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.5).

3-(5-bromo-6-methoxypyridin-2-yl)-5-(6-fluorobenzofuran-2-yl)-5,6-dihydro-4H-1,2,4-oxadiazine To a stirred solution of (Z)-5-bromo-N'-(2-(6-fluorobenzofuran-2-yl)-2-oxoethoxy)-6-methoxypicolinimidamide (730 mg, crude) in MeOH (12 mL) at room temperature under an argon atmosphere was added acetic acid (3 mL). The reaction mixture was stirred for 1 h at room temperature. Then sodium cyanoborohydride (184 mg, 3 mmol) was added to the reaction mixture at room temperature. The reaction mixture was stirred at 80° C. for 16 h. After consumption of starting material (monitored by TLC), the reaction mixture was diluted with saturated sodium bicarbonate solution (20 mL) and extracted with EtOAc (2×20 mL). The combined organic extracts were dried over sodium sulfate, filtered and concentrated in vacuo to afford 3-(5-bromo-6-methoxypyridin-2-yl)-5-(6-fluorobenzofuran-2-yl)-5,6-dihydro-4H-1,2,4-oxadiazine (150 mg) as a brown syrup used in the next step without further purification. LCMS: 99.8%; 407.8 (M+2); (column; Ascentis Express C-18 (50×3.0 mm, 3.5 μm); RT 2.77 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane ($R_f$: 0.4).

Example 52

Synthesis of 5-(6-fluorobenzofuran-2-yl)-3-(6-methoxy-5-(4-methyl-1H-imidazol-1-yl) pyridin-2-yl)-5,6-dihydro-4H-1,2,4-oxadiazine

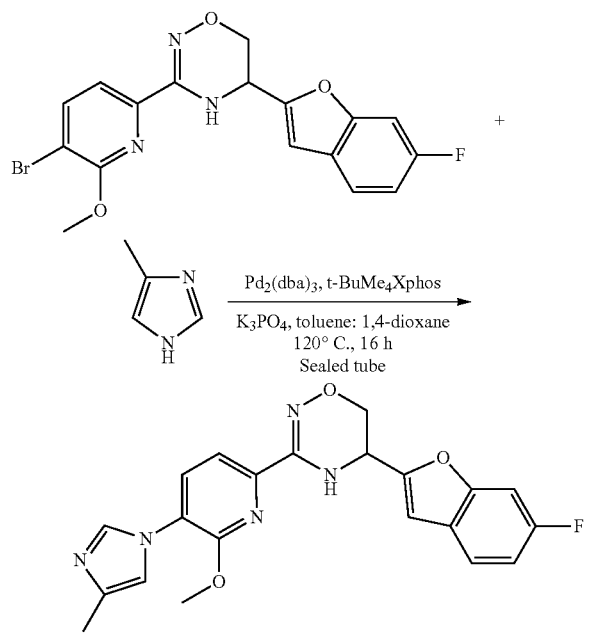

5-(6-fluorobenzofuran-2-yl)-3-(6-methoxy-5-(4-methyl-1H-imidazol-1-yl) pyridin-2-yl)-5,6-dihydro-4H-1,2,4-oxadiazine To a dry vial was added a suspension of Pd$_2$(dba)$_3$ (22 mg, 0.02 mmol) and tert-butyl tetra methyl Xphos (24 mg, 0.05 mmol) in toluene:1,4-dioxane (2:1, 3.75 mL) at room temperature. The suspension was degassed with argon, heated to 120° C., and stirred at 120° C. for 3 min. A mixture of 3-(5-bromo-6-methoxypyridin-2-yl)-5-(6-fluorobenzofuran-2-yl)-5,6-dihydro-4H-1, 2, 4-oxadiazine (200 mg, 0.50 mmol), 4-methyl-1H-imidazole (81 mg, 1.0 mmol) and potassium phosphate (207 mg, 1.0 mmol) in toluene:1,4-dioxane (2:1, 3.75 mL) was degassed and the catalyst premixture was added. The resultant mixture was stirred at 120° C. for 16 h in a sealed tube. After consumption of the starting material (monitored by TLC and LCMS), the reaction mixture was filtered. The filtrate was concentrated in vacuo. The crude material was purified by column chromatography using 2% MeOH: CH$_2$Cl$_2$ to afford 5-(6-fluorobenzofuran-2-yl)-3-(6-methoxy-5-(4-methyl-1H-imidazol-1-yl) pyridin-2-yl)-5,6-dihydro-4H-1,2,4-oxadiazine (125 mg, 57%) as an off-white solid.

Racemic compound of Example 52 was separated using a Chiralpak-IB column (250×20 mm, 5 μm) (30 mg loading; 0.1% DEA in n-Hexane: CH$_2$Cl$_2$:MeOH (80:20) (A:B: 90:10) as mobile phase) to afford the compounds of Example 52A (Fraction (I) (−)) and the compound of Example 52B (Fraction (II) (+)).

Analytical conditions for Example 52A and Example 52B: HPLC: (column; Eclipse XDB C-18, 150×4.6 mm, 5 μm), mobile phase: ACN: 5 mM Aq NH$_4$OAc, flow rate: 1.0 mL/min, Gradient program: T/B % 0.01/80, 3/80, 10/10, 20/10; diluent: CH$_3$CN:Water; Chiral HPLC: (Chiralpak-IB (250×4.6 mm, 5 μm; mobile phase (A) 0.1% DEA in n-Hexane (B) CH$_2$Cl$_2$:MeOH (80:20) (A:B; 70:30); flow Rate: 1.0 mL/min).

Example 52A, (−)-5-(6-fluorobenzofuran-2-yl)-3-(6-methoxy-5-(4-methyl-1H-imidazol-1-yl) pyridin-2-yl)-5,6-dihydro-4H-1,2,4-oxadiazine fraction (I) (−): Mass (ESI): 408.3 [M+1]; HPLC (purity): 98.0%, RT 9.85 min; Chiral HPLC: 99.7%, RT=6.56 min; Optical rotation $[\alpha]_D^{20.00}$: −221.71 (c=0.25, CH$_2$Cl$_2$).

Example 52B, (+)-5-(6-fluorobenzofuran-2-yl)-3-(6-methoxy-5-(4-methyl-1H-imidazol-1-yl) pyridin-2-yl)-5,6-dihydro-4H-1,2,4-oxadiazine fraction (II) (+): $^1$H NMR (CD$_3$OD, 400 MHz): δ 7.98 (s, 1H), 7.88 (d, 1H), 7.64 (d, 1H), 7.53 (dd, 1H), 7.27 (d, 1H), 7.22 (s, 1H), 7.04-7.00 (m, 1H), 6.75 (s, 1H), 5.07 (t, 1H), 4.39 (dd, 1H), 4.13 (s, 3H), 4.07 (dd, 1H), 2.25 (s, 3H); Mass (ESI): 408.3 [M+1]; HPLC (purity): 99.8%, RT 9.85 min; Chiral HPLC: 99.6%, RT=7.60 min; Optical rotation $[\alpha]_D^{20.01}$: +220.76 (c=0.25, CH$_2$Cl$_2$).

Example 53

Synthesis of 3-(5-bromo-6-methoxypyridin-2-yl)-5-(4-methoxyphenyl)-5,6-dihydro-4H-1,2,4-oxadiazine

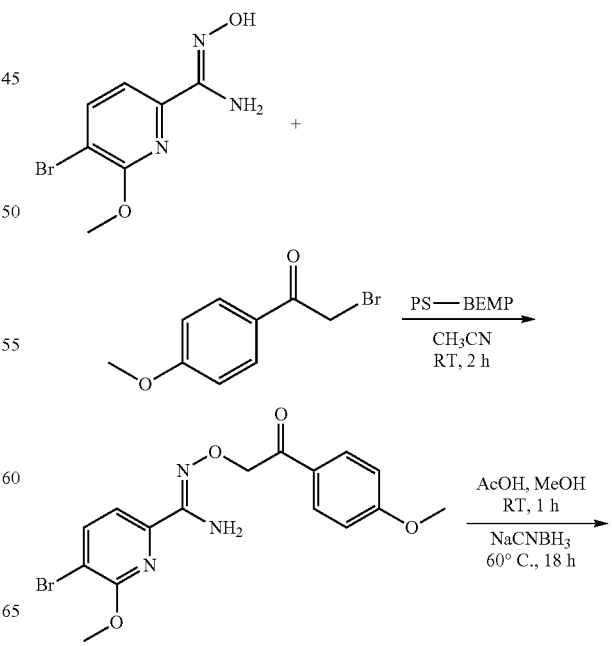

-continued

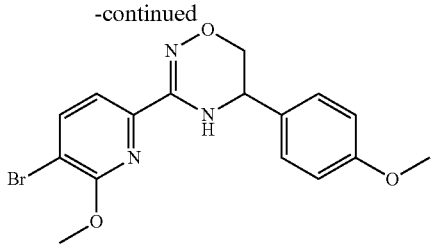

(Z)-5-bromo-6-methoxy-N'-(2-(4-methoxyphenyl)-2-oxoethoxy) picolinimidamide

To a stirred solution of 5-bromo-N'-hydroxy-6-methoxypicolinimidamide (500 mg, 2 mmol) in CH$_3$CN (12 mL) at room temperature under an argon atmosphere was added PS-BEMP (665 mg, 2 mmol). The reaction mixture was stirred for 10 min at room temperature. Then 2-bromo-1-(4-methoxyphenyl) ethan-1-one (698 mg, 3 mmol) in CH$_3$CN (12.5 mL) was added to the reaction mixture at room temperature. The reaction mixture was stirred for 2 h at room temperature. After consumption of starting material (monitored by TLC), the reaction mixture was filtered. The filtrate was concentrated in vacuo to afford (Z)-5-bromo-6-methoxy-N'-(2-(4-methoxyphenyl)-2-oxoethoxy) picolinimidamide (600 mg, crude) as a brown syrup used in the next step without further purification.

LCMS: 51.6%; 395.9 (M+); (column; Ascentis Express C-18 (50×3.0 mm, 3.5 µm); RT 2.74 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane (R$_f$: 0.5).

3-(5-bromo-6-methoxypyridin-2-yl)-5-(4-methoxyphenyl)-5,6-dihydro-4H-1,2,4-oxadiazine To a stirred solution of (Z)-5-bromo-6-methoxy-N'-(2-(4-methoxyphenyl)-2-oxoethoxy) picolinimidamide (600 mg, crude) in MeOH (10 mL) at room temperature under an argon atmosphere was added acetic acid (2.5 mL). The reaction mixture was stirred for 1 h at room temperature. Then sodium cyanoborohydride (144 mg, 2 mmol) was added to the reaction mixture at room temperature. The reaction mixture was stirred at 60° C. for 18 h. After consumption of starting material (monitored by TLC), the reaction mixture was diluted with saturated sodium bicarbonate solution (20 mL) and extracted with EtOAc (2×20 mL). The combined organic extracts were dried over sodium sulfate, filtered and concentrated in vacuo to afford 3-(5-bromo-6-methoxypyridin-2-yl)-5-(4-methoxyphenyl)-5,6-dihydro-4H-1,2,4-oxadiazine (400 mg, crude) as a brown syrup used in the next step without further purification.

LCMS: 56.1%; 377.8 (M+1); (column; Ascentis Express C-18 (50×3.0 mm, 3.5 µm); RT 2.60 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane (R$_f$: 0.4).

Example 54

Synthesis of 5-(3, 4-dichlorophenyl)-3-(6-methoxy-5-(4-methyl-1H-imidazol-1-yl) pyridin-2-yl)-5,6-dihydro-4H-1,2,4-oxadiazine

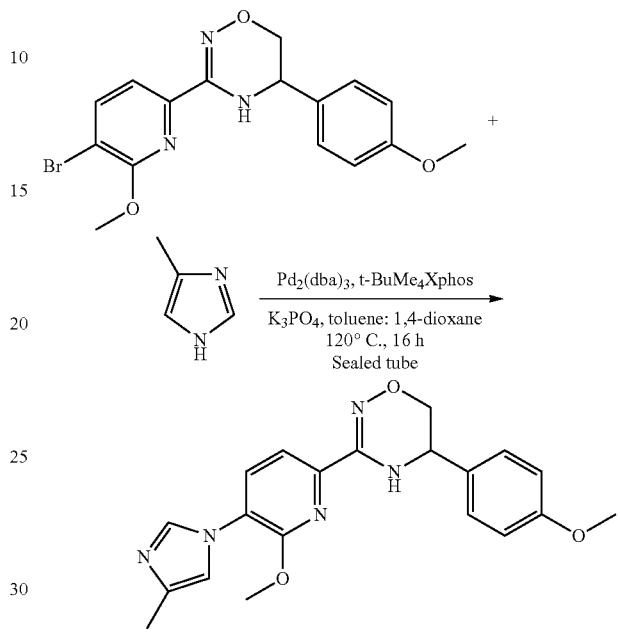

To a dry vial was added a suspension of Pd$_2$(dba)$_3$ (48 mg, 0.05 mmol) and tert-butyl tetramethyl Xphos (51 mg, 0.10 mmol) in toluene:1,4-dioxane (2:1, 6 mL) at room temperature. The suspension was degassed with argon, heated to 120° C., and stirred at 120° C. for 3 min. A mixture of 3-(5-bromo-6-methoxypyridin-2-yl)-5-(4-methoxyphenyl)-5,6-dihydro-4H-1,2,4-oxadiazine (400 mg, 2.0 mmol), 4-methyl-1H-imidazole (130 mg, 2.0 mmol) and potassium phosphate (450 mg, 2.1 mmol) in toluene:1,4-dioxane (2:1, 6 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with CH$_2$Cl$_2$ (2×10 mL). The combined organic extracts were dried over sodium sulfate, filtered and concentrated in vacuo. The crude material was purified by column chromatography using 2-5% MeOH: CH$_2$Cl$_2$ to afford 3-(6-methoxy-5-(4-methyl-1H-imidazol-1-yl) pyridin-2-yl)-5-(4-methoxyphenyl)-5,6-dihydro-4H-1,2,4-oxadiazine (200 mg, 50%) as an off-white solid.

Racemic compound of Example 54 was separated using a Chiralpak-IB column (250×20 mm, 5 µm) (30 mg loading; 0.1% DEA in n-Hexane: CH$_2$Cl$_2$:MeOH (50:50) (A:B: 80:20) as mobile phase) to afford the compounds of Example 54A (Fraction (I) (−)) and the compound of Example 54B (Fraction (II) (+)).

Analytical conditions for Example 54A and Example 54B: HPLC (column; Eclipse XDB C-18, 150×4.6 mm, 5.0 µm), mobile phase: ACN: 0.05% TFA; Gradient program: T/B % 0.01/90, 2/90, 8/10, 15/10; diluent: CH$_3$CN:Water; flow rate: 1.0 mL/min; Chiral HPLC: (Chiralpak-IB (250× 4.6 mm, 5 µm; mobile phase (A) 0.1% DEA in n-Hexane (B) CH$_2$Cl$_2$:MeOH (50:50) (A:B; 80:20); flow Rate: 1.0 mL/min).

Example 54A, (−)-3-(6-methoxy-5-(4-methyl-1H-imidazol-1-yl) pyridin-2-yl)-5-(4-methoxyphenyl)-5,6-dihydro-4H-1,2,4-oxadiazine fraction (I) (−): Mass (ESI): 380.3 [M+1]; HPLC (purity): 98.3%, RT 7.06 min; Chiral HPLC: 99.6%, RT=12.44 min; Optical rotation $[\alpha]_D^{20.00}$: −122.24 (c=0.25, CH$_2$Cl$_2$).

Example 54B, (+)-3-(6-methoxy-5-(4-methyl-1H-imidazol-1-yl) pyridin-2-yl)-5-(4-methoxyphenyl)-5,6-dihydro-4H-1,2,4-oxadiazine fraction (II) (+): $^1$H NMR (CD$_3$OD, 400 MHz): δ 7.99 (br s, 1H), 7.88 (d, 1H), 7.64 (d, 1H), 7.32 (d, 2H), 7.23 (br s, 1H), 6.95 (d, 2H), 4.78 (t, 1H), 4.14 (dd, 1H), 4.07 (s, 3H), 3.82-3.78 (m, 4H), 2.25 (s, 3H); Mass (ESI): 380.3 [M+1]; HPLC (purity): 96.9%, RT 7.06 min; Chiral HPLC: 97.9%, RT=17.18 min; Optical rotation $[\alpha]_D^{20.00}$: +125.47 (c=0.25, CH$_2$Cl$_2$).

Example 55

Synthesis of Synthesis of 2-bromo-1-(5-chlorobenzofuran-2-yl) ethan-1-one

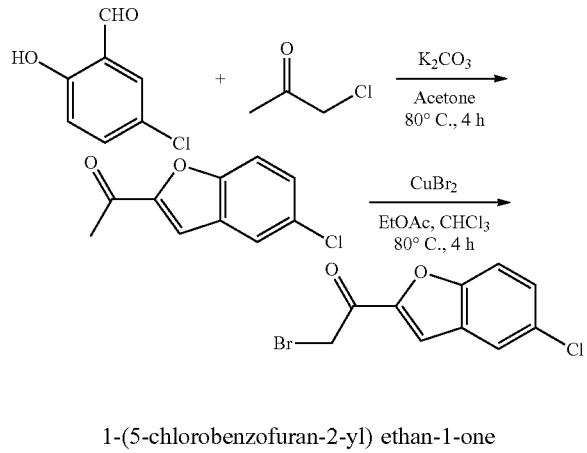

1-(5-chlorobenzofuran-2-yl) ethan-1-one

To a stirred solution of 5-chloro-2-hydroxybenzaldehyde (6 g, 38 mmol) in acetone (80 mL) at room temperature under an argon atmosphere were added potassium carbonate (7.96 g, 58 mmol) and 1-chloropropan-2-one (4.2 g, 46 mmol). The reaction mixture was stirred for 4 h at 80° C. After consumption of starting material (monitored by TLC), the reaction mixture was filtered and the filtrate was concentrated in vacuo. The crude material was purified by column chromatography using 2-3% EtOAc: Hexane to afford 1-(5-chlorobenzofuran-2-yl) ethan-1-one (4.2 g, 56%) as an off-white solid used in the next step without further purification.

$^1$H NMR (DMSO-d$_6$, 400 MHz): δ 8.41 (s, 1H), 8.33 (s, 1H), 8.26 (d, 1H), 8.05 (dd, 1H), 2.99 (s, 3H); LCMS: 98.9%; 195.3 (M+1); (column; X-select CSH C-18 (50×3.0 mm, 3.5 μm); RT 4.01 min; mobile phase: 5 mM Aq NH$_4$OAc: ACN; T/B %: 0.01/10, 0.5/10, 4/90, 9/90; flow rate: 0.8 mL/min) (Gradient); TLC: 5% EtOAc/Hexane (R$_f$: 0.3).

2-bromo-1-(5-chlorobenzofuran-2-yl) ethan-1-one

To a stirred solution of 1-(5-chlorobenzofuran-2-yl) ethan-1-one (4.2 g, 22 mmol) in EtOAc:CHCl$_3$ (3:1, 84 mL) at room temperature under an argon atmosphere was added copper bromide (10.63 g, 48 mmol). The reaction mixture was stirred for 4 h at 80° C. After consumption of starting material (monitored by TLC), the reaction mixture was filtered and the filtrate was concentrated in vacuo. The crude material was purified by column chromatography using 2-3% EtOAc: Hexane to afford 2-bromo-1-(5-chlorobenzofuran-2-yl) ethan-1-one (3 g, 50%) as a pale yellow solid used in the next step without further purification.

$^1$H NMR (DMSO-d$_6$, 400 MHz): δ 8.00 (s, 1H), 7.97 (s, 1H), 7.79 (d, 1H), 7.58 (dd, 1H), 4.81 (s, 2H); LCMS: 96.2%; 273 (M+2); (column; X-select CSH C-18 (50×3.0 mm, 3.5 μm); RT 4.34 min; mobile phase: 5 mM Aq NH$_4$OAc: ACN; T/B %: 0.01/10, 0.5/10, 4/90, 9/90; flow rate: 0.8 mL/min) (Gradient); TLC: 5% EtOAc/Hexane (R$_f$: 0.3).

Example 56

Synthesis of 3-(5-bromo-6-methoxypyridin-2-yl)-5-(5-chlorobenzofuran-2-yl)-5,6-dihydro-4H-1,2,4-oxadiazine

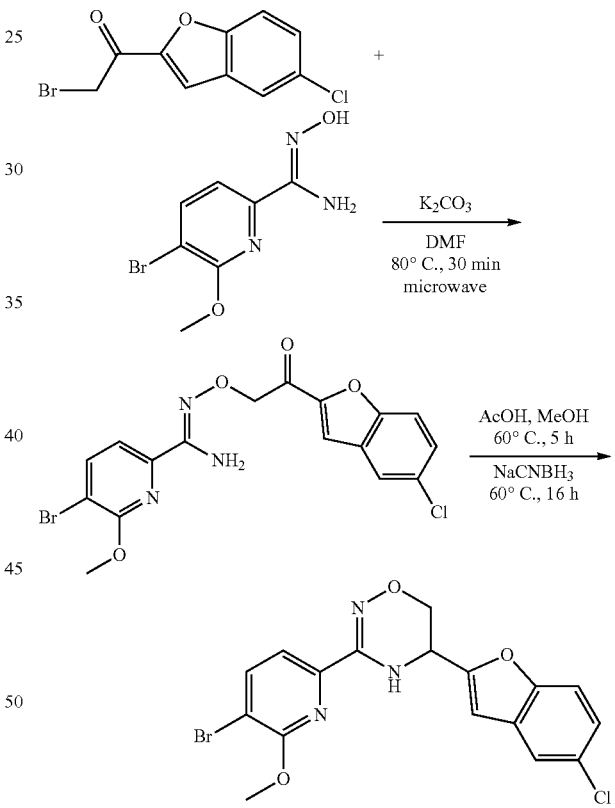

(Z)-5-bromo-N'-(2-(5-chlorobenzofuran-2-yl)-2-oxoethoxy)-6-methoxypicolinimidamide To a stirred solution of 5-bromo-N'-hydroxy-6-methoxypicolinimidamide (800 mg, 3 mmol) in DMF (16 mL) at room temperature under an argon atmosphere were added potassium carbonate (896 mg, 7 mmol) and 2-bromo-1-(5-chlorobenzofuran-2-yl) ethan-1-one (1.33 g, 5 mmol). The reaction mixture was stirred for 30 min at 80° C. in microwave. After consumption of starting material (monitored by TLC), the reaction mixture was diluted with water (20 mL) and extracted with EtOAc (2×20 mL). The combined organic extracts were dried over sodium sulfate, filtered and concentrated in vacuo to afford (Z)-5-bromo-N'-(2-(5-chlorobenzofuran-2-yl)-2-oxoethoxy)-6-methoxypicolinimidamide (900 mg, crude) as an off-white solid used in the next step without further purification.

LCMS: 16.5%; 439.7 (M+2); (column; Ascentis Express C-18 (50×3.0 mm, 3.5 μm); RT 2.75 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane ($R_f$: 0.6).

3-(5-bromo-6-methoxypyridin-2-yl)-5-(5-chlorobenzofuran-2-yl)-5,6-dihydro-4H-1,2,4-oxadiazine To a stirred solution of (Z)-5-bromo-N'-(2-(5-chlorobenzofuran-2-yl)-2-oxoethoxy)-6-methoxypicolinimidamide (900 mg, crude) in MeOH (16 mL) at room temperature under an argon atmosphere was added acetic acid (4 mL). The reaction mixture was stirred for 5 h at 60° C. Then sodium cyanoborohydride (155 mg, 2 mmol) was added to the reaction mixture at room temperature. The reaction mixture was stirred at 60° C. for 16 h. After consumption of starting material (monitored by TLC), the reaction mixture was diluted with water (20 mL) and extracted with EtOAc (2×20 mL). The combined organic extracts were dried over sodium sulfate, filtered and concentrated in vacuo to afford 3-(5-bromo-6-methoxypyridin-2-yl)-5-(5-chlorobenzofuran-2-yl)-5,6-dihydro-4H-1,2,4-oxadiazine (250 mg, 29%) as an off-white solid.

LCMS: 98.6%; 423.7 (M+2); (column; Ascentis Express C-18 (50×3.0 mm, 3.5 μm); RT 2.91 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.4).

Example 57

Synthesis of 5-(5-chlorobenzofuran-2-yl)-3-(6-methoxy-5-(4-methyl-1H-imidazol-1-yl) pyridin-2-yl)-5,6-dihydro-4H-1,2,4-oxadiazine

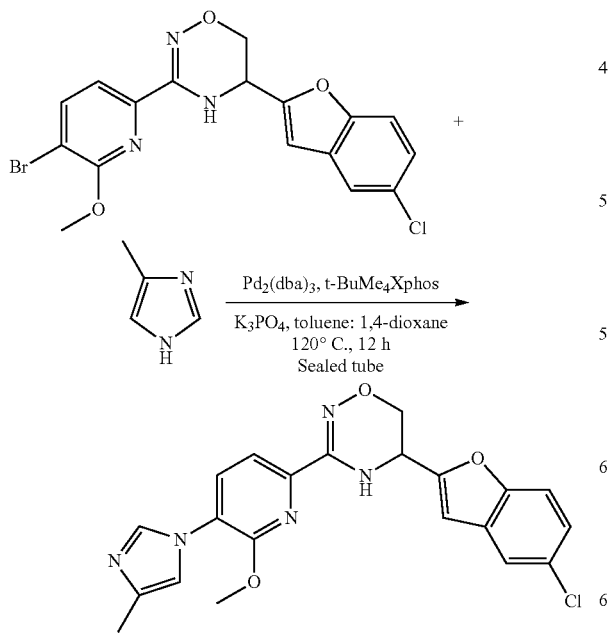

5-(5-chlorobenzofuran-2-yl)-3-(6-methoxy-5-(4-methyl-1H-imidazol-1-yl) pyridin-2-yl)-5,6-dihydro-4H-1,2,4-oxadiazine To a dry vial was added a suspension of $Pd_2(dba)_3$ (24 mg, 0.02 mmol) and tert-butyl tetramethyl Xphos (25 mg, 0.05 mmol) in toluene:1,4-dioxane (2:1, 3.75 mL) at room temperature. The suspension was degassed with argon, heated to 120° C., and stirred at 120° C. for 3 min. A mixture of 3-(5-bromo-6-methoxypyridin-2-yl)-5-(5-chlorobenzofuran-2-yl)-5,6-dihydro-4H-1,2,4-oxadiazine (220 mg, 0.5 mmol), 4-methyl-1H-imidazole (85 mg, 1.0 mmol) and potassium phosphate (429 mg, 1 mmol) in toluene:1,4-dioxane (2:1, 3.75 mL) was degassed, and the catalyst premixture was added. The resultant mixture was stirred at 120° C. for 16 h in a sealed tube. After consumption of the starting material (monitored by TLC and LCMS), the reaction mixture was filtered, and the filtrate was concentrated in vacuo. The crude material was purified by column chromatography using 2% MeOH: $CH_2Cl_2$ to afford 5-(5-chlorobenzofuran-2-yl)-3-(6-methoxy-5-(4-methyl-1H-imidazol-1-yl) pyridin-2-yl)-5,6-dihydro-4H-1,2,4-oxadiazine (125 mg, 57%) as an off-white solid.

Racemic compound of Example 57 was separated using a Chiralpak-IB column (250×4.6 mm, 5 μm) (30 mg loading; 0.1% DEA in n-Hexane: $CH_2Cl_2$:MeOH (50:50) (A:B: 80:20) as mobile phase) to afford the compounds of Example 57A (Fraction (I) (−)) and the compound of Example 57B (Fraction (II) (+)).

Analytical conditions for Example 57A and Example 57B. HPLC (column; YMC Triart C-18, 150×4.6 mm, 3.0 μm), mobile phase: ACN: 0.05% Aq TFA; flow rate: 1.0 mL/min; Gradient program: T/B % 0.01/90, 3/90, 8/10, 15/10; diluent: $CH_3CN$:Water, Chiral HPLC: (Chiralpak-IB (250×4.6 mm, 5 μm; mobile phase (A) 0.1% DEA in n-Hexane (B) $CH_2Cl_2$:MeOH (50:50) (A:B; 80:20); flow Rate: 1.0 mL/min).

Example 57A, (−)-5-(5-chlorobenzofuran-2-yl)-3-(6-methoxy-5-(4-methyl-1H-imidazol-1-yl) pyridin-2-yl)-5,6-dihydro-4H-1,2,4-oxadiazine, fraction (I) (−): Mass (ESI): 424.4 [M+1]; HPLC (purity): 98.7%, RT 8.28 min; Chiral HPLC: 99.8%, RT=13.73 min; Optical rotation $[\alpha]_D^{19.99}$: −296.60 (c=0.25, $CH_2Cl_2$).

Example 57B, (+)-5-(5-chlorobenzofuran-2-yl)-3-(6-methoxy-5-(4-methyl-1H-imidazol-1-yl) pyridin-2-yl)-5,6-dihydro-4H-1,2,4-oxadiazine, fraction (II) (+): $^1$H NMR ($CD_3OD$, 400 MHz) δ 8.00 (s, 1H), 7.90 (d, 1H), 7.65 (d, 1H), 7.57 (s, 1H), 7.45 (d, 1H), 7.25-7.20 (m, 2H), 6.73 (s, 1H), 5.10 (t, 1H), 4.41 (dd, 1H), 4.13 (s, 3H), 4.06 (dd, 1H), 2.23 (s, 3H); Mass (ESI): 424.5 [M+1]; HPLC (purity): 98.2%, RT 8.24 min; Chiral HPLC: 98.9%, RT=19.58 min; Optical rotation $[\alpha]_D^{20.02}$: +296.86 (c=0.25, $CH_2Cl_2$).

Example 58

Synthesis of 3-(5-bromo-6-methoxypyridin-2-yl)-5-(4-(trifluoromethyl) phenyl)-5,6-dihydro-4H-1,2,4-oxadiazine

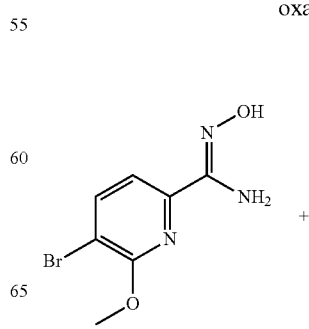

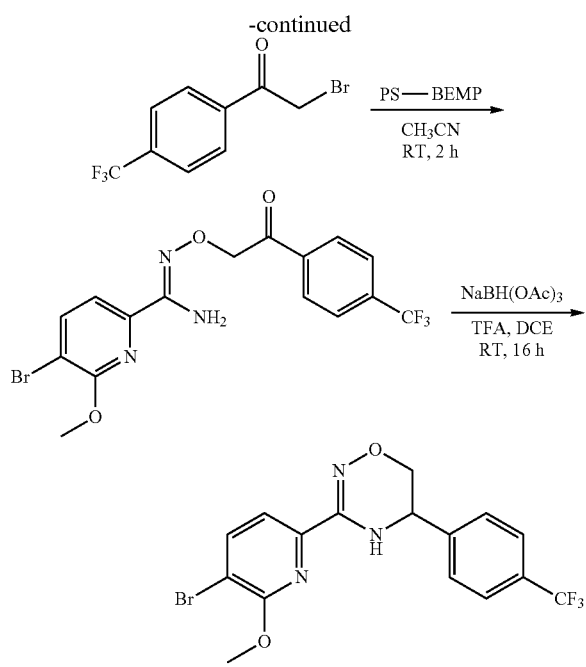

(Z)-5-bromo-6-methoxy-N'-(2-oxo-2-(4-(trifluoromethyl) phenyl) ethoxy) picolinimidamide To a stirred solution of 5-bromo-N'-hydroxy-6-methoxypicolinimidamide (500 mg, 2.0 mmol) in CH₃CN (12.5 mL) at room temperature under an argon atmosphere was added PS-BEMP (665 mg, 2.4 mmol). The reaction mixture was stirred for 5 min at room temperature. Then 2-bromo-1-(4-(trifluoromethyl) phenyl) ethan-1-one (814 mg, 3.0 mmol) in CH₃CN (12.5 mL) was added to the reaction mixture at room temperature. The reaction mixture was stirred for 2 h at room temperature. After consumption of starting material (monitored by TLC), the reaction mixture was filtered and the filtrate was concentrated in vacuo to afford (Z)-5-bromo-6-methoxy-N'-(2-oxo-2-(4-(trifluoromethyl) phenyl) ethoxy) picolinimidamide (600 mg, crude) as a brown syrup used in the next step without further purification.

LCMS: 32.2%; 433.7 (M+2); (column; Ascentis Express C-18 (50×3.0 mm, 3.5 μm); RT 3.06 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane (R_f: 0.5).

3-(5-bromo-6-methoxypyridin-2-yl)-5-(4-(trifluoromethyl) phenyl)-5,6-dihydro-4H-1,2,4-oxadiazine To a stirred solution of (Z)-5-bromo-6-methoxy-N'-(2-oxo-2-(4-(trifluoromethyl) phenyl) ethoxy) picolinimidamide (700 mg, crude) in dichloroethane (10 mL) at room temperature under an argon atmosphere was added trifluoroacetic acid (0.6 mL, 8.1 mmol) and sodium triacetoxyborohydride (1 g, 5.0 mmol). The reaction mixture was stirred for 16 h at room temperature. After consumption of starting material (monitored by TLC), the reaction mixture was diluted with water (20 mL) and 1N sodium hydroxide solution (20 mL) and extracted with EtOAc (2×20 mL). The combined organic extracts were dried over sodium sulfate, filtered and concentrated in vacuo to afford 3-(5-bromo-6-methoxypyridin-2-yl)-5-(4-(trifluoromethyl) phenyl)-5,6-dihydro-4H-1,2,4-oxadiazine (400 mg, crude) as a brown syrup used in the next step without further purification.

LCMS: 58.2%; 415.8 (M+); (column; Ascentis Express C-18 (50×3.0 mm, 3.5 μm); RT 2.85 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane (R_f: 0.5).

Example 59

Synthesis of 3-(6-methoxy-5-(4-methyl-1H-imidazol-1-yl) pyridin-2-yl)-5-(4-(trifluoromethyl) phenyl)-5,6-dihydro-4H-1,2,4-oxadiazine

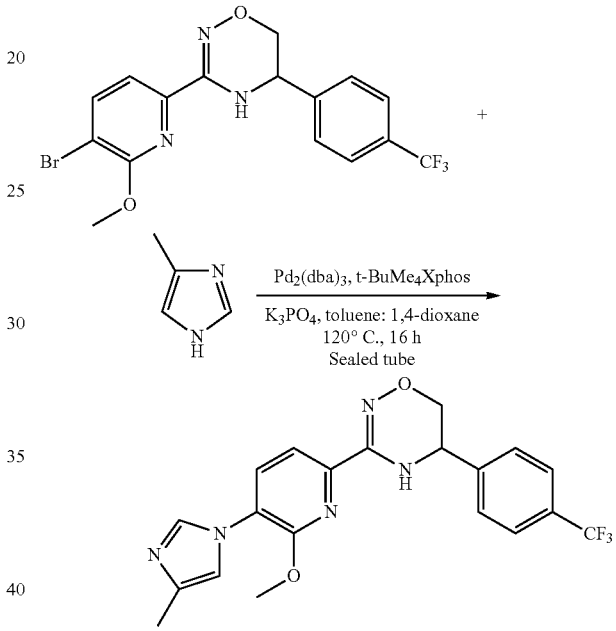

3-(6-methoxy-5-(4-methyl-1H-imidazol-1-yl) pyridin-2-yl)-5-(4-(trifluoromethyl) phenyl)-5,6-dihydro-4H-1,2,4-oxadiazine To a dry vial was added a suspension of Pd₂(dba)₃ (33 mg, 0.03 mmol) and tert-butyl tetramethyl Xphos (35 mg, 0.07 mmol) in toluene:1,4-dioxane (2:1, 4.5 mL) at room temperature. The suspension was degassed with argon, heated to 120° C., and stirred at 120° C. for 3 min. A mixture of 3-(5-bromo-6-methoxypyridin-2-yl)-5-(4-(trifluoromethyl) phenyl)-5,6-dihydro-4H-1,2,4-oxadiazine (300 mg, 1.0 mmol), 4-methyl-1H-imidazole (89 mg, 1.08 mmol) and potassium phosphate (305 mg, 1.44 mmol) in toluene:1,4-dioxane (2:1, 4.5 mL) was degassed and the catalyst pre-mixture was added. The resultant mixture was stirred at 120° C. for 16 h in a sealed tube. After consumption of the starting material (monitored by TLC and LCMS), the reaction mixture was diluted with water (20 mL) and extracted with 5% MeOH: CH₂Cl₂ (2×10 mL). The combined organic extracts were dried over sodium sulfate, filtered and concentrated in vacuo. The crude material was purified by column chromatography using 2-5% MeOH: CH₂Cl₂ to afford 3-(6-methoxy-5-(4-methyl-1H-imidazol-1-yl) pyridin-2-yl)-5-(4-

(trifluoromethyl) phenyl)-5,6-dihydro-4H-1,2,4-oxadiazine (180 mg, 60%) as an off-white solid.

Racemic compound of Example 59 was separated using a Chiralpak-AD-H column (250×20 mm, 5 μm) (19 mg loading; 0.1% DEA in n-Hexane: EtOH:MeOH (50:50) (A:B: 65:35) as mobile phase) to afford the compounds of Example 59A (Fraction (I) (−)) and Example 59B (Fraction (II) (+)).

Analytical conditions for Example 59A and Example 59B. HPLC (column; Zorbax SB C-18, 150×4.6 mm, 5.0 μm), mobile phase: ACN: 0.05% Aq TFA; flow rate: 1.0 mL/min, Gradient program: T/B % 0.01/90, 2/90, 8/10, 15/10, diluent: $CH_3CN$:Water; Chiral HPLC: (Chiralpak-IB (250×4.6 mm, 5 μm; mobile phase (A) 0.1% DEA in n-Hexane (B) $CH_2Cl_2$:MeOH (50:50) (A:B; 80:20); flow Rate: 1.0 mL/min).

Example 59A, (−)-3-(6-methoxy-5-(4-methyl-1H-imidazol-1-yl) pyridin-2-yl)-5-(4-(trifluoromethyl) phenyl)-5,6-dihydro-4H-1,2,4-oxadiazine, fraction (I) (−): Mass (ESI): 418 [M+1]; HPLC (purity): 95.2%, RT 7.63 min; Chiral HPLC: 98.6%, RT=10.92 min; Optical rotation $[\alpha]_D^{20.00}$: −150.38 (c=0.25, $CH_2Cl_2$).

Example 59B, (+)-3-(6-methoxy-5-(4-methyl-1H-imidazol-1-yl) pyridin-2-yl)-5-(4-(trifluoromethyl) phenyl)-5,6-dihydro-4H-1,2,4-oxadiazine, fraction (II) (+): $^1$H NMR ($CD_3OD$, 400 MHz): δ 7.96 (s, 1H), 7.89 (d, 1H), 7.70-7.62 (m, 3H), 7.60-7.56 (m, 2H), 7.21 (s, 1H), 4.98 (t, 1H), 4.13-4.07 (m, 4H), 4.00 (dd 1H), 2.24 (s, 3H); Mass (ESI): 418 [M+1]; HPLC (purity): 97.1%, RT 7.60 min; Chiral HPLC: 100%, RT=14.62; Optical rotation $[\alpha]_D^{19.98}$: +150.20 (c=0.25, $CH_2Cl_2$).

Example 60

Synthesis of 3-(5-bromo-6-methoxypyridin-2-yl)-5-cyclohexyl-5,6-dihydro-4H-1,2,4-oxadiazine

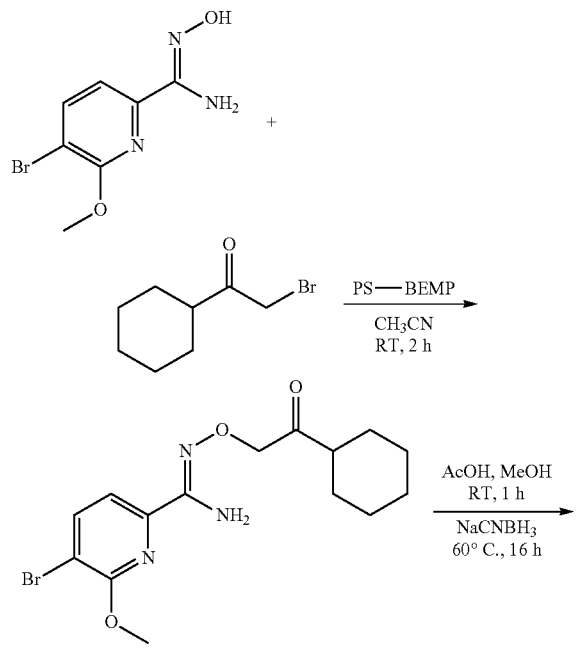

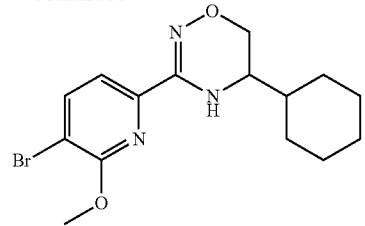

(Z)-5-bromo-N'-(2-cyclohexyl-2-oxoethoxy)-6-methoxypicolinimidamide

To a stirred solution of 5-bromo-N'-hydroxy-6-methoxypicolinimidamide (380 mg, 1.2 mmol) in $CH_3CN$ (10 mL) at room temperature under an argon atmosphere was added PS-BEMP (399 mg, 1.5 mmol). The reaction mixture was stirred for 1 h at room temperature. Then 2-bromo-1-cyclohexylethan-1-one (375 mg, 2.0 mmol) in $CH_3CN$ (5 mL) was added to the reaction mixture at room temperature. The reaction mixture was stirred for 1 h at room temperature. After consumption of starting material (monitored by TLC), the reaction mixture was filtered and the filtrate was concentrated in vacuo to afford (Z)-5-bromo-N'-(2-cyclohexyl-2-oxoethoxy)-6-methoxypicolinimidamide (380 mg, crude) as a brown syrup used in the next step without further purification.

LCMS: 79.9%; 371.8 (M+2); (column; Ascentis Express C-18 (50×3.0 mm, 3.5 μm); RT 2.93 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane ($R_f$: 0.7).

3-(5-bromo-6-methoxypyridin-2-yl)-5-cyclohexyl-5,6-dihydro-4H-1,2,4-oxadiazine

To a stirred solution of (Z)-5-bromo-N'-(2-cyclohexyl-2-oxoethoxy)-6-methoxypicolinimidamide (380 mg, crude) in MeOH (9 mL) at room temperature under an argon atmosphere was added acetic acid (1.5 mL). The reaction mixture was stirred for 1 h at room temperature. Then sodium cyanoborohydride (78 mg, 1.2 mmol) was added to the reaction mixture at room temperature. The reaction mixture was stirred at 60° C. for 16 h. After consumption of starting material (monitored by TLC), the reaction mixture was diluted with saturated sodium bicarbonate solution (20 mL) and extracted with EtOAc (2×20 mL). The combined organic extracts were dried over sodium sulfate, filtered and concentrated in vacuo. The crude material was purified by column chromatography using 15% EtOAc: Hexane to afford 3-(5-bromo-6-methoxypyridin-2-yl)-5-cyclohexyl-5,6-dihydro-4H-1,2,4-oxadiazine Example 18-Br (320 mg, 88%) as a brown syrup.

$^1$H NMR (DMSO-$d_6$, 400 MHz): δ 8.05 (d, 1H), 7.36 (d, 1H), 7.03 (d, 1H), 4.03 (s, 3H), 3.93 (dd, 1H), 3.67 (dd, 1H), 3.32-3.27 (m, 1H), 1.85-1.59 (m, 5H), 1.54-1.44 (m, 1H), 1.26-1.00 (m, 5H); LCMS: 98.9%; 355.8 (M+); (column; Ascentis Express C-18 (50×3.0 mm, 3.5 μm); RT 2.85 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.4).

Example 61

Synthesis of 5-cyclohexyl-3-(6-methoxy-5-(4-methyl-1H-imidazol-1-yl) pyridin-2-yl)-5,6-dihydro-4H-1,2,4-oxadiazine

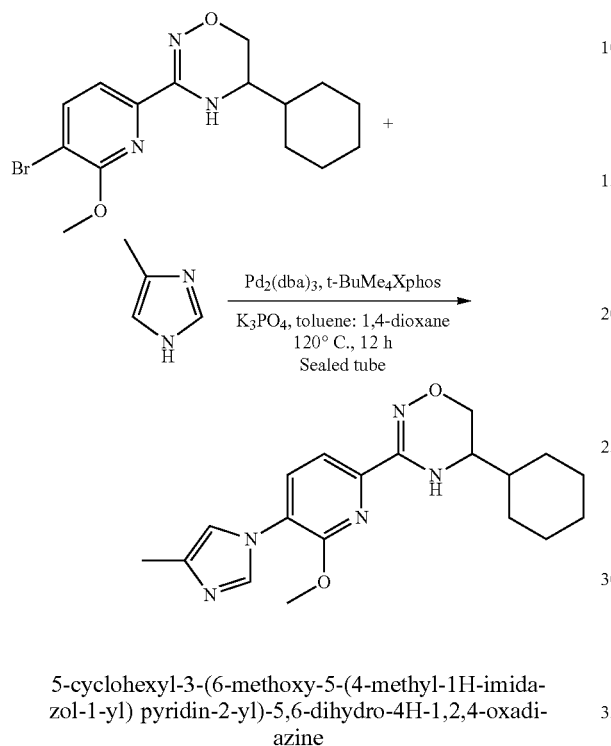

5-cyclohexyl-3-(6-methoxy-5-(4-methyl-1H-imidazol-1-yl) pyridin-2-yl)-5,6-dihydro-4H-1,2,4-oxadiazine To a dry vial was added a suspension of $Pd_2(dba)_3$ (39 mg, 0.04 mmol) and tert-butyl tetramethyl Xphos (61 mg, 0.12 mmol) in toluene:1,4-dioxane (2:1, 5.5 mL) at room temperature. The suspension was degassed with argon, heated to 120° C., and stirred at 120° C. for 3 min. A mixture of 3-(5-bromo-6-methoxypyridin-2-yl)-5-cyclohexyl-5,6-dihydro-4H-1,2,4-oxadiazine (300 mg, 1.0 mmol), 4-methyl-1H-imidazole (139 mg, 2.0 mmol) and potassium phosphate (360 mg, 2.0 mmol) in toluene:1,4-dioxane (2:1, 5.5 mL) was degassed and the catalyst premixture was added. The resultant mixture was stirred at 120° C. for 12 h in a sealed tube. After consumption of the starting material (monitored by TLC and LCMS), the reaction mixture was diluted with water (20 mL) and extracted with 5% MeOH: $CH_2Cl_2$ (2×10 mL). The combined organic extracts were dried over sodium sulfate, filtered and concentrated in vacuo. The crude material was purified by column chromatography using 2% MeOH: $CH_2Cl_2$ to afford 5-cyclohexyl-3-(6-methoxy-5-(4-methyl-1H-imidazol-1-yl) pyridin-2-yl)-5,6-dihydro-4H-1,2,4-oxadiazine (190 mg, 58%) as an off-white solid.

Racemic compound of Example 61 was separated using a Chiralpak-IB column (250×20 mm, 5 μm) (30 mg loading; 0.1% DEA in n-Hexane: $CH_2Cl_2$:MeOH (50:50) (A:B: 80:20) as mobile phase) to afford the compounds of Example 61A (Fraction (I) (−)) and Example 61B (Fraction (II) (+)).

Analytical conditions for Example 61A and Example 61B: HPLC (purity): 95.0%; (column; Eclipse XDB C-18, 150×4.6 mm, 5 μm), mobile phase: ACN: 0.05% Aq TFA; flow rate: 1.0 mL/min; Gradient program: T/B % 0.01/90, 2/90, 8/10, 15/10: Diluent: $CH_3CN$:Water; Chiral HPLC: (Chiralpak-IB (250×4.6 mm, 5 μm; mobile phase (A) 0.1% DEA in n-Hexane (B) $CH_2Cl_2$:MeOH (50:50) (A:B; 80:20); flow Rate: 1.0 mL/min).

Example 61A, (−)-5-cyclohexyl-3-(6-methoxy-5-(4-methyl-1H-imidazol-1-yl) pyridin-2-yl)-5,6-dihydro-4H-1,2,4-oxadiazine, fraction (I) (−): Mass (ESI): 356.3 [M+1]; HPLC (purity): 95.0%, RT 7.44 min; Chiral HPLC: 97.8%, RT=9.37 min; Optical rotation $[\alpha]_D^{19.99}$: −17.05 (c=0.25, $CH_2Cl_2$).

Example 61B, (+)-5-cyclohexyl-3-(6-methoxy-5-(4-methyl-1H-imidazol-1-yl) pyridin-2-yl)-5,6-dihydro-4H-1,2,4-oxadiazine, fraction (II) (+):
$^1$H NMR ($CD_3OD$, 400 MHz): δ 7.97 (s, 1H), 7.85 (d, 1H), 7.56 (d, 1H), 7.21 (s, 1H), 4.11 (s, 3H), 4.01 (dd, 1H), 3.87 (dd, 1H), 3.42-3.38 (m, 1H), 2.25 (s, 3H), 1.97-1.95 (m, 1H), 1.88-1.69 (m, 4H), 1.67-1.57 (m, 1H), 1.37-1.21 (m, 3H), 1.19-1.12 (m, 2H); Mass (ESI): 356.3 [M+1]; HPLC (purity): 98.7%, RT 7.41 min; Chiral HPLC: 98.6%, RT=11.57 min; Optical rotation $[\alpha]_D^{20.00}$: +13.55 (C=0.25, $CH_2Cl_2$).

Example 62

Synthesis of 2-bromo-1-(7-chlorobenzofuran-2-yl) ethan-1-one

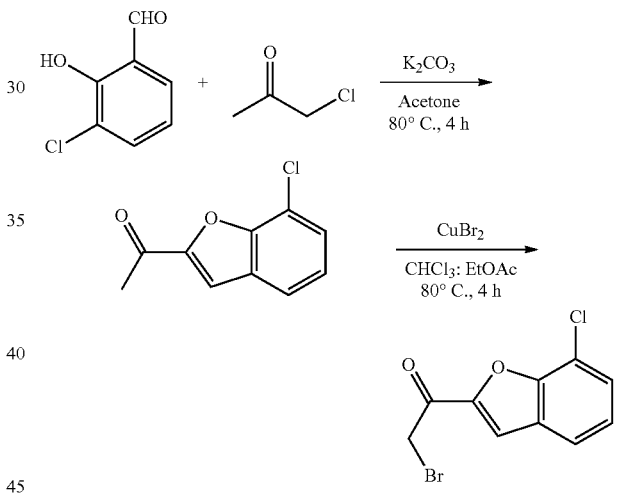

1-(7-chlorobenzofuran-2-yl) ethan-1-one

To a stirred solution of 3-chloro-2-hydroxybenzaldehyde (6 g, 38 mmol) in acetone (80 mL) at room temperature under an argon atmosphere were added potassium carbonate (8 g, 58 mmol) and 1-chloropropan-2-one (4.4 g, 46 mmol). The reaction mixture was stirred at 80° C. for 4 h. After consumption of starting material (monitored by TLC), the reaction mixture was filtered, and the filtrate was concentrated in vacuo. The crude material was purified by column chromatography using 2-5% EtOAc: Hexane to afford 1-(7-chlorobenzofuran-2-yl) ethan-1-one (5.4 g, 72%) as an off-white solid.

$^1$H NMR ($CDCl_3$: 400 MHz): δ 7.61 (dd, 1H), 7.52 (s, 1H), 7.48 (dd, 1H), 7.27 (t, 1H), 2.66 (s, 3H). TLC: 10% EtOAc/Hexane ($R_f$: 0.5).

2-bromo-1-(7-chlorobenzofuran-2-yl) ethan-1-one

To a stirred solution of 1-(7-chlorobenzofuran-2-yl) ethan-1-one (2.4 g, 12 mmol) in chloroform:EtOAc (1:3, 48 mL) at room temperature under an argon atmosphere was added copper bromide (6 g, 27 mmol). The reaction mixture was stirred at 80° C. for 4 h. After consumption of starting material (monitored by TLC), the reaction mixture was filtered, and the filtrate was washed with water (2×50 mL), dried over sodium sulfate, filtered and concentrated in vacuo. The crude material was purified by column chromatography using 2% EtOAc: Hexane to afford 2-bromo-1-(7-chlorobenzofuran-2-yl) ethan-1-one (1.9 g, 56%) as a yellow solid.

$^1$H NMR (CDCl$_3$: 400 MHz): δ 7.68 (s, 1H), 7.61 (dd, 1H), 7.51 (dd, 1H), 7.29 (t, 1H), 4.50 (s, 2H). LCMS: 93.4%; 273.1 (M+1); (column; X-select CSH C-18 (50×3.0 mm, 3.5 µm); RT 4.26 mm 5 mM Aq NH$_4$OAc: ACN; T/B %: 0.01/10, 0.5/10, 4/90, 9/90; 0.8 mL/min); TLC: 5% EtOAc/Hexane (R$_f$: 0.7).

Example 63

Synthesis of 3-(5-bromo-6-methoxypyridin-2-yl)-5-(7-chlorobenzofuran-2-yl)-5,6-dihydro-4H-1,2,4-oxadiazine

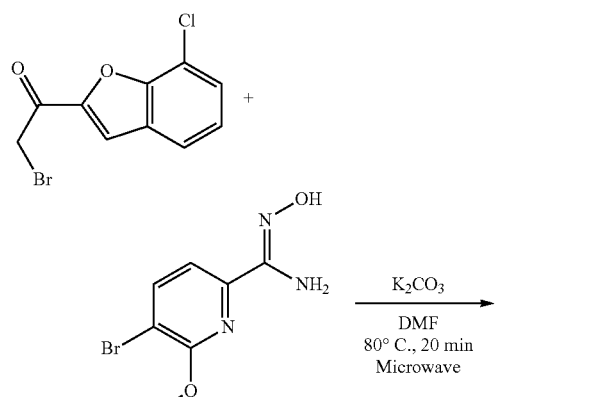

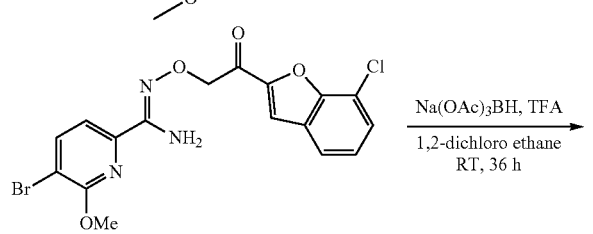

(Z)-5-bromo-N'-(2-(7-chlorobenzofuran-2-yl)-2-oxoethoxy)-6-methoxypicolinimidamide To a stirred solution of 5-bromo-N'-hydroxy-6-methoxypicolinimidamide (500 mg, 2 mmol) in DMF (10 mL) at room temperature under an argon atmosphere were added potassium carbonate (560 mg, 4.06 mmol) and 2-bromo-1-(7-chlorobenzofuran-2-yl) ethan-1-one (832 mg, 3 mmol). The reaction mixture was stirred at 80° C. for 20 min in microwave. After consumption of starting material (monitored by TLC), the reaction mixture was diluted with water (20 mL) and extracted with EtOAc (2×20 mL). The combined organic extracts were dried over sodium sulfate, filtered and concentrated in vacuo to afford (Z)-5-bromo-N'-(2-(7-chlorobenzofuran-2-yl)-2-oxoethoxy)-6-methoxypicolinimidamide (680 mg, crude) as a brown syrup used in the next step without further purification.

LCMS: 38.8%; 439.7 (M+2); (column; Ascentis Express C-18 (50×3.0 mm, 2.7 µm); RT 2.97 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.4).

3-(5-bromo-6-methoxypyridin-2-yl)-5-(7-chlorobenzofuran-2-yl)-5,6-dihydro-4H-1,2,4-oxadiazine To a stirred solution of (Z)-5-bromo-N'-(2-(7-chlorobenzofuran-2-yl)-2-oxoethoxy)-6-methoxypicolinimidamide (680 mg, 1 mmol) in 1,2-dichloro ethane (15 mL) at room temperature under an argon atmosphere was added trifluoroacetic acid (2.5 mL) and sodium triacetoxyborohydride (493 mg, 2 mmol). The reaction mixture was stirred for 36 h at room temperature. After consumption of starting material (monitored by TLC), the reaction mixture was diluted with water (20 mL) and extracted with EtOAc (2×20 mL). The combined organic extracts were dried over sodium sulfate, filtered and concentrated in vacuo to afford 3-(5-bromo-6-methoxypyridin-2-yl)-5-(7-chlorobenzofuran-2-yl)-5,6-dihydro-4H-1,2,4-oxadiazine (150 mg, 30%) as a yellow solid.

LCMS: 74.2%; 423.7 (M+2); (column; Ascentis Express C-18 (50×3.0 mm, 2.7 µm); RT 2.90 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.4).

Example 64

Synthesis of 5-(7-chlorobenzofuran-2-yl)-3-(6-methoxy-5-(4-methyl-1H-imidazol-1-yl) pyridin-2-yl)-5,6-dihydro-4H-1,2,4-oxadiazine

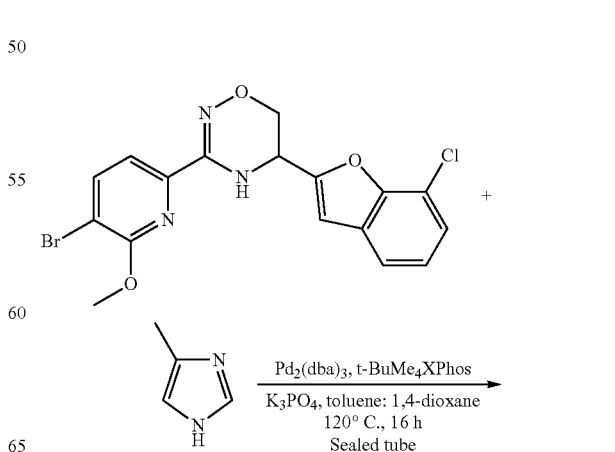

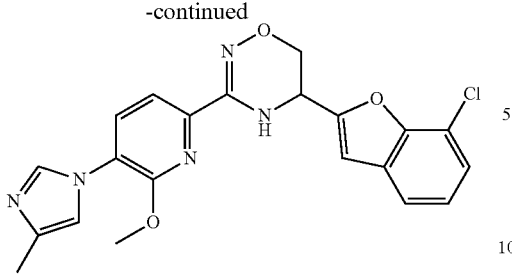

5-(7-chlorobenzofuran-2-yl)-3-(6-methoxy-5-(4-methyl-1H-imidazol-1-yl) pyridin-2-yl)-5,6-dihydro-4H-1,2,4-oxadiazine To a dry vial was added a suspension of $Pd_2(dba)_3$ (30 mg, 0.03 mmol) and tert-butyl tetramethyl XPhos (47 mg, 0.1 mmol) in toluene:1,4-dioxane (2:1, 5.5 mL) at room temperature. The suspension was degassed with argon, heated to 120° C., and stirred at 120° C. for 3 min. A mixture of 3-(5-bromo-6-methoxypyridin-2-yl)-5-(7-chlorobenzofuran-2-yl)-5,6-dihydro-4H-1,2,4-oxadiazine (275 mg, 0.65 mmol), 4-methyl-1H-imidazole (106 mg, 1.30 mmol) and potassium phosphate (276 mg, 1.30 mmol) in toluene:1,4-dioxane (2:1, 5.5 mL) was degassed, and the catalyst pre-mixture was added. The resultant mixture was stirred at 120° C. for 16 h in a sealed tube. After consumption of the starting material (monitored by TLC and LCMS), the reaction mixture was filtered, and the filtrate was concentrated in vacuo. The crude material was purified by preparative HPLC (Column YMC triart C18 column (250×19 mm, 5 μm (50 mg loading; $CH_3CN$: 005% TFA (0.01/90, 2/90, 15/70, 25/30, 30/10, 35/10); Flow rate: 15 mL/min) to afford 5-(7-chlorobenzofuran-2-yl)-3-(6-methoxy-5-(4-methyl-1H-imidazol-1-yl) pyridin-2-yl)-5,6-dihydro-4H-1,2,4-oxadiazine (120 mg, 40%) as an off-white solid.

Racemic compound of Example 64 was separated using a Chiralpak-IB column (250×20 mm, 5 μm) (10 mg loading; 0.1% DEA in n-Hexane: $CH_2Cl_2$:MeOH (80:20) (A:B: 80:20) as mobile phase; flow rate: 18 mL/min) to afford the compounds of Example 64A (Fraction (I) (−)) and Example 64B (Fraction (II) (+)).

Analytical conditions for Example 64A and Example 64B: HPLC (column: zorbax-SB-C-18 150×4.6 mm, 3.5μ), mobile Phase: ACN: 0.05% Aq TFA; flow rate: 1.0 mL/min; Gradient program: T/B % 0.01/90, 2/90, 8/10, 15/10: diluent: $CH_3CN$:Water; Chiral HPLC: (Chiralpak-IB (250× 4.6 mm, 5 μm; mobile phase (A) 0.1% DEA in n-Hexane (B) $CH_2Cl_2$:MeOH (50:50) (A:B; 80:20); flow Rate: 1.0 mL/min).

Example 64A, (−)-5-(7-chlorobenzofuran-2-yl)-3-(6-methoxy-5-(4-methyl-1H-imidazol-1-yl) pyridin-2-yl)-5,6-dihydro-4H-1,2,4-oxadiazine, fraction (I) (−): Mass (ESI): 424.3 [M+1]; HPLC (purity): 97.5%, RT 7.76 min. Chiral HPLC: 100%, RT=13.36 min; Optical rotation $[\alpha]_D^{20.01}$: −211.20 (c=0.25, $CH_2Cl_2$).

Example 64B, (+)-5-(7-chlorobenzofuran-2-yl)-3-(6-methoxy-5-(4-methyl-1H-imidazol-1-yl) pyridin-2-yl)-5,6-dihydro-4H-1,2,4-oxadiazine, fraction (II) (+): $^1H$ NMR ($CD_3OD$, 400 MHz): δ 7.99 (s, 1H), 7.88 (d, 1H), 7.64 (d, 1H), 7.51 (dd, 1H), 7.30 (d, Hz, 1H), 7.26-7.17 (m, 2H), 6.83 (s, 1H), 5.14 (t, 1H), 4.43 (dd, 1H), 4.14 (s, 3H), 4.09 (dd, 1H), 2.26 (s, 3H); Mass (ESI): 424.3 [M+1]; HPLC (purity): 98.4%, RT 7.74 min; Chiral HPLC: 98.8%, RT=14.43 min; Optical rotation $[\alpha]_D^{19.99}$: +217.12 (c=0.25, $CH_2Cl_2$).

Example 65

Synthesis of 2-(3-(5-bromo-6-methoxypyridin-2-yl)-5,6-dihydro-4H-1,2,4-oxadiazin-5-yl)-3-methyl-benzo [b] thiophen-5-ylium

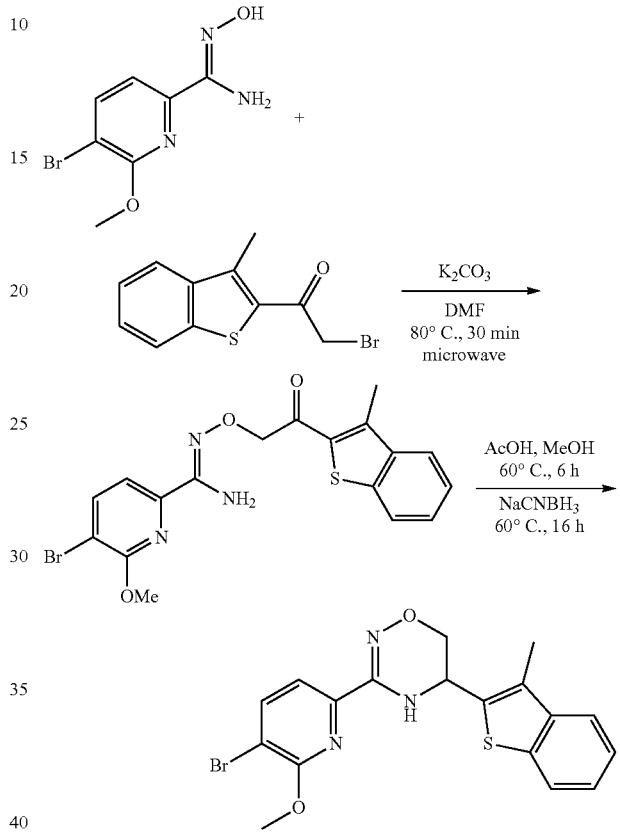

(Z)-5-bromo-6-methoxy-N'-(2-(3-methylbenzo [b] thiophen-2-yl)-2-oxoethoxy) picolinimidamide To a stirred solution of 5-bromo-N'-hydroxy-6-methoxypicolinimidamide (800 mg, 3 mmol) in DMF (16 mL) at room temperature under an argon atmosphere were added potassium carbonate (896 mg, 6 mmol) and 2-bromo-1-(3-methylbenzo [b] thiophen-2-yl) ethan-1-one (1.13 g, 4 mmol). The reaction mixture was stirred for 30 min at 80° C. in microwave. After consumption of starting material (monitored by TLC), the reaction mixture was diluted with water (20 mL) and extracted with EtOAc (2×20 mL). The combined organic extracts were washed with water (20 mL), dried over sodium sulfate, filtered and concentrated in vacuo to afford (Z)-5-bromo-6-methoxy-N'-(2-(3-methylbenzo [b] thiophen-2-yl)-2-oxoethoxy) picolinimidamide (1.2 g, crude) as a brown syrup used in the next step without further purification.

LCMS: 51.7%; 433.8 (M+1); (column; Ascentis Express C-18 (50×3.0 mm, 2.7 μm); RT 3.08 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane ($R_f$: 0.6).

2-(3-(5-bromo-6-methoxypyridin-2-yl)-5,6-dihydro-4H-1,2,4-oxadiazin-5-yl)-3-methylbenzo [b] thiophen-5-ylium To a stirred solution of (Z)-5-bromo-6-methoxy-N'-(2-(3-methylbenzo [b] thiophen-2-yl)-2-oxoethoxy) picolinimidamide (1.2 g, crude) in MeOH (16 mL) at room temperature under an argon atmosphere was added acetic acid (4 mL). The reaction mixture was stirred for 6 h at 60° C. Then sodium cyanoborohydride (246 mg) was added to the reaction mixture at room temperature. The reaction mixture was stirred at 60° C. for 16 h. After consumption of starting material (monitored by TLC), the volatiles were evaporated in vacuo. The residue was diluted with water (50 mL) and extracted with EtOAc (2×50 mL). The combined organic extracts were dried over sodium sulfate, filtered and concentrated in vacuo to afford 2-(3-(5-bromo-6-methoxypyridin-2-yl)-5,6-dihydro-4H-1,2,4-oxadiazin-5-yl)-3-methylbenzo [b] thiophen-5-ylium (150 mg, 13%) as an off-white solid.

LCMS: 99.2%; 419.8 (M+1); (column; Ascentis Express C-18 (50×3.0 mm, 2.7 μm); RT 2.94 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.5).

Example 66

Synthesis of 3-(6-methoxy-5-(4-methyl-1H-imidazol-1-yl) pyridin-2-yl)-5-(2-methylbenzo [b] thiophen-3-yl)-5,6-dihydro-4H-1,2,4-oxadiazine

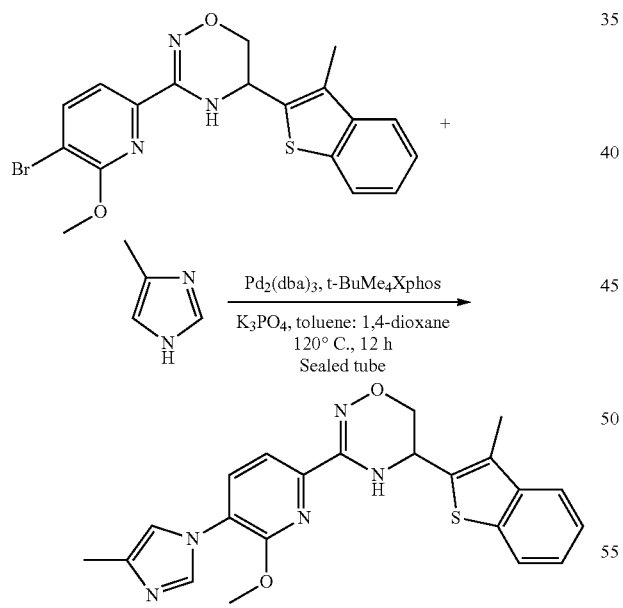

3-(6-methoxy-5-(4-methyl-1H-imidazol-1-yl) pyridin-2-yl)-5-(3-methylbenzo [b] thiophen-2-yl)-5,6-dihydro-4H-1,2,4-oxadiazine To a dry vial was added a suspension of Pd$_2$(dba)$_3$ (22 mg, 0.02 mmol) and tert-butyl tetramethyl Xphos (23 mg, 0.05 mmol) in toluene:1,4-dioxane (2:1, 3.75 mL) at room temperature. The suspension was degassed with argon, heated to 120° C., and stirred at 120° C. for 3 min. A mixture of 2-(3-(5-bromo-6-methoxypyridin-2-yl)-5,6-dihydro-4H-1,2,4-oxadiazin-5-yl)-3-methylbenzo [b] thiophen-5-ylium (200 mg, 0.5 mmol), 4-methyl-1H-imidazole (78 mg, 1.0 mmol) and potassium phosphate (202 mg, 1.0 mmol) in toluene:1,4-dioxane (2:1, 3.75 mL) was degassed and the catalyst premixture was added. The resultant mixture was stirred at 120° C. for 12 h in a sealed tube. After consumption of the starting material (monitored by TLC and LCMS), the reaction mixture was filtered and the filtrate was concentrated in vacuo. The crude material was purified by column chromatography using 2% MeOH: CH$_2$Cl$_2$ to afford 3-(6-methoxy-5-(4-methyl-1H-imidazol-1-yl) pyridin-2-yl)-5-(3-methylbenzo [b] thiophen-2-yl)-5,6-dihydro-4H-1,2,4-oxadiazine (130 mg, 65%) as an off-white solid.

Racemic compound of Example 66 was separated using a Chiralpak-IB column (250×20 mm, 5 μm) (28 mg loading; 0.1% DEA in n-Hexane: CH$_2$Cl$_2$:MeOH (50:50) (A:B: 80:20) as mobile phase; flow rate: 18 mL/min) to afford the compounds of Example 66A (Fraction (I) (−)) and Example 66B (Fraction (II) (+)).

Analytical conditions for Example 66A and Example 66B: HPLC (column; zorbax-SB-C-18 150×4.6 mm, 3.5μ), mobile Phase: ACN: 0.05% Aq TFA; flow rate: 1.0 mL/min; Gradient program: T/B % 0.01/90, 2/90, 8/10, 15/10: diluent: CH$_3$CN:Water; Chiral HPLC: (Chiralpak-IB (250× 4.6 mm, 5 μm; mobile phase (A) 0.1% DEA in n-Hexane (B) CH$_2$Cl$_2$:MeOH (50:50) (A:B; 80:20); flow Rate: 1.0 mL/min).

Example 66A, (−)-3-(6-methoxy-5-(4-methyl-1H-imidazol-1-yl) pyridin-2-yl)-5-(3-methylbenzo [b] thiophen-2-yl)-5,6-dihydro-4H-1,2,4-oxadiazine, fraction (I) (−): Mass (ESI): 420.3 [M+1]; HPLC (purity): 95.4%, RT 7.78 min; Chiral HPLC: 100%, RT=11.03 min, Optical rotation $[\alpha]_D^{19.99}$: −174.16 (c=0.25, CH$_2$Cl$_2$).

Example 66B, (+)-3-(6-methoxy-5-(4-methyl-1H-imidazol-1-yl) pyridin-2-yl)-5-(3-methylbenzo [b] thiophen-2-yl)-5,6-dihydro-4H-1,2,4-oxadiazine, fraction (II) (+): $^1$H NMR (CD$_3$OD, 400 MHz): δ 7.98 (s, 1H), 7.88 (d, 1H), 7.79 (d, 1H), 7.74 (d, 1H), 7.66 (d, 1H), 7.41-7.36 (m, 1H), 7.34-7.31 (m, 1H), 7.22 (s, 1H), 5.41 (t, 1H), 4.22 (dd, 1H), 4.08 (s, 3H), 4.03 (dd, 1H), 2.49 (s, 3H), 2.25 (s, 3H); Mass (ESI): 420.3 [M+1]; HPLC (purity): 99.7%, RT 7.76 min; Chiral HPLC: 100%, RT=15.52 min; Optical rotation $[\alpha]_D^{20.00}$: +163.37 (c=0.25, CH$_2$Cl$_2$).

Example 67

Synthesis of 5-(benzo [b] thiophen-3-yl)-3-(5-bromo-6-methoxypyridin-2-yl)-5,6-dihydro-4H-1,2, 4-oxadiazine

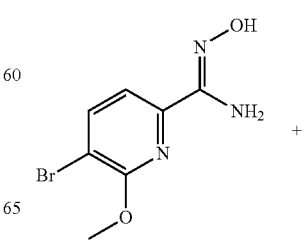

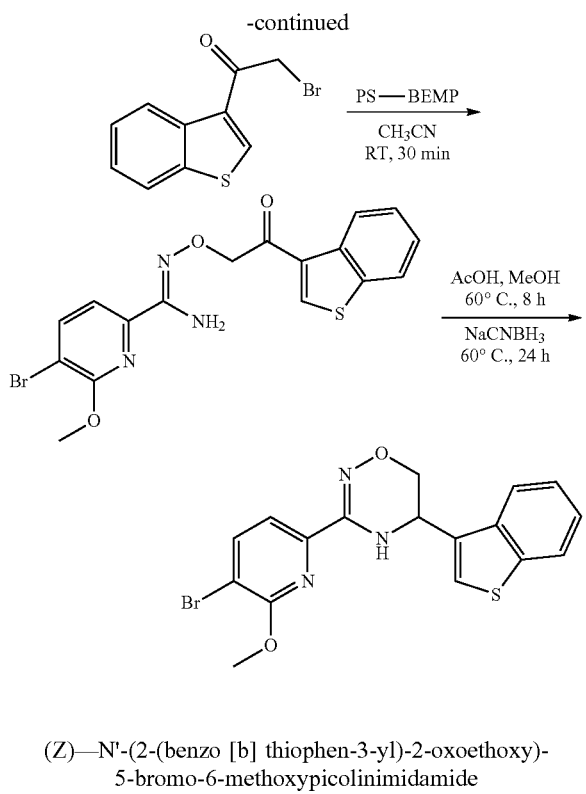

(Z)—N'-(2-(benzo [b] thiophen-3-yl)-2-oxoethoxy)-5-bromo-6-methoxypicolinimidamide To a stirred solution of 5-bromo-N'-hydroxy-6-methoxypicolinimidamide (500 mg, 2 mmol) in $CH_3CN$ (15 mL) at room temperature under an argon atmosphere was added PS-BEMP (1 g, 6 mmol). The reaction mixture was stirred for 10 min at room temperature. Then 1-(benzo [b] thiophen-3-yl)-2-bromoethan-1-one (685 mg, 3 mmol) in $CH_3CN$ (10 mL) was added to the reaction mixture at room temperature. The reaction mixture was stirred for 30 min at room temperature. After consumption of starting material (monitored by TLC), the reaction mixture was filtered and the filtrate was concentrated in vacuo to afford (Z)—N'-(2-(benzo [b] thiophen-3-yl)-2-oxoethoxy)-5-bromo-6-methoxypicolinimidamide (300 mg, crude) as a brown syrup used in the next step without further purification.

LCMS: 42.6%; 419.8 (M+1); (column; Ascentis Express C-18 (50×3.0 mm, 3.5 μm); RT 2.93 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.5).

5-(benzo [b] thiophen-3-yl)-3-(5-bromo-6-methoxy-pyridin-2-yl)-5,6-dihydro-4H-1,2,4-oxadiazine To a stirred solution of (Z)—N'-(2-(benzo [b] thiophen-3-yl)-2-oxoethoxy)-5-bromo-6-methoxypicolinimidamide (450 mg, 1 mmol) in MeOH (10 mL) at room temperature under an argon atmosphere was added acetic acid (1.7 mL). The reaction mixture was stirred for 8 h at 60° C. Then sodium cyanoborohydride (135 mg, 2 mmol) was added to the reaction mixture at room temperature. The reaction mixture was stirred at 60° C. for 24 h. After consumption of starting material (monitored by TLC), the volatiles were evaporated in vacuo. The residue was diluted with saturated sodium bicarbonate solution (20 mL) and extracted with EtOAc (2×20 mL). The combined organic extracts were dried over sodium sulfate, filtered and concentrated in vacuo to afford 5-(benzo [b] thiophen-3-yl)-3-(5-bromo-6-methoxypyridin-2-yl)-5,6-dihydro-4H-1,2,4-oxadiazine (450 mg, crude) as brown syrup used in the next step without further purification.

LCMS: 25.7%; 405.8 (M+3); (column; Ascentis Express C-18 (50×3.0 mm, 3.5 μm); RT 2.84 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.5).

Example 68

Synthesis of 5-(benzo [b] thiophen-3-yl)-3-(6-methoxy-5-(4-methyl-1H-imidazol-1-yl) pyridin-2-yl)-5,6-dihydro-4H-1,2,4-oxadiazine

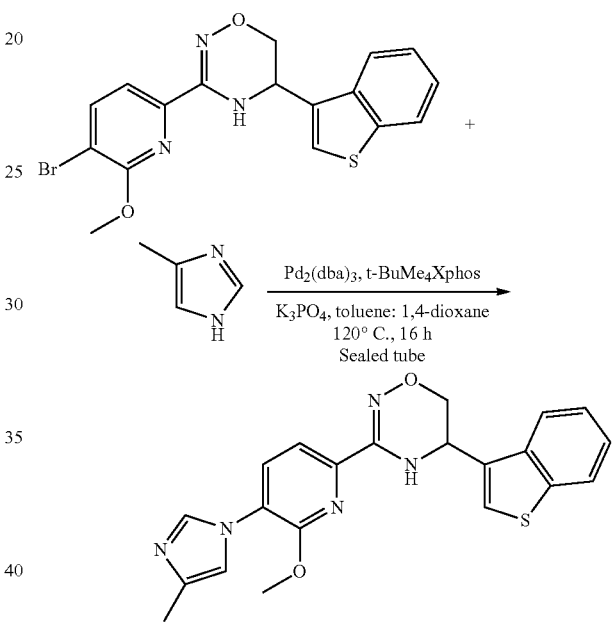

5-(benzo [b] thiophen-3-yl)-3-(6-methoxy-5-(4-methyl-1H-imidazol-1-yl)pyridin-2-yl)-5,6-dihydro-4H-1,2,4-oxadiazine To a dry vial was added a suspension of $Pd_2(dba)_3$ (46 mg, 0.05 mmol) and tert-butyl tetramethyl Xphos (37 mg, 0.09 mmol) in toluene:1,4-dioxane (2:1, 5 mL) at room temperature. The suspension was degassed with argon, heated to 120° C., and stirred at 120° C. for 3 min. A mixture of 5-(benzo [b] thiophen-3-yl)-3-(5-bromo-6-methoxypyridin-2-yl)-5,6-dihydro-4H-1, 2, 4-oxadiazine (400 mg, 1.0 mmol), 4-methyl-1H-imidazole (119 mg, 1.4 mmol) and potassium phosphate (419 mg, 2.0 mmol) in toluene:1,4-dioxane (2:1, 5 mL) was degassed and the catalyst premixture was added. The resultant mixture was stirred at 120° C. for 16 h in a sealed tube. After consumption of the starting material (monitored by TLC and LCMS), the reaction mixture was filtered and the filtrate was concentrated in vacuo. The crude material was purified by column chromatography using 1-2% MeOH: $CH_2Cl_2$ to afford 5-(benzo [b] thiophen-3-yl)-3-(6-methoxy-5-(4-methyl-1H-imidazol-1-yl) pyridin-2-yl)-5,6-dihydro-4H-1,2,4-oxadiazine (160 mg, 40%) as a pale yellow solid.

Racemic compound of Example 68 was separated using a Chiralpak-IB column (250×20 mm, 5 μm) (20 mg loading; 0.1% DEA in n-Hexane: $CH_2Cl_2$:MeOH (50:50) (A:B: 80:20) as mobile phase; flow rate: 18 mL/min) to afford the compounds of Example 68A (Fraction (I) (−)) and Example 68B (Fraction (II) (+)).

Analytical conditions for Example 68A and Example 68B: HPLC (column; zorbax-SB-C-18 (150×4.6 mm, 3.5 μm), mobile Phase: ACN: 0.05% Aq TFA; flow rate: 1.0 mL/min; Gradient program: T/B % 0.01/90, 2/90, 8/10, 15/10: diluent: $CH_3CN$:Water; Chiral HPLC: (Chiralpak-IB (250×4.6 mm, 5 μm; mobile phase (A) 0.1% DEA in n-Hexane (B) $CH_2Cl_2$:MeOH (50:50) (A:B; 80:20); flow Rate: 1.0 mL/min).

Example 68A, (−)-5-(benzo [b] thiophen-3-yl)-3-(6-methoxy-5-(4-methyl-1H-imidazol-1-yl) pyridin-2-yl)-5,6-dihydro-4H-1,2,4-oxadiazine, fraction (I) (−): Mass (ESI): 406.3 [M+1]; HPLC (purity): 98.4%, RT 7.55 min; Chiral HPLC: 100%, RT=13.29 min; Optical rotation $[\alpha]_D^{20.00}$: −212.11 (c=0.25, $CH_2Cl_2$).

Example 68B, (+)-5-(benzo [b] thiophen-3-yl)-3-(6-methoxy-5-(4-methyl-1H-imidazol-1-yl) pyridin-2-yl)-5,6-dihydro-4H-1,2,4-oxadiazine, fraction (II) (+): $^1$H NMR ($CD_3OD$, 400 MHz): δ 7.94-7.91 (m, 2H), 7.90 (d, 2H), 7.67 (d, 1H), 7.53 (s, 1H), 7.42-7.38 (m, 2H), 7.23 (s, 1H), 5.35 (t, 1H), 4.24 (dd, 1H), 4.10 (dd, 1H), 4.07 (s, 3H), 2.26 (s, 3H); Mass (ESI): 406.3 [M+1]; HPLC (purity): 98.6%, RT 7.56 min; Chiral HPLC: 100%, RT=16.55 min; Optical rotation $[\alpha]_D^{20.01}$: +196.30 (c=0.25, $CH_2Cl_2$).

Example 69

Synthesis of 3-(5-bromo-6-methoxypyridin-2-yl)-5-(4-(trifluoromethoxy)phenyl)-5,6-dihydro-4H-1,2,4-oxadiazine

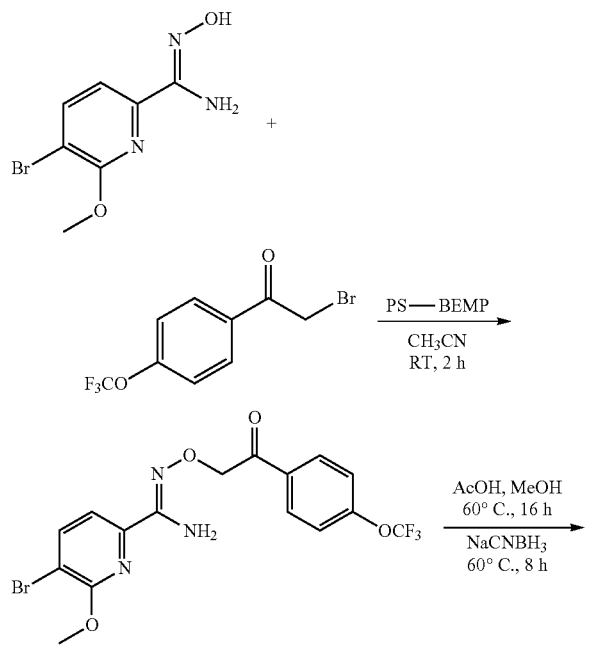

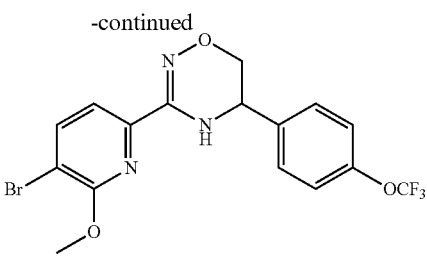

(Z)-5-bromo-6-methoxy-N'-(2-oxo-2-(4-(trifluoromethoxy) phenyl) ethoxy) picolinimidamide To a stirred solution of 5-bromo-N'-hydroxy-6-methoxypicolinimidamide (1 g, 4 mmol) in $CH_3CN$ (15 mL) at room temperature under an argon atmosphere were added PS-BEMP (1.3 g, 5.0 mmol). The reaction mixture was stirred for 5 min at room temperature. Then 2-bromo-1-(4-(trifluoromethoxy) phenyl) ethan-1-one (1.7 g, 6 mmol) in $CH_3CN$ (5 mL) was added to the reaction mixture at room temperature. The reaction mixture was stirred for 2 h at room temperature. After consumption of starting material (monitored by TLC), the reaction mixture was filtered and the filterate was concentrated in vacuo to afford (Z)-5-bromo-6-methoxy-N'-(2-oxo-2-(4-(trifluoromethoxy) phenyl) ethoxy) picolinimidamide (1.1 g, crude) as a pale yellow syrup used in the next step without further purification.

LCMS: 34.6%; 449.7 (M+2); (column; Ascentis Express C-18 (50×3.0 mm, 2.7 μm); RT 2.98 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane ($R_f$: 0.6).

3-(5-bromo-6-methoxypyridin-2-yl)-5-(4-(trifluoromethoxy)phenyl)-5,6-dihydro-4H-1,2,4-oxadiazine To a stirred solution of (Z)-5-bromo-6-methoxy-N'-(2-oxo-2-(4-(trifluoromethoxy) phenyl) ethoxy) picolinimidamide (1.1 g, 2 mmol) in MeOH (15 mL) at room temperature under an argon atmosphere was added acetic acid (5 mL). The reaction mixture was stirred for 16 h at 60° C. Then sodium cyanoborohydride (460 mg, 7 mmol) was added to the reaction mixture at room temperature. The reaction mixture was stirred at 60° C. for 8 h. After consumption of starting material (monitored by TLC), the volatiles were evaporated in vacuo. The residue was diluted with saturated sodium carbonate solution (50 mL) and extracted with EtOAc (2×50 mL). The combined organic extracts were washed with water (20 mL), dried over sodium sulfate, filtered and concentrated in vacuo to afford 3-(5-bromo-6-methoxypyridin-2-yl)-5-(4-(trifluoromethoxy) phenyl)-5,6-dihydro-4H-1,2,4-oxadiazine (500 mg, crude) as a yellow syrup used in the next step without further purification.

LCMS: 35.5%; 431.8 (M+1); (column; Ascentis Express C-18 (50×3.0 mm, 2.7 μm); RT 2.87 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane ($R_f$: 0.7).

Example 70

Synthesis of 3-(6-methoxy-5-(4-methyl-1H-imidazol-1-yl) pyridin-2-yl)-5-(4-(trifluoromethoxy) phenyl)-5,6-dihydro-4H-1,2,4-oxadiazine

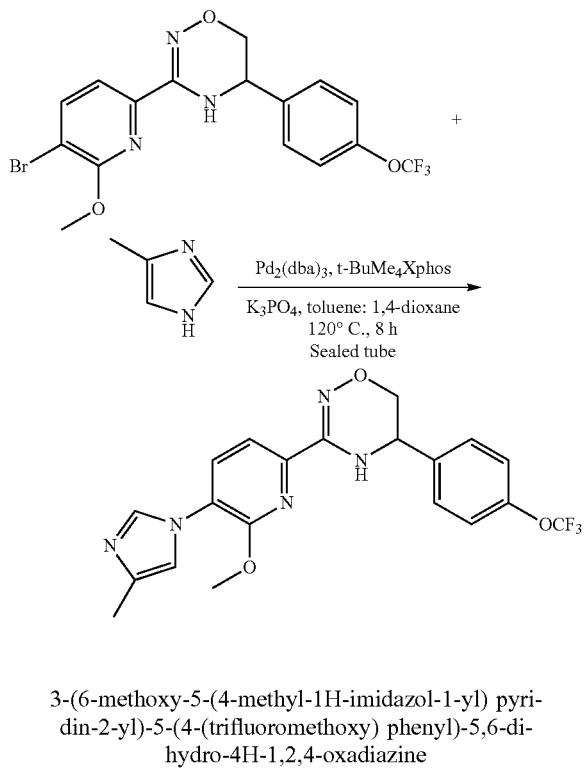

3-(6-methoxy-5-(4-methyl-1H-imidazol-1-yl) pyridin-2-yl)-5-(4-(trifluoromethoxy) phenyl)-5,6-dihydro-4H-1,2,4-oxadiazine To a dry vial was added a suspension of $Pd_2(dba)_3$ (52 mg, 0.05 mmol) and tert-butyl tetramethyl Xphos (55 mg, 0.11 mmol) in toluene:1,4-dioxane (2:1, 7.5 mL) at room temperature. The suspension was degassed with argon, heated to 120° C., and stirred at 120° C. for 3 min. A mixture of 3-(5-bromo-6-methoxypyridin-2-yl)-5-(4-(trifluoromethoxy)phenyl)-5,6-dihydro-4H-1,2,4-oxadiazine (500 mg, 1.15 mmol), 4-methyl-1H-imidazole (110 mg, 1.40 mmol) and potassium phosphate (490 mg, 2.31 mmol) in toluene:1,4-dioxane (2:1, 7.5 mL) was degassed and the catalyst premixture was added. The resultant mixture was stirred at 120° C. for 8 h in a sealed tube. After consumption of the starting material (monitored by TLC and LCMS), the reaction mixture was filtered and the filtrate was concentrated in vacuo. The crude material was purified by column chromatography using 5-8% MeOH: $CH_2Cl_2$ to afford 3-((6-methoxy-5-((4-methyl-1H-imidazol-1-yl) pyridin-2-yl)-5-(4-(trifluoromethoxy) phenyl)-5,6-dihydro-4H-1,2,4-oxadiazine (180 mg, 36%) as an off-white solid.

Racemic compound of Example 70 was separated using a Chiralpak-IB column (250×20 mm, 5 μm) (48 mg loading; 0.1% DEA in n-Hexane: $CH_2Cl_2$:MeOH (50:50) (A:B: 80:20) as mobile phase; flow rate: 18 mL/min) to afford the compounds of Example 70A (Fraction (I) (−)) and Example 70B (Fraction (II) (+)).

Analytical conditions for Example 70A and Example 70B: HPLC (column; zorbax-SB-C-18 150×4.6 mm, 3.5μ), mobile Phase: ACN: 0.05% Aq TFA; flow rate: 1.0 mL/min; Gradient program: T/B % 0.01/90, 2/90, 8/10, 15/10: diluent: $CH_3CN$:Water; Chiral HPLC: (Chiralpak-IB (250× 4.6 mm, 5 μm; mobile phase (A) 0.1% DEA in n-Hexane (B) $CH_2Cl_2$:MeOH (50:50) (A:B; 80:20); flow Rate: 1.0 mL/min).

Example 70A, (−)-3-(6-methoxy-5-(4-methyl-1H-imidazol-1-yl) pyridin-2-yl)-5-(4-(trifluoromethoxy) phenyl)-5,6-dihydro-4H-1,2,4-oxadiazine, fraction (I) (−): Mass (ESI): 434.3 [M+1]; HPLC (purity): 98.2%, RT 7.74 min; Chiral HPLC: 100%, RT=9.73 min; Optical rotation $[\alpha]_D^{19.98}$: −175.26 (c=0.25, $CH_2Cl_2$).

Example 70B, (+)-3-(6-methoxy-5-(4-methyl-1H-imidazol-1-yl) pyridin-2-yl)-5-(4-(trifluoromethoxy) phenyl)-5,6-dihydro-4H-1,2,4-oxadiazine, fraction (II) (+): $^1$H NMR ($CD_3OD$, 400 MHz): δ 7.95 (s, 1H), 7.87 (d, 1H), 7.64 (d, 1H), 7.50 (d, 2H), 7.30 (d, 2H), 7.11 (s, 1H), 4.91 (t, 1H), 4.12 (dd, 1H), 4.10 (s, 3H), 3.92 (dd, 1H), 2.25 (s, 3H); Mass (ESI): 434.3 [M+1]; HPLC (purity): 99.5%, RT 7.74 min; Chiral HPLC: 100%, RT=12.71 min; Optical rotation $[\alpha]_D^{19.99}$: +169.56 (c=0.25, $CH_2Cl_2$).

Example 71

Synthesis of 2-bromo-1-(5-chloro-1-ethyl-6-fluoro-1H-indol-3-yl) ethan-1-one

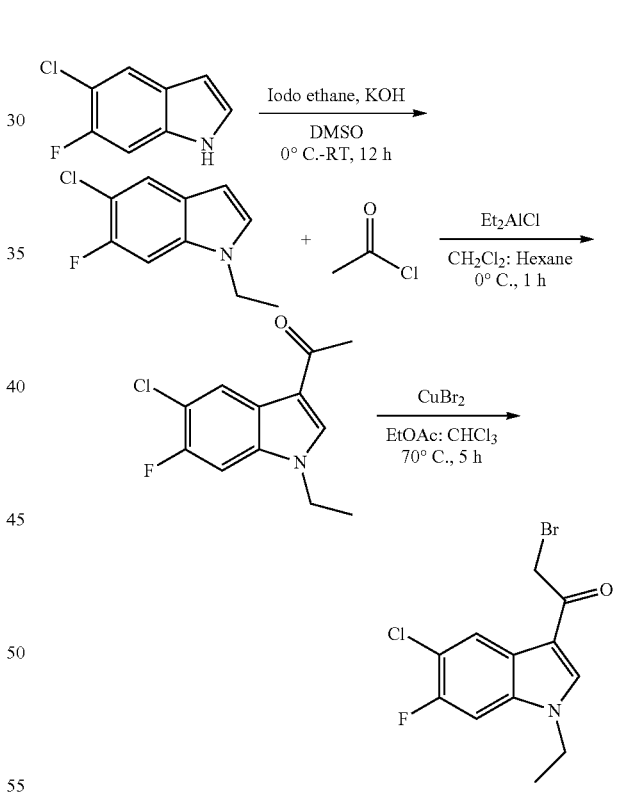

5-chloro-1-ethyl-6-fluoro-1H-indole

To a stirred solution of 5-chloro-6-fluoro-1H-indole (2 g, 12 mmol) in DMSO (10 mL) at 0° C. under an argon atmosphere were added potassium hydroxide (1 g, 18 mmol) and iodoethane (1.2 mL, 15 mmol). The reaction mixture was warmed to room temperature and stirred for 12 h. After consumption of starting material (monitored by TLC), the reaction mixture was diluted with water (50 mL) and extracted with EtOAc (2×50 mL). The combined organic extracts were dried over sodium sulfate, filtered and concentrated in vacuo. The crude material was purified by column chromatography using 5% EtOAc: Hexane to afford 5-chloro-1-ethyl-6-fluoro-1H-indole (2 g, 87%) as a pale yellow solid.

$^1$H NMR (CDCl$_3$, 400 MHz): δ 7.62 (d, 1H), 7.14 (d, 1H), 7.10 (s, 1H), 6.44 (dd, 1H), 4.15-4.10 (m, 2H), 1.48 (t, 3H); LCMS: 96.4%; 197.9 (M+1); (column; Ascentis Express C-18 (50×3.0 mm, 2.7 μm); RT 2.87 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 10% EtOAc/Hexane (R$_f$: 0.5).

1-(5-chloro-1-ethyl-6-fluoro-1H-indol-3-yl) ethan-1-one

To a stirred solution of 5-chloro-1-ethyl-6-fluoro-1H-indole (107 mg, 0.5 mmol) in CH$_2$Cl$_2$:Hexane (3:1, 4 mL) at 0° C. under an argon atmosphere was added Et$_2$AlCl (0.7 mL, 0.70 mmol). The reaction mixture was stirred for 5 min at 0° C. Then acetyl chloride (0.1 mL, 0.7 mmol) was added to the reaction mixture at 0° C. The reaction mixture was stirred for 1 h at 0° C. After consumption of starting material (monitored by TLC), the reaction mixture was diluted with saturated ammonium chloride solution (10 mL) and extracted with EtOAc (2×10 mL). The combined organic extracts were dried over sodium sulfate, filtered and concentrated in vacuo. The crude material was purified by column chromatography using 25% EtOAc: Hexane to afford 1-(5-chloro-1-ethyl-6-fluoro-1H-indol-3-yl) ethan-1-one (80 mg, 61%) as an off-white solid.

$^1$H NMR (DMSO-d$_6$, 400 MHz): δ 8.48 (s, 1H), 8.24 (d, 1H), 7.80 (d, 1H), 4.29-4.21 (m, 2H), 2.42 (s, 3H), 1.40 (t, 3H); LCMS: 98.7%; 239.9 (M+1); (column; Ascentis Express C-18 (50×3.0 mm, 2.7 μm); RT 2.49 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 40% EtOAc/Hexane (R$_f$: 0.4).

2-bromo-1-(5-chloro-1-ethyl-6-fluoro-1H-indol-3-yl) ethan-1-one

To a stirred solution of 1-(5-chloro-1-ethyl-6-fluoro-1H-indol-3-yl) ethan-1-one (100 mg, 0.4 mmol) in EtOAc:chloroform (4:1, 8 mL) at room temperature under an argon atmosphere was added copper bromide (186 mg, 0.8 mmol). The reaction mixture was stirred at 70° C. for 5 h. After consumption of starting material (monitored by TLC), the reaction mixture was filtered, the filtrate was concentrated in vacuo. The crude material was purified by column chromatography using 15% EtOAc: Hexane to afford 2-bromo-1-(5-chloro-1-ethyl-6-fluoro-1H-indol-3-yl) ethan-1-one (50 mg, 38%) as yellow solid.

$^1$H NMR (CDCl$_3$, 400 MHz): δ 8.43 (d, 1H), 7.88 (s, 1H), 7.15 (d, 1H), 4.26 (s, 2H), 4.20-4.13 (m, 2H), 1.56 (t, 3H); LCMS: 92.1%; 317.8 (M+1); (column; Ascentis Express C-18 (50×3.0 mm, 2.7 μm); RT 2.72 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 40% EtOAc/Hexane (R$_f$: 0.5).

Example 72

Synthesis of 3-(5-bromo-6-methoxypyridin-2-yl)-5-(5-chloro-1-ethyl-6-fluoro-1H-indol-3-yl)-5,6-dihydro-4H-1,2,4-oxadiazine

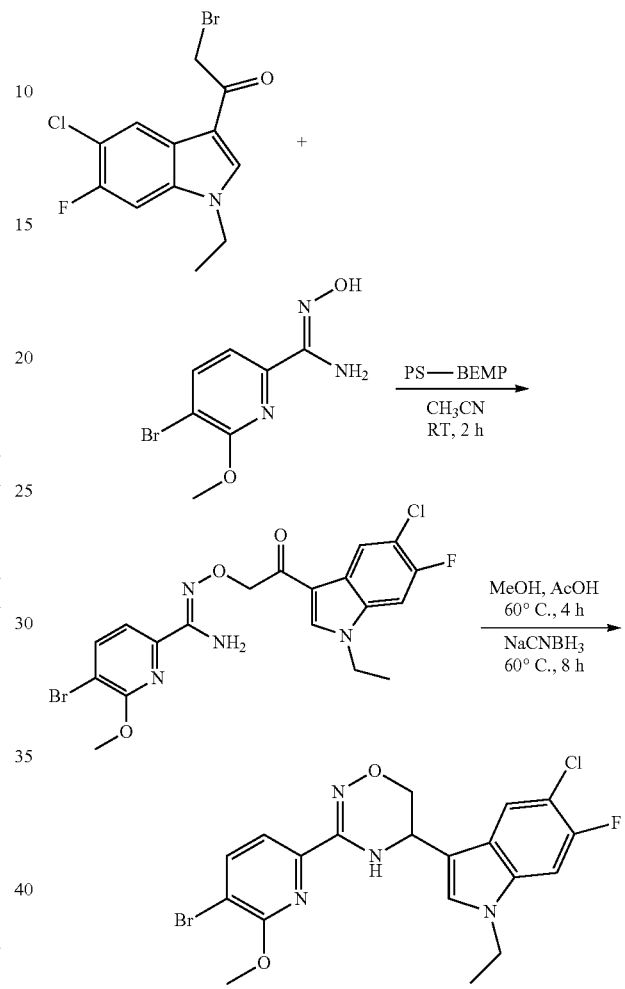

(Z)-5-bromo-N'-(2-(5-chloro-1-ethyl-6-fluoro-1H-indol-3-yl)-2-oxoethoxy)-6-methoxypicolinimidamide To a stirred solution of 5-bromo-N'-hydroxy-6-methoxypicolinimidamide (750 mg, 3 mmol) in CH$_3$CN (5 mL) at room temperature under an argon atmosphere was added PS-BEMP (998 mg, 4 mmol). The reaction mixture was stirred for 10 min at room temperature. Then 2-bromo-1-(5-chloro-1-ethyl-6-fluoro-1H-indol-3-yl) ethan-1-one (1.45 g, 5 mmol) in CH$_3$CN (10 mL) was added to the reaction mixture at room temperature. The reaction mixture was stirred at room temperature for 2 h. After consumption of starting material (monitored by TLC), the reaction mixture was filtered and the filtrate was concentrated in vacuo to afford (Z)-5-bromo-N'-(2-(5-chloro-1-ethyl-6-fluoro-1H-indol-3-yl)-2-oxoethoxy)-6-methoxypicolinimidamide (1.1 g, crude) as a pale yellow syrup used in the next step without further purification.

LCMS: 59.0%; 484.7 (M+3); (column; Ascentis Express C-18 (50×3.0 mm, 2.7 μm); RT 2.97 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 40% EtOAc/Hexane ($R_f$: 0.3).

3-(5-bromo-6-methoxypyridin-2-yl)-5-(5-chloro-1-ethyl-6-fluoro-1H-indol-3-yl)-5,6-dihydro-4H-1,2,4-oxadiazine To a stirred solution of (Z)-5-bromo-N'-(2-(5-chloro-1-ethyl-6-fluoro-1H-indol-3-yl)-2-oxoethoxy)-6-methoxypicolinimidamide (1.1 g, crude) in MeOH (20 mL) at room temperature under an argon atmosphere was added acetic acid (5 mL). The reaction mixture was stirred for 4 h at 60° C. Then sodium cyanoborohydride (430 mg) was added to the reaction mixture at room temperature. The reaction mixture was stirred at 60° C. for 8 h. After consumption of starting material (monitored by TLC), the reaction mixture was diluted with a saturated sodium carbonate solution (50 mL) and extracted with EtOAc (2×50 mL). The combined organic extracts were dried over sodium sulfate, filtered and concentrated in vacuo. The crude material was purified by column chromatography using 10% EtOAc: Hexane to afford 3-(5-bromo-6-methoxypyridin-2-yl)-5-(5-chloro-1-ethyl-6-fluoro-1H-indol-3-yl)-5,6-dihydro-4H-1,2,4-oxadiazine (1 g, crude) as a pale yellow syrup.

LCMS: 41.1%; 468.8 (M+3); (column; Ascentis Express C-18 (50×3.0 mm, 2.7 µm); RT 2.95 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.5).

Example 73

Synthesis of 5-(5-chloro-1-ethyl-6-fluoro-1H-indol-3-yl)-3-(6-methoxy-5-(4-methyl-1H-imidazol-1-yl)pyridin-2-yl)-5,6-dihydro-4H-1,2,4-oxadiazine

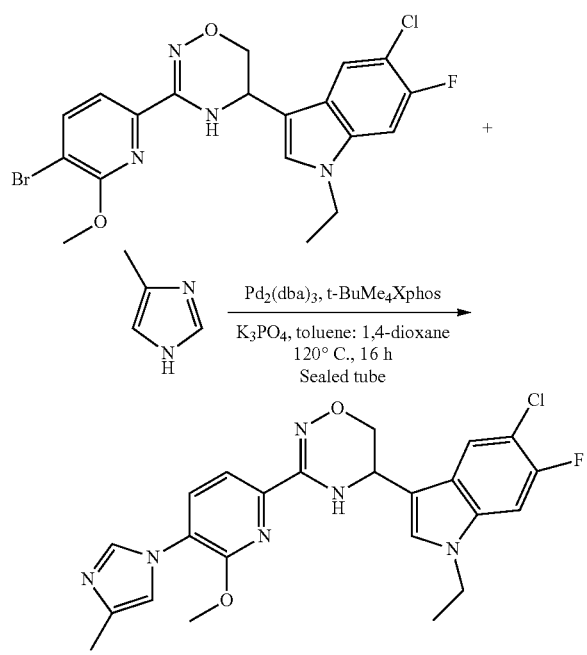

5-(5-chloro-1-ethyl-6-fluoro-1H-indol-3-yl)-3-(6-methoxy-5-(4-methyl-1H-imidazol-1-yl) pyridin-2-yl)-5,6-dihydro-4H-1,2,4-oxadiazine To a dry vial was added a suspension of $Pd_2(dba)_3$ (98 mg, 0.1 mmol) and tert-butyl tetramethyl Xphos (103 mg, 0.2 mmol) in toluene:1,4-dioxane (2:1, 4.5 mL) at room temperature. The suspension was degassed with argon, heated to 120° C., and stirred at 120° C. for 3 min. A mixture of 3-(5-bromo-6-methoxypyridin-2-yl)-5-(5-chloro-1-ethyl-6-fluoro-1H-indol-3-yl)-5,6-dihydro-4H-1, 2, 4-oxadiazine (1 g, 2.1 mmol), 4-methyl-1H-imidazole (211 mg, 3.0 mmol) and potassium phosphate (909 mg, 2.0 mmol) in toluene:1, 4-dioxane (2:1, 2.5 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo. The crude material was purified by column chromatography using 5% MeOH: $CH_2Cl_2$ to afford 5-(5-chloro-1-ethyl-6-fluoro-1H-indol-3-yl)-3-(6-methoxy-5-(4-methyl-1H-imidazol-1-yl) pyridin-2-yl)-5,6-dihydro-4H-1,2,4-oxadiazine (200 mg, 20%) as an off-white solid.

Racemic compound of Example 73 was separated using a Chiralpak-IB column (250×20 mm, 5 µm) (30 mg loading; 0.1% DEA in n-Hexane: $CH_2Cl_2$:MeOH (80:20) (A:B: 80:20) as mobile phase; flow rate: 18 mL/min) to afford the compounds of Example 73A (Fraction (I) (−)) and Example 73B (Fraction (II) (+)).

Analytical conditions for Example 73A and Example 73B: HPLC (column; zorbax-SB-C-18 150×4.6 mm, 3.5µ), mobile Phase: ACN: 0.05% Aq TFA; flow rate: 1.0 mL/min; Gradient program: T/B % 0.01/90, 2/90, 8/10, 15/10: diluent: $CH_3CN$:Water; Chiral HPLC: (Chiralpak-IB (250× 4.6 mm, 5 µm; mobile phase (A) 0.1% DEA in n-Hexane (B) $CH_2Cl_2$:MeOH (80:20) (A:B; 80:20); flow Rate: 1.0 mL/min).

Example 73A, (−)-5-(5-chloro-1-ethyl-6-fluoro-1H-indol-3-yl)-3-(6-methoxy-5-(4-methyl-1H-imidazol-1-yl) pyridin-2-yl)-5,6-dihydro-4H-1,2,4-oxadiazine, fraction (I) (−): Mass (ESI): 469.6 [M+1]; HPLC (purity): 96.5%, RT 7.93 min; Chiral HPLC: 96.0%, RT=21.92 min; Optical rotation $[\alpha]_D^{19.99}$: −109.68 (c=0.25, $CH_2Cl_2$).

Example 73B, (+)-5-(5-chloro-1-ethyl-6-fluoro-1H-indol-3-yl)-3-(6-methoxy-5-(4-methyl-1H-imidazol-1-yl) pyridin-2-yl)-5,6-dihydro-4H-1,2,4-oxadiazine, fraction (II) (+): $^1$H NMR ($CD_3OD$, 400 MHz): δ 7.97 (s, 1H), 7.89 (d, 1H), 7.76 (d, 1H), 7.66 (d, 1H), 7.38 (s, 1H), 7.35 (d, 1H), 7.21 (s, 1H), 5.10 (dd, 1H), 4.23-4.15 (m, 3H), 4.03 (s, 3H), 4.02-3.96 (m, 1H), 2.25 (s, 3H), 1.42 (t, 3H); Mass (ESI): 469.6 [M+1]; HPLC (purity): 99.7%, RT 7.93 min; Chiral HPLC: 96.2%, RT=24.50 min; Optical rotation $[\alpha]_D^{20.01}$: +110.59 (c=0.25, $CH_2Cl_2$).

Example 74

Synthesis of 3-(5-bromo-6-methoxypyridin-2-yl)-5-(3,4-difluorophenyl)-5,6-dihydro-4H-1,2,4-oxadiazine

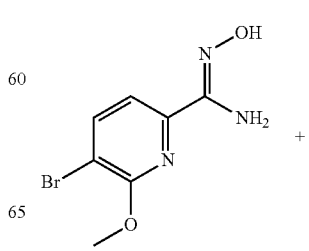

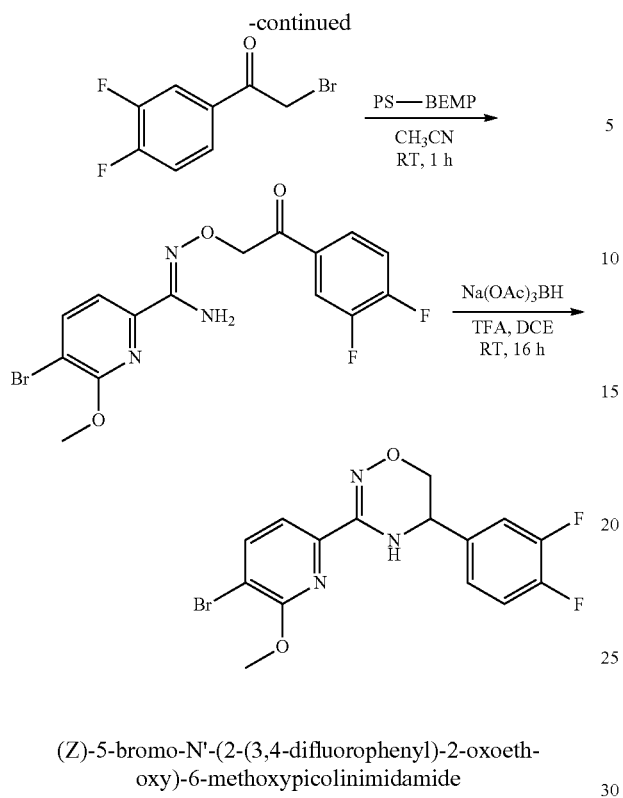

(Z)-5-bromo-N'-(2-(3,4-difluorophenyl)-2-oxoethoxy)-6-methoxypicolinimidamide

To a stirred solution of 5-bromo-N'-hydroxy-6-methoxypicolinimidamide (500 mg, 2 mmol) in CH₃CN (20 mL) at room temperature under an argon atmosphere was added PS-BEMP (665 mg, 2 mmol). The reaction mixture was stirred for 10 min at room temperature. Then 2-bromo-1-(3,4-difluorophenyl) ethan-1-one (716 mg, 3 mmol) in CH₃CN (5 mL) was added to the reaction mixture at room temperature. The reaction mixture was stirred at room temperature for 1 h. After consumption of starting material (monitored by TLC), the reaction mixture was filtered, and the filtrate was concentrated in vacuo to afford (Z)-5-bromo-N'-(2-(3,4-difluorophenyl)-2-oxoethoxy)-6-methoxypicolinimidamide (650 mg, crude) as a brown syrup, used in the next step without further purification.

LCMS: 29.8%; 399.9 (M+); (column; Ascentis Express C-18 (50×3.0 mm, 2.7 μm); RT 2.81 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane ($R_f$: 0.5).

3-(5-bromo-6-methoxypyridin-2-yl)-5-(3,4-difluorophenyl)-5,6-dihydro-4H-1,2,4-oxadiazine To a stirred solution of (Z)-5-bromo-N'-(2-(3, 4-difluorophenyl)-2-oxoethoxy)-6-methoxypicolinimidamide (650 mg, 2 mmol) in 1,2-dichloro ethane (20 mL) at room temperature under an argon atmosphere were added trifluoroacetic acid (0.12 mL, 1.6 mmol) and sodium triacetoxyborohydride (686 mg, 3 mmol). The reaction mixture was stirred for 16 h at room temperature. After consumption of starting material (monitored by TLC), the reaction mixture was diluted with a saturated sodium carbonate solution (20 mL) and extracted with CH₂Cl₂ (2×20 mL). The combined organic extracts were dried over sodium sulfate, filtered and concentrated in vacuo to afford 3-(5-bromo-6-methoxypyridin-2-yl)-5-(3,4-difluorophenyl)-5,6-dihydro-4H-1,2,4-oxadiazine (270 mg, 43%) as a pale yellow solid.

LCMS: 24.2%; 383.8 (M+1); (column; Ascentis Express C-18 (50×3.0 mm, 2.7 μm); RT 2.69 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane ($R_f$: 0.5).

Example 75

Synthesis of 5-(3,4-difluorophenyl)-3-(6-methoxy-5-(4-methyl-1H-imidazol-1-yl) pyridin-2-yl)-5,6-dihydro-4H-1,2,4-oxadiazine

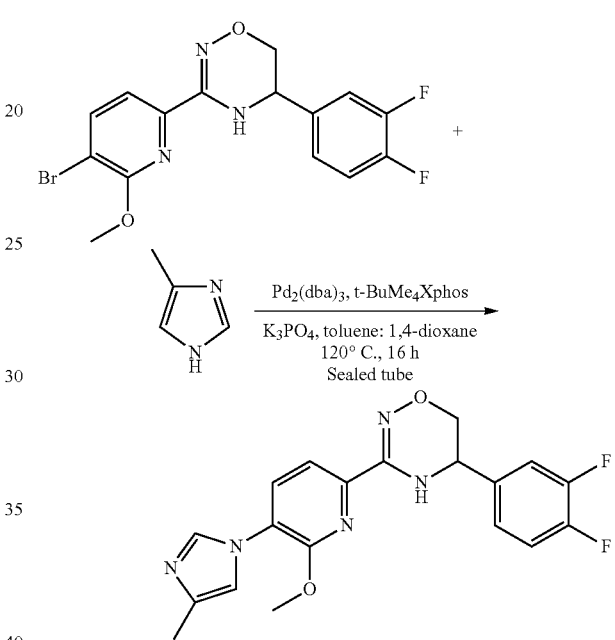

5-(3, 4-difluorophenyl)-3-(6-methoxy-5-(4-methyl-1H-imidazol-1-yl) pyridin-2-yl)-5,6-dihydro-4H-1,2, 4-oxadiazine To a dry vial was added a suspension of Pd₂(dba)₃ (30 mg, 0.03 mmol) and tert-butyl tetramethyl Xphos (32 mg, 0.45 mmol) in toluene:1,4-dioxane (2:1, 3.5 mL) at room temperature. The suspension was degassed with argon, heated to 120° C., and stirred at 120° C. for 3 min. A mixture of 3-(5-bromo-6-methoxypyridin-2-yl)-5-(3, 4-difluorophenyl)-5,6-dihydro-4H-1, 2, 4-oxadiazine (260 mg, 0.7 mmol), 4-methyl-1H-imidazole (83 mg, 1.0 mmol) and potassium phosphate (285 mg, 1.3 mmol) in toluene:1,4-dioxane (2:1, 3.5 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo The crude material was purified by column chromatography using 3-5% MeOH: CH₂Cl₂ to afford 5-(3, 4-difluorophenyl)-3-(6-methoxy-5-(4-methyl-1H-imidazol-1-yl) pyridin-2-yl)-5,6-dihydro-4H-1,2,4-oxadiazine (130 mg, 50%) as an off-white solid.

Racemic compound of Example 75 was separated using a Chiralpak-AD-H column (250×20 mm, 5 μm) (19 mg loading; 0.1% DEA in n-Hexane: EtOH:MeOH (50:50) (A:B: 65:35); as mobile phase flow rate: 18 mL/mm) to afford the compounds of Example 75A (Fraction (I) (−)) and Example 75B (Fraction (II) (+)).

Analytical conditions for Example 75A and Example 75B: HPLC (column; zorbax-SB-C-18 150×4.6 mm, 3.5μ), mobile Phase: ACN: 0.05% Aq TFA; flow rate: 1.0 mL/min; Gradient program: T/B % 0.01/90, 2/90, 8/10, 15/10: diluent: CH$_3$CN:Water; Chiral HPLC: (Chiralpak-ADH (250×4.6 mm, 5 μm; mobile phase (A) 0.1% DEA in n-Hexane (B) EtOH:MeOH (50:50) (A:B; 65:35); flow Rate: 1.0 mL/min).

Example 75A, (−)-5-(3,4-difluorophenyl)-3-(6-methoxy-5-(4-methyl-1H-imidazol-1-yl) pyridin-2-yl)-5,6-dihydro-4H-1,2,4-oxadiazine, fraction (I) (−): Mass (ESI): 386 [M+1]; HPLC (purity): 99.6%, RT 7.29 min; Chiral HPLC: 100%, RT=7.12 mm; Optical rotation $[α]_D^{20.00}$: −136.57 (c=0.25, CH$_2$Cl$_2$).

Example 75B, (+)-5-(3,4-difluorophenyl)-3-(6-methoxy-5-(4-methyl-1H-imidazol-1-yl) pyridin-2-yl)-5,6-dihydro-4H-1,2,4-oxadiazine, fraction (II) (+): $^1$H NMR (CD$_3$OD, 400 MHz): δ 7.95 (s, 1H), 7.89 (d, 1H), 7.65 (d, 1H), 7.30-7.23 (m, 2H), 7.21-7.11 (m, 2H), 4.89 (t, 1H), 4.10 (s, 3H), 4.08 (dd, 1H), 3.98 (dd, 1H), 2.23 (s, 3H); Mass (ESI): 386 [M+1]; HPLC (purity): 99.0%, RT 7.29 min; Chiral HPLC: 100%, RT=11.97 min; Optical rotation $[α]_D^{19.99}$: +143.45 (c=0.25, CH$_2$Cl$_2$).

Example 76

Synthesis of 2-bromo-1-(6-chlorobenzofuran-2-yl) ethan-1-one

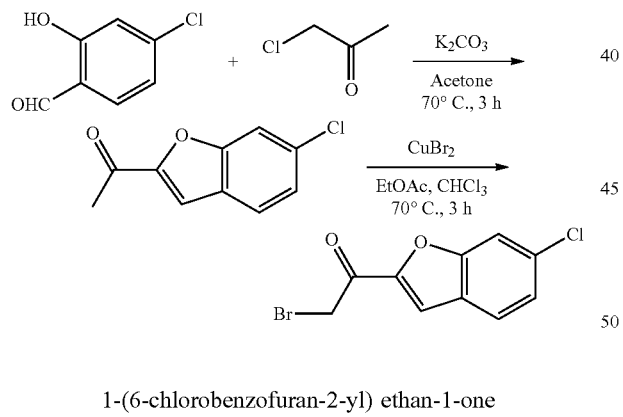

1-(6-chlorobenzofuran-2-yl) ethan-1-one

To a stirred solution of 4-chloro-2-hydroxybenzaldehyde (1 g, 6 mmol) in acetone (10 mL) at room temperature under an argon atmosphere were added potassium carbonate (1.3 g, 10 mmol) and 1-chloropropan-2-one (0.58 mL, 7 mmol). The reaction mixture was stirred at 70° C. for 3 h. After consumption of starting material (monitored by TLC), the volatiles were evaporated in vacuo. The crude material was purified by column chromatography using 5% EtOAc: Hexane to afford 1-(6-chlorobenzofuran-2-yl) ethan-1-one (900 mg, 72%) as white solid.

$^1$H NMR (CDCl$_3$, 500 MHz): δ 7.63 (d, 1H), 7.60 (s, 1H), 7.47 (s, 1H), 7.31 (dd, 1H), 2.61 (s, 3H); TLC: 10% EtOAc/Hexane (R$_f$: 0.3).

2-bromo-1-(6-chlorobenzofuran-2-yl) ethan-1-one

To a stirred solution of 1-(6-chlorobenzofuran-2-yl) ethan-1-one (500 mg, 3 mmol) in chloroform (8 mL) at room temperature under an argon atmosphere was added copper bromide (1.14 g, 5 mmol) in EtOAc (32 mL). The reaction mixture was stirred at 70° C. for 3 h. After consumption of starting material (monitored by TLC), the reaction mixture was filtered. The filtrate was concentrated in vacuo. The crude material was purified by column chromatography using 30% EtOAc: Hexane to afford 2-bromo-1-(6-chlorobenzofuran-2-yl) ethan-1-one (370 mg, 53%) as white solid.

$^1$H NMR (CDCl$_3$, 500 MHz): δ 7.67 (d, 1H), 7.65 (s, 1H), 7.62 (s, 1H), 7.35 (dd, 1H), 4.42 (s, 2H); TLC: 20% CH$_2$Cl$_2$/Hexane (R$_f$: 0.5).

Example 77

Synthesis of 3-(5-bromo-6-methoxypyridin-2-yl)-5-(6-chlorobenzofuran-2-yl)-5,6-dihydro-4H-1,2,4-oxadiazine

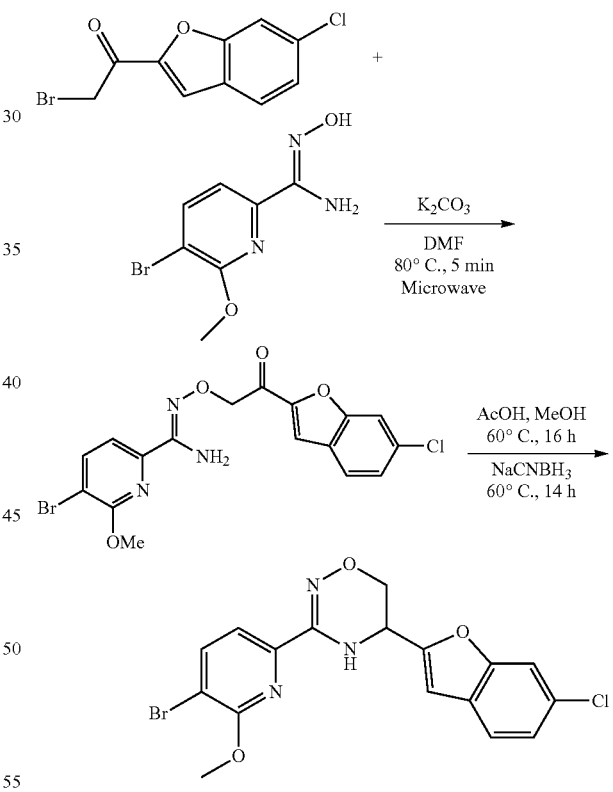

(Z)-5-bromo-N'-(2-(6-chlorobenzofuran-2-yl)-2-oxoethoxy)-6-methoxypicolinimidamide To a stirred solution of 5-bromo-N'-hydroxy-6-methoxypicolinimidamide (40 mg, 0.2 mmol) in DMF (0.4 mL) at room temperature under an argon atmosphere were added potassium carbonate (33 mg, 0.24 mmol) and 2-bromo-1-(6-chlorobenzofuran-2-yl) ethan-1-one (53 mg, 0.2 mmol). The reaction mixture was stirred at 80° C. for 5 min in microwave. After consumption of starting material (monitored by TLC), the reaction mixture was diluted with water (10 mL) and extracted with EtOAc (2×10 mL). The combined organic extracts were dried over sodium sulfate, filtered and concentrated in vacuo to afford (Z)-5-bromo-N'-(2-(6-chlorobenzofuran-2-yl)-2-oxoethoxy)-6-methoxypicolinimidamide (60 mg, crude) as brown syrup used in the next step without further purification.

LCMS: 36.3%; 439.7 (M+2); (column; Ascentis Express C-18 (50×3.0 mm, 2.7 μm); RT 3.01 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.3).

3-(5-bromo-6-methoxypyridin-2-yl)-5-(6-chlorobenzofuran-2-yl)-5,6-dihydro-4H-1,2,4-oxadiazine To a stirred solution of (Z)-5-bromo-N'-(2-(6-chlorobenzofuran-2-yl)-2-oxoethoxy)-6-methoxypicolinimidamide (400 mg, 1.0 mmol) in MeOH (12 mL) at room temperature under an argon atmosphere were added acetic acid (0.6 mL). The reaction mixture was stirred for 16 h at 60° C. Then sodium cyanoborohydride (230 mg, 4 mmol) was added to the reaction mixture at room temperature. The reaction mixture was stirred at 60° C. for 14 h. After consumption of starting material (monitored by TLC), the reaction mixture was diluted with water (20 mL) and extracted with EtOAc (2×20 mL). The combined organic extracts were washed with water (20 mL), dried over sodium sulfate, filtered and concentrated in vacuo to afford 3-(5-bromo-6-methoxypyridin-2-yl)-5-(6-chlorobenzofuran-2-yl)-5,6-dihydro-4H-1,2,4-oxadiazine (400 mg, crude) as white solid. LCMS: 42.4%; 423.7 (M+3); (column; Ascentis Express C-18 (50×3.0 mm, 2.7 μm); RT 2.93 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.3).

Example 78

Synthesis of 5-(6-chlorobenzofuran-2-yl)-3-(6-methoxy-5-(4-methyl-1H-imidazol-1-yl) pyridin-2-yl)-5,6-dihydro-4H-1,2,4-oxadiazine

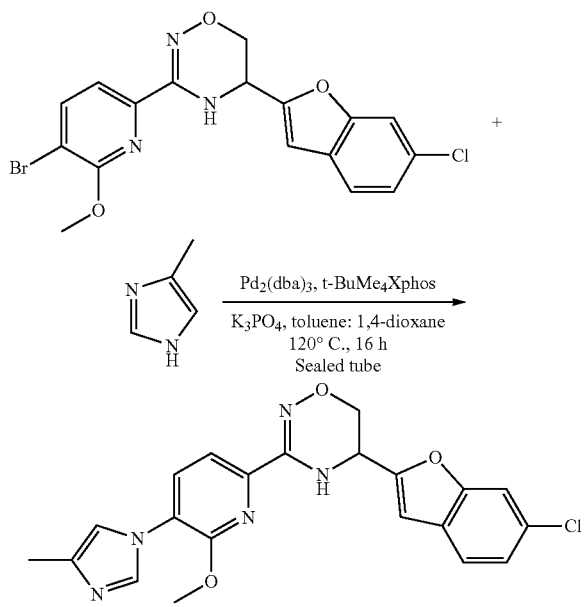

5-(6-chlorobenzofuran-2-yl)-3-(6-methoxy-5-(4-methyl-1H-imidazol-1-yl) pyridin-2-yl)-5,6-dihydro-4H-1,2,4-oxadiazine To a dry vial was added a suspension of $Pd_2(dba)_3$ (43 mg, 0.05 mmol) and tert-butyl tetramethyl Xphos (29 mg, 0.03 mmol) in toluene:1,4-dioxane (2:1, 2.25 mL) at room temperature. The suspension was degassed with argon, heated to 120° C., and stirred at 120° C. for 3 min. A mixture of 3-(5-bromo-6-methoxypyridin-2-yl)-5-(4-chlorobenzofuran-2-yl)-5,6-dihydro-4H-1,2,4-oxadiazine (260 mg, 1.0 mmol), 4-methyl-1H-imidazole (60 mg, 1.0 mmol) and potassium phosphate (260 mg, 1.22 mmol) in toluene:1,4-dioxane (2:1, 2.25 mL) was degassed and the catalyst premixture was added. The resultant mixture was stirred at 120° C. for 12 h in a sealed tube. After consumption of the starting material (monitored by TLC and LCMS), the volatiles were evaporated in vacuo. The crude material was purified by column chromatography using 2% MeOH: $CH_2Cl_2$ to afford 5-(6-chlorobenzofuran-2-yl)-3-(6-methoxy-5-(4-methyl-1H-imidazol-1-yl) pyridin-2-yl)-5,6-dihydro-4H-1,2,4-oxadiazine (50 mg, 22%) as a pale yellow solid.

Racemic compound of Example 78 was separated using a Chiralpak-IB column (250×20 mm, 5 μm) (30 mg loading; 0.1% DEA in n-Hexane: $CH_2Cl_2$:MeOH (50:50) (A:B: 80:20) as mobile phase; flow rate: 18 mL/min) to afford the compounds of Example 78A (Fraction (I) (−)) and Example 78B (Fraction (II) (+)).

Analytical conditions for Example 78A and Example 78B: HPLC (column; zorbax-SB-C-18 150×4.6 mm, 3.5μ), mobile Phase: ACN: 0.05% Aq TFA; flow rate: 1.0 mL/min; Gradient program: T/B % 0.01/90, 2/90, 8/10, 15/10: diluent: $CH_3CN$:Water; Chiral HPLC: (Chiralpak-IB (250× 4.6 mm, 5 μm; mobile phase (A) 0.1% DEA in n-Hexane (B) $CH_2Cl_2$:MeOH (50:50) (A:B; 80:20); flow Rate: 1.0 mL/min).

Example 78A, (−)-5-(6-chlorobenzofuran-2-yl)-3-(6-methoxy-5-(4-methyl-1H-imidazol-1-yl) pyridin-2-yl)-5,6-dihydro-4H-1,2,4-oxadiazine, fraction (I) (−): Mass (ESI): 424.3 [M+1]; HPLC (purity): 95.0%, RT 7.80 min; Chiral HPLC: 100%, RT=10.28 min; Optical rotation $[\alpha]_D^{20.00}$: −264.76 (c=0.25, $CH_2Cl_2$).

Example 78B, (+)-5-(6-chlorobenzofuran-2-yl)-3-(6-methoxy-5-(4-methyl-1H-imidazol-1-yl) pyridin-2-yl)-5,6-dihydro-4H-1,2,4-oxadiazine, fraction (II) (+): $^1$H NMR ($CD_3OD$, 400 MHz): δ 7.98 (s, 1H), 7.88 (d, 1H), 7.64 (d, 1H), 7.57-7.50 (m, 2H), 7.23 (dd, 2H), 6.76 (s, 1H), 5.08 (t, 1H), 4.40 (dd, 1H), 4.13 (s, 3H), 4.07 (dd, 1H), 2.26 (s, 3H); Mass (ESI): 424.3 [M+1]; HPLC (purity): 96.4%, RT 7.79 min; Chiral HPLC: 100%, RT=12.69 min; Optical rotation $[\alpha]_D^{19.99}$: +286.78 (c=0.25, $CH_2Cl_2$).

Example 79

Synthesis of 2-bromo-1-(3,5-difluorophenyl) ethan-1-one

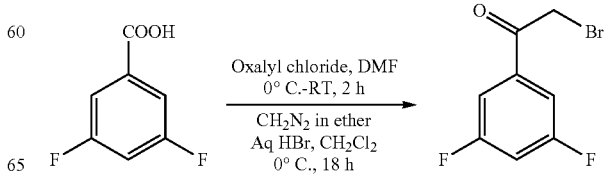

2-bromo-1-(3,5-difluorophenyl) ethan-1-one

To a stirred solution of 3,5-difluorobenzoic acid (10 g, 63 mmol) in $CH_2Cl_2$ (150 mL) at 0° C. under an argon atmosphere was added oxalyl chloride (5.4 mL, 63 mmol) and DMF (1 mL). The reaction mixture was warmed to room temperature and stirred for 2 h. After consumption of acid (monitored by TLC), the volatiles were evaporated in vacuo.

To a stirred solution of the above residue in ether at 0° C. under an argon atmosphere was added $CH_2N_2$ in ether solution (300 mL). The reaction mixture was stirred at 0° C. for 2 h. Then aq. HBr (20 mL) was added to the reaction mixture at 0° C. The reaction mixture was warmed to room temperature and stirred for 18 h. After consumption of the starting material (monitored by TLC), the reaction mixture was neutralized with saturated sodium bicarbonate solution (300 mL) and extracted with EtOAc (2×300 mL). The combined organic extract was washed with water (300 mL), brine (300 mL), dried over sodium sulfate, filtered and concentrated in vacuo to afford 2-bromo-1-(3,5-difluorophenyl) ethan-1-one (6.5 g, 44%) as a pale yellow liquid.

$^1$H NMR (CDCl$_3$, 400 MHz): δ 7.54-7.45 (m, 2H), 7.10-7.05 (m, 1H), 4.63 (s, 1H), 4.38 (s, 1H); TLC: 10% EtOAc/Hexanes (R$_f$: 0.7).

Example 80

Synthesis of 3-(5-bromo-6-methoxypyridin-2-yl)-5-(3,5-difluorophenyl)-5,6-dihydro-4H-1,2,4-oxadiazine

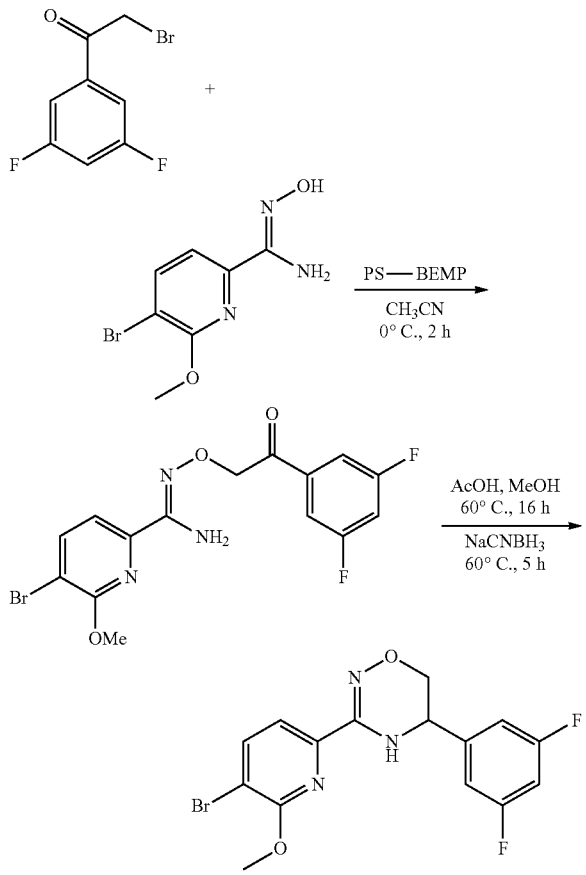

(Z)-5-bromo-N'-(2-(3,5-difluorophenyl)-2-oxoethoxy)-6-methoxypicolinimidamide

To a stirred solution of 5-bromo-N'-hydroxy-6-methoxypicolinimidamide (500 mg, 2 mmol) in CH$_3$CN (15 mL) at 0° C. under an argon atmosphere were added PS-BEMP (665 mg, 2 mmol). The reaction mixture was stirred for 10 min at 0° C. Then 2-bromo-1-(3, 5-difluorophenyl) ethan-1-one (716 mg, 3 mmol) in CH$_3$CN (10 mL) was added to the reaction mixture at 0° C. The reaction mixture was stirred for 2 h at 0° C. After consumption of starting material (monitored by TLC), the reaction mixture was filtered, washed with EtOAc (50 mL) and the filtrate was concentrated in vacuo to afford (Z)-5-bromo-N'-(2-(3, 5-difluorophenyl)-2-oxoethoxy)-6-methoxypicolinimidamide (650 mg, crude) as a brown syrup used in the next step without further purification.

LCMS: 38.4%; 399.8 (M+); (column; Ascentis Express C-18 (50×3.0 mm, 2.7 μm); RT 2.56 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.5).

3-(5-bromo-6-methoxypyridin-2-yl)-5-(3,5-difluorophenyl)-5,6-dihydro-4H-1,2,4-oxadiazine To a stirred solution of (Z)-5-bromo-N'-(2-(3,5-difluorophenyl)-2-oxoethoxy)-6-methoxypicolinimidamide (650 mg, 2.0 mmol) in MeOH (13.5 mL) at room temperature under an argon atmosphere was added acetic acid (2.5 mL). The reaction mixture was stirred for 16 h at 60° C. Then sodium cyanoborohydride (122 mg, 2.0 mmol) was added to the reaction mixture at room temperature. The reaction mixture was stirred at 60° C. for 5 h. After consumption of starting material (monitored by TLC), the volatiles were evaporated in vacuo. The residue was diluted with saturated sodium bicarbonate solution (20 mL) and extracted with EtOAc (2×20 mL). The combined organic extracts were dried over sodium sulfate, filtered and concentrated in vacuo to afford 3-(5-bromo-6-methoxypyridin-2-yl)-5-(3,5-difluorophenyl)-5,6-dihydro-4H-1,2,4-oxadiazine (325 mg, crude) as an off-white solid.

LCMS: 94.6%; 383.8 (M+); (column; Ascentis Express C-18 (50×3.0 mm, 2.7 μm); RT 2.71 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.5).

Example 81

Synthesis of 5-(3,5-difluorophenyl)-3-(6-methoxy-5-(4-methyl-1H-imidazol-1-yl) pyridin-2-yl)-5,6-dihydro-4H-1,2,4-oxadiazine

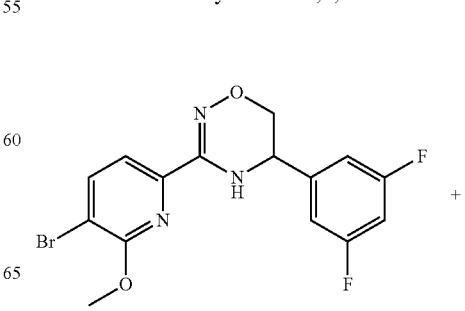

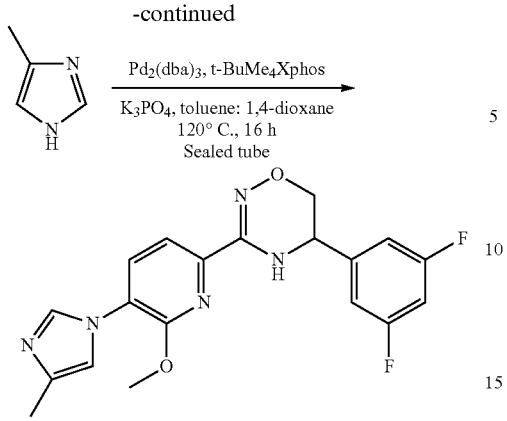

5-(3,5-difluorophenyl)-3-(6-methoxy-5-(4-methyl-1H-imidazol-1-yl) pyridin-2-yl)-5,6-dihydro-4H-1,2,4-oxadiazine To a dry vial was added a suspension of $Pd_2(dba)_3$ (36 mg, 0.04 mmol) and tert-butyl tetramethyl Xphos (56 mg, 0.11 mmol) in toluene:1,4-dioxane (2:1, 5.5 mL) at room temperature. The suspension was degassed with argon, heated to 120° C., and stirred at 120° C. for 3 min. A mixture of 3-(5-bromo-6-methoxypyridin-2-yl)-5-(3,5-difluorophenyl)-5,6-dihydro-4H-1,2,4-oxadiazine (300 mg, 1.0 mmol), 4-methyl-1H-imidazole (128 mg, 2 mmol) and potassium phosphate (330 mg, 2 mmol) in toluene:1,4-dioxane (2:1, 5.5 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo. The crude material was purified by column chromatography using 1-5% MeOH: $CH_2Cl_2$ to afford 5-(3,5-difluorophenyl)-3-(6-methoxy-5-(4-methyl-1H-imidazol-1-yl) pyridin-2-yl)-5,6-dihydro-4H-1,2,4-oxadiazine (130 g, 43%) as an off-white solid.

Racemic compound of Example 81 was separated using a Chiralpak-IB column (250×20 mm, 5 μm) (33.75 mg loading; 0.1% DEA in n-Hexane: $CH_2Cl_2$:MeOH (80:20) (A:B: 80:20) as mobile phase; flow rate: 18 mL/mm) to afford the compounds of Example 81A (Fraction (I) (−)) and Example 81B (Fraction (II) (+)).

Analytical conditions for Example 81A and Example 81B: HPLC (column; zorbax-SB-C-18 150×4.6 mm, 3.5μ), mobile Phase: ACN: 0.05% Aq TFA; flow rate: 1.0 mL/min; Gradient program: T/B % 0.01/90, 2/90, 8/10, 15/10: diluent: $CH_3CN$:Water; Chiral HPLC: (Chiralpak-IB (250× 4.6 mm, 5 μm; mobile phase (A) 0.1% DEA in n-Hexane (B) $CH_2Cl_2$:MeOH (80:20) (A:B; 80:20); flow Rate: 1.0 mL/min).

Example 81A, (−)-5-(3,5-difluorophenyl)-3-(6-methoxy-5-(4-methyl-1H-imidazol-1-yl) pyridin-2-yl)-5,6-dihydro-4H-1,2,4-oxadiazine, fraction (I) (−): Mass (ESI): 386.3 [M+1]; HPLC (purity): 99.3%, RT 7.29 min; Chiral HPLC: 98.9%, RT=15.46 min; Optical rotation $[\alpha]_D^{20.00}$: −19.3 (C=0.25, $CH_2Cl_2$).

Example 81B, (+)-5-(3,5-difluorophenyl)-3-(6-methoxy-5-(4-methyl-1H-imidazol-1-yl) pyridin-2-yl)-5,6-dihydro-4H-1,2,4-oxadiazine, fraction (II) (+): $^1$H NMR ($CD_3OD$, 400 MHz): δ 8.00 (br s, 1H), 7.89 (d, 1H), 7.65 (d, 1H), 7.24 (br s, 1H), 7.01 (dd, 2H), 6.95-6.83 (m, 1H), 4.91 (t, 1H), 4.11 (s, 3H), 4.04 (t, 2H), 2.25 (s, 3H); Mass (ESI): 386.3 [M+1]; HPLC (purity): 99.3%, RT 7.30 min; Chiral HPLC: 98.9%, RT=18.12 min; Optical rotation $[\alpha]_D^{19.99}$: +184.89 (c=0.25, $CH_2Cl_2$).

Example 82

Synthesis of 2-bromo-1-(5-fluorobenzofuran-2-yl)ethan-1-one

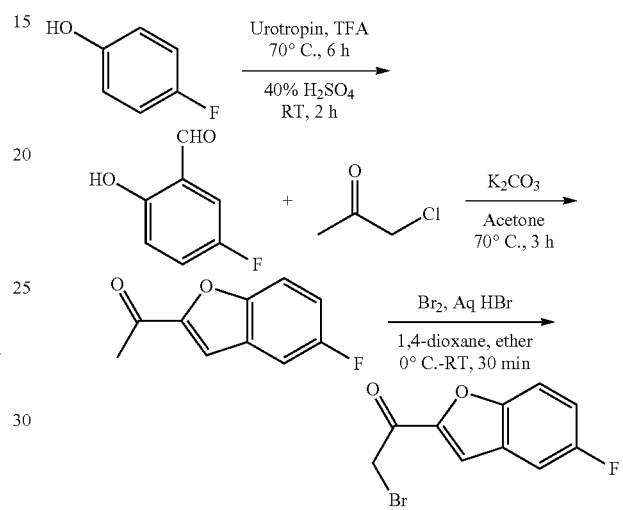

5-fluoro-2-hydroxybenzaldehyde

To a stirred solution of 4-fluorophenol (3 g, 27 mmol) in trifluoroacetic acid (18.6 mL) at room temperature under an argon atmosphere was added urotropin (7.5 g, 54 mmol). The reaction mixture was stirred for 6 h at 70° C. Then 40% $H_2SO_4$ (14 mL) was added to the reaction mixture at room temperature. The reaction mixture was stirred for 2 h at room temperature. After consumption of starting material (monitored by TLC), the reaction mixture was diluted with water (50 mL) and extracted with EtOAc (2×50 mL). The combined organic extracts were dried over sodium sulfate, filtered and concentrated in vacuo to afford 5-fluoro-2-hydroxybenzaldehyde (3.5 g, crude) as brown liquid.

$^1$H NMR ($CDCl_3$, 500 MHz): δ 9.86 (s, 1H), 8.84 (br s, 1H), 7.33-7.24 (m, 1H), 7.00-6.80 (m, 2H); TLC: 10% EtOAc/Hexane ($R_f$: 0.5).

1-(5-fluorobenzofuran-2-yl) ethan-1-one

To a stirred solution of 5-fluoro-2-hydroxybenzaldehyde (3.5 g, crude) in acetone (50 mL) at room temperature under an argon atmosphere were added potassium carbonate (12 g, 88 mmol) and chloro acetone (2.85 g, 30 mmol). The reaction mixture was stirred at 70° C. for 3 h. After consumption of starting material (monitored by TLC), the reaction mixture was filtered and the filterate was concentrated in vacuo. The crude material was purified by column chromatography using 5% EtOAc: Hexane to afford 1-(5-fluorobenzofuran-2-yl) ethan-1-one (900 mg, 20%) as brown solid.

$^1$H NMR (CDCl$_3$, 400 MHz): δ 7.54-7.51 (m, 1H), 7.47 (s, 1H), 7.36 (d, 1H), 7.24-7.19 (m, 1H), 2.61 (s, 3H); LCMS: 93.6%; 178.7 (M+1); (column; Ascentis Express C-18 (50×3.0 mm, 3.5 μm); RT 2.35 min 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 10% EtOAc/Hexane (R$_f$: 0.5).

2-bromo-1-(5-fluorobenzofuran-2-yl) ethan-1-one

To a stirred solution of 1-(5-fluorobenzofuran-2-yl) ethan-1-one (800 mg, 5) in ether:1,4-dioxane (1:5) (96 mL) at 0° C. under an argon atmosphere were added HBr (1 mL) and bromine (0.27 mL, 5 mmol). The reaction mixture was warmed to room temperature and stirred for 30 min. After consumption of starting material (monitored by TLC), the reaction mixture was diluted with water (20 mL) and extracted with ether (2×20 mL). The combined organic extracts were dried over sodium sulfate, filtered and concentrated in vacuo. The crude material was purified by column chromatography using 3% EtOAc: Hexane to afford 2-bromo-1-(5-fluorobenzofuran-2-yl) ethan-1-one (750 mg, 65%) as brown solid.

$^1$H NMR (CDCl$_3$, 400 MHz): δ 7.61 (s, 1H), 7.59-7.54 (m, 1H), 7.38 (dd, 1H), 7.27 (t, 1H), 4.41 (s, 2H); TLC: 5% EtOAc/Hexane (R$_f$: 0.5).

Example 83

Synthesis of 3-(5-bromo-6-methoxypyridin-2-yl)-5-(5-fluorobenzofuran-2-yl)-5,6-dihydro-4H-1,2,4-oxadiazine

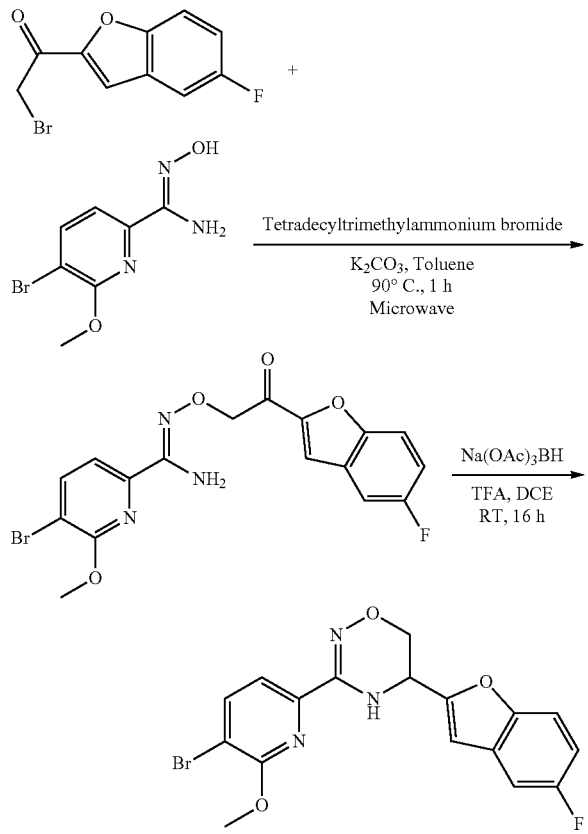

(Z)-5-bromo-N'-(2-(5-fluorobenzofuran-2-yl)-2-oxoethoxy)-6-methoxypicolinimidamide To a stirred solution of 5-bromo-N'-hydroxy-6-methoxypicolinimidamide (500 mg, 2 mmol) in toluene (12.5 mL) at room temperature under an argon atmosphere were added tetradecyl trimethyl ammonium bromide (341 mg, 1 mmol), 2-bromo-1-(5-fluorobenzofuran-2-yl) ethan-1-one (783 mg, 3 mmol) and potassium carbonate (280 mg, 2 mmol). The reaction mixture was stirred for 10 min at 90° C. in microwave. After consumption of starting material (monitored by TLC), the reaction mixture was diluted with water (20 mL) and extracted with EtOAc (2×20 mL). The combined organic extracts were dried over sodium sulfate, filtered and concentrated in vacuo to afford (Z)-5-bromo-N'-(2-(5-fluorobenzofuran-2-yl)-2-oxoethoxy)-6-methoxypicolinimidamide (750 mg, crude) as colorless thick syrup.

LCMS: 14.2%; 423.7 (M+1); (column; Ascentis Express C-18 (50×3.0 mm, 2.7 μm); RT 2.46 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane (R$_f$: 0.5).

3-(5-bromo-6-methoxypyridin-2-yl)-5-(5-fluorobenzofuran-2-yl)-5,6-dihydro-4H-1,2,4-oxadiazine To a stirred solution of (Z)-5-bromo-N'-(2-(5-fluorobenzofuran-2-yl)-2-oxoethoxy)-6-methylpicolinimidamide (750 mg, crude) in dichloroethane (15 mL) at room temperature under an argon atmosphere were added trifluoroacetic acid (0.68 mL, 9.0 mmol) and sodium triacetoxyborohydride (1.13 g, 5.3 mmol). The reaction mixture was stirred for 16 h at room temperature. After consumption of starting material (monitored by TLC), the reaction mixture was diluted with water (20 mL) and extracted with EtOAc (2×20 mL). The combined organic extracts were dried over sodium sulfate, filtered and concentrated in vacuo to afford 3-(5-bromo-6-methoxypyridin-2-yl)-5-(5-fluorobenzofuran-2-yl)-5,6-dihydro-4H-1,2,4-oxadiazine (300 mg, 36%) as colorless thick syrup.

LCMS: 64.7%; 407.8 (M+1); (column; Ascentis Express C-18 (50×3.0 mm, 2.7 μm); RT 2.79 min; mobile phase: 0.025% Aq TFA+5% ACN: ACN+5% 0.025% Aq TFA; T/B %: 0.01/30, 0.5/30, 5/100, 6/100; flow rate: 1.2 mL/min) (Gradient); TLC: 20% EtOAc/Hexane (R$_f$: 0.4).

Example 84

Synthesis of 5-(5-fluorobenzofuran-2-yl)-3-(6-methoxy-5-(4-methyl-1H-imidazol-1-yl) pyridin-2-yl)-5,6-dihydro-4H-1,2,4-oxadiazine

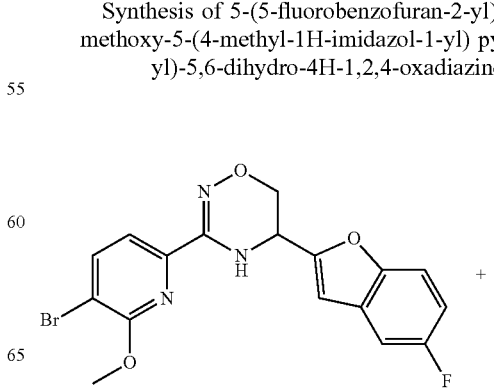

-continued

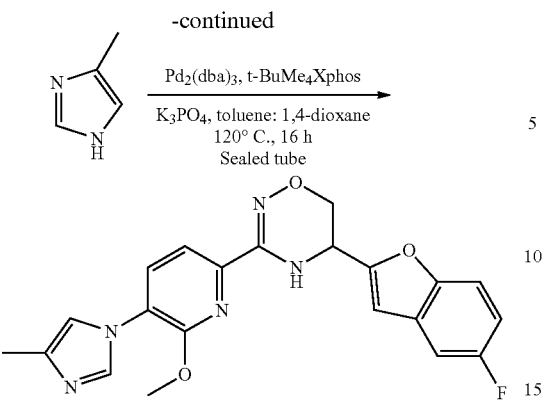

5-(5-fluorobenzofuran-2-yl)-3-(6-methoxy-5-(4-methyl-1H-imidazol-1-yl) pyridin-2-yl)-5,6-dihydro-4H-1,2,4-oxadiazine To a dry vial was added a suspension of Pd₂(dba)₃ (45 mg, 0.05 mmol) and tert-butyl tetramethyl Xphos (47 mg, 0.09 mmol) in toluene:1,4-dioxane (2:1, 6 mL) at room temperature. The suspension was degassed with argon, heated to 120° C., and stirred at 120° C. for 3 min. A mixture of 3-(5-bromo-6-methoxypyridin-2-yl)-5-(5-fluorobenzofuran-2-yl)-5,6-dihydro-4H-1, 2, 4-oxadiazine (400 mg, 1.0 mmol), 4-methyl-1H-imidazole (121 mg, 1.0 mmol) and potassium phosphate (417 mg, 2.0 mmol) in toluene:1,4-dioxane (2:1, 6 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo. The crude material was purified by preparative HPLC (Column YMC triart C18 column (250×20 mm, 5 μm (60 mg loading; CH₃CN: 005% TFA (0.1/90, 2/90, 15/70, 25/35, 30/10, 40/10); flow rate: 15 mL/min) to afford 5-(5-fluorobenzofuran-2-yl)-3-(6-methoxy-5-(4-methyl-1H-imidazol-1-yl) pyridin-2-yl)-5,6-dihydro-4H-1,2,4-oxadiazine (110 mg, 27%) as brown solid.

Racemic compound of Example 84 was separated using a Chiralpak-IB column (250×20 mm, 5 μm) (28.5 mg loading; 0.1% DEA in n-Hexane: CH₂Cl₂:MeOH (80:20) (A:B: 80:20) as mobile phase; flow rate: 18 mL/mm) to afford the compounds of Example 84A (Fraction (I) (−)) and Example 84B (Fraction (II) (+)).

Analytical conditions for Example 84A and Example 84B: HPLC (column; zorbax-SB-C-18 (150×4.6 mm, 3.5 μm), mobile Phase: ACN: 0.05% Aq TFA; flow rate: 1.0 mL/min; Gradient program: T/B % 0.01/90, 2/90, 8/10, 15/10: diluent: CH₃CN:Water; Chiral HPLC: (Chiralpak-IB (250×4.6 mm, 5 μm; mobile phase (A) 0.1% DEA in n-Hexane (B) CH₂Cl₂:MeOH (80:20) (A:B; 80:20); flow Rate: 1.0 mL/min).

Example 84A, (−)-5-(5-fluorobenzofuran-2-yl)-3-(6-methoxy-5-(4-methyl-1H-imidazol-1-yl) pyridin-2-yl)-5,6-dihydro-4H-1,2,4-oxadiazine, fraction (I) (−): Mass (ESI): 408.3 [M+1]; HPLC (purity): 98.8%, RT 7.51 min; Chiral HPLC: 100%, RT=13.69 min; Optical rotation $[\alpha]_D^{20.00}$: −232.78 (c=0.25, CH₂Cl₂).

Example 84B, (+)-5-(5-fluorobenzofuran-2-yl)-3-(6-methoxy-5-(4-methyl-1H-imidazol-1-yl) pyridin-2-yl)-5,6-dihydro-4H-1,2,4-oxadiazine, fraction (II) (+): ¹H NMR (CD₃OD, 400 MHz): δ 7.98 (s, 1H), 7.88 (d, 1H), 7.64 (d, 1H), 7.45 (dd, 1H), 7.26 (dd, 1H), 7.22 (t, 1H), 7.05-6.99 (m, 1H), 6.75 (s, 1H), 5.08 (t, 1H), 4.40 (dd, 1H), 4.13 (s, 3H), 4.06 (dd, 1H), 2.25 (s, 3H); Mass (ESI): 408.3 [M+1]; HPLC (purity): 99.1%, RT 7.50 min; Chiral HPLC: 98.3%, RT=17.37 min; Optical rotation $[\alpha]_D^{20.00}$: +240.70 (c=0.25, CH₂Cl₂).

Example 85

Synthesis of 3-(5-bromo-6-methoxypyridin-2-yl)-5-(4-chloro-3-methylphenyl)-5,6-dihydro-4H-1,2,4-oxadiazine

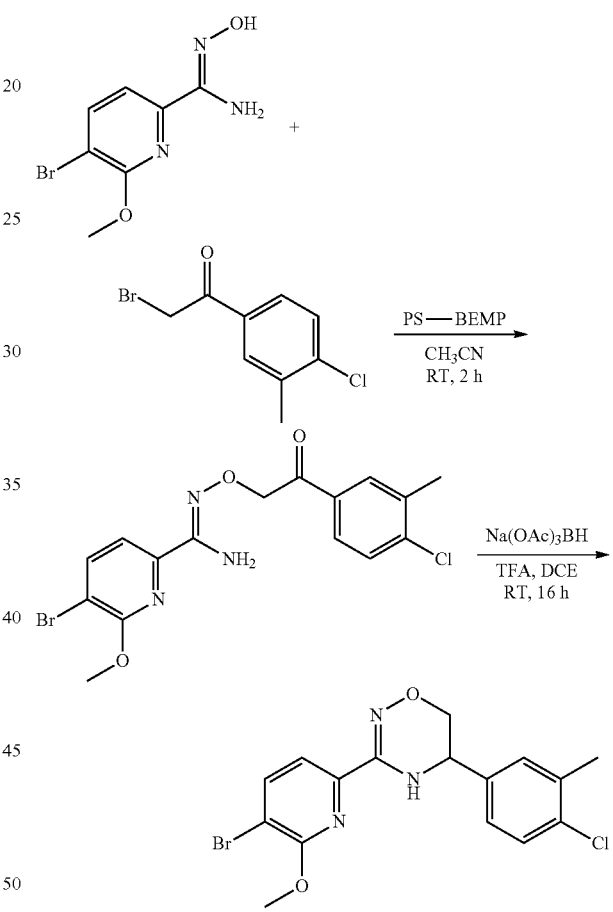

(Z)-5-bromo-N'-(2-(3,4-dimethylphenyl)-2-oxoethoxy)-6-methoxypicolinimidamide

To a stirred solution of 5-bromo-N'-hydroxy-6-methoxypicolinimidamide (600 mg, 2 mmol) in CH₃CN (25 mL) at room temperature under an argon atmosphere was added PS-BEMP (799 mg, 3.0 mmol). The reaction mixture was stirred for 5 min at room temperature. Then 2-bromo-1-(4-chloro-3-methylphenyl) ethan-1-one (903 mg, 4.0 mmol) in CH₃CN (5 mL) was added to the reaction mixture at room temperature. The reaction mixture was stirred for 2 h at room temperature. After consumption of starting material (monitored by TLC), the reaction mixture was filtered and the filtrate was concentrated in vacuo to afford (Z)-5- bromo-N'-(2-(3,4-dimethylphenyl)-2-oxoethoxy)-6-methoxypicolinimidamide (700 mg, crude) as a brown syrup used in the next step without further purification.

LCMS: 47.4%; 413.8 (M+2); (column; Ascentis Express C-18 (50×3.0 mm, 3.5 μm); RT 2.99 min 0.025% Aq TFA+5% ACN: ACN+5% 0.025% Aq TFA; 1.2 mL/min); TLC: 20% EtOAc/Hexane ($R_f$: 0.7).

3-(5-bromo-6-methoxypyridin-2-yl)-5-(4-chloro-3-methylphenyl)-5,6-dihydro-4H-1,2,4-oxadiazine To a stirred solution of (Z)-5-bromo-N'-(2-(3,4-dimethylphenyl)-2-oxoethoxy)-6-methoxypicolinimidamide (700 mg, crude) in dichloroethane (12 mL) at room temperature under an argon atmosphere was added trifluoroacetic acid (0.63 mL, 9 mmol) and sodium triacetoxyborohydride (1 g, 5 mmol). The reaction mixture was stirred for 16 h at room temperature. After consumption of starting material (monitored by TLC), the reaction mixture was diluted with water (20 mL), 1N sodium hydroxide solution (20 mL) and extracted with $CH_2Cl_2$ (2×20 mL). The combined organic extracts were dried over sodium sulfate, filtered and concentrated in vacuo to afford 3-(5-bromo-6-methoxypyridin-2-yl)-5-(4-chloro-3-methylphenyl)-5,6-dihydro-4H-1,2,4-oxadiazine (390 mg, 40%) as colorless thick syrup.

LCMS: 33.6%; 397.7 (M+2); (column; Ascentis Express C-18 (50×3.0 mm, 3.5 μm); RT 2.91 min 0.025% Aq TFA+5% ACN: ACN+5% 0.025% Aq TFA; 1.2 mL/min); TLC: 20% EtOAc/Hexane ($R_f$: 0.4).

Example 86

Synthesis of 5-(4-chloro-3-methylphenyl)-3-(6-methoxy-5-(4-methyl-1H-imidazol-1-yl) pyridin-2-yl)-5,6-dihydro-4H-1,2,4-oxadiazine

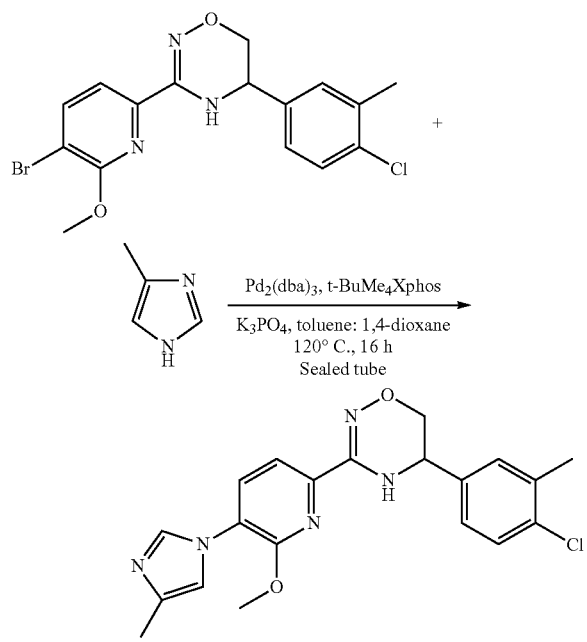

5-(4-chloro-3-methylphenyl)-3-(6-methoxy-5-(4-methyl-1H-imidazol-1-yl) pyridin-2-yl)-5,6-dihydro-4H-1,2,4-oxadiazine To a dry vial was added a suspension of $Pd_2(dba)_3$ (35 mg, 0.04 mmol) and tert-butyl tetramethyl Xphos (36 mg, 0.07 mmol) in toluene:1,4-dioxane (2:1, 4.5 mL) at room temperature. The suspension was degassed with argon, heated to 120° C., and stirred at 120° C. for 3 min. A mixture of 3-(5-bromo-6-methoxypyridin-2-yl)-5-(4-chloro-3-methylphenyl)-5,6-dihydro-4H-1, 2,4-oxadiazine (300 mg, 0.75 mmol), 4-methyl-1H-imidazole (93 mg, 1.13 mmol) and potassium phosphate (321 mg, 1.50 mmol) in toluene:1,4-dioxane (2:1, 4.5 mL) was degassed and the catalyst pre-mixture was added. The resultant mixture was stirred at 120° C. for 16 h in a sealed tube. After consumption of the starting material (monitored by TLC and LCMS), the reaction mixture was diluted with water (20 mL) and extracted with 5% MeOH: $CH_2Cl_2$ (2×20 mL). The combined organic extracts were dried over sodium sulfate, filtered and concentrated in vacuo. The crude material was purified by preparative HPLC (Column X-select C18 column (250×19 mm, 5 μm (50 mg loading; $CH_3CN$: 005% TFA (0.01/95, 2/90, 15/70, 25/35, 25/10, 35/10); flow rate: 15 mL/min) to afford 5-(4-chloro-3-methylphenyl)-3-(6-methoxy-5-(4-methyl-1H-imidazol-1-yl) pyridin-2-yl)-5,6-dihydro-4H-1,2,4-oxadiazine (55 mg, 18%) as colorless thick syrup.

Racemic compound of Example 86 was separated using a Chiralpak-IB column (250×20 mm, 5 μm) (27.5 mg loading; 0.1% DEA in n-Hexane: $CH_2Cl_2$:MeOH (50:50) (A:B: 80:20) as mobile phase; flow rate: 18 mL/min) to afford the compounds of Example 86A (Fraction (I) (−)) and Example 86B (Fraction (II) (+)).

Analytical conditions for Example 86A and Example 86B: HPLC: (column; Zorbax SB C-18, 150×4.6 mm, 3.5 μm), ACN: 0.05% Aq TFA; 1.0 mL/min; Chiral HPLC: (Chiralpak-IB (250×4.6 mm, 5 μm; mobile phase (A) 0.1% DEA in n-Hexane (B) $CH_2Cl_2$: MeOH (50:50) (A:B; 80:20); flow Rate: 1.0 mL/min).

Example 86A, (−)-5-(4-chloro-3-methylphenyl)-3-(6-methoxy-5-(4-methyl-1H-imidazol-1-yl) pyridin-2-yl)-5,6-dihydro-4H-1,2,4-oxadiazine, fraction (I) (−): Mass (ESI): 398.3 [M+1]; HPLC (purity): 98.8%, RT 7.67 min; Chiral HPLC: 99.3%, RT=9.27 min; Optical rotation $[\alpha]_D^{19.98}$: −176.43 (c=0.25, $CH_2Cl_2$).

Example 86B, (+)-5-(4-chloro-3-methylphenyl)-3-(6-methoxy-5-(4-methyl-1H-imidazol-1-yl) pyridin-2-yl)-5,6-dihydro-4H-1,2,4-oxadiazine, fraction (II) (+): $^1H$ NMR ($CD_3OD$, 400 MHz): δ 7.81 (d, 1H), 7.64 (d, 1H), 7.39 (d, 1H), 7.23 (s, 1H), 7.14 (d, 1H), 6.99 (s, 1H), 6.51 (s, 1H), 4.73 (t, 1H), 4.25 (dd, 1H), 4.00 (s, 3H), 3.75 (dd 1H), 2.40 (s, 3H), 2.30 (s, 3H); Mass (ESI): 398.3 [M+1]; HPLC (purity): 99.3%, RT 7.66 min.; Chiral HPLC: 99.7%, RT=11.85 min; Optical rotation $[\alpha]_D^{20.01}$: +163.76 (c=0.25, $CH_2Cl_2$).

Example 87

Synthesis of 2-bromo-1-(7-fluorobenzofuran-2-yl)ethan-1-one

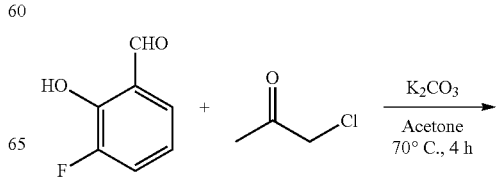

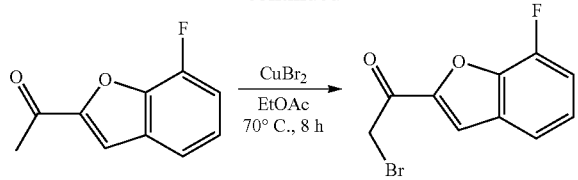

1-(7-fluorobenzofuran-2-yl) ethan-1-one

To a stirred solution 3-fluoro-2-hydroxybenzaldehyde (400 mg, 3 mmol) in acetone (4 mL) at room temperature under an argon atmosphere were added potassium carbonate (471 mg, 3 mmol) and chloro acetone (298 mg, 3 mmol). The reaction mixture was stirred at 70° C. for 4 h. After consumption of starting material (monitored by TLC), the reaction mixture was filtered and the filterate was concentrated in vacuo. The crude material was purified by column chromatography using 2-3% EtOAc: Hexane to afford 1-(7-fluorobenzofuran-2-yl) ethan-1-one (120 mg, 24%) as white solid.

LCMS: 97.6%; 178.7 (M+1); (column; Ascentis Express C-18 (50×3.0 mm, 3.5 μm); RT 2.29 min 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 10% EtOAc/Hexane (R$_f$: 0.5).

2-bromo-1-(7-fluorobenzofuran-2-yl) ethan-1-one

To a stirred solution of 1-(7-fluorobenzofuran-2-yl) ethan-1-one (500 mg, 3 mmol) in EtOAc (10 mL) at room temperature under an argon atmosphere was added copper bromide (936 mg, 4 mmol). The reaction mixture was stirred at 70° C. for 8 h. After consumption of starting material (monitored by TLC), the reaction mixture was filtered. The filterate was washed with saturated sodium bicarbonate solution (20 mL), brine (20 mL), dried over sodium sulfate and concentrated in vacuo. The crude material was purified by column chromatography using 3-5% EtOAc: Hexane to afford 2-bromo-1-(7-fluorobenzofuran-2-yl) ethan-1-one (250 mg, 35%) as white solid.

LCMS: 97.2%; 259.4 (M+1); (column; X-select CSH C-18 (50×3.0 mm, 3.5 μm); RT 4.18 min 5 mM Aq NH$_4$OAc: ACN; T/B %: 0.01/10, 0.5/10, 4/90, 9/90; flow rate: 0.8 mL/min); TLC: 20% CH$_2$Cl$_2$/Hexane (R$_f$: 0.2).

Example 88

Synthesis of 3-(5-bromo-6-methoxypyridin-2-yl)-5-(7-fluorobenzofuran-2-yl)-5,6-dihydro-4H-1,2,4-oxadiazine

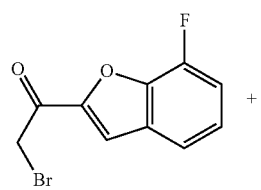

+

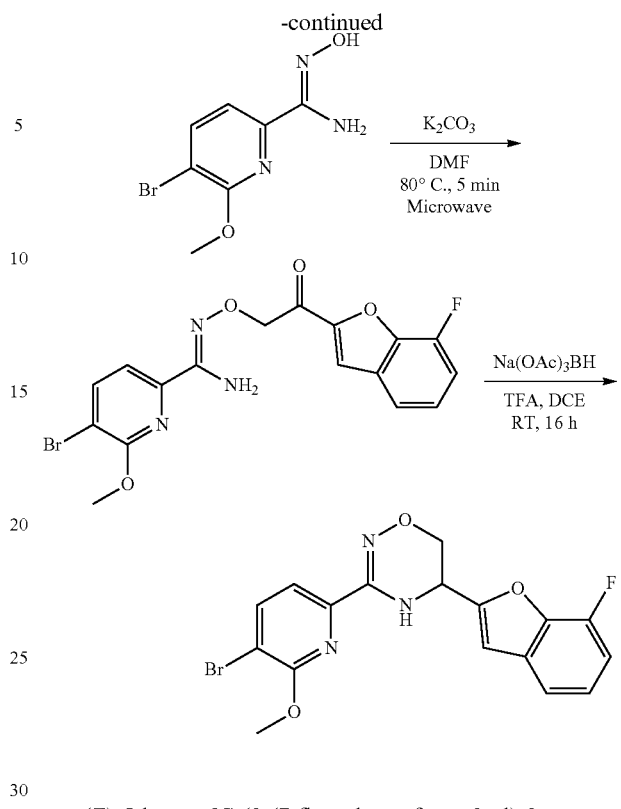

(Z)-5-bromo-N'-(2-(7-fluorobenzofuran-2-yl)-2-oxoethoxy)-6-methoxypicolinimidamide To a stirred solution of 5-bromo-N'-hydroxy-6-methoxypicolinimidamide (700 mg, 3 mmol) in DMF (7 mL) at room temperature under an argon atmosphere was added potassium carbonate (785 mg, 6 mmol) and 2-bromo-1-(7-fluorobenzofuran-2-yl) ethan-1-one (760 mg, 2 mmol). The reaction mixture was stirred at 80° C. for 5 min in microwave. After consumption of starting material (monitored by TLC), the reaction mixture was diluted with water (20 mL) and extracted with EtOAc (2×20 mL). The combined organic extracts were dried over sodium sulfate, filtered and concentrated in vacuo to afford (Z)-5-bromo-N'-(2-(7-fluorobenzofuran-2-yl)-2-oxoethoxy)-6-methoxypicolinimidamide (1 g, crude) as a pale yellow syrup used in the next step without further purification.

LCMS: 30.2%; 423.7 (M+2); (column; Ascentis Express C-18 (50×3.0 mm, 2.7 μm); RT 2.85 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane (R$_f$: 0.5).

3-(5-bromo-6-methoxypyridin-2-yl)-5-(7-fluorobenzofuran-2-yl)-5,6-dihydro-4H-1,2,4-oxadiazine To a stirred solution of (Z)-5-bromo-N'-(2-(7-fluorobenzofuran-2-yl)-2-oxoethoxy)-6-methoxypicolinimidamide (1 g, 2 mmol) in dichloroethane (20 mL) at room temperature under an argon atmosphere were added trifluoroacetic acid (0.9 mL, 8 mmol) and sodium triacetoxyborohydride (1.5 g, 7 mmol). The reaction mixture was stirred for 16 h at room temperature. After consumption of starting material (monitored by TLC), the reaction mixture was diluted with 1N sodium hydroxide solution (20 mL) and extracted with CH$_2$Cl$_2$ (2×20 mL). The combined organic extracts were dried over sodium sulfate, filtered and concentrated in vacuo to afford 3-(5-bromo-6-methoxypyridin-2-yl)-5-(7-fluorobenzofuran-2-yl)-5,6-dihydro-4H-1,2,4-oxadiazine (400 mg, 41%) as colorless thick syrup.

LCMS: 75.9%; 405.8 (M+1); (column; Ascentis Express C-18 (50×3.0 mm, 2.7 μm); RT 2.76 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.4).

Example 89

Synthesis of 5-(7-fluorobenzofuran-2-yl)-3-(6-methoxy-5-(4-methyl-1H-imidazol-1-yl) pyridin-2-yl)-5,6-dihydro-4H-1,2,4-oxadiazine

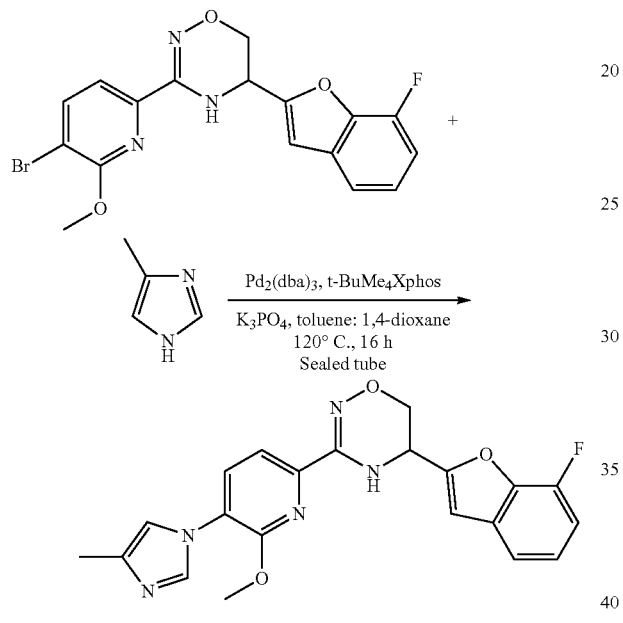

5-(7-fluorobenzofuran-2-yl)-3-(6-methoxy-5-(4-methyl-1H-imidazol-1-yl) pyridin-2-yl)-5,6-dihydro-4H-1,2,4-oxadiazine To a dry vial was added a suspension of $Pd_2(dba)_3$ (34 mg, 0.03 mmol) and tert-butyl tetramethyl Xphos (35 mg, 0.07 mmol) in toluene:1,4-dioxane (2:1, 4.5 mL) at room temperature. The suspension was degassed with argon, heated to 120° C., and stirred at 120° C. for 3 min. A mixture of 3-(5-bromo-6-methoxypyridin-2-yl)-5-(7-fluorobenzofuran-2-yl)-5,6-dihydro-4H-1,2,4-oxadiazine (300 mg, 0.8 mmol), 4-methyl-1H-imidazole (91 mg, 1.1 mmol) and potassium phosphate (313 mg, 1.5 mmol) in toluene: 1,4-dioxane (2:1, 4.5 mL) was degassed and the catalyst pre-mixture was added. The resultant mixture was stirred at 120° C. for 16 h in a sealed tube. After consumption of the starting material (monitored by TLC and LCMS), the reaction mixture was diluted with water (20 mL) and extracted with MeOH: $CH_2Cl_2$ (1:1, 20 mL). The combined organic extracts were dried over sodium sulfate, filtered and concentrated in vacuo. The crude material was purified by column chromatography using 2-5% MeOH: $CH_2Cl_2$ to afford to afford 5-(7-fluorobenzofuran-2-yl)-3-(6-methoxy-5-(4-methyl-1H-imidazol-1-yl) pyridin-2-yl)-5,6-dihydro-4H-1,2,4-oxadiazine (260 mg, 86%) as brown solid.

Racemic compound of Example 89 was separated using a Chiralpak-IB column (250×20 mm, 5 μm) (37.1 mg loading; 0.1% DEA in n-Hexane: $CH_2Cl_2$:MeOH (50:50) (A:B: 80:20) as mobile phase; flow rate: 18 mL/mm) to afford the compounds of Example 89A (Fraction (I) (−)) and Example 89B (Fraction (II) (+)).

Analytical conditions for Example 89A and Example 89B: HPLC (column; Eclipse XDB-C-18 (150×4.6 mm, 3.5 μm), mobile Phase: ACN: 0.05% Aq TFA; flow rate: 1.0 mL/min; Gradient program: T/B % 0.01/90, 2/90, 8/10, 15/10: diluent: $CH_3CN$:Water; Chiral HPLC: (Chiralpak-IB (250×4.6 mm, 5 μm; mobile phase (A) 0.1% DEA in n-Hexane (B) $CH_2Cl_2$:MeOH (50:50) (A:B; 80:20); flow Rate: 1.0 mL/min).

Example 89A, (−)-5-(7-fluorobenzofuran-2-yl)-3-(6-methoxy-5-(4-methyl-1H-imidazol-1-yl) pyridin-2-yl)-5,6-dihydro-4H-1,2,4-oxadiazine, fraction (I) (−): Mass (ESI): 408.3 [M+1]; HPLC (purity): 99.6%, RT 7.63 min; Chiral HPLC: 98.8%, RT=11.01 min; Optical rotation $[\alpha]_D^{20.00}$: −263.85 (c=0.25, $CH_2Cl_2$).

Example 89B, (+)-5-(7-fluorobenzofuran-2-yl)-3-(6-methoxy-5-(4-methyl-1H-imidazol-1-yl) pyridin-2-yl)-5,6-dihydro-4H-1,2,4-oxadiazine, fraction (II) (+): $^1$H NMR ($CD_3OD$, 400 MHz): δ 7.99 (s, 1H), 7.88 (d, 1H), 7.65 (d, 1H), 7.37 (dd, 1H), 7.23 (s, 1H), 7.20-7.16 (m, 1H), 7.08-7.02 (m, 1H), 6.82 (s, 1H), 5.13 (t, 1H), 4.44 (dd, 1H), 4.14 (s, 3H), 4.08 (dd, 1H), 2.26 (s, 3H); Mass (ESI): 408.3 [M+1]; HPLC (purity): 99.4%, RT 7.63 min; Chiral HPLC: 98.8%, RT=12.24 min; Optical rotation $[\alpha]_D^{20.01}$: +262.67 (c=0.25, $CH_2Cl_2$).

Example 90

Synthesis of 3-(5-bromo-6-methoxypyridin-2-yl)-5-(3,4,5-trifluorophenyl)-5,6-dihydro-4H-1,2,4-oxadiazine

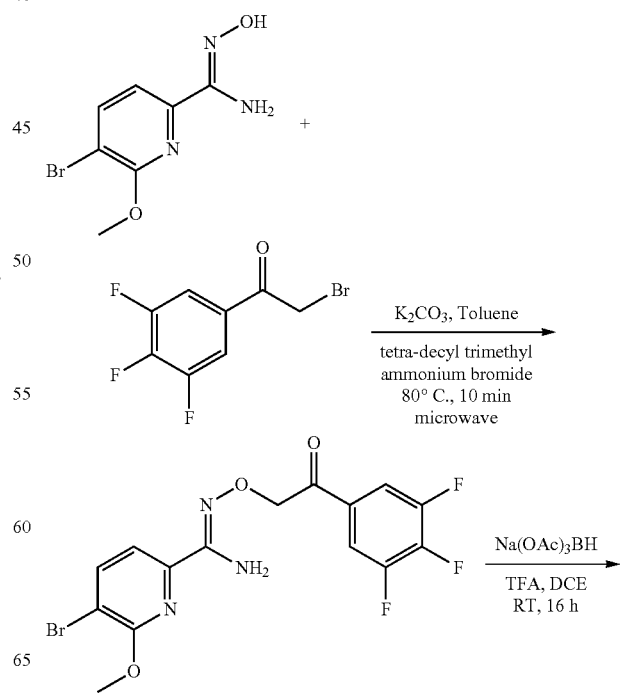

285
-continued

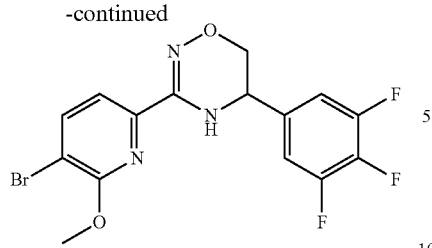

(Z)-5-bromo-6-methoxy-N'-(2-oxo-2-(3,4,5-trifluorophenyl) ethoxy) picolinimidamide To a stirred solution of 5-bromo-N'-hydroxy-6-methoxypicolinimidamide (500 mg, 2 mmol) in toluene (10 mL) at room temperature under an argon atmosphere was added potassium carbonate (280 mg, 2 mmol) and 2-bromo-1-(3, 4, 5-trifluorophenyl) ethan-1-one (771 mg, 3 mmol) and tetra decyl trimethyl ammonium bromide (341 mg, 1 mmol). The reaction mixture was stirred at 80° C. for 10 min in microwave. After consumption of starting material (monitored by TLC), the reaction mixture was diluted with water (10 mL) and extracted with EtOAc (2×10 mL). The combined organic extracts were dried over sodium sulfate, filtered and concentrated in vacuo to afford (Z)-5-bromo-6-methoxy-N'-(2-oxo-2-(3,4,5-trifluorophenyl) ethoxy) picolinimidamide (706 mg, crude) as a pale yellow syrup used in the next step without further purification.

LCMS: 33.3%; 419.7 (M+3); (column; Ascentis Express C-18 (50×3.0 mm, 2.7 μm); RT 2.91 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.5).

3-(5-bromo-6-methoxypyridin-2-yl)-5-(3,4,5-trifluorophenyl)-5,6-dihydro-4H-1,2,4-oxadiazine To a stirred solution of (Z)-5-bromo-6-methoxy-N'-(2-oxo-2-(3,4,5-trifluorophenyl) ethoxy) picolinimidamide (700 mg, crude) in 1, 2-dichloro ethane (1.5 mL) at room temperature under an argon atmosphere was added trifluoroacetic acid (0.63 mL) and sodium triacetoxyborohydride (1.06 g, 8 mmol). The reaction mixture was stirred for 16 h at room temperature. After consumption of starting material (monitored by TLC), the reaction mixture was diluted with 1N sodium hydroxide solution (20 mL) and extracted with CH$_2$Cl$_2$ (2×20 mL). The combined organic extracts were dried over sodium sulfate, filtered and concentrated in vacuo to afford 3-(5-bromo-6-methoxypyridin-2-yl)-5-(3,4,5-trifluorophenyl)-5,6-dihydro-4H-1,2,4-oxadiazine (360 mg, 54%) as a pale yellow solid.

LCMS: 57.1%; 402.2 (M+2); (column; Eclipse XDB C-18 (150×4.6 mm, 5 μm); RT 9.69 min; mobile phase: 5 mM Aq NH$_4$OAc; ACN; T/B %: 0.01/5, 2/5, 8/90, 15/90; flow rate: 1.0 mL/min) (Gradient); TLC: 20% EtOAc/Hexane ($R_f$: 0.5).

286
Example 91

Synthesis of 3-(6-methoxy-5-(4-methyl-1H-imidazol-1-yl) pyridin-2-yl)-5-(3, 4, 5-trifluorophenyl)-5, 6-dihydro-4H-1,2,4-oxadiazine

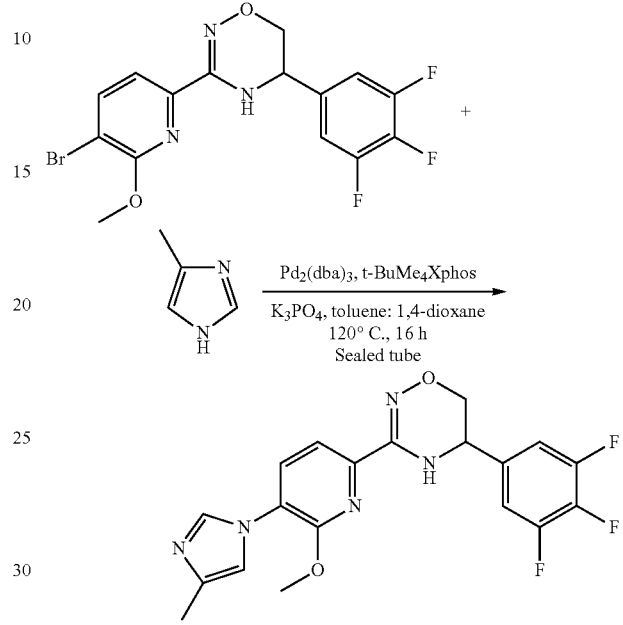

3-(6-methoxy-5-(4-methyl-1H-imidazol-1-yl) pyridin-2-yl)-5-(3,4,5-trifluorophenyl)-5,6-dihydro-4H-1,2,4-oxadiazine To a dry vial was added a suspension of Pd$_2$(dba)$_3$ (62 mg, 0.07 mmol) and tert-butyl tetramethyl Xphos (65 mg, 0.13 mmol) in toluene:1,4-dioxane (2:1, 1.5 mL) at room temperature. The suspension was degassed with argon, heated to 120° C., and stirred at 120° C. for 3 min. A mixture of 3-(5-bromo-6-methoxypyridin-2-yl)-5-(3,4,5-trifluorophenyl)-5,6-dihydro-4H-1,2,4-oxadiazine (550 mg, 1 mmol), 4-methyl-1H-imidazole (168 mg, 2 mmol) and potassium phosphate (580 mg, 3 mmol) in toluene:1,4-dioxane (2:1, 1.5 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo The crude material was purified by column chromatography using 2% MeOH: CH$_2$Cl$_2$ to afford 3-(6-methoxy-5-(4-methyl-1H-imidazol-1-yl) pyridin-2-yl)-5-(3,4,5-trifluorophenyl)-5,6-dihydro-4H-1,2,4-oxadiazine (200 mg, 36%) as white solid.

Racemic compound of Example 91 was separated using a Chiralpak-IB column (250×20 mm, 5 μm) (34 mg loading; 0.1% DEA in n-Hexane: CH$_2$Cl$_2$:MeOH (50:50) (A:B: 85:15) as mobile phase; flow rate: 18 mL/min) to afford the compounds of Example 91A (Fraction (I) (−)) and Example 91B (Fraction (II) (+)).

Analytical conditions for Example 91A and Example 91B: HPLC (column; zorbax-SB-C-18 150×4.6 mm, 3.5μ), mobile Phase: ACN: 0.05% Aq TFA; flow rate: 1.0 mL/min;

Gradient program: T/B % 0.01/90, 2/90, 8/10, 20/10: diluent: CH₃CN:Water; Chiral HPLC: (Chiralpak-IB (250× 4.6 mm, 5 μm; mobile phase (A) 0.1% DEA in n-Hexane (B) CH₂Cl₂:MeOH (50:50) (A:B; 85:15); flow Rate: 1.0 mL/min).

Example 91A, (−)-3-(6-methoxy-5-(4-methyl-1H-imidazol-1-yl) pyridin-2-yl)-5-(3,4,5-trifluorophenyl)-5,6-dihydro-4H-1,2,4-oxadiazine, fraction (I) (−): Mass (ESI): 404.3 [M+1]; HPLC (purity): 99.4%, RT 7.54 min; Chiral HPLC: 95.9%, RT=13.10 min; Optical rotation [α]$_D^{19.99}$: −172.56 (c=0.25, CH₂Cl₂).

Example 91B, (+)-3-(6-methoxy-5-(4-methyl-1H-imidazol-1-yl) pyridin-2-yl)-5-(3,4,5-trifluorophenyl)-5,6-dihydro-4H-1,2,4-oxadiazine, fraction (II) (+): ¹H NMR (CD₃OD, 400 MHz): δ 7.98 (d, 1H), 7.89 (d, 1H), 7.65 (d, 1H), 7.22 (s, 1H), 7.19-7.14 (m, 2H), 4.88 (t, 1H), 4.11 (s, 3H), 4.03 (dd, 2H), 2.25 (s, 3H); Mass (ESI): 404.3 [M+1]; HPLC (purity): 99.6%, RT 7.49 min; Chiral HPLC: 99.7%, RT=16.72 min; Optical rotation [α]$_D^{20.00}$: +187.26 (c=0.25, CH₂Cl₂).

Example 92

Synthesis of 3-(5-bromo-6-methoxypyridin-2-yl)-5-(4-(difluoromethoxy) phenyl)-5,6-dihydro-4H-1,2,4-oxadiazine

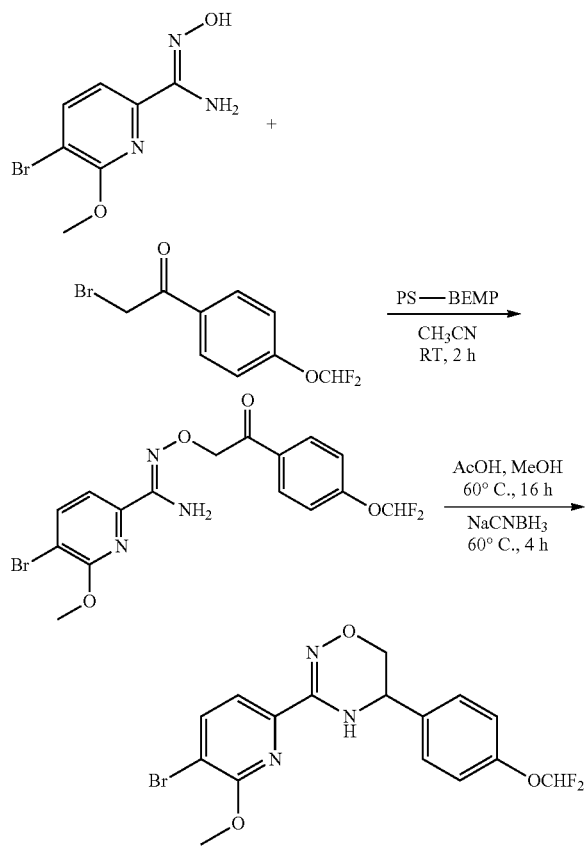

(Z)-5-bromo-N'-(2-(4-(difluoromethoxy) phenyl)-2-oxoethoxy)-6-methoxypicolinimidamide To a stirred solution of 5-bromo-N'-hydroxy-6-methoxypicolinimidamide (800 mg, 3 mmol) in CH₃CN (20 mL) at room temperature under an argon atmosphere was added PS-BEMP (1.06 g, 3 mmol). The reaction mixture was stirred for 10 min at room temperature. Then 2-bromo-1-(4-(difluoromethoxy) phenyl) ethan-1-one (1.3 g, 5 mmol) in CH₃CN (20 mL) was added to the reaction mixture at room temperature. The reaction mixture was stirred at room temperature for 2 h. After consumption of starting material (monitored by TLC), the reaction mixture was filtered and the filtrate was concentrated in vacuo to afford (Z)-5-bromo-N'-(2-(4-(difluoromethoxy) phenyl)-2-oxoethoxy)-6-methoxypicolinimidamide (1.4 g, crude) as brown syrup used in the next step without further purification.

LCMS: 44.6%; 431.7 (M+3); (column; Ascentis Express C-18 (50×3.0 mm, 2.7 μm); RT 2.80 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.3).

3-(5-bromo-6-methoxypyridin-2-yl)-5-(4-(difluoromethoxy) phenyl)-5,6-dihydro-4H-1,2,4-oxadiazine To a stirred solution of (Z)-5-bromo-N'-(2-(4-(difluoromethoxy) phenyl)-2-oxoethoxy)-6-methoxypicolinimidamide (1.4 g, crude) in MeOH (16 mL) at room temperature under an argon atmosphere was added acetic acid (4 mL). The reaction mixture was stirred for 16 h at 60° C. Then sodium cyanoborohydride (250 mg) was added to the reaction mixture at room temperature. The reaction mixture was stirred for 4 h at 60° C. After consumption of starting material (monitored by TLC), the volatiles were evaporated in vacuo. The residue was diluted with water (20 mL) and extracted with CH₂Cl₂ (2×20 mL). The combined organic extracts were dried over sodium sulfate, filtered and concentrated in vacuo to afford 3-(5-bromo-6-methoxypyridin-2-yl)-5-(4-(difluoromethoxy) phenyl)-5,6-dihydro-4H-1,2,4-oxadiazine (450 mg) as an off-white solid.

LCMS: 47.5%; 415.7 (M+2); (column; Ascentis Express C-18 (50×3.0 mm, 2.7 μm); RT 2.71 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.3).

Example 93

Synthesis of 5-(4-(difluoromethoxy) phenyl)-3-(6-methoxy-5-(4-methyl-1H-imidazol-1-yl) pyridin-2-yl)-5,6-dihydro-4H-1,2,4-oxadiazine

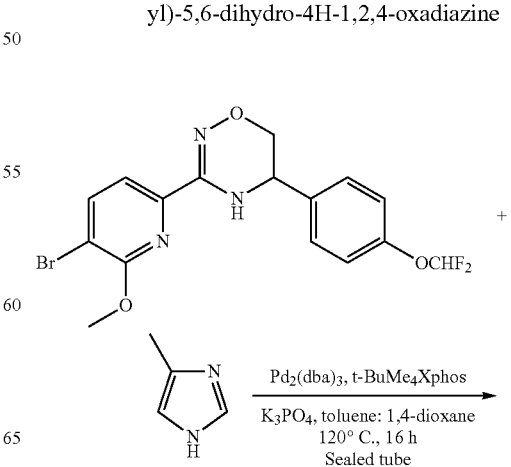

289
-continued

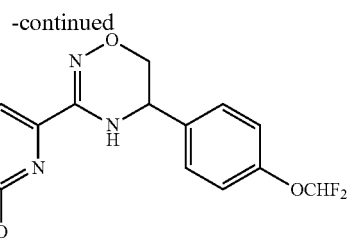

5-(4-(difluoromethoxy) phenyl)-3-(6-methoxy-5-(4-methyl-1H-imidazol-1-yl) pyridin-2-yl)-5,6-dihydro-4H-1,2,4-oxadiazine To a dry vial was added a suspension of Pd$_2$(dba)$_3$ (44 mg, 0.05 mmol) and tert-butyl tetramethyl Xphos (46 mg, 0.09 mmol) in toluene:1,4-dioxane (2:1, 9 mL) at room temperature. The suspension was degassed with argon, heated to 120° C., and stirred at 120° C. for 3 min. A mixture of 3-(5-bromo-6-methoxypyridin-2-yl)-5-(4-(difluoromethoxy) phenyl)-5,6-dihydro-4H-1,2,4-oxadiazine (400 mg, 1 mmol), 4-methyl-1H-imidazole (158 mg, 2 mmol) and potassium phosphate (407 mg, 2 mmol) in toluene:1,4-dioxane (2:1, 9 mL) was degassed and the catalyst premixture was added. The resultant mixture was stirred at 120° C. for 16 h in a sealed tube. After consumption of the starting material (monitored by TLC and LCMS), the reaction mixture was filtered and the filtrate was concentrated in vacuo. The crude material was purified by column chromatography using 3-5% EtOAc: Hexane to afford 5-(4-(difluoromethoxy) phenyl)-3-(6-methoxy-5-(4-methyl-1H-imidazol-1-yl) pyridin-2-yl)-5,6-dihydro-4H-1,2,4-oxadiazine (150 mg, 37%) as an off-white solid.

Racemic compound of Example 93 was separated using a Chiralpak-IB column (250×20 mm, 5 µm) (15.8 mg loading; 0.1% DEA in n-Hexane: CH$_2$Cl$_2$:MeOH (50:50) (A:B: 85:15) as mobile phase; flow rate: 20 mL/min) to afford the compounds of Example 93A (Fraction (I) (−)) and Example 93B (Fraction (II) (+)).

Analytical conditions for Example 93A and Example 93B: HPLC (column; zorbax-SB-C-18 150×4.6 mm, 3.5µ), mobile Phase: ACN: 0.05% Aq TFA; flow rate: 1.0 mL/min; Gradient program: T/B % 0.01/90, 2/90, 8/10, 15/10: diluent: CH$_3$CN:Water; Chiral HPLC: (Chiralpak-IB (250× 4.6 mm, 5 µm; mobile phase (A) 0.1% DEA in n-Hexane (B) CH$_2$Cl$_2$:MeOH (50:50) (A:B; 85:15); flow Rate: 1.0 mL/min).

Example 93A, (−)-5-(4-(difluoromethoxy) phenyl)-3-(6-methoxy-5-(4-methyl-1H-imidazol-1-yl) pyridin-2-yl)-5,6-dihydro-4H-1,2,4-oxadiazine, fraction (I) (−): Mass (ESI): 416.3 [M+1]; HPLC (purity): 99.7%, RT 7.43 min; Chiral HPLC: 100%, RT=16.55 min; Optical rotation [α]$_D^{20.01}$: −165.76 (c=0.25, CH$_2$Cl$_2$).

Example 93B, (+)-5-(4-(difluoromethoxy) phenyl)-3-(6-methoxy-5-(4-methyl-1H-imidazol-1-yl) pyridin-2-yl)-5,6-dihydro-4H-1,2,4-oxadiazine, fraction (II) (+): $^1$H NMR (400 MHz, CD$_3$OD): δ 7.98 (s, 1H), 7.88 (d, 1H), 7.65 (d, 1H), 7.43 (d, 2H), 7.22 (s, 1H), 7.17 (d, 2H), 6.72 (t, 1H), 4.87 (t, 1H), 4.11 (dd, 1H), 4.08 (s, 3H), 3.91 (dd, 1H), 2.25 (s, 3H); Mass (ESI): 416.3 [M+1]; HPLC (purity): 95.2%, RT 7.45 min; Chiral HPLC: 100%, RT=22.32 min; Optical rotation [α]$_D^{20.01}$: +166.92 (c=0.25, CH$_2$Cl$_2$).

290
Example 94

Synthesis of 2-bromo-1-(4-chlorobenzofuran-2-yl) ethan-1-one

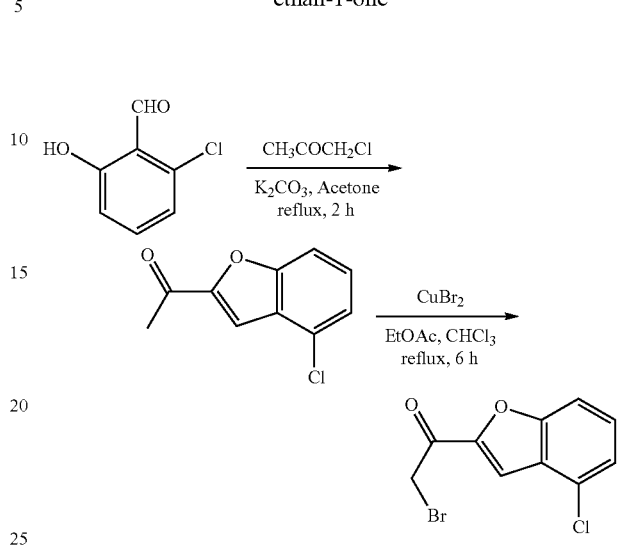

1-(4-chlorobenzofuran-2-yl) ethan-1-one

To a stirred solution of 2-chloro-6-hydroxybenzaldehyde (1 g, 6 mmol) in acetone (25 mL) at room temperature under an argon atmosphere were added potassium carbonate (1.7 g, 13 mmol) and 1-chloropropan-2-one (0.57 mL, 7 mmol). The reaction mixture was stirred at reflux for 2 h. After consumption of starting material (monitored by TLC), the reaction mixture was filtered, the filtrate was diluted with water (50 mL) and extracted with EtOAc (2×50 mL). The combined organic extracts were dried over sodium sulfate, filtered and concentrated in vacuo. The crude material was purified by column chromatography using 20-30% EtOAc: Hexane to afford 1-(4-chlorobenzofuran-2-yl) ethan-1-one (1 g, 80%) as white solid.

$^1$H NMR (CDCl$_3$, 400 MHz): δ 7.58 (s, 1H), 7.52-7.46 (m, 1H), 7.41 (t, 1H), 7.32 (dd, 1H), 2.63 (s, 3H); TLC: 50% EtOAc/Hexane (R$_f$: 0.3).

2-bromo-1-(4-chlorobenzofuran-2-yl) ethan-1-one

To a stirred solution of 1-(4-chlorobenzofuran-2-yl) ethan-1-one (1 g, 5 mmol) in chloroform (40 mL) at room temperature under an argon atmosphere was added copper bromide (2.3 g, 10 mmol) in EtOAc (30 mL). The reaction mixture was stirred at reflux for 6 h. After consumption of starting material (monitored by TLC), the reaction mixture was filtered, washed with EtOAc (2×50 mL). The filtrate was concentrated in vacuo. The crude material was washed with n-pentane (2×10 mL) to afford 2-bromo-1-(4-chlorobenzofuran-2-yl) ethan-1-one (850 mg, 60%) as an off-white solid.

$^1$H NMR (CDCl$_3$, 500 MHz): δ 7.73 (s, 1H), 7.51 (d, 1H), 7.49-7.42 (m, 1H), 7.39-7.31 (m, 1H), 4.44 (s, 2H); TLC: 50% EtOAc/Hexane (R$_f$: 0.5).

Example 95

Synthesis of 3-(5-bromo-6-methoxypyridin-2-yl)-5-(4-chlorobenzofuran-2-yl)-5,6-dihydro-4H-1,2,4-oxadiazine

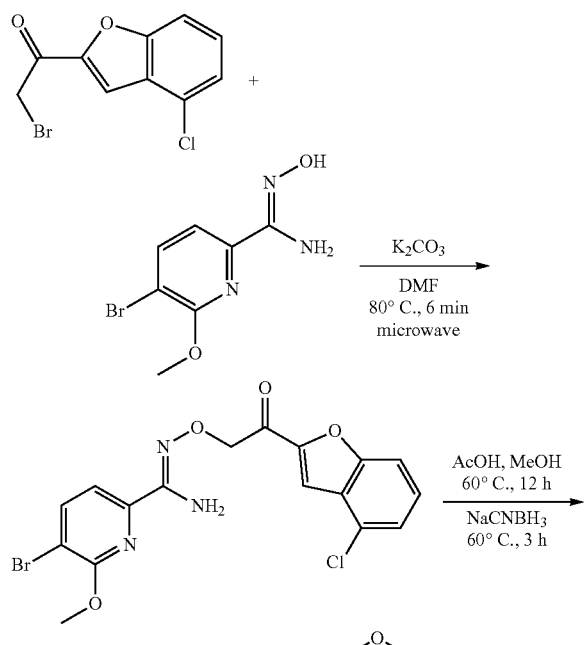

(Z)-5-bromo-N'-(2-(4-chlorobenzofuran-2-yl)-2-oxoethoxy)-6-methoxypicolinimidamide To a stirred solution of 5-bromo-N'-hydroxy-6-methoxypicolinimidamide (1 g, 4 mmol) in DMF (10 mL) at room temperature under an argon atmosphere were added potassium carbonate (1.1 g, 8.12 mmol) and 2-bromo-1-(4-chlorobenzofuran-2-yl) ethan-1-one (1.34 g, 5 mmol). The reaction mixture was stirred at 80° C. for 6 min in microwave. After consumption of starting material (monitored by TLC), the reaction mixture was diluted with water (50 mL) and extracted with EtOAc (2×50 mL). The combined organic extracts were washed with brine solution (30 mL), dried over sodium sulfate, filtered and concentrated in vacuo to afford (Z)-5-bromo-N'-(2-(4-chlorobenzofuran-2-yl)-2-oxoethoxy)-6-methoxypicolinimidamide (2.58 g, crude) as white solid used in the next step without further purification.

LCMS: 21.8%; 439.7 (M+2); (column; Ascentis Express C-18 (50×3.0 mm, 2.7 μm); RT 3.02 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 50% EtOAc/Hexane (R$_f$: 0.3).

3-(5-bromo-6-methoxypyridin-2-yl)-5-(4-chlorobenzofuran-2-yl)-5,6-dihydro-4H-1,2,4-oxadiazine To a stirred solution of (Z)-5-bromo-N'-(2-(4-chlorobenzofuran-2-yl)-2-oxoethoxy)-6-methoxypicolinimidamide (2.5 g, 6 mmol) in MeOH (63 mL) at room temperature under an argon atmosphere was added acetic acid (10 mL). The reaction mixture was stirred for 12 h at 60° C. Then sodium cyanoborohydride (430 mg, 7 mmol) was added to the reaction mixture at room temperature. The reaction mixture was stirred at 60° C. for 3 h. After consumption of starting material (monitored by TLC), the reaction mixture was diluted with water (50 mL) and extracted with EtOAc (2×50 mL). The combined organic extracts were washed with water (50 mL), dried over sodium sulfate, filtered and concentrated in vacuo to afford 3-(5-bromo-6-methoxypyridin-2-yl)-5-(4-chlorobenzofuran-2-yl)-5,6-dihydro-4H-1,2,4-oxadiazine (800 mg, crude) as brown syrup used in the next step without further purification.

LCMS: 34.9%; 423.7 (M+3); (column; Ascentis Express C-18 (50×3.0 mm, 2.7 μm); RT 2.94 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.4).

Example 96

Synthesis of 5-(4-chlorobenzofuran-2-yl)-3-(6-methoxy-5-(4-methyl-1H-imidazol-1-yl) pyridin-2-yl)-5,6-dihydro-4H-1,2,4-oxadiazine

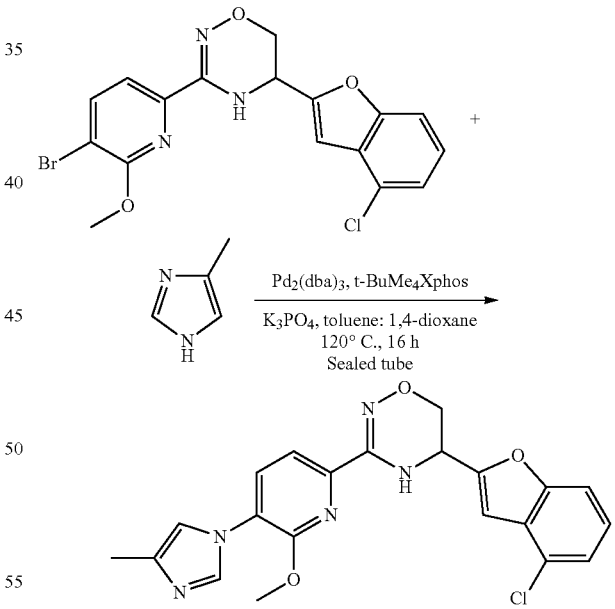

5-(4-chlorobenzofuran-2-yl)-3-(6-methoxy-5-(4-methyl-1H-imidazol-1-yl) pyridin-2-yl)-5,6-dihydro-4H-1,2,4-oxadiazine To a dry vial was added a suspension of Pd$_2$(dba)$_3$ (82 mg, 0.1 mmol) and tert-butyl tetramethyl Xphos (86 mg, 0.1 mmol) in toluene:1,4-dioxane (2:1, 5.62 mL) at room temperature. The suspension was degassed with argon, heated to 120° C., and stirred at 120° C. for 3 min. A mixture of 3-(5-bromo-6-methoxypyridin-2-yl)-5-(4-chlorobenzofuran-2-yl)-5,6-dihydro-4H-1,2,4-oxadiazine (750 mg, 2.0 mmol), 4-methyl-1H-imidazole (175 mg, 2.13 mmol) and potassium phosphate (755 mg, 4.0 mmol) in toluene:1,4-dioxane (2:1, 5 mL) was degassed and the catalyst premixture was added. The resultant mixture was stirred at 120° C. for 16 h in a sealed tube. After consumption of the starting material (monitored by TLC and LCMS), the reaction mixture was filtered and the filtrate was concentrated in vacuo. The crude material was purified by column chromatography using 1-5% MeOH: $CH_2Cl_2$ to afford 5-(4-chlorobenzofuran-2-yl)-3-(6-methoxy-5-(4-methyl-1H-imidazol-1-yl)pyridin-2-yl)-5,6-dihydro-4H-1,2,4-oxadiazine (200 mg, 26%) as a pale yellow solid.

Racemic compound of Example 96 was separated using a Chiralpak-IB column (250×20 mm, 5 μm) (32 mg loading; 0.1% DEA in n-Hexane: $CH_2Cl_2$:MeOH (50:50) (A:B: 85:15) as mobile phase) to afford the compounds of Example 96A (Fraction (I) (−)) and Example 96B (Fraction (II) (+)).

Analytical conditions for Example 96A and Example 96B: HPLC (column; zorbax-SB-C-18 150×4.6 mm, 3.5μ), mobile Phase: ACN: 0.05% Aq TFA; flow rate: 1.0 mL/min; Gradient program: T/B % 0.01/90, 2/90, 8/10, 15/10: diluent: $CH_3CN$:Water; Chiral HPLC: (Chiralpak-IB (250× 4.6 mm, 5 μm; mobile phase (A) 0.1% DEA in n-Hexane (B) $CH_2Cl_2$:MeOH (50:50) (A:B; 85:15); flow Rate: 1.0 mL/min).

Example 96A, (−)-5-(4-chlorobenzofuran-2-yl)-3-(6-methoxy-5-(4-methyl-1H-imidazol-1-yl) pyridin-2-yl)-5,6-dihydro-4H-1,2,4-oxadiazine, fraction (I) (−): Mass (ESI): 424.3 [M+1]; HPLC (purity): 95.3%, RT 7.90 min; Chiral HPLC: 95.7%, RT=16.34 min; Optical rotation $[α]_D^{20.00}$: −301.74 (c=0.25, $CH_2Cl_2$).

Example 96B, (+)-5-(4-chlorobenzofuran-2-yl)-3-(6-methoxy-5-(4-methyl-1H-imidazol-1-yl) pyridin-2-yl)-5,6-dihydro-4H-1,2,4-oxadiazine, fraction (II) (+): $^1$H NMR ($CD_3OD$, 400 MHz): δ 7.99 (s, 1H), 7.88 (d, 1H), 7.65 (d, 1H), 7.47-7.43 (m, 1H), 7.29-7.20 (m, 3H), 6.80 (s, 1H), 5.12 (t, 1H), 4.44 (dd, 1H), 4.14 (s, 3H), 4.07 (dd, 1H), 2.26 (s, 3H); Mass (ESI): 424.3 [M+1]; HPLC (purity): 97.5%, RT 7.89 min; Chiral HPLC: 97.2%, RT=18.02 min; Optical rotation $[α]_D^{20.04}$: +282.65 (c=0.25, $CH_2Cl_2$).

Example 97

Synthesis of 2-bromo-1-(4-fluorobenzofuran-2-yl) ethan-1-one

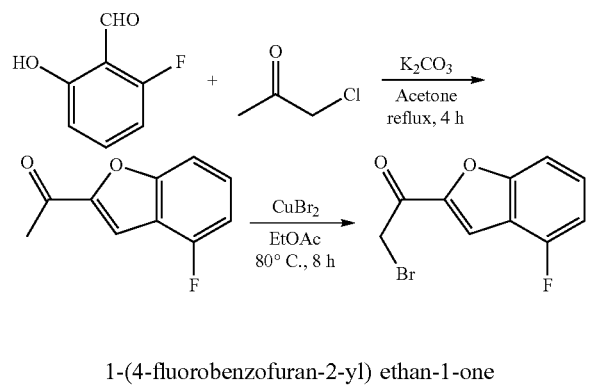

1-(4-fluorobenzofuran-2-yl) ethan-1-one

To a stirred solution of 2-fluoro-6-hydroxybenzaldehyde (3 g, 21 mmol) in acetone (6 mL) at room temperature under an argon atmosphere were added potassium carbonate (4.4 g, 32 mmol) and 1-chloropropan-2-one (2.4 g, 26 mmol). The reaction mixture was stirred at reflux for 4 h. After consumption of starting material (monitored by TLC), the reaction mixture was filtered, the filtrate was concentrated in vacuo. The crude material was purified by column chromatography using 2-3% EtOAc: Hexane to afford 1-(4-fluorobenzofuran-2-yl) ethan-1-one (2.5 g, 66%) as white solid.

$^1$H NMR ($CDCl_3$, 400 MHz): δ 7.58 (s, 1H), 7.45-7.35 (m, 2H), 7.01-6.97 (m, 1H), 2.60 (s, 3H); TLC: 5% EtOAc/Hexane ($R_f$: 0.2).

2-bromo-1-(4-fluorobenzofuran-2-yl) ethan-1-one

To a stirred solution of 1-(4-fluorobenzofuran-2-yl) ethan-1-one (2.5 g, 14 mmol) in EtOAc (5 mL) at room temperature under an argon atmosphere was added copper bromide (4.7 g, 21 mmol). The reaction mixture was stirred at 80° C. for 8 h. After consumption of starting material (monitored by TLC), the reaction mixture was filtered, the filtrate was concentrated in vacuo. The crude material was purified by column chromatography using 2-3% EtOAc: Hexane to afford 2-bromo-1-(4-fluorobenzofuran-2-yl) ethan-1-one (1 g, 30%) as a pale yellow solid.

$^1$H NMR ($CDCl_3$, 500 MHz): δ 7.74 (s, 1H), 7.50-7.46 (m, 1H), 7.44-7.40 (m, 1H), 7.01 (t, 1H), 4.43 (s, 2H); LCMS: 94.6%; 257 (M+2); (column; X-select CSH C-18 (50×3.0 mm, 3.5 μm); RT 4.14 min; mobile phase: 5 mM Aq $NH_4OAc$: ACN; T/B %: 0.01/10, 0.5/10, 4/90, 9/90; flow rate: 0.8 mL/min) (Gradient); TLC: 20% $CH_2Cl_2$/Hexane ($R_f$: 0.5).

Example 98

Synthesis of 3-(5-bromo-6-methoxypyridin-2-yl)-5-(4-fluorobenzofuran-2-yl)-5,6-dihydro-4H-1,2,4-oxadiazine

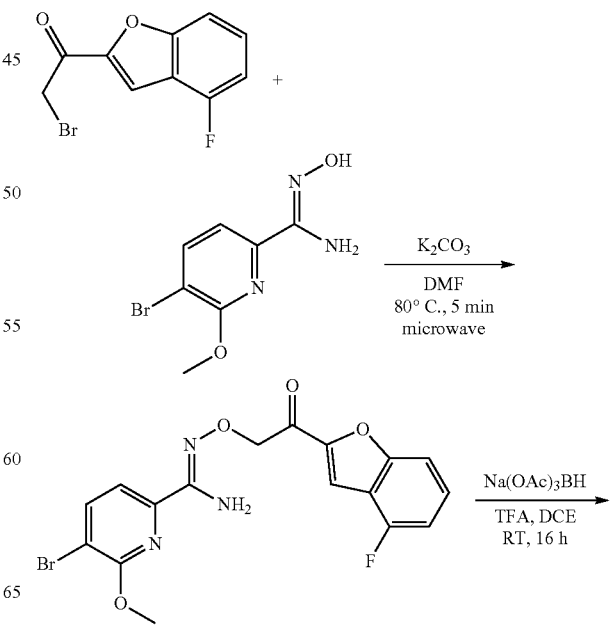

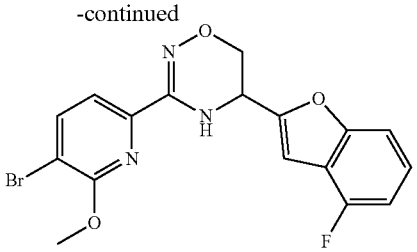

(Z)-5-bromo-N'-(2-(4-fluorobenzofuran-2-yl)-2-ox-oethoxy)-6-methoxypicolinimidamide To a stirred solution of 5-bromo-N'-hydroxy-6-methoxypicolinimidamide (250 mg, 1 mmol) in DMF (5 mL) at room temperature under an argon atmosphere was added potassium carbonate (280 mg, 2 mmol) and 2-bromo-1-(4-fluorobenzofuran-2-yl) ethan-1-one (290 mg, 1 mmol). The reaction mixture was stirred at 80° C. for 5 min in microwave. After consumption of starting material (monitored by TLC), the reaction mixture was diluted with water (10 mL) and extracted with EtOAc (2×10 mL). The combined organic extracts were dried over sodium sulfate, filtered and concentrated in vacuo to afford (Z)-5-bromo-N'-(2-(4-fluorobenzofuran-2-yl)-2-oxoethoxy)-6-methoxypicolinimidamide (300 mg, crude) as brown syrup used in the next step without further purification.

LCMS: 25.4%; 421.8 (M+1); (column; Ascentis Express C-18 (50×3.0 mm, 2.7 μm); RT 2.49 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.3).

3-(5-bromo-6-methoxypyridin-2-yl)-5-(4-fluorobenzofuran-2-yl)-5,6-dihydro-4H-1,2,4-oxadiazine To a stirred solution of (Z)-5-bromo-N'-(2-(6-fluoro-1-methyl-5-(trifluoromethyl)-1H-indol-3-yl)-2-oxoethoxy)-6-methoxypicolinimidamide (580 mg, crude) in 1, 2-dichloro ethane (10 mL) at room temperature under an argon atmosphere was added trifluoroacetic acid (0.5 mL) and sodium triacetoxyborohydride (875 mg, 4.13 mmol). The reaction mixture was stirred for 16 h at room temperature. After consumption of starting material (monitored by TLC), the reaction mixture was diluted with 1N sodium hydroxide solution (20 mL) and extracted with $CH_2Cl_2$ (2×20 mL). The combined organic extracts were dried over sodium sulfate, filtered and concentrated in vacuo to afford 3-(5-bromo-6-methoxypyridin-2-yl)-5-(6-fluoro-1-methyl-5-(trifluoromethyl)-1H-indol-3-yl)-5,6-dihydro-4H-1,2,4-oxadiazine (400 mg, crude) as a pale yellow solid.

LCMS: 62.7%; 405.8 (M+1); (column; Ascentis Express C-18 (50×3.0 mm, 2.7 μm); RT 2.80 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.5).

Example 99

Synthesis of 5-(4-fluorobenzofuran-2-yl)-3-(6-methoxy-5-(4-methyl-1H-imidazol-1-yl) pyridin-2-yl)-5,6-dihydro-4H-1,2,4-oxadiazine

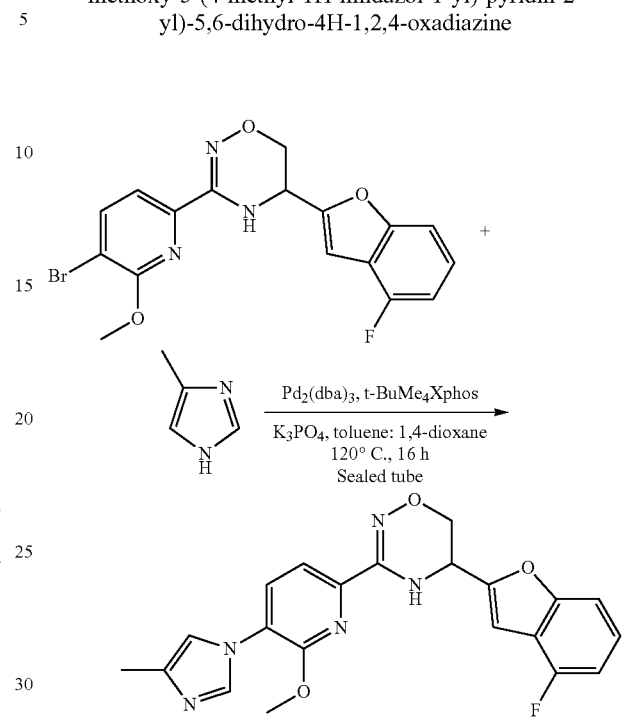

5-(4-fluorobenzofuran-2-yl)-3-(6-methoxy-5-(4-methyl-1H-imidazol-1-yl) pyridin-2-yl)-5,6-dihydro-4H-1,2,4-oxadiazine To a dry vial was added a suspension of $Pd_2(dba)_3$ (46 mg, 0.05 mmol) and tert-butyl tetramethyl Xphos (53 mg, 0.1 mmol) in toluene:1,4-dioxane (2:1, 13.5 mL) at room temperature. The suspension was degassed with argon, heated to 120° C., and stirred at 120° C. for 3 min. A mixture of 3-(5-bromo-6-methoxypyridin-2-yl)-5-(6-fluoro-1-methyl-5-(trifluoromethyl)-1H-indol-3-yl)-5,6-dihydro-4H-1,2,4-oxadiazine (450 mg, 1.1 mmol), 4-methyl-1H-imidazole (136 mg, 1.6 mmol) and potassium phosphate (470 mg, 2.2 mmol) in toluene:1,4-dioxane (2:1, 13.5 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo. The crude material was purified by preparative HPLC (Column X-select C18 column (250×19 mm, 5 μm (52 mg loading; $CH_3CN$: 005% TFA (0.01/95, 2/95, 15/70, 25/30, 30/10, 40/10); flow rate: 15 mL/min) to afford 5-(4-fluorobenzofuran-2-yl)-3-(6-methoxy-5-(4-methyl-1H-imidazol-1-yl) pyridin-2-yl)-5,6-dihydro-4H-1,2,4-oxadiazine (96 mg, 21%) as white solid.

Racemic compound of Example 99 was separated using a Chiralpak-ODH column (250×20 mm, 5 μm) (20 mg loading; 0.1% DEA in n-Hexane: IPA:MeOH (50:50) (A:B: 75:25) as mobile phase; flow rate: 18 mL/mm) to afford the compounds of Example 99A (Fraction (I) (+)) and Example 99B (Fraction (II) (−)).

Analytical conditions for Example 99A and Example 99B: HPLC (column; zorbax-SB-C-18 150×4.6 mm, 3.5µ), mobile Phase: ACN: 0.05% Aq TFA; flow rate: 1.0 mL/min; Gradient program: T/B % 0.01/90, 2/90, 8/10, 15/10: diluent: $CH_3CN$:Water; Chiral HPLC: (Chiralpak-IB (250× 4.6 mm, 5 µm; mobile phase (A) 0.1% DEA in n-Hexane (B) $CH_2Cl_2$:MeOH (50:50) (A:B; 85:15); flow Rate: 1.0 mL/min).

Example 99A, (+)-5-(4-fluorobenzofuran-2-yl)-3-(6-methoxy-5-(4-methyl-1H-imidazol-1-yl) pyridin-2-yl)-5,6-dihydro-4H-1,2,4-oxadiazine, fraction (I) (+): Mass (ESI): 408.3 [M+1]; HPLC (purity): 99.5%, RT 7.59 min; Chiral HPLC: 98.4%, RT=17.61 min; Optical rotation $[\alpha]_D^{20.00}$: +280.09 (c=0.25, $CH_2Cl_2$).

Example 99B, (−)-5-(4-fluorobenzofuran-2-yl)-3-(6-methoxy-5-(4-methyl-1H-imidazol-1-yl) pyridin-2-yl)-5,6-dihydro-4H-1,2,4-oxadiazine, fraction (II) (−): $^1$H NMR ($CD_3OD$, 500 MHz): δ 8.00 (s, 1H), 7.90 (d, 1H), 7.63 (d, 1H), 7.37 (d, 1H), 7.30-7.24 (m, 1H), 7.23 (s, 1H), 6.98 (t, 1H), 6.80 (s, 1H), 5.12 (t, 1H), 4.42 (dd, 1H), 4.14 (s, 3H), 4.08 (dd, 1H), 2.23 (s, 3H); Mass (ESI): 408.3 [M+1]; HPLC (purity): 99.5%, RT 21.85 min; Chiral HPLC: 99.5%, RT=21.85 min; Optical rotation $[\alpha]_D^{20.01}$: −237.68 (c=0.25, $CH_2Cl_2$).

Example 100

Synthesis of 3-(5-bromo-6-methoxypyridin-2-yl)-5-(5-fluoro-3-methylbenzofuran-2-yl)-5,6-dihydro-4H-1,2,4-oxadiazine

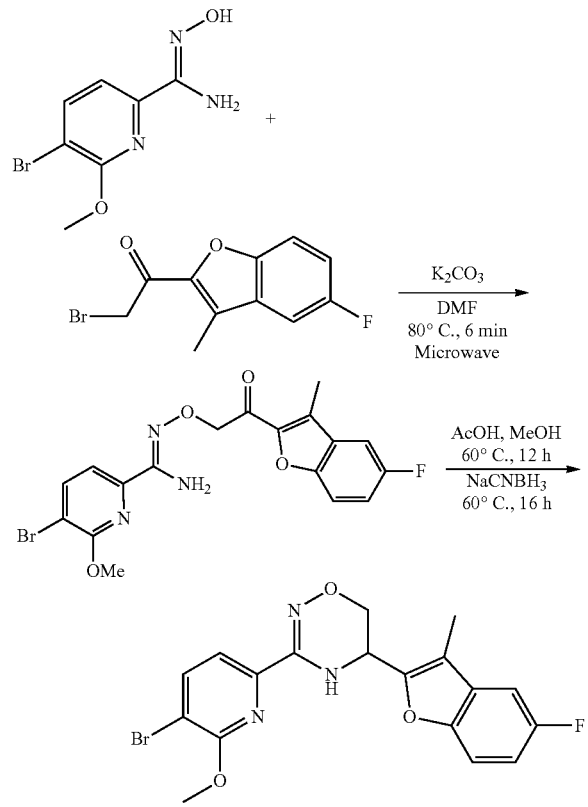

(Z)-5-bromo-N'-(2-(5-fluoro-3-methylbenzofuran-2-yl)-2-oxoethoxy)-6-methoxypicolinimidamide To a stirred solution of 5-bromo-N'-hydroxy-6-methoxypicolinimidamide (300 mg, 1 mmol) in DMF (3 mL) at room temperature under an argon atmosphere were added potassium carbonate (336 mg, 2 mmol) and 2-bromo-1-(5-fluoro-3-methylbenzofuran-2-yl) ethan-1-one (495 mg, 2 mmol). The reaction mixture was stirred at 80° C. for 6 min in microwave. After consumption of starting material (monitored by TLC), the reaction mixture was diluted with water (20 mL) and extracted with EtOAc (2×20 mL). The combined organic extracts were dried over sodium sulfate, filtered and concentrated in vacuo to afford (Z)-5-bromo-N'-(2-(5-fluoro-3-methylbenzofuran-2-yl)-2-oxoethoxy)-6-methoxypicolinimidamide (360 mg, crude) as brown solid used in the next step without further purification.

LCMS: 35.2%; 437.7 (M+2); (column; Ascentis Express C-18 (50×3.0 mm, 2.7 Inn); RT 3.05 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.5).

3-(5-bromo-6-methoxypyridin-2-yl)-5-(5-fluoro-3-methylbenzofuran-2-yl)-5,6-dihydro-4H-1,2,4-oxadiazine To a stirred solution of (Z)-5-bromo-N'-(2-(5-fluoro-3-methylbenzofuran-2-yl)-2-oxoethoxy)-6-methoxypicolinimidamide (720 mg, 2 mmol) in MeOH (12 mL) at room temperature under an argon atmosphere was added acetic acid (2.4 mL). The reaction mixture was stirred at 60° C. for 12 h. Then sodium cyanoborohydride (156 mg, 2 mmol) was added to the reaction mixture at room temperature. The reaction mixture was stirred at 60° C. for 16 h. After consumption of starting material (monitored by TLC), the reaction mixture was diluted with saturated sodium bicarbonate solution (20 mL) and extracted with EtOAc (2×20 mL). The combined organic extracts were dried over sodium sulfate, filtered and concentrated in vacuo to afford 3-(5-bromo-6-methoxypyridin-2-yl)-5-(5-fluoro-3-methylbenzofuran-2-yl)-5,6-dihydro-4H-1,2,4-oxadiazine (300 mg, 43%) as an off-white solid.

LCMS: 78.2%; 419.9 (M+1); (column; Ascentis Express C-18 (50×3.0 mm, 2.7 µm); RT 2.86 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.5).

Example 101

Synthesis of 5-(5-fluoro-3-methylbenzofuran-2-yl)-3-(6-methoxy-5-(4-methyl-1H-imidazol-1-yl) pyridin-2-yl)-5,6-dihydro-4H-1,2,4-oxadiazine

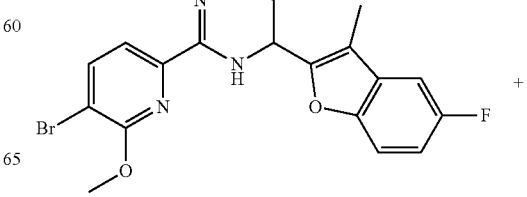

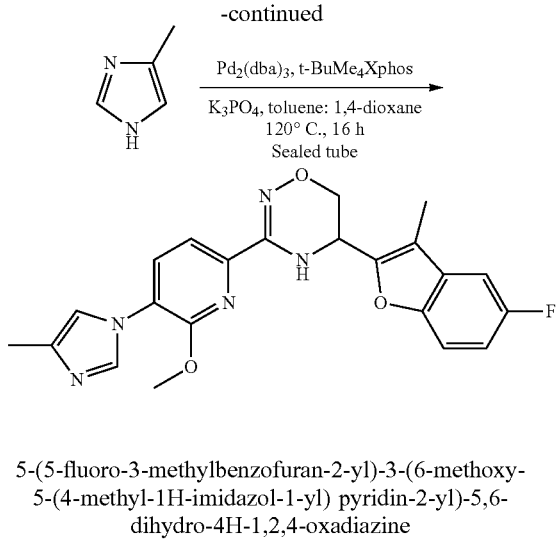

5-(5-fluoro-3-methylbenzofuran-2-yl)-3-(6-methoxy-5-(4-methyl-1H-imidazol-1-yl) pyridin-2-yl)-5,6-dihydro-4H-1,2,4-oxadiazine To a dry vial was added a suspension of Pd$_2$(dba)$_3$ (27 mg, 0.03 mmol) and tert-butyl tetramethyl Xphos (28 mg, 0.06 mmol) in toluene:1,4-dioxane (2:1, 3.75 mL) at room temperature. The suspension was degassed with argon, heated to 120° C., and stirred at 120° C. for 3 min. A mixture of 3-(5-bromo-6-methoxypyridin-2-yl)-5-(5-fluoro-3-methyl-benzofuran-2-yl)-5,6-dihydro-4H-1,2,4-oxadiazine (250 mg, 0.6 mmol), 4-methyl-1H-imidazole (73 mg, 1 mmol) and potassium phosphate (252 mg, 1.2 mmol) in toluene:1,4-dioxane (2:1, 3.75 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo. The crude material was purified by column chromatography using 3% MeOH: CH$_2$Cl$_2$ to afford 5-(5-fluoro-3-methylbenzofuran-2-yl)-3-(6-methoxy-5-(4-methyl-1H-imidazol-1-yl) pyridin-2-yl)-5,6-dihydro-4H-1,2,4-oxadiazine (120 mg, 48%) as an off-white solid.

Racemic compound of Example 101 was separated using a Chiralpak-IB column (250×19 mm, 5 µm) (31 mg loading; 0.1% DEA in n-Hexane: CH$_2$Cl$_2$:MeOH (50:50) (A:B: 85:15) as mobile phase; flow rate: 18 mL/min) to afford the compounds of Example 101A (Fraction (I) (−)) and Example 101B (Fraction (II) (+)).

Analytical conditions for Example 101A and Example 101B: HPLC (column; zorbax-SB-C-18 150×4.6 mm, 3.5µ), mobile Phase: ACN: 0.05% Aq TFA; flow rate: 1.0 mL/min; Gradient program: T/B % 0.01/90, 2/90, 8/10, 15/10: diluent: CH$_3$CN:Water; Chiral HPLC: (Chiralpak-IB (250× 4.6 mm, 5 µm; mobile phase (A) 0.1% DEA in n-Hexane (B) CH$_2$Cl$_2$:MeOH (50:50) (A:B; 85:15); flow Rate: 1.0 mL/min).

Example 101A, (−)-5-(5-fluoro-3-methylbenzofuran-2-yl)-3-(6-methoxy-5-(4-methyl-1H-imidazol-1-yl) pyridin-2-yl)-5,6-dihydro-4H-1,2,4-oxadiazine, fraction (I) (−): Mass (ESI): 422.4 [M+1]; HPLC (purity): 99.3%, RT 7.76 min; Chiral HPLC: 100%, RT=18.58 min; Optical rotation $[\alpha]_D^{19.98}$: −150.32 (c=0.25, CH$_2$Cl$_2$).

Example 101B, (+)-5-(5-fluoro-3-methylbenzofuran-2-yl)-3-(6-methoxy-5-(4-methyl-1H-imidazol-1-yl) pyridin-2-yl)-5,6-dihydro-4H-1,2,4-oxadiazine, fraction (II) (+): $^1$H NMR (CD$_3$OD, 400 MHz): δ 7.98 (s, 1H), 7.88 (d, 1H), 7.66 (d, 1H), 7.39 (dd, 1H), 7.33-7.19 (m, 2H), 7.04-6.99 (m, 1H), 5.16 (t, 1H), 4.23 (dd, 1H), 4.14 (dd, 1H), 4.08 (s, 3H), 2.27 (s, 3H), 2.25 (s, 3H); Mass (ESI): 422.3 [M+1]; HPLC (purity): 99.6%, RT 7.76 min; Chiral HPLC: 99.9%, RT=24.98 min; Optical rotation $[\alpha]_D^{20.00}$: +159.12 (c=0.25, CH$_2$Cl$_2$).

Example 102

Synthesis of 2-bromo-1-(6-fluoro-1-methyl-5-(trifluoromethyl)-1H-indol-3-yl) ethan-1-one

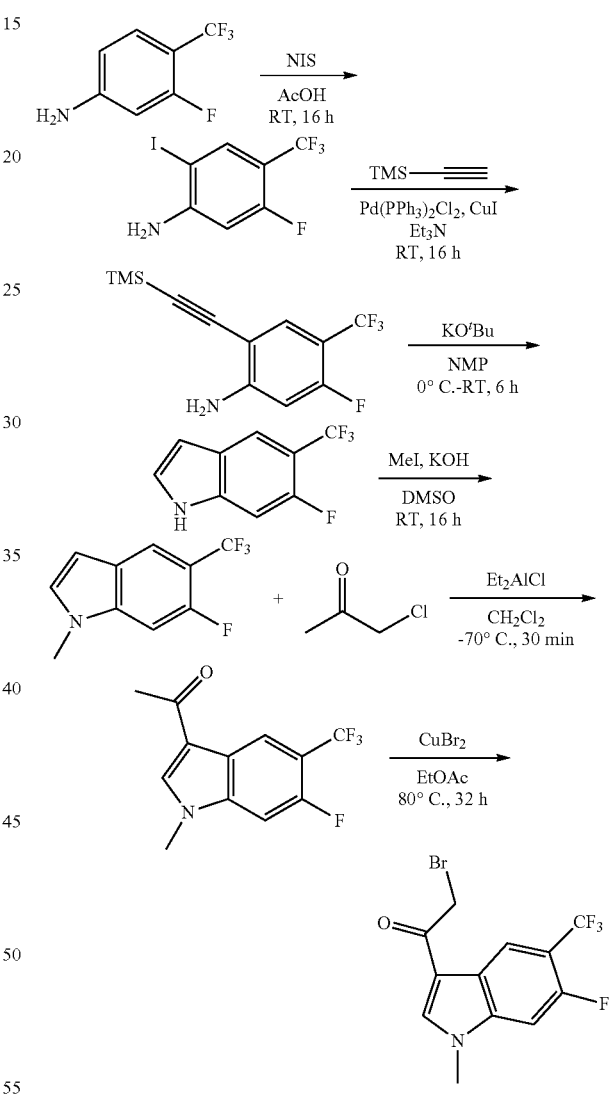

5-fluoro-2-iodo-4-(trifluoromethyl) aniline

To a stirred solution of 3-fluoro-4-(trifluoromethyl) aniline (10 g, 56 mmol) in acetic acid (40 mL) at room temperature under an argon atmosphere was added N-iodo succinimide (12.6 g, 56 mmol). The reaction mixture was stirred at room temperature for 16 h. After consumption of starting material (monitored by TLC), the reaction mixture was diluted with Na$_2$S$_2$O$_3$ solution (100 mL) and extracted with EtOAc (2×100 mL). The combined organic extracts were washed with saturated sodium bicarbonate solution (100 mL), dried over sodium sulfate, filtered and concentrated in vacuo. The crude material was purified by column chromatography using 2-3% EtOAc: Hexane to afford 5-fluoro-2-iodo-4-(trifluoromethyl) aniline (12 g, 70%) as a pale yellow solid. $^1$H NMR (CDCl$_3$, 400 MHz): δ 7.79 (d, 1H), 6.49 (d, 1H), 4.50 (br s, 2H); TLC: 5% EtOAc/Hexane (R$_f$: 0.5).

5-fluoro-4-(trifluoromethyl)-2-((trimethylsilyl) ethynyl) aniline

To a stirred solution of 5-fluoro-2-iodo-4-(trifluoromethyl) aniline (12 g, 40 mmol) in triethylamine (72 mL) at room temperature under an argon atmosphere were added copper iodide (374 mg, 1 mmol), TMS-acetylene (4.2 g, 43.40 mmol) and Pd(PPh$_3$)$_2$Cl$_2$ (1.38 g, 2 mmol). The reaction mixture was stirred at room temperature for 16 h. After consumption of starting material (monitored by TLC), the volatiles were evaporated in vacuo. The crude material was purified by column chromatography using 2-3% EtOAc: Hexane to afford 5-fluoro-4-(trifluoromethyl)-2-((trimethylsilyl) ethynyl) aniline (9 g, 83%) as a pale yellow solid.
$^1$H NMR (CDCl$_3$, 400 MHz): δ 7.50 (d, 1H), 6.43 (d, 1H), 4.65 (br s, 2H), 0.27 (s, 9H); TLC: 5% EtOAc/Hexane (R$_f$: 0.6).

6-fluoro-5-(trifluoromethyl)-1H-indole

To a stirred solution of 5-fluoro-4-(trifluoromethyl)-2-((trimethylsilyl) ethynyl) aniline (9 g, 33 mmol) in N-Methylpyrrolidone (100 mL) at 0° C. under an argon atmosphere was added potassium tert-butoxide (7.3 g, 65 mmol). The reaction mixture was warmed to room temperature and stirred for 6 h. After consumption of starting material (monitored by TLC), the reaction mixture was diluted with water (100 mL) and extracted with EtOAc (2×100 mL). The combined organic extracts were washed with water (100 mL), dried over sodium sulfate, filtered and concentrated in vacuo. The crude material was purified by column chromatography using 2-3% EtOAc: Hexane to afford 6-fluoro-5-(trifluoromethyl)-1H-indole (6 g, 90%) as brown liquid.
$^1$H NMR (CDCl$_3$, 400 MHz): δ 8.47 (br s, 1H), 7.85 (d, 1H), 7.27-7.24 (m, 1H), 7.20 (d, 1H), 6.63 (br s, 1H); TLC: 10% EtOAc/Hexane (R$_f$: 0.5).

6-fluoro-1-methyl-5-(trifluoromethyl)-1H-indole

To a stirred solution of 6-fluoro-5-(trifluoromethyl)-1H-indole (6 g, 30 mmol) in DMSO (30 mL) at room temperature under an argon atmosphere were added potassium hydroxide (2.5 g, 44.30 mmol) and methyl iodide (2.2 mL, 44 mmol). The reaction mixture was stirred at room temperature for 16 h. After consumption of starting material (monitored by TLC), the reaction mixture was diluted with water (100 mL) and extracted with hexane (2×100 mL). The combined organic extracts were dried over sodium sulfate, filtered and concentrated in vacuo. The crude material was purified by column chromatography using 2-3% EtOAc: Hexane to afford 6-fluoro-1-methyl-5-(trifluoromethyl)-1H-indole (5 g, 78%) as brown liquid.
$^1$H NMR (CDCl$_3$, 400 MHz): δ 7.82 (d, 1H), 7.10 (d, 1H), 7.08 (s, 1H), 6.53 (d, 1H), 3.76 (s, 3H), 2.50 (s, 3H); TLC: 5% EtOAc/Hexane (R$_f$: 0.5).

Synthesis of 1-(6-fluoro-1-methyl-5-(trifluoromethyl)-1H-indol-3-yl) ethan-1-one To a stirred solution of 6-fluoro-1-methyl-5-(trifluoromethyl)-1H-indole (250 mg, 1 mmol) in CH$_2$Cl$_2$ (25 mL) at −70° C. under an argon atmosphere was added Et$_2$AlCl (207 mg, 2 mmol). The reaction mixture was stirred for 5 min at −70° C. Then acetyl chloride (136.5 mL, 2 mmol) was added to the reaction mixture at −70° C. The reaction mixture was stirred for 30 min at −70° C. After consumption of starting material (monitored by TLC), the reaction mixture was diluted with saturated sodium bicarbonate solution (10 mL) and extracted with CH$_2$Cl$_2$ (2×10 mL). The combined organic extracts were dried over sodium sulfate, filtered and concentrated in vacuo. The crude material was purified by column chromatography using 20-30% EtOAc: Hexane to afford 1-(6-fluoro-1-methyl-5-(trifluoromethyl)-1H-indol-3-yl) ethan-1-one (110 mg, 38%) as an off-white solid.
$^1$H NMR (CDCl$_3$, 400 MHz): δ 8.66 (d, 1H), 7.71 (s, 1H), 7.11 (d, 1H), 3.81 (s, 3H), 2.50 (s, 3H); TLC: 50% EtOAc/Hexane (R$_f$: 0.3).

2-bromo-1-(6-fluoro-1-methyl-5-(trifluoromethyl)-1H-indol-3-yl) ethan-1-one

To a stirred solution of 1-(6-fluoro-1-methyl-5-(trifluoromethyl)-1H-indol-3-yl) ethan-1-one (50 mg, 0.2 mmol) in EtOAc (5 mL) at room temperature under an argon atmosphere was added copper bromide (64 mg, 0.3 mmol). The reaction mixture was stirred at 80° C. for 32 h. After consumption of starting material (monitored by TLC), the reaction mixture was filtered, the filtrate was concentrated in vacuo. The crude material was purified by column chromatography using 10-15% EtOAc: Hexane to afford 2-bromo-1-(6-fluoro-1-methyl-5-(trifluoromethyl)-1H-indol-3-yl) ethan-1-one (40 mg, 61%) as a pale yellow solid.
$^1$H NMR (CDCl$_3$, 400 MHz): δ 8.63 (d, 1H), 7.88 (s, 1H), 7.15 (d, 1H), 4.24 (s, 2H), 3.88 (s, 3H); LCMS: 90.4%; 339.6 (M+3); (column; Ascentis Express C-18 (50×3.0 mm, 2.7 μm); RT 2.61 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 40% EtOAc/Hexane (R$_f$: 0.5).

Example 103

Synthesis of 3-(5-bromo-6-methoxypyridin-2-yl)-5-(6-fluoro-1-methyl-5-(trifluoromethyl)-1H-indol-3-yl)-5,6-dihydro-4H-1,2,4-oxadiazine

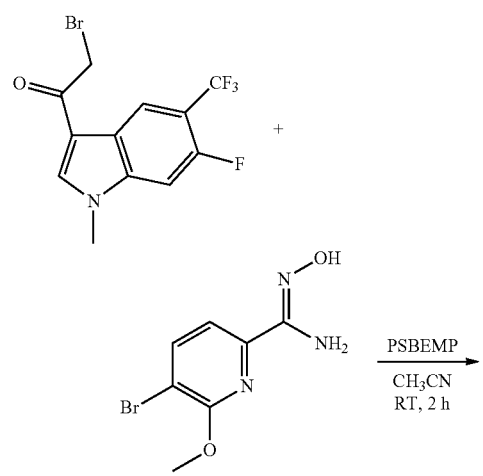

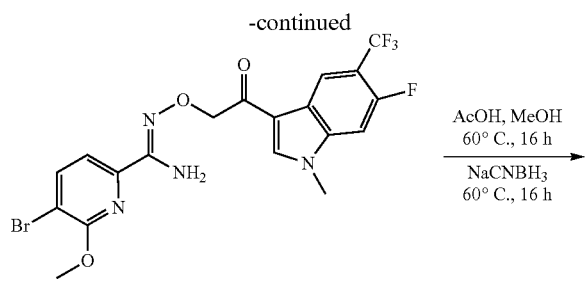

(Z)-5-bromo-N'-(2-(6-fluoro-1-methyl-5-(trifluorom-ethyl)-1H-indol-3-yl)-2-oxoethoxy)-6-methoxypico-linimidamide To a stirred solution of 5-bromo-N'-hydroxy-6-methoxypicolinimidamide (500 mg, 2 mmol) in CH₃CN (25 mL) at room temperature under an argon atmosphere was added PS-BEMP (668 mg, 2 mmol). The reaction mixture was stirred for 10 min at room temperature. Then 2-bromo-1-(6-fluoro-1-methyl-5-(trifluoromethyl)-1H-indol-3-yl) ethan-1-one (760 mg, 2 mmol) in CH₃CN (25 mL) was added to the reaction mixture at room temperature. The reaction mixture was stirred at room temperature for 2 h. After consumption of starting material (monitored by TLC), the reaction mixture was filtered and the filtrate was concentrated in vacuo to afford (Z)-5-bromo-N'-(2-(6-fluoro-1-methyl-5-(trifluoromethyl)-1H-indol-3-yl)-2-oxoethoxy)-6-methoxypicolinimidamide (580 mg, crude) as a pale yellow syrup used in the next step without further purification.

LCMS: 72.7%; 504.6 (M+2); (column; Ascentis Express C-18 (50×3.0 mm, 2.7 μm); RT 2.91 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane (R$_f$: 0.3).

3-(5-bromo-6-methoxypyridin-2-yl)-5-(6-fluoro-1-methyl-5-(trifluoromethyl)-1H-indol-3-yl)-5,6-di-hydro-4H-1,2,4-oxadiazin To a stirred solution of (Z)-5-bromo-N'-(2-(6-fluoro-1-methyl-5-(trifluoromethyl)-1H-indol-3-yl)-2-oxoethoxy)-6-methoxypicolinimidamide (500 mg, crude) in MeOH (10 mL) at room temperature under an argon atmosphere was added acetic acid (2.5 mL). The reaction mixture was stirred at 60° C. for 16 h. Then sodium cyanoborohydride (75 mg, 1 mmol) was added to the reaction mixture at room temperature. The reaction mixture was stirred at 60° C. for 16 h. After consumption of starting material (monitored by TLC), the reaction mixture was diluted with 1N sodium hydroxide solution (20 mL) and extracted with EtOAc (2×20 mL). The combined organic extracts were dried over sodium sulfate, filtered and concentrated in vacuo to afford 3-(5-bromo-6-methoxypyridin-2-yl)-5-(6-fluoro-1-methyl-5-(trifluoromethyl)-1H-indol-3-yl)-5,6-dihydro-4H-1,2,4-oxadiazine (400 mg, crude) as a pale yellow solid.

LCMS: 47.9%; 488.8 (M+3); (column; Ascentis Express C-18 (50×3.0 mm, 2.7 μm); RT 2.88 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane (R$_f$: 0.5).

Example 104

Synthesis of 5-(6-fluoro-1-methyl-5-(trifluorom-ethyl)-1H-indol-3-yl)-3-(6-methoxy-5-(4-methyl-1H-imidazol-1-yl) pyridin-2-yl)-5,6-dihydro-4H-1,2,4-oxadiazine

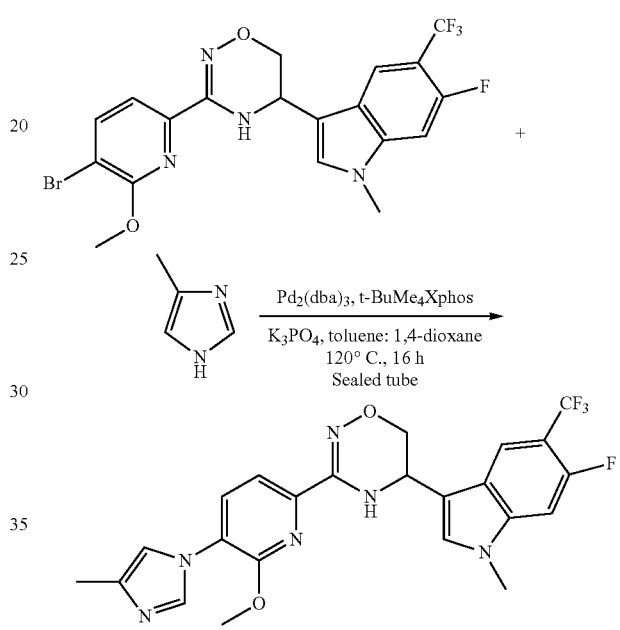

5-(6-fluoro-1-methyl-5-(trifluoromethyl)-1H-indol-3-yl)-3-(6-methoxy-5-(4-methyl-1H-imidazol-1-yl) pyridin-2-yl)-5,6-dihydro-4H-1,2,4-oxadiazine To a dry vial was added a suspension of Pd₂(dba)₃ (46 mg, 0.05 mmol) and tert-butyl tetramethyl Xphos (48 mg, 0.1 mmol) in toluene:1,4-dioxane (2:1, 15 mL) at room temperature. The suspension was degassed with argon, heated to 120° C., and stirred at 120° C. for 3 min. A mixture of 3-(5-bromo-6-methoxypyridin-2-yl)-5-(6-fluoro-1-methyl-5-(trifluoromethyl)-1H-indol-3-yl)-5,6-dihydro-4H-1,2,4-oxadiazine Example (500 mg, 1 mmol), 4-methyl-1H-imidazole (126 mg, 1 mmol) and potassium phosphate (432 mg, 2 mmol) in toluene:1,4-dioxane (2:1, 15 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo. The crude material was purified by preparative HPLC (Column X-select CSH C18 column (250×19 mm, 5 μm (50 mg loading; CH₃CN: 005% TFA (0.01/95, 2/95, 15/70, 25/30, 30/10, 40/10); flow rate: 15 mL/min) to afford 5-(6-fluoro-1-methyl-5-(trifluoromethyl)-

1H-indol-3-yl)-3-(6-methoxy-5-(4-methyl-1H-imidazol-1-yl) pyridin-2-yl)-5,6-dihydro-4H-1,2,4-oxadiazine (110 mg, 22%) as an off-white solid.

Racemic compound of Example 104 was separated using a Chiralpak-AD-H column (250×21 mm, 5 µm) (11.5 mg loading; 0.1% DEA in n-Hexane: EtOH:MeOH (50:50) (A:B: 80:20) as mobile phase; flow rate: 20 mL/min) to afford the compounds of Example 104A (Fraction (I) (−)) and Example 104B (Fraction (II) (+)).

Analytical conditions for Example 104A and Example 104B: HPLC (column; zorbax-SB-C-18 150×4.6 mm, 3.5µ), Phase: ACN: 0.05% Aq TFA; flow rate: 1.0 mL/min; Gradient program: T/B % 0.01/90, 2/90, 8/10, 10/10: diluent: CH$_3$CN:Water; Chiral HPLC: (Chiralcel-ADH (250×4.6 mm, 5 µm; mobile phase (A) 0.1% DEA in n-Hexane (B) MeOH: EtOH (50:50) (A:B; 80:20); flow Rate: 1.0 mL/min).

Example 104A, (−)-5-(6-fluoro-1-methyl-5-(trifluoromethyl)-1H-indol-3-yl)-3-(6-methoxy-5-(4-methyl-1H-imidazol-1-yl) pyridin-2-yl)-5,6-dihydro-4H-1,2,4-oxadiazine, fraction (I) (−): Mass (ESI): 489.3 [M+1]; HPLC (purity): 99.6%, RT 7.87 min; Chiral HPLC: 99.8%, RT=12.10 min; Optical rotation $[\alpha]_D^{20.01}$: −91.92 (c=0.25, CH$_2$Cl$_2$).

Example 104B, (+)-5-(6-fluoro-1-methyl-5-(trifluoromethyl)-1H-indol-3-yl)-3-(6-methoxy-5-(4-methyl-1H-imidazol-1-yl) pyridin-2-yl)-5,6-dihydro-4H-1,2,4-oxadiazine, fraction (II) (+): $^1$H NMR (CD$_3$OD, 400 MHz): δ 8.00 (d, 2H), 7.89 (d, 1H), 7.65 (d, 1H), 7.39 (s, 1H), 7.37 (s, 1H), 7.21 (br s, 1H), 5.18 (t, 1H), 4.20 (dd, 1H), 4.05 (dd, 1H), 4.01 (s, 3H), 3.80 (s, 3H), 2.25 (s, 3H); Mass (ESI): 489.4 [M+1]; HPLC (purity): 99.8%, RT 7.86 min; Chiral HPLC: 99.3%, RT=16.05 min; Optical rotation $[\alpha]_D^{20.03}$=+86.41 (c=0.25, CH$_2$Cl$_2$).

Example 105

Synthesis of 3-(5-bromo-6-methoxypyridin-2-yl)-5-(4-chloro-3-fluorophenyl)-5,6-dihydro-4H-1,2,4-oxadiazine

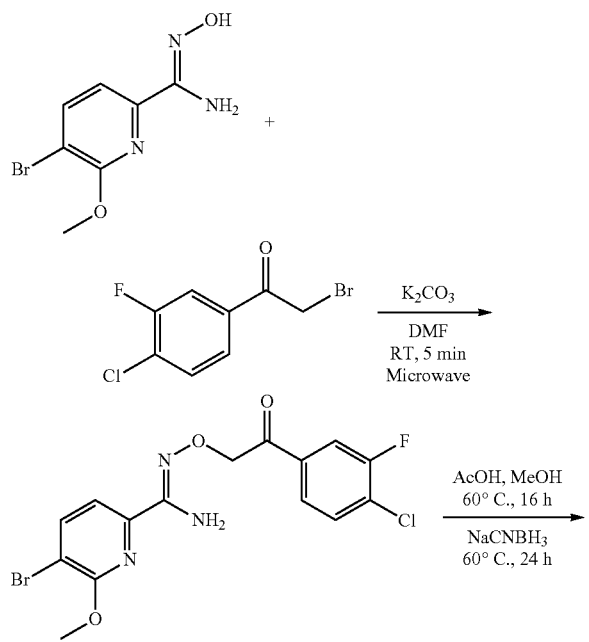

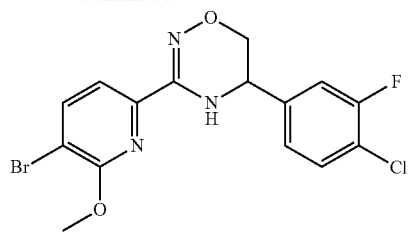

(Z)-5-bromo-N'-(2-(4-chloro-3-fluorophenyl)-2-oxoethoxy)-6-methoxypicolinimidamide To a stirred solution of 5-bromo-N'-hydroxy-6-methoxypicolinimidamide (500 mg, 2 mmol) in DMF (5 mL) at room temperature under an argon atmosphere were added potassium carbonate (420 mg, 3 mmol) and 2-bromo-1-(4-chloro-3-fluorophenyl) ethan-1-one (610 mg, 2 mmol). The reaction mixture was stirred at 80° C. for 5 min in microwave. After consumption of starting material (monitored by TLC), the reaction mixture was diluted with water (20 mL) and extracted with EtOAc (2×20 mL). The combined organic extracts were dried over sodium sulfate, filtered and concentrated in vacuo to afford (Z)-5-bromo-N'-(2-(4-chloro-3-fluorophenyl)-2-oxoethoxy)-6-methoxypicolinimidamide (900 mg, crude) as a pale yellow solid.

LCMS: 31.6%; 417.7 (M+3); (column; Ascentis Express C-18 (50×3.0 mm, 2.7 µm); RT 2.95 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane (R$_f$: 0.4).

3-(5-bromo-6-methoxypyridin-2-yl)-5-(4-chloro-3-fluorophenyl)-5,6-dihydro-4H-1,2,4-oxadiazine To a stirred solution of (Z)-5-bromo-N'-(2-(4-chloro-3-fluorophenyl)-2-oxoethoxy)-6-methoxypicolinimidamide (1 g, 2 mmol) in MeOH (15 mL) at room temperature under an argon atmosphere was added acetic acid (1.5 mL). The reaction mixture was stirred for 16 h at 60° C. Then sodium cyanoborohydride (181 mg, 3 mmol) was added to the reaction mixture at room temperature. The reaction mixture was stirred at 60° C. for 24 h. After consumption of starting material (monitored by TLC), the volatiles were evaporated in vacuo. The residue was diluted with saturated sodium bicarbonate solution (50 mL) and extracted with EtOAc (2×50 mL). The combined organic extracts were washed with water (20 mL), dried over sodium sulfate, filtered and concentrated in vacuo to afford 3-(5-bromo-6-methoxypyridin-2-yl)-5-(4-chloro-3-fluorophenyl)-5,6-dihydro-4H-1,2,4-oxadiazine (800 mg, crude) as yellow syrup used in the next step without further purification.

LCMS: 36.1%; 399.8 (M+1); (column; Ascentis Express C-18 (50×3.0 mm, 2.7 µm); RT 2.83 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 25% EtOAc/Hexane (R$_f$: 0.3).

Example 106

Synthesis of 5-(4-chloro-3-fluorophenyl)-3-(6-methoxy-5-(4-methyl-1H-imidazol-1-yl) pyridin-2-yl)-5,6-dihydro-4H-1,2,4-oxadiazine

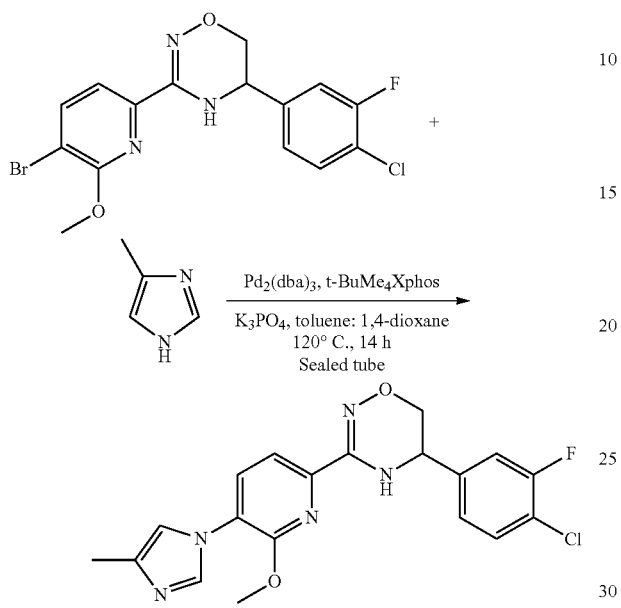

5-(4-chloro-3-fluorophenyl)-3-(6-methoxy-5-(4-methyl-1H-imidazol-1-yl) pyridin-2-yl)-5,6-dihydro-4H-1,2,4-oxadiazine To a dry vial was added a suspension of Pd$_2$(dba)$_3$ (76 mg, 0.08 mmol) and tert-butyl tetramethyl Xphos (76 mg, 0.1 mmol) in toluene:1,4-dioxane (2:1, 15 mL) at room temperature. The suspension was degassed with argon, heated to 120° C., and stirred at 120° C. for 3 min. A mixture of 3-(5-bromo-6-methoxypyridin-2-yl)-5-(4-chloro-3-fluorophenyl)-5,6-dihydro-4H-1, 2, 4-oxadiazine (640 mg, 1.6 mmol), 4-methyl-1H-imidazole (157 mg, 2.0 mmol) and potassium phosphate (678 mg, 3.2 mmol) in toluene:1,4-dioxane (2:1, 15 mL) was degassed and the catalyst pre-mixture was added. The resultant mixture was stirred at 120° C. for 14 h in a sealed tube. After consumption of the starting material (monitored by TLC and LCMS), the reaction mixture was filtered and the filtrate was concentrated in vacuo. The residue was diluted with saturated sodium bicarbonate solution (50 mL) and extracted with EtOAc (2×50 mL). The combined organic extracts were washed with water (20 mL), dried over sodium sulfate, filtered and concentrated in vacuo. The crude material was purified by preparative HPLC (Column X-select C18 column (250×19 mm, 5 µm (50 mg loading; CH$_3$CN: 005% TFA (0.01/95, 2/95, 15/75, 30/35, 35/10, 40/10); flow rate: 15 mL/min) to afford 5-(4-chloro-3-fluorophenyl)-3-(6-methoxy-5-(4-methyl-1H-imidazol-1-yl) pyridin-2-yl)-5,6-dihydro-4H-1,2,4-oxadiazine (400 mg, 67%) as an off-white solid.

Racemic compound of Example 106 was separated using a Chiralpak-IB column (250×20 mm, 5 µm) (30 mg loading; 0.1% DEA in n-Hexane: CH$_2$Cl$_2$:MeOH (50:50) (A:B: 80:20) as mobile phase; flow rate: 20 mL/min) to afford the compounds of Example 106A (Fraction (I) (−)) and Example 106B (Fraction (II) (+)).

Analytical conditions for Example 106A and Example 106B: HPLC (column; zorbax-SB-C-18 150×4.6 mm, 3.5µ), mobile Phase: ACN: 0.05% Aq TFA; flow rate: 1.0 mL/min; Gradient program: T/B % 0.01/90, 2/90, 8/10, 15/10: diluent: CH$_3$CN:Water; Chiral HPLC: (Chiralpak-IB (250× 4.6 mm, 5 µm; mobile phase (A) 0.1% DEA in n-Hexane (B) CH$_2$Cl$_2$:MeOH (50:50) (A:B; 70:30); flow Rate: 1.0 mL/min).

Example 106A, (−)-5-(4-chloro-3-fluorophenyl)-3-(6-methoxy-5-(4-methyl-1H-imidazol-1-yl) pyridin-2-yl)-5,6-dihydro-4H-1,2,4-oxadiazine, fraction (I) (−): Mass (ESI): 354.3 [M+1]; HPLC (purity): 99.5%, RT 6.11 min; Chiral HPLC: 100%, RT=7.66 min; Optical rotation $[\alpha]_D^{19.99}$: −35.48 (c=0.25, CH$_2$Cl$_2$).

Example 106B, (+)-5-(4-chloro-3-fluorophenyl)-3-(6-methoxy-5-(4-methyl-1H-imidazol-1-yl) pyridin-2-yl)-5,6-dihydro-4H-1,2,4-oxadiazine, fraction (II) (+):
$^1$H NMR (CD$_3$OD, 400 MHz): δ 7.97 (s, 1H), 7.87 (d, 1H), 7.63 (d, 1H), 7.47 (t, 1H), 7.26 (dd, 1H), 7.21 (s, 2H), 4.88 (t, 1H), 4.09 (s, 3H), 4.07-3.96 (m, 2H), 2.24 (s, 3H); Mass (ESI): 354.3 [M+1]; HPLC (purity): 98.9%, RT 6.11 min; Chiral HPLC: 99.5%, RT=9.51 min; Optical rotation $[\alpha]_D^{20.00}$: +41.08 (c=0.25, CH$_2$Cl$_2$).

Example 107

Synthesis of 3-(5-bromo-6-methoxypyridin-2-yl)-5-(3-chloro-4-fluorophenyl)-5,6-dihydro-4H-1,2,4-oxadiazine

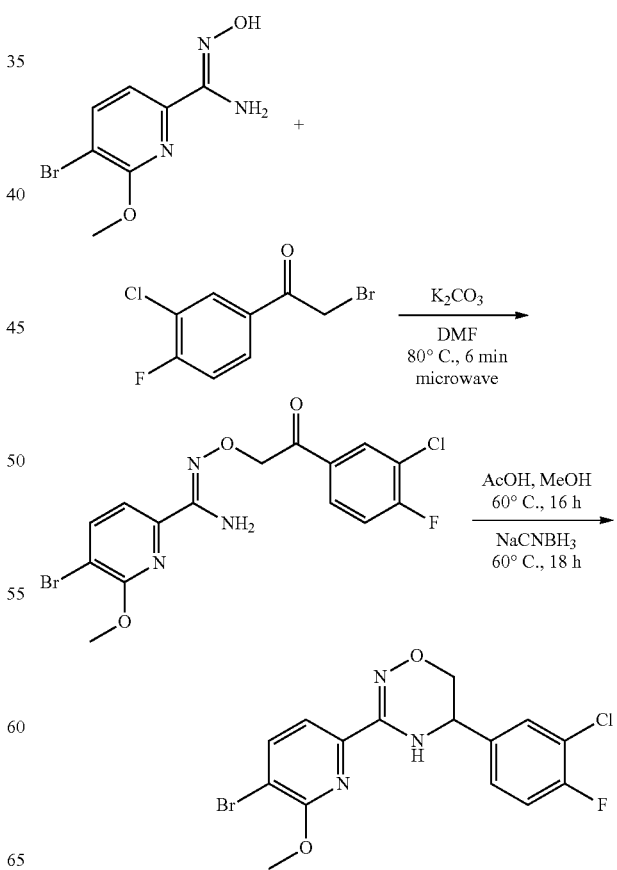

(Z)-5-bromo-N'-(2-(3-chloro-4-fluorophenyl)-2-oxoethoxy)-6-methoxypicolinimidamide To a stirred solution of 5-bromo-N'-hydroxy-6-methoxypicolinimidamide (500 mg, 2 mmol) in DMF (5 mL) at room temperature under an argon atmosphere were added potassium carbonate (560 mg, 4 mmol) and 2-bromo-1-(3-chloro-4-fluorophenyl) ethan-1-one (765 mg, 3 mmol). The reaction mixture was stirred at 80° C. for 6 min in microwave. After consumption of starting material (monitored by TLC), the reaction mixture was diluted with water (20 mL) and extracted with EtOAc (2×20 mL). The combined organic extracts were dried over sodium sulfate, filtered and concentrated in vacuo to afford (Z)-5-bromo-N'-(2-(3-chloro-4-fluorophenyl)-2-oxoethoxy)-6-methoxypicolinimidamide (600 mg, crude) as brown solid used in the next step without further purification.

LCMS: 34.6%; 417.7 (M+3); (column; Ascentis Express C-18 (50×3.0 mm, 2.7 nm); RT 2.94 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.5).

3-(5-bromo-6-methoxypyridin-2-yl)-5-(3-chloro-4-fluorophenyl)-5,6-dihydro-4H-1,2,4-oxadiazine To a stirred solution of (Z)-5-bromo-N'-(2-(3-chloro-4-fluorophenyl)-2-oxoethoxy)-6-methoxypicolinimidamide (500 mg, 1 mmol) in MeOH (10 mL) at room temperature under an argon atmosphere was added acetic acid (2 mL). The reaction mixture was stirred for 16 h at 60° C. Then sodium cyanoborohydride (113 mg, 2 mmol) was added to the reaction mixture at room temperature. The reaction mixture was stirred for 18 h at 60° C. After consumption of starting material (monitored by TLC), the reaction mixture was diluted with saturated sodium bicarbonate solution (20 mL) and extracted with EtOAc (2×20 mL). The combined organic extracts were dried over sodium sulfate, filtered and concentrated in vacuo to afford 3-(5-bromo-6-methoxypyridin-2-yl)-5-(3-chloro-4-fluorophenyl)-5,6-dihydro-4H-1,2,4-oxadiazine (250 mg, 52%) as a pale yellow solid.

LCMS: 50.2%; 401.7 (M+3); (column; Ascentis Express C-18 (50×3.0 mm, 2.7 μm); RT 2.91 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.6).

Example 108

Synthesis of 5-(3-chloro-4-fluorophenyl)-3-(6-methoxy-5-(4-methyl-1H-imidazol-1-yl) pyridin-2-yl)-5,6-dihydro-4H-1,2,4-oxadiazine

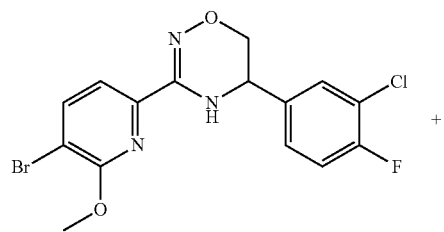

+

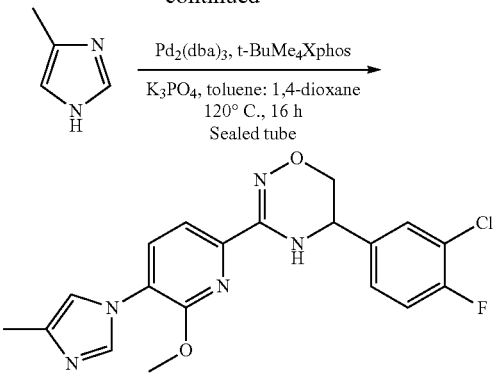

5-(3-chloro-4-fluorophenyl)-3-(6-methoxy-5-(4-methyl-1H-imidazol-1-yl) pyridin-2-yl)-5,6-dihydro-4H-1,2,4-oxadiazine To a dry vial was added a suspension of $Pd_2(dba)_3$ (28 mg, 0.03 mmol) and tert-butyl tetramethyl Xphos (29 mg, 0.06 mmol) in toluene:1,4-dioxane (2:1, 3.25 mL) at room temperature. The suspension was degassed with argon, heated to 120° C., and stirred at 120° C. for 3 min. A mixture of 3-(5-bromo-6-methoxypyridin-2-yl)-5-(3-chloro-4-fluorophenyl)-5,6-dihydro-4H-1,2,4-oxadiazine (250 g, 0.6 mmol), 4-methyl-1H-imidazole (76 mg, 0.9 mmol) and potassium phosphate (264 mg, 1 mmol) in toluene:1,4-dioxane (2:1, 3.25 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with EtOAc (2×20 mL). The combined organic extracts were washed with water (20 mL), dried over sodium sulfate, filtered and concentrated in vacuo. The crude material was purified by preparative HPLC (Column X-select CSH C18 column (250×19 mm, 5 μm (65 mg loading; $CH_3CN$: 005% TFA (0.01/90, 2/90, 15/70, 25/30, 30/10, 35/10); Flow rate: 15 mL/min) to afford 5-(3-chloro-4-fluorophenyl)-3-(6-methoxy-5-(4-methyl-1H-imidazol-1-yl) pyridin-2-yl)-5,6-dihydro-4H-1,2,4-oxadiazine (110 mg, 44%) as a pale yellow solid.

Racemic compound of Example 108 was separated using a Chiralpak-IB column (250×20 mm, 5 μm) (35 mg loading; 0.1% DEA in n-Hexane: $CH_2Cl_2$:MeOH (50:50) (A:B: 80:20) as mobile phase; flow rate: 20 mL/min) to afford the compounds of Example 108A (Fraction (I) (−)) and Example 108B (Fraction (II) (+)).

Analytical conditions for Example 108A and Example 108B: HPLC (column; zorbax-SB-C-18 150×4.6 mm, 5 μm); mobile Phase: ACN: 0.05% Aq TFA; flow rate: 1.0 mL/min; Gradient program: T/B % 0.01/90, 2/90, 8/10, 15/10: diluent: $CH_3CN$:Water; Chiral HPLC: (Chiralpak-IB (250×4.6 mm, 5 μm; mobile phase (A) 0.1% DEA in n-Hexane (B) $CH_2Cl_2$:MeOH (50:50) (A:B; 80:20); flow Rate: 1.0 mL/min).

Example 108A, (−)-5-(3-chloro-4-fluorophenyl)-3-(6-methoxy-5-(4-methyl-1H-imidazol-1-yl) pyridin-2-yl)-5,6-dihydro-4H-1,2,4-oxadiazine, fraction (I) (−): Mass (ESI): 402.3 [M+1]; HPLC (purity): 99.6%, RT 7.64 min; Chiral HPLC: 100%, RT=11.07 min; Optical rotation $[\alpha]_D^{20.01}$: −161.76 (c=0.25, $CH_2Cl_2$).

Example 108B, (+)-5-(3-chloro-4-fluorophenyl)-3-(6-methoxy-5-(4-methyl-1H-imidazol-1-yl) pyridin-2-yl)-5,6-dihydro-4H-1,2,4-oxadiazine, fraction (II) (+): ¹H NMR (CD₃OD, 400 MHz): δ 7.98 (s, 1H), 7.89 (d, 1H), 7.63 (d, 1H), 7.50 (dd, 1H), 7.36-7.30 (m, 1H), 7.25 (d, 1H), 7.20 (s, 1H), 4.89 (t, 1H), 4.10 (s, 3H), 4.08 (dd, 1H), 3.95 (dd, 1H), 2.23 (s, 3H); Mass (ESI): 402.3 [M+1]; HPLC (purity): 99.5%; RT 7.63 min; Chiral HPLC: 100%, RT=14.35 min; Optical rotation $[\alpha]_D^{20.01}$: +164.75 (c=0.25, CH₂Cl₂).

Example 109

Synthesis of 2-bromo-1-(3-chloro-5-fluorophenyl) ethan-1-one

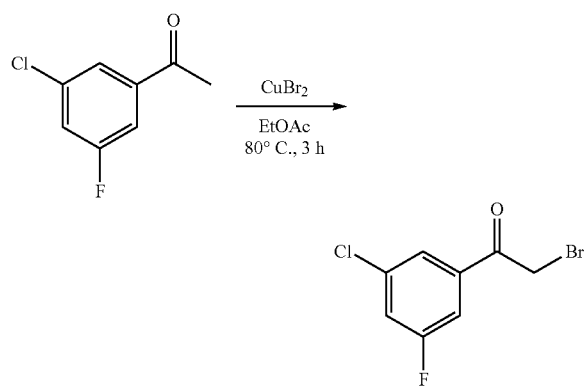

2-bromo-1-(3-chloro-5-fluorophenyl) ethan-1-one

To a stirred solution of 1-(3-chloro-5-fluorophenyl) ethan-1-one (4 g, 23 mmol) in EtOAc (20 mL) at room temperature under an argon atmosphere was added copper bromide (11.4 g, 51 mmol). The reaction mixture was stirred for 3 h at 80° C. After consumption of starting material (monitored by TLC), the reaction mixture was filtered. The filtrate was concentrated in vacuo to afford 2-bromo-1-(3-chloro-5-fluorophenyl) ethan-1-one (5 g, crude) as colorless liquid used in the next step without further purification.

LCMS: 73.3%; 250.9 (M+1); (column; X-select CSH C-18 (50×3.0 mm, 3.5 μm); RT 3.90 min; mobile phase: 5 mM Aq NH₄OAc: ACN; T/B %: 0.01/10, 0.5/10, 4/90, 9/90; flow rate: 0.8 mL/min) (Gradient); TLC: 20% CH₂Cl₂/Hexane (R_f: 0.5).

Example 110

Synthesis of 3-(5-bromo-6-methoxypyridin-2-yl)-5-(3-chloro-5-fluorophenyl)-5,6-dihydro-4H-1,2,4-oxadiazine

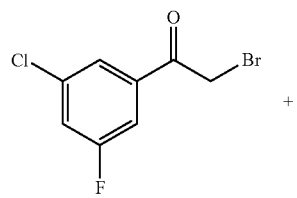

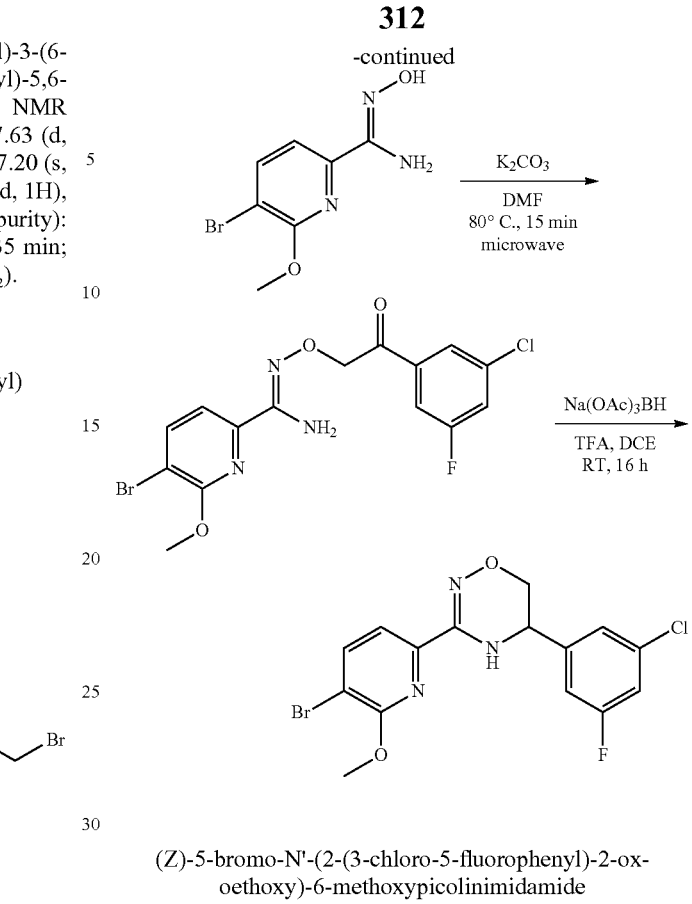

(Z)-5-bromo-N'-(2-(3-chloro-5-fluorophenyl)-2-oxoethoxy)-6-methoxypicolinimidamide To a stirred solution of 5-bromo-N'-hydroxy-6-methoxypicolinimidamide (500 mg, 2 mmol) in DMF (10 mL) at room temperature under an argon atmosphere were added potassium carbonate (560 mg, 4 mmol) and 2-bromo-1-(3-chloro-5-fluorophenyl) ethan-1-one (766 mg, 3 mmol). The reaction mixture was stirred for 15 min at 80° C. in microwave. After consumption of starting material (monitored by TLC), the reaction mixture was diluted with water (10 mL) and extracted with EtOAc (2×10 mL). The combined organic extracts were dried over sodium sulfate, filtered and concentrated in vacuo to afford (Z)-5-bromo-N'-(2-(3-chloro-5-fluorophenyl)-2-oxoethoxy)-6-methoxypicolinimidamide (550 mg, crude) as brown semi solid used in the next step without further purification.

LCMS: 29.0%; 417.7 (M+3); (column; Ascentis Express C-18 (50×3.0 mm, 2.7 μm); RT 2.98 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R_f: 0.5).

3-(5-bromo-6-methoxypyridin-2-yl)-5-(3-chloro-5-fluorophenyl)-5,6-dihydro-4H-1,2,4-oxadiazine To a stirred solution of (Z)-5-bromo-N'-(2-(3-chloro-5-fluorophenyl)-2-oxoethoxy)-6-methoxypicolinimidamide (1.1 g, 2 mmol) in 1, 2-dichloro ethane (20 mL) at room temperature under an argon atmosphere were added trifluoroacetic acid (1.21 mL, 16 mmol) and sodium triacetoxyborohydride (2.24 g, 10 mmol). The reaction mixture was stirred for 16 h at room temperature. After consumption of starting material (monitored by TLC), the reaction mixture was diluted with saturated sodium bicarbonate solution (50 mL) and extracted with CH₂Cl₂ (2×50 mL). The combined organic extracts were dried over sodium sulfate, filtered and concentrated in vacuo to afford 3-(5-bromo-6-methoxypyridin-2-yl)-5-(3-chloro-5-fluorophenyl)-5,6-dihydro-4H-1,2,4-oxadiazine (450 mg, 43%) as brown semi solid.

LCMS: 92.4%; 401.8 (M+3); (column; Ascentis Express C-18 (50×3.0 mm, 2.7 µm); RT 3.13 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane ($R_f$: 0.5).

Example 111

Synthesis of 5-(3-chloro-5-fluorophenyl)-3-(6-methoxy-5-(4-methyl-1H-imidazol-1-yl) pyridin-2-yl)-5,6-dihydro-4H-1,2,4-oxadiazine

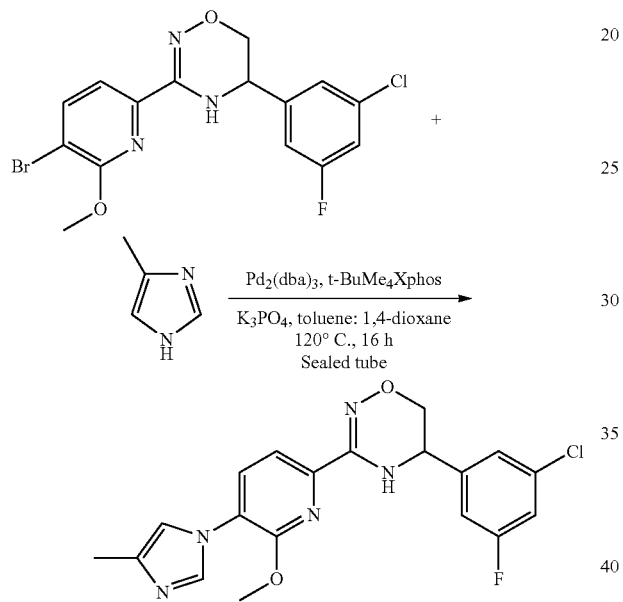

5-(3-chloro-5-fluorophenyl)-3-(6-methoxy-5-(4-methyl-1H-imidazol-1-yl) pyridin-2-yl)-5,6-dihydro-4H-1,2,4-oxadiazine To a dry vial was added a suspension of $Pd_2(dba)_3$ (46 mg, 0.05 mmol) and tert-butyl tetramethyl Xphos (48 mg, 0.1 mmol) in toluene:1,4-dioxane (2:1, 5.25 mL) at room temperature. The suspension was degassed with argon, heated to 120° C., and stirred at 120° C. for 3 min. A mixture of 3-(5-bromo-6-methoxypyridin-2-yl)-5-(3-chloro-5-fluorophenyl)-5,6-dihydro-4H-1,2,4-oxadiazine (400 mg, 1 mmol), 4-methyl-1H-imidazole (82 mg, 1 mmol) and potassium phosphate (424 mg, 2 mmol) in toluene:1,4-dioxane (2:1, 5.25 mL) was degassed and the catalyst premixture was added. The resultant mixture was stirred at 120° C. for 16 h in a sealed tube. After consumption of the starting material (monitored by TLC and LCMS), the reaction mixture was filtered and the filtrate was concentrated in vacuo. The crude material was purified by column chromatography using 2% MeOH: $CH_2Cl_2$ to afford 5-(3-chloro-5-fluorophenyl)-3-(6-methoxy-5-(4-methyl-1H-imidazol-1-yl) pyridin-2-yl)-5,6-dihydro-4H-1,2,4-oxadiazine (120 mg, 30%) as an off-white solid.

Racemic compound of Example 111 was separated using a Chiralpak-IB column (250×20 mm, 5 µm) (20 mg loading; 0.1% DEA in n-Hexane: $CH_2Cl_2$:MeOH (50:50) (A:B: 80:20) as mobile phase; flow rate: 20 mL/min) to afford the compounds of Example 111A (Fraction (I) (−)) and Example 111B (Fraction (II) (+)).

Experimental conditions for Example 111A and Example 111B: HPLC (column; zorbax-SB-C-18 150×4.6 mm, 3.5µ); mobile Phase: ACN: 0.05% Aq TFA; flow rate: 1.0 mL/min; Gradient program: T/B % 0.01/90, 2/90, 8/10, 15/10: diluent: $CH_3CN$:Water; Chiral HPLC: (Chiralpak-IB (250× 4.6 mm, 5 µm; mobile phase (A) 0.1% DEA in n-Hexane (B) $CH_2Cl_2$:MeOH (50:50) (A:B; 80:20); flow Rate: 1.0 mL/min).

Example 111A, (−)-5-(3-chloro-5-fluorophenyl)-3-(6-methoxy-5-(4-methyl-1H-imidazol-1-yl) pyridin-2-yl)-5,6-dihydro-4H-1,2,4-oxadiazine, fraction (I) (−): Mass (ESI): 402.3 [M+1]; HPLC (purity): 98.2%, RT 7.63 min; Chiral HPLC: 98.3%, RT=11.32 min; Optical rotation $[\alpha]_D^{20.00}$: −171.16 (c=0.25, $CH_2Cl_2$).

Example 111B, (+)-5-(3-chloro-5-fluorophenyl)-3-(6-methoxy-5-(4-methyl-1H-imidazol-1-yl) pyridin-2-yl)-5,6-dihydro-4H-1,2,4-oxadiazine, fraction (II) (+): $^1$H NMR ($CD_3OD$, 400 MHz): δ 7.99 (s, 1H), 7.89 (d, 1H), 7.65 (d, 1H), 7.26 (s, 1H), 7.23 (s, 1H), 7.17-7.08 (m, 2H), 4.90 (t, 1H), 4.11 (s, 3H), 4.05-4.03 (m, 2H), 2.26 (s, 3H); Mass (ESI): 402.3 [M+1]; HPLC (purity): 97.2%; RT 7.62 min; Chiral HPLC: 97.3%, RT=12.99 min; Optical rotation $[\alpha]_D^{19.99}$: +178.83 (c=0.25, $CH_2Cl_2$).

Example 112

Synthesis of 3-(5-bromo-6-methoxypyridin-2-yl)-5-(3-(trifluoromethyl) phenyl)-5,6-dihydro-4H-1,2,4-oxadiazine

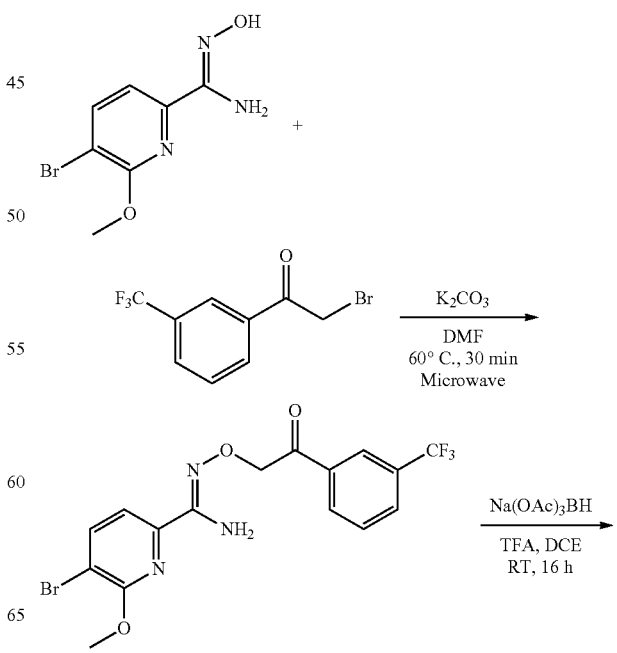

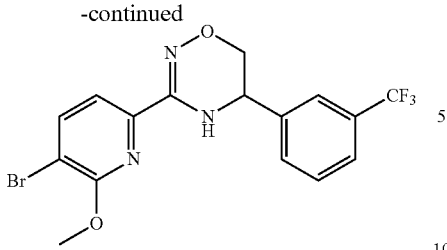

(Z)-5-bromo-6-methoxy-N'-(2-oxo-2-(3-(trifluoromethyl) phenyl) ethoxy) picolinimidamide To a stirred solution of 5-bromo-N'-hydroxy-6-methoxypicolinimidamide (750 mg, 3 mmol) in DMF (7.5 mL) at room temperature under an argon atmosphere were added potassium carbonate (841 mg, 6 mmol) and 2-bromo-1-(3-(trifluoromethyl) phenyl) ethan-1-one (1.2 g, 5 mmol). The reaction mixture was stirred for 30 min at 60° C. in microwave. After consumption of starting material (monitored by TLC), the reaction mixture was diluted with water (20 mL) and extracted with EtOAc (2×20 mL). The combined organic extracts were dried over sodium sulfate, filtered and concentrated in vacuo to afford (Z)-5-bromo-6-methoxy-N'-(2-oxo-2-(3-(trifluoromethyl) phenyl) ethoxy) picolinimidamide (1 g, crude) as yellow solid used in the next step without further purification.

LCMS: 24.0%; 431.8 (M+2); (column; Ascentis Express C-18 (50×3.0 mm, 2.7 μm); RT 2.94 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.6).

3-(5-bromo-6-methoxypyridin-2-yl)-5-(3-(trifluoromethyl) phenyl)-5,6-dihydro-4H-1,2,4-oxadiazine To a stirred solution of (Z)-5-bromo-6-methoxy-N'-(2-oxo-2-(3-(trifluoromethyl) phenyl) ethoxy) picolinimidamide (1 mg, 2 mmol) in 1,2-dichloro ethane (20 mL) at room temperature under an argon atmosphere were added trifluoroacetic acid (0.8 mL, 12 mmol) and sodium triacetoxy borohydride (1.47 g, 7 mmol). The reaction mixture was stirred for 16 h at room temperature. After consumption of starting material (monitored by TLC), the reaction mixture was diluted with 1N sodium hydroxide solution (50 mL) and extracted with EtOAc (2×50 mL). The combined organic extracts were dried over sodium sulfate, filtered and concentrated in vacuo. The crude material was purified by column chromatography using 15-20% EtOAc: Hexane to afford 3-(5-bromo-6-methoxypyridin-2-yl)-5-(3-(trifluoromethyl) phenyl)-5,6-dihydro-4H-1,2,4-oxadiazine (600 mg, 62%) as colorless liquid.

LCMS: 49.3%; 415.8 (M+1); (column; Ascentis Express C-18 (50×3.0 mm, 2.7 μm); RT 2.83 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.4).

Example 113

Synthesis of 3-(6-methoxy-5-(4-methyl-1H-imidazol-1-yl) pyridin-2-yl)-5-(3-(trifluoromethyl) phenyl)-5,6-dihydro-4H-1,2,4-oxadiazine

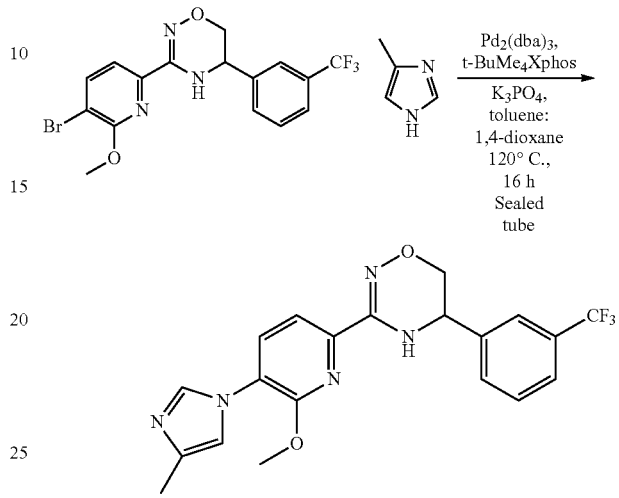

3-(6-methoxy-5-(4-methyl-1H-imidazol-1-yl) pyridin-2-yl)-5-(3-(trifluoromethyl) phenyl)-5,6-dihydro-4H-1,2,4-oxadiazine To a dry vial was added a suspension of $Pd_2(dba)_3$ (11 mg, 0.02 mmol) and tert-butyl tetramethyl Xphos (12 mg, 0.02 mmol) in toluene:1,4-dioxane (2:1, 1.5 mL) at room temperature. The suspension was degassed with argon, heated to 120° C., and stirred at 120° C. for 3 min. A mixture of 3-(5-bromo-6-methoxypyridin-2-yl)-5-(3-(trifluoromethyl) phenyl)-5,6-dihydro-4H-1,2,4-oxadiazine (100 mg, 0.2 mmol), 4-methyl-1H-imidazole (29 mg, 0.4 mmol) and potassium phosphate (102 mg, 0.5 mmol) in toluene:1,4-dioxane (2:1, 1.5 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo. The crude material was purified by column chromatography using 2-5% MeOH: $CH_2Cl_2$ to afford 3-(6-methoxy-5-(4-methyl-1H-imidazol-1-yl) pyridin-2-yl)-5-(3-(trifluoromethyl) phenyl)-5,6-dihydro-4H-1,2,4-oxadiazine (28 mg, 28%) as a pale yellow solid.

Racemic compound of Example 113 was separated using a Chiralpak-IA column (250×20 mm, 5 μm) (25 mg loading; 0.1% DEA in n-Hexane: $CH_2Cl_2$:MeOH (50:50) (A:B: 80:20) as mobile phase; flow rate: 20 mL/min) to afford the compounds of Example 113A (Fraction (I) (−)) and Example 113B (Fraction (II) (+)).

Analytical conditions for Example 113A and Example 113B: HPLC (column; zorbax-SB-C-18 150×4.6 mm, 3.5μ); mobile Phase: ACN: 0.05% Aq TFA; flow rate: 1.0 mL/min; Gradient program: T/B % 0.01/90, 2/90, 8/10, 15/10: diluent: $CH_3CN$:Water; Chiral HPLC: (Chiralpak-IB (250× 4.6 mm, 5 μm; mobile phase (A) 0.1% DEA in n-Hexane (B) $CH_2Cl_2$:MeOH (50:50) (A:B; 90:10); flow Rate: 1.0 mL/min).

Example 113A, (−)-3-(6-methoxy-5-(4-methyl-1H-imidazol-1-yl) pyridin-2-yl)-5-(3-(trifluoromethyl) phenyl)-5,6-dihydro-4H-1,2,4-oxadiazine, fraction (I) (−): Mass (ESI): 418.3 [M+1]; HPLC (purity): 98.6%, RT 7.56 min; Chiral HPLC: 99.4%, RT=24.72 min; Optical rotation $[\alpha]_D^{20.00}$: −153.58 (c=0.25, $CH_2Cl_2$).

Example 113B, (+)-3-(6-methoxy-5-(4-methyl-1H-imidazol-1-yl) pyridin-2-yl)-5-(3-(trifluoromethyl) phenyl)-5,6-dihydro-4H-1,2,4-oxadiazine, fraction (II) (+): $^1$H NMR ($CD_3OD$, 500 MHz): δ 8.00 (s, 1H), 7.90 (d, 1H), 7.70-7.59 (m, 5H), 7.23 (s, 1H), 4.99 (t, 1H), 4.13-4.10 (m, 4H), 3.99 (d, 1H), 2.23 (s, 3H); Mass (ESI): 418.3 [M+1]; HPLC (purity): 99.0%, RT 7.60 min; Chiral HPLC: 98.9%, RT=29.22 min; Optical rotation $[\alpha]_D^{20.00}$: +155.36 (c=0.25, $CH_2Cl_2$).

Example 114

Synthesis of 2-bromo-1-(4-cyclopropylphenyl) ethan-1-one

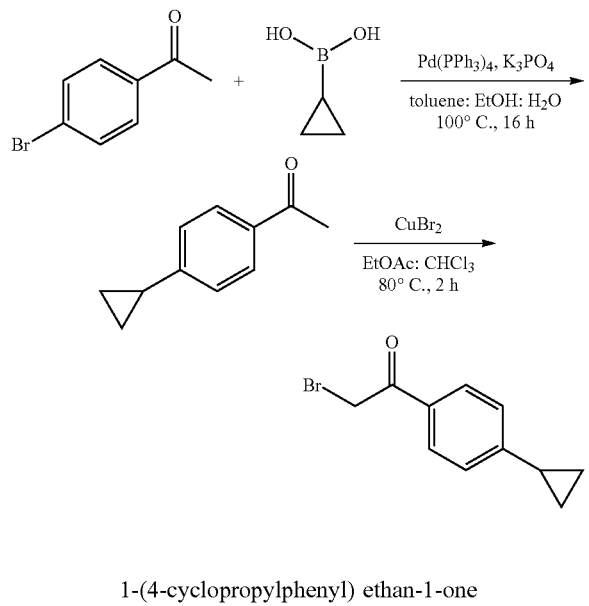

1-(4-cyclopropylphenyl) ethan-1-one

To a stirred solution of 1-(4-bromophenyl) ethan-1-one (2 g, 10 mmol) in toluene:EtOH:water (1:1:1, 20 mL) at room temperature under an argon atmosphere were added cyclopropylboronic acid (1.03 g, 12 mmol), potassium phosphate (4.4 g, 21 mmol) and purged under argon for 15 min. Then Pd(PPh$_3$)$_4$ (580 mg, 0.5 mmol) was added to the reaction mixture at room temperature. The reaction mixture was stirred at 100° C. for 16 h. After consumption of starting material (monitored by TLC), the reaction mixture was filtered. The filtrate was concentrated in vacuo. The crude material was purified by column chromatography using 2-3% EtOAc: Hexane to afford 1-(4-cyclopropylphenyl) ethan-1-one (1.5 g, crude) as colorless liquid. $^1$H NMR (DMSO-d$_6$, 400 MHz): δ 7.83 (d, 2H), 7.20 (d, 2H), 2.57 (s, 3H), 2.04-1.97 (m, 1H), 1.10-0.98 (m, 2H), 0.81-0.72 (m, 2H); LCMS: 91.2%; 160.8 (M+1); (column; Ascentis Express C-18 (50×3.0 mm, 2.7 µm); mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 5% EtOAc/Hexane (R$_f$: 0.4).

2-bromo-1-(4-cyclopropylphenyl) ethan-1-one

To a stirred solution of copper bromide (3 g, 14 mmol) in EtOAc (20 mL) at room temperature under an argon atmosphere was added 1-(4-cyclopropylphenyl) ethan-1-one (1.5 g, 9 mmol) in CHCl$_3$ (5 mL). The reaction mixture was stirred for 2 h at 80° C. After consumption of starting material (monitored by TLC), the reaction mixture was filtered. The filtrate was concentrated in vacuo to afford 2-bromo-1-(4-cyclopropylphenyl) ethan-1-one (800 mg, crude) as colorless liquid used in the next step without further purification. $^1$H NMR (DMSO-d$_6$, 500 MHz): δ 7.87 (d, 2H), 7.21 (d, 2H), 4.88 (s, 2H), 2.03-1.99 (m, 1H), 1.07-1.02 (m, 2H), 0.83-0.79 (m, 2H); LCMS: 68.8%; 240.8 (M+3); (column; Ascentis Express C-18 (50×3.0 mm, 2.7 µm); RT 2.87 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 5% EtOAc/Hexane (R$_f$: 0.4).

Example 115

Synthesis of 3-(5-bromo-6-methoxypyridin-2-yl)-5-(4-cyclopropylphenyl)-5,6-dihydro-4H-1,2,4-oxadiazine

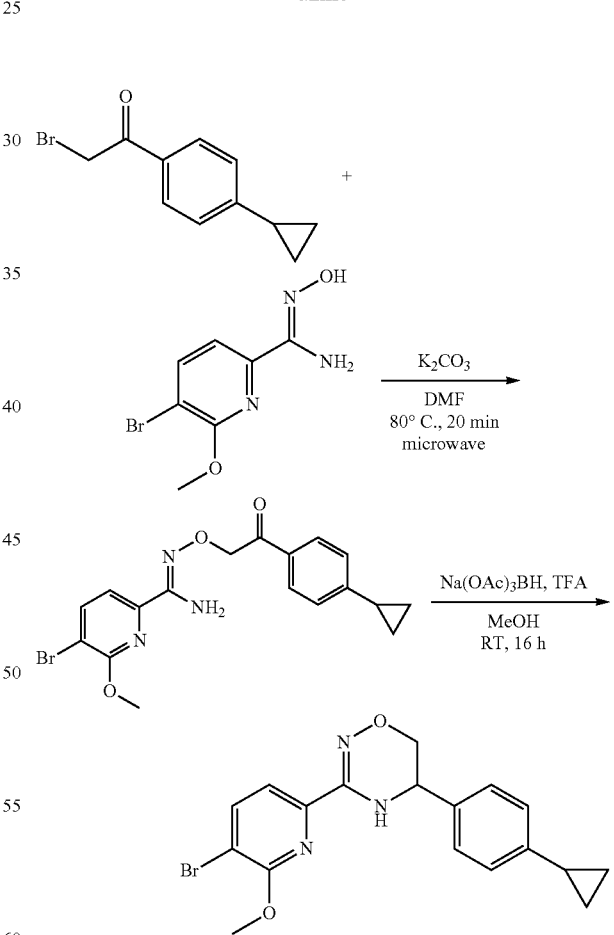

(Z)-5-bromo-N'-(2-(4-cyclopropylphenyl)-2-oxoethoxy)-6-methoxypicolinimidamide

To a stirred solution of 5-bromo-N'-hydroxy-6-methoxypicolinimidamide (300 mg, 1 mmol) in DMF (6 mL) at room temperature under an argon atmosphere were added potassium carbonate (346 mg, 2 mmol) and 2-bromo-1-(4-cyclopropylphenyl) ethan-1-one (435 mg, 2 mmol). The reaction mixture was stirred for 20 min at 80° C. After consumption of starting material (monitored by TLC), the reaction mixture was diluted with water (10 mL) and extracted with EtOAc (2×10 mL). The combined organic extracts were dried over sodium sulfate, filtered and concentrated in vacuo to afford (Z)-5-bromo-N'-(2-(4-cyclopropylphenyl)-2-oxoethoxy)-6-methoxypicolinimidamide (400 mg, crude) as brown solid used in the next step without further purification.

LCMS: 43.1%; 405.8 (M+3); (column; Ascentis Express C-18 (50×3.0 mm, 2.7 µm); RT 3.24 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane ($R_f$: 0.7).

3-(5-bromo-6-methoxypyridin-2-yl)-5-(4-cyclopropylphenyl)-5,6-dihydro-4H-1,2,4-oxadiazine To a stirred solution of (Z)-5-bromo-N'-(2-(4-cyclopropylphenyl)-2-oxoethoxy)-6-methoxypicolinimidamide (50 mg, 0.1 mmol) in 1, 2-dichloro ethane (0.5 mL) at room temperature under an argon atmosphere was added trifluoroacetic acid (0.1 mL) and sodium triacetoxyborohydride (52 mg). The reaction mixture was stirred for 16 h at room temperature. After consumption of starting material (monitored by TLC), the reaction mixture was diluted with 1N sodium hydroxide solution (10 mL) and extracted with EtOAc (2×10 mL). The combined organic extracts were dried over sodium sulfate, filtered and concentrated in vacuo to afford 3-(5-bromo-6-methoxypyridin-2-yl)-5-(4-cyclopropylphenyl)-5,6-dihydro-4H-1,2,4-oxadiazine (50 mg, crude) as yellow liquid.

LCMS: 72.2%; 387.9 (M+1); (column; Ascentis Express C-18 (50×3.0 mm, 2.7 µm); RT 2.89 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.4).

Example 116

Synthesis of 5-(4-cyclopropylphenyl)-3-(6-methoxy-5-(4-methyl-1H-imidazol-1-yl) pyridin-2-yl)-5,6-dihydro-4H-1,2,4-oxadiazine

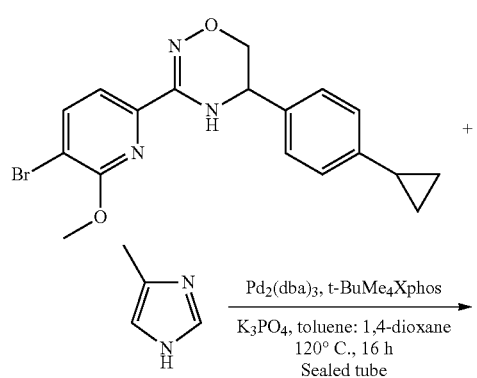

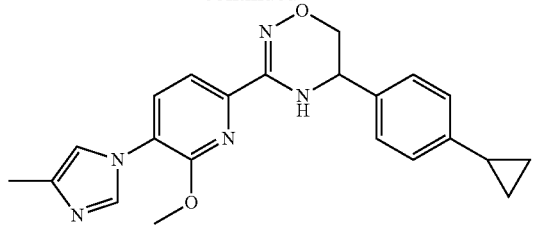

5-(4-cyclopropylphenyl)-3-(6-methoxy-5-(4-methyl-1H-imidazol-1-yl) pyridin-2-yl)-5,6-dihydro-4H-1,2,4-oxadiazine To a dry vial was added a suspension of $Pd_2(dba)_3$ (53 mg, 0.06 mmol) and tert-butyl tetramethyl Xphos (55 mg, 0.1 mmol) in toluene:1,4-dioxane (2:1, 3 mL) at room temperature. The suspension was degassed with argon, heated to 120° C., and stirred at 120° C. for 3 min. A mixture of 3-(5-bromo-6-methoxypyridin-2-yl)-5-(4-cyclopropylphenyl)-5,6-dihydro-4H-1,2,4-oxadiazine (450 mg, 1 mmol), 4-methyl-1H-imidazole (190 mg, 2 mmol) and potassium phosphate (54 mg, 0.2 mmol) in toluene:1,4-dioxane (2:1, 3 mL) was degassed and the catalyst premixture was added. The resultant mixture was stirred at 120° C. for 16 h in a sealed tube. After consumption of the starting material (monitored by TLC and LCMS), the reaction mixture was filtered and the filtrate was concentrated in vacuo. The crude material was purified by column chromatography using 2% MeOH: $CH_2Cl_2$ to afford 5-(4-cyclopropylphenyl)-3-(6-methoxy-5-(4-methyl-1H-imidazol-1-yl) pyridin-2-yl)-5,6-dihydro-4H-1,2,4-oxadiazine (120 mg, 26%) as a pale yellow solid.

Racemic compound of Example 116 was separated using a Chiralpak-IB column (250×20 mm, 5 µm) (20 mg loading; 0.1% DEA in n-Hexane: $CH_2Cl_2$:MeOH (80:20) (A:B: 80:20) as mobile phase; flow rate: 20 mL/min) to afford the compounds of Example 116A (Fraction (I) (−)) and Example 116B (Fraction (II) (+)).

Analytical conditions for Example 116A and Example 116B: HPLC (column; zorbax-SB-C-18 150×4.6 mm, 3.5µ); mobile Phase: ACN: 0.05% Aq TFA; flow rate: 1.0 mL/min; Gradient program: T/B % 0.01/90, 2/90, 8/10, 15/10: diluent: $CH_3CN$:Water; Chiral HPLC: (Chiralpak-IB (250× 4.6 mm, 5 µm; mobile phase (A) 0.1% DEA in n-Hexane (B) $CH_2Cl_2$:MeOH (80:20) (A:B; 80:20); flow Rate: 1.0 mL/min).

Example 116A, (−)-5-(4-cyclopropylphenyl)-3-(6-methoxy-5-(4-methyl-1H-imidazol-1-yl) pyridin-2-yl)-5,6-dihydro-4H-1,2,4-oxadiazine, fraction (I) (−): Mass (ESI): 390.4 [M+1]; HPLC (purity): 99.2%, RT 7.76 min; Chiral HPLC: 100%, RT=13.19 min; Optical rotation $[\alpha]_D^{20.01}$: −144.64 (c=0.25, $CH_2Cl_2$).

Example 116B, (+)-5-(4-cyclopropylphenyl)-3-(6-methoxy-5-(4-methyl-1H-imidazol-1-yl) pyridin-2-yl)-5,6-dihydro-4H-1,2,4-oxadiazine, fraction (II) (+): $^1$H NMR ($CD_3OD$, 400 MHz): δ 7.98 (s, 1H), 7.88 (d, 1H), 7.64 (d, 1H), 7.27 (t, 2H), 7.22 (s, 1H), 7.10 (d, 2H), 4.78 (t, 1H), 4.14 (dd, 1H), 4.07 (s, 3H), 3.81 (dd, 1H), 2.25 (s, 3H), 1.95-1.87 (m, 1H), 0.99-0.93 (m, 2H), 0.69-0.64 (m, 2H); Mass (ESI): 390.3 [M+1]; HPLC (purity): 99.1%, RT 7.73 min; Chiral HPLC: 99.8%, RT=18.65 min; Optical rotation $[\alpha]_D^{20.01}$: +148.49 (c=0.25, $CH_2Cl_2$).

Example 117

Synthesis of 3-(5-bromo-6-methoxypyridin-2-yl)-5-(3,5-dichlorophenyl)-5,6-dihydro-4H-1,2,4-oxadiazine

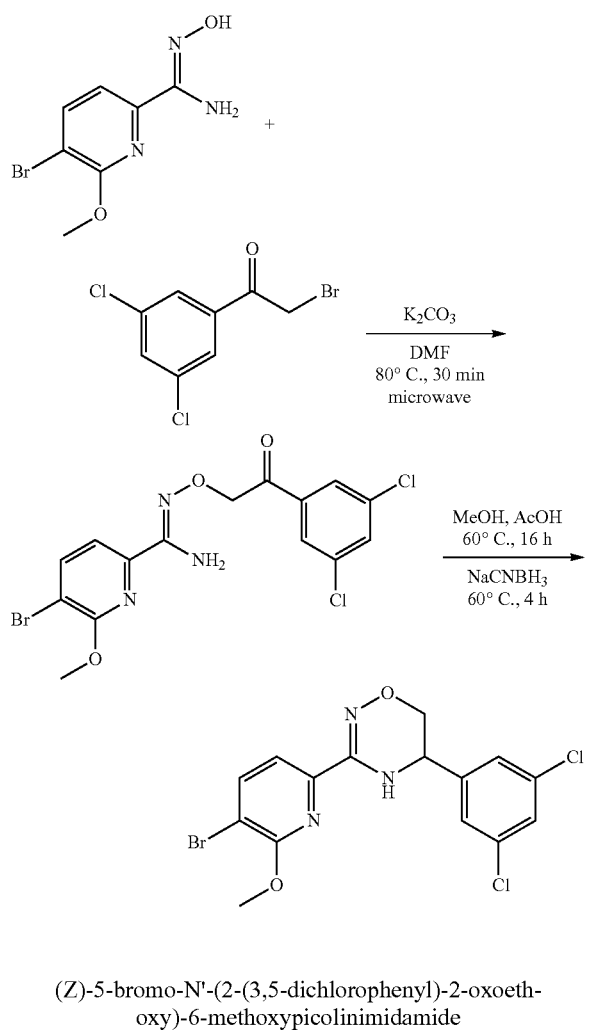

(Z)-5-bromo-N'-(2-(3,5-dichlorophenyl)-2-oxoethoxy)-6-methoxypicolinimidamide

To a stirred solution of 5-bromo-N'-hydroxy-6-methoxypicolinimidamide (500 mg, 2 mmol) in DMF (10 mL) at room temperature under an argon atmosphere were added potassium carbonate (560 mg, 4 mmol) and 2-bromo-1-(3,5-dichlorophenyl) ethan-1-one (817 mg, 3 mmol). The reaction mixture was stirred for 30 min at 80° C. in microwave. After consumption of starting material (monitored by TLC), the reaction mixture was diluted with water (20 mL) and extracted with EtOAc (2×20 mL). The combined organic extracts were dried over sodium sulfate, filtered and concentrated in vacuo to afford (Z)-5-bromo-N'-(2-(3,5-dichlorophenyl)-2-oxoethoxy)-6-methoxypicolinimidamide (600 mg, crude) as brown semi solid used in the next step without further purification.

LCMS: 30.8%; 433.6 (M+3); (column; Ascentis Express C-18 (50×3.0 mm, 2.7 μm); RT 2.88 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane ($R_f$: 0.6).

3-(5-bromo-6-methoxypyridin-2-yl)-5-(3,5-dichlorophenyl)-5,6-dihydro-4H-1,2,4-oxadiazine To a stirred solution of (Z)-5-bromo-N'-(2-(3,5-dichlorophenyl)-2-oxoethoxy)-6-methoxypicolinimidamide (600 mg, crude) in MeOH (10 mL) at room temperature under an argon atmosphere was added acetic acid (2.5 mL). The reaction mixture was stirred for 16 h at 60° C. Then sodium cyanoborohydride (153 mg) was added to the reaction mixture at room temperature. The reaction mixture was stirred for 4 h at 60° C. After consumption of starting material (monitored by TLC), the reaction mixture was diluted with saturated sodium bicarbonate solution (20 mL) and extracted with $CH_2Cl_2$ (2×20 mL). The combined organic extracts were dried over sodium sulfate, filtered and concentrated in vacuo to afford 3-(5-bromo-6-methoxypyridin-2-yl)-5-(3,5-dichlorophenyl)-5,6-dihydro-4H-1,2,4-oxadiazine (200 mg, 32%) as colorless liquid.

LCMS: 79.9%; 417.7 (M+3); (column; Ascentis Express C-18 (50×3.0 mm, 2.7 μm); RT 3.02 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane ($R_f$: 0.4).

Example 118

Synthesis of 5-(3,5-dichlorophenyl)-3-(6-methoxy-5-(4-methyl-1H-imidazol-1-yl) pyridin-2-yl)-5,6-dihydro-4H-1,2,4-oxadiazine

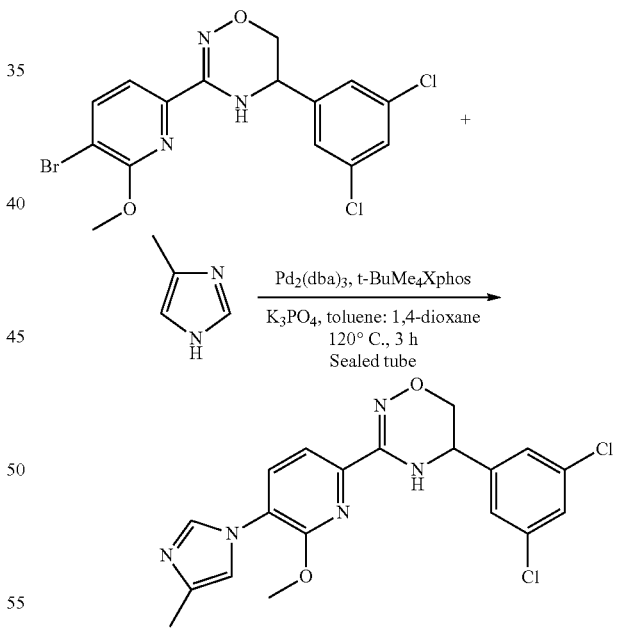

5-(3,5-dichlorophenyl)-3-(6-methoxy-5-(4-methyl-1H-imidazol-1-yl) pyridin-2-yl)-5,6-dihydro-4H-1,2,4-oxadiazine To a dry vial was added a suspension of $Pd_2(dba)_3$ (22 mg, 0.02 mmol) and tert-butyl tetramethyl Xphos (23 mg, 0.05 mmol) in toluene:1,4-dioxane (2:1, 4.5 mL) at room temperature. The suspension was degassed with argon, heated to 120° C., and stirred at 120° C. for 3 min. A mixture of 3-(5-bromo-6-methoxypyridin-2-yl)-5-(3,5-dichlorophenyl)-5,6-dihydro-4H-1,2,4-oxadiazine (200 mg, 0.5 mmol), 4-methyl-1H-imidazole (40 mg, 0.5 mmol) and potassium phosphate (203 mg, 0.9 mmol) in toluene:1,4-dioxane (2:1, 4.5 mL) was degassed and the catalyst premixture was added. The resultant mixture was stirred at 120° C. for 3 h in a sealed tube. After consumption of the starting material (monitored by TLC and LCMS), the reaction mixture was filtered. The filtrate was concentrated in vacuo. The crude material was purified by column chromatography using 2-5% MeOH: $CH_2Cl_2$ to afford 5-(3,5-dichlorophenyl)-3-(6-methoxy-5-(4-methyl-1H-imidazol-1-yl) pyridin-2-yl)-5,6-dihydro-4H-1,2,4-oxadiazine (70 mg, 35%) as a pale yellow solid.

Racemic compound of Example 118 was separated using a Chiralpak-IB column (250×20 mm, 5 μm) (20 mg loading; 0.1% DEA in n-Hexane: $CH_2Cl_2$:MeOH (50:50) (A:B: 80:20) as mobile phase; flow rate: 20 mL/min) to afford the compounds of Example 118A (Fraction (I) (−)) and Example 118B (Fraction (II) (+)).

Analytical conditions for Example 118A and Example 118B: HPLC (column; zorbax-SB-C-18 150×4.6 mm, 3.5μ); mobile Phase: ACN: 0.05% Aq TFA; flow rate: 1.0 mL/min; Gradient program: T/B % 0.01/90, 2/90, 8/10, 15/10: diluent: $CH_3CN$:Water; Chiral HPLC: (Chiralpak-IB (250× 4.6 mm, 5 μm; mobile phase (A) 0.1% DEA in n-Hexane (B) $CH_2Cl_2$:MeOH (50:50) (A:B; 80:20); flow Rate: 1.0 mL/min).

Example 118A, (−)-5-(3,5-dichlorophenyl)-3-(6-methoxy-5-(4-methyl-1H-imidazol-1-yl) pyridin-2-yl)-5,6-dihydro-4H-1,2,4-oxadiazine, fraction (I) (−): Mass (ESI): 417.9 [M+1]; HPLC (purity): 95.7%; RT 8.03 min; Chiral HPLC: 98.1%, RT=13.14 min; Optical rotation $[\alpha]_D^{20.00}$: −194.09 (c=0.25, $CH_2Cl_2$).

Example 118B, (+)-5-(3,5-dichlorophenyl)-3-(6-methoxy-5-(4-methyl-1H-imidazol-1-yl) pyridin-2-yl)-5,6-dihydro-4H-1,2,4-oxadiazine, fraction (II) (+): $^1$H NMR ($CD_3OD$, 400 MHz): δ 7.99 (s, 1H), 7.89 (d, 1H), 7.66 (d, 1H), 7.39 (s, 1H), 7.36 (s, 2H), 7.23 (s, 1H), 4.89 (t, 1H), 4.11 (s, 3H), 4.04 (d, 2H), 2.28 (s, 3H); Mass (ESI): 417.9 [M+1]; HPLC (purity): 95.2%; RT 8.02 min; Chiral HPLC: 97.9%, RT=15.30 min; Optical rotation $[\alpha]_D^{20.00}$: +208.81 (c=0.25, $CH_2Cl_2$).

Example 119

Synthesis of 2-bromo-1-(3-fluoro-4-(trifluoromethyl) phenyl) ethan-1-one

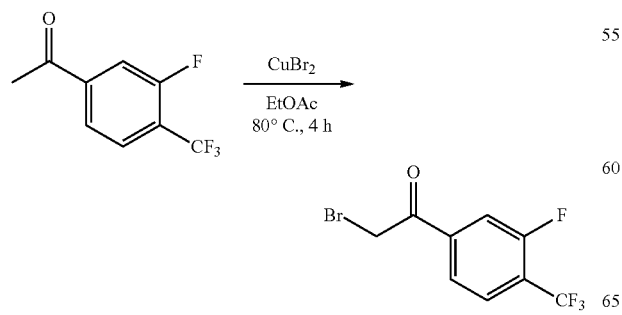

2-bromo-1-(3-fluoro-4-(trifluoromethyl) phenyl) ethan-1-one

To a stirred solution of 1-(3-fluoro-4-(trifluoromethyl) phenyl) ethan-1-one (2.3 g, 11 mmol) in EtOAc (100 mL) at room temperature under an argon atmosphere was added copper bromide (5 g, 24 mmol). The reaction mixture was stirred for 4 h at 80° C. After consumption of starting material (monitored by TLC), the reaction mixture was filtered. The filtrate was concentrated in vacuo to afford 2-bromo-1-(3-fluoro-4-(trifluoromethyl) phenyl) ethan-1-one (2.5 g, crude) as colorless liquid used in the next step without further purification.

$^1$H NMR (DMSO-$d_6$, 500 MHz): δ 8.06-7.97 (m, 3H), 5.00 (s, 2H); LCMS: 73.5%; 283 (M−1); (column; X-select CSH C-18 (50×3.0 mm, 3.5 μm); RT 4.19 min; mobile phase: 5 mM Aq $NH_4OAc$+ ACN; T/B %: 0.01/10, 0.5/10, 5/90, 7/90; flow rate: 0.8 mL/min) (Gradient); TLC: 5% EtOAc/Hexane ($R_f$: 0.5).

Example 120

Synthesis of 3-(5-bromo-6-methoxypyridin-2-yl)-5-(3-fluoro-4-(trifluoromethyl) phenyl)-5,6-dihydro-4H-1,2,4-oxadiazine

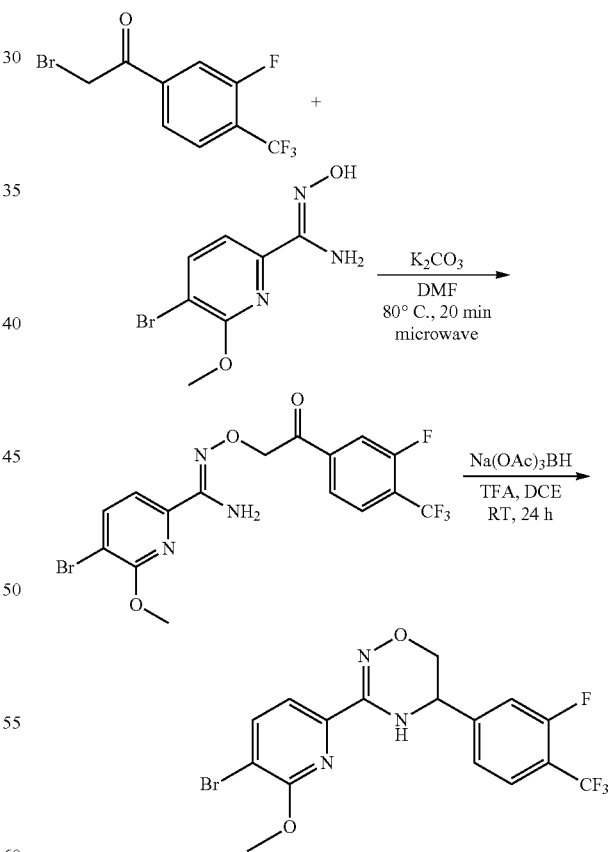

(Z)-5-bromo-N'-(2-(3-fluoro-4-(trifluoromethyl) phenyl)-2-oxoethoxy)-6-methoxypicolinimidamide To a stirred solution of 5-bromo-N'-hydroxy-6-methoxypicolinimidamide (500 mg, 2 mmol) in DMF (10 mL) at room temperature under an argon atmosphere were added potassium carbonate (560 mg, 4 mmol) and 2-bromo-1-(3-fluoro-4-(trifluoromethyl) phenyl) ethan-1-one (868 mg, 3 mmol). The reaction mixture was stirred for 20 min at 80° C. in microwave. After consumption of starting material (monitored by TLC), the reaction mixture was diluted with water (10 mL) and extracted with EtOAc (2×10 mL). The combined organic extracts were dried over sodium sulfate, filtered and concentrated in vacuo to afford (Z)-5-bromo-N'-(2-(3-fluoro-4-(trifluoromethyl) phenyl)-2-oxoethoxy)-6-methoxypicolinimidamide (600 mg, crude) as yellow solid used in the next step without further purification.

LCMS: 22.4%; 449.8 (M+1); (column; Ascentis Express C-18 (50×3.0 mm, 2.7 µm); RT 3.02 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane ($R_f$: 0.5).

3-(5-bromo-6-methoxypyridin-2-yl)-5-(3-fluoro-4-(trifluoromethyl) phenyl)-5,6-dihydro-4H-1,2,4-oxadiazine To a stirred solution of (Z)-5-bromo-N'-(2-(3-fluoro-4-(trifluoromethyl) phenyl)-2-oxoethoxy)-6-methoxypicolinimidamide (600 mg, crude) in 1, 2-dichloro ethane (12 mL) at room temperature under an argon atmosphere were added trifluoroacetic acid (759 mg) and sodium triacetoxy borohydride (847 mg, 4 mmol). The reaction mixture was stirred for 24 h at room temperature. After consumption of starting material (monitored by TLC), the reaction mixture was diluted with saturated sodium bicarbonate solution (20 mL) and extracted with $CH_2Cl_2$ (2×20 mL). The combined organic extracts were dried over sodium sulfate, filtered and concentrated in vacuo. The crude material was purified by column chromatography using 10-20% EtOAc: Hexane to afford 3-(5-bromo-6-methoxypyridin-2-yl)-5-(3-fluoro-4-(trifluoromethyl) phenyl)-5,6-dihydro-4H-1,2,4-oxadiazine (500 mg, 86%) as colorless liquid.

LCMS: 46.3%; 435.8 (M+3); (column; Ascentis Express C-18 (50×3.0 mm, 2.7 µm); RT 2.88 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane ($R_f$: 0.5).

Example 121

Synthesis of 5-(3-fluoro-4-(trifluoromethyl) phenyl)-3-(6-methoxy-5-(4-methyl-1H-imidazol-1-yl) pyridin-2-yl)-5,6-dihydro-4H-1,2,4-oxadiazine

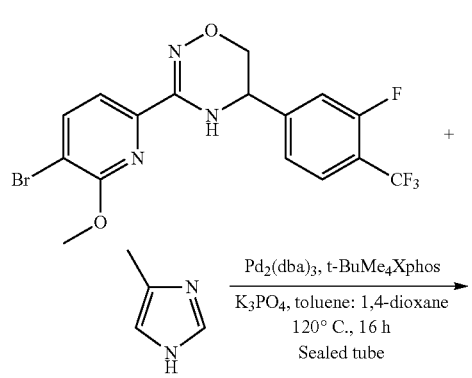

5-(3-fluoro-4-(trifluoromethyl) phenyl)-3-(6-methoxy-5-(4-methyl-1H-imidazol-1-yl) pyridin-2-yl)-5,6-dihydro-4H-1,2,4-oxadiazine

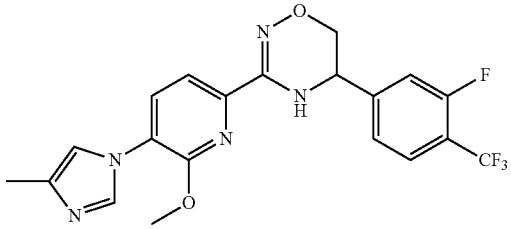

To a dry vial was added a suspension of $Pd_2(dba)_3$ (47 mg, 0.05 mmol) and tert-butyl tetramethyl Xphos (74 mg, 0.1 mmol) in toluene:1,4-dioxane (2:1, 10 mL) at room temperature. The suspension was degassed with argon, heated to 120° C., and stirred at 120° C. for 3 min. A mixture of 3-(5-bromo-6-methoxypyridin-2-yl)-5-(3-fluoro-4-(trifluoromethyl) phenyl)-5,6-dihydro-4H-1,2,4-oxadiazine (450 mg, 1 mmol), 4-methyl-1H-imidazole (102 mg, 1 mmol) and potassium phosphate (440 mg, 2 mmol) in toluene:1,4-dioxane (2:1, 9.75 mL) was degassed and the catalyst premixture was added. The resultant mixture was stirred at 120° C. for 16 h in a sealed tube. After consumption of the starting material (monitored by TLC and LCMS), the reaction mixture was filtered. The filtrate was concentrated in vacuo. The crude material was purified by column chromatography using 2-4% MeOH: $CH_2Cl_2$ to afford 5-(3-fluoro-4-(trifluoromethyl) phenyl)-3-(6-methoxy-5-(4-methyl-1H-imidazol-1-yl) pyridin-2-yl)-5,6-dihydro-4H-1,2,4-oxadiazine (150 mg, 33%) as a pale yellow solid.

Racemic compound of Example 121 was separated using a Chiralpak-IB column (250×20 mm, 5 µm) (28 mg loading; 0.1% DEA in n-Hexane: $CH_2Cl_2$:MeOH (80:20) (A:B: 80:20) as mobile phase; flow rate: 20 mL/min) to afford the compounds of Example 121A (Fraction (I) (−)) and Example 121B (Fraction (II) (+)).

Analytical conditions for Example 121A and Example 121B: HPLC (column; zorbax-SB-C-18 150×4.6 mm, 3.5µ); mobile Phase: ACN: 0.05% Aq TFA; flow rate: 1.0 mL/min; Gradient program: T/B % 0.01/90, 2/90, 8/10, 15/10: diluent: $CH_3CN$:Water; Chiral HPLC: (Chiralpak-IB (250× 4.6 mm, 5 µm; mobile phase (A) 0.1% DEA in n-Hexane (B) $CH_2Cl_2$:MeOH (80:20) (A:B; 80:20); flow Rate: 1.0 mL/min).

Example 121A, (−)-5-(3-fluoro-4-(trifluoromethyl) phenyl)-3-(6-methoxy-5-(4-methyl-1H-imidazol-1-yl) pyridin-2-yl)-5,6-dihydro-4H-1,2,4-oxadiazine, fraction (I) (−): Mass (ESI): 435.9 [M+1]; HPLC (purity): 97.2%, RT 7.77 min; Chiral HPLC: 97.2%, RT=15.13 min; Optical rotation $[\alpha]_D^{19.95}$: −177.55 (c=0.25, $CH_2Cl_2$).

Example 121B, (+)-5-(3-fluoro-4-(trifluoromethyl) phenyl)-3-(6-methoxy-5-(4-methyl-1H-imidazol-1-yl) pyridin-2-yl)-5,6-dihydro-4H-1,2,4-oxadiazine, fraction (II) (+): $^1$H NMR ($CD_3OD$, 400 MHz): δ 7.99 (s, 1H), 7.90 (d, 1H), 7.72 (t, 1H), 7.67 (d, 1H), 7.38 (dd, 2H), 7.23 (t, 1H), 5.00 (t, 1H), 4.12 (s, 3H), 4.09 (d, 2H), 2.27 (s, 3H); Mass (ESI): 435.9 [M+1]; HPLC (purity): 99.7%, RT 7.77 min; Chiral HPLC: 99.8%, RT=21.95 min; Optical rotation $[\alpha]_D^{20.01}$: +185.32 (c=0.25, $CH_2Cl_2$).

Example 122

Synthesis of 2-bromo-1-(1-methyl-1H-indazol-3-yl)ethan-1-one

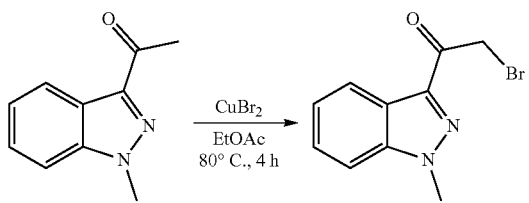

2-bromo-1-(1-methyl-M-indazol-3-yl) ethan-1-one

To a stirred solution of 1-(1-methyl-1H-indazol-3-yl)ethan-1-one (1.5 g, 9 mmol) in EtOAc (150 mL) at room temperature under an argon atmosphere was added copper bromide (2.8 g, 13 mmol). The reaction mixture was stirred for 4 h at 80° C. After consumption of starting material (monitored by TLC), the reaction mixture was filtered. The filtrate was concentrated in vacuo to afford 2-bromo-1-(1-methyl-1H-indazol-3-yl) ethan-1-one (1.5 g, crude) as colorless liquid used in the next step without further purification. $^1$H NMR (CD$_3$OD, 400 MHz): δ 8.35 (d, 1H), 7.53-7.42 (m, 2H), 7.42-7.32 (m, 1H), 4.72 (s, 2H), 4.17 (s, 3H); LCMS: 75.4%; 252.8 (M+1); (column; Ascentis Express C-18 (50×3.0 mm, 2.7 μm); RT 2.45 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 5% EtOAc/Hexane (R$_f$: 0.5).

Example 123

Synthesis of 3-(5-bromo-6-methoxypyridin-2-yl)-5-(1-methyl-1H-indazol-3-yl)-5,6-dihydro-4H-1,2,4-oxadiazine

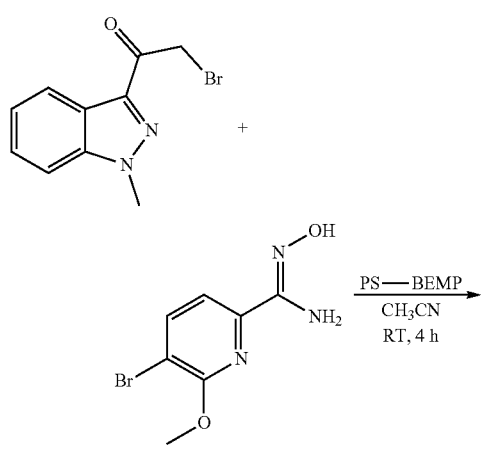

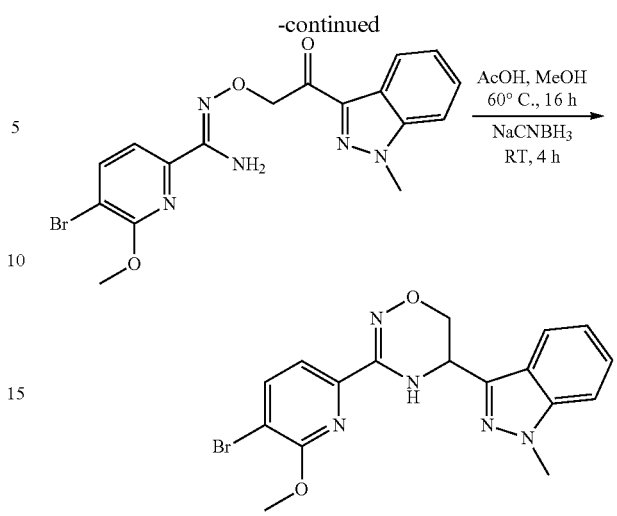

(Z)-5-bromo-6-methoxy-N'-(2-(1-methyl-1H-indazol-3-yl)-2-oxoethoxy) picolinimidamide To a stirred solution of 5-bromo-N'-hydroxy-6-methoxypicolinimidamide (500 mg, 2 mmol) in CH$_3$CN (15 mL) at room temperature under an argon atmosphere was added PS-BEMP (1.1 g). The reaction mixture was stirred for 10 min. Then 2-bromo-1-(1-methyl-1H-indazol-3-yl)ethan-1-one (771 mg, 3 mmol) in CH$_3$CN (10 mL) was added to the reaction mixture at room temperature. The reaction mixture was stirred for 4 h at room temperature. After consumption of starting material (monitored by TLC), the volatiles were evaporated in vacuo to afford (Z)-5-bromo-6-methoxy-N'-(2-(1-methyl-1H-indazol-3-yl)-2-oxoethoxy) picolinimidamide (600 mg, crude) as brown solid used in the next step without further purification.

LCMS: 43.7%; 419.8 (M+3); (column; Ascentis Express C-18 (50×3.0 mm, 2.7 μm); RT 2.77 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.6).

3-(5-bromo-6-methoxypyridin-2-yl)-5-(1-methyl-1H-indazol-3-yl)-5,6-dihydro-4H-1,2,4-oxadiazine To a stirred solution of (Z)-5-bromo-6-methoxy-N'-(2-(1-methyl-1H-indazol-3-yl)-2-oxoethoxy) picolinimidamide (500 mg, 1 mmol) in MeOH (20 mL) at room temperature under an argon atmosphere was added acetic acid (5 mL). The reaction mixture was stirred for 16 h at 60° C. Then sodium cyanoborohydride (90.4 mL, 1 mmol) was added to the reaction mixture. The reaction mixture was stirred for 4 h at room temperature. After consumption of starting material (monitored by TLC), the reaction mixture was diluted with saturated sodium bicarbonate solution (20 mL) and extracted with EtOAc (2×20 mL). The combined organic extracts were dried over sodium sulfate, filtered and concentrated in vacuo. The crude material was purified by column chromatography using 25% EtOAc: Hexane to afford 3-(5-bromo-6-methoxypyridin-2-yl)-5-(1-methyl-1H-indazol-3-yl)-5,6-dihydro-4H-1,2,4-oxadiazine (200 mg, 42%) as brown solid.

LCMS: 72.2%; 403.8 (M+3); (column; Ascentis Express C-18 (50×3.0 mm, 2.7 μm); RT 2.57 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.4).

Example 124

Synthesis of 5-(benzofuran-2-yl)-3-(6-methoxy-5-(4-methyl-1H-imidazol-1-yl)pyridin-2-yl)-5,6-dihydro-4H-1,2,4-oxadiazine

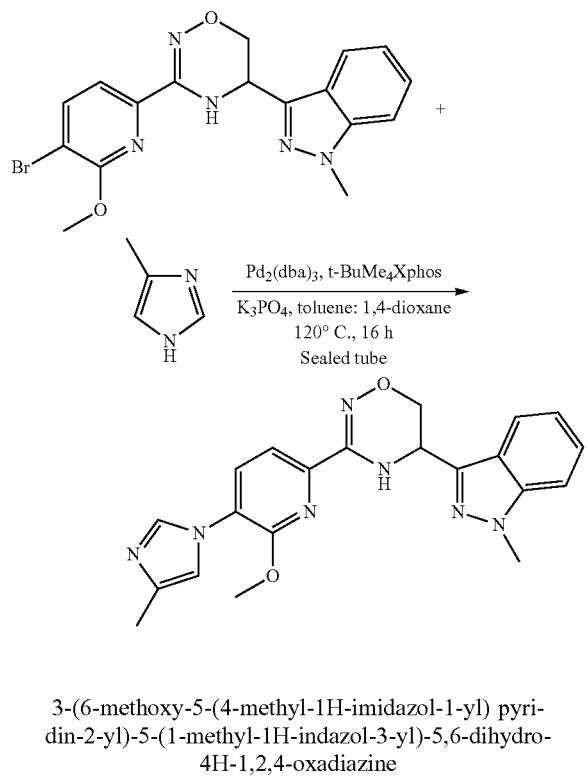

3-(6-methoxy-5-(4-methyl-1H-imidazol-1-yl) pyridin-2-yl)-5-(1-methyl-1H-indazol-3-yl)-5,6-dihydro-4H-1,2,4-oxadiazine To a dry vial was added a suspension of Pd$_2$(dba)$_3$ (23 mg, 0.02 mmol) and tert-butyl tetramethyl Xphos (24 mg, 0.05 mmol) in toluene:1,4-dioxane (2:1, 2 mL) at room temperature. The suspension was degassed with argon, heated to 120° C., and stirred at 120° C. for 3 min. A mixture of 3-(5-bromo-6-methoxypyridin-2-yl)-5-(1-methyl-1H-indazol-3-yl)-5,6-dihydro-4H-1,2,4-oxadiazine (200 mg, 0.5 mmol), 4-methyl-1H-imidazole (81 mg, 1 mmol) and potassium phosphate (210 mg, 1 mmol) in toluene:1,4-dioxane (2:1, 2 mL) was degassed and the catalyst premixture was added. The resultant mixture was stirred at 120° C. for 16 h in a sealed tube. After consumption of the starting material (monitored by TLC and LCMS), the volatiles were evaporated in vacuo. The crude material was purified by column chromatography using 2% MeOH: CH$_2$Cl$_2$ to afford 3-(6-methoxy-5-(4-methyl-1H-imidazol-1-yl) pyridin-2-yl)-5-(1-methyl-1H-indazol-3-yl)-5,6-dihydro-4H-1,2,4-oxadiazine (120 mg, 60%) as an off-white solid used in the next step without further purification.

Racemic compound of Example 124 was separated using a Chiralpak-AD-H column (250×20 mm, 5 μm) (10 mg loading; 0.1% DEA in n-Hexane: EtOH:MeOH (50:50) (A:B; 70:30) as mobile phase; flow rate: 20 mL/min) to afford the compounds of Example 124A (Fraction (I) (−)) and Example 124B (Fraction (II) (+)).

Analytical conditions for Example 124A and Example 124B: HPLC (column; Zorbox SB-C-18 150×4.6 mm, 3.5 μm); mobile Phase: ACN: 0.05% Aq TFA; flow rate: 1.0 mL/min; Gradient program: T/B % 0.01/90, 2/90, 8/10, 15/10: diluent: CH$_3$CN:Water; Chiral HPLC: (Chiralpak-ADH (250×4.6 mm, 5 μm; mobile phase (A) 0.1% DEA in n-Hexane (B) EtOH:MeOH (50:50) (A:B; 70:30); flow Rate: 1.0 mL/min).

Example 124A, (−)-3-(6-methoxy-5-(4-methyl-1H-imidazol-1-yl) pyridin-2-yl)-5-(1-methyl-1H-indazol-3-yl)-5,6-dihydro-4H-1,2,4-oxadiazine, fraction (I) (−): Mass (ESI): 404.3 [M+1]; HPLC (purity): 99.5%, RT 7.13 min; Chiral HPLC: 100%, RT=14.21 min; Optical rotation $[\alpha]_D^{19.96}$: −89.47 (c=0.25, CH$_2$Cl$_2$).

Example 124B, (+)-3-(6-methoxy-5-(4-methyl-1H-imidazol-1-yl) pyridin-2-yl)-5-(1-methyl-1H-indazol-3-yl)-5,6-dihydro-4H-1,2,4-oxadiazine, fraction (II) (+): $^1$H NMR (CD$_3$OD, 400 MHz): δ 7.98 (s, 1H), 7.90 (d, 1H), 7.83 (d, 1H), 7.70 (d, 1H), 7.53 (d, 1H), 7.44-7.40 (m, 1H), 7.23 (s, 1H), 7.14-7.10 (m, 1H), 5.32 (t, 1H), 4.32 (dd, 1H), 4.09 (dd, 1H), 4.06 (s, 6H), 2.25 (s, 3H); Mass (ESI): 404.3 [M+1]; HPLC (purity): 99.8%, RT 7.15 min; Chiral HPLC: 100%, RT=17.56 min; Optical rotation $[\alpha]_D^{19.99}$: +92.51 (c=0.25, CH$_2$Cl$_2$).

Example 125

Synthesis of 2-bromo-1-(3-cyclopropylphenyl) ethan-1-one

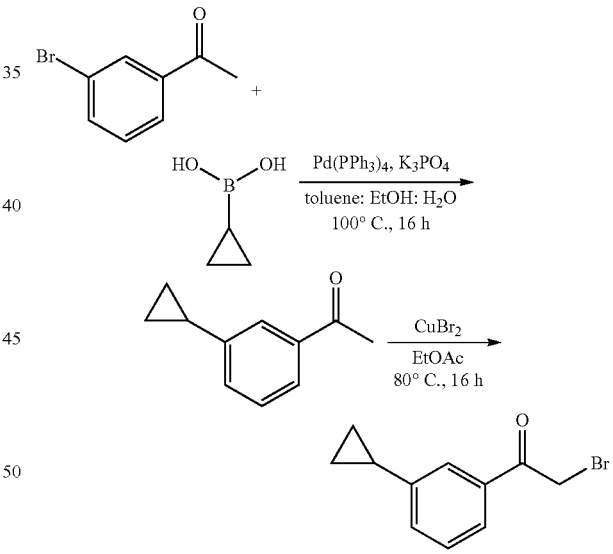

1-(3-cyclopropylphenyl) ethan-1-one

To a stirred solution of 1-(3-bromophenyl) ethan-1-one (2 g, 10 mmol) in toluene:EtOH:water (1:1:1, 40 mL) at room temperature under an argon atmosphere were added cyclopropylboronic acid (1.2 g, 15 mmol), potassium phosphate (4.2 g, 20 mmol) and purged under argon for 15 min. Then Pd(PPh$_3$)$_4$ (580 mg, 0.5 mmol) was added to the reaction mixture at room temperature. The reaction mixture was stirred at 100° C. for 16 h. After consumption of starting material (monitored by TLC), the reaction mixture was diluted with water (50 mL) and extracted with EtOAc (2×50 mL). The combined organic extracts were dried over sodium sulfate, filtered and concentrated in vacuo. The crude material was purified by column chromatography using 5-20% EtOAc: Hexane to afford 1-(3-cyclopropylphenyl) ethan-1-one (1.25 g, crude) as colorless liquid. TLC: 20% EtOAc/Hexane ($R_f$: 0.4).

2-bromo-1-(3-cyclopropylphenyl) ethan-1-one

To a stirred solution of 1-(3-cyclopropylphenyl) ethan-1-one (1.25 g, 8 mmol) in EtOAc (60 mL) at room temperature under an argon atmosphere was added copper bromide (3.5 g, 16 mmol). The reaction mixture was stirred for 16 h at 80° C. After consumption of starting material (monitored by TLC), the reaction mixture was filtered. The filtrate was concentrated in vacuo. The crude material was purified by column chromatography using 5-10% EtOAc: Hexane to afford 2-bromo-1-(3-cyclopropylphenyl) ethan-1-one (1 g, crude) as colorless liquid used in the next step without further purification. $^1$H NMR (DMSO-$d_6$, 400 MHz): δ 7.80-7.73 (m, 1H), 7.68 (s, 1H), 7.56-7.33 (m, 2H), 4.93 (s, 2H), 2.07-1.98 (m, 1H), 1.07-0.94 (m, 2H), 0.80-0.71 (m, 2H); TLC: 20% EtOAc/Hexane ($R_f$: 0.5).

Example 126

Synthesis of 3-(5-bromo-6-methoxypyridin-2-yl)-5-(3-cyclopropylphenyl)-5,6-dihydro-4H-1,2,4-oxadiazine

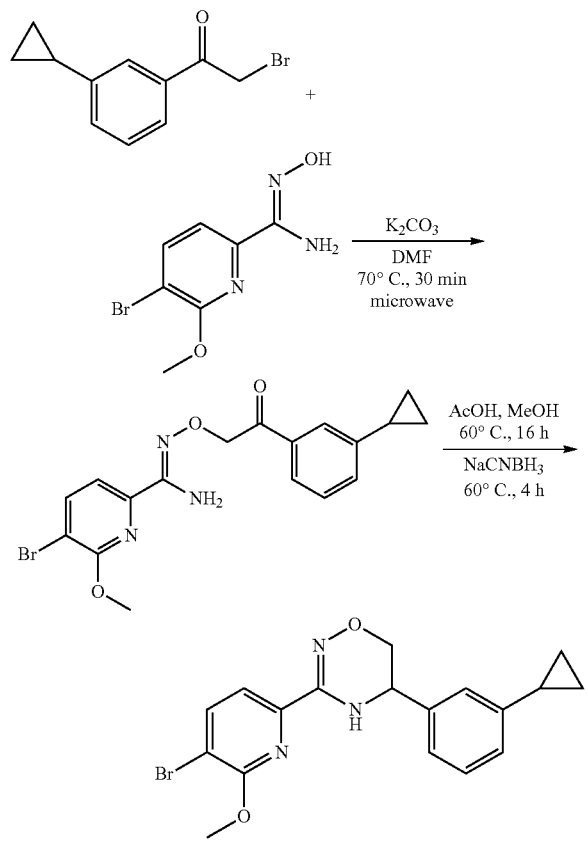

(Z)-5-bromo-N'-(2-(3-cyclopropylphenyl)-2-oxoethoxy)-6-methoxypicolinimidamide

To a stirred solution of 2-bromo-1-(3-cyclopropylphenyl) ethan-1-one (500 mg, 2 mmol) in DMF (5 mL) at room temperature under an argon atmosphere were added potassium carbonate (560 mg, 4.06 mmol) and 2-bromo-1-(3-cyclopropylphenyl) ethan-1-one (728 mg, 3 mmol). The reaction mixture was stirred for 30 min at 70° C. in microwave. After consumption of starting material (monitored by TLC), the reaction mixture was diluted with water (10 mL) and extracted with EtOAc (2×10 mL). The combined organic extracts were dried over sodium sulfate, filtered and concentrated in vacuo to afford (Z)-5-bromo-N'-(2-(3-cyclopropylphenyl)-2-oxoethoxy)-6-methoxypicolinimidamide (750 mg, crude) as yellow solid used in the next step without further purification.

LCMS: 40.1%; 405.8 (M+3); (column; Ascentis Express C-18 (50×3.0 mm, 2.7 μm); RT 2.95 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.6).

3-(5-bromo-6-methoxypyridin-2-yl)-5-(3-cyclopropylphenyl)-5,6-dihydro-4H-1,2,4-oxadiazine To a stirred solution of (Z)-5-bromo-N'-(2-(3-cyclopropylphenyl)-2-oxoethoxy)-6-methoxypicolinimidamide (750 mg, 2 mmol) in MeOH (10 mL) at room temperature under an argon atmosphere was added acetic acid (2.5 mL). The reaction mixture was stirred for 16 h at 60° C. Then sodium cyanoborohydride (155 mg) was added to the reaction mixture. The reaction mixture was stirred for 4 h at 60° C. After consumption of starting material (monitored by TLC), the volatiles were evaporated in vacuo. The residue was diluted with water (20 mL) and extracted with EtOAc (2×20 mL). The combined organic extracts were dried over sodium sulfate, filtered and concentrated in vacuo. The crude material was purified by column chromatography using 15-25% EtOAc: Hexane to afford 3-(5-bromo-6-methoxypyridin-2-yl)-5-(3-cyclopropylphenyl)-5,6-dihydro-4H-1,2,4-oxadiazine (400 mg, crude) as colorless liquid used in the next step without further purification. $^1$H NMR (CDCl$_3$, 500 MHz): δ 7.90 (d, 1H), 7.70 (d, 1H), 7.31 (t, 1H), 7.14 (d, 1H), 7.08 (s, 1H), 7.05 (d, 1H), 6.65 (br s, 1H), 4.77-4.72 (m, 1H), 4.31 (dd, 1H), 3.98 (s, 3H), 3.70 (dd, 1H), 1.95-1.79 (m, 1H), 1.02-0.97 (m, 2H), 0.71-0.69 (m, 2H); LCMS: 94.8%; 387.8 (M+1); (column; Ascentis Express C-18 (50×3.0 mm, 2.7 μm); RT 2.88 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.4).

Example 127

Synthesis of 5-(3-cyclopropylphenyl)-3-(6-methoxy-5-(4-methyl-1H-imidazol-1-yl) pyridin-2-yl)-5,6-dihydro-4H-1,2,4-oxadiazine

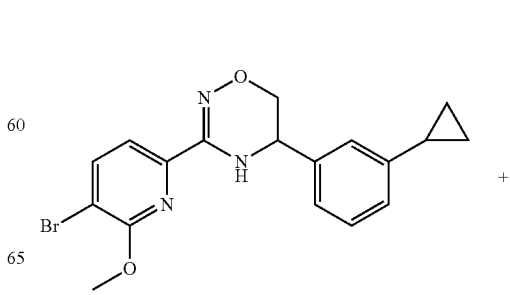

-continued

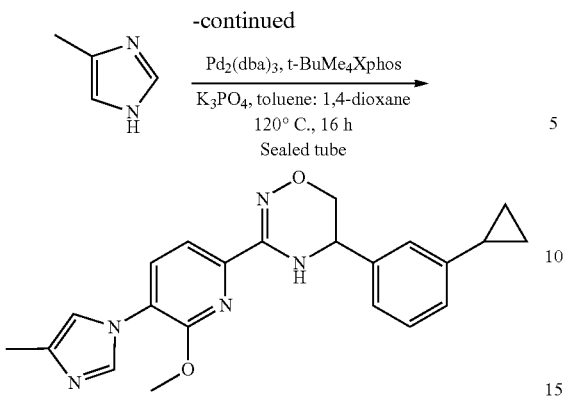

5-(3-cyclopropylphenyl)-3-(6-methoxy-5-(4-methyl-1H-imidazol-1-yl) pyridin-2-yl)-5,6-dihydro-4H-1,2,4-oxadiazine To a dry vial was added a suspension of Pd$_2$(dba)$_3$ (12 mg, 0.01 mmol) and tert-butyl tetramethyl Xphos (12 mg, 0.02 mmol) in toluene:1,4-dioxane (2:1, 1.5 mL) at room temperature. The suspension was degassed with argon, heated to 120° C., and stirred at 120° C. for 3 min. A mixture of 3-(5-bromo-6-methoxypyridin-2-yl)-5-(3-cyclopropylphenyl)-5,6-dihydro-4H-1,2,4-oxadiazine (100 mg, 0.3 mmol), 4-methyl-1H-imidazole (12 mg, 0.4 mmol) and potassium phosphate (109 mg, 0.5 mmol) in toluene:1,4-dioxane (2:1, 1.5 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo. The crude material was purified by column chromatography using 2-5% MeOH: CH$_2$Cl$_2$ to afford 5-(3-cyclopropylphenyl)-3-(6-methoxy-5-(4-methyl-1H-imidazol-1-yl) pyridin-2-yl)-5,6-dihydro-4H-1,2,4-oxadiazine (60 mg, 60%) as a pale yellow solid.

Racemic compound of Example 127 was separated using a Chiralpak-IB column (250×20 mm, 5 µm) (35 mg loading; 0.1% DEA in n-Hexane: CH$_2$Cl$_2$:MeOH (50:50) (A:B: 85:15) as mobile phase; flow rate: 20 mL/min) to afford the compounds of Example 127A (Fraction (I) (−)) and Example 127B (Fraction (II) (+)).

Analytical conditions for Example 127A and Example 127B: HPLC (column; zorbax-SB-C-18 150×4.6 mm, 3.5µ); mobile Phase: ACN: 0.05% Aq TFA; flow rate: 1.0 mL/min; Gradient program: T/B % 0.01/90, 2/90, 8/10, 15/10: diluent: CH$_3$CN:Water; Chiral HPLC: (Chiralpak-IB (250× 4.6 mm, 5 µm; mobile phase (A) 0.1% DEA in n-Hexane (B) CH$_2$Cl$_2$:MeOH (50:50) (A:B; 80:20); flow Rate: 1.0 mL/min).

Example 127A, (−)-5-(3-cyclopropylphenyl)-3-(6-methoxy-5-(4-methyl-1H-imidazol-1-yl) pyridin-2-yl)-5,6-dihydro-4H-1,2,4-oxadiazine, fraction (I) (−): Mass (ESI): 390 [M+1]; HPLC (purity): 99.1%, RT 7.70 min; Chiral HPLC: 99.0%, RT=8.03 min; Optical rotation $[\alpha]_D^{20.00}$: −169.77 (c=0.25, CH$_2$Cl$_2$).

Example 127B, (+)-5-(3-cyclopropylphenyl)-3-(6-methoxy-5-(4-methyl-1H-imidazol-1-yl) pyridin-2-yl)-5,6-dihydro-4H-1,2,4-oxadiazine, fraction (II) (+): $^1$H NMR (CD$_3$OD, 500 MHz): δ 7.99 (s, 1H), 7.89 (d, 1H), 7.64 (d, 1H), 7.28-7.22 (m, 2H), 7.15 (d, 1H), 7.12 (s, 1H), 7.03 (d, 1H), 4.80 (t, 1H), 4.15 (dd, 1H), 4.08 (s, 3H), 3.83 (dd, 1H), 2.25 (s, 3H), 1.95-1.89 (m, 1H), 0.96-0.93 (m, 2H), 0.69-0.66 (m, 2H); Mass (ESI): 390 [M+1]; HPLC (purity): 98.1%, RT 7.70 min; Chiral HPLC: 98.1%, RT=9.25 min (Chiralpak-IB (250×4.6 mm, 5 µm; mobile phase (A) 0.1% DEA in n-Hexane (B) CH$_2$Cl$_2$:MeOH (50:50) (A:B; 80:20); flow Rate: 1.0 mL/min): Optical rotation $[\alpha]_D^{20.00}$: +158.01 (c=0.25, CH$_2$Cl$_2$).

Example 128

Synthesis of 3-(5-bromo-6-methoxypyridin-2-yl)-5-(2,4-difluorophenyl)-5,6-dihydro-4H-1,2,4-oxadiazine

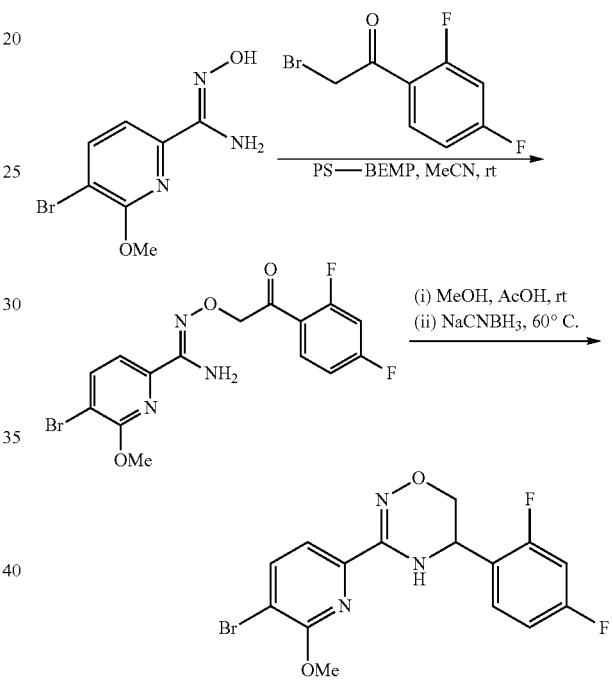

(Z)-5-bromo-N'-(2-(2,4-difluorophenyl)-2-oxoethoxy)-6-methoxypicolinimidamide

The title compound was prepared from 2-bromo-1-(2,4-difluorophenyl)ethanone according to the procedure for Example 43. $^1$H NMR (CDCl$_3$, 400 MHz) δ 8.00 (q, 1H), 7.76 (d, 1H), 7.37 (d, 1H), 6.99 (dt, 1H), 6.92-6.86 (m, 1H), 5.65-5.54 (br s, 2H), 5.22 (d, 2H), 4.04 (s, 3H). UPLC (basic, 1.25 min): RT 0.90 min, [MH]+ 402.2, purity 70%.

3-(5-bromo-6-methoxypyridin-2-yl)-5-(2,4-difluorophenyl)-5,6-dihydro-4H-1,2,4-oxadiazine Example 128 (175 mg, 43% over 2 steps) was prepared from (Z)-5-bromo-N'-(2-(2,4-difluorophenyl)-2-oxoethoxy)-6-methoxypicolinimidamide according to the procedure for Example 43. $^1$H NMR (CDCl$_3$, 400 MHz) δ 7.88 (d, 1H), 7.60 (d, 1H), 7.36 (q, 1H), 6.94-6.81 (m, 2H), 6.56 (s, 1H), 5.16-5.11 (m, 1H), 4.16 (dd, 1H), 4.01 (s, 3H), 3.95 (dd, 1H). UPLC (basic, 1.25 min): RT 0.87 mM, [MH]+ 386.1, purity 66%.

Example 129

Synthesis of 5-(2,4-difluorophenyl)-3-(6-methoxy-5-(4-methyl-1H-imidazol-1-yl)pyridin-2-yl)-5,6-dihydro-4H-1,2,4-oxadiazine

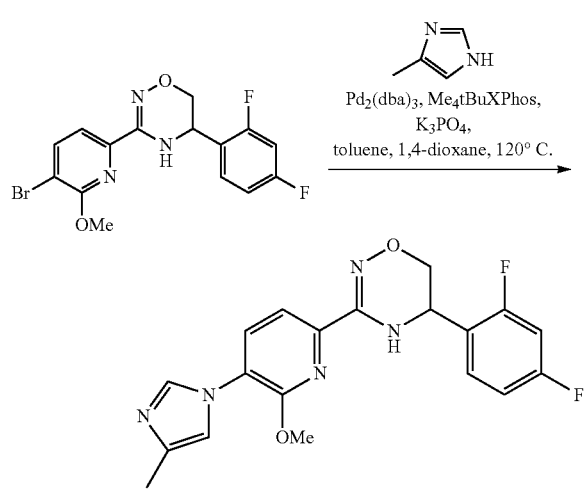

Example 129 (151 mg, 85%) was prepared from 3-(5-bromo-6-methoxypyridin-2-yl)-5-(2,4-difluorophenyl)-5,6-dihydro-4H-1,2,4-oxadiazine according to the procedure for Example 44. The enantiomers were separated by chiral preparative high performance liquid chromatography (HPLC) (Chiralpak IB 20×250 mm) eluting with 4:1 heptane:EtOH (0.1% diethylamine) over 25 minutes (18 mL per minute).

Example 129A, 5-(2,4-difluorophenyl)-3-(6-methoxy-5-(4-methyl-1H-imidazol-1-yl)pyridin-2-yl)-5,6-dihydro-4H-1,2,4-oxadiazine, fraction (I): 36.4 mg; Chiral HPLC: RT 12.92 min, 100% e.e.; LCMS (basic, 11 min): RT 6.02 min, [MH]+ 386.1, purity 100%.

Example 129B, 5-(2,4-difluorophenyl)-3-(6-methoxy-5-(4-methyl-1H-imidazol-1-yl)pyridin-2-yl)-5,6-dihydro-4H-1,2,4-oxadiazine, fraction (II): 20.4 mg; $^1$H NMR (CDCl$_3$, 400 MHz) δ 7.94-7.76 (m, 2H), 7.63 (d, 1H), 7.37 (q, 1H), 6.99 (s, 1H), 6.96-6.81 (m, 2H), 6.58 (s, 1H), 5.15 (s, 1H), 4.18 (dd, 1H), 4.02 (s, 3H), 3.97 (dd, 1H), 2.30 (s, 3H). Chiral HPLC: RT 15.44 min, 92% e.e.; LCMS (basic, 11 min): RT 6.03 min, [MH]+ 386.1, purity 99%.

Example 130

Synthesis of 3-(5-bromo-6-methoxypyridin-2-yl)-5-(o-tolyl)-5,6-dihydro-4H-1,2,4-oxadiazine

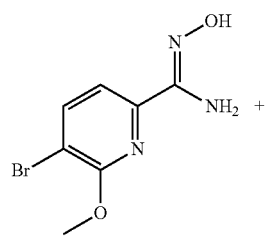

+

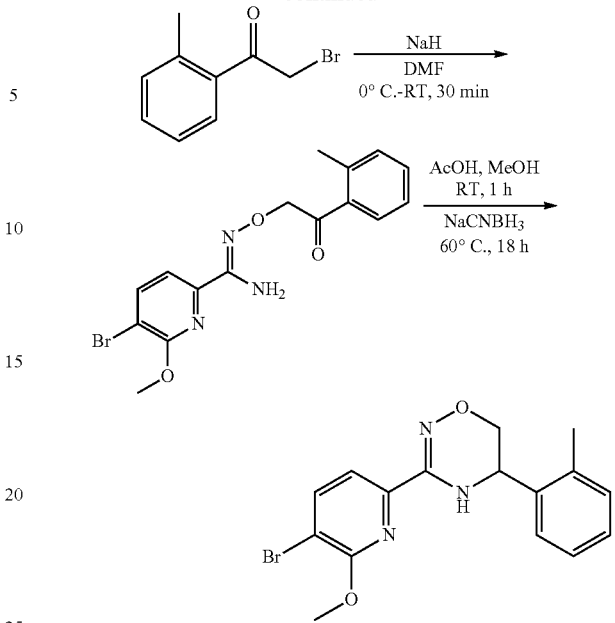

(Z)-5-bromo-6-methoxy-N'-(2-oxo-2-(o-tolyl) ethoxy) picolinimidamide

The title compound was prepared from 2-bromo-1-(o-tolyl)ethanone according to the procedure for Example 35. LCMS: 75.6%; 377.9 (M+2); (column; Ascentis Express C-18 (50×3.0 mm, 3.5 μm); RT 2.87 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.6).

3-(5-bromo-6-methoxypyridin-2-yl)-5-(o-tolyl)-dihydro-4H-1,2,4-oxadiazine

Example 130 (280 mg, crude) was prepared from (Z)-5-bromo-6-methoxy-N'-(2-oxo-2-(o-tolyl) ethoxy) picolinimidamide according to the procedure for Example 35. LCMS: 70.4%; 361.9 (M+); (column; Ascentis Express C-18 (50×3.0 mm, 3.5 μm); RT 2.72 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.6).

Example 131

Synthesis of 3-(6-methoxy-5-(4-methyl-1H-imidazol-1-yl) pyridin-2-yl)-5-(o-tolyl)-5,6-dihydro-4H-1,2,4-oxadiazine

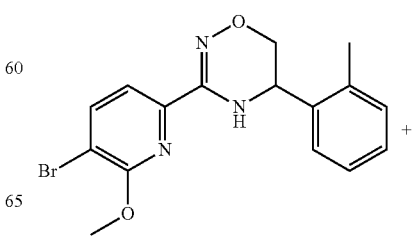

+

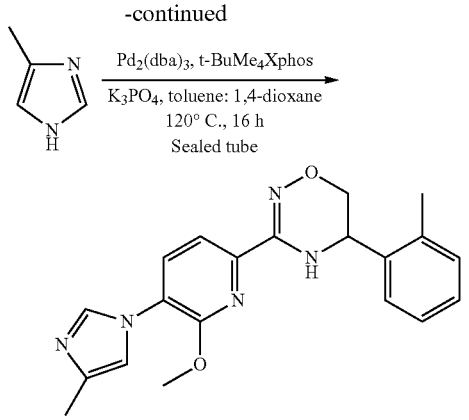

Example 131 (78 mg, 43%) was prepared from 3-(5-bromo-6-methoxypyridin-2-yl)-5-(o-tolyl)-5,6-dihydro-4H-1,2,4-oxadiazine according to the procedure for Example 49.

Racemic compound of Example 131 was separated using a Chiralpak-IC column (250×20 mm, 5 μm) (20 mg loading; 0.1% DEA in n-Hexane: $CH_2Cl_2$:MeOH (50:50) (A:B: 50:50) as mobile phase) to afford the compounds of Example 131A (Fraction (I) (+)) and Example 131B (Fraction (II) (−)).

Analytical conditions for Example 131A and Example 131B: UPLC (column; Acquity UPLC BEH-C-18, 50×2.1 mm, 1.7μ); mobile phase: ACN: 0.025% Aq TFA; flow rate: 0.5 mL/min; Gradient program: T/B % 0.01/90, 0.5/90, 3/10, 6/10: diluent: $CH_3CN$:Water; Chiral HPLC: (Chiralpak-IC (250×4.6 mm, 5 μm; mobile phase (A) 0.1% DEA in n-Hexane (B) $CH_2Cl_2$:MeOH (50:50) (A:B; 50:50); flow Rate: 1.0 mL/min).

Example 131A, (+)-3-(6-methoxy-5-(4-methyl-1H-imidazol-1-yl) pyridin-2-yl)-5-(o-tolyl)-5,6-dihydro-4H-1,2,4-oxadiazine, fraction (I) (+): $^1$H NMR ($CD_3OD$, 400 MHz): δ 7.98 (s, 1H), 7.89 (d, 1H), 7.66 (d, 1H), 7.34-7.29 (m, 1H), 7.22-7.20 (m, 4H), 5.13 (t, 1H), 4.19 (dd, 1H), 4.08 (s, 3H), 3.78 (dd, 1H), 2.44 (s, 3H), 2.26 (s, 3H); Mass (ESI): 364.4 [M+1]; UPLC (purity): 99.7%, RT 1.79 min; Chiral HPLC: 99.8%, RT=14.03 min; Optical rotation $[α]_D^{19.99}$: +178.52 (c=0.25, $CH_2Cl_2$).

Example 131B, (−)-3-(6-methoxy-5-(4-methyl-1H-imidazol-1-yl) pyridin-2-yl)-5-(o-tolyl)-5,6-dihydro-4H-1,2,4-oxadiazine, fraction (II) (−): Mass (ESI): 364.4 [M+1]; UPLC (purity): 99.7%, RT 1.79 min; Chiral HPLC: 99.8%, RT=18.02 min; Optical rotation $[α]_D^{19.99}$: −172.97 (c=0.25, $CH_2Cl_2$).

Example 132

Synthesis of 3-(5-bromo-6-methoxypyridin-2-yl)-5-ethyl-5,6-dihydro-4H-1,2,4-oxadiazine

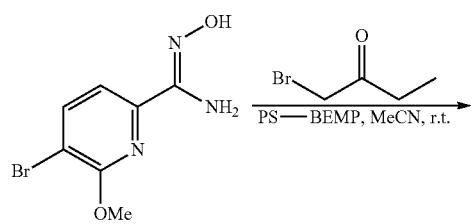

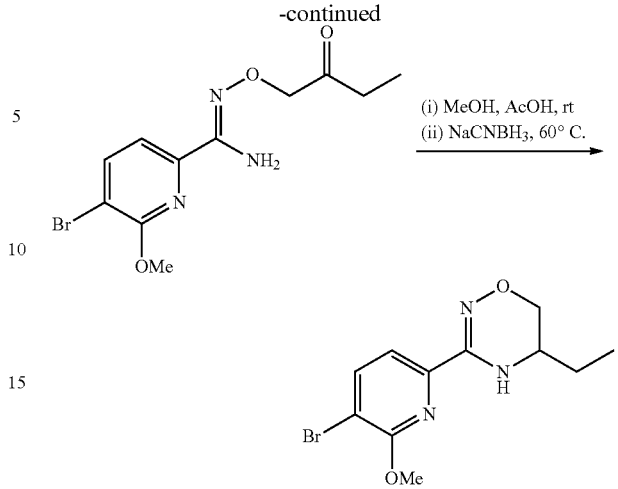

(Z)-5-bromo-6-methoxy-N'-(2-oxobutoxy)picolinimidamide

The title compound was prepared from 1-bromobutan-2-one according to the procedure for Example 43. $^1$H NMR ($CDCl_3$, 400 MHz) δ 7.79 (d, 1H), 7.40 (d, 1H), 5.7-5.4 (br s, 2H), 4.60 (s, 2H), 4.04 (s, 3H), 2.56 (q, 2H), 1.07 (t, 3H). UPLC (basic, 1.25 min): RT 0.81 min, [MH]+ 316.1, purity 88%.

3-(5-bromo-6-methoxypyridin-2-yl)-5-ethyl-5,6-dihydro-4H-1,2,4-oxadiazine

Example 132 (135 mg, 100% over 2 steps) was prepared from (Z)-5-bromo-6-methoxy-N'-(2-oxobutoxy)picolinimidamide according to the procedure for Example 43. $^1$H NMR ($CDCl_3$, 400 MHz) δ 7.83 (d, 1H), 7.52 (d, 1H), 6.30 (s, 1H), 4.10 (dd, 1H), 4.03 (s, 3H), 3.64 (dd, 1H), 3.59-3.51 (m, 1H), 1.64 (p, 2H), 1.04 (t, 3H). UPLC (basic, 1.25 min): RT 0.79 min, [MH]+ 300.1, purity 60%.

Example 133

Synthesis of 5-ethyl-3-(6-methoxy-5-(4-methyl-1H-imidazol-1-yl)pyridin-2-yl)-5,6-dihydro-4H-1,2,4-oxadiazine

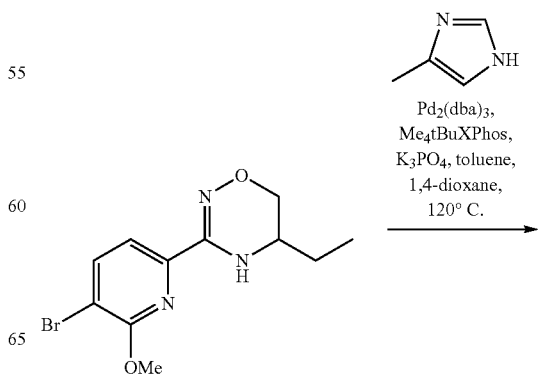

339
-continued

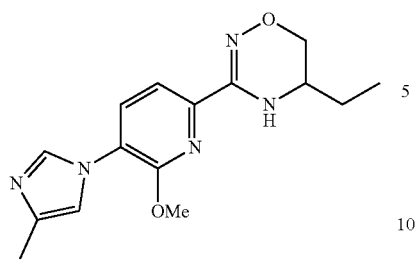

Example 133 (73 mg, 54%) was prepared from 3-(5-bromo-6-methoxypyridin-2-yl)-5-ethyl-5,6-dihydro-4H-1,2,4-oxadiazine according to the procedure for Example 44. The enantiomers were separated by chiral preparative high performance liquid chromatography (HPLC) (Chiralpak IB 20×250 mm) eluting with 95:5 tert-butylmethyl ether:methanol (0.1% ethanolamine) over 30 minutes (18 mL per minute).

Example 133A, 5-ethyl-3-(6-methoxy-5-(4-methyl-1H-imidazol-1-yl)pyridin-2-yl)-5,6-dihydro-4H-1,2,4-oxadiazine, fraction (I): 4 mg; Chiral HPLC: RT 17.74 min, 100% e.e.; UPLC (basic, 4.7 min): RT 1.71 min, [MH]+ 301.0, purity 96%.

Example 133B, 5-ethyl-3-(6-methoxy-5-(4-methyl-1H-imidazol-1-yl)pyridin-2-yl)-5,6-dihydro-4H-1,2,4-oxadiazine, fraction (II): 9 mg; $^1$H NMR (CDCl$_3$, 400 MHz) δ 7.89 (s, 1H), 7.75 (d, 1H), 7.60 (d, 1H), 6.99 (s, 1H), 6.31 (s, 1H), 4.12 (dd, 1H), 4.06 (s, 3H), 3.66 (dd, 1H), 3.63-3.53 (m, 1H), 2.31 (s, 3H), 1.66 (p, 2H), 1.06 (t, 3H). Chiral HPLC: RT 20.16 min, 99% e.e.; UPLC (basic, 4.7 min): RT 1.71 min, [MH]+ 301, purity 100%.

Example 134

Synthesis of 5-cyclopropyl-3-(6-methoxy-5-(4-methyl-1H-imidazol-1-yl)pyridin-2-yl)-5,6-dihydro-4H-1,2,4-oxadiazine

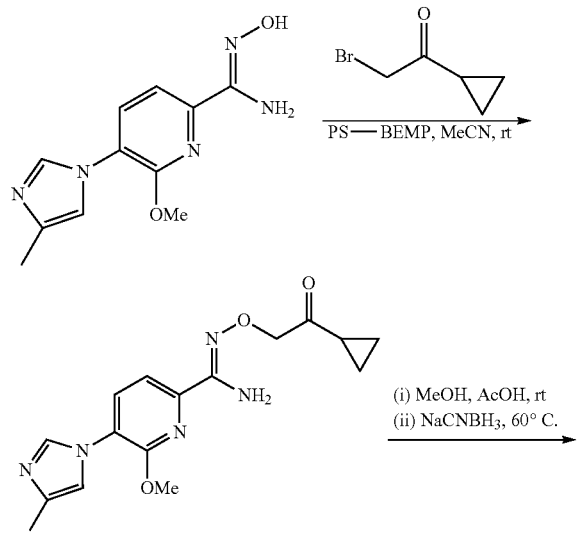

340
-continued

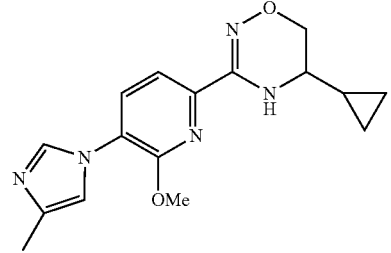

(Z)—N'-(2-cyclopropyl-2-oxoethoxy)-6-methoxy-5-(4-methyl-1H-imidazol-1-yl)picolinimidamide N'-hydroxy-6-methoxy-5-(4-methyl-1H-imidazol-1-yl)picolinimidamide (200 mg, 0.81 mmol) in 1:1 acetonitrile:DMF (8 mL) was added to PS-BEMP (2.2 mmol/g, 450 mg, 0.97 mmol). The mixture was stirred at room temperature for 5 minutes before the addition of 2-bromo-1-cyclopropyl-ethanone (119 μL, 1.21 mmol) in acetonitrile (2 mL). The reaction mixture was stirred overnight, filtered and the solvent was removed under reduced pressure to afford crude (Z)—N'-(2-cyclopropyl-2-oxoethoxy)-6-methoxy-5-(4-methyl-1H-imidazol-1-yl)picolinimidamide, which was used directly in the next step. UPLC (basic, 1.25 min): RT 0.66 min, [MH]+ 330.2, purity 62%.

5-cyclopropyl-3-(6-methoxy-5-(4-methyl-1H-imidazol-1-yl)pyridin-2-yl)-5,6-dihydro-4H-1,2,4-oxadiazine A mixture of (Z)—N'-(2-cyclopropyl-2-oxoethoxy)-6-methoxy-5-(4-methyl-1H-imidazol-1-yl)picolinimidamide (max 0.81 mmol), acetic acid (2 mL) and methanol (8 mL) were heated to 60° C. for 1 hour. To the mixture was added sodium cyanoborohydride (61 mg, 0.92 mmol) and the mixture was stirred at 60° C. for 18 hours. The reaction mixture was diluted with water (20 mL) and extracted into ethyl acetate (2×20 mL). The combined organic extracts were washed with brine (20 mL), dried over magnesium sulfate, filtered, and the solvent was removed under reduced pressure. The crude material was purified by flash column chromatography on silica gel (eluting with 95:5 dichloromethane:methanol) to afford the title compound (33 mg, 13%). The enantiomers were separated by chiral preparative high performance liquid chromatography (HPLC) (Chiralpak IB 20×250 mm) eluting with 95:5 tert-butylmethyl ether:methanol (0.1% ethanolamine) over 30 minutes (18 mL per minute).

Example 134A, 5-cyclopropyl-3-(6-methoxy-5-(4-methyl-1H-imidazol-1-yl)pyridin-2-yl)-5,6-dihydro-4H-1,2,4-oxadiazine, fraction (I): 8.1 mg; Chiral HPLC: RT 17.58 min, 98% e.e.; LCMS (basic, 11 min): RT 5.29 min, [MH]+ 314.1, purity 99%.

Example 134B, 5-cyclopropyl-3-(6-methoxy-5-(4-methyl-1H-imidazol-1-yl)pyridin-2-yl)-5,6-dihydro-4H-1,2,4-oxadiazine, fraction (II): 16.3 mg; $^1$H NMR (CDCl$_3$, 400 MHz) δ 7.95 (s, 1H), 7.77 (d, 1H), 7.61 (d, 1H), 7.00 (s, 1H), 6.31 (s, 1H), 4.25 (dd, 1H), 4.08 (s, 3H), 3.71 (dd, 1H), 2.93-2.84 (m, 1H), 2.34 (s, 3H), 0.99-0.88 (m, 1H), 0.71-0.55 (m, 2H), 0.47-0.30 (m, 2H). Chiral HPLC: RT 20.12 min, 93% e.e.; LCMS (basic, 11 min): RT 5.27 min, [MH]+ 312.3, purity 99%.

Example 135

Synthesis of 3-(5-bromo-6-methoxypyridin-2-yl)-5-(2-chlorophenyl)-5,6-dihydro-4H-1,2,4-oxadiazine

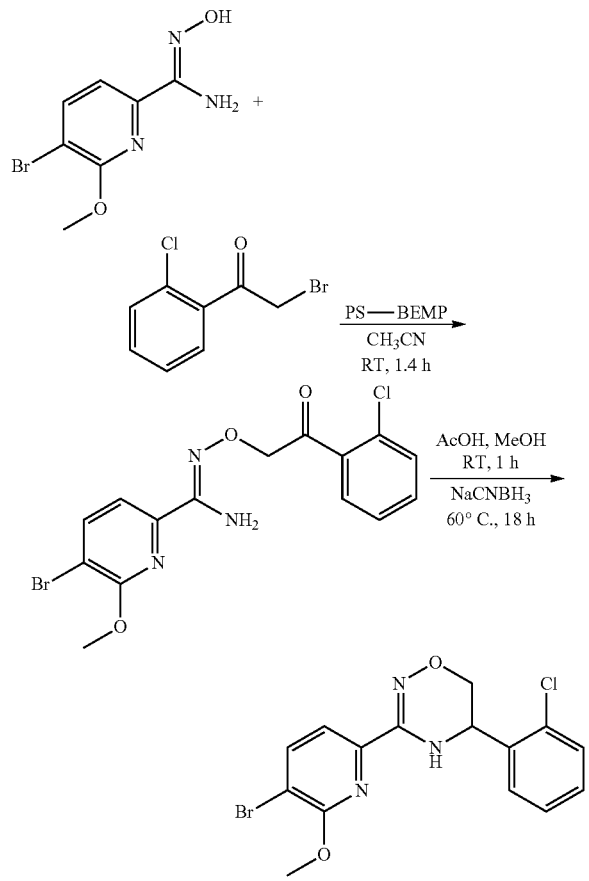

(Z)-5-bromo-N'-(2-(2-chlorophenyl)-2-oxoethoxy)-6-methoxypicolinimidamide

The title compound was prepared from 2-bromo-1-(2-chlorophenyl)ethanone according to the procedure for Example 43. LCMS: 31.5%; 399.8 (M+2); (column; Ascentis Express C-18 (50×3.0 mm, 3.5 μm); RT 2.83 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane ($R_f$: 0.6).

3-(5-bromo-6-methoxypyridin-2-yl)-5-(2-chlorophenyl)-5,6-dihydro-4H-1,2,4-oxadiazine Example 135 (120 mg, crude) was prepared from (Z)-5-bromo-N'-(2-(2-chlorophenyl)-2-oxoethoxy)-6-methoxypicolinimidamide according to the procedure for Example 43. LCMS: 52.7%; 383.7 (M+2); (column; Ascentis Express C-18 (50×3.0 mm, 3.5 μm); RT 2.82 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane ($R_f$: 0.6).

Example 136

Synthesis of 5-(2-chlorophenyl)-3-(6-methoxy-5-(4-methyl-1H-imidazol-1-yl) pyridin-2-yl)-5,6-dihydro-4H-1,2,4-oxadiazine

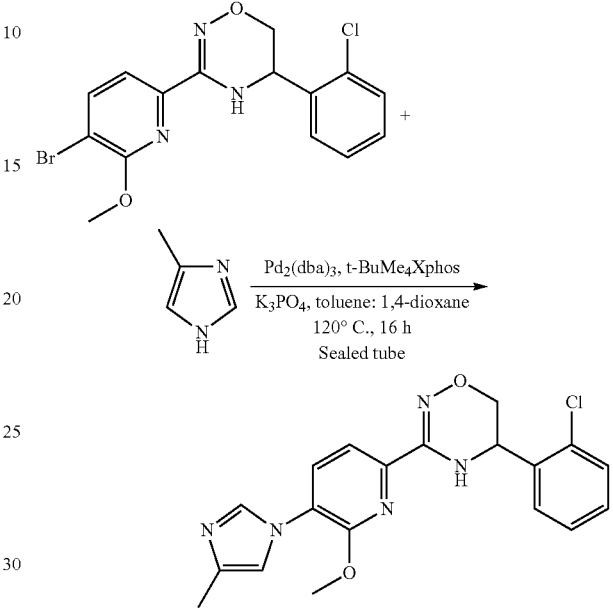

5-(2-chlorophenyl)-3-(6-methoxy-5-(4-methyl-1H-imidazol-1-yl) pyridin-2-yl)-5,6-dihydro-4H-1,2,4-oxadiazine Example 136 (32 mg, 64%) was prepared from 3-(5-bromo-6-methoxypyridin-2-yl)-5-(2-chlorophenyl)-5,6-dihydro-4H-1,2,4-oxadiazine according to the procedure for Example 49. Racemic compound of Example 136 was separated using a Chiralpak-IC column (250×20 mm, 5 μm) (32 mg loading; 0.1% DEA in n-Hexane: $CH_2Cl_2$:MeOH (50:50) (A:B: 50:50) as mobile phase) to afford the compounds of Example 136A (Fraction (I)) and Example 136B (Fraction (II)).

Analytical conditions for Example 136A and Example 136B: UPLC (column; Acquity UPLC BEH-C-18, 50×2.1 mm, 1.7μ); mobile phase: ACN: 0.025% Aq TFA; flow rate: 0.5 mL/min; Gradient program: T/B % 0.01/90, 0.5/90, 3/10, 6/10: diluent: $CH_3CN$:Water; Chiral HPLC: (Chiralpak-IC (250×4.6 mm, 5 μm; mobile phase (A) 0.1% DEA in n-Hexane (B) $CH_2Cl_2$:MeOH (50:50) (A:B; 50:50); flow Rate: 1.0 mL/min).

Example 136A, 5-(2-chlorophenyl)-3-(6-methoxy-5-(4-methyl-1H-imidazol-1-yl) pyridin-2-yl)-5,6-dihydro-4H-1,2,4-oxadiazine, fraction (I): $^1$H NMR ($CD_3OD$, 400 MHz): δ 7.99 (s, 1H), 7.90 (d, 1H), 7.67 (d, 1H), 7.48-7.38 (m, 2H), 7.37-7.28 (m, 2H), 7.23 (s, 1H), 5.34 (t, 1H), 4.11-4.08 (m, 5H), 2.26 (s, 3H); Mass (ESI): 384 [M+1]; UPLC (purity): 97.6%, RT 1.89 min; Chiral HPLC: 100%, RT=13.50 min.

Example 136B, 5-(2-chlorophenyl)-3-(6-methoxy-5-(4-methyl-1H-imidazol-1-yl) pyridin-2-yl)-5,6-dihydro-4H-1,2,4-oxadiazine, fraction (II): Mass (ESI): 384 [M+1]; UPLC (purity): 98.8%, RT 1.90 min; Chiral HPLC: 99.7%, RT=16.09 min.

Example 137

Synthesis of 2-bromo-1-(4,4-difluorocyclohexyl) ethan-1-one

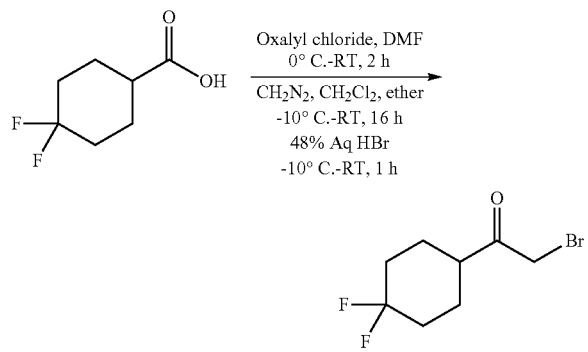

2-bromo-1-(4,4-difluorocyclohexyl) ethan-1-one

To a stirred solution of 4,4-difluorocyclohexane-1-carboxylic acid (1.5 g, 9 mmol) in $CH_2Cl_2$ (10 mL) at 0° C. under argon atmosphere was added oxalyl chloride (0.85 mL, 10 mmol) and DMF (1 drop). The reaction mixture was warmed to room temperature and stirred for 2 h. After consumption of acid (monitored by TLC), the diazomethane solution [20 mL, 10 g of N-nitroso methyl urea was added to 40% aqueous potassium hydroxide solution and ether (50 mL)] was added to the above reaction mixture at −10° C. The reaction mixture was warmed to room temperature and stirred for 16 h. After consumption of starting material (monitored by TLC), the volatiles were evaporated in vacuo. Then a solution of 48% HBr in acetic acid (2 mL) at −10° C. was added drop wise to the above reaction mixture. The reaction mixture was warmed to room temperature and stirred for 1 h. After consumption of the starting material (monitored by TLC), the reaction mixture was quenched with sodium bicarbonate solution (20 mL) and extracted with $CH_2Cl_2$ (2×20 mL). The combined organic extract was washed with brine (20 mL), water (20 mL), dried over sodium sulfate, filtered and concentrated in vacuo to afford 2-bromo-1-(4,4-difluorocyclohexyl) ethan-1-one (2 g, crude) as colorless liquid used in the next step without further purification.

$^1$H-NMR (CDCl$_3$, 400 MHz): δ 3.95 (s, 2H), 2.89-2.83 (m, 1H), 2.20-1.14 (m, 2H), 2.00-1.95 (m, 2H), 1.84-1.75 (m, 4H); TLC: 20% EtOAc/Hexanes (R$_f$: 0.4).

Example 138

Synthesis of 3-(5-bromo-6-methoxypyridin-2-yl)-5-(4,4-difluorocyclohexyl)-5,6-dihydro-4H-1,2,4-oxadiazine

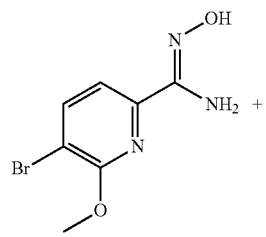

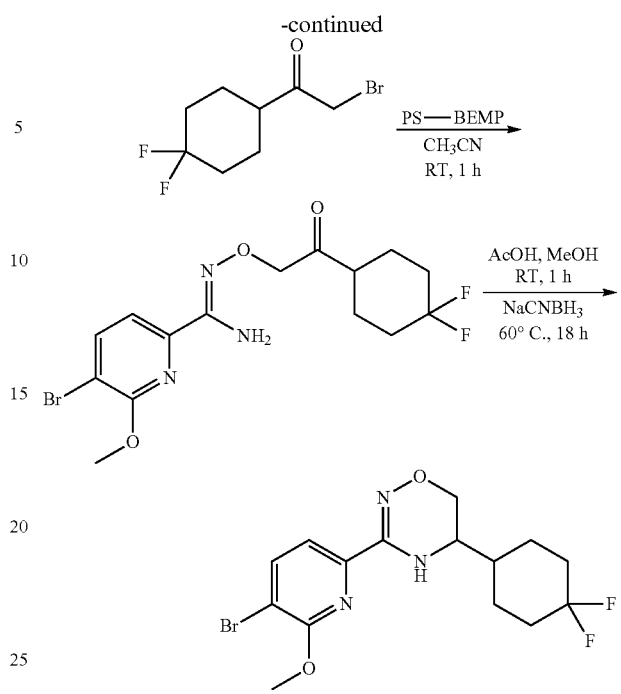

(Z)-5-bromo-N'-(2-(4,4-difluorocyclohexyl)-2-oxoethoxy)-6-methoxypicolinimidamide The title compound was prepared from 2-bromo-1-(4,4-difluorocyclohexyl) ethan-1-one according to the procedure for Example 43. LCMS: 59.6%; 407.8 (M+2); (column; Ascentis Express C-18 (50×3.0 mm, 3.5 µm); RT 2.75 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane (R$_f$: 0.6).

3-(5-bromo-6-methoxypyridin-2-yl)-5-(4,4-difluorocyclohexyl)-5,6-dihydro-4H-1,2,4-oxadiazine Example 138 (300 mg, crude) was prepared from (Z)-5-bromo-N'-(2-(4,4-difluorocyclohexyl)-2-oxoethoxy)-6-methoxypicolinimidamide according to the procedure for Example 43. LCMS: 74.7%; 389.9 (M+1); (column; Ascentis Express C-18 (50×3.0 mm, 3.5 µm); RT 2.62 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane (R$_f$: 0.4).

Example 139

Synthesis of 5-(4, 4-difluorocyclohexyl)-3-(6-methoxy-5-(4-methyl-1H-imidazol-1-yl) pyridin-2-yl)-5,6-dihydro-4H-1,2,4-oxadiazine

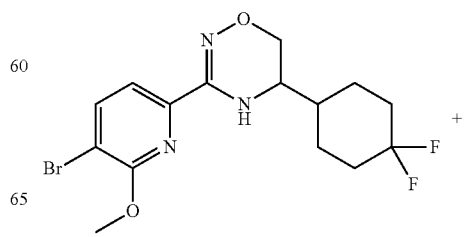

-continued

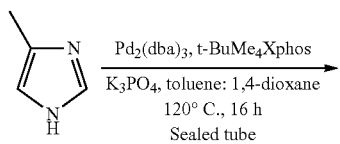

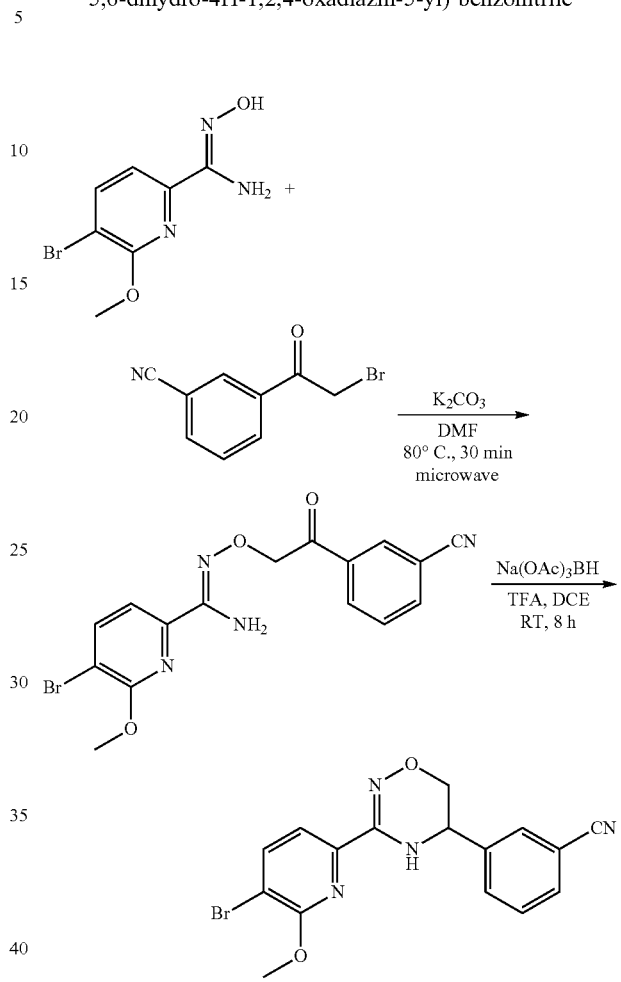

5-(4, 4-difluorocyclohexyl)-3-(6-methoxy-5-(4-methyl-1H-imidazol-1-yl) pyridin-2-yl)-5,6-dihydro-4H-1,2,4-oxadiazine Example 139 (200 mg, 66%) was prepared from 3-(5-bromo-6-methoxypyridin-2-yl)-5-(4,4-difluorocyclohexyl)-5,6-dihydro-4H-1,2,4-oxadiazine according to the procedure for Example 49. Racemic compound of Example 139 was separated using a Chiralpak-IB column (250×20 mm, 5 μm) (25 mg loading; 0.1% DEA in n-Hexane: CH$_2$Cl$_2$:MeOH (80:20) (A:B: 80:20) as mobile phase) to afford the compounds of Example 139A (Fraction (I) (−)) and Example 139B (Fraction (II) (+)).

Analytical conditions for Example 139A and Example 139B: HPLC (column; Zorbax SB C-18, 150×4.6 mm, 3.5 μm); mobile phase: ACN: 0.05% Aq TFA; flow rate: 1.0 mL/min; Gradient program: T/B % 0.01/90, 2/90, 8/10, 15/10: diluent: CH$_3$CN:Water; Chiral HPLC: (Chiralpak-IB (250×4.6 mm, 5 μm; mobile phase (A) 0.1% DEA in n-Hexane (B) CH$_2$Cl$_2$:MeOH (80:20) (A:B; 80:20); flow Rate: 1.0 mL/min).

Example 139A, (−)-5-(4, 4-difluorocyclohexyl)-3-(6-methoxy-5-(4-methyl-1H-imidazol-1-yl) pyridin-2-yl)-5,6-dihydro-4H-1,2,4-oxadiazine, fraction (I) (−): Mass (ESI): 392.4 [M+1]; HPLC (purity): 96.6%, RT 7.23 min; Chiral HPLC: 99.8%, RT=13.78 min; Optical rotation $[\alpha]_D^{20.00}$: −60.83 (c=0.25, CH$_2$Cl$_2$).

Example 139B, (+)-5-(4, 4-difluorocyclohexyl)-3-(6-methoxy-5-(4-methyl-1H-imidazol-1-yl) pyridin-2-yl)-5,6-dihydro-4H-1,2,4-oxadiazine, fraction II (+): $^1$H NMR (CD$_3$OD, 400 MHz): δ 7.98 (s, 1H), 7.86 (d, 1H), 7.57 (d, 1H), 7.22 (s, 1H), 4.15 (dd, 1H), 4.13 (s, 3H), 3.79 (dd, 1H), 3.53-3.49 (m, 1H), 2.26 (s, 3H), 2.16-2.00 (m, 3H), 1.96-1.74 (m, 4H), 1.55-1.42 (m, 2H); Mass (ESI): 392.4 [M+1]; HPLC (purity): 98.8%, RT 7.22 min; Chiral HPLC: 99.5%, RT=24.87; Optical rotation $[\alpha]_D^{20.00}$: +65.36 (c=0.25, CH$_2$Cl$_2$).

Example 140

Synthesis of 3-(3-(5-bromo-6-methoxypyridin-2-yl)-5,6-dihydro-4H-1,2,4-oxadiazin-5-yl) benzonitrile (Z)-5-bromo-N'-(2-(3-cyanophenyl)-2-oxoethoxy)-6-methoxypicolinimidamide The title compound was prepared from 2-bromo-1-(6-fluorobenzofuran-2-yl) ethan-1-one according to the procedure for Example 51. LCMS: 16.4%; 390.4 (M+); (column; Ascentis Express C-18 (50×3.0 mm, 3.5 μm); RT 2.36 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.5).

3-(3-(5-bromo-6-methoxypyridin-2-yl)-5,6-dihydro-4H-1,2,4-oxadiazin-5-yl) benzonitrile Example 140 (320 mg, 27%) was prepared from (Z)-5-bromo-N'-(2-(3-cyanophenyl)-2-oxoethoxy)-6-methoxypicolinimidamide according to the procedure for Example 48. $^1$H NMR (CD$_3$OD, 400 MHz): δ 8.01 (d, 1H), 7.76-7.66 (m, 3H), 7.57 (t, 1H), 7.43 (d, 1H), 4.94 (t, 1H), 4.06-3.99 (m, 5H); LCMS: 97.9%; 374.7 (M+2); (column; Ascentis Express C-18 (50×3.0 mm, 3.5 μm); RT 2.50 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane ($R_f$: 0.4).

Example 141

Synthesis of 3-(3-(6-methoxy-5-(4-methyl-1H-imidazol-1-yl) pyridin-2-yl)-5,6-dihydro-4H-1,2,4-oxadiazin-5-yl) benzonitrile

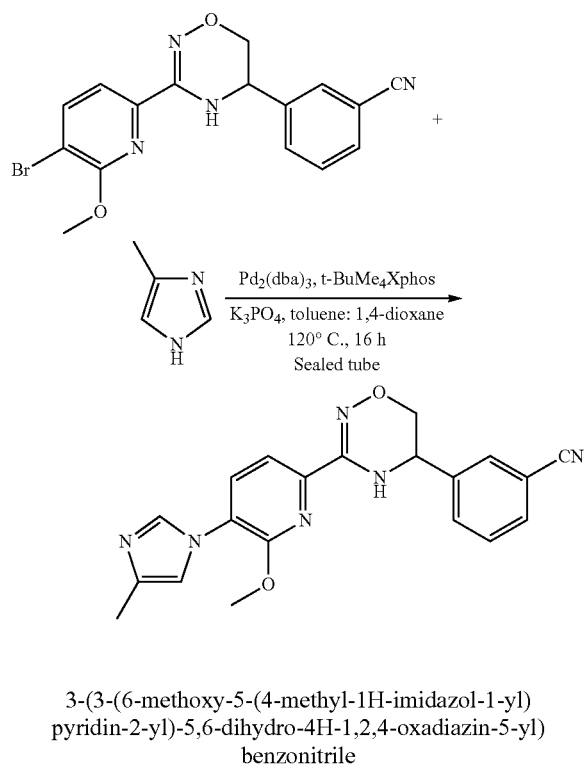

3-(3-(6-methoxy-5-(4-methyl-1H-imidazol-1-yl) pyridin-2-yl)-5,6-dihydro-4H-1,2,4-oxadiazin-5-yl) benzonitrile Example 141 (150 mg, 52%) was prepared from 3-(3-(5-bromo-6-methoxypyridin-2-yl)-5,6-dihydro-4H-1,2,4-oxadiazin-5-yl) benzonitrile according to the procedure for Example 49. Racemic compound of Example 141 was separated using Chiralpak-IB column (250×20 mm, 5 μm) (27 mg loading; 0.1% DEA in n-Hexane: $CH_2Cl_2$: MeOH (50:50) (A:B: 80:20) as mobile phase) to afford the compounds of Example 141A (Fraction (I) (−)) and Example 141B (Fraction (II) (+)).

Analytical conditions for Example 141A and Example 141B: HPLC (column; YMC Triart-C-18, 150×4.6 mm, 3.0 μm); mobile phase: ACN: 0.05% TFA; flow rate: 1.0 mL/min; Gradient program: T/B % 0.01/90, 3/90, 8/10, 15/10; diluent: $CH_3CN$:Water; Chiral HPLC: (Chiralpak-IB (250×4.6 mm, 5 μm; mobile phase (A) 0.1% DEA in n-Hexane (B) $CH_2Cl_2$:MeOH (50:50) (A:B; 80:20); flow Rate: 1.0 mL/min).

Example 141A, (−)-3-(3-(6-methoxy-5-(4-methyl-1H-imidazol-1-yl) pyridin-2-yl)-5,6-dihydro-4H-1,2,4-oxadiazin-5-yl) benzonitrile, fraction (I) (−): Mass (ESI): 375.3 [M+1]; HPLC (purity): 98.6%, RT 7.42 min; Chiral HPLC: 98.7%, RT=18.43 min; Optical rotation $[\alpha]_D^{19.99}$: −244.54 (c=0.25, $CH_2Cl_2$).

Example 141B, (+)-3-(3-(6-methoxy-5-(4-methyl-1H-imidazol-1-yl) pyridin-2-yl)-5,6-dihydro-4H-1,2,4-oxadiazin-5-yl) benzonitrile, fraction (II) (+): $^1$H NMR ($CD_3OD$, 400 MHz): δ 7.99 (s, 1H), 7.89 (d, 1H), 7.74-7.64 (m, 4H), 7.58 (t, 1H), 7.23 (s, 1H), 4.96 (t, 1H), 4.10 (s, 3H), 4.05 (dd, 2H), 2.25 (s, 3H); Mass (ESI): 375.4 [M+1]; HPLC (purity): 99.4%, RT 7.40 min; Chiral HPLC: 99.5%, RT=22.97 min; Optical rotation $[\alpha]_D^{20.01}$: +251.45 (c=0.25, $CH_2Cl_2$).

Example 142

Synthesis of 3-(5-bromo-6-methoxypyridin-2-yl)-5-(tetrahydro-2H-pyran-4-yl)-5,6-dihydro-4H-1,2,4-oxadiazine

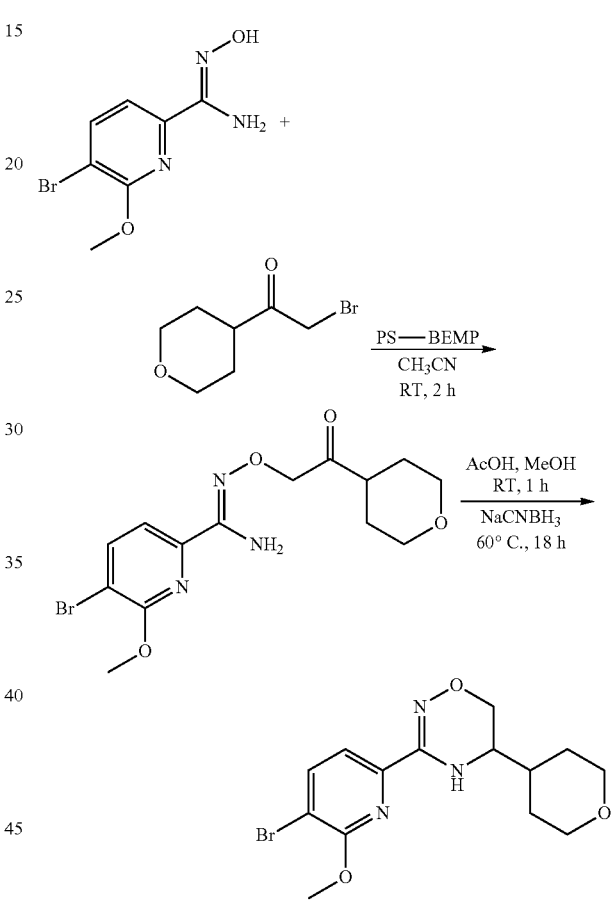

(Z)-5-bromo-6-methoxy-N'-(2-oxo-2-(tetrahydro-2H-pyran-4-yl) ethoxy) picolinimidamide The title compound was prepared from 2-bromo-1-(tetrahydro-2H-pyran-4-yl)ethanone according to the procedure for Example 43. LCMS: 27.0%; 371.9 (M+); (column; Ascentis Express C-18 (50×3.0 mm, 3.5 μm); RT 2.36 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.5).

3-(5-bromo-6-methoxypyridin-2-yl)-5-(tetrahydro-2H-pyran-4-yl)-5,6-dihydro-4H-1,2,4-oxadiazine Example 142 (300 mg, crude) was prepared from (Z)-5-bromo-6-methoxy-N'-(2-oxo-2-(tetrahydro-2H-pyran-4-yl)

ethoxy) picolinimidamide according to the procedure for Example 43. LCMS: 49.3%; 355.8 (M+); (column; Ascentis Express C-18 (50×3.0 mm, 3.5 μm); RT 2.18 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.4).

Example 143

Synthesis of 3-(6-methoxy-5-(4-methyl-1H-imidazol-1-yl)pyridin-2-yl)-5-(tetrahydro-2H-pyran-4-yl)-5,6-dihydro-4H-1,2,4-oxadiazine

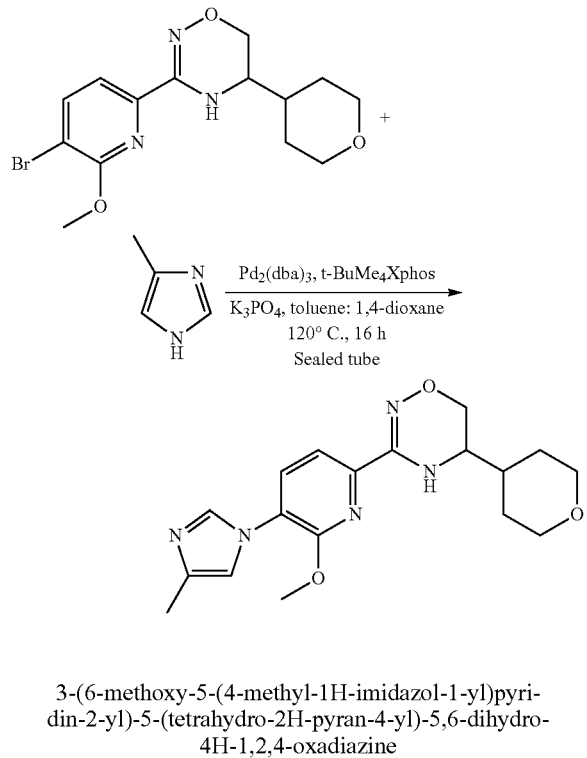

3-(6-methoxy-5-(4-methyl-1H-imidazol-1-yl)pyridin-2-yl)-5-(tetrahydro-2H-pyran-4-yl)-5,6-dihydro-4H-1,2,4-oxadiazine Example 143 (120 mg, 40%) was prepared from 3-(5-bromo-6-methoxypyridin-2-yl)-5-(tetrahydro-2H-pyran-4-yl)-5,6-dihydro-4H-1,2,4-oxadiazine according to the procedure for Example 49. Racemic compound of Example 143 was separated using a Chiralpak-ODH column (250×20 mm, 5 μm) (28 mg loading; 0.1% DEA in n-Hexane: EtOH: MeOH (50:50) (A:B: 65:35) as mobile phase) to afford the compounds of Example 143A (Fraction (I) (−)) and Example 143B (Fraction (II)

Analytical conditions for Example 143A and Example 143B: HPLC (column; Zorbax SB C-18, 150×4.6 mm, 5.0 μm); mobile phase: ACN: 0.05% Aq TFA; Gradient program: T/B % 0.01/90, 2/90, 8/10, 15/10; diluent: $CH_3CN$: Water; flow rate: 1.0 mL/min; Chiral HPLC: (Chiralpak-ODH (250×4.6 mm, 5 μm; mobile phase (A) 0.1% DEA in n-Hexane (B) EtOH:MeOH (50:50) (A:B; 65:35); flow Rate: 1.0 mL/min).

Example 143A, (−)-3-(6-methoxy-5-(4-methyl-1H-imidazol-1-yl)pyridin-2-yl)-5-(tetrahydro-2H-pyran-4-yl)-5,6-dihydro-4H-1,2,4-oxadiazine, fraction (I) (−): Mass (ESI): 358.4 [M+1]; HPLC (purity): 99.6%, RT 6.22 min; Chiral HPLC: 99.9%, RT=11.61 min; Optical rotation $[α]_D^{20.00}$: −47.31 (c=0.25, $CH_2Cl_2$).

Example 143B, (+)-3-(6-methoxy-5-(4-methyl-1H-imidazol-1-yl)pyridin-2-yl)-5-(tetrahydro-2H-pyran-4-yl)-5,6-dihydro-4H-1,2,4-oxadiazine, fraction (II) (+): $^1$H NMR ($CD_3OD$, 500 MHz): δ 7.98 (s, 1H), 7.85 (d, 1H), 7.56 (d, 1H), 7.21 (s, 1H), 4.16 (dd, 1H), 4.12 (s, 3H), 4.03-3.97 (m, 2H), 3.78 (dd, 1H), 3.46-3.40 (m, 3H), 2.25 (s, 3H), 1.95-1.86 (m, 1H), 1.84-1.81 (m, 1H), 1.73-1.71 (m, 1H), 1.56-1.43 (m, 2H); Mass (ESI): 358.4 [M+1]; HPLC (purity): 99.2%, RT 6.23 min; Chiral HPLC: 99.8%, RT=17.91 min; Optical rotation $[α]_D^{20.00}$: +47.90 (c=0.25, $CH_2Cl_2$).

Example 144

Synthesis of 3-(5-bromo-6-methoxypyridin-2-yl)-5-(3-methoxyphenyl)-5,6-dihydro-4H-1,2,4-oxadiazine

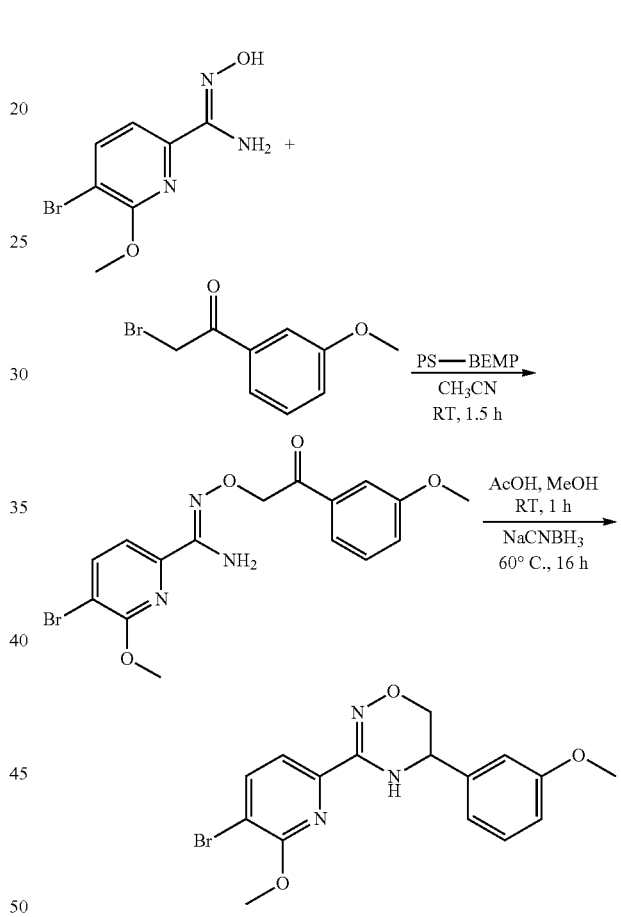

(Z)-5-bromo-6-methoxy-N'-(2-(3-methoxyphenyl)-2-oxoethoxy) picolinimidamide

The title compound was prepared from 2-bromo-1-(3-methoxyphenyl)ethanone according to the procedure for Example 43. LCMS: 45.4%; 393.9 (M+); (column; Ascentis Express C-18 (50×3.0 mm, 3.5 μm); RT 2.77 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane ($R_f$: 0.7).

3-(5-bromo-6-methoxypyridin-2-yl)-5-(3-methoxyphenyl)-5,6-dihydro-4H-1,2,4-oxadiazine Example 144 (250 mg, 27%) was prepared from (Z)-5-bromo-6-methoxy-N'-(2-(3-methoxyphenyl)-2-oxoethoxy)

picolinimidamide according to the procedure for Example 43. LCMS: 31.2%; 379.8 (M+1); (column; Ascentis Express C-18 (50×3.0 mm, 3.5 μm); RT 2.71 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 40% EtOAc/Hexane ($R_f$: 0.4).

Example 145

Synthesis of 3-(6-methoxy-5-(4-methyl-1H-imidazol-1-yl) pyridin-2-yl)-5-(3-methoxyphenyl)-5,6-dihydro-4H-1,2,4-oxadiazine

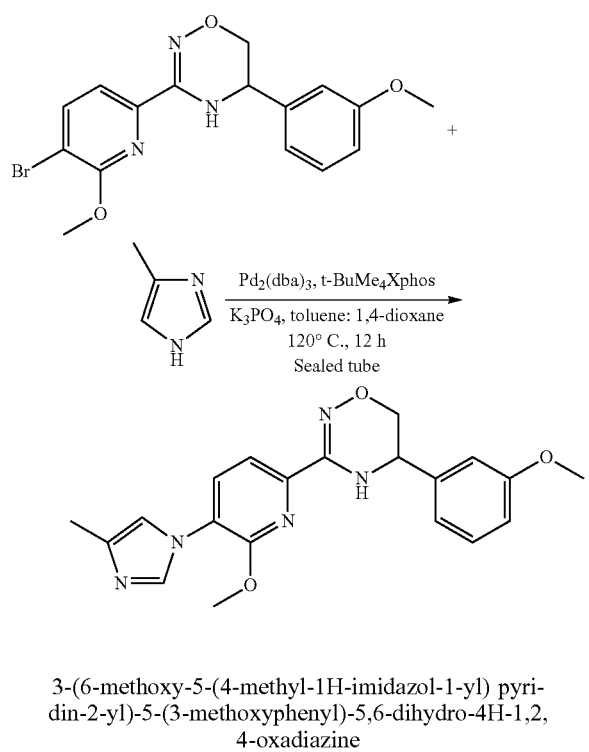

3-(6-methoxy-5-(4-methyl-1H-imidazol-1-yl) pyridin-2-yl)-5-(3-methoxyphenyl)-5,6-dihydro-4H-1,2,4-oxadiazine Example 145 (130 mg, 65%) was prepared from 3-(5-bromo-6-methoxypyridin-2-yl)-5-(3-methoxyphenyl)-5,6-dihydro-4H-1,2,4-oxadiazine according to the procedure for Example 49. Racemic compound of Example 145 was separated using a Chiralpak-AD-H column (250×20 mm, 5 μm) (30 mg loading; 0.1% DEA in n-Hexane: EtOH:MeOH (50:50) (A:B: 65:35) as mobile phase) to afford the compounds of Example 145A (Fraction (I) (−)) and Example 145B (Fraction (II) (+)).

Analytical conditions for Example 145A and Example 145B: HPLC (column; Zorbax SB C-18, 150×4.6 mm, 3.5 μm); mobile phase: ACN: 0.05% Aq TFA; flow rate: 1.0 mL/min; Gradient program: T/B % 0.01/90, 2/90, 8/10, 15/10: Diluent: $CH_3CN$:Water: Chiral HPLC: (Chiralpak-ADH (250×4.6 mm, 5 μm; mobile phase (A) 0.1% DEA in n-Hexane (B) EtOH:MeOH (50:50) (A:B; 65:35); flow Rate: 1.0 mL/min).

Example 145A, (−)-3-(6-methoxy-5-(4-methyl-1H-imidazol-1-yl) pyridin-2-yl)-5-(3-methoxyphenyl)-5,6-dihydro-4H-1,2,4-oxadiazine, fraction (I) (−): Mass (ESI): 380.3 [M+1]; HPLC (purity): 96.2%, RT 7.17 min; Chiral HPLC: 99.3%, RT=7.39 min; Optical rotation $[\alpha]_D^{20.02}$: −131.08 (c=0.25, $CH_2Cl_2$).

Example 145B, (+)-3-(6-methoxy-5-(4-methyl-1H-imidazol-1-yl) pyridin-2-yl)-5-(3-methoxyphenyl)-5,6-dihydro-4H-1,2,4-oxadiazine, fraction (II) (+): $^1$H NMR ($CD_3OD$, 400 MHz): δ 8.00 (br s, 1H), 7.89 (d, 1H), 7.64 (d, 1H), 7.31-7.25 (m, 2H), 6.99-6.95 (m, 2H), 6.90-6.87 (m, 1H), 4.83-4.80 (m, 1H), 4.15 (dd, 1H), 4.05 (s, 3H), 3.87 (dd, 1H), 3.78 (s, 3H), 2.23 (s, 3H); Mass (ESI): 380.3 [M+1]; HPLC (purity): 95.7%, RT 7.17 min; Chiral HPLC: 98.0%, RT=13.17 min; Optical rotation $[\alpha]_D^{19.99}$: +131.05 (c=0.25, $CH_2Cl_2$).

Example 146

Synthesis of 3-(5-bromo-6-methoxypyridin-2-yl)-5-(tert-butyl)-5,6-dihydro-4H-1,2,4-oxadiazine

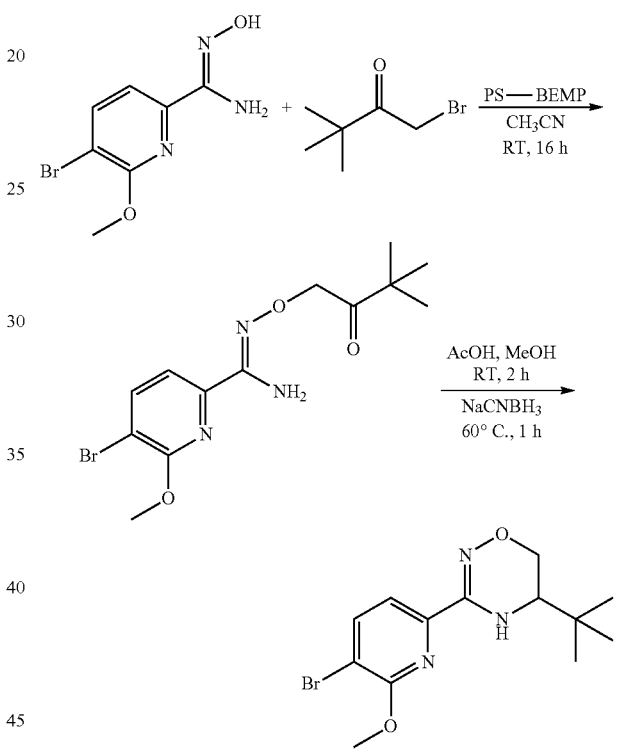

(Z)-5-bromo-N'-(3,3-dimethyl-2-oxobutoxy)-6-methoxypicolinimidamide

The title compound was prepared from 1-bromo-3,3-dimethylbutan-2-one according to the procedure for Example 43. LCMS: 64.9%; 345.8 (M+1); (column; Ascentis Express C-18 (50×3.0 mm, 2.7 μm); RT 2.71 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane ($R_f$: 0.7).

3-(5-bromo-6-methoxypyridin-2-yl)-5-(tert-butyl)-5,6-dihydro-4H-1,2,4-oxadiazine Example 146 (1.0 g, 69%) was prepared from (Z)-5-bromo-N'-(3,3-dimethyl-2-oxobutoxy)-6-methoxypicolinimidamide according to the procedure for Example 43. LCMS: 96.7%; 327.8 (M+1); (column; Ascentis Express C-18 (50×3.0 mm, 2.7 μm); RT 2.66 min; mobile phase:

0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.5).

Example 147

Synthesis of 5-(tert-butyl)-3-(6-methoxy-5-(4-methyl-1H-imidazol-1-yl) pyridin-2-yl)-5,6-dihydro-4H-1,2,4-oxadiazine

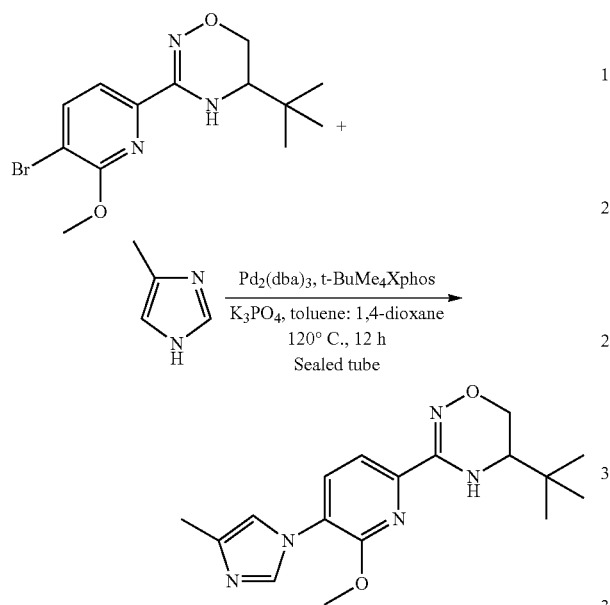

5-(tert-butyl)-3-(6-methoxy-5-(4-methyl-1H-imidazol-1-yl) pyridin-2-yl)-5,6-dihydro-4H-1,2,4-oxadiazine Example 147 (200 mg, 33%) was prepared from 3-(5-bromo-6-methoxypyridin-2-yl)-5-(tert-butyl)-5,6-dihydro-4H-1,2,4-oxadiazine according to the procedure for Example 49. Racemic compound of Example 147 was separated using a Chiralcel-ODH column (250×20 mm, 5 µm) (30 mg loading; 0.1% DEA in n-Hexane: IPA:MeOH (50:50) (A:B: 75:25) as mobile phase flow rate: 18 mL/min) to afford the compounds of Example 147A (Fraction (I) (−)) and Example 147B (Fraction (II) (+)).

Analytical conditions for Example 147A and Example 147B: HPLC (column; zorbax-SB-C-18 150×4.6 mm, 3.5µ); mobile Phase: ACN: 0.05% Aq TFA; flow rate: 1.0 mL/min; Gradient program: T/B % 0.01/90, 2/90, 8/10, 15/10: diluent: CH$_3$CN:Water; Chiral HPLC: (Chiralpak-ODH (250×4.6 mm, 5 µm; mobile phase (A) 0.1% DEA in n-Hexane (B) IPA:MeOH (50:50) (A:B; 75:25); flow Rate: 1.0 mL/min).

Example 147A, (−)-5-(tert-butyl)-3-(6-methoxy-5-(4-methyl-1H-imidazol-1-yl) pyridin-2-yl)-5,6-dihydro-4H-1,2,4-oxadiazine, fraction (I) (−): $^1$H NMR (CD$_3$OD, 400 MHz): δ 7.99 (br s, 1H), 7.86 (d, 1H), 7.58 (d, 1H), 7.22 (br s, 1H), 4.13 (s, 3H), 4.01 (dd, 1H), 3.92 (dd, 1H), 3.40 (t, 1H), 2.25 (s, 3H), 1.05 (s, 9H); Mass (ESI): 330.3 [M+1]; HPLC (purity): 99.6%, RT 7.09 min; Chiral HPLC: 100%, RT=16.76 min; Optical rotation [α]$_D^{19.99}$: −7.36 (c=0.25, CH$_2$Cl$_2$).

Example 147B, (+)-5-(tert-butyl)-3-(6-methoxy-5-(4-methyl-1H-imidazol-1-yl) pyridin-2-yl)-5,6-dihydro-4H-1,2,4-oxadiazine, fraction (II) (+): Mass (ESI): 330.3 [M+1]; HPLC (purity): 99.4%, RT 7.11 min; Chiral HPLC: 98.8%, RT=20.51 min; Optical rotation [α]$_D^{20.00}$: +13.93 (c=0.25, CH$_2$Cl$_2$).

Example 148

Synthesis of 3-(6-methoxy-5-(4-methyl-1H-imidazol-1-yl) pyridin-2-yl)-5-methyl-5,6-dihydro-4H-1,2,4-oxadiazine

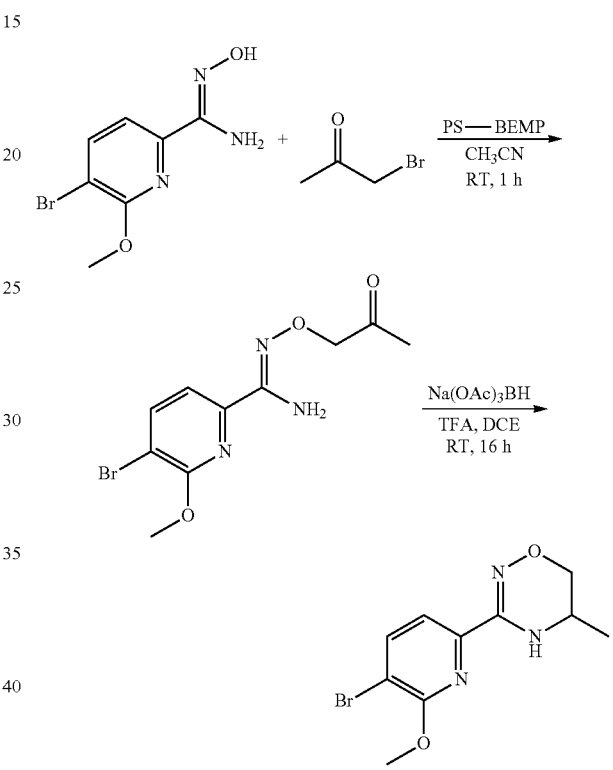

(Z)-5-bromo-6-methoxy-N'-(2-oxopropoxy) picolinimidamide

The title compound was prepared from 1-bromopropan-2-one according to the procedure for Example 43. LCMS: 73.9%; 303.7 (M+3); (column; Ascentis Express C-18 (50× 3.0 mm, 2.7 µm); RT 2.27 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.5).

3-(5-bromo-6-methoxypyridin-2-yl)-5-methyl-5,6-dihydro-4H-1,2,4-oxadiazine

Example 148 (330 mg, 58%) was prepared from (Z)-5-bromo-6-methoxy-N'-(2-oxopropoxy picolinimidamide according to the procedure for Example 48. LCMS: 77.7%; 285.8 (M+1); (column; Ascentis Express C-18 (50×3.0 mm, 2.7 µm); RT 2.11 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.5).

Example 149

Synthesis of 3-(6-methoxy-5-(4-methyl-1H-imidazol-1-yl) pyridin-2-yl)-5-methyl-5,6-dihydro-4H-1,2,4-oxadiazine

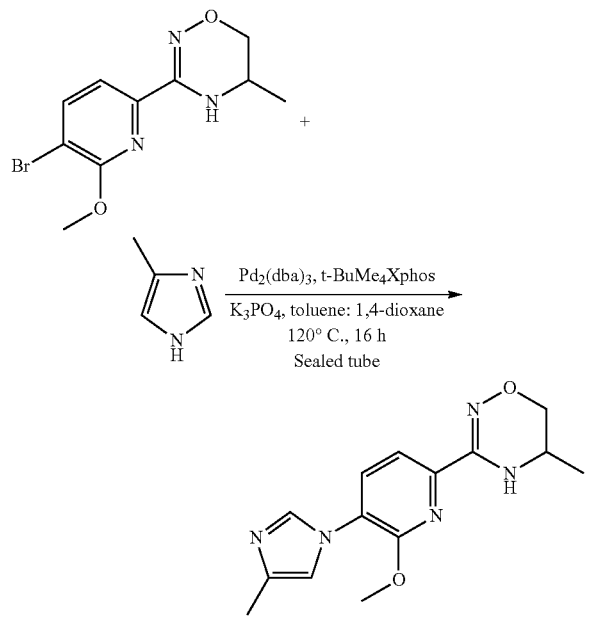

3-(6-methoxy-5-(4-methyl-1H-imidazol-1-yl) pyridin-2-yl)-5-methyl-5,6-dihydro-4H-1,2,4-oxadiazine Example 149 (140 mg, 46%) was prepared from 3-(5-bromo-6-methoxypyridin-2-yl)-5-methyl-5,6-dihydro-4H-1,2,4-oxadiazine according to the procedure for Example 49. Racemic compound of Example 149 was separated using a Chiralpak-IB column (250×20 mm, 5 μm) (27 mg loading; 0.1% DEA in n-Hexane: $CH_2Cl_2$:MeOH (50:50) (A:B: 80:20) as mobile phase; flow rate: 18 mL/min) to afford the compounds of Example 149A (Fraction (I) (+)) and Example 149B (Fraction (II) (−)).

Analytical conditions for Example 149A and Example 149B: HPLC (column; zorbax-SB-C-18 150×4.6 mm, 3.5μ); mobile Phase: ACN: 0.05% Aq TFA; flow rate: 1.0 mL/min; Gradient program: T/B % 0.01/90, 2/90, 8/10, 15/10: diluent: $CH_3CN$:Water; Chiral HPLC: (Chiralpak-IB (250× 4.6 mm, 5 μm; mobile phase (A) 0.1% DEA in n-Hexane (B) $CH_2Cl_2$:MeOH (50:50) (A:B; 80:20); flow Rate: 1.0 mL/min).

Example 149A, (+)-3-(6-methoxy-5-(4-methyl-1H-imidazol-1-yl) pyridin-2-yl)-5-methyl-5,6-dihydro-4H-1,2,4-oxadiazine, fraction (I) (+): $^1$H NMR ($CD_3OD$, 400 MHz): δ 7.97 (s, 1H), 7.84 (d, 1H), 7.57 (d, 1H), 7.21 (s, 1H), 4.12 (s, 3H), 3.99 (dd, 1H), 3.86-3.74 (m, 1H), 3.64 (dd, 1H), 2.26 (s, 3H), 1.33 (d, 3H); Mass (ESI): 288.2 [M+1]; HPLC (purity): 99.7%, RT 6.09 min; Chiral HPLC: 99.7%, RT=11.80 min; Optical rotation $[\alpha]_D^{20.01}$: +13.71 (c=0.25, $CH_2Cl_2$).

Example 149B, (−)-3-(6-methoxy-5-(4-methyl-1H-imidazol-1-yl) pyridin-2-yl)-5-methyl-5,6-dihydro-4H-1,2,4-oxadiazine, fraction (II) (−): Mass (ESI): 288.2 [M+1]; HPLC (purity): 99.8%, RT 6.09 min; Chiral HPLC: 99.0%, RT=14.50 min, Optical rotation $[\alpha]_D^{19.99}$: −11.02 (c=0.25, $CH_2Cl_2$).

Example 150

Synthesis of 4-(3-(5-bromo-6-methoxypyridin-2-yl)-5,6-dihydro-4H-1,2,4-oxadiazin-5-yl) benzonitrile

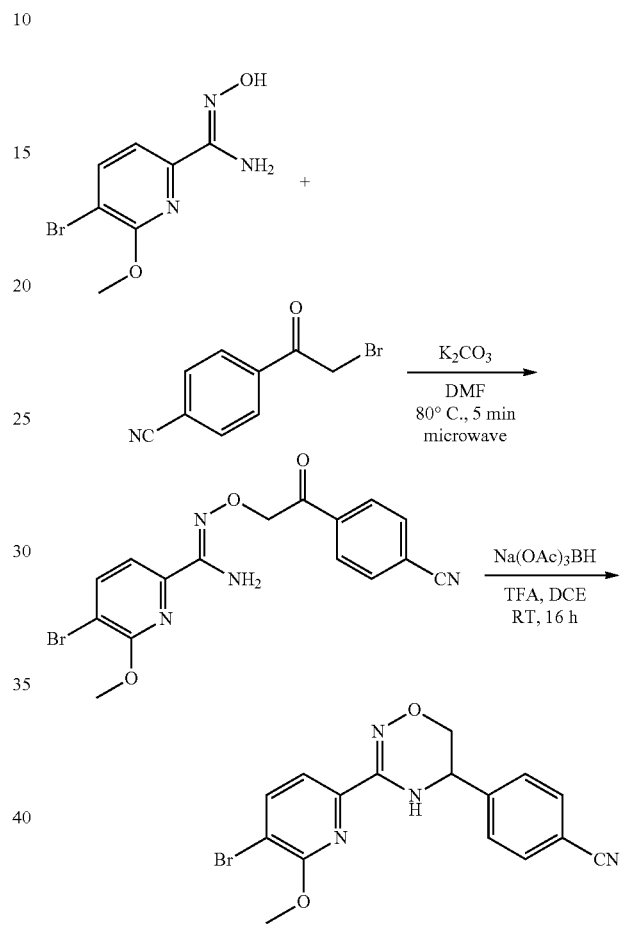

(Z)-5-bromo-N'-(2-(4-cyanophenyl)-2-oxoethoxy)-6-methoxypicolinimidamide

The title compound was prepared from 4-(2-bromoacetyl) benzonitrile according to the procedure for Example 51. LCMS: 30.4%; 388.9 (M+1); (column; Ascentis Express C-18 (50×3.0 mm, 3.5 μm); RT 2.64 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.5).

4-(3-(5-bromo-6-methoxypyridin-2-yl)-5,6-dihydro-4H-1,2,4-oxadiazin-5-yl) benzonitrile Example 150 (800 mg, crude) was prepared from (Z)-5-bromo-N'-(2-(4-cyanophenyl)-2-oxoethoxy)-6-methoxypicolinimidamide according to the procedure for Example 48. LCMS: 40.8%; 372.8 (M+1); (column; Ascentis Express C-18 (50×3.0 mm, 3.5 μm); RT 2.47 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.4).

Example 151

Synthesis of 4-(3-(6-methoxy-5-(4-methyl-1H-imidazol-1-yl) pyridin-2-yl)-5,6-dihydro-4H-1,2,4-oxadiazin-5-yl) benzonitrile

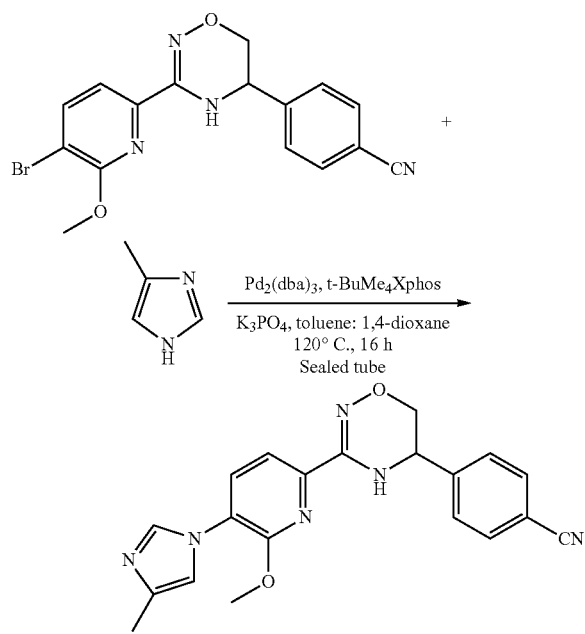

4-(3-(6-methoxy-5-(4-methyl-1H-imidazol-1-yl) pyridin-2-yl)-5,6-dihydro-4H-1,2,4-oxadiazin-5-yl) benzonitrile Example 151 (110 mg, 22%) was prepared from 4-(3-(5-bromo-6-methoxypyridin-2-yl)-5,6-dihydro-4H-1,2,4-oxadiazin-5-yl) benzonitrile according to the procedure for Example 49. Racemic compound of Example 151 was separated using a Chiralpak-IB column (250×20 mm, 5 µm) (26.66 mg loading; 0.1% DEA in n-Hexane:CH$_2$Cl$_2$:MeOH (80:20) (A:B: 75:25) as mobile phase; flow rate: 18 mL/mm) to afford the compounds of Example 151A (Fraction (I) (−)) and Example 151B (Fraction (II) (+)).

Analytical conditions for Example 151A and Example 151B: UPLC (column; zorbax-SB-C-18 150×4.6 mm, 3.5µ); mobile Phase: ACN: 0.05% Aq TFA; flow rate: 1.0 mL/min; Gradient program: T/B % 0.01/90, 2/90, 8/10, 15/10: diluent: CH$_3$CN:Water; Chiral HPLC: (Chiralpak-IB (250× 4.6 mm, 5 µm; mobile phase (A) 0.1% DEA in n-Hexane (B) CH$_2$Cl$_2$:MeOH (80:20) (A:B; 75:25); flow Rate: 1.0 mL/min).

Example 151A, (−)-4-(3-(6-methoxy-5-(4-methyl-1H-imidazol-1-yl) pyridin-2-yl)-5,6-dihydro-4H-1,2,4-oxadiazin-5-yl) benzonitrile, fraction (I) (−): Mass (ESI): 375.3 [M+1]; UPLC (purity): 99.5%, RT 6.94 min; Chiral HPLC: 99.9%, RT=13.16 min; Optical rotation $[\alpha]_D^{20.00}$: −251.02 (c=0.25, CH$_2$Cl$_2$).

Example 151B, (+)-4-(3-(6-methoxy-5-(4-methyl-1H-imidazol-1-yl) pyridin-2-yl)-5,6-dihydro-4H-1,2,4-oxadiazin-5-yl) benzonitrile, fraction (II) (+): $^1$H NMR (CD$_3$OD, 400 MHz): δ 7.98 (s, 1H), 7.89 (d, 1H), 7.76 (d, 2H), 7.66 (d, 1H), 7.59 (d, 2H), 7.23 (s, 1H), 4.98 (t, 1H), 4.10 (s, 3H), 4.06 (dd, 2H), 2.26 (s, 3H); Mass (ESI): 375.3 [M+1]; UPLC (purity): 99.4%; RT 6.95 min; Chiral HPLC: 99.6%, RT=15.54 min; Optical rotation $[\alpha]_D^{20.00}$: +232.75 (c=0.25, CH$_2$Cl$_2$).

Example 152

Synthesis of 1-bromo-4-methylpentan-2-one

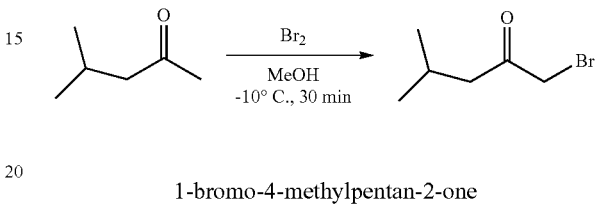

1-bromo-4-methylpentan-2-one

To a stirred solution of 4-methylpentan-2-one (5 g, 50 mmol) in MeOH (50 mL) at −10° C. under an argon atmosphere was added bromine (8 g, 50 mmol) for 10 min. The reaction mixture was stirred for 30 min at −10° C. After consumption of starting material (monitored by TLC), the reaction mixture was quenched with sodium thiosulfate solution (100 mL) and extracted with ether (2×100 mL). The combined organic extracts were dried over sodium sulfate, filtered and concentrated in vacuo to afford 1-bromo-4-methylpentan-2-one (5.5 g, crude) as brown syrup used in the next step without further purification.

$^1$H NMR (CDCl$_3$, 400 MHz): δ 3.86 (s, 2H), 2.53 (d, 2H), 2.21-2.14 (m, 1H), 0.96 (s, 3H), 0.94 (s, 3H); TLC: 20% EtOAc/Hexane ($R_f$: 0.6).

Example 153

Synthesis of 3-(5-bromo-6-methoxypyridin-2-yl)-5-isobutyl-5,6-dihydro-4H-1,2,4-oxadiazine

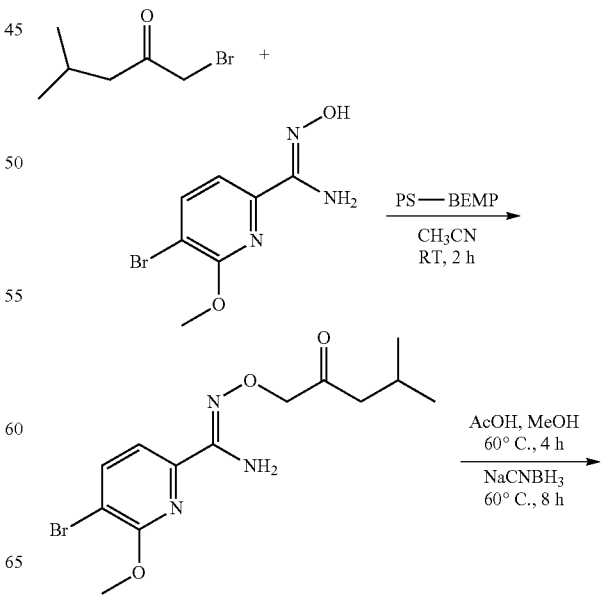

-continued

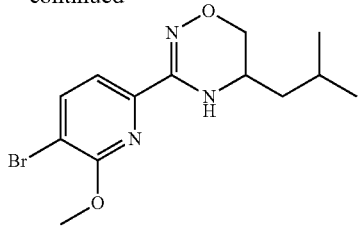

(Z)-5-bromo-6-methoxy-N'-(4-methyl-2-oxopentyl) oxy) picolinimidamide

The title compound was prepared from 1-bromo-4-methylpentan-2-one according to the procedure for Example 43. LCMS: 77.3%; 343.8 (M+1); (column; Ascentis Express C-18 (50×3.0 mm, 2.7 µm); RT 2.75 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane ($R_f$: 0.6).

3-(5-bromo-6-methoxypyridin-2-yl)-5-isobutyl-5,6-dihydro-4H-1,2,4-oxadiazine

Example 153 (200 mg, crude) was prepared from (Z)-5-bromo-6-methoxy-N'-((4-methyl-2-oxopentyl) oxy) picolinimidamide according to the procedure for Example 56. LCMS: 63.0%; 327.8 (M+1); (column; Ascentis Express C-18 (50×3.0 mm, 2.7 µm); RT 2.69 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.5).

Example 154

Synthesis of 5-isobutyl-3-(6-methoxy-5-(4-methyl-1H-imidazol-1-yl) pyridin-2-yl)-5,6-dihydro-4H-1,2,4-oxadiazine 5-isobutyl-3-(6-methoxy-5-(4-methyl-1H-imidazol-1-yl) pyridin-2-yl)-5,6-dihydro-4H-1,2,4-oxadiazine Example 154 (130 mg, 16%) was prepared from 3-(5-bromo-6-methoxypyridin-2-yl)-5-isobutyl-5,6-dihydro-4H-1,2,4-oxadiazine according to the procedure for Example 49. Racemic compound of Example 154 was separated using a Chiralpak-IB column (250×20 mm, 5 µm) (21.6 mg loading; 0.1% DEA in n-Hexane: CH$_2$Cl$_2$:MeOH (50:50) (A:B: 90:10) as mobile phase; flow rate: 18 mL/min) to afford the compounds of Example 154A (Fraction (I) (+)) and Example 154B (Fraction (II) (−)).

Analytical conditions for Example 154A and Example 154B: HPLC (column; zorbax-SB-C-18 150×4.6 mm, 3.5µ); mobile Phase: ACN: 0.05% Aq TFA; flow rate: 1.0 mL/min; Gradient program: T/B % 0.01/90, 2/90, 8/10, 15/10: diluent: CH$_3$CN:Water; Chiral HPLC: (Chiralpak-IB (250× 4.6 mm, 5 µm; mobile phase (A) 0.1% DEA in n-Hexane (B) CH$_2$Cl$_2$:MeOH (50:50) (A:B; 90:10); flow Rate: 1.0 mL/min).

Example 154A, (+)-5-isobutyl-3-(6-methoxy-5-(4-methyl-1H-imidazol-1-yl) pyridin-2-yl)-5,6-dihydro-4H-1,2,4-oxadiazine, fraction (I) (+): Mass (ESI): 330.3 [M+1]; HPLC (purity): 97.6%, RT 7.18 min; Chiral HPLC: 99.5%, RT=15.76 min; Optical rotation $[\alpha]_D^{19.98}$: +20.46 (c=0.25, CH$_2$Cl$_2$).

Example 154B, (−)-5-isobutyl-3-(6-methoxy-5-(4-methyl-1H-imidazol-1-yl) pyridin-2-yl)-5,6-dihydro-4H-1,2,4-oxadiazine, fraction (II) (−): $^1$H NMR (CD$_3$OD, 400 MHz): δ 7.96 (s, 1H), 7.84 (d, 1H), 7.56 (d, 1H), 7.20 (s, 1H), 4.11 (s, 3H), 4.01-3.94 (m, 1H), 3.79-3.71 (m, 2H), 2.25 (s, 3H), 1.88-1.77 (m, 1H), 1.62-1.44 (m, 2H), 1.04 (s, 3H), 1.03 (s, 3H); Mass (ESI): 330.3 [M+1]; HPLC (purity): 99.0%, RT 7.19 min; Chiral HPLC: 98.9%, RT=18.86 min; Optical rotation $[\alpha]_D^{20.00}$: −11.88 (c=0.25, CH$_2$Cl$_2$).

Example 155

Synthesis of 3-(5-bromo-6-methoxypyridin-2-yl)-5-(thiazol-4-yl)-5,6-dihydro-4H-1,2,4-oxadiazine

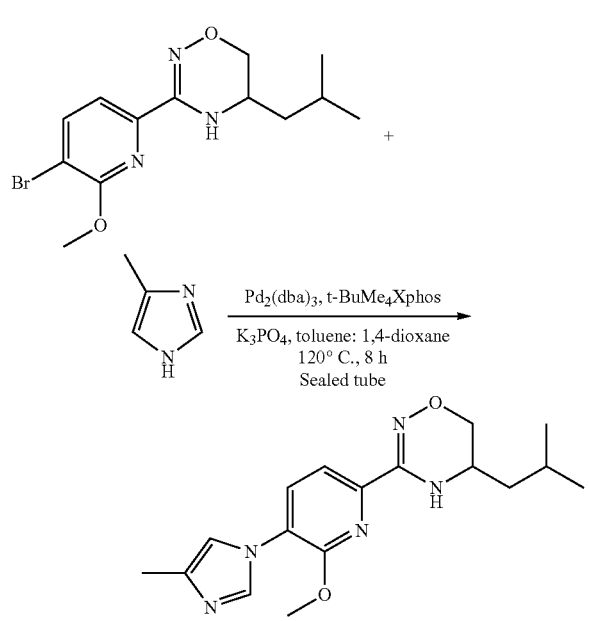

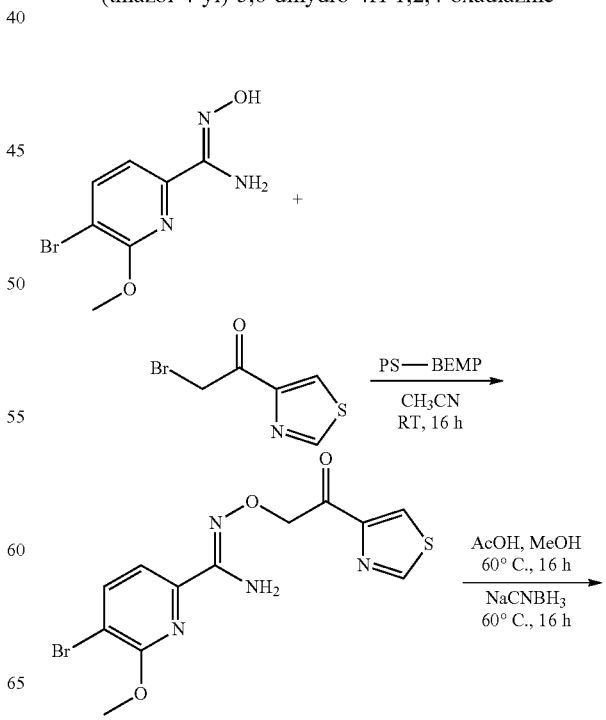

361

-continued

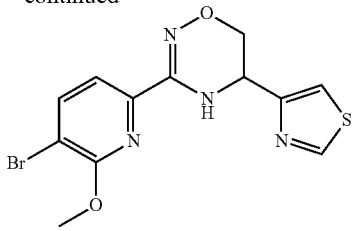

(Z)-5-bromo-6-methoxy-N'-(2-oxo-2-(thiazol-4-yl) ethoxy) picolinimidamide

The title compound was prepared from 2-bromo-1-(thiazol-4-yl) ethan-1-one according to the procedure for Example 43. LCMS: 16.1%; 372.7 (M+2); (column; Ascentis Express C-18 (50×3.0 mm, 2.7 μm); RT 2.32 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 40% EtOAc/Hexane (R$_f$: 0.3).

3-(5-bromo-6-methoxypyridin-2-yl)-5-(thiazol-4-yl)-5,6-dihydro-4H-1,2,4-oxadiazine Example 155 (90 mg, 26%) was prepared from (Z)-5-bromo-6-methoxy-N'-(2-oxo-2-(thiazol-4-yl) ethoxy) picolinimidamide according to the procedure for Example 56. LCMS: 91.9%; 356.8 (M+2); (column; Ascentis Express C-18 (50×3.0 mm, 2.7 μm); RT 2.18 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 50% EtOAc/Hexane (R$_f$: 0.3).

Example 156

Synthesis of 3-(6-methoxy-5-(4-methyl-1H-imidazol-1-yl) pyridin-2-yl)-5-(thiazol-4-yl)-5,6-dihydro-4H-1,2,4-oxadiazine

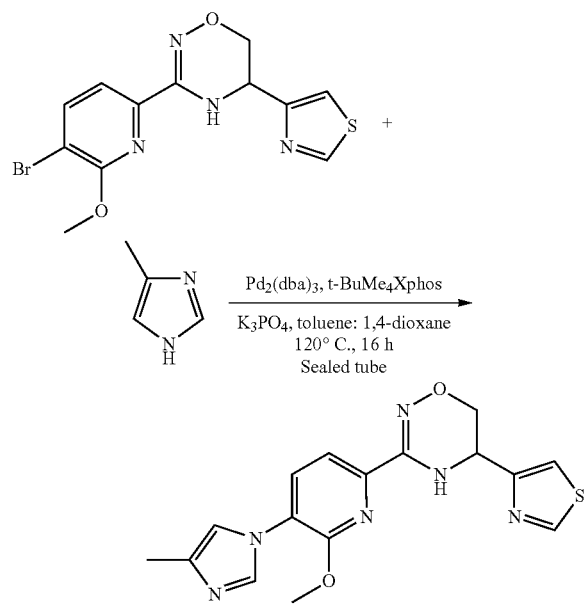

362

3-(6-methoxy-5-(4-methyl-1H-imidazol-1-yl) pyridin-2-yl)-5-(thiazol-4-yl)-5,6-dihydro-4H-1,2,4-oxadiazine Example 156 (95 mg, 78%) was prepared from 3-(5-bromo-6-methoxypyridin-2-yl)-5-(thiazol-4-yl)-5,6-dihydro-4H-1,2,4-oxadiazine according to the procedure for Example 49. Racemic compound of Example 156 was separated using a Chiralpak-ADH column (250×20 mm, 5 μm) (25 mg loading; 0.1% DEA in n-Hexane: EtOH:MeOH (50:50) (A:B: 75:25) as mobile phase; flow rate: 18 mL/min) to afford the compounds of Example 156A (Fraction (I) (−)) and Example 156B (Fraction (II) (+)).

Analytical conditions for Example 156A and Example 156B: UPLC (column; zorbax-SB-C-18 150×4.6 mm, 3.5μ); mobile Phase: ACN: 0.05% Aq TFA; flow rate: 1.0 mL/min; Gradient program: T/B % 0.01/90, 2/90, 8/10, 15/10: diluent: CH$_3$CN:Water; Chiral HPLC: (Chiralpak-ADH (250×4.6 mm, 5 μm; mobile phase (A) 0.1% DEA in n-Hexane (B) EtOH:MeOH (50:50) (A:B; 75:25); flow Rate: 1.0 mL/min).

Example 156A, (+)-3-(6-methoxy-5-(4-methyl-1H-imidazol-1-yl) pyridin-2-yl)-5-(thiazol-4-yl)-5,6-dihydro-4H-1,2,4-oxadiazine, fraction (I) (+): $^1$H NMR (CD$_3$OD, 400 MHz): δ 9.03 (s, 1H), 7.99 (s, 1H), 7.88 (d, 1H), 7.64 (d, 1H), 7.49 (s, 1H), 7.22 (s, 1H), 5.11 (t, 1H), 4.23 (dd, 1H), 4.12 (s, 3H), 4.11-4.09 (m, 1H), 2.26 (s, 3H); Mass (ESI): 357.2 [M+1]; UPLC (purity): 98.8%, RT 6.21 min; Chiral HPLC: 99.6%, RT=19.39 min; Optical rotation [α]$_D^{20.00}$: +213.69 (c=0.25, CH$_2$Cl$_2$).

Example 156B, (−)-3-(6-methoxy-5-(4-methyl-1H-imidazol-1-yl) pyridin-2-yl)-5-(thiazol-4-yl)-5,6-dihydro-4H-1,2,4-oxadiazine, fraction (II) (−): Mass (ESI): 357.2 [M+1]; UPLC (purity): 95.2%, RT 6.22 min; Chiral HPLC: 99.7%, RT=24.98 min; Optical rotation [α]$_D^{20.00}$: −193.15 (c=0.25, CH$_2$Cl$_2$).

Example 157

Synthesis of 1-bromo-3-cyclopropylpropan-2-one

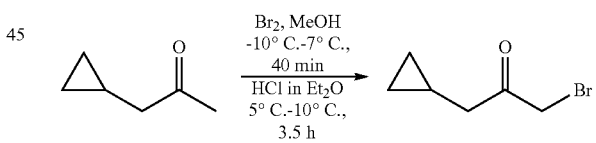

1-bromo-3-cyclopropylpropan-2-one

To a stirred solution of 1-cyclopropylpropan-2-one (200 mg, 2 mmol) in MeOH (2 mL) at −10° C. under an argon atmosphere was added bromine (0.10 mL) for 10 min. The reaction mixture was stirred for 40 min at 7° C. Then HCl in ether (0.04 mL) was added to the reaction mixture at 5° C. The reaction mixture was stirred for 3.5 h at 5° C.-10° C. After consumption of starting material (monitored by TLC), the reaction mixture was diluted with sodium thiosulfate solution (1 mL) and extracted with ether (2×50 mL). The combined organic extracts were washed with saturated sodium bicarbonate solution (10 mL), brine (10 mL), dried over sodium sulfate, filtered and concentrated in vacuo to afford 1-bromo-3-cyclopropylpropan-2-one (320 mg, crude) as a brown syrup used in the next step without further purification. ¹H NMR (CDCl₃, 400 MHz): δ 3.49 (s, 2H), 2.55 (d, 2H), 0.90-0.83 (m, 1H), 0.63-0.58 (m, 2H), 0.23-0.11 (m, 2H).

Example 158

Synthesis of 3-(5-bromo-6-methoxypyridin-2-yl)-5-(cyclopropylmethyl)-5,6-dihydro-4H-1,2,4-oxadiazine

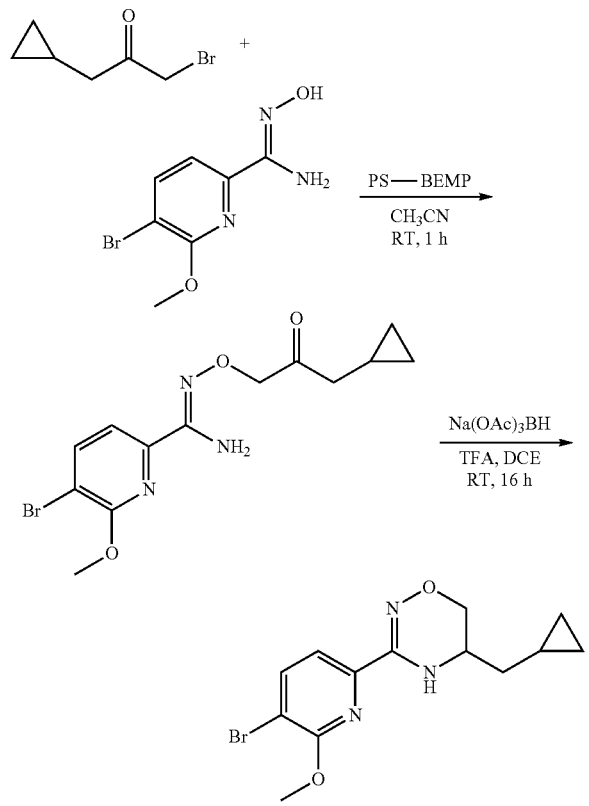

(Z)-5-bromo-N'-(3-cyclopropyl-2-oxopropoxy)-6-methoxypicolinimidamide

The title compound was prepared from 1-bromo-3-cyclopropylpropan-2-one according to the procedure for Example 43. LCMS: 35.1%; 343.7 (M+1); (column; Ascentis Express C-18 (50×3.0 mm, 2.7 μm); RT 2.64 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane ($R_f$: 0.5).

3-(5-bromo-6-methoxypyridin-2-yl)-5-(cyclopropylmethyl)-5,6-dihydro-4H-1,2,4-oxadiazine Example 158 (60 mg, 27%) was prepared from (Z)-5-bromo-N'-(3-cyclopropyl-2-oxopropoxy)-6-methoxypicolinimidamide according to the procedure for Example 48. LCMS: 99.1%; 325.8 (M+1); (column; Ascentis Express C-18 (50×3.0 mm, 2.7 μm); RT 2.57 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane ($R_f$: 0.5).

Example 159

Synthesis of 5-(cyclopropylmethyl)-3-(6-methoxy-5-(4-methyl-1H-imidazol-1-yl) pyridin-2-yl)-5,6-dihydro-4H-1,2,4-oxadiazine

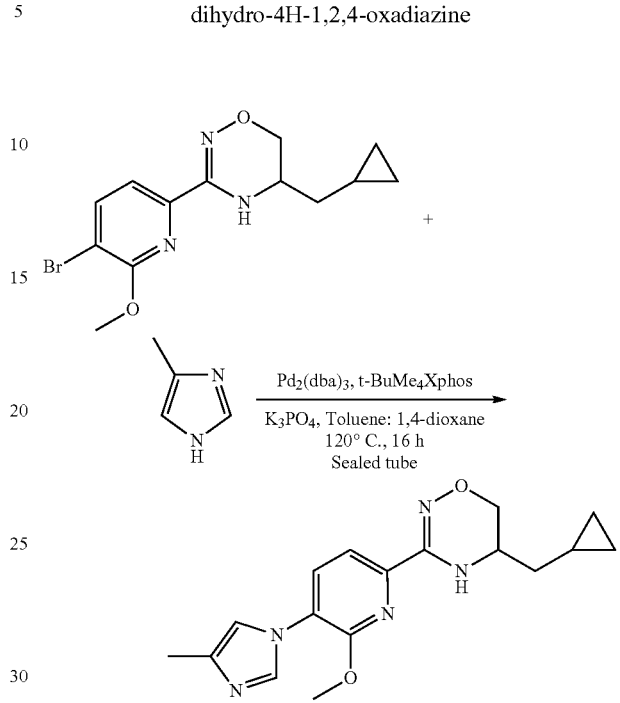

5-(cyclopropylmethyl)-3-(6-methoxy-5-(4-methyl-1H-imidazol-1-yl) pyridin-2-yl)-5,6-dihydro-4H-1,2,4-oxadiazine Example 159 (40 mg, 70%) was prepared from 3-(5-bromo-6-methoxypyridin-2-yl)-5-(cyclopropylmethyl)-5,6-dihydro-4H-1,2,4-oxadiazine according to the procedure for Example 49. Racemic compound of Example 159 was separated using a Chiralpak-IB column (250×20 mm, 5 μm) (24 mg loading; 0.1% DEA in n-Hexane: CH₂Cl₂:MeOH (50:50) (A:B; 80:20) as mobile phase; flow rate: 18 mL/min) to afford the compounds of Example 159A (Fraction (I)) and Example 159B (Fraction (II)).

Analytical conditions for Example 159A and Example 159B: HPLC (column; zorbax-SB-C-18 150×4.6 mm, 3.5μ); mobile Phase: ACN: 0.05% Aq TFA; flow rate: 1.0 mL/min; Gradient program: T/B % 0.01/90, 2/90, 8/10, 25/10: diluent: CH₃CN:Water; Chiral HPLC: (Chiralpak-IB (250×4.6 mm, 5 μm; mobile phase (A) 0.1% DEA in n-Hexane (B) CH₂Cl₂:MeOH (50:50) (A:B; 80:20); Flow Rate: 1.0 mL/min).

Example 159A, 5-(cyclopropylmethyl)-3-(6-methoxy-5-(4-methyl-1H-imidazol-1-yl) pyridin-2-yl)-5,6-dihydro-4H-1,2,4-oxadiazine, fraction (I): Mass (ESI): 328.3 [M+1]; HPLC (purity): 97.8%, RT 6.98 min; Chiral HPLC: 100%, RT=7.62 min.

Example 159B, 5-(cyclopropylmethyl)-3-(6-methoxy-5-(4-methyl-1H-imidazol-1-yl) pyridin-2-yl)-5,6-dihydro-4H-1,2,4-oxadiazine, fraction (II): ¹H NMR (CD₃OD, 400 MHz): δ 7.98 (br s, 1H), 7.83 (d, 1H), 7.55 (d, 1H), 7.21 (br s, 1H), 4.10 (s, 3H), 4.04 (dd, 1H), 3.83-3.73 (m, 2H), 2.23 (s, 3H), 1.70-1.61 (m, 1H), 1.49-1.41 (m, 1H), 0.87-0.78 (m, 1H), 0.60-0.50 (m, 2H), 0.20-0.12 (m, 2H); Mass (ESI):

328.3 [M+1]; HPLC (purity): 96.2%, RT 6.99 min; Chiral HPLC: 99.7%, RT=9.06 min.

Example 160

Synthesis of 3-(5-bromo-6-methoxypyridin-2-yl)-5-(2,4-dimethyloxazol-5-yl)-5,6-dihydro-4H-1,2,4-oxadiazine

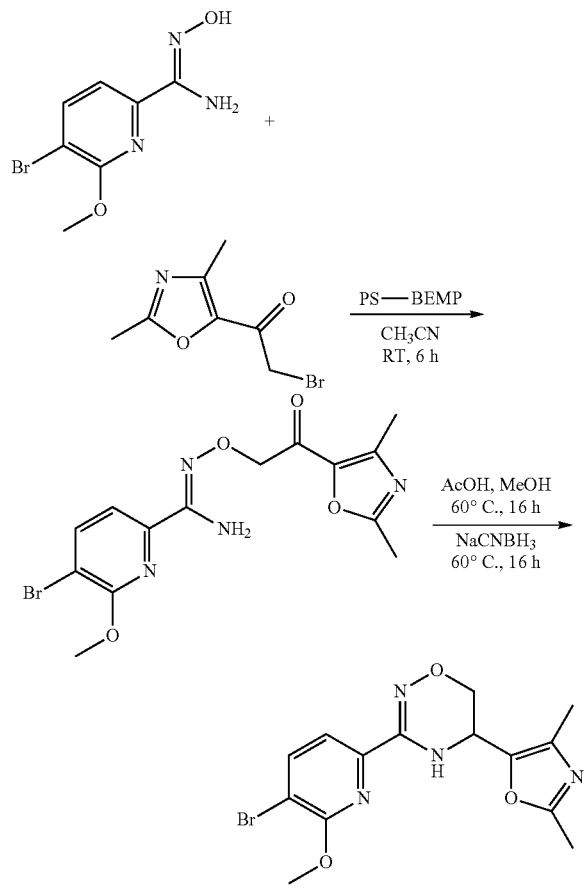

(Z)-5-bromo-N'-(2-(2,4-dimethyloxazol-5-yl)-2-oxoethoxy)-6-methoxypicolinimidamide The title compound was prepared from 2-bromo-1-(2,4-dimethyloxazol-5-yl) ethan-1-one according to the procedure for Example 43. LCMS: 29.8%; 384.6 (M+3); (column; Ascentis Express C-18 (50×3.0 mm, 2.7 μm); RT 2.37 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.4).

3-(5-bromo-6-methoxypyridin-2-yl)-5-(2,4-dimethyloxazol-5-yl)-5,6-dihydro-4H-1,2,4-oxadiazine Example 160 (200 mg, 21%) was prepared from (Z)-5-bromo-N'-(2-(2,4-dimethyloxazol-5-yl)-2-oxoethoxy)-6-methoxypicolinimidamide according to the procedure for Example 56. LCMS: 24.2%; 366.8 (M+1); (column; Ascentis Express C-18 (50×3.0 mm, 2.7 μm); RT 2.16 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.3).

Example 161

Synthesis of 5-(2, 4-dimethyloxazol-5-yl)-3-(6-methoxy-5-(4-methyl-1H-imidazol-1-yl) pyridin-2-yl)-5,6-dihydro-4H-1,2,4-oxadiazine

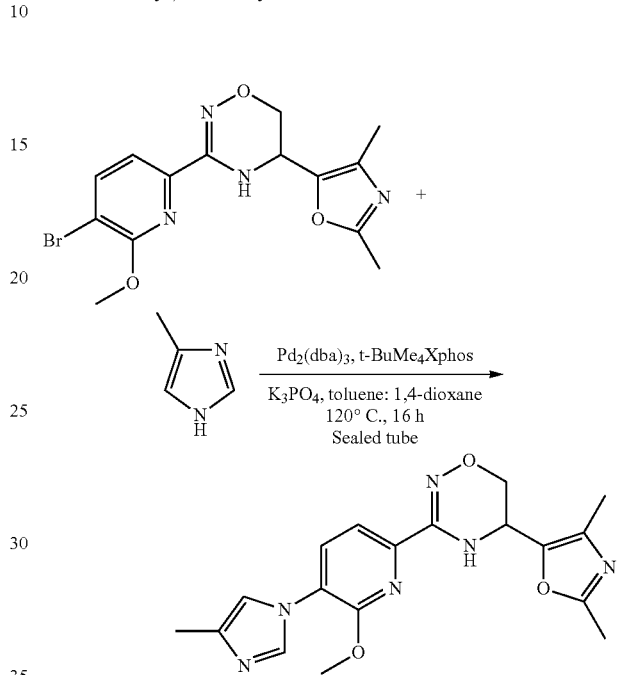

5-(2, 4-dimethyloxazol-5-yl)-3-(6-methoxy-5-(4-methyl-1H-imidazol-1-yl) pyridin-2-yl)-5,6-dihydro-4H-1,2,4-oxadiazine Example 161 (160 mg, 80%) was prepared from 3-(5-bromo-6-methoxypyridin-2-yl)-5-(2,4-dimethyloxazol-5-yl)-5,6-dihydro-4H-1,2,4-oxadiazine according to the procedure for Example 49. Racemic compound of Example 161 was separated using a Chiralpak-IB column (250×20 mm, 5 μm) (25 mg loading; 0.1% DEA in n-Hexane: CH$_2$Cl$_2$: MeOH (50:50) (A:B: 85:15) as mobile phase; flow rate: 18 mL/min) to afford the compounds of Example 161A (Fraction (I) (−)) and Example 161B (Fraction (II) (+)).

Analytical conditions for Example 161A and Example 161B: HPLC (column; zorbax-SB-C-18 150×4.6 mm, 3.5μ); mobile Phase: ACN: 0.05% Aq TFA; flow rate: 1.0 mL/min; Gradient program: T/B % 0.01/90, 2/90, 8/10, 15/10: diluent: CH$_3$CN:Water; Chiral HPLC: (Chiralpak-IB (250× 4.6 mm, 5 μm; mobile phase (A) 0.1% DEA in n-Hexane (B) CH$_2$Cl$_2$:MeOH (50:50) (A:B; 85:15); flow Rate: 1.0 mL/min).

Example 161A, (−)-5-(2, 4-dimethyloxazol-5-yl)-3-(6-methoxy-5-(4-methyl-1H-imidazol-1-yl) pyridin-2-yl)-5,6-dihydro-4H-1,2,4-oxadiazine, fraction (I) (−): Mass (ESI): 369.3 [M+1]; HPLC (purity): 99.6%, RT 6.23 min; Chiral HPLC: 99.5%, RT=15.40 min; Optical rotation [α]$_D^{20.00}$: −70.76 (c=0.25, CH$_2$Cl$_2$).

Example 161B, (+)-5-(2,4-dimethyloxazol-5-yl)-3-(6-methoxy-5-(4-methyl-1H-imidazol-1-yl) pyridin-2-yl)-5,6-dihydro-4H-1,2,4-oxadiazine, fraction (II) (+): $^1$H NMR (CD$_3$OD, 400 MHz): δ 7.97 (s, 1H), 7.87 (d, 1H), 7.62 (d, 1H), 7.21 (s, 1H), 5.00 (t, 1H), 4.13 (dd, 1H), 4.10 (s, 3H), 4.03 (dd, 1H), 2.40 (s, 3H), 2.25 (s, 3H), 2.14 (s, 3H); Mass (ESI): 369.3 [M+1]; HPLC (purity): 99.1%; RT 6.22 min; Chiral HPLC: 99.2%, RT=19.89 min; Optical rotation $[\alpha]_D^{20.00}$: +75.87 (c=0.25, CH$_2$Cl$_2$).

Example 162

Synthesis of 3-(5-bromo-6-methoxypyridin-2-yl)-5-cyclobutyl-5,6-dihydro-4H-1,2,4-oxadiazine

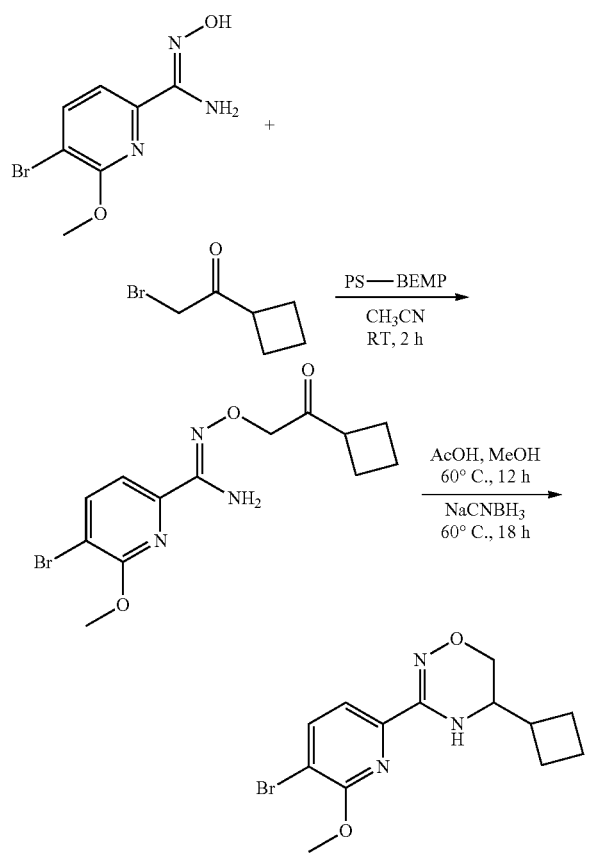

(Z)-5-bromo-N'-(2-cyclobutyl-2-oxoethoxy)-6-methoxypicolinimidamide

The title compound was prepared from 2-bromo-1-cyclobutylethan-1-one according to the procedure for Example 43. LCMS: 39.6%; 341.8 (M+1); (column; Ascentis Express C-18 (50×3.0 mm, 2.7 μm); RT 2.67 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane (R$_f$: 0.5).

3-(5-bromo-6-methoxypyridin-2-yl)-5-cyclobutyl-5,6-dihydro-4H-1,2,4-oxadiazine

Example 162 (300 mg, 52%) was prepared from (Z)-5-bromo-N'-(2-cyclobutyl-2-oxoethoxy)-6-methoxypicolinimidamide according to the procedure for Example 56. LCMS: 92.6%; 325.8 (M+1); (column; Ascentis Express C-18 (50×3.0 mm, 2.7 μm); RT 2.60 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane (R$_f$: 0.5).

Example 163

Synthesis of 5-cyclobutyl-3-(6-methoxy-5-(4-methyl-1H-imidazol-1-yl) pyridin-2-yl)-5,6-dihydro-4H-1,2,4-oxadiazine

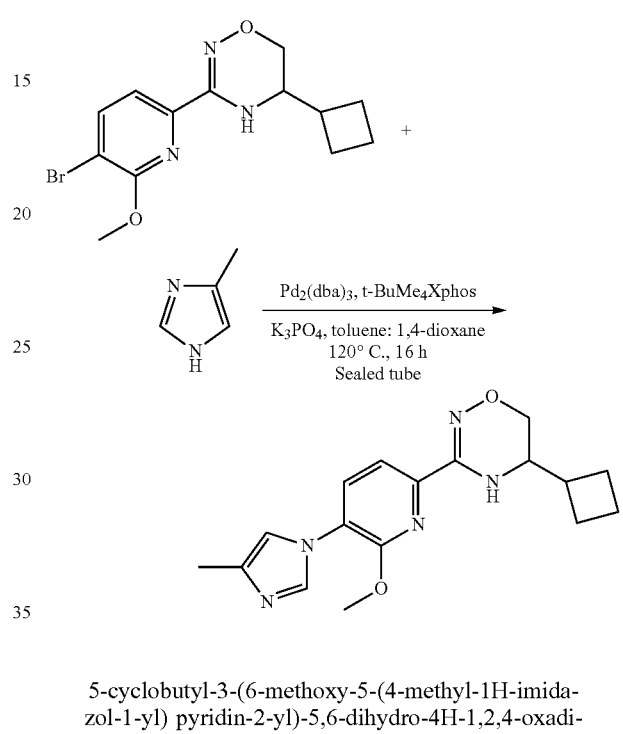

5-cyclobutyl-3-(6-methoxy-5-(4-methyl-1H-imidazol-1-yl) pyridin-2-yl)-5,6-dihydro-4H-1,2,4-oxadiazine Example 163 (165 mg, 66%) was prepared from 3-(5-bromo-6-methoxypyridin-2-yl)-5-cyclobutyl-5,6-dihydro-4H-1,2,4-oxadiazine according to the procedure for Example 49. Racemic compound of Example 163 was separated using a Chiralpak-IA column (250×20 mm, 5 μm) (46.6 mg loading; 0.1% DEA in n-Hexane: CH$_2$Cl$_2$:MeOH (80:20) (A:B: 85:15) as mobile phase; flow rate: 20 mL/min) to afford the compounds of Example 163A (Fraction (I) (+)) and Example 163B (Fraction (II) (−)).

Analytical conditions for Example 163A and Example 163B: HPLC (column; zorbax-SB-C-18 150×4.6 mm, 3.5μ); mobile Phase: ACN: 0.05% Aq TFA; flow rate: 1.0 mL/min; Gradient program: T/B % 0.01/90, 2/90, 8/10, 15/10: diluent: CH$_3$CN:Water; Chiral HPLC: (Chiralpak-IB (250× 4.6 mm, 5 μm; mobile phase (A) 0.1% DEA in n-Hexane (B) CH$_2$Cl$_2$:MeOH (80:20) (A:B; 85:15); flow Rate: 1.0 mL/min).

Example 163A, (+)-5-cyclobutyl-3-(6-methoxy-5-(4-methyl-1H-imidazol-1-yl) pyridin-2-yl)-5,6-dihydro-4H-1,2,4-oxadiazine, fraction (I) (+): Mass (ESI): 328.3 [M+1]; HPLC (purity): 98.8%; RT 6.99 min; Chiral HPLC: 99.0%, RT=20.17 min; Optical rotation $[\alpha]_D^{19.99}$: +22.41 (c=0.25, CH$_2$Cl$_2$).

Example 163B, (−)-5-cyclobutyl-3-(6-methoxy-5-(4-methyl-1H-imidazol-1-yl) pyridin-2-yl)-5,6-dihydro-4H-1,2,4-oxadiazine, fraction (II) (−): $^1$H NMR (CD$_3$OD, 400

MHz): δ 8.04 (br s, 1H), 7.85 (d, 1H), 7.56 (d, 1H), 7.31 (br s, 1H), 4.11 (s, 3H), 3.83 (dd, 1H), 3.77 (dd, 1H), 3.65-3.59 (m, 1H), 2.64-2.53 (m, 1H), 2.25 (s, 3H), 2.18-1.83 (m, 6H); Mass (ESI): 328.3 [M+1]; HPLC (purity): 98.5%, RT 6.99 min; Chiral HPLC: 99.5%, RT=26.89 min; Optical rotation $[\alpha]_D^{20.01}$: −23.10 (c=0.25, CH$_2$Cl$_2$).

Example 164

Synthesis of 2-bromo-1-(1-methyl-1H-pyrazol-4-yl)ethan-1-one

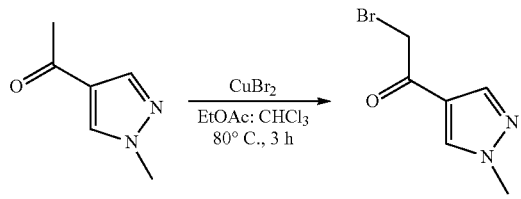

2-bromo-1-(1-methyl-1H-pyrazol-4-yl) ethan-1-one

Example 164 (600 mg, 15%) was prepared from 1-(1-methyl-1H-pyrazol-4-yl) ethan-1-one according to the procedure for Example 62. $^1$H NMR (CDCl$_3$, 500 MHz): δ 7.99 (s, 2H), 4.19 (s, 2H), 3.98 (s, 3H); LCMS: 99.7%; 205.1 (M+2); (column; X-select CSH C-18 (50×3.0 mm, 3.5 μm); RT 1.81 min 5 mM Aq NH$_4$OAc: ACN; T/B %: 0.01/10, 0.5/10, 3.5/90, 7/90; 0.8 mL/min); TLC: 30% EtOAc/Hexane (R$_f$: 0.3).

Example 165

Synthesis of 3-(5-bromo-6-methoxypyridin-2-yl)-5-(1-methyl-1H-pyrazol-4-yl)-5,6-dihydro-4H-1,2,4-oxadiazine

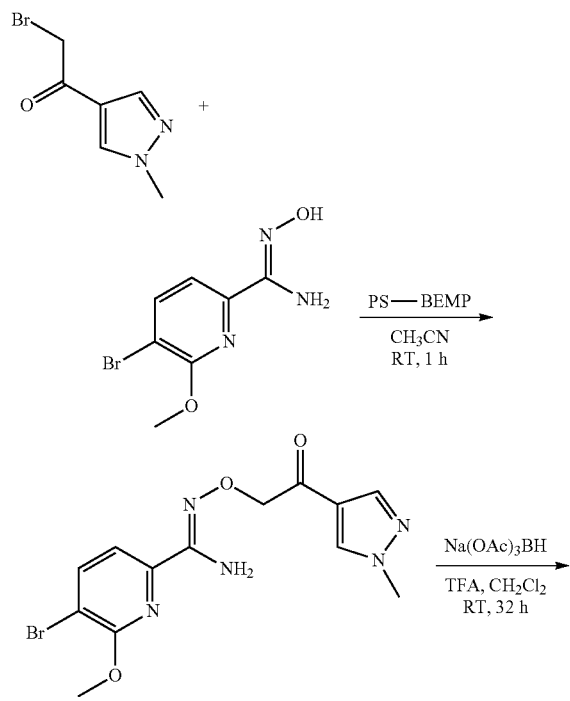

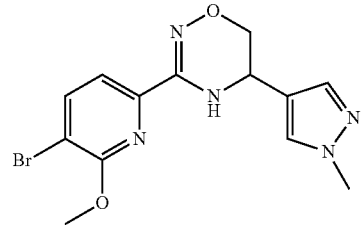

(Z)-5-bromo-6-methoxy-N'-(2-(1-methyl-1H-pyrazol-4-yl)-2-oxoethoxy) picolinimidamide The title compound was prepared from 2-bromo-1-(1-methyl-1H-pyrazol-4-yl) ethan-1-one according to the procedure for Example 43. LCMS: 82.9%; 367.8 (M+1); (column; Ascentis Express C-18 (50×3.0 mm, 2.7 μm); RT 2.39 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.2).

3-(5-bromo-6-methoxypyridin-2-yl)-5-(1-methyl-1H-pyrazol-4-yl)-5,6-dihydro-4H-1,2,4-oxadiazine Example 165 (260 mg, 34%) was prepared from (Z)-5-bromo-6-methoxy-N'-(2-(1-methyl-1H-pyrazol-4-yl)-2-oxoethoxy) picolinimidamide according to the procedure for Example 48. LCMS: 93.6%; 353.7 (M+3); (column; Ascentis Express C-18 (50×3.0 mm, 2.7 μm); RT 2.08 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 50% EtOAc/Hexane (R$_f$: 0.3).

Example 166

Synthesis of 3-(6-methoxy-5-(4-methyl-1H-imidazol-1-yl) pyridin-2-yl)-5-(1-methyl-1H-pyrazol-4-yl)-5,6-dihydro-4H-1,2,4-oxadiazine

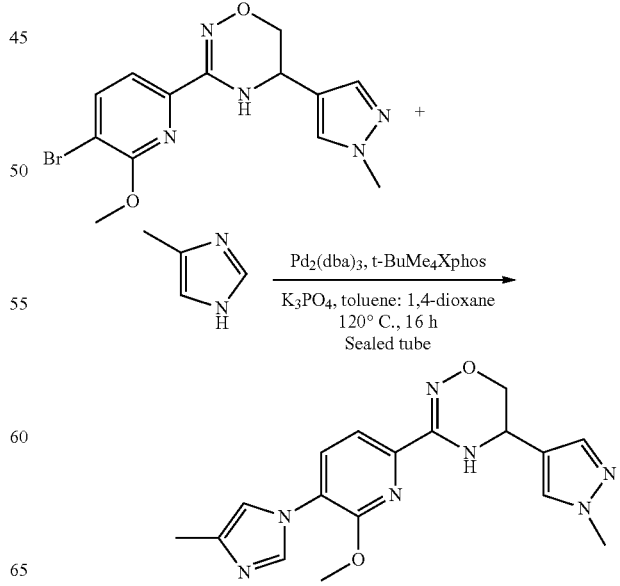

3-(6-methoxy-5-(4-methyl-1H-imidazol-1-yl) pyridin-2-yl)-5-(1-methyl-1H-pyrazol-4-yl)-5,6-dihydro-4H-1,2,4-oxadiazine Example 166 (115 mg, 45%) was prepared from 3-(5-bromo-6-methoxypyridin-2-yl)-5-(1-methyl-1H-pyrazol-4-yl)-5,6-dihydro-4H-1,2,4-oxadiazine according to the procedure for Example 49. Racemic compound of Example 166 was separated using a Chiralpak-IB column (250×20 mm, 5 µm) (30 mg loading; 0.1% DEA in n-Hexane: CH$_2$Cl$_2$: MeOH (80:20) (A:B: 80:20) as mobile phase; flow rate: 20 mL/min) to afford the compounds of Example 166A (Fraction (I) (−)) and Example 166B (Fraction (II) (+)).

Analytical conditions for Example 166A and Example 166B: HPLC (column; zorbax-SB-C-18 150×4.6 mm, 3.5µ); mobile Phase: ACN: 0.05% Aq TFA; flow rate: 1.0 mL/min; Gradient program: T/B % 0.01/90, 2/90, 8/10, 15/10: diluent: CH$_3$CN:Water; Chiral HPLC: (Chiralpak-IB (250×4.6 mm, 5 µm; mobile phase (A) 0.1% DEA in n-Hexane (B) CH$_2$Cl$_2$:MeOH (50:50) (A:B; 70:30); flow Rate: 1.0 mL/min).

Example 166A, (−)-3-(6-methoxy-5-(4-methyl-1H-imidazol-1-yl) pyridin-2-yl)-5-(1-methyl-1H-pyrazol-4-yl)-5,6-dihydro-4H-1,2,4-oxadiazine, fraction (I) (−): Mass (ESI): 354.3 [M+1]; HPLC (purity): 99.5%, RT 6.11 min; Chiral HPLC: 100%, RT=7.66 min, Optical rotation $[\alpha]_D^{19.99}$: −35.48 (c=0.25, CH$_2$Cl$_2$).

Example 166B, (+)-3-(6-methoxy-5-(4-methyl-1H-imidazol-1-yl) pyridin-2-yl)-5-(1-methyl-1H-pyrazol-4-yl)-5,6-dihydro-4H-1,2,4-oxadiazine, fraction (II) (+): $^1$H NMR (CD$_3$OD, 400 MHz): δ 7.97 (s, 1H), 7.86 (d, 1H), 7.65 (s, 1H), 7.61 (d, 1H), 7.52 (s, 1H), 7.21 (s, 1H), 4.83-4.81 (m, 1H), 4.10 (dd, 1H), 4.08 (s, 3H), 3.94 (dd, 1H), 3.88 (s, 3H), 2.25 (s, 3H); Mass (ESI): 354.3 [M+1]; HPLC (purity): 98.9%, RT 6.11 min; Chiral HPLC: 99.5%, RT=9.51 min; Optical rotation $[\alpha]_D^{20.00}$: +41.08 (c=0.25, CH$_2$Cl$_2$).

Example 167

Synthesis of 3-(5-bromo-6-methoxypyridin-2-yl)-5-(pyridin-2-yl)-5,6-dihydro-4H-1,2,4-oxadiazine

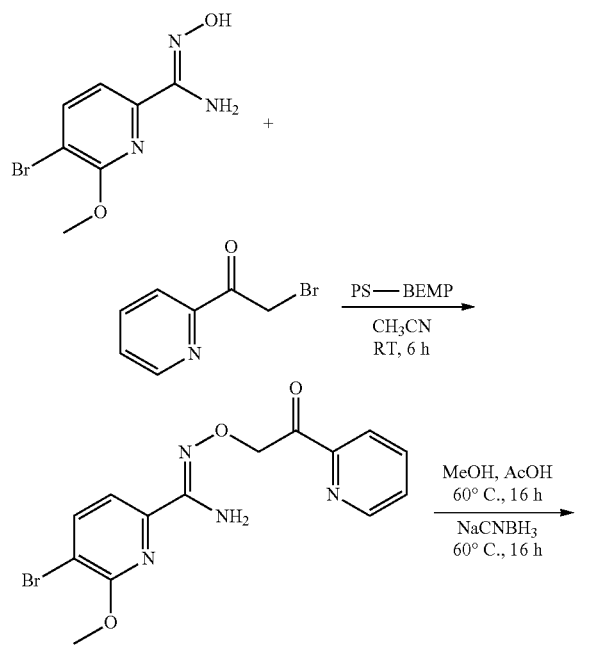

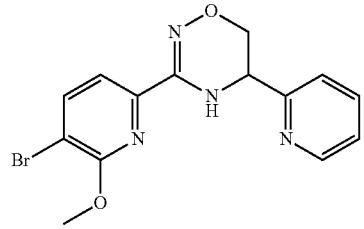

(Z)-5-bromo-6-methoxy-N'-(2-oxo-2-(pyridin-2-yl) ethoxy) picolinimidamide

The title compound was prepared from 2-bromo-1-(pyridin-2-yl) ethan-1-one according to the procedure for Example 43. LCMS: 23.7%; 364.8 (M+1); (column; Ascentis Express C-18 (50×3.0 mm, 2.7 µm); RT 2.57 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane (R$_f$: 0.4).

3-(5-bromo-6-methoxypyridin-2-yl)-5-(pyridin-2-yl)-5,6-dihydro-4H-1,2,4-oxadiazine Example 167 (160 mg, 28%) was prepared from (Z)-5-bromo-6-methoxy-N'-(2-oxo-2-(pyridin-2-yl) ethoxy) picolinimidamide according to the procedure for Example 56. LCMS: 66.6%; 348.8 (M+1); (column; Ascentis Express C-18 (50×3.0 mm, 2.7 µm); RT 2.07 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.3).

Example 168

Synthesis of 3-(6-methoxy-5-(4-methyl-1H-imidazol-1-yl) pyridin-2-yl)-5-(pyridin-2-yl)-5,6-dihydro-4H-1,2,4-oxadiazine

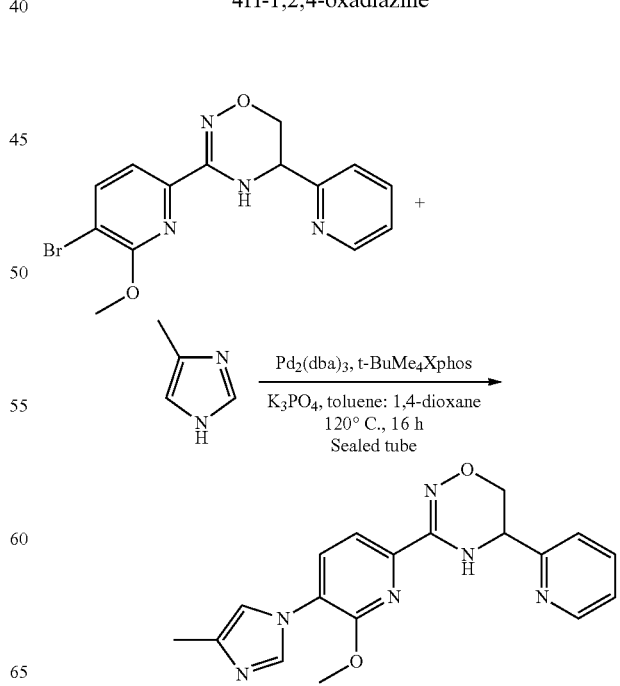

3-(6-methoxy-5-(4-methyl-1H-imidazol-1-yl) pyridin-2-yl)-5-(pyridin-2-yl)-5,6-dihydro-4H-1,2,4-oxadiazine Example 168 (100 mg, 62%) was prepared from 3-(5-bromo-6-methoxypyridin-2-yl)-5-(pyridin-2-yl)-5,6-dihydro-4H-1,2,4-oxadiazine according to the procedure for Example 49. Racemic compound of Example 168 was separated using a Chiralpak-IA column (250×20 mm, 5 μm) (30 mg loading; 0.1% DEA in n-Hexane: CH$_2$Cl$_2$:MeOH (50:50) (A:B: 80:20) as mobile phase; flow rate: 20 mL/min) to afford the compounds of Example 168A (Fraction (I) (+)) and Example 168B (Fraction (II) (−)).

Analytical conditions for Example 168A and Example 168B: HPLC (column; zorbax-SB-C-18 150×4.6 mm, 3.5μ); mobile Phase: ACN: 0.05% Aq TFA; flow rate: 1.0 mL/min; Gradient program: T/B % 0.01/90, 2/90, 8/10, 15/10: diluent: CH$_3$CN:Water; Chiral HPLC: (Chiralpak-IA (250×4.6 mm, 5 μm; mobile phase (A) 0.1% DEA in n-Hexane (B) CH$_2$Cl$_2$:MeOH (50:50) (A:B; 80:20); flow Rate: 1.0 mL/min).

Example 168A, (+)-3-(6-methoxy-5-(4-methyl-1H-imidazol-1-yl) pyridin-2-yl)-5-(pyridin-2-yl)-5,6-dihydro-4H-1,2,4-oxadiazine, fraction (I) (+): $^1$H NMR (CD$_3$OD, 400 MHz): δ 8.60-8.55 (m, 1H), 7.99 (s, 1H), 7.89 (d, 1H), 7.85 (dd, 1H), 7.66 (d, 1H), 7.48 (d, 1H), 7.37-7.35 (m, 1H), 7.23 (s, 1H), 4.97 (t, 1H), 4.14 (d, 2H), 4.13 (s, 3H), 2.26 (s, 3H); Mass (ESI): 351.3 [M+1]; HPLC (purity): 98.0%, RT 5.71 min; Chiral HPLC: 100%, RT=9.22 min; Optical rotation $[\alpha]_D^{20.02}$: +195.37 (c=0.25, CH$_2$Cl$_2$).

Example 168B, (−)-3-(6-methoxy-5-(4-methyl-1H-imidazol-1-yl) pyridin-2-yl)-5-(pyridin-2-yl)-5,6-dihydro-4H-1,2,4-oxadiazine, fraction (II) (−): Mass (ESI): 351.3 [M+1]; HPLC (purity): 99.2%, RT 5.70 min; Chiral HPLC: 99.2%, RT=11.52 min; Optical rotation $[\alpha]_D^{19.99}$: −197.74 (c=0.25, CH$_2$Cl$_2$).

Example 169

Synthesis of 2-bromo-1-cyclopentylethan-1-one

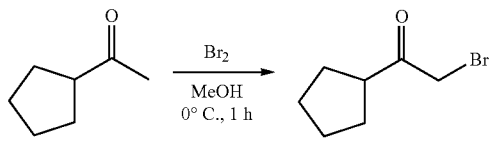

2-bromo-1-cyclopentylethan-1-one

To a stirred solution of 1-cyclopentylethan-1-one (1 g, 8 mmol) in MeOH (5 mL) at 0° C. under an argon atmosphere was added bromine (0.4 mL, 8 mmol). The reaction mixture was stirred at 0° C. for 1 h. After consumption of starting material (monitored by TLC), the reaction mixture was diluted with water (50 mL) and extracted with ether (2×50 mL). The combined organic extracts were dried over sodium sulfate, filtered and concentrated in vacuo to afford 2-bromo-1-cyclopentylethan-1-one (1.5 g, crude) as brown solid used in the next step without further purification.

Example 170

Synthesis of 3-(5-bromo-6-methoxypyridin-2-yl)-5-cyclopentyl-5,6-dihydro-4H-1,2,4-oxadiazine

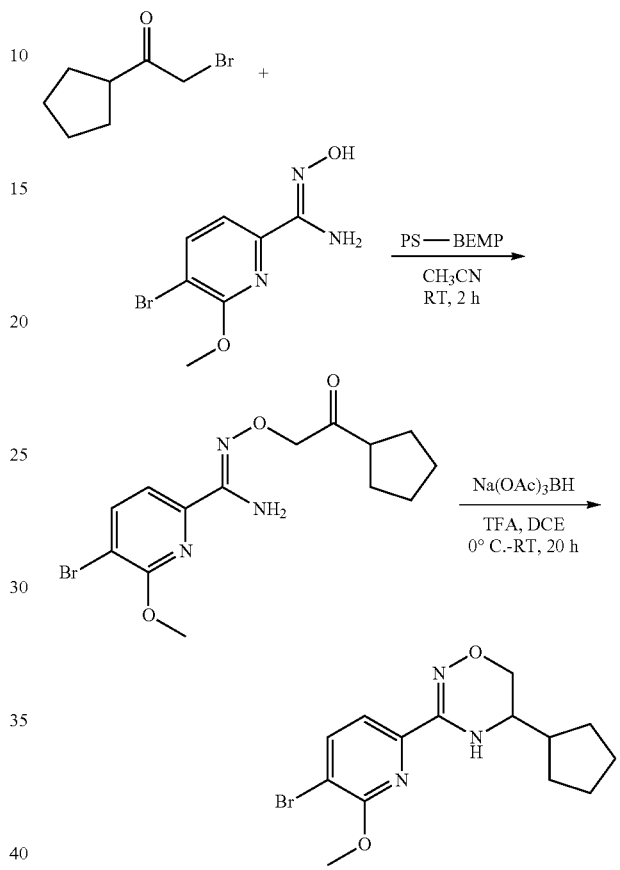

(Z)-5-bromo-N'-(2-cyclopentyl-2-oxoethoxy)-6-methoxypicolinimidamide

The title compound was prepared from 2-bromo-1-cyclopentylethan-1-one according to the procedure for Example 43. LCMS: 74.7%; 357.8 (M+3); (column; Ascentis Express C-18 (50×3.0 mm, 2.7 μm); RT 2.84 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane (R$_f$; 0.4).

3-(5-bromo-6-methoxypyridin-2-yl)-5-cyclopentyl-5,6-dihydro-4H-1,2,4-oxadiazine

Example 170 (460 mg, crude) was prepared from (Z)-5-bromo-N'-(2-cyclopentyl-2-oxoethoxy)-6-methoxypicolinimidamide according to the procedure for Example 48. LCMS: 15.2%; 339.9 (M+1); (column; Ascentis Express C-18 (50×3.0 mm, 2.7 μm); RT 2.77 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane (R$_f$; 0.4).

Example 171

Synthesis of 5-cyclopentyl-3-(6-methoxy-5-(4-methyl-1H-imidazol-1-yl) pyridin-2-yl)-5,6-dihydro-4H-1,2,4-oxadiazine

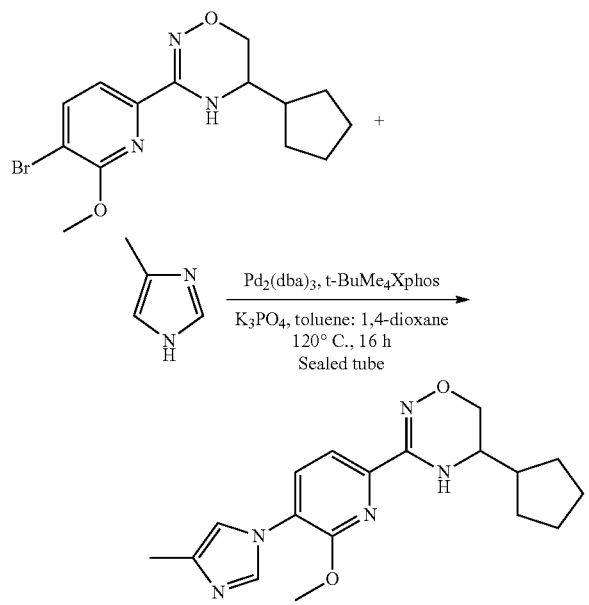

5-cyclopentyl-3-(6-methoxy-5-(4-methyl-1H-imidazol-1-yl) pyridin-2-yl)-5,6-dihydro-4H-1,2,4-oxadiazine Example 171 (90 mg, 13%) was prepared from 3-(5-bromo-6-methoxypyridin-2-yl)-5-cyclopentyl-5,6-dihydro-4H-1,2,4-oxadiazine according to the procedure for Example 49. Racemic compound of Example 171 was separated using a Chiralpak-IB column (250×20 mm, 5 μm) (18 mg loading; 0.1% DEA in n-Hexane: CH$_2$Cl$_2$: MeOH (80:20) (A:B: 80:20) as mobile phase; flow rate: 20 mL/min) to afford the compounds of Example 171A (Fraction (I) (+)) and Example 171B (Fraction (II) (−)).

Analytical conditions for Example 171A and Example 171B: HPLC (column; Zorbax-SB-C-18 150×4.6 mm, 5 μm); mobile Phase: ACN: 0.05% Aq TFA; flow rate: 1.0 mL/min); Gradient program: T/B % 0.01/90, 2/90, 8/10, 15/10: diluent: CH$_3$CN:Water; Chiral HPLC: (Chiralpak-IB (250×4.6 mm, 5 μm; mobile phase (A) 0.1% DEA in n-Hexane (B) CH$_2$Cl$_2$:MeOH (80:20) (A:B; 80:20); flow Rate: 1.0 mL/min).

Example 171A, (+)-5-cyclopentyl-3-(6-methoxy-5-(4-methyl-1H-imidazol-1-yl) pyridin-2-yl)-5,6-dihydro-4H-1,2,4-oxadiazine, fraction (I) (+): Mass (ESI): 342.3 [M+1]; HPLC (purity): 97.5%, RT 7.40 min; Chiral HPLC: 100%, RT=10.50 min; Optical rotation $[\alpha]_D^{20.00}$: +41.96 (c=0.25, CH$_2$Cl$_2$).

Example 171B, (−)-5-cyclopentyl-3-(6-methoxy-5-(4-methyl-1H-imidazol-1-yl) pyridin-2-yl)-5,6-dihydro-4H-1,2,4-oxadiazine, fraction (II) (−): $^1$H NMR (CD$_3$OD, 400 MHz): δ 7.97 (s, 1H), 7.85 (d, 1H), 7.57 (d, 1H), 7.21 (s, 1H), 4.11 (s, 3H), 3.97 (dd, 1H), 3.82 (dd, 1H), 3.51-3.46 (m, 1H), 2.25 (s, 3H), 2.16-2.07 (m, 1H), 1.97-1.79 (m, 2H), 1.76-1.61 (m, 4H), 1.56-1.47 (m, 1H), 1.40-1.27 (m, 1H); Mass (ESI): 342.3 [M+1]; HPLC (purity): 99.1%, RT 7.40 min; Chiral HPLC: 99.4%, RT=11.93 min; Optical rotation $[\alpha]_D^{20.00}$: −41.31 (c=0.25, CH$_2$Cl$_2$).

Example 172

Synthesis of 1-(benzo[d]isoxazol-3-yl)-2-bromoethan-1-one

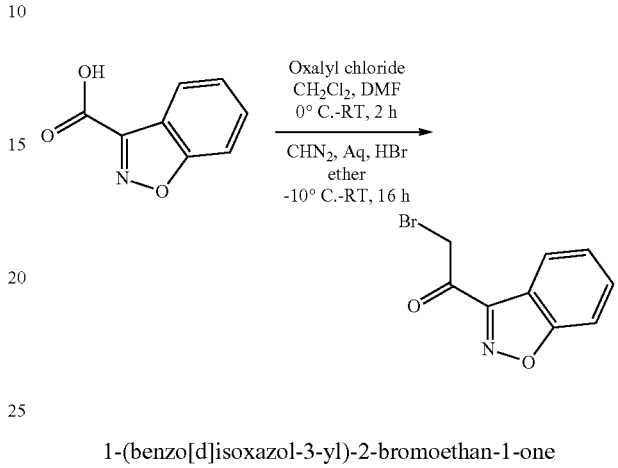

1-(benzo[d]isoxazol-3-yl)-2-bromoethan-1-one

Example 172 (1.2 g, crude) was prepared from benzo[d]isoxazole-3-carboxylic acid according to the procedure for Example 137. $^1$H NMR (CDCl$_3$, 400 MHz): δ 8.04 (d, 1H), 7.76 (d, 1H), 7.46-7.42 (m, 1H), 7.35-7.30 (m, 1H), 4.65 (s, 2H); TLC: 40% EtOAc/Hexane (R$_f$: 0.7).

Example 173

Synthesis of 3-(3-(5-bromo-6-methoxypyridin-2-yl)-5,6-dihydro-4H-1,2,4-oxadiazin-5-yl) benzo [d] isoxazole

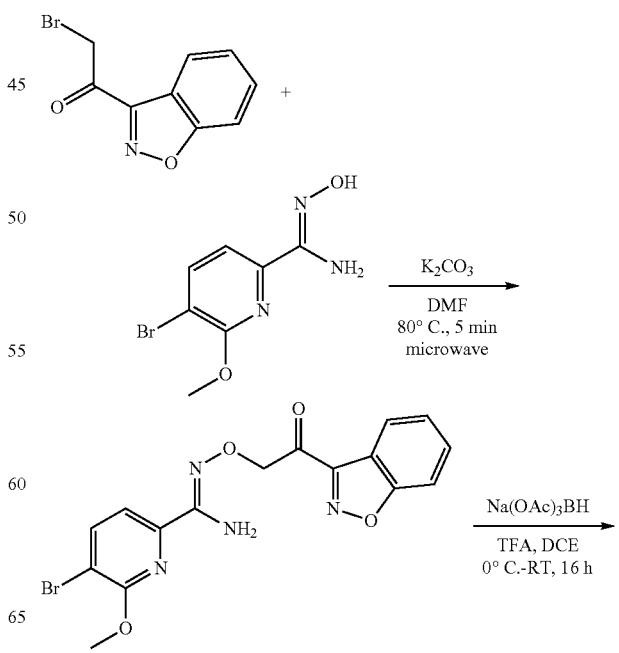

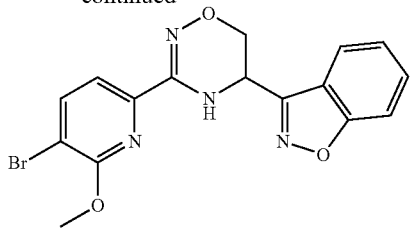

(Z)—N'-(2-(benzo[d]isoxazol-3-yl)-2-oxoethoxy)-5-bromo-6-methoxypicolinimidamide The title compound was prepared from 1-(benzo[d]isoxazol-3-yl)-2-bromoethan-1-one according to the procedure for Example 51. LCMS: 46.8%; 404.9 (M+1); (column; Ascentis Express C-18 (50×3.0 mm, 2.7 μm); RT 2.60 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.3).

3-(3-(5-bromo-6-methoxypyridin-2-yl)-5,6-dihydro-4H-1,2,4-oxadiazin-5-yl) benzo[d]isoxazole Example 173 (60 mg, crude) was prepared from (Z)—N'-(2-(benzo[d]isoxazol-3-yl)-2-oxoethoxy)-5-bromo-6-methoxypicolinimidamide according to the procedure for Example 48. LCMS: 36.3%; 388.8 (M+1); (column; Ascentis Express C-18 (50×3.0 mm, 2.7 μm); RT 2.53 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 40% EtOAc/Hexane ($R_f$: 0.5).

Example 174

Synthesis of 3-(3-(6-methoxy-5-(4-methyl-1H-imidazol-1-yl) pyridin-2-yl)-5,6-dihydro-4H-1,2,4-oxadiazin-5-yl) benzo [d] isoxazole

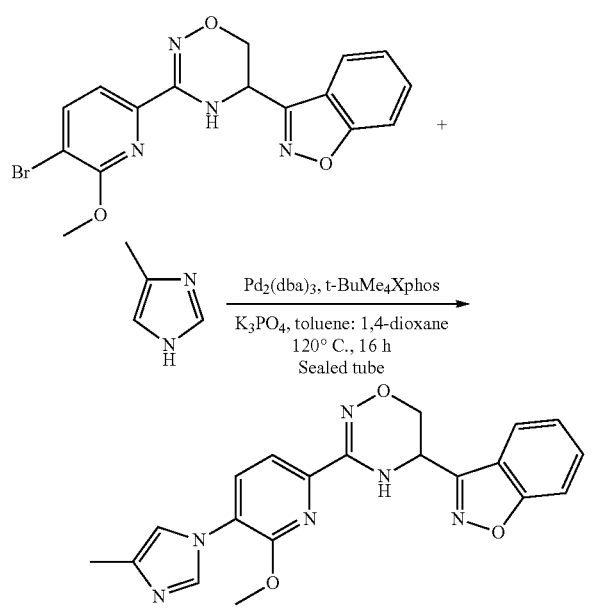

3-(3-(6-methoxy-5-(4-methyl-1H-imidazol-1-yl) pyridin-2-yl)-5,6-dihydro-4H-1,2,4-oxadiazin-5-yl) benzo [d] isoxazole Example 174 (300 mg, 75%) was prepared from 3-(3-(5-bromo-6-methoxypyridin-2-yl)-5,6-dihydro-4H-1,2,4-oxadiazin-5-yl) benzo[d]isoxazole according to the procedure for Example 49. Racemic compound of Example 174 was separated using a Chiralpak-IA column (250×20 mm, 5 μm) (15 mg loading; 0.1% DEA in n-Hexane: CH$_2$Cl$_2$:MeOH (80:20) (A:B: 70:30) as mobile phase; flow rate: 20 mL/min) to afford the compounds of Example 174A (Fraction (I)) and Example 174B (Fraction (II)).

Analytical conditions for Example 174A and Example 174B: HPLC (column; X-select CSH-C-18 150×4.6 mm, 3.5 μm), mobile Phase: ACN: 5 mM NH$_4$OAc; flow rate: 1.0 mL/min; Gradient program: T/B % 0.01/80, 3/80, 10/10, 20/10: diluent: CH$_3$CN:Water; Chiral HPLC: (Chiralpak-IA (250×4.6 mm, 5 μm; mobile phase (A) 0.1% DEA in n-Hexane (B) CH$_2$Cl$_2$:MeOH (80:20) (A:B; 70:30); flow Rate: 1.0 mL/min).

Example 174A, 3-(3-(6-methoxy-5-(4-methyl-1H-imidazol-1-yl) pyridin-2-yl)-5,6-dihydro-4H-1,2,4-oxadiazin-5-yl) benzo[d]isoxazole, fraction (I): Mass (ESI): 391.3 [M+1]; HPLC (purity): 96.1%, RT 8.80 min; Chiral HPLC: 100%, RT=11.74 min.

Example 174B, 3-(3-(6-methoxy-5-(4-methyl-1H-imidazol-1-yl) pyridin-2-yl)-5,6-dihydro-4H-1,2,4-oxadiazin-5-yl) benzo[d]isoxazole, fraction (II): $^1$H NMR (CD$_3$OD, 400 MHz): δ 7.97 (s, 1H), 7.87 (d, 1H), 7.66 (d, 1H), 7.57-7.50 (m, 2H), 7.21 (s, 1H), 6.94 (d, 1H), 6.84 (t, 1H), 4.85-4.82 (m, 1H), 4.07 (s, 3H), 4.05 (d, 1H), 3.80 (d, 1H), 2.25 (s, 3H); Mass (ESI): 391.3 [M+1]; HPLC (purity): 97.8%, RT 8.79 min; Chiral HPLC: 100%, RT=16.85 min.

Example 175

Synthesis of 2-bromo-1-(1,1-dioxidotetrahydro-2H-thiopyran-4-yl) ethan-1-one

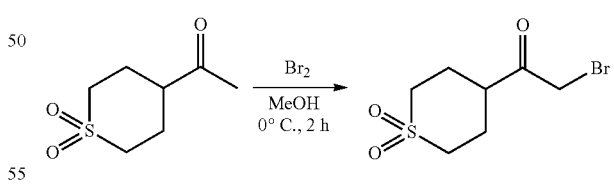

2-bromo-1-(1, 1-dioxidotetrahydro-2H-thiopyran-4-yl) ethan-1-one

Example 175 (400 mg, crude) was prepared from 1-(1,1-dioxidotetrahydro-2H-thiopyran-4-yl) ethan-1-one according to the procedure for Example 169. $^1$H NMR (DMSO-d$_6$, 500 MHz): δ 4.54 (s, 2H), 3.20-3.12 (m, 2H), 3.10-3.03 (m, 2H), 3.00-2.97 (m, 1H), 2.23-2.19 (m, 2H), 1.90-1.84 (m, 2H); TLC: 50% EtOAc/Hexane ($R_f$: 0.3).

Example 176

Synthesis of 4-(3-(5-bromo-6-methoxypyridin-2-yl)-5,6-dihydro-4H-1,2,4-oxadiazin-5-yl) tetrahydro-2H-thiopyran 1,1-dioxide

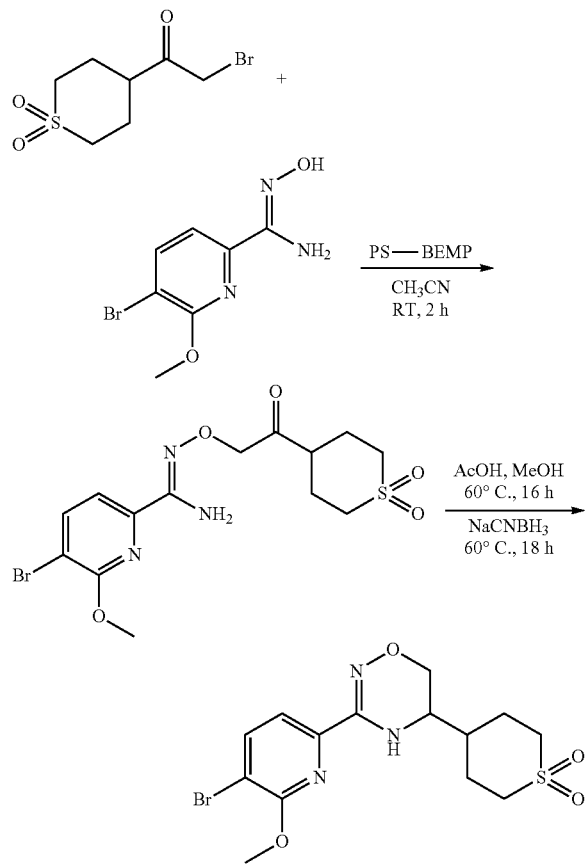

(Z)-5-bromo-N'-(2-(1,1-dioxidotetrahydro-2H-thiopyran-4-yl)-2-oxoethoxy)-6-methoxypicolinimidamide The title compound was prepared from 2-bromo-1-(1,1-dioxidotetrahydro-2H-thiopyran-4-yl) ethan-1-one according to the procedure for Example 43. LCMS: 25.3%; 421.7 (M+3); (column; Ascentis Express C-18 (50×3.0 mm, 2.7 µm); RT 1.93 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.6).

4-(3-(5-bromo-6-methoxypyridin-2-yl)-5,6-dihydro-4H-1,2,4-oxadiazin-5-yl) tetrahydro-2H-thiopyran 1,1-dioxide Example 176 (300 mg, 52%) was prepared from (Z)-5-bromo-N'-(2-(1,1-dioxidotetrahydro-2H-thiopyran-4-yl)-2-oxoethoxy)-6-methoxypicolinimidamide according to the procedure for Example 56. LCMS: 38.0%; 405.7 (M+3); (column; Ascentis Express C-18 (50×3.0 mm, 2.7 µm); RT 2.03 min; mobile phase: 0.025% Aq TFA+5% ACN: ACN+ 5% 0.025% Aq TFA; T/B %: 0.01/5, 0.5/5, 3/100, 5/100; flow rate: 1.2 mL/min) (Gradient); TLC: 20% EtOAc/Hexane ($R_f$: 0.4).

Example 177

Synthesis of 4-(3-(6-methoxy-5-(4-methyl-1H-imidazol-1-yl) pyridin-2-yl)-5,6-dihydro-4H-1,2,4-oxadiazin-5-yl) tetrahydro-2H-thiopyran 1,1-dioxide

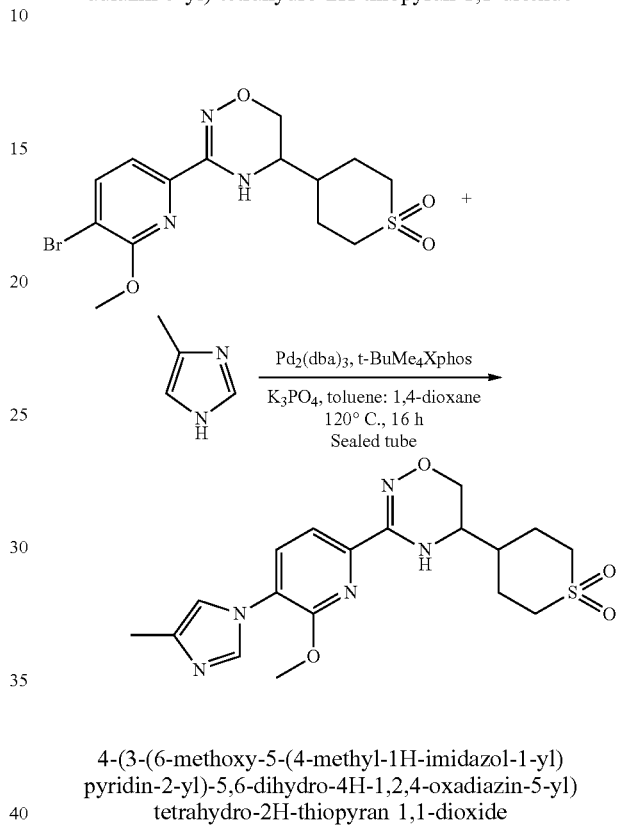

4-(3-(6-methoxy-5-(4-methyl-1H-imidazol-1-yl) pyridin-2-yl)-5,6-dihydro-4H-1,2,4-oxadiazin-5-yl) tetrahydro-2H-thiopyran 1,1-dioxide Example 177 (200 mg, 80%) was prepared from 4-(3-(5-bromo-6-methoxypyridin-2-yl)-5,6-dihydro-4H-1,2,4-oxadiazin-5-yl) tetrahydro-2H-thiopyran 1,1-dioxide according to the procedure for Example 49. Racemic compound of Example 177 was separated using a Chiralpak-IB column (250×20 mm, 5 µm) (35 mg loading; 0.1% DEA in n-Hexane: $CH_2Cl_2$:MeOH (50:50) (A:B: 75:25) as mobile phase; flow rate: 20 mL/min) to afford the compounds of Example 177A (Fraction (I) (+)) and Example 177B (Fraction (II) (−)).

Analytical conditions for Example 177A and Example 177B: HPLC (column; YMC-TRIART-C-18 150×4.6 mm, 3 µm); mobile Phase: ACN: 5 mM $NH_4OAc$; flow rate: 1.0 mL/min; Gradient program: T/B % 0.01/80, 3/80, 10/10, 20/10: diluent: $CH_3CN$:Water; Chiral HPLC: (Chiralpak-IB (250×4.6 mm, 5 µm; mobile phase (A) 0.1% DEA in n-Hexane (B) $CH_2Cl_2$:MeOH (50:50) (A:B; 60:40); flow Rate: 1.0 mL/min).

Example 177A, (+)-4-(3-(6-methoxy-5-(4-methyl-1H-imidazol-1-yl) pyridin-2-yl)-5,6-dihydro-4H-1,2,4-oxadiazin-5-yl) tetrahydro-2H-thiopyran 1,1-dioxide, fraction (I) (+): $^1$H NMR ($CD_3OD$, 400 MHz): δ 7.98 (s, 1H), 7.88-7.83 (m, 1H), 7.57 (d, 1H), 7.21 (s, 1H), 4.24 (dd, 1H), 4.13 (s, 3H), 3.72 (dd, 1H), 3.60 (br s, 1H), 3.22-3.04 (m, 4H), 2.39-2.30 (m, 1H), 2.27-2.20 (m, 4H), 2.03-1.95 (m, 3H); Mass (ESI): 406.3 [M+1]; HPLC (purity): 99.4%, RT 8.31 min; Chiral HPLC: 96.0%, RT=15.78 min; Optical rotation [α]$_D^{20.00}$: +116.19 (c=0.25, CH$_2$Cl$_2$).

Example 177B, (−)-4-(3-(6-methoxy-5-(4-methyl-1H-imidazol-1-yl) pyridin-2-yl)-5,6-dihydro-4H-1,2,4-oxadiazin-5-yl) tetrahydro-2H-thiopyran 1,1-dioxide, fraction (II) (−): Mass (ESI): 406.3 [M+1]; HPLC (purity): 99.8%, RT 8.31 min; Chiral HPLC: 96.5%, RT=18.17 min; Optical rotation [α]$_D^{19.98}$: −110.78 (c=0.25, CH$_2$Cl$_2$).

Example 178

Synthesis of 2-bromo-1-(3,3-difluorocyclobutyl) ethan-1-one

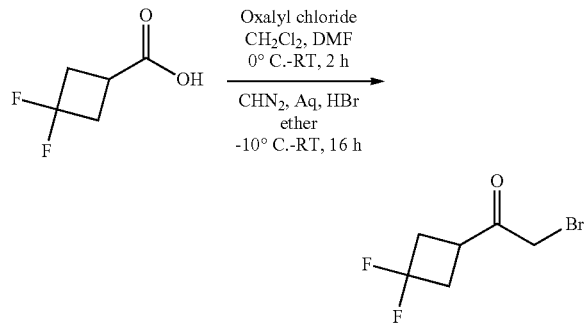

2-bromo-1-(3,3-difluorocyclobutyl) ethan-1-one

Example 178 (2 g, crude) was prepared from 3,3-difluorocyclobutane-1-carboxylic acid according to the procedure for Example 137. $^1$H NMR (CDCl$_3$, 400 MHz): δ 3.92 (s, 2H), 3.49-3.44 (m, 1H), 2.91-2.73 (m, 4H); TLC: 60% EtOAc/Hexane (R$_f$: 0.3).

Example 179

Synthesis of 3-(5-bromo-6-methoxypyridin-2-yl)-5-(3,3-difluorocyclobutyl)-5,6-dihydro-4H-1,2,4-oxadiazine

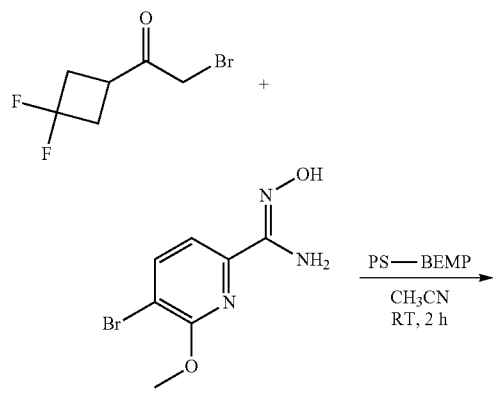

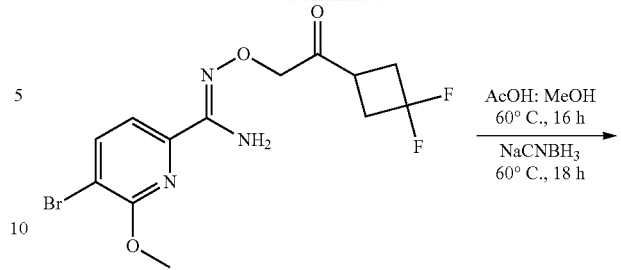

(Z)-5-bromo-N'-(2-(3,3-difluorocyclobutyl)-2-oxoethoxy)-6-methoxypicolinimidamide The title compound was prepared from 2-bromo-1-(3,3-difluorocyclobutyl) ethan-1-one according to the procedure for Example 43. LCMS: 42.9%; 379.6 (M+3); (column; Ascentis Express C-18 (50×3.0 mm, 2.7 μm); RT 2.40 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane (R$_f$: 0.6).

3-(5-bromo-6-methoxypyridin-2-yl)-5-(3,3-difluorocyclobutyl)-5,6-dihydro-4H-1,2,4-oxadiazine

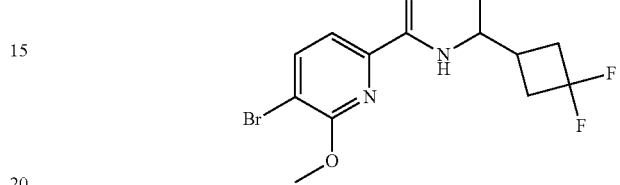

Example 179 (250 mg, crude) was prepared from (Z)-5-bromo-N'-(2-(3,3-difluorocyclobutyl)-2-oxoethoxy)-6-methoxypicolinimidamide according to the procedure for Example 56. LCMS: 47.6%; 361.8 (M+1); (column; Ascentis Express C-18 (50×3.0 mm, 2.7 μm); RT 2.54 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane (Rf: 0.4).

Example 180

Synthesis of 5-(3,3-difluorocyclobutyl)-3-(6-methoxy-5-(4-methyl-1H-imidazol-1-yl) pyridin-2-yl)-5,6-dihydro-4H-1,2,4-oxadiazine

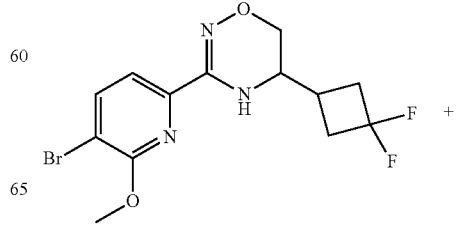

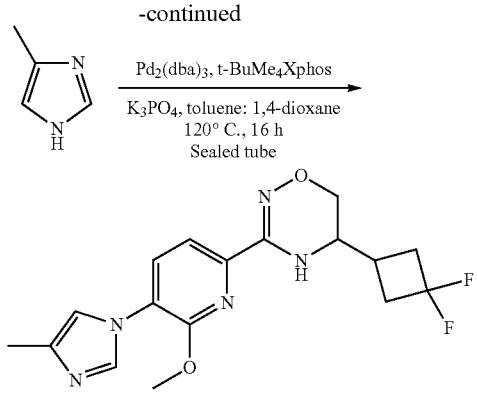

5-(3,3-difluorocyclobutyl)-3-(6-methoxy-5-(4-methyl-1H-imidazol-1-yl) pyridin-2-yl)-5,6-dihydro-4H-1,2,4-oxadiazine Example 179 (110 mg, 55%) was prepared from 3-(5-bromo-6-methoxypyridin-2-yl)-5-(3,3-difluorocyclobutyl)-5,6-dihydro-4H-1,2,4-oxadiazine according to the procedure for Example 49. Racemic compound of Example 180 was separated using a Chiralpak-IB column (250×20 mm, 5 μm) (40 mg loading; 0.1% DEA in n-Hexane: CH$_2$Cl$_2$:MeOH (80:20) (A:B: 80:20) as mobile phase; flow rate: 20 mL/min) to afford the compounds of Example 180A (Fraction (I) (−)) and Example 180B (Fraction (II) (+)).

Analytical conditions for Example 180A and Example 180B: HPLC (column; zorbax-SB-C-18 150×4.6 mm, 3.5 μm); mobile Phase: ACN: 0.05% Aq TFA; flow rate: 1.0 mL/min; Gradient program: T/B % 0.01/90, 2/90, 8/10, 15/10: diluent: CH$_3$CN:Water; Chiral HPLC: (Chiralpak-IB (250×4.6 mm, 5 μm; mobile phase (A) 0.1% DEA in n-Hexane (B) CH$_2$Cl$_2$:MeOH (80:20) (A:B; 80:20); flow Rate: 1.0 mL/min).

Example 180A, (−)-5-(3,3-difluorocyclobutyl)-3-(6-methoxy-5-(4-methyl-1H-imidazol-1-yl) pyridin-2-yl)-5,6-dihydro-4H-1,2,4-oxadiazine, fraction (I) (−): Mass (ESI): 364.1 [M+1]; HPLC (purity): 99.6%; RT 7.02 min; Chiral HPLC: 100%, RT=17.38 min, Optical rotation [α]$_D^{19.97}$: −36.35 (c=0.25, CH$_2$Cl$_2$).

Example 180B, (+)-5-(3,3-difluorocyclobutyl)-3-(6-methoxy-5-(4-methyl-1H-imidazol-1-yl) pyridin-2-yl)-5,6-dihydro-4H-1,2,4-oxadiazine, fraction (II) (+): $^1$H NMR (CD$_3$OD, 400 MHz): δ 7.97 (s, 1H), 7.85 (d, 1H), 7.57 (d, 1H), 7.21 (s, 1H), 4.13 (s, 3H), 4.00 (dd, 1H), 3.78-3.68 (m, 2H), 2.72-2.43 (m, 5H), 2.25 (s, 3H); Mass (ESI): 363.9 [M+1]; HPLC (purity): 99.8%, RT 7.03 min; Chiral HPLC: 98.9%, RT=22.17 min; Optical rotation [α]$_D^{20.01}$: +37.15 (c=0.25, CH$_2$Cl$_2$).

Example 181

Synthesis of 1-(benzo [d] thiazol-6-yl)-2-bromoethan-1-one

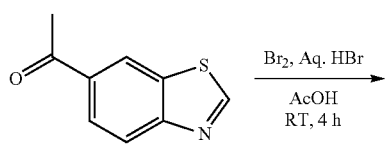

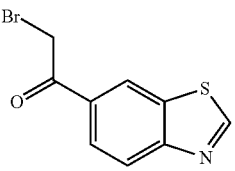

1-(benzo [d] thiazol-6-yl)-2-bromoethan-1-one

To a stirred solution of 1-(benzo [d] thiazol-6-yl) ethan-1-one (1 g, 6 mmol) in AcOH (3 mL) at room temperature under an argon atmosphere were added bromine (0.3 mL, 6 mmol) and 48% Aq.HBr (1 mL). The reaction mixture was stirred for 4 h at room temperature. After consumption of starting material (monitored by TLC), the reaction mixture was diluted with saturated sodium bicarbonate solution (30 mL) and extracted with EtOAc (2×30 mL). The combined organic extracts were dried over sodium sulfate, filtered and concentrated in vacuo. The crude material was purified by column chromatography using 2% EtOAc: Hexane to afford 1-(benzo [d] thiazol-6-yl)-2-bromoethan-1-one (1.1 g, 78%) as a pale yellow solid.

$^1$H NMR (DMSO-d$_6$, 500 MHz): δ 9.63 (s, 1H), 8.92 (s, 1H), 8.21 (d, 1H), 8.04 (d, 1H), 5.01 (s, 2H); LCMS: 85.1%; 257.7 (M+3); (column; Ascentis Express C-18 (50×3.0 mm, 2.7 nm); RT 2.10 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 5% EtOAc/Hexane (R$_f$: 0.4).

Example 182

Synthesis of 5-(benzo [d] thiazol-6-yl)-3-(5-bromo-6-methoxypyridin-2-yl)-5,6-dihydro-4H-1,2,4-oxadiazine

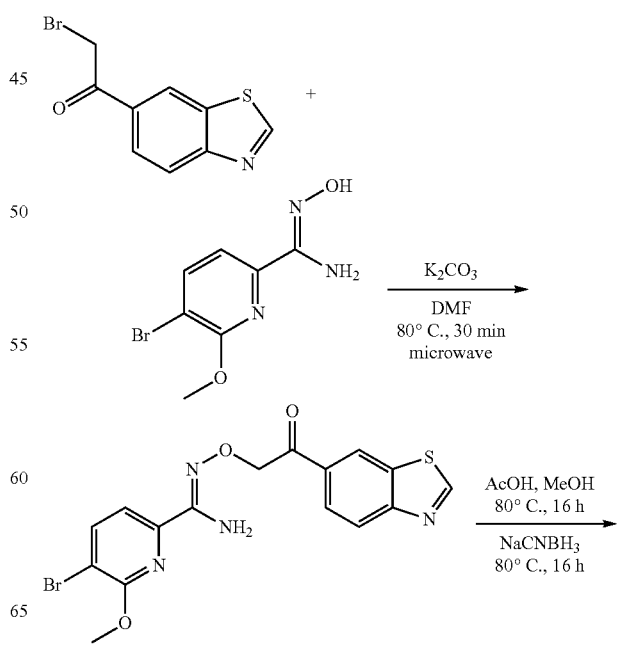

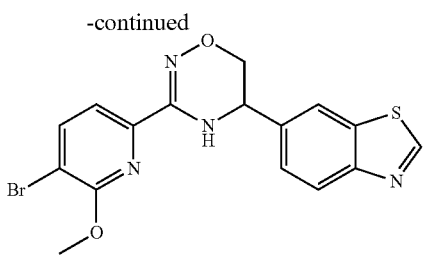

(Z)—N'-(2-(benzo [d] thiazol-6-yl)-2-oxoethoxy)-5-bromo-6-methoxypicolinimidamide The title compound was prepared from 1-(benzo [d] thiazol-6-yl)-2-bromoethan-1-one according to the procedure for Example 51. LCMS: 32.1%; 420.8 (M+1); (column; Ascentis Express C-18 (50×3.0 mm, 2.7 μm); RT 2.57 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 50% EtOAc/Hexane (R$_f$: 0.3).

5-(benzo [d] thiazol-6-yl)-3-(5-bromo-6-methoxy-pyridin-2-yl)-5,6-dihydro-4H-1,2,4-oxadiazine Example 182 (230 mg, 80%) was prepared from (Z)—N'-(2-(benzo [d] thiazol-6-yl)-2-oxoethoxy)-5-bromo-6-methoxypicolinimidamide according to the procedure for Example 56. LCMS: 84.1%; 406.6 (M+2); (column; Ascentis Express C-18 (50×3.0 mm, 2.7 μm); RT 2.42 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 50% EtOAc/Hexane (R$_f$: 0.6).

Example 183

Synthesis of 5-(benzo [d] thiazol-6-yl)-3-(6-methoxy-5-(4-methyl-1H-imidazol-1-yl) pyridin-2-yl)-5,6-dihydro-4H-1,2,4-oxadiazine

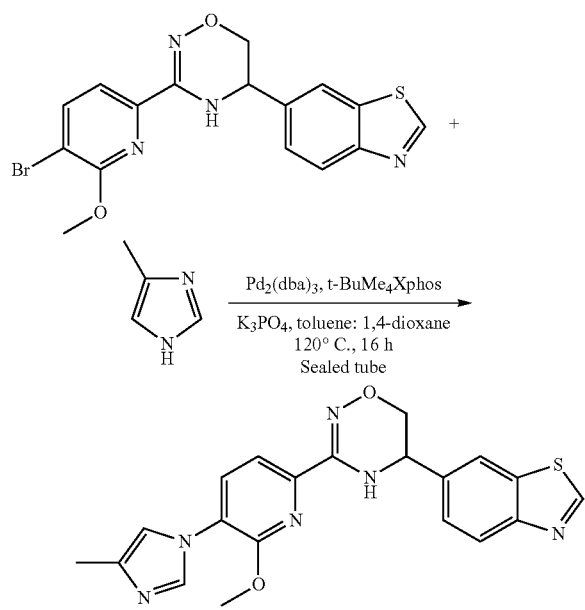

5-(benzo [d] thiazol-6-yl)-3-(6-methoxy-5-(4-methyl-1H-imidazol-1-yl)pyridin-2-yl)-5,6-dihydro-4H-1,2,4-oxadiazine Example 183 (120 mg, 48%) was prepared from 5-(benzo [d] thiazol-6-yl)-3-(5-bromo-6-methoxypyridin-2-yl)-5,6-dihydro-4H-1,2,4-oxadiazine according to the procedure for Example 49. Racemic compound of Example 183 was separated using a Chiralpak-IB column (250×20 mm, 5 μm) (25 mg loading; 0.1% DEA in n-Hexane: CH$_2$Cl$_2$:MeOH (80:20) (A:B: 75:25) as mobile phase; flow rate: 20 mL/min) to afford the compounds of Example 183A (Fraction (I) (−)) and Example 183B (Fraction (II) (+)).

Analytical conditions for Example 183A and Example 183B: HPLC (column; zorbax-SB-C-18 150×4.6 mm, 3.5μ); mobile Phase: ACN: 0.05% Aq TFA; flow rate: 1.0 mL/min; Gradient program: T/B % 0.01/90, 2/90, 8/10, 15/10: diluent: CH$_3$CN:Water; Chiral HPLC: (Chiralpak-IB (250×4.6 mm, 5 μm; mobile phase (A) 0.1% DEA in n-Hexane (B) CH$_2$Cl$_2$:MeOH (80:20) (A:B; 75:25); flow Rate: 1.0 mL/min).

Example 183A, (−)-5-(benzo [d] thiazol-6-yl)-3-(6-methoxy-5-(4-methyl-1H-imidazol-1-yl) pyridin-2-yl)-5,6-dihydro-4H-1,2,4-oxadiazine, fraction (I) (−): Mass (ESI): 407.3 [M+1]; HPLC (purity): 99.2%, RT 6.86 min; Chiral HPLC: 99.9%, RT=11.04 min; Optical rotation $[\alpha]_D^{19.98}$: −235.95 (c=0.25, CH$_2$Cl$_2$).

Example 183B, (+)-5-(benzo [d] thiazol-6-yl)-3-(6-methoxy-5-(4-methyl-1H-imidazol-1-yl) pyridin-2-yl)-5,6-dihydro-4H-1,2,4-oxadiazine, fraction (II) (+): $^1$H NMR (CD$_3$OD, 400 MHz): δ 9.24 (s, 1H), 8.10 (s, 1H), 8.08 (d, 1H), 7.99 (s, 1H), 7.90 (d, 1H), 7.68 (d, 1H), 7.62 (dd, 1H), 7.23 (s, 1H), 5.06 (t, 1H), 4.17 (dd, 1H), 4.09 (s, 3H), 4.04 (dd, 1H), 2.26 (s, 3H); Mass (ESI): 407.3 [M+1]; HPLC (purity): 94.5%; RT 6.84 min; Chiral HPLC: 99.5%, RT=13.62 min; Optical rotation $[\alpha]_D^{20.00}$: +216.33 (c=0.25, CH$_2$Cl$_2$).

Example 184

Synthesis of N'-hydroxy-6-methoxy-5-(4-methyl-1H-imidazol-1-yl) picolinimidamide

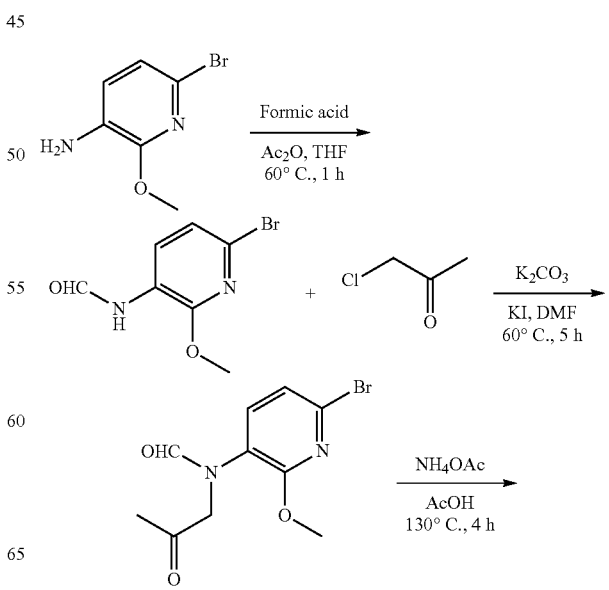

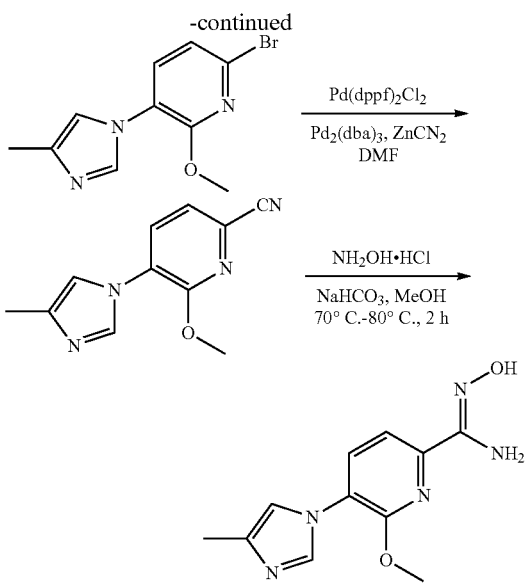

N-(6-bromo-2-methoxypyridin-3-yl) formamide

To the acetic anhydride (8.5 mL) at room temperature under an argon atmosphere was added formic acid (12.5 mL). The reaction mixture was stirred at room temperature for 30 min. Then 6-bromo-2-methoxypyridin-3-amine (5 g, 25 mmol) in THF (22 mL) at room temperature was added to the reaction mixture. The reaction mixture was stirred at 60° C. for 1 h. After consumption of starting material (monitored by TLC), the reaction mixture was diluted with ice cold water (500 mL) stirred for 30 min to afford the solid. The solid was collected by filtration and dried in vacuo to afford N-(6-bromo-2-methoxypyridin-3-yl) formamide (5.5 g, 98%) as an off-white solid.

$^1$H NMR (CDCl$_3$, 500 MHz): δ 8.52-8.50 (m, 2H), 7.61 (br s, 1H), 7.09 (d, 1H), 4.05 (s, 3H); LCMS: 99.8%; 232.7 (M+3); (column; Ascentis Express C-18 (50×3.0 mm, 2.7 μm); RT 2.05 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.3).

N-(6-bromo-2-methoxypyridin-3-yl)-N-(2-oxopropyl) formamide

To a stirred solution of N-(6-bromo-2-methoxypyridin-3-yl) formamide (27 g, 117 mmol) in DMF (216 mL) at room temperature under an argon atmosphere were added potassium carbonate (57 mg, 411 mmol), 1-chloropropan-2-one (28.8 g, 293 mmol) and potassium iodide (1.94 g, 12 mmol). The reaction mixture was stirred at 60° C. for 5 h. After consumption of starting material (monitored by TLC), the reaction mixture was diluted with ice cold water (200 mL) and stirred for 10 min to afford the solid. The solid was collected by filtration and dried in vacuo to afford N-(6-bromo-2-methoxypyridin-3-yl)-N-(2-oxopropyl) formamide (32 g, 94%) as an off-white solid. $^1$H NMR (CDCl$_3$, 500 MHz): δ 8.21 (s, 1H), 7.48 (d, 1H), 7.13 (d, 1H), 4.46 (s, 2H), 4.01 (s, 3H), 2.16 (s, 3H); LCMS: 99.4%; 288.7 (M+3); (column; Ascentis Express C-18 (50×3.0 mm, 2.7 μm); RT 2.05 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 30% EtOAc/Hexane (R$_f$: 0.2).

6-bromo-2-methoxy-3-(4-methyl-1H-imidazol-1-yl) pyridine

The mixture of ammonium acetate (43 g, 553 mmol) in AcOH (208 mL) at room temperature under an argon atmosphere was stirred for 30 min. Then N-(6-bromo-2-methoxypyridin-3-yl)-N-(2-oxopropyl) formamide (32 g, 111 mmol) was added to the reaction mixture at room temperature. The reaction mixture was stirred at 130° C. for 4 h. After consumption of starting material (monitored by TLC), the reaction mixture was diluted with ice cold water (200 mL), the aqueous layer was neutralized with 50% sodium hydroxide solution (200 mL) (pH'7) to afford the solid. The solid was collected by filtration, washed with ether (100 mL) and dried in vacuo to afford 6-bromo-2-methoxy-3-(4-methyl-1H-imidazol-1-yl) pyridine (17.5 g, 60%) as an off-white solid. $^1$H NMR (CDCl$_3$, 400 MHz): δ 7.72 (s, 1H), 7.39 (d, 1H), 7.16 (d, 1H), 6.91 (s, 1H), 4.03 (s, 3H), 2.29 (s, 3H); LCMS: 99.3%; 267.9 (M+1); (column; Ascentis Express C-18 (50×3.0 mm, 2.7 μm); RT 1.54 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 40% EtOAc/Hexane (R$_f$: 0.2).

6-methoxy-5-(4-methyl-M-imidazol-1-yl) picolinonitrile

To a stirred solution of 6-bromo-2-methoxy-3-(4-methyl-1H-imidazol-1-yl) pyridine (20 g, 74 mmol) in DMF (240 mL) at room temperature under an argon atmosphere were added Pd(dppf)$_2$Cl$_2$ (500 mg, 0.9 mmol), Pd$_2$(dba)$_3$ (682 mg, 0.7 mmol) and zinc cyanide (5.3 g, 45 mmol). The reaction mixture was stirred at 140° C. for 2 h. After consumption of starting material (monitored by TLC), the reaction mixture was diluted with 25% NH$_4$OH solution (240 mL) to afford the solid. The solid was collected by filtration and dried in vacuo to afford 6-methoxy-5-(4-methyl-1H-imidazol-1-yl) picolinonitrile (14 g, 88%) as a pale yellow solid.

$^1$H NMR (CDCl$_3$; 400 MHz): δ 7.89 (s, 1H), 7.63 (d, 1H), 7.43 (d, 1H), 7.01 (s, 1H), 4.09 (s, 3H), 2.30 (s, 3H); LCMS: 98.7%; 214.9 (M+1); (column; Ascentis Express C-18 (50× 3.0 mm, 2.7 μm); RT 1.19 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: EtOAc (R$_f$: 0.3).

N'-hydroxy-6-methoxy-5-(4-methyl-M-imidazol-1-yl) picolinimidamide

To a stirred solution of 6-methoxy-5-(4-methyl-1H-imidazol-1-yl) picolinonitrile (4 g, 19 mmol) in MeOH (100 mL) at room temperature under an argon atmosphere were added hydroxyl amine hydrochloride (1.7 g, 24 mmol) and sodium bicarbonate (2.35 g, 28 mmol). The reaction mixture was stirred at 70-80° C. for 2 h. After consumption of starting material (monitored by TLC), the volatiles were evaporated in vacuo. The residue was diluted with ice cold water (100 mL) to afford the solid. The solid was collected by filtration and dried in vacuo to afford N'-hydroxy-6-methoxy-5-(4-methyl-1H-imidazol-1-yl) picolinimidamide (4 g, 87%) as a pale yellow solid.

LCMS: 99.8%; 248 (M+1); (column; Ascentis Express C-18 (50×3.0 mm, 2.7 µm); RT 0.42 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: EtOAc (R$_f$: 0.2).

Example 185

Synthesis of (Z)—N'-(2, 2-dimethoxyethoxy)-6-methoxy-5-(4-methyl-1H-imidazol-1-yl) picolinimidamide

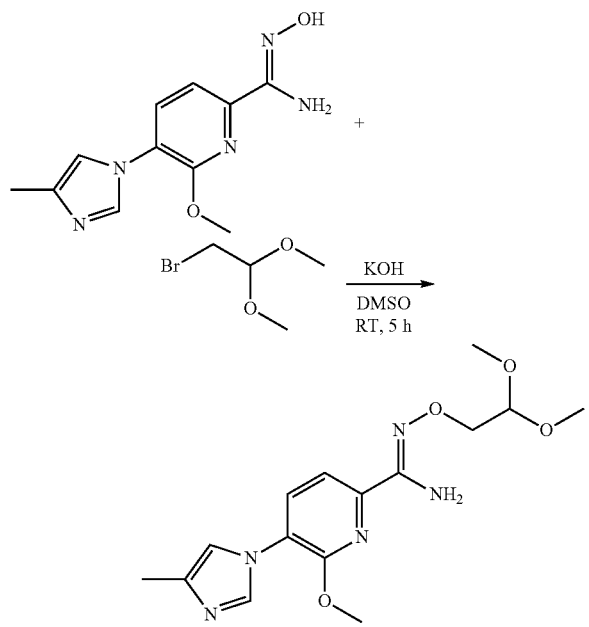

(Z)—N'-(2, 2-dimethoxyethoxy)-6-methoxy-5-(4-methyl-1H-imidazol-1-yl) picolinimidamide To a stirred solution of N'-hydroxy-6-methoxy-5-(4-methyl-1H-imidazol-1-yl) picolinimidamide (500 mg, 2 mmol) in DMSO (2.5 mL) at room temperature under an argon atmosphere were added potassium hydroxide (135 mg, 2 mmol) and 2-bromo-1, 1-dimethoxyethane (0.26 mL, 2 mmol). The reaction mixture was stirred at room temperature for 5 h. After consumption of starting material (monitored by TLC), the reaction mixture was diluted with water (20 mL) and extracted with EtOAc (2×20 mL). The combined organic extracts were dried over sodium sulfate, filtered and concentrated in vacuo to afford (Z)—N'-(2, 2-dimethoxyethoxy)-6-methoxy-5-(4-methyl-1H-imidazol-1-yl) picolinimidamide (500 mg, 74%) as a pale yellow solid. $^1$H NMR (CDCl$_3$, 400 MHz): δ 7.80 (br s, 1H), 7.67 (d, 1H), 7.55 (d, 1H), 6.97 (s, 1H), 5.48 (br s, 2H), 4.75 (t, 1H), 4.15 (d, 2H), 4.05 (s, 3H), 3.45 (s, 6H), 2.30 (s, 3H); LCMS: 97.6%; 335.9 (M+1); (column; Ascentis Express C-18 (50×3.0 mm, 2.7 µm); RT 1.56 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 5% MeOH/CH$_2$Cl$_2$ (R$_f$: 0.4).

Example 186

Synthesis of 5-(benzofuran-2-yl)-3-(6-methoxy-5-(4-methyl-1H-imidazol-1-yl) pyridin-2-yl)-5,6-dihydro-4H-1,2,4-oxadiazine

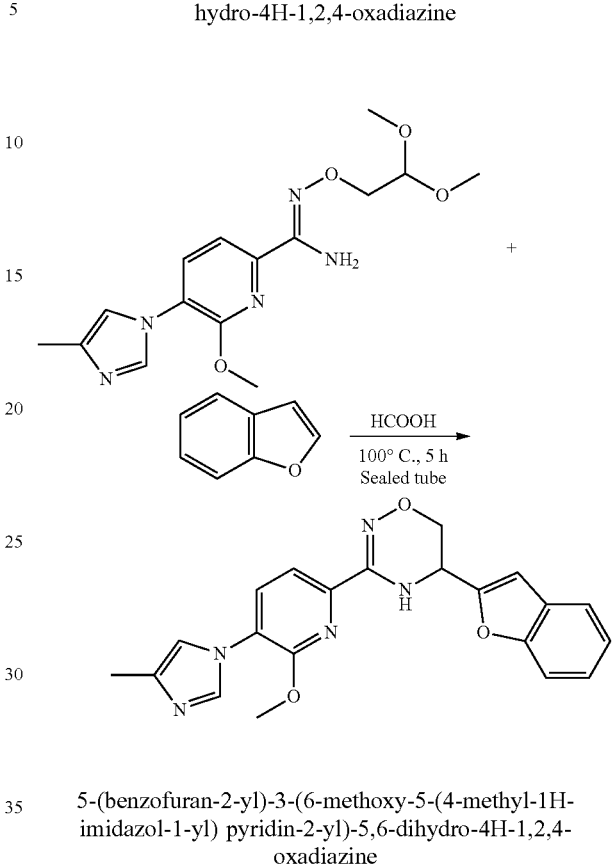

5-(benzofuran-2-yl)-3-(6-methoxy-5-(4-methyl-1H-imidazol-1-yl) pyridin-2-yl)-5,6-dihydro-4H-1,2,4-oxadiazine To a stirred solution of (Z)—N'-(2, 2-dimethoxyethoxy)-6-methoxy-5-(4-methyl-1H-imidazol-1-yl) picolinimidamide (2.5 g, 7 mmol) in formic acid (50 mL) at room temperature under an argon atmosphere was added benzofuran (2 g, 15 mmol). The reaction mixture was stirred at 100° C. for 5 h in a sealed tube. After consumption of starting material (monitored by TLC), the reaction mixture was diluted with saturated sodium bicarbonate solution (100 mL) and extracted with EtOAc (2×50 mL). The combined organic extracts were dried over sodium sulfate, filtered and concentrated in vacuo. The crude material was purified by column chromatography using 5% MeOH: CH$_2$Cl$_2$ to afford 5-(benzofuran-2-yl)-3-(6-methoxy-5-(4-methyl-1H-imidazol-1-yl) pyridin-2-yl)-5,6-dihydro-4H-1,2,4-oxadiazine (1.95 g, 67%) as an off-white solid.

Racemic compound of Example 186 was separated using a Chiralpak-IB column (250×20 mm, 5 µm) (45 mg loading; 0.1% DEA in n-Hexane: CH$_2$Cl$_2$:MeOH (50:50) (A:B: 85:15) as mobile phase; flow rate: 20 mL/min) to afford the compounds of Example 186A (Fraction (I) (−)) and Example 186B (Fraction (II) (+)).

Analytical conditions for Example 186A and Example 186B: HPLC (column; Zorbox SB-C-18 150×4.6 mm, 3.5 µm); mobile Phase: ACN: 0.05% Aq TFA; flow rate: 1.0 mL/min; Gradient program: T/B % 0.01/90, 2/90, 8/10, 15/10; diluent: CH$_3$CN:Water; Chiral HPLC: (Chiralpak-IB (250×4.6 mm, 5 µm; mobile phase (A) 0.1% DEA in n-Hexane (B) CH$_2$Cl$_2$:MeOH (50:50) (A:B; 85:15); flow Rate: 1.0 mL/min).

Example 186A, (−)-5-(benzofuran-2-yl)-3-(6-methoxy-5-(4-methyl-1H-imidazol-1-yl) pyridin-2-yl)-5,6-dihydro-4H-1,2,4-oxadiazine, fraction (I) (−): Mass (ESI): 390.3 [M+1]; HPLC (purity): 99.7%, RT 7.61 min; Chiral HPLC: 99.8%, RT=15.31 min; Optical rotation $[\alpha]_D^{20.00}$: −263.72 (c=0.25, CH$_2$Cl$_2$).

Example 186B, (+)-5-(benzofuran-2-yl)-3-(6-methoxy-5-(4-methyl-1H-imidazol-1-yl) pyridin-2-yl)-5,6-dihydro-4H-1,2,4-oxadiazine, fraction (II) (+): $^1$H NMR (CD$_3$OD, 400 MHz): δ 7.99 (s, 1H), 7.87 (d, 1H), 7.64 (d, 1H), 7.55 (d, 1H), 7.46 (d, 1H), 7.28-7.18 (m, 3H), 6.74 (s, 1H), 5.08 (t, 1H), 4.38 (dd, 1H), 4.12 (s, 3H), 4.09 (dd, 1H), 2.25 (s, 3H); Mass (ESI): 390.3 [M+1]; HPLC (purity): 98.0%, RT 7.62 min; Chiral HPLC: 99.8%, RT=19.72 min; Optical rotation $[\alpha]_D^{20.02}$: +261.24 (c=0.25, CH$_2$Cl$_2$).

Example 187

Synthesis of 3-(5-bromo-6-methoxypyridin-2-yl)-5,6-dihydro-4H-1,2,4-oxadiazin-5-ol

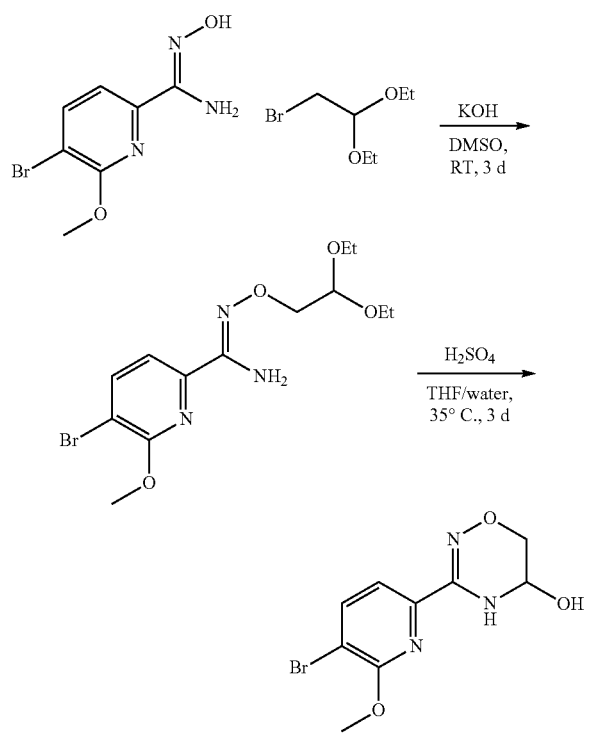

(Z)-5-bromo-N'-(2,2-diethoxyethoxy)-6-methoxypicolinimidamide

To a stirred solution of 5-bromo-N'-hydroxy-6-methoxypicolinimidamide (2.8 g, 11.4 mmol) in dimethylsulfoxide (28 mL) at room temperature were added potassium hydroxide (1.2 g, 20.5 mmol) and bromo acetaldehyde diethylacetal (2.5 g, 12.1 mmol) and the reaction mixture was stirred at room temperature for 3 days. The reaction mixture was diluted with dichloromethane and extracted with 0.1 M NaOH. The layers were separated and the water layer was extracted with dichloromethane twice. The combined organic extracts were washed three times with 0.1 M NaOH, dried over sodium sulfate, filtered and concentrated in vacuo to afford (Z)-5-bromo-N'-(2,2-diethoxyethoxy)-6-methoxypicolinimidamide (3.2 g, 80%) as a yellow oil that solidified upon standing. $^1$H NMR (CDCl$_3$, 300 MHz) δ 7.79 (d, J=8.0 Hz, 1H), 7.45 (d, J=8.0 Hz, 1H), 5.44 (s, 2H), 4.84 (t, J=5.3 Hz, 1H), 4.11 (d, J=5.3 Hz, 2H), 4.04 (s, 3H), 3.83-3.67 (m, 2H), 3.66-3.52 (m, 2H), 1.23 (t, J=7.1 Hz, 6H); LCMS: 97.8%; 362.0 (M+1); RT 2.24 min. (method A); TLC: 25% EtOAc/Heptane (R$_f$: 0.33).

3-(5-bromo-6-methoxypyridin-2-yl)-5,6-dihydro-4H-1,2,4-oxadiazin-5-ol

To a stirred solution of (Z)-5-bromo-N'-(2,2-diethoxyethoxy)-6-methoxypicolinimidamide (3.2 g, 8.9 mmol) in tetrahydrofuran (65 mL), a solution of sulfuric acid (3.8 mL, 71.3 mmol) in water (65 mL) was added and the mixture stirred for 3 days at 35° C. The reaction was quenched using solid NaHCO$_3$. The mixture was diluted with EtOAc and water and the layers were separated. The organic phase was washed with brine, dried over Na$_2$SO$_4$ and concentrated in vacuo to afford 3-(5-bromo-6-methoxypyridin-2-yl)-5,6-dihydro-4H-1,2,4-oxadiazin-5-ol (2.5 g, 97%) as a white solid.
$^1$H NMR (CDCl$_3$, 300 MHz) δ 7.85 (d, J=8.0 Hz, 1H), 7.53 (d, J=8.0 Hz, 1H), 7.16 (s, 1H), 5.27-5.15 (m, 1H), 4.18 (dt, J=11.4, 1.3 Hz, 1H), 4.04 (s, 3H), 3.69 (dd, J=11.4, 1.6 Hz, 1H), 2.95 (d, J=9.0 Hz, 1H); LCMS: 95.9%; 288.0 (M+1); RT 1.75 min (method A).

Example 188

Synthesis of 3-(5-bromo-6-methoxypyridin-2-yl)-5-(1-methyl-1H-indol-3-yl)-5,6-dihydro-4H-1,2,4-oxadiazine

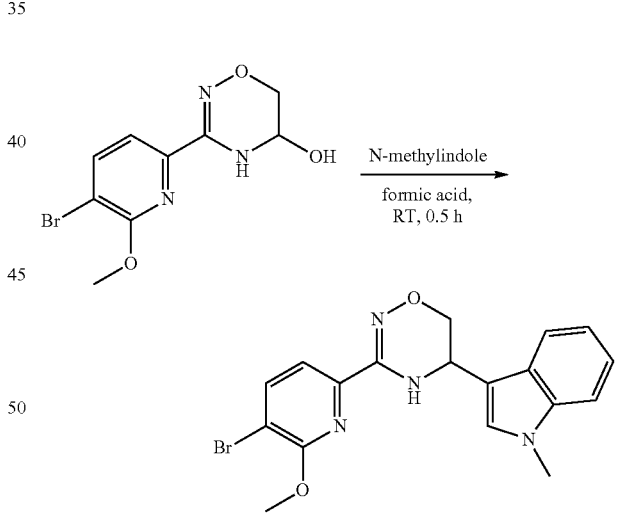

3-(5-bromo-6-methoxypyridin-2-yl)-5-(1-methyl-1H-indol-3-yl)-5,6-dihydro-4H-1,2,4-oxadiazine To a solution of 3-(5-bromo-6-methoxypyridin-2-yl)-5,6-dihydro-4H-1,2,4-oxadiazin-5-ol (50 mg, 0.2 mmol) in formic acid (1 mL), N-methylindole (45 mg, 0.3 mmol) was added and the mixture was stirred at room temperature for 0.5 hours. The mixture was concentrated in vacuo and the residue was purified by silica column chromatography [20% to 50% EtOAc in heptane] to afford 3-(5-bromo-6-methoxypyridin-2-yl)-5-(1-methyl-1H-indol-3-yl)-5,6-dihydro-4H-

1,2,4-oxadiazine (68 mg, 98%) as a white solid. 1H NMR (CDCl₃, 300 MHz) δ 7.88 (d, J=8.0 Hz, 1H), 7.68-7.59 (m, 2H), 7.34 (s, 1H), 7.31-7.23 (m, 1H), 7.16-7.08 (m, 2H), 6.51 (s, 1H), 5.13-5.06 (m, 1H), 4.40-4.32 (m, 1H), 3.98-3.87 (m, 4H), 3.80 (s, 3H); LCMS: 98.7%; 401.0 (M+1); RT 2.28 min (method A); TLC: 50% EtOAc/Heptane (R$_f$ 0.41).

Example 189

Synthesis of 3-(6-methoxy-5-(4-methyl-1H-imidazol-1-yl)pyridin-2-yl)-5-(1-methyl-1H-indol-3-yl)-5,6-dihydro-4H-1,2,4-oxadiazine

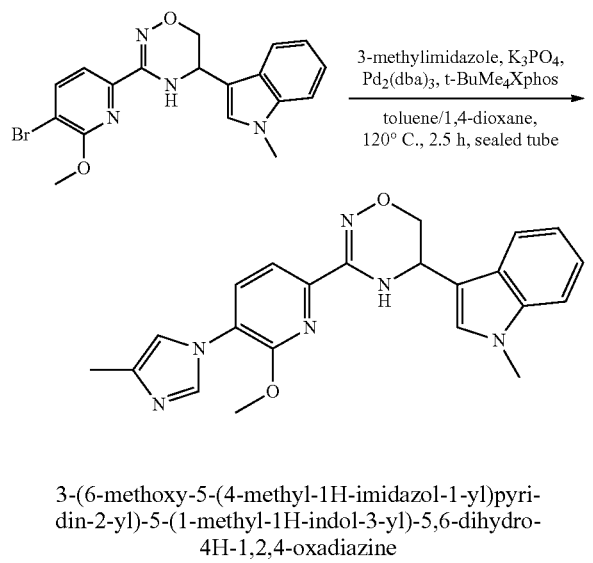

3-(6-methoxy-5-(4-methyl-1H-imidazol-1-yl)pyridin-2-yl)-5-(1-methyl-1H-indol-3-yl)-5,6-dihydro-4H-1,2,4-oxadiazine A dry microwave vial was charged with Pd₂(dba)₃ (30 mg, 0.03 mmol) and tert-butyl tetramethyl Xphos (32 mg, 0.07 mmol) and flushed with argon. Next, an argon-degassed solution of toluene/1,4-dioxane (2/1, 3 mL) was added at room temperature and the resultant suspension was thoroughly degassed with argon. The suspension was placed in a pre-heated oil bath at 120° C. and stirred for 3 minutes. A second dry microwave vial was charged with 3-(5-bromo-6-methoxypyridin-2-yl)-5-(1-methyl-1H-indol-3-yl)-5,6-dihydro-4H-1,2,4-oxadiazine (132 mg, 0.3 mmol), 4-methyl-1H-imidazole (54 mg, 0.7 mmol) and potassium phosphate (140 mg, 0.7 mmol) and flushed with argon. Next, an argon-degassed solution of toluene/1,4-dioxane (2/1, 6 mL) was added at room temperature and the resultant suspension was thoroughly degassed with argon. The catalyst premixture was added, the vial was capped and the resultant mixture was stirred at 120° C. for 2.5 hours. The reaction mixture was filtered, the filtrate was concentrated in vacuo and purified by silica column chromatography [0% to 20% methanol in EtOAc] to afford 3-(6-methoxy-5-(4-methyl-1H-imidazol-1-yl)pyridin-2-yl)-5-(1-methyl-1H-indol-3-yl)-5,6-dihydro-4H-1,2,4-oxadiazine (78 mg, 59%) as a yellow solid.

Racemic compound Example 189 was separated using a Chiralpak-AD-H column (250×20 mm, 5 µm) (45 mg loading; heptane:EtOH (60:40) as mobile phase; flow rate: 18 mL/min) to afford the compounds of Example 189A (Fraction (I) (+)) and Example 189B (Fraction (II) (−)).

Example 189A, (+)-3-(6-methoxy-5-(4-methyl-1H-imidazol-1-yl)pyridin-2-yl)-5-(1-methyl-1H-indol-3-yl)-5,6-dihydro-4H-1,2,4-oxadiazine, Fraction (I) (+): ¹H NMR (CDCl₃, 300 MHz) δ 7.86-7.80 (m, 2H), 7.69-7.65 (m, 1H), 7.63 (d, J=8.0 Hz, 1H), 7.40-7.33 (m, 1H), 7.31-7.27 (m, 1H), 7.17-7.09 (m, 2H), 7.00-6.95 (m, 1H), 6.53 (s, 1H), 5.16-5.07 (m, 1H), 4.37 (dd, J=10.9, 4.2 Hz, 1H), 3.95 (dd, J=10.9, 7.8 Hz, 1H), 3.91 (s, 3H), 3.81 (s, 3H), 2.30 (d, J=0.8 Hz, 3H); LCMS: 97.8%; 403.2 (M+1); RT 3.41 min (method B); Chiral HPLC: 100%; RT=10.75 min (Chiralpak-AD-H (250×4.6 mm, 5 µm; mobile phase heptane:EtOH (60:40); flow Rate: 1.0 mL/min); Optical rotation [α]$_D^{23.0}$: +116.19 (c=0.25, CH₂Cl₂).

Example 189B, (−)-3-(6-methoxy-5-(4-methyl-1H-imidazol-1-yl)pyridin-2-yl)-5-(1-methyl-1H-indol-3-yl)-5,6-dihydro-4H-1,2,4-oxadiazine, fraction (II) (−): LCMS: 96.3%; 403.2 (M+1); RT 3.40 min (method B); Chiral HPLC: 100%; RT=19.91 min (Chiralpak-AD-H (250×4.6 mm, 5 µm; mobile phase heptane:EtOH (60:40); flow Rate: 1.0 mL/min); Optical rotation [α]$_D^{23.0}$: −118.64 (c=0.25, CH₂Cl₂).

Example 190

Synthesis of 5-(5-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine

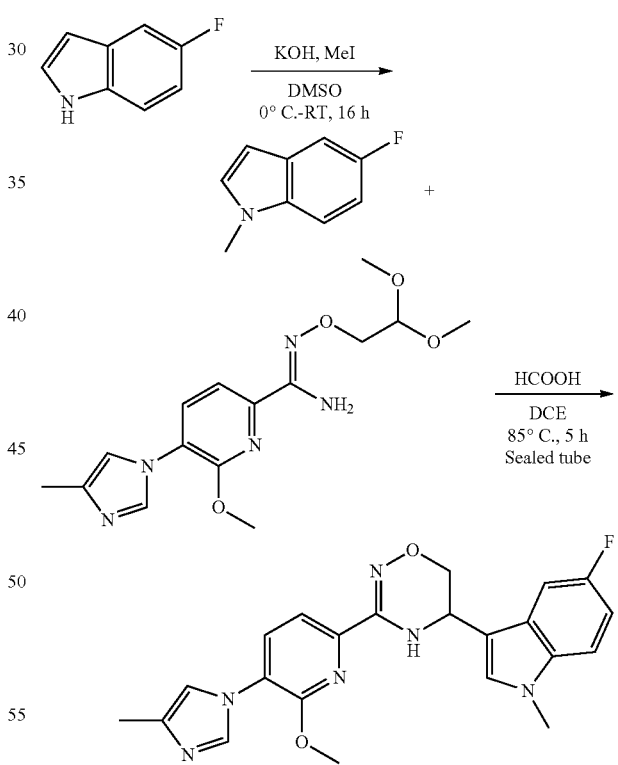

5-fluoro-1-methyl-1H-indole

To a stirred solution of 5-fluoro-1H-indole (5 g, 37 mmol) in DMSO (5 mL) at 0° C. under an argon atmosphere were added potassium hydroxide (3 g, 56 mmol) and methyl iodide (7.94 g, 56 mmol). The reaction mixture was warmed to room temperature and stirred for 16 h. After consumption of starting material (monitored by TLC), the reaction mixture was diluted with ice cold water (50 mL) and extracted with EtOAc (2×50 mL). The combined organic extracts were dried over sodium sulfate, filtered and concentrated in vacuo. The crude material was purified by column chromatography using 2% EtOAc: Hexane to afford 5-fluoro-1-methyl-1H-indole (3.5 g, 63%) as a pale yellow solid. $^1$H NMR (DMSO-$d_6$, 500 MHz): δ 7.55-7.51 (m, 1H), 7.31-7.28 (m, 2H), 6.90-6.85 (m, 1H), 6.42 (s, 1H), 3.75 (s, 3H); LCMS: 94.6%; 149.8 (M+1); (column; Ascentis Express C-18 (50×3.0 mm, 2.7 µm); RT 2.73 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 5% EtOAc/Hexane ($R_f$: 0.5).

5-(5-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine To a stirred solution of (Z)—N'-(2, 2-dimethoxyethoxy)-6-methoxy-5-(4-methyl-1H-imidazol-1-yl) picolinimidamide (310 mg, 1 mmol) in 1, 2-dichloro ethane (6.2 mL) at room temperature under an argon atmosphere were added 5-fluoro-1-methyl-1H-indole (274 mg, 2 mmol) and 85% formic acid (6.2 mL). The reaction mixture was stirred at 85° C. for 5 h in a sealed tube. After consumption of starting material (monitored by TLC), the reaction mixture was diluted with saturated sodium bicarbonate solution (20 mL) and extracted with EtOAc (2×20 mL). The combined organic extracts were dried over sodium sulfate, filtered and concentrated in vacuo. The crude material was purified by column chromatography using 2% MeOH: $CH_2Cl_2$ to afford 5-(5-fluoro-1-methyl-1H-indol-3-yl)-3-(6-methoxy-5-(4-methyl-1H-imidazol-1-yl) pyridin-2-yl)-5,6-dihydro-4H-1, 2,4-oxadiazine (220 mg, 56%) as an off-white solid.

Racemic compound of Example 190 was separated using a Chiralpak-IB column (250×20 mm, 5 µm) (20 mg loading; 0.1% DEA in n-Hexane: $CH_2Cl_2$:MeOH (50:50) (A:B: 80:20) as mobile phase; flow rate: 20 mL/min) to afford the compounds of Example 190A (Fraction (I) (−)) and Example 190B (Fraction (II) (+)).

Analytical conditions for Example 190A and Example 190B: HPLC (column; zorbax-SB-C-18 150×4.6 mm, 3.5µ); mobile Phase: ACN: 0.05% Aq TFA; flow rate: 1.0 mL/min; Gradient program: T/B % 0.01/90, 2/90, 8/10, 15/10: diluent: $CH_3CN$:Water; Chiral HPLC: (Chiralpak-IB (250× 4.6 mm, 5 µm; mobile phase (A) 0.1% DEA in n-Hexane (B) $CH_2Cl_2$:MeOH (50:50) (A:B; 80:20); flow Rate: 1.0 mL/min).

Example 190A, (−)-5-(5-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine, fraction (I) (−): Mass (ESI): 421.4 [M+1]; HPLC (purity): 99.6%, RT 7.53 min; Chiral HPLC: 100%, RT=15.56 min; Optical rotation $[\alpha]_D^{20.01}$: −102.20 (c=0.25, $CH_2Cl_2$).

Example 190B, (+)-5-(5-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine, fraction (II) (+): $^1$H NMR (CD$_3$OD, 400 MHz): δ 7.97 (s, 1H), 7.89 (d, 1H), 7.66 (d, 1H), 7.38-7.34 (m, 2H), 7.31 (s, 1H), 7.21 (s, 1H), 6.99-6.94 (m, 1H), 5.09 (t, 1H), 4.26-4.22 (m, 1H), 4.01 (s, 3H), 3.99-3.95 (m, 1H), 3.79 (s, 3H), 2.25 (s, 3H); Mass (ESI): 421.3 [M+1]; HPLC (purity): 99.4%, RT 7.51 min; Chiral HPLC: 99.3%, RT=18.65 min; Optical rotation $[\alpha]_D^{20.01}$: +80.01 (c=0.25, $CH_2Cl_2$).

Example 191

Synthesis of 5-(5-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine

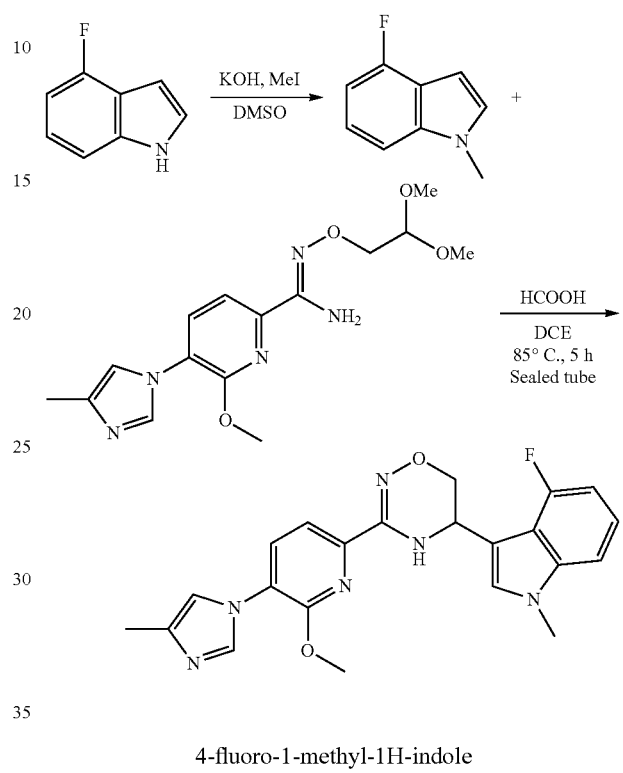

4-fluoro-1-methyl-1H-indole

To a stirred solution of 4-fluoro-1H-indole (5 g, 37 mmol) in DMSO (5 mL) at 0° C. under an argon atmosphere were added potassium hydroxide (3 g, 56 mmol) and methyl iodide (7.94 g, 56 mmol). The reaction mixture was warmed to room temperature and stirred for 16 h. After consumption of starting material (monitored by TLC), the reaction mixture was diluted with ice cold water (50 mL) and extracted with EtOAc (2×50 mL). The combined organic extracts were dried over sodium sulfate, filtered and concentrated in vacuo. The crude material was purified by column chromatography using 2% EtOAc: Hexane to afford 4-fluoro-1-methyl-1H-indole (3.8 g, 70%) as a pale yellow solid. $^1$H NMR (DMSO-$d_6$, 500 MHz): δ 7.58 (s, 1H), 7.42 (d, 1H), 7.39 (d, 1H), 7.12 (d, 1H), 6.40 (d, 1H), 3.77 (s, 3H); LCMS: 94.6%; 149.8 (M+1); (column; Ascentis Express C-18 (50× 3.0 mm, 2.7 µm); RT 2.73 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 10% EtOAc/Hexane ($R_f$: 0.5).

5-(4-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine To a stirred solution of (Z)—N'-(2, 2-dimethoxyethoxy)-6-methoxy-5-(4-methyl-1H-imidazol-1-yl) picolinimidamide (300 mg, 1 mmol) in 1, 2-dichloro ethane (6 mL) at room temperature under an argon atmosphere were added 4-fluoro-1-methyl-1H-indole (266 mg, 2 mmol) and 85% formic acid (6 mL). The reaction mixture was stirred at 85° C. for 5 h in a sealed tube. After consumption of starting material (monitored by TLC), the reaction mixture was diluted with saturated sodium bicarbonate solution (20 mL) and extracted with EtOAc (2×20 mL). The combined organic extracts were dried over sodium sulfate, filtered and concentrated in vacuo. The crude material was purified by column chromatography using 2% MeOH: CH₂Cl₂ to afford 5-(4-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine (250 mg, 66%) as an off-white solid.

Racemic compound of Example 191 was separated using a Chiralpak-IA column (250×20 mm, 5 μm) (250 mg loading; 0.1% DEA in n-Hexane: CH₂Cl₂:MeOH (80:20) (A:B: 80:20) as mobile phase; flow rate: 18 mL/min) to afford the compounds of Example 191A (Fraction (I) (+)) and Example 191A (Fraction (II) (−)).

Analytical conditions for Example 191A and Example 191A: HPLC (column; zorbax-SB-C-18 150×4.6 mm, 3.5μ); mobile Phase: ACN: 0.05% Aq TFA; flow rate: 1.0 mL/min; Gradient program: T/B % 0.01/90, 2/90, 8/10, 15/10: diluent: CH₃CN:Water; Chiral HPLC: (Chiralpak-IA (250× 4.6 mm, 5 μm; mobile phase (A) 0.1% DEA in n-Hexane (B) CH₂Cl₂:MeOH (80:20) (A:B; 80:20); flow Rate: 1.0 mL/min).

Example 191A, (+)-5-(4-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine, fraction (I) (+): ¹H NMR (CD₃OD, 400 MHz): δ 7.97 (s, 1H), 7.87 (d, 1H), 7.64 (d, 1H), 7.24-7.20 (m, 3H), 7.19-7.13 (m, 1H), 6.80-6.75 (m, 1H), 5.24 (t, 1H), 4.27-4.24 (m, 1H), 4.06 (d, 1H), 4.04 (s, 3H), 3.80 (s, 3H), 2.25 (s, 3H); Mass (ESI): 421.3 [M+1]; HPLC (purity): 99.4%, RT 7.69 min; Chiral HPLC: 100%, RT=10.55 min; Optical rotation $[\alpha]_D^{20.00}$: +120.09 (c=0.25, CH₂Cl₂).

Example 191A, (−)-5-(4-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine, fraction (II) (−): Mass (ESI): 421.3 [M+1]; HPLC (purity): 99.0%, RT 7.68 min; Chiral HPLC: 99.5%, RT=12.66 min; Optical rotation $[\alpha]_D^{20.00}$: −120.78 (c=0.25, CH₂Cl₂).

Example 192

Synthesis of 5-(6-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine

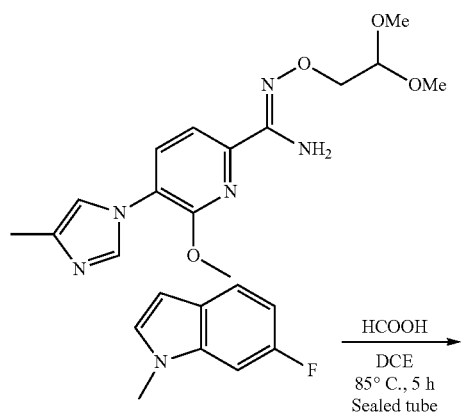

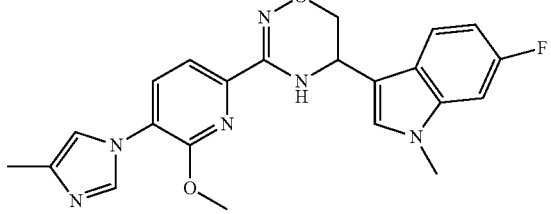

5-(4-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine To a stirred solution of (Z)—N'-(2, 2-dimethoxyethoxy)-6-methoxy-5-(4-methyl-1H-imidazol-1-yl) picolinimidamide (200 mg, 1 mmol) in 1,2-dichloro ethane (6 mL) at room temperature under an argon atmosphere were added 4-fluoro-1H-indole (266 mg, 2 mmol) and 85% formic acid (6 mL). The reaction mixture was stirred at 85° C. for 5 h in a sealed tube. After consumption of starting material (monitored by TLC), the reaction mixture was diluted with saturated sodium bicarbonate solution (20 mL) and extracted with EtOAc (2×20 mL). The combined organic extracts were dried over sodium sulfate, filtered and concentrated in vacuo. The crude material was purified by column chromatography using 2% MeOH: CH₂Cl₂ to afford 5-(4-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine (250 mg, 66%) as an off-white solid.

Racemic compound of Example 192 was separated using a Chiralpak-IB column (250×20 mm, 5 μm) (30 mg loading; 0.1% DEA in n-Hexane: CH₂Cl₂:MeOH (80:20) (A:B: 80:20) as mobile phase; flow rate: 20 mL/min) to afford the compounds of Example 192A (Fraction (I) (−)) and Example 192B (Fraction (II) (+)).

Analytical conditions for Example 192A and Example 192B: HPLC (column; zorbax-SB-C-18 150×4.6 mm, 3.5μ); mobile Phase: ACN: 0.05% Aq TFA; flow rate: 1.0 mL/min; Gradient program: T/B % 0.01/90, 2/90, 8/10, 15/10: diluent: CH₃CN:Water; Chiral HPLC: (Chiralpak-IA (250× 4.6 mm, 5 μm; mobile phase (A) 0.1% DEA in n-Hexane (B) CH₂Cl₂:MeOH (80:20) (A:B; 80:20); flow Rate: 1.0 mL/min).

Example 192A, (−)-5-(6-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine, fraction (I) (−): Mass (ESI): 421.3 [M+1]; HPLC (purity): 99.2%, RT 7.58 min; Chiral HPLC: 100%, RT=16.40 min; Optical rotation $[\alpha]_D^{19.99}$: −108.09 (c=0.25, CH₂Cl₂).

Example 192B, (+)-5-(6-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine, fraction (II) (−): ¹H NMR (CD₃OD, 400 MHz): δ 7.97 (s, 1H), 7.89 (d, 1H), 7.66 (d, 1H), 7.62 (dd, 1H), 7.25 (s, 1H), 7.21 (s, 1H), 7.13 (dd, 1H), 6.86-6.80 (m, 1H), 5.10 (t, 1H), 4.25 (dd, 1H), 3.99 (s, 3H), 3.98-3.94 (m, 1H), 3.76 (s, 3H), 2.25 (s, 3H); Mass (ESI): 421.3 [M+1]; HPLC (purity): 99.7%, RT 7.58 min; Chiral HPLC: 98.7%, RT=19.84 min; Optical rotation $[\alpha]_D^{20.00}$: +109.29 (c=0.25, CH₂Cl₂).

Example 193

Synthesis of 5-(5-chloro-1-methyl-1H-indol-3-yl)-3-(6-methoxy-5-(4-methyl-1H-imidazol-1-yl) pyridin-2-yl)-5,6-dihydro-4H-1,2,4-oxadiazine

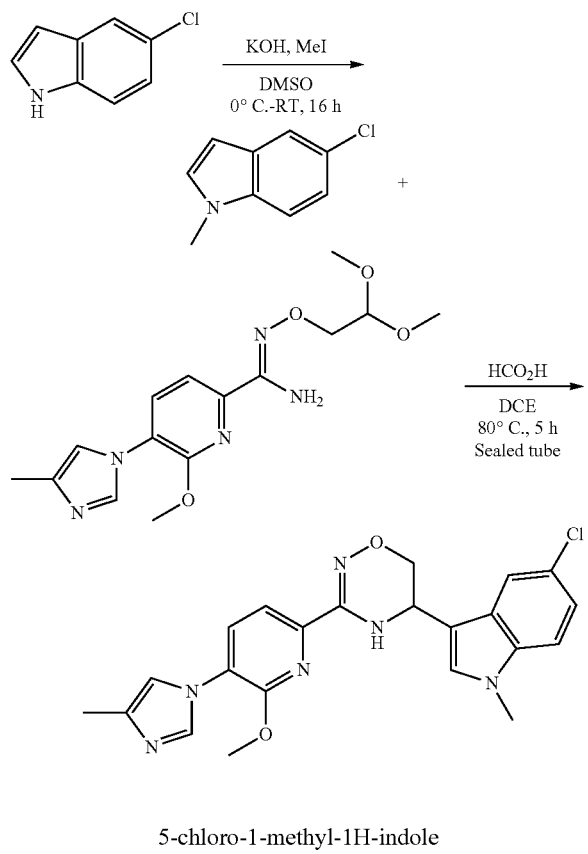

5-chloro-1-methyl-1H-indole

To a stirred solution of 5-chloro-1H-indole (1 g, 6 mmol) in DMSO (10 mL) at 0° C. under an argon atmosphere were added potassium hydroxide (550 mg, 10 mmol) and methyl iodide (1.4 g, 10 mmol). The reaction mixture was warmed to room temperature and stirred for 16 h. After consumption of starting material (monitored by TLC), the reaction mixture was diluted with ice cold water (30 mL) and extracted with EtOAc (2×30 mL). The combined organic extracts were dried over sodium sulfate, filtered and concentrated in vacuo. The crude material was purified by column chromatography using 2% EtOAc: Hexane to afford 5-chloro-1-methyl-1H-indole (740 mg, 68%) as colorless liquid.

$^1$H NMR (DMSO-$d_6$, 500 MHz): δ 7.58 (s, 1H), 7.42 (d, 1H), 7.39 (d, 1H), 7.12 (d, 1H), 6.40 (d, 1H), 3.77 (s, 3H); LCMS: 83.3%; 166.2 (M+1); (column; X-select CSH C-18 (50×3.0 mm, 2.5 μm); RT 3.93 min; mobile phase: 5 mM Aq NH$_4$OAc: ACN; T/B %: 0.01/10, 0.5/10, 3.5/90, 7/90; flow rate: 0.8 mL/min) (Gradient); TLC: 10% EtOAc/Hexane (R$_f$: 0.5).

5-(5-chloro-1-methyl-1H-indol-3-yl)-3-(6-methoxy-5-(4-methyl-1H-imidazol-1-yl) pyridin-2-yl)-5,6-dihydro-4H-1,2,4-oxadiazine To a stirred solution of (Z)—N'-(2,2-dimethoxyethoxy)-6-methoxy-5-(4-methyl-1H-imidazol-1-yl) picolinimidamide (300 mg, 1 mmol) in 1, 2-dichloro ethane (6 mL) at room temperature under an argon atmosphere were added 5-chloro-1-methyl-1H-indole (295 mg, 2 mmol) and 85% formic acid (6 mL). The reaction mixture was stirred at 80° C. for 5 h in a sealed tube. After consumption of starting material (monitored by TLC), the reaction mixture was diluted with water (20 mL) and extracted with EtOAc (2×20 mL). The combined organic extracts were dried over sodium sulfate, filtered and concentrated in vacuo. The crude material was purified by column chromatography using 2% MeOH: CH$_2$Cl$_2$ to afford 5-(5-chloro-1-methyl-1H-indol-3-yl)-3-(6-methoxy-5-(4-methyl-1H-imidazol-1-yl) pyridin-2-yl)-5,6-dihydro-4H-1,2,4-oxadiazine (200 mg, 52%) as an off-white solid.

Racemic compound of Example 193 was separated using a Chiralpak-IB column (250×20 mm, 5 μm) (30 mg loading; 0.1% DEA in n-Hexane: CH$_2$Cl$_2$:MeOH (80:20) (A:B: 80:20) as mobile phase; flow rate: 20 mL/min) to afford the compounds of Example 193A (Fraction (I) (−)) and Example 193B (Fraction (II) (+)).

Analytical conditions for Example 193A and Example 193B: HPLC (column; zorbax-SB-C-18 150×4.6 mm, 3.5μ); mobile Phase: ACN: 0.05% Aq TFA; flow rate: 1.0 mL/min; Gradient program: T/B % 0.01/90, 2/90, 8/10, 15/10: diluent: CH$_3$CN:Water; Chiral HPLC: (Chiralpak-IB (250× 4.6 mm, 5 μm; mobile phase (A) 0.1% DEA in n-Hexane (B) CH$_2$Cl$_2$:MeOH (80:20) (A:B; 80:20); flow Rate: 1.0 mL/min).

Example 193A, (−)-5-(5-chloro-1-methyl-1H-indol-3-yl)-3-(6-methoxy-5-(4-methyl-1H-imidazol-1-yl) pyridin-2-yl)-5,6-dihydro-4H-1,2,4-oxadiazine, fraction (I) (−): Mass (ESI): 437 [M+1]; HPLC (purity): 98.3%; RT 7.74 min; Chiral HPLC: 100%, RT=14.58 min; Optical rotation $[α]_D^{20.00}$: −95.07 (C=0.25, CH$_2$Cl$_2$).

Example 193B, (+)-5-(5-chloro-1-methyl-1H-indol-3-yl)-3-(6-methoxy-5-(4-methyl-1H-imidazol-1-yl) pyridin-2-yl)-5,6-dihydro-4H-1,2,4-oxadiazine, fraction (II) (+): $^1$H NMR (CD$_3$OD, 400 MHz): δ 7.97 (s, 1H), 7.89 (d, 1H), 7.68 (s, 1H), 7.66 (d, 1H), 7.38 (d, 1H), 7.31 (s, 1H), 7.22 (s, 1H), 7.16 (dd, 1H), 5.11 (t, 1H), 4.23 (dd, 1H), 4.02 (s, 3H), 3.98 (dd, 1H), 3.80 (s, 3H), 2.25 (s, 3H); Mass (ESI): 437 [M+1]; HPLC (purity): 99.1%; RT 7.73 min; Chiral HPLC: 99.2%, RT=16.64 min; Optical rotation $[α]_D^{20.00}$: +97.95 (c=0.5, CH$_2$Cl$_2$).

Example 194

Synthesis of 5-(6-chloro-1-methyl-1H-indol-3-yl)-3-(6-methoxy-5-(4-methyl-1H-imidazol-1-yl) pyridin-2-yl)-5,6-dihydro-4H-1,2,4-oxadiazine

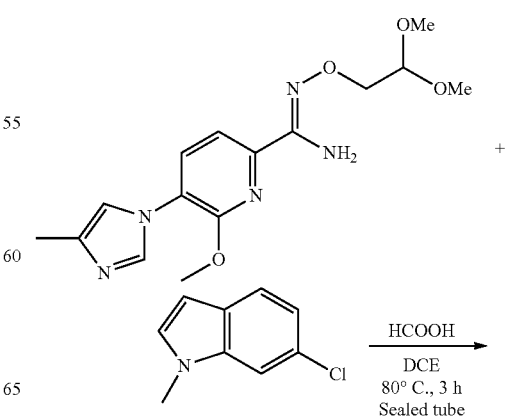

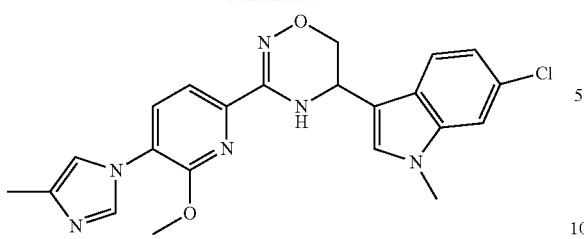

5-(6-chloro-1-methyl-1H-indol-3-yl)-3-(6-methoxy-5-(4-methyl-1H-imidazol-1-yl) pyridin-2-yl)-5,6-dihydro-4H-1,2,4-oxadiazine To a stirred solution of (Z)—N'-(2, 2-dimethoxyethoxy)-6-methoxy-5-(4-methyl-1H-imidazol-1-yl) picolinimidamide (250 mg, 1 mmol) in 1, 2-dichloro ethane (5 mL) under an argon atmosphere were added 6-chloro-1-methyl-1H-indole (248 mg, 2 mmol) and 85% formic acid (5 mL) at room temperature. The reaction mixture was stirred at 80° C. for 3 h in a sealed tube. After consumption of starting material (monitored by TLC), the reaction mixture was diluted with saturated sodium bicarbonate solution (20 mL) and extracted with EtOAc (2×20 mL). The combined organic extracts were dried over sodium sulfate, filtered and concentrated in vacuo. The crude material was purified by column chromatography using 1-5% MeOH: $CH_2Cl_2$ to afford 5-(6-chloro-1-methyl-1H-indol-3-yl)-3-(6-methoxy-5-(4-methyl-1H-imidazol-1-yl) pyridin-2-yl)-5,6-dihydro-4H-1,2,4-oxadiazine (320 mg, 82%) as an off-white solid.

Racemic compound of Example 194 was separated using a Chiralpak-IA column (250×20 mm, 5 µm) (35 mg loading; 0.1% DEA in n-Hexane: $CH_2Cl_2$:MeOH (50:50) (A:B: 85:15) as mobile phase; flow rate: 20 mL/min) to afford the compounds of Example 194A (Fraction (I) (+)) and Example 194B (Fraction (II) (−)).

Analytical conditions for Example 194A and Example 194B: HPLC (column; zorbax-SB-C-18 150×4.6 mm, 3.5µ); mobile Phase: ACN: 0.05% Aq TFA; flow rate: 1.0 mL/min; Gradient program: T/B % 0.01/90, 2/90, 8/10, 15/10: diluent: $CH_3CN$:Water; Chiral HPLC: (Chiralpak-IA (250× 4.6 mm, 5 µm; mobile phase (A) 0.1% DEA in n-Hexane (B) $CH_2Cl_2$:MeOH (50:50) (A:B; 85:15); flow Rate: 1.0 mL/min).

Example 194A, (+)-5-(6-chloro-1-methyl-1H-indol-3-yl)-3-(6-methoxy-5-(4-methyl-1H-imidazol-1-yl) pyridin-2-yl)-5,6-dihydro-4H-1,2,4-oxadiazine, fraction (I) (+): $^1$H NMR ($CD_3OD$, 400 MHz): δ 7.98 (s, 1H), 7.90 (d, 1H), 7.67 (d, 1H), 7.64 (d, 1H), 7.45 (s, 1H), 7.29 (s, 1H), 7.22 (s, 1H), 7.05 (dd, 1H), 5.13 (t, 1H), 4.25 (dd, 1H), 4.01 (s, 3H), 4.00-3.96 (m, 1H), 3.79 (s, 3H), 2.26 (s, 3H); Mass (ESI): 437 [M+1]; HPLC (purity): 99.4%, RT 7.82 min; Chiral HPLC: 100%, RT=16.96 min; Optical rotation $[α]_D^{20.00}$: +102.70 (c=0.25, $CH_2Cl_2$).

Example 194B, (−)-5-(6-chloro-1-methyl-1H-indol-3-yl)-3-(6-methoxy-5-(4-methyl-1H-imidazol-1-yl) pyridin-2-yl)-5,6-dihydro-4H-1,2,4-oxadiazine, fraction (II) (−): Mass (ESI): 437 [M+1]; HPLC (purity): 98.4%, RT 7.81 min; Chiral HPLC: 98.5%, RT=19.70 min; Optical rotation $[α]_D^{20.04}$: −113.42 (c=0.25, $CH_2Cl_2$).

Example 195

Synthesis of 3-(6-methoxy-5-(4-methyl-1H-imidazol-1-yl) pyridin-2-yl)-5-(1-methyl-1H-pyrrolo [2,3-h] pyridin-3-yl)-5,6-dihydro-4H-1,2,4-oxadiazine

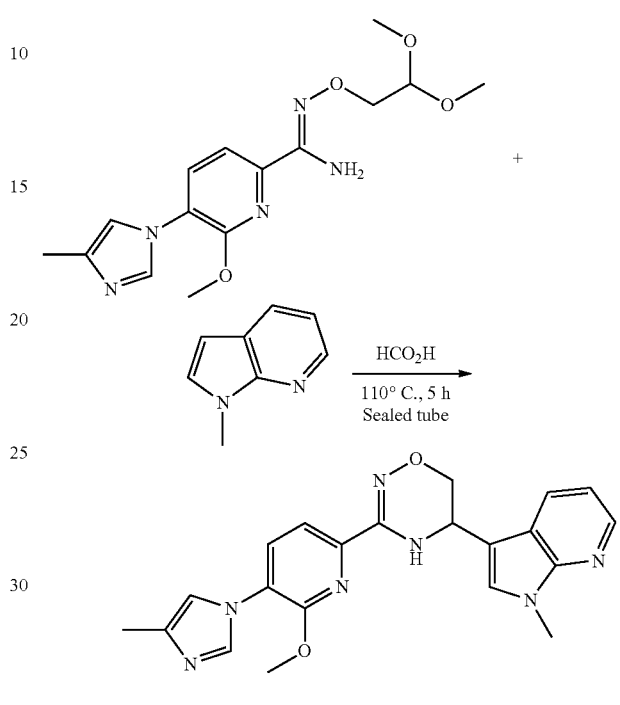

3-(6-methoxy-5-(4-methyl-1H-imidazol-1-yl) pyridin-2-yl)-5-(1-methyl-1H-pyrrolo [2,3-b] pyridin-3-yl)-5,6-dihydro-4H-1,2,4-oxadiazine To a stirred solution of (Z)—N'-(2, 2-dimethoxyethoxy)-6-methoxy-5-(4-methyl-1H-imidazol-1-yl) picolinimidamide (300 mg, 1 mmol) in formic acid (6 mL) at room temperature under an argon atmosphere was added 1-methyl-1H-pyrrolo [2,3-b] pyridine (236 mg, 2 mmol). The reaction mixture was stirred at 110° C. for 5 h in a sealed tube. After consumption of starting material (monitored by TLC), the reaction mixture was diluted with saturated sodium bicarbonate solution (20 mL) and extracted with EtOAc (2×20 mL). The combined organic extracts were dried over sodium sulfate, filtered and concentrated in vacuo. The crude material was purified by column chromatography using 2-5% MeOH: $CH_2Cl_2$ to afford 3-(6-methoxy-5-(4-methyl-1H-imidazol-1-yl) pyridin-2-yl)-5-(1-methyl-1H-pyrrolo [2,3-b] pyridin-3-yl)-5,6-dihydro-4H-1,2,4-oxadiazine (180 mg, 56%) as white solid.

Racemic compound of Example 195 was separated using a Chiralpak-IB column (250×20 mm, 5 µm) (20 mg loading; 0.1% DEA in n-Hexane: $CH_2Cl_2$:MeOH (50:50) (A:B: 80:20) as mobile phase; flow rate: 18 mL/min) to afford the compounds of Example 195A (Fraction (I) (−)) and Example 195B (Fraction (II) (+)).

Analytical conditions for Example 195A and Example 195B: HPLC (column; zorbax-SCB-C-18 150×4.6 mm, 3.5µ); mobile Phase: ACN: 0.05% Aq TFA; flow rate: 1.0 mL/min; Gradient program: T/B % 0.01/90, 2/90, 8/10, 15/10: diluent: $CH_3CN$:Water; Chiral HPLC: (Chiralpak-IB (250×4.6 mm, 5 µm; mobile phase (A) 0.1% DEA in n-Hexane (B) CH$_2$Cl$_2$:MeOH (50:50) (A:B; 80:20); flow Rate: 1.0 mL/min).

Example 195A, (−)-3-(6-methoxy-5-(4-methyl-1H-imidazol-1-yl) pyridin-2-yl)-5-(1-methyl-1H-pyrrolo [2,3-b] pyridin-3-yl)-5,6-dihydro-4H-1,2,4-oxadiazine, fraction (I) (−): Mass (ESI): 404.4 [M+1]; HPLC (purity): 97.3%, RT 6.25 min; Chiral HPLC: 99.8%, RT=14.08 min; Optical rotation $[\alpha]_D^{19.98}$: −121.68 (c=0.25, CH$_2$Cl$_2$).

Example 195B, (+)-3-(6-methoxy-5-(4-methyl-1H-imidazol-1-yl) pyridin-2-yl)-5-(1-methyl-1H-pyrrolo [2,3-b] pyridin-3-yl)-5,6-dihydro-4H-1,2,4-oxadiazine, fraction (II) (+): $^1$H NMR (CD$_3$OD, 400 MHz): δ 8.27 (dd, 1H), 8.12 (dd, 1H), 7.97 (s, 1H), 7.89 (d, 1H), 7.67 (d, 1H), 7.45 (s, 1H), 7.21 (s, 1H), 7.11 (dd, 1H), 5.11 (t, 1H), 4.23 (dd, 1H), 4.07-4.00 (m, 4H), 3.87 (s, 3H), 2.25 (s, 3H); Mass (ESI): 404.3 [M+1]; HPLC (purity): 98.0%, RT 6.31 min; Chiral HPLC: 99.6%, RT=18.93 min; Optical rotation $[\alpha]_D^{20.00}$: +103.69 (c=0.25, CH$_2$Cl$_2$).

Example 196

Synthesis of 5-(4-fluoro-1-isopropyl-1H-indol-3-yl)-3-(6-methoxy-5-(4-methyl-1H-imidazol-1-yl) pyridin-2-yl)-5,6-dihydro-4H-1,2,4-oxadiazine

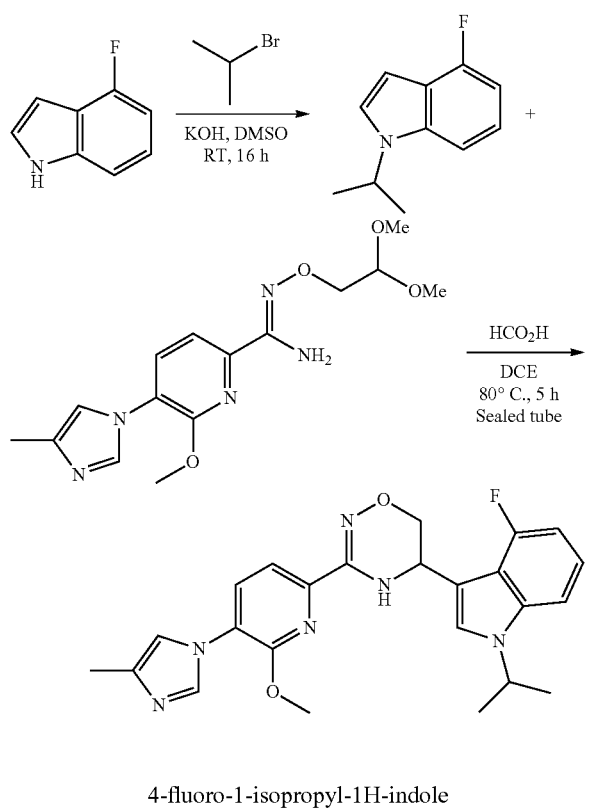

4-fluoro-1-isopropyl-1H-indole

To a stirred solution of 4-fluoro-1H-indole (500 mg, 4 mmol) in DMSO (2.5 mL) at room temperature under an argon atmosphere were added potassium hydroxide (308 mg, 5 mmol) and 2-bromopropane (683 g, 5 mmol). The reaction mixture was stirred at room temperature for 16 h. After consumption of starting material (monitored by TLC), the reaction mixture was diluted with water (20 mL) and extracted with EtOAc (2×20 mL). The combined organic extracts were dried over sodium sulfate, filtered and concentrated in vacuo. The crude material was purified by column chromatography using 2-3% EtOAc: Hexane to afford 4-fluoro-1-isopropyl-1H-indole (450 mg, 98%) as colorless liquid.

$^1$H NMR (DMSO-d$_6$, 500 MHz): δ 7.53 (s, 1H), 7.35 (d, 1H), 7.20-7.16 (m, 1H), 6.80-6.75 (m, 1H), 6.50 (s, 1H), 4.80-4.75 (m, 1H), 1.43 (d, 6H); LCMS: 61.1%; 177.8 (M+1); (column; Ascentis Express C-18 (50×3.0 mm, 2.7 µm); RT 2.90 min; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 10% EtOAc/Hexane (R$_f$: 0.5).

5-(4-fluoro-1-isopropyl-1H-indol-3-yl)-3-(6-methoxy-5-(4-methyl-1H-imidazol-1-yl) pyridin-2-yl)-5,6-dihydro-4H-1,2,4-oxadiazine To a stirred solution of (Z)—N'-(2, 2-dimethoxyethoxy)-6-methoxy-5-(4-methyl-1H-imidazol-1-yl) picolinimidamide (250 mg, 0.7 mmol) in 1,2-dichloro ethane (5 mL) at room temperature under an argon atmosphere were added 4-fluoro-1-isopropyl-1H-indole (260 mg, 1 mmol) and 85% formic acid (5 mL). The reaction mixture was stirred at 80° C. for 5 h in a sealed tube. After consumption of starting material (monitored by TLC), the reaction mixture was diluted with saturated sodium bicarbonate solution (20 mL) and extracted with EtOAc (2×20 mL). The combined organic extracts were dried over sodium sulfate, filtered and concentrated in vacuo. The crude material was purified by column chromatography using 2-3% MeOH: CH$_2$Cl$_2$ to afford 5-(4-fluoro-1-isopropyl-1H-indol-3-yl)-3-(6-methoxy-5-(4-methyl-1H-imidazol-1-yl) pyridin-2-yl)-5,6-dihydro-4H-1,2,4-oxadiazine (180 mg, 54%) as white solid.

Racemic compound of Example 196 was separated using a Chiralpak-ADH column (250×20 mm, 5 µm) (25 mg loading; 0.1% DEA in n-Hexane: EtOH (A:B: 75:25) as mobile phase; flow rate: 18 mL/min) to afford the compounds of Example 196A (Fraction (I) (+)) and Example 196B (Fraction (II) (−)).

Analytical conditions for Example 196A and Example 196B: HPLC (column; zorbax-SB-C-18 150×4.6 mm, 3.5µ); mobile Phase: ACN: 0.05% Aq TFA; flow rate: 1.0 mL/min; Gradient program: T/B % 0.01/90, 2/90, 8/10, 15/10: diluent: CH$_3$CN:Water; Chiral HPLC: (Chiralpak-ADH (250×4.6 mm, 5 µm; mobile phase (A) 0.1% DEA in n-Hexane (B) EtOH (A:B; 75:25); flow Rate: 1.0 mL/min).

Example 196A, (+)-5-(4-fluoro-1-isopropyl-1H-indol-3-yl)-3-(6-methoxy-5-(4-methyl-1H-imidazol-1-yl) pyridin-2-yl)-5,6-dihydro-4H-1,2,4-oxadiazine, fraction (I) (+): $^1$H NMR (CD$_3$OD, 400 MHz): δ 7.91 (s, 1H), 7.85 (d, 1H), 7.62 (d, 1H), 7.39 (s, 1H), 7.29 (d, 1H), 7.20 (s, 1H), 7.18-7.11 (m, 1H), 6.78-6.73 (m, 1H), 5.24 (t, 1H), 4.75-4.70 (m, 1H), 4.27 (dd, 1H), 4.05-4.00 (m, 4H), 2.21 (s, 3H), 1.50 (d, 6H); Mass (ESI): 449.4 [M+1]; HPLC (purity): 97.7%, RT 7.95 min; Chiral HPLC: 99.4%, RT=9.03 min; Optical rotation $[\alpha]_D^{20.00}$: +79.29 (c=0.25, CH$_2$Cl$_2$).

Example 196B, (−)-5-(4-fluoro-1-isopropyl-1H-indol-3-yl)-3-(6-methoxy-5-(4-methyl-1H-imidazol-1-yl) pyridin-2-yl)-5,6-dihydro-4H-1,2,4-oxadiazine, fraction (II) (−): Mass (ESI): 449.4 [M+1]; HPLC (purity): 97.5%, RT 7.95 min; Chiral HPLC: 99.7%, RT=12.48 min; Optical rotation $[\alpha]_D^{19.99}$: −89.45 (c=0.25, CH$_2$Cl$_2$).

Example 197

Synthesis of 3-(6-methoxy-5-(4-methyl-1H-imidazol-1-yl)pyridin-2-yl)-5-(1-methyl-6-(trifluoromethyl)-1H-indol-3-yl)-5,6-dihydro-4H-1,2,4-oxadiazine

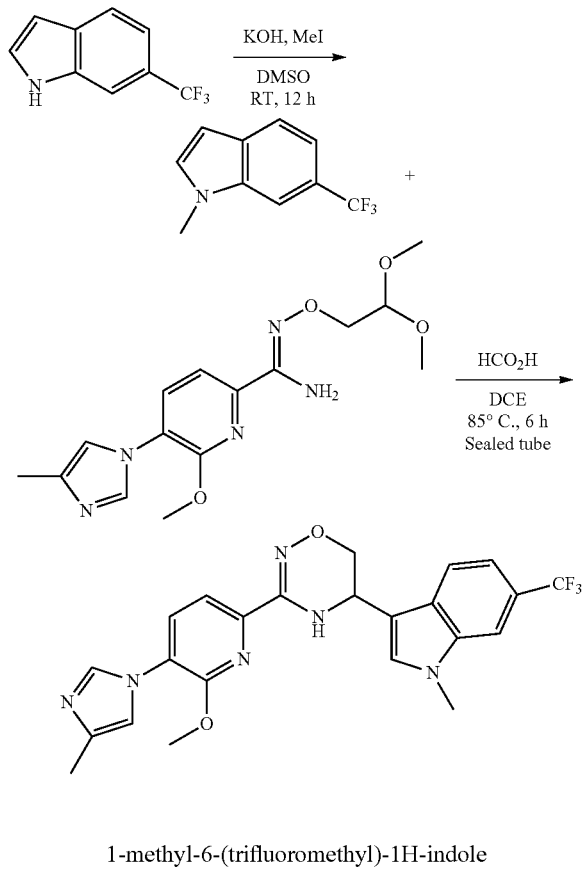

1-methyl-6-(trifluoromethyl)-1H-indole

To a stirred solution of 6-(trifluoromethyl)-1H-indole (2 g, 11 mmol) in DMSO (20 mL) at room temperature under an argon atmosphere were added potassium hydroxide (908 mg, 16 mmol) and methyl iodide (1.01 mL, 16 mmol). The reaction mixture was stirred at room temperature for 12 h. After consumption of starting material (monitored by TLC), the reaction mixture was diluted with water (50 mL) and extracted with EtOAc (2×50 mL). The combined organic extracts were dried over sodium sulfate, filtered and concentrated in vacuo to afford 1-methyl-6-(trifluoromethyl)-1H-indole (2 g, 93%) as colorless liquid. $^1$H NMR (CDCl$_3$, 500 MHz): δ 7.71 (d, 1H), 7.62 (s, 1H), 7.35 (d, 1H), 7.21 (d, 1H), 6.55 (d, 1H), 3.86 (s, 3H); LCMS: 99.7%; 199.8 (M+1); (column; Ascentis Express C-18 (50×3.0 mm, 2.7 μm); RT 2.78 mm; mobile phase: 0.025% Aq TFA+5% ACN: ACN+5% 0.025% Aq TFA; T/B %: 0.01/5, 0.5/5, 3/100, 5/100; flow rate: 1.2 mL/min) (Gradient); TLC: 20% EtOAc/Hexane (R$_f$: 0.5).

3-(6-methoxy-5-(4-methyl-1H-imidazol-1-yl) pyridin-2-yl)-5-(1-methyl-6-(trifluoromethyl)-1H-indol-3-yl)-5,6-dihydro-4H-1,2,4-oxadiazine To a stirred solution of (Z)—N'-(2-dimethoxyethoxy)-6-methoxy-5-(4-methyl-1H-imidazol-1-yl) picolinimidamide (300 mg, 1 mmol) in 1, 2-dichloro ethane (6 mL) at room temperature under an argon atmosphere were added 1-methyl-6-(trifluoromethyl)-1H-indole (355 mg, 2 mmol) and 85% formic acid (6 mL). The reaction mixture was stirred at 85° C. for 6 h in a sealed tube. After consumption of starting material (monitored by TLC), the reaction mixture was diluted with saturated sodium bicarbonate solution (20 mL) and extracted with EtOAc (2×20 mL). The combined organic extracts were dried over sodium sulfate, filtered and concentrated in vacuo. The crude material was purified by column chromatography using 1-5% MeOH: CH$_2$Cl$_2$ to afford 3-(6-methoxy-5-(4-methyl-1H-imidazol-1-yl) pyridin-2-yl)-5-(1-methyl-6-(trifluoromethyl)-1H-indol-3-yl)-5,6-dihydro-4H-1,2,4-oxadiazine (200 mg, 48%) as white solid.

Racemic compound of Example 197 was separated using a Chiralpak-IA column (250×4.6 mm, 5μ) (30 mg loading; CO$_2$: 1% MeOH in NH$_3$: CH$_2$Cl$_2$ (80:20) ISO-25% as mobile phase; flow rate: 3 mL/min) to afford the compounds of Example 197A (Fraction (I) (+)) and Example 197B (Fraction (II) (−)).

Analytical conditions for Example 197A and Example 197B: HPLC (column; zorbax-SB-C-18 150×4.6 mm, 3.5μ); mobile Phase: ACN: 0.05% Aq TFA; flow rate: 1.0 mL/min; Gradient program: T/B % 0.01/90, 2/10, 8/10, 15/10: diluent: CH$_3$CN:Water; Chiral HPLC: (Chiralpak-IA (250× 4.6 mm, 5 μm; mobile phase (A) 0.1% DEA in n-Hexane (B) CH$_2$Cl$_2$:MeOH (50:50) (A:B; 80:20); flow Rate: 1.0 mL/min).

Example 197A, (+)-3-(6-methoxy-5-(4-methyl-1H-imidazol-1-yl) pyridin-2-yl)-5-(1-methyl-6-(trifluoromethyl)-1H-indol-3-yl)-5,6-dihydro-4H-1,2,4-oxadiazine, fraction (I) (+): $^1$H NMR (CD$_3$OD, 400 MHz): δ 8.27 (dd, 1H), 8.12 (dd, 1H), 7.97 (s, 1H), 7.89 (d, 1H), 7.67 (d, 1H), 7.45 (s, 1H), 7.21 (s, 1H), 7.11 (dd, 1H), 5.14 (t, 1H), 4.23 (dd, 1H), 4.07-4.00 (m, 4H), 3.87 (s, 3H), 2.25 (s, 3H); Mass (ESI): 471.3 [M+1]; HPLC (purity): 99.7%; RT 7.93 min; Chiral HPLC: 100%, RT=8.52 min; Optical rotation $[\alpha]_D^{19.99}$: +126.43 (c=0.25, CH$_2$Cl$_2$).

Example 197B, (−)-3-(6-methoxy-5-(4-methyl-1H-imidazol-1-yl) pyridin-2-yl)-5-(1-methyl-6-(trifluoromethyl)-1H-indol-3-yl)-5,6-dihydro-4H-1,2,4-oxadiazine, fraction (II) (−): Mass (ESI): 471.4 [M+1]; HPLC (purity): 99.4%; RT 7.94 min; Chiral HPLC: 98.1%, RT=9.53 min; Optical rotation $[\alpha]_D^{20.00}$: −118.80 (c=0.25, CH$_2$Cl$_2$).

Example 198

Synthesis of 3-(5-bromo-6-methoxypyridin-2-yl)-4-methyl-5,6-dihydro-4H-1,2,4-oxadiazin-5-ol

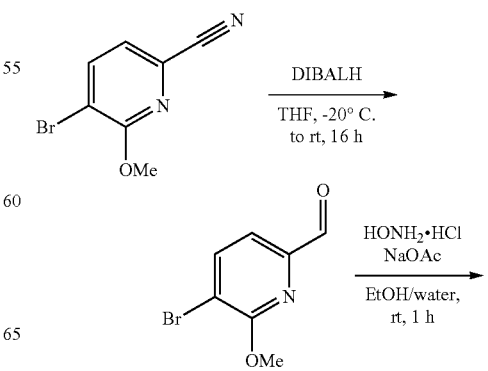

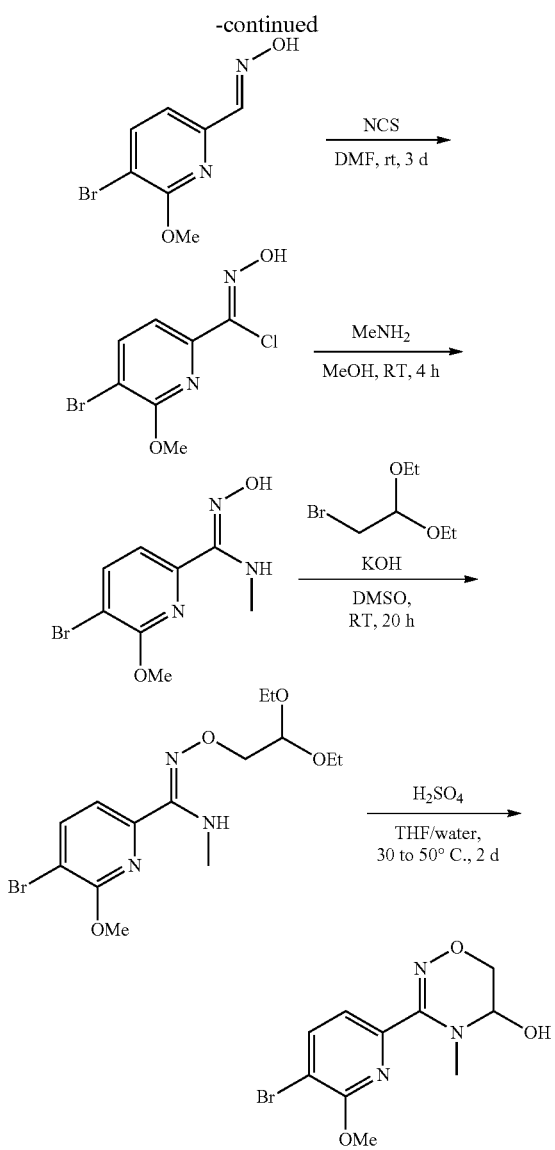

5-bromo-6-methoxypicolinaldehyde

To a stirred solution of 5-bromo-6-methoxypicolinonitrile (2.5 g, 11.7 mmol) in dry tetrahydrofuran (50 mL) at −20° C. under nitrogen atmosphere, DIBAL-H (1 M in hexanes, 17.6 mL, 17.60 mmol) was added and the mixture was allowed to warm to room temperature overnight. The mixture was quenched using aqueous HCl (2M, 15 mL), stirred at rt for 15 minutes, then partially concentrated under reduced pressure. The residue was diluted aqueous HCl (2M, 50 mL) and extracted with EtOAc (3×50 mL). The combined organic layers were washed with 2 M HCl, brine, dried over sodium sulfate and concentrated in vacuo to afford 5-bromo-6-methoxypicolinaldehyde (411 mg, 48%) as a brown solid. $^1$H NMR (CDCl$_3$, 300 MHz) δ 9.94 (d, J=0.7 Hz, 1H), 7.98 (dd, J=7.7, 0.7 Hz, 1H), 7.45 (d, J=7.7 Hz, 1H), 4.12 (s, 3H).

5-bromo-6-methoxypicolinaldehyde oxime

To a stirred suspension of 5-bromo-6-methoxypicolinaldehyde (1.9 g, 8.6 mmol) in EtOH/water (22 mL, 10/1) hydroxylamine hydrochloride (1.2 g, 17.2 mmol) and sodium acetate (2.1 g, 25.8 mmol) were added. The mixture was stirred at room temperature for 1 hour, concentrated in vacuo, water (40 mL) was added and it was stirred for 1 hour. The solids were filtered off and washed with water to afford 5-bromo-6-methoxypicolinaldehyde oxime (1.8 g, 92%) as a beige solid. $^1$H NMR (CDCl$_3$, 300 MHz) δ 8.08 (s, 1H), 7.80 (d, J=7.9 Hz, 1H), 7.54 (s, 1H), 7.21 (d, J=7.9 Hz, 1H), 4.03 (s, 3H).

(Z)-5-bromo-N-hydroxy-6-methoxypicolinimidoyl chloride

To a solution of 5-bromo-6-methoxypicolinaldehyde oxime (1.8 g, 7.9 mmol) in DMF (80 mL), NCS (1.2 g, 8.7 mmol) was added and the mixture was stirred at room temperature for 3 days. The mixture was diluted with EtOAc (200 mL), washed with water (3×150 mL), brine (3×75 mL), dried on sodium sulfate and concentrated in vacuo to afford (Z)-5-bromo-N-hydroxy-6-methoxypicolinimidoyl chloride (2.0 g, 95%) as a pale yellow solid. $^1$H NMR (DMSO-d6, 300 MHz) δ 12.75 (s, 1H), 8.11 (d, J=8.0 Hz, 1H), 7.41 (d, J=8.0 Hz, 1H), 3.98 (s, 3H).

(Z)-5-bromo-N'-hydroxy-6-methoxy-N-methylpicolinimidamide

To a stirred solution of methanamine (2M in THF, 10 mL, 20.00 mmol) in methanol (50 mL), a solution of (Z)-5-bromo-N-hydroxy-6-methoxypicolinimidoyl chloride (1.0 g, 3.8 mmol) in methanol (40 mL) was added over 4 hours using a syringe pump. The mixture was concentrated in vacuo and purified by silica column chromatography [20% EtOAc in heptane] to afford (Z)-5-bromo-N'-hydroxy-6-methoxy-N-methylpicolinimidamide (596 mg, 61%) as a white solid. LCMS: 100%; 260.0 (M+1); RT 1.84 min. (method A); TLC: 20% EtOAc/Heptane (R$_f$: 0.32).

5-bromo-N'-(2,2-diethoxyethoxy)-6-methoxy-N-methylpicolinimidamide

To a stirred solution of (Z)-5-bromo-N'-hydroxy-6-methoxy-N-methylpicolinimidamide (596 mg, 2.3 mmol) in dimethylsulfoxide (15 mL) at room temperature were added potassium hydroxide (231 mg, 4.1 mmol) and bromo acetaldehyde diethylacetal (523 mg, 2.5 mmol) and the reaction mixture was stirred at room temperature for 20 hours. The reaction mixture was diluted with dichloromethane and extracted with 0.1 M NaOH. The layers were separated and the water layer was extracted with dichloromethane twice. The combined organic extracts were washed twice with 0.1 M NaOH, dried over sodium sulfate, filtered, concentrated in vacuo and the residue was purified by silica column chromatography [15% EtOAc in heptane] to afford (Z)-5-bromo-N'-(2,2-diethoxyethoxy)-6-methoxy-N-methylpicolinimidamide (411 mg, 48%) as a colorless oil. LCMS: 100%; 376.0 (M+1); RT 2.25 min. (method A); TLC: 15% EtOAc/Heptane (R$_f$: 0.30).

3-(5-bromo-6-methoxypyridin-2-yl)-4-methyl-5,6-dihydro-4H-1,2,4-oxadiazin-5-ol

To a stirred solution of (Z)-5-bromo-N'-(2,2-diethoxyethoxy)-6-methoxy-N-methylpicolinimidamide (400 mg, 1.1 mmol) in tetrahydrofuran (10 mL), a solution of sulfuric acid (0.28 mL, 5.3 mmol) in water (10 mL) was added and the mixture stirred for 1 day at 30° C. Additional sulfuric acid (0.28 mL, 5.3 mmol) was added and the mixture was stirred for another day at 50° C. The reaction was quenched using solid NaHCO₃. The mixture was extracted with EtOAc twice, the organic phase was washed with brine, dried over Na₂SO₄ and concentrated in vacuo to afford 3-(5-bromo-6-methoxypyridin-2-yl)-4-methyl-5,6-dihydro-4H-1,2,4-oxadiazin-5-ol (321 mg, 100%) as a white solid. LCMS: 74.9%; 302.0 (M+1); RT 1.69 min. (method A).

Example 199

Synthesis of 3-(5-bromo-6-methoxypyridin-2-yl)-4-methyl-5-(1-methyl-1H-indol-3-yl)-5,6-dihydro-4H-1,2,4-oxadiazine

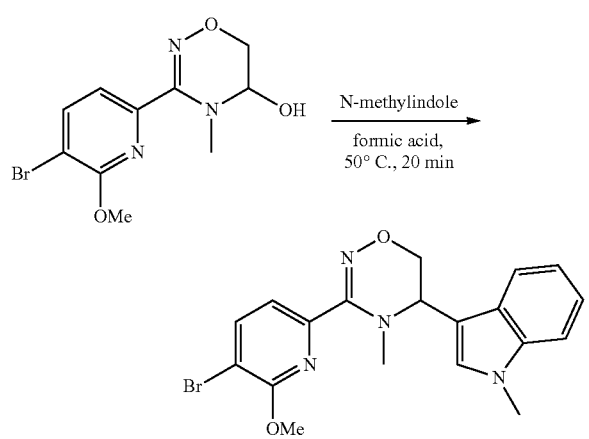

3-(5-bromo-6-methoxypyridin-2-yl)-4-methyl-5-(1-methyl-1H-indol-3-yl)-5,6-dihydro-4H-1,2,4-oxadiazine To a stirred solution of 3-(5-bromo-6-methoxypyridin-2-yl)-4-methyl-5,6-dihydro-4H-1,2,4-oxadiazin-5-ol (321 mg, 1.1 mmol) in formic acid (10 mL), N-methylindole (213 mg, 1.6 mmol) was added and the mixture stirred at 50° C. for 20 minutes. The mixture was concentrated in vacuo and the residue was purified by silica column chromatography [15% EtOAc in heptane] to afford 3-(5-bromo-6-methoxypyridin-2-yl)-4-methyl-5-(1-methyl-1H-indol-3-yl)-5,6-dihydro-4H-1,2,4-oxadiazine (154 mg, 35%) as a beige solid. LCMS: 93.2%; 415.0 (M+1); RT 2.21 min (method A); TLC: 15% EtOAc/Heptane (R$_f$: 0.35).

Example 200

Synthesis of 3-(6-methoxy-5-(4-methyl-1H-imidazol-1-yl)pyridin-2-yl)-4-methyl-5-(1-methyl-1H-indol-3-yl)-5,6-dihydro-4H-1,2,4-oxadiazine

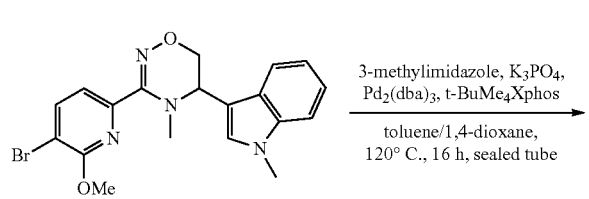

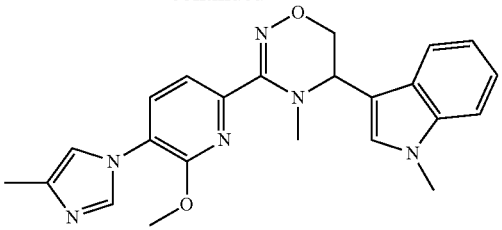

3-(6-methoxy-5-(4-methyl-1H-imidazol-1-yl)pyridin-2-yl)-4-methyl-5-(1-methyl-1H-indol-3-yl)-5,6-dihydro-4H-1,2,4-oxadiazine Example 200 (37 mg, 25%) was prepared from 3-(5-bromo-6-methoxypyridin-2-yl)-4-methyl-5-(1-methyl-1H-indol-3-yl)-5,6-dihydro-4H-1,2,4-oxadiazine according to the procedure for Example 189. Racemic compound Example 200 was separated using a Chiralpak-AD-H column (250×20 mm, 5 μm) (18 mg loading; heptane:EtOH (50:50) as mobile phase; flow rate: 18 mL/min) to afford the compounds of Example 200A (Fraction (I) (+)) and Example 200B (Fraction (II) (−)).

Example 200A, (+)-3-(6-methoxy-5-(4-methyl-1H-imidazol-1-yl)pyridin-2-yl)-4-methyl-5-(1-methyl-1H-indol-3-yl)-5,6-dihydro-4H-1,2,4-oxadiazine, fraction (I) (+): $^1$H NMR (CDCl₃, 400 MHz) δ 8.05-7.98 (m, 1H), 7.90-7.83 (m, 1H), 7.65 (d, J=7.7 Hz, 1H), 7.47 (d, J=7.8 Hz, 1H), 7.41-7.35 (m, 1H), 7.34-7.29 (m, 1H), 7.17 (s, 1H), 7.17-7.12 (m, 1H), 7.05-7.00 (m, 1H), 4.95 (dd, J=7.6, 5.0 Hz, 1H), 4.31 (dd, J=11.6, 5.0 Hz, 1H), 4.25 (dd, J=11.6, 7.6 Hz, 1H), 4.05 (s, 3H), 3.83 (s, 3H), 2.82 (s, 3H), 2.33 (d, J=0.9 Hz, 3H); LCMS: 100%; 417.2 (M+1); RT 3.40 min (method D); Chiral HPLC: 100%; RT=11.67 min (Chiralpak-AD-H (250×4.6 mm, 5 μm; mobile phase heptane:EtOH (60:40); flow Rate: 1.0 mL/min); Optical rotation [α]$_D^{21.7}$: +110.26 (c=0.07, CH₂Cl₂).

Example 200B, (−)-3-(6-methoxy-5-(4-methyl-1H-imidazol-1-yl)pyridin-2-yl)-4-methyl-5-(1-methyl-1H-indol-3-yl)-5,6-dihydro-4H-1,2,4-oxadiazine, fraction (II) (−): LCMS: 100%; 417.2 (M+1); RT 3.40 min (method D); Chiral HPLC: 100%; RT=43.44 min (Chiralpak-AD-H (250×4.6 mm, 5 μm; mobile phase heptane:EtOH (60:40); flow Rate: 1.0 mL/min); Optical rotation [α]$_D^{21.7}$: −190.48 (c=0.06, CH₂Cl₂).

Example 201

Synthesis of 3-(5-bromo-6-methoxypyridin-2-yl)-5,6-dihydro-4H-1,2,4-oxadiazine-5-carboxylic acid

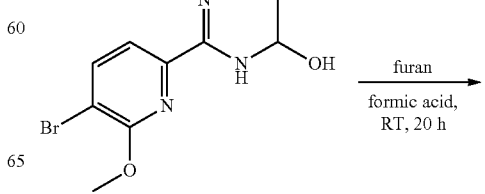

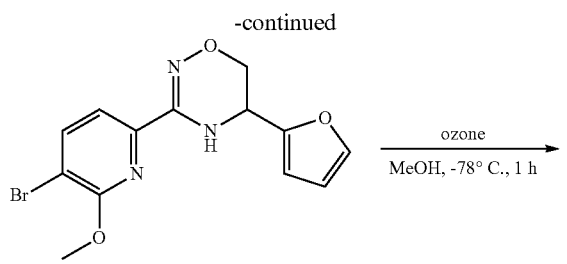

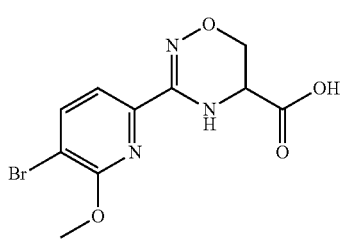

3-(5-bromo-6-methoxypyridin-2-yl)-5-(furan-2-yl)-
5,6-dihydro-4H-1,2,4-oxadiazine To a stirred solution of 3-(5-bromo-6-methoxypyridin-2-yl)-5,6-dihydro-4H-1,2,4-oxadiazin-5-ol (2.5 g, 8.6 mmol) in formic acid (50 mL), furan (2.5 mL, 34.3 mmol) was added and the mixture stirred at room temperature for 20 hours. The mixture was concentrated in vacuo and the residue was purified by silica column chromatography [10% to 20% EtOAc in heptane] to afford 3-(5-bromo-6-methoxypyridin-2-yl)-5-(furan-2-yl)-5,6-dihydro-4H-1,2,4-oxadiazine (2.5 g, 86%) as a white solid. $^1$H NMR (CDCl$_3$, 300 MHz) δ 7.86 (d, J=8.0 Hz, 1H), 7.56 (d, J=8.0 Hz, 1H), 7.42 (dd, J=1.8, 0.8 Hz, 1H), 6.52 (s, 1H), 6.39 (dd, J=3.3, 1.8 Hz, 1H), 6.36-6.31 (m, 1H), 4.91-4.84 (m, 1H), 4.31-4.22 (m, 1H), 4.02 (s, 3H), 3.98 (dd, J=11.0, 6.1 Hz, 1H); LCMS: 99.1%; 338.0 (M+1); RT 2.15 min (method A); TLC: 30% EtOAc/Heptane (R$_f$: 0.4).

3-(5-bromo-6-methoxypyridin-2-yl)-5,6-dihydro-4H-1,2,4-oxadiazine-5-carboxylic acid A stirred solution of 3-(5-bromo-6-methoxypyridin-2-yl)-5-(furan-2-yl)-5,6-dihydro-4H-1,2,4-oxadiazine (710 mg, 2.1 mmol) in methanol (350 mL) was cooled to −78° C. and ozone was passed through until a faint blue colour persisted. Next, excess ozone was removed by bubbling through oxygen for 2 minutes and the reaction mixture was concentrated in vacuo. The residue was partitioned between EtOAc and saturated aqueous Na$_2$CO$_3$, the layers were separated and the water layer was washed with EtOAc. The water layer was acidified to pH=1 using conc. hydrochloric acid and extracted twice with EtOAc. These last extracts were dried over Na$_2$SO$_4$ and concentrated in vacuo to afford 3-(5-bromo-6-methoxypyridin-2-yl)-5,6-dihydro-4H-1,2,4-oxadiazine-5-carboxylic acid (471 mg, 71%) as a light orange foam. LCMS: 98.0%; 316.0 (M+1); RT 1.51 min (method A).

Example 202

Synthesis of 2-(3-(5-bromo-6-methoxypyridin-2-yl)-5,6-dihydro-4H-1,2,4-oxadiazin-5-yl)benzo[d]oxazole

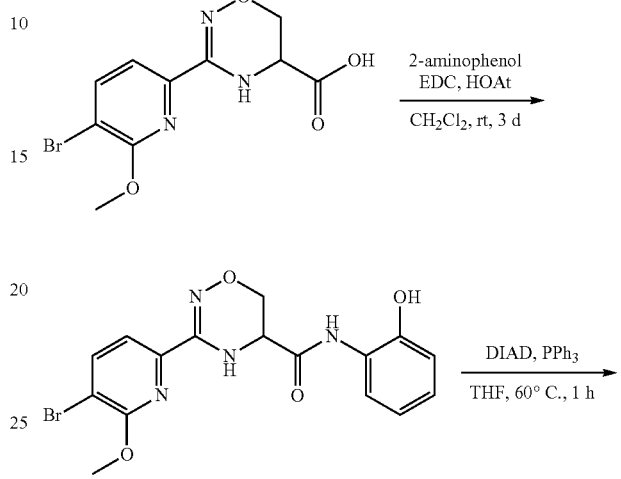

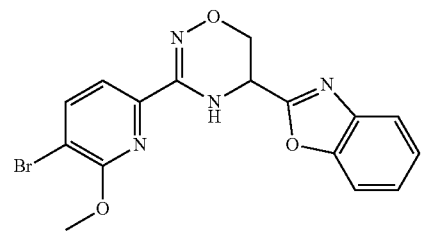

3-(5-bromo-6-methoxypyridin-2-yl)-N-(2-hydroxyphenyl)-5,6-dihydro-4H-1,2,4-oxadiazine-5-carboxamide To a stirred solution of 3-(5-bromo-6-methoxypyridin-2-yl)-5,6-dihydro-4H-1,2,4-oxadiazine-5-carboxylic acid (400 mg, 1.3 mmol) in dichloromethane (100 mL) at 0° C., 2-aminophenol (138 mg, 1.3 mmol), EDC (267 mg, 1.4 mmol) and HOAt (17 mg, 0.1 mmol) were added. The mixture was allowed to come to room temperature and stirred for 3 days. The reaction mixture was washed with water twice, dried over Na$_2$SO$_4$, concentrated onto silica in vacuo and purified by silica column chromatography [20% to 60% EtOAc in heptane] to afford 3-(5-bromo-6-methoxypyridin-2-yl)-N-(2-hydroxyphenyl)-5,6-dihydro-4H-1,2,4-oxadiazine-5-carboxamide (308 mg, 60%) as a white solid. LCMS: 98.0%; 407.0 (M+1); RT 1.99 min (method A); TLC: 60% EtOAc/Heptane (R$_f$: 0.36).

2-(3-(5-bromo-6-methoxypyridin-2-yl)-5,6-dihydro-4H-1,2,4-oxadiazin-5-yl)benzo[d] oxazole To a stirred solution of 3-(5-bromo-6-methoxypyridin-2-yl)-N-(2-hydroxyphenyl)-5,6-dihydro-4H-1,2,4-oxadiazine-5-carboxamide (322 mg, 0.8 mmol) and triphenylphosphine (249 mg, 0.9 mmol) in tetrahydrofuran (25 mL) at 60° C., a solution of diisopropyl azodicarboxylate (0.18 mL, 94%, 0.9 mmol) in tetrahydrofuran (1.5 mL) was added. The mixture was stirred at 60° C. for 1 hour, cooled to rt and poured onto a SCX column: After washing the column with 3 column volumes of methanol, the product was eluted using dichloromethane/7M $NH_3$ in methanol (1/1, v/v). The basic fraction was concentrated in vacuo and purified by silica column chromatography [15% to 30% EtOAc in heptane] to afford 2-(3-(5-bromo-6-methoxypyridin-2-yl)-5,6-dihydro-4H-1,2,4-oxadiazin-5-yl)benzo[d] oxazole (278 mg, 90%) as a white solid. LCMS: 99.1%; 389.0 (M+1); RT 2.11 min (method A)); TLC: 50% EtOAc/Heptane ($R_f$ 0.41).

Example 203

Synthesis of 2-(3-(6-methoxy-5-(4-methyl-1H-imidazol-1-yl)pyridin-2-yl)-5,6-dihydro-4H-1,2,4-oxadiazin-5-yl)benzo[d]oxazole

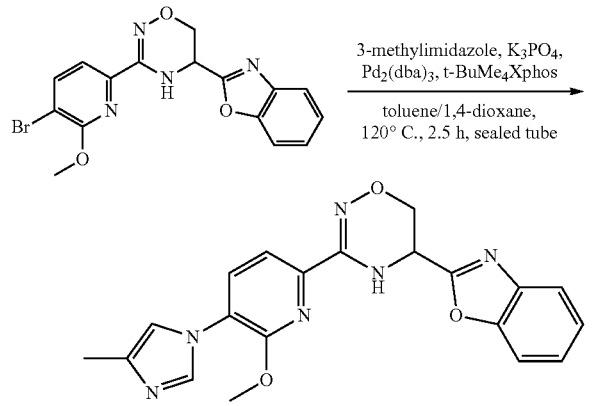

2-(3-(6-methoxy-5-(4-methyl-1H-imidazol-1-yl)pyridin-2-yl)-5,6-dihydro-4H-1,2,4-oxadiazin-5-yl)benzo[d]oxazole Example 203 (155 mg, 59%) was prepared from 2-(3-(5-bromo-6-methoxypyridin-2-yl)-5,6-dihydro-4H-1,2,4-oxadiazin-5-yl)benzo[d]oxazole according to the procedure for Example 189. Racemic compound Example 203 was separated using a Chiralpak-AD-H column (250×20 mm, 5 μm) (15 mg loading; heptane:EtOH (60:40) as mobile phase; flow rate: 18 mL/min) to afford the compounds of Example 203A (Fraction (I) (−)) and Example 203B (Fraction (II) (+)).

Example 203A, (−)-2-(3-(6-methoxy-5-(4-methyl-1H-imidazol-1-yl)pyridin-2-yl)-5,6-dihydro-4H-1,2,4-oxadiazin-5-yl)benzo[d]oxazole, fraction (I) (−): LCMS: 99.7%; 391.0 (M+1); RT 3.12 min (method B); Chiral HPLC: 99.2%, RT; =10.62 min (Chiralpak-AD-H (250×4.6 mm, 5 μm; mobile phase heptane:EtOH (60:40); flow Rate: 1.0 mL/min); Optical rotation $[\alpha]_D^{21.7}$: −287.17 (c=0.25, $CH_2Cl_2$).

Example 203B, (+)-2-(3-(6-methoxy-5-(4-methyl-1H-imidazol-1-yl)pyridin-2-yl)-5,6-dihydro-4H-1,2,4-oxadiazin-5-yl)benzo[d]oxazole, fraction (II) (+): $^1$H NMR (CDCl$_3$, 400 MHz) δ 7.86-7.78 (m, 2H), 7.78-7.71 (m, 1H), 7.64 (d, J=8.0 Hz, 1H), 7.59-7.52 (m, 1H), 7.42-7.34 (m, 2H), 7.09 (d, J=2.5 Hz, 1H), 7.02-6.98 (m, 1H), 5.21-5.15 (m, 1H), 4.54-4.47 (m, 1H), 4.27-4.19 (m, 1H), 4.12 (s, 3H), 2.31 (d, J=0.9 Hz, 3H); LCMS: 99.4%; 391.0 (M+1); RT 3.12 min (method B); Chiral HPLC: 99.7%; RT=14.62 min (Chiralpak-AD-H (250×4.6 mm, 5 μm; mobile phase heptane:EtOH (60:40); flow Rate: 1.0 mL/min); Optical rotation $[\alpha]_D^{21.7}$: +292.95 (c=0.25, $CH_2Cl_2$).

Example 204

Synthesis of (Z)—N'-((2-bromoallyl)oxy)-6-methoxy-5-(4-methyl-1H-imidazol-1-yl)picolinimidamide

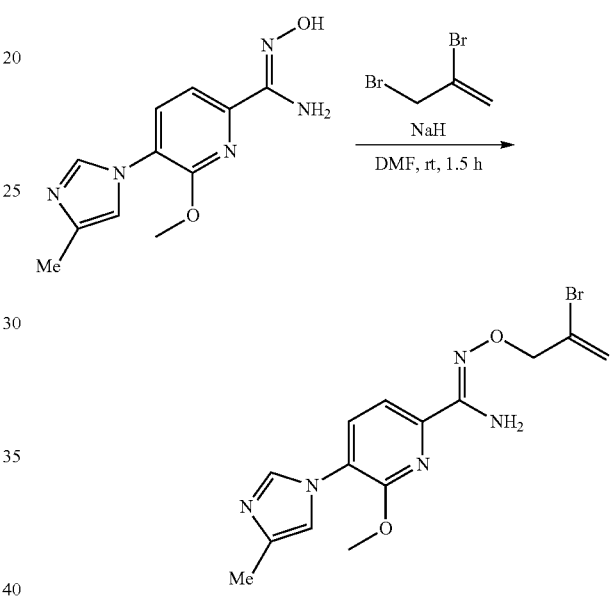

(Z)—N'-((2-bromoallyl)oxy)-6-methoxy-5-(4-methyl-1H-imidazol-1-yl)picolinimidamide To a stirred solution of (Z)—N'-hydroxy-6-methoxy-5-(4-methyl-1H-imidazol-1-yl)picolinimidamide (770 mg, 3.1 mmol) under argon atmosphere in dry N,N-dimethylformamide (30 mL), sodium hydride (131 mg, 3.3 mmol, 60%) was added and the mixture was stirred for 30 minutes. Next, 2,3-dibromopropene (622 mg, 3.11 mmol, 0.305 ml) in dry N,N-Dimethylformamide (8 mL) was added and the mixture was stirred at room temperature for 1.5 hour. The mixture was quenched with water and extracted twice with EtOAc. The combined organic layers were washed with water, brine, dried with sodium sulfate, concentrated in vacuo and the residue was purified by silica column chromatography [EtOAc] to afford (Z)—N'-((2-bromoallyl)oxy)-6-methoxy-5-(4-methyl-1H-imidazol-1-yl)picolinimidamide (1.09 g, 91%) as a colorless oil. $^1$H NMR (CDCl$_3$, 400 MHz) δ 7.82 (d, J=1.3 Hz, 1H), 7.68 (d, J=7.9 Hz, 1H), 7.57 (d, J=8.0 Hz, 1H), 7.03-6.95 (m, 1H), 6.00-5.90 (m, 1H), 5.70-5.63 (m, 1H), 5.55 (s, 2H), 4.78-4.68 (m, 2H), 4.08 (s, 3H), 2.32 (d, J=0.9 Hz, 3H); LCMS: 97.1%; 366.0 (M+1); RT 2.06 min. (method A); TLC: EtOAc ($R_f$ 0.4).

Example 205

Synthesis of 3-(6-methoxy-5-(4-methyl-1H-imidazol-1-yl)pyridin-2-yl)-5-(1-methyl-1H-indol-2-yl)-5,6-dihydro-4H-1,2,4-oxadiazine

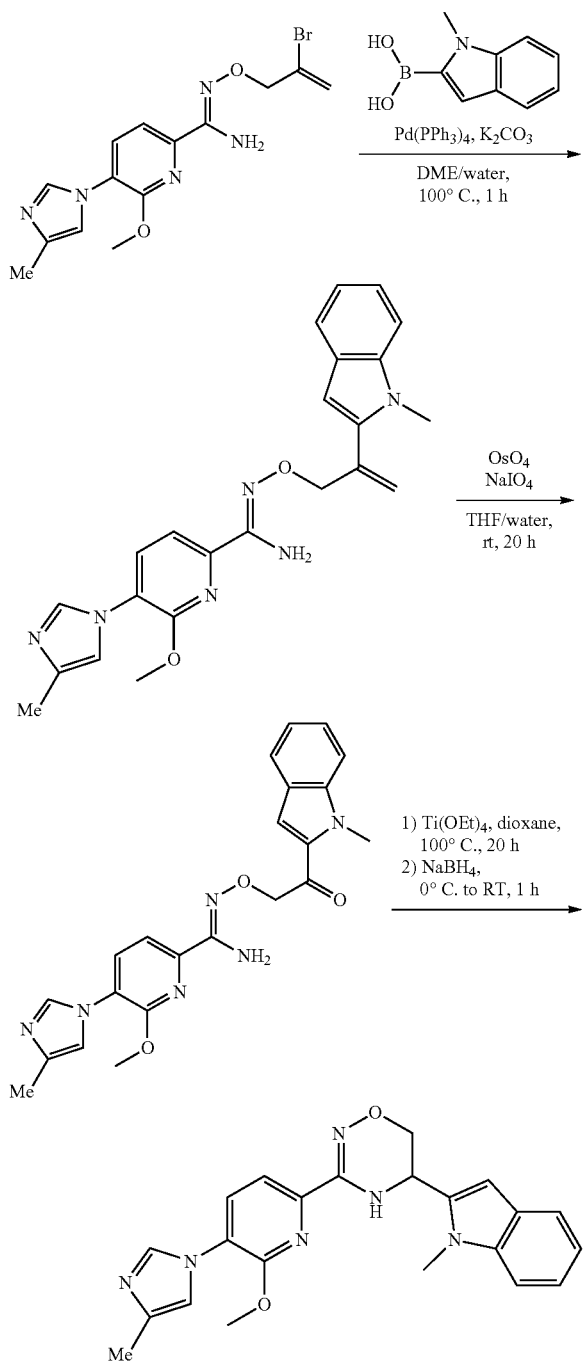

(Z)-6-methoxy-5-(4-methyl-1H-imidazol-1-yl)-N'-((2-(1-methyl-1H-indol-2-yl)allyl)oxy) picolinimidamide Under argon, a microwave vial was charged with (Z)—N'-((2-bromoallyl)oxy)-6-methoxy-5-(4-methyl-1H-imidazol-1-yl)picolinimidamide (600 mg, 1.6 mmol), 1-Methyl-1H-indol-2-yl-2-boronic acid (315 mg, 1.8 mmol), sodium carbonate (521 mg, 4.9 mmol) and Pd(PPh$_3$)$_4$ (95 mg, 0.08 mmol). Next, degassed 1,2-dimethoxyethane (14 mL) and water (4 mL) were added and the resultant mixture was heated in an oil-bath at 100° C. for 1 hour. The mixture was diluted with water and extracted twice with EtOAc. The combined organic layers were washed with water, brine, dried with sodium sulfate, concentrated in vacuo and the residue was purified by silica column chromatography [5% methanol in EtOAc] to afford (Z)-6-methoxy-5-(4-methyl-1H-imidazol-1-yl)-N'-((2-(1-methyl-1H-indol-2-yl)allyl)oxy)picolinimidamide (491 mg, 85%) as a colorless oil. $^1$H NMR (CDCl$_3$, 400 MHz) δ 7.82 (d, J=1.3 Hz, 1H), 7.68 (d, J=8.0 Hz, 1H), 7.65-7.60 (m, 1H), 7.57 (d, J=8.0 Hz, 1H), 7.37-7.32 (m, 1H), 7.28-7.22 (m, 1H), 7.16-7.11 (m, 1H), 7.02-6.97 (m, 1H), 6.59 (d, J=0.7 Hz, 1H), 5.73 (d, J=1.3 Hz, 1H), 5.55-5.31 (m, 3H), 4.98 (s, 2H), 4.07 (s, 3H), 3.81 (s, 3H), 2.32 (d, J=0.9 Hz, 3H); LCMS: 97.7%; 417.2 (M+1); RT 2.24 min. (method A); TLC: 5% MeOH/EtOAc (R$_f$: 0.35).

(Z)-6-methoxy-5-(4-methyl-1H-imidazol-1-yl)-N'-(2-(1-methyl-1H-indol-2-yl)-2-oxoethoxy) picolinimidamide To a stirred solution of (Z)-6-methoxy-5-(4-methyl-1H-imidazol-1-yl)-N'-((2-(1-methyl-1H-indol-2-yl)allyl)oxy)picolinimidamide (485 mg, 1.2 mmol in tetrahydrofuran/water (3/1, 36 mL) ml), osmium tetroxide in water (0.27 mL, 4 wt %, 0.05 mmol) was added followed by sodium periodate (560 mg, 2.6 mmol) and the mixture was stirred at room temperature for 20 hours. Additional sodium periodate (224 mg, 1.0 mmol) was added, the mixture was stirred at room temperature for 3 hours, diluted with water and extracted twice with EtOAc. The combined organic layers were washed with brine, dried with sodium sulfate, concentrated in vacuo and purified by silica column chromatography [5% MeOH in EtOAc], followed by basic preparative MPLC (Linear Gradient: t=0 min 5% A, t=1 min 5% A, t=2 min 30% A; t=17 min 70% A; t=18 min 100%; t=23 min 100% A; detection: 310 nm) to afford (Z)-6-methoxy-5-(4-methyl-1H-imidazol-1-yl)-N'-(2-(1-methyl-1H-indol-2-yl)-2-oxoethoxy)picolinimidamide (184 mg, 38%) as a light yellow solid. $^1$H NMR (CDCl$_3$, 400 MHz) δ 7.82 (d, J=1.2 Hz, 1H), 7.78-7.71 (m, 1H), 7.66 (d, J=8.0 Hz, 1H), 7.55 (d, J=8.0 Hz, 1H), 7.47-7.40 (m, 3H), 7.24-7.16 (m, 1H), 6.99 (s, 1H), 5.68 (s, 2H), 5.34 (s, 2H), 4.13 (s, 3H), 4.09 (s, 3H), 2.31 (d, J=0.9 Hz, 3H); LCMS: 99.1%; 419.2 (M+1); RT 2.17 min. (method A); TLC: 5% MeOH/EtOAc (R$_f$: 0.31).

3-(6-methoxy-5-(4-methyl-1H-imidazol-1-yl)pyridin-2-yl)-5-(1-methyl-1H-indol-2-yl)-5,6-dihydro-4H-1,2,4-oxadiazine To a stirred solution of (Z)-6-methoxy-5-(4-methyl-1H-imidazol-1-yl)-N'-(2-(1-methyl-1H-indol-2-yl)-2-oxoethoxy)picolinimidamide (162 mg, 0.387 mmol) in dry 1,4-dioxane (4 mL) under argon atmosphere Ti(OEt)$_4$ (1.9 mL, 5.8 mmol) was added and the resultant mixture was heated to 100° C. for 20 hours. The mixture was cooled to 0° C., sodium borohydride (37 mg, 1.0 mmol) and methanol (1 mL) were added and the mixture was allowed to reach room temp. The mixture was quenched with water and EtOAc. The suspension was filtered over Celite, washed with EtOAc and the layers were separated. The organic layer was dried with sodium sulfate, concentrated in vacuo and purified by silica column chromatography [10% MeOH in EtOAc] to afford 3-(6-methoxy-5-(4-methyl-1H-imidazol-1-yl)pyridin-2-yl)-5-(1-methyl-1H-indol-2-yl)-5,6-dihydro-4H-1,2,4-oxadiazine (60 mg, 38%) as a light yellow foam.

Racemic compound Example 205 was separated using a Chiralpak-AD-H column (250×20 mm, 5 μm) (22 mg loading; heptane:EtOH (60:40) as mobile phase; flow rate: 18 mL/min) to afford the compounds of Example 205A (Fraction (I) (−)) and Example 205B (Fraction (II) (+)).

Example 205A, (−)-3-(6-methoxy-5-(4-methyl-1H-imidazol-1-yl)pyridin-2-yl)-5-(1-methyl-1H-indol-2-yl)-5,6-dihydro-4H-1,2,4-oxadiazine, fraction (I) (−): LCMS: 100%; 403.2 (M+1); RT 3.50 min (method D); Chiral HPLC: 100%; RT=12.28 min (Chiralpak-AD-H (250×4.6 mm, 5 μm; mobile phase heptane:EtOH (60:40); flow Rate: 1.0 mL/min); Optical rotation $[\alpha]_D^{23.1}$: −209.44 (c=0.10, CH$_2$Cl$_2$).

Example 205B, (+)-3-(6-methoxy-5-(4-methyl-1H-imidazol-1-yl)pyridin-2-yl)-5-(1-methyl-1H-indol-2-yl)-5,6-dihydro-4H-1,2,4-oxadiazine, fraction (II) (+): $^1$H NMR (CDCl$_3$, 400 MHz) δ 7.84 (d, J=1.2 Hz, 1H), 7.83 (d, J=8.0 Hz, 1H), 7.65 (d, J=8.0 Hz, 1H), 7.63-7.58 (m, 1H), 7.39-7.34 (m, 1H), 7.30-7.25 (m, 1H), 7.17-7.12 (m, 1H), 7.02-6.98 (m, 1H), 6.58 (s, 1H), 6.57-6.55 (m, 1H), 5.13-5.06 (m, 1H), 4.54-4.46 (m, 1H), 4.02 (s, 3H), 3.84 (s, 3H), 3.80 (dd, J=11.0, 7.7 Hz, 1H), 2.31 (d, J=0.9 Hz, 3H); LCMS: 100%; 403.2 (M+1); RT 3.50 min (method D); Chiral HPLC: 100%; RT=27.00 min (Chiralpak-AD-H (250×4.6 mm, 5 μm; mobile phase heptane:EtOH (60:40); flow Rate: 1.0 mL/min); Optical rotation $[\alpha]_D^{23.2}$: +209.97 (c=0.10, CH$_2$Cl$_2$).

Example 206

Synthesis of 3-(6-methoxy-5-(4-methyl-1H-imidazol-1-yl) pyridin-2-yl)-5-(1-methyl-5-(trifluoromethyl)-1H-pyrrolo [2,3-b] pyridin-3-yl)-5,6-dihydro-4H-1,2,4-oxadiazine

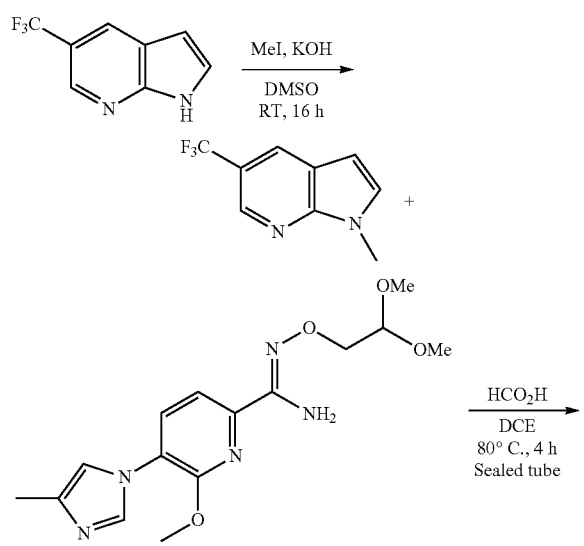

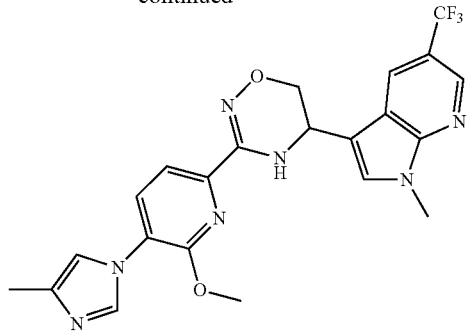

1-methyl-5-(trifluoromethyl)-1H-pyrrolo [2,3-b] pyridine

To a stirred solution of 5-(trifluoromethyl)-1H-pyrrolo [2,3-b] pyridine (1 g, 5 mmol) in DMSO (5 mL) at 0° C. under an argon atmosphere were added potassium hydroxide (600 mg, 11 mmol) and methyl iodide (1.5 g, 11 mmol). The reaction mixture was warmed to room temperature and stirred for 16 h. After consumption of starting material (monitored by TLC), the reaction mixture was diluted with ice cold water (20 mL) and extracted with EtOAc (2×20 mL). The combined organic extracts were dried over sodium sulfate, filtered and concentrated in vacuo to afford 1-methyl-5-(trifluoromethyl)-1H-pyrrolo [2,3-b] pyridine (1 g, 93%) as a pale yellow solid used in the next step without further purification.

$^1$H NMR (CDCl$_3$, 500 MHz): δ 8.60 (s, 1H), 8.17 (s, 1H), 7.31 (d, 1H), 6.57 (d, 1H), 3.95 (s, 3H); LCMS: 95.9%; 200.8 (M+1); (column; X-Select CSH C-18 (50×3.0 mm, 2.5 μm); RT 3.11 min; mobile phase: 2.5 mM NH$_4$OOCH in water+5% ACN: ACN+5% 2.5 mM NH$_4$OOCH in water; T/B %: 0.01/5, 0.5/5, 3.5/100, 6/100; flow rate: 0.8 mL/min) (Gradient); TLC: 20% EtOAc/Hexane (R$_f$: 0.6).

3-(6-methoxy-5-(4-methyl-1H-imidazol-1-yl) pyridin-2-yl)-5-(1-methyl-5-(trifluoromethyl)-1H-pyrrolo [2,3-b] pyridin-3-yl)-5,6-dihydro-4H-1,2,4-oxadiazine To a stirred solution of (Z)—N'-(2,2-dimethoxyethoxy)-6-methoxy-5-(4-methyl-1H-imidazol-1-yl) picolinimidamide (250 mg, 0.7 mmol) in 1,2-dichloroethane (5 mL) at room temperature under an argon atmosphere were added 1-methyl-5-(trifluoromethyl)-1H-pyrrolo [2,3-b] pyridine (300 mg, 1.5 mmol) and formic acid (5 mL). The reaction mixture was stirred at 80° C. for 4 h in a sealed tube. After consumption of starting material (monitored by TLC), the reaction mixture was diluted with saturated sodium bicarbonate solution (10 mL), water (10 mL) and extracted with EtOAc (2×10 mL). The combined organic extracts were dried over sodium sulfate, filtered and concentrated in vacuo. The crude material was purified by column chromatography using 1-5% MeOH: CH$_2$Cl$_2$ to afford 3-(6-methoxy-5-(4-methyl-1H-imidazol-1-yl) pyridin-2-yl)-5-(1-methyl-5-(trifluoromethyl)-1H-pyrrolo [2,3-b] pyridin-3-yl)-5,6-dihydro-4H-1,2,4-oxadiazine (180 mg, 51%) as an off-white solid.

Racemic compound of Example 206 was separated using a Chiralpak-IB column (250×20 mm, 5 μm) (30 mg loading; 0.1% DEA in n-Hexane: CH$_2$Cl$_2$:MeOH (35:65) (A:B:

85:15) as mobile phase; flow rate: 20 mL/min) to afford the compounds of Example 206A (Fraction (I) (−)) and Example 206B (Fraction (II) (+)).

Analytical conditions for Example 206A and Example 206B: HPLC (column; zorbax-SB-C-18 150×4.6 mm, 3.5μ); mobile Phase: ACN: 0.05% Aq TFA; flow rate: 1.0 mL/min; Gradient program: T/B % 0.01/90, 2/90, 8/10, 15/10: diluent: $CH_3CN$:Water; Chiral HPLC: (Chiralpak-IB (250× 4.6 mm, 5 μm; mobile phase (A) 0.1% DEA in n-Hexane (B) $CH_2Cl_2$:MeOH (35:65) (A:B; 85:15); flow Rate: 1.0 mL/min).

Example 206A, (−)-3-(6-methoxy-5-(4-methyl-1H-imidazol-1-yl) pyridin-2-yl)-5-(1-methyl-5-(trifluoromethyl)-1H-pyrrolo [2,3-b]pyridin-3-yl)-5,6-dihydro-4H-1,2,4-oxadiazine, fraction (I) (−): Mass (ESI): 472 [M+1]; HPLC (purity): 97.9%, RT 7.45 min; Chiral HPLC: 99.8%, RT=22.06 min; Optical rotation $[\alpha]_D^{20.00}$: −102.44 (c=0.25, $CH_2Cl_2$).

Example 206B, (+)-3-(6-methoxy-5-(4-methyl-1H-imidazol-1-yl) pyridin-2-yl)-5-(1-methyl-5-(trifluoromethyl)-1H-pyrrolo [2,3-b]pyridin-3-yl)-5,6-dihydro-4H-1,2,4-oxadiazine, fraction (II) (+): $^1H$ NMR ($CD_3OD$, 500 MHz): δ 8.55 (s, 1H), 8.41 (s, 1H), 7.97 (s, 1H), 7.89 (d, 1H), 7.67 (d, 1H), 7.61 (s, 1H), 7.21 (s, 1H), 5.19 (t, 1H), 4.17 (dd, 1H), 4.12 (dd, 1H), 4.03 (s, 3H), 3.91 (s, 3H), 2.24 (s, 3H); Mass (ESI): 472 [M+1]; HPLC (purity): 99.5%, RT 7.45 min; Chiral HPLC: 99.4%, RT=28.59 min; Optical rotation $[\alpha]_D^{19.99}$: +106.73 (c=0.25, $CH_2Cl_2$).

Example 207

Synthesis of 5-(benzo[d]thiazol-2-yl)-3-(5-bromo-6-methoxypyridin-2-yl)-5,6-dihydro-4H-1,2,4-oxadiazine

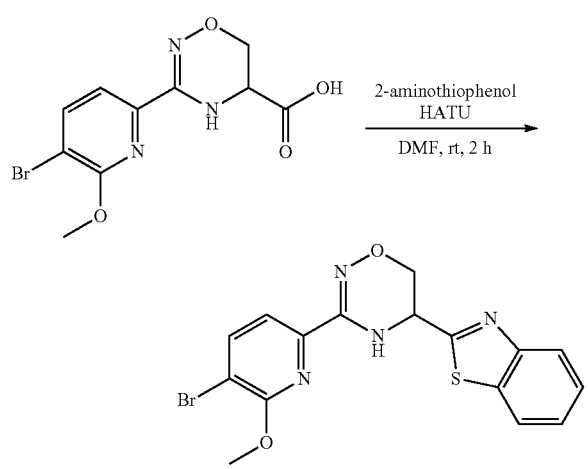

5-(benzo[d]thiazol-2-yl)-3-(5-bromo-6-methoxypyridin-2-yl)-5,6-dihydro-4H-1,2,4-oxadiazine To a stirred solution of 3-(5-bromo-6-methoxypyridin-2-yl)-5,6-dihydro-4H-1,2,4-oxadiazine-5-carboxylic acid (118 mg, 0.4 mmol) in degassed DMF under an argon atmosphere, DIPEA (58 mg, 0.4 mmol) and HATU (142 mg, 0.4 mmol) were added and the mixture was stirred at room temperature for 90 minutes. Additional DIPEA (19 mg, 0.1 mmol mL) and HATU (40 mg, 0.1 mmol) were added and stirring was continued for 30 minutes. Next, 2-aminothiophenol (51 mg, 0.4 mmol) was added and the mixture was stirred for 30 minutes, diluted with EtOAc, washed twice with water, brine, dried over sodium sulfate and concentrated in vacuo. After storage overnight, partial cyclisation was observed. The mixture was at 55° C. in a water bath under vacuum for 30 minutes, resulting in full conversion to the cyclised product. The crude product was purified by silica column chromatography [0% to 3% MeOH in dichloromethane], followed by basic preparative MPLC (Linear Gradient: t=0 min 5% A, t=1 min 5% A, t=2 min 30% A; t=17 min 70% A; t=18 min 100%; t=23 min 100% A; detection: 220/254/300 nm) to afford 5-(benzo[d]thiazol-2-yl)-3-(5-bromo-6-methoxypyridin-2-yl)-5,6-dihydro-4H-1,2,4-oxadiazine (61 mg, 40%) as a white solid. 1H NMR ($CDCl_3$, 400 MHz) δ 8.06 (d, J=8.3 Hz, 1H), 7.97-7.88 (m, 2H), 7.65 (d, J=8.0 Hz, 1H), 7.59-7.51 (m, 1H), 7.50-7.40 (m, 1H), 7.17 (s, 1H), 5.40-5.31 (m, 1H), 4.37 (dd, J=11.2, 3.7 Hz, 1H), 4.32-4.27 (m, 1H), 4.10 (s, 3H); LCMS: 99.6%; 405.0 (M+1); RT 2.23 min (method A); TLC: 2% MeOH/$CH_2Cl_2$ ($R_f$: 0.19).

Example 208

Synthesis of 5-(benzo[d]thiazol-2-yl)-3-(6-methoxy-5-(4-methyl-1H-imidazol-1-yl)pyridin-2-yl)-5,6-dihydro-4H-1,2,4-oxadiazine

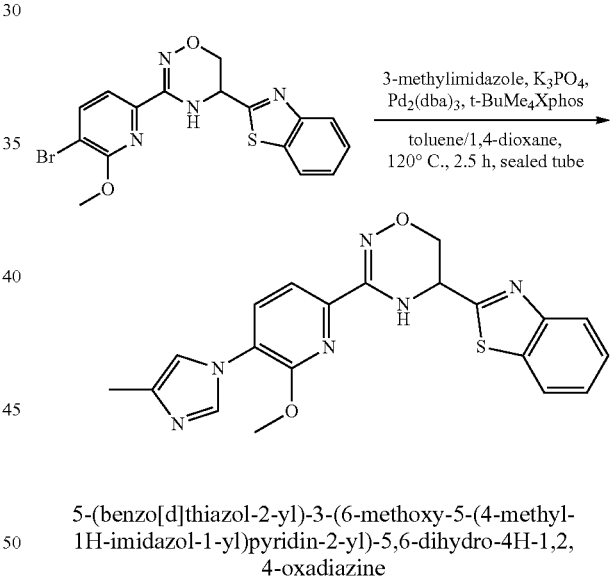

5-(benzo[d]thiazol-2-yl)-3-(6-methoxy-5-(4-methyl-1H-imidazol-1-yl)pyridin-2-yl)-5,6-dihydro-4H-1,2,4-oxadiazine A dry microwave vial was charged with $Pd_2(dba)_3$ (30 mg, 0.03 mmol) and tert-butyl tetramethyl Xphos (32 mg, 0.07 mmol) and flushed with argon. Next, an argon-degassed solution of toluene/1,4-dioxane (2/1, 4.5 mL) was added at room temperature and the resultant suspension was thoroughly degassed with argon. The suspension was placed in a pre-heated oil bath at 120° C. and stirred for 3 minutes. A second dry microwave vial was charged with 5-(benzo[d]thiazol-2-yl)-3-(5-bromo-6-methoxypyridin-2-yl)-5,6-dihydro-4H-1,2,4-oxadiazine (67 mg, 0.2 mmol), 4-methyl-1H-imidazole (27 mg, 0.3 mmol) and potassium phosphate (70 mg, 0.3 mmol) and flushed with argon. Next, an argon-degassed solution of toluene/1,4-dioxane (2/1, 9 mL) was added at room temperature and the resultant suspension was thoroughly degassed with argon. The catalyst premixture was added, the vial was capped and the resultant mixture was stirred at 120° C. for 1 hour. The reaction mixture was filtered, the filtrate was concentrated onto silica in vacuo and purified by silica column chromatography [0% to 7% methanol in $CH_2Cl_2$] to afford 5-(benzo[d]thiazol-2-yl)-3-(6-methoxy-5-(4-methyl-1H-imidazol-1-yl)pyridin-2-yl)-5,6-dihydro-4H-1,2,4-oxadiazine (42 mg, 63%) as an off-white solid.

Racemic compound Example 208 was separated using a Chiralpak-IB column (250×20 mm, 5 μm) (10 mg loading; heptane+0.2% DEA:EtOH (70:30) as mobile phase; flow rate: 18 mL/min) to afford the compounds of Example 208A (Fraction (I) (−)) and compound Example 208B (Fraction (II) (+)).

Example 208A, (−)-5-(benzo[d]thiazol-2-yl)-3-(6-methoxy-5-(4-methyl-1H-imidazol-1-yl)pyridin-2-yl)-5,6-dihydro-4H-1,2,4-oxadiazine, fraction (I) (−): LCMS: 99.6%; 407.0 (M+1); RT 3.24 min (method D); Chiral HPLC: 100% RT; =14.45 min (Chiralpak-IB (250×4.6 mm, 5 μm; mobile phase heptane+0.1% DEA:EtOH (70:30); flow Rate: 1.0 mL/min); Optical rotation $[\alpha]_D^{22.9}$: −335.29 (c=0.05, $CH_2Cl_2$).

Example 208B, (+)-5-(benzo [d] thiazol-2-yl)-3-(6-methoxy-5-(4-methyl-1H-imidazol-1-yl)pyridin-2-yl)-5,6-dihydro-4H-1,2,4-oxadiazine, fraction (II) (+): $^1$H NMR (CDCl$_3$, 400 MHz) δ 8.06-8.01 (m, 1H), 7.93-7.88 (m, 1H), 7.85 (s, 1H), 7.83 (d, J=8.0 Hz, 1H), 7.66 (d, J=8.0 Hz, 1H), 7.56-7.49 (m, 1H), 7.45-7.39 (m, 1H), 7.13 (d, J=3.7 Hz, 1H), 7.00 (s, 1H), 5.36-5.30 (m, 1H), 4.35 (dd, J=11.2, 3.8 Hz, 1H), 4.29 (dd, J=11.1, 3.6 Hz, 1H), 4.09 (s, 3H), 2.31 (s, 3H); LCMS: 100%; 407.0 (M+1); RT 3.25 min (method D); Chiral HPLC: 98.8%; RT=18.63 min (Chiralpak-IB (250× 4.6 mm, 5 μm; mobile phase heptane+0.1% DEA:EtOH (70:30); flow Rate: 1.0 mL/min); Optical rotation $[\alpha]_D^{23.1}$: +304.19 (c=0.04, $CH_2Cl_2$).

Example 209

In Vitro Cell Screening Assay and Quantification of Aβ(1-x) and Aβ(1-((2) Peptides Human neuroglioma H4 cells were transfected with a pcDNA3.1 plasmid expressing human wild type APP751 cDNA and a stable cell line was generated using G418 selection. Cells were plated at 15,000 cells/well in Costar 96-well plates and placed at 37° C. and 5% $CO_2$. Six hours after plating, cells were washed three times with Pro293™ chemically defined medium, followed by addition of compounds (0.003-10 μM, final DMSO concentration of 0.33%). Plates were incubated overnight (16-18 h) and supernatant was removed for quantification of Aβ peptides by sandwich ELISA. Cytotoxicity was evaluated using Cell-Titer 96W AQueous One Solution Cell Proliferation Assay according to the manufacturer's protocol.

ELISA Measurements of Aβ Peptides

Aβ peptide levels were quantified by sandwich ELISA. 96-well plates were coated with C-terminal specific Aβ antibodies recognizing either Aβ37, Aβ38, Aβ40, Aβ42, Aβ43 or a N-terminal specific Aβ antibody to detect Aβ 1-x. Plates were then blocked overnight at 4° C. with 1% bovine serum albumin (BSA) in PBS-T. Plates were washed and 100 μl of cultured cell supernatant or synthetic Aβ peptide standards and a detection antibody (4G8-HRP) were applied to the blocked plate and incubated overnight at 4° C. The next day, wells were washed before the addition of detection substrate (TMB peroxidase). Plates were then read for absorbance at 450 nm on a Molecular Devices SpectraMax M5e Microplate Reader.

Compound-treated samples were normalized to samples treated with DMSO alone (no inhibition) and to samples treated with DAPT. $EC_{50}$ values were calculated from values reported as percent of DMSO controls using nonlinear regression, based on a sigmoidal dose response (variable slope) model. GraphPAD software from Prism used for calculation.

TABLE II

| | Biological Assay | | |
|---|---|---|---|
| Compound of Example | Structure | Name | Aβ42 EC50 (μM) |
| 4 | | (R)-5-(benzofuran-2-yl)-3-(6-methoxy-5-(4-methyl-1H-imidazol-1-yl)pyridin-2-yl)-5,6-dihydro-4H-1,2,4-oxadiazine | 0.0384 |
| 7A | | 3-(6-methoxy-5-(4-methyl-1H-imidazol-1-yl)pyridin-2-yl)-5-(7-methylbenzofuran-2-yl)-5,6-dihydro-4H-1,2,4-oxadiazine | >3 |

TABLE II-continued

Biological Assay

| Compound of Example | Structure | Name | Aβ42 EC50 (μM) |
|---|---|---|---|
| 7B | 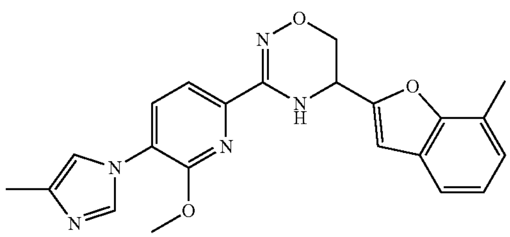 | 3-(6-Methoxy-5-(4-methyl-1H-imidazol-1-yl)pyridin-2-yl)-5-(7-methylbenzofuran-2-yl)-5,6-dihydro-4H-1,2,4-oxadiazine | 0.0233 |
| 10 | 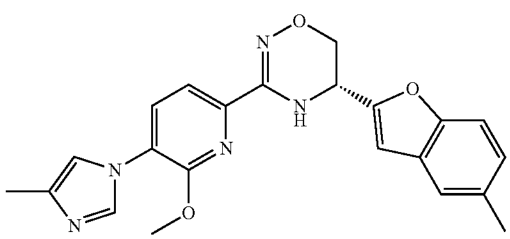 | (R)-3-(6-methoxy-5-(4-methyl-1H-imidazol-1-yl)pyridin-2-yl)-5-(5-methylbenzofuran-2-yl)-5,6-dihydro-4H-1,2,4-oxadiazine | 0.016 |
| 13 | 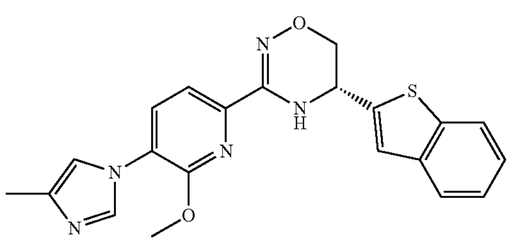 | (R)-5-(benzo[b]thiophen-2-yl)-3-(6-methoxy-5-(4-methyl-1H-imidazol-1-yl)pyridin-2-yl)-5,6-dihydro-4H-1,2,4-oxadiazine | 0.0078 |
| 16A | 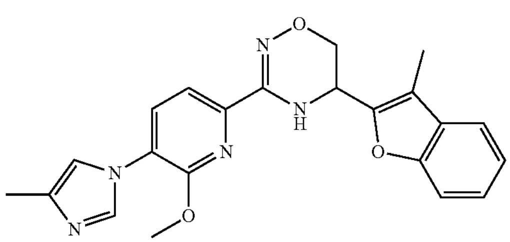 | (−)-3-(6-methoxy-5-(4-methyl-1H-imidazol-1-yl)pyridin-2-yl)-5-(3-methylbenzofuran-2-yl)-5,6-dihydro-4H-1,2,4-oxadiazine | 0.5077 |
| 16B | 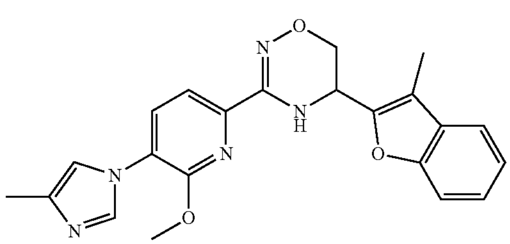 [SMILES: COc1nc(C2=NOCC(c3oc4ccccc4c3C)N2)ccc1-n1cnc(C)c1] | (+)-3-(6-methoxy-5-(4-methyl-1H-imidazol-1-yl)pyridin-2-yl)-5-(3-methylbenzofuran-2-yl)-5,6-dihydro-4H-1,2,4-oxadiazine | 0.0167 |
| 19 | 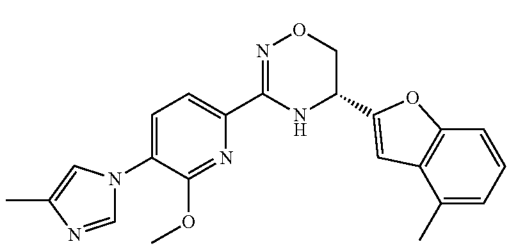 [SMILES: COc1nc(C2=NOC[C@H](c3cc4c(C)cccc4o3)N2)ccc1-n1cnc(C)c1] | (R)-3-(6-methoxy-5-(4-methyl-1H-imidazol-1-yl)pyridin-2-yl)-5-(4-methylbenzofuran-2-yl)-5,6-dihydro-4H-1,2,4-oxadiazine | 0.0115 |

TABLE II-continued

Biological Assay

| Compound of Example | Structure | Name | Aβ42 EC50 (μM) |
|---|---|---|---|
| 22 | 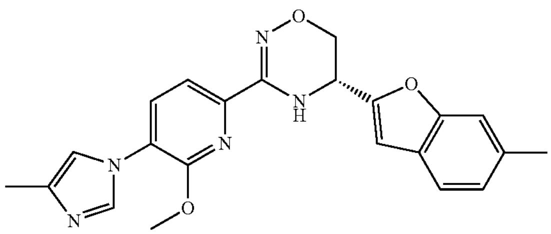 | (R)-3-(6-methoxy-5-(4-methyl-1H-imidazol-1-yl)pyridin-2-yl)-5-(6-methylbenzofuran-2-yl)-5,6-dihydro-4H-1,2,4-oxadiazine | 0.0184 |
| 23 | 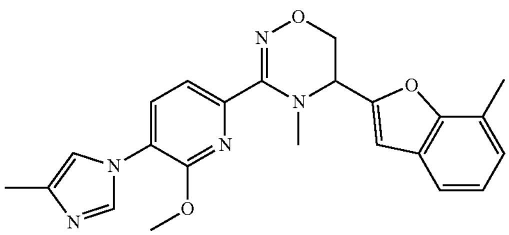 | (+)-3-(6-methoxy-5-(4-methyl-1H-imidazol-1-yl)pyridin-2-yl)-4-methyl-5-(7-methylbenzofuran-2-yl)-5,6-dihydro-4H-1,2,4-oxadiazine | 0.0619 |
| 24 | 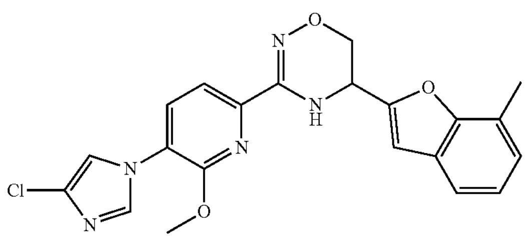 [SMILES: COc1nc(C2=NOCC(c3cc4cccc(C)c4o3)N2)ccc1-n1cnc(Cl)c1] | (+)-3-(5-(4-chloro-1H-imidazol-1-yl)-6-methoxypyridin-2-yl)-5-(7-methylbenzofuran-2-yl)-5,6-dihydro-4H-1,2,4-oxadiazine | 0.0137 |
| 27A | 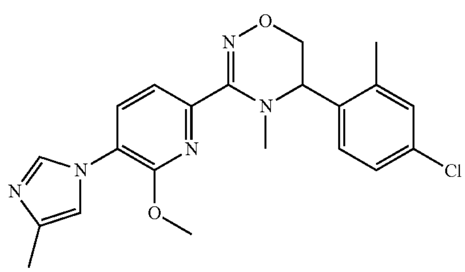 [SMILES: COc1nc(C2=NOCC(c3ccc(Cl)cc3C)N2C)ccc1-n1cnc(C)c1] | 5-(4-chloro-2-methylphenyl)-3-(6-methoxy-5-(4-methyl-1H-imidazol-1-yl)pyridin-2-yl)-4-methyl-5,6-dihydro-4H-1,2,4-oxadiazine | 2.1801 |
| 27B | 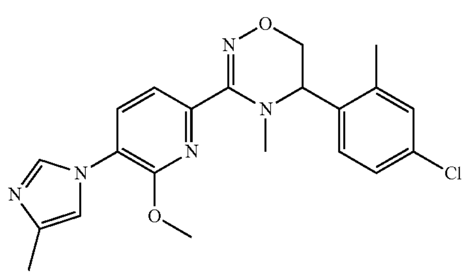 [SMILES: COc1nc(C2=NOCC(c3ccc(Cl)cc3C)N2C)ccc1-n1cnc(C)c1] | 5-(4-chloro-2-methylphenyl)-3-(6-methoxy-5-(4-methyl-1H-imidazol-1-yl)pyridin-2-yl)-4-methyl-5,6-dihydro-4H-1,2,4-oxadiazine | 0.0613 |
| 30A | 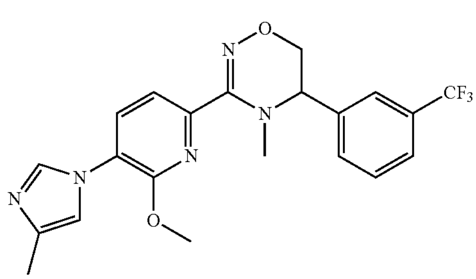 [SMILES: COc1nc(C2=NOCC(c3cccc(C(F)(F)F)c3)N2C)ccc1-n1cnc(C)c1] | 3-(6-methoxy-5-(4-methyl-1H-imidazol-1-yl)pyridin-2-yl)-4-methyl-5-(3-(trifluoromethyl)phenyl)-5,6-dihydro-4H-1,2,4-oxadiazine | 0.0557 |

TABLE II-continued

Biological Assay

| Compound of Example | Structure | Name | Aβ42 EC50 (μM) |
|---|---|---|---|
| 30B | 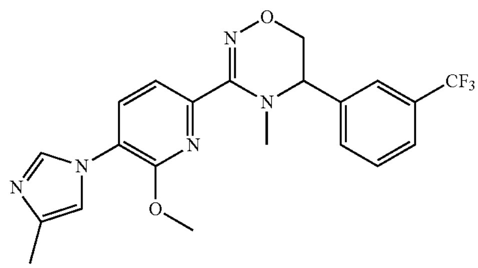 [SMILES: COc1nc(C2=NOCC(c3cccc(C(F)(F)F)c3)N2C)ccc1-n1cnc(C)c1] | 3-(6-methoxy-5-(4-methyl-1H-imidazol-1-yl)pyridin-2-yl)-4-methyl-5-(3-(trifluoromethyl)phenyl)-5,6-dihydro-4H-1,2,4-oxadiazine | >3 |
| 31A | 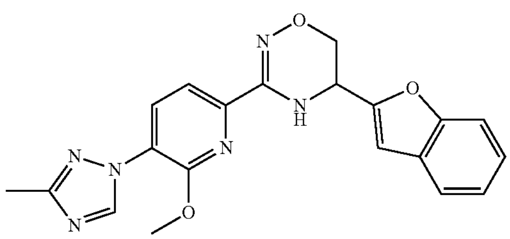 [SMILES: COc1nc(C2=NOCC(c3cc4ccccc4o3)N2)ccc1-n1cnc(C)n1] | (−)-5-(Benzofuran-2-yl)-3-(6-methoxy-5-(3-methyl-1H-1,2,4-triazol-1-yl)pyridin-2-yl)-5,6-dihydro-4H-1,2,4-oxadiazine | >3 |
| 31B | 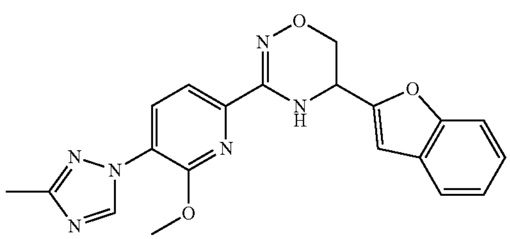 [SMILES: COc1nc(C2=NOCC(c3cc4ccccc4o3)N2)ccc1-n1cnc(C)n1] | (+)-5-(Benzofuran-2-yl)-3-(6-methoxy-5-(3-methyl-1H-1,2,4-triazol-1-yl)pyridin-2-yl)-5,6-dihydro-4H-1,2,4-oxadiazine | 0.6358 |
| 32 | 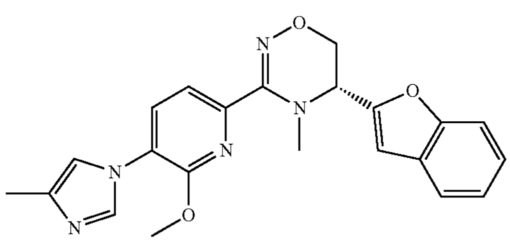 [SMILES: COc1nc(C2=NOC[C@H](c3cc4ccccc4o3)N2C)ccc1-n1cnc(C)c1] | (R)-5-(benzofuran-2-yl)-3-(6-methoxy-5-(4-methyl-1H-imidazol-1-yl)pyridin-2-yl)-4-methyl-5,6-dihydro-4H-1,2,4-oxadiazine | 0.3905 |
| 33 | 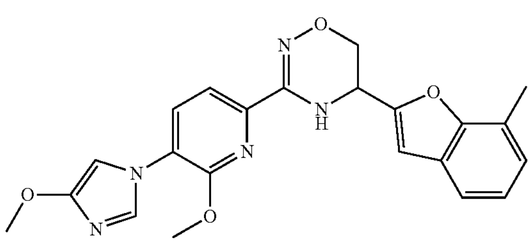 | (+)-3-(6-methoxy-5-(4-methoxy-1H-imidazol-1-yl)pyridin-2-yl)-5-(7-methylbenzofuran-2-yl)-5,6-dihydro-4H-1,2,4-oxadiazine | 0.1472 |
| 36A | 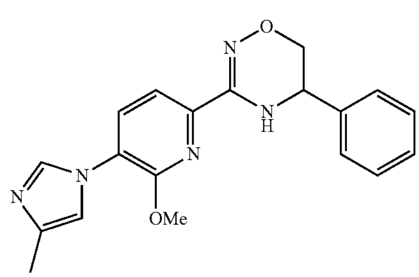 [SMILES: COc1nc(C2=NOCC(c3ccccc3)N2)ccc1-n1cnc(C)c1] | 3-(6-methoxy-5-(4-methyl-1H-imidazol-1-yl)pyridin-2-yl)-5-phenyl-5,6-dihydro-4H-1,2,4-oxadiazine | 2.7432 |

TABLE II-continued

Biological Assay

| Compound of Example | Structure | Name | Aβ42 EC50 (μM) |
|---|---|---|---|
| 36B | 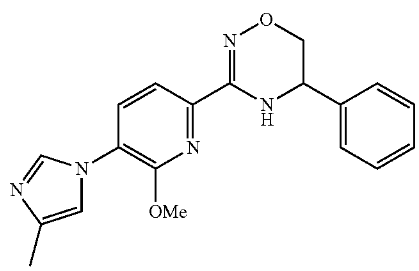 [SMILES: COc1nc(C2=NOCC(c3ccccc3)N2)ccc1-n1cnc(C)c1] | 3-(6-methoxy-5-(4-methyl-1H-imidazol-1-yl)pyridin-2-yl)-5-phenyl-5,6-dihydro-4H-1,2,4-oxadiazine | 0.097 |
| 38A | 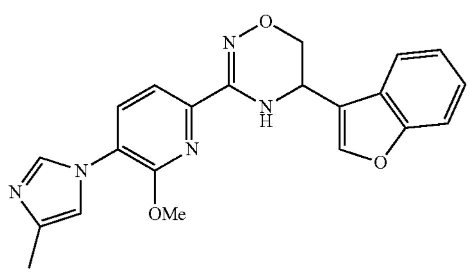 [SMILES: COc1nc(C2=NOCC(c3coc4ccccc34)N2)ccc1-n1cnc(C)c1] | 5-(benzofuran-3-yl)-3-(6-methoxy-5-(4-methyl-1H-imidazol-1-yl)pyridin-2-yl)-5,6-dihydro-4H-1,2,4-oxadiazine | >3 |
| 38B | 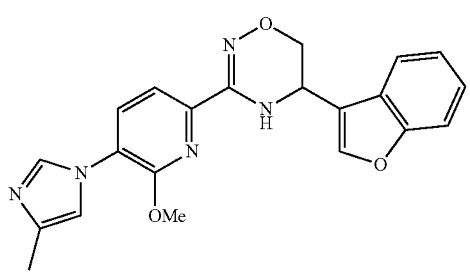 [SMILES: COc1nc(C2=NOCC(c3coc4ccccc34)N2)ccc1-n1cnc(C)c1] | 5-(benzofuran-3-yl)-3-(6-methoxy-5-(4-methyl-1H-imidazol-1-yl)pyridin-2-yl)-5,6-dihydro-4H-1,2,4-oxadiazine | 0.0224 |
| 40A | 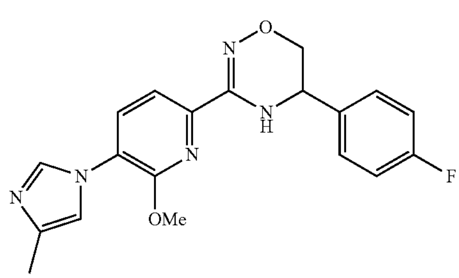 [SMILES: COc1nc(C2=NOCC(c3ccc(F)cc3)N2)ccc1-n1cnc(C)c1] | 5-(4-fluorophenyl)-3-(6-methoxy-5-(4-methyl-1H-imidazol-1-yl)pyridin-2-yl)-5,6-dihydro-4H-1,2,4-oxadiazine | >3 |
| 40B | 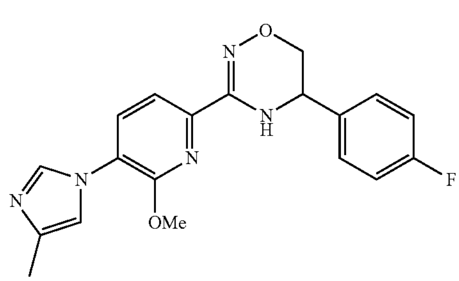 [SMILES: COc1nc(C2=NOCC(c3ccc(F)cc3)N2)ccc1-n1cnc(C)c1] | 5-(4-fluorophenyl)-3-(6-methoxy-5-(4-methyl-1H-imidazol-1-yl)pyridin-2-yl)-5,6-dihydro-4H-1,2,4-oxadiazine | 0.0595 |

TABLE II-continued

Biological Assay

| Compound of Example | Structure | Name | Aβ42 EC50 (μM) |
|---|---|---|---|
| 42A | 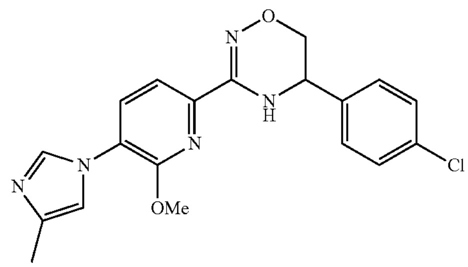 [SMILES: COc1nc(C2=NOCC(c3ccc(Cl)cc3)N2)ccc1-n1cnc(C)c1] | 5-(4-chlorophenyl)-3-(6-methoxy-5-(4-methyl-1H-imidazol-1-yl)pyridin-2-yl)-5,6-dihydro-4H-1,2,4-oxadiazine | >3 |
| 42B | 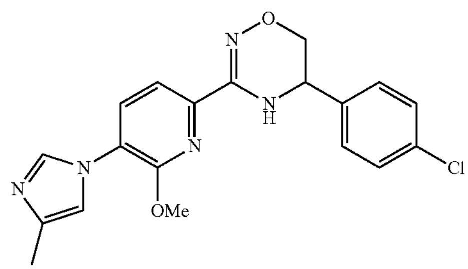 [SMILES: COc1nc(C2=NOCC(c3ccc(Cl)cc3)N2)ccc1-n1cnc(C)c1] | 5-(4-chlorophenyl)-3-(6-methoxy-5-(4-methyl-1H-imidazol-1-yl)pyridin-2-yl)-5,6-dihydro-4H-1,2,4-oxadiazine | 0.0283 |
| 44A | 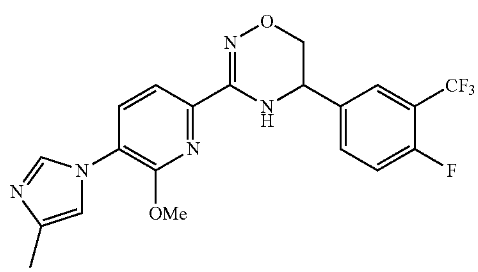 [SMILES: COc1nc(C2=NOCC(c3ccc(F)c(C(F)(F)F)c3)N2)ccc1-n1cnc(C)c1] | 5-(4-fluoro-3-(trifluoromethyl)phenyl)-3-(6-methoxy-5-(4-methyl-1H-imidazol-1-yl)pyridin-2-yl)-5,6-dihydro-4H-1,2,4-oxadiazine | >3 |
| 44B | 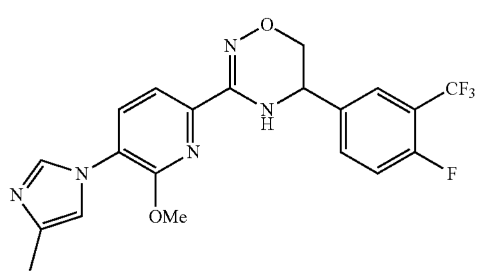 [SMILES: COc1nc(C2=NOCC(c3ccc(F)c(C(F)(F)F)c3)N2)ccc1-n1cnc(C)c1] | 5-(4-fluoro-3-(trifluoromethyl)phenyl)-3-(6-methoxy-5-(4-methyl-1H-imidazol-1-yl)pyridin-2-yl)-5,6-dihydro-4H-1,2,4-oxadiazine | 0.0216 |
| 47A | 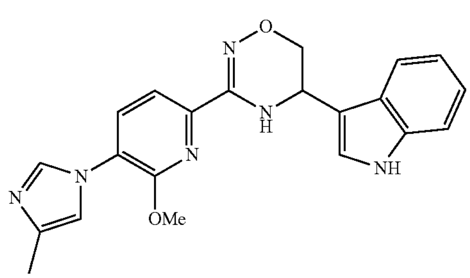 | 5-(1H-indol-3-yl)-3-(6-methoxy-5-(4-methyl-1H-imidazol-1-yl)pyridin-2-yl)-5,6-dihydro-4H-1,2,4-oxadiazine | 0.1358 |

TABLE II-continued

Biological Assay

| Compound of Example | Structure | Name | Aβ42 EC50 (μM) |
|---|---|---|---|
| 47B | 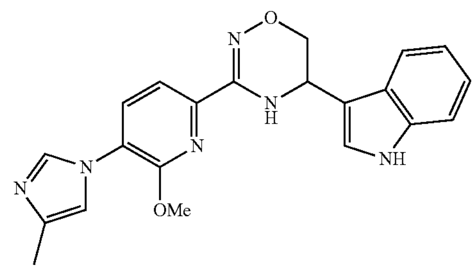 [SMILES: COc1nc(C2=NOCC(c3c[nH]c4ccccc34)N2)ccc1-n1cnc(C)c1] | 5-(1H-indol-3-yl)-3-(6-methoxy-5-(4-methyl-1H-imidazol-1-yl)pyridin-2-yl)-5,6-dihydro-4H-1,2,4-oxadiazine | 0.0231 |
| 49A | 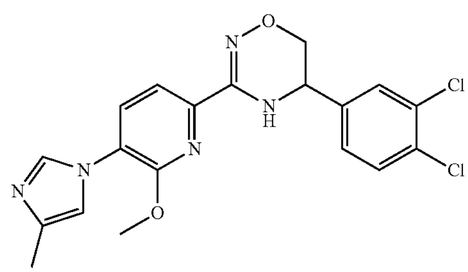 | (−)-5-(3,4-dichlorophenyl)-3-(6-methoxy-5-(4-methyl-1H-imidazol-1-yl)pyridin-2-yl)-5,6-dihydro-4H-1,2,4-oxadiazine | >3 |
| 49B | 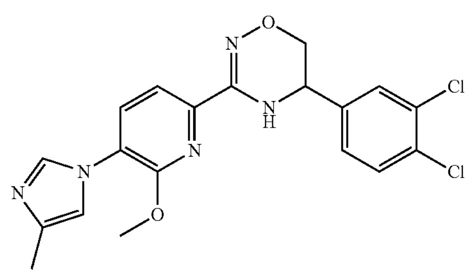 | (+)-5-(3,4-dichlorophenyl)-3-(6-methoxy-5-(4-methyl-1H-imidazol-1-yl)pyridin-2-yl)-5,6-dihydro-4H-1,2,4-oxadiazine | 0.0114 |
| 52A | 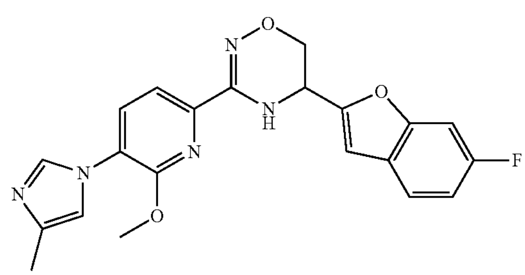 [SMILES: COc1nc(C2=NOCC(c3cc4ccc(F)cc4o3)N2)ccc1-n1cnc(C)c1] | (−)-5-(6-fluorobenzofuran-2-yl)-3-(6-methoxy-5-(4-methyl-1H-imidazol-1-yl)pyridin-2-yl)-5,6-dihydro-4H-1,2,4-oxadiazine | 0.6669 |
| 52B | 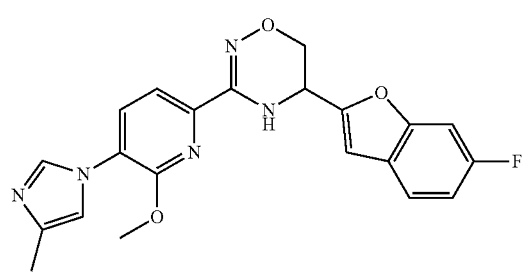 [SMILES: COc1nc(C2=NOCC(c3cc4ccc(F)cc4o3)N2)ccc1-n1cnc(C)c1] | (+)-5-(6-fluorobenzofuran-2-yl)-3-(6-methoxy-5-(4-methyl-1H-imidazol-1-yl)pyridin-2-yl)-5,6-dihydro-4H-1,2,4-oxadiazine | 0.0246 |

TABLE II-continued

Biological Assay

| Compound of Example | Structure | Name | Aβ42 EC50 (μM) |
|---|---|---|---|
| 54A | 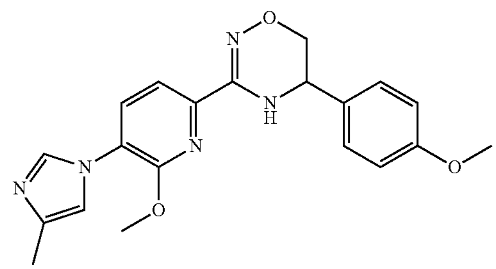 [SMILES: COc1ccc(C2CON=C(c3ccc(-n4cnc(C)c4)c(OC)n3)N2)cc1] | (−)-3-(6-methoxy-5-(4-methyl-1H-imidazol-1-yl)pyridin-2-yl)-5-(4-methoxyphenyl)-5,6-dihydro-4H-1,2,4-oxadiazine | >3 |
| 54B | 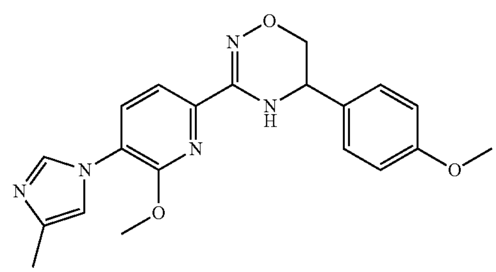 [SMILES: COc1ccc(C2CON=C(c3ccc(-n4cnc(C)c4)c(OC)n3)N2)cc1] | (+)-3-(6-methoxy-5-(4-methyl-1H-imidazol-1-yl)pyridin-2-yl)-5-(4-methoxyphenyl)-5,6-dihydro-4H-1,2,4-oxadiazine | 0.0974 |
| 57A | 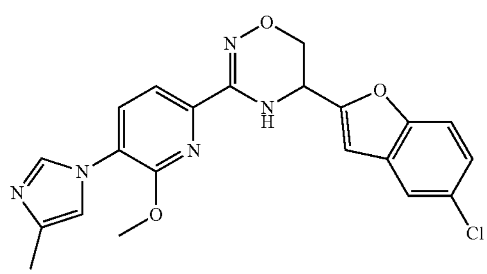 [SMILES: COc1nc(C2=NOCC(c3cc4cc(Cl)ccc4o3)N2)ccc1-n1cnc(C)c1] | (−)-5-(5-chlorobenzofuran-2-yl)-3-(6-methoxy-5-(4-methyl-1H-imidazol-1-yl)pyridin-2-yl)-5,6-dihydro-4H-1,2,4-oxadiazine | 2.2775 |
| 57B | 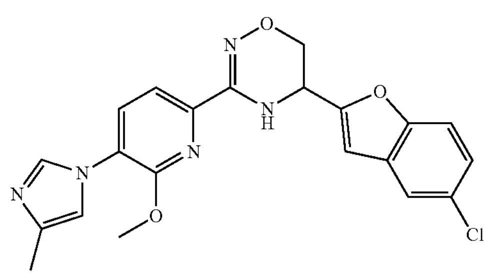 [SMILES: COc1nc(C2=NOCC(c3cc4cc(Cl)ccc4o3)N2)ccc1-n1cnc(C)c1] | (+)-5-(5-chlorobenzofuran-2-yl)-3-(6-methoxy-5-(4-methyl-1H-imidazol-1-yl)pyridin-2-yl)-5,6-dihydro-4H-1,2,4-oxadiazine | 0.0178 |
| 59A | 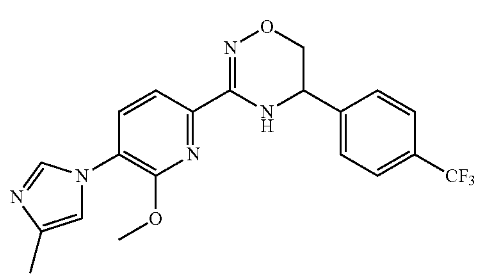 [SMILES: COc1nc(C2=NOCC(c3ccc(C(F)(F)F)cc3)N2)ccc1-n1cnc(C)c1] | (−)-3-(6-methoxy-5-(4-methyl-1H-imidazol-1-yl)pyridin-2-yl)-5-(4-(trifluoromethyl)phenyl)-5,6-dihydro-4H-1,2,4-oxadiazine | >3 |

TABLE II-continued

Biological Assay

| Compound of Example | Structure | Name | Aβ42 EC50 (μM) |
|---|---|---|---|
| 59B | 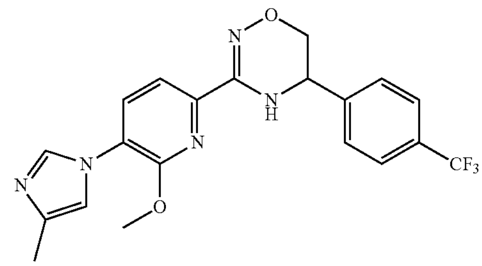 [SMILES: COc1nc(C2=NOCC(c3ccc(C(F)(F)F)cc3)N2)ccc1-n1cnc(C)c1] | (+)-3-(6-methoxy-5-(4-methyl-1H-imidazol-1-yl)pyridin-2-yl)-5-(4-(trifluoromethyl)phenyl)-5,6-dihydro-4H-1,2,4-oxadiazine | 0.0337 |
| 61A | 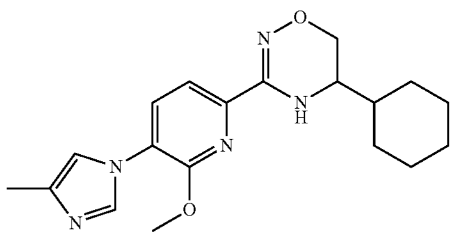 [SMILES: COc1nc(C2=NOCC(C3CCCCC3)N2)ccc1-n1cnc(C)c1] | (−)-5-cyclohexyl-3-(6-methoxy-5-(4-methyl-1H-imidazol-1-yl)pyridin-2-yl)-5,6-dihydro-4H-1,2,4-oxadiazine | 0.7754 |
| 61B | 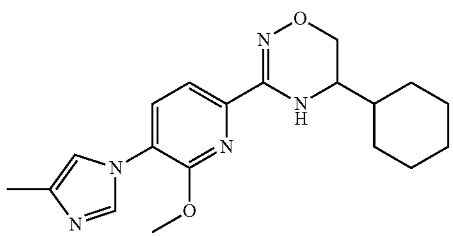 [SMILES: COc1nc(C2=NOCC(C3CCCCC3)N2)ccc1-n1cnc(C)c1] | (+)-5-cyclohexyl-3-(6-methoxy-5-(4-methyl-1H-imidazol-1-yl)pyridin-2-yl)-5,6-dihydro-4H-1,2,4-oxadiazine | 0.0578 |
| 64A | 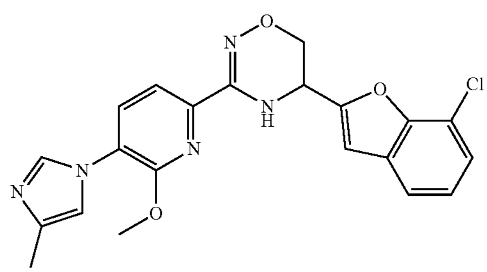 [SMILES: COc1nc(C2=NOCC(c3cc4cccc(Cl)c4o3)N2)ccc1-n1cnc(C)c1] | (−)-5-(7-chlorobenzofuran-2-yl)-3-(6-methoxy-5-(4-methyl-1H-imidazol-1-yl)pyridin-2-yl)-5,6-dihydro-4H-1,2,4-oxadiazine | 0.7589 |
| 64B | 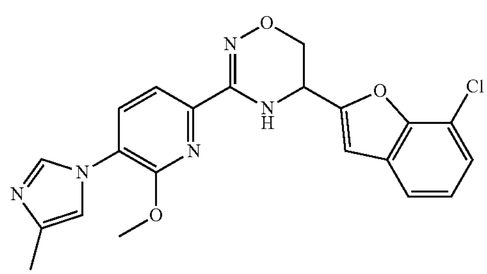 [SMILES: COc1nc(C2=NOCC(c3cc4cccc(Cl)c4o3)N2)ccc1-n1cnc(C)c1] | (+)-5-(7-chlorobenzofuran-2-yl)-3-(6-methoxy-5-(4-methyl-1H-imidazol-1-yl)pyridin-2-yl)-5,6-dihydro-4H-1,2,4-oxadiazine | 0.0122 |
| 66A | 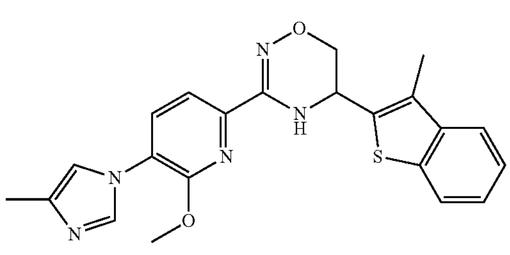 [SMILES: COc1nc(C2=NOCC(c3sc4ccccc4c3C)N2)ccc1-n1cnc(C)c1] | (−)-3-(6-methoxy-5-(4-methyl-1H-imidazol-1-yl)pyridin-2-yl)-5-(3-methylbenzo[b]thiophen-2-yl)-5,6-dihydro-4H-1,2,4-oxadiazine | 0.6512 |

TABLE II-continued

Biological Assay

| Compound of Example | Structure | Name | Aβ42 EC50 (μM) |
|---|---|---|---|
| 66B | 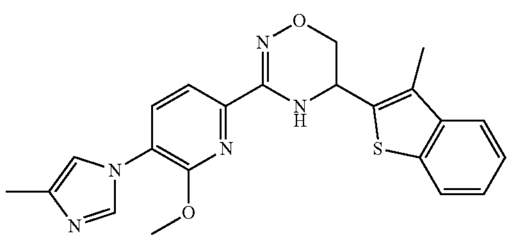 [SMILES: COc1nc(C2=NOCC(c3sc4ccccc4c3C)N2)ccc1-n1cnc(C)c1] | (+)-3-(6-methoxy-5-(4-methyl-1H-imidazol-1-yl)pyridin-2-yl)-5-(3-methylbenzo[b]thiophen-2-yl)-5,6-dihydro-4H-1,2,4-oxadiazine | 0.0091 |
| 68A | 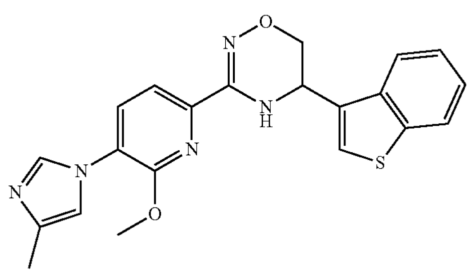 [SMILES: COc1nc(C2=NOCC(c3csc4ccccc34)N2)ccc1-n1cnc(C)c1] | (−)-5-(benzo[b]thiophen-3-yl)-3-(6-methoxy-5-(4-methyl-1H-imidazol-1-yl)pyridin-2-yl)-5,6-dihydro-4H-1,2,4-oxadiazine | 1.0922 |
| 68B | 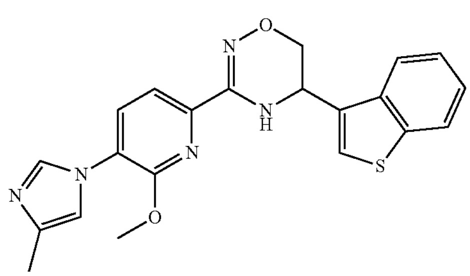 [SMILES: COc1nc(C2=NOCC(c3csc4ccccc34)N2)ccc1-n1cnc(C)c1] | (+)-5-(benzo[b]thiophen-3-yl)-3-(6-methoxy-5-(4-methyl-1H-imidazol-1-yl)pyridin-2-yl)-5,6-dihydro-4H-1,2,4-oxadiazine | 0.0208 |
| 70A | 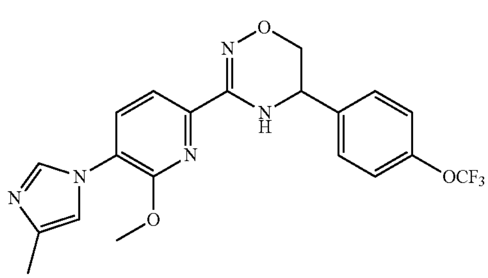 [SMILES: COc1nc(C2=NOCC(c3ccc(OC(F)(F)F)cc3)N2)ccc1-n1cnc(C)c1] | (−)-3-(6-methoxy-5-(4-methyl-1H-imidazol-1-yl)pyridin-2-yl)-5-(4-(trifluoromethoxy)phenyl)-5,6-dihydro-4H-1,2,4-oxadiazine | >3 |
| 70B | 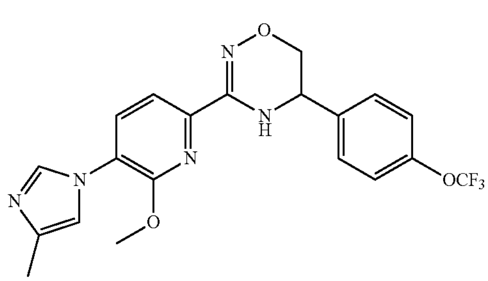 [SMILES: COc1nc(C2=NOCC(c3ccc(OC(F)(F)F)cc3)N2)ccc1-n1cnc(C)c1] | (+)-3-(6-methoxy-5-(4-methyl-1H-imidazol-1-yl)pyridin-2-yl)-5-(4-(trifluoromethoxy)phenyl)-5,6-dihydro-4H-1,2,4-oxadiazine | 0.0218 |

TABLE II-continued

Biological Assay

| Compound of Example | Structure | Name | Aβ42 EC50 (μM) |
|---|---|---|---|
| 73A | 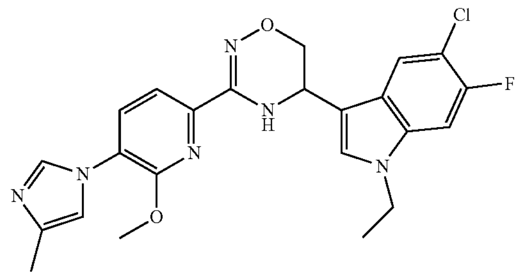 [SMILES: CCn1cc(C2CON=C(c3ccc(-n4cnc(C)c4)c(OC)n3)N2)c2cc(Cl)c(F)cc21] | (−)-5-(5-chloro-1-ethyl-6-fluoro-1H-indol-3-yl)-3-(6-methoxy-5-(4-methyl-1H-imidazol-1-yl)pyridin-2-yl)-5,6-dihydro-4H-1,2,4-oxadiazine | 0.0549 |
| 73B | 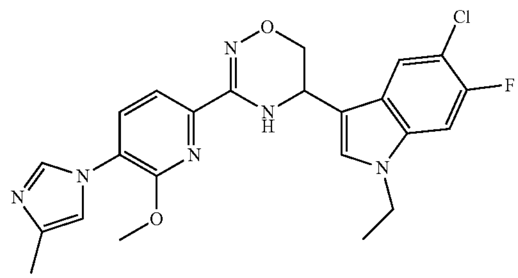 [SMILES: CCn1cc(C2CON=C(c3ccc(-n4cnc(C)c4)c(OC)n3)N2)c2cc(Cl)c(F)cc21] | (+)-5-(5-chloro-1-ethyl-6-fluoro-1H-indol-3-yl)-3-(6-methoxy-5-(4-methyl-1H-imidazol-1-yl)pyridin-2-yl)-5,6-dihydro-4H-1,2,4-oxadiazine | 0.0039 |
| 75A | 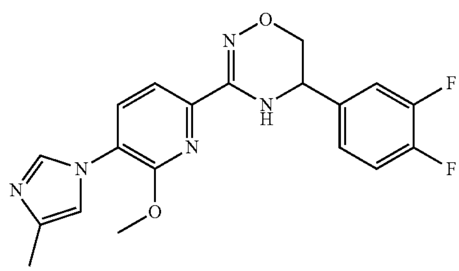 [SMILES: COc1nc(C2=NOCC(c3ccc(F)c(F)c3)N2)ccc1-n1cnc(C)c1] | (−)-5-(3,4-difluorophenyl)-3-(6-methoxy-5-(4-methyl-1H-imidazol-1-yl)pyridin-2-yl)-5,6-dihydro-4H-1,2,4-oxadiazine | >3 |
| 75B | 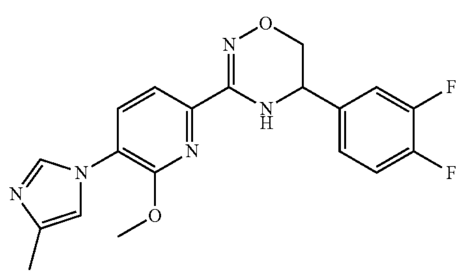 [SMILES: COc1nc(C2=NOCC(c3ccc(F)c(F)c3)N2)ccc1-n1cnc(C)c1] | (+)-5-(3,4-difluorophenyl)-3-(6-methoxy-5-(4-methyl-1H-imidazol-1-yl)pyridin-2-yl)-5,6-dihydro-4H-1,2,4-oxadiazine | 0.0922 |
| 78A | 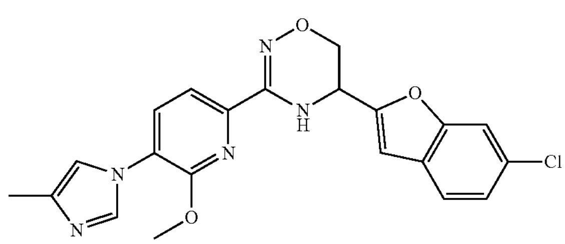 [SMILES: COc1nc(C2=NOCC(c3cc4ccc(Cl)cc4o3)N2)ccc1-n1cnc(C)c1] | (−)-5-(6-chlorobenzofuran-2-yl)-3-(6-methoxy-5-(4-methyl-1H-imidazol-1-yl)pyridin-2-yl)-5,6-dihydro-4H-1,2,4-oxadiazine | 1.2825 |

TABLE II-continued

Biological Assay

| Compound of Example | Structure | Name | Aβ42 EC50 (μM) |
|---|---|---|---|
| 78B | 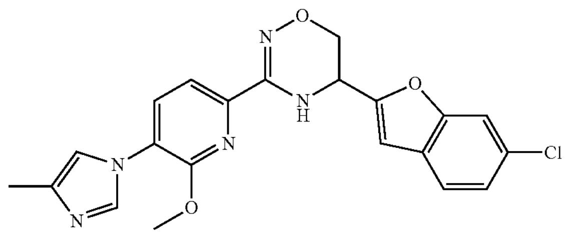 [SMILES: COc1nc(C2=NOCC(c3cc4ccc(Cl)cc4o3)N2)ccc1-n1cnc(C)c1] | (+)-5-(6-chlorobenzofuran-2-yl)-3-(6-methoxy-5-(4-methyl-1H-imidazol-1-yl)pyridin-2-yl)-5,6-dihydro-4H-1,2,4-oxadiazine | 0.0089 |
| 81A | 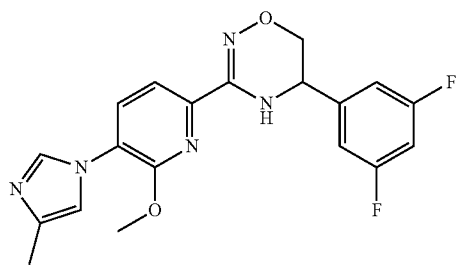 [SMILES: COc1nc(C2=NOCC(c3cc(F)cc(F)c3)N2)ccc1-n1cnc(C)c1] | (−)-5-(3,5-difluorophenyl)-3-(6-methoxy-5-(4-methyl-1H-imidazol-1-yl)pyridin-2-yl)-5,6-dihydro-4H-1,2,4-oxadiazine | >3 |
| 81B | 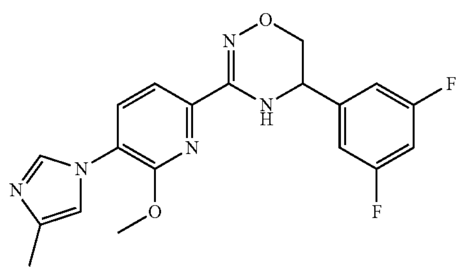 [SMILES: COc1nc(C2=NOCC(c3cc(F)cc(F)c3)N2)ccc1-n1cnc(C)c1] | (+)-5-(3,5-difluorophenyl)-3-(6-methoxy-5-(4-methyl-1H-imidazol-1-yl)pyridin-2-yl)-5,6-dihydro-4H-1,2,4-oxadiazine | 0.0431 |
| 84A | 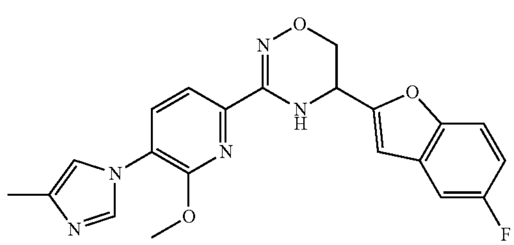 [SMILES: COc1nc(C2=NOCC(c3cc4cc(F)ccc4o3)N2)ccc1-n1cnc(C)c1] | (−)-5-(5-fluorobenzofuran-2-yl)-3-(6-methoxy-5-(4-methyl-1H-imidazol-1-yl)pyridin-2-yl)-5,6-dihydro-4H-1,2,4-oxadiazine | 0.9441 |
| 84B | 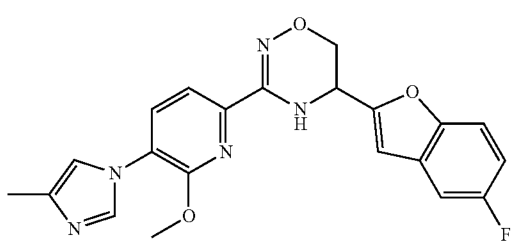 [SMILES: COc1nc(C2=NOCC(c3cc4cc(F)ccc4o3)N2)ccc1-n1cnc(C)c1] | (+)-5-(5-fluorobenzofuran-2-yl)-3-(6-methoxy-5-(4-methyl-1H-imidazol-1-yl)pyridin-2-yl)-5,6-dihydro-4H-1,2,4-oxadiazine | 0.0297 |
| 86A | 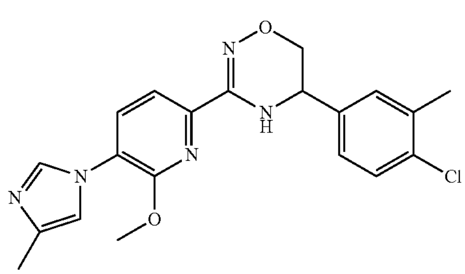 [SMILES: COc1nc(C2=NOCC(c3ccc(Cl)c(C)c3)N2)ccc1-n1cnc(C)c1] | (−)-5-(4-chloro-3-methylphenyl)-3-(6-methoxy-5-(4-methyl-1H-imidazol-1-yl)pyridin-2-yl)-5,6-dihydro-4H-1,2,4-oxadiazine | 1.5495 |

TABLE II-continued

Biological Assay

| Compound of Example | Structure | Name | Aβ42 EC50 (μM) |
|---|---|---|---|
| 86B | 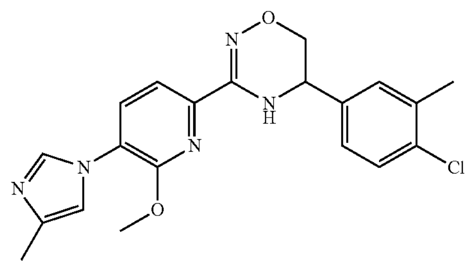 [SMILES: COc1nc(C2=NOCC(c3ccc(Cl)c(C)c3)N2)ccc1-n1cnc(C)c1] | (+)-5-(4-chloro-3-methylphenyl)-3-(6-methoxy-5-(4-methyl-1H-imidazol-1-yl)pyridin-2-yl)-5,6-dihydro-4H-1,2,4-oxadiazine | 0.0104 |
| 89A | 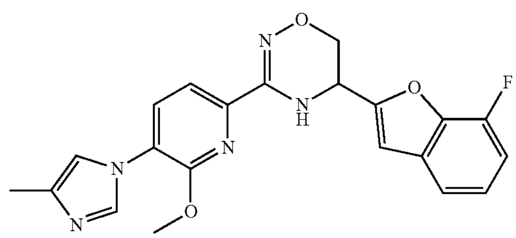 [SMILES: COc1nc(C2=NOCC(c3cc4cccc(F)c4o3)N2)ccc1-n1cnc(C)c1] | (−)-5-(7-fluorobenzofuran-2-yl)-3-(6-methoxy-5-(4-methyl-1H-imidazol-1-yl)pyridin-2-yl)-5,6-dihydro-4H-1,2,4-oxadiazine | 2.3427 |
| 89B | 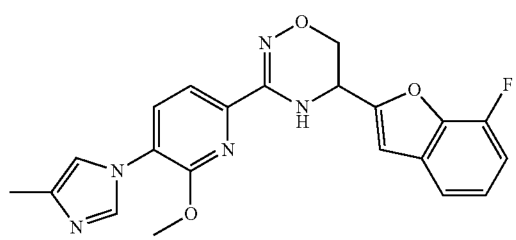 [SMILES: COc1nc(C2=NOCC(c3cc4cccc(F)c4o3)N2)ccc1-n1cnc(C)c1] | (+)-5-(7-fluorobenzofuran-2-yl)-3-(6-methoxy-5-(4-methyl-1H-imidazol-1-yl)pyridin-2-yl)-5,6-dihydro-4H-1,2,4-oxadiazine | 0.0442 |
| 91A | 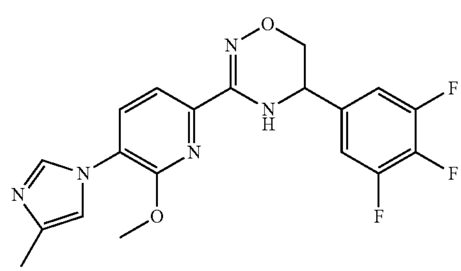 [SMILES: COc1nc(C2=NOCC(c3cc(F)c(F)c(F)c3)N2)ccc1-n1cnc(C)c1] | (−)-3-(6-methoxy-5-(4-methyl-1H-imidazol-1-yl)pyridin-2-yl)-5-(3,4,5-trifluorophenyl)-5,6-dihydro-4H-1,2,4-oxadiazine | >3 |
| 91B | 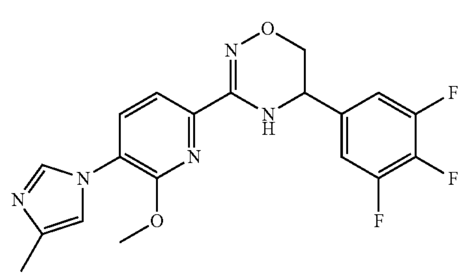 [SMILES: COc1nc(C2=NOCC(c3cc(F)c(F)c(F)c3)N2)ccc1-n1cnc(C)c1] | (+)-3-(6-methoxy-5-(4-methyl-1H-imidazol-1-yl)pyridin-2-yl)-5-(3,4,5-trifluorophenyl)-5,6-dihydro-4H-1,2,4-oxadiazine | 0.0365 |

TABLE II-continued

Biological Assay

| Compound of Example | Structure | Name | Aβ42 EC50 (μM) |
|---|---|---|---|
| 93A | 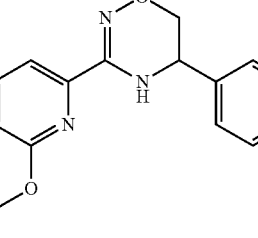 | (−)-5-(4-(difluoromethoxy)phenyl)-3-(6-methoxy-5-(4-methyl-1H-imidazol-1-yl)pyridin-2-yl)-5,6-dihydro-4H-1,2,4-oxadiazine | >3 |
| 93B | 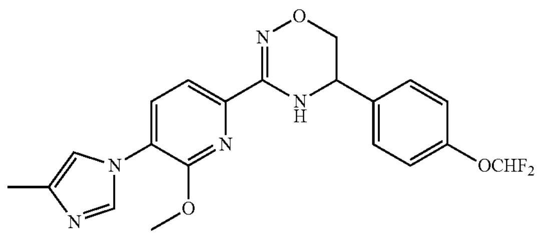 [SMILES: COc1nc(C2=NOCC(c3ccc(OC(F)F)cc3)N2)ccc1-n1cnc(C)c1] | (+)-5-(4-(difluoromethoxy)phenyl)-3-(6-methoxy-5-(4-methyl-1H-imidazol-1-yl)pyridin-2-yl)-5,6-dihydro-4H-1,2,4-oxadiazine | 0.073 |
| 96A | 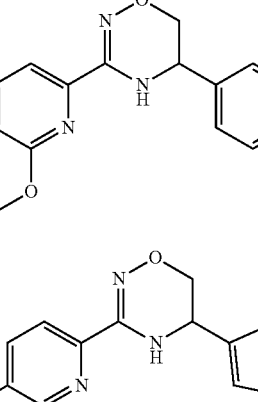 | (−)-5-(4-chlorobenzofuran-2-yl)-3-(6-methoxy-5-(4-methyl-1H-imidazol-1-yl)pyridin-2-yl)-5,6-dihydro-4H-1,2,4-oxadiazine | 1.0109 |
| 96B | 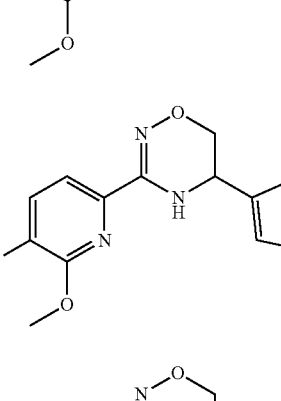 | (+)-5-(4-chlorobenzofuran-2-yl)-3-(6-methoxy-5-(4-methyl-1H-imidazol-1-yl)pyridin-2-yl)-5,6-dihydro-4H-1,2,4-oxadiazine | 0.0127 |
| 99A | 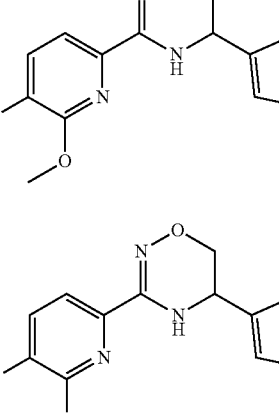 | (+)-5-(4-fluorobenzofuran-2-yl)-3-(6-methoxy-5-(4-methyl-1H-imidazol-1-yl)pyridin-2-yl)-5,6-dihydro-4H-1,2,4-oxadiazine | 0.8559 |
| 99B | 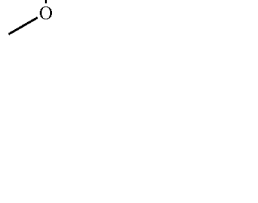 | (−)-5-(4-fluorobenzofuran-2-yl)-3-(6-methoxy-5-(4-methyl-1H-imidazol-1-yl)pyridin-2-yl)-5,6-dihydro-4H-1,2,4-oxadiazine | 0.0257 |

TABLE II-continued

Biological Assay

| Compound of Example | Structure | Name | Aβ42 EC50 (μM) |
|---|---|---|---|
| 101A | 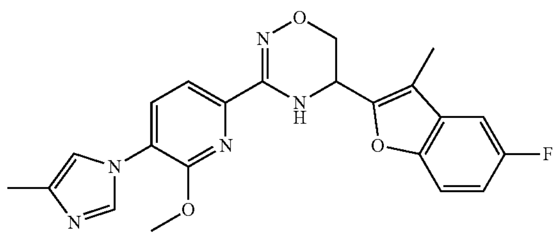 [SMILES: COc1nc(C2=NOCC(c3oc4ccc(F)cc4c3C)N2)ccc1-n1cnc(C)c1] | (−)-5-(5-fluoro-3-methylbenzofuran-2-yl)-3-(6-methoxy-5-(4-methyl-1H-imidazol-1-yl)pyridin-2-yl)-5,6-dihydro-4H-1,2,4-oxadiazine | 1.566 |
| 101B | 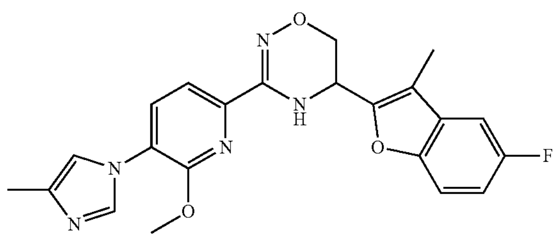 [SMILES: COc1nc(C2=NOCC(c3oc4ccc(F)cc4c3C)N2)ccc1-n1cnc(C)c1] | (+)-5-(5-fluoro-3-methylbenzofuran-2-yl)-3-(6-methoxy-5-(4-methyl-1H-imidazol-1-yl)pyridin-2-yl)-5,6-dihydro-4H-1,2,4-oxadiazine | 0.0108 |
| 104A | 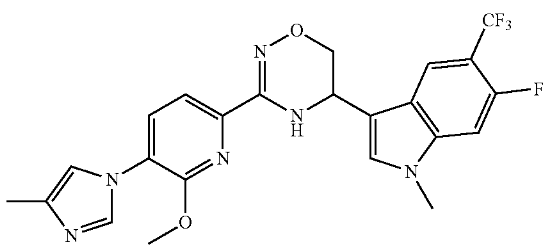 [SMILES: COc1nc(C2=NOCC(c3cn(C)c4cc(F)c(C(F)(F)F)cc34)N2)ccc1-n1cnc(C)c1] | (−)-5-(6-fluoro-1-methyl-5-(trifluoromethyl)-1H-indol-3-yl)-3-(6-methoxy-5-(4-methyl-1H-imidazol-1-yl)pyridin-2-yl)-5,6-dihydro-4H-1,2,4-oxadiazine | 0.1672 |
| 104B | 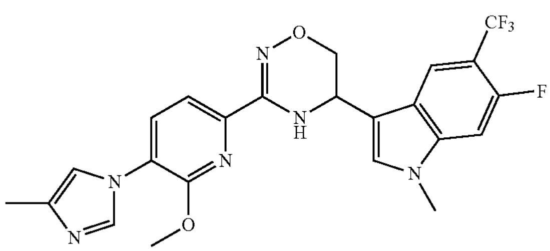 [SMILES: COc1nc(C2=NOCC(c3cn(C)c4cc(F)c(C(F)(F)F)cc34)N2)ccc1-n1cnc(C)c1] | (+)-5-(6-fluoro-1-methyl-5-(trifluoromethyl)-1H-indol-3-yl)-3-(6-methoxy-5-(4-methyl-1H-imidazol-1-yl)pyridin-2-yl)-5,6-dihydro-4H-1,2,4-oxadiazine | 0.0046 |
| 106A | 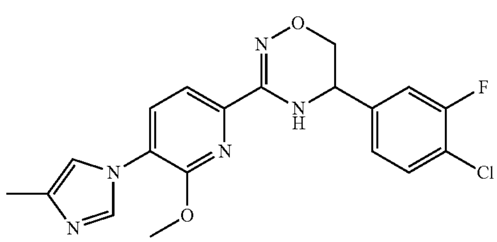 [SMILES: COc1nc(C2=NOCC(c3ccc(Cl)c(F)c3)N2)ccc1-n1cnc(C)c1] | (−)-5-(4-chloro-3-fluorophenyl)-3-(6-methoxy-5-(4-methyl-1H-imidazol-1-yl)pyridin-2-yl)-5,6-dihydro-4H-1,2,4-oxadiazine | >3 |
| 106B | 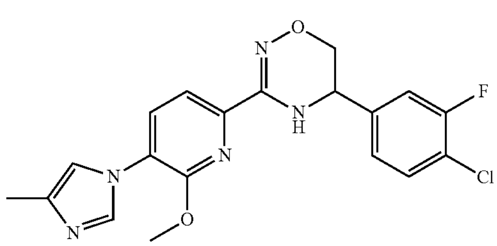 [SMILES: COc1nc(C2=NOCC(c3ccc(Cl)c(F)c3)N2)ccc1-n1cnc(C)c1] | (+)-5-(4-chloro-3-fluorophenyl)-3-(6-methoxy-5-(4-methyl-1H-imidazol-1-yl)pyridin-2-yl)-5,6-dihydro-4H-1,2,4-oxadiazine | 0.0229 |

TABLE II-continued

Biological Assay

| Compound of Example | Structure | Name | Aβ42 EC50 (μM) |
|---|---|---|---|
| 108A | 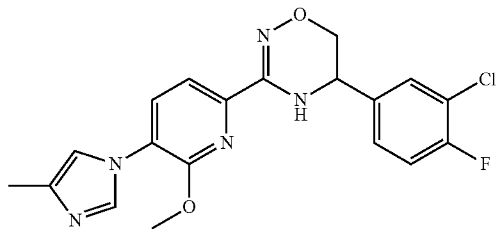 [SMILES: COc1nc(C2=NOCC(c3ccc(F)c(Cl)c3)N2)ccc1-n1cnc(C)c1] | (−)-5-(3-chloro-4-fluorophenyl)-3-(6-methoxy-5-(4-methyl-1H-imidazol-1-yl)pyridin-2-yl)-5,6-dihydro-4H-1,2,4-oxadiazine | 2.6329 |
| 108B | 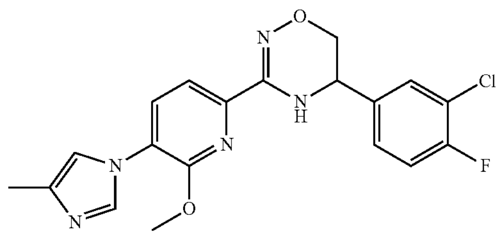 [SMILES: COc1nc(C2=NOCC(c3ccc(F)c(Cl)c3)N2)ccc1-n1cnc(C)c1] | (+)-5-(3-chloro-4-fluorophenyl)-3-(6-methoxy-5-(4-methyl-1H-imidazol-1-yl)pyridin-2-yl)-5,6-dihydro-4H-1,2,4-oxadiazine | 0.0232 |
| 111A | 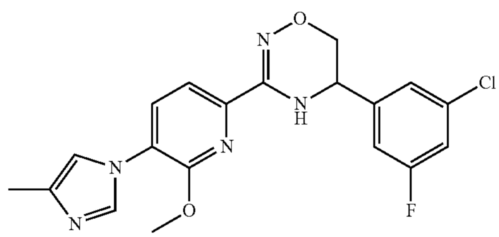 [SMILES: COc1nc(C2=NOCC(c3cc(F)cc(Cl)c3)N2)ccc1-n1cnc(C)c1] | (−)-5-(3-chloro-5-fluorophenyl)-3-(6-methoxy-5-(4-methyl-1H-imidazol-1-yl)pyridin-2-yl)-5,6-dihydro-4H-1,2,4-oxadiazine | >3 |
| 111B | 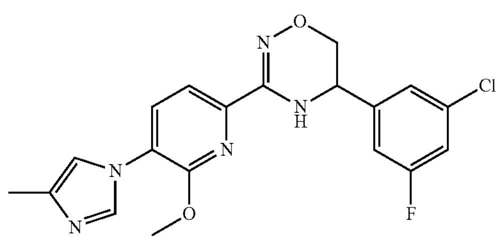 [SMILES: COc1nc(C2=NOCC(c3cc(F)cc(Cl)c3)N2)ccc1-n1cnc(C)c1] | (+)-5-(3-chloro-5-fluorophenyl)-3-(6-methoxy-5-(4-methyl-1H-imidazol-1-yl)pyridin-2-yl)-5,6-dihydro-4H-1,2,4-oxadiazine | 0.0226 |
| 113A | 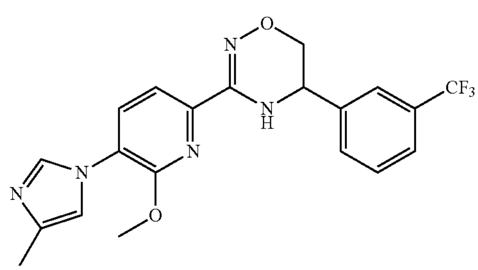 [SMILES: COc1nc(C2=NOCC(c3cccc(C(F)(F)F)c3)N2)ccc1-n1cnc(C)c1] | (−)-3-(6-methoxy-5-(4-methyl-1H-imidazol-1-yl)pyridin-2-yl)-5-(3-(trifluoromethyl)phenyl)-5,6-dihydro-4H-1,2,4-oxadiazine | >3 |
| 113B | 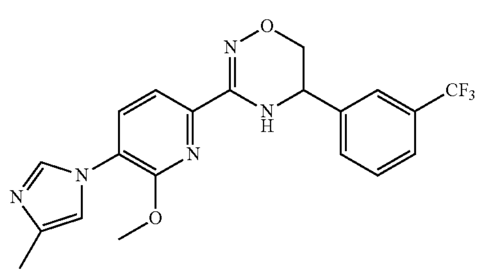 [SMILES: COc1nc(C2=NOCC(c3cccc(C(F)(F)F)c3)N2)ccc1-n1cnc(C)c1] | (+)-3-(6-methoxy-5-(4-methyl-1H-imidazol-1-yl)pyridin-2-yl)-5-(3-(trifluoromethyl)phenyl)-5,6-dihydro-4H-1,2,4-oxadiazine | 0.043 |

TABLE II-continued

Biological Assay

| Compound of Example | Structure | Name | Aβ42 EC50 (μM) |
|---|---|---|---|
| 116A | 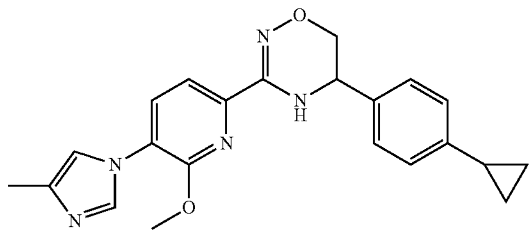 [SMILES: COc1nc(C2=NOCC(c3ccc(C4CC4)cc3)N2)ccc1-n1cnc(C)c1] | (−)-5-(4-cyclopropylphenyl)-3-(6-methoxy-5-(4-methyl-1H-imidazol-1-yl)pyridin-2-yl)-5,6-dihydro-4H-1,2,4-oxadiazine | 0.7669 |
| 116B | 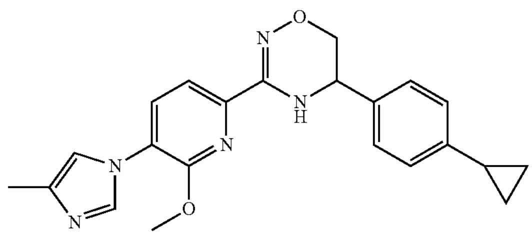 [SMILES: COc1nc(C2=NOCC(c3ccc(C4CC4)cc3)N2)ccc1-n1cnc(C)c1] | (+)-5-(4-cyclopropylphenyl)-3-(6-methoxy-5-(4-methyl-1H-imidazol-1-yl)pyridin-2-yl)-5,6-dihydro-4H-1,2,4-oxadiazine | 0.0388 |
| 118A | 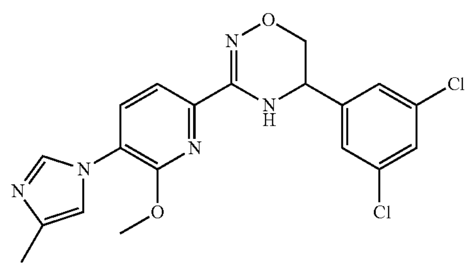 [SMILES: COc1nc(C2=NOCC(c3cc(Cl)cc(Cl)c3)N2)ccc1-n1cnc(C)c1] | (−)-5-(3,5-dichlorophenyl)-3-(6-methoxy-5-(4-methyl-1H-imidazol-1-yl)pyridin-2-yl)-5,6-dihydro-4H-1,2,4-oxadiazine | 1.5053 |
| 118B | 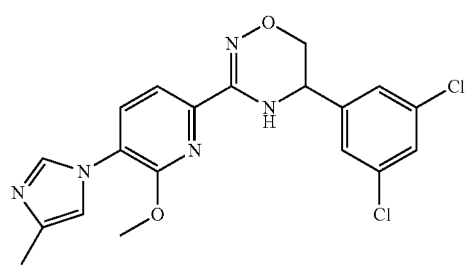 [SMILES: COc1nc(C2=NOCC(c3cc(Cl)cc(Cl)c3)N2)ccc1-n1cnc(C)c1] | (+)-5-(3,5-dichlorophenyl)-3-(6-methoxy-5-(4-methyl-1H-imidazol-1-yl)pyridin-2-yl)-5,6-dihydro-4H-1,2,4-oxadiazine | 0.0099 |
| 121A | 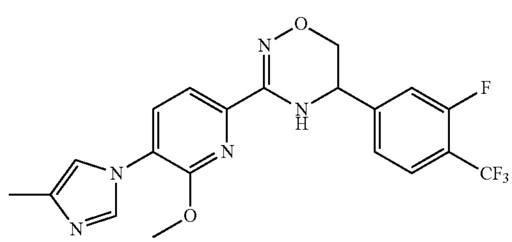 [SMILES: COc1nc(C2=NOCC(c3ccc(C(F)(F)F)c(F)c3)N2)ccc1-n1cnc(C)c1] | (−)-5-(3-fluoro-4-(trifluoromethyl)phenyl)-3-(6-methoxy-5-(4-methyl-1H-imidazol-1-yl)pyridin-2-yl)-5,6-dihydro-4H-1,2,4-oxadiazine | >3 |
| 121B | 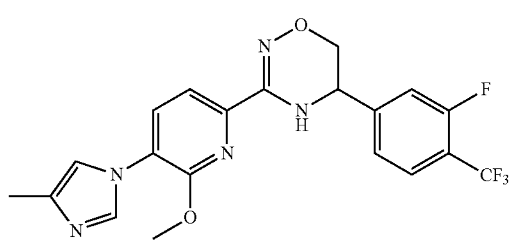 [SMILES: COc1nc(C2=NOCC(c3ccc(C(F)(F)F)c(F)c3)N2)ccc1-n1cnc(C)c1] | (+)-5-(3-fluoro-4-(trifluoromethyl)phenyl)-3-(6-methoxy-5-(4-methyl-1H-imidazol-1-yl)pyridin-2-yl)-5,6-dihydro-4H-1,2,4-oxadiazine | 0.0214 |

TABLE II-continued

Biological Assay

| Compound of Example | Structure | Name | Aβ42 EC50 (μM) |
|---|---|---|---|
| 124A | 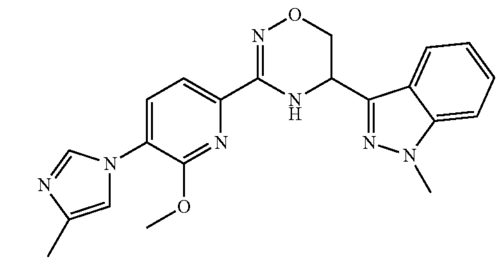 [SMILES: COc1nc(C2=NOCC(c3nn(C)c4ccccc34)N2)ccc1-n1cnc(C)c1] | (−)-3-(6-methoxy-5-(4-methyl-1H-imidazol-1-yl)pyridin-2-yl)-5-(1-methyl-1H-indazol-3-yl)-5,6-dihydro-4H-1,2,4-oxadiazine | 1.0576 |
| 124B | 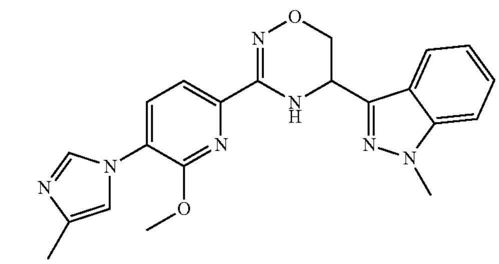 [SMILES: COc1nc(C2=NOCC(c3nn(C)c4ccccc34)N2)ccc1-n1cnc(C)c1] | (+)-3-(6-methoxy-5-(4-methyl-1H-imidazol-1-yl)pyridin-2-yl)-5-(1-methyl-1H-indazol-3-yl)-5,6-dihydro-4H-1,2,4-oxadiazine | 0.0548 |
| 127A | 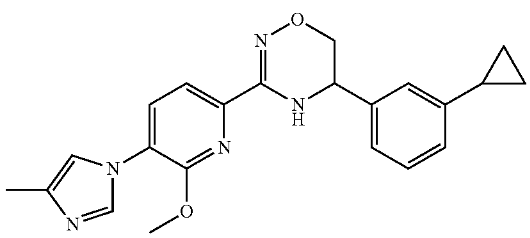 [SMILES: COc1nc(C2=NOCC(c3cccc(C4CC4)c3)N2)ccc1-n1cnc(C)c1] | (−)-5-(3-cyclopropylphenyl)-3-(6-methoxy-5-(4-methyl-1H-imidazol-1-yl)pyridin-2-yl)-5,6-dihydro-4H-1,2,4-oxadiazine | 1.029 |
| 127B | 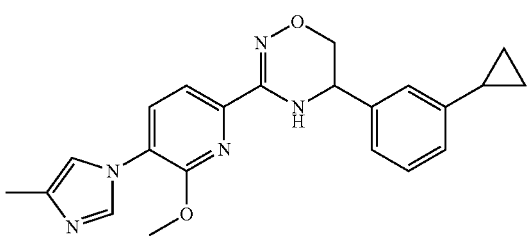 [SMILES: COc1nc(C2=NOCC(c3cccc(C4CC4)c3)N2)ccc1-n1cnc(C)c1] | (+)-5-(3-cyclopropylphenyl)-3-(6-methoxy-5-(4-methyl-1H-imidazol-1-yl)pyridin-2-yl)-5,6-dihydro-4H-1,2,4-oxadiazine | 0.023 |
| 129A | 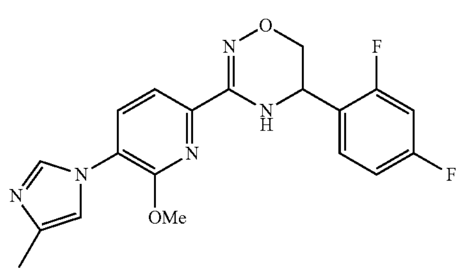 [SMILES: COc1nc(C2=NOCC(c3ccc(F)cc3F)N2)ccc1-n1cnc(C)c1] | 5-(2,4-difluorophenyl)-3-(6-methoxy-5-(4-methyl-1H-imidazol-1-yl)pyridin-2-yl)-5,6-dihydro-4H-1,2,4-oxadiazine | 2.7784 |

TABLE II-continued

| Compound of Example | Structure | Name | Aβ42 EC50 (μM) |
|---|---|---|---|
| 129B | 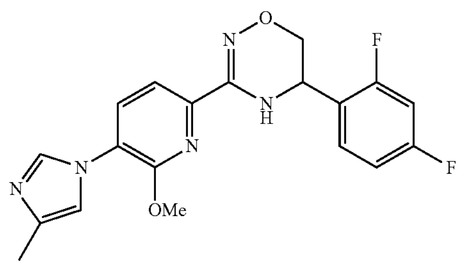 [SMILES: COc1nc(C2=NOCC(c3ccc(F)cc3F)N2)ccc1-n1cnc(C)c1] | 5-(2,4-difluorophenyl)-3-(6-methoxy-5-(4-methyl-1H-imidazol-1-yl)pyridin-2-yl)-5,6-dihydro-4H-1,2,4-oxadiazine | 0.1284 |
| 131A | 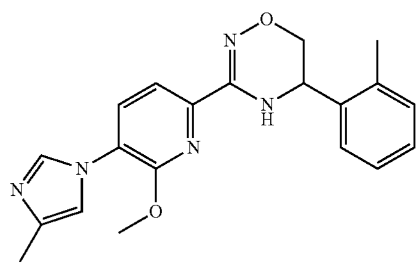 [SMILES: COc1nc(C2=NOCC(c3ccccc3C)N2)ccc1-n1cnc(C)c1] | (+)-3-(6-methoxy-5-(4-methyl-1H-imidazol-1-yl)pyridin-2-yl)-5-(o-tolyl)-5,6-dihydro-4H-1,2,4-oxadiazine | 0.1024 |
| 131B | 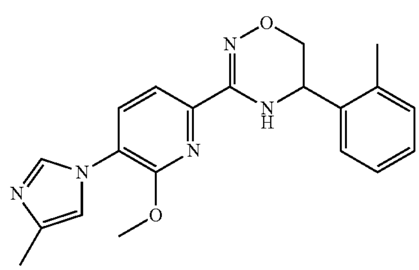 [SMILES: COc1nc(C2=NOCC(c3ccccc3C)N2)ccc1-n1cnc(C)c1] | (−)-3-(6-methoxy-5-(4-methyl-1H-imidazol-1-yl)pyridin-2-yl)-5-(o-tolyl)-5,6-dihydro-4H-1,2,4-oxadiazine | >3 |
| 133A | 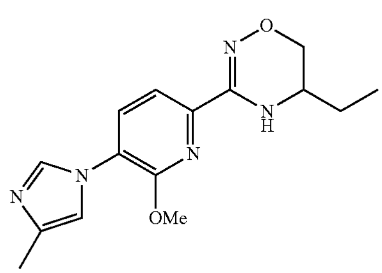 [SMILES: CCC1CON=C(c2ccc(-n3cnc(C)c3)c(OC)n2)N1] | 5-ethyl-3-(6-methoxy-5-(4-methyl-1H-imidazol-1-yl)pyridin-2-yl)-5,6-dihydro-4H-1,2,4-oxadiazine | >3 |
| 133B | 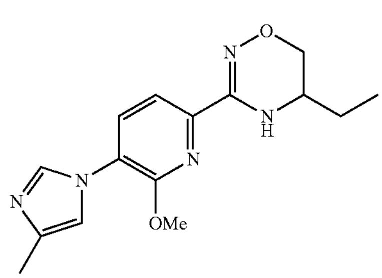 [SMILES: CCC1CON=C(c2ccc(-n3cnc(C)c3)c(OC)n2)N1] | 5-ethyl-3-(6-methoxy-5-(4-methyl-1H-imidazol-1-yl)pyridin-2-yl)-5,6-dihydro-4H-1,2,4-oxadiazine | 0.7279 |

TABLE II-continued

Biological Assay

| Compound of Example | Structure | Name | Aβ42 EC50 (μM) |
|---|---|---|---|
| 134A | 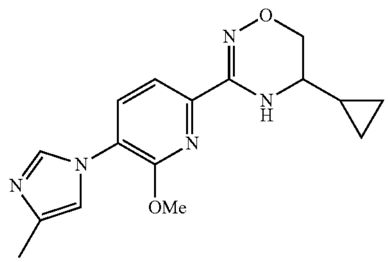 [SMILES: COc1nc(C2=NOCC(C3CC3)N2)ccc1-n1cnc(C)c1] | 5-cyclopropyl-3-(6-methoxy-5-(4-methyl-1H-imidazol-1-yl)pyridin-2-yl)-5,6-dihydro-4H-1,2,4-oxadiazine | >3 |
| 134B | 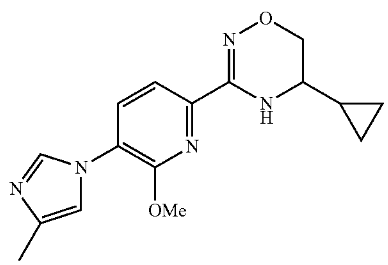 [SMILES: COc1nc(C2=NOCC(C3CC3)N2)ccc1-n1cnc(C)c1] | 5-cyclopropyl-3-(6-methoxy-5-(4-methyl-1H-imidazol-1-yl)pyridin-2-yl)-5,6-dihydro-4H-1,2,4-oxadiazine | 1.1007 |
| 136A | 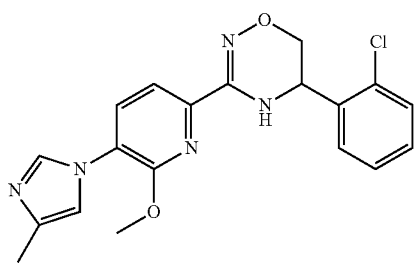 | 5-(2-chlorophenyl)-3-(6-methoxy-5-(4-methyl-1H-imidazol-1-yl)pyridin-2-yl)-5,6-dihydro-4H-1,2,4-oxadiazine | 0.1434 |
| 136B | 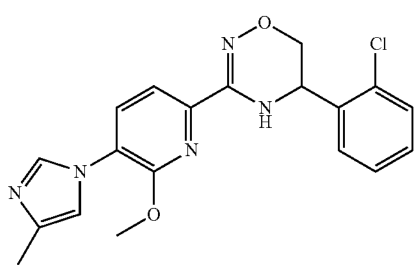 | 5-(2-chlorophenyl)-3-(6-methoxy-5-(4-methyl-1H-imidazol-1-yl)pyridin-2-yl)-5,6-dihydro-4H-1,2,4-oxadiazine | 0.7754 |
| 139A | 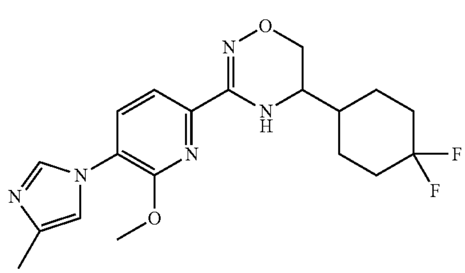 [SMILES: COc1nc(C2=NOCC(C3CCC(F)(F)CC3)N2)ccc1-n1cnc(C)c1] | (−)-5-(4,4-difluorocyclohexyl)-3-(6-methoxy-5-(4-methyl-1H-imidazol-1-yl)pyridin-2-yl)-5,6-dihydro-4H-1,2,4-oxadiazine | 2.1314 |

TABLE II-continued

Biological Assay

| Compound of Example | Structure | Name | Aβ42 EC50 (μM) |
|---|---|---|---|
| 139B | 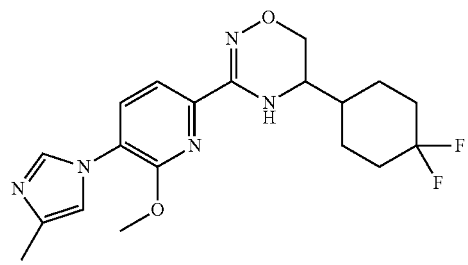 [SMILES: COc1nc(C2=NOCC(C3CCC(F)(F)CC3)N2)ccc1-n1cnc(C)c1] | (+)-5-(4,4-difluorocyclohexyl)-3-(6-methoxy-5-(4-methyl-1H-imidazol-1-yl)pyridin-2-yl)-5,6-dihydro-4H-1,2,4-oxadiazine | 0.2014 |
| 141A | 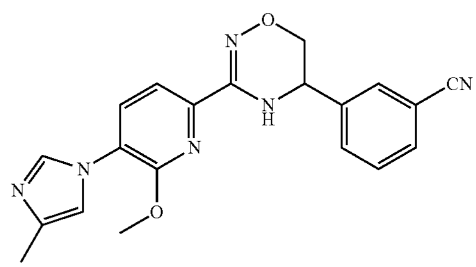 [SMILES: COc1nc(C2=NOCC(c3cccc(C#N)c3)N2)ccc1-n1cnc(C)c1] | (−)-3-(3-(6-methoxy-5-(4-methyl-1H-imidazol-1-yl)pyridin-2-yl)-5,6-dihydro-4H-1,2,4-oxadiazin-5-yl) benzonitrile | >3 |
| 141B | 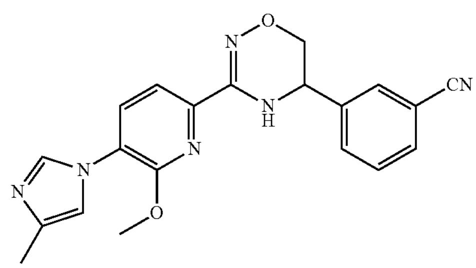 [SMILES: COc1nc(C2=NOCC(c3cccc(C#N)c3)N2)ccc1-n1cnc(C)c1] | (+)-3-(3-(6-methoxy-5-(4-methyl-1H-imidazol-1-yl)pyridin-2-yl)-5,6-dihydro-4H-1,2,4-oxadiazin-5-yl) benzonitrile | 0.2139 |
| 143A | 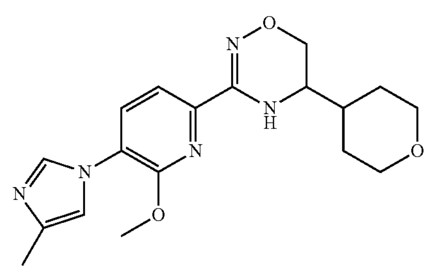 [SMILES: COc1nc(C2=NOCC(C3CCOCC3)N2)ccc1-n1cnc(C)c1] | (−)-3-(6-methoxy-5-(4-methyl-1H-imidazol-1-yl)pyridin-2-yl)-5-(tetrahydro-2H-pyran-4-yl)-5,6-dihydro-4H-1,2,4-oxadiazine | >3 |
| 143B | 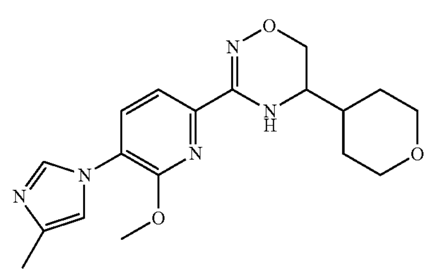 [SMILES: COc1nc(C2=NOCC(C3CCOCC3)N2)ccc1-n1cnc(C)c1] | (+)-3-(6-methoxy-5-(4-methyl-1H-imidazol-1-yl)pyridin-2-yl)-5-(tetrahydro-2H-pyran-4-yl)-5,6-dihydro-4H-1,2,4-oxadiazine | 2.4632 |

TABLE II-continued

Biological Assay

| Compound of Example | Structure | Name | Aβ42 EC50 (μM) |
|---|---|---|---|
| 145A | 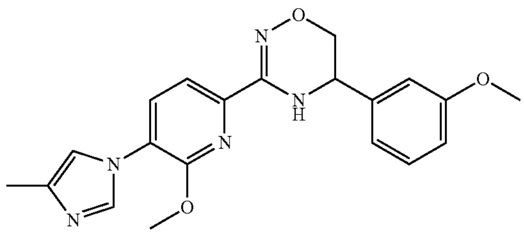 | (−)-3-(6-methoxy-5-(4-methyl-1H-imidazol-1-yl)pyridin-2-yl)-5-(3-methoxyphenyl)-5,6-dihydro-4H-1,2,4-oxadiazine | 2.6728 |
| 145B | 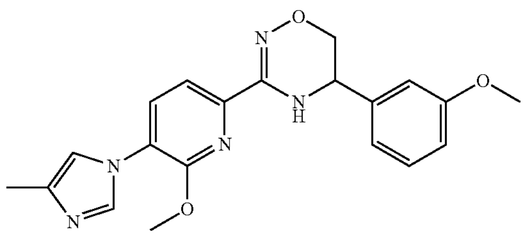 | (+)-3-(6-methoxy-5-(4-methyl-1H-imidazol-1-yl)pyridin-2-yl)-5-(3-methoxyphenyl)-5,6-dihydro-4H-1,2,4-oxadiazine | 0.1967 |
| 147A | 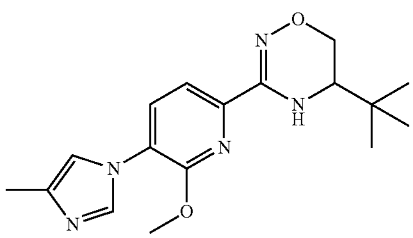 [SMILES: COc1nc(C2=NOCC(C(C)(C)C)N2)ccc1-n1cnc(C)c1] | (−)-5-(tert-butyl)-3-(6-methoxy-5-(4-methyl-1H-imidazol-1-yl)pyridin-2-yl)-5,6-dihydro-4H-1,2,4-oxadiazine | 0.1305 |
| 147B | 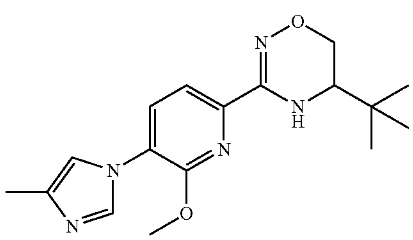 [SMILES: COc1nc(C2=NOCC(C(C)(C)C)N2)ccc1-n1cnc(C)c1] | (+)-5-(tert-butyl)-3-(6-methoxy-5-(4-methyl-1H-imidazol-1-yl)pyridin-2-yl)-5,6-dihydro-4H-1,2,4-oxadiazine | 1.7211 |
| 149A | 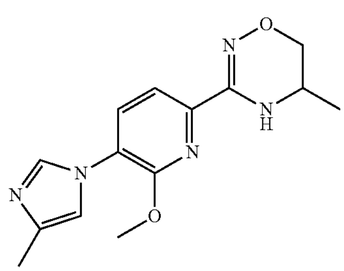 [SMILES: COc1nc(C2=NOCC(C)N2)ccc1-n1cnc(C)c1] | (+)-3-(6-methoxy-5-(4-methyl-1H-imidazol-1-yl)pyridin-2-yl)-5-methyl-5,6-dihydro-4H-1,2,4-oxadiazine | >3 |
| 149B | 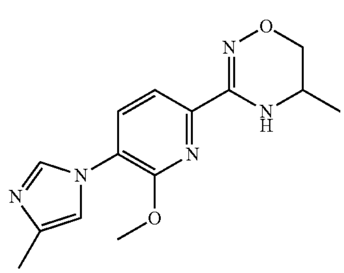 [SMILES: COc1nc(C2=NOCC(C)N2)ccc1-n1cnc(C)c1] | (−)-3-(6-methoxy-5-(4-methyl-1H-imidazol-1-yl)pyridin-2-yl)-5-methyl-5,6-dihydro-4H-1,2,4-oxadiazine | >3 |

TABLE II-continued

Biological Assay

| Compound of Example | Structure | Name | Aβ42 EC50 (μM) |
|---|---|---|---|
| 151A | 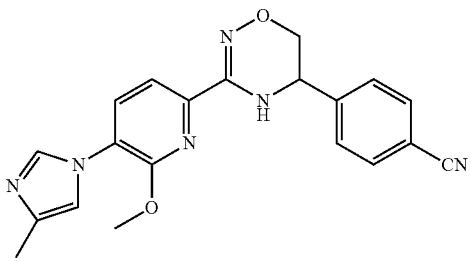 [SMILES: COc1nc(C2=NOCC(c3ccc(C#N)cc3)N2)ccc1-n1cnc(C)c1] | (−)-4-(3-(6-methoxy-5-(4-methyl-1H-imidazol-1-yl)pyridin-2-yl)-5,6-dihydro-4H-1,2,4-oxadiazin-5-yl) benzonitrile | >3 |
| 151B | 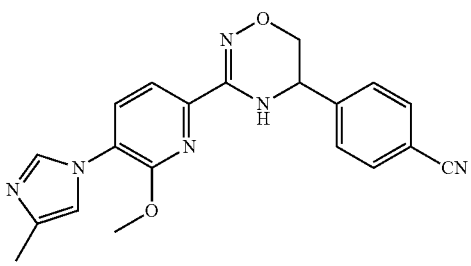 [SMILES: COc1nc(C2=NOCC(c3ccc(C#N)cc3)N2)ccc1-n1cnc(C)c1] | (+)-4-(3-(6-methoxy-5-(4-methyl-1H-imidazol-1-yl)pyridin-2-yl)-5,6-dihydro-4H-1,2,4-oxadiazin-5-yl) benzonitrile | 0.4505 |
| 154A | 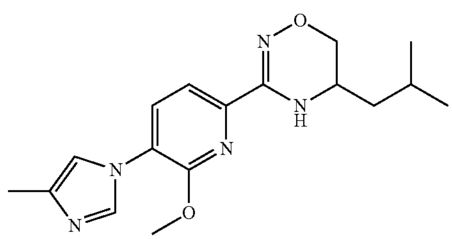 [SMILES: COc1nc(C2=NOCC(CC(C)C)N2)ccc1-n1cnc(C)c1] | (+)-5-isobutyl-3-(6-methoxy-5-(4-methyl-1H-imidazol-1-yl)pyridin-2-yl)-5,6-dihydro-4H-1,2,4-oxadiazine | 0.93 |
| 154B | 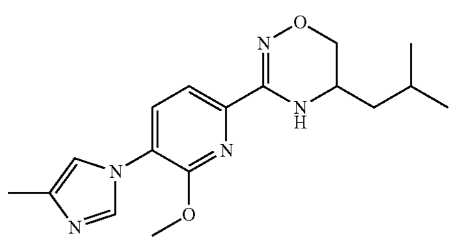 [SMILES: COc1nc(C2=NOCC(CC(C)C)N2)ccc1-n1cnc(C)c1] | (−)-5-isobutyl-3-(6-methoxy-5-(4-methyl-1H-imidazol-1-yl)pyridin-2-yl)-5,6-dihydro-4H-1,2,4-oxadiazine | 0.1992 |
| 156A | 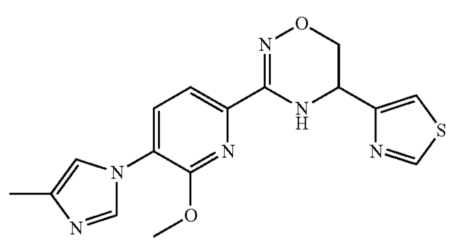 [SMILES: COc1nc(C2=NOCC(c3cscn3)N2)ccc1-n1cnc(C)c1] | (+)-3-(6-methoxy-5-(4-methyl-1H-imidazol-1-yl)pyridin-2-yl)-5-(thiazol-4-yl)-5,6-dihydro-4H-1,2,4-oxadiazine | 1.7254 |
| 156B | 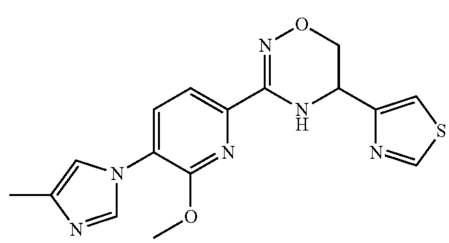 [SMILES: COc1nc(C2=NOCC(c3cscn3)N2)ccc1-n1cnc(C)c1] | (−)-3-(6-methoxy-5-(4-methyl-1H-imidazol-1-yl)pyridin-2-yl)-5-(thiazol-4-yl)-5,6-dihydro-4H-1,2,4-oxadiazine | >3 |

TABLE II-continued

Biological Assay

| Compound of Example | Structure | Name | Aβ42 EC50 (μM) |
|---|---|---|---|
| 159A | 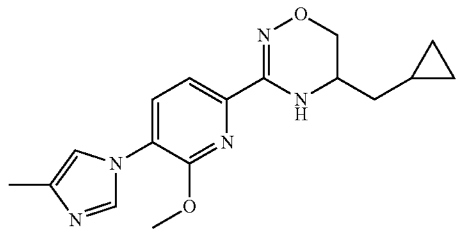 [SMILES: COc1nc(C2=NOCC(CC3CC3)N2)ccc1-n1cnc(C)c1] | 5-(cyclopropylmethyl)-3-(6-methoxy-5-(4-methyl-1H-imidazol-1-yl)pyridin-2-yl)-5,6-dihydro-4H-1,2,4-oxadiazine | >3 |
| 159B | 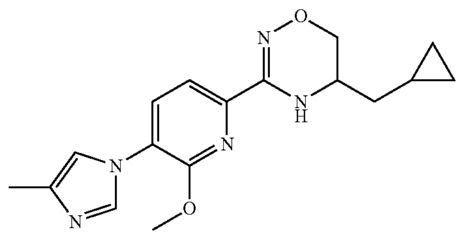 [SMILES: COc1nc(C2=NOCC(CC3CC3)N2)ccc1-n1cnc(C)c1] | 5-(cyclopropylmethyl)-3-(6-methoxy-5-(4-methyl-1H-imidazol-1-yl)pyridin-2-yl)-5,6-dihydro-4H-1,2,4-oxadiazine | 0.6947 |
| 161A | 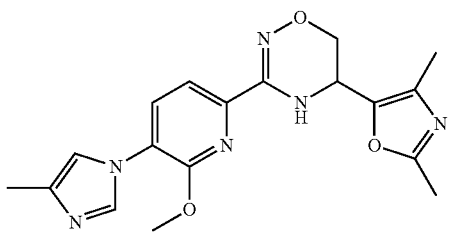 [SMILES: COc1nc(C2=NOCC(c3oc(C)nc3C)N2)ccc1-n1cnc(C)c1] | (−)-5-(2,4-dimethyloxazol-5-yl)-3-(6-methoxy-5-(4-methyl-1H-imidazol-1-yl)pyridin-2-yl)-5,6-dihydro-4H-1,2,4-oxadiazine | >3 |
| 161B | 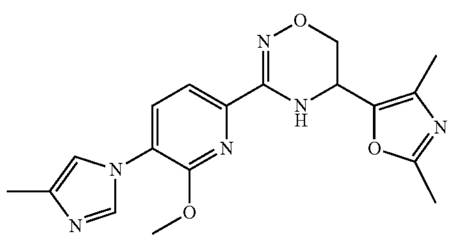 [SMILES: COc1nc(C2=NOCC(c3oc(C)nc3C)N2)ccc1-n1cnc(C)c1] | (+)-5-(2,4-dimethyloxazol-5-yl)-3-(6-methoxy-5-(4-methyl-1H-imidazol-1-yl)pyridin-2-yl)-5,6-dihydro-4H-1,2,4-oxadiazine | >3 |
| 163A | 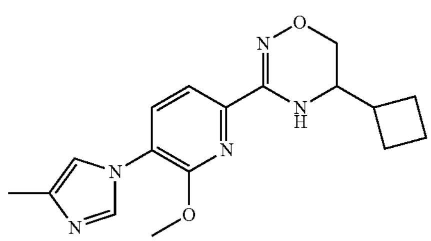 [SMILES: COc1nc(C2=NOCC(C3CCC3)N2)ccc1-n1cnc(C)c1] | (+)-5-cyclobutyl-3-(6-methoxy-5-(4-methyl-1H-imidazol-1-yl)pyridin-2-yl)-5,6-dihydro-4H-1,2,4-oxadiazine | >3 |
| 163B | 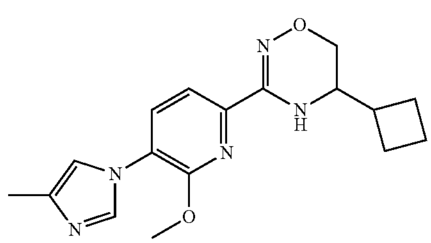 [SMILES: COc1nc(C2=NOCC(C3CCC3)N2)ccc1-n1cnc(C)c1] | (−)-5-cyclobutyl-3-(6-methoxy-5-(4-methyl-1H-imidazol-1-yl)pyridin-2-yl)-5,6-dihydro-4H-1,2,4-oxadiazine | 0.3675 |

TABLE II-continued

Biological Assay

| Compound of Example | Structure | Name | Aβ42 EC50 (μM) |
|---|---|---|---|
| 166A | 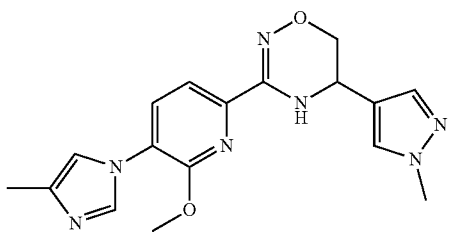 [SMILES: COc1nc(C2=NOCC(c3cnn(C)c3)N2)ccc1-n1cnc(C)c1] | (−)-3-(6-methoxy-5-(4-methyl-1H-imidazol-1-yl)pyridin-2-yl)-5-(1-methyl-1H-pyrazol-4-yl)-5,6-dihydro-4H-1,2,4-oxadiazine | >3 |
| 166B | 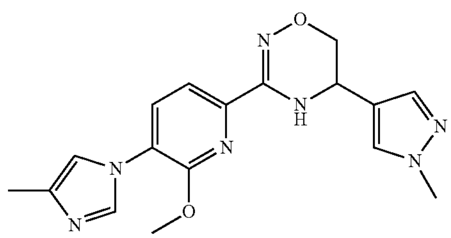 [SMILES: COc1nc(C2=NOCC(c3cnn(C)c3)N2)ccc1-n1cnc(C)c1] | (+)-3-(6-methoxy-5-(4-methyl-1H-imidazol-1-yl)pyridin-2-yl)-5-(1-methyl-1H-pyrazol-4-yl)-5,6-dihydro-4H-1,2,4-oxadiazine | >3 |
| 168A | 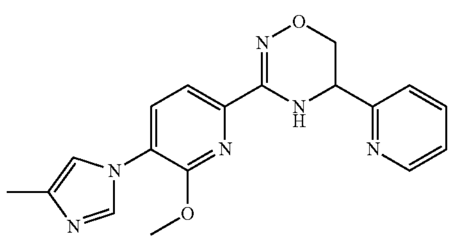 [SMILES: COc1nc(C2=NOCC(c3ccccn3)N2)ccc1-n1cnc(C)c1] | (+)-3-(6-methoxy-5-(4-methyl-1H-imidazol-1-yl)pyridin-2-yl)-5-(pyridin-2-yl)-5,6-dihydro-4H-1,2,4-oxadiazine | >3 |
| 168B | 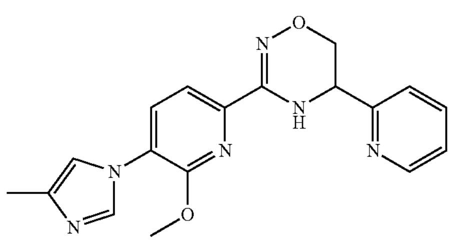 [SMILES: COc1nc(C2=NOCC(c3ccccn3)N2)ccc1-n1cnc(C)c1] | (−)-3-(6-methoxy-5-(4-methyl-1H-imidazol-1-yl)pyridin-2-yl)-5-(pyridin-2-yl)-5,6-dihydro-4H-1,2,4-oxadiazine | >3 |
| 171A | 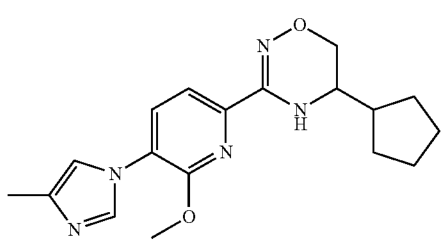 [SMILES: COc1nc(C2=NOCC(C3CCCC3)N2)ccc1-n1cnc(C)c1] | (+)-5-cyclopentyl-3-(6-methoxy-5-(4-methyl-1H-imidazol-1-yl)pyridin-2-yl)-5,6-dihydro-4H-1,2,4-oxadiazine | 0.9176 |
| 171B | 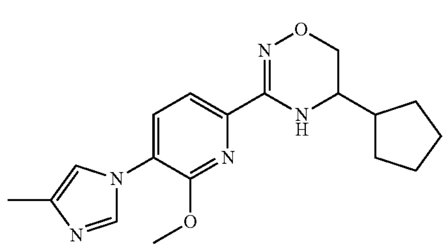 [SMILES: COc1nc(C2=NOCC(C3CCCC3)N2)ccc1-n1cnc(C)c1] | (−)-5-cyclopentyl-3-(6-methoxy-5-(4-methyl-1H-imidazol-1-yl)pyridin-2-yl)-5,6-dihydro-4H-1,2,4-oxadiazine | 0.1068 |

TABLE II-continued

Biological Assay

| Compound of Example | Structure | Name | Aβ42 EC50 (μM) |
|---|---|---|---|
| 174A | 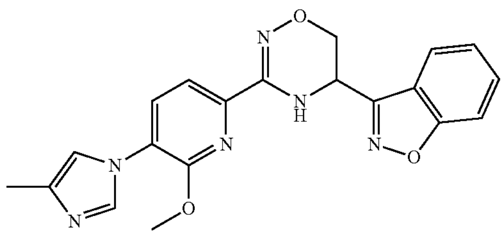 [SMILES: COc1nc(C2=NOCC(c3noc4ccccc34)N2)ccc1-n1cnc(C)c1] | 3-(3-(6-methoxy-5-(4-methyl-1H-imidazol-1-yl)pyridin-2-yl)-5,6-dihydro-4H-1,2,4-oxadiazin-5-yl)benzo[d]isoxazole | >3 |
| 174B | 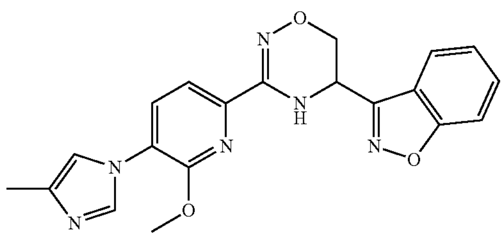 [SMILES: COc1nc(C2=NOCC(c3noc4ccccc34)N2)ccc1-n1cnc(C)c1] | 3-(3-(6-methoxy-5-(4-methyl-1H-imidazol-1-yl)pyridin-2-yl)-5,6-dihydro-4H-1,2,4-oxadiazin-5-yl)benzo[d]isoxazole | 0.2806 |
| 177A | 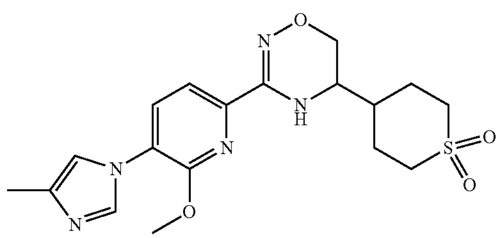 [SMILES: COc1nc(C2=NOCC(C3CCS(=O)(=O)CC3)N2)ccc1-n1cnc(C)c1] | (+)-4-(3-(6-methoxy-5-(4-methyl-1H-imidazol-1-yl)pyridin-2-yl)-5,6-dihydro-4H-1,2,4-oxadiazin-5-yl) tetrahydro-2H-thiopyran 1,1-dioxide | >3 |
| 177B | 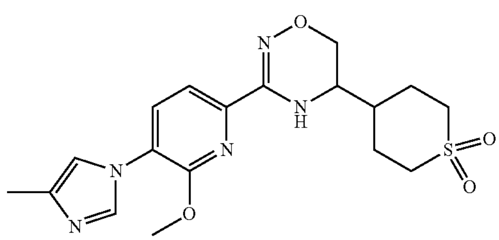 [SMILES: COc1nc(C2=NOCC(C3CCS(=O)(=O)CC3)N2)ccc1-n1cnc(C)c1] | (−)-4-(3-(6-methoxy-5-(4-methyl-1H-imidazol-1-yl)pyridin-2-yl)-5,6-dihydro-4H-1,2,4-oxadiazin-5-yl) tetrahydro-2H-thiopyran 1,1-dioxide | >3 |
| 180A | 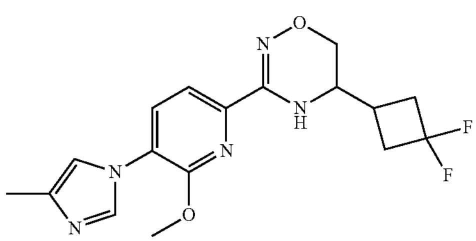 [SMILES: COc1nc(C2=NOCC(C3CC(F)(F)C3)N2)ccc1-n1cnc(C)c1] | (−)-5-(3,3-difluorocyclobutyl)-3-(6-methoxy-5-(4-methyl-1H-imidazol-1-yl)pyridin-2-yl)-5,6-dihydro-4H-1,2,4-oxadiazine | >3 |
| 180B | 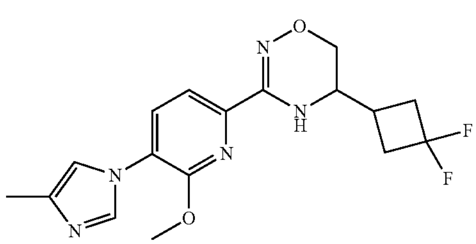 [SMILES: COc1nc(C2=NOCC(C3CC(F)(F)C3)N2)ccc1-n1cnc(C)c1] | (+)-5-(3,3-difluorocyclobutyl)-3-(6-methoxy-5-(4-methyl-1H-imidazol-1-yl)pyridin-2-yl)-5,6-dihydro-4H-1,2,4-oxadiazine | 0.281 |

TABLE II-continued

Biological Assay

| Compound of Example | Structure | Name | Aβ42 EC50 (μM) |
|---|---|---|---|
| 183A | 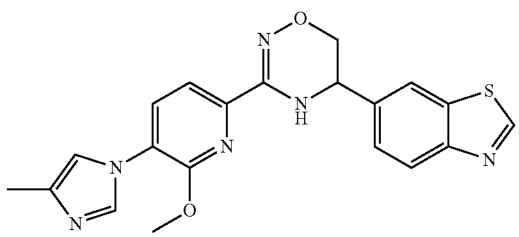 [SMILES: COc1nc(C2=NOCC(c3ccc4ncsc4c3)N2)ccc1-n1cnc(C)c1] | (−)-5-(benzo[d]thiazol-6-yl)-3-(6-methoxy-5-(4-methyl-1H-imidazol-1-yl)pyridin-2-yl)-5,6-dihydro-4H-1,2,4-oxadiazine | 1.7616 |
| 183B | 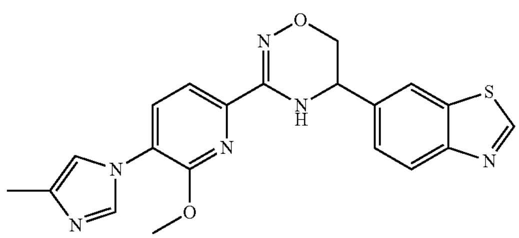 [SMILES: COc1nc(C2=NOCC(c3ccc4ncsc4c3)N2)ccc1-n1cnc(C)c1] | (+)-5-(benzo[d]thiazol-6-yl)-3-(6-methoxy-5-(4-methyl-1H-imidazol-1-yl)pyridin-2-yl)-5,6-dihydro-4H-1,2,4-oxadiazine | 0.2595 |
| 186A | 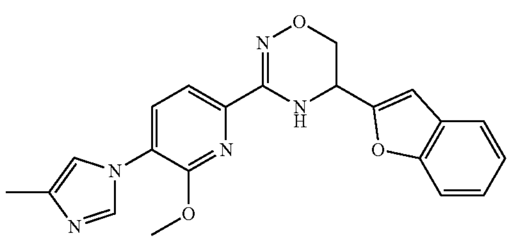 [SMILES: COc1nc(C2=NOCC(c3cc4ccccc4o3)N2)ccc1-n1cnc(C)c1] | (−)-5-(benzofuran-2-yl)-3-(6-methoxy-5-(4-methyl-1H-imidazol-1-yl)pyridin-2-yl)-5,6-dihydro-4H-1,2,4-oxadiazine | 1.1681 |
| 186B | 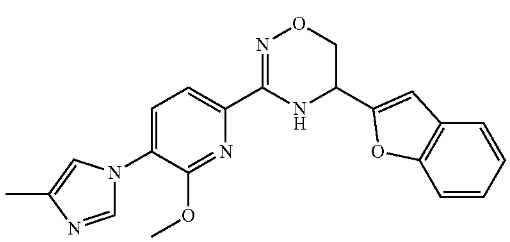 [SMILES: COc1nc(C2=NOCC(c3cc4ccccc4o3)N2)ccc1-n1cnc(C)c1] | (+)-5-(benzofuran-2-yl)-3-(6-methoxy-5-(4-methyl-1H-imidazol-1-yl)pyridin-2-yl)-5,6-dihydro-4H-1,2,4-oxadiazine | 0.0384 |
| 189A | 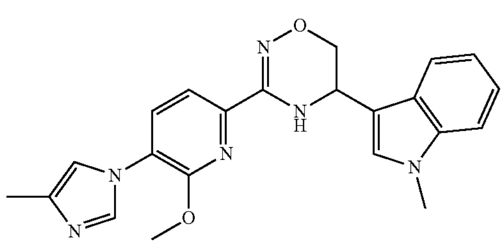 [SMILES: COc1nc(C2=NOCC(c3cn(C)c4ccccc34)N2)ccc1-n1cnc(C)c1] | (+)-3-(6-methoxy-5-(4-methyl-1H-imidazol-1-yl)pyridin-2-yl)-5-(1-methyl-1H-indol-3-yl)-5,6-dihydro-4H-1,2,4-oxadiazine | 0.024 |
| 189B | 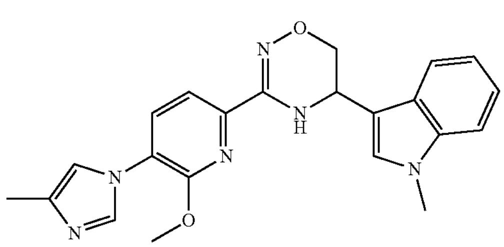 | (−)-3-(6-methoxy-5-(4-methyl-1H-imidazol-1-yl)pyridin-2-yl)-5-(1-methyl-1H-indol-3-yl)-5,6-dihydro-4H-1,2,4-oxadiazine | 0.2522 |

TABLE II-continued

Biological Assay

| Compound of Example | Structure | Name | Aβ42 EC50 (μM) |
|---|---|---|---|
| 190A | 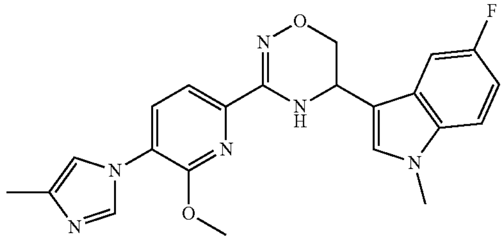 [SMILES: COc1nc(C2=NOCC(c3cn(C)c4ccc(F)cc34)N2)ccc1-n1cnc(C)c1] | (−)-5-(5-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.287 |
| 190B | 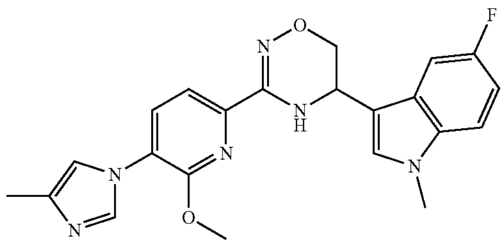 [SMILES: COc1nc(C2=NOCC(c3cn(C)c4ccc(F)cc34)N2)ccc1-n1cnc(C)c1] | (+)-5-(5-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0195 |
| 191A | 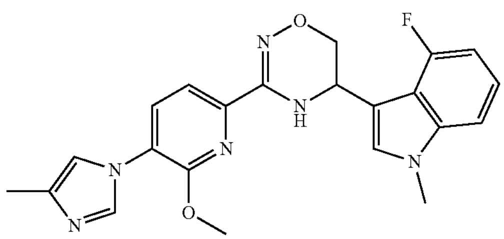 [SMILES: COc1nc(C2=NOCC(c3cn(C)c4cccc(F)c34)N2)ccc1-n1cnc(C)c1] | (+)-5-(4-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0069 |
| 191B | 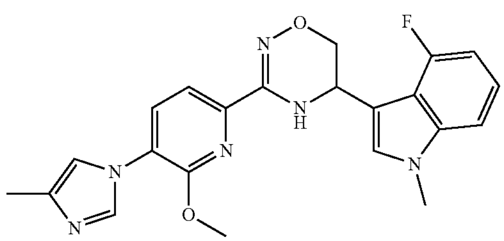 [SMILES: COc1nc(C2=NOCC(c3cn(C)c4cccc(F)c34)N2)ccc1-n1cnc(C)c1] | (−)-5-(4-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0832 |
| 192A | 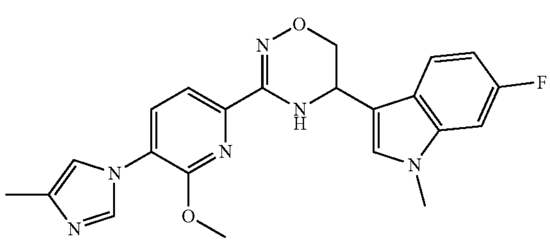 [SMILES: COc1nc(C2=NOCC(c3cn(C)c4cc(F)ccc34)N2)ccc1-n1cnc(C)c1] | (−)-5-(6-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.1704 |
| 192B | 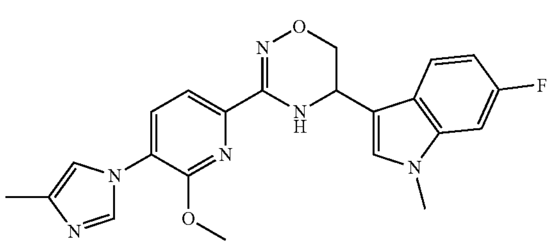 [SMILES: COc1nc(C2=NOCC(c3cn(C)c4cc(F)ccc34)N2)ccc1-n1cnc(C)c1] | (+)-5-(6-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0085 |

TABLE II-continued

Biological Assay

| Compound of Example | Structure | Name | Aβ42 EC50 (μM) |
|---|---|---|---|
| 193A | 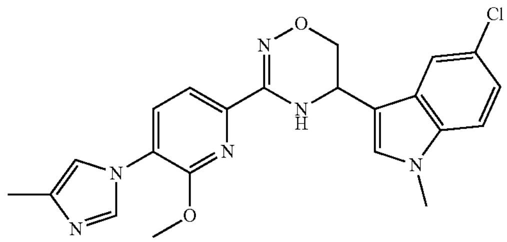 [SMILES: COc1nc(C2=NOCC(c3cn(C)c4ccc(Cl)cc34)N2)ccc1-n1cnc(C)c1] | (−)-5-(5-chloro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.071 |
| 193B | 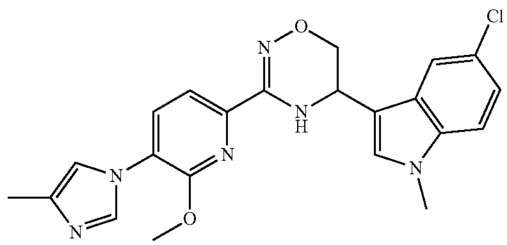 [SMILES: COc1nc(C2=NOCC(c3cn(C)c4ccc(Cl)cc34)N2)ccc1-n1cnc(C)c1] | (+)-5-(5-chloro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0049 |
| 194A | 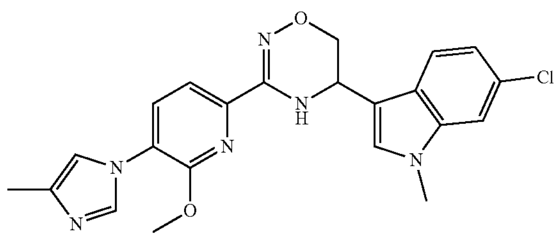 [SMILES: COc1nc(C2=NOCC(c3cn(C)c4cc(Cl)ccc34)N2)ccc1-n1cnc(C)c1] | (+)-5-(6-chloro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0077 |
| 194B | 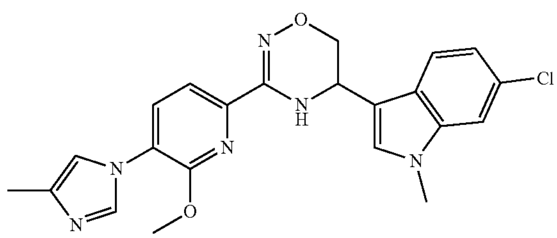 [SMILES: COc1nc(C2=NOCC(c3cn(C)c4cc(Cl)ccc34)N2)ccc1-n1cnc(C)c1] | (−)-5-(6-chloro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.1469 |
| 195A | 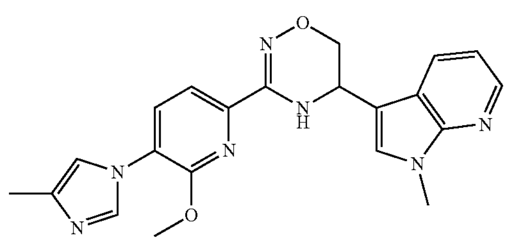 [SMILES: COc1nc(C2=NOCC(c3cn(C)c4ncccc34)N2)ccc1-n1cnc(C)c1] | (−)-3-(6-methoxy-5-(4-methyl-1H-imidazol-1-yl)pyridin-2-yl)-5-(1-methyl-1H-pyrrolo[2,3-b]pyridin-3-yl)-5,6-dihydro-4H-1,2,4-oxadiazine | 2.1122 |
| 195B | 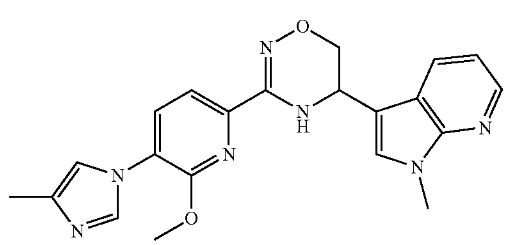 [SMILES: COc1nc(C2=NOCC(c3cn(C)c4ncccc34)N2)ccc1-n1cnc(C)c1] | (+)-3-(6-methoxy-5-(4-methyl-1H-imidazol-1-yl)pyridin-2-yl)-5-(1-methyl-1H-pyrrolo[2,3-b]pyridin-3-yl)-5,6-dihydro-4H-1,2,4-oxadiazine | 0.1632 |

TABLE II-continued

Biological Assay

| Compound of Example | Structure | Name | Aβ42 EC50 (μM) |
|---|---|---|---|
| 196A | 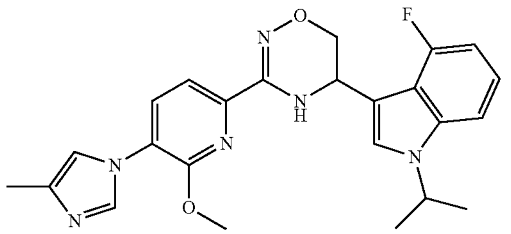 [SMILES: COc1nc(C2=NOCC(c3cn(C(C)C)c4cccc(F)c34)N2)ccc1-n1cnc(C)c1] | (+)-5-(4-fluoro-1-isopropyl-1H-indol-3-yl)-3-(6-methoxy-5-(4-methyl-1H-imidazol-1-yl)pyridin-2-yl)-5,6-dihydro-4H-1,2,4-oxadiazine | 0.0225 |
| 196B | 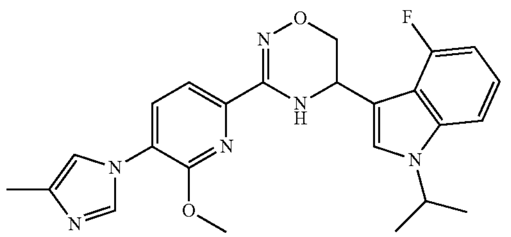 [SMILES: COc1nc(C2=NOCC(c3cn(C(C)C)c4cccc(F)c34)N2)ccc1-n1cnc(C)c1] | (−)-5-(4-fluoro-1-isopropyl-1H-indol-3-yl)-3-(6-methoxy-5-(4-methyl-1H-imidazol-1-yl)pyridin-2-yl)-5,6-dihydro-4H-1,2,4-oxadiazine | 0.2198 |
| 197A | 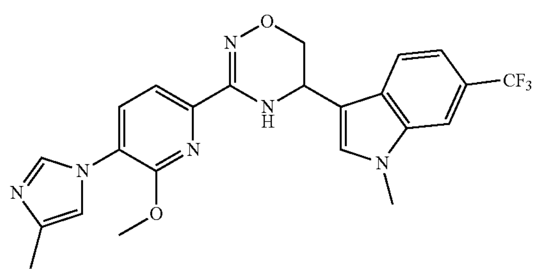 [SMILES: COc1nc(C2=NOCC(c3cn(C)c4cc(C(F)(F)F)ccc34)N2)ccc1-n1cnc(C)c1] | (+)-3-(6-methoxy-5-(4-methyl-1H-imidazol-1-yl)pyridin-2-yl)-5-(1-methyl-6-(trifluoromethyl)-1H-indol-3-yl)-5,6-dihydro-4H-1,2,4-oxadiazine | 0.0034 |
| 197B | 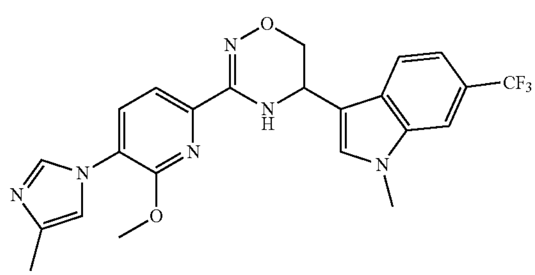 [SMILES: COc1nc(C2=NOCC(c3cn(C)c4cc(C(F)(F)F)ccc34)N2)ccc1-n1cnc(C)c1] | (−)-3-(6-methoxy-5-(4-methyl-1H-imidazol-1-yl)pyridin-2-yl)-5-(1-methyl-6-(trifluoromethyl)-1H-indol-3-yl)-5,6-dihydro-4H-1,2,4-oxadiazine | 0.0905 |
| 200A | 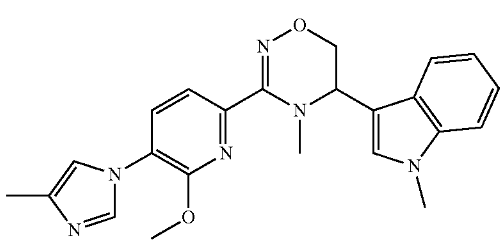 [SMILES: COc1nc(C2=NOCC(c3cn(C)c4ccccc34)N2C)ccc1-n1cnc(C)c1] | (+)-3-(6-methoxy-5-(4-methyl-1H-imidazol-1-yl)pyridin-2-yl)-4-methyl-5-(1-methyl-1H-indol-3-yl)-5,6-dihydro-4H-1,2,4-oxadiazine | 0.154 |
| 200B | 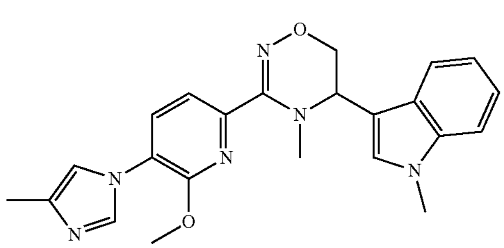 [SMILES: COc1nc(C2=NOCC(c3cn(C)c4ccccc34)N2C)ccc1-n1cnc(C)c1] | (−)-3-(6-methoxy-5-(4-methyl-1H-imidazol-1-yl)pyridin-2-yl)-4-methyl-5-(1-methyl-1H-indol-3-yl)-5,6-dihydro-4H-1,2,4-oxadiazine | 1.2891 |

TABLE II-continued

Biological Assay

| Compound of Example | Structure | Name | Aβ42 EC50 (μM) |
|---|---|---|---|
| 203A | 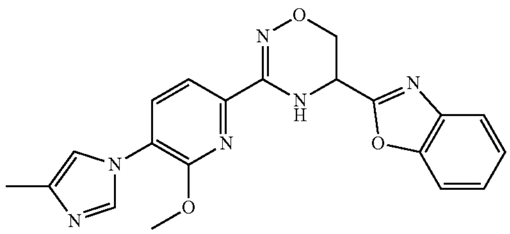 [SMILES: COc1nc(C2=NOCC(c3nc4ccccc4o3)N2)ccc1-n1cnc(C)c1] | (−)-2-(3-(6-methoxy-5-(4-methyl-1H-imidazol-1-yl)pyridin-2-yl)-5,6-dihydro-4H-1,2,4-oxadiazin-5-yl)benzo[d]oxazole | 2.3173 |
| 203B | 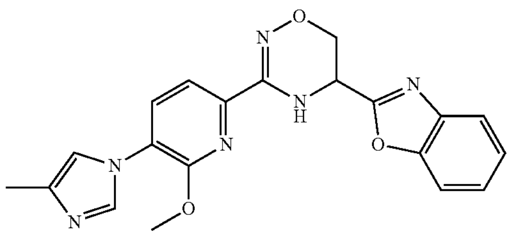 [SMILES: COc1nc(C2=NOCC(c3nc4ccccc4o3)N2)ccc1-n1cnc(C)c1] | (+)-2-(3-(6-methoxy-5-(4-methyl-1H-imidazol-1-yl)pyridin-2-yl)-5,6-dihydro-4H-1,2,4-oxadiazin-5-yl)benzo[d]oxazole | 0.2557 |
| 205A | 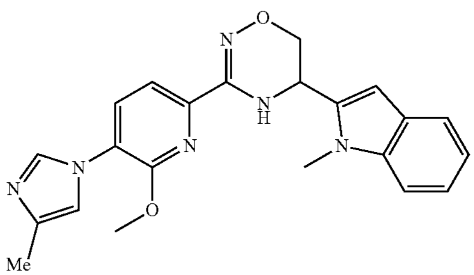 [SMILES: COc1nc(C2=NOCC(c3cc4ccccc4n3C)N2)ccc1-n1cnc(C)c1] | (−)-3-(6-methoxy-5-(4-methyl-1H-imidazol-1-yl)pyridin-2-yl)-5-(1-methyl-1H-indol-2-yl)-5,6-dihydro-4H-1,2,4-oxadiazine | 1.730 |
| 205B | 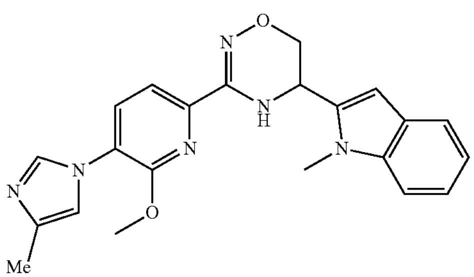 [SMILES: COc1nc(C2=NOCC(c3cc4ccccc4n3C)N2)ccc1-n1cnc(C)c1] | (+)-3-(6-methoxy-5-(4-methyl-1H-imidazol-1-yl)pyridin-2-yl)-5-(1-methyl-1H-indol-2-yl)-5,6-dihydro-4H-1,2,4-oxadiazine | 0.027 |
| 206A | 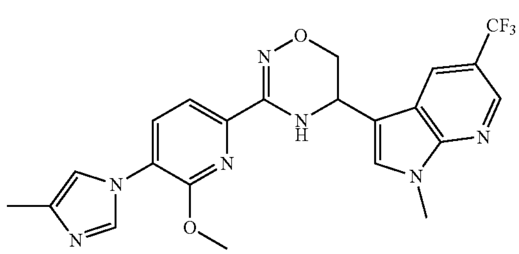 [SMILES: COc1nc(C2=NOCC(c3cn(C)c4ncc(C(F)(F)F)cc34)N2)ccc1-n1cnc(C)c1] | (−)-3-(6-methoxy-5-(4-methyl-1H-imidazol-1-yl)pyridin-2-yl)-5-(1-methyl-5-(trifluoromethyl)-1H-pyrrolo[2,3-b]pyridin-3-yl)-5,6-dihydro-4H-1,2,4-oxadiazine | 0.800 |
| 206B | 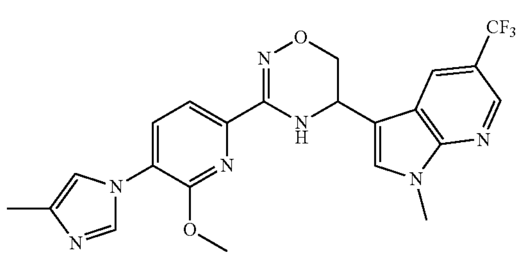 [SMILES: COc1nc(C2=NOCC(c3cn(C)c4ncc(C(F)(F)F)cc34)N2)ccc1-n1cnc(C)c1] | (+)-3-(6-methoxy-5-(4-methyl-1H-imidazol-1-yl)pyridin-2-yl)-5-(1-methyl-5-(trifluoromethyl)-1H-pyrrolo[2,3-b]pyridin-3-yl)-5,6-dihydro-4H-1,2,4-oxadiazine | 0.005 |

TABLE II-continued

Biological Assay

| Compound of Example | Structure | Name | Aβ42 EC50 (μM) |
|---|---|---|---|
| 208A | 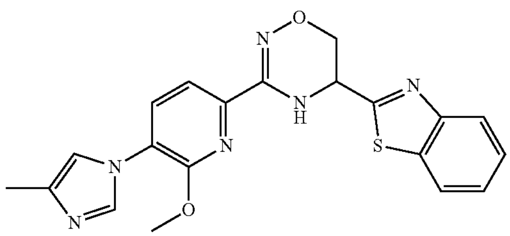 [SMILES: COc1nc(C2=NOCC(c3nc4ccccc4s3)N2)ccc1-n1cnc(C)c1] | (−)-5-(benzo[d]thiazol-2-yl)-3-(6-methoxy-5-(4-methyl-1H-imidazol-1-yl)pyridin-2-yl)-5,6-dihydro-4H-1,2,4-oxadiazine | >3 |
| 208B | 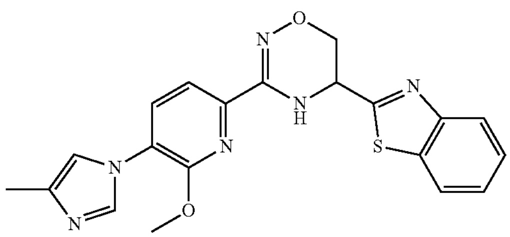 [SMILES: COc1nc(C2=NOCC(c3nc4ccccc4s3)N2)ccc1-n1cnc(C)c1] | (+)-5-(benzo[d]thiazol-2-yl)-3-(6-methoxy-5-(4-methyl-1H-imidazol-1-yl)pyridin-2-yl)-5,6-dihydro-4H-1,2,4-oxadiazine | 0.074 |
| 212A | 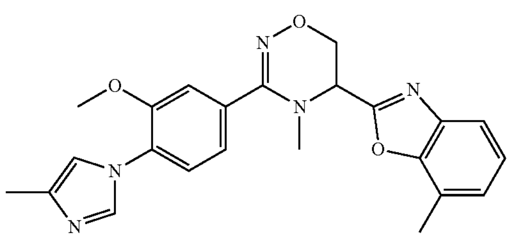 [SMILES: COc1cc(C2=NOCC(c3nc4cccc(C)c4o3)N2C)ccc1-n1cnc(C)c1] | (+)-2-(3-(3-methoxy-4-(4-methyl-1H-imidazol-1-yl)phenyl)-4-methyl-5,6-dihydro-4H-1,2,4-oxadiazin-5-yl)-7-methylbenzo[d]oxazole | 0.789 |
| 212B | 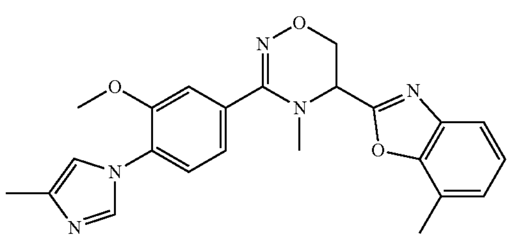 [SMILES: COc1cc(C2=NOCC(c3nc4cccc(C)c4o3)N2C)ccc1-n1cnc(C)c1] | (−)-2-(3-(3-methoxy-4-(4-methyl-1H-imidazol-1-yl)phenyl)-4-methyl-5,6-dihydro-4H-1,2,4-oxadiazin-5-yl)-7-methylbenzo[d]oxazole | >3 |
| 213 | 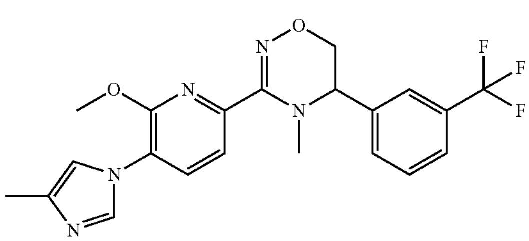 [SMILES: COc1nc(C2=NOCC(c3cccc(C(F)(F)F)c3)N2C)ccc1-n1cnc(C)c1] | 3-(6-methoxy-5-(4-methyl-1H-imidazol-1-yl)pyridin-2-yl)-4-methyl-5-(3-(trifluoromethyl)phenyl)-5,6-dihydro-4H-1,2,4-oxadiazine | 0.0557 |
| 214A | 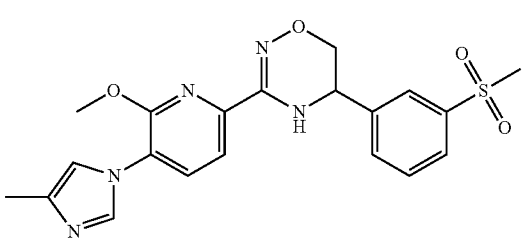 | (−)-3-(6-methoxy-5-(4-methyl-1H-imidazol-1-yl)pyridin-2-yl)-5-(3-(methylsulfonyl)phenyl)-5,6-dihydro-4H-1,2,4-oxadiazine | >3 |

TABLE II-continued

Biological Assay

| Compound of Example | Structure | Name | Aβ42 EC50 (μM) |
|---|---|---|---|
| 214B | 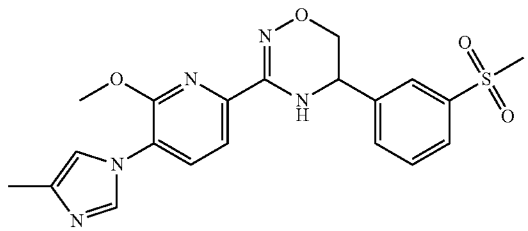 | (+)-3-(6-methoxy-5-(4-methyl-1H-imidazol-1-yl)pyridin-2-yl)-5-(3-(methylsulfonyl)phenyl)-5,6-dihydro-4H-1,2,4-oxadiazine | 0.9043 |
| 215A | 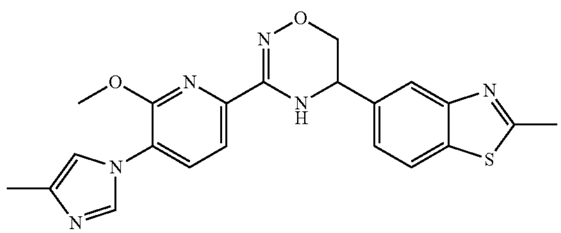 | (−)-3-(6-methoxy-5-(4-methyl-1H-imidazol-1-yl)pyridin-2-yl)-5-(2-methylbenzo[d]thiazol-5-yl)-5,6-dihydro-4H-1,2,4-oxadiazine | 2.2068 |
| 215B | 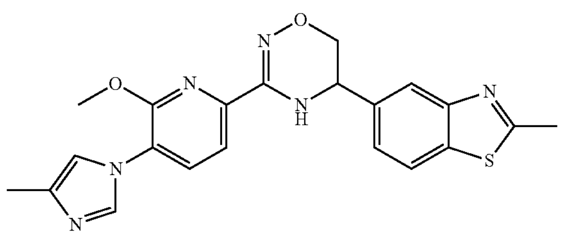 | (+)-3-(6-methoxy-5-(4-methyl-1H-imidazol-1-yl)pyridin-2-yl)-5-(2-methylbenzo[d]thiazol-5-yl)-5,6-dihydro-4H-1,2,4-oxadiazine | 0.0527 |
| 216A | 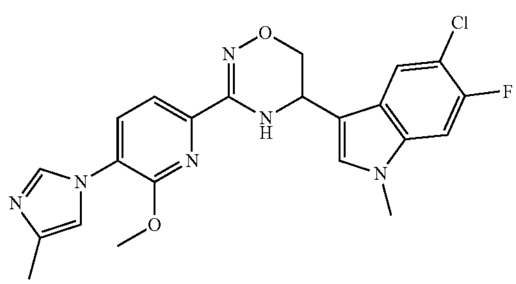 [SMILES: COc1nc(C2=NOCC(c3cn(C)c4cc(F)c(Cl)cc34)N2)ccc1-n1cnc(C)c1] | (−)-5-(5-chloro-6-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0895 |
| 216B | 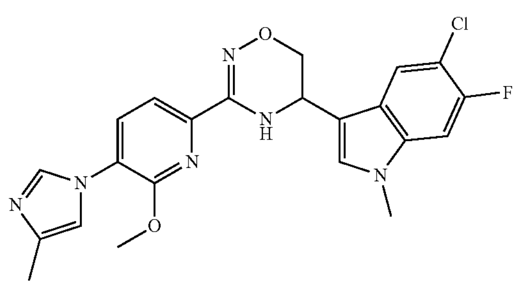 [SMILES: COc1nc(C2=NOCC(c3cn(C)c4cc(F)c(Cl)cc34)N2)ccc1-n1cnc(C)c1] | (+)-5-(5-chloro-6-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0042 |
| 217A | 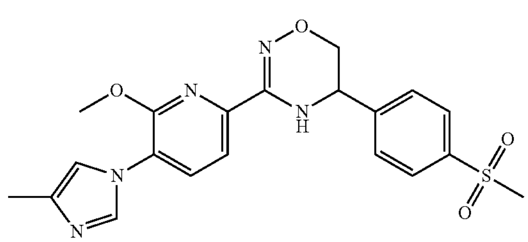 | (−)-3-(6-methoxy-5-(4-methyl-1H-imidazol-1-yl)pyridin-2-yl)-5-(4-(methylsulfonyl)phenyl)-5,6-dihydro-4H-1,2,4-oxadiazine | >3 |

TABLE II-continued

Biological Assay

| Compound of Example | Structure | Name | Aβ42 EC50 (μM) |
|---|---|---|---|
| 217B | 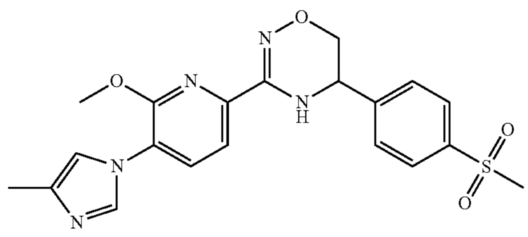 | (+)-3-(6-methoxy-5-(4-methyl-1H-imidazol-1-yl)pyridin-2-yl)-5-(4-(methylsulfonyl)phenyl)-5,6-dihydro-4H-1,2,4-oxadiazine | 2.0548 |
| 218A | 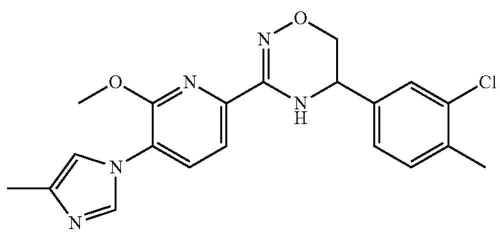 [SMILES: COc1nc(C2=NOCC(c3ccc(C)c(Cl)c3)N2)ccc1-n1cnc(C)c1] | (−)-5-(3-chloro-4-methylphenyl)-3-(6-methoxy-5-(4-methyl-1H-imidazol-1-yl)pyridin-2-yl)-5,6-dihydro-4H-1,2,4-oxadiazine | 1.014 |
| 218B | 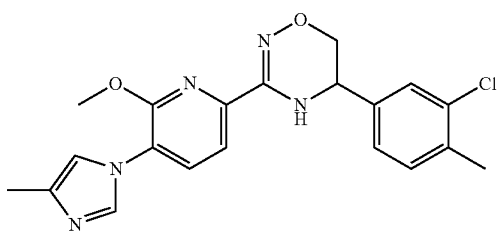 [SMILES: COc1nc(C2=NOCC(c3ccc(C)c(Cl)c3)N2)ccc1-n1cnc(C)c1] | (+)-5-(3-chloro-4-methylphenyl)-3-(6-methoxy-5-(4-methyl-1H-imidazol-1-yl)pyridin-2-yl)-5,6-dihydro-4H-1,2,4-oxadiazine | 0.0141 |
| 219A | 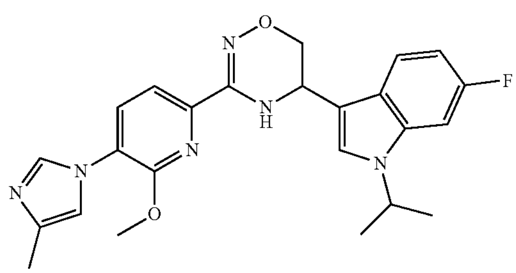 [SMILES: COc1nc(C2=NOCC(c3cn(C(C)C)c4cc(F)ccc34)N2)ccc1-n1cnc(C)c1] | (+)-5-(6-fluoro-1-isopropyl-1H-indol-3-yl)-3-(6-methoxy-5-(4-methyl-1H-imidazol-1-yl)pyridin-2-yl)-5,6-dihydro-4H-1,2,4-oxadiazine | 0.0092 |
| 219B | 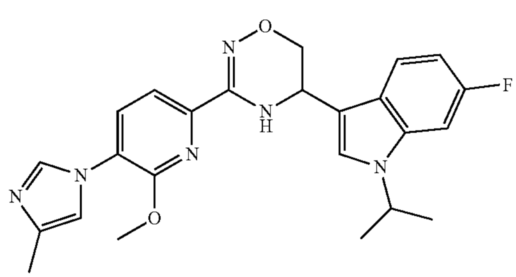 [SMILES: COc1nc(C2=NOCC(c3cn(C(C)C)c4cc(F)ccc34)N2)ccc1-n1cnc(C)c1] | (−)-5-(6-fluoro-1-isopropyl-1H-indol-3-yl)-3-(6-methoxy-5-(4-methyl-1H-imidazol-1-yl)pyridin-2-yl)-5,6-dihydro-4H-1,2,4-oxadiazine | 0.1943 |
| 220A | 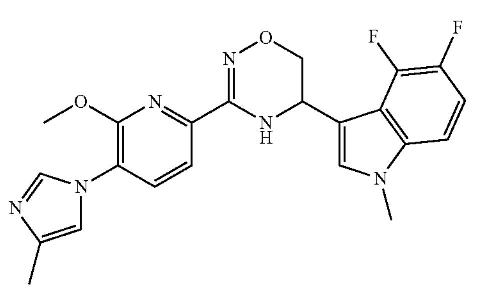 [SMILES: COc1nc(C2=NOCC(c3cn(C)c4ccc(F)c(F)c34)N2)ccc1-n1cnc(C)c1] | (−)-5-(4,5-difluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.1025 |

TABLE II-continued

Biological Assay

| Compound of Example | Structure | Name | Aβ42 EC50 (μM) |
|---|---|---|---|
| 220B | 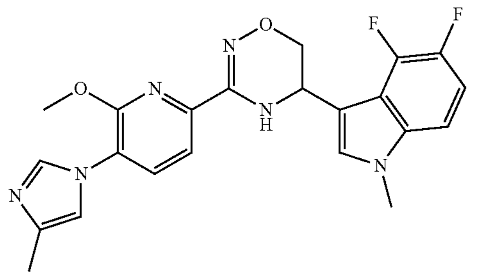 [SMILES: COc1nc(C2=NOCC(c3cn(C)c4ccc(F)c(F)c34)N2)ccc1-n1cnc(C)c1] | (+)-5-(4,5-difluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0055 |
| 221A | 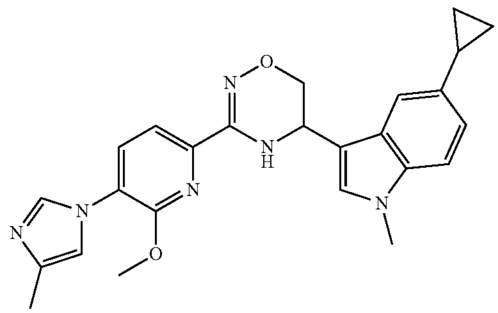 [SMILES: COc1nc(C2=NOCC(c3cn(C)c4ccc(C5CC5)cc34)N2)ccc1-n1cnc(C)c1] | (−)-5-(5-cyclopropyl-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0599 |
| 221B | 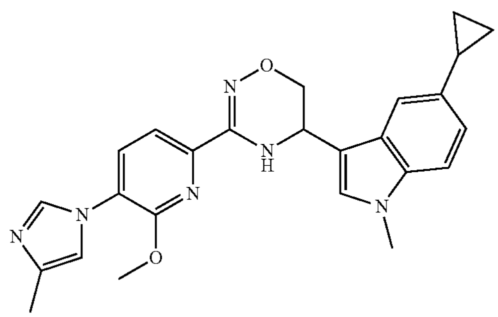 [SMILES: COc1nc(C2=NOCC(c3cn(C)c4ccc(C5CC5)cc34)N2)ccc1-n1cnc(C)c1] | (+)-5-(5-cyclopropyl-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0029 |
| 222A | 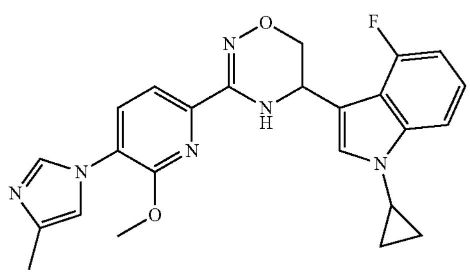 [SMILES: COc1nc(C2=NOCC(c3cn(C4CC4)c4cccc(F)c34)N2)ccc1-n1cnc(C)c1] | (+)-5-(1-cyclopropyl-4-fluoro-1H-indol-3-yl)-3-(6-methoxy-5-(4-methyl-1H-imidazol-1-yl)pyridin-2-yl)-5,6-dihydro-4H-1,2,4-oxadiazine | 0.0112 |
| 222B | 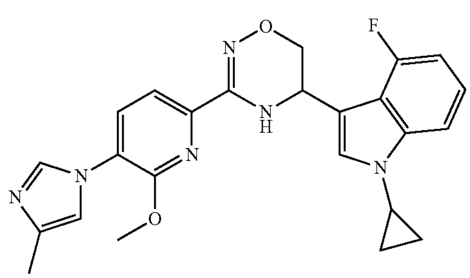 [SMILES: COc1nc(C2=NOCC(c3cn(C4CC4)c4cccc(F)c34)N2)ccc1-n1cnc(C)c1] | (−)-5-(1-cyclopropyl-4-fluoro-1H-indol-3-yl)-3-(6-methoxy-5-(4-methyl-1H-imidazol-1-yl)pyridin-2-yl)-5,6-dihydro-4H-1,2,4-oxadiazine | 0.0686 |

TABLE II-continued

Biological Assay

| Compound of Example | Structure | Name | Aβ42 EC50 (μM) |
|---|---|---|---|
| 223A | 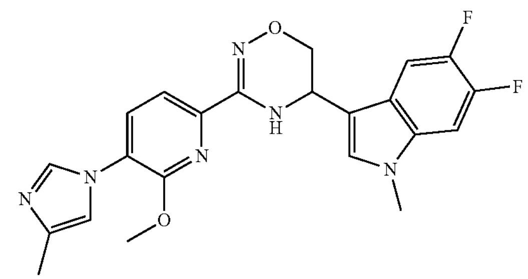 [SMILES: COc1nc(C2=NOCC(c3cn(C)c4cc(F)c(F)cc34)N2)ccc1-n1cnc(C)c1] | (−)-5-(5,6-difluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.1299 |
| 223B | 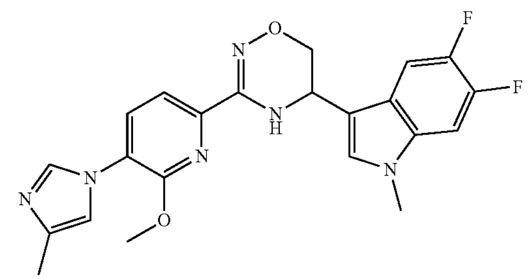 [SMILES: COc1nc(C2=NOCC(c3cn(C)c4cc(F)c(F)cc34)N2)ccc1-n1cnc(C)c1] | (+)-5-(5,6-difluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0062 |
| 224A | 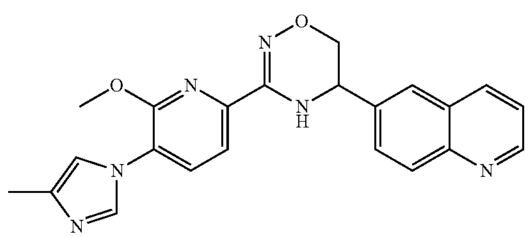 [SMILES: COc1nc(C2=NOCC(c3ccc4ncccc4c3)N2)ccc1-n1cnc(C)c1] | (−)-3-(6-methoxy-5-(4-methyl-1H-imidazol-1-yl)pyridin-2-yl)-5-(quinolin-6-yl)-5,6-dihydro-4H-1,2,4-oxadiazine | >3 |
| 224B | 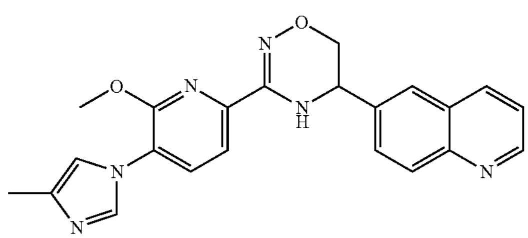 [SMILES: COc1nc(C2=NOCC(c3ccc4ncccc4c3)N2)ccc1-n1cnc(C)c1] | (+)-3-(6-methoxy-5-(4-methyl-1H-imidazol-1-yl)pyridin-2-yl)-5-(quinolin-6-yl)-5,6-dihydro-4H-1,2,4-oxadiazine | 0.294 |
| 225A | 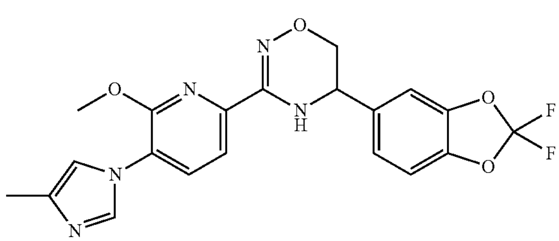 [SMILES: COc1nc(C2=NOCC(c3ccc4c(c3)OC(F)(F)O4)N2)ccc1-n1cnc(C)c1] | (−)-5-(2,2)-difluorobenzo[d][1,3]dioxol-5-yl)-3-(6-methoxy-5-(4-methyl-1H-imidazol-1-yl)pyridin-2-yl)-5,6-dihydro-4H-1,2,4-oxadiazine | >3 |
| 225B | 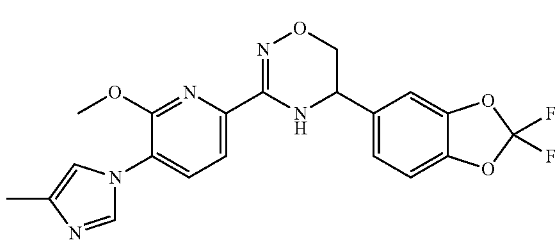 [SMILES: COc1nc(C2=NOCC(c3ccc4c(c3)OC(F)(F)O4)N2)ccc1-n1cnc(C)c1] | (+)-5-(2,2)-difluorobenzo[d][1,3]dioxol-5-yl)-3-(6-methoxy-5-(4-methyl-1H-imidazol-1-yl)pyridin-2-yl)-5,6-dihydro-4H-1,2,4-oxadiazine | 0.014 |

TABLE II-continued

Biological Assay

| Compound of Example | Structure | Name | Aβ42 EC50 (μM) |
|---|---|---|---|
| 226A | 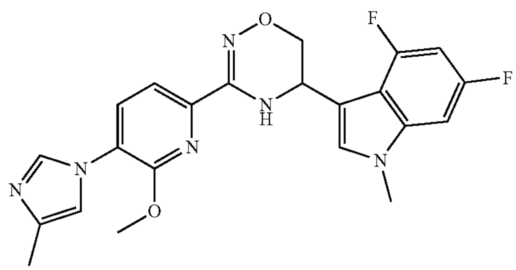 [SMILES: COc1nc(C2=NOCC(c3cn(C)c4cc(F)cc(F)c34)N2)ccc1-n1cnc(C)c1] | (+)-5-(4,6-difluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0094 |
| 226B | 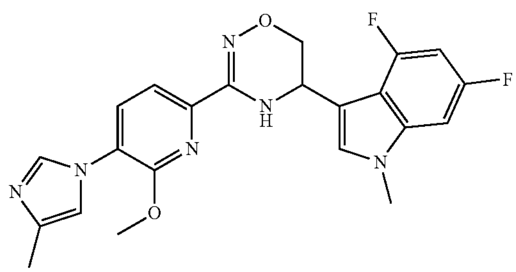 [SMILES: COc1nc(C2=NOCC(c3cn(C)c4cc(F)cc(F)c34)N2)ccc1-n1cnc(C)c1] | (−)-5-(4,6-difluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0714 |
| 227A | 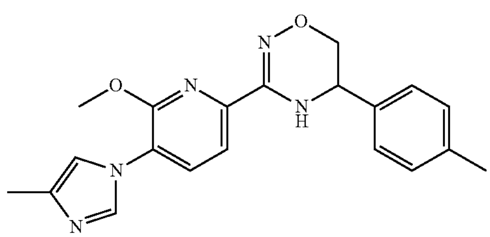 | (−)-3-(6-methoxy-5-(4-methyl-1H-imidazol-1-yl)pyridin-2-yl)-5-(p-tolyl)-5,6-dihydro-4H-1,2,4-oxadiazine | 0.9575 |
| 227B | 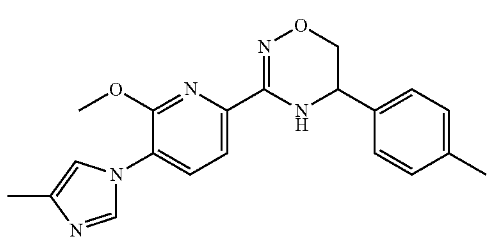 | (+)-3-(6-methoxy-5-(4-methyl-1H-imidazol-1-yl)pyridin-2-yl)-5-(p-tolyl)-5,6-dihydro-4H-1,2,4-oxadiazine | 0.0738 |
| 228A | 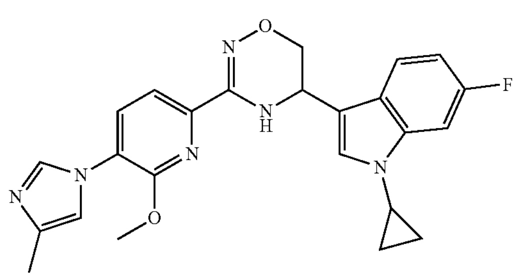 [SMILES: COc1nc(C2=NOCC(c3cn(C4CC4)c4cc(F)ccc34)N2)ccc1-n1cnc(C)c1] | (−)-5-(1-cyclopropyl-6-fluoro-1H-indol-3-yl)-3-(6-methoxy-5-(4-methyl-1H-imidazol-1-yl)pyridin-2-yl)-5,6-dihydro-4H-1,2,4-oxadiazine | 0.2621 |

TABLE II-continued

Biological Assay

| Compound of Example | Structure | Name | Aβ42 EC50 (μM) |
|---|---|---|---|
| 228B | 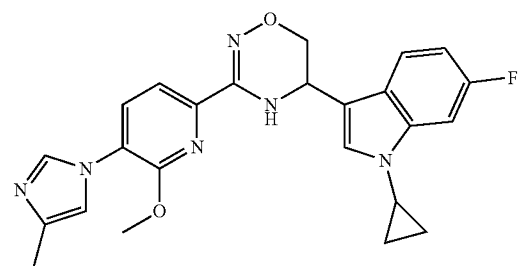 [SMILES: COc1nc(C2=NOCC(c3cn(C4CC4)c4cc(F)ccc34)N2)ccc1-n1cnc(C)c1] | (+)-5-(1-cyclopropyl-6-fluoro-1H-indol-3-yl)-3-(6-methoxy-5-(4-methyl-1H-imidazol-1-yl)pyridin-2-yl)-5,6-dihydro-4H-1,2,4-oxadiazine | 0.0084 |
| 229A | 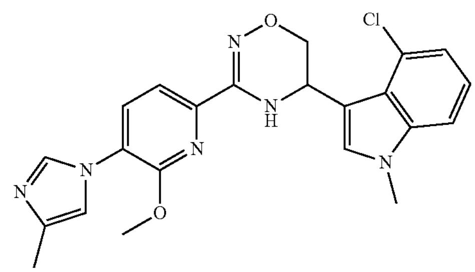 [SMILES: COc1nc(C2=NOCC(c3cn(C)c4cccc(Cl)c34)N2)ccc1-n1cnc(C)c1] | (+)-5-(4-chloro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0288 |
| 229B | 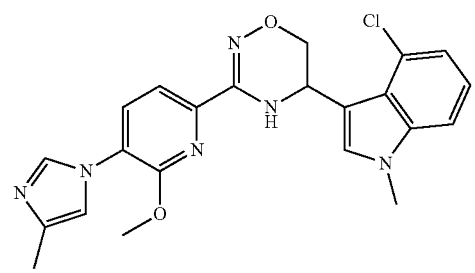 [SMILES: COc1nc(C2=NOCC(c3cn(C)c4cccc(Cl)c34)N2)ccc1-n1cnc(C)c1] | (−)-5-(4-chloro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0244 |
| 230A | 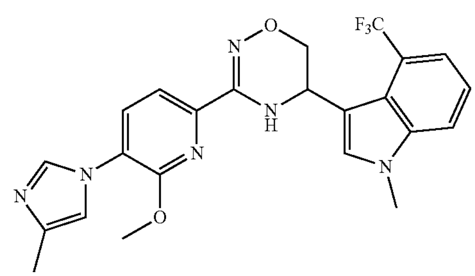 [SMILES: COc1nc(C2=NOCC(c3cn(C)c4cccc(C(F)(F)F)c34)N2)ccc1-n1cnc(C)c1] | (+)-3-(6-methoxy-5-(4-methyl-1H-imidazol-1-yl)pyridin-2-yl)-5-(1-methyl-4-(trifluoromethyl)-1H-indol-3-yl)-5,6-dihydro-4H-1,2,4-oxadiazine | 0.105 |
| 230B | 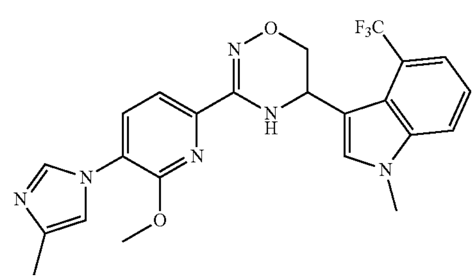 [SMILES: COc1nc(C2=NOCC(c3cn(C)c4cccc(C(F)(F)F)c34)N2)ccc1-n1cnc(C)c1] | (−)-3-(6-methoxy-5-(4-methyl-1H-imidazol-1-yl)pyridin-2-yl)-5-(1-methyl-4-(trifluoromethyl)-1H-indol-3-yl)-5,6-dihydro-4H-1,2,4-oxadiazine | 0.0252 |

TABLE II-continued

Biological Assay

| Compound of Example | Structure | Name | Aβ42 EC50 (μM) |
|---|---|---|---|
| 231A | 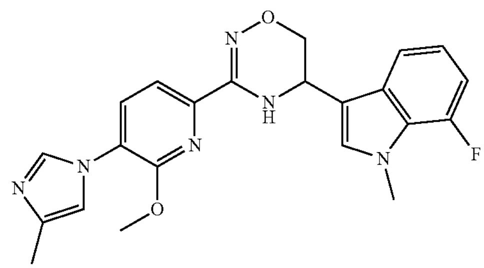 [SMILES: COc1nc(C2=NOCC(c3cn(C)c4c(F)cccc34)N2)ccc1-n1cnc(C)c1] | (−)-5-(7-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.229 |
| 231B | 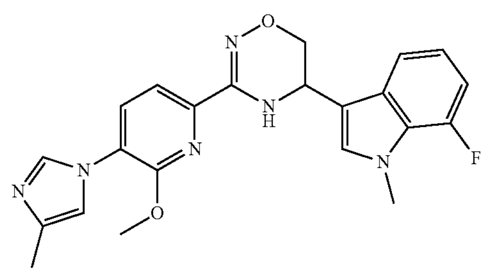 [SMILES: COc1nc(C2=NOCC(c3cn(C)c4c(F)cccc34)N2)ccc1-n1cnc(C)c1] | (+)-5-(7-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0108 |
| 232A | 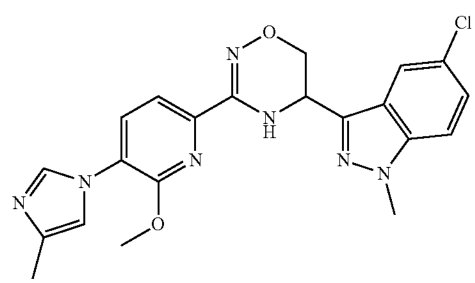 [SMILES: COc1nc(C2=NOCC(c3nn(C)c4ccc(Cl)cc34)N2)ccc1-n1cnc(C)c1] | (−)-5-(5-chloro-1-methyl-1H-indazol-3-yl)-3-(6-methoxy-5-(4-methyl-1H-imidazol-1-yl)pyridin-2-yl)-5,6-dihydro-4H-1,2,4-oxadiazine | 0.2784 |
| 232B | 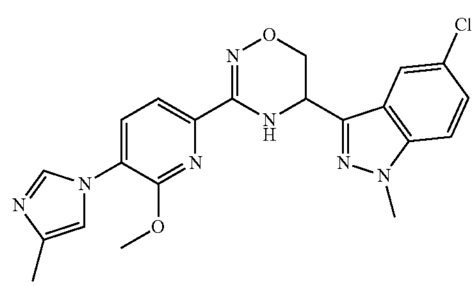 [SMILES: COc1nc(C2=NOCC(c3nn(C)c4ccc(Cl)cc34)N2)ccc1-n1cnc(C)c1] | (+)-5-(5-chloro-1-methyl-1H-indazol-3-yl)-3-(6-methoxy-5-(4-methyl-1H-imidazol-1-yl)pyridin-2-yl)-5,6-dihydro-4H-1,2,4-oxadiazine | 0.0129 |
| 233A | 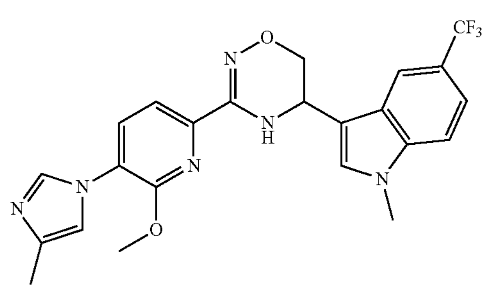 [SMILES: COc1nc(C2=NOCC(c3cn(C)c4ccc(C(F)(F)F)cc34)N2)ccc1-n1cnc(C)c1] | (−)-3-(6-methoxy-5-(4-methyl-1H-imidazol-1-yl)pyridin-2-yl)-5-(1-methyl-5-(trifluoromethyl)-1H-indol-3-yl)-5,6-dihydro-4H-1,2,4-oxadiazine | 0.0945 |

TABLE II-continued

Biological Assay

| Compound of Example | Structure | Name | Aβ42 EC50 (μM) |
|---|---|---|---|
| 233B | 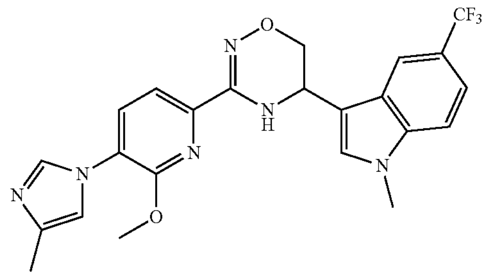 [SMILES: COc1nc(C2=NOCC(c3cn(C)c4ccc(C(F)(F)F)cc34)N2)ccc1-n1cnc(C)c1] | (+)-3-(6-methoxy-5-(4-methyl-1H-imidazol-1-yl)pyridin-2-yl)-5-(1-methyl-5-(trifluoromethyl)-1H-indol-3-yl)-5,6-dihydro-4H-1,2,4-oxadiazine | 0.0017 |
| 234A | 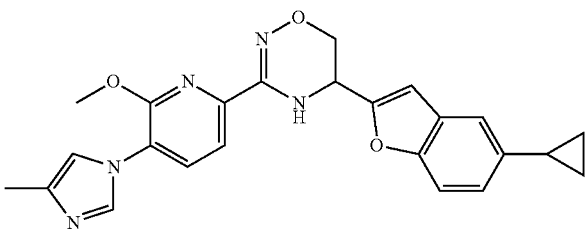 [SMILES: COc1nc(C2=NOCC(c3cc4cc(C5CC5)ccc4o3)N2)ccc1-n1cnc(C)c1] | (−)-5-(5-cyclopropylbenzofuran-2-yl)-3-(6-methoxy-5-(4-methyl-1H-imidazol-1-yl)pyridin-2-yl)-5,6-dihydro-4H-1,2,4-oxadiazine | 0.4254 |
| 234B | 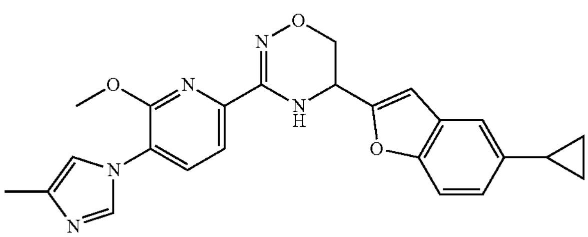 [SMILES: COc1nc(C2=NOCC(c3cc4cc(C5CC5)ccc4o3)N2)ccc1-n1cnc(C)c1] | (+)-5-(5-cyclopropylbenzofuran-2-yl)-3-(6-methoxy-5-(4-methyl-1H-imidazol-1-yl)pyridin-2-yl)-5,6-dihydro-4H-1,2,4-oxadiazine | 0.0095 |
| 235A | 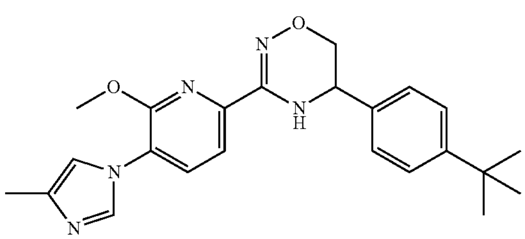 [SMILES: COc1nc(C2=NOCC(c3ccc(C(C)(C)C)cc3)N2)ccc1-n1cnc(C)c1] | (−)-5-(4-(tert-butyl)phenyl)-3-(6-methoxy-5-(4-methyl-1H-imidazol-1-yl)pyridin-2-yl)-5,6-dihydro-4H-1,2,4-oxadiazine | 0.7632 |
| 235B | 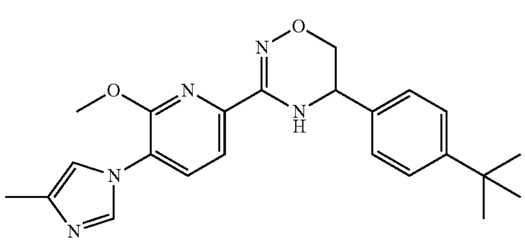 [SMILES: COc1nc(C2=NOCC(c3ccc(C(C)(C)C)cc3)N2)ccc1-n1cnc(C)c1] | (+)-5-(4-(tert-butyl)phenyl)-3-(6-methoxy-5-(4-methyl-1H-imidazol-1-yl)pyridin-2-yl)-5,6-dihydro-4H-1,2,4-oxadiazine | 0.0095 |
| 236A | 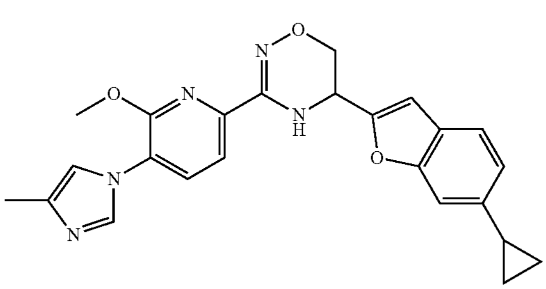 [SMILES: COc1nc(C2=NOCC(c3cc4ccc(C5CC5)cc4o3)N2)ccc1-n1cnc(C)c1] | (−)-5-(6-cyclopropylbenzofuran-2-yl)-3-(6-methoxy-5-(4-methyl-1H-imidazol-1-yl)pyridin-2-yl)-5,6-dihydro-4H-1,2,4-oxadiazine | 0.397 |

TABLE II-continued

Biological Assay

| Compound of Example | Structure | Name | Aβ42 EC50 (μM) |
|---|---|---|---|
| 236B | 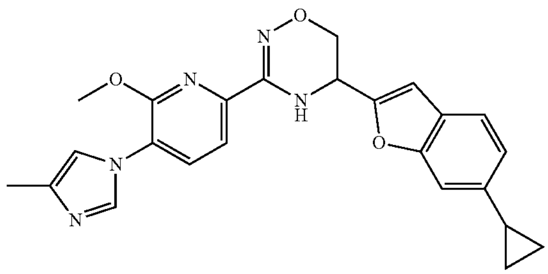 [SMILES: COc1nc(C2=NOCC(c3cc4ccc(C5CC5)cc4o3)N2)ccc1-n1cnc(C)c1] | (+)-5-(6-cyclopropylbenzofuran-2-yl)-3-(6-methoxy-5-(4-methyl-1H-imidazol-1-yl)pyridin-2-yl)-5,6-dihydro-4H-1,2,4-oxadiazine | 0.0092 |
| 237A | 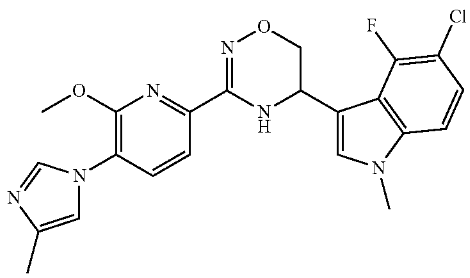 [SMILES: COc1nc(C2=NOCC(c3cn(C)c4ccc(Cl)c(F)c34)N2)ccc1-n1cnc(C)c1] | (+)-5-(5-chloro-4-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.005 |
| 237B | 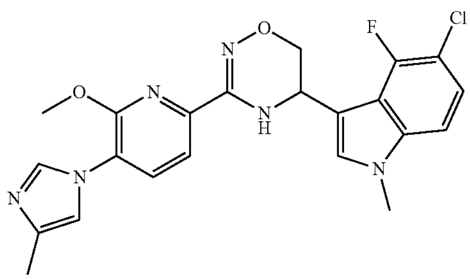 [SMILES: COc1nc(C2=NOCC(c3cn(C)c4ccc(Cl)c(F)c34)N2)ccc1-n1cnc(C)c1] | (−)-5-(5-chloro-4-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0471 |
| 238A | 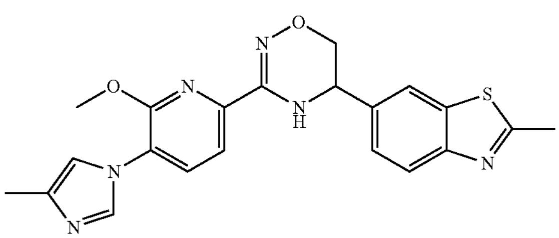 | (−)-3-(6-methoxy-5-(4-methyl-1H-imidazol-1-yl)pyridin-2-yl)-5-(2-methylbenzo[d]thiazol-6-yl)-5,6-dihydro-4H-1,2,4-oxadiazine | >3 |
| 238B | 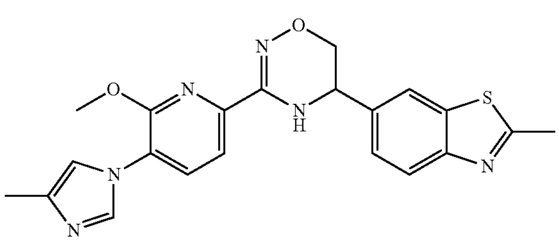 | (+)-3-(6-methoxy-5-(4-methyl-1H-imidazol-1-yl)pyridin-2-yl)-5-(2-methylbenzo[d]thiazol-6-yl)-5,6-dihydro-4H-1,2,4-oxadiazine | 0.1127 |

TABLE II-continued

Biological Assay

| Compound of Example | Structure | Name | Aβ42 EC50 (μM) |
|---|---|---|---|
| 239A | 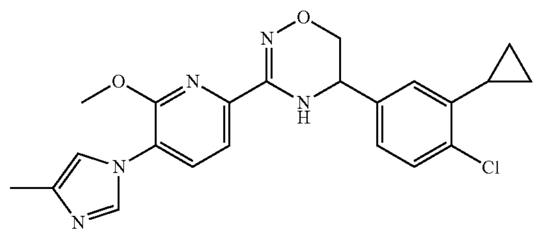 [SMILES: COc1nc(C2=NOCC(c3ccc(Cl)c(C4CC4)c3)N2)ccc1-n1cnc(C)c1] | (−)-5-(4-chloro-3-cyclopropylphenyl)-3-(6-methoxy-5-(4-methyl-1H-imidazol-1-yl)pyridin-2-yl)-5,6-dihydro-4H-1,2,4-oxadiazine | 0.9202 |
| 239B | 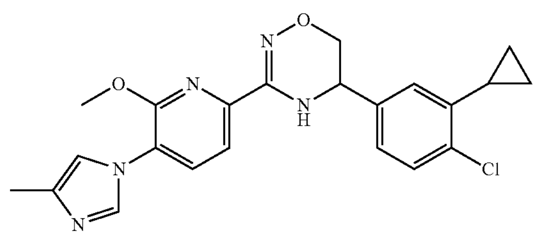 [SMILES: COc1nc(C2=NOCC(c3ccc(Cl)c(C4CC4)c3)N2)ccc1-n1cnc(C)c1] | (+)-5-(4-chloro-3-cyclopropylphenyl)-3-(6-methoxy-5-(4-methyl-1H-imidazol-1-yl)pyridin-2-yl)-5,6-dihydro-4H-1,2,4-oxadiazine | 0.0131 |
| 240A | 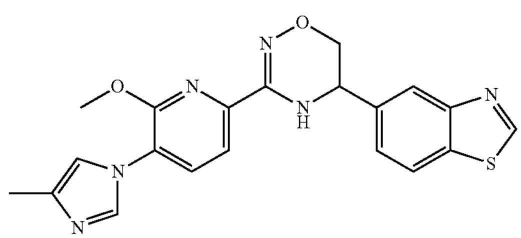 [SMILES: COc1nc(C2=NOCC(c3ccc4scnc4c3)N2)ccc1-n1cnc(C)c1] | (−)-5-(benzo[d]thiazol-5-yl)-3-(6-methoxy-5-(4-methyl-1H-imidazol-1-yl)pyridin-2-yl)-5,6-dihydro-4H-1,2,4-oxadiazine | >3 |
| 240B | 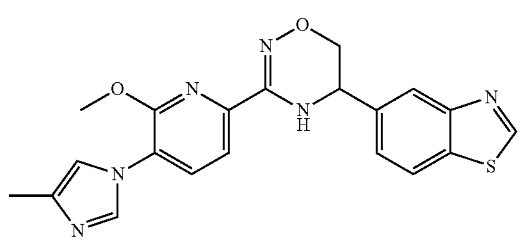 [SMILES: COc1nc(C2=NOCC(c3ccc4scnc4c3)N2)ccc1-n1cnc(C)c1] | (+)-5-(benzo[d]thiazol-5-yl)-3-(6-methoxy-5-(4-methyl-1H-imidazol-1-yl)pyridin-2-yl)-5,6-dihydro-4H-1,2,4-oxadiazine | 0.1087 |
| 241A | 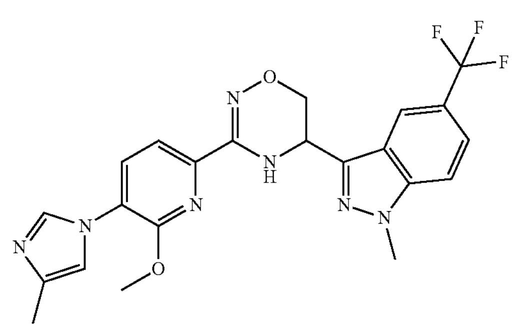 [SMILES: COc1nc(C2=NOCC(c3nn(C)c4ccc(C(F)(F)F)cc34)N2)ccc1-n1cnc(C)c1] | (−)-3-(6-methoxy-5-(4-methyl-1H-imidazol-1-yl)pyridin-2-yl)-5-(1-methyl-5-(trifluoromethyl)-1H-indazol-3-yl)-5,6-dihydro-4H-1,2,4-oxadiazine | 0.3865 |

TABLE II-continued

Biological Assay

| Compound of Example | Structure | Name | Aβ42 EC50 (μM) |
|---|---|---|---|
| 241B | 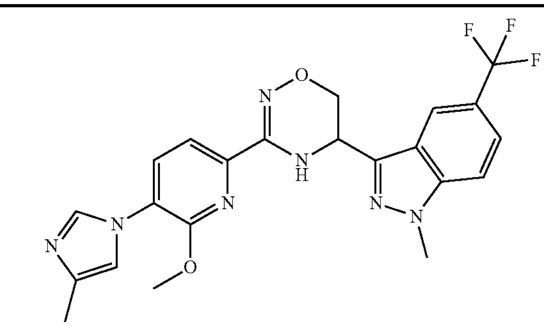 | (+)-3-(6-methoxy-5-(4-methyl-1H-imidazol-1-yl)pyridin-2-yl)-5-(1-methyl-5-(trifluoromethyl)-1H-indazol-3-yl)-5,6-dihydro-4H-1,2,4-oxadiazine | 0.0051 |
| 242A | 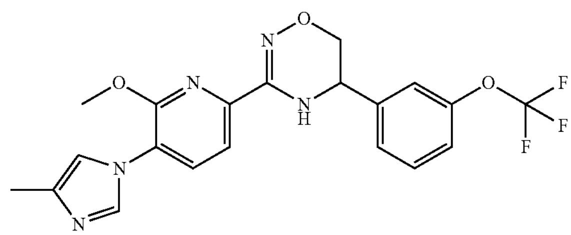 [SMILES: COc1nc(C2=NOCC(c3cccc(OC(F)(F)F)c3)N2)ccc1-n1cnc(C)c1] | (−)-3-(6-methoxy-5-(4-methyl-1H-imidazol-1-yl)pyridin-2-yl)-5-(3-(trifluoromethoxy)phenyl)-5,6-dihydro-4H-1,2,4-oxadiazine | 0.7087 |
| 242B | 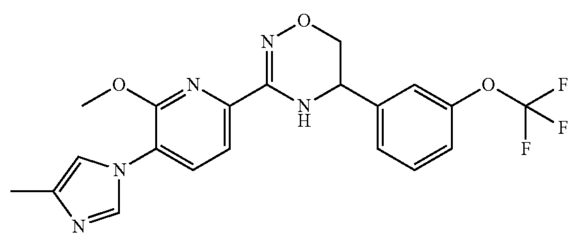 [SMILES: COc1nc(C2=NOCC(c3cccc(OC(F)(F)F)c3)N2)ccc1-n1cnc(C)c1] | (+)-3-(6-methoxy-5-(4-methyl-1H-imidazol-1-yl)pyridin-2-yl)-5-(3-(trifluoromethoxy)phenyl)-5,6-dihydro-4H-1,2,4-oxadiazine | 0.0185 |
| 243A | 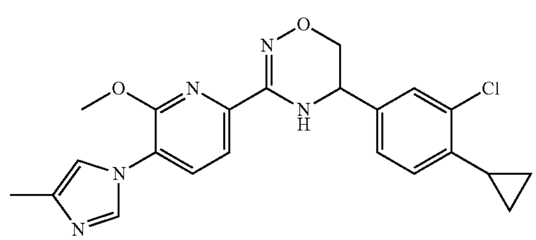 [SMILES: COc1nc(C2=NOCC(c3ccc(C4CC4)c(Cl)c3)N2)ccc1-n1cnc(C)c1] | (−)-5-(3-chloro-4-cyclopropylphenyl)-3-(6-methoxy-5-(4-methyl-1H-imidazol-1-yl)pyridin-2-yl)-5,6-dihydro-4H-1,2,4-oxadiazine | 0.2503 |
| 243B | 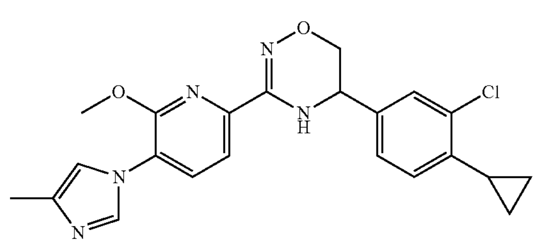 [SMILES: COc1nc(C2=NOCC(c3ccc(C4CC4)c(Cl)c3)N2)ccc1-n1cnc(C)c1] | (+)-5-(3-chloro-4-cyclopropylphenyl)-3-(6-methoxy-5-(4-methyl-1H-imidazol-1-yl)pyridin-2-yl)-5,6-dihydro-4H-1,2,4-oxadiazine | 0.0132 |
| 244A | 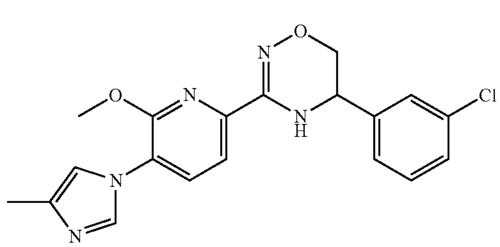 [SMILES: COc1nc(C2=NOCC(c3cccc(Cl)c3)N2)ccc1-n1cnc(C)c1] | (−)-5-(3-chlorophenyl)-3-(6-methoxy-5-(4-methyl-1H-imidazol-1-yl)pyridin-2-yl)-5,6-dihydro-4H-1,2,4-oxadiazine | 0.668 |

TABLE II-continued

Biological Assay

| Compound of Example | Structure | Name | Aβ42 EC50 (μM) |
|---|---|---|---|
| 244B | 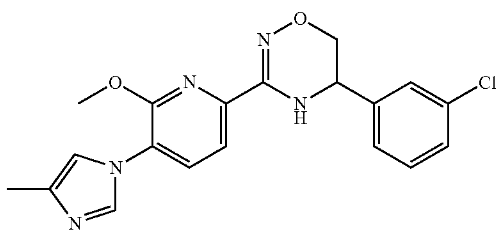 [SMILES: COc1nc(C2=NOCC(c3cccc(Cl)c3)N2)ccc1-n1cnc(C)c1] | (+)-5-(3-chlorophenyl)-3-(6-methoxy-5-(4-methyl-1H-imidazol-1-yl)pyridin-2-yl)-5,6-dihydro-4H-1,2,4-oxadiazine | 0.0263 |
| 245A | 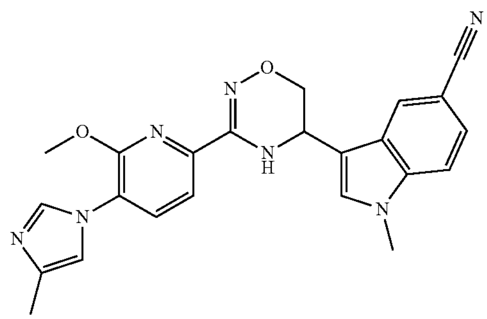 [SMILES: COc1nc(C2=NOCC(c3cn(C)c4ccc(C#N)cc34)N2)ccc1-n1cnc(C)c1] | (−)-3-(3-(6-methoxy-5-(4-methyl-1H-imidazol-1-yl)pyridin-2-yl)-5,6-dihydro-4H-1,2,4-oxadiazin-5-yl)-1-methyl-1H-indole-5-carbonitrile | 0.5537 |
| 245B | 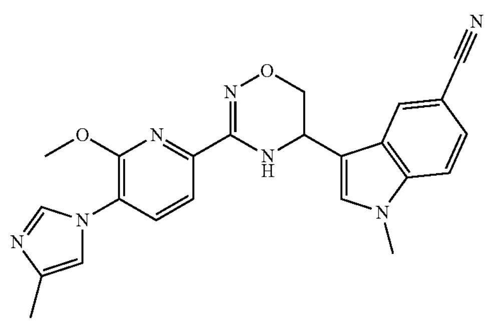 [SMILES: COc1nc(C2=NOCC(c3cn(C)c4ccc(C#N)cc34)N2)ccc1-n1cnc(C)c1] | (+)-3-(3-(6-methoxy-5-(4-methyl-1H-imidazol-1-yl)pyridin-2-yl)-5,6-dihydro-4H-1,2,4-oxadiazin-5-yl)-1-methyl-1H-indole-5-carbonitrile | 0.0185 |
| 246A | 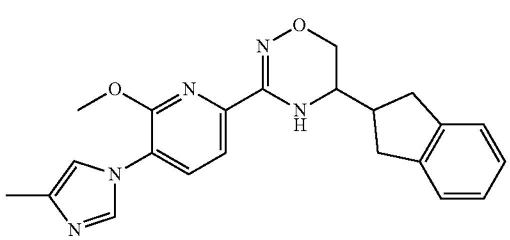 [SMILES: COc1nc(C2=NOCC(C3Cc4ccccc4C3)N2)ccc1-n1cnc(C)c1] | (−)-5-(2,3-dihydro-1H-inden-2-yl)-3-(6-methoxy-5-(4-methyl-1H-imidazol-1-yl)pyridin-2-yl)-5,6-dihydro-4H-1,2,4-oxadiazine | 0.5761 |
| 246B | 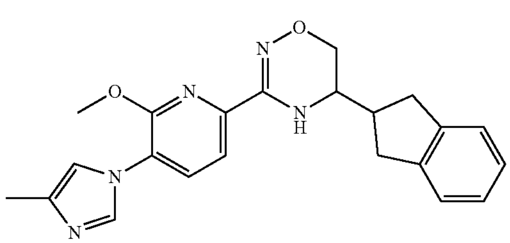 [SMILES: COc1nc(C2=NOCC(C3Cc4ccccc4C3)N2)ccc1-n1cnc(C)c1] | (+)-5-(2,3-dihydro-1H-inden-2-yl)-3-(6-methoxy-5-(4-methyl-1H-imidazol-1-yl)pyridin-2-yl)-5,6-dihydro-4H-1,2,4-oxadiazine | 0.0257 |

TABLE II-continued

Biological Assay

| Compound of Example | Structure | Name | Aβ42 EC50 (μM) |
|---|---|---|---|
| 247A | 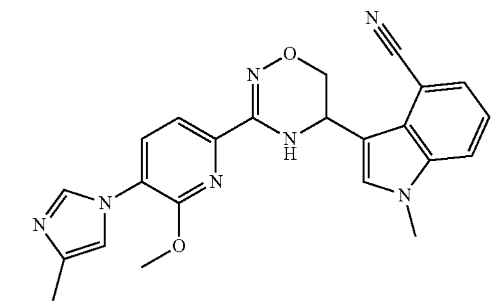 [SMILES: COc1nc(C2=NOCC(c3cn(C)c4cccc(C#N)c34)N2)ccc1-n1cnc(C)c1] | (+)-3-(3-(6-methoxy-5-(4-methyl-1H-imidazol-1-yl)pyridin-2-yl)-5,6-dihydro-4H-1,2,4-oxadiazin-5-yl)-1-methyl-1H-indole-4-carbonitrile | 0.0471 |
| 247B | 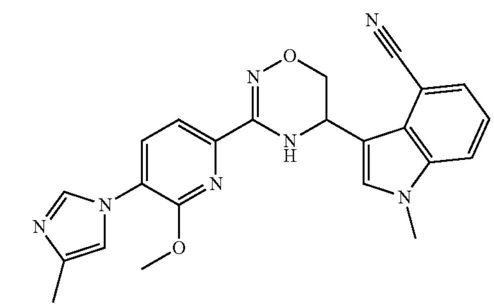 [SMILES: COc1nc(C2=NOCC(c3cn(C)c4cccc(C#N)c34)N2)ccc1-n1cnc(C)c1] | (−)-3-(3-(6-methoxy-5-(4-methyl-1H-imidazol-1-yl)pyridin-2-yl)-5,6-dihydro-4H-1,2,4-oxadiazin-5-yl)-1-methyl-1H-indole-4-carbonitrile | 0.0792 |
| 248A | 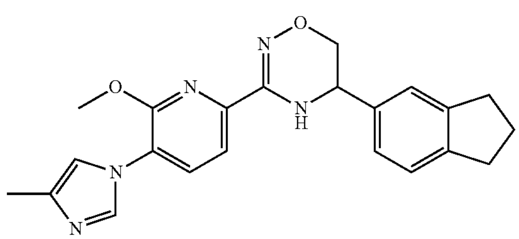 [SMILES: COc1nc(C2=NOCC(c3ccc4c(c3)CCC4)N2)ccc1-n1cnc(C)c1] | (−)-5-(2,3-dihydro-1H-inden-5-yl)-3-(6-methoxy-5-(4-methyl-1H-imidazol-1-yl)pyridin-2-yl)-5,6-dihydro-4H-1,2,4-oxadiazine | 0.4743 |
| 248B | 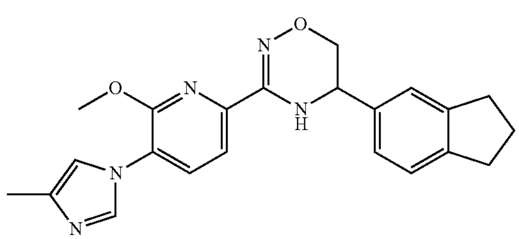 [SMILES: COc1nc(C2=NOCC(c3ccc4c(c3)CCC4)N2)ccc1-n1cnc(C)c1] | (+)-5-(2,3-dihydro-1H-inden-5-yl)-3-(6-methoxy-5-(4-methyl-1H-imidazol-1-yl)pyridin-2-yl)-5,6-dihydro-4H-1,2,4-oxadiazine | 0.0101 |
| 249A | 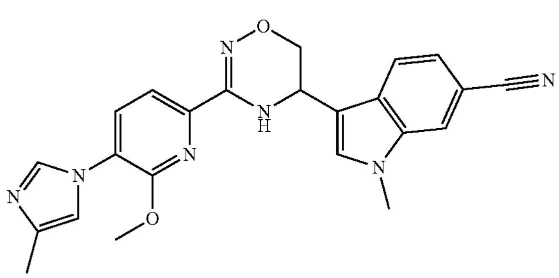 [SMILES: COc1nc(C2=NOCC(c3cn(C)c4cc(C#N)ccc34)N2)ccc1-n1cnc(C)c1] | (−)-3-(3-(6-methoxy-5-(4-methyl-1H-imidazol-1-yl)pyridin-2-yl)-5,6-dihydro-4H-1,2,4-oxadiazin-5-yl)-1-methyl-1H-indole-6-carbonitrile | 0.4291 |

TABLE II-continued

Biological Assay

| Compound of Example | Structure | Name | Aβ42 EC50 (μM) |
|---|---|---|---|
| 249B | 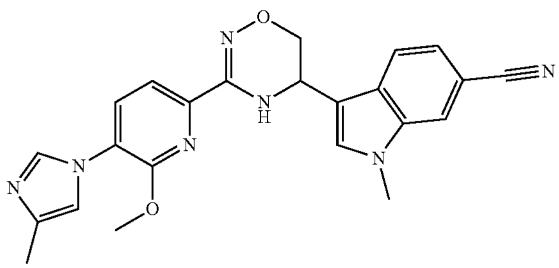 [SMILES: COc1nc(C2=NOCC(c3cn(C)c4cc(C#N)ccc34)N2)ccc1-n1cnc(C)c1] | (+)-3-(3-(6-methoxy-5-(4-methyl-1H-imidazol-1-yl)pyridin-2-yl)-5,6-dihydro-4H-1,2,4-oxadiazin-5-yl)-1-methyl-1H-indole-6-carbonitrile | 0.0302 |
| 250A | 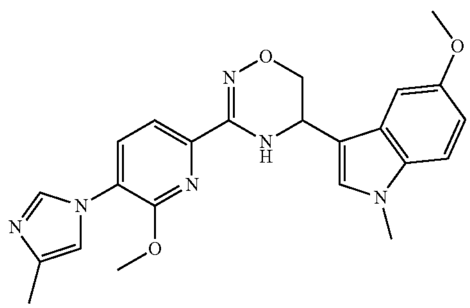 [SMILES: COc1ccc2c(c1)c(C1CON=C(c3ccc(-n4cnc(C)c4)c(OC)n3)N1)cn2C] | (−)-5-(5-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.2015 |
| 250B | 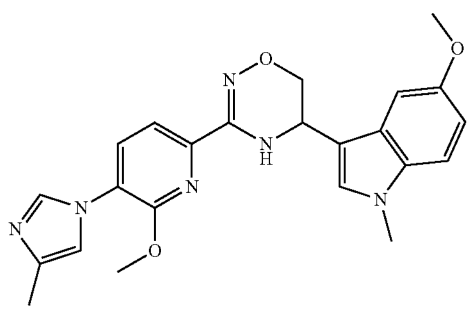 [SMILES: COc1ccc2c(c1)c(C1CON=C(c3ccc(-n4cnc(C)c4)c(OC)n3)N1)cn2C] | (+)-5-(5-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0158 |
| 252A | 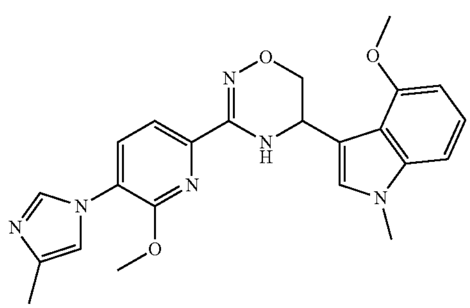 [SMILES: COc1nc(C2=NOCC(c3cn(C)c4cccc(OC)c34)N2)ccc1-n1cnc(C)c1] | (−)-5-(4-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.1584 |
| 252B | 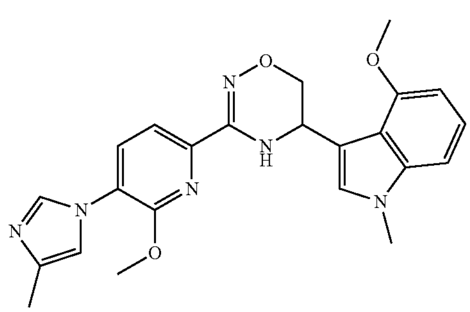 [SMILES: COc1nc(C2=NOCC(c3cn(C)c4cccc(OC)c34)N2)ccc1-n1cnc(C)c1] | (+)-5-(4-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0363 |

TABLE II-continued

Biological Assay

| Compound of Example | Structure | Name | Aβ42 EC50 (μM) |
|---|---|---|---|
| 253A | 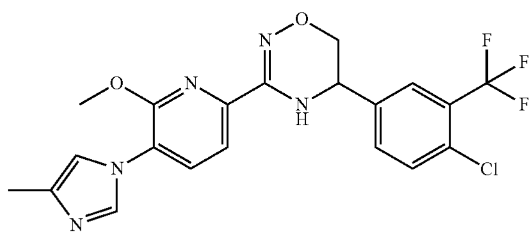 [SMILES: COc1nc(C2=NOCC(c3ccc(Cl)c(C(F)(F)F)c3)N2)ccc1-n1cnc(C)c1] | 5-(4-chloro-3-(trifluoromethyl)phenyl)-3-(6-methoxy-5-(4-methyl-1H-imidazol-1-yl)pyridin-2-yl)-5,6-dihydro-4H-1,2,4-oxadiazine | 0.6536 |
| 253B | 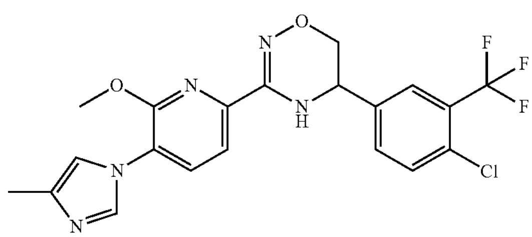 [SMILES: COc1nc(C2=NOCC(c3ccc(Cl)c(C(F)(F)F)c3)N2)ccc1-n1cnc(C)c1] | 5-(4-chloro-3-(trifluoromethyl)phenyl)-3-(6-methoxy-5-(4-methyl-1H-imidazol-1-yl)pyridin-2-yl)-5,6-dihydro-4H-1,2,4-oxadiazine | 0.0084 |
| 254A | 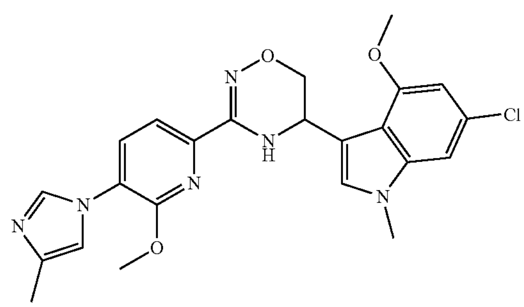 [SMILES: COc1nc(C2=NOCC(c3cn(C)c4cc(Cl)cc(OC)c34)N2)ccc1-n1cnc(C)c1] | (−)-5-(6-chloro-4-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.1484 |
| 254B | 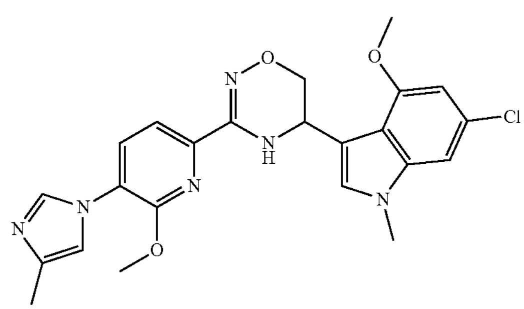 [SMILES: COc1nc(C2=NOCC(c3cn(C)c4cc(Cl)cc(OC)c34)N2)ccc1-n1cnc(C)c1] | (+)-5-(6-chloro-4-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0129 |
| 255A | 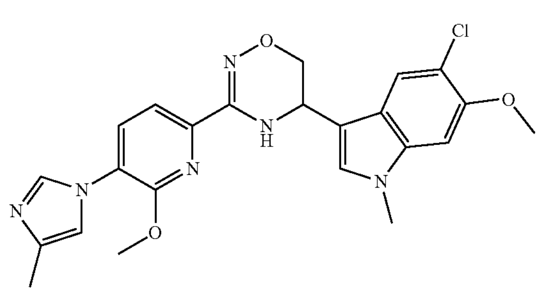 [SMILES: COc1cc2c(cc1Cl)c(C1CON=C(c3ccc(-n4cnc(C)c4)c(OC)n3)N1)cn2C] | (−)-5-(5-chloro-6-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0704 |

TABLE II-continued

Biological Assay

| Compound of Example | Structure | Name | Aβ42 EC50 (μM) |
|---|---|---|---|
| 255B | 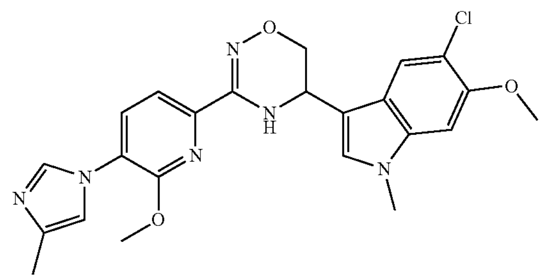 [SMILES: COc1cc2c(cc1Cl)c(C1CON=C(c3ccc(-n4cnc(C)c4)c(OC)n3)N1)cn2C] | (+)-5-(5-chloro-6-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.009 |
| 256A | 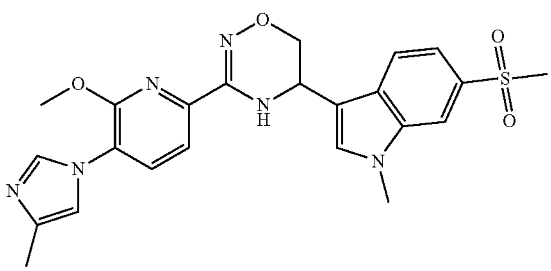 [SMILES: COc1nc(C2=NOCC(c3cn(C)c4cc(S(C)(=O)=O)ccc34)N2)ccc1-n1cnc(C)c1] | (−)-3-(6-methoxy-5-(4-methyl-1H-imidazol-1-yl)pyridin-2-yl)-5-(1-methyl-6-(methylsulfonyl)-1H-indol-3-yl)-5,6-dihydro-4H-1,2,4-oxadiazine | 2.5921 |
| 256B | 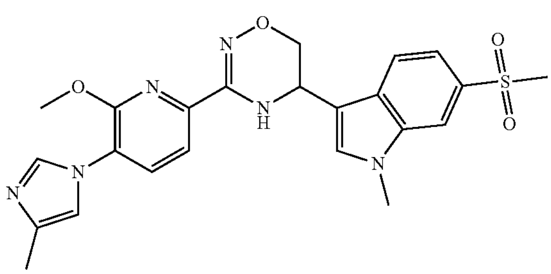 [SMILES: COc1nc(C2=NOCC(c3cn(C)c4cc(S(C)(=O)=O)ccc34)N2)ccc1-n1cnc(C)c1] | (+)-3-(6-methoxy-5-(4-methyl-1H-imidazol-1-yl)pyridin-2-yl)-5-(1-methyl-6-(methylsulfonyl)-1H-indol-3-yl)-5,6-dihydro-4H-1,2,4-oxadiazine | 0.4223 |
| 257A | 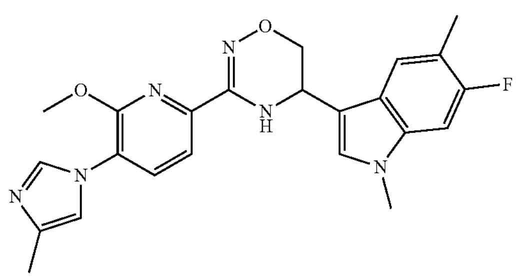 [SMILES: COc1nc(C2=NOCC(c3cn(C)c4cc(F)c(C)cc34)N2)ccc1-n1cnc(C)c1] | (−)-5-(6-fluoro-1,5-dimethyl-1H-indol-3-yl)-3-(6-methoxy-5-(4-methyl-1H-imidazol-1-yl)pyridin-2-yl)-5,6-dihydro-4H-1,2,4-oxadiazine | 0.1199 |
| 257B | 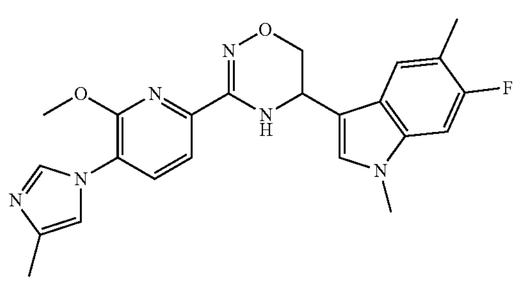 [SMILES: COc1nc(C2=NOCC(c3cn(C)c4cc(F)c(C)cc34)N2)ccc1-n1cnc(C)c1] | (+)-5-(6-fluoro-1,5-dimethyl-1H-indol-3-yl)-3-(6-methoxy-5-(4-methyl-1H-imidazol-1-yl)pyridin-2-yl)-5,6-dihydro-4H-1,2,4-oxadiazine | 0.0049 |

TABLE II-continued

Biological Assay

| Compound of Example | Structure | Name | Aβ42 EC50 (μM) |
|---|---|---|---|
| 258A | 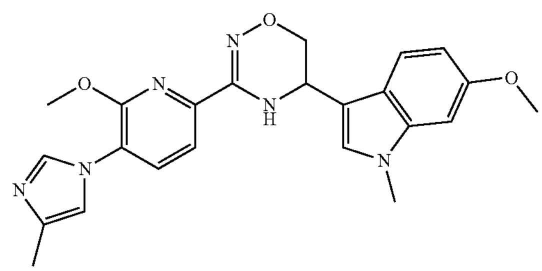 [SMILES: COc1ccc2c(C3CON=C(c4ccc(-n5cnc(C)c5)c(OC)n4)N3)cn(C)c2c1] | (−)-5-(6-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.1541 |
| 258B | 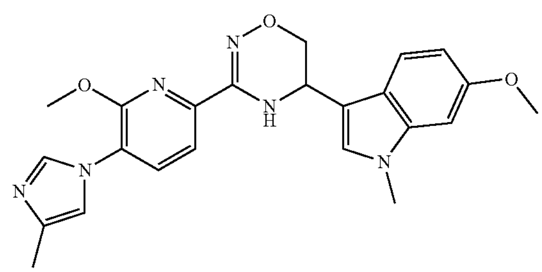 [SMILES: COc1ccc2c(C3CON=C(c4ccc(-n5cnc(C)c5)c(OC)n4)N3)cn(C)c2c1] | (+)-5-(6-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0235 |
| 259A | 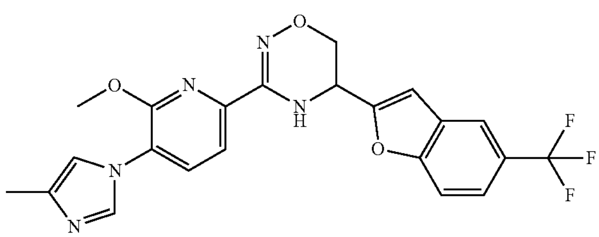 [SMILES: COc1nc(C2=NOCC(c3cc4cc(C(F)(F)F)ccc4o3)N2)ccc1-n1cnc(C)c1] | (−)-3-(6-methoxy-5-(4-methyl-1H-imidazol-1-yl)pyridin-2-yl)-5-(5-(trifluoromethyl)benzofuran-2-yl)-5,6-dihydro-4H-1,2,4-oxadiazine | 2.4557 |
| 259B | 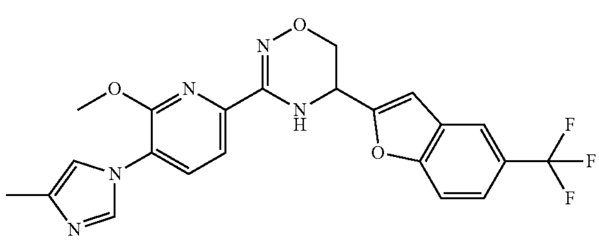 [SMILES: COc1nc(C2=NOCC(c3cc4cc(C(F)(F)F)ccc4o3)N2)ccc1-n1cnc(C)c1] | (+)-3-(6-methoxy-5-(4-methyl-1H-imidazol-1-yl)pyridin-2-yl)-5-(5-(trifluoromethyl)benzofuran-2-yl)-5,6-dihydro-4H-1,2,4-oxadiazine | 0.009 |
| 260A | 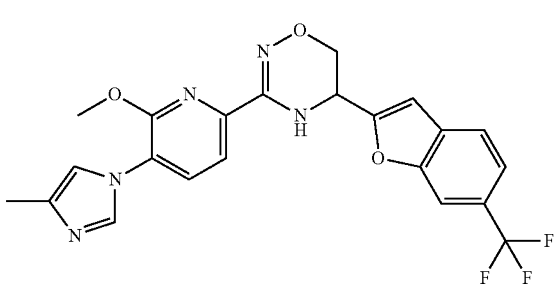 [SMILES: COc1nc(C2=NOCC(c3cc4ccc(C(F)(F)F)cc4o3)N2)ccc1-n1cnc(C)c1] | (−)-3-(6-methoxy-5-(4-methyl-1H-imidazol-1-yl)pyridin-2-yl)-5-(6-(trifluoromethyl)benzofuran-2-yl)-5,6-dihydro-4H-1,2,4-oxadiazine | 2.3176 |

TABLE II-continued

Biological Assay

| Compound of Example | Structure | Name | Aβ42 EC50 (μM) |
|---|---|---|---|
| 260B | 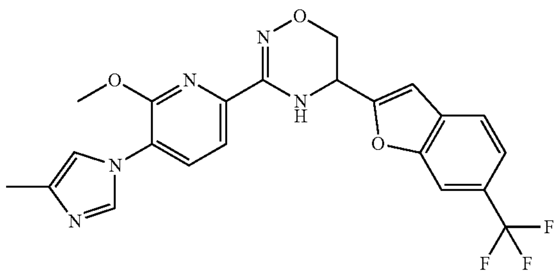 [SMILES: COc1nc(C2=NOCC(c3cc4ccc(C(F)(F)F)cc4o3)N2)ccc1-n1cnc(C)c1] | (+)-3-(6-methoxy-5-(4-methyl-1H-imidazol-1-yl)pyridin-2-yl)-5-(6-(trifluoromethyl)benzofuran-2-yl)-5,6-dihydro-4H-1,2,4-oxadiazine | 0.0048 |
| 261A | 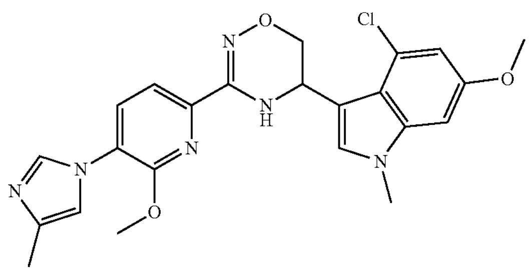 [SMILES: COc1cc(Cl)c2c(C3CON=C(c4ccc(-n5cnc(C)c5)c(OC)n4)N3)cn(C)c2c1] | (+)-5-(4-chloro-6-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0387 |
| 261B | 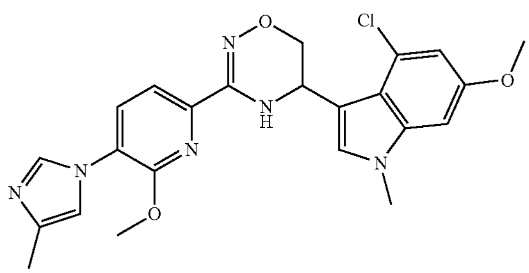 [SMILES: COc1cc(Cl)c2c(C3CON=C(c4ccc(-n5cnc(C)c5)c(OC)n4)N3)cn(C)c2c1] | (−)-5-(4-chloro-6-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 0.0212 |
| 262A | 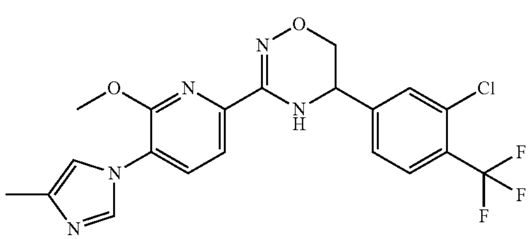 [SMILES: COc1nc(C2=NOCC(c3ccc(C(F)(F)F)c(Cl)c3)N2)ccc1-n1cnc(C)c1] | (−)-5-(3-chloro-4-(trifluoromethyl)phenyl)-3-(6-methoxy-5-(4-methyl-1H-imidazol-1-yl)pyridin-2-yl)-5,6-dihydro-4H-1,2,4-oxadiazine | >3 |
| 262B | 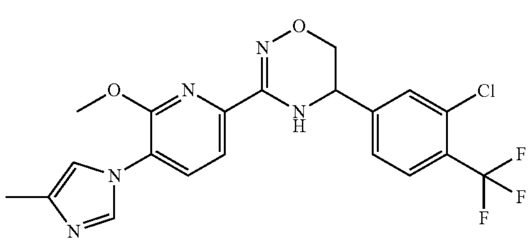 [SMILES: COc1nc(C2=NOCC(c3ccc(C(F)(F)F)c(Cl)c3)N2)ccc1-n1cnc(C)c1] | (+)-5-(3-chloro-4-(trifluoromethyl)phenyl)-3-(6-methoxy-5-(4-methyl-1H-imidazol-1-yl)pyridin-2-yl)-5,6-dihydro-4H-1,2,4-oxadiazine | 0.01 |

TABLE II-continued

Biological Assay

| Compound of Example | Structure | Name | Aβ42 EC50 (μM) |
|---|---|---|---|
| 264A | 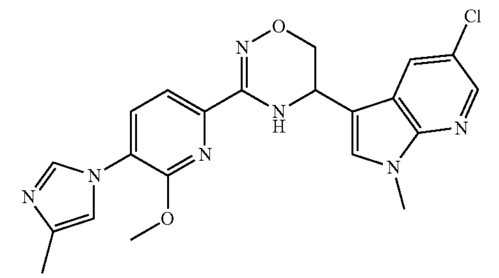 [SMILES: COc1nc(C2=NOCC(c3cn(C)c4ncc(Cl)cc34)N2)ccc1-n1cnc(C)c1] | (−)-5-(5-chloro-1-methyl-1H-pyrrolo[2,3-b]pyridin-3-yl)-3-(6-methoxy-5-(4-methyl-1H-imidazol-1-yl)pyridin-2-yl)-5,6-dihydro-4H-1,2,4-oxadiazine | 0.3207 |
| 264B | 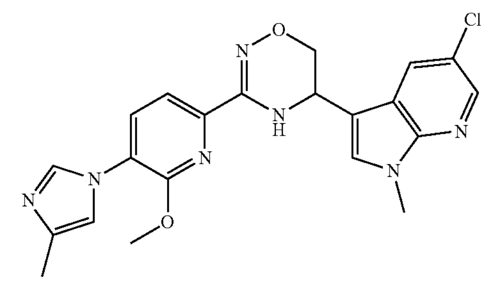 [SMILES: COc1nc(C2=NOCC(c3cn(C)c4ncc(Cl)cc34)N2)ccc1-n1cnc(C)c1] | (+)-5-(5-chloro-1-methyl-1H-pyrrolo[2,3-b]pyridin-3-yl)-3-(6-methoxy-5-(4-methyl-1H-imidazol-1-yl)pyridin-2-yl)-5,6-dihydro-4H-1,2,4-oxadiazine | 0.0095 |
| 266A | 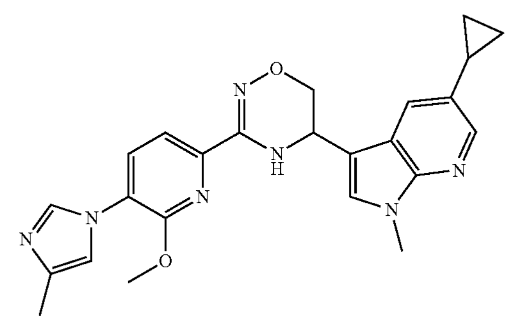 [SMILES: COc1nc(C2=NOCC(c3cn(C)c4ncc(C5CC5)cc34)N2)ccc1-n1cnc(C)c1] | (−)-5-(5-cyclopropyl-1-methyl-1H-pyrrolo[2,3-b]pyridin-3-yl)-3-(6-methoxy-5-(4-methyl-1H-imidazol-1-yl)pyridin-2-yl)-5,6-dihydro-4H-1,2,4-oxadiazine | 0.4503 |
| 266B | 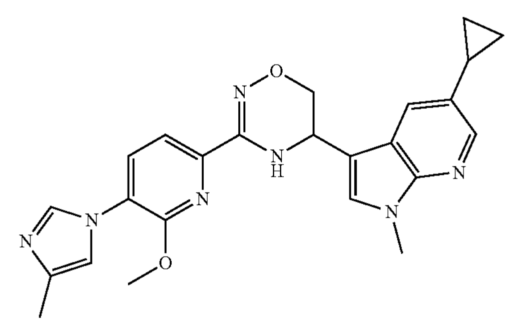 [SMILES: COc1nc(C2=NOCC(c3cn(C)c4ncc(C5CC5)cc34)N2)ccc1-n1cnc(C)c1] | (+)-5-(5-cyclopropyl-1-methyl-1H-pyrrolo[2,3-b]pyridin-3-yl)-3-(6-methoxy-5-(4-methyl-1H-imidazol-1-yl)pyridin-2-yl)-5,6-dihydro-4H-1,2,4-oxadiazine | 0.0155 |
| 267A | 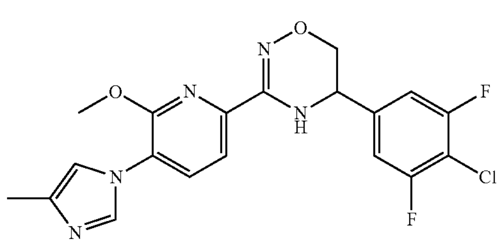 [SMILES: COc1nc(C2=NOCC(c3cc(F)c(Cl)c(F)c3)N2)ccc1-n1cnc(C)c1] | (−)-5-(4-chloro-3,5-difluorophenyl)-3-(6-methoxy-5-(4-methyl-1H-imidazol-1-yl)pyridin-2-yl)-5,6-dihydro-4H-1,2,4-oxadiazine | >3 |

TABLE II-continued

Biological Assay

| Compound of Example | Structure | Name | Aβ42 EC50 (μM) |
|---|---|---|---|
| 267B | 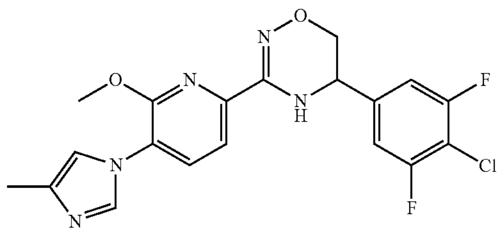 [SMILES: COc1nc(C2=NOCC(c3cc(F)c(Cl)c(F)c3)N2)ccc1-n1cnc(C)c1] | (+)-5-(4-chloro-3,5-difluorophenyl)-3-(6-methoxy-5-(4-methyl-1H-imidazol-1-yl)pyridin-2-yl)-5,6-dihydro-4H-1,2,4-oxadiazine | 0.0249 |
| 268A | 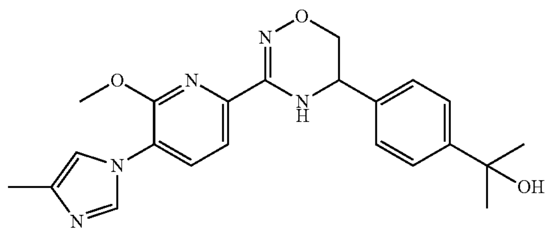 [SMILES: COc1nc(C2=NOCC(c3ccc(C(C)(C)O)cc3)N2)ccc1-n1cnc(C)c1] | (−)-2-(4-(3-(6-methoxy-5-(4-methyl-1H-imidazol-1-yl)pyridin-2-yl)-5,6-dihydro-4H-1,2,4-oxadiazin-5-yl)phenyl)propan-2-ol | 1.4447 |
| 268B | 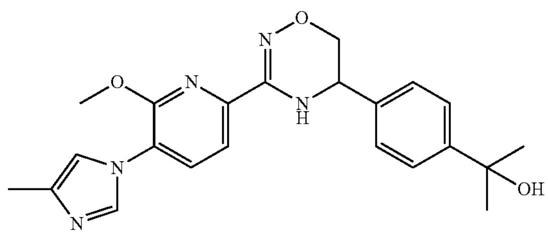 [SMILES: COc1nc(C2=NOCC(c3ccc(C(C)(C)O)cc3)N2)ccc1-n1cnc(C)c1] | (+)-2-(4-(3-(6-methoxy-5-(4-methyl-1H-imidazol-1-yl)pyridin-2-yl)-5,6-dihydro-4H-1,2,4-oxadiazin-5-yl)phenyl)propan-2-ol | 0.2698 |
| 269A | 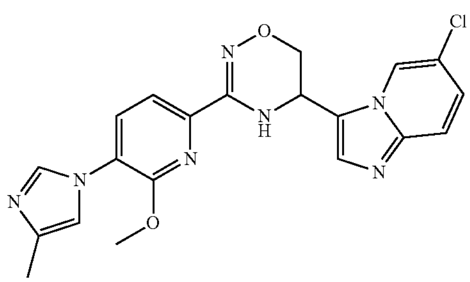 [SMILES: COc1nc(C2=NOCC(c3cnc4ccc(Cl)cn34)N2)ccc1-n1cnc(C)c1] | (−)-5-(6-chloroimidazo[1,2-a]pyridin-3-yl)-3-(6-methoxy-5-(4-methyl-1H-imidazol-1-yl)pyridin-2-yl)-5,6-dihydro-4H-1,2,4-oxadiazine | >3 |
| 269B | 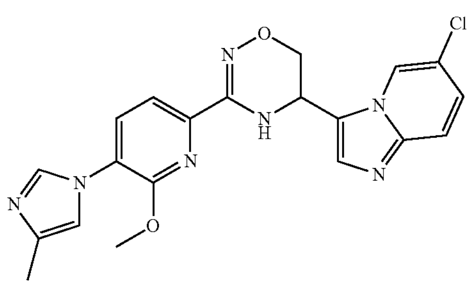 [SMILES: COc1nc(C2=NOCC(c3cnc4ccc(Cl)cn34)N2)ccc1-n1cnc(C)c1] | (+)-5-(6-chloroimidazo[1,2-a]pyridin-3-yl)-3-(6-methoxy-5-(4-methyl-1H-imidazol-1-yl)pyridin-2-yl)-5,6-dihydro-4H-1,2,4-oxadiazine | 0.2399 |
| 270A | 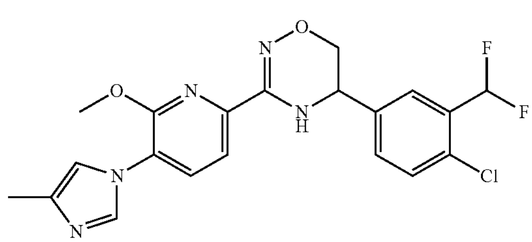 [SMILES: COc1nc(C2=NOCC(c3ccc(Cl)c(C(F)F)c3)N2)ccc1-n1cnc(C)c1] | (−)-5-(4-chloro-3-(difluoromethyl)phenyl)-3-(6-methoxy-5-(4-methyl-1H-imidazol-1-yl)pyridin-2-yl)-5,6-dihydro-4H-1,2,4-oxadiazine | 0.4179 |

TABLE II-continued

Biological Assay

| Compound of Example | Structure | Name | Aβ42 EC50 (μM) |
|---|---|---|---|
| 270B | 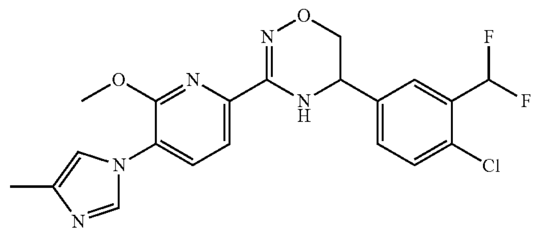 [SMILES: COc1nc(C2=NOCC(c3ccc(Cl)c(C(F)F)c3)N2)ccc1-n1cnc(C)c1] | (+)-5-(4-chloro-3-(difluoromethyl)phenyl)-3-(6-methoxy-5-(4-methyl-1H-imidazol-1-yl)pyridin-2-yl)-5,6-dihydro-4H-1,2,4-oxadiazine | 0.0214 |

Examples 212-250, 252-262, 264, 266-270

Synthesis of Additional Oxadiazine Compounds

Following the synthetic schemes described above and the procedures described in Examples 1-209, the following compounds were prepared and characterized:

TABLE III

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 212A | (+)-2-(3-(3-methoxy-4-(4-methyl-1H-imidazol-1-yl)phenyl)-4-methyl-5,6-dihydro-4H-1,2,4-oxadiazin-5-yl)-7-methylbenzo[d]oxazole | 1.75 min (column; Acquity BEH C-18, 50 × 2.1 mm, 1.7μ); RT 1.75 min; mobile phase: ACN: 0.025% Aq TFA; flow rate: 0.5 mL/min; Gradient programe: T/B % 0.01/90, 0.5/90, 3/10, 6/10; diluent: CH$_3$CN:Water | 417.46 | 418.5 [M + 1] | 92.44 C = 0.25, CH$_2$Cl$_2$ |
| 212B | (-)-2-(3-(3-methoxy-4-(4-methyl-1H-imidazol-1-yl)phenyl)-4-methyl-5,6-dihydro-4H-1,2,4-oxadiazin-5-yl)-7-methylbenzo[d]oxazole | 1.74 min (column; Acquity BEH C-18, 50 × 2.1 mm, 1.7μ); RT 1.75 min; mobile phase: ACN: 0.025% Aq TFA; flow rate: 0.5 mL/min; Gradient programe: T/B % 0.01/90, 0.5/90, 3/10, 6/10; diluent: CH$_3$CN:Water | 417.46 | 418.4 [M + 1] | −78.4 C = 0.25, CH$_2$Cl$_2$ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 213 | 3-(6-methoxy-5-(4-methyl-1H-imidazol-1-yl)pyridin-2-yl)-4-methyl-5-(3-(trifluoromethyl)phenyl)-5,6-dihydro-4H-1,2,4-oxadiazine | 7.45 min (column; Eclipse XDB-C-18, 150 × 4.6 mm, 5.0 µm); mobile phase: ACN: 0.05% Aq TFA; flow rate: 1.0 mL/min; Gradient programe: T/B % 0.01/90, 2/90, 8/10, 15/10: diluent: CH₃CN:Water | 431.41 | 432.4 [M + 1] | |
| 214A | (−)-3-(6-methoxy-5-(4-methyl-1H-imidazol-1-yl)pyridin-2-yl)-5-(3-(methylsulfonyl)phenyl)-5,6-dihydro-4H-1,2,4-oxadiazine | 6.65 min (column; zorbax-SB-C-18 150 × 4.6 mm, 5 µm); mobile Phase: ACN: 0.05% Aq TFA; flow rate: 1.0 mL/min; Gradient programme: T/B % 0.01/90, 2/90, 8/10, 15/10: diluent: CH₃CN:Water | 427.48 | 428.3 [M + 1] | −202.72 C = 0.25, CH₂Cl₂ |
| 214B | (+)-3-(6-methoxy-5-(4-methyl-1H-imidazol-1-yl)pyridin-2-yl)-5-(3-(methylsulfonyl)phenyl)-5,6-dihydro-4H-1,2,4-oxadiazine | 6.66 min (column; zorbax-SB-C-18 150 × 4.6 mm, 5 µm); mobile Phase: ACN: 0.05% Aq TFA; flow rate: 1.0 mL/min; Gradient programme: T/B % 0.01/90, 2/90, 8/10, 15/10: diluent: CH₃CN:Water | 427.48 | 428.3 [M + 1] | 175.5 C = 0.25, CH₂Cl₂ |
| 215A | (−)-3-(6-methoxy-5-(4-methyl-1H-imidazol-1-yl)pyridin-2-yl)-5-(2-methylbenzo[d]thiazol-5-yl)-5,6-dihydro-4H-1,2,4-oxadiazine | 7.06 min (column; zorbax-SB-C-18 150 × 4.6 mm, 5µ); mobile Phase: ACN: 0.05% Aq TFA; flow rate: 1.0 mL/min; Gradient programme: T/B % 0.01/90, 2/90, 8/10, 15/10: diluent: CH₃CN:Water | 420.49 | 421.3 [M + 1] | −178.64 C = 0.25, CH₂Cl₂ |
| 215B | (+)-3-(6-methoxy-5-(4-methyl-1H-imidazol-1-yl)pyridin-2-yl)-5-(2-methylbenzo[d]thiazol-5-yl)-5,6-dihydro-4H-1,2,4-oxadiazine | 7.08 min (column; zorbax-SB-C-18 150 × 4.6 mm, 5µ); mobile Phase: ACN: 0.05% Aq TFA; flow rate: 1.0 mL/min; Gradient programme: T/B % 0.01/90, 2/90, 8/10, 15/10: diluent: CH₃CN:Water | 420.49 | 421.3 [M + 1] | 187.32 C = 0.25, CH₂Cl₂ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 216A | (−)-5-(5-chloro-6-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.78 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 2/90, 8/10, 15/10: diluent: CH$_3$CN:Water | 454.88 | 455.4 [M + 1] | −79.37 C = 0.25, CH$_2$Cl$_2$ |
| 216B | (+)-5-(5-chloro-6-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.78 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 2/90, 8/10, 15/10: diluent: CH$_3$CN:Water | 454.88 | 455.3 [M + 1] | 90.3 C = 0.25, CH$_2$Cl$_2$ |
| 217A | (−)-3-(6-methoxy-5-(4-methyl-1H-imidazol-1-yl)pyridin-2-yl)-5-(4-(methylsulfonyl)phenyl)-5,6-dihydro-4H-1,2,4-oxadiazine | 6.56 min (column; zorbax-SB-C-18 150 × 4.6 mm, 5 μm); mobile Phase: ACN: 0.05% Aq TFA; flow rate: 1.0 mL/min; Gradient programme: T/B % 0.01/90, 2/10, 8/10, 15/10: diluent: CH$_3$CN:Water | 427.48 | 428.3 [M + 1] | −200.65 C = 0.25, CH$_2$Cl$_2$ |
| 217B | (+)-3-(6-methoxy-5-(4-methyl-1H-imidazol-1-yl)pyridin-2-yl)-5-(4-(methylsulfonyl)phenyl)-5,6-dihydro-4H-1,2,4-oxadiazine | 6.56 min (column; zorbax-SB-C-18 150 × 4.6 mm, 5 μm); mobile Phase: ACN: 0.05% Aq TFA; flow rate: 1.0 mL/min; Gradient programme: T/B % 0.01/90, 2/10, 8/10, 15/10: diluent: CH$_3$CN:Water | 427.48 | 428.3 [M + 1] | 208.2 C = 0.25, CH$_2$Cl$_2$ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 218A | (−)-5-(3-chloro-4-methylphenyl)-3-(6-methoxy-5-(4-methyl-1H-imidazol-1-yl)pyridin-2-yl)-5,6-dihydro-4H-1,2,4-oxadiazine | 7.82 min (column; zorbax-SB-C-18 150 × 4.6 mm, 5 μm); mobile Phase: ACN: 0.05% Aq TFA; flow rate: 1.0 mL/min; Gradient programme: T/B % 0.01/90, 2/90, 8/10, 15/10: diluent: $CH_3CN$:Water | 397.86 | 398.3 [M + 1] | −235.58 C = 0.25, $CH_2Cl_2$ |
| 218B | (+)-5-(3-chloro-4-methylphenyl)-3-(6-methoxy-5-(4-methyl-1H-imidazol-1-yl)pyridin-2-yl)-5,6-dihydro-4H-1,2,4-oxadiazine | 7.81 min (column; zorbax-SB-C-18 150 × 4.6 mm, 5 μm); mobile Phase: ACN: 0.05% Aq TFA; flow rate: 1.0 mL/min; Gradient programme: T/B % 0.01/90, 2/90, 8/10, 15/10: diluent: $CH_3CN$:Water | 397.86 | 398.3 [M + 1] | 218.96 C = 0.25, $CH_2Cl_2$ |
| 219A | (+)-5-(6-fluoro-1-isopropyl-1H-indol-3-yl)-3-(6-methoxy-5-(4-methyl-1H-imidazol-1-yl)pyridin-2-yl)-5,6-dihydro-4H-1,2,4-oxadiazine | 7.96 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 2/90, 8/10, 15/10: diluent: $CH_3CN$:Water | 448.49 | 449.4 [M + 1] | 89.18 C = 0.25, $CH_2Cl_2$ |
| 219B | (−)-5-(6-fluoro-1-isopropyl-1H-indol-3-yl)-3-(6-methoxy-5-(4-methyl-1H-imidazol-1-yl)pyridin-2-yl)-5,6-dihydro-4H-1,2,4-oxadiazine | 7.94 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 2/90, 8/10, 15/10: diluent: $CH_3CN$:Water | 448.49 | 449.4 [M + 1] | −86.06 C = 0.25, $CH_2Cl_2$ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 220A | (−)-5-(4,5-difluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.62 min (column; zorbax-SB-C-18 150 × 4.6 mm, 3.5µ); mobile Phase: ACN: 0.05% Aq TFA; flow rate: 1.0 mL/min; Gradient programme: T/B % 0.01/90, 2/90, 8/10, 15/10: diluent: $CH_3CN$:Water | 438.43 | 439 [M + 1] | −126.14 C = 0.25, $CH_2Cl_2$ |
| 220B | (+)-5-(4,5-difluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.62 min (column; zorbax-SB-C-18 150 × 4.6 mm, 3.5µ); mobile Phase: ACN: 0.05% Aq TFA; flow rate: 1.0 mL/min; Gradient programme: T/B % 0.01/90, 2/90, 8/10, 15/10: diluent: $CH_3CN$:Water | 438.43 | 438.9 [M + 1] | 107.28 C = 0.25, $CH_2Cl_2$ |
| 221A | (−)-5-(5-cyclopropyl-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.81 min (column; zorbax-SB-C-18 150 × 4.6 mm, 3.5µ); mobile Phase: ACN: 0.05% Aq TFA; flow rate: 1.0 mL/min; Gradient programme: T/B % 0.01/90, 2/90, 8/10, 15/10: diluent: $CH_3CN$:Water | 442.51 | 443.4 [M + 1] | −77.71 C = 0.25, $CH_2Cl_2$ |
| 221B | (+)-5-(5-cyclopropyl-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.82 min (column; zorbax-SB-C-18 150 × 4.6 mm, 3.5µ); mobile Phase: ACN: 0.05% Aq TFA; flow rate: 1.0 mL/min; Gradient programme: T/B % 0.01/90, 2/90, 8/10, 15/10: diluent: $CH_3CN$:Water | 442.51 | 443.4 [M + 1] | 72.25 C = 0.25, $CH_2Cl_2$ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 222A | (+)-5-(1-cyclopropyl-4-fluoro-1H-indol-3-yl)-3-(6-methoxy-5-(4-methyl-1H-imidazol-1-yl)pyridin-2-yl)-5,6-dihydro-4H-1,2,4-oxadiazine | 7.89 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 2/90, 8/10, 15/10: diluent: $CH_3CN$:Water | 446.48 | 447.3 [M + 1] | 126.94 C = 0.25, $CH_2Cl_2$ |
| 222B | (−)-5-(1-cyclopropyl-4-fluoro-1H-indol-3-yl)-3-(6-methoxy-5-(4-methyl-1H-imidazol-1-yl)pyridin-2-yl)-5,6-dihydro-4H-1,2,4-oxadiazine | 7.90 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 2/90, 8/10, 15/10: diluent: $CH_3CN$:Water | 446.48 | 447.3 [M + 1] | −119.79 C = 0.25, $CH_2Cl_2$ |
| 223A | (−)-5-(5,6-difluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.48 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 2/90, 8/10, 15/10: diluent: $CH_3CN$:Water | 438.43 | 439 [M + 1] | −112.33 C = 0.25, $CH_2Cl_2$ |
| 223B | (+)-5-(5,6-difluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.49 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 2/90, 8/10, 15/10: diluent: $CH_3CN$:Water | 438.43 | 439 [M + 1] | 116.11 C = 0.25, $CH_2Cl_2$ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 224A | (−)-3-(6-methoxy-5-(4-methyl-1H-imidazol-1-yl)pyridin-2-yl)-5-(quinolin-6-yl)-5,6-dihydro-4H-1,2,4-oxadiazine | 9.10 min (column; X-select CSH-C-18 150 × 4.6 mm, 3.5 μm); mobile Phase: ACN: 5 mM NH4OAc; flow rate: 1.0 mL/min; Gradient programme: T/B % 0.01/80, 3/80, 10/10, 20/10: diluent: CH$_3$CN:Water | 400.43 | 401.1 [M + 1] | −194.56 C = 0.25, CH$_2$Cl$_2$ |
| 224B | (+)-3-(6-methoxy-5-(4-methyl-1H-imidazol-1-yl)pyridin-2-yl)-5-(quinolin-6-yl)-5,6-dihydro-4H-1,2,4-oxadiazine | 9.13 min (column; X-select CSH-C-18 150 × 4.6 mm, 3.5 μm); mobile Phase: ACN: 5 mM NH4OAc; flow rate: 1.0 mL/min; Gradient programme: T/B % 0.01/80, 3/80, 10/10, 20/10: diluent: CH$_3$CN:Water | 400.43 | 401 [M + 1] | 187.34 C = 0.25, CH$_2$Cl$_2$ |
| 225A | (−)-5-(2,2-difluorobenzo[d][1,3]dioxol-5-yl)-3-(6-methoxy-5-(4-methyl-1H-imidazol-1-yl)pyridin-2-yl)-5,6-dihydro-4H-1,2,4-oxadiazine | 7.65 min (column; zorbax-SB-C-18 150 × 4.6 mm, 5 μm); mobile Phase: ACN: 0.05% Aq TFA; flow rate: 1.0 mL/min; Gradient programme: T/B % 0.01/90, 2/90, 8/10, 15/10: diluent: CH$_3$CN:Water | 429.38 | 430 [M + 1] | −183.61 C = 0.25, CH$_2$Cl$_2$ |
| 225B | (+)-5-(2,2-difluorobenzo[d][1,3]dioxol-5-yl)-3-(6-methoxy-5-(4-methyl-1H-imidazol-1-yl)pyridin-2-yl)-5,6-dihydro-4H-1,2,4-oxadiazine | 7.66 min (column; zorbax-SB-C-18 150 × 4.6 mm, 5 μm); mobile Phase: ACN: 0.05% Aq TFA; flow rate: 1.0 mL/min; Gradient programme: T/B % 0.01/90, 2/90, 8/10, 15/10: diluent: CH$_3$CN:Water | 429.38 | 429.9 [M + 1] | 190.09 C = 0.25, CH$_2$Cl$_2$ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 226A | 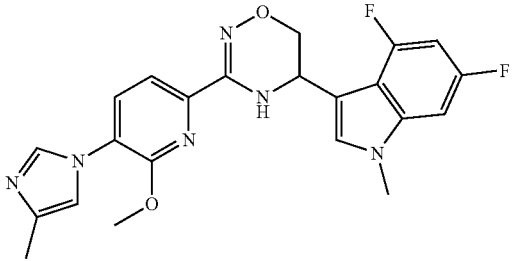<br>(+)-5-(4,6-difluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.67 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 2/90, 10/10, 15/10: diluent: $CH_3CN$:Water | 438.43 | 439.1 [M + 1] | 116.86 C = 0.25, $CH_2Cl_2$ |
| 226B | 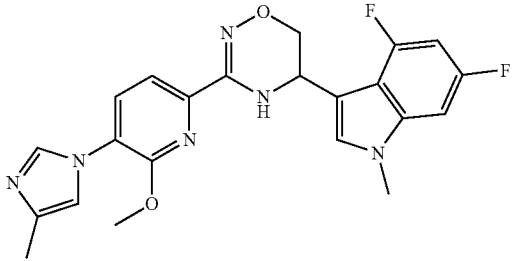<br>(-)-5-(4,6-difluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.67 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 2/90, 10/10, 15/10: diluent: $CH_3CN$:Water | 438.43 | 439 [M + 1] | -118.81 C = 0.25, $CH_2Cl_2$ |
| 227A | 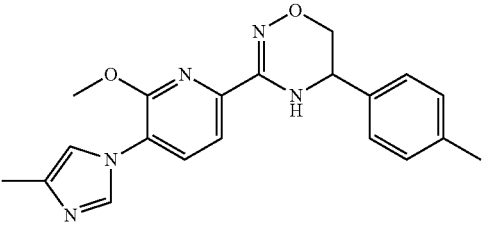<br>(-)-3-(6-methoxy-5-(4-methyl-1H-imidazol-1-yl)pyridin-2-yl)-5-(p-tolyl)-5,6-dihydro-4H-1,2,4-oxadiazine | 7.42 min (column; zorbax-SB-C-18 150 × 4.6 mm, 5 μm); mobile Phase: ACN: 0.05% Aq TFA; flow rate: 1.0 mL/min; Gradient programme: T/B % 0.01/90, 2/90, 8/10, 15/10: diluent: $CH_3CN$:Water | 363.41 | 364.1 [M + 1] | -170.09 C = 0.25, $CH_2Cl_2$ |
| 227B | 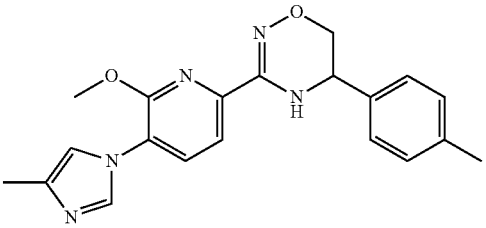<br>(+)-3-(6-methoxy-5-(4-methyl-1H-imidazol-1-yl)pyridin-2-yl)-5-(p-tolyl)-5,6-dihydro-4H-1,2,4-oxadiazine | 7.39 min (column; zorbax-SB-C-18 150 × 4.6 mm, 5 μm); mobile Phase: ACN: 0.05% Aq TFA; flow rate: 1.0 mL/min; Gradient programme: T/B % 0.01/90, 2/90, 8/10, 15/10: diluent: $CH_3CN$:Water | 363.41 | 363.9 [M + 1] | 173.32 C = 0.25, $CH_2Cl_2$ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 228A | 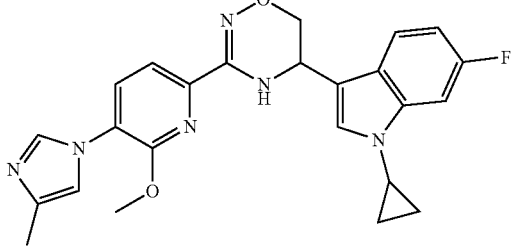<br>(−)-5-(1-cyclopropyl-6-fluoro-1H-indol-3-yl)-3-(6-methoxy-5-(4-methyl-1H-imidazol-1-yl)pyridin-2-yl)-5,6-dihydro-4H-1,2,4-oxadiazine | 7.79 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 2/90, 8/10, 15/10: diluent: CH$_3$CN:Water | 446.48 | 447.1 [M + 1] | −97.84 C = 0.25, CH$_2$Cl$_2$ |
| 228B | 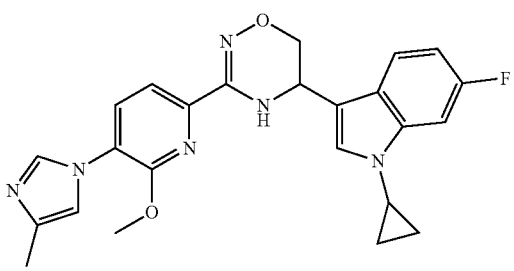<br>(+)-5-(1-cyclopropyl-6-fluoro-1H-indol-3-yl)-3-(6-methoxy-5-(4-methyl-1H-imidazol-1-yl)pyridin-2-yl)-5,6-dihydro-4H-1,2,4-oxadiazine | 7.77 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 2/90, 8/10, 15/10: diluent: CH$_3$CN:Water | 446.48 | 447 [M + 1] | 81.69 C = 0.25, CH$_2$Cl$_2$ |
| 229A | 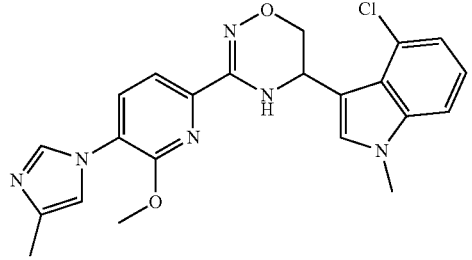<br>(+)-5-(4-chloro-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.69 min (column; zorbax-SB-C-18 150 × 4.6 mm, 5 μm); mobile Phase: ACN: 0.05% Aq TFA; flow rate: 1.0 mL/min; Gradient programme: T/B % 0.01/90, 2/90, 8/10, 15/10: diluent: CH$_3$CN:Water | 436.89 | 437.3 [M + 1] | 107.84 C = 0.25, CH$_2$Cl$_2$ |
| 229B | 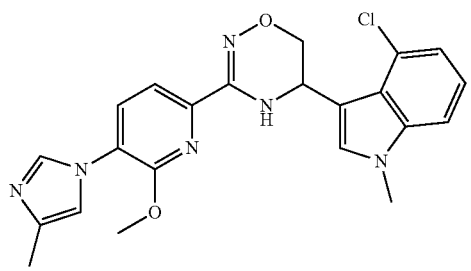<br>(−)-5-(4-chloro-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.69 min (column; zorbax-SB-C-18 150 × 4.6 mm, 5 μm); mobile Phase: ACN: 0.05% Aq TFA; flow rate: 1.0 mL/min; Gradient programme: T/B % 0.01/90, 2/90, 8/10, 15/10: diluent: CH$_3$CN:Water | 436.89 | 437.3 [M + 1] | −105.07 C = 0.25, CH$_2$Cl$_2$ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 230A | 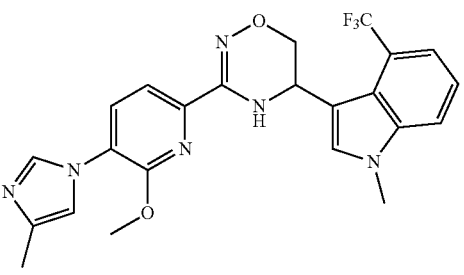<br>(+)-3-(6-methoxy-5-(4-methyl-1H-imidazol-1-yl)pyridin-2-yl)-5-(1-methyl-4-(trifluoromethyl)-1H-indol-3-yl)-5,6-dihydro-4H-1,2,4-oxadiazine | 7.86 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 2/90, 8/10, 15/10: diluent: CH$_3$CN:Water | 470.45 | 471 [M + 1] | 51.79 C = 0.25, CH$_2$Cl$_2$ |
| 230B | 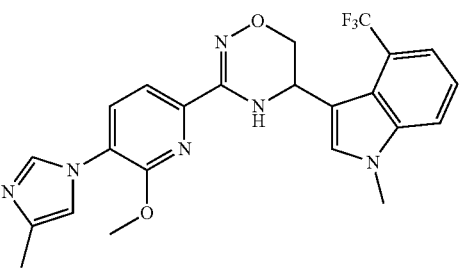<br>(−)-3-(6-methoxy-5-(4-methyl-1H-imidazol-1-yl)pyridin-2-yl)-5-(1-methyl-4-(trifluoromethyl)-1H-indol-3-yl)-5,6-dihydro-4H-1,2,4-oxadiazine | 7.87 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 2/90, 8/10, 15/10: diluent: CH$_3$CN:Water | 470.45 | 471 [M + 1] | −51.42 C = 0.25, CH$_2$Cl$_2$ |
| 231A | 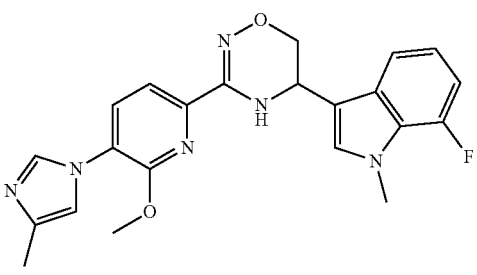<br>(−)-5-(7-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.64 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 2/90, 10/10, 15/10: diluent: CH$_3$CN:Water | 420.44 | 421.1 [M + 1] | −84.28 C = 0.25, CH$_2$Cl$_2$ |
| 231B | 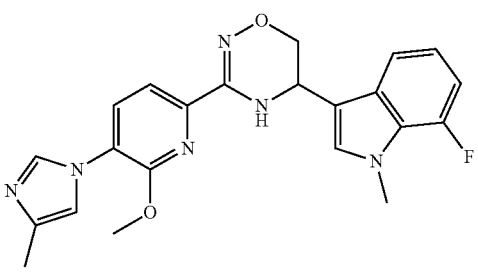<br>(+)-5-(7-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.65 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 2/90, 10/10, 15/10: diluent: CH$_3$CN:Water | 420.44 | 421 [M + 1] | 88.99 C = 0.25, CH$_2$Cl$_2$ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 232A | 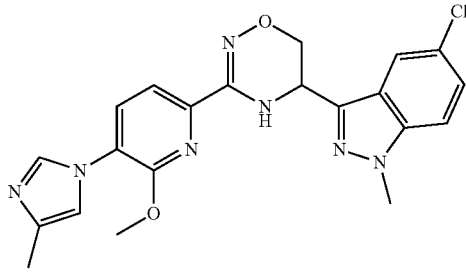<br>(−)-5-(5-chloro-1-methyl-1H-indazol-3-yl)-3-(6-methoxy-5-(4-methyl-1H-imidazol-1-yl)pyridin-2-yl)-5,6-dihydro-4H-1,2,4-oxadiazine | 3.32 min (column: Phenomenex Gemini-NX-C18, 50 × 2.0 mm, 3 μm); Flow: 0.8 mL/min; Column temp: 25° C.; Eluent A: 95% acetonitrile + 5% 10 mM ammoniumbicarbonate in water; Eluent B: 10 mM ammoniumbicarbonate in water pH = 9.0; Linear Gradient: t = 0 min 5% A, 1 = 3.5 min 98% A, t = 6 min 98% A; detection: DAD (220-320 nm) | 437.88 | 438 M + H | −206.7 c = 0.25, $CH_2Cl_2$, 22.1° C., 589 nm |
| 232B | 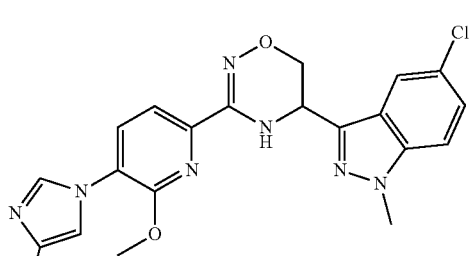<br>(+)-5-(5-chloro-1-methyl-1H-indazol-3-yl)-3-(6-methoxy-5-(4-methyl-1H-imidazol-1-yl)pyridin-2-yl)-5,6-dihydro-4H-1,2,4-oxadiazine | 3.32 min (column: Phenomenex Gemini-NX-C18, 50 × 2.0 mm, 3 μm); Flow: 0.8 mL/min; Column temp: 25° C.; Eluent A: 95% acetonitrile + 5% 10 mM ammoniumbicarbonate in water; Eluent B: 10 mM ammoniumbicarbonate in water pH = 9.0; Linear Gradient: t = 0 min 5% A, 1 = 3.5 min 98% A, t = 6 min 98% A; detection: DAD (220-320 nm) | 437.88 | 438 M + H | 215.9 c = 0.25, $CH_2Cl_2$, 22.2° C., 589 nm |
| 233A | 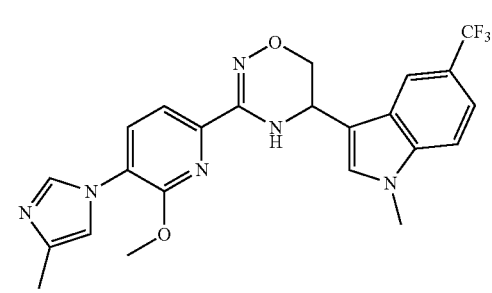<br>(−)-3-(6-methoxy-5-(4-methyl-1H-imidazol-1-yl)pyridin-2-yl)-5-(1-methyl-5-(trifluoromethyl)-1H-indol-3-yl)-5,6-dihydro-4H-1,2,4-oxadiazine | 7.98 min (column; zorbax-SB-C-18 150 × 4.6 mm, 5 μm); mobile Phase: ACN: 0.05% Aq TFA; flow rate: 1.0 mL/min; Gradient programme: T/B % 0.01/90, 2/90, 8/10, 15/10: diluent: $CH_3CN$:Water | 470.45 | 471 [M + 1] | −101.32 C = 0.25, $CH_2Cl_2$ |
| 233B | 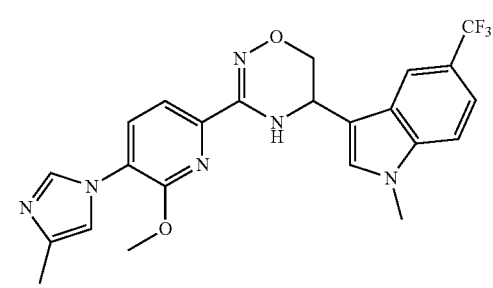<br>(+)-3-(6-methoxy-5-(4-methyl-1H-imidazol-1-yl)pyridin-2-yl)-5-(1-methyl-5-(trifluoromethyl)-1H-indol-3-yl)-5,6-dihydro-4H-1,2,4-oxadiazine | 7.97 min (column; zorbax-SB-C-18 150 × 4.6 mm, 5 μm); mobile Phase: ACN: 0.05% Aq TFA; flow rate: 1.0 mL/min; Gradient programme: T/B % 0.01/90, 2/90, 8/10, 15/10: diluent: $CH_3CN$:Water | 470.45 | 471 [M + 1] | 100.16 C = 0.25, $CH_2Cl_2$ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 234A | 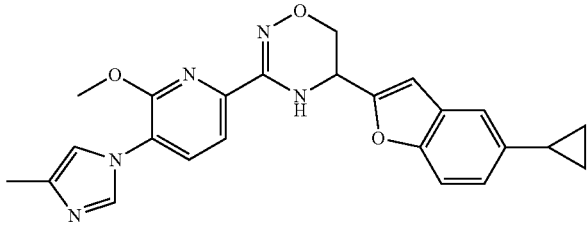<br>(−)-5-(5-cyclopropylbenzofuran-2-yl)-3-(6-methoxy-5-(4-methyl-1H-imidazol-1-yl)pyridin-2-yl)-5,6-dihydro-4H-1,2,4-oxadiazine | 8.02 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 2/90, 8/10, 15/10: diluent: CH$_3$CN:Water | 429.47 | 430 [M + 1] | −240.76 C = 0.25, CH$_2$Cl$_2$ |
| 234B | 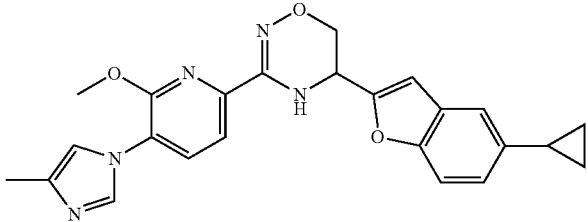<br>(+)-5-(5-cyclopropylbenzofuran-2-yl)-3-(6-methoxy-5-(4-methyl-1H-imidazol-1-yl)pyridin-2-yl)-5,6-dihydro-4H-1,2,4-oxadiazine | 8.02 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 2/90, 8/10, 15/10: diluent: CH$_3$CN:Water | 429.47 | 430 [M + 1] | 218.24 C = 0.25, CH$_2$Cl$_2$ |
| 235A | 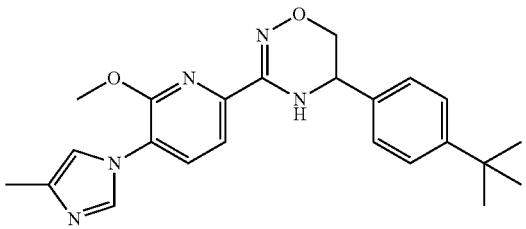<br>(−)-5-(4-(tert-butyl)phenyl)-3-(6-methoxy-5-(4-methyl-1H-imidazol-1-yl)pyridin-2-yl)-5,6-dihydro-4H-1,2,4-oxadiazine | 7.98 min (column; zorbax-SB-C-18 150 × 4.6 mm, 5 μm); mobile Phase: ACN: 0.05% Aq TFA; flow rate: 1.0 mL/min; Gradient programme: T/B % 0.01/90, 2/90, 8/10, 15/10: diluent: CH$_3$CN:Water | 405.49 | 406.1 [M + 1] | −151.12 C = 0.25, CH$_2$Cl$_2$ |
| 235B | 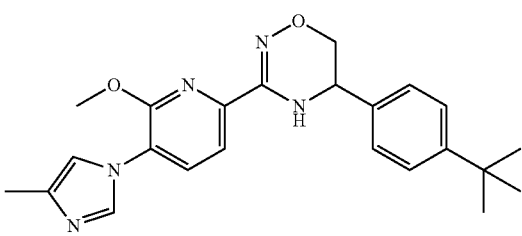<br>(+)-5-(4-(tert-butyl)phenyl)-3-(6-methoxy-5-(4-methyl-1H-imidazol-1-yl)pyridin-2-yl)-5,6-dihydro-4H-1,2,4-oxadiazine | 7.99 min (column; zorbax-SB-C-18 150 × 4.6 mm, 5 μm); mobile Phase: ACN: 0.05% Aq TFA; flow rate: 1.0 mL/min; Gradient programme: T/B % 0.01/90, 2/90, 8/10, 15/10: diluent: CH$_3$CN:Water | 405.49 | 406 [M + 1] | 156.44 C = 0.25, CH$_2$Cl$_2$ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 236A | (−)-5-(6-cyclopropylbenzofuran-2-yl)-3-(6-methoxy-5-(4-methyl-1H-imidazol-1-yl)pyridin-2-yl)-5,6-dihydro-4H-1,2,4-oxadiazine | 8.16 min (column; zorbax-SB-C-18 150 × 4.6 mm, 5μ); mobile Phase: ACN: 0.05% Aq TFA; flow rate: 1.0 mL/min; Gradient programme: T/B % 0.01/90, 2/90, 8/10, 15/10: diluent: CH$_3$CN:Water | 429.47 | 430.1 [M + 1] | −197.24 C = 0.25, CH$_2$Cl$_2$ |
| 236B | (+)-5-(6-cyclopropylbenzofuran-2-yl)-3-(6-methoxy-5-(4-methyl-1H-imidazol-1-yl)pyridin-2-yl)-5,6-dihydro-4H-1,2,4-oxadiazine | 8.15 min (column; zorbax-SB-C-18 150 × 4.6 mm, 5μ); mobile Phase: ACN: 0.05% Aq TFA; flow rate: 1.0 mL/min; Gradient programme: T/B % 0.01/90, 2/90, 8/10, 15/10: diluent: CH$_3$CN:Water | 429.47 | 430 [M + 1] | 187.84 C = 0.25, CH$_2$Cl$_2$ |
| 237A | (+)-5-(5-chloro-4-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.66 min (column; zorbax-SB-C-18 150 × 4.6 mm, 5μ); mobile Phase: ACN + 5% 0.05% TFA; 0.05% TFA + 5% ACN; flow rate: 1.0 mL/min; Gradient programme: T/B % 0.01/90, 2/90, 8/10, 15/10: diluent: CH$_3$CN:Water | 454.88 | 455 [M + 1] | 80.84 C = 0.25, CH$_2$Cl$_2$ |
| 237B | (−)-5-(5-chloro-4-fluoro-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.55 min (column; zorbax-SB-C-18 150 × 4.6 mm, 5μ); mobile Phase: ACN + 5% 0.05% TFA; 0.05% TFA + 5% ACN; flow rate: 1.0 mL/min; Gradient programme: T/B % 0.01/90, 2/90, 8/10, 15/10: diluent: CH$_3$CN:Water | 454.88 | 455 [M + 1] | −92.01 C = 0.25, CH$_2$Cl$_2$ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 238A | (−)-3-(6-methoxy-5-(4-methyl-1H-imidazol-1-yl)pyridin-2-yl)-5-(2-methylbenzo[d]thiazol-6-yl)-5,6-dihydro-4H-1,2,4-oxadiazine | 6.62 min (column; zorbax-SB-C-18 150 × 4.6 mm, 5 μm); mobile Phase: ACN + 5% 0.05% Aq TFA; 0.05% TFA + 5% ACN; flow rate: 1.0 mL/min; Gradient programme: T/B % 0.01/90, 2/90, 8/10, 15/10: diluent: CH$_3$CN:Water | 420.49 | 421 [M + 1] | −193.61 C = 0.25, CH$_2$Cl$_2$ |
| 238B | (+)-3-(6-methoxy-5-(4-methyl-1H-imidazol-1-yl)pyridin-2-yl)-5-(2-methylbenzo[d]thiazol-6-yl)-5,6-dihydro-4H-1,2,4-oxadiazine | 6.62 min (column; zorbax-SB-C-18 150 × 4.6 mm, 5 μm); mobile Phase: ACN + 5% 0.05% Aq TFA; 0.05% TFA + 5% ACN; flow rate: 1.0 mL/min; Gradient programme: T/B % 0.01/90, 2/90, 8/10, 15/10: diluent: CH$_3$CN:Water | 420.49 | 421 [M + 1] | 206.64 C = 0.25, CH$_2$Cl$_2$ |
| 239A | (−)-5-(4-chloro-3-cyclopropylphenyl)-3-(6-methoxy-5-(4-methyl-1H-imidazol-1-yl)pyridin-2-yl)-5,6-dihydro-4H-1,2,4-oxadiazine | 8.17 min (column; X-select CSH-C-18 150 × 4.6 mm, 2.5 μm); mobile Phase: ACN + 0.05% TFA; flow rate: 0.8 mL/min; Gradient programme: T/B % 0.01/90, 10/05, 20/05: diluent: CH$_3$CN | 423.90 | 423.9 [M + 1] | −172.64 C = 0.25, CH$_2$Cl$_2$ |
| 239B | (+)-5-(4-chloro-3-cyclopropylphenyl)-3-(6-methoxy-5-(4-methyl-1H-imidazol-1-yl)pyridin-2-yl)-5,6-dihydro-4H-1,2,4-oxadiazine | 8.15 min (column; X-select CSH-C-18 150 × 4.6 mm, 2.5 μm); mobile Phase: ACN + 0.05% TFA; flow rate: 0.8 mL/min; Gradient programme: T/B % 0.01/90, 10/05, 20/05: diluent: CH$_3$CN | 423.90 | 423.9 [M + 1] | 167 C = 0.25, CH$_2$Cl$_2$ |
| 240A | (−)-5-(benzo[d]thiazol-5-yl)-3-(6-methoxy-5-(4-methyl-1H-imidazol-1-yl)pyridin-2-yl)-5,6-dihydro-4H-1,2,4-oxadiazine | 5.54 min (column; zorbax-SB-C-18 150 × 4.6 mm, 3.5 μm); mobile Phase: ACN + 5% 0.05% TFA: 0.05% TFA + 5% ACN; flow rate: 1.0 mL/min; Gradient programme: T/B % 0.01/90, 10/10, 15/10: diluent: CH$_3$CN:Water | 406.46 | 407 [M + 1] | −164.08 C = 0.25, CH$_2$Cl$_2$ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 240B | (+)-5-(benzo[d]thiazol-5-yl)-3-(6-methoxy-5-(4-methyl-1H-imidazol-1-yl)pyridin-2-yl)-5,6-dihydro-4H-1,2,4-oxadiazine | 5.53 min (column; zorbax-SB-C-18 150 × 4.6 mm, 3.5 μm); mobile Phase: ACN + 5% 0.05% TFA: 0.05% TFA + 5% ACN; flow rate: 1.0 mL/min; Gradient programme: T/B % 0.01/90, 10/10, 15/10: diluent: CH$_3$CN:Water | 406.46 | 406.9 [M + 1] | 166.78 C = 0.25, CH$_2$Cl$_2$ |
| 241A | (−)-3-(6-methoxy-5-(4-methyl-1H-imidazol-1-yl)pyridin-2-yl)-5-(1-methyl-5-(trifluoromethyl)-1H-indazol-3-yl)-5,6-dihydro-4H-1,2,4-oxadiazine | 3.44 min (column: Phenomenex Gemini-NX-C18, 50 × 2.0 mm, 3 μm); Flow: 0.8 mL/min; Column temp: 25° C.; Eluent A: 95% acetonitrile + 5% 10 mM ammoniumbicarbonate in water; Eluent B: 10 mM ammoniumbicarbonate in water pH = 9.0; Linear Gradient: t = 0 min 5% A, t = 3.5 min 98% A, t = 6 min 98% A; detection: DAD (220-320 nm) | 471.44 | 472 M + H | −140.3 c = 0.05, CH$_2$Cl$_2$, 22.7° C., 589 nm |
| 241B | (+)-3-(6-methoxy-5-(4-methyl-1H-imidazol-1-yl)pyridin-2-yl)-5-(1-methyl-5-(trifluoromethyl)-1H-indazol-3-yl)-5,6-dihydro-4H-1,2,4-oxadiazine | 3.44 min (column: Phenomenex Gemini-NX-C18, 50 × 2.0 mm, 3 μm); Flow: 0.8 mL/min; Column temp: 25° C.; Eluent A: 95% acetonitrile + 5% 10 mM ammoniumbicarbonate in water; Eluent B: 10 mM ammoniumbicarbonate in water pH = 9.0; Linear Gradient: t = 0 min 5% A, t = 3.5 min 98% A, t = 6 min 98% A; detection: DAD (220-320 nm) | 471.44 | 472 M + H | 159.9 c = 0.05, CH$_2$Cl$_2$, 22.7° C., 589 nm |
| 242A | (−)-3-(6-methoxy-5-(4-methyl-1H-imidazol-1-yl)pyridin-2-yl)-5-(3-(trifluoromethoxy)phenyl)-5,6-dihydro-4H-1,2,4-oxadiazine | 7.31 min (column; zorbax-SB-C-18 150 × 4.6 mm, 3.5 μm); mobile Phase: ACN + 5% Aq TFA: 0.05% TFA + 5% ACN; flow rate: 1.0 mL/min; Gradient programme: T/B % 0.01/90, 10/10, 15/10: diluent: CH$_3$CN:Water | 433.38 | 433.9 [M + 1] | −150.59 C = 0.25, CH$_2$Cl$_2$ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 242B | (+)-3-(6-methoxy-5-(4-methyl-1H-imidazol-1-yl)pyridin-2-yl)-5-(3-(trifluoromethoxy)phenyl)-5,6-dihydro-4H-1,2,4-oxadiazine | 7.32 min (column; zorbax-SB-C-18 150 × 4.6 mm, 3.5 µm); mobile Phase: ACN + 5% Aq TFA: 0.05% TFA + 5% ACN; flow rate: 1.0 mL/min; Gradient programme: T/B % 0.01/90, 10/10, 15/10: diluent: CH$_3$CN:Water | 433.38 | 434 [M + 1] | 168.56 C = 0.25, CH$_2$Cl$_2$ |
| 243A | (−)-5-(3-chloro-4-cyclopropylphenyl)-3-(6-methoxy-5-(4-methyl-1H-imidazol-1-yl)pyridin-2-yl)-5,6-dihydro-4H-1,2,4-oxadiazine | 7.76 min (column; zorbax-SB-C-18 150 × 4.6 mm, 3.5 µm); mobile Phase: ACN + 5% Aq TFA: 0.05% TFA + 5% ACN; flow rate: 1.0 mL/min; Gradient programme: T/B % 0.01/90, 10/10, 15/10: diluent: CH$_3$CN:Water | 423.90 | 424 [M + 1] | −111.55 C = 0.25, CH$_2$Cl$_2$ |
| 243B | (+)-5-(3-chloro-4-cyclopropylphenyl)-3-(6-methoxy-5-(4-methyl-1H-imidazol-1-yl)pyridin-2-yl)-5,6-dihydro-4H-1,2,4-oxadiazine | 7.74 min (column; zorbax-SB-C-18 150 × 4.6 mm, 3.5 µm); mobile Phase: ACN + 5% Aq TFA: 0.05% TFA + 5% ACN; flow rate: 1.0 mL/min; Gradient programme: T/B % 0.01/90, 10/10, 15/10: diluent: CH$_3$CN:Water | 423.90 | 423.9 [M + 1] | 102.32 C = 0.25, CH$_2$Cl$_2$ |
| 244A | (−)-5-(3-chlorophenyl)-3-(6-methoxy-5-(4-methyl-1H-imidazol-1-yl)pyridin-2-yl)-5,6-dihydro-4H-1,2,4-oxadiazine | 6.60 min (column; zorbax-SB-C-18 150 × 4.6 mm, 3.5 µm); mobile Phase: ACN + 5% 0.05% TFA: 0.05% TFA + 5% ACN; flow rate: 1.0 mL/min; Gradient programme: T/B % 0.01/90, 10/10, 15/10: diluent: CH$_3$CN:Water | 383.83 | 383.9 [M + 1] | −226.09 C = 0.25, CH$_2$Cl$_2$ |
| 244B | (+)-5-(3-chlorophenyl)-3-(6-methoxy-5-(4-methyl-1H-imidazol-1-yl)pyridin-2-yl)-5,6-dihydro-4H-1,2,4-oxadiazine | 6.60 min (column; zorbax-SB-C-18 150 × 4.6 mm, 3.5 µm); mobile Phase: ACN + 5% 0.05% TFA: 0.05% TFA + 5% ACN; flow rate: 1.0 mL/min; Gradient programme: T/B % 0.01/90, 10/10, 15/10: diluent: CH$_3$CN:Water | 383.83 | 383.9 [M + 1] | 207.79 C = 0.25, CH$_2$Cl$_2$ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 245A | 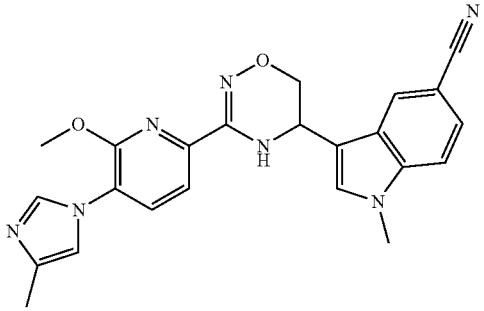<br>(−)-3-(3-(6-methoxy-5-(4-methyl-1H-imidazol-1-yl)pyridin-2-yl)-5,6-dihydro-4H-1,2,4-oxadiazin-5-yl)-1-methyl-1H-indole-5-carbonitrile | 5.97 min (column; zorbax-SB-C-18 150 × 4.6 mm, 3.5μ); mobile Phase: ACN: 5% 0.05% TFA; 0.05% TFA + 5% ACN; flow rate: 1.0 mL/min; Gradient programme: T/B % 0.01/90, 10/10, 15/10: diluent: CH₃CN:Water | 427.46 | 428 [M + 1] | −123.24 C = 0.25, CH₂Cl₂ |
| 245B | 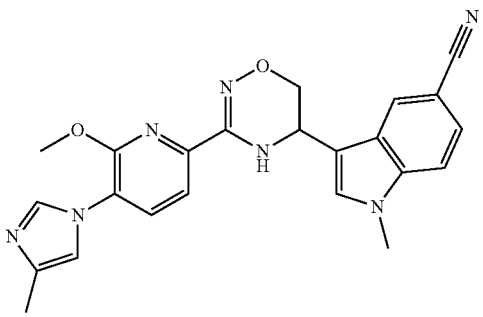<br>(+)-3-(3-(6-methoxy-5-(4-methyl-1H-imidazol-1-yl)pyridin-2-yl)-5,6-dihydro-4H-1,2,4-oxadiazin-5-yl)-1-methyl-1H-indole-5-carbonitrile | 5.94 min (column; zorbax-SB-C-18 150 × 4.6 mm, 3.5μ); mobile Phase: ACN: 5% 0.05% TFA; 0.05% TFA + 5% ACN; flow rate: 1.0 mL/min; Gradient programme: T/B % 0.01/90, 10/10, 15/10: diluent: CH₃CN:Water | 427.46 | 428 [M + 1] | 133.05 C = 0.25, CH₂Cl₂ |
| 246A | 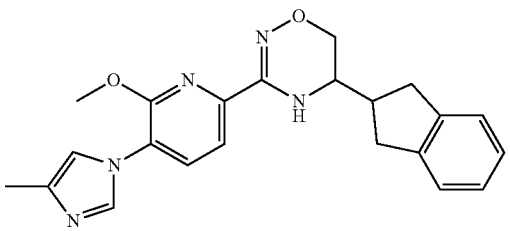<br>(−)-5-(2,3-dihydro-1H-inden-2-yl)-3-(6-methoxy-5-(4-methyl-1H-imidazol-1-yl)pyridin-2-yl)-5,6-dihydro-4H-1,2,4-oxadiazine | 7.40 min (column; zorbax-SB-C-18 150 × 4.6 mm, 3.5μ); mobile Phase: ACN: 5% 0.05% TFA; 0.05% TFA + 5% ACN; flow rate: 1.0 mL/min; Gradient programme: T/B % 0.01/90, 10/10, 15/10: diluent: CH₃CN:Water | 389.45 | 390 [M + 1] | −27.31 C = 0.25, CH₂Cl₂ |
| 246B | 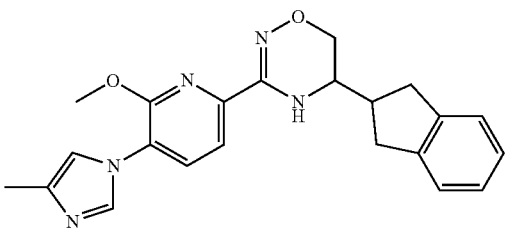<br>(+)-5-(2,3-dihydro-1H-inden-2-yl)-3-(6-methoxy-5-(4-methyl-1H-imidazol-1-yl)pyridin-2-yl)-5,6-dihydro-4H-1,2,4-oxadiazine | 7.39 min (column; zorbax-SB-C-18 150 × 4.6 mm, 3.5μ); mobile Phase: ACN: 5% 0.05% TFA; 0.05% TFA + 5% ACN; flow rate: 1.0 mL/min; Gradient programme: T/B % 0.01/90, 10/10, 15/10: diluent: CH₃CN:Water | 389.45 | 390 [M + 1] | 16.35 C = 0.25, CH₂Cl₂ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 247A | 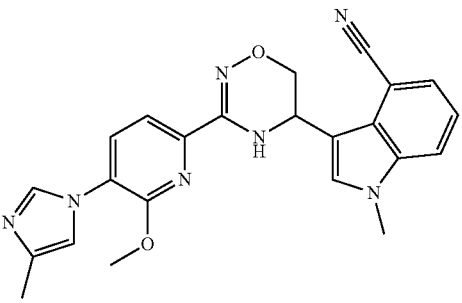<br>(+)-3-(3-(6-methoxy-5-(4-methyl-1H-imidazol-1-yl)pyridin-2-yl)-5,6-dihydro-4H-1,2,4-oxadiazin-5-yl)-1-methyl-1H-indole-4-carbonitrile | 6.91 min (column; zorbax-SB-C-18 150 × 4.6 mm, 3.5μ); mobile Phase: ACN: 5% 0.05% Aq TFA; 0.05% TFA + 5% ACN; flow rate: 1.0 mL/min; Gradient programme: T/B % 0.01/90, 10/10, 15/10: diluent: CH₃CN:Water | 427.46 | 428 [M + 1] | 24.67 C = 0.25, CH₂Cl₂ |
| 247B | 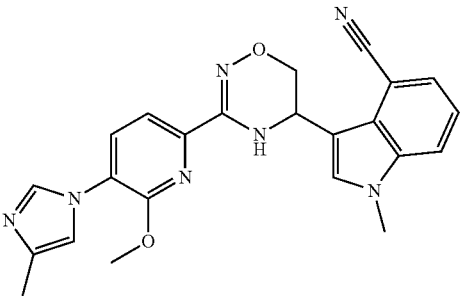<br>(−)-3-(3-(6-methoxy-5-(4-methyl-1H-imidazol-1-yl)pyridin-2-yl)-5,6-dihydro-4H-1,2,4-oxadiazin-5-yl)-1-methyl-1H-indole-4-carbonitrile | 6.91 min (column; zorbax-SB-C-18 150 × 4.6 mm, 3.5μ); mobile Phase: ACN: 5% 0.05% Aq TFA; 0.05% TFA + 5% ACN; flow rate: 1.0 mL/min; Gradient programme: T/B % 0.01/90, 10/10, 15/10: diluent: CH₃CN:Water | 427.46 | 428 [M + 1] | −17.39 C = 0.25, CH₂Cl₂ |
| 248A | 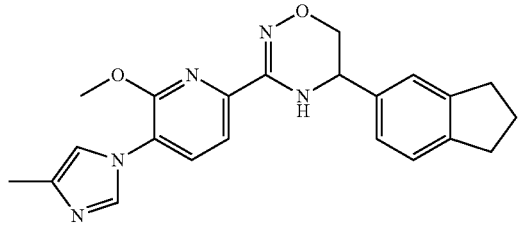<br>(−)-5-(2,3-dihydro-1H-inden-5-yl)-3-(6-methoxy-5-(4-methyl-1H-imidazol-1-yl)pyridin-2-yl)-5,6-dihydro-4H-1,2,4-oxadiazine | 7.67 min (column; zorbax-SB-C-18 150 × 4.6 mm, 5 μm); mobile Phase: ACN + 5% 0.05% TFA: 0.05% TFA + 5% ACN; flow rate: 1.0 mL/min; Gradient programme: T/B % 0.01/90, 10/10, 15/10: diluent: CH₃CN:Water | 389.45 | 390 [M + 1] | −162.59 C = 0.25, CH₂Cl₂ |
| 248B | 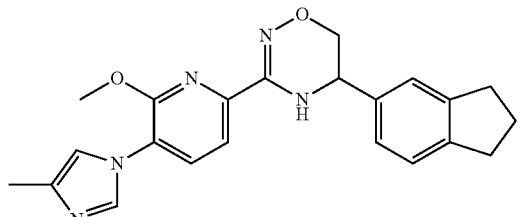<br>(+)-5-(2,3-dihydro-1H-inden-5-yl)-3-(6-methoxy-5-(4-methyl-1H-imidazol-1-yl)pyridin-2-yl)-5,6-dihydro-4H-1,2,4-oxadiazine | 7.63 min (column; zorbax-SB-C-18 150 × 4.6 mm, 5 μm); mobile Phase: ACN + 5% 0.05% TFA: 0.05% TFA + 5% ACN; flow rate: 1.0 mL/min; Gradient programme: T/B % 0.01/90, 10/10, 15/10: diluent: CH₃CN:Water | 389.45 | 390 [M + 1] | 144.81 C = 0.25, CH₂Cl₂ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 249A | 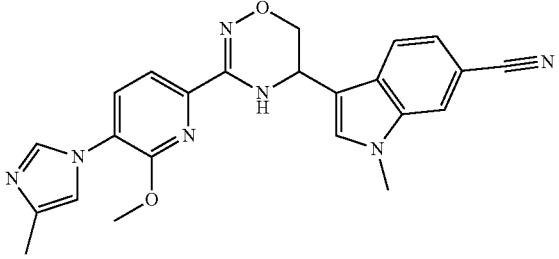<br>(−)-3-(3-(6-methoxy-5-(4-methyl-1H-imidazol-1-yl)pyridin-2-yl)-5,6-dihydro-4H-1,2,4-oxadiazin-5-yl)-1-methyl-1H-indole-6-carbonitrile | 6.88 min (column; zorbax-SB-C-18 150 × 4.6 mm, 3.5μ); mobile Phase: ACN + 0.5% TFA: 0.5% TFA + 5% ACN; flow rate: 1.0 mL/min; Gradient programme: T/B % 0.01/90, 10/10, 15/10: diluent: CH$_3$CN:Water | 427.46 | 428 [M + 1] | −121.74 C = 0.25, CH$_2$Cl$_2$ |
| 249B | 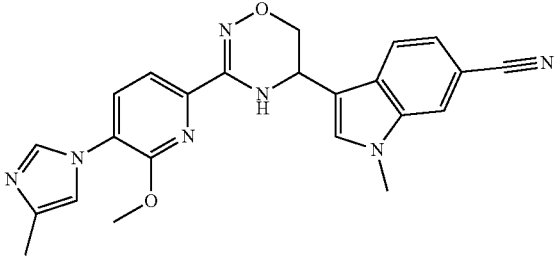<br>(+)-3-(3-(6-methoxy-5-(4-methyl-1H-imidazol-1-yl)pyridin-2-yl)-5,6-dihydro-4H-1,2,4-oxadiazin-5-yl)-1-methyl-1H-indole-6-carbonitrile | 6.88 min (column; zorbax-SB-C-18 150 × 4.6 mm, 3.5μ); mobile Phase: ACN + 0.5% TFA: 0.5% TFA + 5% ACN; flow rate: 1.0 mL/min; Gradient programme: T/B % 0.01/90, 10/10, 15/10: diluent: CH$_3$CN:Water | 427.46 | 428 [M + 1] | 96.6 C = 0.25, CH$_2$Cl$_2$ |
| 250A | 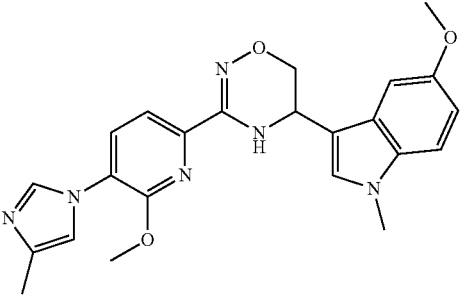<br>(−)-5-(5-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.01 min (column; zorbax-SB-C-18 150 × 4.6 mm, 3.5μ); mobile Phase: ACN + 0.5% TFA; 0.5% TFA + 5% ACN; flow rate: 1.0 mL/min; Gradient programme: T/B % 0.01/90, 10/10, 15/10: diluent: CH$_3$CN:Water | 432.48 | 433 [M + 1] | −64.68 C = 0.25, CH$_2$Cl$_2$ |
| 250B | 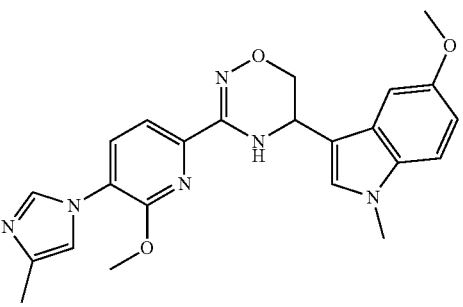<br>(+)-5-(5-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.00 min (column; zorbax-SB-C-18 150 × 4.6 mm, 3.5μ); mobile Phase: ACN + 0.5% TFA; 0.5% TFA + 5% ACN; flow rate: 1.0 mL/min; Gradient programme: T/B % 0.01/90, 10/10, 15/10: diluent: CH$_3$CN:Water | 432.48 | 432.9 [M + 1] | 53.12 C = 0.25, CH$_2$Cl$_2$ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 252A | 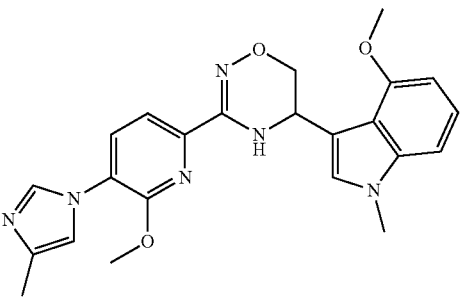<br>(−)-5-(4-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.24 min (column; zorbax-SB-C-18 150 × 4.6 mm, 3.5µ); mobile Phase: ACN + 5% 0.05% TFA; 0.05% TFA + 5% ACN: Gradient programme: T/B % 0.01/90, 10/10, 15/10: diluent: CH$_3$CN:Water | 432.48 | 433 [M + 1] | −51.61 C = 0.25, CH$_2$Cl$_2$ |
| 252B | 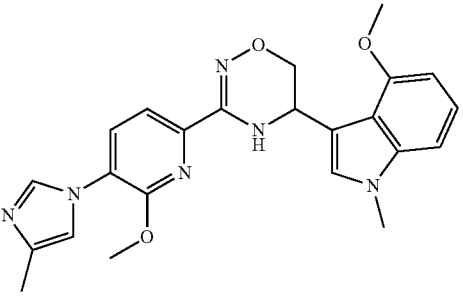<br>(+)-5-(4-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.23 min (column; zorbax-SB-C-18 150 × 4.6 mm, 3.5µ); mobile Phase: ACN + 5% 0.05% TFA; 0.05% TFA + 5% ACN: Gradient programme: T/B % 0.01/90, 10/10, 15/10: diluent: CH$_3$CN:Water | 432.48 | 433 [M + 1] | 57.93 C = 0.25, CH$_2$Cl$_2$ |
| 253A | 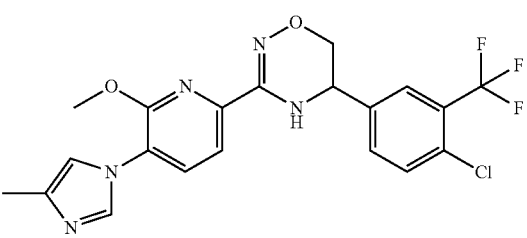<br>5-(4-chloro-3-(trifluoromethyl)phenyl)-3-(6-methoxy-5-(4-methyl-1H-imidazol-1-yl)pyridin-2-yl)-5,6-dihydro-4H-1,2,4-oxadiazine | 7.97 min (Fr-I) (column; zorbax-SB-C-18 150 × 4.6 mm, 5 µm); mobile Phase: ACN: 0.05% TFA; flow rate: 1.0 mL/min; Gradient programme: T/B % 0.01/90, 10/10, 15/10: diluent: CH$_3$CN:Water | 451.83 | 451.9 [M + 1] | |
| 253B | 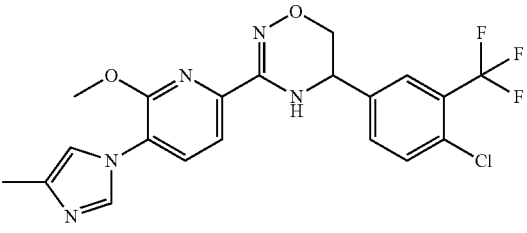<br>5-(4-chloro-3-(trifluoromethyl)phenyl)-3-(6-methoxy-5-(4-methyl-1H-imidazol-1-yl)pyridin-2-yl)-5,6-dihydro-4H-1,2,4-oxadiazine | 7.94 min (Fr-II) (column; zorbax-SB-C-18 150 × 4.6 mm, 5 µm); mobile Phase: ACN: 0.05% TFA; flow rate: 1.0 mL/min; Gradient programme: T/B % 0.01/90, 10/10, 15/10: diluent: CH$_3$CN:Water | 451.83 | 452 [M + 1] | |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 254A | (-)-5-(6-chloro-4-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.95 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 10/10, 15/10: diluent: CH$_3$CN:Water | 466.92 | 467 [M + 1] | −58.28 C = 0.25, CH$_2$Cl$_2$ |
| 254B | (+)-5-(6-chloro-4-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.96 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 10/10, 15/10: diluent: CH$_3$CN:Water | 466.92 | 466.9 [M + 1] | 61.5 C = 0.25, CH$_2$Cl$_2$ |
| 255A | (-)-5-(5-chloro-6-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.35 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 10/10, 15/10: diluent: CH$_3$CN:Water | 466.92 | 467 [M + 1] | −119.98 C = 0.25, CH$_2$Cl$_2$ |
| 255B | (+)-5-(5-chloro-6-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.36 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 10/10, 15/10: diluent: CH$_3$CN:Water | 466.92 | 467 [M + 1] | 116.27 C = 0.25, CH$_2$Cl$_2$ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 256A | 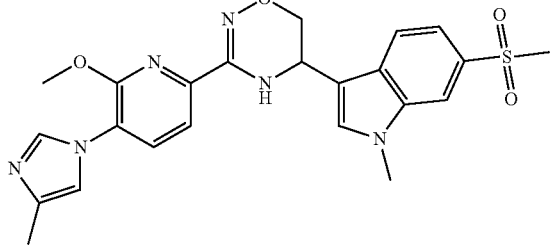<br>(−)-3-(6-methoxy-5-(4-methyl-1H-imidazol-1-yl)pyridin-2-yl)-5-(1-methyl-6-(methylsulfonyl)-1H-indol-3-yl)-5,6-dihydro-4H-1,2,4-oxadiazine | 5.98 min (column; zorbax-SB-C-18 150 × 4.6 mm, 3.5µ); mobile Phase: ACN: 5% 0.05% Aq TFA; 0.05% TFA: 5% ACN; flow rate: 1.0 mL/min; Gradient programme: T/B % 0.01/90, 10/10, 15/10: diluent: CH$_3$CN:Water | 480.54 | 481 [M + 1] | −137.28 C = 0.25, CH$_2$Cl$_2$ |
| 256B | 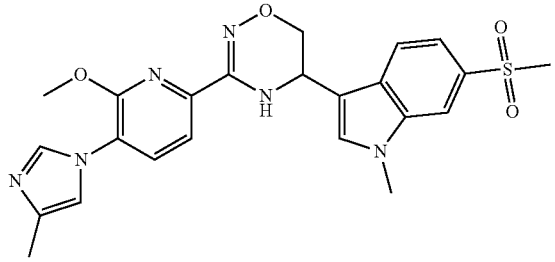<br>(+)-3-(6-methoxy-5-(4-methyl-1H-imidazol-1-yl)pyridin-2-yl)-5-(1-methyl-6-(methylsulfonyl)-1H-indol-3-yl)-5,6-dihydro-4H-1,2,4-oxadiazine | 5.94 min (column; zorbax-SB-C-18 150 × 4.6 mm, 3.5µ); mobile Phase: ACN: 5% 0.05% Aq TFA; 0.05% TFA: 5% ACN; flow rate: 1.0 mL/min; Gradient programme: T/B % 0.01/90, 10/10, 15/10: diluent: CH$_3$CN:Water | 480.54 | 481 [M + 1] | 135.42 C = 0.25, CH$_2$Cl$_2$ |
| 257A | 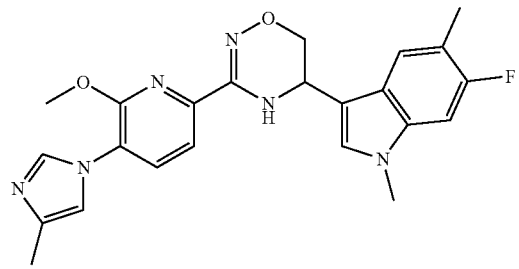<br>(−)-5-(6-fluoro-1,5-dimethyl-1H-indol-3-yl)-3-(6-methoxy-5-(4-methyl-1H-imidazol-1-yl)pyridin-2-yl)-5,6-dihydro-4H-1,2,4-oxadiazine | 7.73 min (column; zorbax-SB-C-18 150 × 4.6 mm, 3.5µ); mobile Phase: ACN: 0.05% Aq TFA; flow rate: 1.0 mL/min; Gradient programme: T/B % 0.01/90, 10/10, 15/10: diluent: CH$_3$CN:Water | 434.47 | 435 [M + 1] | −78.57 C = 0.25, CH$_2$Cl$_2$ |
| 257B | 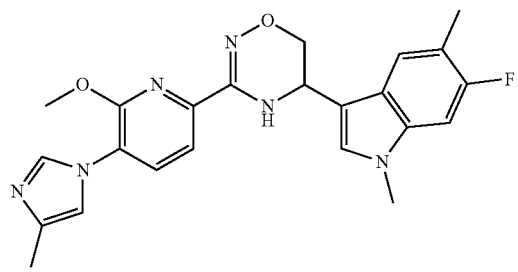<br>(+)-5-(6-fluoro-1,5-dimethyl-1H-indol-3-yl)-3-(6-methoxy-5-(4-methyl-1H-imidazol-1-yl)pyridin-2-yl)-5,6-dihydro-4H-1,2,4-oxadiazine | 7.71 min (column; zorbax-SB-C-18 150 × 4.6 mm, 3.5µ); mobile Phase: ACN: 0.05% Aq TFA; flow rate: 1.0 mL/min; Gradient programme: T/B % 0.01/90, 10/10, 15/10: diluent: CH$_3$CN:Water | 434.47 | 435 [M + 1] | 86.17 C = 0.25, CH$_2$Cl$_2$ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 258A | (−)-5-(6-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 6.95 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 10/10, 15/10: diluent: CH$_3$CN:Water | 432.48 | 433 [M + 1] | −100.86 C = 0.25, CH$_2$Cl$_2$ |
| 258B | (+)-5-(6-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 6.97 min (column; zorbax-SB-C-18 150 × 4.6 mm, 3.5μ); mobile Phase: ACN: 0.05% Aq TFA; flow rate: 1.0 mL/min; Gradient programme: T/B % 0.01/90, 10/10, 15/10: diluent: CH$_3$CN:Water | 432.48 | 433 [M + 1] | 105.37 C = 0.25, CH$_2$Cl$_2$ |
| 259A | (−)-3-(6-methoxy-5-(4-methyl-1H-imidazol-1-yl)pyridin-2-yl)-5-(5-(trifluoromethyl)benzofuran-2-yl)-5,6-dihydro-4H-1,2,4-oxadiazine | 7.84 min (column; zorbax-SB-C-18 150 × 4.6 mm, 5 μm); mobile Phase: ACN + 5% 0.05% Aq TFA; 0.05% TFA + 5% ACN; flow rate: 1.0 mL/min; Gradient programme: T/B % 0.01/90, 10/10, 15/10: diluent: CH$_3$CN:Water | 457.41 | 458 [M + 1] | −209.5 C = 0.25, CH$_2$Cl$_2$ |
| 259B | (+)-3-(6-methoxy-5-(4-methyl-1H-imidazol-1-yl)pyridin-2-yl)-5-(5-(trifluoromethyl)benzofuran-2-yl)-5,6-dihydro-4H-1,2,4-oxadiazine | 7.85 min (column; zorbax-SB-C-18 150 × 4.6 mm, 5 μm); mobile Phase: ACN + 5% 0.05% Aq TFA; 0.05% TFA + 5% ACN; flow rate: 1.0 mL/min; Gradient programme: T/B % 0.01/90, 10/10, 15/10: diluent: CH$_3$CN:Water | 457.41 | 457.9 [M + 1] | 246.01 C = 0.25, CH$_2$Cl$_2$ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 260A | (−)-3-(6-methoxy-5-(4-methyl-1H-imidazol-1-yl)pyridin-2-yl)-5-(6-(trifluoromethyl)benzofuran-2-yl)-5,6-dihydro-4H-1,2,4-oxadiazine | 7.69 min (column; zorbax-SB-C-18 150 × 4.6 mm, 5 µm); mobile Phase: ACN + 5% 0.05% Aq TFA; 0.05% TFA + 5% ACN; flow rate: 1.0 mL/min; Gradient programme: T/B % 0.01/90, 10/10, 15/10: diluent: CH$_3$CN:Water | 457.41 | 458 [M + 1] | −230.59 C = 0.25, CH$_2$Cl$_2$ |
| 260B | (+)-3-(6-methoxy-5-(4-methyl-1H-imidazol-1-yl)pyridin-2-yl)-5-(6-(trifluoromethyl)benzofuran-2-yl)-5,6-dihydro-4H-1,2,4-oxadiazine | 7.68 min (column; zorbax-SB-C-18 150 × 4.6 mm, 5 µm); mobile Phase: ACN + 5% 0.05% Aq TFA; 0.05% TFA + 5% ACN; flow rate: 1.0 mL/min; Gradient programme: T/B % 0.01/90, 10/10, 15/10: diluent: CH$_3$CN:Water | 457.41 | 458 [M + 1] | 230.86 C = 0.25, CH$_2$Cl$_2$ |
| 261A | (+)-5-(4-chloro-6-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.41 min (column; zorbax-SB-C-18 150 × 4.6 mm, 3.5µ); mobile Phase: ACN: 5% 0.05% Aq TFA: 0.05% TFA + 5% ACN; flow rate: 1.0 mL/min; Gradient programme: T/B % 0.01/90, 10/10, 15/10: diluent: CH$_3$CN:Water | 466.92 | 467 [M + 1] | 104.97 C = 0.25, CH$_2$Cl$_2$ |
| 261B | (−)-5-(4-chloro-6-methoxy-1-methyl-1H-indol-3-yl)-3-(6-methoxy-5-(4-methyl-1H-imidazol-1-yl)pyridin-2-yl)-5,6-dihydro-4H-1,2,4-oxadiazine | 7.43 min (column; zorbax-SB-C-18 150 × 4.6 mm, 3.5µ); mobile Phase: ACN: 5% 0.05% Aq TFA: 0.05% TFA + 5% ACN; flow rate: 1.0 mL/min; Gradient programme: T/B % 0.01/90, 10/10, 15/10: diluent: CH$_3$CN:Water | 466.92 | 467 [M + 1] | −104.3 C = 0.25, CH$_2$Cl$_2$ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 262A | (−)-5-(3-chloro-4-(trifluoromethyl)phenyl)-3-(6-methoxy-5-(4-methyl-1H-imidazol-1-yl)pyridin-2-yl)-5,6-dihydro-4H-1,2,4-oxadiazine | 7.56 min (column; zorbax-SB-C-18 150 × 4.6 mm, 5 μm); mobile Phase: ACN + 5% 0.05% Aq TFA; 0.05% TFA + 5% ACN; flow rate: 1.0 mL/min; Gradient programme: T/B % 0.01/90, 10/10, 15/10: diluent: CH₃CN:Water; | 451.83 | 452 [M + 1] | −165.64 C = 0.25, CH₂Cl₂ |
| 262B | (+)-5-(3-chloro-4-(trifluoromethyl)phenyl)-3-(6-methoxy-5-(4-methyl-1H-imidazol-1-yl)pyridin-2-yl)-5,6-dihydro-4H-1,2,4-oxadiazine | 7.58 min (column; zorbax-SB-C-18 150 × 4.6 mm, 5 μm); mobile Phase: ACN + 5% 0.05% Aq TFA; 0.05% TFA + 5% ACN; flow rate: 1.0 mL/min; Gradient programme: T/B % 0.01/90, 10/10, 15/10: diluent: CH₃CN:Water; | 451.83 | 452 [M + 1] | 180.38 C = 0.25, CH₂Cl₂ |
| 264A | (−)-5-(5-chloro-1-methyl-1H-pyrrolo[2,3-b]pyridin-3-yl)-3-(6-methoxy-5-(4-methyl-1H-imidazol-1-yl)pyridin-2-yl)-5,6-dihydro-4H-1,2,4-oxadiazine | 6.43 min (column; zorbax-SB-C-18 150 × 4.6 mm, 3.5μ); mobile Phase: ACN: 5% 0.05% Aq TFA; 0.05% TFA + 5% ACN; flow rate: 1.0 mL/min; Gradient programme: T/B % 0.01/90, 10/10, 15/10: diluent: CH₃CN:Water | 437.88 | 438 [M + 1] | −146.32 C = 0.25, CH₂Cl₂ |
| 264B | (+)-5-(5-chloro-1-methyl-1H-pyrrolo[2,3-b]pyridin-3-yl)-3-(6-methoxy-5-(4-methyl-1H-imidazol-1-yl)pyridin-2-yl)-5,6-dihydro-4H-1,2,4-oxadiazine | 6.45 min (column; zorbax-SB-C-18 150 × 4.6 mm, 3.5μ); mobile Phase: ACN: 5% 0.05% Aq TFA; 0.05% TFA + 5% ACN; flow rate: 1.0 mL/min; Gradient programme: T/B % 0.01/90, 10/10, 15/10: diluent: CH₃CN:Water | 437.88 | 438 [M + 1] | 126.44 C = 0.25, CH₂Cl₂ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 266A | 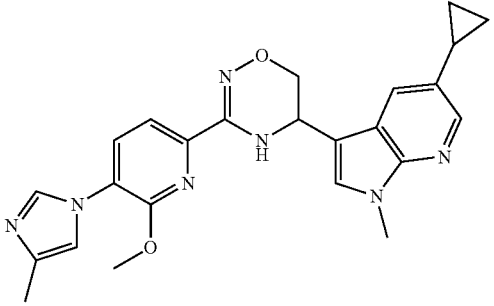<br>(−)-5-(5-cyclopropyl-1-methyl-1H-pyrrolo[2,3-b]pyridin-3-yl)-3-(6-methoxy-5-(4-methyl-1H-imidazol-1-yl)pyridin-2-yl)-5,6-dihydro-4H-1,2,4-oxadiazine | 5.71 min (column; Zorbax SB-C-18 (150 × 4.6 mm, 3.5 μm); mobile Phase: CH$_3$CN: 0.05% TFA; flow rate: 1.0 mL/min; Gradient programme: T/B % 0.01/90, 10/10, 15/10; diluent: CH$_3$CN:Water | 443.50 | 444 [M + 1] | −133.63 C = 0.25, CH$_2$Cl$_2$ |
| 266B | 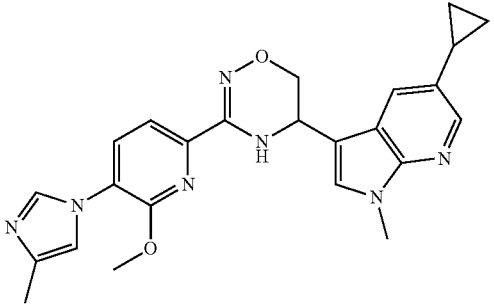<br>(+)-5-(5-cyclopropyl-1-methyl-1H-pyrrolo[2,3-b]pyridin-3-yl)-3-(6-methoxy-5-(4-methyl-1H-imidazol-1-yl)pyridin-2-yl)-5,6-dihydro-4H-1,2,4-oxadiazine | 5.72 min (column; Zorbax SB-C-18 (150 × 4.6 mm, 3.5 μm); mobile Phase: CH$_3$CN: 0.05% TFA; flow rate: 1.0 mL/min; Gradient programme: T/B % 0.01/90, 10/10, 15/10; diluent: CH$_3$CN:Water | 443.50 | 444 [M + 1] | 143.18 C = 0.25, CH$_2$Cl$_2$ |
| 267A | 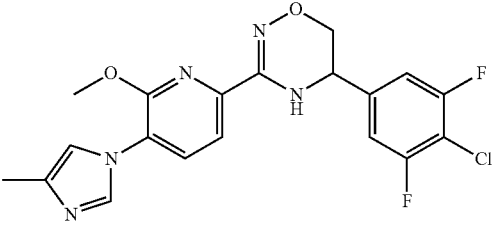<br>(−)-5-(4-chloro-3,5-difluorophenyl)-3-(6-methoxy-5-(4-methyl-1H-imidazol-1-yl)pyridin-2-yl)-5,6-dihydro-4H-1,2,4-oxadiazine | 7.23 min (column; Zorbax SB-C-18 (150 × 4.6 mm, 3.5 μm); mobile Phase: CH$_3$CN: 0.05% TFA; flow rate: 1.0 mL/min; Gradient programme: T/B % 0.01/90, 10/10, 15/10; diluent: CH$_3$CN:Water | 419.81 | 419.9 [M + 1] | −187.04 C = 0.25, CH$_2$Cl$_2$ |
| 267B | 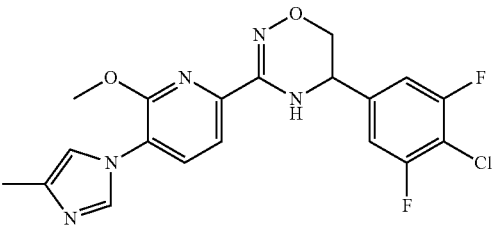<br>(+)-5-(4-chloro-3,5-difluorophenyl)-3-(6-methoxy-5-(4-methyl-1H-imidazol-1-yl)pyridin-2-yl)-5,6-dihydro-4H-1,2,4-oxadiazine | 7.25 min (column; Zorbax SB-C-18 (150 × 4.6 mm, 3.5 μm); mobile Phase: CH$_3$CN: 0.05% TFA; flow rate: 1.0 mL/min; Gradient programme: T/B % 0.01/90, 10/10, 15/10; diluent: CH$_3$CN:Water | 419.81 | 419.9 [M + 1] | 161.72 C = 0.25, CH$_2$Cl$_2$ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 268A | 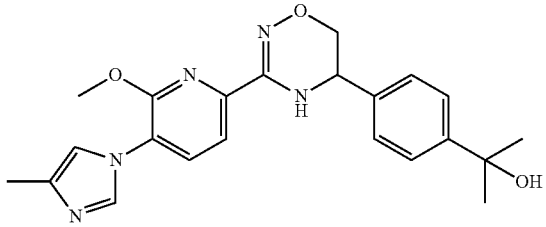<br>(−)-2-(4-(3-(6-methoxy-5-(4-methyl-1H-imidazol-1-yl)pyridin-2-yl)-5,6-dihydro-4H-1,2,4-oxadiazin-5-yl)phenyl)propan-2-ol | 5.67 min (column; zorbax-SB-C-18 150 × 4.6 mm, 3.5µ); mobile Phase: ACN: 0.05% TFA; flow rate: 1.0 mL/min; Gradient programme: T/B % 0.01/90, 10/10, 15/10: diluent: CH₃CN:Water | 407.47 | 408.1 [M + 1] | −183.58 C = 0.25, CH₂Cl₂ |
| 268B | 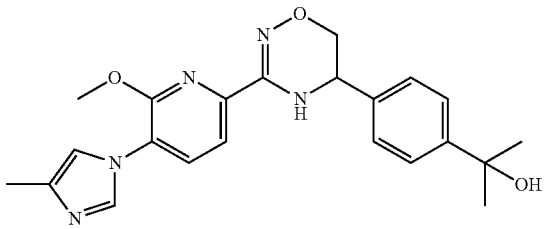<br>(+)-2-(4-(3-(6-methoxy-5-(4-methyl-1H-imidazol-1-yl)pyridin-2-yl)-5,6-dihydro-4H-1,2,4-oxadiazin-5-yl)phenyl)propan-2-ol | 5.66 min (column; zorbax-SB-C-18 150 × 4.6 mm, 3.5µ); mobile Phase: ACN: 0.05% TFA; flow rate: 1.0 mL/min; Gradient programme: T/B % 0.01/90, 10/10, 15/10: diluent: CH₃CN:Water | 407.47 | 408 [M + 1] | 185.04 C = 0.25, CH₂Cl₂ |
| 269A | 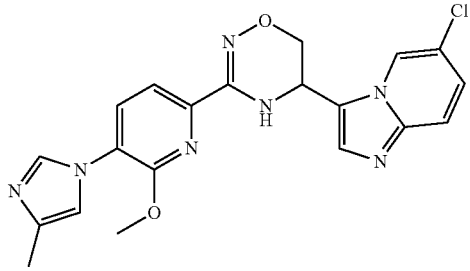<br>(−)-5-(6-chloroimidazo[1,2-a]pyridin-3-yl)-3-(6-methoxy-5-(4-methyl-1H-imidazol-1-yl)pyridin-2-yl)-5,6-dihydro-4H-1,2,4-oxadiazine | 4.28 min (column; Zorbax SBC-C-18 150 × 4.6 mm, 3.5µ); mobile Phase: ACN: 0.05% TFA; flow rate: 1.0 mL/min; Gradient programme: T/B % 0.01/90, 10/10, 15/10: diluent: CH₃CN:Water | 423.86 | 423.9 [M + 1] | −63.2 C = 0.25, CH₂Cl₂ |
| 269B | 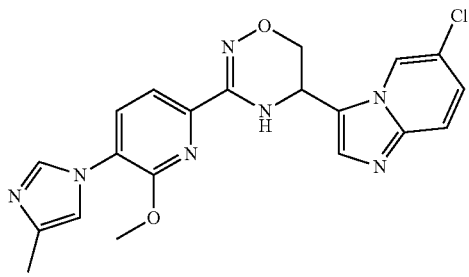<br>(+)-5-(6-chloroimidazo[1,2-a]pyridin-3-yl)-3-(6-methoxy-5-(4-methyl-1H-imidazol-1-yl)pyridin-2-yl)-5,6-dihydro-4H-1,2,4-oxadiazine | 4.27 min (column; Zorbax SBC-C-18 150 × 4.6 mm, 3.5µ); mobile Phase: ACN: 0.05% TFA; flow rate: 1.0 mL/min; Gradient programme: T/B % 0.01/90, 10/10, 15/10: diluent: CH₃CN:Water | 423.86 | 424 [M + 1] | 71.95 C = 0.25, CH₂Cl₂ |

TABLE III-continued

Characterization Data for Additional Oxadiazine Compounds

| Compound of Example | Structure and Name | HPLC Retention Time and Condition | Molecular Weight | ESI Mass Observed And Mass Ion (M + H or other) | Optical Rotation And Optical Rotation Condition |
|---|---|---|---|---|---|
| 270A | (-)-5-(4-chloro-3-(difluoromethyl)phenyl)-3-(6-methoxy-5-(4-methyl-1H-imidazol-1-yl)pyridin-2-yl)-5,6-dihydro-4H-1,2,4-oxadiazine | 7.21 min (column; Zorbax SB-C-18 150 × 4.6 mm, 3.5 µm); mobile Phase: ACN: 0.05% TFA; flow rate: 1.0 mL/min; Gradient programme: T/B % 0.01/90, 10/10, 15/10: diluent: CH$_3$CN:Water | 433.84 | 433.9 [M + 1] | −197.74 C = 0.25, CH$_2$Cl$_2$ |
| 270B | (+)-5-(4-chloro-3-(difluoromethyl)phenyl)-3-(6-methoxy-5-(4-methyl-1H-imidazol-1-yl)pyridin-2-yl)-5,6-dihydro-4H-1,2,4-oxadiazine | 7.16 min (column; Zorbax SB-C-18 150 × 4.6 mm, 3.5 µm); mobile Phase: ACN: 0.05% TFA; flow rate: 1.0 mL/min; Gradient programme: T/B % 0.01/90, 10/10, 15/10: diluent: CH$_3$CN:Water | 433.84 | 433.9 [M + 1] | 199.48 C = 0.25, CH$_2$Cl$_2$ |

We claim:

1. A compound of Formula (I)

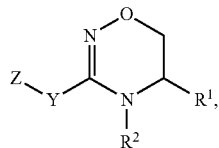

(I)

or a pharmaceutically acceptable salt thereof,
wherein:
$R^1$ is —$C_1$-$C_6$ alkyl, —$C_3$-$C_8$ monocyclic cycloalkyl, —$C_1$-$C_4$ alkylene-$C_3$-$C_8$ monocyclic cycloalkyl, phenyl, 5- to 6-membered aromatic heterocycle, 3- to 7-membered monocyclic heterocycle, 8- to 10-membered bicyclic heterocycle, each of which is unsubstituted or substituted with one or more substituents independently selected from the group consisting of -halo, —CN, —$C_1$-$C_4$ alkyl, —$C_3$-$C_8$ monocyclic cycloalkyl, halo-substituted $C_1$-$C_4$ alkyl, —$C_1$-$C_4$ alkoxy, halo-substituted $C_1$-$C_4$ alkoxy and oxo;
$R^2$ is hydrogen or —$C_1$-$C_4$ alkyl;
Y is pyridinyl which is unsubstituted or substituted with one or more substituents independently selected from the group consisting of -halo, —$C_1$-$C_4$ alkoxy, halo-substituted $C_1$-$C_4$ alkoxy, —$C_1$-$C_4$ alkyl, halo-substituted $C_1$-$C_4$ alkyl, —CN and —OH; and
Z is nitrogen-containing 3- to 7-membered monocyclic heterocycle which is unsubstituted or substituted with one or more substituents independently selected from the group consisting of -halo, —$C_1$-$C_4$ alkyl, halo-substituted $C_1$-$C_4$ alkyl, —$C_1$-$C_4$ alkoxy and —OCF$_3$.

2. A compound of claim 1, wherein $R^1$ is —$C_1$-$C_6$ alkyl, —$C_3$-$C_8$ monocyclic cycloalkyl, phenyl, 8- to 10-membered bicyclic heterocycle, each of which is unsubstituted or substituted with one or more substituents independently selected from the group consisting of -halo, —CN, —$C_1$-$C_4$ alkyl, —$C_3$-$C_8$ monocyclic cycloalkyl, halo-substituted $C_1$-$C_4$ alkyl, —$C_1$-$C_4$ alkoxy and halo-substituted $C_1$-$C_4$ alkoxy; or a pharmaceutically acceptable salt thereof.

3. A compound of claim 1, wherein $R^1$ is —$C_3$-$C_8$ monocyclic cycloalkyl, phenyl, 8- to 10-membered bicyclic heterocycle, each of which is unsubstituted or substituted with one or more substituents independently selected from the group consisting of -halo, —$C_1$-$C_4$ alkyl, —$C_3$-$C_8$ monocyclic cycloalkyl, halo-substituted $C_1$-$C_4$ alkyl, and halo-substituted $C_1$-$C_4$ alkoxy; or a pharmaceutically acceptable salt thereof.

4. A compound of claim 1, wherein $R^1$ is 8- to 10-membered bicyclic heterocycle, each of which is unsubstituted or substituted with one or more substituents independently selected from the group consisting of -halo, —$C_1$-$C_4$ alkyl, and halo-substituted $C_1$-$C_4$ alkyl; or a pharmaceutically acceptable salt thereof.

5. A compound of claim 1, wherein $R^1$ is phenyl, each of which is unsubstituted or substituted with one or more substituents independently selected from the group consisting of -halo, —CN, —$C_1$-$C_4$ alkyl, —$C_3$-$C_8$ monocyclic cycloalkyl, halo-substituted $C_1$-$C_4$ alkyl, —$C_1$-$C_4$ alkoxy and halo-substituted $C_1$-$C_4$ alkoxy; or a pharmaceutically acceptable salt thereof.

6. A compound of claim 1, wherein R¹ is —C₁-C₆ alkyl which is unsubstituted; or a pharmaceutically acceptable salt thereof.

7. A compound of claim 1, wherein R¹ is —C₃-C₈ monocyclic cycloalkyl, each of which is unsubstituted or substituted with one or more -halo; or a pharmaceutically acceptable salt thereof.

8. A compound of claim 1, wherein R¹ is —C₃-C₈ monocyclic cycloalkyl which is unsubstituted; or a pharmaceutically acceptable salt thereof.

9. A compound of claim 1, wherein Y is pyridinyl which is unsubstituted or substituted with one or more —C₁-C₄ alkoxy, halo-substituted C₁-C₄ alkoxy; or a pharmaceutically acceptable salt thereof.

10. A compound of claim 1, wherein Z is nitrogen-containing 3- to 7-membered monocyclic heterocycle which is unsubstituted or substituted with one or more —C₁-C₄ alkyl; or a pharmaceutically acceptable salt thereof.

11. A compound of claim 1, wherein Z is imidazolyl which is unsubstituted or substituted with one methyl; or a pharmaceutically acceptable salt thereof.

12. A compound of claim 1, wherein:
R¹ is

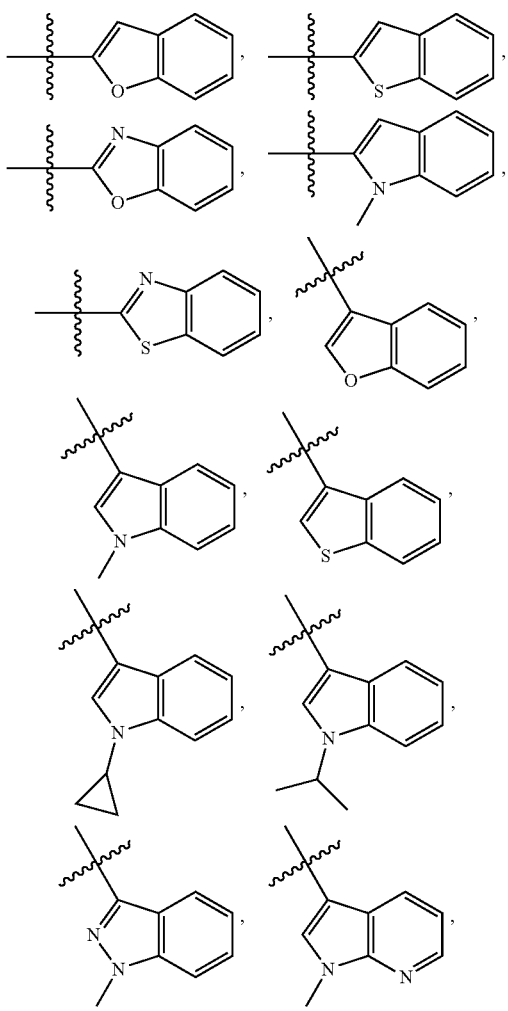

-continued

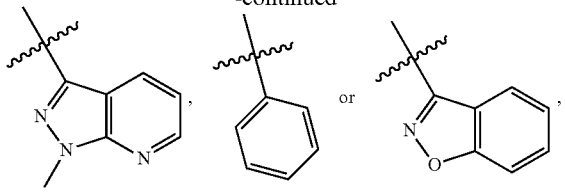

each of which is optionally further substituted with -halo, —CF₃ or —C₁-C₄ alkyl; and
Z is

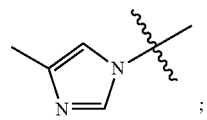 [SMILES: *n1cnc(C)c1]

or a pharmaceutically acceptable salt thereof.

13. The compound of claim 12, wherein Y is

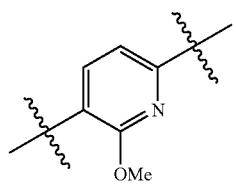 [SMILES: *c1ccc(*)c(OC)n1]

wherein the left most radical is connected to the Z group in Formula (I); or a pharmaceutically acceptable salt thereof.

14. A compound selected from the group consisting of:
(R)-5-(benzofuran-2-yl)-3-(6-methoxy-5-(4-methyl-1H-imidazol-1-yl)pyridin-2-yl)-5, 6-dihydro-4H-1,2,4-oxadiazine;
3-(6-Methoxy-5-(4-methyl-1H-imidazol-1-yl)pyridin-2-yl)-5-(7-methylbenzofuran-2-yl)-5,6-dihydro-4H-1,2,4-oxadiazine;
(R)-3-(6-methoxy-5-(4-methyl-1H-imidazol-1-yl)pyridin-2-yl)-5-(5-methylbenzofuran-2-yl)-5,6-dihydro-4H-1,2,4-oxadiazine;
(R)-5-(benzo[b]thiophen-2-yl)-3-(6-methoxy-5-(4-methyl-1H-imidazol-1-yl)pyridin-2-yl)-5,6-dihydro-4H-1,2,4-oxadiazine;
(+)-3-(6-methoxy-5-(4-methyl-1H-imidazol-1-yl)pyridin-2-yl)-5-(3-methylbenzofuran-2-yl)-5,6-dihydro-4H-1,2,4-oxadiazine;
(R)-3-(6-methoxy-5-(4-methyl-1H-imidazol-1-yl)pyridin-2-yl)-5-(4-methylbenzofuran-2-yl)-5,6-dihydro-4H-1,2,4-oxadiazine;
(R)-3-(6-methoxy-5-(4-methyl-1H-imidazol-1-yl)pyridin-2-yl)-5-(6-methylbenzofuran-2-yl)-5,6-dihydro-4H-1,2,4-oxadiazine;
(+)-3-(6-methoxy-5-(4-methyl-1H-imidazol-1-yl)pyridin-2-yl)-4-methyl-5-(7-methylbenzofuran-2-yl)-5,6-dihydro-4H-1,2,4-oxadiazine;
(+)-3-(5-(4-chloro-1H-imidazol-1-yl)-6-methoxypyridin-2-yl)-5-(7-methylbenzofuran-2-yl)-5, 6-dihydro-4H-1,2,4-oxadiazine;
5-(4-chloro-2-methylphenyl)-3-(6-methoxy-5-(4-methyl-1H-imidazol-1-yl) pyridin-2-yl)-4-methyl-5,6-dihydro-4H-1,2,4-oxadiazine;
3-(6-methoxy-5-(4-methyl-1H-imidazol-1-yl) pyridin-2-yl)-4-methyl-5-(3-(trifluoromethyl) phenyl)-5, 6-dihydro-4H-1,2,4-oxadiazine;
(+)-3-(6-methoxy-5-(4-methoxy-1H-imidazol-1-yl)pyridin-2-yl)-5-(7-methylbenzofuran-2-yl)-5,6-dihydro-4H-1,2,4-oxadiazine;

3-(6-methoxy-5-(4-methyl-1H-imidazol-1-yl)pyridin-2-yl)-5-phenyl-5,6-dihydro-4H-1,2,4-oxadiazine;

5-(benzofuran-3-yl)-3-(6-methoxy-5-(4-methyl-1H-imidazol-1-yl)pyridin-2-yl)-5,6-dihydro-4H-1,2,4-oxadiazine;

5-(4-fluorophenyl)-3-(6-methoxy-5-(4-methyl-H-imidazol-1-yl)pyridin-2-yl)-5,6-dihydro-4H-1,2,4-oxadiazine;

5-(4-chlorophenyl)-3-(6-methoxy-5-(4-methyl-1H-imidazol-1-yl)pyridin-2-yl)-5,6-dihydro-4H-1,2,4-oxadiazine;

5-(4-fluoro-3-(trifluoromethyl)phenyl)-3-(6-methoxy-5-(4-methyl-1H-imidazol-1-yl)pyridin-2-yl)-5,6-dihydro-4H-1,2,4-oxadiazine;

5-(1H-indol-3-yl)-3-(6-methoxy-5-(4-methyl-1H-imidazol-1-yl)pyridin-2-yl)-5,6-dihydro-4H-1,2,4-oxadiazine;

(+)-5-(3, 4-dichlorophenyl)-3-(6-methoxy-5-(4-methyl-1H-imidazol-1-yl) pyridin-2-yl)-5,6-dihydro-4H-1,2,4-oxadiazine;

(+)-5-(6-fluorobenzofuran-2-yl)-3-(6-methoxy-5-(4-methyl-H-imidazol-1-yl) pyridin-2-yl)-5,6-dihydro-4H-1,2,4-oxadiazine;

(+)-3-(6-methoxy-5-(4-methyl-1H-imidazol-1-yl) pyridin-2-yl)-5-(4-methoxyphenyl)-5,6-dihydro-4H-1,2,4-oxadiazine;

(+)-5-(5-chlorobenzofuran-2-yl)-3-(6-methoxy-5-(4-methyl-H-imidazol-1-yl) pyridin-2-yl)-5,6-dihydro-4H-1,2,4-oxadiazine;

(+)-3-(6-methoxy-5-(4-methyl-1H-imidazol-1-yl) pyridin-2-yl)-5-(4-(trifluoromethyl) phenyl)-5,6-dihydro-4H-1,2,4-oxadiazine;

(+)-5-cyclohexyl-3-(6-methoxy-5-(4-methyl-1H-imidazol-1-yl) pyridin-2-yl)-5,6-dihydro-4H-1,2,4-oxadiazine;

(+)-5-(7-chlorobenzofuran-2-yl)-3-(6-methoxy-5-(4-methyl-H-imidazol-1-yl) pyridin-2-yl)-5,6-dihydro-4H-1,2,4-oxadiazine;

(+)-3-(6-methoxy-5-(4-methyl-1H-imidazol-1-yl) pyridin-2-yl)-5-(3-methylbenzo [b] thiophen-2-yl)-5,6-dihydro-4H-1,2,4-oxadiazine;

(+)-5-(benzo [b] thiophen-3-yl)-3-(6-methoxy-5-(4-methyl-1H-imidazol-1-yl) pyridin-2-yl)-5,6-dihydro-4H-1,2,4-oxadiazine;

(+)-3-(6-methoxy-5-(4-methyl-1H-imidazol-1-yl) pyridin-2-yl)-5-(4-(trifluoromethoxy) phenyl)-5,6-dihydro-4H-1,2,4-oxadiazine;

(−)-5-(5-chloro-1-ethyl-6-fluoro-1H-indol-3-yl)-3-(6-methoxy-5-(4-methyl-1H-imidazol-1-yl) pyridin-2-yl)-5,6-dihydro-4H-1,2,4-oxadiazine;

(+)-5-(5-chloro-1-ethyl-6-fluoro-1H-indol-3-yl)-3-(6-methoxy-5-(4-methyl-1H-imidazol-1-yl) pyridin-2-yl)-5,6-dihydro-4H-1,2,4-oxadiazine;

(+)-5-(3,4-difluorophenyl)-3-(6-methoxy-5-(4-methyl-1H-imidazol-1-yl) pyridin-2-yl)-5,6-dihydro-4H-1,2,4-oxadiazine;

(+)-5-(6-chlorobenzofuran-2-yl)-3-(6-methoxy-5-(4-methyl-H-imidazol-1-yl) pyridin-2-yl)-5,6-dihydro-4H-1,2,4-oxadiazine;

(+)-5-(3,5-difluorophenyl)-3-(6-methoxy-5-(4-methyl-1H-imidazol-1-yl) pyridin-2-yl)-5,6-dihydro-4H-1,2,4-oxadiazine;

(+)-5-(5-fluorobenzofuran-2-yl)-3-(6-methoxy-5-(4-methyl-H-imidazol-1-yl) pyridin-2-yl)-5,6-dihydro-4H-1,2,4-oxadiazine;

(+)-5-(4-chloro-3-methylphenyl)-3-(6-methoxy-5-(4-methyl-1H-imidazol-1-yl) pyridin-2-yl)-5,6-dihydro-4H-1,2,4-oxadiazine;

(+)-5-(7-fluorobenzofuran-2-yl)-3-(6-methoxy-5-(4-methyl-H-imidazol-1-yl) pyridin-2-yl)-5,6-dihydro-4H-1,2,4-oxadiazine;

(+)-3-(6-methoxy-5-(4-methyl-1H-imidazol-1-yl) pyridin-2-yl)-5-(3,4,5-trifluorophenyl)-5,6-dihydro-4H-1,2,4-oxadiazine;

(+)-5-(4-(difluoromethoxy) phenyl)-3-(6-methoxy-5-(4-methyl-1H-imidazol-1-yl) pyridin-2-yl)-5,6-dihydro-4H-1,2,4-oxadiazine;

(+)-5-(4-chlorobenzofuran-2-yl)-3-(6-methoxy-5-(4-methyl-H-imidazol-1-yl) pyridin-2-yl)-5,6-dihydro-4H-1,2,4-oxadiazine;

(−)-5-(4-fluorobenzofuran-2-yl)-3-(6-methoxy-5-(4-methyl-1H-imidazol-1-yl) pyridin-2-yl)-5,6-dihydro-4H-1,2,4-oxadiazine;

(+)-5-(5-fluoro-3-methylbenzofuran-2-yl)-3-(6-methoxy-5-(4-methyl-1H-imidazol-1-yl) pyridin-2-yl)-5,6-dihydro-4H-1,2,4-oxadiazine;

(−)-5-(6-fluoro-1-methyl-5-(trifluoromethyl)-1H-indol-3-yl)-3-(6-methoxy-5-(4-methyl-1H-imidazol-1-yl) pyridin-2-yl)-5,6-dihydro-4H-1,2,4-oxadiazine;

(+)-5-(6-fluoro-1-methyl-5-(trifluoromethyl)-1H-indol-3-yl)-3-(6-methoxy-5-(4-methyl-1H-imidazol-1-yl) pyridin-2-yl)-5,6-dihydro-4H-1,2,4-oxadiazine;

(+)-5-(4-chloro-3-fluorophenyl)-3-(6-methoxy-5-(4-methyl-1H-imidazol-1-yl) pyridin-2-yl)-5,6-dihydro-4H-1,2,4-oxadiazine;

(+)-5-(3-chloro-4-fluorophenyl)-3-(6-methoxy-5-(4-methyl-1H-imidazol-1-yl) pyridin-2-yl)-5,6-dihydro-4H-1,2,4-oxadiazine;

(+)-5-(3-chloro-5-fluorophenyl)-3-(6-methoxy-5-(4-methyl-1H-imidazol-1-yl) pyridin-2-yl)-5,6-dihydro-4H-1,2,4-oxadiazine;

(+)-3-(6-methoxy-5-(4-methyl-1H-imidazol-1-yl) pyridin-2-yl)-5-(3-(trifluoromethyl) phenyl)-5,6-dihydro-4H-1,2,4-oxadiazine;

(+)-5-(4-cyclopropylphenyl)-3-(6-methoxy-5-(4-methyl-1H-imidazol-1-yl) pyridin-2-yl)-5,6-dihydro-4H-1,2,4-oxadiazine;

(+)-5-(3,5-dichlorophenyl)-3-(6-methoxy-5-(4-methyl-1H-imidazol-1-yl) pyridin-2-yl)-5,6-dihydro-4H-1,2,4-oxadiazine;

(+)-5-(3-fluoro-4-(trifluoromethyl) phenyl)-3-(6-methoxy-5-(4-methyl-1H-imidazol-1-yl) pyridin-2-yl)-5,6-dihydro-4H-1,2,4-oxadiazine;

(+)-3-(6-methoxy-5-(4-methyl-1H-imidazol-1-yl) pyridin-2-yl)-5-(1-methyl-1H-indazol-3-yl)-5,6-dihydro-4H-1,2,4-oxadiazine;

(+)-5-(3-cyclopropylphenyl)-3-(6-methoxy-5-(4-methyl-1H-imidazol-1-yl) pyridin-2-yl)-5,6-dihydro-4H-1,2,4-oxadiazine;

5-(2,4-difluorophenyl)-3-(6-methoxy-5-(4-methyl-1H-imidazol-1-yl)pyridin-2-yl)-5,6-dihydro-4H-1,2,4-oxadiazine;

(+)-3-(6-methoxy-5-(4-methyl-1H-imidazol-1-yl) pyridin-2-yl)-5-(o-tolyl)-5,6-dihydro-4H-1,2,4-oxadiazine;

5-(2-chlorophenyl)-3-(6-methoxy-5-(4-methyl-1H-imidazol-1-yl) pyridin-2-yl)-5,6-dihydro-4H-1,2,4-oxadiazine:

(+)-5-(4, 4-difluorocyclohexyl)-3-(6-methoxy-5-(4-methyl-1H-imidazol-1-yl) pyridin-2-yl)-5,6-dihydro-4H-1,2,4-oxadiazine;

(+)-3-(3-(6-methoxy-5-(4-methyl-1H-imidazol-1-yl) pyridin-2-yl)-5,6-dihydro-4H-1,2,4-oxadiazin-5-yl) benzonitrile;

(+)-3-(6-methoxy-5-(4-methyl-1H-imidazol-1-yl) pyridin-2-yl)-5-(3-methoxyphenyl)-5,6-dihydro-4H-1,2,4-oxadiazine;

(−)-5-(tert-butyl)-3-(6-methoxy-5-(4-methyl-H-imidazol-1-yl) pyridin-2-yl)-5,6-dihydro-4H-1,2,4-oxadiazine;

(−)-5-isobutyl-3-(6-methoxy-5-(4-methyl-1H-imidazol-1-yl) pyridin-2-yl)-5,6-dihydro-4H-1,2,4-oxadiazine;

(−)-5-cyclopentyl-3-(6-methoxy-5-(4-methyl-1H-imidazol-1-yl) pyridin-2-yl)-5,6-dihydro-4H-1,2,4-oxadiazine;

(+)-3-(6-methoxy-5-(4-methyl-1H-imidazol-1-yl)pyridin-2-yl)-5-(1-methyl-1H-indol-3-yl)-5,6-dihydro-4H-1,2,4-oxadiazine;

(−)-3-(6-methoxy-5-(4-methyl-1H-imidazol-1-yl)pyridin-2-yl)-5-(1-methyl-1H-indol-3-yl)-5,6-dihydro-4H-1,2,4-oxadiazine;

(+)-5-(5-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine;

(+)-5-(4-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine;

(−)-5-(4-fluoro-1-methyl-1H-indol-3-yl)-3-(6-methoxy-5-(4-methyl-H-imidazol-1-yl) pyridin-2-yl)-5,6-dihydro-4H-1,2,4-oxadiazine;

(−)-5-(6-fluoro-1-methyl-1H-indol-3-yl)-3-(6-methoxy-5-(4-methyl-H-imidazol-1-yl) pyridin-2-yl)-5,6-dihydro-4H-1,2,4-oxadiazine;

(+)-5-(6-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine;

(−)-5-(5-chloro-1-methyl-1H-indol-3-yl)-3-(6-methoxy-5-(4-methyl-1H-imidazol-1-yl) pyridin-2-yl)-5,6-dihydro-4H-1,2,4-oxadiazine;

(+)-5-(5-chloro-1-methyl-1H-indol-3-yl)-3-(6-methoxy-5-(4-methyl-1H-imidazol-1-yl) pyridin-2-yl)-5,6-dihydro-4H-1,2,4-oxadiazine;

(+)-5-(6-chloro-1-methyl-1H-indol-3-yl)-3-(6-methoxy-5-(4-methyl-1H-imidazol-1-yl) pyridin-2-yl)-5,6-dihydro-4H-1,2,4-oxadiazine;

(−)-5-(6-chloro-1-methyl-1H-indol-3-yl)-3-(6-methoxy-5-(4-methyl-1H-imidazol-1-yl) pyridin-2-yl)-5,6-dihydro-4H-1,2,4-oxadiazine;

(+)-3-(6-methoxy-5-(4-methyl-1H-imidazol-1-yl) pyridin-2-yl)-5-(1-methyl-1H-pyrrolo [2,3-b]pyridin-3-yl)-5,6-dihydro-4H-1,2,4-oxadiazine;

(+)-5-(4-fluoro-1-isopropyl-1H-indol-3-yl)-3-(6-methoxy-5-(4-methyl-1H-imidazol-1-yl) pyridin-2-yl)-5,6-dihydro-4H-1,2,4-oxadiazine;

(−)-5-(4-fluoro-1-isopropyl-1H-indol-3-yl)-3-(6-methoxy-5-(4-methyl-1H-imidazol-1-yl) pyridin-2-yl)-5,6-dihydro-4H-1,2,4-oxadiazine;

(+)-3-(6-methoxy-5-(4-methyl-1H-imidazol-1-yl) pyridin-2-yl)-5-(1-methyl-6-(trifluoromethyl)-1H-indol-3-yl)-5,6-dihydro-4H-1,2,4-oxadiazine;

(−)-3-(6-methoxy-5-(4-methyl-1H-imidazol-1-yl) pyridin-2-yl)-5-(1-methyl-6-(trifluoromethyl)-1H-indol-3-yl)-5,6-dihydro-4H-1,2,4-oxadiazine;

(+)-3-(6-methoxy-5-(4-methyl-1H-imidazol-1-yl)pyridin-2-yl)-4-methyl-5-(1-methyl-1H-indol-3-yl)-5,6-dihydro-4H-1,2,4-oxadiazine;

(+)-2-(3-(6-methoxy-5-(4-methyl-1H-imidazol-1-yl)pyridin-2-yl)-5,6-dihydro-4H-1,2,4-oxadiazin-5-yl)benzo[d]oxazole;

(+)-3-(6-methoxy-5-(4-methyl-1H-imidazol-1-yl)pyridin-2-yl)-5-(1-methyl-1H-indol-2-yl)-5,6-dihydro-4H-1,2,4-oxadiazine;

(+)-3-(6-methoxy-5-(4-methyl-1H-imidazol-1-yl) pyridin-2-yl)-5-(1-methyl-5-(trifluoromethyl)-1H-pyrrolo[2,3-b] pyridin-3-yl)-5,6-dihydro-4H-1,2,4-oxadiazine; and (+)-5-(benzo[d]thiazol-2-yl)-3-(6-methoxy-5-(4-methyl-1H-imidazol-1-yl)pyridin-2-yl)-5,6-dihydro-4H-1,2,4-oxadiazine;

or a pharmaceutically acceptable salt thereof.

15. The compound of claim 14, selected from the group consisting of:

(R)-5-(benzofuran-2-yl)-3-(6-methoxy-5-(4-methyl-1H-imidazol-1-yl)pyridin-2-yl)-5, 6-dihydro-4H-1,2,4-oxadiazine;

3-(6-Methoxy-5-(4-methyl-1H-imidazol-1-yl)pyridin-2-yl)-5-(7-methylbenzofuran-2-yl)-5,6-dihydro-4H-1,2,4-oxadiazine;

(R)-3-(6-methoxy-5-(4-methyl-1H-imidazol-1-yl)pyridin-2-yl)-5-(5-methylbenzofuran-2-yl)-5,6-dihydro-4H-1,2,4-oxadiazine;

(R)-5-(benzo[b]thiophen-2-yl)-3-(6-methoxy-5-(4-methyl-1H-imidazol-1-yl)pyridin-2-yl)-5,6-dihydro-4H-1,2,4-oxadiazine;

(+)-3-(6-methoxy-5-(4-methyl-1H-imidazol-1-yl)pyridin-2-yl)-5-(3-methylbenzofuran-2-yl)-5,6-dihydro-4H-1,2,4-oxadiazine;

(R)-3-(6-methoxy-5-(4-methyl-1H-imidazol-1-yl)pyridin-2-yl)-5-(4-methylbenzofuran-2-yl)-5,6-dihydro-4H-1,2,4-oxadiazine;

(R)-3-(6-methoxy-5-(4-methyl-1H-imidazol-1-yl)pyridin-2-yl)-5-(6-methylbenzofuran-2-yl)-5,6-dihydro-4H-1,2,4-oxadiazine;

(+)-3-(5-(4-chloro-1H-imidazol-1-yl)-6-methoxypyridin-2-yl)-5-(7-methylbenzofuran-2-yl)-5, 6-dihydro-4H-1,2,4-oxadiazine;

5-(4-chloro-2-methylphenyl)-3-(6-methoxy-5-(4-methyl-1H-imidazol-1-yl) pyridin-2-yl)-4-methyl-5,6-dihydro-4H-1,2,4-oxadiazine;

3-(6-methoxy-5-(4-methyl-1H-imidazol-1-yl) pyridin-2-yl)-4-methyl-5-(3-(trifluoromethyl) phenyl)-5, 6-dihydro-4H-1,2,4-oxadiazine;

5-(benzofuran-3-yl)-3-(6-methoxy-5-(4-methyl-1H-imidazol-1-yl)pyridin-2-yl)-5, 6-dihydro-4H-1,2,4-oxadiazine;

5-(4-fluorophenyl)-3-(6-methoxy-5-(4-methyl-H-imidazol-1-yl)pyridin-2-yl)-5,6-dihydro-4H-1,2,4-oxadiazine;

5-(4-fluoro-3-(trifluoromethyl)phenyl)-3-(6-methoxy-5-(4-methyl-1H-imidazol-1-yl)pyridin-2-yl)-5,6-dihydro-4H-1,2,4-oxadiazine;

5-(1H-indol-3-yl)-3-(6-methoxy-5-(4-methyl-1H-imidazol-1-yl)pyridin-2-yl)-5,6-dihydro-4H-1,2,4-oxadiazine;

(+)-5-(3, 4-dichlorophenyl)-3-(6-methoxy-5-(4-methyl-1H-imidazol-1-yl) pyridin-2-yl)-5,6-dihydro-4H-1,2,4-oxadiazine;

(+)-5-(6-fluorobenzofuran-2-yl)-3-(6-methoxy-5-(4-methyl-H-imidazol-1-yl) pyridin-2-yl)-5,6-dihydro-4H-1,2,4-oxadiazine;

(+)-5-(5-chlorobenzofuran-2-yl)-3-(6-methoxy-5-(4-methyl-H-imidazol-1-yl) pyridin-2-yl)-5,6-dihydro-4H-1,2,4-oxadiazine;

(+)-3-(6-methoxy-5-(4-methyl-1H-imidazol-1-yl) pyridin-2-yl)-5-(4-(trifluoromethyl) phenyl)-5,6-dihydro-4H-1,2,4-oxadiazine;

(+)-5-cyclohexyl-3-(6-methoxy-5-(4-methyl-1H-imidazol-1-yl) pyridin-2-yl)-5,6-dihydro-4H-1,2,4-oxadiazine;

(+)-5-(7-chlorobenzofuran-2-yl)-3-(6-methoxy-5-(4-methyl-H-imidazol-1-yl) pyridin-2-yl)-5,6-dihydro-4H-1,2,4-oxadiazine;

(+)-3-(6-methoxy-5-(4-methyl-1H-imidazol-1-yl) pyridin-2-yl)-5-(3-methylbenzo [b] thiophen-2-yl)-5,6-dihydro-4H-1,2,4-oxadiazine;

(+)-5-(benzo [b] thiophen-3-yl)-3-(6-methoxy-5-(4-methyl-1H-imidazol-1-yl) pyridin-2-yl)-5,6-dihydro-4H-1,2,4-oxadiazine;

(+)-3-(6-methoxy-5-(4-methyl-1H-imidazol-1-yl) pyridin-2-yl)-5-(4-(trifluoromethoxy) phenyl)-5,6-dihydro-4H-1,2,4-oxadiazine;

(−)-5-(5-chloro-1-ethyl-6-fluoro-1H-indol-3-yl)-3-(6-methoxy-5-(4-methyl-1H-imidazol-1-yl) pyridin-2-yl)-5,6-dihydro-4H-1,2,4-oxadiazine;

(+)-5-(5-chloro-1-ethyl-6-fluoro-1H-indol-3-yl)-3-(6-methoxy-5-(4-methyl-1H-imidazol-1-yl) pyridin-2-yl)-5,6-dihydro-4H-1,2,4-oxadiazine;

(+)-5-(6-chlorobenzofuran-2-yl)-3-(6-methoxy-5-(4-methyl-H-imidazol-1-yl) pyridin-2-yl)-5,6-dihydro-4H-1,2,4-oxadiazine;

(+)-5-(3,5-difluorophenyl)-3-(6-methoxy-5-(4-methyl-1H-imidazol-1-yl) pyridin-2-yl)-5,6-dihydro-4H-1,2,4-oxadiazine;

(+)-5-(5-fluorobenzofuran-2-yl)-3-(6-methoxy-5-(4-methyl-H-imidazol-1-yl) pyridin-2-yl)-5,6-dihydro-4H-1,2,4-oxadiazine;

(+)-5-(4-chloro-3-methylphenyl)-3-(6-methoxy-5-(4-methyl-1H-imidazol-1-yl) pyridin-2-yl)-5,6-dihydro-4H-1,2,4-oxadiazine;

(+)-5-(7-fluorobenzofuran-2-yl)-3-(6-methoxy-5-(4-methyl-H-imidazol-1-yl) pyridin-2-yl)-5,6-dihydro-4H-1,2,4-oxadiazine;

(+)-3-(6-methoxy-5-(4-methyl-1H-imidazol-1-yl) pyridin-2-yl)-5-(3,4,5-trifluorophenyl)-5,6-dihydro-4H-1,2,4-oxadiazine;

(+)-5-(4-chlorobenzofuran-2-yl)-3-(6-methoxy-5-(4-methyl-H-imidazol-1-yl) pyridin-2-yl)-5,6-dihydro-4H-1,2,4-oxadiazine;

(−)-5-(4-fluorobenzofuran-2-yl)-3-(6-methoxy-5-(4-methyl-1H-imidazol-1-yl) pyridin-2-yl)-5,6-dihydro-4H-1,2,4-oxadiazine;

(+)-5-(5-fluoro-3-methylbenzofuran-2-yl)-3-(6-methoxy-5-(4-methyl-1H-imidazol-1-yl) pyridin-2-yl)-5,6-dihydro-4H-1,2,4-oxadiazine;

(+)-5-(6-fluoro-1-methyl-5-(trifluoromethyl)-1H-indol-3-yl)-3-(6-methoxy-5-(4-methyl-1H-imidazol-1-yl) pyridin-2-yl)-5,6-dihydro-4H-1,2,4-oxadiazine;

(+)-5-(4-chloro-3-fluorophenyl)-3-(6-methoxy-5-(4-methyl-1H-imidazol-1-yl) pyridin-2-yl)-5,6-dihydro-4H-1,2,4-oxadiazine;

(+)-5-(3-chloro-4-fluorophenyl)-3-(6-methoxy-5-(4-methyl-1H-imidazol-1-yl) pyridin-2-yl)-5,6-dihydro-4H-1,2,4-oxadiazine;

(+)-5-(3-chloro-5-fluorophenyl)-3-(6-methoxy-5-(4-methyl-1H-imidazol-1-yl) pyridin-2-yl)-5,6-dihydro-4H-1,2,4-oxadiazine;

(+)-3-(6-methoxy-5-(4-methyl-1H-imidazol-1-yl) pyridin-2-yl)-5-(3-(trifluoromethyl) phenyl)-5,6-dihydro-4H-1,2,4-oxadiazine;

(+)-5-(4-cyclopropylphenyl)-3-(6-methoxy-5-(4-methyl-1H-imidazol-1-yl) pyridin-2-yl)-5,6-dihydro-4H-1,2,4-oxadiazine;

(+)-5-(3,5-dichlorophenyl)-3-(6-methoxy-5-(4-methyl-1H-imidazol-1-yl) pyridin-2-yl)-5,6-dihydro-4H-1,2,4-oxadiazine;

(+)-5-(3-fluoro-4-(trifluoromethyl) phenyl)-3-(6-methoxy-5-(4-methyl-1H-imidazol-1-yl) pyridin-2-yl)-5,6-dihydro-4H-1,2,4-oxadiazine;

(+)-3-(6-methoxy-5-(4-methyl-1H-imidazol-1-yl) pyridin-2-yl)-5-(i-methyl-1H-indazol-3-yl)-5,6-dihydro-4H-1,2,4-oxadiazine;

(+)-5-(3-cyclopropylphenyl)-3-(6-methoxy-5-(4-methyl-1H-imidazol-1-yl) pyridin-2-yl)-5,6-dihydro-4H-1,2,4-oxadiazine;

(+)-3-(6-methoxy-5-(4-methyl-1H-imidazol-1-yl)pyridin-2-yl)-5-(1-methyl-1H-indol-3-yl)-5,6-dihydro-4H-1,2,4-oxadiazine;

(+)-5-(5-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine;

(+)-5-(4-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine;

(+)-5-(6-fluoro-1-methyl-1H-indol-3-yl)-3-(6-methoxy-5-(4-methyl-1H-imidazol-1-yl) pyridin-2-yl)-5,6-dihydro-4H-1,2,4-oxadiazine;

(+)-5-(5-chloro-1-methyl-1H-indol-3-yl)-3-(6-methoxy-5-(4-methyl-1H-imidazol-1-yl) pyridin-2-yl)-5,6-dihydro-4H-1,2,4-oxadiazine;

(+)-5-(6-chloro-1-methyl-1H-indol-3-yl)-3-(6-methoxy-5-(4-methyl-1H-imidazol-1-yl) pyridin-2-yl)-5,6-dihydro-4H-1,2,4-oxadiazine;

(+)-5-(4-fluoro-1-isopropyl-H-indol-3-yl)-3-(6-methoxy-5-(4-methyl-1H-imidazol-1-yl) pyridin-2-yl)-5,6-dihydro-4H-1,2,4-oxadiazine;

(+)-3-(6-methoxy-5-(4-methyl-1H-imidazol-1-yl) pyridin-2-yl)-5-(1-methyl-6-(trifluoromethyl)-1H-indol-3-yl)-5,6-dihydro-4H-1,2,4-oxadiazine;

(+)-3-(6-methoxy-5-(4-methyl-1H-imidazol-1-yl)pyridin-2-yl)-5-(1-methyl-1H-indol-2-yl)-5,6-dihydro-4H-1,2,4-oxadiazine; and (+)-3-(6-methoxy-5-(4-methyl-1H-imidazol-1-yl) pyridin-2-yl)-5-(1-methyl-5-(trifluoromethyl)-1H-pyrrolo [2,3-b] pyridin-3-yl)-5,6-dihydro-4H-1,2,4-oxadiazine;

or a pharmaceutically acceptable salt thereof.

16. The levorotatory isomer of the compound of claim 1 or a pharmaceutically acceptable salt thereof.

17. The dextrorotatory isomer of the compound of claim 1 or a pharmaceutically acceptable salt thereof.

18. A pharmaceutical composition comprising a pharmaceutically acceptable carrier or vehicle and an effective amount of a compound of claim 1 or a pharmaceutically acceptable salt thereof.

19. A method for treating a neurodegenerative disease, comprising administering to a subject in need thereof an effective amount of a compound of claim 1 or a pharmaceutically acceptable salt thereof, wherein the neurodegenerative disease is panic disorder, obsessive compulsive disorder, delusional disorder, drug-induced psychosis, post-traumatic stress disorder, age-related cognitive decline, attention deficit/hyperactivity disorder, personality disorder of the paranoid type, personality disorder of the schizoid type, dyskinesia, choreiform condition, psychosis associated with Parkinson's disease, psychotic symptoms associated with Alzheimer's disease, mood disorder, or dementia.

* * * * *

UNITED STATES PATENT AND TRADEMARK OFFICE
CERTIFICATE OF CORRECTION

PATENT NO. : 9,802,927 B2
APPLICATION NO. : 15/178626
DATED : October 31, 2017
INVENTOR(S) : Raksha Acharya et al.

Page 1 of 6

It is certified that error appears in the above-identified patent and that said Letters Patent is hereby corrected as shown below:

In the Claims

Column 582, Line 33, Claim 14, please delete "-5, 6-dihydro-" and insert -- -5,6-dihydro- --;

Column 582, Line 57, Claim 14, please delete "-5, 6-dihydro-" and insert -- -5,6-dihydro- --;

Column 582, Line 60, Claim 14, please delete "-1-yl) pyridin-" and insert -- -1-yl)pyridin- --;

Column 582, Line 60, Claim 14, please delete "-1-yl) pyridin-" and insert -- -1-yl)pyridin- --;

Column 582, Line 63, Claim 14, please delete "(trifluoromethyl) phenyl)-5, 6-dihydro-" and insert -- (trifluoromethyl)phenyl)-5,6-dihydro- --;

Column 583, Line 19, Claim 14, please delete "(3, 4-dichlorophenyl" and insert -- (3,4-dichlorophenyl --;

Column 583, Line 20, Claim 14, please delete "-1-yl) pyridin-" and insert -- -1-yl)pyridin- --;

Column 583, Line 23, Claim 14, please delete "-1-yl) pyridin-" and insert -- -1-yl)pyridin- --;

Column 583, Line 25, Claim 14, please delete "-1-yl) pyridin-" and insert -- -1-yl)pyridin- --;

Column 583, Line 29, Claim 14, please delete "-1-yl) pyridin-" and insert -- -1-yl)pyridin- --;

Column 583, Line 31, Claim 14, please delete "-1-yl) pyridin-" and insert -- -1-yl)pyridin- --;

Column 583, Line 32, Claim 14, please delete "(trifluoromethyl) phenyl)-" and insert -- (trifluoromethyl)phenyl)- --;

Signed and Sealed this
Nineteenth Day of June, 2018

Andrei Iancu
*Director of the United States Patent and Trademark Office*

Column 583, Line 35, Claim 14, please delete "-1-yl) pyridin-" and insert -- -1-yl)pyridin- --;

Column 583, Line 38, Claim 14, please delete "-1-yl) pyridin-" and insert -- -1-yl)pyridin- --;

Column 583, Line 40, Claim 14, please delete "-1-yl) pyridin-" and insert -- -1-yl)pyridin- --;

Column 583, Line 45, Claim 14, please delete "-1-yl) pyridin-" and insert -- -1-yl)pyridin- --;

Column 583, Line 47, Claim 14, please delete "-1-yl) pyridin-" and insert -- -1-yl)pyridin- --;

Column 583, Line 48, Claim 14, please delete "(trifluoromethyl) phenyl)-" and insert -- (trifluoromethyl)phenyl)- --;

Column 583, Line 51, Claim 14, please delete "-1-yl) pyridin-" and insert -- -1-yl)pyridin- --;

Column 583, Line 54, Claim 14, please delete "-1-yl) pyridin-" and insert -- -1-yl)pyridin- --;

Column 583, Line 57, Claim 14, please delete "-1-yl) pyridin-" and insert -- -1-yl)pyridin- --;

Column 583, Line 60, Claim 14, please delete "-1-yl) pyridin-" and insert -- -1-yl)pyridin- --;

Column 583, Line 63, Claim 14, please delete "-1-yl) pyridin-" and insert -- -1-yl)pyridin- --;

Column 583, Line 66, Claim 14, please delete "-1-yl) pyridin-" and insert -- -1-yl)pyridin- --;

Column 584, Line 2, Claim 14, please delete "-1-yl) pyridin-" and insert -- -1-yl)pyridin- --;

Column 584, Line 5, Claim 14, please delete "-1-yl) pyridin-" and insert -- -1-yl)pyridin- --;

Column 584, Line 7, Claim 14, please delete "-1-yl) pyridin-" and insert -- -1-yl)pyridin- --;

Column 584, Line 10, Claim 14, please delete "(difluoromethoxy) phenyl)-" and insert -- (difluoromethoxy)phenyl)- --;

Column 584, Line 11, Claim 14, please delete "-1-yl) pyridin-" and insert -- -1-yl)pyridin- --;

Column 584, Line 14, Claim 14, please delete "-1-yl) pyridin-" and insert -- -1-yl)pyridin- --;

Column 584, Line 17, Claim 14, please delete "-1-yl) pyridin-" and insert -- -1-yl)pyridin- --;

Column 584, Line 21, Claim 14, please delete "-1-yl) pyridin-" and insert -- -1-yl)pyridin- --;

Column 584, Line 24, Claim 14, please delete "-1-yl) pyridin-" and insert -- -1-yl)pyridin- --;

Column 584, Line 27, Claim 14, please delete "-1-yl) pyridin-" and insert -- -1-yl)pyridin- --;

Column 584, Line 30, Claim 14, please delete "-1-yl) pyridin-" and insert -- -1-yl)pyridin- --;

Column 584, Line 33, Claim 14, please delete "-1-yl) pyridin-" and insert -- -1-yl)pyridin- --;

Column 584, Line 36, Claim 14, please delete "-1-yl) pyridin-" and insert -- -1-yl)pyridin- --;

Column 584, Line 39, Claim 14, please delete "-1-yl) pyridin-" and insert -- -1-yl)pyridin- --;

Column 584, Line 40, Claim 14, please delete "(trifluoromethyl) phenyl)-" and insert -- (trifluoromethyl)phenyl)- --;

Column 584, Line 43, Claim 14, please delete "-1-yl) pyridin-" and insert -- -1-yl)pyridin- --;

Column 584, Line 46, Claim 14, please delete "-1-yl) pyridin-" and insert -- -1-yl)pyridin- --;

Column 584, Line 48, Claim 14, please delete "(trifluoromethyl) phenyl)-" and insert -- (trifluoromethyl)phenyl)- --;

Column 584, Line 49, Claim 14, please delete "-1-yl) pyridin-" and insert -- -1-yl)pyridin- --;

Column 584, Line 51, Claim 14, please delete "-1-yl) pyridin-" and insert -- -1-yl)pyridin- --;

Column 584, Line 55, Claim 14, please delete "-1-yl) pyridin-" and insert -- -1-yl)pyridin- --;

Column 584, Line 60, Claim 14, please delete "-1-yl) pyridin-" and insert -- -1-yl)pyridin- --;

Column 584, Line 63, Claim 14, please delete "-1-yl) pyridin-" and insert -- -1-yl)pyridin- --;

Column 584, Line 65, Claim 14, please delete "-(4, 4-dichlorocyclohexyl)-" and insert -- -(4,4-dichlorocyclohexyl)- --;

Column 584, Line 66, Claim 14, please delete "-1-yl) pyridin-" and insert -- -1-yl)pyridin- --;

Column 585, Line 4, Claim 14, please delete "-1-yl) pyridin-" and insert -- -1-yl)pyridin- --;

Column 585, Line 8, Claim 14, please delete "-1-yl) pyridin-" and insert -- -1-yl)pyridin- --;

Column 585, Line 10, Claim 14, please delete "-1-yl) pyridin-" and insert -- -1-yl)pyridin- --;

Column 585, Line 12, Claim 14, please delete "-1-yl) pyridin-" and insert -- -1-yl)pyridin- --;

Column 585, Line 21, Claim 14, please delete "-1-yl) pyridin-" and insert -- -1-yl)pyridin- --;

Column 585, Line 24, Claim 14, please delete "-1-yl) pyridin-" and insert -- -1-yl)pyridin- --;

Column 585, Line 27, Claim 14, please delete "-1-yl) pyridin-" and insert -- -1-yl)pyridin- --;

CERTIFICATE OF CORRECTION (continued)
U.S. Pat. No. 9,802,927 B2

Column 585, Line 30, Claim 14, please delete "-1-yl) pyridin-" and insert -- -1-yl)pyridin- --;

Column 585, Line 33, Claim 14, please delete "-1-yl) pyridin-" and insert -- -1-yl)pyridin- --;

Column 585, Line 36, Claim 14, please delete "-1-yl) pyridin-" and insert -- -1-yl)pyridin- --;

Column 585, Line 39, Claim 14, please delete "-1-yl) pyridin-" and insert -- -1-yl)pyridin- --;

Column 585, Line 42, Claim 14, please delete "-1-yl) pyridin-" and insert -- -1-yl)pyridin- --;

Column 585, Line 45, Claim 14, please delete "-1-yl) pyridin-" and insert -- -1-yl)pyridin- --;

Column 585, Line 47, Claim 14, please delete "-1-yl) pyridin-" and insert -- -1-yl)pyridin- --;

Column 585, Line 51, Claim 14, please delete "-1-yl) pyridin-" and insert -- -1-yl)pyridin- --;

Column 585, Line 54, Claim 14, please delete "-1-yl) pyridin-" and insert -- -1-yl)pyridin- --;

Column 585, Line 56, Claim 14, please delete "-1-yl) pyridin-" and insert -- -1-yl)pyridin- --;

Column 585, Line 59, Claim 14, please delete "-1-yl) pyridin-" and insert -- -1-yl)pyridin- --;

Column 586, Line 4, Claim 14, please delete "-1-yl) pyridin-" and insert -- -1-yl)pyridin- --;

Column 586, Line 15, Claim 15, please delete "-5, 6-dihydro-" and insert -- -5,6-dihydro- --;

Column 586, Line 36, Claim 15, please delete "-5, 6-dihydro-" and insert -- -5,6-dihydro- --;

Column 586, Line 41, Claim 15, please delete "-1-yl) pyridin-" and insert -- -1-yl)pyridin- --;

Column 586, Line 42, Claim 15, please delete "(trifluoromethyl) phenyl)-" and insert -- (trifluoromethyl)phenyl)- --;

Column 586, Line 42, Claim 15, please delete "-5, 6-dihydro-" and insert -- -5,6-dihydro- --;

Column 586, Line 45, Claim 15, please delete "-5, 6-dihydro-" and insert -- -5,6-dihydro- --;

Column 586, Line 56, Claim 15, please delete "-(3, 4-dichlorophenyl)-" and insert -- -(3,4-dichlorophenyl)- --;

Column 586, Line 60, Claim 15, please delete "-1-yl) pyridin-" and insert -- -1-yl)pyridin- --;

Column 586, Line 63, Claim 15, please delete "-1-yl) pyridin-" and insert -- -1-yl)pyridin- --;

Column 586, Line 65, Claim 15, please delete "-1-yl) pyridin-" and insert -- -1-yl)pyridin- --;

CERTIFICATE OF CORRECTION (continued)
U.S. Pat. No. 9,802,927 B2

Column 586, Line 66, Claim 15, please delete "(trifluoromethyl) phenyl)-" and insert
-- (trifluoromethyl)phenyl)- --;

Column 587, Line 2, Claim 15, please delete "-1-yl) pyridin-" and insert -- -1-yl)pyridin- --;

Column 587, Line 5, Claim 15, please delete "-1-yl) pyridin-" and insert -- -1-yl)pyridin- --;

Column 587, Line 7, Claim 15, please delete "-1-yl) pyridin-" and insert -- -1-yl)pyridin- --;

Column 587, Line 11, Claim 15, please delete "-1-yl) pyridin-" and insert -- -1-yl)pyridin- --;

Column 587, Line 13, Claim 15, please delete "-1-yl) pyridin-" and insert -- -1-yl)pyridin- --;

Column 587, Line 14, Claim 15, please delete "(trifluoromethyl) phenyl)-" and insert
-- (trifluoromethyl)phenyl)- --;

Column 587, Line 17, Claim 15, please delete "-1-yl) pyridin-" and insert -- -1-yl)pyridin- --;

Column 587, Line 20, Claim 15, please delete "-1-yl) pyridin-" and insert -- -1-yl)pyridin- --;

Column 587, Line 23, Claim 15, please delete "-1-yl) pyridin-" and insert -- -1-yl)pyridin- --;

Column 587, Line 26, Claim 15, please delete "-1-yl) pyridin-" and insert -- -1-yl)pyridin- --;

Column 587, Line 29, Claim 15, please delete "-1-yl) pyridin-" and insert -- -1-yl)pyridin- --;

Column 587, Line 32, Claim 15, please delete "-1-yl) pyridin-" and insert -- -1-yl)pyridin- --;

Column 587, Line 35, Claim 15, please delete "-1-yl) pyridin-" and insert -- -1-yl)pyridin- --;

Column 587, Line 37, Claim 15, please delete "-1-yl) pyridin-" and insert -- -1-yl)pyridin- --;

Column 587, Line 41, Claim 15, please delete "-methyl-H-imidazol-" and insert
-- -methyl-1H-imidazol- --;

Column 587, Line 41, Claim 15, please delete "-1-yl) pyridin-" and insert -- -1-yl)pyridin- --;

Column 587, Line 44, Claim 15, please delete "-1-yl) pyridin-" and insert -- -1-yl)pyridin- --;

Column 587, Line 47, Claim 15, please delete "-1-yl) pyridin-" and insert -- -1-yl)pyridin- --;

Column 587, Line 50, Claim 15, please delete "-1-yl) pyridin-" and insert -- -1-yl)pyridin- --;

Column 587, Line 53, Claim 15, please delete "-1-yl) pyridin-" and insert -- -1-yl)pyridin- --;

Column 587, Line 56, Claim 15, please delete "-1-yl) pyridin-" and insert -- -1-yl)pyridin- --;

CERTIFICATE OF CORRECTION (continued)
U.S. Pat. No. 9,802,927 B2

Column 587, Line 59, Claim 15, please delete "-1-yl) pyridin-" and insert -- -1-yl)pyridin- --;

Column 587, Line 61, Claim 15, please delete "-1-yl) pyridin-" and insert -- -1-yl)pyridin- --;

Column 587, Line 62, Claim 15, please delete "(trifluoromethyl) phenyl)-" and insert -- (trifluoromethyl)phenyl)- --;

Column 587, Line 65, Claim 15, please delete "-1-yl) pyridin-" and insert -- -1-yl)pyridin- --;

Column 588, Line 2, Claim 15, please delete "-1-yl) pyridin-" and insert -- -1-yl)pyridin- --;

Column 588, Line 4, Claim 15, please delete "(trifluoromethyl) phenyl)-" and insert -- (trifluoromethyl)phenyl)- --;

Column 588, Line 5, Claim 15, please delete "-1-yl) pyridin-" and insert -- -1-yl)pyridin- --;

Column 588, Line 7, Claim 15, please delete "-1-yl) pyridin-" and insert -- -1-yl)pyridin- --;

Column 588, Line 8, Claim 15, please delete "-5-(i-methyl-" and insert -- -5-(1-methyl- --;

Column 588, Line 11, Claim 15, please delete "-1-yl) pyridin-" and insert -- -1-yl)pyridin- --;

Column 588, Line 17, Claim 15, please delete "-1-yl) pyridin-" and insert -- -1-yl)pyridin- --;

Column 588, Line 20, Claim 15, please delete "-1-yl) pyridin-" and insert -- -1-yl)pyridin- --;

Column 588, Line 24, Claim 15, please delete "-1-yl) pyridin-" and insert -- -1-yl)pyridin- --;

Column 588, Line 27, Claim 15, please delete "-1-yl) pyridin-" and insert -- -1-yl)pyridin- --;

Column 588, Line 30, Claim 15, please delete "-1-yl) pyridin-" and insert -- -1-yl)pyridin- --;

Column 588, Line 33, Claim 15, please delete "-1-yl) pyridin-" and insert -- -1-yl)pyridin- --;

Column 588, Line 35, Claim 15, please delete "-1-yl) pyridin-" and insert -- -1-yl)pyridin- --;

Column 588, Line 42, Claim 15, please delete "-1-yl) pyridin-" and insert -- -1-yl)pyridin- -- therefor.